US008173410B2

(12) United States Patent
Bott et al.

(10) Patent No.: US 8,173,410 B2
(45) Date of Patent: May 8, 2012

(54) ISOPRENE SYNTHASE VARIANTS FOR IMPROVED MICROBIAL PRODUCTION OF ISOPRENE

(75) Inventors: Richard R. Bott, Burlingame, CA (US); Marguerite A. Cervin, Redwood City, CA (US); James T. Kellis, Jr., Palo Alto, CA (US); Joseph C. McAuliffe, Sunnyvale, CA (US); Andrei Miasnikov, Mountain View, CA (US); Caroline M. Peres, Palo Alto, CA (US); Christopher Lee Rife, Redwood City, CA (US); Derek H. Wells, Palo Alto, CA (US); Walter Weyler, San Francisco, CA (US); Gregory M. Whited, Belmont, CA (US)

(73) Assignee: Danisco US Inc., Palo Alto, CA (US)

( * ) Notice: Subject to any disclaimer, the term of this patent is extended or adjusted under 35 U.S.C. 154(b) by 215 days.

(21) Appl. No.: 12/429,143

(22) Filed: Apr. 23, 2009

(65) Prior Publication Data

US 2010/0003716 A1    Jan. 7, 2010

Related U.S. Application Data

(60) Provisional application No. 61/125,336, filed on Apr. 23, 2008.

(51) Int. Cl.
*C12N 9/88* (2006.01)
*C12N 15/09* (2006.01)
*C12N 15/00* (2006.01)
*C12N 1/20* (2006.01)
*C12P 5/02* (2006.01)
*C07H 21/04* (2006.01)
*C07K 1/00* (2006.01)

(52) U.S. Cl. ............ 435/232; 435/69.1; 435/320.1; 435/167; 435/252.3; 435/252.33; 435/254.11; 435/254.2; 435/254.21; 435/254.6; 536/23.1; 536/23.2; 536/23.6; 530/350

(58) Field of Classification Search ............ 435/232, 435/69.1, 320.1, 167, 252.3, 252.33, 254.11, 435/254.2, 254.21, 254.6; 536/23.1, 23.2, 536/23.6; 530/350

See application file for complete search history.

(56) References Cited

U.S. PATENT DOCUMENTS

| | | |
|---|---|---|
| 1,344,713 A | 6/1920 | Peters |
| 3,686,349 A | 8/1972 | Schliebs et al. |
| 4,570,029 A | 2/1986 | Kulprathipanja et al. |
| 4,647,344 A | 3/1987 | Lindner et al. |
| 4,683,195 A | 7/1987 | Mullis et al. |
| 4,683,202 A | 7/1987 | Mullis |
| 4,703,007 A | 10/1987 | Mulholland et al. |
| 4,846,872 A | 7/1989 | Kamuro et al. |
| 4,965,188 A | 10/1990 | Mullis et al. |
| 5,322,770 A | 6/1994 | Gelfand |
| 5,349,126 A | 9/1994 | Chappell et al. |
| 5,380,831 A | 1/1995 | Adang et al. |
| 5,436,391 A | 7/1995 | Fujimoto et al. |
| 5,545,816 A | 8/1996 | Ausiche et al. |
| 5,849,970 A | 12/1998 | Fall et al. |
| 5,874,276 A | 2/1999 | Fowler et al. |
| 6,022,725 A | 2/2000 | Fowler et al. |
| 6,106,888 A | 8/2000 | Dale et al. |
| 6,176,176 B1 | 1/2001 | Dale et al. |
| 6,268,328 B1 | 7/2001 | Mitchinson et al. |
| 6,270,739 B1 | 8/2001 | Barnicki et al. |
| 6,294,653 B1 | 9/2001 | Mayfield |
| 6,582,914 B1 | 6/2003 | Caldwell et al. |
| 6,806,076 B1 | 10/2004 | Miyake et al. |
| 6,989,257 B2 | 1/2006 | Berry et al. |
| 6,998,471 B2 | 2/2006 | Hallahan et al. |
| 7,129,392 B2 | 10/2006 | Hahn et al. |
| 7,132,268 B2 | 11/2006 | Miyake et al. |
| 7,132,527 B2 | 11/2006 | Payne et al. |
| 7,172,886 B2 | 2/2007 | Keasling et al. |
| 7,183,089 B2 | 2/2007 | Keasling et al. |
| 7,208,298 B2 | 4/2007 | Miyake et al. |
| 7,241,587 B2 | 7/2007 | Dodge et al. |
| 7,262,041 B2 | 8/2007 | Baldwin et al. |
| 7,364,885 B2 | 4/2008 | Miyake et al. |
| 7,531,333 B2 | 5/2009 | Miyake et al. |
| 2002/0095818 A1 | 7/2002 | Jain et al. |
| 2003/0033626 A1 | 2/2003 | Hahn et al. |
| 2004/0005678 A1 | 1/2004 | Keasling et al. |
| 2004/0219629 A1 | 11/2004 | Cheng et al. |
| 2005/0287655 A1 | 12/2005 | Tabata et al. |
| 2006/0009647 A1 | 1/2006 | Yeates et al. |

(Continued)

FOREIGN PATENT DOCUMENTS

DE     196 29 568 C1     1/1998

(Continued)

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Kozak M., Structural features in eukaryotic mRNAs that modulate the initiation of translation. J. Biol. Chem., 1991, vol. 266 (30): 19867-19870.*

(Continued)

*Primary Examiner* — Ganapathirama Raghu
(74) *Attorney, Agent, or Firm* — Morrison & Foerster LLP

(57) ABSTRACT

The present invention provides methods and compositions comprising at least one isoprene synthase enzyme with improved catalytic activity and/or solubility. In particular, the present invention provides variant plant isoprene synthases for increased isoprene production in microbial host cells. Biosynthetically produced isoprene of the present invention finds use in the manufacture of rubber and elastomers.

22 Claims, 156 Drawing Sheets

U.S. PATENT DOCUMENTS

| | | | |
|---|---|---|---|
| 2006/0020095 A1 | 1/2006 | Gandon-Pain | |
| 2008/0178354 A1 | 7/2008 | Chappell et al. | |
| 2009/0155874 A1 | 6/2009 | Clark et al. | |
| 2009/0203102 A1 | 8/2009 | Cervin et al. | |
| 2010/0048964 A1 | 2/2010 | Calabria et al. | |
| 2010/0086978 A1 | 4/2010 | Beck et al. | |
| 2010/0113846 A1 | 5/2010 | McAuliffe et al. | |
| 2010/0196982 A1 | 8/2010 | Anderson | |
| 2011/0045563 A1* | 2/2011 | Melis | 435/167 |

FOREIGN PATENT DOCUMENTS

| | | |
|---|---|---|
| EP | 0 215 594 A2 | 3/1987 |
| EP | 0 215 594 A3 | 3/1987 |
| EP | 0 215 594 B1 | 3/1987 |
| EP | 0 215 594 B2 | 3/1987 |
| EP | 0 238 023 A2 | 9/1987 |
| EP | 0 238 023 A3 | 9/1987 |
| EP | 0 238 023 B1 | 9/1987 |
| EP | 0 238 023 B2 | 9/1987 |
| EP | 0 244 234 A2 | 11/1987 |
| EP | 0 244 234 A3 | 11/1987 |
| EP | 0 244 234 B1 | 11/1987 |
| EP | 0 244 234 B2 | 11/1987 |
| EP | 1 118 855 A2 | 7/2001 |
| EP | 1 118 855 A3 | 7/2001 |
| JP | 2008-035831 A | 2/2008 |
| WO | WO-95/04134 A1 | 2/1995 |
| WO | WO-96/35796 A1 | 11/1996 |
| WO | WO-98/02550 A2 | 1/1998 |
| WO | WO-98/02550 A3 | 1/1998 |
| WO | WO-00/17327 A2 | 3/2000 |
| WO | WO-00/17327 A3 | 3/2000 |
| WO | WO-00/17327 C2 | 3/2000 |
| WO | WO-01/58839 A1 | 8/2001 |
| WO | WO-02/099095 A2 | 12/2002 |
| WO | WO-02/099095 A3 | 12/2002 |
| WO | WO-2004/033646 A2 | 4/2004 |
| WO | WO-2004/033646 A3 | 4/2004 |
| WO | WO-2004/111214 A1 | 12/2004 |
| WO | WO-2005/001036 A2 | 1/2005 |
| WO | WO-2005/001036 C1 | 1/2005 |
| WO | WO-2005/007682 A2 | 1/2005 |
| WO | WO-2005/007682 A3 | 1/2005 |
| WO | WO-2005/078074 A2 | 8/2005 |
| WO | WO-2005/078074 A3 | 8/2005 |
| WO | WO-2006/063752 A1 | 6/2006 |
| WO | WO-2006/085899 A2 | 8/2006 |
| WO | WO-2006/085899 A3 | 8/2006 |
| WO | WO-2007/018062 A1 | 2/2007 |
| WO | WO-2007/136847 A2 | 11/2007 |
| WO | WO-2007/136847 A3 | 11/2007 |
| WO | WO-2007/140339 A2 | 12/2007 |
| WO | WO-2007/140339 A3 | 12/2007 |
| WO | WO-2007/140339 A8 | 12/2007 |
| WO | WO-2008/003078 A2 | 1/2008 |
| WO | WO-2008/003078 A3 | 1/2008 |
| WO | WO-2008/003078 A8 | 1/2008 |
| WO | WO2008/003078 * | 3/2008 |
| WO | WO-2008/137092 A2 | 11/2008 |
| WO | WO-2008/137092 A3 | 11/2008 |
| WO | WO-2008/153925 A2 | 12/2008 |
| WO | WO-2008/153925 A3 | 12/2008 |
| WO | WO-2008/153925 A9 | 12/2008 |
| WO | WO-2008/153934 A2 | 12/2008 |
| WO | WO-2008/153934 A3 | 12/2008 |
| WO | WO-2008/153935 A2 | 12/2008 |
| WO | WO-2008/153935 A3 | 12/2008 |
| WO | WO-2009/076676 A2 | 6/2009 |
| WO | WO-2009/076676 A3 | 6/2009 |
| WO | WO-2009/132220 A2 | 10/2009 |
| WO | WO-2009/132220 A3 | 10/2009 |
| WO | WO-2009/132220 A9 | 10/2009 |
| WO | WO-2010/003007 A2 | 1/2010 |
| WO | WO-2010/005525 A1 | 1/2010 |
| WO | WO-2010/031062 A1 | 3/2010 |
| WO | WO-2010/031068 A1 | 3/2010 |
| WO | WO-2010/031076 A2 | 3/2010 |
| WO | WO-2010/031077 A1 | 3/2010 |
| WO | WO-2010/031079 A1 | 3/2010 |
| WO | WO-2010/078457 A2 | 7/2010 |
| WO | WO-2010/078457 A3 | 7/2010 |

OTHER PUBLICATIONS

Kozak M., Initiation of translation in prokaryotes and eukaryotes. Gene, 1999, vol. 234: 187-208.*

Sasaki et al., Gene expression and characterization of isoprene synthase from *Populus alba*. FEBS Letters, 2005, vol. 579: 2514-2518.*

Sen et al., Developments in directed evolution for improving enzyme functions. Appl. Biochem. Biotechnol., 2007, vol. 143: 212-223.*

Whisstock et al., Prediction of protein function from protein sequence. Q. Rev. Biophysics., 2003, vol. 36 (3): 307-340.*

Wishart et al., A single mutation converts a novel phosphotyrosine binding domain into a dual-specificity phosphatase. J. Biol. Chem., 1995, vol. 270(45): 26782-26785.*

Witkowski et al., Conversion of b-ketoacyl synthase to a Malonyl Decarboxylase by replacement of the active cysteine with glutamine. Biochemistry, 1999, vol. 38: 11643-11650.*

Albrecht, M. at al. (Aug. 2000). "Novel Hydroxycarotenoids with Improved Antioxidive Properties Produced by Gene Combination in *Escherichia coli*," *Nature Biotechnology* 18:843-846.

Alexopoulos, C.J. (1962). *Introductory Mycology*, Wiley: New York, NY, pp. ix-x, (Table of Contents Only).

Allison, R. at al. (1986). "The Nucleotide Sequence of the Coding Region of Tobacco Etch Virus Genomic RNA: Evidence for the Synthesis of a Single Polyprotein," *Virology* 154:9-20.

Alper, H. et al. (2008). "Uncovering the Gene Knockout Landscape for Improved Lycopene Production in *E. coli*," *Appl. Microbiol. Biotechnol.* 10 pages.

Alterthum, F. et al. (Aug. 1989). "Efficient Ethanol Production from Glucose, Lactose, and Xylose by Recombinant *Escherichia coli*," *Applied Environmental Microbiology* 55(8):1943-1948.

Altschul, S.F. et al. (1990). "Basic Local Alignment Search Tool," *J Mol Biol.* 215:403-410.

Altschul, S.F. et al. (1996). "Local Alignment Statistics," Chapter 27 in *Multiple Alignment and Phylogenetic Trees*, American Press, Inc. 266:460-480.

Alves, R. et al. (Nov. 2000). "Effect of Overall Feedback Inhibition in Unbranched Biosynthetic Pathways," *Biophysical Journal* 79(5):2290-2304.

Anderson, M.S. et al. (Nov. 15, 1989). "Isopentenyl Diphosphate: Dimethylallyl Diphosphate Isomerare. An Improved Purification of the Enzyme and Isolation of the Gene From *Saccharomyces cerevisia*," *J. Biol. Chem.* 264(32):19169-19175.

Andreassi, J.L. et al. (2004, e-pub. Dec. 4, 2004). "*Streptococcus pneumoniae* Isoprenoid Biosynthesis Is Downregulated by Diphosphomevalonate: An Antimicrobial Target," *Biochemistry* 43(51):16461-16466.

Andreassi, J.L. et al. (2007, e-pub. Mar. 30, 2007). "Crystal Structure of the *Streptococcus pneumoniae* Mevalonate Kinase in Complex with Diphosphomevalonate," *Protein Science* 16:983-989.

Aon, J.C. et al. (Feb. 2008, e-pub. Dec. 14, 2007). "Suppressing Posttranslational Gluconoylation of Heterologous Proteins by Metabolic Engineering of *Escherichia coli*," *Applied and Environmental Microbiology* 74(4):950-958.

Arai, Y. et al. (2004). "Production of Polyhydroxybutyrate by Polycistronic Expression of Bacterial Genes in Tobacco Plastid," *Plant Cell Physiol* 45(9):1176-1184.

Ashby, M.N. et al. (Aug. 5, 1990). "Elucidation of the Deficiency in Two Yeast Coenzyme Q Mutants: Characterization of the Structural Gene Encoding Hexaprenyl Pyrophosphate Synthetase," *The Journal of Biological Chemistry* 265(22):13157-13164.

Ausubel, F.M. et al. eds. (1987). *Current Protocols in Molecular Biology*, John Wiley and Sons, Inc., pp. 1-13, (Table of Contents Only).

Ausubel, F.M. et al. eds. (1994). *Current Protocols in Molecular Biology*, John Wiley and Sons, Inc., pp. 1-7, (Table of Contents Only).

Baba, T. et al. (Feb. 21, 2006). "Construction of *Escherichia coli* K-12 In-Frame, Single-Gene Knockout Mutants: The Keio Collection," *Molecular Systems Biology* pp. 1-11.

Ballas, N. et al. (1989). "Efficient Functioning of Plant Promoters and Poly(A) Sites in *Xenopus oocytes*," *Nucleic Acids Research* 17(19):7891-7903.

Barkovich, R. et al. (2001, e-pub. Dec. 1, 2000). "Metabolic Engineering of Isoprenoids," *Metabolic Engineering* 3:27-29.

Beaucage, S.L. et al. (1981). "Deoxynucleoside Phosphoramidites—A New Class of Key Intermediates for Deoxypolynucleotide Synthesis," *Tetrahedron Letters* 22(20):1859-1862.

Bellion, E. et al. (1993). "Methylamine Utilization in Yeast and Bacteria: Studies Using in vivo NMR," Chapter 32 in *Microbial Growth $C_1$ Compounds*, Muerrell, J.C. et al. eds, Intercept Ltd: Andover, UK, pp. 415-432.

Bennett, J.W. et al. eds. (1991). "Gene Cloning and Analysis," Chapter 3 in *More Gene Manipulations in Fungi*, Academic Press, San Diego, CA pp. 70-76.

Berman, H. et al. (2007, e-published Nov. 16, 2006). "The Worldwide Protein Data Bank (wwPDB): Ensuring a Single, Uniform Archive of PBD Data," *Nucleic Acids Research* 35:D301-D303.

Beytia, E. et al. (Oct. 25, 1970). "Purification and Mechanism of Action of Hog Liver Mevalonic Kinase," *The Journal of Biological Chemistry* 245(20):5450-5458.

Bock, R. et al. (2000). "Extranuclear Inheritance: Plastid Genetic: Manipulation of Plastid Genomes and Biotechnological Applications," *Progress in Botany* 61:76-90.

Bock, R. (2001). "Transgenic Plastids in Basic Research and Plant Biotechnology," *J. Mol. Biol.* 312:425-438.

Bock, R. et al. (Jun. 2004). "Taming Plastids for a Green Future," *Trends Biotechnology* 22(6):311-318.

Boel, E. et al. (1984). "Two Different Types of Intervening Sequences in the Glucoamylase Gene from *Aspergillus niger*," *The EMBO Journal* 3(7):1581-1585.

Bouvier, F. et al. (2005). "Biogenesis, Molecular Regulation and Function of Plant Isoprenoids," *Progress in Lipid Res*. 44:357-429.

Boynton, J.E. et al. (1993). "Chloroplast Transformation in *Chlamydomonas*," *Methods in Enzymology* 217(37):510-536.

Bubunenko, M. et al. (Apr. 2007). "Essentiality of Ribosomal and Transcription Antitermination Proteins Analyzed by Systemic Gene Replacement in *Escherichia coli*," *Journal of Bacteriology* 189(7):2844-2853.

Campbell, E.I. et al. (1989). "Improved Transformation Efficiency of *Aspergillus niger* Using the Homologus *niaD* Gene for Nitrate Reductase," *Curr. Genet.* 16:53-56.

Campbell, J.W. et al. (Oct. 2001). "*Escherichia coli* FadR Positively Regulates Transcription of the *fabB* Fatty Acid Biosynthetic Gene," *J. Bacteriol.* 183(20):5982-5990.

Campos, N. et al. (2001). "*Escherichia coli* Engineering to Synthesize Isopentenyl Diphosphate and Dimethylallyl Diphosphate from Mevalonate: A Novel System for the Genetic Analysis of the 2-C-Methyl-D-Erythritol 4-Phospate Pathway for Isoprenoid Biosynthesis," *Biochem. J.* 353:59-67.

Cao, Q-N. et al. (2000). "Penicillopepsin-JT2, a Recombinant Enzyme from *Penicillium janthinellum* and the Contribution of a Hydrogen Bond in Subsite $S_3$ to $k_{cat}$," *Protein Science* 9:991-1001.

Chamberlin, M. et al. (Oct. 17, 1970). "New RNA Polymerase from *Escherichia coli* Infected with Bacteriophase T7," *Nature* 228:227-231.

Champenoy, S. et al. (1998). "Expression of the Yeast Mevalonate Kinase Gene in Transgenic Tobacco," *Molecular Breeding* 4:291-300.

Chan, W. et al. (2007, e-pub. Apr. 10, 2007). "A Recombineering Based Approach for High-Throughput Conditional Knockout Targeting Vector Construction," *Nucleic Acids Research* 35(8):e64, 13 pages.

Chappell J. et al. (1995). "Is the Reaction Catalyzed by 3-Hydroxy-3-Methylglutaryl—Coenzyme A Reductase a Rate-Limiting Step for Isoprenoid Biosynthesis in Plants?" *Plant Physiology* 109:1337-1343.

Chemler, J.A. et al. (May 23, 2006). "Biosynthesis of Isoprenoids, Polyunsaturated Fatty Acids and Flavonoids in *Saccharomyces cerevisiae*," *Microbial Cell Factories* 5:20, 9 pages.

Cho, H-J. et al. (1995). "Expression Pattern of Bacterial Polycistronic Genes in Tobacco Cells," *Journal of Fermentation and Bioengineering* 80(2):111-117.

Clarke, S. (1992). "Protein Isoprenylation and Methylation at Carboxyl-Terminal Cysteine Residues," *Annu. Rev. Biochem.* 61:355-386.

Clough, S.J. et al. (1998). "Floral Dip: Simplified Method for *Agrobacterium*-Mediated Transformation of *Arabidopsis thaliana*," *The Plant Journal* 16(6):735-743.

Cordier, H. et al. (1999). "Heterologous Expression in *Saccharomyces cerevisiae* of an *Arabidopsis thaliana* cDNA Encoding Mevalonate Diphosphate Decarboxylase," *Plant Molecular Biology* 39:953-967.

Crueger, W. et al. (1989). *Biotechnology: A Textbook of Industrial Microbiology*, Second Edition, T.D. ed., Sinauer Associates, Inc.: Sunderland, MA, pp. vii-x, (Table of Contents Only).

Cunningham, F.X. et al. (1998). "Genes and Enzymes of Carotenoid Biosynthesis in Plants," *Ann. Rev. Plant Mol. Biol.* 49:557-583.

Cunningham, F.X. et al. (Oct. 2000). "Evidence of a Role for LytB in the Nonmevalonate Pathway of Isoprenoid Biosynthesis," *Journal of Bacteriology* 182(20):5841-5848.

Dale, P. J. (1992). "Spread of Engineered Genes to Wild Relatives," *Plant Physiol.* 100:13-15.

Daniell, H. (1997). "Transformation and Foreign Gene Expression in Plants Mediated by Microprojectile Bombardment," Chapter 35 in *Methods in Molecular Biology, Recombinant Gene Expression Protocols*, Tuan, R S. ed., Humana Press: Totowa, NJ, 62:463-489.

Daniell, H. et al. (Apr. 1998) "Containment of Herbicide Resistance Through Genetic Engineering of the Chloroplast Genome," *Nature Biotechnology* 16:345-348.

Datsenko, K.A. et al. (Jun. 6, 2000). "One-Step Inactivation of Chromosomal Genes in *Escherichia coli* K-12 Using PCR Products," *PNAS* 97(12):6640-6645.

Datta, S. et al. (2006). "A Set of Recombineering Plasmids for Gram-Negative Bacteria," *Gene* 379:109-115.

Datukishvili, N.T. et al. (2001). "Isolation and Purification of Protein Responsible for the Conversion of Dimethylallylpyrophosphate from Poplar Leaves into Isoprene," *Russian Journal of Plant Physiology* 48(2):222-225.

Davidson, S. (Oct.-Dec. 2003). "Light Factories," located at <http://www.publish.csiro.au/?act=view_file&file_id=EC117p10.pdf>, last visited on Oct. 2, 2008.

Davis, I.W. et al. (2007). "MolProbity: All-Atom Contacts and Structure Validation for Proteins and Nucleic Acids," *Nucleic Acids Research* 35:W375-W383.

De Cosa, B. et al. (Jan. 2001). "Overexpression of the *Bt cry*2Aa2 Operon in Chloroplasts Leads to Formation of Insecticidal Crystals," *Nature Biotechnology* 19:71-74.

Del Campo, E. M. et al. (1997). "Plastid *ndhD* Gene of Barley, Sequence and Transcript Editing (Accesion No. Y12258) (PGR 97-090)," *Plant Physiol* 114:747-749.

Della-Cioppa, G. et al. (1987). "Protein Trafficking in Plant Cells," *Plant Physiol* 84:965-968.

Deppenmeier, U. et al. (2002). "The Genome of methanosarcina mazei: Evidence for Lateral Gene Transfer Between Bacteria and Archaea," *J. Mol. Microbiol. Biotechnol.* 4(4):453-461.

Deroles, S.C. et al. (1988). "Expression and Inheritance of Kanamycin Resistance in a Large Number of Transgenic Petunias Generated by *Agrobacteriu*-Mediated Transformation," *Plant Molecular Biology* 11:355-364.

Dettmer, K. et al. (2000). "Stability of Reactive Low Boiling Hydrocarbons on Carbon Based Dsorbents Typically Used for Adsorptive Enrichment and Thermal Desorption," *Fresenius J. Anal. Chem.* 366:70-78.

Devereux, J. et al. (1984). "A Comprehensive Set of Sequence Analysis Programs for the VAX," *Nucleic Acids Research* 12(1):387-395.

Dewick, P.M. et al. (2002, e-pub. Jan. 22, 2002). "The Biosynthesis of $C_5$-$C_{25}$ Terpenoid Compounds," *Nat. Prod. Rep.* 19:181-222.

Dhe-Paganon, S. et al. (1994). "Mechanism of Mevalonate Pyrophosphate Decarboxylase: Evidence for a Carbocationic Transition State," *Biochemistry* 33(45):13355-13362.

Dorsey, J.K. et al. (Sep. 25, 1968). "The Inhibition of Mevalonic Kinase by Geranyl and Farnesyl Pyrophosphates," *The Journal of Biological Chemistry* 243(18):4667-4670.

Doumith, M. et al. (2000, e-pub. Aug. 25, 2000). "Analysis of Genes Involved in 6-Deoxyhexose Biosynthesis and Transfer in *Saccharopolyspora erythraea*," *Mol. Gen Genet.* 264:477-485.

Dynan, W.S. et al. (Aug. 29, 1985). "Control of Eukaryotic Messenger RNA Synthesis by Sequence-Specific DNA-Binding Proteins," *Nature* 316:774-778.

Eisenreich, W. et al. (Sep. 1998). "The Deoxyxylulose Phosphate Pathway of Terpenoid Biosynthesis in Plants and Microorganisms," *Chemistry and Biology* 5(9):R221-R233.

Eisenreich, W. et al, (Feb. 2001). "Deoxyxylulose Phosphate Pathway to Terpenoids," *Trends in Plant Science* 6(2):78-84.

Elroy-Stein, O. et al. (Aug. 1989). "Cap-Independent Translation of mRNA Conferred by Encephalomyocarditis Virus 5' Sequence Improves the Performance of the Vaccinia Virus/Bacteriophage T7 Hybrid Expression System," *PNAS USA* 86:6126-6130.

EMBL-EBI Accession No. A0PFK2, last updated on Mar. 2, 2010, located at <http://srs.ebi.ac.uk/srsbin/cgi-bin/wgetz?-e+[UNIPROT:A0PFK2_POPNI]+-newId>, last visited on Jun. 2, 2010, 2 pages.

EMBL-EBI Accession No. A9PGR5, last updated on Mar. 2, 2010, located at <http://srs.ebi.ac.uk/srsbin/cgi-bin/wgetz?-e+[UNIPROT:A9PGR5_POPTR]+-newId>, last visited on Jun. 2, 2010, 2 pages.

EMBL-EBI Accession No. AB198180, last updated May 10, 2005, located at <http://www.ebi.ac.uk/cgi-bin/dbfetch?db=embl&id=ab198180&Subm...>, last visited on Aug. 7, 2009, 2 pages.

EMBL-EBI Accession No. AY341431, last updated Apr. 16, 2005, located at <http://www.ebi.ac.uk/cgi-bin/dbfetch?db=embl&id=AY341431&Sub...>, last visited on Nov. 26, 2009, 2 pages.

Emsley, P. et al. (2004). "*Coot*: Model-Building Tools for Molecular Graphics," *Acta Crystallographica* D60:2126-2132.

Fall, R. (Sep. 12, 2003). "Final Technical Report: DE-FG03-97ER20274, 'Microbial Production of Isoprene'," located at <http://www.osti.gov/bridge/product.biblio.jsp?query_id=1&page=0&osti_id=814920>, last visited on May 26, 2010, 4 pages.

Farmer, W.R. et al. (May 2000). "Improving Lycopene Production in *Escherichia coli* by Engineering Metabolic Control," *Nature Biotechnology* 18:533-537.

Feng, E-F. et al. (1987). "Progressive Sequence Alignment as a Prerequisite to Correct Phylogenetic Trees," Journal of Molecular Evolution 25:351-360.

Finkelstein, D.B. (1992). "Transformation," Chapter 6 in *Biotechnology of Filamentous Fungi*, Butterworth-Heinemann: Boston, MA, pp. 113-156.

Flores, S. et al. (Aug. 20, 2004, e-pub. Jul. 23, 2004). "Growth-Rate Recovery of *Escherichia coli* Cultures Carrying a Multicopy Plasmid, by Engineering of the Pentose-Phosphate Pathway," *Biotechnology and Bioengineering* 87(4):485-494.

Fu, Z. et al. (2008, e-pub. Feb. 27, 2008). "Biochemical and Structural Basis for Feedback Inhibition of Mevalonate Kinase and Isoprenoid Metabolism," *Biochemistry* 47:3715-3724.

Gallie, D.R. et al. (1989). "Eukaryotic Viral 5'-Leader Sequences Act as Translational Enhancers in Eukaryotes and Prokaryotes," in *Molecular Biology of RNA*, Cech, T.R. ed. Alan R. Liss, Inc: New York, NY, pp. 237-256.

Garret, T.A. et al. (May 15, 1998). "Accumulation of a Lipid A Precursor Lacking the 4'-Phosphate Following Inactivation of the *Escherichia coli IpxK* Gene," *The Journal of Biological Chemistry* 273(20):12457-12465.

GenBank Accession No. AB198180, last updated on May 10, 2005, located at <http://www.ncbi.nlm.nih.gov/nuccore/63108309>, last visited on Jun. 2, 2010, 2 pages.

GenBank Accession No. AJ457070, last updated on Apr. 15, 2005, located at <http://www.ncbi.nlm.nih.gov/nuccore/38092202>, last visited on Jun. 2, 2010, 2 pages.

GenBank Accession No. AY182241, last updated on May 4, 2004, located at <http://www.ncbi.nlm.nih.gov/nuccore/32265057>, last visited on Jun. 2, 2010, 2 pages.

GenBank Accession No. AY279379, last updated on Mar. 11, 2005, located at <http://www.ncbi.nlm.nih.gov/nuccore/30984014>, last visited on Jun. 2, 2010, 2 pages.

GenBank Accession No. AY316691, last updated on Feb. 15, 2005, located at <http://www.ncbi.nlm.nih.gov/nuccore/35187003>, last visited on Jun. 2, 2010, 2 pages.

GenBank Accession No. AY341431, last updated on Feb. 15, 2005, located at <http://www.ncbi.nlm.nih.gov/nuccore/33358228>, last visited on Jun. 2, 2010, 3 pages.

GenBank Accession No. CAC35696, last updated Apr. 15, 2005, located at <http://www.ncbi.nlm.nih.gov/protein/CAC35696>, last visited on Apr. 6, 2011, 2 pages.

GenBank Accession No. EU693027, last updated on May 27, 2008, located at <http://www.ncbi.nlm.nih.gov/nuccore/189017053>, last visited on Jun. 2, 2010, 2 pages.

Gerhardt, P. et al. eds. (1994). *Methods for General and Molecular Bacteriology*, American Society for Microbiology: Washington, D.C., p. v, (Table of Contents Only).

Goedegebuur, F. et al. (2002, e-pub. May 7, 2002). "Cloning and Relational Analysis of 15 Novel Fungal Endoglucanases form Family 12 Glycosyl Hydrolase," *Curr. Genet.* 41:89-98.

Goldschmidt-Clermont, M. (1991). "Transgenic Expression of Aminoglycoside Adenine Transferase in the Chloroplast: A Selectable Marker for Site-Directed Transformation of Chlamydomonas," *Nucleic Acids Res.* 19(15):4083-4089.

Goodwin, T.W. (1971). "Biosynthesis of Carotenoids and Plant Triterpenes: The Fifth CIBA Medal Lecture," *Biochem. J.* 123(3):293-329.

Gottschalk, G. (1986). *Bacterial Metabolism*, Second Edition, Springer Verlag: New York, NY, pp. xi-xiii, (Table of Contents Only).

Grӓwert, T. et al. (2004, e-pub. Sep. 21, 2004). "IspH Protein of *Escherichia coli*: Studies on Iron-Sulfur Cluster Implementation and Catalysis," *Journal American Chemistry Society* 126:12847-12855.

Greenberg, J.P. et al. (1993). "Sub-Parts Per Billion Detection of Isoprene Using a Reduction Gas Detector with a Portable Gas Chormatograph," *Atmos. Environ.* 27A(16):2689-2692.

Grochowski, L.L. et al. (May 2006). "*Methanocaldococcus jannaschii* Uses a Modified Mevalonate Pathway for Biosynthesis of Isopentenyl Diphosphate," *Journal of Bacteriology* 188(9):3192-3198.

Guda, C. et al. (2000). "Stable Expression for a Biodegradable Protein-Based Polymer in Tobacco Chloroplasts," *Plant Cell Reports* 19:257-262.

Guerineau, F. et al. (1991). "Effect of Deletions in the Cauliflower Mosaic Virus Polyadenylation Sequence on the Choice of the Polyadenylation Sites in Tobacco Protoplasts," *Mol. Gen. Genet* 226:141-144.

Guo, D-A. et al. (1995). "Developmental Regulation of Sterol Biosynthesis in *Zea mays*," *Lipids* 30(3):203-219.

Hahn, F.M. et al. (May 12, 1995). "Isolation of *Schizosaccharomyces pombe* Isopentenyl Diphosphate Isomerase in cDNA Clones by Complementation and Synthesis of the Enzyme in *Escherichia coli*," *The Journal of Biological Chemistry* 270(19):11298-11303.

Hahn, F.M. et al. (Feb. 1996). "Open Reading Frame 176 in the Photosynthesis Gene Cluster of *Rhodobacter capsulatus* Encodes *idi*, a Gene for Isopentenyl Diphosphate Isomerase," *Journal of Bacteriology* 178(3):619-624.

Hahn, F.M. et al. (Aug. 1999). "*Escherichia coli* Open Reading Frame 696 Is *idi*, a Nonessential Gene Encoding Isopentenyl Diphosphate Isomerase," *Journal of Bacteriology* 181(15):4499-4504.

Hahn, F.M. et al. (Jan. 2001). "1-Deoxy D-Xylulose 5-Phosphate Synthase, the Gene Product of Open Reading Frame (ORF) 2816 and ORF 2895 in *Rhodobacter capsulatus*," *Journal of Bacteriology* 183(1):1-11.

Hale, W.G. et al. (1991). *The Harper Collins Dictionary of Biology*, Ehrlich, E. ed., Harper Perennial: New York, NY, 2 pages.

Hamano, Y. et al. (2001). "Cloning of a Gene Cluster Encoding Enzymes Responsible for the Mevalonate Pathway from a Terpenoid-Antibiotic-Producing *Streptomyces* Strain," *Biosci. Biotechnol. Biochem.* 65(7):1627-1635.

Hamilton, C.M. et al. (Sep. 1989). "New Method for Generating Deletions and Gene Replacements in *Escherichia coli*," *Journal of Bacteriology* 171(9):4617-4622.

Hanai, T. et al. (Dec. 2007). "Engineered Synthetic Pathway for Isopropanol Production in *Escherichia coli*," *Applied and Environmental Microbiology* 73(24):7814-7818.

Harker, M. et al. (1999). "Expression of Prokaryotic 1-Deoxy-D-Xylulose-5-Phosphatases in *Escherichia coli* Increases Cartenoid and Ubiquinone Biosynthesis," *FEBS Letters* 448:115-119.

Harkki, A. et al. (Jun. 1989). "A Novel Fungal Expression System: Secretion of Active Calf Chymosin From the Filamentous Fungus *Trichoderma ressei*," *Bio. Technol.* 7:596-603.

Hedl, M. et al. (Apr. 2002). "*Enterococcus faecalis* Acetoacetyl-Coenzyme A Thiolase/3-Hydroxy-3-Methyglutaryl-Coenzyme A Reductase, A Dual-Function Protein of Isopentenyl Diphosphate Biosynthesis," *J. Bacteriol.* 184(8):2116-2122.

Hedl, M. et al. (Apr. 2004). "Class II 3-Hydroxy-3-Methylglutaryl Coenzyme A Reductases," *Journal of Bacteriology* 186(7):1927-1932.

Hellman, U. et al. (1995). "Improvement of an "In-Gel" Digestion Procedure for the Micropreparation of Internal Protein Fragments for Amino Acid Fragments for Amino Acid Sequencing," *Analytical Biochemistry* 224:451-455.

Herbers, K. et al. (Jun. 1996). "Manipulating Metabolic Partitioning in Transgenic Plants", *TIBTECH* 14:198-205.

Herz, S. et al. (Mar. 14, 2000). "Biosynthesis of Terpenoids: YgbB Protein Converts 4-Diphosphocytidyl-2C-Methyl-D-Erythritol 2-Phosphate to 2C-Methyl-D-Erythritol 2,4-Cyclodiphosphate," *Proc. Natl. Acad. Sci. USA* 97(6):2486-2490.

Higgins, D.G. et al. (1989). "Fast and Sensitive Multiple Sequence Alignments on a Microcomputer," *Cabios Communications* 5(2):151-153.

Hinson, D.D. et al. (1997). "Post-Translation Regulation of Mevalonate Kinase by Intermediates of the Cholesterol and Nonsterol Isoprene Biosynthetic Pathways," *Journal of Lipid Research* 38:2216-2223.

Hoeffler, J-F. et al. (2002). "Isoprenoid Biosynthesis via the Methylerythritol Phosphate Pathway. Mechanistic Investigations of the 1-Deoxy-$_D$-Xylulose 5-Phosphate Reductiosimerase," *Eur. J. Biochem.* 269:4446-4457.

Huang, K-X. et al. (1999). "Overexpression, Purification, and Characterization of the Thermostable Mevalonate Kinase from *Methanococcus jannaschii*," *Protein Expression and Purification* 17:33-40.

Hunter, B.K. (1985). "Formaldehyde Metabolism by *Escherichia coli*. Carbon and Solvent Deuterium Incoproration into Glycerol, 1,2-Propanediol, and 1,3-Propanediol," *Biochemistry* 24(15):4148-4155.

Hyatt, D.C. et al. (Mar. 27, 2007). "Structure of Limonene synthase, A Simple Model for Terpenoid Cyclase Catalysis," PNAS 104(13):5360-5365.

Ilmen, M. et al. (Apr. 1997). "Regulation of Cellulase Gene Expression in the Filamentous Fungus *Trichoderma reesei*," *Appl. Environ. Microbiol.* 63(4):1298-1306.

Innis, M.A. et al. (Apr. 5, 1985). "Expression, Glycosylation, and Secretion of an *Aspergillus* Glucoamylase by *Saccharomyces cerevisiae*," *Science* 228:21-26.

International Search Report mailed on Jun. 18, 2009, for PCT Patent Application No. PCT/US08/86869, filed on Dec. 15, 2008, 1 page.

Jenkins, L.S. et al. (Jan. 1987). "Genetic and Molecular Characterization of the Genes Involved in Short-Chain Fatty Acid Degradation in *Escherichia coli*: The *ato* System," *Journal of Bacteriology* 169(1):42-52.

Jeong, S.-W. et al. (2004, e-published Jan. 21, 2004). "Dicistronic Expression of the Green Fluorescent Protein and Antibiotic Resistance Genes in the Plastid for Selection and Tracking of Plastid-Transformed Cells in Tobacco," *Plant Cell Rep* 22:747-751.

Jobling, S.A. et al. (Feb. 12, 1987). "Enhanced Translation of Chimaeric Messenger RNAs Containing a Plant Viral Untranslated Leader Sequence," *Nature* 235:622-625.

Jones, K.L. et al. (2000). "Low-Copy Plasmids Can Perform as Well as or Better Than High-Copy Plasmids for Metabolic Engineering of Bacteria," *Metabolic Engineering* 2:238-338.

Joshi, C.P. (1987). "Putative Polyadenylation Signals in Nuclear Genes of Higher Plants: A Compilation and Analysis," *Nucleic Acid Research* 15(23):9627-9640.

Julsing, M.K. et al. (2007). "Functional Analysis of Genes Involved in the Biosynthesis of Isoprene in *Bacillus subtilis*," *Applied Microbiol. Biotechnol.* 75:1377-1384.

Kacian, D.L. et al. (Oct. 1972). "A Replicating RNA Molecule Suitable for a Detailed Analysis of Extracellular Evolution and Replication," *Proc Natl Acad Sci USA* 69(10):3038-3042.

Kajiwara, S. et al. (1997). "Expression of an Exogenous Isopentenyl Diphosphate Isomerase Gene Enhances Isoprenoid Biosynthesis in *Escherichia coli*," *Biochem. J.* 324:421-426.

Kaneda, K. et al. (Jan. 30, 2001). "An Unusual Isopentenyl Diphosphate Isomerase Found in the Mevalonate Pathway Gene Cluster from *Streptomyces* sp. Strain CL190," *PNAS* 98(3):932-937.

Karl, T. et al. (2003). "Dynamic Measurements of Partition Coefficients Using Proton-Transfer-Reaction Mass Spectrometry (PTR-MS)," *International Journal of Mass Spectrometry* 223-224:383-295.

Karlin, S. (Jun. 1993). "Applications and Statistics for Muliple High-Scoring Segments in Molecular Sequences," *Proc Natl Acad Sci USA* 90:5873-5787.

Kavanagh, T.A. et al. (Jul. 1999). "Homeologous Plastid DNA Transformation in Tobacco is Mediated by Multiple Recombination Events," *Genetics* 52:1111-1122.

Keasling, J.D. (Mar. 29, 2004). "Genetic Tools for Metabolic Enzyme Production in *Escherichia Coli*," presented at NIGMS 2004 PSI Protein Production & Crystallization Workshop, Bethesda, MD, Mar. 29-31, 2004, located at <http://www-nmr.cabm.rutgers.edu/labdocuments/workshops/psi_ppcw_32904/ppcw_32904.html>, last visited on Jun. 4, 2010, 66 pages.

Keasling, J.D. (May 7, 2005). "Drugs from Bugs: Engineering Microorganisms to Produce New Drugs," presented at Engineering a Better World: *Our Environment, Our Health*, Berkeley, CA, May 7, 2005, 62 pages.

Keasling, J.D. (Sep. 23, 2007). "Engineering Microbes for Production of Low-Cost, Effective, Anti-Malarial Drugs," *presented at Enzyme Engineering XIX*, Harrison Hot Springs, British Columbia, Canada, Sep. 23-28, 2007, 152 pages.

Keegan, R.M. et al. (2007). "Automated Search-Model Discovery and preparation for Structure Solution by Molecular Replacement," *Acta Crystallographica* D63:447-457.

Keeler, K.H. et al. (1996). "Movement of Crop Transgenes into Wild Plants," Chapter 20 in *Herbicide Resistant Crops: Agricultural, Economic, Environmental, RegUlatory and Technological Aspects*, Duke, S.O. ed., Lewis Publishers: Boca Raton, FL., pp. 303-330.

Kelly, J.M. et al. (1985). "Transformation of *Aspergillus niger* by the *amdS* Gene of *Asperfillus nidulans*," *The Embo Journal* 4(2):475-479.

Khan, M.S. et al. (Sep. 1999). "Fluorescent Antibiotic Resistance Marker for Tracking Plastid Transformation in Higher Plants," *Nature Biotechnology* 17:910-914.

Kieser, T. eds. et al. (Jul. 2000). "Introduction of DNA into *Streptomyces*," Chapter 10 in *Practical Streptomyces Genetics*, pp. 229-252.

Kinghorn, J.R. et al. (1992). *Applied Molecular Genetics of Filamentous Fungi*, Blackie Academic Professional and Chapman and Hall: London, 3 pages, (Table of Contents Only).

Klein-Marcuschamer, D. et al. (2007, e-pub. Aug. 2, 2007). "Engineering Microbial cell Factories for Biosynthesis of Isoprenoid Molecules: Beyond Lycopene," *TRENDS in Biotechnology* 25(9):417-424.

Klein-Marcuschamer, D. et al. (Feb. 19, 2008). "Assessing the Potential of Mutational Strategies to Elicit New Phenotypes in Industrial Strains," *Proc. Natl. Acad. Sci.* 105(7):2319-2324.

Koga, Y. et al. (Mar. 2007). "Biosynthesis of Ether-Type Polar Lipids in Archaea and Evolutionary Considerations," *Microbiology and Molecular Biology Reviews* 71(1):97-120.

Kooter, J. M., et al. (Sep. 1999). "Listening to the Silent Genes: Transgene Silencing, Gene Regulation and Pathogen Control," *Trends in Plant Science* 4(9):340-347.

Kota, M. et al. (Mar. 1999). "Overexpression of the *Bacililus thuringiensis* (Bt) Cry2Aa2 Protein in Chloroplasts Confers Resistance to Plants Against Susceptible and Bt-Resistant Insects," *Proc. Natl. Acad. Sci. USA* 96:1840-1845.

Kreigler, M. (1990). *Gene Transfer and Expression: A Laboratory Manual*, W.H. Freeman and Company: New York, NY, pp. Vii-x, (Table of Contents Only).

Kunkel, T. A. (Jan. 1985). "Rapid and Efficient Site-Specific Mutagenesis without Phenotypic Selection," *Proc. Natl. Acad. Sci. USA* 82:488-492.

Kuzma, J. et al. (1995). "Bacteria Produce the Volatile Hydrocarbon Isoprene," *Current Microbiology* 30:97-103.

Kuzuyama, T. et al. (1998). "Direct Formation of 2-C Methyl-D-Erythritoi 4-Phosphate by 1-Deoxy-D-Xylulose 5-Phosphate Reductoisomerase, a New Enzyme in the Non-Mevalonate Pathway to Isopentenyl Diphosphate," *Tetrahedron Letters* 39:4509-4512.

Kuzuyama, T. et al. (1998). "Fosmidomycin, a Specific Inhibitor of 1-Deoxy-D-Xylulose 5-Phosphate Reductoisomerase in the Nonmevalonate Pathway for Terpenoid Biosynthesis," *Tetrahedron Letters* 39:7913-7916.

Lange, B.M. et al. (Nov. 23, 1999). "Isopentenyl Diphosphate Biosynthesis via a Mevalonate-Independent Pathway: Isopentenyl Monophosphate Kinase Catalyzes the Terminal Enzymatic Step," *PNAS* 96(24):13714-13719.

Lange, B.M. et al. (Sep. 2001). "Isoprenoid Biosynthesis. Metabolite Profiling of Peppermint Oil Gland Secretory Cells and Application to Herbicide Target Analysis," *Plant Physiology* 127:305-314.

Law, C.K. (1984). "Heat and Mass Transfer in Combustion: Fundamental Concepts and Analytical Techniques," *Progress in Energy and Combustion Science* 10:295-318.

Lehning, A. et al. (1999). "Isoprene Synthase Activity and Its Relation to Isoprene Emission in *Quercus robur* L. Leaves," *Plant, Cell and Environment* 22:495-504.

Learner, C.G. et al. (1990). "Low Copy Number Plasmids for Regulated Low-Level Expression of Cloned Genes in *Escherichia coli* with Blue/White Insear Screening Capability," *Nucl Acids Res* 18(15):4631.

Lichtenthaler, H.K. et al. (1997). "Biosynthesis of Isoprenoids in Higher Plant Chloroplasts Proceeds Via a Mevalonate-Independent Pathway," *FEBS Letters* 400:271-274.

Lichtenthaler, H. K. (1999). "The 1-Deoxy-D-Xylulose-5-Phosphate Pathway of Isopenoid Bosynthesis in Plants," *Annu Rev Plant Physiol Plant Mol Biol.* 50:47-65.

Lin, X-M. et al. (2008, e-pub. Apr. 26, 2008). "Proteomic Analysis of Nalidixic Acid Resistance in *Escherichia coli*: Identification and Functional Characterization of OM Proteins," *Journal of Proteome Research* pp. A-G.

Lluch, M.A. et al. (2000). "Molecular Cloning and Expression Analysis of the Mevalonate Kinase Gene from *Arobidopsis thallana*," *Plant Molecular Biology* 42:365-376.

Lois, L.M. et al. (Mar. 1998). "Cloning and Characterization of a Gene from *Escherichia coli* Encoding a Transketolase-Like Enzyme that Catalyzes the Synthesis of D-1-Deoxyxylulose 5-Phosphate, a Common Precursor for Isoprenoid, Thiamin, and Pyridoxal Biosynthesis," *Proc. Natl. Acad. Sci. USA* 95:2105-2110.

Loivamäki, M. et al. (Jun. 2007). "Arabidopsis, A Model to Study Biological Functions of Isoprene Emission?" *Plant Physiology* 144:1066-1078.

Lommel, S.A. et al. (1991). "Identification of the Maize Chlorotic Mottle Virus Capsid Protein Cistron and Characterization of its Subgenomic Messenger RNA," *Virolog* 181:382-385.

Lücker, J. et al. (2002). "Monoterpene Biosynthesis in Lemon (Citrus Limon). cDNA Isolation and Functional Analysis of Four Monoterpene Synthases," *European Journal of Biochemistry* 269:3160-3171.

Luli, G.W. et al. (Apr. 1990). "Comparison of Growth, Acetate Production, and Acetate Inhibition of *Escherichia coli* in Batch and Fed-Batch Fermentations," *Applied and Environmental Microbiology* 56(4):1004-1011.

Lüttgen, H. et al. (Feb. 1, 2000). "Biosynthesis of Terpenoids: YchB Protein *Escherichia coli* Phosphorylates the 2-Hydroxy Group of 4-Diphosphocytidy1-2C-Methyl-$_D$-Erythritol," *PNAS* 97(3):1062-1067.

Macejak, D.G. et al. (Sep. 5, 1991). "Internal Initiation of Translation Mediated by the 5' Leader of a Cellular mRNA," *Nature* 353:90-94.

Mahmoud, S.S. et al. (Jul. 17, 2001). "Metabolic Engineering of Essential Oil Yield and Composition in Mint by Altering Expression of Deoxyxylulose Phosphate Reductoisomerase and Menthofuran Synthase," *PNAS* 98(15):8915-8920.

Maldonado-Mendoza, I.E. et al. (1997). "Molecular Characterization of Three Differentially Expressed Members of the *Camptotheca acuminate* 3-Hydroxy-3-Methylglutaryl CoA Reductase (HMGR) Gene Family," *Plant Molecular Biology* 134:781-790.

Mann, V. et al. (Aug. 2000). "Metabolic Engineering of Astaxanthin Production in Tobacco Flowers," *Nature Biotechnology* 18:888-892.

Martin, V.J.J. et al. (Dec. 5, 2001). "The in Vivo Synthesis of Plant Sesquiterpenes by *Escherichia coli*," *Biotechnology and Bioengineering* 75(5):497-503.

Martin, V.J.J. et al. (Jul. 2003). "Engineering a Mevalonate Pathway in *Escherichia coli* for Production of Terpenoids," *Nature Biotechnology* 21(7):796-802.

Martin, W. et al. (May 14, 1998). "Gene Transfer to the Nucleus and the Evolution of Chloroplasts," *Nature* 393:162-165.

Mashego, M.R. et al. (2007, e-pub. Nov. 8, 2006). "Microbial Metabolomics: Past, Present and Future Methodologies," *Biotechnol. Lett.* 29:1-16.

Matsuoka, S. et al. (Feb. 25, 1991). "Variable Product Specificity of Microsomal Dehydrodolichyl Diphosphate Synthase from Rat Liver," *The Journal of Biological Chemistry* 266(6):3464-3468.

Matteucci, M.D. et al. (1981). "Synthesis of Deoxyoligonucleotides on a Polymer Support," *J. American Chemical Society* 103(11):3185-3191.

Matthews, P.D. et al. (2000). "Metabolic Engineering of Carotenoid Accumulation in *Escherichia coli* by Modulation of the Isoprenoid Precursor Pool with Expression of Deoxyxylulose Phosphate Synthase," *Appl Microbiol Biotechnol* 53:396-400.

Maury, J. et al. (2005, e-pub. Jul. 5, 2005). "Microbial Isoprenoid Production: An Example of Green Chemistry through Metabolic Engineering," *Adv. Biochem. Engin/Biotechnol.* 100:19-51.

Meinkoth, J. et al. (1984). "Hybridization of Nucleic Acids Immobilized on Solid Supports," *Analytical Biochemistry* 138:267-284.

Meyer, P. et al. (1996). "Homology-Dependent Gene Silencing in Plants," *Ann. Rev. Plat. Physiol. Mol. Biol.* 47:23-48.

Millen, R.S. et al. (Mar. 2001). "Many Parallel Losses of *infA* from Chloroplast DNA During Angiosperm Evolution with Multiple Independent Transfers to the Nucleus," *The Plant Cell* 13:645-658.

Miller, B. et al. (2001, e-pub. May 10, 2001). "First Isolation of an Isoprene Synthase Gene from Poplar and Successful Expression of the Gene in *Escherichia coli*," *Planta* 213:483-487.

Milne, P.J. et al. (1995). "Measurement of Vertical Distribution of Isoprene in Surface Seawater, Its Chemical Fate, and Its Emission from Several Phytoplankton Monocultures," *Marine Chemistry* 48:237-244.

Mo, H. et al. (2004). "Studies of the Isoprenoid-Mediated Inhibition of Mevaloante Synthesis Applied to Cancer Chemotherapy and Chemoprevention," *Exp. Biol. Med.* 229:567-585.

Mogen, B.D. et al. (Dec. 1990). "Upstream Sequences Other than AAUAAA are Required for Efficient Messenger RNA 3'-End Formation in Plants," *The Plant Cell* 2:1261-1272.

Monson, R.K. et al. (1992). "Relationships Among Isoprene Emission Rate, Photosynthesis, and Isoprene Synthase Activity as Influenced by Temperature," *Plant Physiol.* 98:1175-1180.

Munroe, D. et al. (1990). "Tales of Poly(A): a Review," *Gene* 91:151-158.

Murray, E.E. et al. (1989). "Codon Usage in Plant Genes," *Nucleic Acids Research* 17(2): 477-498.

Nakamura, C.E. et al. (2003). "Metabolic Engineering for the Microbial Production of 1,3-Propanediol," *Current Opinion in Biotechnology* 14:454-459.

Nanchen, A. et al. (Apr. 2008, e-pub. Jan. 25, 2008). "Cyclic AMP-Dependent Catabolite Repression Is the Dominant Control Mechanism for Metabolic Fluxes under Glucose Limitation in *Escherichia coli*," *Journal of Bacteriology* 190(7):2323-2330.

Nawrath, C. et al. (Dec. 1994). "Targeting of the Polyhydroxybutyrate Biosynthetic Pathway to the Plastids of *Arabidopsis thaliana* Results in High Levels of Polymer Accumulation," *Proc. Natl. Acad. Sci. USA* 91:12760-12764.

Needleman, S. B. et al. (1970). "A General Method Applicable to the Search for Similarities in the Amino Acid Sequence of Two Proteins," *J. Mol. Biol.* 48:443-453.

Neidhardt, F.C. et al. (Sep. 1974). "Culture Medium for Enterobacteria," *J. Bacteriology* 119(3):736-747.

Nevalainen, K.M.H. et al. (1992). "The Molecular Biology of *Trichoderma* and Its Application to the Expression of Both Homologous and Heterologous Genes," Chapter 6 in *Molecular Industrial Mycology, Systems and Applications for Filamentous Fungi*, Leong, S.A. et al. eds., Marcel Dekker Inc.: New York, NY, pp. 129-148.

Newman, J.D. et al. (Nov. 5, 2006, e-pub. Jul. 28, 2006). "High-Level Production of Amorpha-4,11-Diene in a Two-Phase Partitioning Bioreactor of Metabolically Engineered *Escherichia coli*," *Biotechnology and Bioengineering* 95(4):684-691.

Newman, T. et al. (1994). "Genes Galore: A Summary of Methods for Accessing Results from Large-Scale Partial Sequencing of Anonymous *Arabidopsis* cDNA Clones," *Plant Physiology* 106:1241-1255.

Nielsen, K.M. et al. (1997). "Analysis and Developmental Profile of Carotenoid Pigments in Petals of Three Yellow Petunia Cultivars," *Scientia Horticulturae* 71:257-266.

Niinements, Ü. et al. (Nov. 2002). "Stomatal Constraints May Affect Emission of Oxygenated Monoterpenoids from the Foliage of *Pinus pinea*," *Plant Physiology* 130:1371-1385.

Noronha, S.B. et al. (May 5, 2000). "Investigation of the TCA Cycle and the Glyoxylate Shunt in *Escherichia coli* BL21 and JM109 Using $^{13}$C-NMR/MS," *Biotechnol. Bioeng.* 68(3):316-327.

Nunberg, J.H. et al. (Nov. 1984). "Molecular Cloning and Characterization of the Glucoamylase Gene of *Aspergillus awamori*," *Mol. Cell. Biol.* 4(11):2306-2315.

Oh, M-K. et al. (Apr. 12, 2002). "Global Expression Profiling of Acetate-Grown *Escherichia coli*," *The Journal of Biological Chemistry* 277(15):13175-13183.

Oulmouden, A. et al. (1991). "Nucleotide Sequence of the ERG12 Gene of *Saccharomyces cerevisiae* Encoding Mevalonate Kinase," *Curr. Genet.* 19:9-14.

Pachuk, C.J. et al. (2000). "Chain Reaction Cloning: A One-Step Method for Directional Ligation of Multiple DNA Fragments," *Gene* 243:19-25.

Pearson, W.R. et al. (Apr. 1988). "Improved Tools for Biological Sequence Comparison," *Proc. Natl. Acad. Sci.* 85:2444-2448.

Pegg, S.C-H. et al. (2006). "Leveraging Enzyme Structure-Function Relationships for Functional Inference and Experimental Design: The Structure-Function Linkage Database," *Biochemistry* 45:2545-2555.

Penttila, M. et al. (1987). "A Versatile Transformation System for the Cellulolytic Filamentous Fungus *Trichoderma reesei*," *Gene* 61:155-164.

Perego, M. (1993). "Integrational Vectors for Genetic Manipulation in *Bacillus subtilis*," Chapter 42 in *Bacillus subtilis and Other Gram-Positive Bacteria: Biochemistry, Physiology, and Molecular Genetics*, Sonenshein et al. eds., American Society for Microbiology: Washington, D.C., pp. 615-624.

Phan, R.M. et al. (2001, e-pub. Sep. 13, 2001). "Synthesis of (*S*)-Isoprenoid Thiodiphosphates as Substrates and Inhibitors," *J. Org. Chem.* 66(20):6705-6710.

Phillips, T.A. et al. (Jul. 1984). "Ion Gene Product of *Escherichia coli* Is a Heat-Shock Protein," *Journal of Bacteriology* 159(1):283-287.

Phue, J-N. et al. (2004). "Transcription Levels of Key Metabolic Genes are the Cause for Different Glucose Utilization Pathways in *E. coli* B (BL21) and *E. coli* K (JM109)," *Journal of Biotechnology* 109:21-30.

Phue, J-N. et al. (2005, e-pub. Aug. 11, 2005). "Impact of Dissolved Oxygen Concentration on Acetate Accumulation and Physiology of *E. coli* BL21, Evaluating Transcription Levels of Key Genes at Different Dissolved Oxygen Conditions," *Metabolic Engineering* 7:353-363.

Pillof, D. et al. (Feb. 14, 2003). "The Kinetic Mechanism of Phosphomevalonate Kinase," *The Journal of Biological Chemistry* 278(7):4510-4515.

Pitera, D.J. et al. (2007, e-pub. Nov. 23, 2006). "Balancing a Heterologous Mevalonate Pathway for Improved Isoprenoid Production in *Escherichia coli*," *Metabolic Engineering* 9:193-207.

Pommer, H. et al. (1975). "Industrial Synthesis of Terpene Compounds," *Pure and Applied Chemistry* 43(3-4):527-551.

Potter, D. et al. (Oct. 10, 1997). "Identification of Catalytic Residues in Human Mevalonate Kinase," *The Journal of Biological Chemistry* 272(41):25449-25454.

Pourquie, J. et al. (1988). "Scale Up of Cellulase Production and Utilization," in *Biochemistry and Genetics of Cellulose Degradation*, Aubert, J.-P. et al. eds., Academic Press: San Diego, CA, pp. 71-86.

Proudfoot, N. (Feb. 22, 1991). "Poly(A) Signals," *Cell* 64:671-674.

Ramos-Valdivia, A.C. et al. (1997). "Isopentenyl Diphosphate Isomerase: A Core Enzyme in Isoprenoid Biosynthesis: A Review of its Biochemistry and Function," *Nature Product Report* 6:591-603.

Raschke, M. et al. (2004, e-pub. Oct. 28, 2004). "A High-Performance Liquid Chromatography Methods for the Analysis of Intermediates of the Deoxyxylulose Phosphate Pathway," *Analytical Biochemistry* 335:235-243.

Re, E.B. et al. (1995). "Co-Expression of Native and Introduced Genes Reveals Cryptic Regulation of HMG CoA Reductase Expression in *Arabidopsis*," *The Plant Journal* 7(5):771-789.

Rodriguez-Concepción, M. et al. (2000). "Genetic Evidence of Branching in the Isoprenoid Pathway for the Production of Isopentenyl Diphosphate and Dimethyl Diphosphate in *Escherichia coli*," *FES Letters* 473:328-332.

Rodriguez-Concepción, M. et al. (Nov. 2002). "Elucidation of the Methylerythritol Phosphate Pathway for Isoprenoid Biosynthesis in Bacteria and Plastids. A Metabolic Milestone Achieved Through Genomics," *Plant Physiology* 130:1079-1089.

Rodríguez-Villalón, A. et al. (2008). "Cartenoid Accumulation in Bacteria with Enhanced Supply of Isoprenoid Precursors by Upregulation of Exogenous or Endogenous Pathways," *Journal of Biotechnology* 135:78-84.

Rohdich, F. et al. (Oct. 12, 1999). "Cytidine 5'-Triphosphate-Dependent Biosynthesis of Isoprenoids: YgbP Protein of *Escherichia coli* Catalyzes the Formation of 4-Diphosphocytidyl-2-C-Methylerythritol," *PNAS* 96(21):11758-11763.

Rohdich, F. et al. (Jun. 6, 2000). "Biosynthesis of Terpenoids: 4-Diphosphocytidyl-2C-Methyl-$_D$-Erythritol Synthase of *Arabidopsis thaliana*," *PNAS* 97(12):6451-6456.

Rohmer, M. (1998). "Isoprenoid Biosynthesis Via the Mevalonate-Independent Route, a Novel Target for Antibacterial Drugs?" *Progress in Drug Research* 50:137-154.

Röhrich, R.C. et al. (2005, e-pub. Nov. 2, 2005). "Reconstitution of an Apicoplast-Localised Electron Transfer Pathway Involved in the Isoprenoid Biosynthesis of *Plasmodium falciparum*," *FEBS Letters* 579:6433-6439.

Rondon, M.R. et al. (May 1999). "Toward Functional Genomics in Bacteria: Analysis of Gene Expression in *Escherichia coli* from a Bacterial Artificial Chromosome Library of *Bacillus cereus*," *Proc. Natl. Acad. Sci. USA* 96:6451-6455.

Rosenfeld, J. et al. (1992). "In-Gel Digestion of Proteins for Internal Sequence Analysis After One- or Two-Dimensional Gel Electrophoresis," *Analytical Biochemistry* 203:173-179.

Rost, B. et al. (2004). "The PredictProtein Server," *Nucleic Acids Research* 32:W321-W326.

Sambrook, J. et al. (1982). Molecular Cloning: A Laboratory Manual, 2nd edition, Cold Spring Harbor Laboratory Press: New York, NY, pp. xi-xxxviii (Table of Contents Only).

Sambrook, J. et al. (1989). *Molecular Cloning: A Laboratory Manual*, $2^{nd}$ edition, Cold Spring Harbor Laboratory Press: New York, NY, pp. xi-xxxviii (Table of Contents Only).

Sánchez, C. et al. (Apr. 2002). "The Biosynthetic Gene Cluster for the Antitumor Rebeccamycin: Characterization and Generation of Indolocarbazole Derivatives," *Chem. Biol.* 9(4):519-531.

Sander, R. (Apr. 8, 1999). Compilation of Henry's Law Constants for Inorganic and Organic Species of Potential Importance in Environmental Chemistry, 3:1-107.

Sanfaçon, H. et al. (1991). "A Dissection of the Cauliflower Mosaic Virus Polyadenylation Signal," *Genes & Development* 5:141-149.

Sasaki, K. et al. (2005, e-pub. Apr. 7, 2005). "Gene Expression and Characterization of Isoprene Synthase from *Populas alba*," *FEBS Letters* 579:2514-2518.

Schneider, D. et al. (2002). "Genomic Comparisons Among *Escherichia coli* Strains B. K-12, and OI57:H7 Using IS Elements as Molecular Markers," *BMC Microbiology* 2:18, 8 pages.

Schnitzler, J.-P. et al. (2005, e-pub. Jul. 29, 2005). "Biochemical Properties of Isoprene Synthase in Poplar (*Populus x canescens*)," *Planta* 222(5):777-786.

Schöller, C. et al. (1997). "Volatile Metabolites from some Gram-Negative Bacteria," *Chemosphere* 35(7):1487-1495.

Scott, E. et al. (2007, e-pub. Mar. 27, 2007). "Biomass in the Manufacture of Industrial Products—The Use of Proteins and Amino Acids," *Appl. Microbiol. Biotehcnol.* 75:751-762.

Serino, G. et al. (1997). "A Negative Selection Scheme Based in the Expression of Cytosine Deaminase in Plastids," *The Plant Journal* 12(3): 697-701.

Sharkey, T.D. et al. (Feb. 2005). "Evolution of the Isoprene Biosynthetic Pathway in Kudzu," *Plant Physiology* 137:700-712.

Sharkey, T.D. et al. (Feb. 1, 2005). "Supplemental data for: Evolution of the Isoprene Biosynthetic Pathway in Kudzu," *Plant Physiology*, located at <http://www.plantphysiol.org/cgi/conten t/full/pp.104.054445/DC1,> last visited Nov. 26, 2009, 137(2):700-712.

Sheir-Neiss, G. et al. (Jul. 1984). "Characterization of the Secreted Ceullulases of *Trichoderma ressei* Wild Type and Mutants During Controlled Fermentations," *Appl. Microbiol. Biotechnol.* 20(1):46-53.

Shelton, D. et al. (2004, e-pub. Nov. 26, 2004). "Isolation and Partial Characterization of a Putative Monoterpene Synthase from *Melalecua alternifolia*," *Plant Physiology and Biochemistry* 42:875-882.

Shinozaki, K. et al. (1986). "The Complete Nucleotide Sequence of the Tobacco Chloroplast Genome: its Gene Organization and Expression," *The EMBO Journal* 5(9):2043-2049.

Shirk, M.C. et al. (2002, e-pub. Jul. 27, 2002). "Isoprene Formation in *Bacillus subtilis*: A Barometer of Central Carbon Assimilation in a Bioreactor?" *Bitoechnol. Prog.* 18(5):1109-1115.

Silver, G.M. et al. (1991). "Enzymatic Synthesis of Isoprene from Dimethylallyl Diphosphate in Aspen Leaf Extracts," *Plant Physiol.* 97:1588-1591.

Silver, G.M. et al. (Jun. 2, 1995). "Characterization of Aspen Isoprene Synthase, an Enzyme Responsible for Leaf Isoprene Emission to the Atmosphere," *The Journal of Biological Chemistry* 270(22):13010-1316.

Sivy, T.L. at al. (2002). "Isoprene Synthase Activity Parallels Fluctuations of Isoprene Release During Growth of *Bacillus Subtilis*," *Biochemical and Biophysical Research Communications* 294:71-75.

Siwko, M.E. et al. (2007, e-published Oct. 4, 2006). "Does Isoprene Protect Plant Membranes from Thermal Shock? A Molecular Dynamics Study," *Biochimica et Biophysica Acta* 1768:198-206.

Slater, S. et al. (Apr. 1992). "Production of Poly-(3-Hydroxybutyrate-co-3-Hydroxyvalerate) in a Recombinant *Escherichia coli* Strain," Applied and Environmental Microbiology 58(4):1089-1094.

Slater, S. et al. (1999). "Metabolic Engineering of *Arabidopsis* and *Brassica* for Poly(3-Hydroxybutyrate-co-3-Hydroxyvalerate) Copolymer Production," *Nature Biotechnology* 17:1011-1016.

Smit, A. et al. (2000). "Biosynthesis of Isoprenoids via Mevalonate in Archaea: The Lost Pathway," *Genome Research* 10:1468-1484.

Smith, T. et al. (1981). "Comparison of Biosequences." *Advances in Applied Mathematics* 2:482-489.

Sprenger, G.A. et al. (Nov. 1997). Identification of a Thiamin-Dependent Synthase in *Escherichia coli* Required for the Formation of the 1-Deoxy-$_D$-Xylulose 5-Phosphate Precursor to Isoprenoids, Thiamin, and Pyridoxol *PNAS* 94:12857-12862.

Starks, C.M. et al. (Sep. 10, 1997). "Structural Basis for Cyclic Terpene Biosynthesis by Tobacco 5-Epi-Aristolochene Synthase," Science 277:1815-1820.

Staub, J. M. et al. (1995). "Expression of a Chimeric *uidA* Gene Indicates that Polycistronic mRNAs are Efficiently Translated in Tobacco Plastids," *The Plant Journal* 7(5):845-848.

Staub, J. M. et al. (Mar. 2000). "High-Yield Production of a Human Therapeutic Protein in Tobacco Chloroplast," *Nature Biotechnology* 18:333-338.

Steibüchel, A. (2003). "Production of Rubber-Like Polymers by Microorganisms," *Current Opinion in Microbiology* 6:261-270.

Steller, I. et al. (1997). "An Algorithm for Automatic Indexing of Oscillation Images using Fourier Analysis," Journal of Applied Crystallography 30:1036.1040.

Stermer, B. A. et al. (1994). "Regulation of HMG-CoA Reductase Activity in Plants," *Journal of Lipid Research* 35:1133-1140.

Stevens, D.R. et al. (1997). "Genetic Engineering of Eukaryotic Algae: Progress and Prospects," *J. Phycol.* 33:713-722.

Sulter, G.J. et al. (1990). "Proliferation and Metabolic Significance of Peroxisomes in *Candida boidinii* During Growth on D-Alanine or Oleic Acid as the Sole Carbon Source," *Arch. Microbiol.* 153:485-489.

Sutherlin, A. et al. (Aug. 2002). "*Enterococcus faecalis* 3-Hydroxy-3-Methylglutaryl Coenzyme A Synthase, an Enzyme of Isopentenyl Diphosphate Biosynthesis," *J. Bacteriol.* 184(15):4065-4070.

Takagi, M. et al. (Aug. 2000). "A Gene Cluster for the Mevalonate Pathway from *Streptomyces* sp. Strain CL190," *Journal of Bacteriology* 182(15):4153-4157.

Takahashi, S. et al. (Feb. 1999). "Purification, Characterization, and Cloning of a Eubacterial 3-Hydroxy-3-Methylglutaryl Coenzyme A Reductase, a Key Enzyme Involved in Biosynthesis of Terpenoids," *Journal of Bacteriology* 181(4):1256-1263.

Takara Bio Inc. (Feb. 2008). "Chaperon Plasmid Set," Cat. # 3340, pp. 1-8.

Teymouri, F. et al. (2005, e-pub. Feb. 24, 2005). "Optimization of the Ammonia Fiber Explosion (AFEX) Treatment Parameters for Enzymeatic Hydrolysis of Corn Stover," *Bioresource Technology* 96:2014-2018.

Thomas, F. et al. (1988). "Expression of the *rp123*, *rp12* and *rps19* Genes in Spinach Chloroplasts," *Nucleic Acids Research* 16(6):2461-2472.

Thomason, L.C. et al. (2007, e-pub. Apr. 16, 2007). "Multicopy Plasmid Modification with Phage λ Red Recombineering," *Plasmid* 58:148-158.

Thouvenot, B. et al. (2004). "The Strong Efficiency of the *Escherichia coli gapA* P1 Promoter Depends on a Complex Combination of Functional Determinants," *Biochem. J.* 383:371-382.

Timberlake, W.E. (1991). "Gene Cloning and Analysis" in Chapter 3 in *More Gene Manipulations in Fungi*, Bennett et al. eds., Academic Press: San Diego, CA, pp. 70-76.

Toriyama, K. et al. (1985). "Cell Suspension and Protoplast Culture in Rice," *Plant Science* 41:179-183.

Tsay, Y.H. et al. (Feb. 1991). "Cloning and Characterization of *ERG8*, an Essential Gene of *Saccharomyces cerevisiae* That Encodes Phosphomevalonate Kinase," *Mol. Cell Biol.* 11(2):620-631.

Tsudsuki, T. (Apr. 27, 1988). "Direct submission, bases 1-155939", *Data Processing Center*, 1998, Aichi-Gakuin University, Aixhi, Japan, 12 pages.

Vadali, R.V. et al. (2005, e-publsihed Sep. 2, 2005). "Enhanced Lycopene Productivity by Manipulation of Carbon Flow to Isopentenyl Diphosphate in *Escherichia coli*," *Biotechnol. Prog.* 21(5):1558-1561.

Vagin, A. et al. (1997). "MOLREP: An Automated Program for Molecular Replacement," *Journal of Applied Crystallography* 30:1022-1025.

Van De Walle, M. et al. (Jan. 5, 1998). "Proposed Mechanism of Acetate Accumulation in Two Recombinant *Escherichia coli* Strains During High Density Fermentation," *Biotechnol. Bioeng.* 57(1):71-78.

Van Den Hondel, C.A.M.J.J. et al. (1991). "Heterologous Gene Expression in Filamentous Fungi," Chapter 18 in *More Gene Manipulations in Fungi*, Bennet, J.W. et al. eds., Academic Press, Inc.: San Diego, CA, pp. 396-428.

Van Hylckama, J.E.T. et al. (Apr. 2000). "Characterization of the Gene Cluster Involved in Isoprene Metabolism in *Rhodococcus* sp. Strain AD45," *Journal of Bacteriology* 182(7):1956-1963.

Vandamme, E.J. et al. (e-pub. 2002). "Bioflavours and Fragrances via Fermentation and Biocatalysis," *Journal of Chemical Technology and Biotechnology* 77:1323-1332.

Vane, L.M. (2005, e-pub. Apr. 21, 2005). "A Review of Pervaporation for Product Recovery from Biomass Fermentation Processes," *Journal of Chemical Technology and Biotechnology* 80:603-629.

Velikova, V. et al. (2005). "Consequences of Inhibition of Isoprene Synthesis in *Phragmites australis* Leaves Exposed to Elevated Temperatures," *Agriculture Ecosystems & Environment* 106:209-217.

Vidal, M. et al. (2006, e-pub. Nov. 23, 2005). "Evaluation of Lower Flammability Limits of Fuel-Air-Diluent Mixtures Using Calculated Adiabatic Flame Temperatures," *Journal of Hazardous Materials* 130:21-27.

Voynova, N.E. et al. (Jan. 2004). "*Staphylococcus aureus* Mevalonate Kinase: Isolation and Characterization of an Enzyme of the Isoprenoid Biosyntheitc Pathway," *Journal of Bacteriology* 186(1):61-67.

Wagner, W.P. et al. (Aug. 1999). "Three Distinct Phases of Isoprene Formation During Growth and Sporulation of *Bacillus subtilis*," *Journal of Bacteriology* 181(15):4700-4703.

Wagner, W.P. et al. (Jan. 2000, e-pub. Nov. 18, 1999). "Isoprene Biosynthesis in *Bacillus subtilis* via the Methylerythritol Phosphate Pathway," *J. Nat. Prod.* 63(1):37-40.

Wang, C-W. et al. (Jan. 20, 1999). "Engineered Isoprenoid Pathway Enhances Astaxanthin Production in *Escherichia coli*," *Biotechnol. Bioeng.* 62(2):235-241.

Ward, M. et al. (Aug. 1993). "Use of *Aspergillus* Overproducing Mutants, Cured for lntergrated Plasmid, to Overproduce Heterologous Proteins," *Appl. Microbiol. Biotechnol.* 39(6):738-743.

Weissermel, K. et al. (2003). Industrial Organic Chemistry, 4th, Completely Revised Edition, translated by Lindley, C.R. et al., Wiley-VCH GmbH & Co. KGaA, Weinheim, Germany, pp. 117-222.

Whittington, D.A. et al. (Nov. 26, 2002). "Bornyl Diphosphate Synthase: Structure and Strategy for Carbocation Manipulation by a Terpenoid Cyclase," *PNAS* 99(24):15375-15380.

Wildermuth, M.C. et al. (1998). "Biochemical Characterization of Stromal and Thylakoid-Bound Isoforms of Isoprene Synthase in Willow Leaves," *Plant Physiology* 116:1111-1123.

Wilding, E.I. et al. (Aug. 2000). "Identification, Evolution, and Essentiality of the Mevalonate Pathway for Isopentenyl Diphosphate Biosynthesis in Gram-Positive Cocci," *Journal of Bacteriology* 182(15):4319-4327.

Wilkins, K. (1996). "Volatile Metabolites from Actinomycetes," *Chemosphere* 32(7):1427-1434.

Williams, D.C. et al. (1998). "Truncation of Limonene Synthase Preprotein Provides a Fully Active 'Pseudomature' Form of This Monoterpene Cyclase and Reveals the Function of the Amino-Terminal Arginine Pair," *Biochemistry* 37(35):12213-12220.

Withers, S.T. et al. (Oct. 2007, e-pub. Aug. 10, 2007). "Identification of Isopentenol Biosynthetic from *Bacillus subtilis* by a Screening Method Based on Isorpenoid Precursor Toxicity," *Appl. Environ Microbiol.* 73(19):6277-6283.

Wolfertz, M. et al. (2003). "Biochemical Regulation of Isoprene Emission," *Plant, Cell and Environment* 26:1357-1364.

Wolfertz, M. et al. (Aug. 2004). "Rapid Regulation of the Methylerythritol 4-Phosphate Pathway during Isoprene Synthesis," *Plant Physiology* 135:1939-1945.

Wu, D.Y. et al. (1989). "The Ligation Amplification Reaction (LAR)—Amplification of Specific DNA Sequences Using Sequential Rounds of Template-Dependent Ligation," *Genomics* 4:560-569.

Xia, X-X. et al. (2008). "Comparison of the Extracellular Proteomes of *Escherichia coli* B and K-12 Strains During High Cell Density Cultivation," *Proteomics* 8:1-15.

Yamada, K. et al. (1989). "Production of Glycerol from Methanol by a Mutant Strain of *Candida boidinii* No. 2201," *Agric. Biol. Chem.* 53(2):541-543.

Yang, D. et al. (Mar. 15, 2002, published ahead of print Dec. 19, 2001). "Structure of the *Methanococcus jannaschii* Mevalonate Kinase, a Member of the GHMP Kinase Superfamily," *The Journal of Biological Chemistry* 277(11):9462-9467.

Ye, X. et al. (Jan. 14, 2000). "Engineering the Provitamin A (β-Carotene) Biosynthetic Pathway into (Carotenoid-Free) Rice Endosperm," *Science* 287:303-305.

Yelton, M.M. et al. (Mar. 1984). "Transformation of *Aspergillus nidulans* by Using a *trpC* Plasmid," *PNAS* 81:1470-1474.

Yoon, S-H. at al. (2007, e-pub. May 15, 2007). "Increased β-Carotene Production in Recombinant *Escherichia coli* Harboring an Engineered Isoprenoid Precursor Pathway with Mevalonate Addition," *Biotechnol. Prog.* 23(3):599-605.

Yoon, S-H. et al. (2009). "Combinatorial Expression of Bacterial Whole Mevalonate Pathway for the Production of β-Carotene in *E. coli*," *Journal of Biotechnology* 140:218-226.

Zepeck, F. et al. (2005, e-pub. Oct. 14, 2005). "Biosynthesis of Isoprenoids. Purification and Properties of IspG Protein from *Escherichia coli*," *J. Org. Chem.* 70:9168-9174.

Collaborative Computational Project, No. 4. (1994). "The CCP4 Suite: Programs for Protein Crystallography," *Acta Cryst.* D50:760-763.

Extended European Search Report mailed on Jun. 14, 2011, for EP Patent Application No. 08860589.4, filed on Dec. 15, 2008, 10 pages.

Kampranis, S.C. et al. (Jun. 2007). "Rational Conversion of Substrate and Product Specificity in a *Salvia* Monoterpene Synthase: Structural Insights into the Evolution of Terpene Synthase Function," *The Plant Cell* 19:1994-2005.

Köksal, M. et al. (2010, e-pub. Jul. 17, 2010). "Structure of Isoprene Synthase Illuminates the Chemical Mechanism of Teragram Atmospheric Carbon Emission," *J. Mol. Biol.* pp. 1-11.

Li, W. et al. (2010, e-pub. Nov. 1, 2009). "Non-Redundant Patent Sequence Databases with Value-Added Annotations at Two Levels," *Nucleic Acids Research* 38:D52-D56.

Miller, B. (2001). "Erstmalige Isolierung Eines Isoprenysthase-Gens und Heterologe Expression Des Aus Der Pappel Stammenden Gens Sowie Charakterisierung der Eingangsgene des Mevalonateunabhängigen lsoprenoidbiosyntheseweges aus dem Cyanobakterium *Synechococcus leopoliensis*," located at <http://kups.ub.uni-koeln.de/883/>, last visited on Jun. 23, 2011, English Translation included, 2 pages.

Ondrey, G. et al. (Oct. 2008). "Bio-Based Isoprene," *Chemical Engineering, Access Intelligence Association*, Rockville, MA, 115(1):14.

Reiling, K.K. et al. (Jul. 20, 2004, e-pub. Jun. 18, 2004). "Mono and Diterpene Production in *Escherichia coli*," *Biotechnology and Bioengineering* 87(2):200-212.

UniProt Database Accession No. A2XGY9, last updated Jul. 27, 2011, located at <http://www.uniprot.org/jobs/201109112CDIG8GYZL.txt>, last visited on Sep. 11, 2011, 2 pages.

UniProt Database Accession No. A5AR04, last updated Jul. 27, 2011, located at <http://www.uniprot.org/jobs/20110911315BAWWKZ7.txt>, last visited on Sep. 11, 2011, 1 page.

UniProt Database Accession No. A5B7V4, last updated Jul. 27, 2011, located at <http://www.uniprot.org/jobs/2011091150O6CWCI3L.txt>, last visited on Sep. 11, 2011, 1 page.

UniProt Database Accession No. A5BKK1, last updated Jul. 27, 2011, located at <http://www.uniprot.org/jobs/20110911315BB1QWK6.txt>, last visited on Sep. 11, 2011, 1 page.

UniProt Database Accession No. A5BLS5, last updated Jul. 27, 2011, located at <http://www.uniprot.org/jobs/201109112CDIFUU28L.txt>, last visited on Sep. 11, 2011, 1 page.

UniProt Database Accession No. A9PGR5, last updated Jul. 27, 2011, located at <http://www.uniprot.org/jobs/201109112CDIFT06PL.txt>, last visited on Sep. 11, 2011, 1 page.

UniProt Database Accession No. B1P189, last updated Jul. 27, 2011, located at <http://www.uniprot.org/jobs/201109112CDIFXI7BK.txt>, last visited on Sep. 11, 2011, 1 page.

UniProt Database Accession No. B3GEM8, last updated Jul. 27, 2011, located at <http://www.uniprot.org/jobs/20110911315BAG9N17.txt>, last visited on Sep. 11, 2011, 1 page.

UniProt Database Accession No. B7FLI6, last updated Jul. 27, 2011, located at <http://www.uniprot.org/jobs/20110911315BAXCRQU.txt>, last visited on Sep. 11, 2011, 1 page.

UniProt Database Accession No. B9HE95, last updated Jul. 27, 2011, located at <http://www.uniprot.org/jobs/201109112CDIFY9X6U.txt>, last visited on Sep. 11, 2011, 2 pages.

UniProt Database Accession No. B9MXU1, last updated Jul. 27, 2011, located at < http://www.uniprot.org/jobs/201109112CDIFV8DIC.txt>, last visited on Sep. 11, 2011, 2 pages.

UniProt Database Accession No. B9PAP5, last updated Jul. 27, 2011, located at <http://www.uniprot.org/jobs/201109112CDIG1HNFH.txt>, last visited on Sep. 11, 2011, 2 pages.

UniProt Database Accession No. B9T537, last updated Nov. 30, 2010, located at <http://www.uniprot.org/jobs/20110911315BB065GR.txt>, last visited on Sep. 11, 2011, 1 page.

UniProt Database Accession No. B9T825, last updated Jul. 27, 2011, located at <http://www.uniprot.org/jobs/20110911315BALANC9.txt>, last visited on Sep. 11, 2011, 1 page.

UniProt Database Accession No. Q0PCI3, last updated Jul. 27, 2011, located at <http://www.uniprot.org/jobs/20110911315BAPL92C.txt>, last visited on Sep. 11, 2011, 1 page.

UniProt Database Accession No. Q0PCI4, last updated Jul. 27, 2011, located at <http://www.uniprot.org/jobs/20110911315BAQURQ8.txt>, last visited on Sep. 11, 2011, 1 page.

UniProt Database Accession No. Q50L36, last updated May 31, 2011, located at <http://www.uniprot.org/jobs/201109112CDIGBF1M4.txt>, last visited on Sep. 11, 2011, 2 pages.

UniProt Database Accession No. Q5SBP1, last updated Apr. 5, 2011, located at < http://www.uniprot.org/jobs/201109112CDIGFFR1Q.txt>, last visited on Sep. 11, 2011, 2 pages.

UniProt Database Accession No. Q5SBP2, last updated Apr. 5, 2011, located at <http://www.uniprot.org/jobs/201109112CDIG4W1U8.txt>, last visited on Sep. 11, 2011, 2 pages.

UniProt Database Accession No. Q5SBP4, last updated Jul. 27, 2011, located at <http://www.uniprot.org/jobs/2011091140O0OYGHJF.txt>, last visited on Sep. 11, 2011, 2 pages.

UniProt Database Accession No. Q5UB07, last updated Jul. 27, 2011, located at <http://www.uniprot.org/jobs/201109112CDIFZCWUC.txt>, last visited on Sep. 11, 2011, 1 page.

UniProt Database Accession No. Q672F7, last updated Jul. 27, 2011, located at <http://www.uniprot.org/jobs/201109112CDIFWBP6O.txt >, last visited on Sep. 11, 2011, 1 page.

UniProt Database Accession No. Q6EJ97, last updated Apr. 5, 2011, located at <http://www.uniprot.org/jobs/20110911315BARZM8D.txt>, last visited on Sep. 11, 2011, 2 pages.

UniProt Database Accession No. Q7Y1V1, last updated Jul. 27, 2011, located at <http://www.uniprot.org/jobs/201109112CDIGOLK2O.txt>, last visited on Sep. 11, 2011, 1 page.

UniProt Database Accession No. Q941 H1, last updated Jul. 27, 2011, located at <http://www.uniprot.org/jobs/201109112CDIG6PW6Y.txt>, last visited on Sep. 11, 2011, 1 page.

UniProt Database Accession No. Q9AR86, last updated May 31, 2011, located at <http://www.uniprot.org/jobs/2011091140O0P1KMN7.txt>, last visited on Sep. 11, 2011, 2 pages.

UniProt Database Accession No. Q9LIA1; Q84UU7, last updated Jul. 27, 2011, located at <http://www.uniprot.org/jobs/20110911315BB4RI8G.txt>, last visited on Sep. 11, 2011, 3 pages.

UniProt Database Accession no. Q7XAS7, last updated Apr. 5, 2011, located at <http://www.uniprot.org/jobs/201109112CDIGCK99G.txt>, last visited on Sep. 11, 2011, 2 pages.

UniProt Database Accession no. Q9FQ26, last updated Jul. 27, 2011, located at <http://www.uniprot.org/jobs/20110911315BB3SH2Y.txt>, last visited on Sep. 11, 2011, 1 page.

Voss, S. et al. (1997). "Mutagenesis of a Flexible Loop in Streptavidin Leads to Higher Affinity for the *Strep*-tag II Peptide and Improved Performance in Recombinant Protein Purification," *Protein Engineering* 10(8):975-982.

\* cited by examiner

Figure. 1

Kudzu IspS DNA for E. coli (SEQ ID NO:1)

atgtgtgcgacctcttctcaatttactcagattaccgagcataattcccgtcgttccgcaaactatcagccaaacct
gtggaatttcgaattcctgcaatccctggagaacgacctgaaagtggaaaagctggaggagaaagcgaccaaactgg
aggaagaagttcgctgcatgatcaaccgtgtagacacccagccgctgtccctgctggagctgatcgacgatgtgcag
cgcctgggtctgacctacaaatttgaaaaagacatcattaaagccctggaaaacatcgtactgctggacgaaaacaa
aaagaacaaatctgacctgcacgcaaccgctctgtctttccgtctgctgcgtcagcacggtttcgaggtttctcagg
atgtttttgagcgtttcaaggataaagaaggtggtttcagcggtgaactgaaaggtgacgtccaaggcctgctgagc
ctgtatgaagcgtcttacctgggtttcgagggtgagaacctgctggaggaggcgcgtaccttttccatcacccacct
gaagaacaacctgaaagaaggcattaataccaaggttgcagaacaagtgagccacgccctggaactgccatatcacc
agcgtctgcaccgtctggaggcacgttggttcctggataaatacgaaccgaaagaaccgcatcaccagctgctgctg
gagctggcgaagctggattttaacatggtacagaccctgcaccagaaagagctgcaagatctgtcccgctggtggac
cgagatgggcctggctagcaaactggattttgtacgcgaccgcctgatggaagtttatttctgggcactgggtatgg
cgccagacccgcagtttggtgaatgtcgcaaagctgttactaaaatgtttggtctggtgacgatcatcgatgacgtg
tatgacgtttatggcactctggacgaactgcaactgttcaccgatgctgtagagcgctgggacgttaacgctattaa
caccctgccggactatatgaaactgtgtttcctggcactgtacaacaccgttaacgacacgtcctattctattctga
aagagaaaggtcataacaacctgtcctatctgacgaaaagctggcgtgaactgtgcaaagcctttctgcaagaggcg
aaatggtccaacaacaaaattatcccggctttctccaagtacctggaaaacgccagcgtttcctcctccggtgtagc
gctgctggcgccgtcttacttttccgtatgccagcagcaggaagacatctccgaccacgcgctgcgttccctgaccg
acttccatggtctggtgcgttctagctgcgttatcttccgcctgtgcaacgatctggccacctctgcggcggagctg
gaacgtggcgagactaccaattctatcattagctacatgcacgaaaacgatggtaccagcgaggaacaggcccgcga
agaactgcgtaaactgatcgacgccgaatggaaaaagatgaatcgtgaacgcgttagcgactccaccctgctgccta
aagcgttcatggaaatcgcagttaacatggcacgtgtttcccactgcacctaccagtatggcgatggtctgggtcgc
ccagactacgcgactgaaaaccgcatcaaactgctgctgattgaccctttcccgattaaccagctgatgtatgtc**ta
a**

Figure 2

Kudzu IspS protein (SEQ ID NO:2)

MCATSSQFTQITEHNSRRSANYQPNLWNFEFLQSLENDLKVEKLEEKATKLEEEVRCMINRVDTQPLSLLELIDDVQ
RLGLTYKFEKDIIKALENIVLLDENKKNKSDLHATALSFRLLRQHGFEVSQDVFERFKDKEGGFSGELKGDVQGLLS
LYEASYLGFEGENLLEEARTFSITHLKNNLKEGINTKVAEQVSHALELPYHQRLHRLEARWFLDKYEPKEPHHQLLL
ELAKLDFNMVQTLHQKELQDLSRWWTEMGLASKLDFVRDRLMEVYFWALGMAPDPQFGECRKAVTKMFGLVTIIDDV
YDVYGTLDELQLFTDAVERWDVNAINTLPDYMKLCFLALYNTVNDTSYSILKEKGHNNLSYLTKSWRELCKAFLQEA
KWSNNKIIPAFSKYLENASVSSSGVALLAPSYFSVCQQQEDISDHALRSLTDFHGLVRSSCVIFRLCNDLATSAAEL
ERGETTNSIISYMHENDGTSEEQAREELRKLIDAEWKKMNRERVSDSTLLPKAFMEIAVNMARVSHCTYQYGDGLGR
PDYATENRIKLLLIDPFPINQLMYV

Figure 3

Poplar IspS DNA for *E. coli* (SEQ ID NO:6)

atgtgctctgtttctaccgagaacgtttccttcactgagacggaaaccgaggcacgtcgtagcgcgaactacgagcc
gaatagctgggactacgatttcctgctgtcttccgatactgacgaatctattgaggtgtacaaagacaaagcaaaga
aactggaggctgaagtgcgccgcgaaattaacaacgagaaagctgaattcctgactctgctggagctgatcgataac
gtacagcgcctgggtctgggttaccgcttcgaatctgatatccgtcgcgcactggatcgtttcgtaagcagcggcgg
tttcgatggcgtgaccaaaacgagcctgcacgctaccgcgctgtccttccgtctgctgcgtcagcacggcttcgaag
tttctcaggaagcattctccggtttcaaagatcaaaacggtaacttcctggaaaacctgaaagaagacactaaggcg
atcctgagcctgtatgaggcaagctttctggccctggagggtgagaacatcctggatgaggcgcgcgtattcgccat
ctcccatctgaaagagctgtctgaagagaaaatcggtaaggaactggcagagcaggttaatcacgcactggaactgc
cgctgcatcgtcgtacccagcgtctggaggcggtttggtccatcgaagcgtaccgcaaaaaggaggatgctaaccag
gttctgctggaactggccatcctggactacaacatgatccagtccgtttaccagcgtgatctgcgtgaaacctcccg
ttggtggcgccgtgtgggcctggcgaccaaactgcacttcgctaaggaccgcctgattgagtcttttactgggcag
tcggcgttgcgttcgaacctcagtattctgactgccgtaacagcgttgcgaaaatgttcagcttcgttactattatc
gacgacatctacgacgtttacggtactctggacgagctggaactgtttaccgacgctgtcgaacgttgggatgttaa
cgccatcaacgatctgcctgactacatgaaactgtgcttcctggcactgtataacacgatcaacgaaattgcatacg
acaacctgaaagacaaaggtgaaaacatcctgccgtacctgactaaagcgtgggcggatctgtgtaacgctttttctg
caagaagcgaaatggctgtataacaaatccactccgacctttgacgattatttcggcaatgcctggaaatccagctc
tggcccgctgcaactgatcttcgcttattttgcggttgtccaaaacatcaaaaaggaggaaattgaaacctgcaaa
aataccacgatatcattagccgtccttctcatatctttcgcctgtgcaacgacctggcaagcgcgtccgcagagatc
gcacgtggcgaaaccgctaactctgtttcctgctacatgcgcaccaagggcatttccgaagagctggcaaccgagag
cgtaatgaatctgatcgacgaaacctgtaagaaaatgaacaaagaaaaactgggtggctccctgttcgctaaaccgt
tcgtagagactgctattaacctggcacgtcagagccactgcacctaccacaatggtgacgcacatactagcccggat
gaactgactcgtaaacgtgtactgtctgttatcaccgaaccgattctgccgttcgaacgttaa

Figure 4

Poplar IspS protein (SEQ ID NO:7)

```
MCSVSTENVSFTETETEARRSANYEPNSWDYDFLLSSDTDESIEVYKDKAKKLEAEVRREINNEKAEFLTLLELIDN
VQRLGLGYRFESDIRRALDRFVSSGGFDGVTKTSLHATALSFRLLRQHGFEVSQEAFSGFKDQNGNFLENLKEDTKA
ILSLYEASFLALEGENILDEARVFAISHLKELSEEKIGKELAEQVNHALELPLHRRTQRLEAVWSIEAYRKKEDANQ
VLLELAILDYNMIQSVYQRDLRETSRWWRRVGLATKLHFAKDRLIESFYWAVGVAFEPQYSDCRNSVAKMFSFVTII
DDIYDVYGTLDELELFTDAVERWDVNAINDLPDYMKLCFLALYNTINEIAYDNLKDKGENILPYLTKAWADLCNAFL
QEAKWLYNKSTPTFDDYFGNAWKSSSGPLQLIFAYFAVVQNIKKEEIENLQKYHDIISRPSHIFRLCNDLASASAEI
ARGETANSVSCYMRTKGISEELATESVMNLIDETCKKMNKEKLGGSLFAKPFVETAINLARQSHCTYHNGDAHTSPD
ELTRKRVLSVITEPILPFER
```

Figure 10A plasmid MCM93 = pCR2.1-Kudzu (SEQ ID NO:22)
aagggcgaattctgcagatatccatcacactggcggccgctcgagcatgcatctagagggcccaattcgccctatag
tgagtcgtattacaattcactggccgtcgttttacaacgtcgtgactgggaaaaccctggcgttacccaacttaatc
gccttgcagcacatccccctttcgccagctggcgtaatagcgaagaggcccgcaccgatcgcccttcccaacagttg
cgcagcctgaatggcgaatggacgcgccctgtagcggcgcattaagcgcggcgggtgtggtggttacgcgcagcgtg
accgctacacttgccagcgccctagcgcccgctcctttcgctttcttcccttcctttctcgccacgttcgccggctt
tccccgtcaagctctaaatcgggggctccctttagggttccgatttagtgctttacggcacctcgaccccaaaaaac
ttgattagggtgatggttcacgtagtgggccatcgccctgatagacggttttcgccctttgacgttggagtccacg
ttctttaatagtggactcttgttccaaactggaacaacactcaaccctatctcggtctattcttttgatttataagg
gattttgccgatttcggcctattggttaaaaaatgagctgatttaacaaaaatttaacgcgaattttaacaaaattc
agggcgcaagggctgctaaaggaagcggaacacgtagaaagccagtccgcagaaacggtgctgacccggatgaatg
tcagctactgggctatctggacaagggaaaacgcaagcgcaaagagaaagcaggtagcttgcagtgggcttacatgg
cgatagctagactgggcggttttatggacagcaagcgaaccggaattgccagctggggcgccctctggtaaggttgg
gaagccctgcaaagtaaactggatggctttcttgccgccaaggatctgatggcgcaggggatcaagatctgatcaag
agacaggatgaggatcgtttcgcatgattgaacaagatggattgcacgcaggttctccggccgcttgggtggagagg
ctattcggctatgactgggcacaacagacaatcggctgctctgatgccgccgtgttccggctgtcagcgcaggggcg
cccggttcttttgtcaagaccgacctgtccggtgccctgaatgaactgcaggacgaggcagcgcggctatcgtggc
tggccacgacgggcgttccttgcgcagctgtgctcgacgttgtcactgaagcgggaagggactggctgctattgggc
gaagtgccggggcaggatctcctgtcatcccaccttgctcctgccgagaaagtatccatcatggctgatgcaatgcg
gcggctgcatacgcttgatccggctacctgcccattcgaccaccaagcgaaacatcgcatcgagcgagcacgtactc
ggatggaagccggtcttgtcgatcaggatgatctctggacgaagagcatcaggggctcgcgccagccgaactgttcgcc
aggctcaaggcgcgcatgcccgacggcgaggatctcgtcgtgacccatggcgatgcctgcttgccgaatatcatggt
ggaaaatggccgcttttctggattcatcgactgtggccggctgggtgtggcggaccgctatcaggacatagcgttgg
ctacccgtgatattgctgaagagcttggcggcgaatgggctgaccgcttcctcgtgctttacggtatcgccgctccc
gattcgcagcgcatcgccttctatcgccttcttgacgagttcttctgaattgaaaaaggaagagtatgagtattcaa
catttccgtgtcgcccttattccctttttgcggcattttgccttcctgttttgctcacccagaaacgctggtgaa
agtaaaagatgctgaagatcagttgggtgcacgagtgggttacatcgaactggatctcaacagcggtaagatccttg
agagttttcgccccgaagaacgttttccaatgatgagcacttttaaagttctgctatgtggcgcggtattatcccgt
attgacgccgggcaagagcaactcggtcgccgcatacactattctcagaatgacttggttgagtactcaccagtcac
agaaaagcatcttacggatggcatgacagtaagagaattatgcagtgctgccataaccatgagtgataacactgcgg
ccaacttacttctgacaacgatcggaggaccgaaggagctaaccgcttttttgcacaacatgggggatcatgtaact
cgccttgatcgttgggaaccggagctgaatgaagccataccaaacgacgagcgtgacaccacgatgcctgtagcaat
ggcaacaacgttgcgcaaactattaactggcgaactacttactctagcttcccggcaacaattaatagactggatgg
aggcggataaagttgcaggaccacttctgcgctcggcccttccggctggctggtttattgctgataaatctggagcc
ggtgagcgtgggtctcgcggtatcattgcagcactggggccagatggtaagccctcccgtatcgtagttatctacac
gacggggagtcaggcaactatggatgaacgaaatagacagatcgctgagataggtgcctcactgattaagcattggt
aactgtcagaccaagtttactcatatatactttagattgatttaaaacttcatttttaatttaaaaggatctaggtg
aagatcctttttgataatctcatgaccaaaatcccttaacgtgagttttcgttccactgagcgtcagaccccgtaga
aaagatcaaaggatcttcttgagatcctttttttctgcgcgtaatctgctgcttgcaaacaaaaaaaccaccgctac
cagcggtggtttgtttgccggatcaagagctaccaactctttttccgaaggtaactggcttcagcagagcgcagata
ccaaatactgttcttctagtgtagccgtagttaggccaccacttcaagaactctgtagcaccgcctacatacctcgc
tctgctaatcctgttaccagtggctgctgccagtggcgataagtcgtgtcttaccgggttggactcaagacgatagt
taccggataaggcgcagcggtcgggctgaacggggggttcgtgcacacagcccagcttggagcgaacgacctacacc
gaactgagatacctacagcgtgagctatgagaaagcgccacgcttcccgaagggagaaaggcggacaggtatccggt
aagcggcagggtcggaacaggagagcgcacgagggagcttccagggggaaacgcctggtatctttatagtcctgtcg
ggtttcgccacctctgacttgagcgtcgatttttgtgatgctcgtcaggggggcggagcctatggaaaaacgccagc
aacgcggcctttttacggttcctggccttttgctggccttttgctcacatgttctttcctgcgttatcccctgattc
tgtggataaccgtattaccgcctttgagtgagctgataccgctcgccgcagccgaacgaccgagcgcagcgagtcag
tgagcgaggaagcggaagagcgcccaatacgcaaaccgcctctccccgcgcgttggccgattcattaatgcagctgg
cacgacaggtttcccgactggaaagcgggcagtgagcgcaacgcaattaatgtgagttagctcactcattaggcacc
ccaggctttacactttatgcttccggctcgtatgttgtgtggaattgtgagcggataacaatttcacacaggaaaca
gctatgaccatgattacgccaagcttggtaccgagctcggatccnctagtaacggccgccagtgtgctggaattcgc
ccttgatcatgcattcgcccttaggaggtaaaaaaacatgtgtgcgacctcttctcaatttactcagattaccgagc
ataattcccgtcgttccgcaaactatcagccaaacctgtggaatttcgaattcctgcaatccctggagaacgacctg

Figure 10B

```
aaagtggaaaagctggaggagaaagcgaccaaactggaggaagaagttcgctgcatgatcaaccgtgtagacaccca
gccgctgtccctgctggagctgatcgacgatgtgcagcgcctgggtctgacctacaaatttgaaaagacatcatta
aagccctggaaaacatcgtactgctggacgaaaacaaaaagaacaaatctgacctgcacgcaaccgctctgtctttc
cgtctgctgcgtcagcacggtttcgaggtttctcaggatgtttttgagcgtttcaaggataaagaaggtggtttcag
cggtgaactgaaaggtgacgtccaaggcctgctgagcctgtatgaagcgtcttacctgggtttcgagggtgagaacc
tgctggaggaggcgcgtaccttttccatcacccacctgaagaacaacctgaaagaaggcattaataccaaggttgca
gaacaagtgagccacgccctggaactgccatatcaccagcgtctgcaccgtctggaggcacgttggttcctggataa
atacgaaccgaaagaaccgcatcaccagctgctgctggagctggcgaagctggattttaacatggtacagaccctgc
accagaaagagctgcaagatctgtcccgctggtggaccgagatgggcctggctagcaaactggattttgtacgcgac
cgcctgatggaagtttatttctgggcactgggtatggcgccagacccgcagtttggtgaatgtcgcaaagctgttac
taaaatgtttggtctggtgacgatcatcgatgacgtgtatgacgtttatggcactctggacgaactgcaactgttca
ccgatgctgtagagcgctgggacgttaacgctattaacaccctgccggactatatgaaactgtgtttcctggcactg
tacaacaccgttaacgacacgtcctattctattctgaaagagaaaggtcataacaacctgtcctatctgacgaaaag
ctggcgtgaactgtgcaaagcctttctgcaagaggcgaaatggtccaacaacaaaattatcccggctttctccaagt
acctggaaaacgccagcgtttcctcctccggtgtagcgctgctggcgccgtcttacttttccgtatgccagcagcag
gaagacatctccgaccacgcgctgcgttccctgaccgacttccatggtctggtgcgttctagctgcgttatcttccg
cctgtgcaacgatctggccacctctgcggcgagctggaacgtggcgagactaccaattctatcattagctacatgc
acgaaaacgatggtaccagcgaggaacaggcccgcgaagaactgcgtaaactgatcgacgccgaatggaaaaagatg
aatcgtgaacgcgttagcgactccaccctgctgcctaaagcgttcatggaaatcgcagttaacatggcacgtgtttc
ccactgcacctaccagtatggcgatggtctgggtcgcccagactacgcgactgaaaaccgcatcaaactgctgctga
ttgacccttttcccgattaaccagctgatgtatgtctaactgcagggatccgtcgaccg
```

Figure 12A pET24D-Kudzu (SEQ ID NO:23) Kudzu IspS ORF 48-1742 (complementary)
gtgcggccgcaagcttgtcgacggagctcgaattcggatccctgcagttagacatacatcagctggttaatcgggaa
agggtcaatcagcagcagtttgatgcggttttcagtcgcgtagtctgggcgacccagaccatcgccatactggtagg
tgcagtgggaaacacgtgccatgttaactgcgatttccatgaacgctttaggcagcagggtggagtcgctaacgcgt
tcacgattcatcttttccattcggcgtcgatcagtttacgcagttcttcgcgggcctgttcctcgctggtaccatc
gttttcgtgcatgtagctaatgatagaattggtagtctcgccacgttccagctccgccgcagaggtggccagatcgt
tgcacaggcggaagataacgcagctagaacgcaccagaccatggaagtcggtcagggaacgcagcgcgtggtcggag
atgtcttcctgctgctggcatacggaaaagtaagacggcagcgcgctacaccggaggaggaaacgctggcgtt
ttccaggtacttggagaaagccgggataattttgttgttggaccatttcgcctcttgcagaaaggctttgcacagtt
cacgccagcttttcgtcagataggacaggttgttatgacctttctctttcagaatagaataggacgtgtcgttaacg
gtgttgtacagtgccaggaaacacagtttcatatagtccggcagggtgttaatagcgttaacgtcccagcgctctac
agcatcggtgaacagttgcagttcgtccagagtgccataaacgtcatacacgtcatcgatgatcgtcaccagaccaa
acattttagtaacagctttgcgacattcaccaaactgcgggtctggcgccatacccagtgcccagaaataaacttcc
atcaggcggtcgcgtacaaaatccagtttgctagccaggccatctcggtccaccagcgggacagatcttgcagctc
tttctggtgcagggtctgtaccatgttaaaatccagcttcgccagctccagcagcagctggtgatgcggttctttcg
gttcgtatttatccaggaaccaacgtgcctccagacggtgcagacgctggtgatatggcagttccagggcgtggctc
acttgttctgcaaccttggtattaatgccttctttcaggttgttcttcaggtgggtgatggaaaaggtacgcgcctc
ctccagcaggttctcaccctcgaaacccaggtaagacgcttcatacaggctcagcaggccttggacgtcaccttca
gttcaccgctgaaaccaccttctttatccttgaaacgctcaaaaacatcctgagaaacctcgaaaccgtgctgacgc
agcagacggaaagacagagcggttgcgtgcaggtcagatttgttctttttgttttcgtccagcagtacgatgttttc
cagggctttaatgatgtcttttttcaaatttgtaggtcagacccaggcgctgcacatcgtcgatcagctccagcaggg
acagcggctgggtgtctacacggttgatcatgcagcgaacttcttcctccagtttggtcgctttctcctccagcttt
tccactttcaggtcgttctccaggattgcaggaattcgaaattccacaggtttggctgatagtttgcggaacgacg
ggaattatgctcggtaatctgagtaaattgagaagaggtcgcacacatggtatatctccttcttaaagttaaacaaa
attatttctagaggggaattgttatccgctcacaattcccctatagtgagtcgtattaatttcgcgggatcgagatc
tcgatcctctacgccggacgcatcgtggccggcatcaccggcgccacaggtgcggttgctggcgcctatatcgccga
catcaccgatggggaagatcgggctcgccacttcgggctcatgagcgcttgttcggcgtgggtatggtggcaggcc
ccgtggccggggactgttgggcgccatctccttgcatgcaccattccttgcggcggcggtgctcaacggcctcaac
ctactactgggctgcttcctaatgcaggagtcgcataaggagagcgtcgagatcccggacaccatcgaatggcgca
aaacctttcgcggtatggcatgatagcgcccggaagagagtcaattcagggtggtgaatgtgaaaccagtaacgtta
tacgatgtcgcagagtatgccggtgtctcttatcagaccgtttcccgcgtggtgaaccaggccagccacgtttctgc
gaaaacgcgggaaaaagtggaagcggcgatgcggagctgaattacattcccaaccgcgtggcacaacaactggcgg
gcaaacagtcgttgctgattggcgttgccacctccagtctggccctgcacgcgccgtcgcaaattgtcgcggcgatt
aaatctcgcgccgatcaactgggtgccagcgtggtggtgtcgatggtagaacgaagcggcgtcgaagcctgtaaagc
ggcggtgcacaatcttctcgcgcaacgcgtcagtgggctgatcattaactatccgctggatgaccaggatgccattg
ctgtggaagctgcctgcactaatgttccggcgttatttcttgatgtctctgaccagacacccatcaacagtattatt
ttctcccatgaagacgctacgcgactgggcgtggagcatctggtcgcattgggtcaccagcaaatcgcgctgttagc
gggccattaagttctgtctcggcgcgtctgcgtctggctggctggcataaatatctcactcgcaatcaaattcagc
cgatagcggaacgggaaggcgactggagtgccatgtccggttttcaacaaaccatgcaaatgctgaatgagggcatc
gttcccactgcgatgctggttgccaacgatcagatggcgctgggcgcaatgcgcgccattaccgagtccggctgcg
cgttggtgcggatatctcggtagtgggatacgacgataccgaagacagctcatgttatatccgccgttaaccacca
tcaaacaggattttcgcctgctggggcaaaccagcgtggaccgcttgctgcaactctctcagggccaggcggtgaag
ggcaatcagctgttgcccgtctcactggtgaaagaaaaaccaccctggcgcccaatacgcaaaccgcctctcccg
cgcgttggccgattcattaatgcagctggcacgacaggtttcccgactggaaagcgggcagtgagcgcaacgcaatt
aatgtaagttagctcactcattaggcaccgggatctcgaccgatgcccttgagagccttcaacccagtcagctcctt
ccggtgggcgcggggcatgactatcgtcgccgcacttatgactgtcttctttatcatgcaactcgtaggacaggtgc
cggcagcgctctgggtcattttcggcgaggaccgctttcgctggagcgcgacgatgatcggcctgtcgcttcggta
ttcggaatcttgcacgccctcgctcaagccttcgtcactgtccccaccaaacgtttcggcgagaagcaggccat
tatcgccggcatggcggccccacgggtgcgcatgatcgtgctcctgtcgttgaggacccggctaggctggcggggtt
gccttactggttagcagaatgaatcaccgatacgcgagcgaacgtgaagcgactgctgctgcaaaacgtctgcgacc
tgagcaacaacatgaatggtcttcggtttccgtgtttcgtaaagtctggaaacgcggaagtcagcgccctgcaccat
tatgttccggatctgcatcgcaggatgctgctggctaccctgtggaacacctacatctgtattaacgaagcgctggc
attgaccctgagtgattttctctggtcccgccgcatccataccgccagttgtttaccctcacaacgttccagtaac
cgggcatgttcatcatcagtaacccgtatcgtgagcatcctctctcgtttcatcggtatcattaccccatgaacag

Figure 12B

```
aaatccccttacacggaggcatcagtgaccaaacaggaaaaaaccgcccttaacatggcccgctttatcagaagcc
agacattaacgcttctggagaaactcaacgagctggacgcggatgaacaggcagacatctgtgaatcgcttcacgac
cacgctgatgagctttaccgcagctgcctcgcgcgtttcggtgatgacggtgaaaacctctgacacatgcagctccc
ggagacggtcacagcttgtctgtaagcggatgccgggagcagacaagcccgtcagggcgcgtcagcgggtgttggcg
ggtgtcggggcgcagccatgacccagtcacgtagcgatagcggagtgtatactggcttaactatgcggcatcagagc
agattgtactgagagtgcaccatatatgcggtgtgaaataccgcacagatgcgtaaggagaaaataccgcatcaggc
gctcttccgcttcctcgctcactgactcgctgcgctcggtcgttcggctgcggcgagcggtatcagctcactcaaag
gcggtaatacggttatccacagaatcaggggataacgcaggaaagaacatgtgagcaaaaggccagcaaaaggccag
gaaccgtaaaaaggccgcgttgctggcgtttttccataggctccgcccccctgacgagcatcacaaaaatcgacgct
caagtcagaggtggcgaaacccgacaggactataaagataccaggcgtttccccctggaagctccctcgtgcgctct
cctgttccgaccctgccgcttaccggatacctgtccgcctttctcccttcgggaagcgtggcgctttctcatagctc
acgctgtaggtatctcagttcggtgtaggtcgttcgctccaagctgggctgtgtgcacgaaccccccgttcagcccg
accgctgcgccttatccggtaactatcgtcttgagtccaacccggtaagacacgacttatcgccactggcagcagcc
actggtaacaggattagcagagcgaggtatgtaggcggtgctacagagttcttgaagtggtggcctaactacggcta
cactagaaggacagtatttggtatctgcgctctgctgaagccagttaccttcggaaaaagagttggtagctcttgat
ccggcaaacaaaccaccgctggtagcggtggtttttttgtttgcaagcagcagattacgcgcagaaaaaaaggatct
caagaagatcctttgatcttttctacggggtctgacgctcagtggaacgaaaactcacgttaagggattttggtcat
gaacaataaaactgtctgcttacataaacagtaatacaaggggtgttatgagccatattcaacgggaaacgtcttgc
tctaggccgcgattaaattccaacatgatgctgatttatatgggtataaatgggctcgcgataatgtcgggcaatc
aggtgcgacaatctatcgattgtatgggaagcccgatgcgccagagttgtttctgaaacatggcaaaggtagcgttg
ccaatgatgttacagatgagatggtcagactaaactggctgacggaatttatgcctcttccgaccatcaagcatttt
atccgtactcctgatgatgcatggttactcaccactgcgatccccgggaaaacagcattccaggtattagaagaata
tcctgattcaggtgaaaatattgttgatgcgctggcagtgttcctgcgccggttgcattcgattcctgtttgtaatt
gtcctttttaacagcgatcgcgtatttcgtctcgctcaggcgcaatcacgaatgaataacggtttggttgatgcgagt
gatttgatgacgagcgtaatggctggcctgttgaacaagtctggaaagaaatgcataaacttttgccattctcacc
ggattcagtcgtcactcatggtgatttctcacttgataaaccttatttttgacgaggggaaattaataggttgtattg
atgttggacgagtcggaatcgcagaccgataccaggatcttgccatcctatggaactgcctcggtgagttttctcct
tcattacagaaacggctttttcaaaaatatggtattgataatcctgatatgaataaattgcagtttcatttgatgct
cgatgagttttttctaagaattaattcatgagcggatacatatttgaatgtatttagaaaaataaacaaatagggg tt
ccgcgcacatttccccgaaaagtgccacctgaaattgtaaacgttaatattttgttaaaattcgcgttaaattttg
ttaaatcagctcatttttttaaccaataggccgaaatcggcaaaatcccttataaatcaaaagaatagaccgagatag
ggttgagtgttgttccagtttggaacaagagtccactattaaagaacgtggactccaacgtcaaagggcgaaaaacc
gtctatcagggcgatggcccactacgtgaaccatcaccctaatcaagttttttggggtcgaggtgccgtaaagcact
aaatcggaaccctaaagggagcccccgatttagagcttgacggggaaagccggcgaacgtggcgagaaaggaaggga
agaaagcgaaaggagcgggcgctagggcgctggcaagtgtagcggtcacgctgcgcgtaaccaccacacccgccgcg
cttaatgcgccgctacagggcgcgtcccattcgccaatccggatatagttcctcctttcagcaaaaaacccctcaag
acccgtttagaggccccaaggggttatgctagttattgctcagcggtggcagcagccaactcagcttcctttcgggc
tttgttagcagccggatctcagtggtggtggtggtggtgctcga
```

Figure 17

Amino acid sequence of 6XHis N-terminally tagged *P. alba* IspS (SEQ ID NO:118)

MRGSHHHHHHGMASMTGGQQMGRDLYDDDDKDHPFTMRCSVSTENVSFTETETEARRSANYEPN
SWDYDYLLSSDTDESIEVYKDKAKKLEAEVRREINNEKAEFLTLLELIDNVQRLGLGYRFESDI
RGALDRFVSSGGFDAVTKTSLHGTALSFRLLRQHGFEVSQEAFSGFKDQNGNFLENLKEDIKAI
LSLYEASFLALEGENILDEAKVFAISHLKELSEEKIGKELAEQVNHALELPLHRRTQRLEAVWS
IEAYRKKEDANQVLLELAILDYNMIQSVYQRDLRETSRWWRRVGLATKLHFARDRLIESFYWAV
GVAFEPQYSDCRNSVAKMFSFVTIIDDIYDVYGTLDELELFTDAVERWDVNAINDLPDYMKLCF
LALYNTINEIAYDNLKDKGENILPYLTKAWADLCNAFLQEAKWLYNKSTPTFDDYFGNAWKSSS
GPLQLVFAYFAVVQNIKKEEIENLQKYHDTISRPSHIFRLCNDLASASAEIARGETANSVSCYM
RTKGISEELATESVMNLIDETWKKMNKEKLGGSLFAKPFVETAINLARQSHCTYHNGDAHTSPD
ELTRKRVLSVITEPILPFER

Figure 18A

Nucleotide sequence of pDu27 (SEQ ID NO:119)

```
aagggcgagctcaacgatccggctgctaacaaagcccgaaaggaagctgagttggctgctgcca
ccgctgagcaataactagcataaccccttggggcctctaaacgggtcttgaggagttttttgct
gaaaggaggaactatatccggatatcccgcaagaggcccggcagtaccggcataaccaagccta
tgcctacagcatccagggtgacggtgccgaggatgacgatgagcgcattgttagatttcataca
cggtgcctgactgcgttagcaatttaactgtgataaactaccgcattaaagcttatcgatgata
agctgtcaaacatgagaattaattcttgaagacgaaagggcctcgtgatacgcctatttttata
ggttaatgtcatgataataatggtttcttagacgtcaggtggcacttttcggggaaatgtgcgc
ggaacccctatttgtttatttttctaaatacattcaaatatgtatccgctcatgagacaataac
cctgataaatgcttcaataatattgaaaaaggaagagtatgattgaacaagatggattgcacgc
aggttctccggccgcttgggtggagaggctattcggctatgactgggcacaactgacaatcggc
tgctctgatgccgccgtgttccggctgtcagcgcaggggcgcccggttcttttttgtcaagaccg
acctgtccggtgccctgaatgaactgcaggacgaggcagcgcggctatcgtggctggccacgac
gggcgttccttgcgcagctgtgctcgacgttgtcactgaagcgggaagggactggctgctattg
ggcgaagtgccggggcaggatctcctgtcatctcaccttgctcctgccgagaaagtatccatca
tggctgatgcaatgcggcggctgcatacgcttgatccggctacctgcccattcgaccaccaagc
gaaacatcgcatcgagcgggcacgtactcggatggaagccggtcttgtcgatcaggatgatctg
gacgaagagcatcaggggctcgcgccagccgaactgttcgccaggctcaaggcgcgcatgcccg
acggcgaggatctcgtcgtgacacatggcgatgcctgcttgccgaatatcatggtggaaaatgg
ccgcttttctggattcatcgactgtggccggctgggtgtggcggaccgctatcaggacatagcg
ttggctacccgtgatattgctgaagagcttggcggcgaatgggctgaccgcttcctcgtgcttt
acggtatcgccgctcccgattcgcagcgcatcgccttctatcgccttcttgacgagttcttctg
agcgggactctggggttcgaaatgaccgaccaagcgacgcctaactgtcagaccaagtttactc
atatatactttagattgatttaaaacttcatttttaatttaaaaggatctaggtgaagatcctt
tttgataatctcatgaccaaaatcccttaacgtgagttttcgttccactgagcgtcagacccccg
tagaaaagatcaaaggatcttcttgagatcctttttttctgcgcgtaatctgctgcttgcaaac
aaaaaaaccaccgctaccagcggtggtttgtttgccggatcaagagctaccaactctttttccg
aaggtaactggcttcagcagagcgcagataccaaatactgtccttctagtgtagccgtagttag
gccaccacttcaagaactctgtagcaccgcctacatacctcgctctgctaatcctgttaccagt
ggctgctgccagtggcgataagtcgtgtcttaccgggttggactcaagacgatagttaccggat
aaggcgcagcggtcgggctgaacggggggttcgtgcacacagcccagcttggagcgaacgacct
acaccgaactgagatacctacagcgtgagctatgagaaagcgccacgcttcccgaagggagaaa
ggcggacaggtatccggtaagcggcagggtcggaacaggagagcgcacgagggagcttccaggg
ggaaacgcctggtatctttatagtcctgtcgggtttcgccacctctgacttgagcgtcgatttt
tgtgatgctcgtcaggggggcggagcctatggaaaaacgccagcaacgcggcctttttacggtt
cctggccttttgctggccttttgctcacatgttctttcctgcgttatccctgattctgtggat
aaccgtattaccgcctttgagtgagctgataccgctcgccgcagccgaacgaccgagcgcagcg
agtcagtgagcgaggaagcggaagagcgcctgatgcggtattttctccttacgcatctgtgcgg
tatttcacaccgcaatggtgcactctcagtacaatctgctctgatgccgcatagttaagccagt
atacactccgctatcgctacgtgactgggtcatggctgcgccccgacacccgccaacacccgct
gacgcgccctgacgggcttgtctgctcccggcatccgcttacagacaagctgtgaccgtctccg
ggagctgcatgtgtcagaggttttcaccgtcatcaccgaaacgcgcgaggcagctgcggtaaag
ctcatcagcgtggtcgtgaagcgattcacagatgtctgcctgttcatccgcgtccagctcgttg
agtttctccagaagcgttaatgtctggcttctgataaagcgggccatgttaagggcggttttt
```

Figure 18B

Nucleotide sequence of pDu27 cctgtttggtcactgatgcctccgtgtaaggggatttctgttcatggggtaatgataccgat
gaaacgagagaggatgctcacgatacgggttactgatgatgaacatgcccggttactggaacgt
tgtgagggtaaacaactggcggtatggatgcggcgggaccagagaaaaatcactcagggtcaat
gccagcgcttcgttaatacagatgtaggtgttccacagggtagccagcagcatcctgcgatgca
gatccggaacataatggtgcagggcgctgacttccgcgtttccagactttacgaaacacggaaa
ccgaagaccattcatgttgttgctcaggtcgcagacgttttgcagcagcagtcgcttcacgttc
gctcgcgtatcggtgattcattctgctaaccagtaaggcaaccccgccagcctagccgggtcct
caacgacaggagcacgatcatgcgcacccgtggccaggacccaacgctgcccgagatgcgccgc
gtgcggctgctggagatggcggacgcgatggatatgttctgccaagggttggtttgcgcattca
cagttctccgcaagaattgattggctccaattcttggagtggtgaatccgttagcgaggtgccg
ccggcttccattcaggtcgaggtggcccggctccatgcaccgcgacgcaacgcggggaggcaga
caaggtatagggcggcgcctacaatccatgccaacccgttccatgtgctcgccgaggcggcata
aatcgccgtgacgatcagcggtccaatgatcgaagttaggctggtaagagccgcgagcgatcct
tgaagctgtccctgatggtcgtcatctacctgcctggacagcatggcctgcaacgcgggcatcc
cgatgccgccggaagcgagaagaatcataatggggaaggccatccagcctcgcgtcgcgaacgc
cagcaagacgtagcccagcgcgtcggccgccatgccggcgataatggcctgcttctcgccgaaa
cgtttggtggcgggaccagtgacgaaggcttgagcgagggcgtgcaagattccgaataccgcaa
gcgacaggccgatcatcgtcgcgctccagcgaaagcggtcctcgccgaaaatgacccagagcgc
tgccggcacctgtcctacgagttgcatgataaagaagacagtcataagtgcggcgacgatagtc
atgccccgcgccaccggaaggagctgactgggttgaaggctctcaagggcatcggtcgagatc
ccggtgcctaatgagtgagctaacttacattaattgcgttgcgctcactgcccgctttccagtc
gggaaacctgtcgtgccagctgcattaatgaatcggccaacgcgcggggagaggcggtttgcgt
attgggcgccagggtggttttcttttcaccagtgagacgggcaacagctgattgcccttcacc
gcctggccctgagagagttgcagcaagcggtccacgctggtttgccccagcaggcgaaaatcct
gtttgatggtggttaacggcgggatataacatgagctgtcttcggtatcgtcgtatcccactac
cgagatatccgcaccaacgcgcagcccggactcggtaatggcgcgcattgcgcccagcgccatc
tgatcgttggcaaccagcatcgcagtgggaacgatgccctcattcagcatttgcatggtttgtt
gaaaaccggacatggcactccagtcgccttcccgttccgctatcggctgaatttgattgcgagt
gagatatttatgccagccagccagacgcagacgcgccgagacagaacttaatgggcccgctaac
agcgcgatttgctggtgacccaatgcgaccagatgctccacgcccagtcgcgtaccgtcttcat
gggagaaaataatactgttgatgggtgtctggtcagagacatcaagaaataacgccggaacatt
agtgcaggcagcttccacagcaatggcatcctggtcatccagcggatagttaatgatcagccca
ctgacgcgttgcgcgagaagattgtgaccgccgctttacaggcttcgacgccgcttcgttcta
ccatcgacaccaccacgctggcacccagttgatcggcgcgagatttaatcgccgcgacaatttg
cgacggcgcgtgcagggccagactggaggtggcaacgccaatcagcaacgactgtttgcccgcc
agttgttgtgccacgcggtgggaatgtaattcagctccgccatcgccgcttccactttttccc
gcgttttcgcagaaacgtggctggcctggttcaccacgcgggaaacggtctgataagagacacc
ggcatactctgcgacatcgtataacgttactggtttcacattcaccaccctgaattgactctct
tccgggcgctatcatgccataccgcgaaaggttttgcgccattcgatggtgtccgggatctcga
cgctctcccttatgcgactcctgcattaggaagcagcccagtagtaggttgaggccgttgagca
ccgccgccgcaaggaatggtgcatgcaaggagatggcgcccaacagtccccggccacggggcc
tgccaccatacccacgccgaaacaagcgctcatgagcccgaagtggcgagcccgatcttcccca

Figure 18C

Nucleotide sequence of pDu27

```
tcggtgatgtcggcgatataggcgccagcaaccgcacctgtggcgccggtgatgccggccacga
tgcgtccggcgtagaggatcgagatctcgatcccgcgaaattaatacgactcactatagggga
ttgtgagcggataacaattcccctctagaaataattttgtttaactttaagaaggagatataca
tatgcggggttctcatcatcatcatcatggtatggctagcatgactggtggacagcaaatg
ggtcgggatctgtacgacgatgacgataaggatcatcccttcaccatgcgttgtagcgtgtcca
ccgaaaatgtgtctttcaccgaaactgaaaccgaagctcgtcgttctgcgaactacgacctaa
cagctgggactatgattacctgctgtcctccgacacggacgagtccatcgaagtatacaaagac
aaagcgaaaaagctggaagccgaagttcgtcgcgagattaataacgaaaaagcagaatttctga
ccctgctggaactgattgacaacgtccagcgcctgggcctgggttaccgtttcgagtctgatat
ccgtggtgcgctggatcgcttcgtttcctccggcggcttcgatgcggtaaccaagacttccctg
cacggtacggcactgtctttccgtctgctgcgtcaacacggttttgaggtttctcaggaagcgt
tcagcggcttcaaagaccaaaacggcaacttcctggagaacctgaaggaagatatcaaagctat
cctgagcctgtacgaggccagcttcctggctctggaaggcgaaaacatcctggacgaggcgaag
gttttcgcaatctctcatctgaaagaactgtctgaagaaaagatcggtaaagagctggcagaac
aggtgaaccatgcactggaactgccactgcatcgccgtactcagcgtctggaagcagtatggtc
tatcgaggcctaccgtaaaaaggaggacgcgaatcaggttctgctggagctggcaattctggat
tacaacatgatccagtctgtataccagcgtgatctgcgtgaaacgtcccgttggtggcgtcgtg
tgggtctggcgaccaaactgcactttgctcgtgaccgcctgattgagcttctactgggccgt
gggtgtagcattcgaaccgcaatactccgactgccgtaactccgtcgcaaaaatgttttctttc
gtaaccattatcgacgatatctacgatgtatacggcaccctggacgaactggagctgtttactg
atgcagttgagcgttgggacgtaaacgccatcaacgacctgccggattacatgaaactgtgctt
tctggctctgtataacactattaacgaaatcgcctacgacaacctgaaagataaaggtgagaac
atcctgccgtatctgaccaaagcctgggctgacctgtgcaacgctttcctgcaagaagccaagt
ggctgtacaacaaatctactccgacctttgacgactacttcggcaacgcatggaaatcctcttc
tggcccgctgcaactggtgttcgcttacttcgctgtcgtgcagaacattaaaaaggaagagatc
gaaaacctgcaaaaataccatgacaccatctctcgtccttcccatatcttccgtctgtgcaatg
acctggctagcgcgtctgcggaaattgcgcgtggtgaaaccgcaaatagcgtttcttgttacat
gcgcactaaaggtatctccgaagaactggctaccgaaagcgtgatgaatctgatcgatgaaacc
tggaaaagatgaacaaggaaaaactgggtggtagcctgttcgcgaaaccgttcgtggaaaccg
cgatcaacctggcacgtcaatctcactgcacttatcataacggcgacgcgcatacctctccgga
tgagctgacccgcaaacgcgttctgtctgtaatcactgaaccgattctgccgtttgaacgctaa
```

Figure 19

Amino acid sequence of full length *P. alba* IspS in P. alba (SEQ ID NO:120)

```
MRCSVSTENVSFTETETEARRSANYEPNSWDYDYLLSSDTDESIEVYKDKAKKLEAEVRREINN
EKAEFLTLLELIDNVQRLGLGYRFESDIRGALDRFVSSGGFDAVTKTSLHGTALSFRLLRQHGF
EVSQEAFSGFKDQNGNFLENLKEDIKAILSLYEASFLALEGENILDEAKVFAISHLKELSEEKI
GKELAEQVNHALELPLHRRTQRLEAVWSIEAYRKKEDANQVLLELAILDYNMIQSVYQRDLRET
SRWWRRVGLATKLHFARDRLIESFYWAVGVAFEPQYSDCRNSVAKMFSFVTIIDDIYDVYGTLD
ELELFTDAVERWDVNAINDLPDYMKLCFLALYNTINEIAYDNLKDKGENILPYLTKAWADLCNA
FLQEAKWLYNKSTPTFDDYFGNAWKSSSGPLQLVFAYFAVVQNIKKEEIENLQKYHDTISRPSH
IFRLCNDLASASAEIARGETANSVSCYMRTKGISEELATESVMNLIDETWKKMNKEKLGGSLFA
KPFVETAINLARQSHCTYHNGDAHTSPDELTRKRVLSVITEPILPFER
```

Figure 20A

Nucleotide sequence of P. alba pET24a (SEQ ID NO:121)

```
tggcgaatgggacgcgccctgtagcggcgcattaagcgcggcgggtgtggtggttacgcgcagc
gtgaccgctacacttgccagcgccctagcgcccgctcctttcgctttcttcccttcctttctcg
ccacgttcgccggctttccccgtcaagctctaaatcggggctccctttagggttccgatttag
tgctttacggcacctcgaccccaaaaaacttgattagggtgatggttcacgtagtgggccatcg
ccctgatagacggttttcgcccttgacgttggagtccacgttctttaatagtggactcttgt
tccaaactggaacaacactcaaccctatctcggtctattcttttgatttataagggatttgcc
gatttcggcctattggttaaaaaatgagctgatttaacaaaaatttaacgcgaattttaacaaa
atattaacgtttacaatttcaggtggcacttttcggggaaatgtgcgcggaaccctatttgtt
tattttctaaatacattcaaatatgtatccgctcatgaattaattcttagaaaaactcatcga
gcatcaaatgaaactgcaatttattcatatcaggattatcaataccatatttttgaaaaagccg
tttctgtaatgaaggagaaaactcaccgaggcagttccataggatggcaagatcctggtatcgg
tctgcgattccgactcgtccaacatcaatacaacctattaatttcccctcgtcaaaaataaggt
tatcaagtgagaaatcaccatgagtgacgactgaatccggtgagaatggcaaaagtttatgcat
ttctttccagacttgttcaacaggccagccattacgctcgtcatcaaaatcactcgcatcaacc
aaaccgttattcattcgtgattgcgcctgagcgagacgaaatacgcgatcgctgttaaaggac
aattacaaacaggaatcgaatgcaaccggcgcaggaacactgccagcgcatcaacaatattttc
acctgaatcaggatattcttctaatacctggaatgctgttttcccggggatcgcagtggtgagt
aaccatgcatcatcaggagtacggataaaatgcttgatggtcggaagaggcataaattccgtca
gccagtttagtctgaccatctcatctgtaacatcattggcaacgctacctttgccatgtttcag
aaacaactctggcgcatcgggcttcccatacaatcgatagattgtcgcacctgattgcccgaca
ttatcgcgagcccatttatacccatataaatcagcatccatgttggaatttaatcgcggcctag
agcaagacgtttcccgttgaatatggctcataacaccccttgtattactgtttatgtaagcaga
cagttttattgttcatgaccaaaatcccttaacgtgagttttcgttccactgagcgtcagaccc
cgtagaaaagatcaaaggatcttcttgagatcctttttttctgcgcgtaatctgctgcttgcaa
acaaaaaaaccaccgctaccagcggtggtttgtttgccggatcaagagctaccaactctttttc
cgaaggtaactggcttcagcagagcgcagataccaaatactgtccttctagtgtagccgtagtt
aggccaccacttcaagaactctgtagcaccgcctacatacctcgctctgctaatcctgttacca
gtggctgctgccagtggcgataagtcgtgtcttaccgggttggactcaagacgatagttaccgg
ataaggcgcagcggtcgggctgaacggggggttcgtgcacacagcccagcttggagcgaacgac
ctacaccgaactgagatacctacagcgtgagctatgagaaagcgccacgcttcccgaagggaga
aaggcggacaggtatccggtaagcggcagggtcggaacaggagagcgcacgagggagcttccag
ggggaaacgcctggtatctttatagtcctgtcgggtttcgccacctctgacttgagcgtcgatt
tttgtgatgctcgtcaggggggcggagcctatggaaaaacgccagcaacgcggcctttttacgg
ttcctggccttttgctggccttttgctcacatgttctttcctgcgttatcccctgattctgtgg
ataaccgtattaccgcctttgagtgagctgataccgctcgccgcagccgaacgaccgagcgcag
cgagtcagtgagcgaggaagcggaagagcgcctgatgcggtattttctccttacgcatctgtgc
ggtatttcacaccgcatatatggtgcactctcagtacaatctgctctgatgccgcatagttaag
ccagtatacactccgctatcgctacgtgactgggtcatggctgcgccccgacacccgccaacac
ccgctgacgcgccctgacgggcttgtctgctcccggcatccgcttacagacaagctgtgaccgt
ctccgggagctgcatgtgtcagaggttttcaccgtcatcaccgaaacgcgcgaggcagctgcgg
taaagctcatcagcgtggtcgtgaagcgattcacagatgtctgcctgttcatccgcgtccagct
cgttgagtttctccagaagcgttaatgtctggcttctgataaagcgggccatgttaagggcggt
ttttcctgtttggtcactgatgcctccgtgtaaggggggattctgttcatgggggtaatgata
```

Figure 20B

Nucleotide sequence of P. alba pET24a ccgatgaaacgagagaggatgctcacgatacgggttactgatgatgaacatgcccggttactgg
aacgttgtgagggtaaacaactggcggtatggatgcggcgggaccagagaaaaatcactcaggg
tcaatgccagcgcttcgttaatacagatgtaggtgttccacagggtagccagcagcatcctgcg
atgcagatccggaacataatggtgcagggcgctgacttccgcgtttccagactttacgaaacac
ggaaaccgaagaccattcatgttgttgctcaggtcgcagacgttttgcagcagcagtcgcttca
cgttcgctcgcgtatcggtgattcattctgctaaccagtaaggcaaccccgccagcctagccgg
gtcctcaacgacaggagcacgatcatgcgcacccgtggggccgccatgccggcgataatggcct
gcttctcgccgaaacgtttggtggcgggaccagtgacgaaggcttgagcgagggcgtgcaagat
tccgaataccgcaagcgacaggccgatcatcgtcgcgctccagcgaaagcggtcctcgccgaaa
atgacccagagcgctgccggcacctgtcctacgagttgcatgataaagaagacagtcataagtg
cggcgacgatagtcatgccccgcgcccaccggaaggagctgactgggttgaaggctctcaaggg
catcggtcgagatcccggtgcctaatgagtgagctaacttacattaattgcgttgcgctcactg
cccgcttttccagtcgggaaacctgtcgtgccagctgcattaatgaatcggccaacgcgcgggga
gaggcggtttgcgtattgggcgccagggtggttttcttttcaccagtgagacgggcaacagct
gattgcccttcaccgcctggccctgagagagttgcagcaagcggtccacgctggtttgccccag
caggcgaaaatcctgtttgatggtggttaacggcgggatataacatgagctgtcttcggtatcg
tcgtatcccactaccgagatatccgcaccaacgcgcagcccggactcggtaatggcgcgcattg
cgcccagcgccatctgatcgttggcaaccagcatcgcagtgggaacgatgccctcattcagcat
ttgcatggtttgttgaaaaccggacatggcactccagtcgccttcccgttccgctatcggctga
atttgattgcgagtgagatatttatgccagccagccagacgcagacgcgccgagacagaactta
atgggcccgctaacagcgcgatttgctggtgacccaatgcgaccagatgctccacgcccagtcg
cgtaccgtcttcatgggagaaaataatactgttgatgggtgtctggtcagagacatcaagaaat
aacgccggaacattagtgcaggcagcttccacagcaatggcatcctggtcatccagcggatagt
taatgatcagcccactgacgcgttgcgcgagaagattgtgcaccgccgctttacaggcttcgac
gccgcttcgttctaccatcgacaccaccacgctggcacccagttgatcggcgcgagatttaatc
gccgcgacaatttgcgacggcgcgtgcagggccagactggaggtggcaacgccaatcagcaacg
actgtttgcccgccagttgttgtgccacgcggttgggaatgtaattcagctccgccatcgccgc
ttccacttttttcccgcgttttcgcagaaacgtggctggcctggttcaccacgcgggaaacggtc
tgataagagacaccggcatactctgcgacatcgtataacgttactggtttcacattcaccaccc
tgaattgactctcttccgggcgctatcatgccataccgcgaaaggttttgcgccattcgatggt
gtccgggatctcgacgctctcccttatgcgactcctgcattaggaagcagcccagtagtaggtt
gaggccgttgagcaccgccgccgcaaggaatggtgcatgcaaggagatggcgcccaacagtccc
ccggccacggggcctgccaccatacccacgccgaaacaagcgctcatgagcccgaagtggcgag
cccgatcttccccatcggtgatgtcggcgatataggcgccagcaaccgcacctgtggcgccggt
gatgccggccacgatgcgtccggcgtagaggatcgagatctcgatcccgcgaaattaatacgac
tcactatagggggaattgtgagcggataacaattcccctctagaaataattttgtttaactttaa
gaaggagatatacatatgcgttgtagcgtgtccaccgaaaatgtgtctttcaccgaaactgaaa
ccgaagctcgtcgttctgcgaactacgaacctaacagctgggactatgattacctgctgtcctc
cgacacggacgagtccatcgaagtatacaaagacaaagcgaaaaagctggaagccgaagttcgt
cgcgagattaataacgaaaagcagaatttctgaccctgctggaactgattgacaacgtccagc
gcctgggcctgggttaccgtttcgagtctgatatccgtggtgcgctggatcgcttcgtttcctc
cggcggcttcgatgcggtaaccaagacttccctgcacggtacggcactgtctttccgtctgctg
cgtcaacacggttttgaggtttctcaggaagcgttcagcggcttcaaagaccaaaacggcaact

Figure 20C

Nucleotide sequence of P. alba pET24a

```
tcctggagaacctgaaggaagatatcaaagctatcctgagcctgtacgaggccagcttcctggc
tctggaaggcgaaaacatcctggacgaggcgaaggttttcgcaatctctcatctgaaagaactg
tctgaagaaaagatcggtaaagagctggcagaacaggtgaaccatgcactggaactgccactgc
atcgccgtactcagcgtctggaagcagtatggtctatcgaggcctaccgtaaaaggaggacgc
gaatcaggttctgctggagctggcaattctggattacaacatgatccagtctgtataccagcgt
gatctgcgtgaaacgtcccgttggtggcgtcgtgtgggtctggcgaccaaactgcactttgctc
gtgaccgcctgattgagagcttctactgggccgtgggtgtagcattcgaaccgcaatactccga
ctgccgtaactccgtcgcaaaaatgttttctttcgtaaccattatcgacgatatctacgatgta
tacggcaccctggacgaactggagctgtttactgatgcagttgagcgttgggacgtaaacgcca
tcaacgacctgccggattacatgaaactgtgctttctggctctgtataacactattaacgaaat
cgcctacgacaacctgaaagataaaggtgagaacatcctgccgtatctgaccaaagcctgggct
gacctgtgcaacgctttcctgcaagaagccaagtggctgtacaacaaatctactccgacctttg
acgactacttcggcaacgcatggaaatcctcttctggcccgctgcaactggtgttcgcttactt
cgctgtcgtgcagaacattaaaaaggaagagatcgaaaacctgcaaaaataccatgacaccatc
tctcgtccttcccatatcttccgtctgtgcaatgacctggctagcgcgtctgcggaaattgcgc
gtggtgaaaccgcaaatagcgtttcttgttacatgcgcactaaaggtatctccgaagaactggc
taccgaaagcgtgatgaatctgatcgatgaaacctggaaaaagatgaacaaggaaaaactgggt
ggtagcctgttcgcgaaaccgttcgtggaaaccgcgatcaacctggcacgtcaatctcactgca
cttatcataacggcgacgcgcatacctctccggatgagctgacccgcaaacgcgttctgtctgt
aatcactgaaccgattctgccgtttgaacgctaaggatccgaattcgagctccgtcgacaagct
tgcggccgcactcgagcaccaccaccaccaccactgagatccggctgctaacaaagcccgaaag
gaagctgagttggctgctgccaccgctgagcaataactagcataacccttggggcctctaaac
gggtcttgaggggttttttgctgaaaggaggaactatatccggat
```

10% NUPAGE Bis-Tris Gel, Reduced

| Lane | Gel No. 1 Volume | Description |
|---|---|---|
| 1 | 10 | MW Marker |
| 2 | 1.5 | Purif IsoS 0.5 ug |
| 3 | 3.1 | Purif IsoS 1 ug |
| 4 | 6.3 | Purif IsoS 2 ug |
| 5 | 15 | P alba Uninduced |
| 6 | 15 | P alba Induced |
| 7 | 15 | P alba Lysate |
| 8 | 15 | P alba Supernatant |
| 9 | 10 | P alba Pellet |
| 10 | 0 | Blank |
| Function | | Coomassie Stain |

Figure 25

Amino acid sequence of "MEA" variant of P. alba IspS (SEQ ID NO:122)

```
MEARRSANYEPNSWDYDYLLSSDTDESIEVYKDKAKKLEAEVRREINNEKAEFLTLLELIDNVQ
RLGLGYRFESDIRGALDRFVSSGGFDAVTKTSLHGTALSFRLLRQHGFEVSQEAFSGFKDQNGN
FLENLKEDIKAILSLYEASFLALEGENILDEAKVFAISHLKELSEEKIGKELAEQVNHALELPL
HRRTQRLEAVWSIEAYRKKEDANQVLLELAILDYNMIQSVYQRDLRETSRWWRRVGLATKLHFA
RDRLIESFYWAVGVAFEPQYSDCRNSVAKMFSFVTIIDDIYDVYGTLDELELFTDAVERWDVNA
INDLPDYMKLCFLALYNTINEIAYDNLKDKGENILPYLTKAWADLCNAFLQEAKWLYNKSTPTF
DDYFGNAWKSSSGPLQLVFAYFAVVQNIKKEEIENLQKYHDTISRPSHIFRLCNDLASASAEIA
RGETANSVSCYMRTKGISEELATESVMNLIDETWKKMNKEKLGGSLFAKPFVETAINLARQSHC
TYHNGDAHTSPDELTRKRVLSVITEPILPFER
```

Figure 26A

Nucleotide sequence of pDu39 (SEQ ID NO:123)

```
tggcgaatgggacgcgccctgtagcggcgcattaagcgcggcgggtgtggtggttacgcgcagc
gtgaccgctacacttgccagcgccctagcgcccgctcctttcgctttcttcccttcctttctcg
ccacgttcgccggctttccccgtcaagctctaaatcggggctccctttagggttccgatttag
tgctttacggcacctcgaccccaaaaaacttgattagggtgatggttcacgtagtgggccatcg
ccctgatagacggttttttcgcccttgacgttggagtccacgttctttaatagtggactcttgt
tccaaactggaacaacactcaaccctatctcggtctattcttttgatttataagggattttgcc
gatttcggcctattggttaaaaaatgagctgatttaacaaaaatttaacgcgaattttaacaaa
atattaacgtttacaatttcaggtggcacttttcggggaaatgtgcgcggaaccccctatttgtt
tattttctaaatacattcaaatatgtatccgctcatgaattaattcttagaaaaactcatcga
gcatcaaatgaaactgcaatttattcatatcaggattatcaataccatattttgaaaaagccg
tttctgtaatgaaggagaaaactcaccgaggcagttccataggatggcaagatcctggtatcgg
tctgcgattccgactcgtccaacatcaatacaacctattaatttcccctcgtcaaaaataaggt
tatcaagtgagaaatcaccatgagtgacgactgaatccggtgagaatggcaaaagtttatgcat
ttctttccagacttgttcaacaggccagccattacgctcgtcatcaaaatcactcgcatcaacc
aaaccgttattcattcgtgattgcgcctgagcgagacgaaatacgcgatcgctgttaaaggac
aattacaaacaggaatcgaatgcaaccggcgcaggaacactgccagcgcatcaacaatattttc
acctgaatcaggatattcttctaatacctggaatgctgttttcccggggatcgcagtggtgagt
aaccatgcatcatcaggagtacggataaaatgcttgatggtcggaagaggcataaattccgtca
gccagtttagtctgaccatctcatctgtaacatcattggcaacgctacctttgccatgtttcag
aaacaactctggcgcatcgggcttcccatacaatcgatagattgtcgcacctgattgcccgaca
ttatcgcgagcccatttatacccatataaatcagcatccatgttggaatttaatcgcggcctag
agcaagacgtttcccgttgaatatggctcataacacccttgtattactgtttatgtaagcaga
cagttttattgttcatgaccaaaatcccttaacgtgagttttcgttccactgagcgtcagaccc
cgtagaaaagatcaaaggatcttcttgagatcctttttttctgcgcgtaatctgctgcttgcaa
acaaaaaaaccaccgctaccagcggtggtttgtttgccggatcaagagctaccaactctttttc
cgaaggtaactggcttcagcagagcgcagataccaaatactgtccttctagtgtagccgtagtt
aggccaccacttcaagaactctgtagcaccgcctacatacctcgctctgctaatcctgttacca
gtggctgctgccagtggcgataagtcgtgtcttaccgggttggactcaagacgatagttaccgg
ataaggcgcagcggtcgggctgaacggggggttcgtgcacacagcccagcttggagcgaacgac
ctacaccgaactgagatacctacagcgtgagctatgagaaagcgccacgcttcccgaagggaga
aaggcggacaggtatccggtaagcggcagggtcggaacaggagagcgcacgagggagcttccag
ggggaaacgcctggtatctttatagtcctgtcgggtttcgccacctctgacttgagcgtcgatt
tttgtgatgctcgtcaggggggcggagcctatggaaaaacgccagcaacgcggcctttttacgg
ttcctggccttttgctggccttttgctcacatgttctttcctgcgttatcccctgattctgtgg
ataaccgtattaccgcctttgagtgagctgataccgctcgccgcagccgaacgaccgagcgcag
cgagtcagtgagcgaggaagcggaagagcgcctgatgcggtattttctccttacgcatctgtgc
ggtatttcacaccgcatatatggtgcactctcagtacaatctgctctgatgccgcatagttaag
ccagtatacactccgctatcgctacgtgactgggtcatggctgcgccccgacacccgccaacac
ccgctgacgcgccctgacgggcttgtctgctcccggcatccgcttacagacaagctgtgaccgt
ctccgggagctgcatgtgtcagaggttttcaccgtcatcaccgaaacgcgcgaggcagctgcgg
taaagctcatcagcgtggtcgtgaagcgattcacagatgtctgcctgttcatccgcgtccagct
cgttgagtttctccagaagcgttaatgtctggcttctgataaagcgggccatgttaagggcggt
ttttcctgtttggtcactgatgcctccgtgtaagggggatttctgttcatgggggtaatgata
```

Figure 26B

Nucleotide sequence of pDu39

```
ccgatgaaacgagagaggatgctcacgatacgggttactgatgatgaacatgcccggttactgg
aacgttgtgagggtaaacaactggcggtatggatgcggcgggaccagagaaaaatcactcaggg
tcaatgccagcgcttcgttaatacagatgtaggtgttccacagggtagccagcagcatcctgcg
atgcagatccggaacataatggtgcagggcgctgacttccgcgtttccagactttacgaaacac
ggaaaccgaagaccattcatgttgttgctcaggtcgcagacgttttgcagcagcagtcgcttca
cgttcgctcgcgtatcggtgattcattctgctaaccagtaaggcaaccccgccagcctagccgg
gtcctcaacgacaggagcacgatcatgcgcacccgtggggccgccatgccggcgataatggcct
gcttctcgccgaaacgtttggtggcgggaccagtgacgaaggcttgagcgagggcgtgcaagat
tccgaataccgcaagcgacaggccgatcatcgtcgcgctccagcgaaagcggtcctcgccgaaa
atgacccagagcgctgccggcacctgtcctacgagttgcatgataaagaagacagtcataagtg
cggcgacgatagtcatgccccgcgcccaccggaaggagctgactgggttgaaggctctcaaggg
catcggtcgagatcccggtgcctaatgagtgagctaacttacattaattgcgttgcgctcactg
cccgctttccagtcgggaaacctgtcgtgccagctgcattaatgaatcggccaacgcgcgggga
gaggcggtttgcgtattgggcgccagggtggttttcttttcaccagtgagacgggcaacagct
gattgcccttcaccgcctggccctgagagagttgcagcaagcggtccacgctggtttgccccag
caggcgaaaatcctgtttgatggtggttaacggcgggatataacatgagctgtcttcggtatcg
tcgtatcccactaccgagatatccgcaccaacgcgcagcccggactcggtaatggcgcgcattg
cgcccagcgccatctgatcgttggcaaccagcatcgcagtgggaacgatgccctcattcagcat
ttgcatggtttgttgaaaaccggacatggcactccagtcgccttcccgttccgctatcggctga
atttgattgcgagtgagatatttatgccagccagccagacgcagacgcgccgagacagaactta
atgggcccgctaacagcgcgatttgctggtgacccaatgcgaccagatgctccacgcccagtcg
cgtaccgtcttcatgggagaaaataatactgttgatgggtgtctggtcagagacatcaagaaat
aacgccggaacattagtgcaggcagcttccacagcaatggcatcctggtcatccagcggatagt
taatgatcagcccactgacgcgttgcgcgagaagattgtgcaccgccgctttacaggcttcgac
gccgcttcgttctaccatcgacaccaccacgctggcacccagttgatcggcgcgagatttaatc
gccgcgacaatttgcgacggcgcgtgcagggccagactggaggtggcaacgccaatcagcaacg
actgtttgcccgccagttgttgtgccacgcggttgggaatgtaattcagctccgccatcgccgc
ttccacttttttcccgcgttttcgcagaaacgtggctggcctggttcaccacgcgggaaacggtc
tgataagagacaccggcatactctgcgacatcgtataacgttactggtttcacattcaccaccc
tgaattgactctcttccgggcgctatcatgccataccgcgaaaggttttgcgccattcgatggt
gtccgggatctcgacgctctcccttatgcgactcctgcattaggaagcagcccagtagtaggtt
gaggccgttgagcaccgccgccgcaaggaatggtgcatgcaaggagatggcgcccaacagtccc
ccggccacggggcctgccaccatacccacgccgaaacaagcgctcatgagcccgaagtggcgag
cccgatcttccccatcggtgatgtcggcgatataggcgccagcaaccgcacctgtggcgccggt
gatgccggccacgatgcgtccggcgtagaggatcgagatctcgatcccgcgaaattaatacgac
tcactatagggaattgtgagcggataacaattcccctctagaaataattttgtttaactttaa
gaaggagatatacatatggaagctcgtcgttctgcgaactacgaacctaacagctgggactatg
attacctgctgtcctccgacacggacgagtccatcgaagtatacaaagacaaagcgaaaaagct
ggaagccgaagttcgtcgcgagattaataacgaaaaagcagaatttctgaccctgctggaactg
attgacaacgtccagcgcctgggcctgggttaccgtttcgagtctgatatccgtggtgcgctgg
atcgcttcgtttcctccggcggcttcgatgcggtaaccaagacttccctgcacggtacggcact
gtctttccgtctgctgcgtcaacacggttttgaggtttctcaggaagcgttcagcggcttcaaa
gaccaaaacggcaacttcctggagaacctgaaggaagatatcaaagctatcctgagcctgtacg
```

Figure 26C

Nucleotide sequence of pDu39

```
aggccagcttcctggctctggaaggcgaaaacatcctggacgaggcgaaggttttcgcaatctc
tcatctgaaagaactgtctgaagaaaagatcggtaaagagctggcagaacaggtgaaccatgca
ctggaactgccactgcatcgccgtactcagcgtctggaagcagtatggtctatcgaggcctacc
gtaaaaaggaggacgcgaatcaggttctgctggagctggcaattctggattacaacatgatcca
gtctgtataccagcgtgatctgcgtgaaacgtcccgttggtggcgtcgtgtgggtctggcgacc
aaactgcactttgctcgtgaccgcctgattgagagcttctactgggccgtgggtgtagcattcg
aaccgcaatactccgactgccgtaactccgtcgcaaaaatgttttctttcgtaaccattatcga
cgatatctacgatgtatacggcaccctggacgaactggagctgtttactgatgcagttgagcgt
tgggacgtaaacgccatcaacgacctgccggattacatgaaactgtgctttctggctctgtata
acactattaacgaaatcgcctacgacaacctgaaagataaaggtgagaacatcctgccgtatct
gaccaaagcctgggctgacctgtgcaacgcttttcctgcaagaagccaagtggctgtacaacaaa
tctactccgacctttgacgactacttcggcaacgcatggaaatcctcttctggcccgctgcaac
tggtgttcgcttacttcgctgtcgtgcagaacattaaaaaggaagagatcgaaaacctgcaaaa
ataccatgacaccatctctcgtccttcccatatcttccgtctgtgcaatgacctggctagcgcg
tctgcggaaattgcgcgtggtgaaaccgcaaatagcgtttcttgttacatgcgcactaaaggta
tctccgaagaactggctaccgaaagcgtgatgaatctgatcgatgaaacctggaaaaagatgaa
caaggaaaaactgggtggtagcctgttcgcgaaaccgttcgtggaaaccgcgatcaacctggca
cgtcaatctcactgcacttatcataacggcgacgcgcatacctctccggatgagctgacccgca
aacgcgttctgtctgtaatcactgaaccgattctgccgtttgaacgctaaggatccgaattcga
gctccgtcgacaagcttgcggccgcactcgagcaccaccaccaccaccactgagatccggctgc
taacaaagcccgaaaggaagctgagttggctgctgccaccgctgagcaataactagcataaccc
cttggggcctctaaacgggtcttgaggggttttttgctgaaaggaggaactatatccggat
```

Figure 27

Amino acid sequence of truncated "MSV" variant of *P. alba* IspS (SEQ ID NO:124)

```
MSVSTENVSFTETETEARRSANYEPNSWDYDYLLSSDTDESIEVYKDKAKKLEAEVRREINNEK
AEFLTLLELIDNVQRLGLGYRFESDIRGALDRFVSSGGFDAVTKTSLHGTALSFRLLRQHGFEV
SQEAFSGFKDQNGNFLENLKEDIKAILSLYEASFLALEGENILDEAKVFAISHLKELSEEKIGK
ELAEQVNHALELPLHRRTQRLEAVWSIEAYRKKEDANQVLLELAILDYNMIQSVYQRDLRETSR
WWRRVGLATKLHFARDRLIESFYWAVGVAFEPQYSDCRNSVAKMFSFVTIIDDIYDVYGTLDEL
ELFTDAVERWDVNAINDLPDYMKLCFLALYNTINEIAYDNLKDKGENILPYLTKAWADLCNAFL
QEAKWLYNKSTPTFDDYFGNAWKSSSGPLQLVFAYFAVVQNIKKEEIENLQKYHDTISRPSHIF
RLCNDLASASAEIARGETANSVSCYMRTKGISEELATESVMNLIDETWKKMNKEKLGGSLFAKP
FVETAINLARQSHCTYHNGDAHTSPDELTRKRVLSVITEPILPFER
```

Figure 28A

Nucleotide sequence of pDu41 (pET24a-P.alba (MSV) Untagged) (SEQ ID NO:125)

```
tggcgaatgggacgcgccctgtagcggcgcattaagcgcggcgggtgtggtggttacgcgcagc
gtgaccgctacacttgccagcgccctagcgcccgctcctttcgctttcttcccttcctttctcg
ccacgttcgccggctttccccgtcaagctctaaatcgggggctcccctttagggttccgatttag
tgctttacggcacctcgaccccaaaaaacttgattagggtgatggttcacgtagtgggccatcg
ccctgatagacggttttttcgccctttgacgttggagtccacgttctttaatagtggactcttgt
tccaaactggaacaacactcaaccctatctcggtctattcttttgatttataagggattttgcc
gatttcggcctattggttaaaaaatgagctgatttaacaaaatttaacgcgaattttaacaaa
atattaacgtttacaatttcaggtggcacttttcggggaaatgtgcgcggaaccccatttgtt
tatttttctaaatacattcaaatatgtatccgctcatgaattaattcttagaaaaactcatcga
gcatcaaatgaaactgcaatttattcatatcaggattatcaataccatattttgaaaaagccg
tttctgtaatgaaggagaaaactcaccgaggcagttccataggatggcaagatcctggtatcgg
tctgcgattccgactcgtccaacatcaatacaacctattaatttccctcgtcaaaaataaggt
tatcaagtgagaaatcaccatgagtgacgactgaatccggtgagaatggcaaaagtttatgcat
ttctttccagacttgttcaacaggccagccattacgctcgtcatcaaaatcactcgcatcaacc
aaaccgttattcattcgtgattgcgcctgagcgagacgaaatacgcgatcgctgttaaaggac
aattacaaacaggaatcgaatgcaaccggcgcaggaacactgccagcgcatcaacaatattttc
acctgaatcaggatattcttctaatacctggaatgctgttttcccggggatcgcagtggtgagt
aaccatgcatcatcaggagtacggataaaatgcttgatggtcggaagaggcataaattccgtca
gccagtttagtctgaccatctcatctgtaacatcattggcaacgctacctttgccatgtttcag
aaacaactctggcgcatcgggcttcccatacaatcgatagattgtcgcacctgattgcccgaca
ttatcgcgagcccatttatacccatataaatcagcatccatgttggaatttaatcgcggcctag
agcaagacgtttcccgttgaatatggctcataacacccttgtattactgtttatgtaagcaga
cagttttattgttcatgaccaaaatcccttaacgtgagttttcgttccactgagcgtcagaccc
cgtagaaaagatcaaaggatcttcttgagatccttttttttctgcgcgtaatctgctgcttgcaa
acaaaaaaaccaccgctaccagcggtggtttgtttgccggatcaagagctaccaactctttttc
cgaaggtaactggcttcagcagagcgcagataccaaatactgtccttctagtgtagccgtagtt
aggccaccacttcaagaactctgtagcaccgcctacatacctcgctctgctaatcctgttacca
gtggctgctgccagtggcgataagtcgtgtcttaccgggttggactcaagacgatagttaccgg
ataaggcgcagcggtcgggctgaacggggggttcgtgcacacagcccagcttggagcgaacgac
ctacaccgaactgagatacctacagcgtgagctatgagaaagcgccacgcttcccgaagggaga
aaggcggacaggtatccggtaagcggcaggtcggaacaggagagcgcacgagggagcttccag
ggggaaacgcctggtatctttatagtcctgtcgggtttcgccacctctgacttgagcgtcgatt
tttgtgatgctcgtcaggggggcggagcctatggaaaaacgccagcaacgcggcctttttacgg
ttcctggccttttgctggccttttgctcacatgttctttcctgcgttatcccctgattctgtgg
ataaccgtattaccgcctttgagtgagctgataccgctcgccgcagccgaacgaccgagcgcag
cgagtcagtgagcgaggaagcggaagagcgcctgatgcggtattttctccttacgcatctgtgc
ggtatttcacaccgcatatatggtgcactctcagtacaatctgctctgatgccgcatagttaag
ccagtatacactccgctatcgctacgtgactgggtcatggctgcgccccgacacccgccaacac
ccgctgacgcgccctgacgggcttgtctgctcccggcatccgcttacagacaagctgtgaccgt
ctccgggagctgcatgtgtcagaggttttcaccgtcatcaccgaaacgcgcgaggcagctgcgg
taaagctcatcagcgtggtcgtgaagcgattcacagatgtctgcctgttcatccgcgtccagct
cgttgagtttctccagaagcgttaatgtctggcttctgataaagcgggccatgttaagggcggt
```

Figure 28B

Nucleotide sequence of pDu41 (pET24a-P.alba (MSV) Untagged)

ttttcctgtttggtcactgatgcctccgtgtaaggggatttctgttcatgggggtaatgata
ccgatgaaacgagagaggatgctcacgatacgggttactgatgatgaacatgcccggttactgg
aacgttgtgagggtaaacaactggcggtatggatgcggcgggaccagagaaaaatcactcaggg
tcaatgccagcgcttcgttaatacagatgtaggtgttccacagggtagccagcagcatcctgcg
atgcagatccggaacataatggtgcagggcgctgacttccgcgtttccagactttacgaaacac
ggaaaccgaagaccattcatgttgttgctcaggtcgcagacgttttgcagcagcagtcgcttca
cgttcgctcgcgtatcggtgattcattctgctaaccagtaaggcaaccccgccagcctagccgg
gtcctcaacgacaggagcacgatcatgcgcacccgtggggccgccatgccggcgataatggcct
gcttctcgccgaaacgtttggtggcgggaccagtgacgaaggcttgagcgagggcgtgcaagat
tccgaataccgcaagcgacaggccgatcatcgtcgcgctccagcgaaagcggtcctcgccgaaa
atgacccagagcgctgccggcacctgtcctacgagttgcatgataaagaagacagtcataagtg
cggcgacgatagtcatgccccgcgccaccggaaggagctgactggttgaaggctctcaaggg
catcggtcgagatcccggtgcctaatgagtgagctaacttacattaattgcgttgcgctcactg
cccgctttccagtcgggaaacctgtcgtgccagctgcattaatgaatcggccaacgcgcgggga
gaggcggtttgcgtattgggcgccagggtggttttcttttcaccagtgagacgggcaacagct
gattgcccttcaccgcctggccctgagagagttgcagcaagcggtccacgctggtttgccccag
caggcgaaaatcctgtttgatggtggttaacggcgggatataacatgagctgtcttcggtatcg
tcgtatcccactaccgagatatccgcaccaacgcgcagcccggactcggtaatggcgcgcattg
cgcccagcgccatctgatcgttggcaaccagcatcgcagtgggaacgatgccctcattcagcat
ttgcatggttttgttgaaaaccggacatggcactccagtcgccttcccgttccgctatcggctga
atttgattgcgagtgagatatttatgccagccagccagacgcagacgcgccgagacagaactta
atgggcccgctaacagcgcgatttgctggtgacccaatgcgaccagatgctccacgcccagtcg
cgtaccgtcttcatgggagaaaataatactgttgatgggtgtctggtcagagacatcaagaaat
aacgccggaacattagtgcaggcagcttccacagcaatggcatcctggtcatccagcggatagt
taatgatcagcccactgacgcgttgcgcgagaagattgtgcaccgccgctttacaggcttcgac
gccgcttcgttctaccatcgacaccaccacgctggcacccagttgatcggcgcgagatttaatc
gccgcgacaatttgcgacggcgcgtgcagggccagactggaggtggcaacgccaatcagcaacg
actgtttgcccgccagttgttgtgccacgcggttgggaatgtaattcagctccgccatcgccgc
ttccactttttcccgcgttttcgcagaaacgtggctggcctggttcaccacgcgggaaacggtc
tgataagagacaccggcatactctgcgacatcgtataacgttactggtttcacattcaccaccc
tgaattgactctcttccgggcgctatcatgccataccgcgaaaggttttgcgccattcgatggt
gtccgggatctcgacgctctcccttatgcgactcctgcattaggaagcagcccagtagtaggtt
gaggccgttgagcaccgccgccgcaaggaatggtgcatgcaaggagatggcgcccaacagtccc
ccggccacggggcctgccaccatacccacgccgaaacaagcgctcatgagcccgaagtggcgag
cccgatcttccccatcggtgatgtcggcgatataggcgccagcaaccgcacctgtggcgccggt
gatgccggccacgatgcgtccggcgtagaggatcgagatctcgatcccgcgaaattaatacgac
tcactatagggaattgtgagcggataacaattcccctctagaaataattttgtttaactttaa
gaaggagatatacatatgagcgtgtccaccgaaaatgtgtctttcaccgaaactgaaaccgaag
ctcgtcgttctgcgaactacgaacctaacagctgggactatgattacctgctgtcctccgacac
ggacgagtccatcgaagtatacaaagacaaagcgaaaaagctggaagccgaagttcgtcgcgag
attaataacgaaaagcagaatttctgaccctgctggaactgattgacaacgtccagcgcctgg
gcctgggttaccgtttcgagtctgatatccgtggtgcgctggatcgcttcgtttcctccggcgg
cttcgatgcggtaaccaagacttccctgcacggtacggcactgtctttccgtctgctgcgtcaa

Figure 28C

Nucleotide sequence of pDu41 (pET24a-P.alba (MSV) Untagged)

```
cacggttttgaggtttctcaggaagcgttcagcggcttcaaagaccaaaacggcaacttcctgg
agaacctgaaggaagatatcaaagctatcctgagcctgtacgaggccagcttcctggctctgga
aggcgaaaacatcctggacgaggcgaaggttttcgcaatctctcatctgaaagaactgtctgaa
gaaaagatcggtaaagagctggcagaacaggtgaaccatgcactggaactgccactgcatcgcc
gtactcagcgtctggaagcagtatggtctatcgaggcctaccgtaaaaaggaggacgcgaatca
ggttctgctggagctggcaattctggattacaacatgatccagtctgtataccagcgtgatctg
cgtgaaacgtcccgttggtggcgtcgtgtgggtctggcgaccaaactgcactttgctcgtgacc
gcctgattgagagcttctactgggccgtgggtgtagcattcgaaccgcaatactccgactgccg
taactccgtcgcaaaaatgttttctttcgtaaccattatcgacgatatctacgatgtatacggc
accctggacgaactggagctgtttactgatgcagttgagcgttgggacgtaaacgccatcaacg
acctgccggattacatgaaactgtgctttctggctctgtataacactattaacgaaatcgccta
cgacaacctgaaagataaaggtgagaacatcctgccgtatctgaccaaagcctgggctgacctg
tgcaacgctttcctgcaagaagccaagtggctgtacaacaaatctactccgacctttgacgact
acttcggcaacgcatggaaatcctcttctggcccgctgcaactggtgttcgcttacttcgctgt
cgtgcagaacattaaaaaggaagagatcgaaaacctgcaaaaataccatgacaccatctctcgt
ccttcccatatcttccgtctgtgcaatgacctggctagcgcgtctgcggaaattgcgcgtggtg
aaaccgcaaatagcgtttcttgttacatgcgcactaaaggtatctccgaagaactggctaccga
aagcgtgatgaatctgatcgatgaaacctggaaaaagatgaacaaggaaaaactgggtggtagc
ctgttcgcgaaaccgttcgtggaaaccgcgatcaacctggcacgtcaatctcactgcacttatc
ataacggcgacgcgcatacctctccggatgagctgacccgcaaacgcgttctgtctgtaatcac
tgaaccgattctgccgtttgaacgctaaggatccgaattcgagctccgtcgacaagcttgcggc
cgcactcgagcaccaccaccaccaccactgagatccggctgctaacaaagcccgaaaggaagct
gagttggctgctgccaccgctgagcaataactagcataacccctggggcctctaaacgggtct
tgaggggttttttgctgaaaggaggaactatatccggat
```

Figure 29

Amino acid sequence of truncated "MVS" Variant of *P. alba* IspS (SEQ ID NO:126)

```
MVSTENVSFTETETEARRSANYEPNSWDYDYLLSSDTDESIEVYKDKAKKLEAEVRREINNEKA
EFLTLLELIDNVQRLGLGYRFESDIRGALDRFVSSGGFDAVTKTSLHGTALSFRLLRQHGFEVS
QEAFSGFKDQNGNFLENLKEDIKAILSLYEASFLALEGENILDEAKVFAISHLKELSEEKIGKE
LAEQVNHALELPLHRRTQRLEAVWSIEAYRKKEDANQVLLELAILDYNMIQSVYQRDLRETSRW
WRRVGLATKLHFARDRLIESFYWAVGVAFEPQYSDCRNSVAKMFSFVTIIDDIYDVYGTLDELE
LFTDAVERWDVNAINDLPDYMKLCFLALYNTINEIAYDNLKDKGENILPYLTKAWADLCNAFLQ
EAKWLYNKSTPTFDDYFGNAWKSSSGPLQLVFAYFAVVQNIKKEEIENLQKYHDTISRPSHIFR
LCNDLASASAEIARGETANSVSCYMRTKGISEELATESVMNLIDETWKKMNKEKLGGSLFAKPF
VETAINLARQSHCTYHNGDAHTSPDELTRKRVLSVITEPILPFER
```

Figure 30A

Nucleotide sequence of pDu43 (pET24a-P.alba (MVS) Untagged) (SEQ ID NO:127)

```
tggcgaatgggacgcgccctgtagcggcgcattaagcgcggcgggtgtggtggttacgcgcagc
gtgaccgctacacttgccagcgccctagcgcccgctcctttcgctttcttcccttcctttctcg
ccacgttcgccggctttccccgtcaagctctaaatcgggggctcccttttagggttccgatttag
tgctttacggcacctcgaccccaaaaaacttgattagggtgatggttcacgtagtgggccatcg
ccctgatagacggtttttcgccctttgacgttggagtccacgttctttaatagtggactcttgt
tccaaactggaacaacactcaaccctatctcggtctattcttttgatttataagggattttgcc
gatttcggcctattggttaaaaaatgagctgatttaacaaaaatttaacgcgaattttaacaaa
atattaacgtttacaatttcaggtggcacttttcggggaaatgtgcgcggaacccctatttgtt
tatttttctaaatacattcaaatatgtatccgctcatgaattaattcttagaaaaactcatcga
gcatcaaatgaaactgcaatttattcatatcaggattatcaataccatattttttgaaaaagccg
tttctgtaatgaaggagaaaactcaccgaggcagttccataggatggcaagatcctggtatcgg
tctgcgattccgactcgtccaacatcaatacaacctattaatttcccctcgtcaaaaataaggt
tatcaagtgagaaatcaccatgagtgacgactgaatccggtgagaatggcaaaagtttatgcat
ttctttccagacttgttcaacaggccagccattacgctcgtcatcaaaatcactcgcatcaacc
aaaccgttattcattcgtgattgcgcctgagcgagacgaaatacgcgatcgctgttaaaaggac
aattacaaacaggaatcgaatgcaaccggcgcaggaacactgccagcgcatcaacaatatttc
acctgaatcaggatattcttctaatacctggaatgctgttttcccggggatcgcagtggtgagt
aaccatgcatcatcaggagtacggataaaatgcttgatggtcggaagaggcataaattccgtca
gccagtttagtctgaccatctcatctgtaacatcattggcaacgctacctttgccatgtttcag
aaacaactctggcgcatcgggcttcccatacaatcgatagattgtcgcacctgattgcccgaca
ttatcgcgagcccatttatacccatataaatcagcatccatgttggaatttaatcgcggcctag
agcaagacgtttccgttgaatatggctcataacacccccttgtattactgtttatgtaagcaga
cagttttattgttcatgaccaaaatcccttaacgtgagttttcgttccactgagcgtcagaccc
cgtagaaaagatcaaaggatcttcttgagatcctttttttctgcgcgtaatctgctgcttgcaa
acaaaaaaaccaccgctaccagcggtggtttgtttgccggatcaagagctaccaactctttttc
cgaaggtaactggcttcagcagagcgcagataccaaatactgtccttctagtgtagccgtagtt
aggccaccacttcaagaactctgtagcaccgcctacatacctcgctctgctaatcctgttacca
gtggctgctgccagtggcgataagtcgtgtcttaccgggttggactcaagacgatagttaccgg
ataaggcgcagcggtcgggctgaacggggggttcgtgcacacagcccagcttggagcgaacgac
ctacaccgaactgagatacctacagcgtgagctatgagaaagcgccacgcttcccgaagggaga
aaggcggacaggtatccggtaagcggcagggtcggaacaggagagcgcacgagggagcttccag
ggggaaacgcctggtatctttatagtcctgtcgggtttcgccacctctgacttgagcgtcgatt
tttgtgatgctcgtcaggggggcggagcctatggaaaaacgccagcaacgcggcctttttacgg
ttcctggccttttgctggccttttgctcacatgttctttcctgcgttatccctgattctgtgg
ataaccgtattaccgcctttgagtgagctgataccgctcgccgcagccgaacgaccgagcgcag
cgagtcagtgagcgaggaagcggaagagcgcctgatgcggtattttctccttacgcatctgtgc
ggtatttcacaccgcatatatggtgcactctcagtacaatctgctctgatgccgcatagttaag
ccagtatacactccgctatcgctacgtgactgggtcatggctgcgccccgacacccgccaacac
ccgctgacgcgccctgacgggcttgtctgctcccggcatccgcttacagacaagctgtgaccgt
ctccgggagctgcatgtgtcagaggttttcaccgtcatcaccgaaacgcgcgaggcagctgcgg
taaagctcatcagcgtggtcgtgaagcgattcacagatgtctgcctgttcatccgcgtccagct
cgttgagtttctccagaagcgttaatgtctggcttctgataaagcgggccatgttaagggcggt
ttttcctgtttggtcactgatgcctccgtgtaaggggggatttctgttcatgggggtaatgata
```

Figure 30B

Nucleotide sequence of pDu43 (pET24a-P.alba (MVS) Untagged)

ccgatgaaacgagagaggatgctcacgatacgggttactgatgatgaacatgcccggttactgg
aacgttgtgagggtaaacaactggcggtatggatgcggcgggaccagagaaaaatcactcaggg
tcaatgccagcgcttcgttaatacagatgtaggtgttccacagggtagccagcagcatcctgcg
atgcagatccggaacataatggtgcagggcgctgacttccgcgtttccagactttacgaaacac
ggaaaccgaagaccattcatgttgttgctcaggtcgcagacgttttgcagcagcagtcgcttca
cgttcgctcgcgtatcggtgattcattctgctaaccagtaaggcaaccccgccagcctagccgg
gtcctcaacgacaggagcacgatcatgcgcaccgtggggccgccatgccggcgataatggcct
gcttctcgccgaaacgtttggtggcgggaccagtgacgaaggcttgagcgagggcgtgcaagat
tccgaataccgcaagcgacaggccgatcatcgtcgcgctccagcgaaagcggtcctcgccgaaa
atgacccagagcgctgccggcacctgtcctacgagttgcatgataaagaagacagtcataagtg
cggcgacgatagtcatgccccgcgccaccggaaggagctgactgggttgaaggctctcaaggg
catcggtcgagatcccggtgcctaatgagtgagctaacttacattaattgcgttgcgctcactg
cccgctttccagtcgggaaacctgtcgtgccagctgcattaatgaatcggccaacgcgcggga
gaggcggtttgcgtattgggcgccagggtggttttttcttttcaccagtgagacgggcaacagct
gattgcccttcaccgcctggccctgagagagttgcagcaagcggtccacgctggtttgccccag
caggcgaaaatcctgtttgatggtggttaacggcgggatataacatgagctgtcttcggtatcg
tcgtatcccactaccgagatatccgcaccaacgcgcagcccggactcggtaatggcgcgcattg
cgcccagcgccatctgatcgttggcaaccagcatcgcagtgggaacgatgccctcattcagcat
ttgcatggtttgttgaaaaccggacatggcactccagtcgccttcccgttccgctatcggctga
atttgattgcgagtgagatatttatgccagccagccagacgcagacgcgccgagacagaactta
atgggcccgctaacagcgcgatttgctggtgacccaatgcgaccagatgctccacgcccagtcg
cgtaccgtcttcatgggagaaaataatactgttgatgggtgtctggtcagagacatcaagaaat
aacgccggaacattagtgcaggcagcttccacagcaatggcatcctggtcatccagcggatagt
taatgatcagcccactgacgcgttgcgcgagaagattgtgcaccgccgctttacaggcttcgac
gccgcttcgttctaccatcgacaccaccacgctggcacccagttgatcggcgcgagatttaatc
gccgcgacaatttgcgacggcgcgtgcagggccagactggaggtggcaacgccaatcagcaacg
actgtttgcccgccagttgttgtgccacgcggtgggaatgtaattcagctccgccatcgccgc
ttccactttttcccgcgttttcgcagaaacgtggctggcctggttcaccacgcgggaaacggtc
tgataagagacaccggcatactctgcgacatcgtataacgttactggtttcacattcaccaccc
tgaattgactctcttccgggcgctatcatgccataccgcgaaaggttttgcgccattcgatggt
gtccgggatctcgacgctctcccttatgcgactcctgcattaggaagcagcccagtagtaggtt
gaggccgttgagcaccgccgccgcaaggaatggtgcatgcaaggagatggcgcccaacagtccc
ccggccacggggcctgccaccatacccacgccgaaacaagcgctcatgagcccgaagtggcgag
cccgatcttccccatcggtgatgtcggcgatataggcgccagcaaccgcacctgtggcgccggt
gatgccggccacgatgcgtccggcgtagaggatcgagatctcgatcccgcgaaattaatacgac
tcactatagggaattgtgagcggataacaattcccctctagaaataattttgtttaactttaa
gaaggagatatacatatggtgtccaccgaaatgtgtctttcaccgaaactgaaaccgaagctc
gtcgttctgcgaactacgaacctaacagctgggactatgattacctgctgtcctccgacacgga
cgagtccatcgaagtatacaaagacaaagcgaaaaagctggaagccgaagttcgtcgcgagatt
aataacgaaaaagcagaatttctgaccctgctggaactgattgacaacgtccagcgcctgggcc
tgggttaccgtttcgagtctgatatccgtggtgcgctggatcgcttcgtttcctccggcggctt
cgatgcggtaaccaagacttccctgcacggtacggcactgtctttccgtctgctgcgtcaacac
ggttttgaggtttctcaggaagcgttcagcggcttcaaagaccaaaacggcaacttcctggaga

Figure 30C

Nucleotide sequence of pDu43 (pET24a-P.alba (MVS) Untagged)

```
acctgaaggaagatatcaaagctatcctgagcctgtacgaggccagcttcctggctctggaagg
cgaaaacatcctggacgaggcgaaggttttcgcaatctctcatctgaaagaactgtctgaagaa
aagatcggtaaagagctggcagaacaggtgaaccatgcactggaactgccactgcatcgccgta
ctcagcgtctggaagcagtatggtctatcgaggcctaccgtaaaaaggaggacgcgaatcaggt
tctgctggagctggcaattctggattacaacatgatccagtctgtataccagcgtgatctgcgt
gaaacgtcccgttggtggcgtcgtgtgggtctggcgaccaaactgcactttgctcgtgaccgcc
tgattgagagcttctactgggccgtgggtgtagcattcgaaccgcaatactccgactgccgtaa
ctccgtcgcaaaaatgttttctttcgtaaccattatcgacgatatctacgatgtatacggcacc
ctggacgaactggagctgtttactgatgcagttgagcgttgggacgtaaacgccatcaacgacc
tgccggattacatgaaactgtgctttctggctctgtaacactattaacgaaatcgcctacga
caacctgaaagataaaggtgagaacatcctgccgtatctgaccaaagcctgggctgacctgtgc
aacgctttcctgcaagaagccaagtggctgtacaacaaatctactccgacctttgacgactact
tcggcaacgcatggaaatcctcttctggcccgctgcaactggtgttcgcttacttcgctgtcgt
gcagaacattaaaaaggaagagatcgaaaacctgcaaaaataccatgacaccatctctcgtcct
tcccatatcttccgtctgtgcaatgacctggctagcgcgtctgcggaaattgcgcgtggtgaaa
ccgcaaatagcgtttcttgttacatgcgcactaaaggtatctccgaagaactggctaccgaaag
cgtgatgaatctgatcgatgaaacctggaaaaagatgaacaaggaaaaactgggtggtagcctg
ttcgcgaaaccgttcgtggaaaccgcgatcaacctggcacgtcaatctcactgcacttatcata
acggcgacgcgcataccttccggatgagctgacccgcaaacgcgttctgtctgtaatcactga
accgattctgccgtttgaacgctaaggatccgaattcgagctccgtcgacaagcttgcggccgc
actcgagcaccaccaccaccaccactgagatccggctgctaacaaagcccgaaaggaagctgag
ttggctgctgccaccgctgagcaataactagcataacccttggggcctctaaacgggtcttga
ggggttttttgctgaaaggaggaactatatccggat
```

Figure 31

Amino acid sequence of truncated "MTE" variant of *P. alba* IspS (SEQ ID NO:128)

```
MTENVSFTETETEARRSANYEPNSWDYDYLLSSDTDESIEVYKDKAKKLEAEVRREINNEKAEF
LTLLELIDNVQRLGLGYRFESDIRGALDRFVSSGGFDAVTKTSLHGTALSFRLLRQHGFEVSQE
AFSGFKDQNGNFLENLKEDIKAILSLYEASFLALEGENILDEAKVFAISHLKELSEEKIGKELA
EQVNHALELPLHRRTQRLEAVWSIEAYRKKEDANQVLLELAILDYNMIQSVYQRDLRETSRWWR
RVGLATKLHFARDRLIESFYWAVGVAFEPQYSDCRNSVAKMFSFVTIIDDIYDVYGTLDELELF
TDAVERWDVNAINDLPDYMKLCFLALYNTINEIAYDNLKDKGENILPYLTKAWADLCNAFLQEA
KWLYNKSTPTFDDYFGNAWKSSSGPLQLVFAYFAVVQNIKKEEIENLQKYHDTISRPSHIFRLC
NDLASASAEIARGETANSVSCYMRTKGISEELATESVMNLIDETWKKMNKEKLGGSLFAKPFVE
TAINLARQSHCTYHNGDAHTSPDELTRKRVLSVITEPILPFER
```

Figure 32A

Nucleotide sequence of pDu42 (pET24a-P.alba (MTE) Untagged) (SEQ ID NO:129)

```
tggcgaatgggacgcgccctgtagcggcgcattaagcgcggcgggtgtggtggttacgcgcagc
gtgaccgctacacttgccagcgccctagcgcccgctcctttcgctttcttcccttcctttctcg
ccacgttcgccggctttccccgtcaagctctaaatcgggggctccctttagggttccgatttag
tgctttacggcacctcgaccccaaaaaacttgatttagggtgatggttcacgtagtgggccatcg
ccctgatagacggttttttcgccctttgacgttggagtccacgttctttaatagtggactcttgt
tccaaactggaacaacactcaaccctatctcggtctattcttttgatttataagggatttttgcc
gatttcggcctattggttaaaaaatgagctgatttaacaaaaatttaacgcgaattttaacaaa
atattaacgtttacaatttcaggtggcacttttcggggaaatgtgcgcggaacccctatttgtt
tattttctaaatacattcaaatatgtatccgctcatgaattaattcttagaaaaactcatcga
gcatcaaatgaaactgcaatttattcatatcaggattatcaataccatattttttgaaaaagccg
tttctgtaatgaaggagaaaactcaccgaggcagttccataggatggcaagatcctggtatcgg
tctgcgattccgactcgtccaacatcaatacaacctattaatttcccctcgtcaaaaataaggt
tatcaagtgagaaatcaccatgagtgacgactgaatccggtgagaatggcaaaagtttatgcat
ttctttccagacttgttcaacaggccagccattacgctcgtcatcaaaatcactcgcatcaacc
aaaccgttattcattcgtgattgcgcctgagcgagacgaaatacgcgatcgctgttaaaaggac
aattacaaacaggaatcgaatgcaaccggcgcaggaacactgccagcgcatcaacaatattttc
acctgaatcaggatattcttctaatacctggaatgctgttttcccggggatcgcagtggtgagt
aaccatgcatcatcaggagtacggataaaatgcttgatggtcggaagaggcataaattccgtca
gccagtttagtctgaccatctcatctgtaacatcattggcaacgctacctttgccatgtttcag
aaacaactctggcgcatcgggcttcccatacaatcgatagattgtcgcacctgattgcccgaca
ttatcgcgagcccatttatacccatataaatcagcatccatgttggaatttaatcgcggcctag
agcaagacgtttcccgttgaatatggctcataacaccccttgtattactgtttatgtaagcaga
cagttttattgttcatgaccaaaatcccttaacgtgagttttcgttccactgagcgtcagaccc
cgtagaaaagatcaaaggatcttcttgagatcctttttttctgcgcgtaatctgctgcttgcaa
acaaaaaaaccaccgctaccagcggtggtttgtttgccggatcaagagctaccaactctttttc
cgaaggtaactggcttcagcagagcgcagataccaaatactgtccttctagtgtagccgtagtt
aggccaccacttcaagaactctgtagcaccgcctacatacctcgctctgctaatcctgttacca
gtggctgctgccagtggcgataagtcgtgtcttaccgggttggactcaagacgatagttaccgg
ataaggcgcagcggtcgggctgaacggggggttcgtgcacacagcccagcttggagcgaacgac
ctacaccgaactgagatacctacagcgtgagctatgagaaagcgccacgcttcccgaagggaga
aaggcggacaggtatccggtaagcggcaggtcggaacaggagagcgcacgagggagcttccag
ggggaaacgcctggtatctttatagtcctgtcgggtttcgccacctctgacttgagcgtcgatt
tttgtgatgctcgtcaggggggcggagcctatggaaaaacgccagcaacgcggcctttttacgg
ttcctggccttttgctggccttttgctcacatgttctttcctgcgttatccctgattctgtgg
ataaccgtattaccgcctttgagtgagctgataccgctcgccgcagccgaacgaccgagcgcag
cgagtcagtgagcgaggaagcggaagagcgcctgatgcggtattttctccttacgcatctgtgc
ggtatttcacaccgcatatatggtgcactctcagtacaatctgctctgatgccgcatagttaag
ccagtatacactccgctatcgctacgtgactgggtcatggctgcgccccgacacccgccaacac
ccgctgacgcgccctgacgggcttgtctgctcccggcatccgcttacagacaagctgtgaccgt
ctccgggagctgcatgtgtcagaggttttcaccgtcatcaccgaaacgcgcgaggcagctgcgg
taaagctcatcagcgtggtcgtgaagcgattcacagatgtctgcctgttcatccgcgtccagct
cgttgagtttctccagaagcgttaatgtctggcttctgataaagcgggccatgttaagggcggt
ttttcctgtttggtcactgatgcctccgtgtaaggggggattctgttcatgggggtaatgata
```

Figure 32B

Nucleotide sequence of pDu42 (pET24a-P.alba (MTE) Untagged)

ccgatgaaacgagagaggatgctcacgatacgggttactgatgatgaacatgcccggttactgg
aacgttgtgagggtaaacaactggcggtatggatgcggcgggaccagagaaaaatcactcaggg
tcaatgccagcgcttcgttaatacagatgtaggtgttccacagggtagccagcagcatcctgcg
atgcagatccggaacataatggtgcagggcgctgacttccgcgtttccagactttacgaaacac
ggaaaccgaagaccattcatgttgttgctcaggtcgcagacgttttgcagcagcagtcgcttca
cgttcgctcgcgtatcggtgattcattctgctaaccagtaaggcaaccccgccagcctagccgg
gtcctcaacgacaggagcacgatcatgcgcacccgtggggccgccatgccggcgataatggcct
gcttctcgccgaaacgtttggtggcgggaccagtgacgaaggcttgagcgagggcgtgcaagat
tccgaataccgaagcgacaggccgatcatcgtcgcgctccagcgaaagcggtcctcgccgaaa
atgacccagagcgctgccggcacctgtcctacgagttgcatgataaagaagacagtcataagtg
cggcgacgatagtcatgccccgcgccaccggaaggagctgactgggttgaaggctctcaaggg
catcggtcgagatcccggtgcctaatgagtgagctaacttacattaattgcgttgcgctcactg
cccgctttccagtcgggaaacctgtcgtgccagctgcattaatgaatcggccaacgcgcgggga
gaggcggtttgcgtattgggcgccagggtggttttcttttcaccagtgagacgggcaacagct
gattgcccttcaccgcctggccctgagagagttgcagcaagcggtccacgctggtttgccccag
caggcgaaaatcctgtttgatggtggttaacggcgggatataacatgagctgtcttcggtatcg
tcgtatcccactaccgagatatccgcaccaacgcgcagcccggactcggtaatggcgcgcattg
cgcccagcgccatctgatcgttggcaaccagcatcgcagtgggaacgatgccctcattcagcat
ttgcatggtttgttgaaaaccggacatggcactccagtcgccttcccgttccgctatcggctga
atttgattgcgagtgagatatttatgccagccagccagacgcagacgcgccgagacagaactta
atgggcccgctaacagcgcgatttgctggtgacccaatgcgaccagatgctccacgcccagtcg
cgtaccgtcttcatgggagaaaataatactgttgatgggtgtctggtcagagacatcaagaaat
aacgccggaacattagtgcaggcagcttccacagcaatggcatcctggtcatccagcggatagt
taatgatcagcccactgacgcgttgcgcgagaagattgtgcaccgccgctttacaggcttcgac
gccgcttcgttctaccatcgacaccaccacgctggcacccagttgatcggcgcgagatttaatc
gccgcgacaatttgcgacggcgcgtgcagggccagactggaggtggcaacgccaatcagcaacg
actgtttgcccgccagttgttgtgccacgcggttgggaatgtaattcagctccgccatcgccgc
ttccacttttttcccgcgttttcgcagaaacgtggctggcctggttcaccacgcgggaaacggtc
tgataagagacaccggcatactctgcgacatcgtataacgttactggtttcacattcaccaccc
tgaattgactctcttccgggcgctatcatgccataccgcgaaaggttttgcgccattcgatggt
gtccgggatctcgacgctctcccttatgcgactcctgcattaggaagcagcccagtagtaggtt
gaggccgttgagcaccgccgccgcaaggaatggtgcatgcaaggagatggcgcccaacagtccc
ccggccacggggcctgccaccatacccacgccgaaacaagcgctcatgagcccgaagtggcgag
cccgatcttccccatcggtgatgtcggcgatataggcgccagcaaccgcacctgtggcgccgt
gatgccggccacgatgcgtccggcgtagaggatcgagatctcgatcccgcgaaattaatacgac
tcactatagggaattgtgagcggataacaattcccctctagaaataatttgtttaactttaa
gaaggagatatacatatgaccgaaatgtgtctttcaccgaaactgaaaccgaagctcgtcgtt
ctgcgaactacgaacctaacagctgggactatgattacctgctgtcctccgacacggacgagtc
catcgaagtatacaaagacaaagcgaaaagctggaagccgaagttcgtcgcgagattaataac
gaaaagcagaatttctgaccctgctggaactgattgacaacgtccagcgcctgggcctgggtt
accgtttcgagtctgatatccgtggtgcgctggatcgcttcgtttcctccggcggcttcgatgc
ggtaaccaagacttccctgcacggtacggcactgtctttccgtctgctgcgtcaacacggtttt
gaggtttctcaggaagcgttcagcggcttcaaagaccaaaacggcaacttcctggagaacctga

Figure 32C

Nucleotide sequence of pDu42 (pET24a-P.alba (MTE) Untagged)

aggaagatatcaaagctatcctgagcctgtacgaggccagcttcctggctctggaaggcgaaaa
catcctggacgaggcgaaggttttcgcaatctctcatctgaaagaactgtctgaagaaaagatc
ggtaaagagctggcagaacaggtgaaccatgcactggaactgccactgcatcgccgtactcagc
gtctggaagcagtatggtctatcgaggcctaccgtaaaaaggaggacgcgaatcaggttctgct
ggagctggcaattctggattacaacatgatccagtctgtataccagcgtgatctgcgtgaaacg
tcccgttggtggcgtcgtgtgggtctggcgaccaaactgcactttgctcgtgaccgcctgattg
agagcttctactgggccgtgggtgtagcattcgaaccgcaatactccgactgccgtaactccgt
cgcaaaaatgttttctttcgtaaccattatcgacgatatctacgatgtatacggcaccctggac
gaactggagctgtttactgatgcagttgagcgttgggacgtaaacgccatcaacgacctgccgg
attacatgaaactgtgctttctggctctgtataacactattaacgaaatcgcctacgacaacct
gaaagataaaggtgagaacatcctgccgtatctgaccaaagcctgggctgacctgtgcaacgct
ttcctgcaagaagccaagtggctgtacaacaaatctactccgacctttgacgactacttcggca
acgcatggaaatcctcttctggcccgctgcaactggtgttcgcttacttcgctgtcgtgcagaa
cattaaaaaggaagagatcgaaaacctgcaaaaataccatgacaccatctctcgtccttcccat
atcttccgtctgtgcaatgacctggctagcgcgtctgcggaaattgcgcgtggtgaaaccgcaa
atagcgtttcttgttacatgcgcactaaaggtatctccgaagaactggctaccgaaagcgtgat
gaatctgatcgatgaaacctggaaaaagatgaacaaggaaaaactgggtggtagcctgttcgcg
aaaccgttcgtggaaaccgcgatcaacctggcacgtcaatctcactgcacttatcataacggcg
acgcgcatacctctccggatgagctgacccgcaaacgcgttctgtctgtaatcactgaaccgat
tctgccgtttgaacgctaaggatccgaattcgagctccgtcgacaagcttgcggccgcactcga
gcaccaccaccaccaccactgagatccggctgctaacaaagcccgaaaggaagctgagttggct
gctgccaccgctgagcaataactagcataaccccttggggcctctaaacgggtcttgaggggtt
ttttgctgaaaggaggaactatatccggat

Figure 33

Amino acid Sequence of truncated "MNV" variant of *P. alba* IspS (SEQ ID NO:130)

```
MNVSFTETETEARRSANYEPNSWDYDYLLSSDTDESIEVYKDKAKKLEAEVRREINNEKAEFLT
LLELIDNVQRLGLGYRFESDIRGALDRFVSSGGFDAVTKTSLHGTALSFRLLRQHGFEVSQEAF
SGFKDQNGNFLENLKEDIKAILSLYEASFLALEGENILDEAKVFAISHLKELSEEKIGKELAEQ
VNHALELPLHRRTQRLEAVWSIEAYRKKEDANQVLLELAILDYNMIQSVYQRDLRETSRWWRRV
GLATKLHFARDRLIESFYWAVGVAFEPQYSDCRNSVAKMFSFVTIIDDIYDVYGTLDELELFTD
AVERWDVNAINDLPDYMKLCFLALYNTINEIAYDNLKDKGENILPYLTKAWADLCNAFLQEAKW
LYNKSTPTFDDYFGNAWKSSSGPLQLVFAYFAVVQNIKKEEIENLQKYHDTISRPSHIFRLCND
LASASAEIARGETANSVSCYMRTKGISEELATESVMNLIDETWKKMNKEKLGGSLFAKPFVETA
INLARQSHCTYHNGDAHTSPDELTRKRVLSVITEPILPFER
```

Figure 34A

Nucleotide sequence of pDu40 (pET24a-P.alba (MNV) Untagged) (SEQ ID NO:131)

```
tggcgaatgggacgcgccctgtagcggcgcattaagcgcggcgggtgtggtggttacgcgcagc
gtgaccgctacacttgccagcgccctagcgcccgctcctttcgctttcttcccttcctttctcg
ccacgttcgccggctttccccgtcaagctctaaatcgggggctcccctttagggttccgatttag
tgctttacggcacctcgaccccaaaaaacttgattagggtgatggttcacgtagtgggccatcg
ccctgatagacggttttcgcccttgacgttggagtccacgttctttaatagtggactcttgt
tccaaactggaacaacactcaaccctatctcggtctattcttttgatttataagggattgcc
gatttcggcctattggttaaaaaatgagctgatttaacaaaaatttaacgcgaattttaacaaa
atattaacgtttacaatttcaggtggcacttttcggggaaatgtgcgcggaacccctatttgtt
tattttctaaatacattcaaatatgtatccgctcatgaattaattcttagaaaaactcatcga
gcatcaaatgaaactgcaatttattcatatcaggattatcaataccatattttgaaaaagccg
tttctgtaatgaaggagaaaactcaccgaggcagttccataggatggcaagatcctggtatcgg
tctgcgattccgactcgtccaacatcaatacaacctattaatttcccctcgtcaaaaataaggt
tatcaagtgagaaatcaccatgagtgacgactgaatccggtgagaatggcaaaagtttatgcat
ttctttccagacttgttcaacaggccagccattacgctcgtcatcaaaatcactcgcatcaacc
aaaccgttattcattcgtgattgcgcctgagcgagacgaaatacgcgatcgctgttaaaaggac
aattacaaacaggaatcgaatgcaaccggcgcaggaacactgccagcgcatcaacaatattttc
acctgaatcaggatattcttctaatacctggaatgctgttttccggggatcgcagtggtgagt
aaccatgcatcatcaggagtacggataaaatgcttgatggtcggaagaggcataaattccgtca
gccagtttagtctgaccatctcatctgtaacatcattggcaacgctaccttcgccatgtttcag
aaacaactctggcgcatcgggcttcccatacaatcgatagattgtcgcacctgattgcccgaca
ttatcgcgagcccatttatacccatataaatcagcatccatgttggaatttaatcgcggcctag
agcaagacgtttcccgttgaatatggctcataacacccccttgtattactgtttatgtaagcaga
cagttttattgttcatgaccaaaatcccttaacgtgagttttcgttccactgagcgtcagaccc
cgtagaaaagatcaaaggatcttcttgagatcctttttttctgcgcgtaatctgctgcttgcaa
acaaaaaaaccaccgctaccagcggtggtttgtttgccggatcaagagctaccaactctttttc
cgaaggtaactggcttcagcagagcgcagataccaaatactgtccttctagtgtagccgtagtt
aggccaccacttcaagaactctgtagcaccgcctacatacctcgctctgctaatcctgttacca
gtggctgctgccagtggcgataagtcgtgtcttaccgggttggactcaagacgatagttaccgg
ataaggcgcagcggtcgggctgaacggggggttcgtgcacacagcccagcttggagcgaacgac
ctacaccgaactgagatacctacagcgtgagctatgagaaagcgccacgcttcccgaagggaga
aaggcggacaggtatccggtaagcggcagggtcggaacaggagagcgcacgagggagcttccag
ggggaaacgcctggtatctttatagtcctgtcgggtttcgccacctctgacttgagcgtcgatt
tttgtgatgctcgtcaggggggcggagcctatggaaaaacgccagcaacgcggcctttttacgg
ttcctggccttttgctggccttttgctcacatgttcttcctgcgttatcccctgattctgtgg
ataaccgtattaccgcctttgagtgagctgataccgctcgccgcagccgaacgaccgagcgcag
cgagtcagtgagcgaggaagcggaagagcgcctgatgcggtattttctccttacgcatctgtgc
ggtatttcacaccgcatatatggtgcactctcagtacaatctgctctgatgccgcatagttaag
ccagtatacactccgctatcgctacgtgactgggtcatggctgcgccccgacacccgccaacac
ccgctgacgcgccctgacgggcttgtctgctcccggcatccgcttacagacaagctgtgaccgt
ctccgggagctgcatgtgtcagaggttttcaccgtcatcaccgaaacgcgcgaggcagctgcgg
taaagctcatcagcgtggtcgtgaagcgattcacagatgtctgcctgttcatccgcgtccagct
cgttgagtttctccagaagcgttaatgtctggcttctgataaagcgggccatgttaagggcggt
ttttcctgtttggtcactgatgcctccgtgtaagggggatttctgttcatgggggtaatgata
```

Figure 34B

Nucleotide sequence of pDu40 (pET24a-P.alba (MNV) Untagged)

ccgatgaaacgagagaggatgctcacgatacgggttactgatgatgaacatgcccggttactgg
aacgttgtgagggtaaacaactggcggtatggatgcggcgggaccagagaaaaatcactcaggg
tcaatgccagcgcttcgttaatacagatgtaggtgttccacagggtagccagcagcatcctgcg
atgcagatccggaacataatggtgcagggcgctgacttccgcgtttccagactttacgaaacac
ggaaaccgaagaccattcatgttgttgctcaggtcgcagacgttttgcagcagcagtcgcttca
cgttcgctcgcgtatcggtgattcattctgctaaccagtaaggcaaccccgccagcctagccgg
gtcctcaacgacaggagcacgatcatgcgcaccgtggggccgccatgccggcgataatggcct
gcttctcgccgaaacgtttggtggcgggaccagtgacgaaggcttgagcgagggcgtgcaagat
tccgaataccgcaagcgacaggccgatcatcgtcgcgctccagcgaaagcggtcctcgccgaaa
atgacccagagcgctgccggcacctgtcctacgagttgcatgataaagaagacagtcataagtg
cggcgacgatagtcatgccccgcgccaccggaaggagctgactggggttgaaggctctcaaggg
catcggtcgagatcccggtgcctaatgagtgagctaacttacattaattgcgttgcgctcactg
cccgctttccagtcgggaaacctgtcgtgccagctgcattaatgaatcggccaacgcgcgggga
gaggcggtttgcgtattgggcgccagggtggttttttcttttcaccagtgagacgggcaacagct
gattgcccttcaccgcctggccctgagagagttgcagcaagcggtccacgctggtttgccccag
caggcgaaaatcctgtttgatggtggttaacggcgggatataacatgagctgtcttcggtatcg
tcgtatcccactaccgagatatccgcaccaacgcgcagcccggactcggtaatggcgcgcattg
cgcccagcgccatctgatcgttggcaaccagcatcgcagtgggaacgatgccctcattcagcat
ttgcatggtttgttgaaaaccggacatggcactccagtcgccttcccgttccgctatcggctga
atttgattgcgagtgagatatttatgccagccagccagacgcagacgcgccgagacagaactta
atgggcccgctaacagcgcgatttgctggtgacccaatgcgaccagatgctccacgcccagtcg
cgtaccgtcttcatgggagaaaataatactgttgatgggtgtctggtcagagacatcaagaaat
aacgccggaacattagtgcaggcagcttccacagcaatggcatcctggtcatccagcggatagt
taatgatcagcccactgacgcgttgcgcgagaagattgtgcaccgccgctttacaggcttcgac
gccgcttcgttctaccatcgacaccaccacgctggcacccagttgatcggcgcgagatttaatc
gccgcgacaatttgcgacggcgcgtgcagggccagactggaggtggcaacgccaatcagcaacg
actgtttgcccgccagttgttgtgccacgcggttgggaatgtaattcagctccgccatcgccgc
ttccacttttttcccgcgttttcgcagaaacgtggctggcctggttcaccacgcgggaaacggtc
tgataagagacaccggcatactctgcgacatcgtataacgttactggtttcacattcaccaccc
tgaattgactctcttccgggcgctatcatgccataccgcgaaaggttttgcgccattcgatggt
gtccgggatctcgacgctctcccttatgcgactcctgcattaggaagcagcccagtagtaggtt
gaggccgttgagcaccgccgccgcaaggaatggtgcatgcaaggagatggcgcccaacagtccc
ccggccacggggcctgccaccatacccacgccgaaacaagcgctcatgagcccgaagtggcgag
cccgatcttccccatcggtgatgtcggcgatataggcgccagcaaccgcacctgtggcgccggt
gatgccggccacgatgcgtccggcgtagaggatcgagatctcgatcccgcgaaattaatacgac
tcactatagggaattgtgagcggataacaattcccctctagaaataatttttgtttaactttaa
gaaggagatatacatatgaatgtgtctttcaccgaaactgaaaccgaagctcgtcgttctgcga
actacgaacctaacagctgggactatgattacctgctgtcctcgacacggacgagtccatcga
agtatacaaagacaaagcgaaaaagctggaagccgaagttcgtcgcgagattaataacgaaaaa
gcagaatttctgaccctgctggaactgattgacaacgtccagcgcctgggcctgggttaccgtt
tcgagtctgatatccgtggtgcgctggatcgcttcgtttcctccggcggcttcgatgcggtaac
caagacttccctgcacggtacggcactgtctttccgtctgctgcgtcaacacggttttgaggtt
tctcaggaagcgttcagcggcttcaaagaccaaaacggcaacttcctggagaacctgaaggaag

Figure 34C

Nucleotide sequence of pDu40 (pET24a-P.alba (MNV) Untagged)

atatcaaagctatcctgagcctgtacgaggccagcttcctggctctggaaggcgaaaacatcct
ggacgaggcgaaggttttcgcaatctctcatctgaaagaactgtctgaagaaaagatcggtaaa
gagctggcagaacaggtgaaccatgcactggaactgccactgcatcgccgtactcagcgtctgg
aagcagtatggtctatcgaggcctaccgtaaaaaggaggacgcgaatcaggttctgctggagct
ggcaattctggattacaacatgatccagtctgtataccagcgtgatctgcgtgaaacgtcccgt
tggtggcgtcgtgtgggtctggcgaccaaactgcactttgctcgtgaccgcctgattgagagct
tctactgggccgtgggtgtagcattcgaaccgcaatactccgactgccgtaactccgtcgcaaa
aatgttttctttcgtaaccattatcgacgatatctacgatgtatacggcaccctggacgaactg
gagctgtttactgatgcagttgagcgttgggacgtaaacgccatcaacgacctgccggattaca
tgaaactgtgctttctggctctgtataacactattaacgaaatcgcctacgacaacctgaaaga
taaaggtgagaacatcctgccgtatctgaccaaagcctgggctgacctgtgcaacgctttcctg
caagaagccaagtggctgtacaacaaatctactccgacctttgacgactacttcggcaacgcat
ggaaatcctcttctggcccgctgcaactggtgttcgcttacttcgctgtcgtgcagaacattaa
aaaggaagagatcgaaaacctgcaaaaataccatgacaccatctctcgtccttcccatatcttc
cgtctgtgcaatgacctggctagcgcgtctgcggaaattgcgcgtggtgaaaccgcaaatagcg
tttcttgttacatgcgcactaaaggtatctccgaagaactggctaccgaaagcgtgatgaatct
gatcgatgaaacctggaaaaagatgaacaaggaaaaactgggtggtagcctgttcgcgaaacg
ttcgtggaaaccgcgatcaacctggcacgtcaatctcactgcacttatcataacggcgacgcgc
atacctctccggatgagctgacccgcaaacgcgttctgtctgtaatcactgaaccgattctgcc
gtttgaacgctaaggatccgaattcgagctccgtcgacaagcttgcggccgcactcgagcacca
ccaccaccaccactgagatccggctgctaacaaagcccgaaaggaagctgagttggctgctgcc
accgctgagcaataactagcataacccttggggcctctaaacgggtcttgaggggttttttgc
tgaaaggaggaactatatccggat

Figure 36

Amino acid sequence of *P. alba* MEA(+)TEV (SEQ ID NO:132)

```
MEARRSANYEPNSWDYDYLLSSDTDESIEVYKDKAKKLEAEVRREINNEKAEFLTLLELIDNVQ
RLGLGYRFESDIRGALDRFVSSGGFDAVTKTSLHGTALSFRLLRQHGFEVSQEAFSGFKDQNGN
FLENLKEDIKAILSLYEASFLALEGENILDEAKVFAISHLKELSEEKIGKELAEQVNHALELPL
HRRTQRLEAVWSIEAYRKKEDANQVLLELAILDYNMIQSVYQRDLRETSRWWRRVGLATKLHFA
RDRLIESFYWAVGVAFEPQYSDCRNSVAKMFSFVTIIDDIYDVYGTLDELELFTDAVERWDVNA
INDLPDYMKLCFLALYNTINEIAYDNLKDKGENILPYLTKAWADLCNAFLQEAKWLYNKSTPTF
DDYFGNAWKSSSGPLQLVFAYFAVVQNIKKEEIENLQKYHDTISRPSHIFRLCNDLASASAEIA
RGETANSVSCYMRTKGISEELATESVMNLIDETWKKMNKEKLGGSLFAKPFVETAINLARQSHC
TYHNGDAHTSPDELTRKRVLSVITEPILPFERENLYFQGLEHHHHHH
```

Figure 37A

Nucleotide sequence of MD09-163 (pET24a-P. alba MEA(+)TEV) (SEQ ID NO:133)

```
tggcgaatgggacgcgccctgtagcggcgcattaagcgcggcgggtgtggtggttacgcgcagc
gtgaccgctacacttgccagcgccctagcgcccgctcctttcgctttcttcccttcctttctcg
ccacgttcgccggctttccccgtcaagctctaaatcgggggctcccttagggttccgatttag
tgctttacggcacctcgaccccaaaaaacttgattagggtgatggttcacgtagtgggccatcg
ccctgatagacggttttcgcccttttgacgttggagtccacgttctttaatagtggactcttgt
tccaaactggaacaacactcaaccctatctcggtctattcttttgatttataagggattttgcc
gatttcggcctattggttaaaaaatgagctgatttaacaaaaatttaacgcgaattttaacaaa
atattaacgtttacaatttcaggtggcacttttcggggaaatgtgcgcggaacccctatttgtt
tatttttctaaatacattcaaatatgtatccgctcatgaattaattcttagaaaaactcatcga
gcatcaaatgaaactgcaatttattcatatcaggattatcaataccatattttgaaaaagccg
tttctgtaatgaaggagaaaactcaccgaggcagttccataggatggcaagatcctggtatcgg
tctgcgattccgactcgtccaacatcaatacaacctattaatttcccctcgtcaaaaataaggt
tatcaagtgagaaatcaccatgagtgacgactgaatccggtgagaatggcaaaagtttatgcat
ttctttccagacttgttcaacaggccagccattacgctcgtcatcaaaatcactcgcatcaacc
aaaccgttattcattcgtgattgcgcctgagcgagacgaaatacgcgatcgctgttaaaaggac
aattacaaacaggaatcgaatgcaaccggcgcaggaacactgccagcgcatcaacaatatttc
acctgaatcaggatattcttctaatacctggaatgctgttttcccggggatcgcagtggtgagt
aaccatgcatcatcaggagtacggataaaatgcttgatggtcggaagaggcataaattccgtca
gccagtttagtctgaccatctcatctgtaacatcattggcaacgctacctttgccatgtttcag
aaacaactctggcgcatcgggcttcccatacaatcgatagattgtcgcacctgattgcccgaca
ttatcgcgagcccatttatacccatataaatcagcatccatgttggaatttaatcgcggcctag
agcaagacgtttcccgttgaatatggctcataacacccttgtattactgtttatgtaagcaga
cagttttattgttcatgaccaaaatcccttaacgtgagttttcgttccactgagcgtcagaccc
cgtagaaaagatcaaaggatcttcttgagatcctttttttctgcgcgtaatctgctgcttgcaa
acaaaaaaaccaccgctaccagcggtggtttgtttgccggatcaagagctaccaactctttttc
cgaaggtaactggcttcagcagagcgcagataccaaatactgtccttctagtgtagccgtagtt
aggccaccacttcaagaactctgtagcaccgcctacatacctcgctctgctaatcctgttacca
gtggctgctgccagtggcgataagtcgtgtcttaccgggttggactcaagacgatagttaccgg
ataaggcgcagcggtcgggctgaacggggggttcgtgcacacagcccagcttggagcgaacgac
ctacaccgaactgagatacctacagcgtgagctatgagaaagcgccacgcttcccgaagggaga
aaggcggacaggtatccggtaagcggcagggtcggaacaggagagcgcacgagggagcttccag
ggggaaacgcctggtatctttatagtcctgtcgggtttcgccacctctgacttgagcgtcgatt
tttgtgatgctcgtcaggggggcggagcctatggaaaaacgccagcaacgcggcctttttacgg
ttcctggccttttgctggccttttgctcacatgttctttcctgcgttatcccctgattctgtgg
ataaccgtattaccgcctttgagtgagctgataccgctcgccgcagccgaacgaccgagcgcag
cgagtcagtgagcgaggaagcggaagagcgcctgatgcggtattttctccttacgcatctgtgc
ggtatttcacaccgcatatatggtgcactctcagtacaatctgctctgatgccgcatagttaag
ccagtatacactccgctatcgctacgtgactgggtcatggctgcgccccgacacccgccaacac
ccgctgacgcgccctgacgggcttgtctgctcccggcatccgcttacagacaagctgtgaccgt
ctccgggagctgcatgtgtcagaggttttcaccgtcatcaccgaaacgcgcgaggcagctgcgg
taaagctcatcagcgtggtcgtgaagcgattcacagatgtctgcctgttcatccgcgtccagct
cgttgagtttctccagaagcgttaatgtctggcttctgataaagcgggccatgttaagggcggt
```

Figure 37B

Nucleotide sequence of MD09-163 (pET24a-P. alba MEA(+)TEV)

```
tttttcctgtttggtcactgatgcctccgtgtaaggggatttctgttcatggggtaatgata
ccgatgaaacgagagaggatgctcacgatacgggttactgatgatgaacatgcccggttactgg
aacgttgtgagggtaaacaactggcggtatggatgcggcgggaccagagaaaaatcactcaggg
tcaatgccagcgcttcgttaatacagatgtaggtgttccacagggtagccagcagcatcctgcg
atgcagatccggaacataatggtgcagggcgctgacttccgcgtttccagactttacgaaacac
ggaaaccgaagaccattcatgttgttgctcaggtcgcagacgttttgcagcagcagtcgcttca
cgttcgctcgcgtatcggtgattcattctgctaaccagtaaggcaaccccgccagcctagccgg
gtcctcaacgacaggagcacgatcatgcgcacccgtggggccgccatgccggcgataatggcct
gcttctcgccgaaacgtttggtggcgggaccagtgacgaaggcttgagcgagggcgtgcaagat
tccgaataccgcaagcgacaggccgatcatcgtcgcgctccagcgaaagcggtcctcgccgaaa
atgacccagagcgctgccggcacctgtcctacgagttgcatgataaagaagacagtcataagtg
cggcgacgatagtcatgccccgcgcccaccggaaggagctgactgggttgaaggctctcaaggg
catcggtcgagatcccggtgcctaatgagtgagctaacttacattaattgcgttgcgctcactg
cccgctttccagtcgggaaacctgtcgtgccagctgcattaatgaatcggccaacgcgcgggga
gaggcggtttgcgtattgggcgccagggtggttttcttttcaccagtgagacgggcaacagct
gattgcccttcaccgcctggccctgagagagttgcagcaagcggtccacgctggtttgcccag
caggcgaaaatcctgtttgatggtggttaacggcgggatataacatgagctgtcttcggtatcg
tcgtatcccactaccgagatatccgcaccaacgcgcagcccggactcggtaatggcgcgcattg
cgcccagcgccatctgatcgttggcaaccagcatcgcagtgggaacgatgccctcattcagcat
ttgcatggtttgttgaaaaccggacatggcactccagtcgccttcccgttccgctatcggctga
atttgattgcgagtgagatatttatgccagccagccagacgcagacgcgccgagacagaactta
atgggcccgctaacagcgcgatttgctggtgacccaatgcgaccagatgctccacgcccagtcg
cgtaccgtcttcatgggagaaaataatactgttgatgggtgtctggtcagagacatcaagaaat
aacgccggaacattagtgcaggcagcttccacagcaatggcatcctggtcatccagcggatagt
taatgatcagcccactgacgcgttgcgcgagaagattgtgcaccgccgctttacaggcttcgac
gccgcttcgttctaccatcgacaccaccacgctggcacccagttgatcggcgcgagatttaatc
gccgcgacaatttgcgacggcgcgtgcagggccagactggaggtggcaacgccaatcagcaacg
actgtttgcccgccagttgttgtgccacgcggttgggaatgtaattcagctccgccatcgccgc
ttccacttttttcccgcgttttcgcagaaacgtggctggcctggttcaccacgcgggaaacggtc
tgataagagacaccggcatactctgcgacatcgtataacgttactggtttcacattcaccaccc
tgaattgactctcttccgggcgctatcatgccataccgcgaaaggttttgcgccattcgatggt
gtccgggatctcgacgctctcccttatgcgactcctgcattaggaagcagcccagtagtaggtt
gaggccgttgagcaccgccgccgcaaggaatggtgcatgcaaggagatggcgcccaacagtccc
ccggccacggggcctgccaccatacccacgccgaaacaagcgctcatgagcccgaagtggcgag
cccgatcttccccatcggtgatgtcggcgatataggcgccagcaaccgcacctgtggcgccggt
gatgccggccacgatgcgtccggcgtagaggatcgagatctcgatcccgcgaaattaatacgac
tcactataggggaattgtgagcggataacaattcccctctagaaataattttgtttaactttaa
gaaggagatatacatatggaagctcgtcgttctgcgaactacgaacctaacagctgggactatg
attacctgctgtcctccgacacggacgagtccatcgaagtatacaaagacaaagcgaaaaagct
ggaagccgaagttcgtcgcgagattaataacgaaaaagcagaatttctgaccctgctggaactg
attgacaacgtccagcgcctgggcctgggttaccgtttcgagtctgatatccgtggtgcgctgg
atcgcttcgtttcctccggcggcttcgatgcggtaaccaagacttccctgcacggtacggcact
gtctttccgtctgctgcgtcaacacggttttgaggtttctcaggaagcgttcagcggcttcaaa
```

Figure 37C

Nucleotide sequence of MD09-163 (pET24a-P. alba MEA(+)TEV)

```
gaccaaaacggcaacttcctggagaacctgaaggaagatatcaaagctatcctgagcctgtacg
aggccagcttcctggctctggaaggcgaaaacatcctggacgaggcgaaggttttcgcaatctc
tcatctgaaagaactgtctgaagaaaagatcggtaaagagctggcagaacaggtgaaccatgca
ctggaactgccactgcatcgccgtactcagcgtctggaagcagtatggtctatcgaggcctacc
gtaaaaaggaggacgcgaatcaggttctgctggagctggcaattctggattacaacatgatcca
gtctgtataccagcgtgatctgcgtgaaacgtcccgttggtggcgtcgtgtgggtctggcgacc
aaactgcactttgctcgtgaccgcctgattgagagcttctactgggccgtgggtgtagcattcg
aaccgcaatactccgactgccgtaactccgtcgcaaaaatgttttctttcgtaaccattatcga
cgatatctacgatgtatacggcaccctggacgaactggagctgtttactgatgcagttgagcgt
tgggacgtaaacgccatcaacgacctgccggattacatgaaactgtgctttctggctctgtata
acactattaacgaaatcgcctacgacaacctgaaagataaaggtgagaacatcctgccgtatct
gaccaaagcctgggctgacctgtgcaacgctttcctgcaagaagccaagtggctgtacaacaaa
tctactccgacctttgacgactacttcggcaacgcatggaaatcctcttctggcccgctgcaac
tggtgttcgcttacttcgctgtcgtgcagaacattaaaaaggaagagatcgaaaacctgcaaaa
ataccatgacaccatctctcgtccttcccatatcttccgtctgtgcaatgacctggctagcgcg
tctgcggaaattgcgcgtggtgaaaccgcaaatagcgtttcttgttacatgcgcactaaaggta
tctccgaagaactggctaccgaaagcgtgatgaatctgatcgatgaaacctggaaaaagatgaa
caaggaaaaactgggtggtagcctgttcgcgaaaccgttcgtggaaaccgcgatcaacctggca
cgtcaatctcactgcacttatcataacggcgacgcgcataCctctccggatgagctgacccgca
aacgcgttctgtctgtaatcactgaaccgattctgccgtttgaacgcgaaaacctgtatttca
gggcctcgagcaccaccaccaccaccactgagatccggctgctaacaaagcccgaaaggaagct
gagttggctgctgccaccgctgagcaataactagcataaccccttggggcctctaaacgggtct
tgagggtttttttgctgaaaggaggaactatatccggat
```

Figure 38

Amino acid sequence of *P. alba* FL (+) TEV (SEQ ID NO:134)

```
MRCSVSTENVSFTETETEARRSANYEPNSWDYDYLLSSDTDESIEVYKDKAKKLEAEVRREINN
EKAEFLTLLELIDNVQRLGLGYRFESDIRGALDRFVSSGGFDAVTKTSLHGTALSFRLLRQHGF
EVSQEAFSGFKDQNGNFLENLKEDIKAILSLYEASFLALEGENILDEAKVFAISHLKELSEEKI
GKELAEQVNHALELPLHRRTQRLEAVWSIEAYRKKEDANQVLLELAILDYNMIQSVYQRDLRET
SRWWRRVGLATKLHFARDRLIESFYWAVGVAFEPQYSDCRNSVAKMFSFVTIIDDIYDVYGTLD
ELELFTDAVERWDVNAINDLPDYMKLCFLALYNTINEIAYDNLKDKGENILPYLTKAWADLCNA
FLQEAKWLYNKSTPTFDDYFGNAWKSSSGPLQLVFAYFAVVQNIKKEEIENLQKYHDTISRPSH
IFRLCNDLASASAEIARGETANSVSCYMRTKGISEELATESVMNLIDETWKKMNKEKLGGSLFA
KPFVETAINLARQSHCTYHNGDAHTSPDELTRKRVLSVITEPILPFERENLYFQGLEHHHHHH
```

Figure 39A

Nucleotide sequence of MD09-161 (pET24a-P. alba FL(+)TEV) (SEQ ID NO:135)

```
tggcgaatgggacgcgccctgtagcggcgcattaagcgcggcgggtgtggtggttacgcgcagc
gtgaccgctacacttgccagcgccctagcgcccgctcctttcgctttcttcccttcctttctcg
ccacgttcgccggctttccccgtcaagctctaaatcggggggctcccttagggttccgatttag
tgctttacggcacctcgaccccaaaaaacttgattagggtgatggttcacgtagtgggccatcg
ccctgatagacggtttttcgccctttgacgttggagtccacgttctttaatagtggactcttgt
tccaaactggaacaacactcaaccctatctcggtctattcttttgatttataagggattttgcc
gatttcggcctattggttaaaaaatgagctgatttaacaaaaatttaacgcgaattttaacaaa
atattaacgtttacaatttcaggtggcacttttcggggaaatgtgcgcggaaccccatttgtt
tattttctaaatacattcaaatatgtatccgctcatgaattaattcttagaaaaactcatcga
gcatcaaatgaaactgcaatttattcatatcaggattatcaataccatattttgaaaaagccg
tttctgtaatgaaggagaaaactcaccgaggcagttccataggatggcaagatcctggtatcgg
tctgcgattccgactcgtccaacatcaatacaacctattaatttcccctcgtcaaaaataaggt
tatcaagtgagaaatcaccatgagtgacgactgaatccggtgagaatggcaaaagtttatgcat
ttctttccagacttgttcaacaggccagccattacgctcgtcatcaaaatcactcgcatcaacc
aaaccgttattcattcgtgattgcgcctgagcgagacgaaatacgcgatcgctgttaaaggac
aattacaaacaggaatcgaatgcaaccggcgcaggaacactgccagcgcatcaacaatattttc
acctgaatcaggatattcttctaatacctggaatgctgttttcccggggatcgcagtggtgagt
aaccatgcatcatcaggagtacggataaaatgcttgatggtcggaagaggcataaattccgtca
gccagtttagtctgaccatctcatctgtaacatcattggcaacgctacctttgccatgtttcag
aaacaactctggcgcatcgggcttcccatacaatcgatagattgtcgcacctgattgcccgaca
ttatcgcgagcccatttatacccatataaatcagcatccatgttggaatttaatcgcggcctag
agcaagacgtttcccgttgaatatggctcataacacccctgtattactgtttatgtaagcaga
cagtttattgttcatgaccaaaatcccttaacgtgagttttcgttccactgagcgtcagaccc
cgtagaaaagatcaaaggatcttcttgagatccttttttctgcgcgtaatctgctgcttgcaa
acaaaaaaaccaccgctaccagcggtggtttgtttgccggatcaagagctaccaactctttttc
cgaaggtaactggcttcagcagagcgcagataccaaatactgtccttctagtgtagccgtagtt
aggccaccacttcaagaactctgtagcaccgcctacatacctcgctctgctaatcctgttacca
gtggctgctgccagtggcgataagtcgtgtcttaccgggttggactcaagacgatagttaccgg
ataaggcgcagcggtcgggctgaacggggggttcgtgcacacagcccagcttggagcgaacgac
ctacaccgaactgagatacctacagcgtgagctatgagaaagcgccacgcttcccgaagggaga
aaggcggacaggtatccggtaagcggcagggtcggaacaggagagcgcacgagggagcttccag
ggggaaacgcctggtatctttatagtcctgtcgggtttcgccacctctgacttgagcgtcgatt
tttgtgatgctcgtcaggggggcggagcctatggaaaaacgccagcaacgcggcctttttacgg
ttcctggccttttgctggccttttgctcacatgttctttcctgcgttatcccctgattctgtgg
ataaccgtattaccgcctttgagtgagctgataccgctcgccgcagccgaacgaccgagcgcag
cgagtcagtgagcgaggaagcggaagagcgcctgatgcggtattttctccttacgcatctgtgc
ggtatttcacaccgcatatatggtgcactctcagtacaatctgctctgatgccgcatagttaag
ccagtatacactccgctatcgctacgtgactgggtcatggctgcgccccgacacccgccaacac
cgctgacgcgccctgacgggcttgtctgctcccggcatccgcttacagacaagctgtgaccgt
ctccgggagctgcatgtgtcagaggttttcaccgtcatcaccgaaacgcgcgaggcagctgcgg
taaagctcatcagcgtggtcgtgaagcgattcacagatgtctgcctgttcatccgcgtccagct
cgttgagtttctccagaagcgttaatgtctggcttctgataaagcgggccatgttaagggcggt
```

Figure 39B

Nucleotide sequence of MD09-161 (pET24a-P. alba FL(+)TEV)

```
tttttcctgtttggtcactgatgcctccgtgtaaggggatttctgttcatgggggtaatgata
ccgatgaaacgagagaggatgctcacgatacgggttactgatgatgaacatgcccggttactgg
aacgttgtgagggtaaacaactggcggtatggatgcggcgggaccagagaaaaatcactcaggg
tcaatgccagcgcttcgttaatacagatgtaggtgttccacagggtagccagcagcatcctgcg
atgcagatccggaacataatggtgcagggcgctgacttccgcgtttccagactttacgaaacac
ggaaaccgaagaccattcatgttgttgctcaggtcgcagacgttttgcagcagcagtcgcttca
cgttcgctcgcgtatcggtgattcattctgctaaccagtaaggcaacccgccagcctagccgg
gtcctcaacgacaggagcacgatcatgcgcaccgtggggccgccatgccggcgataatggcct
gcttctcgccgaaacgtttggtggcgggaccagtgacgaaggcttgagcgagggcgtgcaagat
tccgaataccgcaagcgacaggccgatcatcgtcgcgctccagcgaaagcggtcctcgccgaaa
atgacccagagcgctgccggcacctgtcctacgagttgcatgataaagaagacagtcataagtg
cggcgacgatagtcatgccccgcgccaccggaaggagctgactgggttgaaggctctcaaggg
catcggtcgagatcccggtgcctaatgagtgagctaacttacattaattgcgttgcgctcactg
cccgctttccagtcgggaaacctgtcgtgccagctgcattaatgaatcggccaacgcgcgggga
gaggcggtttgcgtattgggcgccagggtggttttcttttcaccagtgagacgggcaacagct
gattgcccttcaccgcctggccctgagagagttgcagcaagcggtccacgctggtttgccccag
caggcgaaaatcctgtttgatggtggttaacggcgggatataacatgagctgtcttcggtatcg
tcgtatcccactaccgagatatccgcaccaacgcgcagcccggactcggtaatggcgcgcattg
cgcccagcgccatctgatcgttggcaaccagcatcgcagtgggaacgatgccctcattcagcat
ttgcatggtttgttgaaaaccggacatggcactccagtcgccttcccgttccgctatcggctga
atttgattgcgagtgagatatttatgccagccagccagacgcagacgcgccgagacagaactta
atgggcccgctaacagcgcgatttgctggtgacccaatgcgaccagatgctccacgcccagtcg
cgtaccgtcttcatgggagaaaataatactgttgatgggtgtctggtcagagacatcaagaaat
aacgccggaacattagtgcaggcagcttccacagcaatggcatcctggtcatccagcggatagt
taatgatcagcccactgacgcgttgcgcgagaagattgtgcaccgccgctttacaggcttcgac
gccgcttcgttctaccatcgacaccaccacgctggcacccagttgatcggcgcgagatttaatc
gccgcgacaatttgcgacggcgcgtgcagggccagactggaggtggcaacgccaatcagcaacg
actgtttgcccgccagttgttgtgccacgcggttgggaatgtaattcagctccgccatcgccgc
ttccacttttttcccgcgttttcgcagaaacgtggctggcctggttcaccacgcgggaaacggtc
tgataagagacaccggcatactctgcgacatcgtataacgttactggtttcacattcaccaccc
tgaattgactctcttccgggcgctatcatgccataccgcgaaaggttttgcgccattcgatggt
gtccgggatctcgacgctctcccttatgcgactcctgcattaggaagcagcccagtagtaggtt
gaggccgttgagcaccgccgccgcaaggaatggtgcatgcaaggagatggcgcccaacagtccc
ccggccacggggcctgccaccatacccacgccgaaacaagcgctcatgagcccgaagtggcgag
cccgatcttccccatcggtgatgtcggcgatataggcgccagcaaccgcacctgtggcgccggt
gatgccggccacgatgcgtccggcgtagaggatcgagatctcgatcccgcgaaattaatacgac
tcactatagggaattgtgagcggataacaattcccctctagaaataattttgtttaactttaa
gaaggagatatacatatgcgttgtagcgtgtccaccgaaaatgtgtctttcaccgaaactgaaa
ccgaagctcgtcgttctgcgaactacgaacctaacagctgggactatgattacctgctgtcctc
cgacacggacgagtccatcgaagtatacaaagacaaagcgaaaaagctggaagccgaagttcgt
cgcgagattaataacgaaaaagcagaatttctgaccctgctggaactgattgacaacgtccagc
gcctgggcctgggttaccgtttcgagtctgatatccgtggtgcgctggatcgcttcgtttcctc
cggcggcttcgatgcggtaaccaagacttccctgcacggtacggcactgtctttccgtctgctg
```

Figure 39C

Nucleotide sequence of MD09-161 (pET24a-P. alba FL(+)TEV)

cgtcaacacggttttgaggtttctcaggaagcgttcagcggcttcaaagaccaaaacggcaact
tcctggagaacctgaaggaagatatcaaagctatcctgagcctgtacgaggccagcttcctggc
tctggaaggcgaaaacatcctggacgaggcgaaggttttcgcaatctctcatctgaaagaactg
tctgaagaaaagatcggtaaagagctggcagaacaggtgaaccatgcactggaactgccactgc
atcgccgtactcagcgtctggaagcagtatggtctatcgaggcctaccgtaaaaaggaggacgc
gaatcaggttctgctggagctggcaattctggattacaacatgatccagtctgtataccagcgt
gatctgcgtgaaacgtcccgttggtggcgtcgtgtgggtctggcgaccaaactgcactttgctc
gtgaccgcctgattgagagcttctactgggccgtgggtgtagcattcgaaccgcaatactccga
ctgccgtaactccgtcgcaaaaatgttttctttcgtaaccattatcgacgatatctacgatgta
tacggcaccctggacgaactggagctgtttactgatgcagttgagcgttgggacgtaaacgcca
tcaacgacctgccggattacatgaaactgtgctttctggctctgtataacactattaacgaaat
cgcctacgacaacctgaaagataaaggtgagaacatcctgccgtatctgaccaaagcctgggct
gacctgtgcaacgctttcctgcaagaagccaagtggctgtacaacaaatctactccgacctttg
acgactacttcggcaacgcatggaaatcctcttctggcccgctgcaactggtgttcgcttactt
cgctgtcgtgcagaacattaaaaaggaagagatcgaaaacctgcaaaataccatgacaccatc
tctcgtccttcccatatcttccgtctgtgcaatgacctggctagcgcgtctgcggaaattgcgc
gtggtgaaaccgcaaatagcgtttcttgttacatgcgcactaaaggtatctccgaagaactggc
taccgaaagcgtgatgaatctgatcgatgaaacctggaaaaagatgaacaaggaaaaactgggt
ggtagcctgttcgcgaaaccgttcgtggaaccgcgatcaacctggcacgtcaatctcactgca
cttatcataacggcgacgcgcatacctctccggatgagctgacccgcaaacgcgttctgtctgt
aatcactgaaccgattctgccgtttgaacgcgaaaacctgtattttcagggcctcgagcaccac
caccaccaccactgagatccggctgctaacaaagcccgaaaggaagctgagttggctgctgcca
ccgctgagcaataactagcataacccttggggcctctaaacgggtcttgaggggttttttgct
gaaaggaggaactatatccggat Figure 43
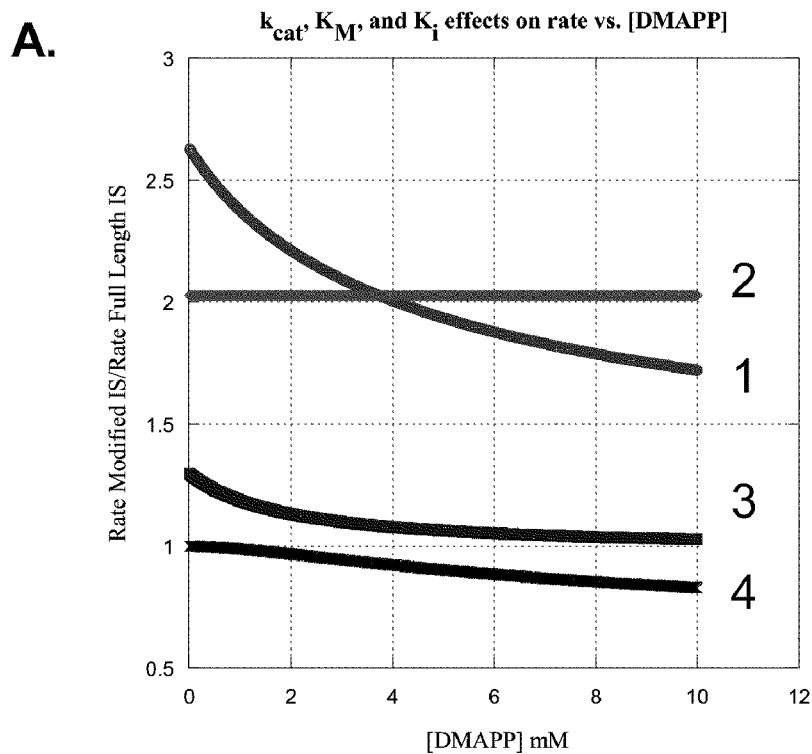
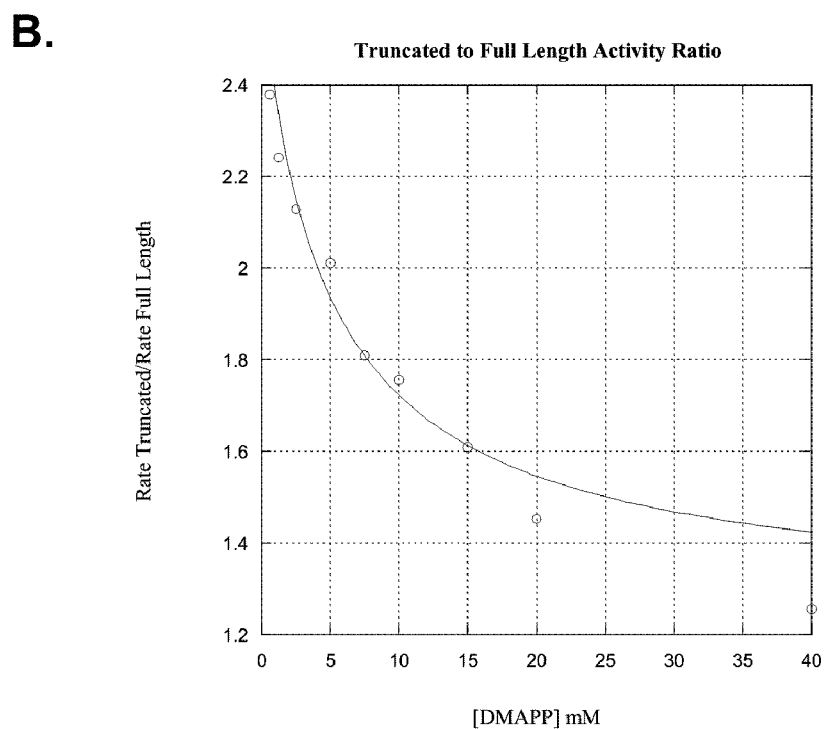

Figure 48
A.
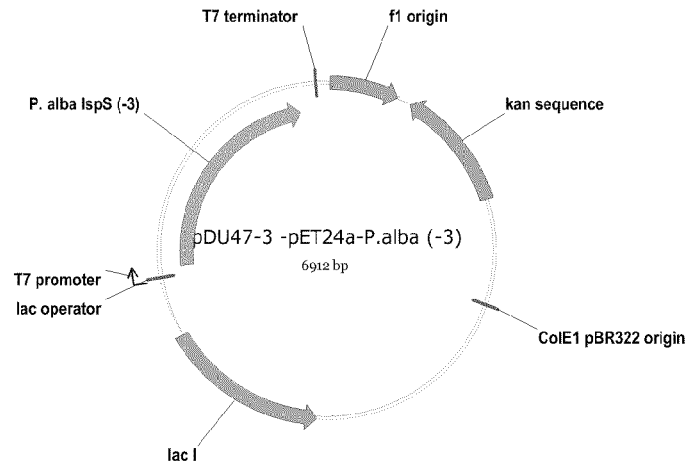
B.
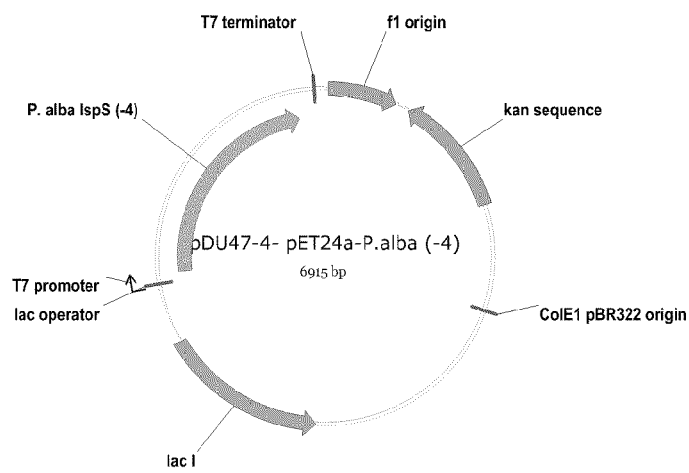
C.
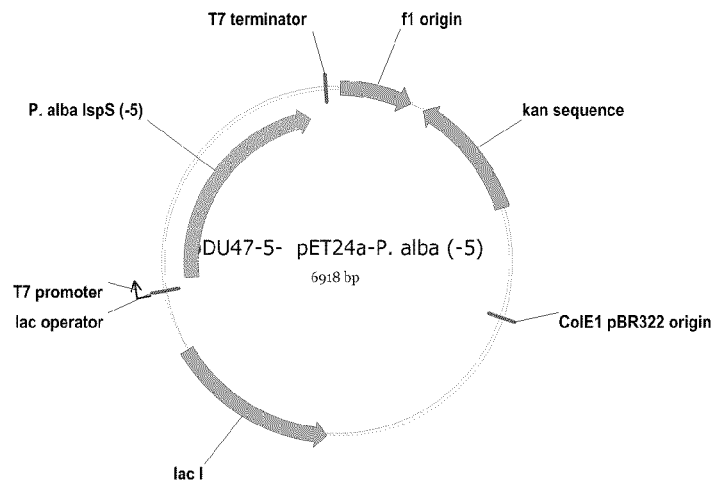

Figure 49
A.
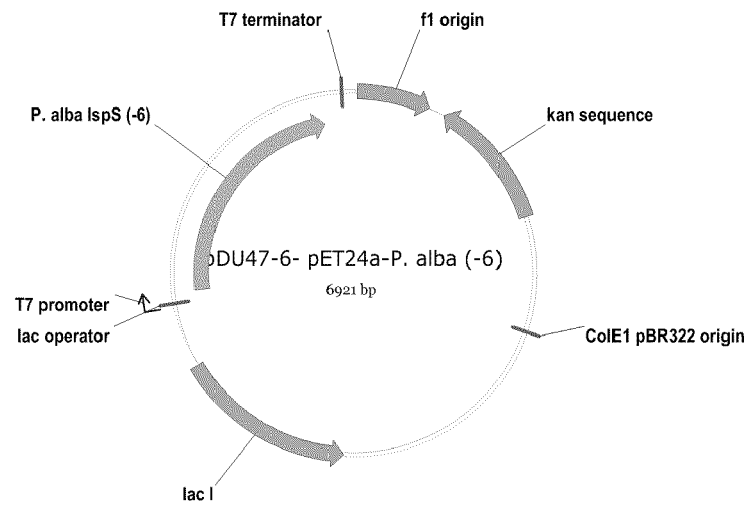
B.
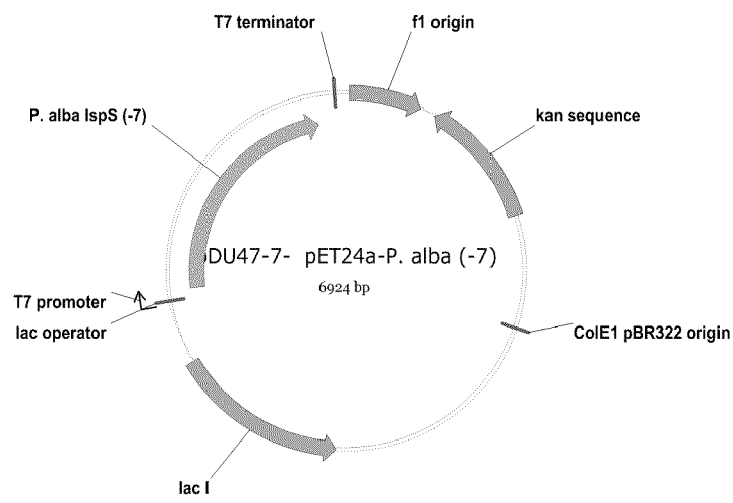
C.
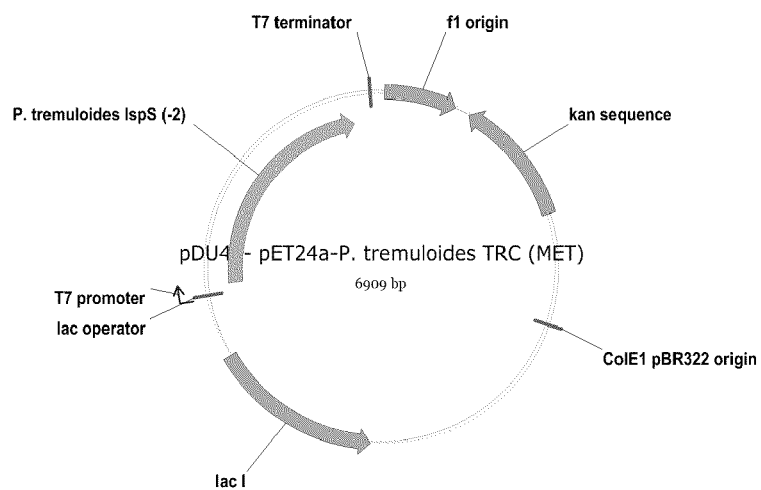

Figure 50
A.
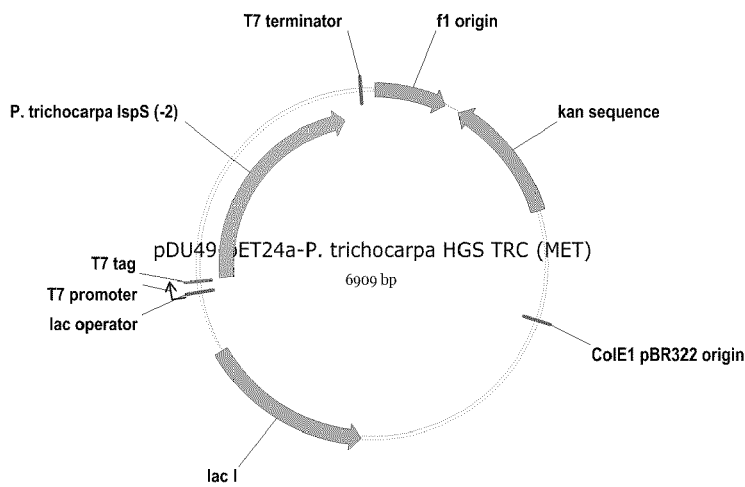
B.
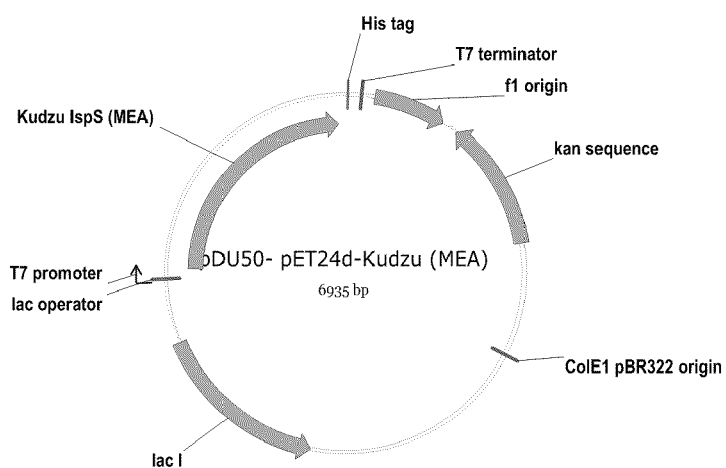
C.
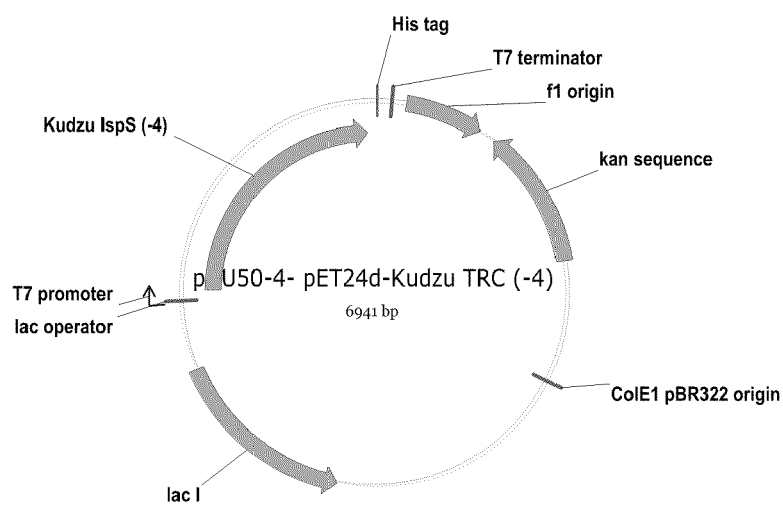

Figure 51

Amino acid sequence of *P.alba* TRC (-3) (SEQ ID NO:136)

```
MTEARRSANYEPNSWDYDYLLSSDTDESIEVYKDKAKKLEAEVRREINNEKAEFLTLLELIDNV
QRLGLGYRFESDIRGALDRFVSSGGFDAVTKTSLHGTALSFRLLRQHGFEVSQEAFSGFKDQNG
NFLENLKEDIKAILSLYEASFLALEGENILDEAKVFAISHLKELSEEKIGKELAEQVNHALELP
LHRRTQRLEAVWSIEAYRKKEDANQVLLELAILDYNMIQSVYQRDLRETSRWWRRVGLATKLHF
ARDRLIESFYWAVGVAFEPQYSDCRNSVAKMFSFVTIIDDIYDVYGTLDELELFTDAVERWDVN
AINDLPDYMKLCFLALYNTINEIAYDNLKDKGENILPYLTKAWADLCNAFLQEAKWLYNKSTPT
FDDYFGNAWKSSSGPLQLVFAYFAVVQNIKKEEIENLQKYHDTISRPSHIFRLCNDLASASAEI
ARGETANSVSCYMRTKGISEELATESVMNLIDETWKKMNKEKLGGSLFAKPFVETAINLARQSH
CTYHNGDAHTSPDELTRKRVLSVITEPILPFER
```

Figure 52A

Nucleotide sequence of pDu47-3 (SEQ ID NO:137)

```
tggcgaatgggacgcgccctgtagcggcgcattaagcgcggcgggtgtggtggttacgcgcagc
gtgaccgctacacttgccagcgccctagcgcccgctcctttcgctttcttcccttcctttctcg
ccacgttcgccggctttccccgtcaagctctaaatcgggggctcccctttagggttccgatttag
tgctttacggcacctcgaccccaaaaaacttgatttagggtgatggttcacgtagtgggccatcg
ccctgatagacggtttttcgccctttgacgttggagtccacgttctttaatagtggactcttgt
tccaaactggaacaacactcaaccctatctcggtctattcttttgatttataagggattttgcc
gatttcggcctattggttaaaaatgagctgatttaacaaaaatttaacgcgaattttaacaaa
atattaacgtttacaatttcaggtggcacttttcggggaaatgtgcgcggaacccctatttgtt
tatttttctaaatacattcaaatatgtatccgctcatgaattaattcttagaaaaactcatcga
gcatcaaatgaaactgcaatttattcatatcaggattatcaataccatatttttgaaaaagccg
tttctgtaatgaaggagaaaactcaccgaggcagttccataggatggcaagatcctggtatcgg
tctgcgattccgactcgtccaacatcaatacaacctattaatttcccctcgtcaaaaataaggt
tatcaagtgagaaatcaccatgagtgacgactgaatccggtgagaatggcaaaagtttatgcat
ttctttccagacttgttcaacaggccagccattacgctcgtcatcaaaatcactcgcatcaacc
aaaccgttattcattcgtgattgcgcctgagcgagacgaaatacgcgatcgctgttaaaggac
aattacaaacaggaatcgaatgcaaccggcgcaggaacactgccagcgcatcaacaatattttc
acctgaatcaggatattcttctaatacctggaatgctgttttcccggggatcgcagtggtgagt
aaccatgcatcatcaggagtacggataaaatgcttgatggtcggaagaggcataaattccgtca
gccagtttagtctgaccatctcatctgtaacatcattggcaacgctacctttgccatgtttcag
aaacaactctggcgcatcgggcttcccatacaatcgatagattgtcgcacctgattgcccgaca
ttatcgcgagcccatttatacccatataaatcagcatccatgttggaatttaatcgcggcctag
agcaagacgtttccgttgaatatggctcataacacccttgtattactgtttatgtaagcaga
cagttttattgttcatgaccaaaatcccttaacgtgagttttcgttccactgagcgtcagaccc
cgtagaaaagatcaaaggatcttcttgagatcctttttttctgcgcgtaatctgctgcttgcaa
acaaaaaaaccaccgctaccagcggtggtttgtttgccggatcaagagctaccaactctttttc
cgaaggtaactggcttcagcagagcgcagataccaaatactgtccttctagtgtagccgtagtt
aggccaccacttcaagaactctgtagcaccgcctacatacctcgctctgctaatcctgttacca
gtggctgctgccagtggcgataagtcgtgtcttaccgggttggactcaagacgatagttaccgg
ataaggcgcagcggtcgggctgaacggggggttcgtgcacacagcccagcttggagcgaacgac
ctacaccgaactgagatacctacagcgtgagctatgagaaagcgccacgcttcccgaagggaga
aaggcggacaggtatccggtaagcggcagggtcggaacaggagagcgcacgagggagcttccag
ggggaaacgcctggtatctttatagtcctgtcgggtttcgccacctctgacttgagcgtcgatt
tttgtgatgctcgtcaggggggcggagcctatggaaaaacgccagcaacgcggcctttttacgg
ttcctggccttttgctggccttttgctcacatgttctttcctgcgttatcccctgattctgtgg
ataaccgtattaccgcctttgagtgagctgataccgctcgccgcagccgaacgaccgagcgcag
cgagtcagtgagcgaggaagcggaagagcgcctgatgcggtattttctccttacgcatctgtgc
ggtatttcacaccgcatatatggtgcactctcagtacaatctgctctgatgccgcatagttaag
ccagtatacactccgctatcgctacgtgactgggtcatggctgcgccccgacacccgccaacac
ccgctgacgcgccctgacgggcttgtctgctcccggcatccgcttacagacaagctgtgaccgt
ctccgggagctgcatgtgtcagaggttttcaccgtcatcaccgaaacgcgcgaggcagctgcgg
taaagctcatcagcgtggtcgtgaagcgattcacagatgtctgcctgttcatccgcgtccagct
cgttgagtttctccagaagcgttaatgtctggcttctgataaagcgggccatgttaagggcggt
ttttcctgtttggtcactgatgcctccgtgtaaggggggatttctgttcatggggtaatgata
```

Figure 52B

Nucleotide sequence of pDu47-3

```
ccgatgaaacgagagaggatgctcacgatacgggttactgatgatgaacatgcccggttactgg
aacgttgtgagggtaaacaactggcggtatggatgcggcgggaccagagaaaaatcactcaggg
tcaatgccagcgcttcgttaatacagatgtaggtgttccacagggtagccagcagcatcctgcg
atgcagatccggaacataatggtgcagggcgctgacttccgcgtttccagactttacgaaacac
ggaaaccgaagaccattcatgttgttgctcaggtcgcagacgttttgcagcagcagtcgcttca
cgttcgctcgcgtatcggtgattcattctgctaaccagtaaggcaacccgccagcctagccgg
gtcctcaacgacaggagcacgatcatgcgcacccgtggggccgccatgccggcgataatggcct
gcttctcgccgaaacgtttggtggcgggaccagtgacgaaggcttgagcgagggcgtgcaagat
tccgaataccgcaagcgacaggccgatcatcgtcgcgctccagcgaaagcggtcctcgccgaaa
atgacccagagcgctgccggcacctgtcctacgagttgcatgataaagaagacagtcataagtg
cggcgacgatagtcatgccccgcgcccaccggaaggagctgactgggttgaaggctctcaaggg
catcggtcgagatcccggtgcctaatgagtgagctaacttacattaattgcgttgcgctcactg
cccgctttccagtcgggaaacctgtcgtgccagctgcattaatgaatcggccaacgcgcgggga
gaggcggtttgcgtattgggcgccagggtggtttttcttttcaccagtgagacgggcaacagct
gattgcccttcaccgcctggccctgagagagttgcagcaagcggtccacgctggtttgccccag
caggcgaaaatcctgtttgatggtggttaacggcgggatataacatgagctgtcttcggtatcg
tcgtatcccactaccgagatatccgcaccaacgcgcagcccggactcggtaatggcgcgcattg
cgcccagcgccatctgatcgttggcaaccagcatcgcagtgggaacgatgccctcattcagcat
ttgcatggtttgttgaaaaccggacatggcactccagtcgccttcccgttccgctatcggctga
atttgattgcgagtgagatatttatgccagccagccagacgcagacgcgccgagacagaactta
atgggcccgctaacagcgcgatttgctggtgacccaatgcgaccagatgctccacgcccagtcg
cgtaccgtcttcatgggagaaaataatactgttgatgggtgtctggtcagagacatcaagaaat
aacgccggaacattagtgcaggcagcttccacagcaatggcatcctggtcatccagcggatagt
taatgatcagcccactgacgcgttgcgcgagaagattgtgcaccgccgctttacaggcttcgac
gccgcttcgttctaccatcgacaccaccacgctggcacccagttgatcggcgcgagatttaatc
gccgcgacaatttgcgacggcgcgtgcagggccagactggaggtggcaacgccaatcagcaacg
actgtttgcccgccagttgttgtgccacgcggttgggaatgtaattcagctccgccatcgccgc
ttccacttttttcccgcgttttcgcagaaacgtggctggcctggttcaccacgcgggaaacggtc
tgataagagacaccggcatactctgcgacatcgtataacgttactggtttcacattcaccaccc
tgaattgactctcttccgggcgctatcatgccataccgcgaaaggttttgcgccattcgatggt
gtccgggatctcgacgctctcccttatgcgactcctgcattaggaagcagcccagtagtaggtt
gaggccgttgagcaccgccgccgcaaggaatggtgcatgcaaggagatggcgcccaacagtccc
ccggccacggggcctgccaccatacccacgccgaaacaagcgctcatgagcccgaagtggcgag
cccgatcttccccatcggtgatgtcggcgatataggcgccagcaaccgcacctgtggcgccggt
gatgccggccacgatgcgtccggcgtagaggatcgagatctcgatcccgcgaaattaatacgac
tcactatagggaattgtgagcggataacaattcccctctagaaataattttgtttaactttaa
gaaggagatatacatatgaccgaagctcgtcgttctgcgaactacgaacctaacagctgggact
atgattacctgctgtcctccgacacggacgagtccatcgaagtatacaaagacaaagcgaaaaa
gctggaagccgaagttcgtcgcgagattaataacgaaaaagcagaatttctgaccctgctggaa
ctgattgacaacgtccagcgcctgggcctgggttaccgtttcgagtctgatatccgtggtgcgc
tggatcgcttcgttcctccggcggcttcgatgcggtaaccaagacttccctgcacggtacggc
actgtctttccgtctgctgcgtcaacacggttttgaggtttctcaggaagcgttcagcggcttc
aaagaccaaaacggcaacttcctggagaacctgaaggaagatatcaaagctatcctgagcctgt
```

Figure 52C

Nucleotide sequence of pDu47-3

```
acgaggccagcttcctggctctggaaggcgaaaacatcctggacgaggcgaaggttttcgcaat
ctctcatctgaaagaactgtctgaagaaaagatcggtaaagagctggcagaacaggtgaaccat
gcactggaactgccactgcatcgccgtactcagcgtctggaagcagtatggtctatcgaggcct
accgtaaaaaggaggacgcgaatcaggttctgctggagctggcaattctggattacaacatgat
ccagtctgtataccagcgtgatctgcgtgaaacgtcccgttggtggcgtcgtgtgggtctggcg
accaaactgcactttgctcgtgaccgcctgattgagagcttctactgggccgtgggtgtagcat
tcgaaccgcaatactccgactgccgtaactccgtcgcaaaaatgttttctttcgtaaccattat
cgacgatatctacgatgtatacggcaccctggacgaactggagctgtttactgatgcagttgag
cgttgggacgtaaacgccatcaacgacctgccggattacatgaaactgtgctttctggctctgt
ataacactattaacgaaatcgcctacgacaacctgaaagataaaggtgagaacatcctgccgta
tctgaccaaagcctgggctgacctgtgcaacgctttcctgcaagaagccaagtggctgtacaac
aaatctactccgacctttgacgactacttcggcaacgcatggaaatcctcttctggcccgctgc
aactggtgttcgcttacttcgctgtcgtgcagaacattaaaaaggaagagatcgaaaacctgca
aaaataccatgacaccatctctcgtccttcccatatcttccgtctgtgcaatgacctggctagc
gcgtctgcggaaattgcgcgtggtgaaaccgcaaatagcgtttcttgttacatgcgcactaaag
gtatctccgaagaactggctaccgaaagcgtgatgaatctgatcgatgaaacctggaaaaagat
gaacaaggaaaaactgggtggtagcctgttcgcgaaaccgttcgtggaaaccgcgatcaacctg
gcacgtcaatctcactgcacttatcataacggcgacgcgcatacctctccggatgagctgaccc
gcaaacgcgttctgtctgtaatcactgaaccgattctgccgtttgaacgctaaggatccgaatt
cgagctccgtcgacaagcttgcggccgcactcgagcaccaccaccaccactgagatccggc
tgctaacaaagcccgaaaggaagctgagttggctgctgccaccgctgagcaataactagcataa
ccccttggggcctctaaacgggtcttgaggggttttttgctgaaaggaggaactatatccggat
```

Figure 53

Amino acid sequence of *P.alba* TRC (-4) (SEQ ID NO:138)

```
METEARRSANYEPNSWDYDYLLSSDTDESIEVYKDKAKKLEAEVRREINNEKAEFLTLLELIDN
VQRLGLGYRFESDIRGALDRFVSSGGFDAVTKTSLHGTALSFRLLRQHGFEVSQEAFSGFKDQN
GNFLENLKEDIKAILSLYEASFLALEGENILDEAKVFAISHLKELSEEKIGKELAEQVNHALEL
PLHRRTQRLEAVWSIEAYRKKEDANQVLLELAILDYNMIQSVYQRDLRETSRWWRRVGLATKLH
FARDRLIESFYWAVGVAFEPQYSDCRNSVAKMFSFVTIIDDIYDVYGTLDELELFTDAVERWDV
NAINDLPDYMKLCFLALYNTINEIAYDNLKDKGENILPYLTKAWADLCNAFLQEAKWLYNKSTP
TFDDYFGNAWKSSSGPLQLVFAYFAVVQNIKKEEIENLQKYHDTISRPSHIFRLCNDLASASAE
IARGETANSVSCYMRTKGISEELATESVMNLIDETWKKMNKEKLGGSLFAKPFVETAINLARQS
HCTYHNGDAHTSPDELTRKRVLSVITEPILPFER
```

Figure 54A

Nucleotide sequence of pDu47-4 (SEQ ID NO:139)

```
tggcgaatgggacgcgccctgtagcggcgcattaagcgcggcgggtgtggtggttacgcgcagc
gtgaccgctacacttgccagcgccctagcgcccgctcctttcgctttcttccttcctttctcg
ccacgttcgccggctttccccgtcaagctctaaatcgggggctcccttttagggttccgatttag
tgctttacggcacctcgaccccaaaaaacttgattagggtgatggttcacgtagtgggccatcg
ccctgatagacggttttttcgcccttttgacgttggagtccacgttctttaatagtggactcttgt
tccaaactggaacaacactcaaccctatctcggtctattcttttgatttataagggatttttgcc
gatttcggcctattggttaaaaaatgagctgatttaacaaaaatttaacgcgaattttaacaaa
atattaacgtttacaatttcaggtggcacttttcggggaaatgtgcgcggaaccccctattttgtt
tatttttctaaatacattcaaatatgtatccgctcatgaattaattcttagaaaaactcatcga
gcatcaaatgaaactgcaatttattcatatcaggattatcaataccatatttttgaaaaagccg
tttctgtaatgaaggagaaaactcaccgaggcagttccataggatggcaagatcctggtatcgg
tctgcgattccgactcgtccaacatcaatacaacctattaatttccctcgtcaaaaataaggt
tatcaagtgagaaatcaccatgagtgacgactgaatccggtgagaatggcaaaagtttatgcat
ttctttccagacttgttcaacaggccagccattacgctcgtcatcaaaatcactcgcatcaacc
aaaccgttattcattcgtgattgcgcctgagcgagacgaaatacgcgatcgctgttaaaaggac
aattacaaacaggaatcgaatgcaaccggcgcaggaacactgccagcgcatcaacaatattttc
acctgaatcaggatattcttctaatacctggaatgctgttttcccggggatcgcagtggtgagt
aaccatgcatcatcaggagtacggataaaatgcttgatggtcggaagaggcataaattccgtca
gccagtttagtctgaccatctcatctgtaacatcattggcaacgctacctttgccatgtttcag
aaacaactctggcgcatcgggcttcccatacaatcgatagattgtcgcacctgattgcccgaca
ttatcgcgagcccatttatacccatataaatcagcatccatgttggaatttaatcgcggcctag
agcaagacgtttcccgttgaatatggctcataacacccttgtattactgtttatgtaagcaga
cagtttttattgttcatgaccaaaatcccttaacgtgagttttcgttccactgagcgtcagaccc
cgtagaaaagatcaaaggatcttcttgagatcctttttttctgcgcgtaatctgctgcttgcaa
acaaaaaaaccaccgctaccagcggtggtttgtttgccggatcaagagctaccaactctttttc
cgaaggtaactggcttcagcagagcgcagataccaaatactgtccttctagtgtagccgtagtt
aggccaccacttcaagaactctgtagcaccgcctacatacctcgctctgctaatcctgttacca
gtggctgctgccagtggcgataagtcgtgtcttaccgggttggactcaagacgatagttaccgg
ataaggcgcagcggtcgggctgaacggggggttcgtgcacacagcccagcttggagcgaacgac
ctacaccgaactgagatacctacagcgtgagctatgagaaagcgccacgcttcccgaagggaga
aaggcggacaggtatccggtaagcggcagggtcggaacaggagagcgcacgagggagcttccag
ggggaaacgcctggtatctttatagtcctgtcgggtttcgccacctctgacttgagcgtcgatt
tttgtgatgctcgtcaggggggcggagcctatggaaaaacgccagcaacgcggcctttttacgg
ttcctggccttttgctggccttttgctcacatgttctttcctgcgttatcccctgattctgtgg
ataaccgtattaccgcctttgagtgagctgataccgctcgccgcagccgaacgaccgagcgcag
cgagtcagtgagcgaggaagcggaagagcgcctgatgcggtattttctccttacgcatctgtgc
ggtatttcacaccgcatatatggtgcactctcagtacaatctgctctgatgccgcatagttaag
ccagtatacactccgctatcgctacgtgactgggtcatggctgcgccccgacacccgccaacac
ccgctgacgcgccctgacgggcttgtctgctcccggcatccgcttacagacaagctgtgaccgt
ctccgggagctgcatgtgtcagaggttttcaccgtcatcaccgaaacgcgcgaggcagctgcgg
taaagctcatcagcgtggtcgtgaagcgattcacagatgtctgcctgttcatccgcgtccagct
cgttgagtttctccagaagcgttaatgtctggcttctgataaagcgggccatgttaagggcggt
ttttcctgtttggtcactgatgcctccgtgtaagggggatttctgttcatgggggtaatgata
```

Figure 54B

Nucleotide sequence of pDu47-4

```
ccgatgaaacgagagaggatgctcacgatacgggttactgatgatgaacatgcccggttactgg
aacgttgtgagggtaaacaactggcggtatggatgcggcgggaccagagaaaaatcactcaggg
tcaatgccagcgcttcgttaatacagatgtaggtgttccacagggtagccagcagcatcctgcg
atgcagatccggaacataatggtgcagggcgctgacttccgcgtttccagactttacgaaacac
ggaaaccgaagaccattcatgttgttgctcaggtcgcagacgttttgcagcagcagtcgcttca
cgttcgctcgcgtatcggtgattcattctgctaaccagtaaggcaacccgccagcctagccgg
gtcctcaacgacaggagcacgatcatgcgcacccgtggggccgccatgccggcgataatggcct
gcttctcgccgaaacgtttggtggcgggaccagtgacgaaggcttgagcgagggcgtgcaagat
tccgaataccgcaagcgacaggccgatcatcgtcgcgctccagcgaaagcggtcctcgccgaaa
atgacccagagcgctgccggcacctgtcctacgagttgcatgataaagaagacagtcataagtg
cggcgacgatagtcatgccccgcgccaccggaaggagctgactgggttgaaggctctcaaggg
catcggtcgagatcccggtgcctaatgagtgagctaacttacattaattgcgttgcgctcactg
cccgctttccagtcgggaaacctgtcgtgccagctgcattaatgaatcggccaacgcgcggga
gaggcggtttgcgtattgggcgccagggtggttttcttttcaccagtgagacgggcaacagct
gattgcccttcaccgcctggccctgagagagttgcagcaagcggtccacgctggtttgcccag
caggcgaaaatcctgtttgatggtggttaacggcgggatataacatgagctgtcttcggtatcg
tcgtatcccactaccgagatatccgcaccaacgcgcagcccggactcggtaatggcgcgcattg
cgcccagcgccatctgatcgttggcaaccagcatcgcagtgggaacgatgccctcattcagcat
ttgcatggttttgttgaaaaccggacatggcactccagtcgccttcccgttccgctatcggctga
atttgattgcgagtgagatatttatgccagccagccagacgcagacgcgccgagacagaactta
atgggcccgctaacagcgcgatttgctggtgacccaatgcgaccagatgctccacgccagtcg
cgtaccgtcttcatgggagaaaataatactgttgatgggtgtctggtcagagacatcaagaaat
aacgccggaacattagtgcaggcagcttccacagcaatggcatcctggtcatccagcggatagt
taatgatcagcccactgacgcgttgcgcgagaagattgtgcaccgccgctttacaggcttcgac
gccgcttcgttctaccatcgacaccaccacgctggcacccagttgatcggcgcgagatttaatc
gccgcgacaatttgcgacggcgcgtgcagggccagactggaggtggcaacgccaatcagcaacg
actgtttgcccgccagttgttgtgccacgcggttgggaatgtaattcagctccgccatcgccgc
ttccacttttcccgcgttttcgcagaaacgtggctggcctggttcaccacgcgggaaacggtc
tgataagagacaccggcatactctgcgacatcgtataacgttactggtttcacattcaccaccc
tgaattgactctcttccgggcgctatcatgccataccgcgaaaggttttgcgccattcgatggt
gtccgggatctcgacgctctcccttatgcgactcctgcattaggaagcagcccagtagtaggtt
gaggccgttgagcaccgccgccgcaaggaatggtgcatgcaaggagatggcgcccaacagtccc
ccggccacggggcctgccaccatacccacgccgaaacaagcgctcatgagcccgaagtggcgag
cccgatcttccccatcggtgatgtcggcgatataggcgccagcaaccgcacctgtggcgccggt
gatgccggccacgatgcgtccggcgtagaggatcgagatctcgatcccgcgaaattaatacgac
tcactatagggaattgtgagcggataacaattcccctctagaaataattttgtttaactttaa
gaaggagatatacatatggaaaccgaagctcgtcgttctgcgaactacgaacctaacagctggg
actatgattacctgctgtcctccgacacggacgagtccatcgaagtatacaaagacaaagcgaa
aaagctggaagccgaagttcgtcgcgagattaataacgaaaaagcagaatttctgaccctgctg
gaactgattgacaacgtccagcgcctgggcctgggttaccgtttcgagtctgatatccgtggtg
cgctggatcgcttcgtttcctccggcggcttcgatgcggtaaccaagacttccctgcacggtac
ggcactgtctttccgtctgctgcgtcaacacggttttgaggtttctcaggaagcgttcagcggc
ttcaaagaccaaaacggcaacttcctggagaacctgaaggaagatatcaaagctatcctgagcc
```

Figure 54C

Nucleotide sequence of pDu47-4

```
tgtacgaggccagcttcctggctctggaaggcgaaaacatcctggacgaggcgaaggttttcgc
aatctctcatctgaaagaactgtctgaagaaaagatcggtaaagagctggcagaacaggtgaac
catgcactggaactgccactgcatcgccgtactcagcgtctggaagcagtatggtctatcgagg
cctaccgtaaaaaggaggacgcgaatcaggttctgctggagctggcaattctggattacaacat
gatccagtctgtataccagcgtgatctgcgtgaaacgtcccgttggtggcgtcgtgtgggtctg
gcgaccaaactgcactttgctcgtgaccgcctgattgagagcttctactgggccgtgggtgtag
cattcgaaccgcaatactccgactgccgtaactccgtcgcaaaaatgttttctttcgtaaccat
tatcgacgatatctacgatgtatacggcaccctggacgaactggagctgtttactgatgcagtt
gagcgttgggacgtaaacgccatcaacgacctgccggattacatgaaactgtgctttctggctc
tgtataacactattaacgaaatcgcctacgacaacctgaaagataaaggtgagaacatcctgcc
gtatctgaccaaagcctgggctgacctgtgcaacgctttcctgcaagaagccaagtggctgtac
aacaaatctactccgacctttgacgactacttcggcaacgcatggaaatcctcttctggcccgc
tgcaactggtgttcgcttacttcgctgtcgtgcagaacattaaaaaggaagagatcgaaaacct
gcaaaaataccatgacaccatctctcgtccttcccatatcttccgtctgtgcaatgacctggct
agcgcgtctgcggaaattgcgcgtggtgaaaccgcaaatagcgtttcttgttacatgcgcacta
aaggtatctccgaagaactggctaccgaaagcgtgatgaatctgatcgatgaaacctggaaaaa
gatgaacaaggaaaaactgggtggtagcctgttcgcgaaaccgttcgtggaaaccgcgatcaac
ctggcacgtcaatctcactgcacttatcataacggcgacgcgcatacctctccggatgagctga
cccgcaaacgcgttctgtctgtaatcactgaaccgattctgccgtttgaacgctaaggatccga
attcgagctccgtcgacaagcttgcggccgcactcgagcaccaccaccaccactgagatcc
ggctgctaacaaagcccgaaaggaagctgagttggctgctgccaccgctgagcaataactagca
taaccccttggggcctctaaacgggtcttgaggggttttttgctgaaaggaggaactatatccg
gat
```

Figure 55

Amino acid sequence of *P.alba* TRC (-5) (SEQ ID NO:140)

MTETEARRSANYEPNSWDYDYLLSSDTDESIEVYKDKAKKLEAEVRREINNEKAEFLTLLELID
NVQRLGLGYRFESDIRGALDRFVSSGGFDAVTKTSLHGTALSFRLLRQHGFEVSQEAFSGFKDQ
NGNFLENLKEDIKAILSLYEASFLALEGENILDEAKVFAISHLKELSEEKIGKELAEQVNHALE
LPLHRRTQRLEAVWSIEAYRKKEDANQVLLELAILDYNMIQSVYQRDLRETSRWWRRVGLATKL
HFARDRLIESFYWAVGVAFEPQYSDCRNSVAKMFSFVTIIDDIYDVYGTLDELELFTDAVERWD
VNAINDLPDYMKLCFLALYNTINEIAYDNLKDKGENILPYLTKAWADLCNAFLQEAKWLYNKST
PTFDDYFGNAWKSSSGPLQLVFAYFAVVQNIKKEEIENLQKYHDTISRPSHIFRLCNDLASASA
EIARGETANSVSCYMRTKGISEELATESVMNLIDETWKKMNKEKLGGSLFAKPFVETAINLARQ
SHCTYHNGDAHTSPDELTRKRVLSVITEPILPFER

Figure 56A

Nucleotide sequence of pDu47-5 (SEQ ID NO:141)

tggcgaatgggacgcgccctgtagcggcgcattaagcgcggcgggtgtggtggttacgcgcagc
gtgaccgctacacttgccagcgccctagcgcccgctcctttcgctttcttcccttcctttctcg
ccacgttcgccggctttccccgtcaagctctaaatcgggggctcccctttagggttccgatttag
tgctttacggcacctcgaccccaaaaaacttgatttagggtgatggttcacgtagtgggccatcg
ccctgatagacggtttttcgccctttgacgttggagtccacgttctttaatagtggactcttgt
tccaaactggaacaacactcaaccctatctcggtctattcttttgatttataagggattttgcc
gatttcggcctattggttaaaaaatgagctgatttaacaaaaatttaacgcgaattttaacaaa
atattaacgtttacaatttcaggtggcacttttcggggaaatgtgcgcggaacccctatttgtt
tatttttctaaatacattcaaatatgtatccgctcatgaattaattcttagaaaaactcatcga
gcatcaaatgaaactgcaatttattcatatcaggattatcaataccatattttgaaaaagccg
tttctgtaatgaaggagaaaactcaccgaggcagttccataggatggcaagatcctggtatcgg
tctgcgattccgactcgtccaacatcaatacaacctattaatttcccctcgtcaaaaataaggt
tatcaagtgagaaatcaccatgagtgacgactgaatccggtgagaatggcaaaagtttatgcat
ttctttccagacttgttcaacaggccagccattacgctcgtcatcaaaatcactcgcatcaacc
aaaccgttattcattcgtgattgcgcctgagcgagacgaaatacgcgatcgctgttaaaaggac
aattacaaacaggaatcgaatgcaaccggcgcaggaacactgccagcgcatcaacaatattttc
acctgaatcaggatattcttctaatacctggaatgctgttttcccggggatcgcagtggtgagt
aaccatgcatcatcaggagtacggataaaatgcttgatggtcggaagaggcataaattccgtca
gccagtttagtctgaccatctcatctgtaacatcattggcaacgctacctttgccatgtttcag
aaacaactctggcgcatcggcttcccatacaatcgatagattgtcgcacctgattgcccgaca
ttatcgcgagcccatttatacccatataaatcagcatccatgttggaatttaatcgcggcctag
agcaagacgtttccgttgaatatggctcataacacccctgtattactgtttatgtaagcaga
cagttttattgttcatgaccaaaatcccttaacgtgagttttcgttccactgagcgtcagaccc
cgtagaaaagatcaaaggatcttcttgagatcctttttttctgcgcgtaatctgctgcttgcaa
acaaaaaaaccaccgctaccagcggtggtttgtttgccggatcaagagctaccaactctttttc
cgaaggtaactggcttcagcagagcgcagataccaaatactgtccttctagtgtagccgtagtt
aggccaccacttcaagaactctgtagcaccgcctacatacctcgctctgctaatcctgttacca
gtggctgctgccagtggcgataagtcgtgtcttaccgggttggactcaagacgatagttaccgg
ataaggcgcagcggtcgggctgaacggggggttcgtgcacacagcccagcttggagcgaacgac
ctacaccgaactgagatacctacagcgtgagctatgagaaagcgccacgcttccgaagggaga
aaggcggacaggtatccggtaagcggcagggtcggaacaggagagcgcacgagggagcttccag
ggggaaacgcctggtatctttatagtcctgtcgggtttcgccacctctgacttgagcgtcgatt
tttgtgatgctcgtcagggggcggagcctatggaaaaacgccagcaacgcggcctttttacgg
ttcctggccttttgctggccttttgctcacatgttctttcctgcgttatccctgattctgtgg
ataaccgtattaccgcctttgagtgagctgataccgctcgccgcagccgaacgaccgagcgcag
cgagtcagtgagcgaggaagcggaagagcgcctgatgcggtattttctccttacgcatctgtgc
ggtatttcacaccgcatatatggtgcactctcagtacaatctgctctgatgccgcatagttaag
ccagtatacactccgctatcgctacgtgactgggtcatggctgcgccccgacacccgccaacac
ccgctgacgcgccctgacgggcttgtctgctcccggcatccgcttacagacaagctgtgaccgt
ctccgggagctgcatgtgtcagaggttttcaccgtcatcaccgaaacgcgcgaggcagctgcgg
taaagctcatcagcgtggtcgtgaagcgattcacagatgtctgcctgttcatccgcgtccagct
cgttgagtttctccagaagcgttaatgtctggcttctgataaagcgggccatgttaagggcggt
ttttcctgtttggtcactgatgcctccgtgtaagggggatttctgttcatggggtaatgata

Figure 56B

Nucleotide sequence of pDu47-5

```
ccgatgaaacgagagaggatgctcacgatacgggttactgatgatgaacatgcccggttactgg
aacgttgtgagggtaaacaactggcggtatggatgcggcgggaccagagaaaaatcactcaggg
tcaatgccagcgcttcgttaatacagatgtaggtgttccacagggtagccagcagcatcctgcg
atgcagatccggaacataatggtgcaggcgctgacttccgcgtttccagactttacgaaacac
ggaaaccgaagaccattcatgttgttgctcaggtcgcagacgttttgcagcagcagtcgcttca
cgttcgctcgcgtatcggtgattcattctgctaaccagtaaggcaaccccgccagcctagccgg
gtcctcaacgacaggagcacgatcatgcgcacccgtggggccgccatgccggcgataatggcct
gcttctcgccgaaacgtttggtggcgggaccagtgacgaaggcttgagcgagggcgtgcaagat
tccgaataccgcaagcgacaggccgatcatcgtcgcgctccagcgaaagcggtcctcgccgaaa
atgacccagagcgctgccggcacctgtcctacgagttgcatgataaagaagacagtcataagtg
cggcgacgatagtcatgccccgcgcccaccggaaggagctgactgggttgaaggctctcaaggg
catcggtcgagatcccggtgcctaatgagtgagctaacttacattaattgcgttgcgctcactg
cccgctttccagtcgggaaacctgtcgtgccagctgcattaatgaatcggccaacgcgcgggga
gaggcggtttgcgtattgggcgccagggtggttttcttttcaccagtgagacgggcaacagct
gattgcccttcaccgcctggccctgagagagttgcagcaagcggtccacgctggtttgccccag
caggcgaaaatcctgtttgatggtggttaacggcgggatataacatgagctgtcttcggtatcg
tcgtatcccactaccgagatatccgcaccaacgcgcagcccggactcggtaatggcgcgcattg
cgcccagcgccatctgatcgttggcaaccagcatcgcagtgggaacgatgccctcattcagcat
ttgcatggtttgttgaaaaccggacatggcactccagtcgccttcccgttccgctatcggctga
atttgattgcgagtgagatatttatgccagccagccagacgcagacgcgccgagacagaactta
atgggcccgctaacagcgcgatttgctggtgacccaatgcgaccagatgctccacgcccagtcg
cgtaccgtcttcatgggagaaaataatactgttgatgggtgtctggtcagagacatcaagaaat
aacgccggaacattagtgcaggcagcttccacagcaatggcatcctggtcatccagcggatagt
taatgatcagcccactgacgcgttgcgcgagaagattgtgcaccgccgctttacaggcttcgac
gccgcttcgttctaccatcgacaccaccacgctggcacccagttgatcggcgcgagatttaatc
gccgcgacaatttgcgacggcgcgtgcagggccagactggaggtggcaacgccaatcagcaacg
actgtttgcccgccagttgttgtgccacgcggttgggaatgtaattcagctccgccatcgccgc
ttccacttttttcccgcgttttcgcagaaacgtggctggcctggttcaccacgcgggaaacggtc
tgataagagacaccggcatactctgcgacatcgtataacgttactggtttcacattcaccaccc
tgaattgactctcttccgggcgctatcatgccataccgcgaaaggttttgcgccattcgatggt
gtccgggatctcgacgctctcccttatgcgactcctgcattaggaagcagcccagtagtaggtt
gaggccgttgagcaccgccgccgcaaggaatggtgcatgcaaggagatggcgcccaacagtccc
ccggccacggggcctgccaccatacccacgccgaaacaagcgctcatgagcccgaagtggcgag
cccgatcttccccatcggtgatgtcggcgatataggcgccagcaaccgcacctgtggcgccggt
gatgccggccacgatgcgtccggcgtagaggatcgagatctcgatcccgcgaaattaatacgac
tcactataggggaattgtgagcggataacaattcccctctagaaataattttgtttaactttaa
gaaggagatatacatatgactgaaaccgaagctcgtcgttctgcgaactacgaacctaacagct
gggactatgattacctgctgtcctcgacacggacgagtccatcgaagtatacaaagacaaagc
gaaaaagctggaagccgaagttcgtcgcgagattaataacgaaaaagcagaatttctgaccctg
ctggaactgattgacaacgtccagcgcctgggcctgggttaccgtttcgagtctgatatccgtg
gtgcgctggatcgcttcgtttcctccggcggcttcgatgcggtaaccaagacttccctgcacgg
tacggcactgtctttccgtctgctgcgtcaacacggttttgaggtttctcaggaagcgttcagc
ggcttcaaagaccaaaacggcaacttcctggagaacctgaaggaagatatcaaagctatcctga
```

Figure 56C

Nucleotide sequence of pDu47-5

```
gcctgtacgaggccagcttcctggctctggaaggcgaaaacatcctggacgaggcgaaggtttt
cgcaatctctcatctgaaagaactgtctgaagaaaagatcggtaaagagctggcagaacaggtg
aaccatgcactggaactgccactgcatcgccgtactcagcgtctggaagcagtatggtctatcg
aggcctaccgtaaaaaggaggacgcgaatcaggttctgctggagctggcaattctggattacaa
catgatccagtctgtataccagcgtgatctgcgtgaaacgtcccgttggtggcgtcgtgtgggt
ctggcgaccaaactgcactttgctcgtgaccgcctgattgagagcttctactgggccgtgggtg
tagcattcgaaccgcaatactccgactgccgtaactccgtcgcaaaaatgttttctttcgtaac
cattatcgacgatatctacgatgtatacggcaccctggacgaactggagctgtttactgatgca
gttgagcgttgggacgtaaacgccatcaacgacctgccggattacatgaaactgtgctttctgg
ctctgtataacactattaacgaaatcgcctacgacaacctgaaagataaaggtgagaacatcct
gccgtatctgaccaaagcctgggctgacctgtgcaacgctttcctgcaagaagccaagtggctg
tacaacaaatctactccgacctttgacgactacttcggcaacgcatggaaatcctcttctggcc
cgctgcaactggtgttcgcttacttcgctgtcgtgcagaacattaaaaaggaagagatcgaaaa
cctgcaaaaataccatgacaccatctctcgtccttcccatatcttccgtctgtgcaatgacctg
gctagcgcgtctgcggaaattgcgcgtggtgaaaccgcaaatagcgtttcttgttacatgcgca
ctaaaggtatctccgaagaactggctaccgaaagcgtgatgaatctgatcgatgaaacctggaa
aaagatgaacaaggaaaaactgggtggtagcctgttcgcgaaaccgttcgtggaaaccgcgatc
aacctggcacgtcaatctcactgcacttatcataacggcgacgcgcatacctctccggatgagc
tgacccgcaaacgcgttctgtctgtaatcactgaaccgattctgccgtttgaacgctaaggatc
cgaattcgagctccgtcgacaagcttgcggccgcactcgagcaccaccaccaccaccactgaga
tccggctgctaacaaagcccgaaaggaagctgagttggctgctgccaccgctgagcaataacta
gcataaccccttggggcctctaaacgggtcttgaggggttttttgctgaaaggaggaactatat
ccggat
```

Figure 57

Amino acid sequence of *P.alba* TRC (-6) (SEQ ID NO:142)

```
METETEARRSANYEPNSWDYDYLLSSDTDESIEVYKDKAKKLEAEVRREINNEKAEFLTLLELI
DNVQRLGLGYRFESDIRGALDRFVSSGGFDAVTKTSLHGTALSFRLLRQHGFEVSQEAFSGFKD
QNGNFLENLKEDIKAILSLYEASFLALEGENILDEAKVFAISHLKELSEEKIGKELAEQVNHAL
ELPLHRRTQRLEAVWSIEAYRKKEDANQVLLELAILDYNMIQSVYQRDLRETSRWWRRVGLATK
LHFARDRLIESFYWAVGVAFEPQYSDCRNSVAKMFSFVTIIDDIYDVYGTLDELELFTDAVERW
DVNAINDLPDYMKLCFLALYNTINEIAYDNLKDKGENILPYLTKAWADLCNAFLQEAKWLYNKS
TPTFDDYFGNAWKSSSGPLQLVFAYFAVVQNIKKEEIENLQKYHDTISRPSHIFRLCNDLASAS
AEIARGETANSVSCYMRTKGISEELATESVMNLIDETWKKMNKEKLGGSLFAKPFVETAINLAR
QSHCTYHNGDAHTSPDELTRKRVLSVITEPILPFER
```

Figure 58A

Nucleotide sequence of pDu47-6 (SEQ ID NO:143)

```
tggcgaatgggacgcgccctgtagcggcgcattaagcgcggcgggtgtggtggttacgcgcagc
gtgaccgctacacttgccagcgccctagcgcccgctcctttcgctttcttccctttcctttctcg
ccacgttcgccggctttccccgtcaagctctaaatcgggggctccctttagggttccgatttag
tgctttacggcacctcgaccccaaaaaacttgattagggtgatggttcacgtagtgggccatcg
ccctgatagacggttttttcgccctttgacgttggagtccacgttctttaatagtggactcttgt
tccaaactggaacaacactcaaccctatctcggtctattcttttgatttataagggattttgcc
gatttcggcctattggttaaaaaatgagctgatttaacaaaaatttaacgcgaattttaacaaa
atattaacgtttacaatttcaggtggcacttttcggggaaatgtgcgcggaacccctatttgtt
tatttttctaaatacattcaaatatgtatccgctcatgaattaattcttagaaaaactcatcga
gcatcaaatgaaactgcaatttattcatatcaggattatcaataccatattttgaaaaagccg
tttctgtaatgaaggagaaaactcaccgaggcagttccataggatggcaagatcctggtatcgg
tctgcgattccgactcgtccaacatcaatacaacctattaatttcccctcgtcaaaaataaggt
tatcaagtgagaaatcaccatgagtgacgactgaatccggtgagaatggcaaaagtttatgcat
ttctttccagacttgttcaacaggccagccattacgctcgtcatcaaaatcactcgcatcaacc
aaaccgttattcattcgtgattgcgcctgagcgagacgaaatacgcgatcgctgttaaaggac
aattacaaacaggaatcgaatgcaaccggcgcaggaacactgccagcgcatcaacaatattttc
acctgaatcaggatattcttctaatacctggaatgctgttttcccggggatcgcagtggtgagt
aaccatgcatcatcaggagtacggataaaatgcttgatggtcggaagaggcataaattccgtca
gccagtttagtctgaccatctcatctgtaacatcattggcaacgctacctttgccatgtttcag
aaacaactctggcgcatcgggcttcccatacaatcgatagattgtcgcacctgattgcccgaca
ttatcgcgagcccatttatacccatataaatcagcatccatgttggaatttaatcgcggcctag
agcaagacgtttcccgttgaatatggctcataacacccctttgtattactgtttatgtaagcaga
cagttttattgttcatgaccaaaatcccttaacgtgagttttcgttccactgagcgtcagaccc
cgtagaaaagatcaaaggatcttcttgagatcctttttttctgcgcgtaatctgctgcttgcaa
acaaaaaaaccaccgctaccagcggtggtttgtttgccggatcaagagctaccaactctttttc
cgaaggtaactggcttcagcagagcgcagataccaaatactgtccttctagtgtagccgtagtt
aggccaccacttcaagaactctgtagcaccgcctacatacctcgctctgctaatcctgttacca
gtggctgctgccagtggcgataagtcgtgtcttaccgggttggactcaagacgatagttaccgg
ataaggcgcagcggtcgggctgaacggggggttcgtgcacacagcccagcttggagcgaacgac
ctacaccgaactgagatacctacagcgtgagctatgagaaagcgccacgcttcccgaagggaga
aaggcggacaggtatccggtaagcggcaggtcggaacaggagagcgcacgagggagcttccag
ggggaaacgcctggtatctttatagtcctgtcgggtttcgccacctctgacttgagcgtcgatt
tttgtgatgctcgtcaggggggcggagcctatggaaaaacgccagcaacgcggcctttttacgg
ttcctggccttttgctggccttttgctcacatgttctttcctgcgttatcccctgattctgtgg
ataaccgtattaccgcctttgagtgagctgataccgctcgccgcagccgaacgaccgagcgcag
cgagtcagtgagcgaggaagcggaagagcgcctgatgcggtattttctccttacgcatctgtgc
ggtatttcacaccgcatatatggtgcactctcagtacaatctgctctgatgccgcatagttaag
ccagtatacactccgctatcgctacgtgactgggtcatggctgcgccccgacacccgccaacac
ccgctgacgcgccctgacgggcttgtctgctcccggcatccgcttacagacaagctgtgaccgt
ctccgggagctgcatgtgtcagaggttttcaccgtcatcaccgaaacgcgcgaggcagctgcgg
taaagctcatcagcgtggtcgtgaagcgattcacagatgtctgcctgttcatccgcgtccagct
cgttgagtttctccagaagcgttaatgtctggcttctgataaagcgggccatgttaagggcggt
ttttcctgtttggtcactgatgcctccgtgtaagggggatttctgttcatgggggtaatgata
```

Figure 58B

Nucleotide sequence of pDu47-6

```
ccgatgaaacgagagaggatgctcacgatacgggttactgatgatgaacatgcccggttactgg
aacgttgtgagggtaaacaactggcggtatggatgcggcgggaccagagaaaaatcactcaggg
tcaatgccagcgcttcgttaatacagatgtaggtgttccacagggtagccagcagcatcctgcg
atgcagatccggaacataatggtgcagggcgctgacttccgcgtttccagactttacgaaacac
ggaaaccgaagaccattcatgttgttgctcaggtcgcagacgttttgcagcagcagtcgcttca
cgttcgctcgcgtatcggtgattcattctgctaaccagtaaggcaaccccgccagcctagccgg
gtcctcaacgacaggagcacgatcatgcgcacccgtggggccgccatgccggcgataatggcct
gcttctcgccgaaacgtttggtggcgggaccagtgacgaaggcttgagcgagggcgtgcaagat
tccgaataccgcaagcgacaggccgatcatcgtcgcgctccagcgaaagcggtcctcgccgaaa
atgacccagagcgctgccggcacctgtcctacgagttgcatgataaagaagacagtcataagtg
cggcgacgatagtcatgccccgcgcccaccggaaggagctgactgggttgaaggctctcaaggg
catcggtcgagatcccggtgcctaatgagtgagctaacttacattaattgcgttgcgctcactg
cccgctttccagtcgggaaacctgtcgtgccagctgcattaatgaatcggccaacgcgcgggga
gaggcggtttgcgtattgggcgccagggtggttttttcttttcaccagtgagacgggcaacagct
gattgcccttcaccgcctggccctgagagagttgcagcaagcggtccacgctggtttgccccag
caggcgaaaatcctgtttgatggtggttaacggcgggatataacatgagctgtcttcggtatcg
tcgtatcccactaccgagatatccgcaccaacgcgcagcccggactcggtaatggcgcgcattg
cgcccagcgccatctgatcgttggcaaccagcatcgcagtgggaacgatgccctcattcagcat
ttgcatggtttgttgaaaaccggacatggcactccagtcgccttcccgttccgctatcggctga
atttgattgcgagtgagatatttatgccagccagccagacgcagacgcgccgagacagaactta
atgggcccgctaacagcgcgatttgctggtgacccaatgcgaccagatgctccacgcccagtcg
cgtaccgtcttcatgggagaaaataatactgttgatgggtgtctggtcagagacatcaagaaat
aacgccggaacattagtgcaggcagcttccacagcaatggcatcctggtcatccagcggatagt
taatgatcagcccactgacgcgttgcgcgagaagattgtgcaccgccgctttacaggcttcgac
gccgcttcgttctaccatcgacaccaccacgctggcacccagttgatcggcgcgagatttaatc
gccgcgacaatttgcgacggcgcgtgcagggccagactggaggtggcaacgccaatcagcaacg
actgtttgccgccagttgttgtgccacgcggttgggaatgtaattcagctccgccatcgccgc
ttccacttttttcccgcgttttcgcagaaacgtggctggcctggttcaccacgcgggaaacggtc
tgataagagacaccggcatactctgcgacatcgtataacgttactggtttcacattcaccaccc
tgaattgactctcttccgggcgctatcatgccataccgcgaaaggttttgcgccattcgatggt
gtccgggatctcgacgctctcccttatgcgactcctgcattaggaagcagcccagtagtaggtt
gaggccgttgagcaccgccgccgcaaggaatggtgcatgcaaggagatggcgcccaacagtccc
ccggccacggggcctgccaccatacccacgccgaaacaagcgctcatgagcccgaagtggcgag
cccgatcttccccatcggtgatgtcggcgatataggcgccagcaaccgcacctgtggcgccggt
gatgccggccacgatgcgtccggcgtagaggatcgagatctcgatcccgcgaaattaatacgac
tcactataggggaattgtgagcggataacaattcccctctagaaataattttgtttaacttta
gaaggagatatacatatggaaactgaaaccgaagctcgtcgttctgcgaactacgaacctaaca
gctgggactatgattacctgctgtcctccgacacggacgagtccatcgaagtatacaaagacaa
agcgaaaaagctggaagccgaagttcgtcgcgagattaataacgaaaagcagaatttctgacc
ctgctggaactgattgacaacgtccagcgcctgggcctgggttaccgtttcgagtctgatatcc
gtggtgcgctggatcgcttcgtttcctccggcggcttcgatgcggtaaccaagacttccctgca
cggtacggcactgtctttccgtctgctgcgtcaacacggttttgaggtttctcaggaagcgttc
agcggcttcaaagaccaaaacggcaacttcctggagaacctgaaggaagatatcaaagctatcc
```

Figure 58C

Nucleotide sequence of pDu47-6

```
tgagcctgtacgaggccagcttcctggctctggaaggcgaaaacatcctggacgaggcgaaggt
tttcgcaatctctcatctgaaagaactgtctgaagaaaagatcggtaaagagctggcagaacag
gtgaaccatgcactggaactgccactgcatcgccgtactcagcgtctggaagcagtatggtcta
tcgaggcctaccgtaaaaaggaggacgcgaatcaggttctgctggagctggcaattctggatta
caacatgatccagtctgtataccagcgtgatctgcgtgaaacgtcccgttggtggcgtcgtgtg
ggtctggcgaccaaactgcactttgctcgtgaccgcctgattgagagcttctactgggccgtgg
gtgtagcattcgaaccgcaatactccgactgccgtaactccgtcgcaaaaatgttttctttcgt
aaccattatcgacgatatctacgatgtatacggcaccctggacgaactggagctgtttactgat
gcagttgagcgttgggacgtaaacgccatcaacgacctgccggattacatgaaactgtgctttc
tggctctgtataacactattaacgaaatcgcctacgacaacctgaaagataaaggtgagaacat
cctgccgtatctgaccaaagcctgggctgacctgtgcaacgctttcctgcaagaagccaagtgg
ctgtacaacaaatctactccgacctttgacgactacttcggcaacgcatggaaatcctcttctg
gcccgctgcaactggtgttcgcttacttcgctgtcgtgcagaacattaaaaaggaagagatcga
aaacctgcaaaaataccatgacaccatctctcgtccttcccatatcttccgtctgtgcaatgac
ctggctagcgcgtctgcggaaattgcgcgtggtgaaaccgcaaatagcgtttcttgttacatgc
gcactaaaggtatctccgaagaactggctaccgaaagcgtgatgaatctgatcgatgaaacctg
gaaaaagatgaacaaggaaaaactgggtggtagcctgttcgcgaaaccgttcgtggaaaccgcg
atcaacctggcacgtcaatctcactgcacttatcataacggcgacgcgcatacctctccggatg
agctgacccgcaaacgcgttctgtctgtaatcactgaaccgattctgccgtttgaacgctaagg
atccgaattcgagctccgtcgacaagcttgcggccgcactcgagcaccaccaccaccaccactg
agatccggctgctaacaaagcccgaaaggaagctgagttggctgctgccaccgctgagcaataa
ctagcataacccttggggcctctaaacgggtcttgaggggttttttgctgaaaggaggaacta
tatccggat
```

Figure 59

Amino acid sequence of *P.alba* TRC (-7) (SEQ ID NO:144)

```
MTETETEARRSANYEPNSWDYDYLLSSDTDESIEVYKDKAKKLEAEVRREINNEKAEFLTLLEL
IDNVQRLGLGYRFESDIRGALDRFVSSGGFDAVTKTSLHGTALSFRLLRQHGFEVSQEAFSGFK
DQNGNFLENLKEDIKAILSLYEASFLALEGENILDEAKVFAISHLKELSEEKIGKELAEQVNHA
LELPLHRRTQRLEAVWSIEAYRKKEDANQVLLELAILDYNMIQSVYQRDLRETSRWWRRVGLAT
KLHFARDRLIESFYWAVGVAFEPQYSDCRNSVAKMFSFVTIIDDIYDVYGTLDELELFTDAVER
WDVNAINDLPDYMKLCFLALYNTINEIAYDNLKDKGENILPYLTKAWADLCNAFLQEAKWLYNK
STPTFDDYFGNAWKSSSGPLQLVFAYFAVVQNIKKEEIENLQKYHDTISRPSHIFRLCNDLASA
SAEIARGETANSVSCYMRTKGISEELATESVMNLIDETWKKMNKEKLGGSLFAKPFVETAINLA
RQSHCTYHNGDAHTSPDELTRKRVLSVITEPILPFER
```

Figure 60A

Nucleotide sequence of pDu47-7 (SEQ ID NO:145)

```
tggcgaatgggacgcgccctgtagcggcgcattaagcgcggcgggtgtggtggttacgcgcagc
gtgaccgctacacttgccagcgccctagcgcccgctcctttcgctttcttcccttcctttctcg
ccacgttcgccggctttccccgtcaagctctaaatcgggggctccctttagggttccgatttag
tgctttacggcacctcgaccccaaaaaacttgattagggtgatggttcacgtagtgggccatcg
ccctgatagacggttttcgccctttgacgttggagtccacgttctttaatagtggactcttgt
tccaaactggaacaacactcaaccctatctcggtctattcttttgatttataagggattttgcc
gatttcggcctattggttaaaaaatgagctgatttaacaaaaatttaacgcgaattttaacaaa
atattaacgtttacaatttcaggtggcacttttcggggaaatgtgcgcggaacccctatttgtt
tatttttctaaatacattcaaatatgtatccgctcatgaattaattcttagaaaaactcatcga
gcatcaaatgaaactgcaatttattcatatcaggattatcaataccatattttgaaaaagccg
tttctgtaatgaaggagaaaactcaccgaggcagttccataggatggcaagatcctggtatcgg
tctgcgattccgactcgtccaacatcaatacaacctattaatttcccctcgtcaaaaataaggt
tatcaagtgagaaatcaccatgagtgacgactgaatccggtgagaatggcaaaagtttatgcat
ttctttccagacttgttcaacaggccagccattacgctcgtcatcaaaatcactcgcatcaacc
aaaccgttattcattcgtgattgcgcctgagcgagacgaaatacgcgatcgctgttaaaggac
aattacaaacaggaatcgaatgcaaccggcgcaggaacactgccagcgcatcaacaatattttc
acctgaatcaggatattcttctaatacctggaatgctgttttcccggggatcgcagtggtgagt
aaccatgcatcatcaggagtacggataaaatgcttgatggtcggaagaggcataaattccgtca
gccagtttagtctgaccatctcatctgtaacatcattggcaacgctacctttgccatgtttcag
aaacaactctggcgcatcgggcttcccatacaatcgatagattgtcgcacctgattgcccgaca
ttatcgcgagcccatttatacccatataaatcagcatccatgttggaatttaatcgcggcctag
agcaagacgtttcccgttgaatatggctcataacacccttgtattactgtttatgtaagcaga
cagttttattgttcatgaccaaaatcccttaacgtgagttttcgttccactgagcgtcagaccc
cgtagaaaagatcaaaggatcttcttgagatcctttttttctgcgcgtaatctgctgcttgcaa
acaaaaaaaccaccgctaccagcggtggtttgtttgccggatcaagagctaccaactctttttc
cgaaggtaactggcttcagcagagcgcagataccaaatactgtccttctagtgtagccgtagtt
aggccaccacttcaagaactctgtagcaccgcctacatacctcgctctgctaatcctgttacca
gtggctgctgccagtggcgataagtcgtgtcttaccgggttggactcaagacgatagttaccgg
ataaggcgcagcggtcgggctgaacggggggttcgtgcacacagcccagcttggagcgaacgac
ctacaccgaactgagatacctacagcgtgagctatgagaaagcgccacgcttcccgaagggaga
aaggcggacaggtatccggtaagcggcagggtcggaacaggagagcgcacgagggagcttccag
ggggaaacgcctggtatctttatagtcctgtcgggtttcgccacctctgacttgagcgtcgatt
tttgtgatgctcgtcaggggggcggagcctatggaaaaacgccagcaacgcggcctttttacgg
ttcctggccttttgctggccttttgctcacatgttcttcctgcgttatccctgattctgtgg
ataaccgtattaccgcctttgagtgagctgataccgctcgccgcagccgaacgaccgagcgcag
cgagtcagtgagcgaggaagcggaagagcgcctgatgcggtattttctccttacgcatctgtgc
ggtatttcacaccgcatatatggtgcactctcagtacaatctgctctgatgccgcatagttaag
ccagtatacactccgctatcgctacgtgactgggtcatggctgcgccccgacacccgccaacac
ccgctgacgcgccctgacgggcttgtctgctcccggcatccgcttacagacaagctgtgaccgt
ctccgggagctgcatgtgtcagaggttttcaccgtcatcaccgaaacgcgcgaggcagctgcgg
taaagctcatcagcgtggtcgtgaagcgattcacagatgtctgcctgttcatccgcgtccagct
cgttgagtttctccagaagcgttaatgtctggcttctgataaagcgggccatgttaagggcggt
ttttcctgtttggtcactgatgcctccgtgtaagggggatttctgttcatggggtaatgata
```

Figure 60B

Nucleotide sequence of pDu47-7

```
ccgatgaaacgagagaggatgctcacgatacgggttactgatgatgaacatgcccggttactgg
aacgttgtgagggtaaacaactggcggtatggatgcggcgggaccagagaaaaatcactcaggg
tcaatgccagcgcttcgttaatacagatgtaggtgttccacagggtagccagcagcatcctgcg
atgcagatccggaacataatggtgcagggcgctgacttccgcgtttccagactttacgaaacac
ggaaaccgaagaccattcatgttgttgctcaggtcgcagacgttttgcagcagcagtcgcttca
cgttcgctcgcgtatcggtgattcattctgctaaccagtaaggcaaccccgccagcctagccgg
gtcctcaacgacaggagcacgatcatgcgcacccgtggggccgccatgccggcgataatggcct
gcttctcgccgaaacgtttggtggcgggaccagtgacgaaggcttgagcgagggcgtgcaagat
tccgaataccgcaagcgacaggccgatcatcgtcgcgctccagcgaaagcggtcctcgccgaaa
atgacccagagcgctgccggcacctgtcctacgagttgcatgataaagaagacagtcataagtg
cggcgacgatagtcatgccccgcgcccaccggaaggagctgactggttgaaggctctcaaggg
catcggtcgagatcccggtgcctaatgagtgagctaacttacattaattgcgttgcgctcactg
cccgctttccagtcgggaaacctgtcgtgccagctgcattaatgaatcggccaacgcgcgggga
gaggcggtttgcgtattgggcgccagggtggtttttcttttcaccagtgagacgggcaacagct
gattgcccttcaccgcctggccctgagagagttgcagcaagcggtccacgctggtttgccccag
caggcgaaaatcctgtttgatggtggttaacggcgggatataacatgagctgtcttcggtatcg
tcgtatcccactaccgagatatccgcaccaacgcgcagcccggactcggtaatggcgcgcattg
cgcccagcgccatctgatcgttggcaaccagcatcgcagtgggaacgatgccctcattcagcat
ttgcatggtttgttgaaaaccggacatggcactccagtcgccttcccgttccgctatcggctga
atttgattgcgagtgagatatttatgccagccagccagacgcagacgcgccgagacagaactta
atgggcccgctaacagcgcgatttgctggtgacccaatgcgaccagatgctccacgcccagtcg
cgtaccgtcttcatgggagaaaataatactgttgatgggtgtctggtcagagacatcaagaaat
aacgccggaacattagtgcaggcagcttccacagcaatggcatcctggtcatccagcggatagt
taatgatcagcccactgacgcgttgcgcgagaagattgtgcaccgccgctttacaggcttcgac
gccgcttcgttctaccatcgacaccaccacgctggcacccagttgatcggcgcgagatttaatc
gccgcgacaatttgcgacggcgcgtgcagggccagactggaggtggcaacgccaatcagcaacg
actgtttgcccgccagttgttgtgccacgcggttgggaatgtaattcagctccgccatcgccgc
ttccactttttcccgcgttttcgcagaaacgtggctggcctggttcaccacgcgggaaacggtc
tgataagagacaccggcatactctgcgacatcgtataacgttactggtttcacattcaccaccc
tgaattgactctcttccgggcgctatcatgccataccgcgaaaggttttgcgccattcgatggt
gtccgggatctcgacgctctcccttatgcgactcctgcattaggaagcagcccagtagtaggtt
gaggccgttgagcaccgccgccgcaaggaatggtgcatgcaaggagatggcgcccaacagtccc
ccggccacggggcctgccaccatacccacgccgaaacaagcgctcatgagcccgaagtggcgag
cccgatcttccccatcggtgatgtcggcgatataggcgccagcaaccgcacctgtggcgccggt
gatgccggccacgatgcgtccggcgtagaggatcgagatctcgatcccgcgaaattaatacgac
tcactatagggaattgtgagcggataacaattcccctctagaaataattttgtttaactttaa
gaaggagatatacatatgaccgaaactgaaaccgaagctcgtcgttctgcgaactacgaaccta
acagctgggactatgattacctgctgtcctcgacacggacgagtccatcgaagtatacaaaga
caaagcgaaaagctggaagccgaagttcgtcgcgagattaataacgaaaaagcagaatttctg
accctgctggaactgattgacaacgtccagcgcctgggcctgggttaccgtttcgagtctgata
tccgtggtgcgctggatcgcttcgtttcctccggcggcttcgatgcggtaaccaagacttccct
gcacggtacggcactgtctttccgtctgctgcgtcaacacggttttgaggtttctcaggaagcg
ttcagcggcttcaaagaccaaaacggcaacttcctggagaacctgaaggaagatatcaaagcta
```

Figure 60C

Nucleotide sequence of pDu47-7

```
tcctgagcctgtacgaggccagcttcctggctctggaaggcgaaaacatcctggacgaggcgaa
ggttttcgcaatctctcatctgaaagaactgtctgaagaaaagatcggtaaagagctggcagaa
caggtgaaccatgcactggaactgccactgcatcgccgtactcagcgtctggaagcagtatggt
ctatcgaggcctaccgtaaaaaggaggacgcgaatcaggttctgctggagctggcaattctgga
ttacaacatgatccagtctgtataccagcgtgatctgcgtgaaacgtcccgttggtggcgtcgt
gtgggtctggcgaccaaactgcactttgctcgtgaccgcctgattgagagcttctactgggccg
tgggtgtagcattcgaaccgcaatactccgactgccgtaactccgtcgcaaaaatgttttcttt
cgtaaccattatcgacgatatctacgatgtatacggcaccctggacgaactggagctgtttact
gatgcagttgagcgttgggacgtaaacgccatcaacgacctgccggattacatgaaactgtgct
ttctggctctgtataacactattaacgaaatcgcctacgacaacctgaaagataaaggtgagaa
catcctgccgtatctgaccaaagcctgggctgacctgtgcaacgctttcctgcaagaagccaag
tggctgtacaacaaatctactccgaccttttgacgactacttcggcaacgcatggaaatcctctt
ctggcccgctgcaactggtgttcgcttacttcgctgtcgtgcagaacattaaaaaggaagagat
cgaaaacctgcaaaaataccatgacaccatctctcgtccttcccatatcttccgtctgtgcaat
gacctggctagcgcgtctgcggaaattgcgcgtggtgaaaccgcaaatagcgtttcttgttaca
tgcgcactaaaggtatctccgaagaactggctaccgaaagcgtgatgaatctgatcgatgaaac
ctggaaaaagatgaacaaggaaaaactgggtggtagcctgttcgcgaaaccgttcgtggaaacc
gcgatcaacctggcacgtcaatctcactgcacttatcataacggcgacgcgcatacctctccgg
atgagctgacccgcaaacgcgttctgtctgtaatcactgaaccgattctgccgtttgaacgcta
aggatccgaattcgagctccgtcgacaagcttgcggccgcactcgagcaccaccaccaccacca
ctgagatccggctgctaacaaagcccgaaaggaagctgagttggctgctgccaccgctgagcaa
taactagcataacccccttggggcctctaaacgggtcttgaggggttttttgctgaaaggaggaa
ctatatccggat
```

Figure 61

Amino acid sequence of *P. tremu* TRC (MET) (SEQ ID NO:146)

```
METRRSANYEPNSWDYDYLLSSDTDESIEVHKDKAKKLEAEVRREINNEKAEFLTLLELIDNVQ
RLGLGYRFESDIRRALDRFVSSGGFDGVTKTSLHGTALSFRLLRQHGFEVSQEAFSGFKDQNGN
FLENLKEDIKAILSLYEASFLALEGENILDEAKVFAISHLKELSEEKIGKELAEQVSHALELPL
HRRTQRLEAVWSIEAYRKKEDANQVLLELAILDYNMIQSVYQRDLRETSRWWRRVGLATKLHFA
RDRLIESFYWAVGVAFEPQYSDCRNSVAKMFSFVTIIDDIYDVYGTLDELELFTDAVERWDVNA
INDLPDYMKLCFLALYNTINEIAYDNLKDKGENILPYLTKAWADLCNAFLQEAKWLYNKSTPTF
DDYFGNAWKSSSGPLQLIFAYFAVVQNIKKEEIENLQKYHDIISRPSHIFRLCNDLASASAEIA
RGETANSVSCYMRTKGISEELATESVMNLIDETWKKMNKEKLGGSLFAKPFVETAINLARQSHC
TYHNGDAHTSPDELTRKRVLSVITEPILPFER
```

Figure 62A

Nucleotide sequence of pDu48 (SEQ ID NO:147)

```
tggcgaatgggacgcgccctgtagcggcgcattaagcgcggcgggtgtggtggttacgcgcagc
gtgaccgctacacttgccagcgccctagcgcccgctcctttcgctttcttccttcctttctcg
ccacgttcgccggctttccccgtcaagctctaaatcgggggctcccctttagggttccgatttag
tgctttacggcacctcgaccccaaaaaacttgattagggtgatggttcacgtagtgggccatcg
ccctgatagacggttttttcgccctttgacgttggagtccacgttctttaatagtggactcttgt
tccaaactggaacaacactcaaccctatctcggtctattcttttgatttataagggattttgcc
gatttcggcctattggttaaaaaatgagctgatttaacaaaaatttaacgcgaattttaacaaa
atattaacgtttacaatttcaggtggcacttttcggggaaatgtgcgcggaacccctatttgtt
tatttttctaaatacattcaaatatgtatccgctcatgaattaattcttagaaaaactcatcga
gcatcaaatgaaactgcaatttattcatatcaggattatcaataccatattttgaaaaagccg
tttctgtaatgaaggagaaaactcaccgaggcagttccataggatggcaagatcctggtatcgg
tctgcgattccgactcgtccaacatcaatacaacctattaatttcccctcgtcaaaataaggt
tatcaagtgagaaatcaccatgagtgacgactgaatccggtgagaatggcaaagtttatgcat
ttctttccagacttgttcaacaggccagccattacgctcgtcatcaaaatcactcgcatcaacc
aaaccgttattcattcgtgattgcgcctgagcgagacgaaatacgcgatcgctgttaaaaggac
aattacaaacaggaatcgaatgcaaccggcgcaggaacactgccagcgcatcaacaatattttc
acctgaatcaggatattcttctaatacctggaatgctgttttcccggggatcgcagtggtgagt
aaccatgcatcatcaggagtacggataaaatgcttgatggtcggaagaggcataaattccgtca
gccagtttagtctgaccatctcatctgtaacatcattggcaacgctacctttgccatgtttcag
aaacaactctggcgcatcgggcttcccatacaatcgatagattgtcgcacctgattgcccgaca
ttatcgcgagcccatttataccctataaatcagcatccatgttggaatttaatcgcggcctag
agcaagacgtttcccgttgaatatggctcataacaccccttgtattactgtttatgtaagcaga
cagttttattgttcatgaccaaaatcccttaacgtgagttttcgttccactgagcgtcagaccc
cgtagaaaagatcaaaggatcttcttgagatccttttttctgcgcgtaatctgctgcttgcaa
acaaaaaaaccaccgctaccagcggtggtttgtttgccggatcaagagctaccaactctttttc
cgaaggtaactggcttcagcagagcgcagataccaaatactgtccttctagtgtagccgtagtt
aggccaccacttcaagaactctgtagcaccgcctacatacctcgctctgctaatcctgttacca
gtggctgctgccagtggcgataagtcgtgtcttaccgggttggactcaagacgatagttaccgg
ataaggcgcagcggtcgggctgaacggggggttcgtgcacacagcccagcttggagcgaacgac
ctacaccgaactgagatacctacagcgtgagctatgagaaagcgccacgcttcccgaagggaga
aaggcggacaggtatccggtaagcggcagggtcggaacaggagagcgcacgagggagcttccag
ggggaaacgcctggtatctttatagtcctgtcgggtttcgccacctctgacttgagcgtcgatt
tttgtgatgctcgtcaggggggcggagcctatggaaaaacgccagcaacgcggcctttttacgg
ttcctggccttttgctggccttttgctcacatgttctttcctgcgttatcccctgattctgtgg
ataaccgtattaccgcctttgagtgagctgataccgctcgccgcagccgaacgaccgagcgcag
cgagtcagtgagcgaggaagcggaagagcgcctgatgcggtattttctccttacgcatctgtgc
ggtatttcacaccgcatatatggtgcactctcagtacaatctgctctgatgccgcatagttaag
ccagtatacactccgctatcgctacgtgactgggtcatggctgcgccccgacacccgccaacac
ccgctgacgcgccctgacgggcttgtctgctcccggcatccgcttacagacaagctgtgaccgt
ctccgggagctgcatgtgtcagaggttttcaccgtcatcaccgaaacgcgcgaggcagctgcgg
taaagctcatcagcgtggtcgtgaagcgattcacagatgtctgcctgttcatccgcgtccagct
cgttgagtttctccagaagcgttaatgtctggcttctgataaagcgggccatgttaagggcggt
ttttcctgtttggtcactgatgcctccgtgtaagggggattctgttcatggggtaatgata
```

Figure 62B

Nucleotide sequence of pDu48

```
ccgatgaaacgagagaggatgctcacgatacgggttactgatgatgaacatgcccggttactgg
aacgttgtgagggtaaacaactggcggtatggatgcggcgggaccagagaaaaatcactcaggg
tcaatgccagcgcttcgttaatacagatgtaggtgttccacagggtagccagcagcatcctgcg
atgcagatccggaacataatggtgcagggcgctgacttccgcgtttccagactttacgaaacac
ggaaaccgaagaccattcatgttgttgctcaggtcgcagacgttttgcagcagcagtcgcttca
cgttcgctcgcgtatcggtgattcattctgctaaccagtaaggcaaccccgccagcctagccgg
gtcctcaacgacaggagcacgatcatgcgcaccgtggggccgccatgccggcgataatggcct
gcttctcgccgaaacgtttggtggcgggaccagtgacgaaggcttgagcgagggcgtgcaagat
tccgaataccgcaagcgacaggccgatcatcgtcgcgctccagcgaaagcggtcctcgccgaaa
atgacccagagcgctgccggcacctgtcctacgagttgcatgataaagaagacagtcataagtg
cggcgacgatagtcatgccccgcgcccaccggaaggagctgactgggttgaaggctctcaaggg
catcggtcgagatcccggtgcctaatgagtgagctaacttacattaattgcgttgcgctcactg
cccgctttccagtcgggaaacctgtcgtgccagctgcattaatgaatcggccaacgcgcgggga
gaggcggtttgcgtattgggcgccagggtggttttcttttcaccagtgagacgggcaacagct
gattgcccttcaccgcctggccctgagagagttgcagcaagcggtccacgctggtttgccccag
caggcgaaaatcctgtttgatggtggttaacggcgggatataacatgagctgtcttcggtatcg
tcgtatcccactaccgagatatccgcaccaacgcgcagcccggactcggtaatggcgcgcattg
cgcccagcgccatctgatcgttggcaaccagcatcgcagtgggaacgatgccctcattcagcat
ttgcatggtttgttgaaaaccggacatggcactccagtcgccttcccgttccgctatcggctga
atttgattgcgagtgagatatttatgccagccagccagacgcagacgcgccgagacagaactta
atgggcccgctaacagcgcgatttgctggtgacccaatgcgaccagatgctccacgcccagtcg
cgtaccgtcttcatgggagaaaataatactgttgatgggtgtctggtcagagacatcaagaaat
aacgccggaacattagtgcaggcagcttccacagcaatggcatcctggtcatccagcggatagt
taatgatcagcccactgacgcgttgcgcgagaagattgtgcaccgccgctttacaggcttcgac
gccgcttcgttctaccatcgacaccaccacgctggcacccagttgatcggcgcgagatttaatc
gccgcgacaatttgcgacggcgcgtgcagggccagactggaggtggcaacgccaatcagcaacg
actgtttgccgccagttgttgtgccacgcggttgggaatgtaattcagctccgccatcgccgc
ttccacttttttcccgcgttttcgcagaaacgtggctggcctggttcaccacgcgggaaacggtc
tgataagagacaccggcatactctgcgacatcgtataacgttactggtttcacattcaccaccc
tgaattgactctcttccgggcgctatcatgccataccgcgaaaggttttgcgccattcgatggt
gtccgggatctcgacgctctcccttatgcgactcctgcattaggaagcagcccagtagtaggtt
gaggccgttgagcaccgccgccgcaaggaatggtgcatgcaaggagatggcgcccaacagtccc
ccggccacggggcctgccaccatacccacgccgaaacaagcgctcatgagcccgaagtggcgag
cccgatcttccccatcggtgatgtcggcgatataggcgccagcaaccgcacctgtggcgccggt
gatgccggccacgatgcgtccggcgtagaggatcgagatctcgatcccgcgaaattaatacgac
tcactatagggaattgtgagcggataacaattcccctctagaaataattttgtttaactttaa
gaaggagatatacatatggaaacgcgtcgttctgcgaactacgaacctaacagctgggactatg
attacctgctgtcctccgacacggacgagtccatcgaagtacacaaagacaaagcgaaaaagct
ggaagccgaagttcgtcgcgagattaataacgaaaagcagaatttctgacctgctggaactg
attgacaacgtccagcgcctgggcctgggttaccgtttcgagtctgatatccgtcgtgcgctgg
atcgcttcgtttcctccggcggcttcgatggcgtaaccaagacttccctgcacggtacggcact
gtcttttccgtctgctgcgtcaacacggttttgaggtttctcaggaagcgttcagcggcttcaaa
gaccaaaacggcaacttcctggagaacctgaaggaagatatcaaagctatcctgagcctgtacg
```

Figure 62C

Nucleotide sequence of pDu48 aggccagcttcctggctctggaaggcgaaaacatcctggacgaggcgaaggttttcgcaatctc
tcatctgaaagaactgtctgaagaaaagatcggtaaagagctggcagaacaggtgtcccatgca
ctggaactgccactgcatcgccgtactcagcgtctggaagcagtatggtctatcgaggcctacc
gtaaaaaggaggacgcgaaccaggttctgctggagctggcaattctggattacaacatgatcca
gtctgtataccagcgtgatctgcgtgaaacgtcccgttggtggcgtcgtgtgggtctggcgacc
aaactgcactttgctcgtgaccgcctgattgagagcttctactgggccgtgggtgtagcattcg
aaccgcaatactccgactgccgtaactccgtcgcaaaaatgttttctttcgtaaccattatcga
cgatatctacgatgtatacggcaccctggacgaactggagctgtttactgatgcagttgagcgt
tgggacgtaaacgccatcaacgacctgccggattacatgaaactgtgctttctggctctgtata
acactattaacgaaatcgcctacgacaacctgaaagataaaggtgagaacatcctgccgtatct
gaccaaagcctgggctgacctgtgcaacgcttcctgcaagaagccaagtggctgtacaacaaa
tctactccgacctttgacgactacttcggcaacgcatggaaatcctcttctggcccgctgcaac
tgatcttcgcttacttcgctgtcgtgcagaacattaaaaaggaagagatcgaaaacctgcaaaa
ataccatgacatcatctctcgtccttcccatatcttccgtctgtgcaatgacctggctagcgcg
tctgcggaaattgcgcgtggtgaaaccgcaaatagcgtttcttgttacatgcgcactaaaggta
tctccgaagaactggctaccgaaagcgtgatgaatctgatcgatgaaacctggaaaaagatgaa
caaggaaaaactgggtggtagcctgttcgcgaaaccgttcgtggaaaccgcgatcaacctggca
cgtcaatctcactgcacttatcataacggcgacgcgcatacctctccggatgagctgacccgca
aacgcgttctgtctgtaatcactgaaccgattctgccgtttgaacgctaaggatccgaattcga
gctccgtcgacaagcttgcggccgcactcgagcaccaccaccaccaccactgagatccggctgc
taacaaagcccgaaaggaagctgagttggctgctgccaccgctgagcaataactagcataaccc
cttggggcctctaaacgggtcttgaggggttttttgctgaaaggaggaactatatccggat

Figure 63

Amino acid sequence of *P. tricho* (TRC) (SEQ ID NO:148)

```
METRRSANYEPNSWDYDYLLSSDTDESIEVYKDKAKKLEAEVRREINNEKAEFLTLLELIDNVQ
RLGLGYRFESDIRRALDRFVSSGGFDAVTKTSLHATALSFRLLRQHGFEVSQEAFSGFKDQNGN
FLENLKEDIKAILSLYEASFLALEGENILDEAKVFAISHLKELSEEKIGKDLAEQVNHALELPL
HRRTQRLEAVLSIEAYRKKEDADQVLLELAILDYNMIQSVYQRDLRETSRWWRRVGLATKLHFA
RDRLIESFYWAVGVAFEPQYSDCRNSVAKMFSFVTIIDDIYDVYGTLDELELFTNAVERWDVNA
IDDLPDYMKLCFLALYNTINEIAYDNLKEKGENILPYLTKAWADLCNAFLQEAKWLYNKSTPTF
DEYFGNAWKSSSGPLQLVFAYFAVVQNIKKEEIENLQKYHDIISRPSHIFRLCNDLASASAEIA
RGETANSVSCYMRTKGISEELATESVMNLIDETWKKMNKEKLGGSLFAKPFVETAINLARQSHC
TYHNGDAHTSPDELTRKRVLSVITEPILPFER
```

Figure 64A

Nucleotide sequence of pDu49 (SEQ ID NO:149)

```
tggcgaatgggacgcgccctgtagcggcgcattaagcgcggcgggtgtggtggttacgcgcagc
gtgaccgctacacttgccagcgccctagcgcccgctcctttcgctttcttcccttcctttctcg
ccacgttcgccggctttccccgtcaagctctaaatcgggggctcccttagggttccgatttag
tgctttacggcacctcgacccaaaaaacttgattagggtgatggttcacgtagtgggccatcg
ccctgatagacggttttcgccttgacgttggagtccacgttctttaatagtggactcttgt
tccaaactggaacaacactcaacccatctcggtctattcttttgatttataagggattttgcc
gatttcggcctattggttaaaaatgagctgatttaacaaaaatttaacgcgaattttaacaaa
atattaacgtttacaatttcaggtggcacttttcggggaaatgtgcgcggaacccctatttgtt
tatttttctaaatacattcaaatatgtatccgctcatgaattaattcttagaaaaactcatcga
gcatcaaatgaaactgcaatttattcatatcaggattatcaataccatattttgaaaaagccg
tttctgtaatgaaggagaaaactcaccgaggcagttccataggatggcaagatcctggtatcgg
tctgcgattccgactcgtccaacatcaatacaacctattaatttcccctcgtcaaaataaggt
tatcaagtgagaaatcaccatgagtgacgactgaatccggtgagaatggcaaagtttatgcat
ttctttccagacttgttcaacaggccagccattacgctcgtcatcaaaatcactcgcatcaacc
aaaccgttattcattcgtgattgcgcctgagcgagacgaaatacgcgatcgctgttaaaaggac
aattacaaacaggaatcgaatgcaaccggcgcaggaacactgccagcgcatcaacaatattttc
acctgaatcaggatattcttctaatacctggaatgctgttttcccggggatcgcagtggtgagt
aaccatgcatcatcaggagtacggataaaatgcttgatggtcggaagaggcataaattccgtca
gccagtttagtctgaccatctcatctgtaacatcattggcaacgctacctttgccatgtttcag
aaacaactctggcgcatcgggcttcccatacaatcgatagattgtcgcacctgattgcccgaca
ttatcgcgagcccatttatacccatataaatcagcatccatgttggaatttaatcgcggcctag
agcaagacgtttcccgttgaatatggctcataacacccttgtattactgtttatgtaagcaga
cagttttattgttcatgaccaaaatcccttaacgtgagttttcgttccactgagcgtcagaccc
cgtagaaaagatcaaaggatcttcttgagatccttttttctgcgcgtaatctgctgcttgcaa
acaaaaaaaccaccgctaccagcggtggtttgtttgccggatcaagagctaccaactctttttc
cgaaggtaactggcttcagcagagcgcagataccaaatactgtccttctagtgtagccgtagtt
aggccaccacttcaagaactctgtagcaccgcctacatacctcgctctgctaatcctgttacca
gtggctgctgccagtggcgataagtcgtgtcttaccgggttggactcaagacgatagttaccgg
ataaggcgcagcggtcgggctgaacggggggttcgtgcacacagcccagcttggagcgaacgac
ctacaccgaactgagatacctacagcgtgagctatgagaaagcgccacgcttcccgaagggaga
aaggcggacaggtatccggtaagcggcagggtcggaacaggagagcgcacgagggagcttccag
ggggaaacgcctggtatctttatagtcctgtcgggtttcgccacctctgacttgagcgtcgatt
tttgtgatgctcgtcaggggggcggagcctatggaaaaacgccagcaacgcggcctttttacgg
ttcctggccttttgctggccttttgctcacatgttctttcctgcgttatccctgattctgtgg
ataaccgtattaccgcctttgagtgagctgataccgctcgccgcagccgaacgaccgagcgcag
cgagtcagtgagcgaggaagcggaagagcgcctgatgcggtattttctccttacgcatctgtgc
ggtatttcacaccgcatatatggtgcactctcagtacaatctgctctgatgccgcatagttaag
ccagtatacactccgctatcgctacgtgactgggtcatggctgcgccccgacacccgccaacac
ccgctgacgcgccctgacgggcttgtctgctcccggcatccgcttacagacaagctgtgaccgt
ctccgggagctgcatgtgtcagaggttttcaccgtcatcaccgaaacgcgcgaggcagctgcgg
taaagctcatcagcgtggtcgtgaagcgattcacagatgtctgcctgttcatccgcgtccagct
cgttgagtttctccagaagcgttaatgtctggcttctgataaagcgggccatgttaagggcggt
ttttcctgtttggtcactgatgcctccgtgtaaggggggatttctgttcatgggggtaatgata
```

Figure 64B

Nucleotide sequence of pDu49

```
ccgatgaaacgagagaggatgctcacgatacgggttactgatgatgaacatgcccggttactgg
aacgttgtgagggtaaacaactggcggtatggatgcggcgggaccagagaaaaatcactcaggg
tcaatgccagcgcttcgttaatacagatgtaggtgttccacagggtagccagcagcatcctgcg
atgcagatccggaacataatggtgcagggcgctgacttccgcgtttccagactttacgaaacac
ggaaaccgaagaccattcatgttgttgctcaggtcgcagacgttttgcagcagcagtcgcttca
cgttcgctcgcgtatcggtgattcattctgctaaccagtaaggcaaccccgccagcctagccgg
gtcctcaacgacaggagcacgatcatgcgcacccgtggggccgccatgccggcgataatggcct
gcttctcgccgaaacgtttggtggcgggaccagtgacgaaggcttgagcgagggcgtgcaagat
tccgaataccgcaagcgacaggccgatcatcgtcgcgctccagcgaaagcggtcctcgccgaaa
atgacccagagcgctgccggcacctgtcctacgagttgcatgataaagaagacagtcataagtg
cggcgacgatagtcatgccccgcgcccaccggaaggagctgactggttgaaggctctcaaggg
catcggtcgagatcccggtgcctaatgagtgagctaacttacattaattgcgttgcgctcactg
cccgctttccagtcgggaaacctgtcgtgccagctgcattaatgaatcggccaacgcgcgggga
gaggcggtttgcgtattgggcgccagggtggttttcttttcaccagtgagacgggcaacagct
gattgcccttcaccgcctggccctgagagagttgcagcaagcggtccacgctggtttgccccag
caggcgaaaatcctgtttgatggtggttaacggcgggatataacatgagctgtcttcggtatcg
tcgtatcccactaccgagatatccgcaccaacgcgcagcccggactcggtaatggcgcgcattg
cgcccagcgccatctgatcgttggcaaccagcatcgcagtgggaacgatgccctcattcagcat
ttgcatggtttgttgaaaaccggacatggcactccagtcgccttcccgttccgctatcggctga
atttgattgcgagtgagatatttatgccagccagccagacgcagacgcgccgagacagaactta
atgggcccgctaacagcgcgatttgctggtgacccaatgcgaccagatgctccacgcccagtcg
cgtaccgtcttcatgggagaaaataatactgttgatgggtgtctggtcagagacatcaagaaat
aacgccggaacattagtgcaggcagcttccacagcaatggcatcctggtcatccagcggatagt
taatgatcagcccactgacgcgttgcgcgagaagattgtgcaccgccgctttacaggcttcgac
gccgcttcgttctaccatcgacaccaccacgctggcacccagttgatcggcgcgagatttaatc
gccgcgacaatttgcgacggcgcgtgcagggccagactggaggtggcaacgccaatcagcaacg
actgtttgcccgccagttgttgtgccacgcggttgggaatgtaattcagctccgccatcgccgc
ttccactttttcccgcgttttcgcagaaacgtggctggcctggttcaccacgcgggaaacggtc
tgataagagacaccggcatactctgcgacatcgtataacgttactggtttcacattcaccaccc
tgaattgactctcttccgggcgctatcatgccataccgcgaaaggttttgcgccattcgatggt
gtccgggatctcgacgctctcccttatgcgactcctgcattaggaagcagcccagtagtaggtt
gaggccgttgagcaccgccgcgcaaggaatggtgcatgcaaggagatggcgcccaacagtccc
ccggccacggggcctgccaccatacccacgccgaaacaagcgctcatgagcccgaagtggcgag
cccgatcttccccatcggtgatgtcggcgatataggcgccagcaaccgcacctgtggcgccggt
gatgccggccacgatgcgtccggcgtagaggatcgagatctcgatcccgcgaaattaatacgac
tcactatagggaattgtgagcggataacaattcccctctagaaataattttgtttaactttaa
gaaggagatatacatatggaaacgcgtcgttctgcgaactacgaacctaacagctgggactatg
attacctgctgtcctcgacacggacgagtccatcgaagtatacaaagacaaagcgaaaaagct
ggaagccgaagttcgtcgcgagattaataacgaaaaagcagaatttctgaccctgctggaactg
attgacaacgtccagcgcctgggcctgggttaccgtttcgagtctgatatccgtcgtgcgctgg
atcgcttcgtttcctccggcggcttcgatgcggtaaccaagacttccctgcacgcgacggcact
gtcttttcgtctgctgcgtcaacacggttttgaggtttctcaggaagcgttcagcggcttcaaa
gaccaaaacggcaacttcctggagaacctgaaggaagatatcaaagctatcctgagcctgtacg
```

Figure 64C

Nucleotide sequence of pDu49

```
aggccagcttcctggctctggaaggcgaaaacatcctggacgaggcgaaggttttcgcaatctc
tcatctgaaagaactgtctgaagaaaagatcggtaaagatctggcagaacaggtgaaccatgca
ctggaactgccactgcatcgccgtactcagcgtctggaagcagtactgtctatcgaggcctacc
gtaaaaaggaggacgcggatcaggttctgctggagctggcaattctggattacaacatgatcca
gtctgtataccagcgtgatctgcgtgaaacgtcccgttggtggcgtcgtgtgggtctggcgacc
aaactgcactttgctcgtgaccgcctgattgagagcttctactgggccgtgggtgtagcattcg
aaccgcaatactccgactgccgtaactccgtcgcaaaaatgttttctttcgtaaccattatcga
cgatatctacgatgtatacggcacctggacgaactggagctgtttactaacgcagttgagcgt
tgggacgtaaacgccatcgacgatctgccggattacatgaaactgtgctttctggctctgtata
acactattaacgaaatcgcctacgacaacctgaaagaaaaaggtgagaacatcctgccgtatct
gaccaaagcctgggctgacctgtgcaacgctttcctgcaagaagccaagtggctgtacaacaaa
tctactccgacctttgacgaatacttcggcaacgcatggaaatcctcttctggcccgctgcaac
tggtgttcgcttacttcgctgtcgtgcagaacattaaaaaggaagagatcgaaaacctgcaaaa
ataccatgacatcatctctcgtccttcccatatcttccgtctgtgcaatgacctggctagcgcg
tctgcggaaattgcgcgtggtgaaaccgcaaatagcgtttcttgttacatgcgcactaaaggta
tctccgaagaactggctaccgaaagcgtgatgaatctgatcgatgaaacctggaaaaagatgaa
caaggaaaaactgggtggtagcctgttcgcgaaaccgttcgtggaaaccgcgatcaacctggca
cgtcaatctcactgcacttatcataacggcgacgcgcatacctctccggatgagctgacccgca
aacgcgttctgtctgtaatcactgaaccgattctgccgtttgaacgctaaggatccgaattcga
gctccgtcgacaagcttgcggccgcactcgagcaccaccaccaccactgagatccggctgc
taacaaagcccgaaaggaagctgagttggctgctgccaccgctgagcaataactagcataaccc
cttggggcctctaaacgggtcttgaggggttttttgctgaaaggaggaactatatccggat
```

Figure 65

Amino acid sequence of kudzu TRC (MEA) (SEQ ID NO:150)

```
MEARRSANYQPNLWNFEFLQSLENDLKVEKLEEKATKLEEEVRCMINRVDTQPLSLLELIDDVQ
RLGLTYKFEKDIIKALENIVLLDENKKNKSDLHATALSFRLLRQHGFEVSQDVFERFKDKEGGF
SGELKGDVQGLLSLYEASYLGFEGENLLEEARTFSITHLKNNLKEGINTKVAEQVSHALELPYH
QRLHRLEARWFLDKYEPKEPHHQLLLELAKLDFNMVQTLHQKELQDLSRWWTEMGLASKLDFVR
DRLMEVYFWALGMAPDPQFGECRKAVTKMFGLVTIIDDVYDVYGTLDELQLFTDAVERWDVNAI
NTLPDYMKLCFLALYNTVNDTSYSILKEKGHNNLSYLTKSWRELCKAFLQEAKWSNNKIIPAFS
KYLENASVSSSGVALLAPSYFSVCQQQEDISDHALRSLTDFHGLVRSSCVIFRLCNDLATSAAE
LERGETTNSIISYMHENDGTSEEQAREELRKLIDAEWKKMNRERVSDSTLLPKAFMEIAVNMAR
VSHCTYQYGDGLGRPDYATENRIKLLLIDPFPINQLMYV
```

Figure 66A

Nucleotide sequence of pDu50 (SEQ ID NO:151)

```
tcgagcaccaccaccaccaccactgagatccggctgctaacaaagcccgaaaggaagctgagtt
ggctgctgccaccgctgagcaataactagcataaccccttggggcctctaaacgggtcttgagg
ggttttttgctgaaaggaggaactatatccggattggcgaatgggacgcgcctgtagcggcgc
attaagcgcggcgggtgtggtggttacgcgcagcgtgaccgctacacttgccagcgccctagcg
cccgctcctttcgctttcttcccttcctttctcgccacgttcgccggctttccccgtcaagctc
taaatcgggggctcccttagggttccgatttagtgctttacggcacctcgaccccaaaaaact
tgattagggtgatggttcacgtagtgggccatcgccctgatagacggttttcgccctttgacg
ttggagtccacgttctttaatagtggactcttgttccaaactggaacaacactcaaccctatct
cggtctattcttttgatttataagggattttgccgatttcggcctattggttaaaaaatgagct
gatttaacaaaaatttaacgcgaattttaacaaaatattaacgtttacaatttcaggtggcact
tttcggggaaatgtgcgcggaacccctatttgtttatttttctaaatacattcaaatatgtatc
cgctcatgaattaattcttagaaaaactcatcgagcatcaaatgaaactgcaatttattcatat
caggattatcaataccatattttgaaaaagccgtttctgtaatgaaggagaaaactcaccgag
gcagttccataggatggcaagatcctggtatcggtctgcgattccgactcgtccaacatcaata
caacctattaatttcccctcgtcaaaaataaggttatcaagtgagaaatcaccatgagtgacga
ctgaatccggtgagaatggcaaaagtttatgcatttctttccagacttgttcaacaggccagcc
attacgctcgtcatcaaaatcactcgcatcaaccaaaccgttattcattcgtgattgcgcctga
gcgagacgaaatacgcgatcgctgttaaaaggacaattacaaacaggaatcgaatgcaaccggc
gcaggaacactgccagcgcatcaacaatattttcacctgaatcaggatattcttctaatacctg
gaatgctgttttcccggggatcgcagtggtgagtaaccatgcatcatcaggagtacggataaaa
tgcttgatggtcggaagaggcataaattccgtcagccagtttagtctgaccatctcatctgtaa
catcattggcaacgctacctttgccatgtttcagaaacaactctggcgcatcgggcttcccata
caatcgatagattgtcgcacctgattgcccgacattatcgcgagcccatttatacccatataaa
tcagcatccatgttggaatttaatcgcggcctagagcaagacgtttcccgttgaatatggctca
taacaccccttgtattactgtttatgtaagcagacagttttattgttcatgaccaaaatccctt
aacgtgagttttcgttccactgagcgtcagaccccgtagaaaagatcaaaggatcttcttgaga
tcctttttttctgcgcgtaatctgctgcttgcaaacaaaaaaaccaccgctaccagcggtggtt
tgtttgccggatcaagagctaccaactctttttccgaaggtaactggcttcagcagagcgcaga
taccaaatactgtccttctagtgtagccgtagttaggccaccacttcaagaactctgtagcacc
gcctacatacctcgctctgctaatcctgttaccagtggctgctgccagtggcgataagtcgtgt
cttaccgggttggactcaagacgatagttaccggataaggcgcagcggtcgggctgaacggggg
gttcgtgcacacagcccagcttggagcgaacgacctacaccgaactgagatacctacagcgtga
gctatgagaaagcgccacgcttcccgaagggagaaaggcggacaggtatccggtaagcggcagg
gtcggaacaggagagcgcacgagggagcttccaggggaaacgcctggtatctttatagtcctg
tcgggtttcgccacctctgacttgagcgtcgatttttgtgatgctcgtcaggggggcggagcct
atggaaaaacgccagcaacgcggccttttacggttcctggccttttgctggccttttgctcac
atgttcttcctgcgttatcccctgattctgtggataaccgtattaccgcctttgagtgagctg
ataccgctcgccgcagccgaacgaccgagcgcagcgagtcagtgagcgaggaagcggaagagcg
cctgatgcggtattttctccttacgcatctgtgcggtatttcacaccgcatatggtgcactc
tcagtacaatctgctctgatgccgcatagttaagccagtatacactccgctatcgctacgtgac
tgggtcatggctgcgccccgacacccgccaacacccgctgacgcgccctgacgggcttgtctgc
tcccggcatccgcttacagacaagctgtgaccgtctccgggagctgcatgtgtcagaggttttc
accgtcatcaccgaaacgcgcgaggcagctgcggtaaagctcatcagcgtggtcgtgaagcgat
```

Figure 66B

Nucleotide sequence of pDu50

```
tcacagatgtctgcctgttcatccgcgtccagctcgttgagtttctccagaagcgttaatgtct
ggcttctgataaagcgggccatgttaagggcggttttttcctgtttggtcactgatgcctccgt
gtaaggggatttctgttcatggggtaatgataccgatgaaacgagagaggatgctcacgata
cgggttactgatgatgaacatgcccggttactggaacgttgtgagggtaaacaactggcggtat
ggatgcggcgggaccagagaaaaatcactcagggtcaatgccagcgcttcgttaatacagatgt
aggtgttccacagggtagccagcagcatcctgcgatgcagatccggaacataatggtgcagggc
gctgacttccgcgtttccagactttacgaaacacggaaaccgaagaccattcatgttgttgctc
aggtcgcagacgttttgcagcagcagtcgcttcacgttcgctcgcgtatcggtgattcattctg
ctaaccagtaaggcaaccccgccagcctagccgggtcctcaacgacaggagcacgatcatgcgc
acccgtggggccgccatgccggcgataatggcctgcttctcgccgaaacgtttggtggcgggac
cagtgacgaaggcttgagcgagggcgtgcaagattccgaataccgcaagcgacaggccgatcat
cgtcgcgctccagcgaaagcggtcctcgccgaaaatgacccagagcgctgccggcacctgtcct
acgagttgcatgataaagaagacagtcataagtgcggcgacgatagtcatgccccgcgcccacc
ggaaggagctgactggttgaaggctctcaagggcatcggtcgagatcccggtgcctaatgagt
gagctaacttacattaattgcgttgcgctcactgcccgctttccagtcgggaaacctgtcgtgc
cagctgcattaatgaatcggccaacgcgcggggagaggcggtttgcgtattgggcgccagggtg
gtttttcttttcaccagtgagacgggcaacagctgattgcccttcaccgcctggccctgagaga
gttgcagcaagcggtccacgctggtttgccccagcaggcgaaaatcctgtttgatggtggttaa
cggcgggatataacatgagctgtcttcggtatcgtcgtatcccactaccgagatatccgcacca
acgcgcagcccggactcggtaatggcgcgcattgcgcccagcgccatctgatcgttggcaacca
gcatcgcagtgggaacgatgccctcattcagcatttgcatggtttgttgaaaaccggacatggc
actccagtcgccttcccgttccgctatcggctgaatttgattgcgagtgagatatttatgccag
ccagccagacgcagacgcgccgagacagaacttaatgggcccgctaacagcgcgatttgctggt
gacccaatgcgaccagatgctccacgcccagtcgcgtaccgtcttcatgggagaaaataatact
gttgatgggtgtctggtcagagacatcaagaaataacgccggaacattagtgcaggcagcttcc
acagcaatggcatcctggtcatccagcggatagttaatgatcagcccactgacgcgttgcgcga
gaagattgtgcaccgccgctttacaggcttcgacgccgcttcgttctaccatcgacaccaccac
gctggcacccagttgatcggcgcgagatttaatcgccgcgacaatttgcgacggcgcgtgcagg
gccagactggaggtggcaacgccaatcagcaacgactgtttgcccgccagttgttgtgccacgc
ggttgggaatgtaattcagctccgccatcgccgcttccacttttccgcgttttcgcagaaac
gtggctggcctggttcaccacgcgggaaacggtctgataagagacaccggcatactctgcgaca
tcgtataacgttactggtttcacattcaccaccctgaattgactctcttccgggcgctatcatg
ccataccgcgaaaggttttgcgccattcgatggtgtccgggatctcgacgctctcccttatgcg
actcctgcattaggaagcagcccagtagtaggttgaggccgttgagcaccgccgccgcaaggaa
tggtgcatgcaaggagatggcgcccaacagtccccggccacggggcctgccaccatacccacg
ccgaaacaagcgctcatgagcccgaagtggcgagcccgatcttccccatcggtgatgtcggcga
tataggcgccagcaaccgcacctgtggcgccggtgatgccggccacgatgcgtccggcgtagag
gatcgagatctcgatcccgcgaaattaatacgactcactatagggaattgtgagcggataaca
attccccctctagaaataattttgtttaactttaagaaggagatataccatggaagctcgtcgtt
ccgcaaactatcagccaaacctgtggaatttcgaattcctgcaatccctggagaacgacctgaa
agtggaaaagctggaggagaaagcgaccaaactggaggaagaagttcgctgcatgatcaaccgt
gtagacacccagccgctgtccctgctggagctgatcgacgatgtgcagcgcctggtctgacct
acaaatttgaaaagacatcattaaagccctggaaaacatcgtactgctggacgaaaacaaaaa
```

Figure 66C

Nucleotide sequence of pDu50

```
gaacaaatctgacctgcacgcaaccgctctgtctttccgtctgctgcgtcagcacggtttcgag
gtttctcaggatgttttttgagcgtttcaaggataaagaaggtggtttcagcggtgaactgaaag
gtgacgtccaaggcctgctgagcctgtatgaagcgtcttacctgggtttcgagggtgagaacct
gctggaggaggcgcgtacctttttccatcacccacctgaagaacaacctgaaagaaggcattaat
accaaggttgcagaacaagtgagccacgccctggaactgccatatcaccagcgtctgcaccgtc
tggaggcacgttggttcctggataaatacgaaccgaaagaaccgcatcaccagctgctgctgga
gctggcgaagctggattttaacatggtacagaccctgcaccagaaagagctgcaagatctgtcc
cgctggtggaccgagatgggcctggctagcaaactggattttgtacgcgaccgcctgatggaag
tttatttctgggcactgggtatggcgccagacccgcagtttggtgaatgtcgcaaagctgttac
taaaatgtttggtctggtgacgatcatcgatgacgtgtatgacgtttatggcactctggacgaa
ctgcaactgttcaccgatgctgtagagcgctgggacgttaacgctattaacaccctgccggact
atatgaaactgtgtttcctggcactgtacaacaccgttaacgacacgtcctattctattctgaa
agagaaaggtcataacaacctgtcctatctgacgaaaagctggcgtgaactgtgcaaagccttt
ctgcaagaggcgaaatggtccaacaacaaaattatcccggctttctccaagtacctggaaaacg
ccagcgtttcctcctccggtgtagcgctgctggcgccgtcttacttttccgtatgccagcagca
ggaagacatctccgaccacgcgctgcgttccctgaccgacttccatggtctggtgcgttctagc
tgcgttatcttccgcctgtgcaacgatctggccacctctgcggcggagctggaacgtggcgaga
ctaccaattctatcattagctacatgcacgaaaacgatggtaccagcgaggaacaggcccgcga
agaactgcgtaaactgatcgacgccgaatggaaaaagatgaatcgtgaacgcgttagcgactcc
accctgctgcctaaagcgttcatggaaatcgcagttaacatggcacgtgtttcccactgcacct
accagtatggcgatggtctgggtcgcccagactacgcgactgaaaaccgcatcaaactgctgct
gattgacccttttcccgattaaccagctgatgtatgtctaactgcagggatccgaattcgagctc
cgtcgacaagcttgcggccgcac
```

Figure 67

Amino acid sequence of kudzu TRC (-4) (SEQ ID NO:152)

MEHNSRRSANYQPNLWNFEFLQSLENDLKVEKLEEKATKLEEEVRCMINRVDTQPLSLLELIDD
VQRLGLTYKFEKDIIKALENIVLLDENKKNKSDLHATALSFRLLRQHGFEVSQDVFERFKDKEG
GFSGELKGDVQGLLSLYEASYLGFEGENLLEEARTFSITHLKNNLKEGINTKVAEQVSHALELP
YHQRLHRLEARWFLDKYEPKEPHHQLLLELAKLDFNMVQTLHQKELQDLSRWWTEMGLASKLDF
VRDRLMEVYFWALGMAPDPQFGECRKAVTKMFGLVTIIDDVYDVYGTLDELQLFTDAVERWDVN
AINTLPDYMKLCFLALYNTVNDTSYSILKEKGHNNLSYLTKSWRELCKAFLQEAKWSNNKIIPA
FSKYLENASVSSSGVALLAPSYFSVCQQQEDISDHALRSLTDFHGLVRSSCVIFRLCNDLATSA
AELERGETTNSIISYMHENDGTSEEQAREELRKLIDAEWKKMNRERVSDSTLLPKAFMEIAVNM
ARVSHCTYQYGDGLGRPDYATENRIKLLLIDPFPINQLMYV

Figure 68A

Nucleotide sequence of pDu50-4 (SEQ ID NO:153)

```
tcgagcaccaccaccaccaccactgagatccggctgctaacaaagcccgaaaggaagctgagtt
ggctgctgccaccgctgagcaataactagcataaccccttggggcctctaaacgggtcttgagg
ggttttttgctgaaaggaggaactatatccggattggcgaatgggacgcgccctgtagcggcgc
attaagcgcggcgggtgtggtggttacgcgcagcgtgaccgctacacttgccagcgccctagcg
cccgctcctttcgctttcttcccttcctttctcgccacgttcgccggcttccccgtcaagctc
taaatcgggggctcccctttagggttccgatttagtgctttacggcacctcgaccccaaaaaact
tgattagggtgatggttcacgtagtgggccatcgccctgatagacggttttttcgccctttgacg
ttggagtccacgttctttaatagtggactcttgttccaaactggaacaacactcaaccctatct
cggtctattcttttgatttataagggattttgccgatttcggcctattggttaaaaaatgagct
gatttaacaaaaatttaacgcgaattttaacaaaatattaacgtttacaatttcaggtggcact
tttcggggaaatgtgcgcggaacccctatttgtttattttctaaatacattcaaatatgtatc
cgctcatgaattaattcttagaaaaactcatcgagcatcaaatgaaactgcaatttattcatat
caggattatcaataccatattttttgaaaaagccgtttctgtaatgaaggagaaaactcaccgag
gcagttccataggatggcaagatcctggtatcggtctgcgattccgactcgtccaacatcaata
caacctattaatttcccctcgtcaaaaataaggttatcaagtgagaaatcaccatgagtgacga
ctgaatccggtgagaatggcaaaagtttatgcatttctttccagacttgttcaacaggccagcc
attacgctcgtcatcaaaatcactcgcatcaaccaaaccgttattcattcgtgattgcgcctga
gcgagacgaaatacgcgatcgctgttaaaaggacaattacaaacaggaatcgaatgcaaccggc
gcaggaacactgccagcgcatcaacaatatttcacctgaatcaggatattcttctaatacctg
gaatgctgttttcccggggatcgcagtggtgagtaaccatgcatcatcaggagtacggataaaa
tgcttgatggtcggaagaggcataaattccgtcagccagtttagtctgaccatctcatctgtaa
catcattggcaacgctacctttgccatgtttcagaaacaactctggcgcatcgggcttcccata
caatcgatagattgtcgcacctgattgcccgacattatcgcgagcccatttataccatataaa
tcagcatccatgttggaatttaatcgcggcctagagcaagacgtttcccgttgaatatggctca
taacacccttgtattactgtttatgtaagcagacagttttattgttcatgaccaaaatccctt
aacgtgagttttcgttccactgagcgtcagaccccgtagaaaagatcaaaggatcttcttgaga
tccttttttctgcgcgtaatctgctgcttgcaaacaaaaaaaccaccgctaccagcggtggtt
tgtttgccggatcaagagctaccaactctttttccgaaggtaactggcttcagcagagcgcaga
taccaaatactgtccttctagtgtagccgtagttaggccaccacttcaagaactctgtagcacc
gcctacatacctcgctctgctaatcctgttaccagtggctgctgccagtggcgataagtcgtgt
cttaccgggttggactcaagacgatagttaccggataaggcgcagcggtcgggctgaacggggg
gttcgtgcacacagcccagcttggagcgaacgacctacaccgaactgagatacctacagcgtga
gctatgagaaagcgccacgcttcccgaagggagaaaggcggacaggtatccggtaagcggcagg
gtcggaacaggagagcgcacgagggagcttccaggggaaacgcctggtatctttatagtcctg
tcgggtttcgccacctctgacttgagcgtcgatttttgtgatgctcgtcaggggggcggagcct
atggaaaaacgccagcaacgcggcctttttacggttcctggccttttgctggccttttgctcac
atgttctttcctgcgttatcccctgattctgtggataaccgtattaccgcctttgagtgagctg
ataccgctcgccgcagccgaacgaccgagcgcagcgagtcagtgagcgaggaagcggaagagcg
cctgatgcggtattttctccttacgcatctgtgcggtatttcacaccgcatatggtgcactc
tcagtacaatctgctctgatgccgcatagttaagccagtatacactccgctatcgctacgtgac
tgggtcatggctgcgccccgacacccgccaacacccgctgacgcgccctgacgggcttgtctgc
tcccggcatccgcttacagacaagctgtgaccgtctccgggagctgcatgtgtcagaggttttc
accgtcatcaccgaaacgcgcgaggcagctgcggtaaagctcatcagcgtggtcgtgaagcgat
```

Figure 68B

Nucleotide sequence of pDu50-4

```
tcacagatgtctgcctgttcatccgcgtccagctcgttgagtttctccagaagcgttaatgtct
ggcttctgataaagcgggccatgttaagggcggttttttcctgtttggtcactgatgcctccgt
gtaaggggatttctgttcatgggggtaatgataccgatgaaacgagagaggatgctcacgata
cgggttactgatgatgaacatgcccggttactggaacgttgtgagggtaaacaactggcggtat
ggatgcggcgggaccagagaaaaatcactcagggtcaatgccagcgcttcgttaatacagatgt
aggtgttccacagggtagccagcagcatcctgcgatgcagatccggaacataatggtgcagggc
gctgacttccgcgtttccagactttacgaaacacggaaaccgaagaccattcatgttgttgctc
aggtcgcagacgttttgcagcagcagtcgcttcacgttcgctcgcgtatcggtgattcattctg
ctaaccagtaaggcaaccccgccagcctagccgggtcctcaacgacaggagcacgatcatgcgc
acccgtggggccgccatgccggcgataatggcctgcttctcgccgaaacgtttggtggcgggac
cagtgacgaaggcttgagcgagggcgtgcaagattccgaataccgcaagcgacaggccgatcat
cgtcgcgctccagcgaaagcggtcctcgccgaaaatgacccagagcgctgccggcacctgtcct
acgagttgcatgataaagaagacagtcataagtgcggcgacgatagtcatgccccgcgcccacc
ggaaggagctgactgggttgaaggctctcaagggcatcggtcgagatcccggtgcctaatgagt
gagctaacttacattaattgcgttgcgctcactgcccgctttccagtcgggaaacctgtcgtgc
cagctgcattaatgaatcggccaacgcgcggggagaggcggtttgcgtattgggcgccagggtg
gtttttcttttcaccagtgagacgggcaacagctgattgcccttaccgcctggccctgagaga
gttgcagcaagcggtccacgctggtttgcccagcaggcgaaaatcctgtttgatggtggttaa
cggcgggatataacatgagctgtcttcggtatcgtcgtatcccactaccgagatatccgcacca
acgcgcagcccggactcggtaatggcgcgcattgcgcccagcgccatctgatcgttggcaacca
gcatcgcagtgggaacgatgccctcattcagcatttgcatggtttgttgaaaaccggacatggc
actccagtcgccttcccgttccgctatcggctgaatttgattgcgagtgagatatttatgccag
ccagccagacgcagacgcgccgagacagaacttaatgggcccgctaacagcgcgatttgctggt
gacccaatgcgaccagatgctccacgcccagtcgcgtaccgtcttcatgggagaaaataatact
gttgatgggtgtctggtcagagacatcaagaaataacgccggaacattagtgcaggcagcttcc
acagcaatggcatcctggtcatccagcggatagttaatgatcagcccactgacgcgttgcgcga
gaagattgtgcaccgccgctttacaggcttcgacgccgcttcgttctaccatcgacaccaccac
gctggcacccagttgatcggcgcgagatttaatcgccgcgacaatttgcgacggcgcgtgcagg
gccagactggaggtggcaacgccaatcagcaacgactgtttgcccgccagttgttgtgccacgc
ggttgggaatgtaattcagctccgccatcgccgcttccacttttttcccgcgttttcgcagaaac
gtggctggcctggttcaccacgcgggaaacggtctgataagagacaccggcatactctgcgaca
tcgtataacgttactggttttcacattcaccaccctgaattgactctcttccgggcgctatcatg
ccataccgcgaaaggttttgcgccattcgatggtgtccgggatctcgacgctctcccttatgcg
actcctgcattaggaagcagcccagtagtaggttgaggccgttgagcaccgccgccgcaaggaa
tggtgcatgcaaggagatggcgcccaacagtcccccggccacggggcctgccaccatacccacg
ccgaaacaagcgctcatgagcccgaagtggcgagcccgatcttccccatcggtgatgtcggcga
tataggcgccagcaaccgcacctgtggcgccggtgatgccggccacgatgcgtccggcgtagag
gatcgagatctcgatcccgcgaaattaatacgactcactatagggaattgtgagcggataaca
attcccctctagaaataattttgtttaactttaagaaggagatataccatggagcataattccc
gtcgttccgcaaactatcagccaaacctgtggaatttcgaattcctgcaatccctggagaacga
cctgaaagtggaaaagctggaggagaaagcgaccaaactggaggaagaagttcgctgcatgatc
aaccgtgtagacacccagccgctgtccctgctggagctgatcgacgatgtgcagcgcctgggtc
tgacctacaaatttgaaaaagacatcattaaagccctggaaaacatcgtactgctggacgaaaa
```

Figure 68C

Nucleotide sequence of pDu50-4 caaaaagaacaaatctgacctgcacgcaaccgctctgtctttccgtctgctgcgtcagcacggt
ttcgaggtttctcaggatgtttttgagcgtttcaaggataaagaaggtggtttcagcggtgaac
tgaaaggtgacgtccaaggcctgctgagcctgtatgaagcgtcttacctgggtttcgagggtga
gaacctgctggaggaggcgcgtaccttttccatcacccacctgaagaacaacctgaaagaaggc
attaataccaaggttgcagaacaagtgagccacgccctggaactgccatatcaccagcgtctgc
accgtctggaggcacgttggttcctggataaatacgaaccgaaagaaccgcatcaccagctgct
gctggagctggcgaagctggattttaacatggtacagaccctgcaccagaaagagctgcaagat
ctgtcccgctggtggaccgagatgggcctggctagcaaactggattttgtacgcgaccgcctga
tggaagtttatttctgggcactgggtatggcgccagacccgcagtttggtgaatgtcgcaaagc
tgttactaaaatgtttggtctggtgacgatcatcgatgacgtgtatgacgtttatggcactctg
gacgaactgcaactgttcaccgatgctgtagagcgctgggacgttaacgctattaacaccctgc
cggactatatgaaactgtgtttcctggcactgtacaacaccgttaacgacacgtcctattctat
tctgaaagagaaaggtcataacaacctgtcctatctgacgaaaagctggcgtgaactgtgcaaa
gcctttctgcaagaggcgaaatggtccaacaacaaaattatcccggctttctccaagtacctgg
aaaacgccagcgtttcctcctccggtgtagcgctgctggcgccgtcttacttttccgtatgcca
gcagcaggaagacatctccgaccacgcgctgcgttccctgaccgacttccatggtctggtgcgt
tctagctgcgttatcttccgcctgtgcaacgatctggccacctctgcggcggagctggaacgtg
gcgagactaccaattctatcattagctacatgcacgaaaacgatggtaccagcgaggaacaggc
ccgcgaagaactgcgtaaactgatcgacgccgaatggaaaaagatgaatcgtgaacgcgttagc
gactccaccctgctgcctaaagcgttcatggaaatcgcagttaacatggcacgtgtttcccact
gcacctaccagtatggcgatggtctgggtcgcccagactacgcgactgaaaaccgcatcaaact
gctgctgattgacccttcccgattaaccagctgatgtatgtctaactgcagggatccgaattc
gagctccgtcgacaagcttgcggccgcac Figure 69
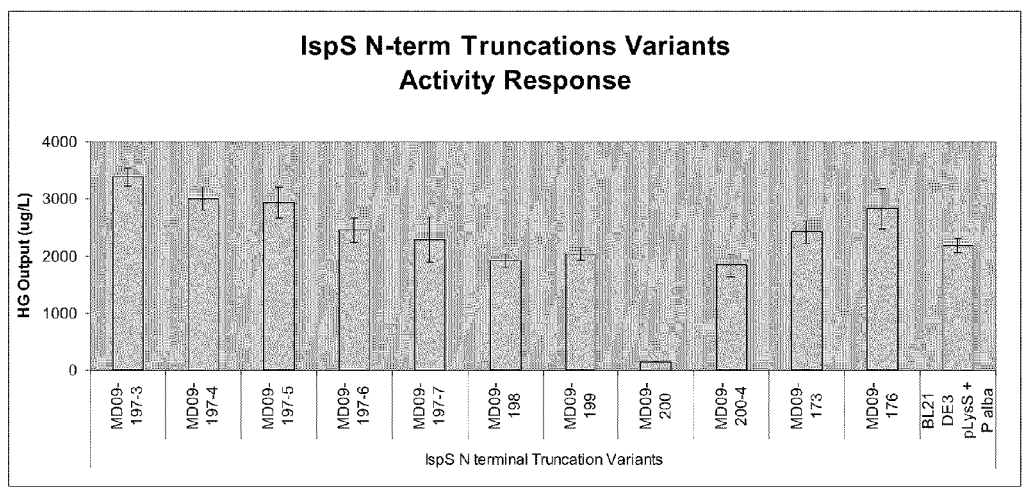
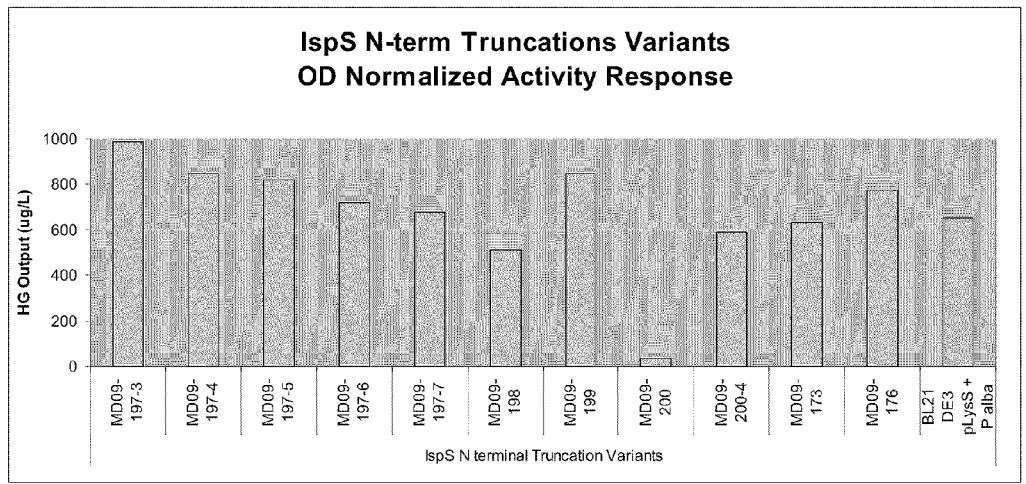

Figure 72A

Nucleotide sequence of p9795 (SEQ ID NO:154)

```
tagaaaaactcatcgagcatcaaatgaaactgcaatttattcatatcaggattatcaat
accatattttgaaaaagccgtttctgtaatgaaggagaaaactcaccgaggcagttcc
ataggatggcaagatcctggtatcggtctgcgattccgactcgtccaacatcaatacaa
cctattaatttccctcgtcaaaaataaggttatcaagtgagaaatcaccatgagtgac
gactgaatccggtgagaatggcaaagtttatgcatttctttccagacttgttcaacag
gccagccattacgctcgtcatcaaaatcactcgcatcaaccaaaccgttattcattcgt
gattgcgcctgagcgaggcgaaatacgcgatcgctgttaaaaggacaattacaaacagg
aatcgagtgcaaccggcgcaggaacactgccagcgcatcaacaatattttcacctgaat
caggatattcttctaatacctggaacgctgtttttccggggatcgcagtggtgagtaac
catgcatcatcaggagtacggataaaatgcttgatggtcggaagtggcataaattccgt
cagccagtttagtctgaccatctcatctgtaacatcattggcaacgctacctttgccat
gtttcagaaacaactctggcgcatcgggcttcccatacaagcgatagattgtcgcacct
gattgcccgacattatcgcgagcccatttatacccatataaatcagcatccatgttgga
atttaatcgcggcctcgacgtttccgttgaatatggctcatattcttccttttcaat
attattgaagcatttatcagggttattgtctcatgagcggatacatatttgaatgtatt
tagaaaataaacaaatagggtcagtgttacaaccaattaaccaattctgaacattat
cgcgagcccatttatacctgaatatggctcataacacccttgtttgcctggcggcagt
agcgcggtggtcccacctgacccatgccgaactcagaagtgaaacgccgtagcgccga
tggtagtgtggggactccccatgcgagagtagggaactgccaggcatcaaataaaacga
aaggctcagtcgaaagactgggccttcgcccgggctaattagggggtgtcgcctttc
gattgacgctgcagttagacatacatcagctggttaatcgggaaagggtcaatcagcag
cagtttgatgcggttttcagtcgcgtagtctgggcgacccagaccatcgccatactggt
aggtgcagtgggaaacacgtgccatgttaactgcgatttccatgaacgctttaggcagc
agggtggagtcgctaacgcgttcacgattcatcttttttccattcggcgtcgatcagttt
acgcagttcttcgcgggcctgttcctcgctggtaccatcgttttcgtgcatgtagctaa
tgatagaattggtagtctcgccacgttccagctccgccgcagaggtggccagatcgttg
cacaggcggaagataacgcagctagaacgcaccagaccatggaagtcggtcagggaacg
cagcgcgtggtcggagatgtcttcctgctgctggcatacggaaaagtaagacggcgcca
gcagcgctacaccggaggaggaaacgctggcgttttccaggtacttggagaaagccggg
ataattttgttgttggaccatttcgcctcttgcagaaaggctttgcacagttcacgcca
gcttttcgtcagataggacaggttgttatgacctttctctttcagaatagaataggacg
tgtcgttaacggtgttgtacagtgccaggaaacacagtttcatatagtccggcagggtg
ttaatagcgttaacgtcccagcgctctacagcatcggtgaacagttgcagttcgtccag
agtgccataaacgtcatacacgtcatcgatgatcgtcaccagaccaaacattttagtaa
cagctttgcgacattcaccaaactgcgggtctggcgccatacccagtgcccagaaataa
acttccatcaggcggtcgcgtacaaatccagtttgctagccaggcccatctcggtcca
ccagcgggacagatcttgcagctctttctggtgcagggtctgtaccatgttaaaatcca
gcttcgccagctccagcagcagctggtgatgcggttctttcggttcgtatttatccagg
aaccaacgtgcctccagacggtgcagacgctggtgatatggcagttccagggcgtggct
cacttgttctgcaaccttggtattaatgccttcttcaggttgttcttcaggtgggtga
tggaaaaggtacgcgcctcctccagcaggttctcaccctcgaaacccaggtaagacgct
tcatacaggctcagcaggccttggacgtcacctttcagttcaccgctgaaaccaccttc
tttatccttgaaacgctcaaaaacatcctgagaaacctcgaaaccgtgctgacgcagca
```

Figure 72B

Nucleotide sequence of p9795

```
gacggaaagacagagcggttgcgtgcaggtcagatttgttcttttttgttttcgtccagc
agtacgatgttttccagggctttaatgatgtcttttttcaaatttgtaggtcagacccag
gcgctgcacatcgtcgatcagctccagcagggacagcggctgggtgtctacacggttga
tcatgcagcgaacttcttcctccagtttggtcgctttctcctccagcttttccactttc
aggtcgttctccagggattgcaggaattcgaaattccacaggtttggctgatagtttgc
ggaacgacgggaattatgctcggtaatctgagtaaattgagaagaggtcgcacacatgt
tcagcgacaagggcgacacaaaatttattctaaatgcataataaatactgataacatct
tatagtttgtattatattttgtattatcgttgacatgtataattttgatatcaaaaact
gattttcccttattattttcgagatttatttttcttaattctctttaacaaactagaaa
tattgtatatacaaaaaatcataaataatagatgaatagtttaattataggtgttcatc
aatcgaaaagcaacgtatcttatttaaagtgcgttgcttttttctcatttataaggtt
aaataattctcatatatcaagcaaagtgacaggcgcccttaaatattctgacaaatgct
ctttccctaaactcccccccataaaaaaacccgccgaagcgggttttttacgttatttgcg
gattaacgattactcgttatcagaaccgcccaggggcccgagcttaagactggccgtc
gttttacaacacagaaagagtttgtagaaacgcaaaaaggccatccgtcaggggccttc
tgcttagtttgatgcctggcagttccctactctcgccttccgcttcctcgctcactgac
tcgctgcgctcggtcgttcggctgcggcgagcggtatcagctcactcaaaggcggtaat
acggttatccacagaatcaggggataacgcaggaaagaacatgtgagcaaaaggccagc
aaaaggccaggaaccgtaaaaaggccgcgttgctggcgttttttccataggctccgcccc
cctgacgagcatcacaaaaatcgacgctcaagtcagaggtggcgaaacccgacaggact
ataaagataccaggcgtttccccctggaagctccctcgtgcgctctcctgttccgaccc
tgccgcttaccggatacctgtccgcctttctcccttcgggaagcgtggcgctttctcat
agctcacgctgtaggtatctcagttcggtgtaggtcgttcgctccaagctgggctgtgt
gcacgaaccccccgttcagcccgaccgctgcgccttatccggtaactatcgtcttgagt
ccaacccggtaagacacgacttatcgccactggcagcagccactggtaacaggattagc
agagcgaggtatgtaggcggtgctacagagttcttgaagtggtgggctaactacggcta
cactagaagaacagtatttggtatctgcgctctgctgaagccagttaccttcggaaaaa
gagttggtagctcttgatccggcaaacaaaccaccgctggtagcggtggttttttgtt
tgcaagcagcagattacgcgcagaaaaaaggatctcaagaagatcctttgatcttttc
tacggggtctgacgctcagtggaacgacgcgcgcgtaactcacgttaagggattttggt
catgagcttgcgccgtcccgtcaagtcagcgtaatgctctgcttt
```

Figure 74A

Nucleotide sequence of pTrcKudzu (SEQ ID NO:155)

```
gtttgacagcttatcatcgactgcacggtgcaccaatgcttctggcgtcaggcagccat
cggaagctgtggtatggctgtgcaggtcgtaaatcactgcataattcgtgtcgctcaag
gcgcactcccgttctggataatgttttttgcgccgacatcataacggttctggcaaata
ttctgaaatgagctgttgacaattaatcatccggctcgtataatgtgtggaattgtgag
cggataacaatttcacacaggaaacagcgccgctgagaaaaagcgaagcggcactgctc
tttaacaatttatcagacaatctgtgtgggcactcgaccggaattatcgattaacttta
ttattaaaaattaaagaggtatatattaatgtatcgattaaataaggaggaataaacca
tgtgtgcgacctcttctcaatttactcagattaccgagcataattcccgtcgttccgca
aactatcagccaaacctgtggaatttcgaattcctgcaatccctggagaacgacctgaa
agtggaaaagctggaggagaaagcgaccaaactggaggaagaagttcgctgcatgatca
accgtgtagacacccagccgctgtcctgctggagctgatcgacgatgtgcagcgcctg
ggtctgacctacaaatttgaaaaagacatcattaaagccctggaaaacatcgtactgct
ggacgaaaacaaaagaacaaatctgacctgcacgcaaccgctctgtctttccgtctgc
tgcgtcagcacggtttcgaggtttctcaggatgttttgagcgtttcaaggataaagaa
ggtggtttcagcggtgaactgaaaggtgacgtccaaggcctgctgagcctgtatgaagc
gtcttacctgggtttcgagggtgagaacctgctggaggaggcgcgtaccttttccatca
cccacctgaagaacaacctgaaagaaggcattaataccaaggttgcagaacaagtgagc
cacgccctggaactgccatatcaccagcgtctgcaccgtctggaggcacgttggttcct
ggataaatacgaaccgaaagaaccgcatcaccagctgctgctggagctggcgaagctgg
atttaacatggtacagaccctgcaccagaaagagctgcaagatctgtcccgctggtgg
accgagatgggcctggctagcaaactggattttgtacgcgaccgcctgatggaagttta
tttctgggcactgggtatggcgccagacccgcagtttggtgaatgtcgcaaagctgtta
ctaaaatgtttggtctggtgacgatcatcgatgacgtgtatgacgtttatggcactctg
gacgaactgcaactgttcaccgatgctgtagagcgctgggacgttaacgctattaacac
cctgccggactatatgaaactgtgtttcctggcactgtacaacaccgttaacgacacgt
cctattctattctgaaagagaaaggtcataacaacctgtcctatctgacgaaaagctgg
cgtgaactgtgcaaagcctttctgcaagaggcgaaatggtccaacaacaaaattatccc
ggctttctccaagtacctggaaaacgccagcgtttcctcctccggtgtagcgctgctgg
cgccgtcttacttttccgtatgccagcagcaggaagacatctccgaccacgcgctgcgt
tccctgaccgacttccatggtctggtgcgttctagctgcgttatcttccgcctgtgcaa
cgatctggccacctctgcggcggagctggaacgtggcgagactaccaattctatcatta
gctacatgcacgaaaacgatggtaccagcgaggaacaggcccgcgaagaactgcgtaaa
ctgatcgacgccgaatggaaaaagatgaatcgtgaacgcgttagcgactccaccctgct
gcctaaagcgttcatggaaatcgcagttaacatggcacgtgtttcccactgcacctacc
agtatggcgatggtctgggtcgcccagactacgcgactgaaaaccgcatcaaactgctg
ctgattgacccttcccgattaaccagctgatgtatgtctaactgcagctggtaccata
tgggaattcgaagctttctagaacaaaaactcatctcagaagaggatctgaatagcgcc
gtcgaccatcatcatcatcatcattgagtttaaacggtctccagcttggctgttttggc
ggatgagagaagattttcagcctgatacagattaaatcgaacgcagaagcggtctgat
aaaacagaatttgcctggcggcagtagcgcggtggtcccacctgaccccatgccgaact
cagaagtgaaacgccgtagcgccgatggtagtgtggggtctccccatgcgagagtaggg
aactgccaggcatcaaataaaacgaaaggctcagtcgaaagactgggcctttcgtttta
tctgttgtttgtcggtgaacgctctcctgagtaggacaaatccgccgggagcggatttg
```

Figure 74B

Nucleotide sequence of pTrcKudzu

```
aacgttgcgaagcaacggcccggagggtggcgggcaggacgcccgccataaactgccag
gcatcaaattaagcagaaggccatcctgacggatggccttttgcgtttctacaaactc
ttttgttatttttctaaatacattcaaatatgtatccgctcatgagacaataaccct
gataaatgcttcaataatattgaaaaggaagagtatgagtattcaacatttccgtgtc
gcccttattcccttttttgcggcattttgccttcctgttttgctcacccagaaacgct
ggtgaaagtaaaagatgctgaagatcagttgggtgcacgagtgggttacatcgaactgg
atctcaacagcggtaagatccttgagagttttcgccccgaagaacgttttccaatgatg
agcacttttaaagttctgctatgtggcgcggtattatcccgtgttgacgccgggcaaga
gcaactcggtcgccgcatacactattctcagaatgacttggttgagtactcaccagtca
cagaaaagcatcttacggatggcatgacagtaagagaattatgcagtgctgccataacc
atgagtgataacactgcggccaacttacttctgacaacgatcggaggaccgaaggagct
aaccgcttttttgcacaacatgggggatcatgtaactcgccttgatcgttgggaaccgg
agctgaatgaagccataccaaacgacgagcgtgacaccacgatgcctgtagcaatggca
acaacgttgcgcaaactattaactggcgaactacttactctagcttcccggcaacaatt
aatagactggatggaggcggataaagttgcaggaccacttctgcgctcggcccttccgg
ctggctggtttattgctgataaatctggagccggtgagcgtgggtctcgcggtatcatt
gcagcactggggccagatggtaagccctcccgtatcgtagttatctacacgacggggag
tcaggcaactatggatgaacgaaatagacagatcgctgagataggtgcctcactgatta
agcattggtaactgtcagaccaagtttactcatatactttagattgatttaaaactt
cattttaatttaaaaggatctaggtgaagatcctttttgataatctcatgaccaaaat
cccttaacgtgagttttcgttccactgagcgtcagaccccgtagaaaagatcaaaggat
cttcttgagatcctttttttctgcgcgtaatctgctgcttgcaaacaaaaaaaccaccg
ctaccagcggtggtttgtttgccggatcaagagctaccaactctttttccgaaggtaac
tggcttcagcagagcgcagataccaaatactgtccttctagtgtagccgtagttaggcc
accacttcaagaactctgtagcaccgcctacatacctcgctctgctaatcctgttacca
gtggctgctgccagtggcgataagtcgtgtcttaccgggttggactcaagacgatagtt
accggataaggcgcagcggtcgggctgaacggggggttcgtgcacacagcccagcttgg
agcgaacgacctacaccgaactgagatacctacagcgtgagctatgagaaagcgccacg
cttcccgaagggagaaaggcggacaggtatccggtaagcggcagggtcggaacaggaga
gcgcacgagggagcttccagggggaaacgcctggtatctttatagtcctgtcgggtttc
gccacctctgacttgagcgtcgatttttgtgatgctcgtcaggggggcggagcctatgg
aaaacgccagcaacgcggcctttttacggttcctggccttttgctggccttttgctca
catgttctttcctgcgttatccctgattctgtggataaccgtattaccgcctttgagt
gagctgataccgctcgccgcagccgaacgaccgagcgcagcgagtcagtgagcgaggaa
gcggaagagcgcctgatgcggtattttctccttacgcatctgtgcggtatttcacaccg
catatggtgcactctcagtacaatctgctctgatgccgcatagttaagccagtatacac
tccgctatcgctacgtgactgggtcatggctgcgccccgacacccgccaacacccgctg
acgcgccctgacgggcttgtctgctcccggcatccgcttacagacaagctgtgaccgtc
tccgggagctgcatgtgtcagaggttttcaccgtcatcaccgaaacgcgcgaggcagca
gatcaattcgcgcgcgaaggcgaagcggcatgcatttacgttgacaccatcgaatggtg
caaaacctttcgcggtatggcatgatagcgcccggaagagagtcaattcagggtggtga
atgtgaaaccagtaacgttatacgatgtcgcagagtatgccggtgtctcttatcagacc
gtttcccgcgtggtgaaccaggccagccacgtttctgcgaaaacgcgggaaaaagtgga
```

Figure 74C

Nucleotide sequence of pTrcKudzu

```
agcggcgatggcggagctgaattacattcccaaccgcgtggcacaacaactggcgggca
aacagtcgttgctgattggcgttgccacctccagtctggccctgcacgcgccgtcgcaa
attgtcgcggcgattaaatctcgcgccgatcaactgggtgccagcgtggtggtgtcgat
ggtagaacgaagcggcgtcgaagcctgtaaagcggcggtgcacaatcttctcgcgcaac
gcgtcagtgggctgatcattaactatccgctggatgaccaggatgccattgctgtggaa
gctgcctgcactaatgttccggcgttatttcttgatgtctctgaccagacacccatcaa
cagtattattttctcccatgaagacggtacgcgactgggcgtggagcatctggtcgcat
tgggtcaccagcaaatcgcgctgttagcgggcccattaagttctgtctcggcgcgtctg
cgtctggctggctggcataaatatctcactcgcaatcaaattcagccgatagcggaacg
ggaaggcgactggagtgccatgtccggttttcaacaaaccatgcaaatgctgaatgagg
gcatcgttcccactgcgatgctggttgccaacgatcagatggcgctgggcgcaatgcgc
gccattaccgagtccgggctgcgcgttggtgcggatatctcggtagtgggatacgacga
taccgaagacagctcatgttatatcccgccgtcaaccaccatcaaacaggattttcgcc
tgctggggcaaaccagcgtggaccgcttgctgcaactctctcagggccaggcggtgaag
ggcaatcagctgttgcccgtctcactggtgaaaagaaaaaccacctggcgcccaatac
gcaaaccgcctctccccgcgcgttggccgattcattaatgcagctggcacgacaggttt
cccgactggaaagcgggcagtgagcgcaacgcaattaatgtgagttagcgcgaattgat
ctg
```

Figure 76A

Nucleotide sequence of pMAL-C4X (SEQ ID NO:156)

```
ccgacaccatcgaatggtgcaaaacctttcgcggtatggcatgatagcgcccggaagag
agtcaattcagggtggtgaatgtgaaaccagtaacgttatacgatgtcgcagagtatgc
cggtgtctcttatcagaccgtttcccgcgtggtgaaccaggccagccacgtttctgcga
aaacgcgggaaaagtggaagcggcgatggcggagctgaattacattcccaaccgcgtg
gcacaacaactggcgggcaaacagtcgttgctgattggcgttgccacctccagtctggc
cctgcacgcgccgtcgcaattgtcgcggcgattaaatctcgcgccgatcaactgggtg
ccagcgtggtggtgtcgatggtagaacgaagcggcgtcgaagcctgtaaagcggcggtg
cacaatcttctcgcgcaacgcgtcagtgggctgatcattaactatccgctggatgacca
ggatgccattgctgtggaagctgcctgcactaatgttccggcgttatttcttgatgtct
ctgaccagacacccatcaacagtattattttctcccatgaagacggtacgcgactgggc
gtggagcatctggtcgcattgggtcaccagcaaatcgcgctgttagcgggccattaag
ttctgtctcggcgcgtctgcgtctggctggctggcataaatatctcactcgcaatcaaa
ttcagccgatagcggaacgggaaggcgactggagtgccatgtccggttttcaacaaacc
atgcaaatgctgaatgagggcatcgttcccactgcgatgctggttgccaacgatcagat
ggcgctgggcgcaatgcgcgccattaccgagtccgggctgcgcgttggtgcggatatct
cggtagtgggatacgacgataccgaagacagctcatgttatatcccgccgttaaccacc
atcaaacaggattttcgcctgctggggcaaaccagcgtggaccgcttgctgcaactctc
tcagggccaggcggtgaagggcaatcagctgttgcccgtctcactggtgaaagaaaaa
ccaccctggcgcccaatacgcaaaccgcctctccccgcgcgttggccgattcattaatg
cagctggcacgacaggtttcccgactggaaagcgggcagtgagcgcaacgcaattaatg
taagttagctcactcattaggcacaattctcatgtttgacagcttatcatcgactgcac
ggtgcaccaatgcttctggcgtcaggcagccatcggaagctgtggtatggctgtgcagg
tcgtaaatcactgcataattcgtgtcgctcaaggcgcactcccgttctggataatgttt
tttgcgccgacatcataacggttctggcaaatattctgaaatgagctgttgacaattaa
tcatcggctcgtataatgtgtggaattgtgagcggataacaatttcacacaggaaacag
ccagtccgtttaggtgttttcacgagcacttcaccaacaaggaccatagcatatgaaaa
tcgaagaaggtaaactggtaatctggattaacggcgataaaggctataacggtctcgct
gaagtcggtaagaaattcgagaagataccggaattaaagtcaccgttgagcatccgga
taaactggaagagaaattcccacaggttgcggcaactggcgatggccctgacattatct
tctgggcacacgaccgctttggtggctacgctcaatctggcctgttggctgaaatcacc
ccggacaaagcgttccaggacaagctgtatccgtttacctgggatgccgtacgttacaa
cggcaagctgattgcttacccgatcgctgttgaagcgttatcgctgatttataacaaag
atctgctgccgaacccgccaaaaacctgggaagagatcccggcgctggataaagaactg
aaagcgaaaggtaagagcgcgctgatgttcaacctgcaagaaccgtacttcacctggcc
gctgattgctgctgacggggttatgcgttcaagtatgaaaacggcaagtacgacatta
agacgtgggcgtggataacgctggcgcgaaagcgggtctgaccttctggttgacctg
attaaaaacaaacacatgaatgcagacaccgattactccatcgcagaagctgcctttaa
taaaggcgaaacagcgatgaccatcaacggcccgtgggcatggtccaacatcgacacca
gcaaagtgaattatggtgtaacggtactgccgaccttcaagggtcaaccatccaaaccg
ttcgttggcgtgctgagcgcaggtattaacgccgccagtccgaacaaagagctggcaaa
agagttcctcgaaaactatctgctgactgatgaaggtctggaagcggttaataaagaca
aaccgctgggtgccgtagcgctgaagtcttacgaggaagagttggtgaaagatccgcgg
attgccgccactatggaaaacgcccagaaaggtgaaatcatgccgaacatcccgcagat
```

Figure 76B

Nucleotide sequence of pMAL-C4X

```
gtccgctttctggtatgccgtgcgtactgcggtgatcaacgccgccagcggtcgtcaga
ctgtcgatgaagccctgaaagacgcgcagactaattcgagctcgaacaacaacaacaat
aacaataacaacaacctcgggatcgagggaaggatttcagaattcggatcctctagagt
cgacctgcaggcaagcttggcactggccgtcgttttacaacgtcgtgactgggaaaacc
ctggcgttacccaacttaatcgccttgcagcacatccccctttcgccagctggcgtaat
agcgaagaggcccgcaccgatcgcccttcccaacagttgcgcagcctgaatggcgaatg
gcagcttggctgttttggcggatgagataagattttcagcctgatacagattaaatcag
aacgcagaagcggtctgataaaacagaatttgcctggcggcagtagcgcggtggtccca
cctgacccatgccgaactcagaagtgaaacgccgtagcgccgatggtagtgtggggtc
tccccatgcgagagtagggaactgccaggcatcaaataaaacgaaaggctcagtcgaaa
gactgggcctttcgttttatctgttgtttgtcggtgaacgctctcctgagtaggacaaa
tccgccgggagcggatttgaacgttgcgaagcaacggcccggagggtggcgggcaggac
gcccgccataaactgccaggcatcaaattaagcagaaggccatcctgacggatggcctt
tttgcgtttctacaaactcttttgtttatttttctaaatacattcaaatatgtatccg
ctcatgagacaataaccctgataaatgcttcaataatattgaaaaaggaagagtatgag
tattcaacatttccgtgtcgcccttattcccttttttgcggcattttgccttcctgttt
ttgctcacccagaaacgctggtgaaagtaaaagatgctgaagatcagttgggtgcacga
gtgggttacatcgaactggatctcaacagcggtaagatccttgagagttttcgccccga
agaacgttctccaatgatgagcacttttaaagttctgctatgtggcgcggtattatccc
gtgttgacgccgggcaagagcaactcggtcgccgcatacactattctcagaatgacttg
gttgagtactcaccagtcacagaaaagcatcttacggatggcatgacagtaagagaatt
atgcagtgctgccataaccatgagtgataacactgcggccaacttacttctgacaacga
tcggaggaccgaaggagctaaccgcttttttgcacaacatgggggatcatgtaactcgc
cttgatcgttgggaaccggagctgaatgaagccataccaaacgacgagcgtgacaccac
gatgcctgtagcaatggcaacaacgttgcgcaaactattaactggcgaactacttactc
tagcttcccggcaacaattaatagactggatggaggcggataaagttgcaggaccactt
ctgcgctcggcccttccggctggctggtttattgctgataaatctggagccggtgagcg
tgggtctcgcggtatcattgcagcactggggccagatggtaagccctcccgtatcgtag
ttatctacacgacggggagtcaggcaactatggatgaacgaaatagacagatcgctgag
ataggtgcctcactgattaagcattggtaactgtcagaccaagtttactcatatatact
ttagattgatttaccccggttgataatcagaaaagccccaaaaacaggaagattgtata
agcaaatatttaaattgtaaacgttaatattttgttaaaattcgcgttaaattttgtt
aaatcagctcatttttaaccataggccgaaatcggcaaaatcccttataaatcaaaa
gaatagaccgagatagggttgagtgttgttccagtttggaacaagagtccactattaaa
gaacgtggactccaacgtcaaagggcgaaaaaccgtctatcagggcgatggcccactac
gtgaaccatcacccaaatcaagttttttggggtcgaggtgccgtaaagcactaaatcgg
aaccctaaagggagcccccgatttagagcttgacggggaaagccggcgaacgtggcgag
aaaggaagggaagaaagcgaaaggagcgggcgctagggcgctggcaagtgtagcggtca
cgctgcgcgtaaccaccacacccgccgcgcttaatgcgccgctacagggcgcgtaaaag
gatctaggtgaagatccttttgataatctcatgaccaaaatcccttaacgtgagtttt
cgttccactgagcgtcagaccccgtagaaaagatcaaaggatcttcttgagatccttt
tttctgcgcgtaatctgctgcttgcaaacaaaaaaaccaccgctaccagcggtggtttg
tttgccggatcaagagctaccaactctttttccgaaggtaactggcttcagcagagcgc
```

Figure 76C

Nucleotide sequence of pMAL-C4X

```
agataccaaatactgtccttctagtgtagccgtagttaggccaccacttcaagaactct
gtagcaccgcctacatacctcgctctgctaatcctgttaccagtggctgctgccagtgg
cgataagtcgtgtcttaccggggttggactcaagacgatagttaccggataaggcgcagc
ggtcgggctgaacggggggttcgtgcacacagcccagcttggagcgaacgacctacacc
gaactgagatacctacagcgtgagctatgagaaagcgccacgcttcccgaagggagaaa
ggcggacaggtatccggtaagcggcagggtcggaacaggagagcgcacgagggagcttc
cagggggaaacgcctggtatctttatagtcctgtcgggtttcgccacctctgacttgag
cgtcgattttgtgatgctcgtcagggggcggagcctatggaaaaacgccagcaacgc
ggccttttacggttcctggccttttgctggccttttgctcacatgttctttcctgcgt
tatccctgattctgtggataaccgtattaccgcctttgagtgagctgataccgctcgc
cgcagccgaacgaccgagcgcagcgagtcagtgagcgaggaagcggaagagcgcctgat
gcggtattttctccttacgcatctgtgcggtatttcacaccgcatatggtgcactct
cagtacaatctgctctgatgccgcatagttaagccagtatacactccgctatcgctacg
tgactgggtcatggctgcgccccgacacccgccaacacccgctgacgcgccctgacggg
cttgtctgctcccggcatccgcttacagacaagctgtgaccgtctccgggagctgcatg
tgtcagaggttttcaccgtcatcaccgaaacgcgcgaggcagctgcggtaaagctcatc
agcgtggtcgtgcagcgattcacagatgtctgcctgttcatccgcgtccagctcgttga
gtttctccagaagcgttaatgtctggcttctgataaagcgggccatgttaagggcggtt
ttttcctgtttggtcactgatgcctccgtgtaagggggatttctgttcatggggtaat
gataccgatgaaacgagagaggatgctcacgatacgggttactgatgatgaacatgccc
ggttactggaacgttgtgagggtaaacaactggcggtatggatgcggcgggaccagaga
aaaatcactcagggtcaatgccagcgcttcgttaatacagatgtaggtgttccacaggg
tagccagcagcatcctgcgatgcagatccggaacataatggtgcagggcgctgacttcc
gcgtttccagactttacgaaacacggaaaccgaagaccattcatgttgttgctcaggtc
gcagacgttttgcagcagcagtcgcttcacgttcgctcgcgtatcggtgattcattctg
ctaaccagtaaggcaacccgccagcctagccgggtcctcaacgacaggagcacgatca
tgcgcacccgtggccaggacccaacgctgcccgaatt
```

Figure 78A

Nucleotide sequence of pMAL-C4X Kudzu (SEQ ID NO:157)

```
ccgacaccatcgaatggtgcaaaacctttcgcggtatggcatgatagcgcccggaagag
agtcaattcagggtggtgaatgtgaaaccagtaacgttatacgatgtcgcagagtatgc
cggtgtctcttatcagaccgtttcccgcgtggtgaaccaggccagccacgtttctgcga
aaacgcgggaaaaagtggaagcggcgatggcggagctgaattacattcccaaccgcgtg
gcacaacaactggcgggcaaacagtcgttgctgattggcgttgccacctccagtctggc
cctgcacgcgccgtcgcaaattgtcgcggcgattaaatctcgcgccgatcaactgggtg
ccagcgtggtggtgtcgatggtagaacgaagcggcgtcgaagcctgtaaagcggcggtg
cacaatcttctcgcgcaacgcgtcagtgggctgatcattaactatccgctggatgacca
ggatgccattgctgtggaagctgcctgcactaatgttccggcgttatttcttgatgtct
ctgaccagacacccatcaacagtattattttctcccatgaagacggtacgcgactgggc
gtggagcatctggtcgcattgggtcaccagcaaatcgcgctgttagcgggcccattaag
ttctgtctcggcgcgtctgcgtctggctggctggcataaatatctcactcgcaatcaaa
ttcagccgatagcggaacgggaaggcgactggagtgccatgtccggttttcaacaaacc
atgcaaatgctgaatgagggcatcgttcccactgcgatgctggttgccaacgatcagat
ggcgctgggcgcaatgcgcgccattaccgagtccgggctgcgcgttggtgcggatatct
cggtagtgggatacgacgataccgaagacagctcatgttatatcccgccgttaaccacc
atcaaacaggattttcgcctgctggggcaaaccagcgtggaccgcttgctgcaactctc
tcagggccaggcggtgaagggcaatcagctgttgcccgtctcactggtgaaaagaaaaa
ccaccctggcgcccaatacgcaaaccgcctctccccgcgcgttggccgattcattaatg
cagctggcacgacaggtttcccgactggaaagcgggcagtgagcgcaacgcaattaatg
taagttagctcactcattaggcacaattctcatgtttgacagcttatcatcgactgcac
ggtgcaccaatgcttctggcgtcaggcagccatcggaagctgtggtatggctgtgcagg
tcgtaaatcactgcataattcgtgtcgctcaaggcgcactcccgttctggataatgttt
tttgcgccgacatcataacggttctggcaaatattctgaaatgagctgttgacaattaa
tcatcggctcgtataatgtgtggaattgtgagcggataacaatttcacacaggaaacag
ccagtccgtttaggtgttttcacgagcacttcaccaacaaggaccatagcatatgaaaa
tcgaagaaggtaaactggtaatctggattaacggcgataaaggctataacggtctcgct
gaagtcggtaagaaattcgagaaagataccggaattaaagtcaccgttgagcatccgga
taaactggaagagaaattcccacaggttgcggcaactggcgatggccctgacattatct
tctgggcacacgaccgctttggtggctacgctcaatctggcctgttggctgaaatcacc
ccggacaaagcgttccaggacaagctgtatccgtttacctgggatgccgtacgttacaa
cggcaagctgattgcttacccgatcgctgttgaagcgttatcgctgatttataacaaag
atctgctgccgaacccgccaaaaacctgggaagagatcccggcgctggataaagaactg
aaagcgaaaggtaagagcgcgctgatgttcaacctgcaagaaccgtacttcacctggcc
gctgattgctgctgacgggggttatgcgttcaagtatgaaaacggcaagtacgacatta
aagacgtgggcgtggataacgctggcgcgaaagcgggtctgaccttcctggttgacctg
attaaaaacaaacacatgaatgcagacaccgattactccatcgcagaagctgcctttaa
taaaggcgaaacagcgatgaccatcaacggcccgtgggcatggtccaacatcgacacca
gcaaagtgaattatggtgtaacggtactgccgaccttcaagggtcaaccatccaaaccg
ttcgttggcgtgctgagcgcaggtattaacgccgccagtccgaacaaagagctggcaaa
agagttcctcgaaaactatctgctgactgatgaaggtctggaagcggttaataaagaca
aaccgctgggtgccgtagcgctgaagtcttacgaggaagagttggtgaaagatccgcgg
attgccgccactatggaaaacgcccagaaaggtgaaatcatgccgaacatcccgcagat
```

Figure 78B

Nucleotide sequence of pMAL-C4X Kudzu

```
gtccgctttctggtatgccgtgcgtactgcggtgatcaacgccgccagcggtcgtcaga
ctgtcgatgaagccctgaaagacgcgcagactaattcgagctcgaacaacaacaacaat
aacaataacaacaacctcgggatcgagggaaggatttcagaattctgtgcgacctcttc
tcaatttactcagattaccgagcataattcccgtcgttccgcaaactatcagccaaacc
tgtggaatttcgaattcctgcaatccctggagaacgacctgaaagtggaaaagctggag
gagaaagcgaccaaactggaggaagaagttcgctgcatgatcaacgtgtagacaccca
gccgctgtccctgctggagctgatcgacgatgtgcagcgcctgggtctgacctacaaat
ttgaaaagacatcattaaagccctggaaaacatcgtactgctggacgaaaacaaaaag
aacaaatctgacctgcacgcaaccgctctgtctttccgtctgctgcgtcagcacggttt
cgaggtttctcaggatgttttgagcgtttcaaggataaagaaggtggtttcagcggtg
aactgaaaggtgacgtccaaggcctgctgagcctgtatgaagcgtcttacctgggtttc
gagggtgagaacctgctggaggaggcgcgtaccttttccatcacccacctgaagaacaa
cctgaaagaaggcattaataccaaggttgcagaacaagtgagccacgccctggaactgc
catatcaccagcgtctgcaccgtctggaggcacgttggttcctggataaatacgaaccg
aaagaaccgcatcaccagctgctgctggagctggcgaagctggattttaacatggtaca
gaccctgcaccagaaagagctgcaagatctgtcccgctggtggaccgagatgggcctgg
ctagcaaactggattttgtacgcgaccgcctgatggaagtttatttctgggcactgggt
atggcgccagacccgcagtttggtgaatgtcgcaaagctgttactaaaatgtttggtct
ggtgacgatcatcgatgacgtgtatgacgtttatggcactctggacgaactgcaactgt
tcaccgatgctgtagagcgctgggacgttaacgctattaacaccctgccggactatatg
aaactgtgtttcctggcactgtacaacaccgttaacgacacgtcctattctattctgaa
agagaaaggtcataacaacctgtcctatctgacgaaaagctggcgtgaactgtgcaaag
cctttctgcaagaggcgaaatggtccaacaacaaaattatcccggctttctccaagtac
ctggaaaacgccagcgtttcctcctccggtgtagcgctgctggcgccgtcttacttttc
cgtatgccagcagcaggaagacatctccgaccacgcgctgcgttccctgaccgacttcc
atggtctggtgcgttctagctgcgttatcttccgcctgtgcaacgatctggccacctct
gcggcggagctggaacgtggcgagactaccaattctatcattagctacatgcacgaaaa
cgatggtaccagcgaggaacaggcccgcgaagaactgcgtaaactgatcgacgccgaat
ggaaaaagatgaatcgtgaacgcgttagcgactccaccctgctgcctaaagcgttcatg
gaaatcgcagttaacatggcacgtgtttcccactgcacctaccagtatggcgatggtct
gggtcgcccagactacgcgactgaaaaccgcatcaaactgctgctgattgacccttcc
cgattaaccagctgatgtatgtctaagcttggcactggccgtcgttttacaacgtcgtg
actgggaaaaccctggcgttacccaacttaatcgccttgcagcacatccccctttcgcc
agctggcgtaatagcgaagaggcccgcaccgatcgcccttcccaacagttgcgcagcct
gaatggcgaatggcagcttggctgttttggcggatgagataagatttcagcctgatac
agattaaatcagaacgcagaagcggtctgataaaacagaatttgcctggcggcagtagc
gcggtggtcccacctgaccccatgccgaactcagaagtgaaacgccgtagcgccgatgg
tagtgtggggtctcccatgcgagagtagggaactgccaggcatcaaataaaacgaaag
gctcagtcgaaagactgggcctttcgttttatctgttgtttgtcggtgaacgctctcct
gagtaggacaaatccgccgggagcggatttgaacgttgcgaagcaacggcccggagggt
ggcgggcaggacgcccgccataaactgccaggcatcaaattaagcagaaggccatcctg
acggatggcctttttgcgtttctacaaactcttttgtttatttttctaaatacattca
aatatgtatccgctcatgagacaataaccctgataaatgcttcaataatattgaaaag
```

Figure 78C

Nucleotide sequence of pMAL-C4X Kudzu

```
gaagagtatgagtattcaacatttccgtgtcgcccttattccttttttgcggcatttt
gccttcctgttttgctcacccagaaacgctggtgaaagtaaaagatgctgaagatcag
ttgggtgcacgagtgggttacatcgaactggatctcaacagcggtaagatccttgagag
ttttcgccccgaagaacgttctccaatgatgagcacttttaaagttctgctatgtggcg
cggtattatcccgtgttgacgccgggcaagagcaactcggtcgccgcatacactattct
cagaatgacttggttgagtactcaccagtcacagaaaagcatcttacggatggcatgac
agtaagagaattatgcagtgctgccataaccatgagtgataacactgcggccaacttac
ttctgacaacgatcggaggaccgaaggagctaaccgcttttttgcacaacatgggggat
catgtaactcgccttgatcgttgggaaccggagctgaatgaagccataccaaacgacga
gcgtgacaccacgatgcctgtagcaatggcaacaacgttgcgcaaactattaactggcg
aactacttactctagcttcccggcaacaattaatagactggatggaggcggataaagtt
gcaggaccacttctgcgctcggcccttccggctggctggtttattgctgataaatctgg
agccggtgagcgtgggtctcgcggtatcattgcagcactggggccagatggtaagccct
cccgtatcgtagttatctacacgacggggagtcaggcaactatggatgaacgaaataga
cagatcgctgagataggtgcctcactgattaagcattggtaactgtcagaccaagttta
ctcatatactttagattgatttaccccggttgataatcagaaaagccccaaaaacag
gaagattgtataagcaaatatttaaattgtaaacgttaatattttgttaaaattcgcgt
taaattttgttaaatcagctcattttttaaccaataggccgaaatcggcaaaatccct
tataaatcaaaagaatagaccgagatagggttgagtgttgttccagtttggaacaagag
tccactattaaagaacgtggactccaacgtcaaagggcgaaaaaccgtctatcagggcg
atggcccactacgtgaaccatcacccaaatcaagttttttggggtcgaggtgccgtaaa
gcactaaatcggaaccctaaagggagcccccgatttagagcttgacggggaaagccggc
gaacgtggcgagaaaggaagggaagaaagcgaaggagcgggcgctagggcgctggcaa
gtgtagcggtcacgctgcgcgtaaccaccacacccgccgcgcttaatgcgccgctacag
ggcgcgtaaaaggatctaggtgaagatcctttttgataatctcatgaccaaaatcccttg
aacgtgagttttcgttccactgagcgtcagaccccgtagaaaagatcaaaggatcttct
tgagatcctttttttctgcgcgtaatctgctgcttgcaaacaaaaaaaccaccgctacc
agcggtggtttgtttgccggatcaagagctaccaactcttttccgaaggtaactggct
tcagcagagcgcagataccaaatactgtccttctagtgtagccgtagttaggccaccac
ttcaagaactctgtagcaccgcctacatacctcgctctgctaatcctgttaccagtggc
tgctgccagtggcgataagtcgtgtcttaccgggttggactcaagacgatagttaccgg
ataaggcgcagcggtcgggctgaacggggggttcgtgcacacagcccagcttggagcga
acgacctacaccgaactgagatacctacagcgtgagctatgagaaagcgccacgcttcc
cgaagggagaaaggcggacaggtatccggtaagcggcagggtcggaacaggagagcgca
cgagggagcttccaggggaaacgcctggtatctttatagtcctgtcgggtttcgccac
ctctgacttgagcgtcgatttttgtgatgctcgtcaggggggcggagcctatggaaaaa
cgccagcaacgcggcctttttacggttcctggccttttgctggccttttgctcacatgt
tctttcctgcgttatcccctgattctgtggataaccgtattaccgcctttgagtgagct
gataccgctcgccgcagccgaacgaccgagcgcagcgagtcagtgagcgaggaagcgga
agagcgcctgatgcggtattttctccttacgcatctgtgcggtatttcacaccgcatat
atggtgcactctcagtacaatctgctctgatgccgcatagttaagccagtatacactcc
gctatcgctacgtgactgggtcatggctgcgccccgacacccgccaacacccgctgacg
cgccctgacgggcttgtctgctcccggcatccgcttacagacaagctgtgaccgtctcc
```

Figure 78D

Nucleotide sequence of pMAL-C4X Kudzu

```
gggagctgcatgtgtcagaggttttcaccgtcatcaccgaaacgcgcgaggcagctgcg
gtaaagctcatcagcgtggtcgtgcagcgattcacagatgtctgcctgttcatccgcgt
ccagctcgttgagtttctccagaagcgttaatgtctggcttctgataaagcgggccatg
ttaagggcggttttttcctgtttggtcactgatgcctccgtgtaagggggatttctgtt
catgggggtaatgataccgatgaaacgagagaggatgctcacgatacgggttactgatg
atgaacatgcccggttactggaacgttgtgagggtaaacaactggcggtatggatgcgg
cgggaccagagaaaaatcactcagggtcaatgccagcgcttcgttaatacagatgtagg
tgttccacagggtagccagcagcatcctgcgatgcagatccggaacataatggtgcagg
gcgctgacttccgcgtttccagactttacgaaacacggaaaccgaagaccattcatgtt
gttgctcaggtcgcagacgttttgcagcagcagtcgcttcacgttcgctcgcgtatcgg
tgattcattctgctaaccagtaaggcaaccccgccagcctagccgggtcctcaacgaca
ggagcacgatcatgcgcacccgtggccaggacccaacgctgcccgaatt
```

Figure 79
A.
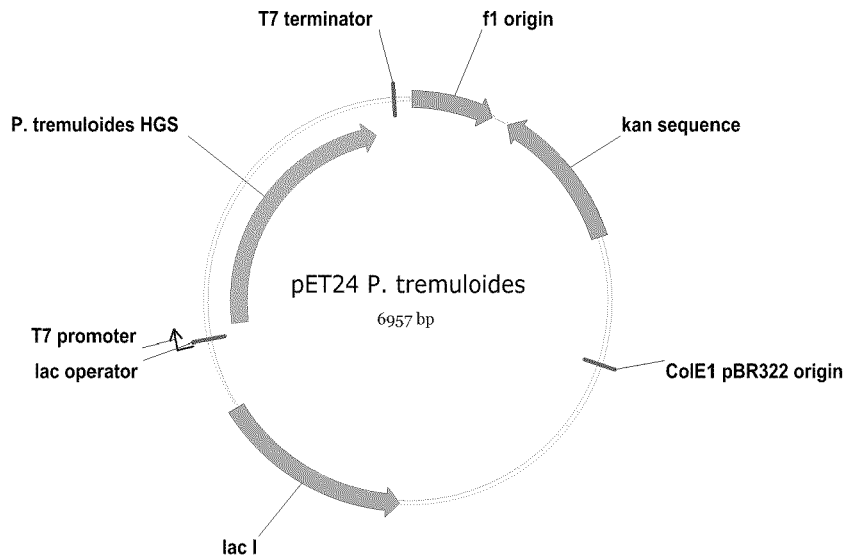
B.
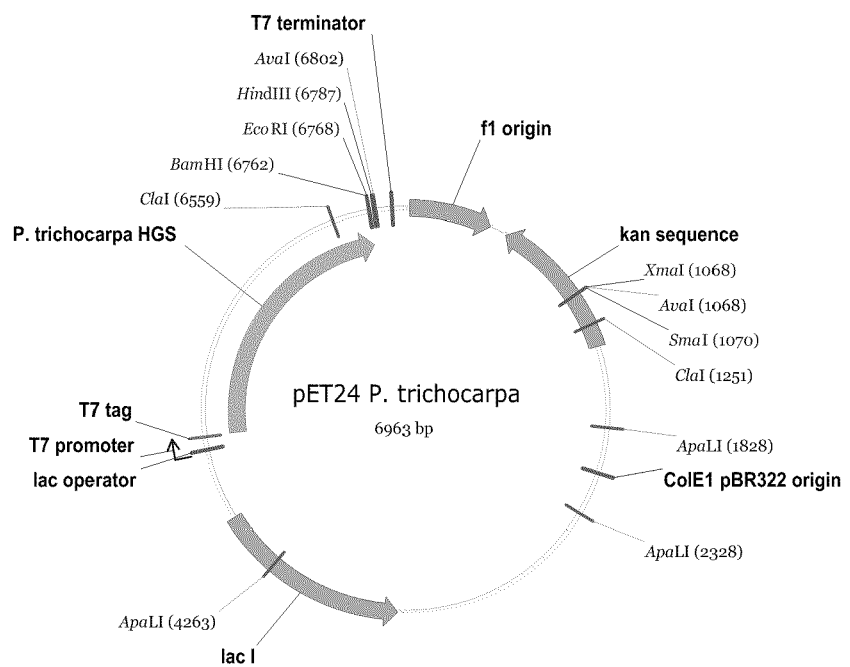

Figure 80

Amino acid sequence of *P. tremuloides* IspS (SEQ ID NO:158)

```
MRCSVSTENVSFSETETETRRSANYEPNSWDYDYLLSSDTDESIEVHKDKAKKLEAEVR
REINNEKAEFLTLLELIDNVQRLGLGYRFESDIRRALDRFVSSGGFDGVTKTSLHGTAL
SFRLLRQHGFEVSQEAFSGFKDQNGNFLENLKEDIKAILSLYEASFLALEGENILDEAK
VFAISHLKELSEEKIGKELAEQVSHALELPLHRRTQRLEAVWSIEAYRKKEDANQVLLE
LAILDYNMIQSVYQRDLRETSRWWRRVGLATKLHFARDRLIESFYWAVGVAFEPQYSDC
RNSVAKMFSFVTIIDDIYDVYGTLDELELFTDAVERWDVNAINDLPDYMKLCFLALYNT
INEIAYDNLKDKGENILPYLTKAWADLCNAFLQEAKWLYNKSTPTFDDYFGNAWKSSSG
PLQLIFAYFAVVQNIKKEEIENLQKYHDIISRPSHIFRLCNDLASASAEIARGETANSV
SCYMRTKGISEELATESVMNLIDETWKKMNKEKLGGSLFAKPFVETAINLARQSHCTYH
NGDAHTSPDELTRKRVLSVITEPILPFER
```

Figure 81A

Nucleotide sequence of P. tremuloides pET24a (SEQ ID NO:159)

```
tggcgaatgggacgcgccctgtagcggcgcattaagcgcggcgggtgtggtggttacgc
gcagcgtgaccgctacacttgccagcgccctagcgcccgctccttcgctttcttccct
tcctttctcgccacgttcgccggctttccccgtcaagctctaaatcgggggctcccttt
agggttccgatttagtgctttacggcacctcgaccccaaaaaacttgattagggtgatg
gttcacgtagtgggccatcgccctgatagacggttttcgcccttgacgttggagtcc
acgttctttaatagtggactcttgttccaaactggaacaacactcaacccatctcggt
ctattcttttgatttataagggattttgccgatttcggcctattggttaaaaaatgagc
tgatttaacaaaaatttaacgcgaattttaacaaaatattaacgtttacaatttcaggt
ggcacttttcggggaaatgtgcgcggaacccctatttgtttattttctaaatacattc
aaatatgtatccgctcatgaattaattcttagaaaaactcatcgagcatcaaatgaaac
tgcaatttattcatatcaggattatcaataccatatttttgaaaaagccgtttctgtaa
tgaaggagaaaactcaccgaggcagttccataggatggcaagatcctggtatcggtctg
cgattccgactcgtccaacatcaatacaacctattaatttcccctcgtcaaaaataagg
ttatcaagtgagaaatcaccatgagtgacgactgaatccggtgagaatggcaaaagttt
atgcatttctttccagacttgttcaacaggccagccattacgctcgtcatcaaaatcac
tcgcatcaaccaaaccgttattcattcgtgattgcgcctgagcgagacgaaatacgcga
tcgctgttaaaaggacaattacaaacaggaatcgaatgcaaccggcgcaggaacactgc
cagcgcatcaacaatattttcacctgaatcaggatattcttctaatacctggaatgctg
ttttcccggggatcgcagtggtgagtaaccatgcatcatcaggagtacggataaaatgc
ttgatggtcggaagaggcataaattccgtcagccagtttagtctgaccatctcatctgt
aacatcattggcaacgctacctttgccatgtttcagaaacaactctggcgcatcgggct
tcccatacaatcgatagattgtcgcacctgattgcccgacattatcgcgagcccattta
tacccatataaatcagcatccatgttggaatttaatcgcggcctagagcaagacgtttc
ccgttgaatatggctcataacacccccttgtattactgtttatgtaagcagacagtttta
ttgttcatgaccaaaatcccttaacgtgagttttcgttccactgagcgtcagacccgt
agaaaagatcaaaggatcttcttgagatccttttttctgcgcgtaatctgctgcttgc
aaacaaaaaaaccaccgctaccagcggtggtttgtttgccggatcaagagctaccaact
ctttttccgaaggtaactggcttcagcagagcgcagataccaaatactgtccttctagt
gtagccgtagttaggccaccacttcaagaactctgtagcaccgcctacatacctcgctc
tgctaatcctgttaccagtggctgctgccagtggcgataagtcgtgtcttaccgggttg
gactcaagacgatagttaccggataaggcgcagcggtcgggctgaacggggggttcgtg
cacacagcccagcttggagcgaacgacctacaccgaactgagatacctacagcgtgagc
tatgagaaagcgccacgcttcccgaagggagaaaggcggacaggtatccggtaagcggc
agggtcggaacaggagagcgcacgagggagcttccagggggaaacgcctggtatcttta
tagtcctgtcgggtttcgccacctctgacttgagcgtcgatttttgtgatgctcgtcag
gggggcggagcctatggaaaaacgccagcaacgcggcctttttacggttcctggccttt
tgctggccttttgctcacatgttctttcctgcgttatccctgattctgtggataaccg
tattaccgcctttgagtgagctgataccgctcgccgcagccgaacgaccgagcgcagcg
agtcagtgagcgaggaagcggaagagcgcctgatgcggtattttctccttacgcatctg
tgcggtatttcacaccgcatatggtgcactctcagtacaatctgctctgatgccgca
tagttaagccagtatacactccgctatcgctacgtgactgggtcatggctgcgccccga
cacccgccaacacccgctgacgcgccctgacgggcttgtctgctcccggcatccgctta
cagacaagctgtgaccgtctccgggagctgcatgtgtcagaggttttcaccgtcatcac
```

Figure 81B

Nucleotide sequence of P. tremuloides pET24a cgaaacgcgcgaggcagctgcggtaaagctcatcagcgtggtcgtgaagcgattcacag
atgtctgcctgttcatccgcgtccagctcgttgagtttctccagaagcgttaatgtctg
gcttctgataaagcgggccatgttaagggcggttttttcctgtttggtcactgatgcct
ccgtgtaaggggatttctgttcatggggtaatgataccgatgaaacgagagaggatg
ctcacgatacgggttactgatgatgaacatgcccggttactggaacgttgtgagggtaa
acaactggcggtatggatgcggcgggaccagagaaaaatcactcagggtcaatgccagc
gcttcgttaatacagatgtaggtgttccacagggtagccagcagcatcctgcgatgcag
atccggaacataatggtgcagggcgctgacttccgcgtttccagactttacgaaacacg
gaaaccgaagaccattcatgttgttgctcaggtcgcagacgttttgcagcagcagtcgc
ttcacgttcgctcgcgtatcggtgattcattctgctaaccagtaaggcaaccccgccag
cctagccgggtcctcaacgacaggagcacgatcatgcgcacccgtggggccgccatgcc
ggcgataatggcctgcttctcgccgaaacgtttggtggcgggaccagtgacgaaggctt
gagcgagggcgtgcaagattccgaataccgcaagcgacaggccgatcatcgtcgcgctc
cagcgaaagcggtcctcgccgaaaatgacccagagcgctgccggcacctgtcctacgag
ttgcatgataaagaagacagtcataagtgcggcgacgatagtcatgccccgcgcccacc
ggaaggagctgactgggttgaaggctctcaagggcatcggtcgagatcccggtgcctaa
tgagtgagctaacttacattaattgcgttgcgctcactgcccgctttccagtcgggaaa
cctgtcgtgccagctgcattaatgaatcggccaacgcgcggggagaggcggtttgcgta
ttgggcgccagggtggtttttcttttcaccagtgagacgggcaacagctgattgcccctt
caccgcctggccctgagagagttgcagcaagcggtccacgctggtttgcccagcaggc
gaaaatcctgtttgatggtggttaacggcgggatataacatgagctgtcttcggtatcg
tcgtatcccactaccgagatatccgcaccaacgcgcagcccggactcggtaatggcgcg
cattgcgcccagcgccatctgatcgttggcaaccagcatcgcagtgggaacgatgccct
cattcagcatttgcatggtttgttgaaaaccggacatggcactccagtcgccttcccgt
tccgctatcggctgaatttgattgcgagtgagatatttatgccagccagccagacgcag
acgcgccgagacagaacttaatgggcccgctaacagcgcgatttgctggtgacccaatg
cgaccagatgctccacgcccagtcgcgtaccgtcttcatgggagaaaataatactgttg
atgggtgtctggtcagagacatcaagaaataacgccggaacattagtgcaggcagcttc
cacagcaatggcatcctggtcatccagcggatagttaatgatcagcccactgacgcgtt
gcgcgagaagattgtgcaccgccgctttacaggcttcgacgccgcttcgttctaccatc
gacaccaccacgctggcacccagttgatcggcgcgagatttaatcgccgcgacaatttg
cgacggcgcgtgcagggccagactggaggtggcaacgccaatcagcaacgactgtttgc
ccgccagttgttgtgccacgcggttgggaatgtaattcagctccgccatcgccgcttcc
acttttcccgcgttttcgcagaaacgtggctggcctggttcaccacgcgggaaacggt
ctgataagagacaccggcatactctgcgacatcgtataacgttactggtttcacattca
ccaccctgaattgactctcttccgggcgctatcatgccataccgcgaaaggttttgcgc
cattcgatggtgtccgggatctcgacgctctccttatgcgactcctgcattaggaagc
agcccagtagtaggttgaggccgttgagcaccgccgccgcaaggaatggtgcatgcaag
gagatggcgcccaacagtccccggccacggggcctgccaccatacccacgccgaaaca
agcgctcatgagcccgaagtggcgagcccgatcttccccatcggtgatgtcggcgatat
aggcgccagcaaccgcacctgtggcgccggtgatgccggccacgatgcgtccggcgtag
aggatcgagatctcgatcccgcgaaattaatacgactcactatagggaattgtgagcg
gataacaattcccctctagaaataattttgtttaactttaagaaggagatatacatatg

Figure 81C

Nucleotide sequence of P. tremuloides pET24a

```
cgttgtagcgtgtccaccgaaaatgtgtctttctctgaaactgaaaccgaaacgcgtcg
ttctgcgaactacgaacctaacagctgggactatgattacctgctgtcctccgacacgg
acgagtccatcgaagtacacaaagacaaagcgaaaaagctggaagccgaagttcgtcgc
gagattaataacgaaaaagcagaatttctgaccctgctggaactgattgacaacgtcca
gcgcctgggcctgggttaccgtttcgagtctgatatccgtcgtgcgctggatcgcttcg
tttcctccggcggcttcgatggcgtaaccaagacttcctgcacggtacggcactgtct
ttccgtctgctgcgtcaacacggttttgaggtttctcaggaagcgttcagcggcttcaa
agaccaaaacggcaacttcctggagaacctgaaggaagatatcaaagctatcctgagcc
tgtacgaggccagcttcctggctctggaaggcgaaaacatcctggacgaggcgaaggtt
ttcgcaatctctcatctgaaagaactgtctgaagaaagatcggtaaagagctggcaga
acaggtgtcccatgcactggaactgccactgcatcgccgtactcagcgtctggaagcag
tatggtctatcgaggcctaccgtaaaaaggaggacgcgaaccaggttctgctggagctg
gcaattctggattacaacatgatccagtctgtataccagcgtgatctgcgtgaaacgtc
ccgttggtggcgtcgtgtgggtctggcgaccaaactgcactttgctcgtgaccgcctga
ttgagagcttctactgggccgtgggtgtagcattcgaaccgcaatactccgactgccgt
aactccgtcgcaaaaatgttttctttcgtaaccattatcgacgatatctacgatgtata
cggcaccctggacgaactggagctgtttactgatgcagttgagcgttgggacgtaaacg
ccatcaacgacctgccggattacatgaaactgtgctttctggctctgtataacactatt
aacgaaatcgcctacgacaacctgaaagataaaggtgagaacatcctgccgtatctgac
caaagcctgggctgacctgtgcaacgcttcctgcaagaagccaagtggctgtacaaca
aatctactccgacctttgacgactacttcggcaacgcatggaaatcctcttctggcccg
ctgcaactgatcttcgcttacttcgctgtcgtgcagaacattaaaaaggaagagatcga
aaacctgcaaaaataccatgacatcatctctcgtccttcccatatcttccgtctgtgca
atgacctggctagcgcgtctgcggaaattgcgcgtggtgaaaccgcaaatagcgtttct
tgttacatgcgcactaaaggtatctccgaagaactggctaccgaaagcgtgatgaatct
gatcgatgaaacctggaaaaagatgaacaaggaaaaactgggtggtagcctgttcgcga
aaccgttcgtggaaccgcgatcaacctggcacgtcaatctcactgcacttatcataac
ggcgacgcgcatacctctccggatgagctgacccgcaaacgcgttctgtctgtaatcac
tgaaccgattctgccgtttgaacgctaaggatccgaattcgagctccgtcgacaagctt
gcggccgcactcgagcaccaccaccaccaccactgagatccggctgctaacaaagcccg
aaaggaagctgagttggctgctgccaccgctgagcaataactagcataacccttgggg
cctctaaacgggtcttgaggggttttttgctgaaggaggaactatatccggat
```

Figure 82

Amino acid sequence of *P. trichocharpa* IspS (SEQ ID NO:160)

```
MRCSVSTENVSFTETETETRRSANYEPNSWDYDYLLSSDTDESIEVYKDKAKKLEAEVR
REINNEKAEFLTLLELIDNVQRLGLGYRFESDIRRALDRFVSSGGFDAVTKTSLHATAL
SFRLLRQHGFEVSQEAFSGFKDQNGNFLENLKEDIKAILSLYEASFLALEGENILDEAK
VFAISHLKELSEEKIGKDLAEQVNHALELPLHRRTQRLEAVLSIEAYRKKEDADQVLLE
LAILDYNMIQSVYQRDLRETSRWWRRVGLATKLHFARDRLIESFYWAVGVAFEPQYSDC
RNSVAKMFSFVTIIDDIYDVYGTLDELELFTNAVERWDVNAIDDLPDYMKLCFLALYNT
INEIAYDNLKEKGENILPYLTKAWADLCNAFLQEAKWLYNKSTPTFDEYFGNAWKSSSG
PLQLVFAYFAVVQNIKKEEIENLQKYHDIISRPSHIFRLCNDLASASAEIARGETANSV
SCYMRTKGISEELATESVMNLIDETWKKMNKEKLGGSLFAKPFVETAINLARQSHCTYH
NGDAHTSPDELTRKRVLSVITEPILPFER
```

Figure 83A

Nucleotide sequence of P. trichocharpa pET24a (SEQ ID NO:161)

```
tggcgaatgggacgcgccctgtagcggcgcattaagcgcggcgggtgtggtggttacgc
gcagcgtgaccgctacacttgccagcgccctagcgcccgctcctttcgctttcttccct
tcctttctcgccacgttcgccggcttccccgtcaagctctaaatcggggctcccttt
agggttccgatttagtgctttacggcacctcgaccccaaaaaacttgattagggtgatg
gttcacgtagtgggccatcgccctgatagacggttttcgccctttgacgttggagtcc
acgttctttaatagtggactcttgttccaaactggaacaacactcaccctatctcggt
ctattcttttgatttataagggattttgccgatttcggcctattggttaaaaaatgagc
tgatttaacaaaaatttaacgcgaattttaacaaaatattaacgtttacaatttcaggt
ggcacttttcggggaaatgtgcgcggaacccctatttgtttattttctaaatacattc
aaatatgtatccgctcatgaattaattcttagaaaaactcatcgagcatcaaatgaaac
tgcaatttattcatatcaggattatcaataccatattttgaaaaagccgtttctgtaa
tgaaggagaaaactcaccgaggcagttcataggatggcaagatcctggtatcggtctg
cgattccgactcgtccaacatcaatacaacctattaatttccctcgtcaaaaataagg
ttatcaagtgagaaatcaccatgagtgacgactgaatccggtgagaatggcaaaagttt
atgcatttctttccagacttgttcaacaggccagccattacgctcgtcatcaaaatcac
tcgcatcaaccaaaccgttattcattcgtgattgcgcctgagcgagacgaaatacgcga
tcgctgttaaaggacaattacaaacaggaatcgaatgcaaccggcgcaggaacactgc
cagcgcatcaacaatattttcacctgaatcaggatattcttctaatacctggaatgctg
ttttcccggggatcgcagtggtgagtaaccatgcatcatcaggagtacggataaaatgc
ttgatggtcggaagaggcataaattccgtcagccagtttagtctgaccatctcatctgt
aacatcattggcaacgctacctttgccatgtttcagaaacaactctggcgcatcgggct
tcccatacaatcgatagattgtcgcacctgattgcccgacattatcgcgagcccattta
tacccatataaatcagcatccatgttggaatttaatcgcggcctagagcaagacgtttc
ccgttgaatatggctcataacacccttgtattactgtttatgtaagcagacagtttta
ttgttcatgaccaaaatcccttaacgtgagttttcgttccactgagcgtcagacccgt
agaaaagatcaaaggatcttcttgagatccttttttctgcgcgtaatctgctgcttgc
aaacaaaaaaaccaccgctaccagcggtggtttgtttgccggatcaagagctaccaact
ctttttccgaaggtaactggcttcagcagagcgcagataccaaatactgtccttctagt
gtagccgtagttaggccaccacttcaagaactctgtagcaccgcctacatacctcgctc
tgctaatcctgttaccagtggctgctgccagtggcgataagtcgtgtcttaccgggttg
gactcaagacgatagttaccggataaggcgcagcggtcgggctgaacggggggttcgtg
cacacagcccagcttggagcgaacgacctacaccgaactgagatacctacagcgtgagc
tatgagaaagcgccacgcttcccgaagggagaaaggcggacaggtatccggtaagcggc
agggtcggaacaggagagcgcacgagggagcttccaggggaaacgcctggtatcttta
tagtcctgtcgggtttcgccacctctgacttgagcgtcgatttttgtgatgctcgtcag
ggggcggagcctatggaaaaacgccagcaacgcggcctttttacggttcctggcctt
tgctggccttttgctcacatgttcttcctgcgttatcccctgattctgtggataaccg
tattaccgcctttgagtgagctgataccgctcgccgcagccgaacgaccgagcgcagcg
agtcagtgagcgaggaagcggaagagcgcctgatgcggtattttctccttacgcatctg
tgcggtatttcacaccgcatatatggtgcactctcagtacaatctgctctgatgccgca
tagttaagccagtatacactccgctatcgctacgtgactgggtcatggctgcgccga
cacccgccaacacccgctgacgcgccctgacgggcttgtctgctcccggcatccgctta
cagacaagctgtgaccgtctccgggagctgcatgtgtcagaggttttcaccgtcatcac
```

Figure 83B

Nucleotide sequence of P. trichocharpa pET24a cgaaacgcgcgaggcagctgcggtaaagctcatcagcgtggtcgtgaagcgattcacag
atgtctgcctgttcatccgcgtccagctcgttgagtttctccagaagcgttaatgtctg
gcttctgataaagcgggccatgttaagggcggttttttcctgtttggtcactgatgcct
ccgtgtaagggggatttctgttcatggggtaatgataccgatgaaacgagagaggatg
ctcacgatacgggttactgatgatgaacatgcccggttactggaacgttgtgagggtaa
acaactggcggtatggatgcggcgggaccagagaaaaatcactcagggtcaatgccagc
gcttcgttaatacagatgtaggtgttccacagggtagccagcagcatcctgcgatgcag
atccggaacataatggtgcagggcgctgacttccgcgtttcagactttacgaaacacg
gaaaccgaagaccattcatgttgttgctcaggtcgcagacgttttgcagcagcagtcgc
ttcacgttcgctcgcgtatcggtgattcattctgctaaccagtaaggcaaccccgccag
cctagccgggtcctcaacgacaggagcacgatcatgcgcacccgtggggccgccatgcc
ggcgataatggcctgcttctcgccgaaacgtttggtggcgggaccagtgacgaaggctt
gagcgagggcgtgcaagattccgaataccgcaagcgacaggccgatcatcgtcgcgctc
cagcgaaagcggtcctcgccgaaaatgacccagagcgctgccggcacctgtcctacgag
ttgcatgataaagaagacagtcataagtgcggcgacgatagtcatgccccgcgcccacc
ggaaggagctgactgggttgaaggctctcaagggcatcggtcgagatcccggtgcctaa
tgagtgagctaacttacattaattgcgttgcgctcactgcccgctttccagtcgggaaa
cctgtcgtgccagctgcattaatgaatcggccaacgcgcggggagaggcggtttgcgta
ttgggcgccagggtggttttcttttcaccagtgagacgggcaacagctgattgcccctt
caccgcctggccctgagagagttgcagcaagcggtccacgctggtttgcccagcaggc
gaaaatcctgtttgatggtggttaacggcgggataacatgagctgtcttcggtatcg
tcgtatcccactaccgagatatccgcaccaacgcgcagcccggactcggtaatggcgcg
cattgcgcccagcgccatctgatcgttggcaaccagcatcgcagtgggaacgatgccct
cattcagcatttgcatggtttgttgaaaaccggacatggcactccagtcgccttcccgt
tccgctatcggctgaatttgattgcgagtgagatatttatgccagccagccagacgcag
acgcgccgagacagaacttaatgggcccgctaacagcgcgatttgctggtgacccaatg
cgaccagatgctccacgcccagtcgcgtaccgtcttcatgggagaaaataatactgttg
atgggtgtctggtcagagacatcaagaaataacgccggaacattagtgcaggcagcttc
cacagcaatggcatcctggtcatccagcggatagttaatgatcagcccactgacgcgtt
gcgcgagaagattgtgcaccgccgctttacaggcttcgacgccgcttcgttctaccatc
gacaccaccacgctggcacccagttgatcggcgcgagatttaatcgccgcgacaatttg
cgacggcgcgtgcagggccagactggaggtggcaacgccaatcagcaacgactgtttgc
ccgccagttgttgtgccacgcggttgggaatgtaattcagctccgccatcgccgcttcc
acttttttcccgcgttttcgcagaaacgtggctggcctggttcaccacgcgggaaacggt
ctgataagagacaccggcatactctgcgacatcgtataacgttactggtttcacattca
ccaccctgaattgactctcttccgggcgctatcatgccataccgcgaaaggttttgcgc
cattcgatggtgtccgggatctcgacgctctccttatgcgactcctgcattaggaagc
agcccagtagtaggttgaggccgttgagcaccgccgcgcaaggaatggtgcatgcaag
gagatggcgcccaacagtccccggccacgggcctgccaccatacccacgccgaaaca
agcgctcatgagcccgaagtggcgagcccgatcttccccatcggtgatgtcggcgatat
aggcgccagcaaccgcacctgtggcgccggtgatgccggccacgatgcgtccggcgtag
aggatcgagatctcgatcccgcgaattaatacgactcactatagggaattgtgagcg
gataacaattcccctctagaaataattttgtttaactttaagaaggagatatacatatg

Figure 83C

Nucleotide sequence of P. trichocharpa pET24a catatgcgttgtagcgtgtccaccgaaaatgtgtcttccaccgaaactgaaaccgaaac
gcgtcgttctgcgaactacgaacctaacagctgggactatgattacctgctgtcctccg
acacggacgagtccatcgaagtatacaaagacaaagcgaaaaagctggaagccgaagtt
cgtcgcgagattaataacgaaaaagcagaatttctgaccctgctggaactgattgacaa
cgtccagcgcctgggcctgggttaccgtttcgagtctgatatccgtcgtgcgctggatc
gcttcgtttcctccggcggcttcgatgcggtaaccaagactccctgcacgcgacggca
ctgtctttccgtctgctgcgtcaacacggttttgaggtttctcaggaagcgttcagcgg
cttcaaagaccaaaacggcaacttcctggagaacctgaaggaagatatcaaagctatcc
tgagcctgtacgaggccagcttcctggctctggaaggcgaaaacatcctggacgaggcg
aaggttttcgcaatctctcatctgaaagaactgtctgaagaaaagatcggtaaagatct
ggcagaacaggtgaaccatgcactggaactgccactgcatcgccgtactcagcgtctgg
aagcagtactgtctatcgaggcctaccgtaaaaaggaggacgcggatcaggttctgctg
gagctggcaattctggattacaacatgatccagtctgtataccagcgtgatctgcgtga
aacgtcccgttggtggcgtcgtgtgggtctggcgaccaaactgcactttgctcgtgacc
gcctgattgagagcttctactgggccgtggtgtagcattcgaaccgcaatactccgac
tgccgtaactccgtcgcaaaaatgttttctttcgtaaccattatcgacgatatctacga
tgtatacggcaccctggacgaactggagctgtttactaacgcagttgagcgttgggacg
taaacgccatcgacgatctgccggattacatgaaactgtgctttctggctctgtataac
actattaacgaaatcgcctacgacaacctgaaagaaaaaggtgagaacatcctgccgta
tctgaccaaagcctgggctgacctgtgcaacgctttcctgcaagaagccaagtggctgt
acaacaaatctactccgaccttgacgaatacttcggcaacgcatggaaatcctcttct
ggcccgctgcaactggtgttcgcttacttcgctgtcgtgcagaacattaaaaaggaaga
gatcgaaaacctgcaaaaataccatgacatcatctctcgtccttcccatatcttccgtc
tgtgcaatgacctggctagcgcgtctgcggaaattgcgcgtggtgaaaccgcaaatagc
gtttcttgttacatgcgcactaaaggtatctccgaagaactggctaccgaaagcgtgat
gaatctgatcgatgaaacctggaaaaagatgaacaaggaaaaactgggtggtagcctgt
tcgcgaaaccgttcgtggaaaccgcgatcaacctggcacgtcaatctcactgcacttat
cataacggcgacgcgcatacctctccggatgagctgacccgcaaacgcgttctgtctgt
aatcactgaaccgattctgccgtttgaacgctaaggatccgaattcgagctccgtcgac
aagcttgcggccgcactcgagcaccaccaccaccaccactgagatccggctgctaacaa
agcccgaaaggaagctgagttggctgctgccaccgctgagcaataactagcataacccc
ttggggcctctaaacgggtcttgaggggttttttgctgaaaggaggaactatatccgga
t Figure 84
A.
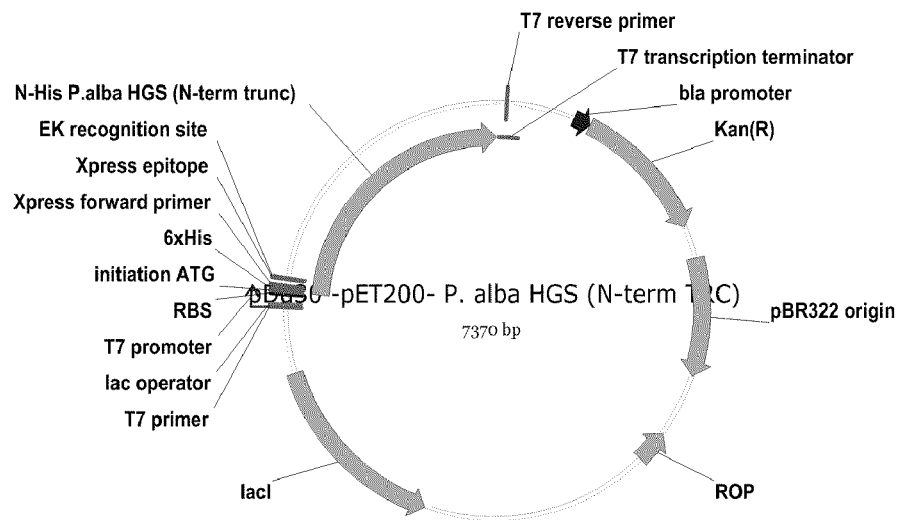
B.
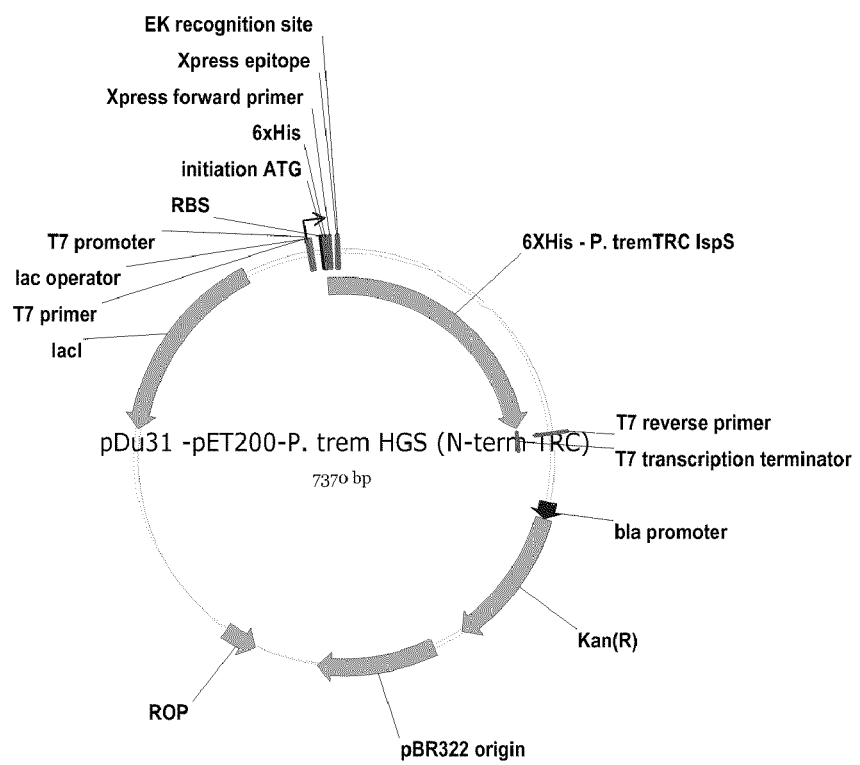

Figure 85

Amino acid sequence of IspS variant P. albaTRC-pET200 (SEQ ID NO:162)

```
MRGSHHHHHHGMASMTGGQQMGRDLYDDDDKDHPFTMRRSANYEPNSWDYDYLLSSDTD
ESIEVYKDKAKKLEAEVRREINNEKAEFLTLLELIDNVQRLGLGYRFESDIRGALDRFV
SSGGFDAVTKTSLHGTALSFRLLRQHGFEVSQEAFSGFKDQNGNFLENLKEDIKAILSL
YEASFLALEGENILDEAKVFAISHLKELSEEKIGKELAEQVNHALELPLHRRTQRLEAV
WSIEAYRKKEDANQVLLELAILDYNMIQSVYQRDLRETSRWWRRVGLATKLHFARDRLI
ESFYWAVGVAFEPQYSDCRNSVAKMFSFVTIIDDIYDVYGTLDELELFTDAVERWDVNA
INDLPDYMKLCFLALYNTINEIAYDNLKDKGENILPYLTKAWADLCNAFLQEAKWLYNK
STPTFDDYFGNAWKSSSGPLQLVFAYFAVVQNIKKEEIENLQKYHDTISRPSHIFRLCN
DLASASAEIARGETANSVSCYMRTKGISEELATESVMNLIDETWKKMNKEKLGGSLFAK
PFVETAINLARQSHCTYHNGDAHTSPDELTRKRVLSVITEPILPFER
```

Figure 86A

Nucleotide Sequence of pDu30 (SEQ ID NO:163)

```
aagggcgagctcaacgatccggctgctaacaaagcccgaaaggaagctgagttggctgc
tgccaccgctgagcaataactagcataaccccttggggcctctaaacgggtcttgagga
gttttttgctgaaaggaggaactatatccggatatcccgcaagaggcccggcagtaccg
gcataaccaagcctatgcctacagcatccagggtgacggtgccgaggatgacgatgagc
gcattgttagatttcatacacggtgcctgactgcgttagcaatttaactgtgataaact
accgcattaaagcttatcgatgataagctgtcaaacatgagaattaattcttgaagacg
aaagggcctcgtgatacgcctatttttataggttaatgtcatgataataatggtttctt
agacgtcaggtggcacttttcggggaaatgtgcgcggaaccccatttgtttattttc
taaatacattcaaatatgtatccgctcatgagacaataaccctgataaatgcttcaata
atattgaaaaaggaagagtatgattgaacaagatggattgcacgcaggttctccggccg
cttgggtggagaggctattcggctatgactgggcacaactgacaatcggctgctctgat
gccgccgtgttccggctgtcagcgcaggggcgcccggttcttttgtcaagaccgacct
gtccggtgccctgaatgaactgcaggacgaggcagcgcggctatcgtggctggccacga
cgggcgttccttgcgcagctgtgctcgacgttgtcactgaagcgggaagggactggctg
ctattgggcgaagtgccggggcaggatctcctgtcatctcaccttgctcctgccgagaa
agtatccatcatggctgatgcaatgcggcggctgcatacgcttgatccggctacctgcc
cattcgaccaccaagcgaaacatcgcatcgagcgggcacgtactcggatggaagccgt
cttgtcgatcaggatgatctggacgaagagcatcaggggctcgcgccagccgaactgtt
cgccaggctcaaggcgcgcatgcccgacggcgaggatctcgtcgtgacacatggcgatg
cctgcttgccgaatatcatggtggaaaatggccgcttttctggattcatcgactgtggc
cggctgggtgtggcggaccgctatcaggacatagcgttggctacccgtgatattgctga
agagcttggcggcgaatgggctgaccgcttcctcgtgctttacggtatcgccgctcccg
attcgcagcgcatcgccttctatcgccttcttgacgagttcttctgagcgggactctgg
ggttcgaaatgaccgaccaagcgacgcctaactgtcagaccaagtttactcatatatac
tttagattgatttaaaacttcattttaatttaaaaggatctaggtgaagatcctttt
gataatctcatgaccaaaatcccttaacgtgagttttcgttccactgagcgtcagaccc
cgtagaaaagatcaaaggatcttcttgagatcctttttttctgcgcgtaatctgctgct
tgcaaacaaaaaaaccaccgctaccagcggtggtttgtttgccggatcaagagctacca
actcttttccgaaggtaactggcttcagcagagcgcagataccaaatactgtccttct
agtgtagccgtagttaggccaccacttcaagaactctgtagcaccgcctacatacctcg
ctctgctaatcctgttaccagtggctgctgccagtggcgataagtcgtgtcttaccggg
ttggactcaagacgatagttaccggataaggcgcagcggtcgggctgaacggggggttc
gtgcacacagcccagcttggagcgaacgacctacaccgaactgagatacctacagcgtg
agctatgagaaagcgccacgcttcccgaagggagaaaggcggacaggtatccggtaagc
ggcagggtcggaacaggagagcgcacgagggagcttccaggggaaacgcctggtatct
ttatagtcctgtcgggtttcgccacctctgacttgagcgtcgatttttgtgatgctcgt
caggggggcggagcctatggaaaaacgccagcaacgcggcctttttacggttcctggcc
ttttgctggccttttgctcacatgttctttcctgcgttatccctgattctgtggataa
ccgtattaccgcctttgagtgagctgataccgctcgccgcagccgaacgaccgagcgca
gcgagtcagtgagcgaggaagcggaagagcgcctgatgcggtattttctccttacgcat
ctgtgcggtatttcacaccgcaatggtgcactctcagtacaatctgctctgatgccgca
tagttaagccagtatacactccgctatcgctacgtgactgggtcatggctgcgccccga
cacccgccaacacccgctgacgcgccctgacgggcttgtctgctcccggcatccgctta
```

Figure 86B

Nucleotide Sequence of pDu30 cagacaagctgtgaccgtctccgggagctgcatgtgtcagaggttttcaccgtcatcac
cgaaacgcgcgaggcagctgcggtaaagctcatcagcgtggtcgtgaagcgattcacag
atgtctgcctgttcatccgcgtccagctcgttgagtttctccagaagcgttaatgtctg
gcttctgataaagcgggccatgttaagggcggttttttcctgtttggtcactgatgcct
ccgtgtaagggggatttctgttcatgggggtaatgataccgatgaaacgagagaggatg
ctcacgatacgggttactgatgatgaacatgcccggttactggaacgttgtgagggtaa
acaactggcggtatggatgcggcgggaccagagaaaaatcactcagggtcaatgccagc
gcttcgttaatacagatgtaggtgttccacagggtagccagcagcatcctgcgatgcag
atccggaacataatggtgcagggcgctgacttccgcgtttccagactttacgaaacacg
gaaaccgaagaccattcatgttgttgctcaggtcgcagacgttttgcagcagcagtcgc
ttcacgttcgctcgcgtatcggtgattcattctgctaaccagtaaggcaaccccgccag
cctagccgggtcctcaacgacaggagcacgatcatgcgcacccgtggccaggacccaac
gctgcccgagatgcgccgcgtgcggctgctggagatggcggacgcgatggatatgttct
gccaagggttggtttgcgcattcacagttctccgcaagaattgattggctccaattctt
ggagtggtgaatccgttagcgaggtgccgccggcttccattcaggtcgaggtggcccgg
ctccatgcaccgcgacgcaacgcggggaggcagacaaggtatagggcggcgcctacaat
ccatgccaacccgttccatgtgctcgccgaggcggcataaatcgccgtgacgatcagcg
gtccaatgatcgaagttaggctggtaagagccgcgagcgatccttgaagctgtccctga
tggtcgtcatctacctgcctggacagcatggcctgcaacgcgggcatcccgatgccgcc
ggaagcgagaagaatcataatggggaaggccatccagcctcgcgtcgcgaacgccagca
agacgtagcccagcgcgtcggccgccatgccggcgataatggcctgcttctcgccgaaa
cgtttggtggcgggaccagtgacgaaggcttgagcgagggcgtgcaagattccgaatac
cgcaagcgacaggccgatcatcgtcgcgctccagcgaaagcggtcctcgccgaaaatga
cccagagcgctgccggcacctgtcctacgagttgcatgataaagaagacagtcataagt
gcggcgacgatagtcatgccccgcgcccaccggaaggagctgactgggttgaaggctct
caagggcatcggtcgagatcccggtgcctaatgagtgagctaacttacattaattgcgt
tgcgctcactgcccgctttccagtcgggaaacctgtcgtgccagctgcattaatgaatc
ggccaacgcgcggggagaggcggtttgcgtattgggcgccagggtggttttcttttca
ccagtgagacgggcaacagctgattgcccttcaccgcctggccctgagagagttgcagc
aagcggtccacgctggtttgccccagcaggcgaaaatcctgtttgatggtggttaacgg
cgggatataacatgagctgtcttcggtatcgtcgtatcccactaccgagatatccgcac
caacgcgcagcccggactcggtaatggcgcgcattgcgcccagcgccatctgatcgttg
gcaaccagcatcgcagtgggaacgatgccctcattcagcatttgcatggtttgttgaaa
accggacatggcactccagtcgccttcccgttccgctatcggctgaatttgattgcgag
tgagatatttatgccagccagccagacgcagacgcgccgagacagaacttaatgggccc
gctaacagcgcgatttgctggtgacccaatgcgaccagatgctccacgcccagtcgcgt
accgtcttcatgggagaaaataatactgttgatgggtgtctggtcagagacatcaagaa
ataacgccggaacattagtgcaggcagcttccacagcaatggcatcctggtcatccagc
ggatagttaatgatcagcccactgacgcgttgcgcgagaagattgtgcaccgccgcttt
acaggcttcgacgccgcttcgttctaccatcgacaccaccacgctggcacccagttgat
cggcgcgagatttaatcgccgcgacaatttgcgacggcgcgtgcagggccagactggag
gtggcaacgccaatcagcaacgactgtttgccgccagttgttgtgccacgcggttggg
aatgtaattcagctccgccatcgccgcttccacttttcccgcgttttcgcagaaacgt

Figure 86C

Nucleotide Sequence of pDu30

```
ggctggcctggttcaccacgcgggaaacggtctgataagagacaccggcatactctgcg
acatcgtataacgttactggtttcacattcaccaccctgaattgactctcttccgggcg
ctatcatgccataccgcgaaaggttttgcgccattcgatggtgtccgggatctcgacgc
tctcccttatgcgactcctgcattaggaagcagcccagtagtaggttgaggccgttgag
caccgccgccgcaaggaatggtgcatgcaaggagatggcgcccaacagtccccggcca
cggggcctgccaccatacccacgccgaaacaagcgctcatgagcccgaagtggcgagcc
cgatcttccccatcggtgatgtcggcgatataggcgccagcaaccgcacctgtggcgcc
ggtgatgccggccacgatgcgtccggcgtagaggatcgagatctcgatcccgcgaaatt
aatacgactcactatagggaattgtgagcggataacaattcccctctagaaataattt
tgtttaactttaagaaggagatatacatatgcggggttctcatcatcatcatcatcatg
gtatggctagcatgactggtggacagcaaatgggtcgggatctgtacgacgatgacgat
aaggatcatcccttcaccatgcgtcgttctgcgaactacgaacctaacagctgggacta
tgattacctgctgtcctccgacacggacgagtccatcgaagtatacaaagacaaagcga
aaaagctggaagccgaagttcgtcgcgagattaataacgaaaagcagaatttctgacc
ctgctggaactgattgacaacgtccagcgcctgggcctgggttaccgtttcgagtctga
tatccgtggtgcgctggatcgcttcgtttcctccggcggcttcgatgcggtaaccaaga
cttccctgcacggtacggcactgtctttccgtctgctgcgtcaacacggttttgaggtt
tctcaggaagcgttcagcggcttcaaagaccaaaacggcaacttcctggagaacctgaa
ggaagatatcaaagctatcctgagcctgtacgaggccagcttcctggctctggaaggcg
aaaacatcctggacgaggcgaaggttttcgcaatctctcatctgaaagaactgtctgaa
gaaaagatcggtaaagagctggcagaacaggtgaaccatgcactggaactgccactgca
tcgccgtactcagcgtctggaagcagtatggtctatcgaggcctaccgtaaaaaggagg
acgcgaatcaggttctgctggagctggcaattctggattacaacatgatccagtctgta
taccagcgtgatctgcgtgaaacgtcccgttggtggcgtcgtgtgggtctggcgaccaa
actgcactttgctcgtgaccgcctgattgagagcttctactgggccgtgggtgtagcat
tcgaaccgcaatactccgactgccgtaactccgtcgcaaaaatgttttctttcgtaacc
attatcgacgatatctacgatgtatacggcaccctggacgaactggagctgtttactga
tgcagttgagcgttgggacgtaaacgccatcaacgacctgccggattacatgaaactgt
gctttctggctctgtataacactattaacgaaatcgcctacgacaacctgaaagataaa
ggtgagaacatcctgccgtatctgaccaaagcctgggctgacctgtgcaacgctttcct
gcaagaagccaagtggctgtacaacaaatctactccgacctttgacgactacttcggca
acgcatggaaatcctcttctggcccgctgcaactggtgttcgcttacttcgctgtcgtg
cagaacattaaaaggaagagatcgaaaacctgcaaaaataccatgacaccatctctcg
tccttcccatatcttccgtctgtgcaatgacctggctagcgcgtctgcggaaattgcgc
gtggtgaaaccgcaaatagcgtttcttgttacatgcgcactaaaggtatctccgaagaa
ctggctaccgaaagcgtgatgaatctgatcgatgaaacctggaaaagatgaacaagga
aaaactgggtggtagcctgttcgcgaaaccgttcgtggaaccgcgatcaacctggcac
gtcaatctcactgcacttatcataacggcgacgcgcatacctctccggatgagctgacc
cgcaaacgcgttctgtctgtaatcactgaaccgattctgccgtttgaacgctaa
```

Figure 87

Amino acid sequence of IspS variant *P.trem*TRC-pET200 (SEQ ID NO:164)

```
MRGSHHHHHHGMASMTGGQQMGRDLYDDDDKDHPFTMRRSANYEPNSWDYDYLLSSDTD
ESIEVHKDKAKKLEAEVRREINNEKAEFLTLLELIDNVQRLGLGYRFESDIRRALDRFV
SSGGFDGVTKTSLHGTALSFRLLRQHGFEVSQEAFSGFKDQNGNFLENLKEDIKAILSL
YEASFLALEGENILDEAKVFAISHLKELSEEKIGKELAEQVSHALELPLHRRTQRLEAV
WSIEAYRKKEDANQVLLELAILDYNMIQSVYQRDLRETSRWWRRVGLATKLHFARDRLI
ESFYWAVGVAFEPQYSDCRNSVAKMFSFVTIIDDIYDVYGTLDELELFTDAVERWDVNA
INDLPDYMKLCFLALYNTINEIAYDNLKDKGENILPYLTKAWADLCNAFLQEAKWLYNK
STPTFDDYFGNAWKSSSGPLQLIFAYFAVVQNIKKEEIENLQKYHDIISRPSHIFRLCN
DLASASAEIARGETANSVSCYMRTKGISEELATESVMNLIDETWKKMNKEKLGGSLFAK
PFVETAINLARQSHCTYHNGDAHTSPDELTRKRVLSVITEPILPFER
```

Figure 88A

Nucleotide sequence of pDu31 (SEQ ID NO:165)

```
cgtcgttctgcgaactacgaacctaacagctgggactatgattacctgctgtcctccga
cacggacgagtccatcgaagtacacaaagacaaagcgaaaaagctggaagccgaagttc
gtcgcgagattaataacgaaaaagcagaatttctgaccctgctggaactgattgacaac
gtccagcgcctgggcctgggttaccgtttcgagtctgatatccgtcgtgcgctggatcg
cttcgtttcctccggcggcttcgatggcgtaaccaagacttcctgcacggtacggcac
tgtcttccgtctgctgcgtcaacacggttttgaggtttctcaggaagcgttcagcggc
ttcaaagaccaaaacggcaacttcctggagaacctgaaggaagatatcaaagctatcct
gagcctgtacgaggccagcttcctggctctggaaggcgaaaacatcctggacgaggcga
aggttttcgcaatctctcatctgaaagaactgtctgaagaaaagatcggtaaagagctg
gcagaacaggtgtcccatgcactggaactgccactgcatcgccgtactcagcgtctgga
agcagtatggtctatcgaggcctaccgtaaaaaggaggacgcgaaccaggttctgctgg
agctggcaattctggattacaacatgatccagtctgtataccagcgtgatctgcgtgaa
acgtcccgttggtggcgtcgtgtgggtctggcgaccaaactgcactttgctcgtgaccg
cctgattgagagcttctactgggccgtggtgtagcattcgaaccgcaatactccgact
gccgtaactccgtcgcaaaaatgttttctttcgtaaccattatcgacgatatctacgat
gtatacggcaccctggacgaactggagctgtttactgatgcagttgagcgttgggacgt
aaacgccatcaacgacctgccggattacatgaaactgtgctttctggctctgtataaca
ctattaacgaaatcgcctacgacaacctgaaagataaaggtgagaacatcctgccgtat
ctgaccaaagcctgggctgacctgtgcaacgctttcctgcaagaagccaagtggctgta
caacaaatctactccgacctttgacgactacttcggcaacgcatggaaatcctcttctg
gcccgctgcaactgatcttcgcttacttcgctgtcgtgcagaacattaaaaaggaagag
atcgaaaacctgcaaaaataccatgacatcatctctcgtccttcccatatcttccgtct
gtgcaatgacctggctagcgcgtctgcggaaattgcgcgtggtgaaaccgcaaatagcg
tttcttgttacatgcgcactaaaggtatctccgaagaactggctaccgaaagcgtgatg
aatctgatcgatgaaacctggaaaaagatgaacaaggaaaaactgggtggtagcctgtt
cgcgaaaccgttcgtggaaaccgcgatcaacctggcacgtcaatctcactgcacttatc
ataacggcgacgcgcatacctctccggatgagctgacccgcaaacgcgttctgtctgta
atcactgaaccgattctgccgtttgaacgctaaaagggcgagctcaacgatccggctgc
taacaaagcccgaaaggaagctgagttggctgctgccaccgctgagcaataactagcat
aacccctgggggcctctaaacgggtcttgaggagttttttgctgaaaggaggaactata
tccggatatcccgcaagaggcccggcagtaccggcataaccaagcctatgcctacagca
tccagggtgacggtgccgaggatgacgatgagcgcattgttagatttcatacacggtgc
ctgactgcgttagcaatttaactgtgataaactaccgcattaaagcttatcgatgataa
gctgtcaaacatgagaattaattcttgaagacgaaagggcctcgtgatacgcctatttt
tataggttaatgtcatgataataatggtttcttagacgtcaggtggcacttttcgggga
aatgtgcgcggaacccctatttgtttattttctaaatacattcaaatatgtatccgct
catgagacaataaccctgataaatgcttcaataatattgaaaaaggaagagtatgattg
aacaagatggattgcacgcaggttctccggccgcttgggtggagaggctattcggctat
gactgggcacaactgacaatcggctgctctgatgccgccgtgttccggctgtcagcgca
ggggcgcccggttcttttgtcaagaccgacctgtccggtgccctgaatgaactgcagg
acgaggcagcgcggctatcgtggctggccacgacgggcgttccttgcgcagctgtgctc
gacgttgtcactgaagcgggaagggactggctgctattgggcgaagtgccggggcagga
tctcctgtcatctcaccttgctcctgccgagaaagtatccatcatggctgatgcaatgc
```

Figure 88B

Nucleotide sequence of pDu31

```
ggcggctgcatacgcttgatccggctacctgcccattcgaccaccaagcgaaacatcgc
atcgagcgggcacgtactcggatggaagccggtcttgtcgatcaggatgatctggacga
agagcatcaggggctcgcgccagccgaactgttcgccaggctcaaggcgcgcatgcccg
acggcgaggatctcgtcgtgacacatggcgatgcctgcttgccgaatatcatggtggaa
aatggccgcttttctggattcatcgactgtggccggctgggtgtggcggaccgctatca
ggacatagcgttggctaccgtgatattgctgaagagcttggcggcgaatgggctgacc
gcttcctcgtgctttacggtatcgccgctcccgattcgcagcgcatcgccttctatcgc
cttcttgacgagttcttctgagcgggactctggggttcgaaatgaccgaccaagcgacg
cctaactgtcagaccaagtttactcatatactttagattgatttaaaacttcatttt
taatttaaaaggatctaggtgaagatcctttttgataatctcatgaccaaaatcccttta
acgtgagttttcgttccactgagcgtcagaccccgtagaaaagatcaaaggatcttctt
gagatcctttttttctgcgcgtaatctgctgcttgcaaacaaaaaaaccaccgctacca
gcggtggtttgtttgccggatcaagagctaccaactcttttccgaaggtaactggctt
cagcagagcgcagataccaaatactgtccttctagtgtagccgtagttaggccaccact
tcaagaactctgtagcaccgcctacatacctcgctctgctaatcctgttaccagtggct
gctgccagtggcgataagtcgtgtcttaccgggttggactcaagacgatagttaccgga
taaggcgcagcggtcgggctgaacggggggttcgtgcacacagcccagcttggagcgaa
cgacctacaccgaactgagatacctacagcgtgagctatgagaaagcgccacgcttccc
gaagggagaaaggcggacaggtatccggtaagcggcagggtcggaacaggagagcgcac
gagggagcttccaggggaaacgcctggtatctttatagtcctgtcgggtttcgccacc
tctgacttgagcgtcgattttgtgatgctcgtcaggggcggagcctatggaaaaac
gccagcaacgcggccttttacggttcctggccttttgctggccttttgctcacatgtt
ctttcctgcgttatcccctgattctgtggataaccgtattaccgcctttgagtgagctg
ataccgctcgccgcagccgaacgaccgagcgcagcgagtcagtgagcgaggaagcggaa
gagcgcctgatgcggtattttctccttacgcatctgtgcggtatttcacaccgcaatgg
tgcactctcagtacaatctgctctgatgccgcatagttaagccagtatacactccgcta
tcgctacgtgactgggtcatggctgcgccccgacacccgccaacacccgctgacgcgcc
ctgacgggcttgtctgctcccggcatccgcttacagacaagctgtgaccgtctccggga
gctgcatgtgtcagaggttttcaccgtcatcaccgaaacgcgcgaggcagctgcggtaa
agctcatcagcgtggtcgtgaagcgattcacagatgtctgcctgttcatccgcgtccag
ctcgttgagtttctccagaagcgttaatgtctggcttctgataaagcgggccatgttaa
gggcggttttttcctgtttggtcactgatgcctccgtgtaaggggatttctgttcatg
ggggtaatgataccgatgaaacgagagaggatgctcacgatacgggttactgatgatga
acatgcccggttactggaacgttgtgagggtaaacaactggcggtatggatgcggcggg
accagagaaaaatcactcagggtcaatgccagcgcttcgttaatacagatgtaggtgtt
ccacagggtagccagcagcatcctgcgatgcagatccggaacataatggtgcagggcgc
tgacttccgcgtttccagactttacgaaacacggaaaccgaagaccattcatgttgttg
ctcaggtcgcagacgttttgcagcagcagtcgcttcacgttcgctcgcgtatcggtgat
tcattctgctaaccagtaaggcaaccccgccagcctagccgggtcctcaacgacaggag
cacgatcatgcgcacccgtggccaggacccaacgctgcccgagatgcgccgcgtgcggc
tgctggagatggcggacgcgatggatatgttctgccaagggttggtttgcgcattcaca
gttctccgcaagaattgattggctccaattcttggagtggtgaatccgttagcgaggtg
ccgccggcttccattcaggtcgaggtggcccggctccatgcaccgcgacgcaacgcggg
```

Figure 88C

Nucleotide sequence of pDu31

```
gaggcagacaaggtatagggcggcgcctacaatccatgccaacccgttccatgtgctcg
ccgaggcggcataaatcgccgtgacgatcagcggtccaatgatcgaagttaggctggta
agagccgcgagcgatccttgaagctgtccctgatggtcgtcatctacctgcctggacag
catggcctgcaacgcgggcatcccgatgccgccggaagcgagaagaatcataatgggga
aggccatccagcctcgcgtcgcgaacgccagcaagacgtagcccagcgcgtcggccgcc
atgccggcgataatggcctgcttctcgccgaaacgtttggtggcgggaccagtgacgaa
ggcttgagcgagggcgtgcaagattccgaataccgcaagcgacaggccgatcatcgtcg
cgctccagcgaaagcggtcctcgccgaaaatgacccagagcgctgccggcacctgtcct
acgagttgcatgataaagaagacagtcataagtgcggcgacgatagtcatgccccgcgc
ccaccggaaggagctgactgggttgaaggctctcaagggcatcggtcgagatcccggtg
cctaatgagtgagctaacttacattaattgcgttgcgctcactgcccgctttccagtcg
ggaaacctgtcgtgccagctgcattaatgaatcggccaacgcgcggggagaggcggttt
gcgtattgggcgccagggtggttttcttttcaccagtgagacgggcaacagctgattg
cccttcaccgcctggccctgagagagttgcagcaagcggtccacgctggtttgccccag
caggcgaaaatcctgtttgatggtggttaacggcgggatataacatgagctgtcttcgg
tatcgtcgtatcccactaccgagatatccgcaccaacgcgcagcccggactcggtaatg
gcgcgcattgcgcccagcgccatctgatcgttggcaaccagcatcgcagtgggaacgat
gccctcattcagcatttgcatggtttgttgaaaaccggacatggcactccagtcgcctt
cccgttccgctatcggctgaatttgattgcgagtgagatatttatgccagccagccaga
cgcagacgcgccgagacagaacttaatgggcccgctaacagcgcgatttgctggtgacc
caatgcgaccagatgctccacgcccagtcgcgtaccgtcttcatgggagaaaataatac
tgttgatgggtgtctggtcagagacatcaagaaataacgccggaacattagtgcaggca
gcttccacagcaatggcatcctggtcatccagcggatagttaatgatcagcccactgac
gcgttgcgcgagaagattgtgcaccgccgctttacaggcttcgacgccgcttcgttcta
ccatcgacaccaccacgctggcacccagttgatcggcgcgagatttaatcgccgcgaca
atttgcgacggcgcgtgcagggccagactggaggtggcaacgccaatcagcaacgactg
tttgcccgccagttgttgtgccacgcggttgggaatgtaattcagctccgccatcgccg
cttccacttttcccgcgttttcgcagaaacgtggctggcctggttcaccacgcgggaa
acggtctgataagagacaccggcatactctgcgacatcgtataacgttactggtttcac
attcaccaccctgaattgactctcttccgggcgctatcatgccataccgcgaaggttt
tgcgccattcgatggtgtccgggatctcgacgctctcccttatgcgactcctgcattag
gaagcagcccagtagtaggttgaggccgttgagcaccgccgccgcaaggaatggtgcat
gcaaggagatggcgcccaacagtccccggccacggggcctgccaccatacccacgccg
aaacaagcgctcatgagcccgaagtggcgagcccgatcttccccatcggtgatgtcggc
gatataggcgccagcaaccgcacctgtggcgccggtgatgccggcacgatgcgtccgg
cgtagaggatcgagatctcgatcccgcgaaattaatacgactcactatagggaattgt
gagcggataacaattcccctctagaaataattttgtttaactttaagaaggagatatac
atatgcggggttctcatcatcatcatcatcatggtatggctagcatgactggtggacag
caaatgggtcgggatctgtacgacgatgacgataaggatcatcccttcaccatg
```

Figure 89

Amino acid sequence of IspS variant P.trichTRC-pET200 (SEQ ID NO:166)

```
MRGSHHHHHHGMASMTGGQQMGRDLYDDDDKDHPFTMRRSANYEPNSWDYDYLLSSDTD
ESIEVYKDKAKKLEAEVRREINNEKAEFLTLLELIDNVQRLGLGYRFESDIRRALDRFV
SSGGFDAVTKTSLHATALSFRLLRQHGFEVSQEAFSGFKDQNGNFLENLKEDIKAILSL
YEASFLALEGENILDEAKVFAISHLKELSEEKIGKDLAEQVNHALELPLHRRTQRLEAV
LSIEAYRKKEDADQVLLELAILDYNMIQSVYQRDLRETSRWWRRVGLATKLHFARDRLI
ESFYWAVGVAFEPQYSDCRNSVAKMFSFVTIIDDIYDVYGTLDELELFTNAVERWDVNA
IDDLPDYMKLCFLALYNTINEIAYDNLKEKGENILPYLTKAWADLCNAFLQEAKWLYNK
STPTFDEYFGNAWKSSSGPLQLVFAYFAVVQNIKKEEIENLQKYHDIISRPSHIFRLCN
DLASASAEIARGETANSVSCYMRTKGISEELATESVMNLIDETWKKMNKEKLGGSLFAK
PFVETAINLARQSHCTYHNGDAHTSPDELTRKRVLSVITEPILPFER
```

Figure 90A

Nucleotide Sequence of pDu32 (SEQ ID NO:167)

```
cgtcgttctgcgaactacgaacctaacagctgggactatgattacctgctgtcctccga
cacggacgagtccatcgaagtatacaaagacaaagcgaaaaagctggaagccgaagttc
gtcgcgagattaataacgaaaaagcagaatttctgaccctgctggaactgattgacaac
gtccagcgcctgggcctgggttaccgtttcgagtctgatatccgtcgtgcgctggatcg
cttcgtttcctccggcggcttcgatgcggtaaccaagacttcctgcacgcgacggcac
tgtctttccgtctgctgcgtcaacacggttttgaggtttctcaggaagcgttcagcggc
ttcaaagaccaaaacggcaacttcctggagaacctgaaggaagatatcaaagctatcct
gagcctgtacgaggccagcttcctggctctggaaggcgaaaacatcctggacgaggcga
aggttttcgcaatctctcatctgaaagaactgtctgaagaaaagatcggtaaagatctg
gcagaacaggtgaaccatgcactggaactgccactgcatcgccgtactcagcgtctgga
agcagtactgtctatcgaggcctaccgtaaaaaggaggacgcggatcaggttctgctgg
agctggcaattctggattacaacatgatccagtctgtataccagcgtgatctgcgtgaa
acgtcccgttggtggcgtcgtgtgggtctggcgaccaaactgcactttgctcgtgaccg
cctgattgagagcttctactgggccgtgggtgtagcattcgaaccgcaatactccgact
gccgtaactccgtcgcaaaaatgttttctttcgtaaccattatcgacgatatctacgat
gtatacggcaccctggacgaactggagctgtttactaacgcagttgagcgttgggacgt
aaacgccatcgacgatctgccggattacatgaaactgtgctttctggctctgtataaca
ctattaacgaaatcgcctacgacaacctgaaagaaaaaggtgagaacatcctgccgtat
ctgaccaaagcctgggctgacctgtcaacgctttcctgcaagaagccaagtggctgta
caacaaatctactccgacctttgacgaatacttcggcaacgcatggaaatcctcttctg
gcccgctgcaactggtgttcgcttacttcgctgtcgtgcagaacattaaaaaggaagag
atcgaaaacctgcaaaaataccatgacatcatctctcgtccttcccatatcttccgtct
gtgcaatgacctggctagcgcgtctgcggaaattgcgcgtggtgaaaccgcaaatagcg
tttcttgttacatgcgcactaaaggtatctccgaagaactggctaccgaaagcgtgatg
aatctgatcgatgaaacctggaaaagatgaacaaggaaaaactgggtggtagcctgtt
cgcgaaaccgttcgtggaaaccgcgatcaacctggcacgtcaatctcactgcacttatc
ataacggcgacgcgcatacctctccggatgagctgacccgcaaacgcgttctgtctgta
atcactgaaccgattctgccgtttgaacgctaaaagggcgagctcaacgatccggctgc
taacaaagcccgaaggaagctgagttggctgctgccaccgctgagcaataactagcat
aacccttggggcctctaaacgggtcttgaggagttttttgctgaaaggaggaactata
tccggatatcccgcaagaggcccggcagtaccggcataaccaagcctatgcctacagca
tccagggtgacggtgccgaggatgacgatgagcgcattgttagatttcatacacggtgc
ctgactgcgttagcaatttaactgtgataaactaccgcattaaagcttatcgatgataa
gctgtcaaacatgagaattaattcttgaagacgaaagggcctcgtgatacgcctatttt
tataggttaatgtcatgataataatggtttcttagacgtcaggtggcacttttcgggga
aatgtgcgcggaacccctatttgtttatttttctaaatacattcaaatatgtatccgct
catgagacaataaccctgataaatgcttcaataatattgaaaaggaagagtatgattg
aacaagatggattgcacgcaggttctccggccgcttgggtggagaggctattcggctat
gactgggcacaactgacaatcggctgctctgatgccgcgtgttccggctgtcagcgca
ggggcgcccggttcttttttgtcaagaccgacctgtccggtgccctgaatgaactgcagg
acgaggcagcgcggctatcgtggctggccacgacgggcgttccttgcgcagctgtgctc
gacgttgtcactgaagcgggaagggactggctgctattgggcgaagtgccggggcagga
tctcctgtcatctcaccttgctcctgccgagaaagtatccatcatggctgatgcaatgc
```

Figure 90B

Nucleotide Sequence of pDu32 ggcggctgcatacgcttgatccggctacctgcccattcgaccaccaagcgaaacatcgc
atcgagcgggcacgtactcggatggaagccggtcttgtcgatcaggatgatctggacga
agagcatcaggggctcgcgccagccgaactgttcgccaggctcaaggcgcgcatgcccg
acggcgaggatctcgtcgtgacacatggcgatgcctgcttgccgaatatcatggtggaa
aatggccgcttttctggattcatcgactgtggccggctgggtgtggcggaccgctatca
ggacatagcgttggctacccgtgatattgctgaagagcttggcggcgaatgggctgacc
gcttcctcgtgctttacggtatcgccgctcccgattcgcagcgcatcgccttctatcgc
cttcttgacgagttcttctgagcgggactctggggttcgaaatgaccgaccaagcgacg
cctaactgtcagaccaagtttactcatatactttagattgatttaaaacttcatttt
taatttaaaaggatctaggtgaagatcctttttgataatctcatgaccaaaatcccta
acgtgagttttcgttccactgagcgtcagaccccgtagaaaagatcaaaggatcttctt
gagatcctttttttctgcgcgtaatctgctgcttgcaaacaaaaaaaccaccgctacca
gcggtggtttgtttgccggatcaagagctaccaactctttttccgaaggtaactggctt
cagcagagcgcagataccaaatactgtccttctagtgtagccgtagttaggccaccact
tcaagaactctgtagcaccgcctacatacctcgctctgctaatcctgttaccagtggct
gctgccagtggcgataagtcgtgtcttaccgggttggactcaagacgatagttaccgga
taaggcgcagcggtcgggctgaacggggggttcgtgcacacagcccagcttggagcgaa
cgacctacaccgaactgagatacctacagcgtgagctatgagaaagcgccacgcttccc
gaagggagaaaggcggacaggtatccggtaagcggcagggtcggaacaggagagcgcac
gagggagcttccaggggaaacgcctggtatctttatagtcctgtcgggtttcgccacc
tctgacttgagcgtcgatttttgtgatgctcgtcaggggggcggagcctatggaaaaac
gccagcaacgcggcctttttacggttcctggccttttgctggccttttgctcacatgtt
ctttcctgcgttatccctgattctgtggataaccgtattaccgcctttgagtgagctg
ataccgctcgccgcagccgaacgaccgagcgcagcgagtcagtgagcgaggaagcggaa
gagcgcctgatgcggtattttctccttacgcatctgtgcggtatttcacaccgcaatgg
tgcactctcagtacaatctgctctgatgccgcatagttaagccagtatacactccgcta
tcgctacgtgactgggtcatggctgcgccccgacacccgccaacacccgctgacgcgcc
ctgacgggcttgtctgctcccggcatccgcttacagacaagctgtgaccgtctccggga
gctgcatgtgtcagaggttttcaccgtcatcaccgaaacgcgcgaggcagctgcggtaa
agctcatcagcgtggtcgtgaagcgattcacagatgtctgcctgttcatccgcgtccag
ctcgttgagtttctccagaagcgttaatgtctggcttctgataaagcgggccatgttaa
gggcggttttttcctgtttggtcactgatgcctccgtgtaaggggatttctgttcatg
ggggtaatgataccgatgaaacgagagaggatgctcacgatacgggttactgatgatga
acatgcccggttactggaacgttgtgagggtaaacaactggcggtatggatgcggcggg
accagagaaaaatcactcagggtcaatgccagcgcttcgttaatacagatgtaggtgtt
ccacagggtagccagcagcatcctgcgatgcagatccggaacataatggtgcagggcgc
tgacttccgcgtttccagactttacgaaacacggaaaccgaagaccattcatgttgttg
ctcaggtcgcagacgttttgcagcagcagtcgcttcacgttcgctcgcgtatcggtgat
tcattctgctaaccagtaaggcaaccccgccagcctagccgggtcctcaacgacaggag
cacgatcatgcgcacccgtggccaggacccaacgctgcccgagatgcgccgcgtgcggc
tgctggagatggcggacgcgatggatatgttctgccaaggggttggtttgcgcattcaca
gttctccgcaagaattgattggctccaattcttggagtggtgaatccgttagcgaggtg
ccgccggcttccattcaggtcgaggtggcccggctccatgcaccgcgacgcaacgcggg

Figure 90C

Nucleotide Sequence of pDu32

```
gaggcagacaaggtatagggcggcgcctacaatccatgccaacccgttccatgtgctcg
ccgaggcggcataaatcgccgtgacgatcagcggtccaatgatcgaagttaggctggta
agagccgcgagcgatccttgaagctgtccctgatggtcgtcatctacctgcctggacag
catggcctgcaacgcgggcatcccgatgccgccggaagcgagaagaatcataatgggga
aggccatccagcctcgcgtcgcgaacgccagcaagacgtagcccagcgcgtcggccgcc
atgccggcgataatggcctgcttctcgccgaaacgtttggtggcgggaccagtgacgaa
ggcttgagcgagggcgtgcaagattccgataccgcaagcgacaggccgatcatcgtcg
cgctccagcgaaagcggtcctcgccgaaaatgacccagagcgctgccggcacctgtcct
acgagttgcatgataaagaagacagtcataagtgcggcgacgatagtcatgccccgcgc
ccaccggaaggagctgactgggttgaaggctctcaagggcatcggtcgagatcccggtg
cctaatgagtgagctaacttacattaattgcgttgcgctcactgcccgctttccagtcg
ggaaacctgtcgtgccagctgcattaatgaatcggccaacgcgcggggagaggcggttt
gcgtattgggcgccagggtggttttcttttcaccagtgagacgggcaacagctgattg
cccttcaccgcctggccctgagagagttgcagcaagcggtccacgctggtttgccccag
caggcgaaaatcctgtttgatggtggttaacggcgggatataacatgagctgtcttcgg
tatcgtcgtatcccactaccgagatatccgcaccaacgcgcagcccggactcggtaatg
gcgcgcattgcgcccagcgccatctgatcgttggcaaccagcatcgcagtgggaacgat
gccctcattcagcatttgcatggtttgttgaaaaccggacatggcactccagtcgcctt
cccgttccgctatcggctgaatttgattgcgagtgagatatttatgccagccagccaga
cgcagacgcgccgagacagaacttaatgggcccgctaacagcgcgatttgctggtgacc
caatgcgaccagatgctccacgcccagtcgcgtaccgtcttcatgggagaaaataatac
tgttgatgggtgtctggtcagagacatcaagaaataacgccggaacattagtgcaggca
gcttccacagcaatggcatcctggtcatccagcggatagttaatgatcagcccactgac
gcgttgcgcgagaagattgtgcaccgccgctttacaggcttcgacgccgcttcgttcta
ccatcgacaccaccacgctggcacccagttgatcggcgcgagatttaatcgccgcgaca
atttgcgacggcgcgtgcagggccagactggaggtggcaacgccaatcagcaacgactg
tttgcccgccagttgttgtgccacgcggttgggaatgtaattcagctccgccatcgccg
cttccactttttcccgcgttttcgcagaaacgtggctggcctggttcaccacgcgggaa
acggtctgataagagacaccggcatactctgcgacatcgtataacgttactggtttcac
attcaccaccctgaattgactctcttccgggcgctatcatgccataccgcgaaaggttt
tgcgccattcgatggtgtccgggatctcgacgctctcccttatgcgactcctgcattag
gaagcagcccagtagtaggttgaggccgttgagcaccgccgccgcaaggaatggtgcat
gcaaggagatggcgcccaacagtccccggccacggggcctgccaccataccacgccg
aaacaagcgctcatgagcccgaagtggcgagcccgatcttccccatcggtgatgtcggc
gataggcgccagcaaccgcacctgtggcgccggtgatgccggccacgatgcgtccgg
cgtagaggatcgagatctcgatcccgcgaattaatacgactcactatagggaattgt
gagcggataacaattcccctctagaaataattttgtttaactttaagaaggagatatac
atatgcggggttctcatcatcatcatcatggtatggctagcatgactggtggacag
caaatgggtcgggatctgtacgacgatgacgataaggatcatcccttcaccatg
```

ISOPRENE SYNTHASE VARIANTS FOR IMPROVED MICROBIAL PRODUCTION OF ISOPRENE

CROSS-REFERENCE TO RELATED APPLICATIONS

This application claims the benefit of U.S. provisional application Ser. No. 61/125,336 filed Apr. 23, 2008, which is hereby incorporated by reference in its entirety.

FIELD OF THE INVENTION

The present invention provides methods and compositions comprising at least one isoprene synthase enzyme with improved catalytic activity and/or solubility. In particular, the present invention provides variant plant isoprene synthases for increased isoprene production in microbial host cells. Biosynthetically produced isoprene of the present invention finds use in the manufacture of rubber and elastomers.

BACKGROUND OF THE INVENTION

Isoprenoids are isoprene polymers that find use in pharmaceuticals, neutraceuticals, flavors, fragrances, and rubber products. Natural isoprenoid supplies, however, are limited due to ecological concerns. For this reason, and to provide isoprenoid compositions having fewer impurities and greater uniformity, isoprenoids such as rubber are often produced synthetically.

Isoprene(2-methyl-1,3-butadiene) is a volatile hydrocarbon that is insoluble in water and soluble in alcohol. Commercially viable quantities of isoprene can be obtained by direct isolation from petroleum C5 cracking fractions or by dehydration of C5 isoalkanes or isoalkenes (Weissermel and Arpe, Industrial Organic Chemistry, 4$^{th}$ ed., Wiley-VCH, pp. 117-122, 2003). The C5 skeleton can also be synthesized from smaller subunits. It would be desirable, however, to have a commercially viable method of producing isoprene that was independent of nonrenewable resources.

Biosynthetic production of isoprene occurs by two distinct metabolic pathways (Julsing et al., Appl Microbiol Biotechnol, 75:1377-1384, 2007). In eukaryotes and archae, isoprene is formed via the mevalonate (MVA) pathway, while some eubacteria and higher plants produce isoprene via the methylerythritol phosphate (MEP) pathway. Isoprene emissions from plants are light and temperature-dependent with increases linked to leaf development. An isoprene-producing enzyme, isoprene synthase, has been identified in Aspen trees (Silver and Fall, Plant Physiol, 97:1588-1591, 1991; and Silver and Fall, J Biol Chem, 270:13010-13016, 1995) and is believed to be responsible for the in vivo production of isoprene from whole leaves. Bacterial production of isoprene has also been described (Kuzma et al., Curr Microbiol, 30:97-103, 1995; and Wilkins, Chemosphere, 32:1427-1434, 1996), and varies in amount with the phase of bacterial growth and the nutrient content of the culture medium (U.S. Pat. No. 5,849,970 to Fall et al.; and Wagner et al., J Bacteriol, 181: 4700-4703, 1999, both herein incorporated by reference in their entirety). The levels of isoprene obtainable through bacterial systems of the prior art, however, are insufficient for commercial uses.

Thus what the art needs is an efficient, large scale, bacterial isoprene production process to provide feedstock for the manufacture of isoprenoids.

All patents, patent applications, articles and publications mentioned herein are hereby expressly incorporated herein by reference.

SUMMARY OF THE INVENTION

The present invention provides methods and compositions comprising at least one isoprene synthase enzyme with improved catalytic activity and/or solubility. In particular, the present invention provides variant plant isoprene synthases for increased isoprene production in microbial host cells. Biosynthetically produced isoprene of the present invention finds use in the manufacture of rubber and elastomers.

Specifically, the present invention provides isolated isoprene synthase variants, wherein the variant comprises a substitution at a position corresponding to one or more residues (one, two, three, four, five, six, seven, eight, nine or ten) of a kudzu isoprene synthase comprising the amino acid sequence set forth in SEQ ID NO: 2. In some embodiments, the isoprene synthase variant is a kudzu (*Pueraria* sp.) isoprene synthase variant or a poplar (*Populus* sp.) isoprene synthase variant. In some embodiments, the one or more residues are selected from but not limited to the group consisting of L26, E30, F31, Q33, L35, E36, N37, L39, K40, V41, K43, L44, R61, V62, D63, Q65, K87, E94, N95, L99, D100, N105, K137, E138, G143, E144, N182, L184, K185, G187, N189, T190, P225, H226, K247, T257, E258, M259, D266, N334, D353, S357, I358I, E361, N389, I392, I393, K398, E401, C421, Q423, Q424, E425, D426, H430, L432, R433, S434, D437, R443, L462, E463, H476, N478, D479, Q485, D508, P513, A515, Q532, Y533, L537, G538, R539, Y542, A543, and P557. In some embodiments, the one or more residues are selected from but not limited to the group consisting of P24, N25, Y309, D310, L377, F381, E384, Y399, N402, A403, S406, S407, G409, A411, L413, F449, A456, T457, S458, A459, A460, E461, L462, E463, R464, G465, E466, T467, T468, N469, M523, S527, and Y531. In some embodiments, the one or more residues are selected from but not limited to the group consisting of A20, N21, Y22, Q23, R271, W278, F299, V302, and S408. The present invention also provides an isolated isoprene synthase variant having an A20G substitution in a kudzu isoprene synthase having the amino acid sequence set forth in SEQ ID NO: 2. In a subset of these embodiments, the variant comprises at least two substitutions (two, three, four, five, six, seven, eight, nine or ten), wherein one of the substitutions is an A20G substitution in a kudzu isoprene synthase having the amino acid sequence set forth in SEQ ID NO: 2. The present invention also provides an isolated isoprene synthase variant having an S408D substitution in a kudzu isoprene synthase having the amino acid sequence set forth in SEQ ID NO: 2. In a subset of these embodiments, the variant comprises at least two substitutions (two, three, four, five, six, seven, eight, nine or ten), wherein one of the substitutions is an S408D substitution in a kudzu isoprene synthase having the amino acid sequence set forth in SEQ ID NO: 2. In some preferred embodiments, the isoprene synthase variant has at least one improved property as compared to wild-type isoprene synthase. In some particularly preferred embodiments, the at least one improved property is selected from but not limited to the group consisting of specific activity (production of isoprene from dimethylallyl diphosphate), and solubility.

In addition, the present invention further provides a polynucleotide sequence encoding the isoprene synthase variant. Also provided is an expression vector comprising a polynucleotide sequence encoding the isoprene synthase variant in operable combination with a promoter. In further embodiments, the present invention provides a host cell comprising the expression vector. Also provided is a lysate of the host cell, wherein the lysate further comprises lysozyme. In some embodiments, the lysate has a neutral pH (6.5 to 7.5), while in other embodiments the lysate has a basic pH (above 7.5 and below 9.5). The present invention also provides methods of producing isoprene, comprising: (a) providing host cells comprising the expression vector; and (b) culturing the host cells under conditions suitable for producing isoprene. In some embodiments, the methods further comprise (c) recovering the isoprene. In still further embodiments, the methods further comprise (d) polymerizing the isoprene. The present invention further provides methods of detecting isoprene synthase activity, comprising: (a) culturing host cells comprising the expression vector under conditions suitable for producing the isoprene synthase variant; (b) lysing the host cells with a lysis buffer comprising lysozyme to produce a cell lysate; and (c) detecting isoprene synthase activity in the cell lysate by measuring isoprene production from dimethylallyl diphosphate (DMAPP). In some embodiments, the host is selected from but not limited to the group consisting of gram-positive bacterial cells, gram-negative bacterial cells, filamentous fungal cells, and yeast cells. In some preferred embodiments, the host is selected from but not limited to the group consisting of *Escherichia* sp. (*E. coli*), *Panteoa* sp. (*P. citrea*), *Bacillus* sp. (*B. subtilis*), *Yarrowia* sp. (*Y. lipolytica*), and *Trichoderma* (*T. reesei*). In some embodiments, the host cells are cultured in a medium that includes a carbon source selected from but not limited to the group consisting of glucose, glycerol, glycerine, dihydroxyacetone, yeast extract, biomass, molasses, sucrose, and oil.

Moreover, the present invention provides methods of detecting isoprene in a plurality of samples (high-throughput screening), comprising: (a) providing: i) a plurality of samples each comprising isoprene synthase; ii) a glass plate comprising a plurality of wells; and iii) a seal for the glass plate; (b) placing the plurality of samples in the plurality of wells of the glass plate; (c) sealing the glass plate with the seal to produce a sealed glass plate having a headspace associated with the sample in each of the plurality of wells; (d) incubating the glass plate under conditions in which the isoprene synthase is active; and (e) detecting isoprene in the headspace. In some embodiments, the isoprene is detected by gas chromatography-mass spectrometry (GC-MS). In some embodiments, the plurality of samples comprise host cells comprising an expression vector comprising a polynucleotide sequence encoding an isoprene synthase variant in operable combination with a promoter. In some embodiments, the plurality of samples comprise a lysate of the host cells, lysozyme, and dimethylallyl diphosphate (DMAPP). In some preferred embodiments, the glass plate is a deep-well glass block. In some preferred embodiments, the plurality of wells comprises at least 24 wells (preferably at least 48 wells, more preferably at least 96 wells, still more preferably at least 192 wells, and most preferably at least 384 wells). In particularly preferred embodiments, the plurality of wells each comprise a volume of 2 ml or less (preferably 2 ml to 0.2 ml).

Additionally the present invention provides a host cell comprising a heterologous polynucleotide sequence encoding an isoprene synthase variant in operable combination with a promoter, wherein the isoprene synthase variant comprises a substitution at a position corresponding to one or more residues (one, two, three, four, five, six, seven, eight, nine or ten) of a kudzu isoprene synthase comprising the amino acid sequence set forth in SEQ ID NO: 2. In some embodiments, the one or more residues are selected from but not limited to the group consisting of L26, E30, F31, Q33, L35, E36, N37, L39, K40, V41, K43, L44, R61, V62, D63, Q65, K87, E94, N95, L99, D100, N105, K137, E138, G143, E144, N182, L184, K185, G187, N189, T190, P225, H226, K247, T257, E258, M259, D266, N334, D353, S357, I358I, E361, N389, I392, I393, K398, E401, C421, Q423, Q424, E425, D426, H430, L432, R433, S434, D437, R443, L462, E463, H476, N478, D479, Q485, D508, P513, A515, Q532, Y533, L537, G538, R539, Y542, A543, and P557. In some embodiments, the one or more residues are selected from but not limited to the group consisting of P24, N25, Y309, D310, L377, F381, E384, Y399, N402, A403, S406, S407, G409, A411, L413, F449, A456, T457, S458, A459, A460, E461, L462, E463, R464, G465, E466, T467, T468, N469, M523, S527, and Y531. In some embodiments, the one or more residues are selected from but not limited to the group consisting of A20, N21, Y22, Q23, R271, W278, F299, V302, and S408. The present invention also provides an isolated isoprene synthase variant having an A20G substitution and/or an S408D substitution in a kudzu isoprene synthase having the amino acid sequence set forth in SEQ ID NO: 2. In some preferred embodiments, the isoprene synthase variant has at least one improved property as compared to wild-type isoprene synthase. In some particularly preferred embodiments, the at least one improved property is selected from but not limited to the group consisting of specific activity (production of isoprene from dimethylallyl diphosphate), and solubility. In some preferred embodiments, the polynucleotide sequence is contained within a plasmid. In other preferred embodiments, the polynucleotide sequence is integrated into a chromosome of the host cell. In some embodiments, the host is selected from but not limited to the group consisting of gram-positive bacterial cells, gram-negative bacterial cells, filamentous fungal cells, and yeast cells. In some preferred embodiments, the host is selected from but not limited to the group consisting of *Escherichia* sp. (*E. coli*), *Panteoa* sp. (*P. citrea*), *Bacillus* sp. (*B. subtilis*), *Yarrowia* sp. (*Y. lipolytica*), and *Trichoderma* (*T. reesei*). In some embodiments, the host cells are cultured in a medium that includes a carbon source selected from but not limited to the group consisting of glucose, glycerol, glycerine, dihydroxyacetone, yeast extract, biomass, molasses, sucrose, and oil. In some embodiments, the host cell further comprises a heterologous or native nucleic acid encoding an IDI polypeptide and/or a heterologous or native nucleic acid encoding a DXS polypeptide, sometimes in combination with the native DXP pathway (for example, expression of dxs and idi in *E. coli* in addition to the native DXP pathway). Alternatively the entire DXP pathway (FIG. 15) may be expressed on a plasmid or integrated on the chromosome as an operon, with a single promoter controlling expression, or promoters of varying strengths (example GI 1.20, GI 1.5, or GI 1.6) controlling one or more of the individual genes. In some embodiments, the host cell further comprises one or more nucleic acids encoding an IDI polypeptide and a DXS polypeptide, while in some preferred embodiments, one vector encodes the isoprene synthase variant, the IDI polypeptide, and the DXS polypeptide. In some embodiments, the host cell further comprises a heterologous nucleic acid encoding an MVA pathway polypeptide (e.g., an MVA pathway polypeptide from *Saccharomyces cerevisia* or *Enterococcus faecalis*). In some embodiments, the host cell further comprises one or more nucleic acids encoding an MVA pathway polypeptide and a DXS polypeptide, while in some preferred embodiments, one vector encodes the isoprene synthase variant, the MVA pathway polypeptide, and the DXS polypeptide. In some preferred embodiments, the host cell further comprises one or more nucleic acids encoding a DXS polypeptide, an IDI polypeptide, or one or more of the rest of the DXP pathway polypeptides, and a MVA pathway polypeptide. In some embodiments, the vector further comprises a selectable marker (e.g., antibiotic resistance nucleic acid). Also provided are methods of producing isoprene, comprising: (a) culturing the host cells under suitable culture conditions for production of isoprene; and (b) producing the isoprene. In some embodiments, the methods further comprise (c) recovering the isoprene. In some preferred embodiments, the methods further comprise (d) polymerizing isoprene. The present invention also provides methods of producing isoprene synthase, comprising: (a) providing: (i) a host cell; and (ii) a nucleic acid encoding an isoprene synthase variant in operable combination with a promoter, wherein the isoprene synthase variant comprises a substitution at a position corresponding to one or more residues (one, two, three, four, five, six, seven, eight, nine or ten) of a kudzu isoprene synthase comprising the amino acid sequence set forth in SEQ ID NO: 2; (b) contacting the host cell with the nucleic acid to produce a transformed host cell; and (c) culturing the transformed host cells under suitable culture conditions for production of isoprene synthase.

In another aspect, the invention provides for isolated poplar isoprene synthase variants. In one embodiment, the variant comprises a truncation in the N-terminal portion of isoprene synthase. In another embodiment, the isoprene synthase variant has an increased specific activity compared to a full length isoprene synthase. In another embodiment, the isoprene synthase is P. alba isoprene synthase of SEQ ID NO:120. In another embodiment, wherein the variant is selected from the group consisting of: an MEA variant (SEQ ID NO:122), an MSV variant (SEQ ID NO:124), an MVS variant (SEQ ID NO:126), an MTE variant (SEQ ID NO:128), an MNV variant (SEQ ID NO:130). In another embodiment, the variant is an MEA variant (SEQ ID NO:122). In another embodiment, the variant is selected from the group consisting of: a TRC (−3) variant (SEQ ID NO:136), a TRC (−4) variant (SEQ ID NO:138), a TRC (−5) variant (SEQ ID NO:140), a TRC (−6) variant (SEQ ID NO:142) and a TRC (−7) variant (SEQ ID NO:144). In another embodiment, the variant is a MET variant of P. tremuloides isoprene synthase (SEQ ID NO:146). In another embodiment, the variant is a MET variant of P. trichocharpa isoprene synthase (SEQ ID NO:148).

In another aspect, the invention provides for isolated poplar isoprene synthase variants, wherein the variant comprises a substitution of one or more amino acid residues of a wild type isoprene synthase; and wherein the isoprene synthase variant has increased isoprene synthase activity compared to a wild type isoprene synthase. In one embodiment, the increased isoprene synthase activity is indicated by a host cell comprising the isoprene variant growing at a faster rate in the presence of dimethylallyl pyrophosphate (DMAPP) compared to a host cell comprising a parent isoprene synthase. In another embodiment, the isoprene synthase is the P. alba isoprene synthase of SEQ ID NO:120. In another embodiment, the variant comprises one of more amino acid substitutions selected from the group consisting of V10M, F12S, T15A, E18G, V58I, V58F, L70Q, L70V, L70T, T71P, V79L, E89D, G94A, S119F, F120L, G127R, E175V, T212I, S257A, R262G, A266G, F280L, N297K, F305L, L319M, E323K, A328T, D342E, A359T, K366N, E368D, L374M, S396T, V418S, K438N, H440R, T442I, T442A, I449V, A469S, K500R, K505Q, G507S, S509N, F511Y, and N532K. In another embodiment, at least one amino acid substitution is a L70R substitution. In another embodiment, the variant comprises one of more amino acid substitutions selected from the group consisting of G127R/F511Y, L70Q/G94A/R262G/ F305L, F12S/T15A/E18G/N297K, S396T/T442I, V10M/ E323K, F120L/A266G, K438N/K500R, V79L/S509N, E175V/S257A/E368D/A469S, T71P/L374M, F280L/ H440R, E89D/H440R, V58F/A328T/N532K, S119F/ D342E/I449V, and K366N/G507S.

In another aspect, the invention provides for a crystalline form of a polypeptide comprising the amino acid residues of SEQ ID NO:120 (FIG. 19).

In another aspect, the invention provides for methods of producing isoprene, comprising: (a) providing a host cell comprising an expression vector comprising a polynucleotide sequence encoding an isoprene synthase variant; and (b) culturing the host cell under conditions suitable for producing isoprene. In one embodiment, the method further comprises (c) recovering the isoprene. In another embodiment, the method further comprises (d) polymerizing the isoprene.

In another aspect, the invention provides for methods of detecting isoprene synthase activity, comprising: (a) culturing a host cell comprising the expression vector under conditions suitable for producing an isoprene synthase variant; (b) lysing the host cells with a lysis buffer comprising lysozyme to produce a cell lysate; and (c) detecting isoprene synthase activity in the cell lysate by measuring isoprene production from dimethylallyl diphosphate (DMAPP). In one embodiment, the host cell is selected from the group consisting of gram-positive bacterial cells, gram-negative bacterial cells, filamentous fungal cells, and yeast cells. In another embodiment, the host cell is selected from the group consisting of *Escherichia* sp. (*E. coli*), *Panteoa* sp. (*P. citrea*), *Bacillus* sp. (*B. subtilis*), *Yarrowia* sp. (*Y. lipolytica*), and *Trichoderma* (*T. reesei*). In another embodiment, the host cell is cultured in a medium that includes a carbon source selected from the group consisting of glucose, glycerol, glycerine, dihydroxyacetone, yeast extract, biomass, molasses, sucrose, and oil.

In another aspect, the invention provides for host cells comprising a heterologous polynucleotide sequence encoding an isoprene synthase variant in operable combination with a promoter, wherein the isoprene synthase variant comprises a substitution at a position corresponding to one or more residues (one, two, three, four, five, six, seven, eight, nine or ten) of a poplar isoprene synthase. In one embodiment, the isoprene synthase is the P. alba isoprene synthase of SEQ ID NO:120. In another embodiment, the variant is selected from the group consisting of: an MEA variant (SEQ ID NO:122), an MSV variant (SEQ ID NO:124), an MVS variant (SEQ ID NO:126), an MTE variant (SEQ ID NO:128), an MNV variant (SEQ ID NO:130). In another embodiment, the variant is selected from the group consisting of: a TRC (−3) variant (SEQ ID NO:136), a TRC (−4) variant (SEQ ID NO:138), a TRC (−5) variant (SEQ ID NO:140), a TRC (−6) variant (SEQ ID NO:142) and a TRC (−7) variant (SEQ ID NO:144). In another embodiment, the variant is a MET variant of P. tremuloides isoprene synthase (SEQ ID NO:146). In another embodiment, the variant is a MET variant of P. trichocharpa isoprene synthase (SEQ ID NO:148). In another embodiment, the variant comprises one of more amino acid substitutions selected from the group consisting of V10M, F12S, T15A, E18G, V58I, V58F, L70Q, L70V, L70T, T71P, V79L, E89D, G94A, S119F, F120L, G127R, E175V, T212I, S257A, R262G, A266G, F280L, N297K, F305L, L319M, E323K, A328T, D342E, A359T, K366N, E368D, L374M, S396T, V418S, K438N, H440R, T442I, T442A, I449V, A469S, K500R, K505Q, G507S, S509N, F511Y, and N532K. In another embodiment, at least one amino acid substitution is a L70R substitution. In another embodiment, the variant comprises one of more amino acid substitutions selected from the group consisting of G127R/F511Y, L70Q/G94A/R262G/

F305L, F12S/T15A/E18G/N297K, S396T/T442I, V10M/E323K, F120L/A266G, K438N/K500R, V79L/S509N, E175V/S257A/E368D/A469S, T71P/L374M, F280L/H440R, E89D/H440R, V58F/A328T/N532K, S119F/D342E/I449V, and K366N/G507S. In another embodiment, the polynucleotide sequence is contained within a plasmid. In another embodiment, the polynucleotide sequence is integrated into a chromosome of the host cell. In another embodiment, the host is selected from the group consisting of gram-positive bacterial cells, gram-negative bacterial cells, filamentous fungal cells, and yeast cells. In another embodiment, the host is selected from the group consisting of *Escherichia* sp. (*E. coli*), *Panteoa* sp. (*P. citrea*), *Bacillus* sp. (*B. subtilis*), *Yarrowia* sp. (*Y. lipolytica*), and *Trichoderma* (*T. reesei*). In another embodiment, the host cell is cultured in a medium comprising a carbon source selected from the group consisting of glucose, glycerol, glycerine, dihydroxyacetone, yeast extract, biomass, molasses, sucrose, and oil. In another embodiment, the host cell further comprises a heterologous or native nucleic acid encoding an IDI polypeptide and/or a heterologous or native nucleic acid encoding a DXS polypeptide, optionally in combination with the native DXP pathway. In another embodiment, the host cell further comprises one or more nucleic acids encoding an IDI polypeptide and a DXS polypeptide. In another embodiment, the host cell comprises one vector encoding the isoprene synthase variant, the IDI polypeptide, and the DXS polypeptide. In another embodiment, the host cell further comprises a heterologous nucleic acid encoding an MVA pathway polypeptide selected from the group consisting of an MVA pathway polypeptide from *Saccharomyces cerevisia* and *Enterococcus faecalis*. In another embodiment, the host cell further comprises one or more nucleic acids encoding an MVA pathway polypeptide and a DXS polypeptide and wherein one vector encodes the isoprene synthase variant, the MVA pathway polypeptide, and the DXS polypeptide. In another embodiment, the host cell further comprises one or more nucleic acids encoding a DXS polypeptide, an IDI polypeptide, or one or more of the rest of the DXP pathway polypeptides, and a MVA pathway polypeptide.

In another aspect, the invention provides for methods of producing isoprene, comprising: (a) culturing the host cells comprising a heterologous polynucleotide sequence encoding an isoprene synthase variant in operable combination with a promoter, wherein the isoprene synthase variant comprises a substitution at a position corresponding to one or more residues (one, two, three, four, five, six, seven, eight, nine or ten) of a poplar isoprene synthase under suitable culture conditions for production of isoprene; and (b) producing the isoprene. In one embodiment, the method further comprises (c) recovering the isoprene. In another embodiment, the method further comprises (d) polymerizing isoprene.

In another aspect, the invention provides for methods of producing isoprene synthase, comprising: (a) providing: (i) a host cell; and (ii) a nucleic acid encoding an isoprene synthase variant in operable combination with a promoter, wherein the isoprene synthase variant comprises a substitution at a position corresponding to one or more residues (one, two, three, four, five, six, seven, eight, nine or ten) of a *P. alba* isoprene synthase of SEQ ID NO:120; (b) contacting the host cell with the nucleic acid to produce a transformed host cell; and (c) culturing the transformed host cells under suitable culture conditions for production of isoprene synthase.

BRIEF DESCRIPTION OF THE DRAWINGS

FIG. 1 provides the coding sequence (SEQ ID NO:1) of kudzu (*Pueraria montana*) isoprene synthase, codon-optimized for expression in *Escherichia coli*.

FIG. 2 provides the amino acid sequence (SEQ ID NO:2) of kudzu isoprene synthase.

FIG. 3 provides the coding sequence (SEQ ID NO:6) of poplar (*Populus alba* x *tremula*) isoprene synthase, codon-optimized for expression in *Escherichia coli*.

FIG. 4 provides the amino acid sequence (SEQ ID NO:7) of poplar (*Populus alba* x *tremula*) isoprene synthase.

FIG. 10 provides the nucleotide sequence of plasmid MCM93 (SEQ ID NO:22).

FIG. 12 provides the nucleotide sequence of pET24D-Kudzu (SEQ ID NO:23).

Assay: PNAS, 94:12857-62, 1997; DXR; 1-Deoxy-D-xylulose 5-phosphate reductoisomerase, dxr, EC 2.2.1.7. Assay: Eur. J. Biochem. 269:4446-4457, 2002; MCT; 4-Diphosphocytidyl-2C-methyl-D-erythritol synthase, IspD, EC 2.7.7.60. Assay: PNAS, 97: 6451-6456, 2000; CMK; 4-Diphosphocytidyl-2-C-methyl-D-erythritol kinase, IspE, EC 2.7.1.148. Assay: PNAS, 97:1062-1067, 2000; MCS; 2C-Methyl-D-erythritol 2,4-cyclodiphosphate synthase, IspF, EC 4.6.1.12. Assay: PNAS, 96:11758-11763, 1999; HDS; 1-Hydroxy-2-methyl-2-(E)-butenyl 4-diphosphate synthase, ispG, EC 1.17.4.3. Assay: J. Org. Chem., 70:9168-9174, 2005; HDR; 1-Hydroxy-2-methyl-2-(E)-butenyl 4-diphosphate reductase, IspH, EC 1.17.1.2. Assay: JACS, 126:12847-12855, 2004.

Figure 16:
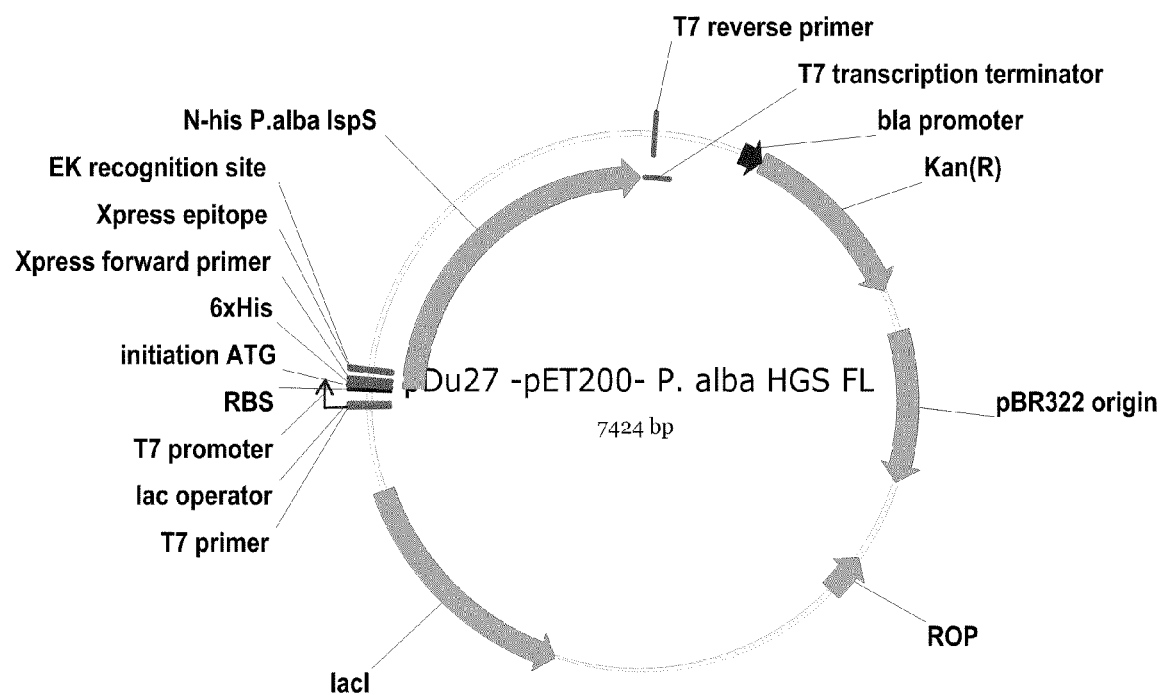

FIG. 16 provides a map of pDu27.

FIG. 17 provides the amino acid sequence (SEQ ID NO:118) of 6Xhis N-terminally tagged *P. alba* IspS in pDu27.

FIG. 18 provides the nucleotide sequence (SEQ ID NO:119) of plasmid pDu27.

FIG. 19 provides the amino acid sequence (SEQ ID NO:120) of full length *P. alba* IspS in pET24a. Underlined residues indicate the locations of N-terminal truncations in IspS in plasmids pDu39 through pDu43.

FIG. 20 provides the nucleotide sequence (SEQ ID NO:121) of plasmid *P. alba* pET24a.

Figure 21:
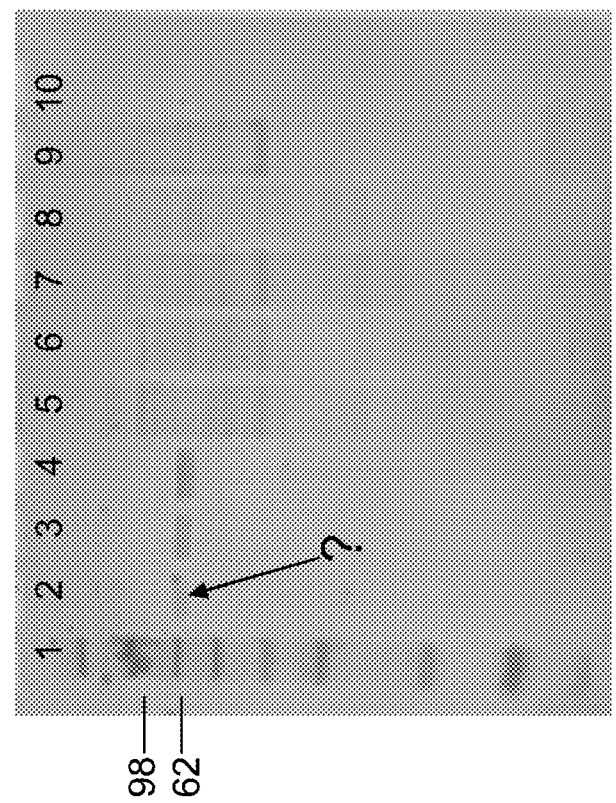

FIG. 21 shows purified IspS displays a lower molecular weight "doublet" by SDS-PAGE analysis.

Figure 22:
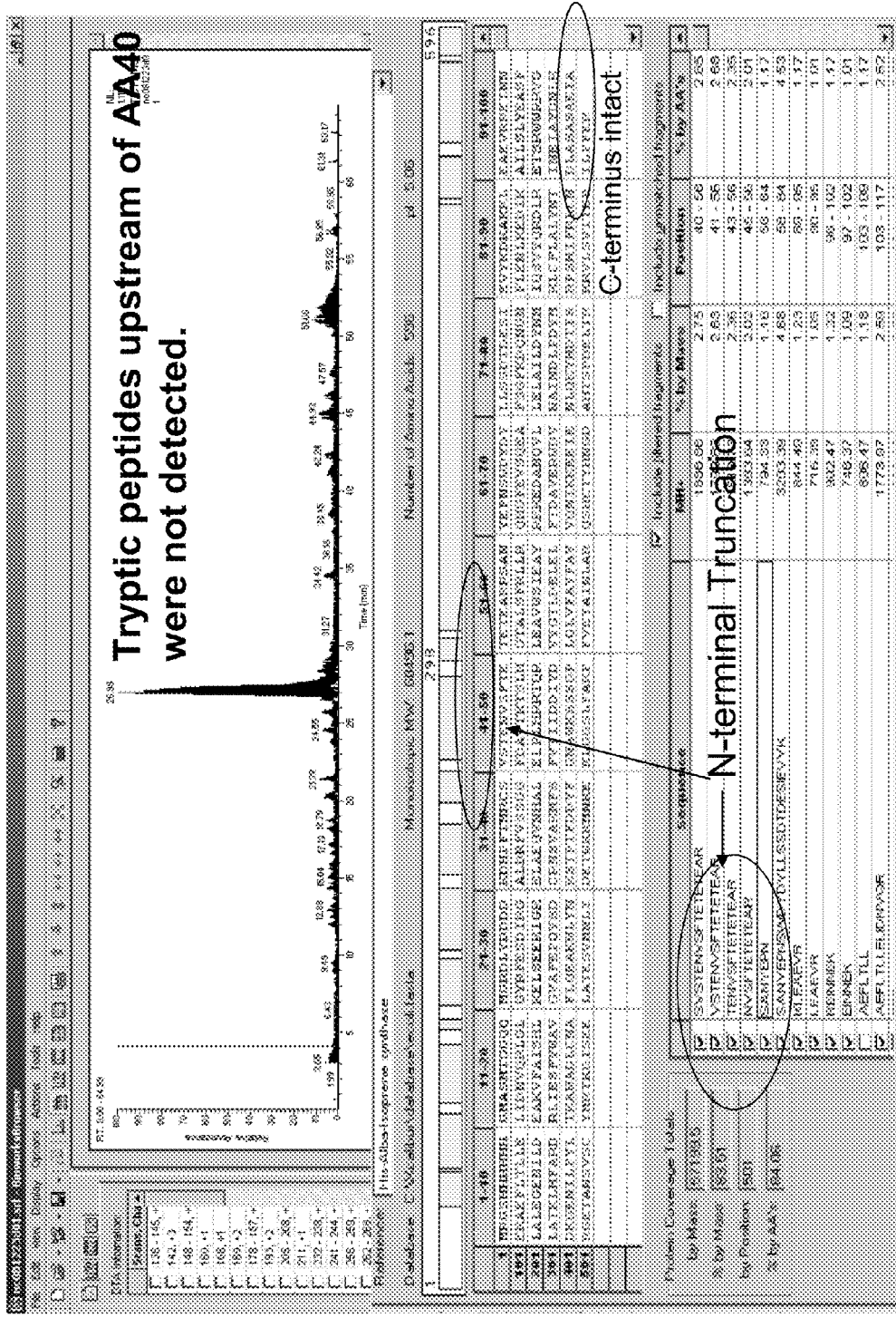

FIG. 22 shows tryptic peptides identified by mass spectrometry.

Figure 23:
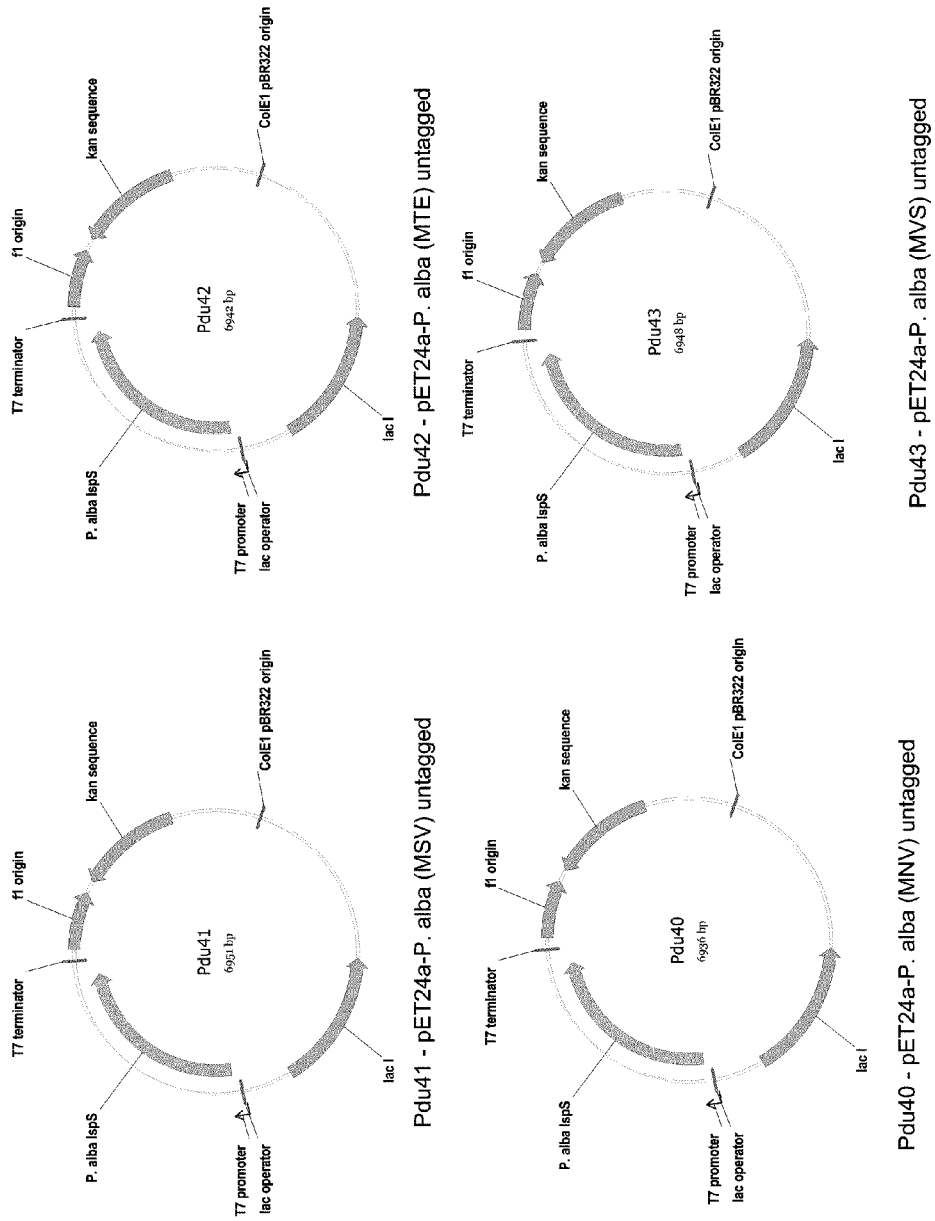

FIG. 23 provides maps of pDu40, pDu41, pDu42 and pDu43 harboring N-terminal truncations of *P. alba* IspS.

Figure 24:
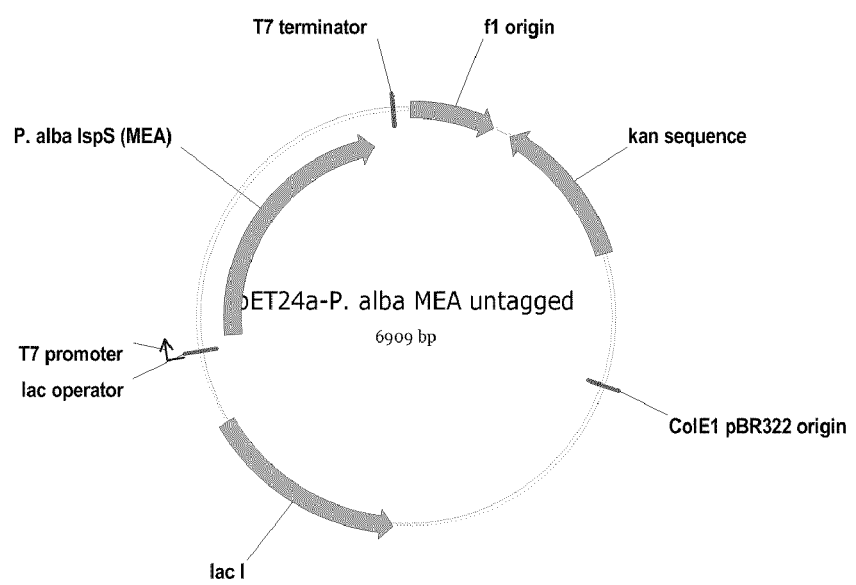

FIG. 24 provides a map of Pdu39 which is pET24a-*P. alba* MEA untagged (in strain MD09-173).

FIG. 25 provides the amino acid sequence (SEQ ID NO:122) of truncated "MEA" variant of *P. alba* IspS in pDu39.

FIG. 26 provides the nucleotide sequence (SEQ ID NO:123) of plasmid pDu39.

FIG. 27 provides the amino acid sequence (SEQ ID NO:124) of truncated "MSV" variant *P. alba* IspS in pDu41.

FIG. 28 provides the nucleotide sequence (SEQ ID NO:125) of plasmid pDu41 (pET24a-*P. alba*(MSV) Untagged).

FIG. 29 provides the amino acid sequence (SEQ ID NO:126) of truncated "MVS" variant *P. alba* IspS in pDu43.

FIG. 30 provides the nucleotide sequence (SEQ ID NO:127) of plasmid pDu43 (pET24a-*P. alba*(MVS) Untagged).

FIG. 31 provides the amino acid sequence (SEQ ID NO:128) of truncated "MTE" variant of *P. alba* IspS in pDu42.

FIG. 32 provides the nucleotide sequence (SEQ ID NO:129) of plasmid pDu42 (pET24a-*P. alba*(MTE) Untagged).

FIG. 33 provides the amino acid sequence (SEQ ID NO:130) of truncated "MNV" *P. alba* IspS in pDu40.

FIG. 34 provides the nucleotide sequence (SEQ ID NO:131) of plasmid pDu40 (pET24a-*P. alba*(MNV) Untagged).

Figure 35:
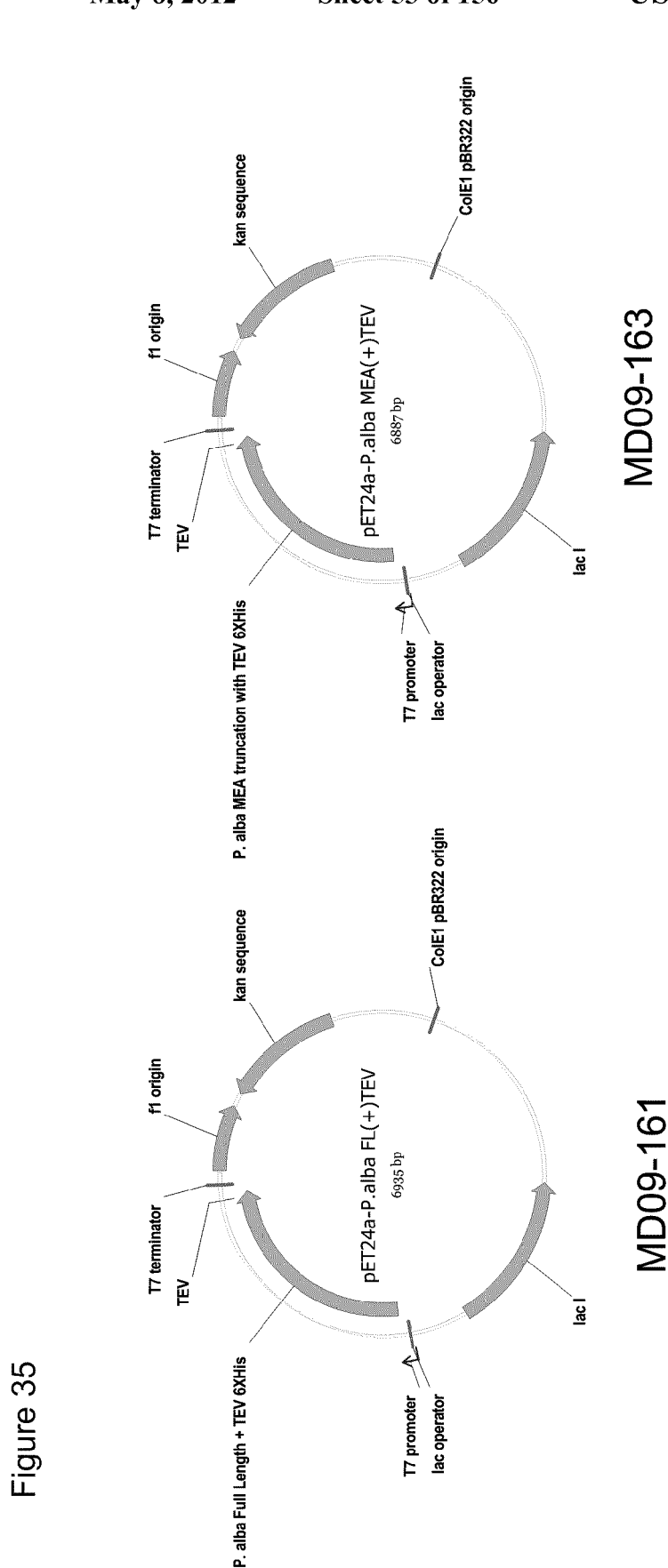

FIG. 35 provides maps of MD09-161 and MD09-163, C-terminally TEV, 6XHis-tagged IspS variants.

FIG. 36 provides the amino acid sequence (SEQ ID NO:132) of *P. alba* MEA(+)TEV in MD09-163.

FIG. 37 provides the nucleotide sequence (SEQ ID NO:133) of plasmid MD09-163 (pET24a-*P. alba* MEA(+) TEV. CDS is underlined, TEV protease site is bold.

FIG. 38 provides the amino acid sequence (SEQ ID NO:134) of *P. alba* FL(+)TEV in MD09-161.

FIG. 39 provides the nucleotide sequence (SEQ ID NO:135) of plasmid MD09-161 (pET24a-*P. alba* FL(+)TEV. CDS is underlined, TEV protease site is bold.

Figure 40:
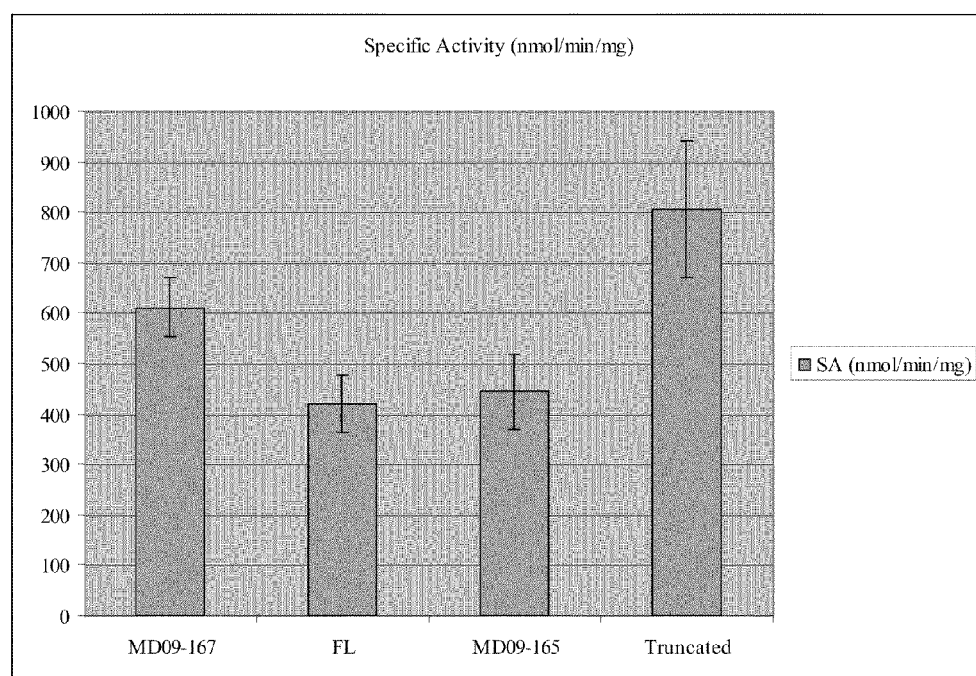

FIG. 40 shows a graph representing specific activities of MD09-167, Full length (FL), MD09-165, and Truncated isoprene synthase (MD09-173). Reactions were run at 30° C. for 15 minutes in a solution containing 100 mM Tris, 100 mM NaCl, 50 mM $MgCl_2$, 5 mM DMAPP, and 2.5-4.5 µg isoprene synthase in the supernatant of whole cell lysate.

Figure 41:
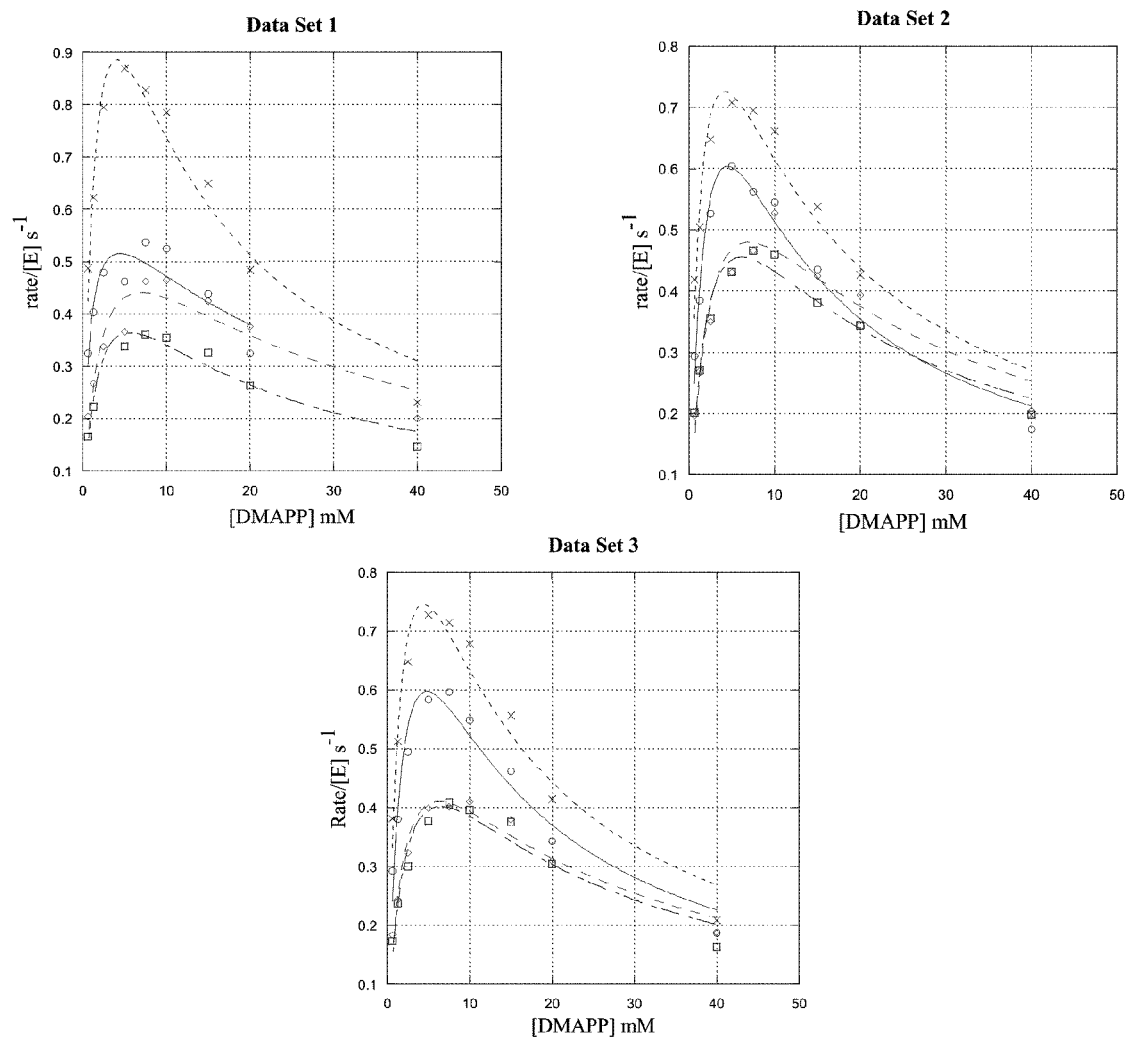

FIG. 41 shows graphs demonstrating Rate/[E] vs. [DMAPP]. X's represent MD09-173, circles represent MD09-167, diamonds represent MD09-165 and squares represent full length IspS.

Figure 42:
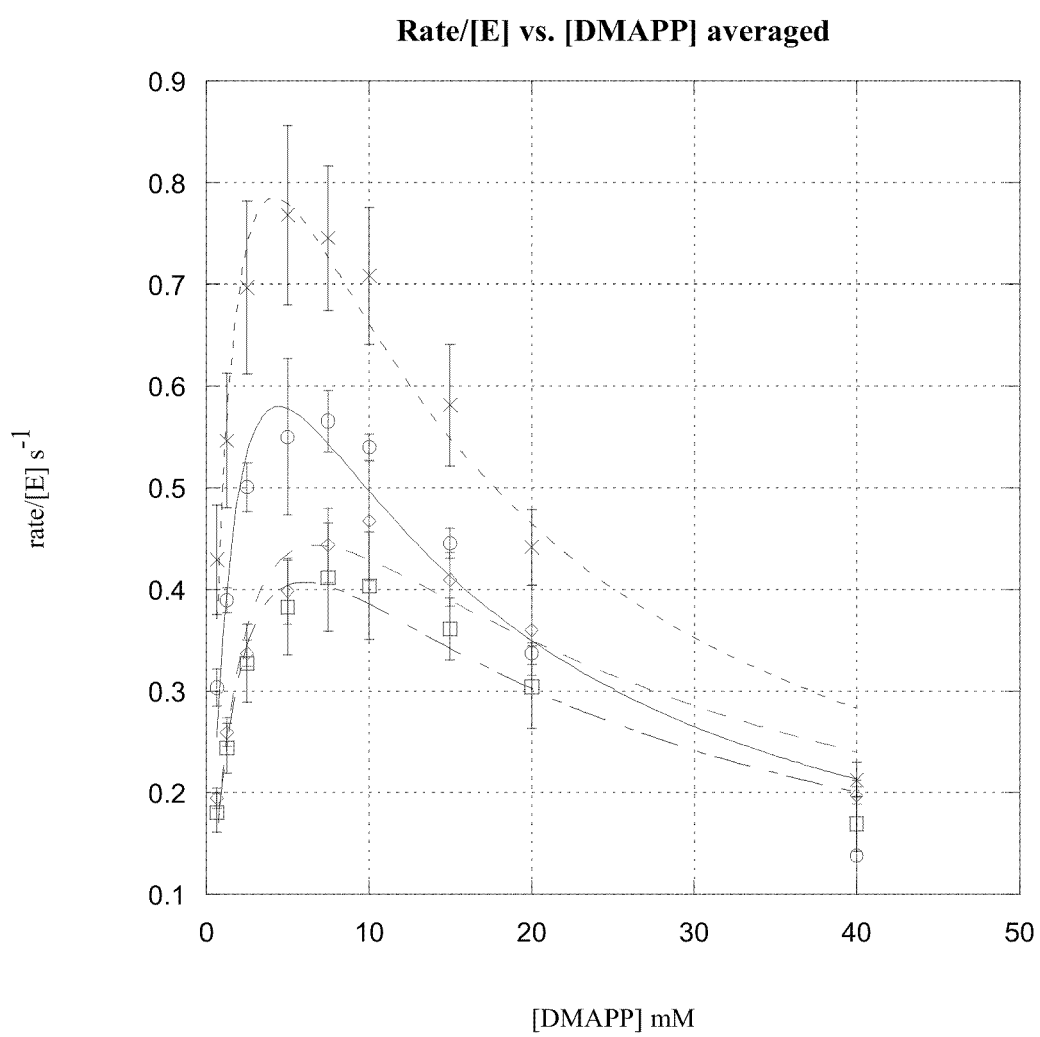

FIG. 42 shows a graph showing Isoprene synthase activity vs. [DMAPP]. X's represent data generated with MD09-173 truncated isoprene synthase. Circles represent data generated with MD09-167 isoprene synthase. Diamonds represent data generated with MD09-165 isoprene synthase. Squares represent data generated with full length isoprene synthase. Each data set was run in triplicate from independently grown cultures.

FIG. 43 shows graphs demonstrating the effects of varying $k_{cat}$ and $K_M$ and $K_i$ on reaction rate. In panel A, line 1 represents the rate equation of truncated isoprene synthase activity divided by the rate equation of full length isoprene synthase plotted at varying DMAPP concentrations. Line 2 represents the rate equation of full length isoprene synthase in which the $k_{cat}$ has been substituted by the $k_{cat}$ of the truncated isoprene synthase divided by the rate equation of the full length isoprene synthase. Line 3 represents the rate equation of full length isoprene synthase in which the $K_M$ has been substituted by the $K_M$ of the truncated isoprene synthase divided by the rate equation of the full length isoprene synthase. Line 4 represents the rate equation of full length isoprene synthase in which the $K_i$ has been substituted by the $K_i$ of the truncated isoprene synthase divided by the rate equation of the full length isoprene synthase. Panel B shows a graph demonstrating data fit to the ratio of the rate equation of truncated isoprene synthase to full length isoprene synthase vs. [DMAPP].

Figure 44:
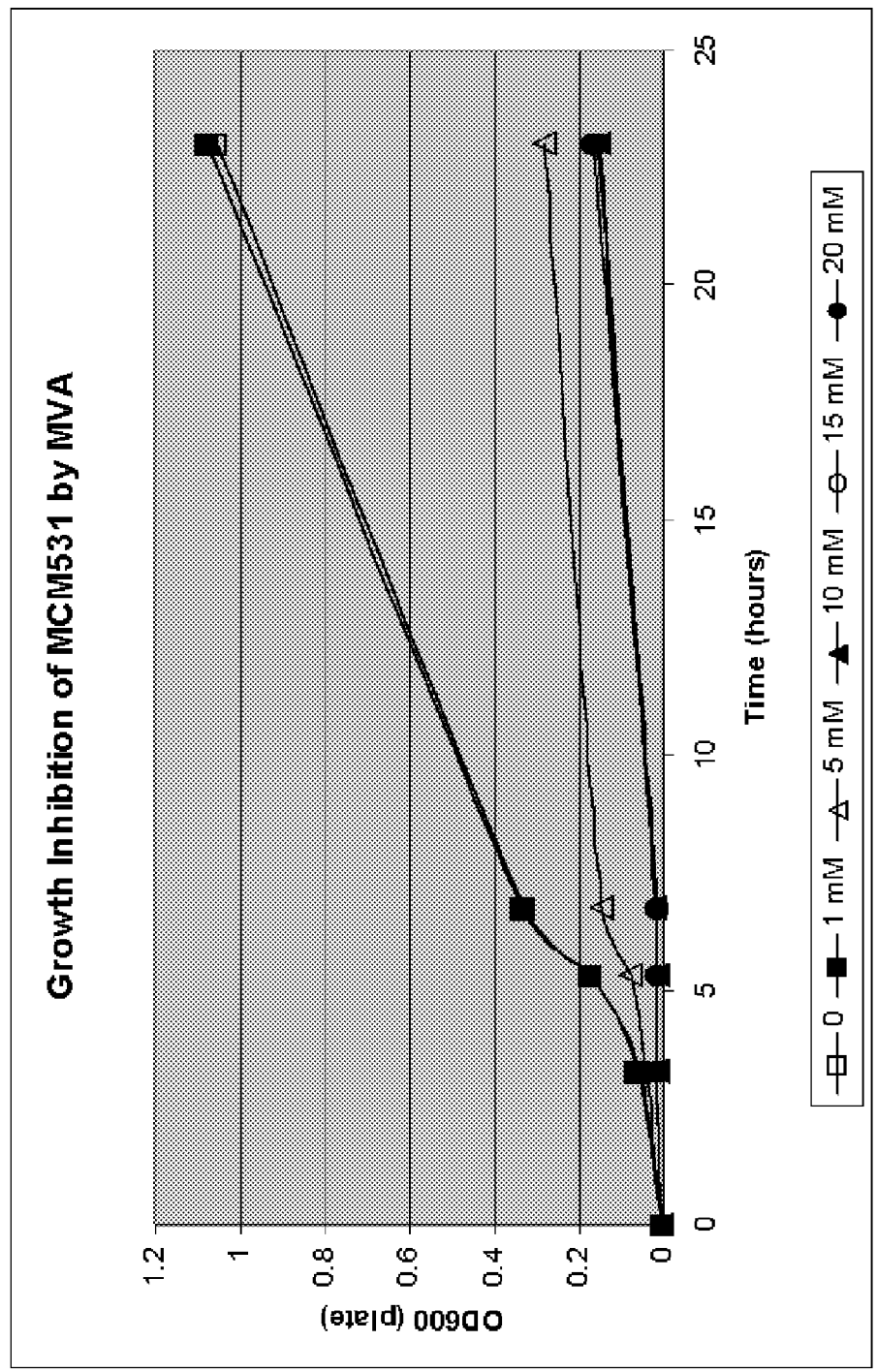

FIG. 44 shows a graph demonstrating growth inhibition of MCM531 by Mevalonic Acid (MVA). Cells were grown in TM3 medium in a microtiter plate with different concentrations of MVA. $OD_{600}$ of quadruplicate wells was measured at the indicated times.

Figure 45:
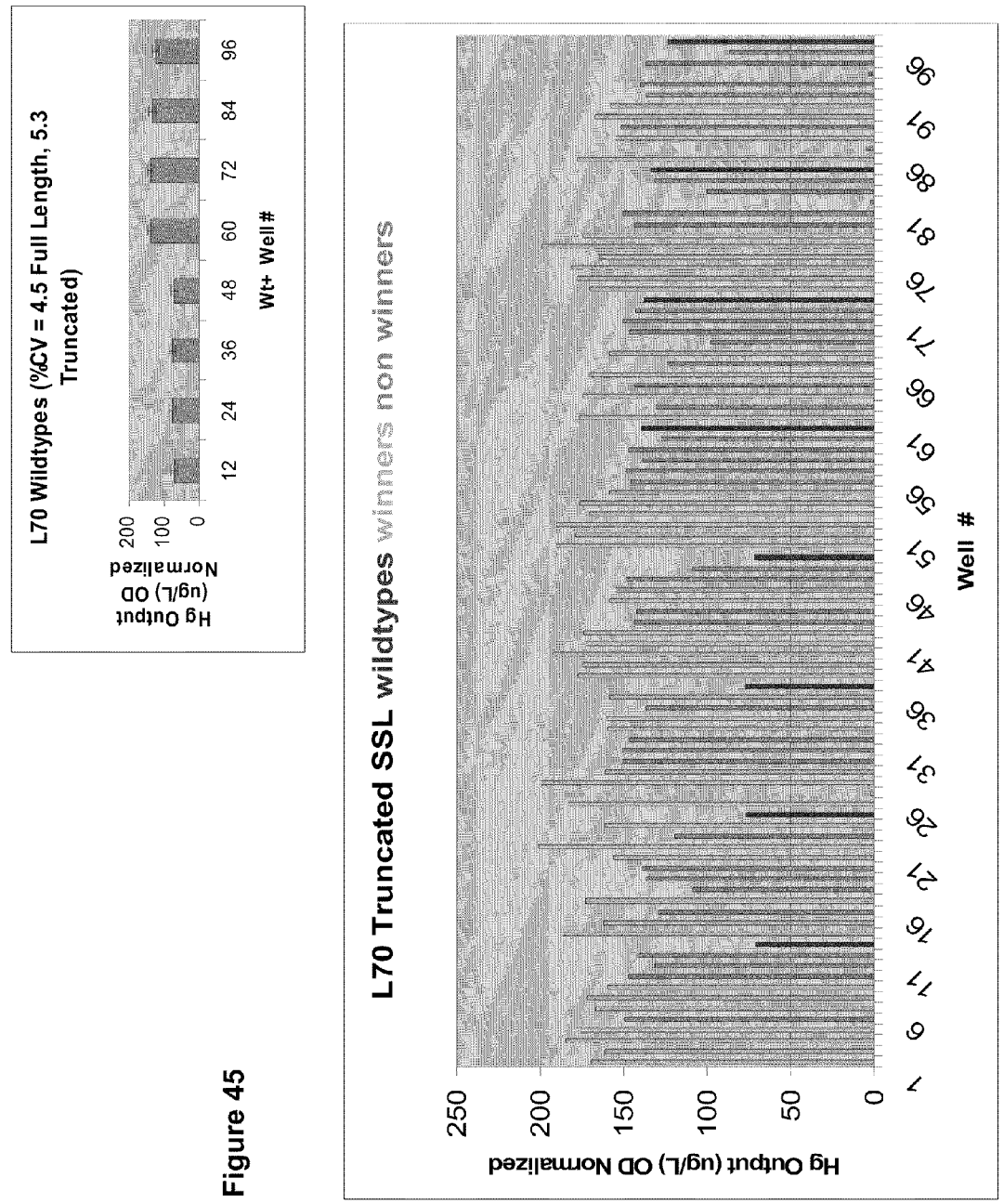

FIG. 45 shows graphs demonstrating DMAPP assays of L70 SSL plate. Dark bars represent either the full length (*P. alba* pET24a) or pDU39 (truncated) controls. The variants in wells C3 (27), D3 (39), or E3 (51) were chosen for further analysis.

Figure 46:
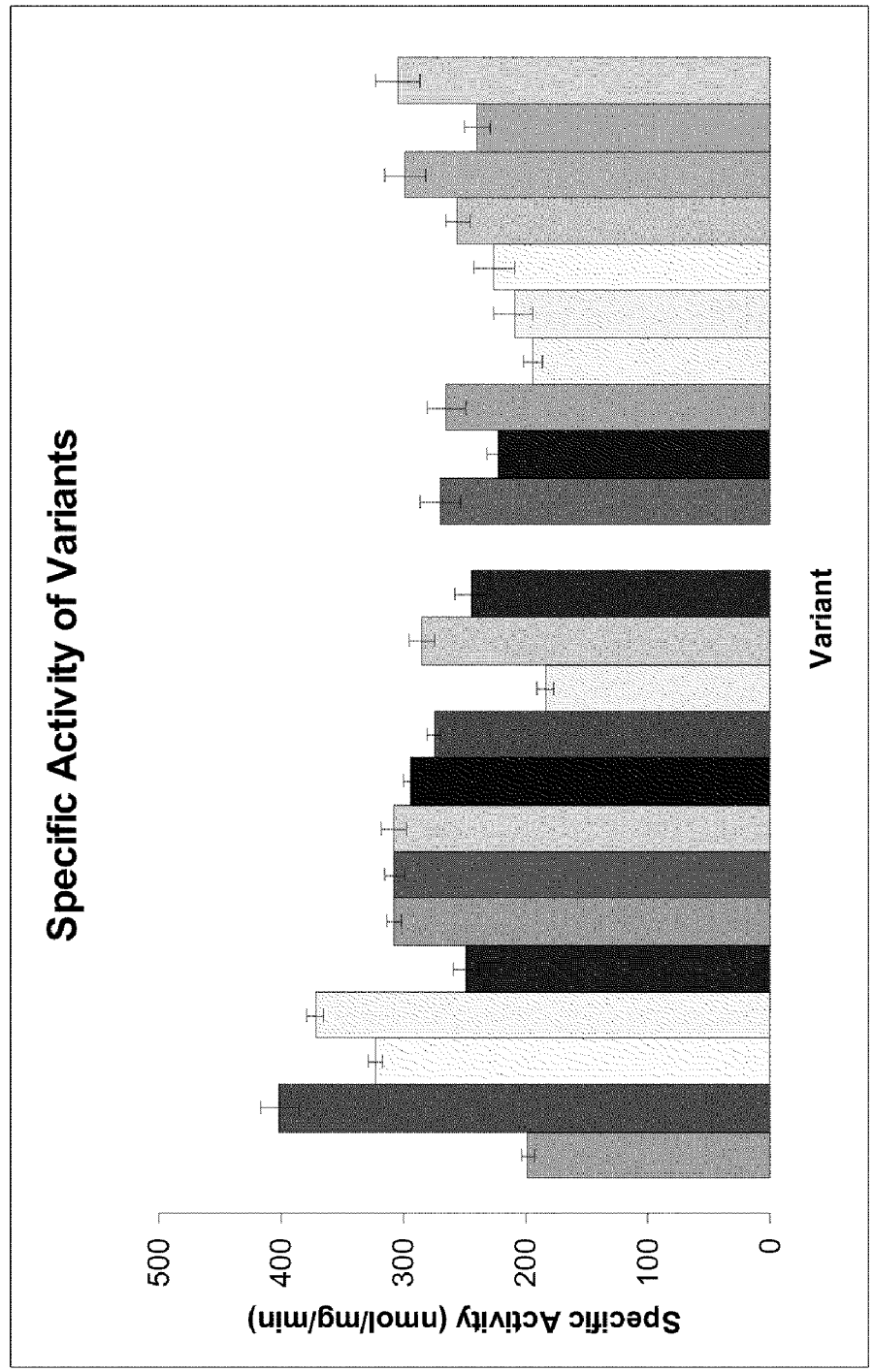

FIG. 46 shows a graph demonstrating the average specific activity of all variants selected for DMAPP assay with protein determination. Error bars show one standard deviation. All 3 L70R variants display higher activity than the control (WT).

Figure 47:
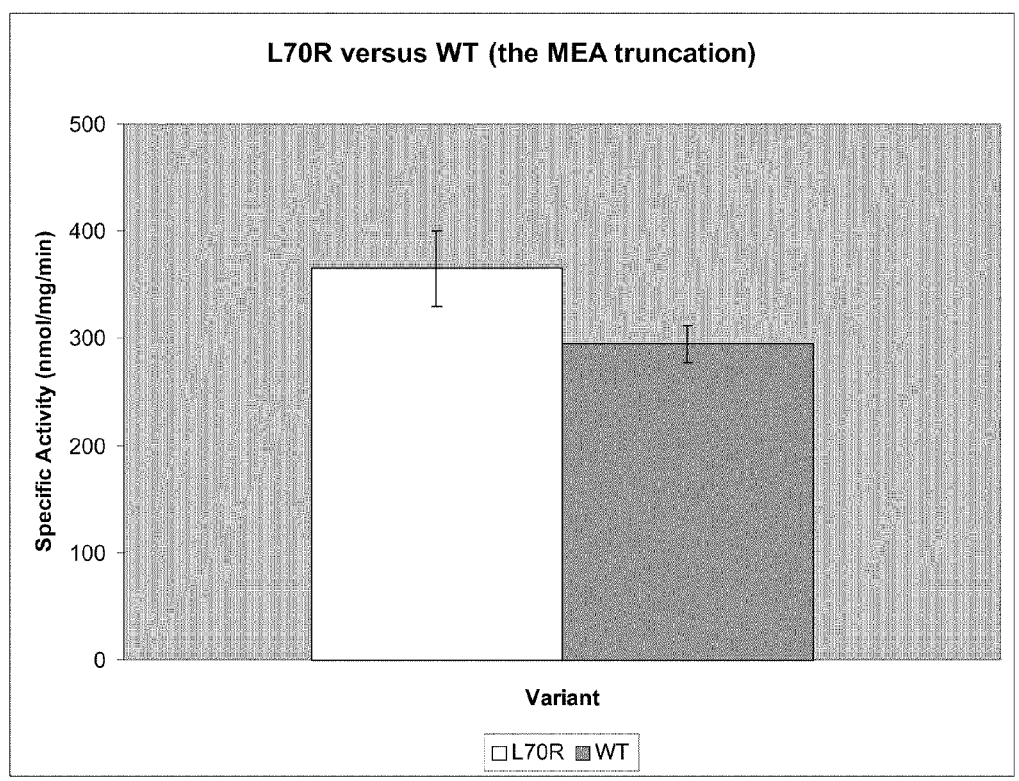

FIG. 47 shows a graph demonstrating the average specific activity of all 3 L70R variants compared to the "MEA" truncated *P. alba* IspS enzyme. Error bars show one standard deviation.

FIG. 48 provides maps of plasmids pDu47-3, pDu47-4, and pDu47-5.

FIG. 49 provides maps of plasmids pDu47-6, pDu47-7, and pDu48.

FIG. 50 provides maps of plasmids pDu49, pDu50 and pDu50-4.

FIG. 51 provides the amino acid sequence (SEQ ID NO:136) of *P. alba* TRC (−3) in pDu47-3.

FIG. 52 provides the nucleotide sequence (SEQ ID NO:137) of plasmid pDu47-3.

FIG. 53 provides the amino acid sequence (SEQ ID NO:138) of *P. alba* TRC (−4) in pDu47-4.

FIG. 54 provides the nucleotide sequence (SEQ ID NO:139) of plasmid pDu47-4.

FIG. 55 provides the amino acid sequence (SEQ ID NO:140) of *P. alba* TRC (−5) in pDu47-5.

FIG. 56 provides the nucleotide sequence (SEQ ID NO:141) of plasmid pDu47-5.

FIG. 57 provides the amino acid sequence (SEQ ID NO:142) of *P. alba* TRC (−6) in pDu47-6.

FIG. 58 provides the nucleotide sequence (SEQ ID NO:143) of plasmid pDu47-6.

FIG. 59 provides the amino acid sequence (SEQ ID NO:144) of *P. alba* TRC (−7) in pDu47-7.

FIG. 60 provides the nucleotide sequence (SEQ ID NO:145) of plasmid pDu47-7.

FIG. 61 provides the amino acid sequence (SEQ ID NO:146) of *P. tremuloides* TRC (MET) in pDu48.

FIG. 62 provides the nucleotide sequence (SEQ ID NO:147) of plasmid pDu48.

FIG. 63 provides the amino acid sequence (SEQ ID NO:148) of *P. trichocarpa* (TRC) in pDu49.

FIG. 64 provides the nucleotide sequence (SEQ ID NO:149) of plasmid pDu49.

FIG. 65 provides the amino acid sequence (SEQ ID NO:150) of Kudzu TRC (MEA) in pDu50.

FIG. 66 provides the nucleotide sequence (SEQ ID NO:151) of plasmid pDu50.

FIG. 67 provides the amino acid sequence (SEQ ID NO:152) of KudzuTRC (−4) in pDu50-4.

FIG. 68 provides the nucleotide sequence (SEQ ID NO:153) of plasmid pDu50-4.

FIG. 69 shows graphs demonstrating raw and OD-normalized data from DMAPP assay of truncated variants of IspS.

Figure 70:
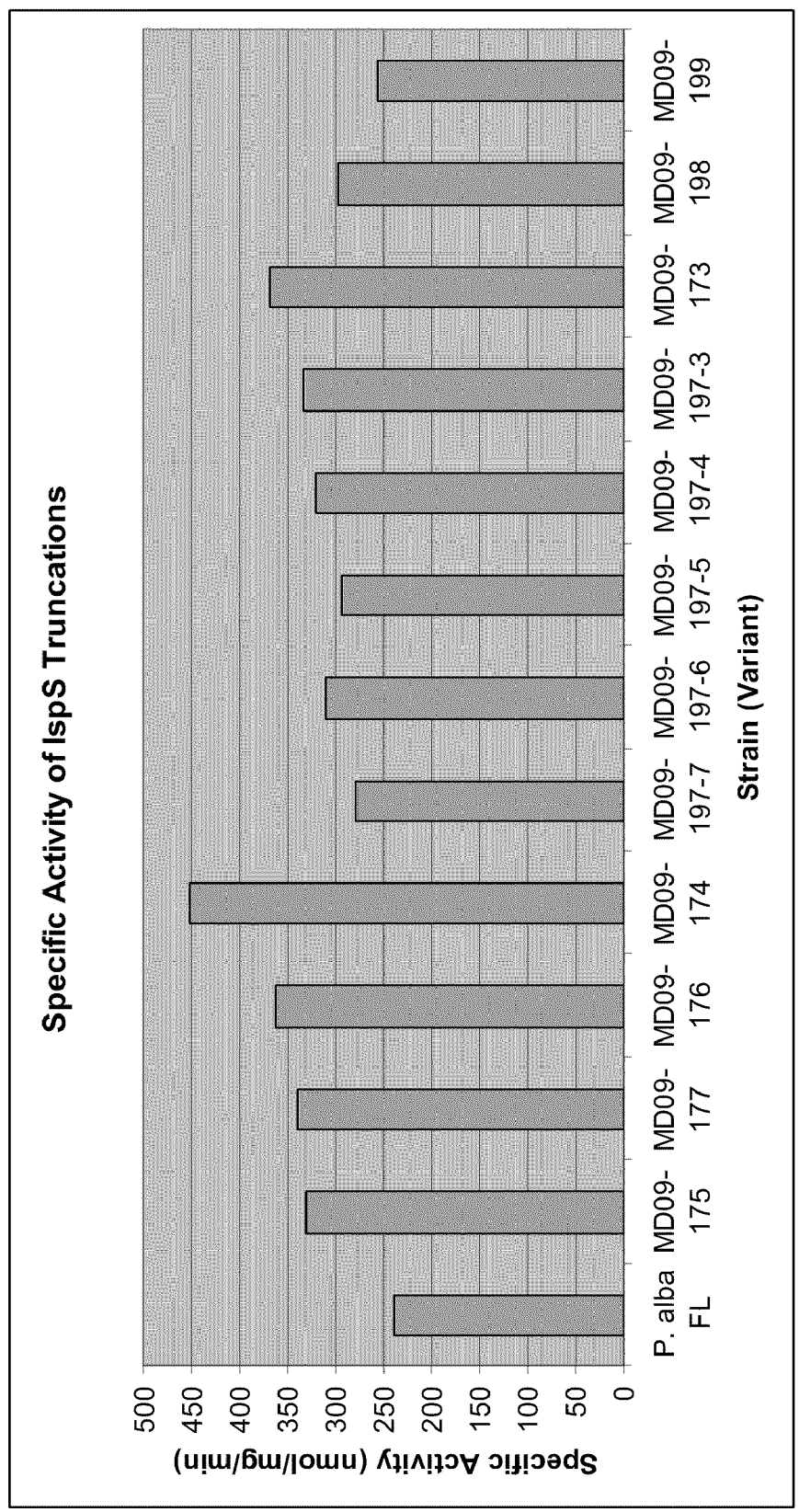

FIG. 70 shows a graph representing the specific activity of IspS truncations. *P. alba*, *P. tremuloides* and *P. trichocharpa* truncations were compared for specific activity relative to the *P. alba* "full length" variant.

Figure 71:
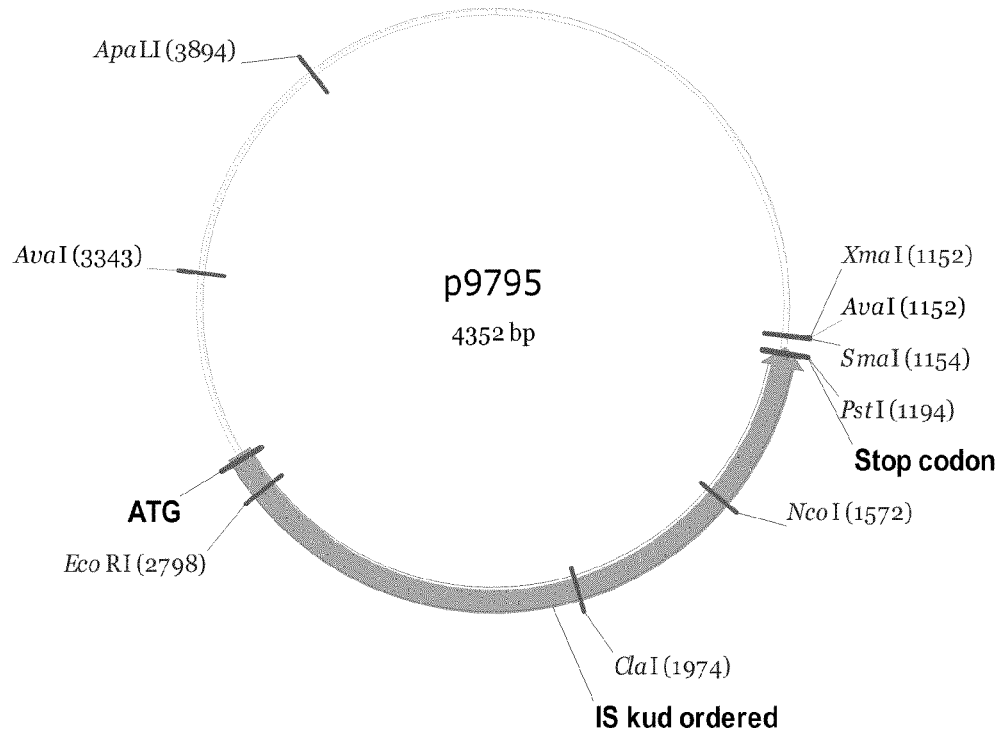

FIG. 71 provides a map of plasmid p9795.

FIG. 72 provides the nucleotide sequence of plasmid p9795 (SEQ ID NO:154).

Figure 73:
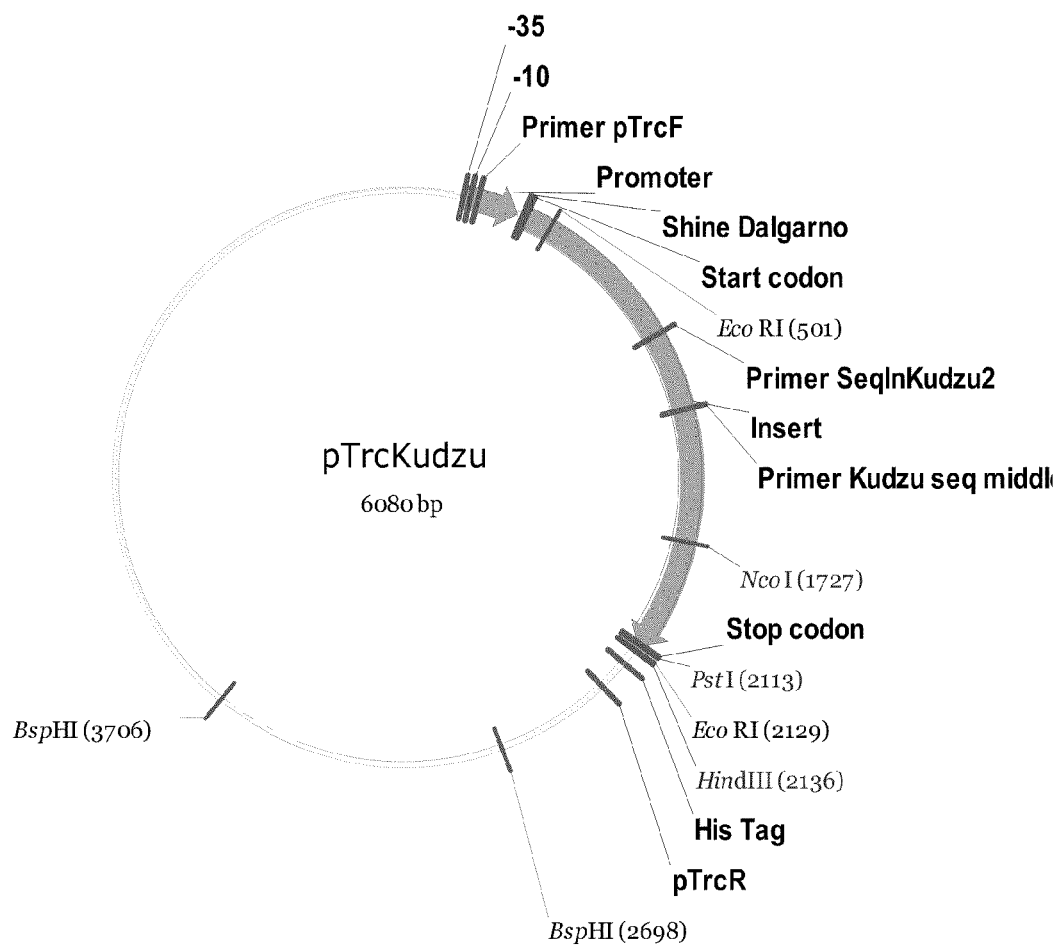

FIG. 73 provides a map of plasmid pTrcKudzu.

FIG. 74 provides the nucleotide sequence (SEQ ID NO:155) of plasmid pTrcKudzu.

Figure 75:
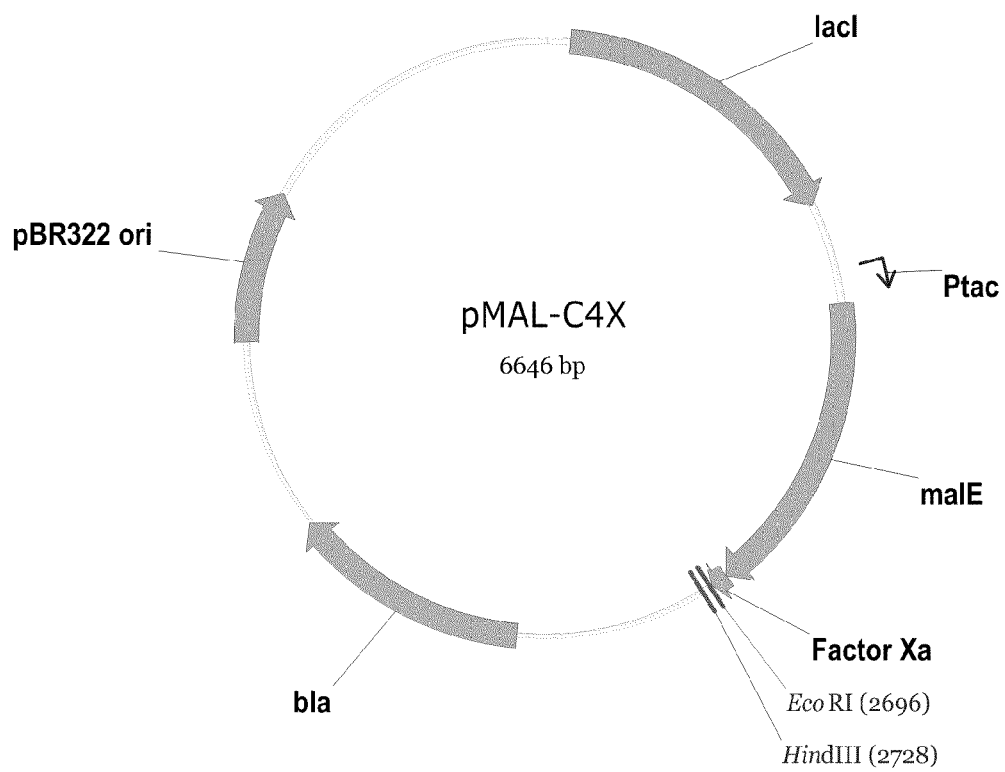

FIG. 75 provides a map of plasmid pMAL-C4X.

FIG. 76 provides the nucleotide sequence (SEQ ID NO:156) of plasmid pMAL-C4X.

Figure 77:
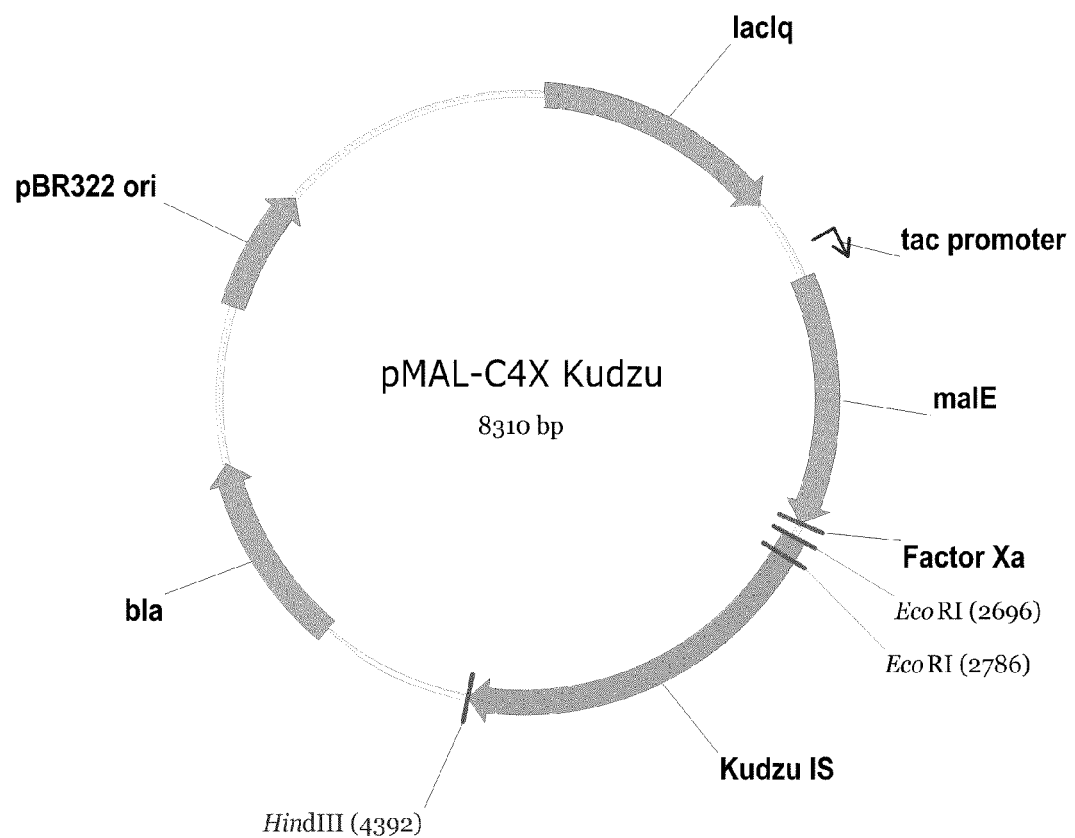

FIG. 77 provides a map of plasmid pMAL-C4X-Kudzu.

FIG. 78 provides the nucleotide sequence (SEQ ID NO:157) of plasmid pMAL-C4X-Kudzu.

FIG. 79 provides maps of plasmids pET24 *P. tremuloides* pET24a and *P. trichocarpa* pET24a.

FIG. 80 provides the amino acid sequence (SEQ ID NO:158) of *P. tremuloides* IspS in *P. trichocharpa* pET24a.

FIG. 81 provides the nucleotide sequence (SEQ ID NO:159) of plasmid *P. tremuloides* pET24a.

FIG. 82 provides the amino acid sequence (SEQ ID NO:160) of *P. trichocarpa* IspS in *P. trichocarpa* pET24a.

FIG. 83 provides the nucleotide sequence (SEQ ID NO:161) of plasmid *P. trichocarpa* pET24a.

Figure 84C:
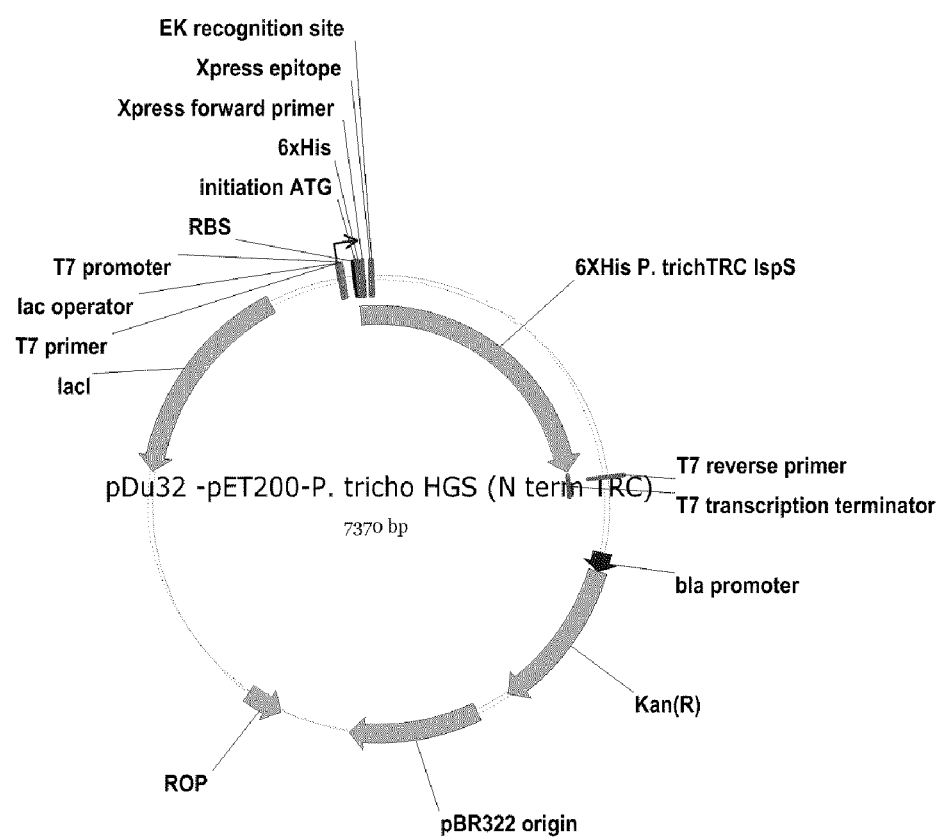

FIG. 84 provides maps of plasmids pDu30, pDu31, and pDu32.

FIG. 85 provides the amino acid sequence (SEQ ID NO:162) of IspS variant *P. alba*TRC-pET200 in pDu30.

FIG. 86 provides the nucleotide sequence (SEQ ID NO:163) of pDu30.

FIG. 87 provides the amino acid sequence (SEQ ID NO:164) of IspS variant *P. trem*TRC-pET200 in pDu31.

FIG. 88 provides the nucleotide sequence (SEQ ID NO:165) of pDu31.

FIG. 89 provides the amino acid sequence (SEQ ID NO:166) of IspS variant *P. trich*TRC-pET200 in pDu32.

FIG. 90 provides the nucleotide sequence (SEQ ID NO:167) of pDu32.

Figure 91:
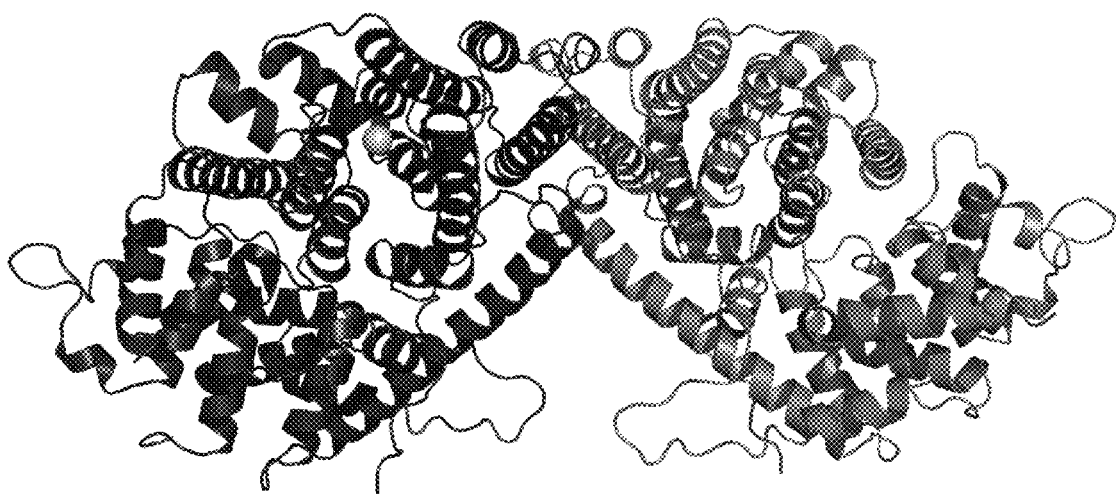

FIG. 91 provides the three-dimensional structure of *P. tremuloides* IspS shown as a dimer. Chain A is in dark gray, chain B is in medium gray and the single magnesium ion found in each active site is light gray.

Figure 92:
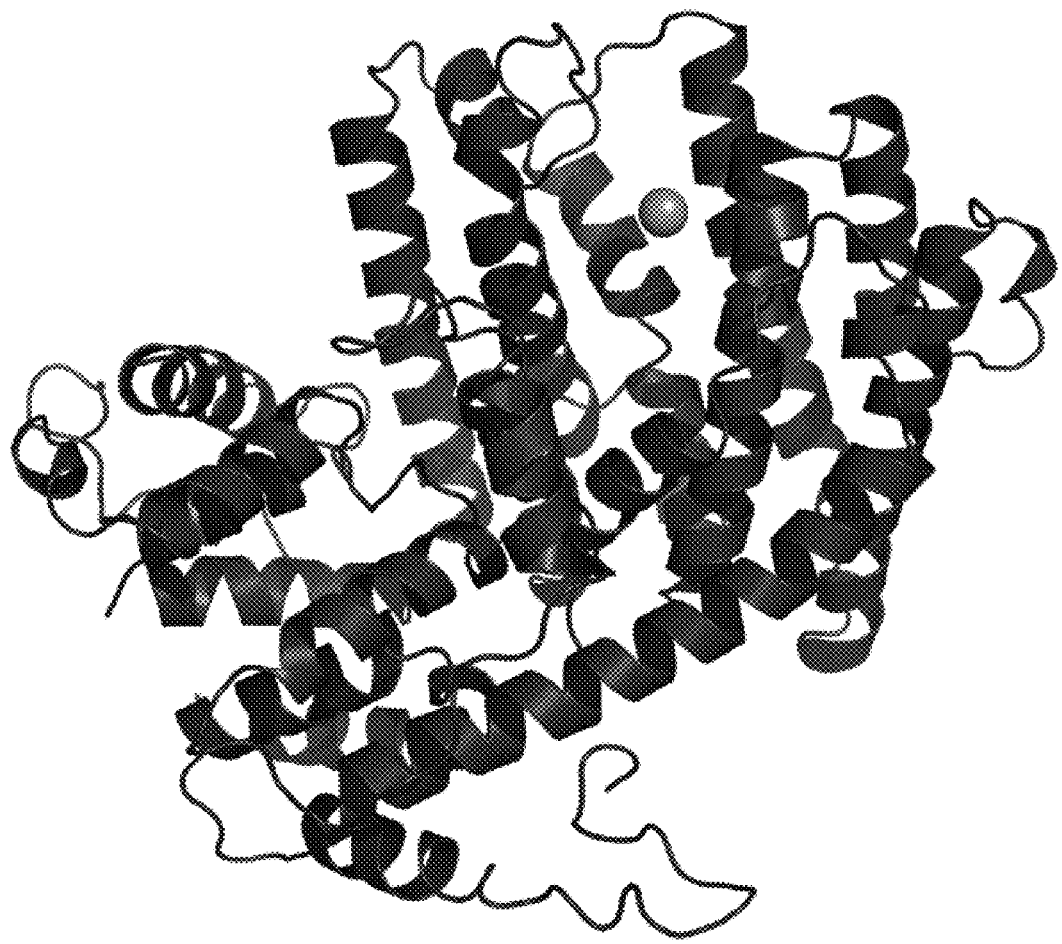

FIG. 92 provides a monomer view of the structure of *P. tremuloides* IspS. The magnesium is shown as a light gray sphere and the N- and C-terminals are indicated.

Figure 93:
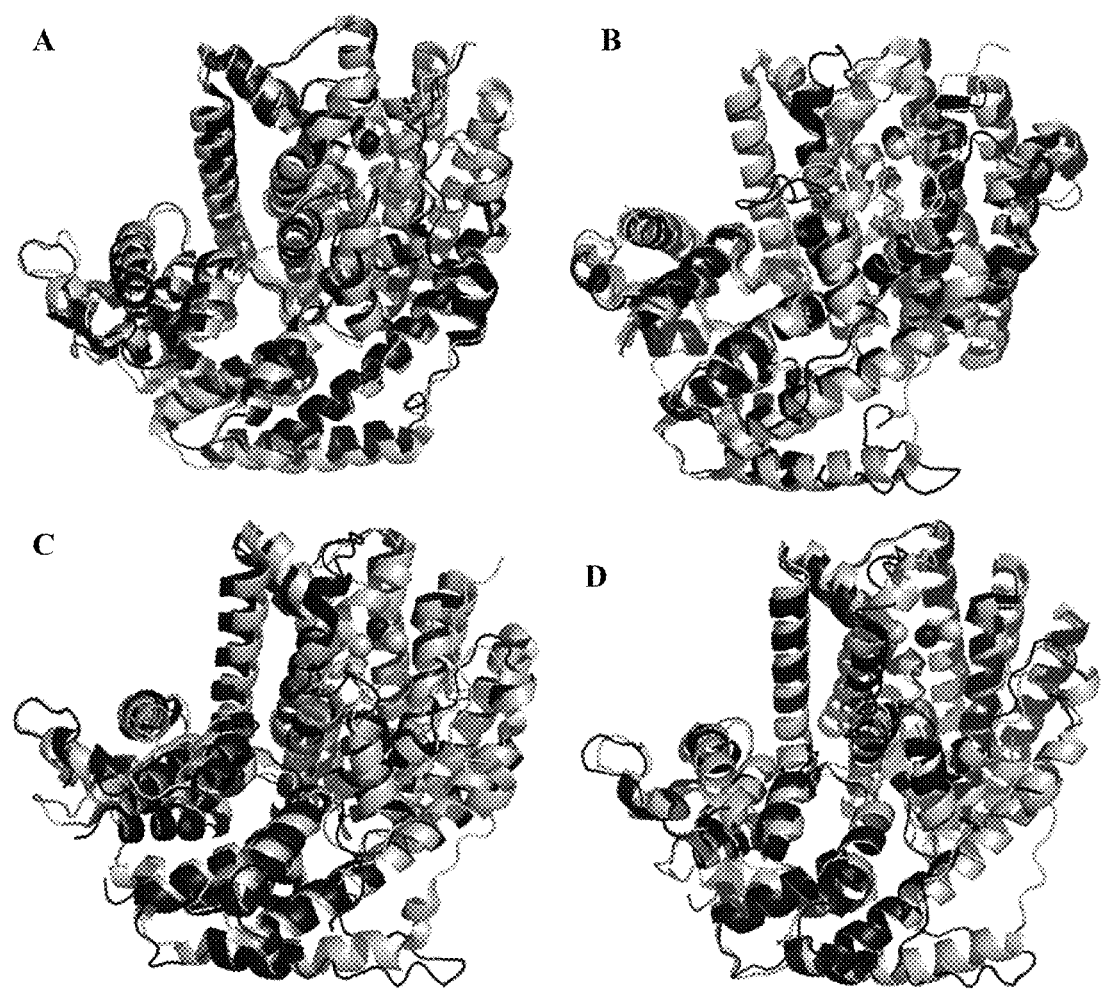

FIG. 93 shows the structural alignments between (A) BdpS and LS, (B) BdpS and poplar IspS, (C) LS and poplar IspS, and (D) TEAS and poplar IspS. In each case the first structure is in light gray and the second is in dark gray. Divalent cations are shown as spheres.

Figure 94:
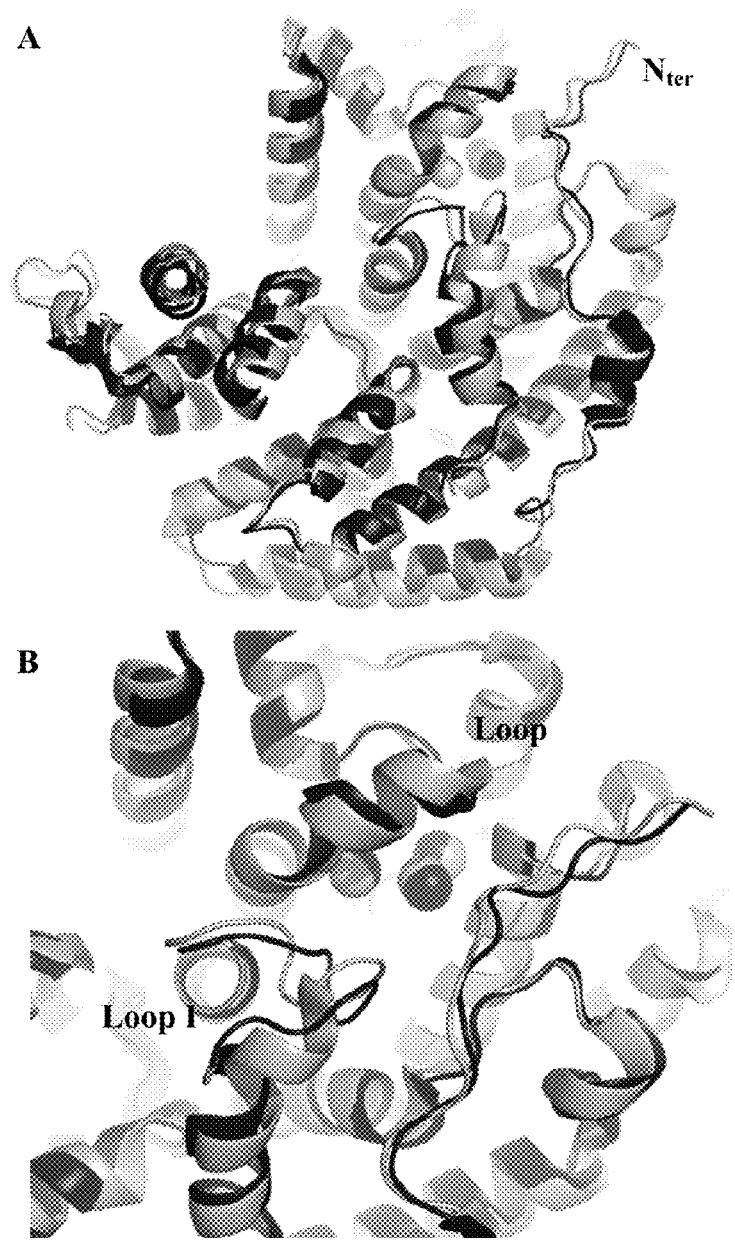

FIG. 94 shows the three dimensional structure of loops in BdpS and LS. Panel A shows the N-terminal loop of Ls in light gray and the N-terminal loop of BdpS in dark gray. Panel B shows that Loop I and Loop II are structurally homologous.

Figure 95:
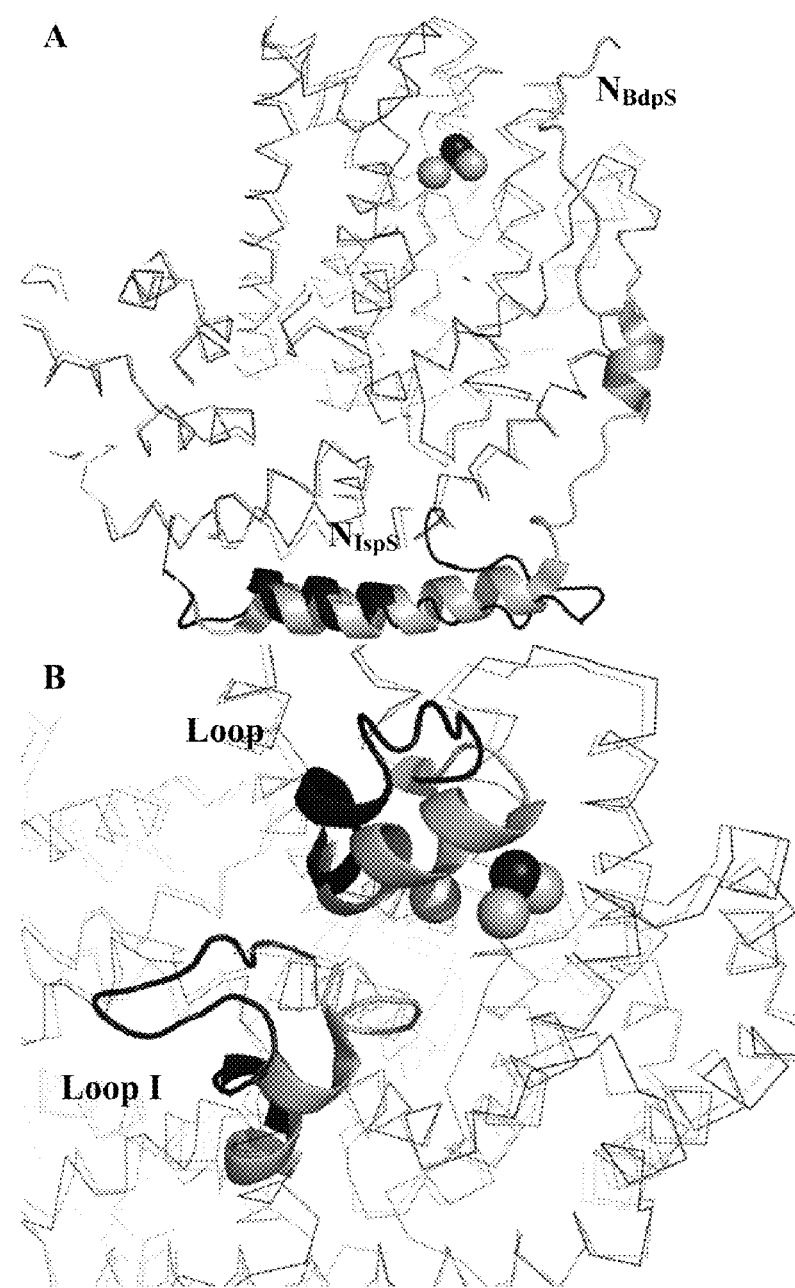

FIG. 95 shows the N-terminal loop of BdpS (dark gray) and poplar IspS (light gray) are structurally divergent. Panel A shows the N-terminal loop and panel B shows Loop I and Loop II.

Figure 96:
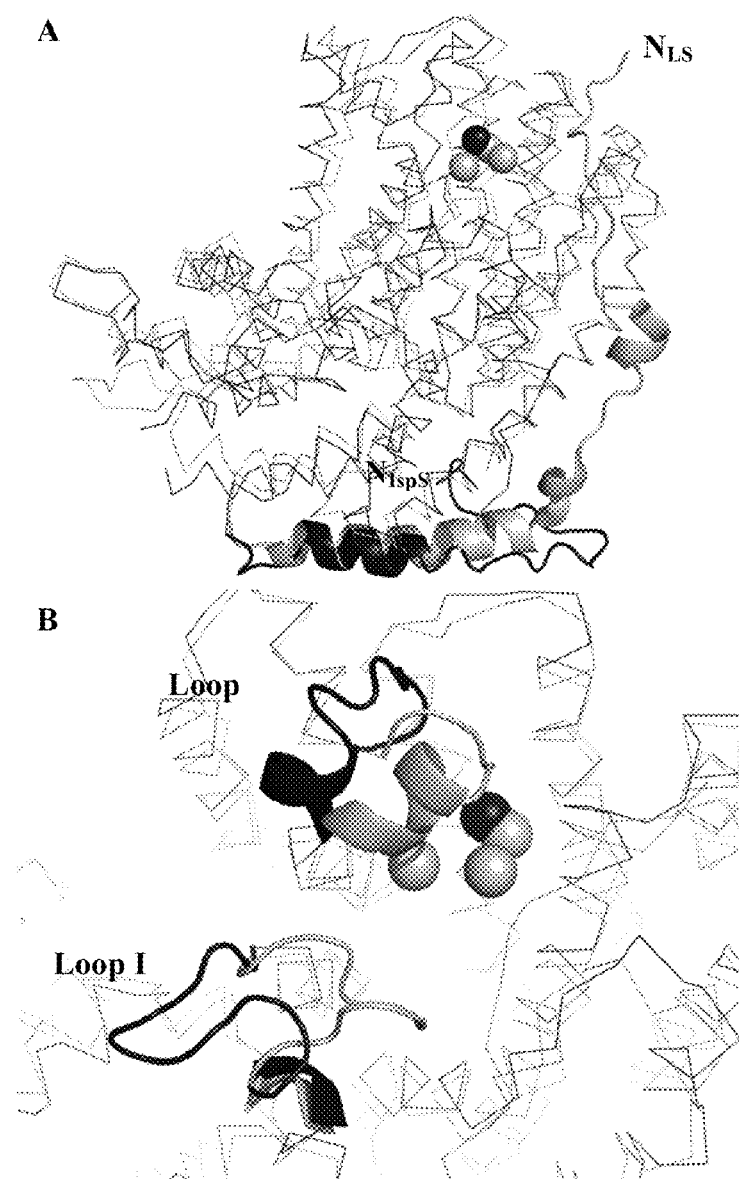

FIG. 96 shows the N-terminal loop of LS (light gray) and poplar IspS (dark gray) are structurally divergent. Panel A shows the N-terminal loop and panel B shows Loop I and Loop II.

Figure 97:
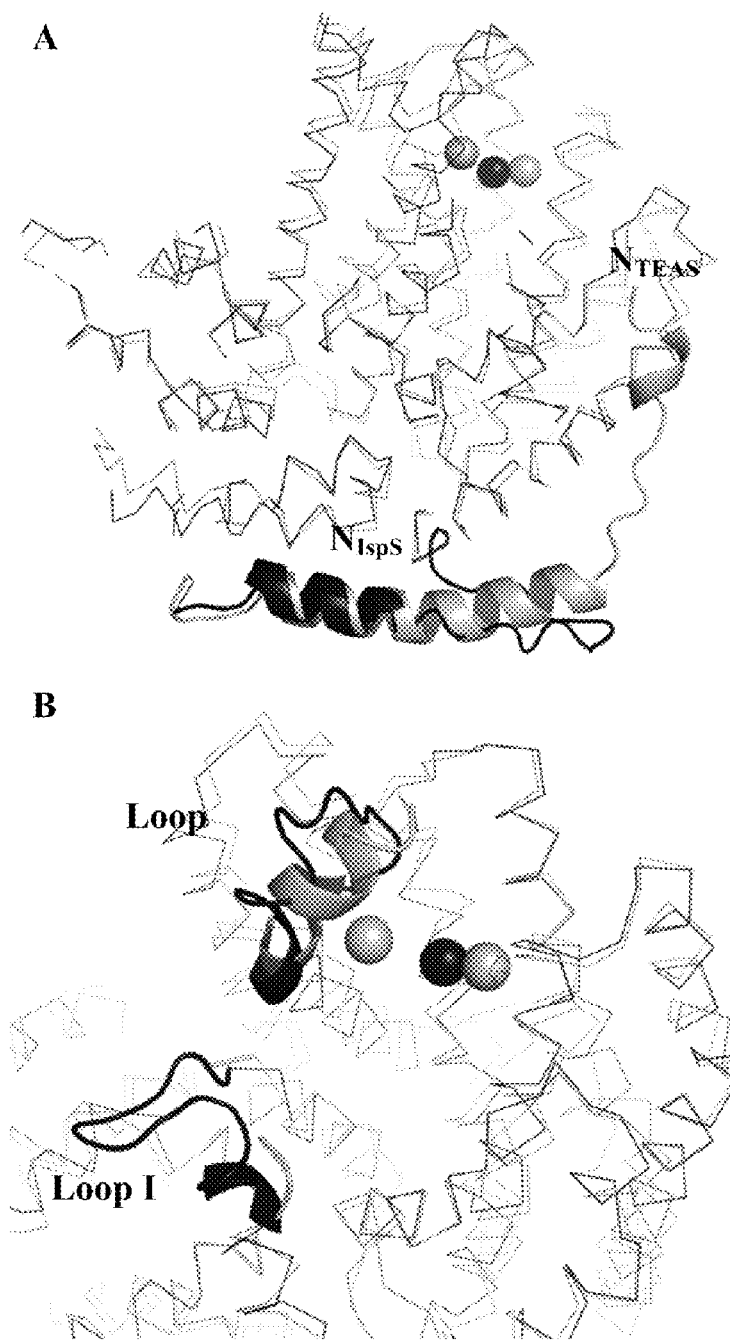

FIG. 97 shows the N-terminal loop of TEAS (light gray) and poplar IspS (dark gray) are structurally divergent. Panel A shows the N-terminal loop and panel B shows Loop I and Loop II. Loop I is disordered in TEAS.

GENERAL DESCRIPTION OF THE INVENTION

The present invention provides methods and compositions comprising at least one isoprene synthase enzyme with improved catalytic activity and/or solubility. In particular, the present invention provides variant plant isoprene synthases for increased isoprene production in microbial host cells. Biosynthetically produced isoprene of the present invention finds use in the manufacture of rubber and elastomers.

Unless otherwise indicated, the practice of the present invention involves conventional techniques commonly used in molecular biology, microbiology, and recombinant DNA, which are within the skill of the art. Such techniques are known to those of skill in the art and are described in numerous texts and reference works (See e.g., Sambrook et al., "Molecular Cloning: A Laboratory Manual," Second Edition, Cold Spring Harbor, 1989; and Ausubel et al., "Current Protocols in Molecular Biology," 1987).

Unless defined otherwise herein, all technical and scientific terms used herein have the same meaning as commonly understood by one of ordinary skill in the art to which this invention pertains. For example, Singleton and Sainsbury, Dictionary of Microbiology and Molecular Biology, 2d Ed., John Wiley and Sons, NY (1994); and Hale and Marham, The Harper Collins Dictionary of Biology, Harper Perennial, NY (1991) provide those of skill in the art with a general dictionaries of many of the terms used in the invention. Although any methods and materials similar or equivalent to those described herein find use in the practice of the present invention, the preferred methods and materials are described herein. Accordingly, the terms defined immediately below are more fully described by reference to the Specification as a whole.

Furthermore, the headings provided herein are not limitations of the various aspects or embodiments of the invention, which can be had by reference to the specification as a whole. Accordingly, the terms defined immediately below are more fully defined by reference to the specification as a whole. Nonetheless, in order to facilitate understanding of the invention, a number of terms are defined below.

Definitions

Unless defined otherwise herein, all technical and scientific terms used herein have the same meaning as commonly understood by one of ordinary skill in the art to which this invention pertains. Although any methods and materials similar or equivalent to those described herein find use in the practice of the present invention, the preferred methods and materials are described herein. Accordingly, the terms defined immediately below are more fully described by reference to the Specification as a whole.

As used herein, the singular terms "a," "an," and "the" include the plural reference unless the context clearly indicates otherwise. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All documents cited are, in relevant part, incorporated herein by reference. However, the citation of any document is not to be construed as an admission that it is prior art with respect to the present invention.

As used herein, the term 2-methyl-1,3-butadiene (CAS #78-79-5 ) ("isoprene") refers to the direct and final volatile C5 hydrocarbon product from the elimination of pyrophosphate from 3,3-dimethylallyl pyrophosphate (DMAPP), and does not involve the linking or polymerization of [an] IPP molecule(s) to [a] DMAPP molecule(s). As used herein, the terms "isoprene synthase," and "IspS," refer to the enzymes that catalyze the elimination or pyrophosphate from diemethylallyl diphosphate (DMAPP) to form isoprene. In some preferred embodiments, the IspS is an enzyme obtained from plants such as kudzu, poplar or red oak. In some embodiments, the term "IspS" refers to a naturally occurring mature enzyme or portion thereof.

Related (and derivative) proteins comprise "variant proteins." In some preferred embodiments, variant proteins differ from a parent protein (e.g., kudzu IspS set forth as SEQ ID NO:2 or poplar IspS) and one another by a small number of amino acid residues. The number of differing amino acid residues may be one or more, preferably 1, 2, 3, 4, 5, 10, 15, 20, 30, 40, 50, or more amino acid residues. In some preferred embodiments, the number of different amino acids between variants is between 1 and 10. In some particularly preferred embodiments, related proteins and particularly variant proteins comprise at least 35%, 40%, 45%, 50%, 55%, 60%, 65%, 70%, 75%, 80%, 85%, 90%, 95%, 97%, 98%, or 99% amino acid sequence identity. Additionally, a related protein or a variant protein as used herein refers to a protein that differs from another related protein or a parent protein in the number of prominent regions. For example, in some embodiments, variant proteins have 1, 2, 3, 4, 5, or 10 corresponding prominent regions that differ from the parent protein.

Several methods are known in the art that are suitable for generating variants of the enzymes of the present invention, including but not limited to site-saturation mutagenesis, scanning mutagenesis, insertional mutagenesis, random mutagenesis, site-directed mutagenesis, and directed-evolution, as well as various other recombinatorial approaches.

Characterization of wild-type and mutant proteins is accomplished via any means or "test" suitable and is preferably based on the assessment of properties of interest. For example one or more of the following properties are assessed in some embodiments of the present invention: pH stability; temperature stability; oxidative stability; proteolytic stability; solubility; Km and/or specific activity of the conversion of DMAPP to isoprene in vitro; Km and/or specific activity of the conversion of DMAPP to isoprene in vivo in the context of a host organism (e.g., *E. coli*); and expression of enzyme(s) of the DXP pathway and/or the MVA pathway. Indeed, it is contemplated that enzymes having various degrees of stability, solubility, activity, and/or expression level in one or more of test conditions will find use in the present invention.

As used herein the term "gene" refers to a polynucleotide (e.g., a DNA segment) that encodes a polypeptide and includes regions preceding and following the coding regions as well as intervening sequences (introns) between individual coding segments (exons).

As used herein, "homologous genes" refers to a pair of genes from different, but usually related species, which correspond to each other and which are identical or very similar to each other. The term encompasses genes that are separated by speciation (i.e., the development of new species) (e.g., orthologous genes), as well as genes that have been separated by genetic duplication (e.g., paralogous genes).

As used herein, "ortholog" and "orthologous genes" refer to genes in different species that have evolved from a common ancestral gene (i.e., a homologous gene) by speciation. Typically, orthologs retain the same function during the course of evolution. Identification of orthologs finds use in the reliable prediction of gene function in newly sequenced genomes.

As used herein, "paralog" and "paralogous genes" refer to genes that are related by duplication within a genome. While orthologs retain the same function through the course of evolution, paralogs evolve new functions, even though some functions are often related to the original one.

As used herein, "homology" refers to sequence similarity or identity, with identity being preferred. This homology is determined using standard techniques known in the art (See e.g., Smith and Waterman, Adv Appl Math, 2:482, 1981; Needleman and Wunsch, J Mol Biol, 48:443, 1970; Pearson and Lipman, Proc Natl Acad Sci USA, 85:2444, 1988; programs such as GAP, BESTFIT, FASTA, and TFASTA in the Wisconsin Genetics Software Package, Genetics Computer Group, Madison, Wis.; and Devereux et al., Nucl Acid Res, 12:387-395, 1984).

As used herein, an "analogous sequence" is one wherein the function of the gene is essentially the same as the gene based on the kudzu isoprene synthase (IspS) or poplar IspS (IspS). Additionally, analogous genes include at least 45%, 50%, 55%, 60%, 65%, 70%, 75%, 80%, 85%, 90%, 95%, 97%, 98%, 99% or 100% sequence identity with the sequence of the kudzu isoprene synthase. In additional embodiments more than one of the above properties applies to the sequence. Analogous sequences are determined by known methods of sequence alignment. A commonly used alignment method is BLAST, although as indicated above and below, there are other methods that also find use in aligning sequences.

One example of a useful algorithm is PILEUP. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle (Feng and Doolittle, J Mol Evol, 35:351-360, 1987). The method is similar to that described by Higgins and Sharp (Higgins and Sharp, CABIOS 5:151-153, 1989). Useful PILEUP parameters including a default gap weight of 3.00, a default gap length weight of 0.10, and weighted end gaps.

Another example of a useful algorithm is the BLAST algorithm, described by Altschul et al., (Altschul et al., J Mol Biol, 215:403-410, 1990; and Karlin et al., Proc Natl Acad Sci USA, 90:5873-5787, 1993). A particularly useful BLAST program is the WU-BLAST-2 program (See, Altschul et al., Meth Enzymol, 266:460-480, 1996). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. However, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

Thus, "percent (%) nucleic acid sequence identity" is defined as the percentage of nucleotide residues in a candidate sequence that are identical to the nucleotide residues of the starting sequence (i.e., the sequence of interest). A preferred method utilizes the BLASTN module of WU-BLAST-2 set to the default parameters, with overlap span and overlap fraction set to 1 and 0.125, respectively.

As used herein, the term "hybridization" refers to the process by which a strand of nucleic acid joins with a complementary strand through base pairing, as known in the art.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm-5° C. (5° below the Tm of the probe); "high stringency" at about 5-10° C. below the Tm; "intermediate stringency" at about 10-20° C. below the Tm of the probe; and "low stringency" at about 20-25° C. below the Tm. Functionally, maximum stringency conditions may be used to identify sequences having strict identity or near-strict identity with the hybridization probe; while intermediate or low stringency hybridization can be used to identify or detect polynucleotide sequence homologs.

Moderate and high stringency hybridization conditions are well known in the art. An example of high stringency conditions includes hybridization at about 42° C. in 50% formamide, 5×SSC, 5× Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C. An example of moderate stringent conditions include an overnight incubation at 37° C. in a solution comprising 20% formamide, 5 ×SSC (150 mM NaCl, 15 mM trisodium citrate), 50 mM sodium phosphate (pH 7.6), 5× Denhardt's solution, 10% dextran sulfate and 20 mg/ml denatured sheared salmon sperm DNA, followed by washing the filters in 1×SSC at about 37-50° C. Those of skill in the art know how to adjust the temperature, ionic strength, etc. as necessary to accommodate factors such as probe length and the like.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. "Recombination," "recombining," and generating a "recombined" nucleic acid are generally the assembly of two or more nucleic acid fragments wherein the assembly gives rise to a chimeric gene.

In a preferred embodiment, mutant DNA sequences are generated with site saturation mutagenesis in at least one codon. In another preferred embodiment, site saturation mutagenesis is performed for two or more codons. In a further embodiment, mutant DNA sequences have more than 50%, more than 55%, more than 60%, more than 65%, more than 70%, more than 75%, more than 80%, more than 85%, more than 90%, more than 95%, or more than 98% homology with the wild-type sequence. In alternative embodiments, mutant DNA is generated in vivo using any known mutagenic procedure such as, for example, radiation, nitrosoguanidine and the like. The desired DNA sequence is then isolated and used in the methods provided herein.

As used herein, the term "target sequence" refers to a DNA sequence in the host cell that encodes the sequence where it is desired for the incoming sequence to be inserted into the host cell genome. In some embodiments, the target sequence encodes a functional wild-type gene or operon, while in other embodiments the target sequence encodes a functional mutant gene or operon, or a non-functional gene or operon.

As used herein, a "flanking sequence" refers to any sequence that is either upstream or downstream of the sequence being discussed (e.g., for genes A-B-C, gene B is flanked by the A and C gene sequences). In a preferred embodiment, the incoming sequence is flanked by a homology box on each side. In another embodiment, the incoming sequence and the homology boxes comprise a unit that is flanked by stuffer sequence on each side. In some embodiments, a flanking sequence is present on only a single side (either 3' or 5'), but in preferred embodiments, it is on each side of the sequence being flanked. In some embodiments, a flanking sequence is present on only a single side (either 3' or 5'), while in preferred embodiments, it is present on each side of the sequence being flanked.

As used herein, the term "stuffer sequence" refers to any extra DNA that flanks homology boxes (typically vector sequences). However, the term encompasses any non-homologous DNA sequence. Not to be limited by any theory, a stuffer sequence provides a noncritical target for a cell to initiate DNA uptake.

As used herein, the terms "amplification" and "gene amplification" refer to a process by which specific DNA sequences are disproportionately replicated such that the amplified gene becomes present in a higher copy number than was initially present in the genome. In some embodiments, selection of cells by growth in the presence of a drug (e.g., an inhibitor of an inhibitable enzyme) results in the amplification of either the endogenous gene encoding the gene product required for growth in the presence of the drug or by amplification of exogenous (i.e., input) sequences encoding this gene product, or both.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

As used herein, the term "co-amplification" refers to the introduction into a single cell of an amplifiable marker in conjunction with other gene sequences (i.e., comprising one or more non-selectable genes such as those contained within an expression vector) and the application of appropriate selective pressure such that the cell amplifies both the amplifiable marker and the other, non-selectable gene sequences. The amplifiable marker may be physically linked to the other gene sequences or alternatively two separate pieces of DNA, one containing the amplifiable marker and the other containing the non-selectable marker, may be introduced into the same cell.

As used herein, the terms "amplifiable marker," "amplifiable gene," and "amplification vector" refer to a gene or a vector encoding a gene, which permits the amplification of that gene under appropriate growth conditions.

"Template specificity" is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (See e.g., Kacian et al., Proc Natl Acad Sci USA 69:3038, 1972) and other nucleic acids are not replicated by this amplification enzyme. Similarly, in the case of T7 RNA polymerase, this amplification enzyme has a stringent specificity for its own promoters (See, Chamberlin et al., Nature 228:227, 1970). In the case of T4 DNA ligase, the enzyme will not ligate the two oligonucleotides or polynucleotides, where there is a mismatch between the oligonucleotide or polynucleotide substrate and the template at the ligation junction (See, Wu and Wallace, Genomics 4:560, 1989). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences.

As used herein, the term "amplifiable nucleic acid" refers to nucleic acids, which may be amplified by any amplification method. It is contemplated that "amplifiable nucleic acid" will usually comprise "sample template."

As used herein, the term "sample template" refers to nucleic acid originating from a sample, which is analyzed for the presence of "target" (defined below). In contrast, "background template" is used in reference to nucleic acid other than sample template, which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, in one embodiment, the term "polymerase chain reaction" ("PCR") refers to the methods of U.S. Pat. Nos. 4,683,195 4,683,202, and 4,965,188, hereby incorporated by reference, which include methods for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "RT-PCR" refers to the replication and amplification of RNA sequences. In this method, reverse transcription is coupled to PCR, most often using a one enzyme procedure in which a thermostable polymerase is employed, as described in U.S. Pat. No. 5,322,770, herein incorporated by reference. In RT-PCR, the RNA template is converted to cDNA due to the reverse transcriptase activity of the polymerase, and then amplified using the polymerizing activity of the polymerase (i.e., as in other PCR methods).

As used herein, the terms "restriction endonucleases" and "restriction enzymes" refer to bacterial enzymes, each of which cut double-stranded DNA at or near a specific nucleotide sequence.

A "restriction site" refers to a nucleotide sequence recognized and cleaved by a given restriction endonuclease and is frequently the site for insertion of DNA fragments. In certain embodiments of the invention restriction sites are engineered into the selective marker and into 5' and 3' ends of the DNA construct.

As used herein, the term "chromosomal integration" refers to the process whereby an incoming sequence is introduced into the chromosome of a host cell. The homologous regions of the transforming DNA align with homologous regions of the chromosome. Subsequently, the sequence between the homology boxes is replaced by the incoming sequence in a double crossover (i.e., homologous recombination). In some embodiments of the present invention, homologous sections of an inactivating chromosomal segment of a DNA construct align with the flanking homologous regions of the indigenous chromosomal region of the Escherichia chromosome. Subsequently, the indigenous chromosomal region is deleted by the DNA construct in a double crossover (i.e., homologous recombination).

"Homologous recombination" means the exchange of DNA fragments between two DNA molecules or paired chromosomes at the site of identical or nearly identical nucleotide sequences. In a preferred embodiment, chromosomal integration is homologous recombination.

"Homologous sequences" as used herein means a nucleic acid or polypeptide sequence having 100%, 99%, 98%, 97%, 96%, 95%, 94%, 93%, 92%, 91%, 90%, 88%, 85%, 80%, 75%, or 70% sequence identity to another nucleic acid or polypeptide sequence when optimally aligned for comparison. In some embodiments, homologous sequences have between 85% and 100% sequence identity, while in other embodiments there is between 90% and 100% sequence identity, and in more preferred embodiments, there is 95% and 100% sequence identity.

As used herein "amino acid" refers to peptide or protein sequences or portions thereof. The terms "protein," "peptide," and "polypeptide" are used interchangeably.

As used herein, the term "heterologous protein" refers to a protein or polypeptide that does not naturally occur in the host cell. Examples of heterologous proteins include enzymes such as isoprene synthases. In some embodiments, the genes encoding the proteins are naturally occurring genes, while in other embodiments mutated and/or synthetic genes are used.

As used herein, "homologous protein" refers to a protein or polypeptide native or naturally occurring in a cell. In preferred embodiments, the cell is a Gram-negative cell, while in particularly preferred embodiments the cell is an Escherichia host cell.

An enzyme is "overexpressed" in a host cell if the enzyme is expressed in the cell at a higher level that the level at which it is expressed in a corresponding wild-type cell.

The terms "protein" and "polypeptide" are used interchangeability herein. The 3-letter code for amino acids as defined in conformity with the IUPAC-IUB Joint Commission on Biochemical Nomenclature (JCBN) is used through out this disclosure. It is also understood that a polypeptide may be coded for by more than one nucleotide sequence due to the degeneracy of the genetic code.

The term "mature" form of a protein or peptide refers to the final functional form of the protein or peptide. To exemplify, a mature form of kudzu isoprene synthase includes the amino acid sequence of SEQ ID NO:2.

The term "precursor" form of a protein or peptide refers to a mature form of the protein having a prosequence operably linked to the amino or carbonyl terminus of the protein. The precursor may also have a "signal" sequence operably linked, to the amino terminus of the prosequence. The precursor may also have additional polynucleotides that are involved in post-translational activity (e.g., polynucleotides cleaved therefrom to leave the mature form of a protein or peptide).

"Naturally occurring enzyme" refers to an enzyme having the unmodified amino acid sequence identical to that found in nature. Naturally occurring enzymes include native enzymes, those enzymes naturally expressed or found in the particular microorganism.

The term "identical" in the context of two nucleic acids or polypeptide sequences refers to the residues in the two sequences that are the same when aligned for maximum correspondence, as measured using one of the following sequence comparison or analysis algorithms.

The term "optimal alignment" refers to the alignment giving the highest percent identity score.

"Percent sequence identity," "percent amino acid sequence identity," "percent gene sequence identity," and/or "percent nucleic acid/polynucloetide sequence identity," with respect to two amino acid, polynucleotide and/or gene sequences (as appropriate), refer to the percentage of residues that are identical in the two sequences when the sequences are optimally aligned. Thus, 80% amino acid sequence identity means that 80% of the amino acids in two optimally aligned polypeptide sequences are identical.

The phrase "substantially identical" in the context of two nucleic acids or polypeptides thus refers to a polynucleotide or polypeptide that comprising at least 70% sequence identity, preferably at least 75%, preferably at least 80%, preferably at least 85%, preferably at least 90%, preferably at least 95%, preferably at least 97%, preferably at least 98% and preferably at least 99% sequence identity as compared to a reference sequence using the programs or algorithms (e.g., BLAST, ALIGN, CLUSTAL) using standard parameters. One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

The term "isolated" or "purified" refers to a material that is removed from its original environment (e.g., the natural environment if it is naturally occurring). For example, the material is said to be "purified" when it is present in a particular composition in a higher or lower concentration than exists in a naturally occurring or wild type organism (e.g., kudzu) or in combination with components not normally present upon expression from a naturally occurring or wild type organism. For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector, and/or such polynucleotides or polypeptides could be part of a composition, and still be isolated in that such vector or composition is not part of its natural environment. In preferred embodiments, a nucleic acid or protein is said to be purified, for example, if it gives rise to essentially one band in an electrophoretic gel or blot.

The term "isolated", when used in reference to a DNA sequence, refers to a DNA sequence that has been removed from its natural genetic milieu and is thus free of other extraneous or unwanted coding sequences, and is in a form suitable for use within genetically engineered protein production systems. Similarly, the term "isolated", when used in reference to a recombinant DNA sequence, refers to a DNA sequence that has been removed from the genetic milieu of the host organism and is thus free of other extraneous or unwanted coding sequences (e.g., kudzu IspS expression vector propagated in *E. coli*). Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (See e.g., Dynan and Tijan, Nature 316:774-78, 1985). The term "an isolated DNA sequence" is alternatively referred to as "a cloned DNA sequence".

The term "isolated," when used in reference to a protein, refers to a protein that is found in a condition other than its native environment. In a preferred form, the isolated protein is substantially free of other proteins, particularly other homologous proteins. Similarly, the term "isolated", when used in reference to a recombinantly produced protein, refers to a protein that has been removed from the proteinaceous milieu of the host organism and is thus free of other extraneous or unwanted proteins (e.g., recombinant kudzu IspS produced in *E. coli*). An isolated protein is more than 10% pure, preferably more than 20% pure, and even more preferably more than 30% pure, as determined by SDS-PAGE. Further aspects of the invention encompass the protein in a highly purified form (i.e., more than 40% pure, more than 60% pure, more than 80% pure, more than 90% pure, more than 95% pure, more than 97% pure, and even more than 99% pure), as determined by SDS-PAGE.

The following cassette mutagenesis method may be used to facilitate the construction of the enzyme variants of the present invention, although other methods may be used. First, as described herein, a naturally-occurring gene encoding the enzyme is obtained and sequenced in whole or in part. Then, the sequence is scanned for a point at which it is desired to make a mutation (deletion, insertion or substitution) of one or more amino acids in the encoded enzyme. The sequences flanking this point are evaluated for the presence of restriction sites for replacing a short segment of the gene with an oligonucleotide pool which when expressed will encode various mutants. Such restriction sites are preferably unique sites within the protein gene so as to facilitate the replacement of the gene segment. However, any convenient restriction site that is not overly redundant in the enzyme gene may be used, provided the gene fragments generated by restriction digestion can be reassembled in proper sequence. If restriction sites are not present at locations within a convenient distance from the selected point (from 10 to 15 nucleotides), such sites are generated by substituting nucleotides in the gene in such a fashion that neither the reading frame nor the amino acids encoded are changed in the final construction. Mutation of the gene in order to change its sequence to conform to the desired sequence is accomplished by M13 primer extension in accord with generally known methods. The task of locating suitable flanking regions and evaluating the needed changes to arrive at two convenient restriction site sequences is made routine by the redundancy of the genetic code, a restriction enzyme map of the gene and the large number of different restriction enzymes. Note that if a convenient flanking restriction site is available, the above method need be used only in connection with the flanking region that does not contain a site.

Once the naturally-occurring DNA and/or synthetic DNA is cloned, the restriction sites flanking the positions to be mutated are digested with the cognate restriction enzymes and a plurality of end termini-complementary oligonucleotide cassettes are ligated into the gene. The mutagenesis is simplified by this method because all of the oligonucleotides can be synthesized so as to have the same restriction sites, and no synthetic linkers are necessary to create the restriction sites.

As used herein, "corresponding to," refers to a residue at the enumerated position in a protein or peptide, or a residue that is analogous, homologous, or equivalent to an enumerated residue in a protein or peptide. As used herein, "corresponding region," generally refers to an analogous position along related proteins or a parent protein.

As used herein, the term, "combinatorial mutagenesis" refers to methods in which libraries of variants of a starting sequence are generated. In these libraries, the variants contain one or several mutations chosen from a predefined set of mutations. In addition, the methods provide means to introduce random mutations, which were not members of the predefined set of mutations. In some embodiments, the methods include those set forth in U.S. application Ser. No. 09/699,250, hereby incorporated by reference. In alternative embodiments, combinatorial mutagenesis methods encompass commercially available kits (e.g., QUIKCHANGE Multisite mutagenesis kit, Stratagene, San Diego, Calif.).

As used herein, the term "library of mutants" refers to a population of cells which are identical in most of their genome but include different homologues of one or more genes. Such libraries can be used, for example, to identify genes or operons with improved traits.

As used herein, the terms "starting gene" and "parent gene" refer to a gene of interest that encodes a protein of interest that is to be improved and/or changed using the present invention.

As used herein, the terms "multiple sequence alignment" and "MSA" refer to the sequences of multiple homologs of a starting gene that are aligned using an algorithm (e.g., Clustal W).

As used herein, the terms "consensus sequence" and "canonical sequence" refer to an archetypical amino acid sequence against which all variants of a particular protein or sequence of interest are compared. The terms also refer to a sequence that sets forth the nucleotides that are most often present in a DNA sequence of interest. For each position of a gene, the consensus sequence gives the amino acid that is most abundant in that position in the MSA.

As used herein, the term "consensus mutation" refers to a difference in the sequence of a starting gene and a consensus sequence. Consensus mutations are identified by comparing the sequences of the starting gene and the consensus sequence obtained from a MSA. In some embodiments, consensus mutations are introduced into the starting gene such that it becomes more similar to the consensus sequence. Consensus mutations also include amino acid changes that change an amino acid in a starting gene to an amino acid that is more frequently found in an MSA at that position relative to the frequency of that amino acid in the starting gene. Thus, the term consensus mutation comprises all single amino acid changes that replace an amino acid of the starting gene with an amino acid that is more abundant than the amino acid in the MSA.

The terms "modified sequence" and "modified genes" are used interchangeably herein to refer to a sequence that includes a deletion, insertion or interruption of naturally occurring nucleic acid sequence. In some preferred embodiments, the expression product of the modified sequence is a truncated protein (e.g., if the modification is a deletion or interruption of the sequence). In some particularly preferred embodiments, the truncated protein retains biological activity. In alternative embodiments, the expression product of the modified sequence is an elongated protein (e.g., modifications comprising an insertion into the nucleic acid sequence). In some embodiments, an insertion leads to a truncated protein (e.g., when the insertion results in the formation of a stop codon). Thus, an insertion may result in either a truncated protein or an elongated protein as an expression product.

As used herein, the terms "mutant sequence" and "mutant gene" are used interchangeably and refer to a sequence that has an alteration in at least one codon occurring in a host cell's wild-type sequence. The expression product of the mutant sequence is a protein with an altered amino acid sequence relative to the wild-type. The expression product may have an altered functional capacity (e.g., enhanced enzymatic activity).

The terms "mutagenic primer" or "mutagenic oligonucleotide" (used interchangeably herein) are intended to refer to oligonucleotide compositions which correspond to a portion of the template sequence and which are capable of hybridizing thereto. With respect to mutagenic primers, the primer will not precisely match the template nucleic acid, the mismatch or mismatches in the primer being used to introduce the desired mutation into the nucleic acid library. As used herein, "non-mutagenic primer" or "non-mutagenic oligonucleotide" refers to oligonucleotide compositions that match precisely to the template nucleic acid. In one embodiment of the invention, only mutagenic primers are used. In another preferred embodiment of the invention, the primers are designed so that for at least one region at which a mutagenic primer has been included, there is also non-mutagenic primer included in the oligonucleotide mixture. By adding a mixture of mutagenic primers and non-mutagenic primers corresponding to at least one of the mutagenic primers, it is possible to produce a resulting nucleic acid library in which a variety of combinatorial mutational patterns are presented. For example, if it is desired that some of the members of the mutant nucleic acid library retain their parent sequence at certain positions while other members are mutant at such sites, the non-mutagenic primers provide the ability to obtain a specific level of non-mutant members within the nucleic acid library for a given residue. The methods of the invention employ mutagenic and non-mutagenic oligonucleotides which are generally between 10-50 bases in length, more preferably about 15-45 bases in length. However, it may be necessary to use primers that are either shorter than 10 bases or longer than 50 bases to obtain the mutagenesis result desired. With respect to corresponding mutagenic and non-mutagenic primers, it is not necessary that the corresponding oligonucleotides be of identical length, but only that there is overlap in the region corresponding to the mutation to be added.

Primers may be added in a pre-defined ratio according to the present invention. For example, if it is desired that the resulting library have a significant level of a certain specific mutation and a lesser amount of a different mutation at the same or different site, by adjusting the amount of primer added, it is possible to produce the desired biased library. Alternatively, by adding lesser or greater amounts of non-mutagenic primers, it is possible to adjust the frequency with which the corresponding mutation(s) are produced in the mutant nucleic acid library.

The terms "wild-type sequence" or "wild-type gene" are used interchangeably herein, to refer to a sequence that is native or naturally occurring in a host cell. In some embodiments, the wild-type sequence refers to a sequence of interest that is the starting point of a protein-engineering project. The wild-type sequence may encode either a homologous or heterologous protein. A homologous protein is one the host cell would produce without intervention. A heterologous protein is one that the host cell would not produce but for the intervention.

As used herein the term "lysate" refers to a solution containing the contents of lysed cells. In some embodiments, the lysate is a bacterial cell lysate (e.g., *E. coli* cells lysed using READYLYSE™ lysozyme solution from Epicentre; or *E. coli* cells lysed using a French Pressure cell).

As used herein the term "lysozyme" refers to a glycosidase that hydrolyzes the bond between N-acetyl muramic acid and N-acetul glucosamine, thus cleaving an important polymer in the cell wall of many bacteria. Suitable lysozymes for use with the present invention include but are not limited to hen egg white lysozyme (Sigma), T4 lysozyme, recombinant non-mammalian, non-avian lysozyme (READYLYSE™), or a fungal lysozyme.

As used herein, the term "headspace" refers to the vapor/air mixture trapped above a solid or liquid sample in a sealed vessel.

As used herein, the terms "high throughput screening" and "HTS" refer to measuring isoprene in at least 96 samples in 4 hours or less. In preferred embodiments, the sample volume is less than 2 mL.

Unless otherwise noted, all component or composition levels are in reference to the active level of that component or composition, and are exclusive of impurities, for example, residual solvents or by-products, which may be present in commercially available sources.

Enzyme components weights are based on total active protein. All percentages and ratios are calculated by weight unless otherwise indicated. All percentages and ratios are calculated based on the total composition unless otherwise.

DETAILED DESCRIPTION OF THE INVENTION

Isoprene monomer is employed in the manufacture of polyisoprene and various copolymers (with isobutylene, butadiene, styrene, or other monomers). To build a strain (prokaryotic or eukaryotic) capable of producing commercially viable levels of isoprene requires optimization of the entire pathway, either MVA to isoprene or DXP to isoprene. A key enzyme in the pathway is isoprene synthase (IspS), which converts the precursor DMAPP to isoprene. The only isoprene synthases (IspS) identified to date are those from plants such as poplar, English oak and kudzu vine. Although some bacteria, such as *Bacillus subtilis*, also produce isoprene, a prokaryotic IspS has yet to be identified and the native IspS activity in *Bacillus* is not sufficient for a commercial process. The plant IspS enzymes identified to date have been partially characterized in part by expression in *E. coli* and some of the kinetic parameters of these enzymes have been determined in vitro with purified protein. However, the kinetic parameters (Km, rate etc) of the native IspS enzymes are insufficient for commercial production of isoprene in a biological host.

To solve this problem as described herein, a plant IspS is expressed in a bacterial host. In addition the IspS is engineered for a change in a property of interest. Characterization of wild-type and mutant IspS is accomplished via any means or "test" suitable and is preferably based on the assessment of properties of interest. Properties of interest include but are not limited to: pH optima, temperature stability (e.g., $T_m$ value), intracellular and extracellular solubility, $K_m$ value, $k_{cat}$ value, or specific activity, as well as sensitivity to potential inhibitors including substrate or product inhibition. Oxidative and proteolytic stability are also of interest. Furthermore, activation or inhibition due to metal ion effects and ionic strength is of interest. These properties and parameters can be assessed by the conversion of DMAPP to isoprene in vitro with purified or partially purified isoprene synthase or in vivo in the context of a host organism such as *E. coli* expressing the DXP pathway, the MVA pathway, or both. It is contemplated that enzymes having various degrees of stability, solubility, activity, and/or expression level in one or more of test conditions will find use in the present invention for the production of isoprene in a diversity of hosts. High throughput methods such as those described in Example 10 are required to investigate these properties in an economical manner.

The invention features compositions and methods for the production of increased amounts of isoprene. In particular, these compositions and methods increase the rate of isoprene production and increase the total amount of isoprene that is produced. The biosynthetic processes for isoprene production described herein are a desirable alternative to using natural rubber. As discussed further below, the amount of isoprene produced by cells can be greatly increased by introducing a heterologous nucleic acid encoding an isoprene synthase (IspS) polypeptide into the cells. Isoprene synthase polypeptides convert dimethylallyl diphosphate (DMAPP) into isoprene. As shown in the examples, a heterologous *Pueraria montana* (kudzu) isoprene synthase polypeptide and variants thereof was expressed in Gram-negative bacterial cells (e.g., *Escherichia coli*). Also shown in the examples and contemplated within the scope of the invention are poplar isoprene synthase polypeptide and variants thereof was expressed in Gram-negative bacterial cells (e.g., *Escherichia coli*).

Heterologous expression of a plant IspS in bacterial host cells resulted in the production of more isoprene than the corresponding cells lacking the plant IspS.

It has been shown that mutating amino-acid residues on the surface of protease enzymes can improve their activity, expression, and stability (WO2008/153925, WO2008/153934, WO2008/153935). Surprisingly, we have found that mutating amino-acid residues on the surface of a completely different enzyme, isoprene synthase, can enhance its expression, solubility, and activity. L70R is an example of such a beneficial surface mutation.

Elucidation of the three-dimensional structure of an enzyme is essential for accurately identifying amino-acid residues on its surface. Homology modeling using structures with sequences approximately 40% identical to isoprene synthase (e.g., bornyl synthase and limonene synthase, the enzymes of known structure with closest identity to isoprene synthase) can reveal gross aspects of the modeled enzyme structure, but is insufficient to precisely identify surface-exposed residues and quantify their degree of surface exposure. Surface exposure of an amino-acid residue is quantified by the percentage of solvent-accessible surface area of its side chain.

The following classes of mutations in isoprene synthase may improve solubility of the enzyme by targeting amino-acid residues that are >50% solvent-exposed, preferably >65% solvent-exposed, and most preferably >85% solvent-exposed:

Hydrophobic→positively charged, and vice versa
Hydrophobic→negatively charged, and vice versa
Hydrophobic→neutral polar, and vice versa
Neutral polar→positively charged, and vice versa
Neutral polar→negatively charged, and vice versa
Positively charged→negatively charged, and vice versa Additionally isoprene production by cells containing a heterologous isoprene synthase nucleic acid can be enhanced by increasing the amount of a 1-deoxy-D-xylulose-5-phosphate synthase (DXS) polypeptide, and/or an isopentenyl diphosphate isomerase (IDI) polypeptide, expressed by the cells. For example, a DXS nucleic acid and/or an IDI nucleic acid can be introduced into the cells. The DXS nucleic acid may be a heterologous nucleic acid or a duplicate copy of an endogenous nucleic acid. Similarly, the IDI nucleic acid may be a heterologous nucleic acid or a duplicate copy of an endogenous nucleic acid. In some embodiments, the amount of DXS and/or IDI polypeptide is increased by replacing the endogenous DXS and/or IDI promoters or regulatory regions with other promoters and/or regulatory regions that result in greater transcription of the DXS and/or IDI nucleic acids. In some embodiments, the cells contain both a heterologous nucleic acid encoding an isoprene synthase polypeptide (e.g., a plant isoprene synthase nucleic acid) and a duplicate copy of an endogenous nucleic acid encoding an isoprene synthase polypeptide.

Figure 15:
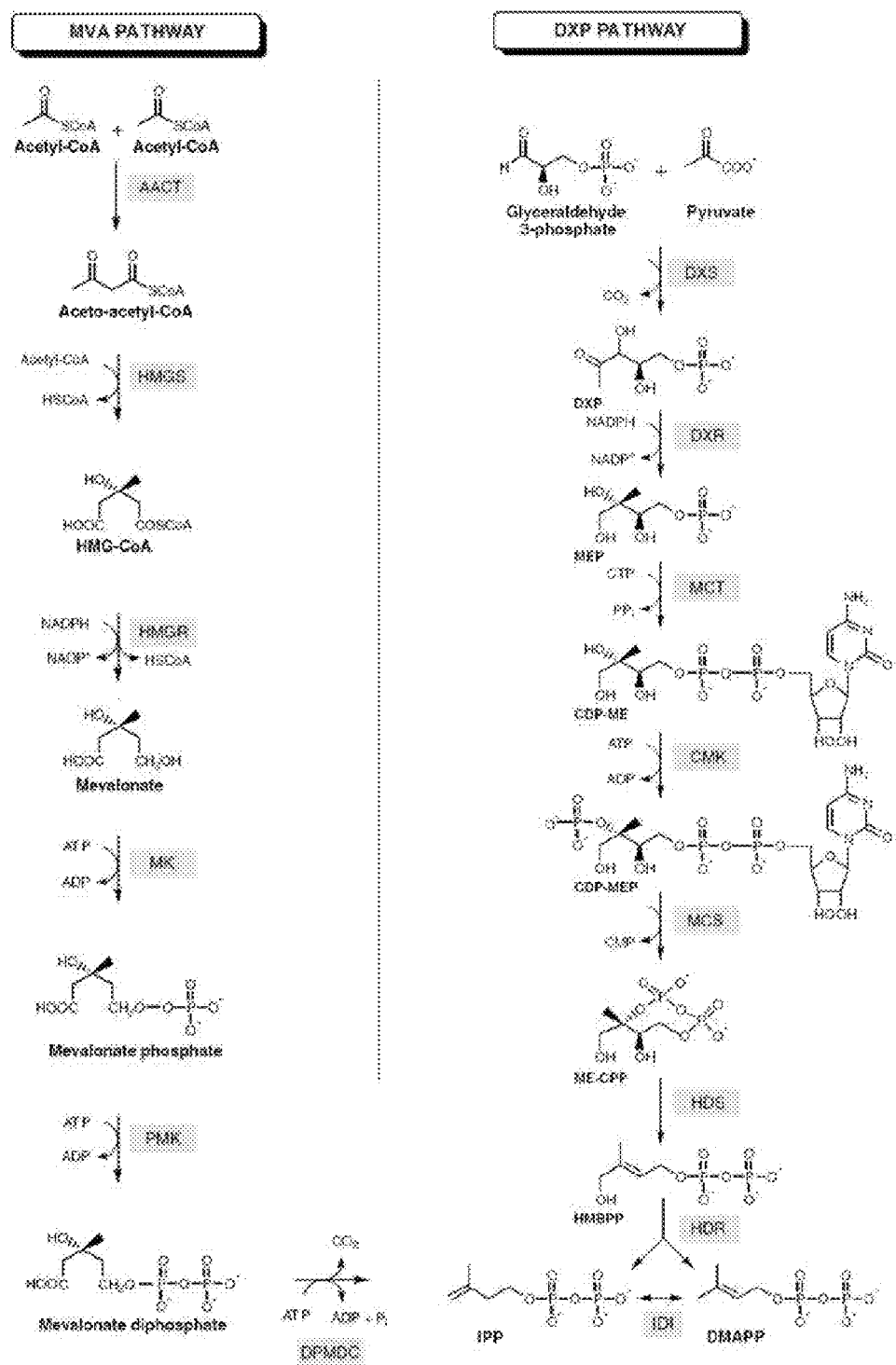
FIG. 15 shows the MVA and DXP metabolic pathways for isoprene (based on F. Bouvier et al., Progress in Lipid Res. 44: 357-429, 2005). The following description includes alternative names for each polypeptide in the pathways and a reference that discloses an assay for measuring the activity of the indicated polypeptide (each of these references are each hereby incorporated by reference in their entireties, particularly with respect to assays for polypeptide activity for polypeptides in the MVA and DXP pathways). Mevalonate Pathway: AACT; Acetyl-CoA acetyltransferase, MvaE, EC 2.3.1.9. Assay: J. Bacteriol., 184: 2116-2122, 2002; HMGS; Hydroxymethylglutaryl-CoA synthase, MvaS, EC 2.3.3.10. Assay: J. Bacteriol., 184: 4065-4070, 2002; HMGR; 3-Hydroxy-3-methylglutaryl-CoA reductase, MvaE, EC 1.1.1.34. Assay: J. Bacteriol., 184: 2116-2122, 2002; MVK; Mevalonate kinase, ERG12, EC 2.7.1.36. Assay: Curr Genet 19:9-14, 1991. PMK; Phosphomevalonate kinase, ERG8, EC 2.7.4.2, Assay: Mol Cell Biol., 11:620-631, 1991; DPMDC; Diphosphomevalonate decarboxylase, MVD1, EC 4.1.1.33. Assay: Biochemistry, 33:13355-13362, 1994; IDI; Isopentenyl-diphosphate delta-isomerase, IDI1, EC 5.3.3.2. Assay: J. Biol. Chem. 264:19169-19175, 1989. DXP Pathway: DXS; 1-Deoxyxylulose-5-phosphate synthase, dxs, EC 2.2.1.7.

The encoded DXS and IDI polypeptides are part of the DXP pathway for the biosynthesis of isoprene (FIG. 15). DXS polypeptides convert pyruvate and D-glyceraldehyde-3-phosphate into 1-deoxy-D-xylulose-5-phosphate. While not intending to be bound by any particular theory, it is believed that increasing the amount of DXS polypeptide increases the flow of carbon through the DXP pathway, leading to greater isoprene production. IDI polypeptides catalyze the interconversion of isopentenyl diphosphate (IPP) and dimethylallyl diphosphate (DMAPP). While not intending to be bound by any particular theory, it is believed that increasing the amount of IDI polypeptide in cells increases the amount of IPP that is converted into DMAPP, which in turn is converted into isoprene.

In some embodiments the production of isoprene by cells containing a heterologous isoprene synthase nucleic acid can be augmented by increasing expression of a MVA polypeptide in the cells (FIG. 15). Exemplary MVA pathways polypeptides include any of the following polypeptides: acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonte decarboxylase (MVD) polypeptides, IDI polypeptides, and polypeptides (e.g., fusion polypeptides) having an activity of two or more MVA pathway polypeptides. For example, one or more MVA pathway nucleic acids can be introduced into the cells. In some embodiments, the cells contain the upper MVA pathway, which includes AA-CoA thiolase, HMG-CoA synthase, and HMG-CoA reductase nucleic acids. In some embodiments, the cells contain the lower MVA pathway, which includes MVK, PMK, MVD, and IDI nucleic acids. In some embodiments, the cells contain the entire MVA pathway, which includes AA-CoA thiolase, HMG-CoA synthase, HMG-CoA reductase, MVK, PMK, MVD, and IDI nucleic acids. The MVA pathway nucleic acids may be heterologous nucleic acids or duplicate copies of endogenous nucleic acids. In some embodiments, the amount of one or more MVA pathway polypeptides is increased by replacing the endogenous promoters or regulatory regions for the MVA pathway nucleic acids with other promoters and/or regulatory regions that result in greater transcription of the MVA pathway nucleic acids. In some embodiments, the cells contain both a heterologous nucleic acid encoding an isoprene synthase polypeptide (e.g., a plant isoprene synthase nucleic acid) and a duplicate copy of an endogenous nucleic acid encoding an isoprene synthase polypeptide.

In some embodiments, at least a portion of the cells maintain the heterologous isoprene synthase, DXS, IDI, and/or MVA pathway nucleic acid for at least about 5, 10, 20, 50, 75, 100, 200, 300, or more cell divisions in a continuous culture (such as a continuous culture without dilution). In some embodiments of any of the aspects of the invention, the nucleic acid comprising the heterologous or duplicate copy of an endogenous isoprene synthase, DXS, IDI, and/or MVA pathway nucleic acid also comprises a selective marker, such as a kanamycin, ampicillin, carbenicillin, gentamicin, hygromycin, phleomycin, bleomycin, neomycin, or chloramphenicol antibiotic resistance nucleic acid.

I. Exemplary Polypeptides and Nucleic Acids

Various isoprene synthase, DXS, IDI, and/or MVA pathway polypeptides and nucleic acids can be used in the compositions and methods of the invention.

As used herein, "polypeptides" includes polypeptides, proteins, peptides, fragments of polypeptides, and fusion polypeptides that include part or all of a first polypeptide (e.g., an isoprene synthase, DXS, IDI, or MVA pathway polypeptide) and part or all of a second polypeptide (e.g., a peptide that facilitates purification or detection of the fusion polypeptide, such as a His-tag). In some embodiments, the fusion polypeptide has an activity of two or more MVA pathway polypeptides (such as AA-CoA thiolase and HMG-CoA reductase polypeptides). In some embodiments, the polypeptide is a naturally-occurring polypeptide (such as the polypeptide encoded by an *Enterococcus faecalis* mvaE nucleic acid) that has an activity of two or more MVA pathway polypeptides.

In various embodiments, a polypeptide has at least or about 50, 100, 150, 175, 200, 250, 300, 350, 400, or more amino acids. In some embodiments, the polypeptide fragment contains at least or about 25, 50, 75, 100, 150, 200, 300, or more contiguous amino acids from a full-length polypeptide and has at least or about 5%, 10%, 20%, 30%, 40%, 50%, 60%, 70%, 80%, 90%, 95%, or 100% of an activity of a corresponding full-length polypeptide. In particular embodiments the polypeptide includes a segment of or the entire amino acid sequence of any naturally-occurring isoprene synthase, DXS, IDI, or MVA pathway polypeptide. In some embodiments, the polypeptide has one or more mutations compared to the sequence of a wild-type (i.e., a sequence occurring in nature) isoprene synthase, DXS, IDI, or MVA pathway polypeptide.

In some embodiments, the polypeptide is an isolated polypeptide. As used herein, an "isolated polypeptide" is not part of a library of polypeptides, such as a library of 2, 5, 10, 20, 50 or more different polypeptides and is separated from at least one component with which it occurs in nature. An isolated polypeptide can be obtained, for example, by expression of a recombinant nucleic acid encoding the polypeptide.

In some embodiments, the polypeptide is a heterologous polypeptide. By "heterologous polypeptide" is meant a polypeptide whose amino acid sequence is not identical to that of another polypeptide naturally expressed in the same host cell.

As used herein, a "nucleic acid" refers to two or more deoxyribonucleotides and/or ribonucleotides in either single or double-stranded form. In some embodiments, the nucleic acid is a recombinant nucleic acid. By "recombinant nucleic acid" means a nucleic acid of interest that is free of one or more nucleic acids (e.g., genes), which in the genome occurring in nature of the organism from which the nucleic acid of interest is derived, flank the nucleic acid of interest. The term therefore includes, for example, a recombinant DNA which is incorporated into a vector, into an autonomously replicating plasmid or virus, or into the genomic DNA of a prokaryote or eukaryote, or which exists as a separate molecule (e.g., a cDNA, a genomic DNA fragment, or a cDNA fragment produced by PCR or restriction endonuclease digestion) independent of other sequences.

In various embodiments, the nucleic acid is a recombinant nucleic acid. For instance, in some embodiments, an isoprene synthase, DXS, IDI, or MVA pathway nucleic acid is operably linked to another nucleic acid encoding all or a portion of another polypeptide such that the recombinant nucleic acid encodes a fusion polypeptide that includes an isoprene synthase, DXS, IDI, or MVA pathway polypeptide and all or part of another polypeptide (e.g., a peptide that facilitates purification or detection of the fusion polypeptide, such as a His-tag). In some embodiments, part or all of a recombinant nucleic acid is chemically synthesized. In some embodiments, the nucleic acid is a heterologous nucleic acid. By "heterologous nucleic acid" is meant a nucleic acid whose nucleic acid sequence is not identical to that of another nucleic acid naturally found in the same host cell.

In particular embodiments the nucleic acid includes a segment of or the entire nucleic acid sequence of any naturally-occurring isoprene synthase, DXS, IDI, or MVA pathway nucleic acid. In some embodiments, the nucleic acid includes at least or about 50, 100, 150, 200, 300, 400, 500, 600, 700, 800, or more contiguous nucleotides from a naturally-occurring isoprene synthase nucleic acid DXS, IDI, or MVA pathway nucleic acid. In some embodiments, the nucleic acid has one or more mutations compared to the sequence of a wild-type (i.e., a sequence occurring in nature) isoprene synthase, DXS, IDI, or MVA pathway nucleic acid. In some embodiments, the nucleic acid has one or more mutations (e.g., a silent mutation) that increase the transcription or translation of isoprene synthase, DXS, IDI, or MVA pathway nucleic acid. In some embodiments, the nucleic acid is a degenerate variant of any nucleic acid encoding an isoprene synthase, DXS, IDI, or MVA pathway polypeptide.

"Codon degeneracy" refers to divergence in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a nucleic acid for improved expression in a host cell, it is desirable in some embodiments to design the nucleic acid such that its frequency of codon usage approaches the frequency of preferred codon usage of the host cell.

The accession numbers of exemplary isoprene synthase, DXS, IDI, and/or MVA pathway polypeptides and nucleic acids are listed in Appendix 1 of U.S. Application No. 61/013,574, herein incorporated by reference in its entirety, particularly with respect to the amino acid and nucleic acid sequences of isoprene synthase, DXS, IDI, and/or MVA pathway polypeptides and nucleic acids). The Kegg database also contains the amino acid and nucleic acid sequences of numerous exemplary isoprene synthase, DXS, IDI, and/or MVA pathway polypeptides and nucleic acids (See, e.g., the worldwide web at "genome.jp/kegg/pathway/map/map00100.html" and the sequences therein, which are each hereby incorporated by reference in their entireties, particularly with respect to the amino acid and nucleic acid sequences of isoprene synthase, DXS, IDI, and/or MVA pathway polypeptides and nucleic acids). In some embodiments, one or more of the isoprene synthase, DXS, IDI, and/or MVA pathway polypeptides and/or nucleic acids have a sequence identical to a sequence publicly available on Dec. 12, 2007, such as any of the sequences that correspond to any of the accession numbers in Appendix 1 of U.S. Application No. 61/013,574, or any of the sequences present in the Kegg database as of the date of this filing. Additional exemplary isoprene synthase, DXS, IDI, and/or MVA pathway polypeptides and nucleic acids are described further below.

Exemplary Isoprene Synthase Polypeptides and Nucleic Acids

As noted above, isoprene synthase polypeptides convert dimethylallyl diphosphate (DMAPP) into isoprene. Exemplary isoprene synthase polypeptides include polypeptides, fragments of polypeptides, peptides, and fusions polypeptides that have at least one activity of an isoprene synthase polypeptide. Standard methods can be used to determine whether a polypeptide has isoprene synthase polypeptide activity by measuring the ability of the polypeptide to convert DMAPP into isoprene in vitro, in a cell extract, or in vivo. Isoprene synthase polypeptide activity in the cell extract can be measured, for example, as described in Silver et al., J. Biol. Chem. 270:13010-13016, 1995 and references therein, which are each hereby incorporated by reference in their entireties, particularly with respect to assays for isoprene synthase polypeptide activity. DMAPP (Sigma) is evaporated to dryness under a stream of nitrogen and rehydrated to a concentration of 100 mM in 100 mM potassium phosphate buffer pH 8.2 and stored at −20° C. To perform the assay, a solution of 5 µl of 1M $MgCl_2$, 1 mM (250 µg/ml) DMAPP, 65 µl of Plant Extract Buffer (PEB) (50 mM Tris-HCl, pH 8.0, 20 mM $MgCl_2$, 5% glycerol, and 2 mM DTT) is added to 25 µl of cell extract in a 20 ml Headspace vial with a metal screw cap and teflon coated silicon septum (Agilent Technologies) and cultured at 37° C. for 15 minutes with shaking. The reaction is quenched by adding 200 µl of 250 mM EDTA or by heat inactivation, and isoprene is quantified by GC/MS.

Exemplary isoprene synthase nucleic acids include nucleic acids that encode a polypeptide, fragment of a polypeptide, peptide, or fusion polypeptide that has at least one activity of an isoprene synthase polypeptide. Exemplary isoprene synthase polypeptides and nucleic acids include naturally-occurring polypeptides and nucleic acids from any of the source organisms described herein as well as mutant polypeptides and nucleic acids derived from any of the source organisms described herein.

In some embodiments, the isoprene synthase polypeptide or nucleic acid is from the family Fabaceae, the family Salicaceae, or the family Fagaceae. In some embodiments, the isoprene synthase polypeptide or nucleic acid is a naturally-occurring polypeptide or nucleic acid from *Pueraria montana* (kudzu) (Sharkey et al., Plant Physiology 137: 700-712, 2005), poplar (such as *Populus alba* x *tremula* CAC35696) Miller et al., Planta 213: 483-487, 2001) aspen (such as *Populus tremuloides*) Silver et al., JBC 270(22): 13010-1316, 1995), or English Oak (*Quercus robur*) (Zimmer et al., WO 98/02550), which are each hereby incorporated by reference in their entireties, particularly with respect to isoprene synthase nucleic acids and the expression of isoprene synthase polypeptides. Suitable isoprene synthases include, but are not limited to, those identified by GenBank Accession Nos. AY341431, AY316691, AY279379, AJ457070, and AY182241, which are each hereby incorporated by reference in their entireties, particularly with respect to sequences of isoprene synthase nucleic acids and polypeptides. In some embodiments, the isoprene synthase polypeptide or nucleic acid is not a naturally-occurring polypeptide or nucleic acid from *Quercus robur* (i.e., the isoprene synthase polypeptide or nucleic acid is an isoprene synthase polypeptide or nucleic acid other than a naturally-occurring polypeptide or nucleic acid from *Quercus robur*). In some embodiments, the isoprene synthase nucleic acid or polypeptide is not a naturally-occurring polypeptide or nucleic acid from poplar (such as *Populus alba* x *tremula* CAC35696).

Exemplary DXS Polypeptides and Nucleic Acids

As noted above, 1-deoxy-D-xylulose-5-phosphate synthase (DXS) polypeptides convert pyruvate and D-glyceraldehyde-3-phosphate into 1-deoxy-D-xylulose-5-phosphate. Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde-3-phosphate into 1-deoxy- D-xylulose-5-phosphate in vitro, in a cell extract, or in vivo. Exemplary DXS nucleic acids include nucleic acids that encode a polypeptide, fragment of a polypeptide, peptide, or fusion polypeptide that has at least one activity of a DXS polypeptide. Exemplary DXS polypeptides and nucleic acids include naturally-occurring polypeptides and nucleic acids from any of the source organisms described herein as well as mutant polypeptides and nucleic acids derived from any of the source organisms described herein.

Exemplary IDI Polypeptides and Nucleic Acids

Isopentenyl diphosphate isomerase polypeptides (isopentenyl-diphosphate delta-isomerase or IDI) catalyzes the interconversion of isopentenyl diphosphate (IPP) and dimethylallyl diphosphate (DMAPP) (e.g., converting IPP into DMAPP and/or converting DMAPP into IPP). Exemplary IDI polypeptides include polypeptides, fragments of polypeptides, peptides, and fusions polypeptides that have at least one activity of an IDI polypeptide. Standard methods (such as those described herein) can be used to determine whether a polypeptide has IDI polypeptide activity by measuring the ability of the polypeptide to interconvert IPP and DMAPP in vitro, in a cell extract, or in vivo. Exemplary IDI nucleic acids include nucleic acids that encode a polypeptide, fragment of a polypeptide, peptide, or fusion polypeptide that has at least one activity of an IDI polypeptide. Exemplary IDI polypeptides and nucleic acids include naturally-occurring polypeptides and nucleic acids from any of the source organisms described herein as well as mutant polypeptides and nucleic acids derived from any of the source organisms described herein.

Exemplary MVA Pathway Polypeptides and Nucleic Acids

Exemplary MVA pathway polypeptides include acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonte decarboxylase (MVD) polypeptides, IDI polypeptides, and polypeptides (e.g., fusion polypeptides) having an activity of two or more MVA pathway polypeptides. In particular, MVA pathway polypeptides include polypeptides, fragments of polypeptides, peptides, and fusions polypeptides that have at least one activity of an MVA pathway polypeptide. Exemplary MVA pathway nucleic acids include nucleic acids that encode a polypeptide, fragment of a polypeptide, peptide, or fusion polypeptide that has at least one activity of an MVA pathway polypeptide. Exemplary MVA pathway polypeptides and nucleic acids include naturally-occurring polypeptides and nucleic acids from any of the source organisms described herein as well as mutant polypeptides and nucleic acids derived from any of the source organisms described herein.

In particular, acetyl-CoA acetyltransferase polypeptides (AA-CoA thiolase or AACT) convert two molecules of acetyl-CoA into acetoacetyl-CoA. Standard methods (such as those described herein) can be used to determine whether a polypeptide has AA-CoA thiolase polypeptide activity by measuring the ability of the polypeptide to convert two molecules of acetyl-CoA into acetoacetyl-CoA in vitro, in a cell extract, or in vivo.

3-hydroxy-3-methylglutaryl-CoA synthase (HMG-CoA synthase or HMGS) polypeptides convert acetoacetyl-CoA into 3-hydroxy-3-methylglutaryl-CoA. Standard methods (such as those described herein) can be used to determine whether a polypeptide has HMG-CoA synthase polypeptide activity by measuring the ability of the polypeptide to convert acetoacetyl-CoA into 3-hydroxy-3-methylglutaryl-CoA in vitro, in a cell extract, or in vivo.

3-hydroxy-3-methylglutaryl-CoA reductase (HMG-CoA reductase or HMGR) polypeptides convert 3-hydroxy-3-methylglutaryl-CoA into mevalonate. Standard methods (such as those described herein) can be used to determine whether a polypeptide has HMG-CoA reductase polypeptide activity by measuring the ability of the polypeptide to convert 3-hydroxy-3-methylglutaryl-CoA into mevalonate in vitro, in a cell extract, or in vivo.

Mevalonate kinase (MVK) polypeptides phosphorylates mevalonate to form mevalonate-5-phosphate. Standard methods (such as those described herein) can be used to determine whether a polypeptide has MVK polypeptide activity by measuring the ability of the polypeptide to convert mevalonate into mevalonate-5-phosphate in vitro, in a cell extract, or in vivo.

Phosphomevalonate kinase (PMK) polypeptides phosphorylates mevalonate-5-phosphate to form mevalonate-5-diphosphate. Standard methods (such as those described herein) can be used to determine whether a polypeptide has PMK polypeptide activity by measuring the ability of the polypeptide to convert mevalonate-5-phosphate into mevalonate-5-diphosphate in vitro, in a cell extract, or in vivo.

Diphosphomevalonte decarboxylase (MVD or DPMDC) polypeptides convert mevalonate-5-diphosphate into isopentenyl diphosphate polypeptides (IPP). Standard methods (such as those described herein) can be used to determine whether a polypeptide has MVD polypeptide activity by measuring the ability of the polypeptide to convert mevalonate-5-diphosphate into IPP in vitro, in a cell extract, or in vivo.

Exemplary Methods for Isolating Nucleic Acids

Isoprene synthase, DXS, IDI, and/or MVA pathway nucleic acids can be isolated using standard methods. Methods of obtaining desired nucleic acids from a source organism of interest (such as a bacterial genome) are common and well known in the art of molecular biology (see, for example, WO 2004/033646 and references cited therein, which are each hereby incorporated by reference in their entireties, particularly with respect to the isolation of nucleic acids of interest). For example, if the sequence of the nucleic acid is known (such as any of the known nucleic acids described herein), suitable genomic libraries may be created by restriction endonuclease digestion and may be screened with probes complementary to the desired nucleic acid sequence. Once the sequence is isolated, the DNA may be amplified using standard primer directed amplification methods such as polymerase chain reaction (PCR) (U.S. Pat. No. 4,683,202, which is incorporated by reference in its entirety, particularly with respect to PCR methods) to obtain amounts of DNA suitable for transformation using appropriate vectors. Alternatively, isoprene synthase, DXS, IDI, and/or MVA pathway nucleic acids (such as any isoprene synthase, DXS, IDI, and/or MVA pathway nucleic acids with a known nucleic acid sequence) can be chemically synthesized using standard methods.

Additional isoprene synthase, DXS, IDI, or MVA pathway polypeptides and nucleic acids that may be suitable for use in the compositions and methods described herein can be identified using standard methods. For example, cosmid libraries of the chromosomal DNA of organisms known to produce isoprene naturally can be constructed in organisms such as *E. coli*, and then screened for isoprene production. Additional methods for obtaining isoprene synthase, DXS, IDI, and/or MVA pathway nucleic acids include screening a metagenomic library by assay (such as the headspace assay described herein) or by PCR using primers directed against nucleotides encoding for a length of conserved amino acids (for example, at least 3 conserved amino acids). Conserved amino acids can be identified by aligning amino acid sequences of known isoprene synthase, DXS, IDI, and/or MVA pathway polypeptides. Conserved amino acids for isoprene synthase polypeptides can be identified based on aligned sequences of known isoprene synthase polypeptides. An organism found to produce isoprene naturally can be subjected to standard protein purification methods (which are well known in the art) and the resulting purified polypeptide can be sequenced using standard methods. Other methods are found in the literature (See, e.g., Julsing et al., Applied. Microbiol. Biotechnol. 75: 1377-84, 2007; and Withers et al., Appl Environ Microbiol. 73:6277-83, 2007, which are each hereby incorporated by reference in their entireties, particularly with respect to identification of nucleic acids involved in the synthesis of isoprene).

Additionally, standard sequence alignment and/or structure prediction programs can be used to identify additional DXS, IDI, or MVA pathway polypeptides and nucleic acids based on the similarity of their primary and/or predicted polypeptide secondary structure with that of known DXS, IDI, or MVA pathway polypeptides and nucleic acids. Standard databases such as the swissprot-trembl database (world-wide web at "expasy.org", Swiss Institute of Bioinformatics Swiss-Prot group CMU-1 rue Michel Servet CH-1211 Geneva 4, Switzerland) can also be used to identify isoprene synthase, DXS, IDI, or MVA pathway polypeptides and nucleic acids. The secondary and/or tertiary structure of an isoprene synthase, DXS, IDI, or MVA pathway polypeptide can be predicted using the default settings of standard structure prediction programs, such as PredictProtein (Rost et al., The PredictProtein Server. Nucleic Acids Research 32(Web Server issue):W321-W326, 2004). Alternatively, the actual secondary and/or tertiary structure of an isoprene synthase, DXS, IDI, or MVA pathway polypeptide can be determined using standard methods. Additional isoprene synthase, DXS, IDI, or MVA pathway nucleic acids can also be identified by hybridization to probes generated from known isoprene synthase, DXS, IDI, or MVA pathway nucleic acids.

Exemplary Promoters and Vectors

Any of the isoprene synthase, DXS, IDI, or MVA pathway nucleic acid described herein can be included in one or more vectors. Accordingly, the invention also features vectors with one more nucleic acids encoding any of the isoprene synthase, DXS, IDI, or MVA pathway polypeptides that are described herein. As used herein, a "vector" means a construct that is capable of delivering, and desirably expressing one or more nucleic acids of interest in a host cell. Examples of vectors include, but are not limited to, plasmids, viral vectors, DNA or RNA expression vectors, cosmids, and phage vectors. In some embodiments, the vector contains a nucleic acid under the control of an expression control sequence.

As used herein, an "expression control sequence" means a nucleic acid sequence that directs transcription of a nucleic acid of interest. An expression control sequence can be a promoter, such as a constitutive or an inducible promoter, or an enhancer. An "inducible promoter" is a promoter that is active under environmental or developmental regulation. The expression control sequence is operably linked to the nucleic acid segment to be transcribed.

In some embodiments, the vector contains a selective marker. The term "selective marker" refers to a nucleic acid capable of expression in a host cell that allows for ease of selection of those host cells containing an introduced nucleic acid or vector. Examples of selectable markers include, but are not limited to, antibiotic resistance nucleic acids (e.g., kanamycin, ampicillin, carbenicillin, gentamicin, hygromycin, phleomycin, bleomycin, neomycin, or chloramphenicol) and/or nucleic acids that confer a metabolic advantage, such as a nutritional advantage on the host cell. In some embodiments, an isoprene synthase, DXS, IDI, or MVA pathway nucleic acid integrates into a chromosome of the cells without a selective marker.

Suitable vectors are those that are compatible with the host cell employed. Suitable vectors can be derived, for example, from a bacterium, a virus (such as bacteriophage T7 or a M-13 derived phage), a cosmid, a yeast, or a plant. Protocols for obtaining and using such vectors are known in the art (See, e.g., Sambrook et al., Molecular Cloning: A Laboratory Manual, $2^{nd}$ ed., Cold Spring Harbor, 1989, which is hereby incorporated by reference in its entirety, particularly with respect to the use of vectors).

Promoters are well known in the art. Any promoter that functions in the host cell can be used for expression of an isoprene synthase, DXS, IDI, or MVA pathway nucleic acid in the host cell. Initiation control regions or promoters, which are useful to drive expression of isoprene synthase, DXS, IDI, or MVA pathway nucleic acids in various host cells are numerous and familiar to those skilled in the art (see, for example, WO 2004/033646 and references cited therein, which are each hereby incorporated by reference in their entireties, particularly with respect to vectors for the expression of nucleic acids of interest). Virtually any promoter capable of driving these nucleic acids is suitable for the present invention including, but not limited to lac, trp, $\lambda P_L$, $\lambda P_R$, T7, tac, and trc (useful for expression in E. coli).

In some embodiments, a glucose isomerase promoter is used (see, for example, U.S. Pat. No. 7,132,527 and references cited therein, which are each hereby incorporated by reference in their entireties, particularly with respect promoters and plasmid systems for expressing polypeptides of interest). Reported glucose isomerase promoter mutants can be used to vary the level of expression of the polypeptide encoded by a nucleic acid operably linked to the glucose isomerase promoter (U.S. Pat. No. 7,132,527). In various embodiments, the glucose isomerase promoter is contained in a low, medium, or high copy plasmid (U.S. Pat. No. 7,132, 527).

In various embodiments, an isoprene synthase, DXS, IDI, and/or MVA pathway nucleic acid is contained in a low copy plasmid (e.g., a plasmid that is maintained at about 1 to about 4 copies per cell), medium copy plasmid (e.g., a plasmid that is maintained at about 10 to about 15 copies per cell), or high copy plasmid (e.g., a plasmid that is maintained at about 50 or more copies per cell). In some embodiments, the heterologous or extra endogenous isoprene synthase, DXS, IDI, or MVA pathway nucleic acid is operably linked to a T7 promoter. In some embodiments, the heterologous or extra endogenous isoprene synthase, DXS, IDI, or MVA pathway nucleic acid operably linked to a T7 promoter is contained in a medium or high copy plasmid. In some embodiments, the heterologous or extra endogenous isoprene synthase, DXS, IDI, or MVA pathway nucleic acid is operably linked to a Trc promoter. In some embodiments, the heterologous or extra endogenous isoprene synthase, DXS, IDI, or MVA pathway nucleic acid operably linked to a Trc promoter is contained in a medium or high copy plasmid. In some embodiments, the heterologous or extra endogenous isoprene synthase, DXS, IDI, or MVA pathway nucleic acid is operably linked to a Lac promoter. In some embodiments, the heterologous or extra endogenous isoprene synthase, DXS, IDI, or MVA pathway nucleic acid operably linked to a Lac promoter is contained in a low copy plasmid. In some embodiments, the heterologous or extra endogenous isoprene synthase, DXS, IDI, or MVA pathway nucleic acid is operably linked to an endogenous promoter, such as an endogenous *Escherichia, Panteoa, Bacillus, Yarrowia, Streptomyces*, or *Trichoderma* promoter or an endogenous alkaline serine protease, isoprene synthase, DXS, IDI, or MVA pathway promoter. In some embodiments, the heterologous or extra endogenous isoprene synthase, DXS, IDI, or MVA pathway nucleic acid operably linked to an endogenous promoter is contained in a high copy plasmid. In some embodiments, the vector is a replicating plasmid that does not integrate into a chromosome in the cells. In some embodiments part or all of the vector integrates into a chromosome in the cells.

In some embodiments, the expression vector also includes a termination sequence. Termination control regions may also be derived from various genes native to the host cell. In some embodiments, the termination sequence and the promoter sequence are derived from the same source. In another embodiment, the termination sequence is endogenous to the host cell.

In some embodiments, the promoter, coding, region, and terminator all originate from the isoprene synthase, DXS, IDI, or MVA pathway nucleic acid to be expressed. In some embodiments, the coding region for an isoprene synthase, DXS, IDI, or MVA pathway nucleic acid is inserted into a general-purpose expression vector such that it is under the transcriptional control of the expression construct promoter and terminator sequences. In some embodiments, genes or part thereof are inserted downstream of the strong cbh1 promoter.

An isoprene synthase, DXS, IDI, or MVA pathway nucleic acid can be incorporated into a vector, such as an expression vector, using standard techniques (Sambrook et al., Molecular Cloning: A Laboratory Manual, Cold Spring Harbor, 1982, which is hereby incorporated by reference in its entirety, particularly with respect to the screening of appropriate DNA sequences and the construction of vectors). Methods used to ligate the DNA construct comprising a nucleic acid of interest (such as an isoprene synthase, DXS, IDI, or MVA pathway nucleic acid), a promoter, a terminator, and other sequences and to insert them into a suitable vector are well known in the art. For example, restriction enzymes can be used to cleave the isoprene synthase, DXS, IDI, or MVA pathway nucleic acid and the vector. Then, the compatible ends of the cleaved isoprene synthase, DXS, IDI, or MVA pathway nucleic acid and the cleaved vector can be ligated. Linking is generally accomplished by ligation at convenient restriction sites. If such sites do not exist, the synthetic oligonucleotide linkers are used in accordance with conventional practice (see, Sambrook et al., Molecular Cloning: A Laboratory Manual, $2^{nd}$ ed., Cold Spring Harbor, 1989, and Bennett and Lasure, More Gene Manipulations in Fungi, Academic Press, San Diego, pp 70-76, 1991, which are each hereby incorporated by reference in their entireties, particularly with respect to oligonucleotide linkers). Additionally, vectors can be constructed using known recombination techniques (e.g., Invitrogen Life Technologies, Gateway Technology).

In some embodiments, it may be desirable to over-express isoprene synthase, DXS, IDI, or MVA pathway nucleic acids at levels far higher than currently found in naturally-occurring cells. This result may be accomplished by the selective cloning of the nucleic acids encoding those polypeptides into multicopy plasmids or placing those nucleic acids under a strong inducible or constitutive promoter. Methods for over-expressing desired polypeptides are common and well known in the art of molecular biology and examples may be found in Sambrook et al., Molecular Cloning: A Laboratory Manual, $2^{nd}$ ed., Cold Spring Harbor, 1989, which is hereby incorporated by reference in its entirety, particularly with respect to cloning techniques.

The following resources include descriptions of additional general methodology useful in accordance with the invention: Kreigler, Gene Transfer and Expression; A Laboratory Manual, 1990; and Ausubel et al., Eds. Current Protocols in Molecular Biology, 1994, which are each hereby incorporated by reference in their entireties, particularly with respect to molecular biology and cloning techniques.

Exemplary Source Organisms

Isoprene synthase, DXS, IDI, or MVA pathway nucleic acids (and their encoded polypeptides) can be obtained from any organism that naturally contains isoprene synthase, DXS, IDI, and/or MVA pathway nucleic acids. As noted above, isoprene is formed naturally by a variety of organisms, such as bacteria, yeast, plants, and animals. Organisms contain the MVA pathway, DXP pathway, or both the MVA and DXP pathways for producing isoprene (FIG. 15). Thus, DXS nucleic acids can be obtained, e.g., from any organism that contains the DXP pathway or contains both the MVA and DXP pathways. IDI and isoprene synthase nucleic acids can be obtained, e.g., from any organism that contains the MVA pathway, DXP pathway, or both the MVA and DXP pathways. MVA pathway nucleic acids can be obtained, e.g., from any organism that contains the MVA pathway or contains both the MVA and DXP pathways.

In some embodiments, the nucleic acid sequence of the isoprene synthase, DXS, IDI, or MVA pathway nucleic is identical to the sequence of a nucleic acid that is produced by any of the following organisms in nature. In some embodiments, the amino acid sequence of the isoprene synthase, DXS, IDI, or MVA pathway polypeptide is identical to the sequence of a polypeptide that is produced by any of the following organisms in nature. In some embodiments, the isoprene synthase, DXS, IDI, or MVA pathway nucleic acid or polypeptide is a mutant nucleic acid or polypeptide derived from any of the organisms described herein. As used herein, "derived from" refers to the source of the nucleic acid or polypeptide into which one or more mutations is introduced. For example, a polypeptide that is "derived from a plant polypeptide" refers to polypeptide of interest that results from introducing one or more mutations into the sequence of a wild-type (i.e., a sequence occurring in nature) plant polypeptide.

In some embodiments, the source organism is a bacterium, such as strains of *Escherichia* (e.g., *E. coli*), or strains of *Bacillus* (e.g., *B. subtilis*).

As used herein, "the genus *Escherichia*" includes all species within the genus "*Escherichia*," as known to those of skill in the art, including but not limited to *E. coli, E. adecarboxylata, E. albertii, E. blattae, E. fergusonii, E. hermannii, E. senegalensis*, and *E. vulneris*. The genus "*Escherichia*" is defined as Gram-negative, non-spore forming, facultatively anaerobic, rod-shaped bacteria are classified as members of the Family Enterobacteriaceae, Order Enterobacteriales, Class Gamma Proteobacteria.

As used herein, "the genus *Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus.*" The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus*, and *Virgibacillus*.

Exemplary Host Cells

A variety of host cells can be used to express isoprene synthase, DXS, IDI, and/or MVA pathway polypeptides and to produce isoprene in the methods of the claimed invention. Exemplary host cells include cells from any of the organisms listed in the prior section under the heading "Exemplary Source Organisms." The host cell may be a cell that naturally produces isoprene or a cell that does not naturally produce isoprene. In some embodiments, the host cell naturally produces isoprene using the DXP pathway, and an isoprene synthase, DXS, and/or IDI nucleic acid is added to enhance production of isoprene using this pathway. In some embodiments, the host cell naturally produces isoprene using the MVA pathway, and an isoprene synthase and/or one or more MVA pathway nucleic acids are added to enhance production of isoprene using this pathway. In some embodiments, the host cell naturally produces isoprene using the DXP pathway and one or more MVA pathway nucleic acids are added to produce isoprene using part or all of the MVA pathway as well as the DXP pathway. In some embodiments, the host cell naturally produces isoprene using both the DXP and MVA pathways and one or more isoprene synthase, DXS, IDI, or MVA pathway nucleic acids are added to enhance production of isoprene by one or both of these pathways.

Exemplary Transformation Methods

Isoprene synthase, DXS, IDI, and/or MVA pathway nucleic acids or vectors containing them can be inserted into a host cell (e.g., a bacterial cell) using standard techniques for expression of the encoded isoprene synthase, DXS, IDI, and/or MVA pathway polypeptide. Introduction of a DNA construct or vector into a host cell can be performed using techniques such as transformation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion. General transformation techniques are known in the art (see, e.g., Current Protocols in Molecular Biology (F. M. Ausubel et al. (eds) Chapter 9, 1987; Sambrook et al., Molecular Cloning: A Laboratory Manual, $2^{nd}$ ed., Cold Spring Harbor, 1989; and Campbell et al., Curr Genet, 16:53-56, 1989, which are each hereby incorporated by reference in their entireties, particularly with respect to transformation methods). The introduced nucleic acids may be integrated into chromosomal DNA or maintained as extrachromosomal replicating sequences.

Exemplary Cell Culture Media

The invention also includes a cell or a population of cells in culture that produce isoprene. By "cells in culture" is meant two or more cells in a solution (e.g., a cell medium) that allows the cells to undergo one or more cell divisions. "Cells in culture" do not include plant cells that are part of a living, multicellular plant containing cells that have differentiated into plant tissues. In various embodiments, the cell culture includes at least or about 10, 20, 50, 100, 200, 500, 1,000, 5,000, 10,000 or more cells.

Any carbon source can be used to cultivate the host cells. The term "carbon source" refers to one or more carbon-containing compounds capable of being metabolized by a host cell or organism. For example, the cell medium used to cultivate the host cells may include any carbon source suitable for maintaining the viability or growing the host cells.

In some embodiments, the carbon source is a carbohydrate (such as monosaccharide, disaccharide, oligosaccharide, or polysaccharides), invert sugar (e.g., enzymatically treated sucrose syrup), glycerol, glycerine (e.g., a glycerine byproduct of a biodiesel or soap-making process), dihydroxyacetone, one-carbon source, fatty acid (e.g., a saturated fatty acid, unsaturated fatty acid, or polyunsaturated fatty acid), lipid, phospholipid, glycerolipid, monoglyceride, diglyceride, triglyceride, polypeptide (e.g., a microbial or plant protein or peptide), renewable carbon source (e.g., a biomass carbon source such as a hydrolyzed biomass carbon source; beet sugar or cane sugar molasses), yeast extract, component from a yeast extract, polymer, acid, alcohol, aldehyde, ketone, amino acid, succinate, lactate, acetate, ethanol, or any combination of two or more of the foregoing. In some embodiments, the carbon source is a product of photosynthesis, including, but not limited to, glucose.

Exemplary monosaccharides include glucose and fructose; exemplary oligosaccharides include lactose and sucrose, and exemplary polysaccharides include starch and cellulose. Exemplary carbohydrates include C6 sugars (e.g., fructose, mannose, galactose, or glucose) and C5 sugars (e.g., xylose or arabinose). In some embodiments, the cell medium includes a carbohydrate as well as a carbon source other than a carbohydrate (e.g., glycerol, glycerine, dihydroxyacetone, one-carbon source, fatty acid, lipid, phospholipid, glycerolipid, monoglyceride, diglyceride, triglyceride, renewable carbon source, or a component from a yeast extract). In some embodiments, the cell medium includes a carbohydrate as well as a polypeptide (e.g., a microbial or plant protein or peptide). In some embodiments, the microbial polypeptide is a polypeptide from yeast or bacteria. In some embodiments, the plant polypeptide is a polypeptide from soy, corn, canola, jatropha, palm, peanut, sunflower, coconut, mustard, rapeseed, cottonseed, palm kernel, olive, safflower, sesame, or linseed.

In some embodiments, the concentration of the carbohydrate is at least or about 5 grams per liter of broth (g/L, wherein the volume of broth includes both the volume of the cell medium and the volume of the cells), such as at least or about 10, 15, 20, 30, 40, 50, 60, 80, 100, 150, 200, 300, 400, or more g/L. In some embodiments, the concentration of the carbohydrate is between about 50 and about 400 g/L, such as between about 100 and about 360 g/L, between about 120 and about 360 g/L, or between about 200 and about 300 g/L. In some embodiments, this concentration of carbohydrate includes the total amount of carbohydrate that is added before and/or during the culturing of the host cells.

Exemplary lipids are any substance containing one or more fatty acids that are C4 and above fatty acids that are saturated, unsaturated, or branched.

Exemplary fatty acids include compounds of the formula R—COOH, where "R" is a hydrocarbon. Exemplary unsaturated fatty acids include compounds where "R" includes at least one carbon-carbon double bond. Exemplary unsaturated fatty acids include, but are not limited to, oleic acid, vaccenic acid, linoleic acid, palmitelaidic acid, and arachidonic acid. Exemplary polyunsaturated fatty acids include compounds where "R" includes a plurality of carbon-carbon double bonds. Exemplary saturated fatty acids include compounds where "R" is a saturated aliphatic group. In some embodiments, the carbon source includes one or more $C_{12}$-$C_{22}$ fatty acids, such as a $C_{12}$ saturated fatty acid, a $C_{14}$ saturated fatty acid, a $C_{16}$ saturated fatty acid, a $C_{18}$ saturated fatty acid, a $C_{20}$ saturated fatty acid, or a $C_{22}$ saturated fatty acid. In an exemplary embodiment, the fatty acid is palmitic acid. In some embodiments, the carbon source is a salt of a fatty acid (e.g., an unsaturated fatty acid), a derivative of a fatty acid (e.g., an unsaturated fatty acid), or a salt of a derivative of fatty acid (e.g., an unsaturated fatty acid). Suitable salts include, but are not limited to, lithium salts, potassium salts, sodium salts, and the like. Di- and triglycerols are fatty acid esters of glycerol.

In some embodiments, the concentration of the lipid, fatty acid, monoglyceride, diglyceride, or triglyceride is at least or about 1 gram per liter of broth (g/L, wherein the volume of broth includes both the volume of the cell medium and the volume of the cells), such as at least or about 5, 10, 15, 20, 30, 40, 50, 60, 80, 100, 150, 200, 300, 400, or more g/L. In some embodiments, the concentration of the lipid, fatty acid, monoglyceride, diglyceride, or triglyceride is between about 10 and about 400 g/L, such as between about 25 and about 300 g/L, between about 60 and about 180 g/L, or between about 75 and about 150 g/L. In some embodiments, the concentration includes the total amount of the lipid, fatty acid, monoglyceride, diglyceride, or triglyceride that is added before and/or during the culturing of the host cells. In some embodiments, the carbon source includes both (i) a lipid, fatty acid, monoglyceride, diglyceride, or triglyceride and (ii) a carbohydrate, such as glucose. In some embodiments, the ratio of the lipid, fatty acid, monoglyceride, diglyceride, or triglyceride to the carbohydrate is about 1:1 on a carbon basis (i.e., one carbon in the lipid, fatty acid, monoglyceride, diglyceride, or triglyceride per carbohydrate carbon). In particular embodiments, the amount of the lipid, fatty acid, monoglyceride, diglyceride, or triglyceride is between about 60 and 180 g/L, and the amount of the carbohydrate is between about 120 and 360 g/L.

Exemplary microbial polypeptide carbon sources include one or more polypeptides from yeast or bacteria. Exemplary plant polypeptide carbon sources include one or more polypeptides from soy, corn, canola, jatropha, palm, peanut, sunflower, coconut, mustard, rapeseed, cottonseed, palm kernel, olive, safflower, sesame, or linseed.

Exemplary renewable carbon sources include cheese whey permeate, cornsteep liquor, sugar beet molasses, barley malt, and components from any of the foregoing. Exemplary renewable carbon sources also include glucose, hexose, pentose and xylose present in biomass, such as corn, switchgrass, sugar cane, cell waste of fermentation processes, and protein by-product from the milling of soy, corn, or wheat. In some embodiments, the biomass carbon source is a lignocellulosic, hemicellulosic, or cellulosic material such as, but are not limited to, a grass, wheat, wheat straw, bagasse, sugar cane bagasse, soft wood pulp, corn, corn cob or husk, corn kernel, fiber from corn kernels, corn stover, switch grass, rice hull product, or a by-product from wet or dry milling of grains (e.g., corn, sorghum, rye, triticate, barley, wheat, and/or distillers grains). Exemplary cellulosic materials include wood, paper and pulp waste, herbaceous plants, and fruit pulp. In some embodiments, the carbon source includes any plant part, such as stems, grains, roots, or tubers. In some embodiments, all or part of any of the following plants are used as a carbon source: corn, wheat, rye, sorghum, triticate, rice, millet, barley, cassava, legumes, such as beans and peas, potatoes, sweet potatoes, bananas, sugarcane, and/or tapioca. In some embodiments, the carbon source is a biomass hydrolysate, such as a biomass hydrolysate that includes both xylose and glucose or that includes both sucrose and glucose.

In some embodiments, the renewable carbon source (such as biomass) is pretreated before it is added to the cell culture medium. In some embodiments, the pretreatment includes enzymatic pretreatment, chemical pretreatment, or a combination of both enzymatic and chemical pretreatment (see, for example, Farzaneh et al., *Bioresource Technology* 96 (18): 2014-2018, 2005; U.S. Pat. Nos. 6,176,176; 6,106,888; which are each hereby incorporated by reference in their entireties, particularly with respect to the pretreatment of renewable carbon sources). In some embodiments, the renewable carbon source is partially or completely hydrolyzed before it is added to the cell culture medium.

In some embodiments, the renewable carbon source (such as corn stover) undergoes ammonia fiber expansion (AFEX) pretreatment before it is added to the cell culture medium (see, for example, Farzaneh et al., *Bioresource Technology* 96 (18): 2014-2018, 2005). During AFEX pretreatment, a renewable carbon source is treated with liquid anhydrous ammonia at moderate temperatures (such as about 60 to about 100° C.) and high pressure (such as about 250 to about 300 psi) for about 5 minutes. Then, the pressure is rapidly released. In this process, the combined chemical and physical effects of lignin solubilization, hemicellulose hydrolysis, cellulose decrystallization, and increased surface area enables near complete enzymatic conversion of cellulose and hemicellulose to fermentable sugars. AFEX pretreatment has the advantage that nearly all of the ammonia can be recovered and reused, while the remaining serves as nitrogen source for microbes in downstream processes. Also, a wash stream is not required for AFEX pretreatment. Thus, dry matter recovery following the AFEX treatment is essentially 100%. AFEX is basically a dry-to-dry process. The treated renewable carbon source is stable for long periods and can be fed at very high solid loadings in enzymatic hydrolysis or fermentation processes. Cellulose and hemicellulose are well preserved in the AFEX process, with little or no degradation. There is no need for neutralization prior to the enzymatic hydrolysis of a renewable carbon source that has undergone AFEX pretreatment. Enzymatic hydrolysis of AFEX-treated carbon sources produces clean sugar streams for subsequent fermentation use.

In some embodiments, the concentration of the carbon source (e.g., a renewable carbon source) is equivalent to at least or about 0.1, 0.5, 1, 1.5 2, 3, 4, 5, 10, 15, 20, 30, 40, or 50% glucose (w/v). The equivalent amount of glucose can be determined by using standard HPLC methods with glucose as a reference to measure the amount of glucose generated from the carbon source. In some embodiments, the concentration of the carbon source (e.g., a renewable carbon source) is equivalent to between about 0.1 and about 20% glucose, such as between about 0.1 and about 10% glucose, between about 0.5 and about 10% glucose, between about 1 and about 10% glucose, between about 1 and about 5% glucose, or between about 1 and about 2% glucose.

In some embodiments, the carbon source includes yeast extract or one or more components of yeast extract. In some embodiments, the concentration of yeast extract is at least 1 gram of yeast extract per liter of broth (g/L, wherein the volume of broth includes both the volume of the cell medium and the volume of the cells), such at least or about 5, 10, 15, 20, 30, 40, 50, 60, 80, 100, 150, 200, 300, or more g/L. In some embodiments, the concentration of yeast extract is between about 1 and about 300 g/L, such as between about 1 and about 200 g/L, between about 5 and about 200 g/L, between about 5 and about 100 g/L, or between about 5 and about 60 g/L. In some embodiments, the concentration includes the total amount of yeast extract that is added before and/or during the culturing of the host cells. In some embodiments, the carbon source includes both yeast extract (or one or more components thereof) and another carbon source, such as glucose. In some embodiments, the ratio of yeast extract to the other carbon source is about 1:5, about 1:10, or about 1:20 (w/w).

Additionally the carbon source may also be one-carbon substrates such as carbon dioxide, or methanol. Glycerol production from single carbon sources (e.g., methanol, formaldehyde, or formate) has been reported in methylotrophic yeasts (Yamada et al., *Agric. Biol. Chem.*, 53(2) 541-543, 1989, which is hereby incorporated by reference in its entirety, particularly with respect to carbon sources) and in bacteria (Hunter et. al., *Biochemistry*, 24, 4148-4155, 1985, which is hereby incorporated by reference in its entirety, particularly with respect to carbon sources). These organisms can assimilate single carbon compounds, ranging in oxidation state from methane to formate, and produce glycerol. The pathway of carbon assimilation can be through ribulose monophosphate, through serine, or through xylulose-momophosphate (Gottschalk, *Bacterial Metabolism*, Second Edition, Springer-Verlag: New York, 1986, which is hereby incorporated by reference in its entirety, particularly with respect to carbon sources). The ribulose monophosphate pathway involves the condensation of formate with ribulose-5-phosphate to form a six carbon sugar that becomes fructose and eventually the three carbon product glyceraldehyde-3-phosphate. Likewise, the serine pathway assimilates the one-carbon compound into the glycolytic pathway via methylenetetrahydrofolate.

In addition to one and two carbon substrates, methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth Cl Compd.*, [Int. Symp.], $7^{th}$ ed., 415-32. Editors: Murrell et al., Publisher: Intercept, Andover, UK, 1993, which is hereby incorporated by reference in its entirety, particularly with respect to carbon sources). Similarly, various species of Candida metabolize alanine or oleic acid (Sulter et al., *Arch. Microbiol.* 153(5), 485-9, 1990, which is hereby incorporated by reference in its entirety, particularly with respect to carbon sources).

In some embodiments, cells are cultured in a standard medium containing physiological salts and nutrients (see, e.g., Pourquie, J. et al., Biochemistry and Genetics of Cellulose Degradation, eds. Aubert et al., Academic Press, pp. 71-86, 1988; and Ilmen et al., *Appl. Environ. Microbiol.* 63:1298-1306, 1997, hereby incorporated by reference, particularly with respect to cell media). Exemplary growth media are common commercially prepared media such as Luria Bertani (LB) broth, Sabouraud Dextrose (SD) broth, or Yeast medium (YM) broth. Other defined or synthetic growth media may also be used, and the appropriate medium for growth of particular host cells are known by someone skilled in the art of microbiology or fermentation science.

In addition to an appropriate carbon source, the cell medium desirably contains suitable minerals, salts, cofactors, buffers, and other components known to those skilled in the art suitable for the growth of the cultures or the enhancement of isoprene production (see, for example, WO 2004/033646 and references cited therein and WO 96/35796 and references cited therein, which are each hereby incorporated by reference in their entireties, particularly with respect cell medias and cell culture conditions). In some embodiments where an isoprene synthase, DXS, IDI, and/or MVA pathway nucleic acid is under the control of an inducible promoter, the inducing agent (e.g., a sugar, metal salt or antimicrobial), is desirably added to the medium at a concentration effective to induce expression of an isoprene synthase, DXS, IDI, and/or MVA pathway polypeptide. In some embodiments, cell medium has an antibiotic (such as kanamycin) that corresponds to the antibiotic resistance nucleic acid (such as a kanamycin resistance nucleic acid) on a vector that has one or more DXS, IDI, or MVA pathway nucleic acids.

Exemplary Production of Isoprene

In some embodiments, the cells are cultured in a culture medium under conditions permitting the production of isoprene by the cells. In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, or more nmole of isoprene/gram of cells for the wet weight of the cells/hour (nmole/$g_{wcm}$/hr). In some embodiments, the amount of isoprene is between about 2 to about 5,000 nmole/$g_{wcm}$/hr, such as between about 2 to about 100 nmole/$g_{wcm}$/hr, about 100 to about 500 nmole/$g_{wcm}$/hr, about 150 to about 500 nmole/$g_{wcm}$/hr, about 500 to about 1,000 nmole/$g_{wcm}$/hr, about 1,000 to about 2,000 nmole/$g_{wcm}$/hr, or about 2,000 to about 5,000 nmole/$g_{wcm}$/hr. The amount of isoprene in units of nmole/$g_{wcm}$/hr can be measured as disclosed in U.S. Pat. No. 5,849,970, which is hereby incorporated by reference in its entirety, particularly with respect to the measurement of isoprene production. For example, two mL of headspace (e.g., headspace from a culture such as 2 mL of culture cultured in sealed vials at 32° C. with shaking at 200 rpm for approximately 3 hours) are analyzed for isoprene using a standard gas chromatography system, such as a system operated isothermally (85° C.) with an n-octane/porasil C column (Alltech Associates, Inc., Deerfield, Ill.) and coupled to a RGD2 mercuric oxide reduction gas detector (Trace Analytical, Menlo Park, Calif.) (see, for example, Greenberg et al, *Atmos. Environ.* 27A: 2689-2692, 1993; Silver et al., *Plant Physiol.* 97:1588-1591, 1991, which are each hereby incorporated by reference in their entireties, particularly with respect to the measurement of isoprene production). The gas chromatography area units are converted to nmol isoprene via a standard isoprene concentration calibration curve. In some embodiments, the value for the grams of cells for the wet weight of the cells is calculated by obtaining the $A_{600}$ value for a sample of the cell culture, and then converting the $A_{600}$ value to grams of cells based on a calibration curve of wet weights for cell cultures with a known $A_{600}$ value. In some embodiments, the grams of the cells is estimated by assuming that one liter of broth (including cell medium and cells) with an $A_{600}$ value of 1 has a wet cell weight of 1 gram. The value is also divided by the number of hours the culture has been incubating for, such as three hours.

In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/$g_{wcm}$/h). In some embodiments, the amount of isoprene is between about 2 to about 5,000 ng/$g_{wcm}$/h, such as between about 2 to about 100 ng/$g_{wcm}$/h, about 100 to about 500 ng/$g_{wcm}$/h, about 500 to about 1,000 ng/$g_{wcm}$/h, about 1,000 to about 2,000 ng/$g_{wcm}$/h, or about 2,000 to about 5,000 ng/$g_{wcm}$/h. The amount of isoprene in ng/$g_{wcm}$/h can be calculated by multiplying the value for isoprene production in the units of nmole/$g_{wcm}$/hr discussed above by 68.1 (as described in Equation 5 below).

In some embodiments, the cells in culture produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium). In some embodiments, the amount of isoprene is between about 2 to about 5,000 mg/$L_{broth}$, such as between about 2 to about 100 mg/$L_{broth}$, about 100 to about 500 mg/$L_{broth}$, about 500 to about 1,000 mg/$L_{broth}$, about 1,000 to about 2,000 mg/$L_{broth}$, or about 2,000 to about 5,000 mg/$L_{broth}$. The specific productivity of isoprene in mg of isoprene/L of headspace from shake flask or similar cultures can be measured by taking a 1 ml sample from the cell culture at an $OD_{600}$ value of approximately 1.0, putting it in a 20 mL vial, incubating for 30 minutes, and then measuring the amount of isoprene in the headspace. If the $OD_{600}$ value is not 1.0, then the measurement can be normalized to an $OD_{600}$ value of 1.0 by dividing by the $OD_{600}$ value. The value of mg isoprene/L headspace can be converted to mg/$L_{broth}$/hr/$OD_{600}$ of culture broth by multiplying by a factor of 38. The value in units of mg/$L_{broth}$/hr/$OD_{600}$ can be multiplied by the number of hours and the $OD_{600}$ value to obtain the cumulative titer in units of mg of isoprene/L of broth.

The instantaneous isoprene production rate in mg/$L_{broth}$/hr in a fermentor can be measured by taking a sample of the fermentor off-gas, analyzing it for the amount of isoprene (in units such as mg of isoprene per $L_{gas}$), and multiplying this value by the rate at which off-gas is passed though each liter of broth (e.g., at 1 vvm (volume of air/volume of broth/minute) this is 60 $L_{gas}$ per hour). Thus, an off-gas level of 1 mg/$L_{gas}$ corresponds to an instantaneous production rate of 60 mg/$L_{broth}$/hr at air flow of 1 vvm. If desired, the value in the units mg/$L_{broth}$/hr can be divided by the $OD_{600}$ value to obtain the specific rate in units of mg/$L_{broth}$/hr/OD. The average value of mg isoprene/$L_{gas}$ can be converted to the total product productivity (grams of isoprene per liter of fermentation broth, mg/$L_{broth}$) by multiplying this average off-gas isoprene concentration by the total amount of off-gas sparged per liter of fermentation broth during the fermentation. Thus, an average off-gas isoprene concentration of 0.5 mg/$L_{broth}$/hr over 10 hours at 1 vvm corresponds to a total product concentration of 300 mg isoprene/$L_{broth}$.

In some embodiments, the cells in culture convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, or 1.6% of the carbon in the cell culture medium into isoprene. In some embodiments, the percent conversion of carbon into isoprene is between about 0.002 to about 1.6%, such as about 0.002 to about 0.005%, about 0.005 to about 0.01%, about 0.01 to about 0.05%, about 0.05 to about 0.15%, 0.15 to about 0.2%, about 0.2 to about 0.3%, about 0.3 to about 0.5%, about 0.5 to about 0.8%, about 0.8 to about 1.0%, or about 1.0 to about 1.6%. The percent conversion of carbon into isoprene (also referred to as "% carbon yield") can be measured by dividing the moles carbon in the isoprene produced by the moles carbon in the carbon source (such as the moles of carbon in batched and fed glucose and yeast extract). This number is multiplied by 100% to give a percentage value (as indicated in Equation 1).

$$\% \text{ Carbon Yield} = (\text{moles carbon in isoprene produced})/(\text{moles carbon in carbon source}) * 100 \quad \text{Equation 1}$$

For this calculation, yeast extract can be assumed to contain 50% w/w carbon.

$$\% \text{ Carbon Yield} = (39.1 \text{ g isoprene} * 1/68.1 \text{ mol/g} * 5 \text{ C/mol})/[(181221 \text{ g glucose} * 1/180 \text{ mol/g} * 6 \text{ C/mol}) + (17780 \text{ g yeast extract} * 0.5 * 1/12 \text{ mol/g})] * 100 = 0.042\% \quad \text{Equation 2}$$

One skilled in the art can readily convert the rates of isoprene production or amount of isoprene produced into any other units. Exemplary equations are listed below for inter-converting between units.

Units for Rate of Isoprene Production (Total and Specific)

$$1 \text{ g isoprene/}L_{broth}/\text{hr} = 14.7 \text{ mmol isoprene/}L_{broth}/\text{hr} \text{ (total volumetric rate)} \quad \text{Equation 3}$$

$$1 \text{ nmol isoprene/}g_{wcm}/\text{hr} = 1 \text{ nmol isoprene/}L_{broth}/\text{hr/}OD_{600} \text{ (This conversion assumes that one liter of broth with an } OD_{600} \text{ value of 1 has a wet cell weight of 1 gram.)} \quad \text{Equation 4}$$

$$1 \text{ nmol isoprene/}g_{wcm}/\text{hr} = 68.1 \text{ ng isoprene/}g_{wcm}/\text{hr} \text{ (given the molecular weight of isoprene)} \quad \text{Equation 5}$$

$$1 \text{ nmol isoprene/}L_{gas} \, O_2/\text{hr} = 90 \text{ nmol isoprene/}L_{broth}/\text{hr (at an } O_2 \text{ flow rate of 90 L/hr per L of culture broth)} \quad \text{Equation 6}$$

$$1 \text{ µg isoprene/}L_{gas} \text{ isoprene in off-gas} = 60 \text{ µg isoprene/}L_{broth}/\text{hr at a flow rate of 60 } L_{gas} \text{ per } L_{broth} \text{ (1 vvm)} \quad \text{Equation 7}$$

Units for Titer (Total and Specific)

$$1 \text{ nmol isoprene/mg cell protein} = 150 \text{ nmol isoprene/}L_{broth}/OD_{600} \text{ (This conversion assumes that one liter of broth with an } OD_{600} \text{ value of 1 has a total cell protein of approximately 150 mg)(specific productivity)} \quad \text{Equation 8}$$

$$1 \text{ g isoprene/}L_{broth} = 14.7 \text{ mmol isoprene/}L_{broth} \text{ (total titer)} \quad \text{Equation 9}$$

If desired, Equation 10 can be used to convert any of the units that include the wet weight of the cells into the corresponding units that include the dry weight of the cells.

$$\text{Dry weight of cells} = (\text{wet weight of cells})/3.3 \quad \text{Equation 10}$$

In some embodiments encompassed by the invention, a cell comprising a heterologous nucleic acid encoding an isoprene synthase polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acid encoding the isoprene synthase polypeptide.

In some embodiments encompassed by the invention, a cell comprising a heterologous nucleic acid encoding an isoprene synthase polypeptide and one or more heterologous nucleic acids encoding a DXS, IDI, and/or MVA pathway polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acids.

Exemplary Isoprene Purification Methods

In some embodiments, any of the methods described herein further include recovering the isoprene. For example, the isoprene produced using the compositions and methods of the invention can be recovered using standard techniques. such as gas stripping, fractionation, adsorption/desorption, pervaporation, thermal or vacuum desorption of isoprene from a solid phase, or extraction of isoprene immobilized or absorbed to a solid phase with a solvent (see, for example, U.S. Pat. Nos. 4,703,007 and 4,570,029, which are each hereby incorporated by reference in their entireties, particularly with respect to isoprene recovery and purification methods). In some embodiments, the recovery of isoprene involves the isolation of isoprene in a liquid form (such as a neat solution of isoprene or a solution of isoprene in a solvent). Gas stripping involves the removal of isoprene vapor from the fermentation off-gas stream in a continuous manner. Such removal can be achieved in several different ways including, but not limited to, adsorption to a solid phase, partition into a liquid phase, or direct condensation. In some embodiments, membrane enrichment of a dilute isoprene vapor stream above the dew point of the vapor resulting in the condensation of liquid isoprene.

The recovery of isoprene may involve one step or multiple steps. In some embodiments, the removal of isoprene vapor from the fermentation off-gas and the conversion of isoprene to a liquid phase are performed simultaneously. For example, isoprene can be directly condensed from the off-gas stream to form a liquid. In some embodiments, the removal of isoprene vapor from the fermentation off-gas and the conversion of isoprene to a liquid phase are performed sequentially. For example, isoprene may be adsorbed to a solid phase and then extracted from the solid phase with a solvent.

In some embodiments, any of the methods described herein further include purifying the isoprene. For example, the isoprene produced using the compositions and methods of the invention can be purified using standard techniques. Purification refers to a process through which isoprene is separated from one or more components that are present when the isoprene is produced. In some embodiments, the isoprene is obtained as a substantially pure liquid. Examples of purification methods include (i) distillation from a solution in a liquid extractant and (ii) chromatography. As used herein, "purified isoprene" means isoprene that has been separated from one or more components that are present when the isoprene is produced. In some embodiments, the isoprene is at least about 20%, by weight, free from other components that are present when the isoprene is produced. In various embodiments, the isoprene is at least or about 25%, 30%, 40%, 50%, 60%, 70%, 75%, 80%, 90%, 95%, or 99%, by weight, pure. Purity can be assayed by any appropriate method, e.g., by column chromatography, HPLC analysis, or GC-MS analysis.

Crystal Structure of Isoprene Synthase

The invention also contemplates crystalline forms of plant isoprene synthase (e.g., poplar and kudzu) and its variants as described supra and in the Examples. In one embodiment, the invention comprises any polypeptide which has the crystal structure of poplar isoprene synthase as disclosed in Table 16-7.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: ° C. (degrees Centigrade); rpm (revolutions per minute); $H_2O$ (water); $diH_2O$ (deionized water); aa and AA (amino acid); bp (base pair); kb (kilobase pair); kD (kilodaltons); gm (grams); μg and ug (micrograms); mg (milligrams); ng (nanograms); μl and ul (microliters); ml (milliliters); mm (millimeters); qs (quantity sufficient); nm (nanometers); μm and um (micrometer); M (molar); mM (millimolar); μM and uM (micromolar); pM (picomolar); U (units); MW (molecular weight); sec (seconds); min (minute/minutes); hr (hour/hours); $OD_{600}$ (optical density at 600 nm); BSA (bovine serum albumin); DMAPP (dimethylallyl diphosphate); DTT (dithiothreitol); EtOH (ethanol); IPTG (isopropyl-beta-D-thiogalactopyranoside); isoprene(2-methyl-1,3-butadiene); IspS (isoprene synthase); PAGE (polyacrylamide gel electrophoresis); PBS (phosphate buffered saline [150 mM NaCl, 10 mM sodium phosphate buffer, pH 7.2]); and SDS (sodium dodecyl sulfate).

The following abbreviations apply to companies whose products or services may have been referred to in the experimental examples: Agilent (Agilent Technologies, Santa Clara, Calif.); Becton Coulter (Becton Coulter, Inc., Fullerton, Calif.); Bio-Rad (Bio-Rad Laboratories, Hercules, Calif.); Cayman Chemical (Cayman Chemical Co., Ann Arbor, Mich.); CTC Analytics (CTC Analytics A.G., Zwingen, Switzerland); EMS (Electron Microscopy Supply, Hatfield, Pa.); Epicentre (Epicentre Biotechnologies, Madison, Wis.); Integrated DNA Technologies (Integrated DNA Technologies, Coralville, Iowa); Invitrogen (Invitrogen Corp., Carlsbad, Calif.); Molecular Dynamics (Molecular Dynamics, Sunnyvale, Calif.); Novagen (Novagen, Inc., Madison, Wis.); Perkin Elmer (Perkin Elmer, Waltham, Mass.); Roche (Roche Applied Science, Indianapolis, Ind.); Sigma (Sigma-Aldrich, St. Louis, Mo.); Stratagene (Stratagene Cloning Systems, La Jolla, Calif.); Qiagen (Qiagen, Inc., Valencia, Calif.); Takara (Takara Bio USA, Madison, Wis.); Thomson Instrument (Thomson Instrument Co., Oceanside, Calif.); V&P Scientific (V&P Scientific, Inc., San Diego, Calif.); and Zinsser (Zinsser North America, Northridge, Calif.).

Example 1

Cloning of Kudzu Isoprene Synthase for Expression in Recombinant Bacteria

In this example, methods used to produce kudzu isoprene synthase (IspS) in *E. coli* are described. The protein sequence for the kudzu (*Pueraria montana*) isoprene synthase gene (IspS) was obtained from GenBank (AAQ84170). A kudzu isoprene synthase gene, optimized for *E. coli* codon usage, was purchased from DNA2.0 (Menlo Park, Calif.), and is set forth as SEQ ID NO:1 (FIG. 1). The isoprene synthase gene was removed from the supplied plasmid by restriction endonuclease digestion with BspLU11I/PstI, gel-purified, and ligated into pTrcHis2B (Invitrogen) that had been digested with NcoI/PstI. The construct was designed such that the stop codon in the isoprene synthase gene was 5' to the PstI site. As a result, when the construct was expressed the His-Tag is not attached to the isoprene synthase protein. The resulting plasmid, pTrcKudzu, was verified by sequencing.

The isoprene synthase gene was also cloned into pET16b (Novagen). In this case, the isoprene synthase gene was inserted into pET16b such that the recombinant isoprene synthase protein contained the N-terminal His tag. The isoprene synthase gene was amplified from pTrcKudzu by PCR using the primer set pET-His-Kudzu-2F: 5'-CGTGAGATCA TATGTGTGCG ACCTCTTCTC AATTTAC (SEQ ID NO:3) and pET-His-Kudzu-R: 5'-CGGTCGACGG ATCCCTGCAG TTAGACATAC ATCAGCTG (SEQ ID NO:4). These primers added an NdeI site at the 5'-end and a BamH1 site at the 3' end of the gene respectively. The plasmid pTrcKudzu, described above, was used as template DNA, HERCULASE DNA polymerase (Stratagene) was used according to manufacturer's directions, and primers were added at a concentration of 10 pM. The PCR was carried out in a total volume of 25 µl. The PCR product was digested with NdeI/BamH1 and cloned into pET16b digested with the same enzymes. The ligation mix was transformed into *E. coli* Top10 (Invitrogen) and the correct clone selected by sequencing. The resulting plasmid designated pETNHisKudzu is then transformed into BL21(λDE3)pLysS (Novagen) cells for expression from the T7 promoter.

The kudzu isoprene synthase gene was also cloned into the low copy number plasmid pCL1920 (Lerner and Inouye, Nucl Acids Res, 18:4631, 1990). Primers were used to amplify the kudzu isoprene synthase gene from pTrcKudzu described above. The forward primer added a HindIII site and an *E. coli* consensus RBS to the 5' end. The PstI cloning site was already present in pTrcKudzu just 3' of the stop codon so the reverse primer was constructed such that the final PCR product includes the PstI site. The sequences of the primers were: HindIII-rbs-Kudzu F: 5'-CATATGAAAG CTTG-TATCGA TTAAATAAGG AGGAATAAAC C (SEQ ID NO:5) and BamH1-Kudzu R: 5'-CGGTCGACGG ATCCCT-GCAG TTAGACATAC ATCAGCTG (SEQ ID NO:4). The PCR product was amplified using HERCULASE DNA polymerase (Stratagene) with primers at a concentration of 10 pM and with 1 ng of template DNA (pTrcKudzu). The amplification protocol included 30 cycles of (95° C. for 1 minute, 60° C. for 1 minute, 72° C. for 2 minutes). The product was digested with HindIII and PstI and ligated into pCL1920, which had also been digested with HindIII and PstI. The ligation mix was transformed into *E. coli* Top10. Several transformants were verified by sequence analysis. The resulting plasmid was designated pCL-lac-Kudzu.

In order to remove the beta-lactamase gene, pTrcKudzu was digested with BspHI, treated with shrimp alkaline phosphatase (SAP), incubated at 65° C. for 10 min to heat kill the SAP, then end-filled by incubating with 2 units of Klenow fragment (New England BioLabs) and dNTPS. The 5 kb fragment was purified from an agarose gel and ligated to the Kan(R) gene. The Kan(R) gene was prepared by PCR amplification from pCR-Blunt-II-TOPO (Invitrogen) using primers MCM22 and MCM23 and Taq DNA polymerase according to the Manufacturer's instructions. The PCR fragment was digested with HindIII and PvuI, and end-filled using Klenow Fragment and dNTPs. The ligation mixture was transformed into *E. coli* Top 10 chemically competent cells and a transformant carrying a plasmid conferring kanamycin resistance, pTrcKudzu(kan), was selected on Luria Agar containing kanamycin (50 µg/ml). The sequences of the primers were: MCM22 5'-gatcaagctt AACCGGAATTGCCAGCTG (SEQ ID NO:15); and MCM23 5'-gatccgatcgTCAGAA-GAACTCGTCAAGAAGGC (SEQ ID NO:16).

Example 2

Cloning of Poplar Isoprene Synthase for Expression in Recombinant Bacteria

In this example, methods used to produce poplar isoprene synthase (IspS) in *E. coli* are described. The protein sequence for the poplar (*Populus alba* x *Populus tremula*) isoprene synthase (Schnitzler et al., Planta 222:777-786, 2005) was obtained from GenBank (CAC35696). A gene, codon optimized for *E. coli*, was purchased from DNA2.0 and is set forth as SEQ ID NO:6 (FIG. 3). The isoprene synthase gene was removed from the supplied plasmid (p9796-poplar) by restriction endonuclease digestion with BspLU11I/PstI, gel-purified, and ligated into pTrcHis2B that had been digested with NcoI/PstI. The construct is cloned such that the stop codon in the insert is before the PstI site, which results in a construct in which the His-Tag is not attached to the isoprene synthase protein. The resulting plasmid, pTrcPoplar, was verified by sequencing using commercially available primers that hybridize within the vector sequence (Forward and Reverse), as well as the primer Poplar InSeq 5'-GAGAAAATCG GTAAGGAACT GG (SEQ ID NO:8).

Example 3

Isoprene Production in Recombinant Bacteria

In this example, methods used to produce and measure isoprene in recombinant *E. coli* are described.

I. Determination of isoprene Production

For the shake flask cultures, one ml of a culture was transferred from shake flasks to 20 ml CTC headspace vials (Agilent vial Catalog No. 5188 2753, and cap Catalog No. 5188 2759). The cap was screwed on tightly and the vials incubated at the equivalent temperature with shaking at 250 rpm. After 30 minutes, the vials were removed from the incubator and analyzed as described below. In cases where isoprene production in fermentors was determined, samples were taken from the off-gas of the fermentor and analyzed directly.

The analysis was performed using an Agilent 6890 GC/MS system interfaced with a CTC Analytics CombiPAL autosampler operating in headspace mode. An Agilent HP-5MS GC/MS column (30 m×0.25 mm; 0.25 µm film thickness) was used for separation of analytes. The sampler was set up to inject 500 µL of headspace gas. The GC/MS method utilized helium as the carrier gas at a flow of 1 ml/min. The injection port was held at 250° C. with a split ratio of 50:1. The oven temperature was held at 37° C. for the 2 min duration of the analysis. The Agilent 5793N mass selective detector was run in single ion monitoring (SIM) mode on m/z 67. The detector was switched off from 1.4 to 1.7 minutes to allow the elution of permanent gases. Under these conditions, isoprene(2-methyl-1,3-butadiene) was observed to elute at 1.78 minutes. A calibration table was used to quantify the absolute amount of isoprene and was found to be linear from 1 µg/L to 200 µg/L. The limit of detection was estimated to be 50 to 100 ng/L using this method.

II. Production of isoprene in Shake Flasks

The vectors described above were introduced into *E. coli* strain BL21(λDE3)pLysS (Novagen) to produce strains BL21/ptrcKudzu, BL21/pCL-lac-Kudzu and BL21/pETHis-Kudzu. The strains were spread for isolation onto LA (Luria agar) containing the appropriate antibiotic (50 µg/ml carbenicillin for BL21/ptrcKudzu and BL21/pETHisKudzu or 50 µg/ml spectinomycin for BL21/pCL-lac-Kudzu) and incubated overnight at 37° C. Single colonies were inoculated into 250 ml baffled shake flasks containing 20 ml Luria Bertani broth (LB) and the appropriate antibiotic. Cultures were grown overnight at 20° C. with shaking at 200 rpm. The $OD_{600}$ of the overnight cultures was measured and the cultures were diluted into a 250 ml baffled shake flask containing 30 ml MAGICMEDIA expression medium (Invitrogen) containing the appropriate antibiotic to an $OD_{600}$ ~0.05. The culture was incubated at 30° C. with shaking at 200 rpm. When the $OD_{600}$ ~0.5-0.8, 400 µM IPTG was added and the cells were incubated for a further 6 hours at 30° C. with shaking at 200 rpm. At 0, 2, 4 and 6 hours after induction with IPTG, 1 ml aliquots of the cultures were collected, the $OD_{600}$ was determined and the amount of isoprene produced was measured as described above.

III. Production of Isoprene from BL21/ptrcKudzu in 14 Liter Fermentation

Large-scale production of isoprene from *E. coli* containing the recombinant kudzu isoprene synthase gene was determined from a fed-batch culture. The recipe for the fermentation media (TM2) per liter of fermentation medium was as follows: $K_2HPO_4$ 13.6 g, $KH_2PO_4$ 13.6 g, $MgSO_4*7H_2O$ 2 g, citric acid monohydrate 2 g, ferric ammonium citrate 0.3 g, $(NH_4)_2SO_4$ 3.2 g, yeast extract 5 g, 1000× Modified Trace Metal Solution 1 ml. All of the components were added together and dissolved in $diH_2O$. The pH was adjusted to 6.8 with potassium hydroxide (KOH) and qs to volume. The final product was filter sterilized with 0.22 μM filter, but not autoclaved. The recipe for 1000× Modified Trace Metal Solution was as follows: Citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO*7H_2O$ 1 g, $CuSO_4*5H_2O$ 100 mg, $H_3BO_3$ 100 mg, $NaMoO_4*2H_2O$ 100 mg. Each component was dissolved one at a time in $diH_2O$, the pH was adjusted to 3.0 with HCl/NaOH, then qs to volume and filter sterilized with a 0.22μfilter.

This experiment was carried out in 14 L bioreactor to monitor isoprene formation from glucose at the desired fermentation, pH 6.7 and temperature 34° C. An inoculum of *E. coli* strain BL21/ptrcKudzu taken from a frozen vial was prepared in soytone-yeast extract-glucose medium in two 600 ml flasks. After the inoculum grew to $OD_{550}$=0.6, two 600 ml flasks were centrifuged and the contents resuspended in 70 ml supernatant to transfer the cell pellet (70 ml of OD 3.1 material) to the bioreactor. At various times after inoculation, samples were removed and the amount of isoprene produced was determined as described above.

Example 4

Selection of Sites for Improvement of Plant Isoprene Synthases

The isoprene synthases of plants were expected to be homologous to the terpene synthases. The three-dimensional structures of two homologous terpene synthases have been determined from bornyl diphosphate synthase (pdb entry 1N1B) and 5-epi-aristolochene synthase (pdb entry 5EAU). These enzymes share only 32% homology but their tertiary structure is conserved. In addition, the structures of intermediate complexes with both enzymes have shown that not only tertiary folding, but also detailed interactions in the active sites of these enzymes are highly conserved.

The kudzu and poplar isoprene synthases have higher sequence identity than was seen between the bornyl diphosphate synthase and the 5-epi-aristolochene synthase as shown in Table 4-1 below.

TABLE 4-1

| Percent Identity of Various Enzymes | | | |
|---|---|---|---|
| | BDP-synthase | 5EA-synthase | Kudzu IspS |
| Poplar IspS | 40.1 | 32.9 | 54.4 |
| Kudzu IspS | 40.7 | 33.8 | |
| 5ES synthase | 31.9 | | |

A homology model of the poplar isoprene synthase has been made based on the bornyl diphosphate synthase (BDP-synthase) pdb entry 1N24 (~40% sequence identity). The homology model appears to be plausible based on the close similarity of 10 trial models created using the program MOE written and supported by The Chemical Computing Group, Inc. The plausibility is based on the conservation of common amino acid residues at sites found to be involved in catalysis in the BDP-synthase structure.

A comparison of the active site from the structure of BDP-synthase and the homology model of poplar IspS indicates that the active site involved in metal ion binding and phosphate recognition is conserved. In particular, Lys 272, Asp 309, Asp 313, Glu 387, Arg 450 and Asn 453 of poplar IspS were observed to overlap equivalent residues in BDP-synthase. In this example, amino acid residue positions for poplar IspS are derived from SEQ ID NO:7. The positioning of an intermediate of the BDP-synthase was also compared with the poplar IspS homology model. Based on this, it was possible to identify the analogous binding region and the approach direction that isopentenyl diphosphate would require in order to bind and react with the poplar IspS enzyme.

A homology model of the kudzu isoprene synthase has been made based on bornyl diphosphate synthase pdb entry 1N24 having (~40% sequence identity). A comparison of the active site from the structure of BDP-synthase with the homology model of kudzu IspS indicates that numerous active site residues involved in metal ion binding and phosphate recognition are conserved. In particular, Arg 269, Asp 306, Asp 310, Glu 384, Arg 450 and Asn 453 of kudzu IspS were observed to overlap equivalent residues in BDP-synthase.

A comparison of the active site residues identified in the homology models of poplar and kudzu IspS revealed that residues from one homology model are also quite homologous with similar residues, appearing with only minor shifts in the relative position numbers for some of the residues, in the other homology model. Based on the homology models, sites in poplar and kudzu IspS were identified as candidates for mutagenesis to produce variant IspS enzymes with improved performance. Briefly, sites were selected in the IspS that might alter the interaction of the metal binding, the diphosphate recognition, the IPP chain binding and/or the approach to the active site.

I. Diphosphate/Metal Binding Sites

The side chains of amino acid residues in the poplar IspS that are found in proximity to the metal and diphosphate (DPP) binding side chains were identified. These residues include Phe 384, Tyr 402, Ala 406, Ser 409, Ala 460 and Asn 469. The inventors note that Lys 272 is incorrect based on homology to other known poplar IspS sequences, which have an Arg at this position.

II. Substrate Access Loop

The substrate access loop of poplar IspS is in a region that deviates from the BDP-synthase structure. In the BDP-synthase structure the residues form a segment that creates a cover. Without being bound by theory, the inventors expect that this segment in the actual three-dimensional structure of poplar IspS will form a similar structure. As such the residues in this loop, including residues 455-466, will be in a position to alter the activity of the poplar IspS enzyme. In the poplar IspS enzyme residues 454-466 have the following sequence: LASASAEIARGET (SEQ ID NO:9).

III. Isoprenyl Binding Site

The complex of BDP-synthase and the product of the reaction, bornyl diphosphate (pdb entry 1N24), was used to identify residues in the poplar model that may modulate substrate specificity and/or reaction rate (altered on and off rates of substrate and product). These residues include Arg 274, Trp 281 Phe 302, Val 305, Ser 411, Gln 415, Phe 449, Ser 537 and Glu 540.

TABLE 4-2

Candidate Mutagenesis Sites

| | Poplar Amino Acid | Kudzu Amino Acid/codon |
|---|---|---|
| DPP/metal sites | Phe 384 | Phe 381/1141-1143 |
| | Tyr 402 | Tyr 399/1195-1197 |
| | Ala 406 | Ala 403/1207-1209 |
| | Ser 409 | Ser 406/1216-1218 |
| | Asn 469 | Asn 469/1405-1407 |
| Extra DPP sites | Tyr 312 | Tyr 309/925-927 |
| | Asp 313 | Asp 310/928-930 |
| | Leu 380 | Leu 377/1129-1131 |
| | Glu 387 | Glu 384/1150-1152 |
| | Asn 404 | Asn 402/1204-1206 |
| | Ser 410 | Ser 407/1219-1221 |
| N_terminal access segment | 22 | 20/58-60 |
| | 23 | 21/61-63 |
| | 24 | 22/64-66 |
| | 25 | 23/67-69 |
| | 26 | 24/70-72 |
| | 27 | 25/73-75 |
| Substrate access loop | Leu 454 | Ala 456/4102-4104 |
| | Ala 455 | Thr 457/4105-4107 |
| | Ser 456 | Ser 458/4108-4110 |
| | Ala 457 | Ala 459/4111-4113 |
| | Ser 458 | Ala 460/4114-4116 |
| | Ala 459 | Glu 461/4117-4119 |
| | Glu 460 | Leu 462/4120-4122 |
| | Ile 461 | Glu 463/4123-4125 |
| | Ala 462 | |
| | Arg 463 | Arg 464/4126-4128 |
| | Gly 464 | Gly 465/4129-4131 |
| | Glu 465 | Glu 466/4132-4134 |
| | Thr 466 | Thr 467/4135-4137 |
| | | Thr 468/4138-4140 |
| Isoprenyl binding site | Arg 274 | Arg 271/811-813 |
| | Trp 281 | Trp 278/832-834 |
| | Phe 302 | Phe 299/895-897 |
| | Val 305 | Val 302/904-906 |
| | Ser 411 | Ser 408/1222-1224 |
| | Gln 415 | |
| | Phe 449 | Phe 449/1345-1347 |
| | Ser 537 | Ser 458/1372-1374 |
| | Glu 540 | Tyr 531/1591-1593 |
| Extra Isoprenyl sites | Gly 412 | Gly 409/1225-1227 |
| | Leu 414 | Ala 411/1231-1233 |
| | Leu 416 | Leu 413/1237-1239 |
| | Leu 521 | Met 523/1567-1569 |
| | Ser 525 | Ser 527/1579-1581 |

Example 5

Mutation of Non-Conserved Cysteines in Kudzu Isoprene Synthase

Figure 5:
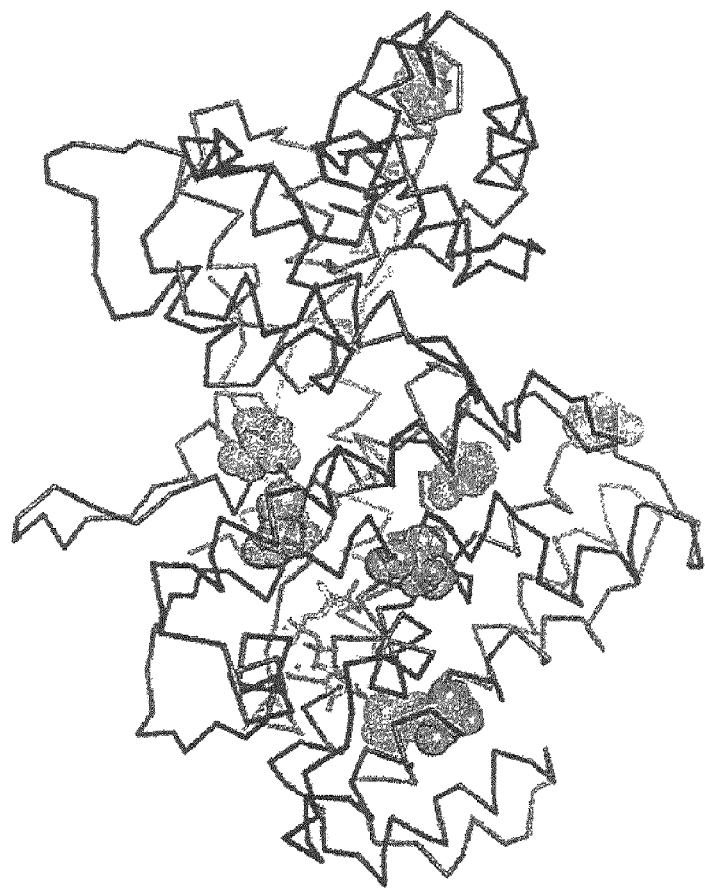
FIG. 5 provides a kudzu isoprene synthase homology model with the cysteine residues highlighted as space filling molecules.
Figure 6:
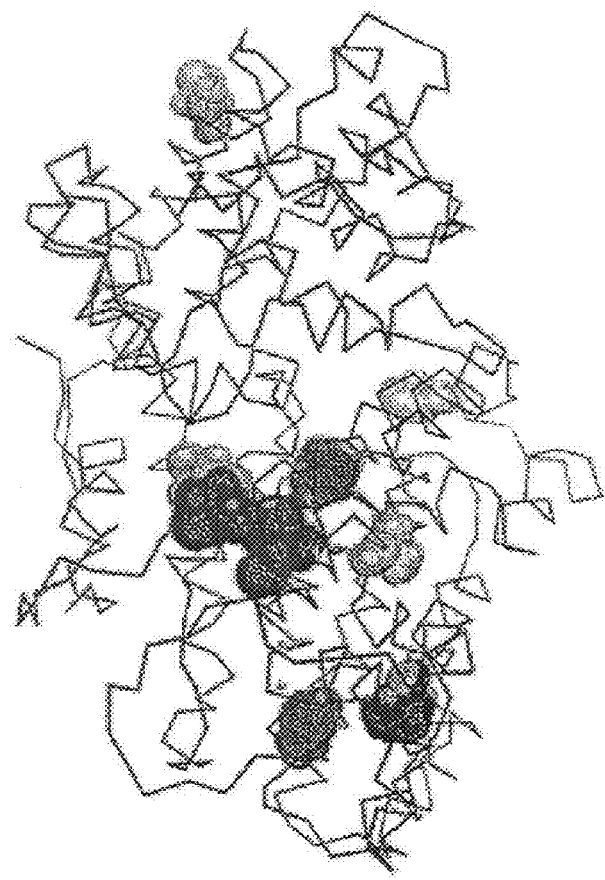
FIG. 6 provides a poplar isoprene synthase homology model with the cysteine residues highlighted as space filling molecules (dark grey). In addition, the cysteine residues from the kudzu model of FIG. 5 are superimposed on the poplar model as space filling molecules (light grey).

The kudzu and poplar isoprene synthase (IspS) homology models, based on the bornyl diphosphate synthase crystal structure, were compared with respect to the positions of the cysteine residues. Cysteines have the potential to form disulfide bonds and stabilize structures. The non-conserved cysteines, contemplated to affect solubility and/or activity, were altered by site-directed mutagenesis. The kudzu IspS amino acid sequence used for the modeling is shown in FIG. 2 (SEQ ID NO:2). There are eight cysteines in kudzu IspS at positions 57, 291, 343, 378, 421, 446, 451 and 529 (relative to the mature form of the protein) as shown in the homology model of FIG. 5. In contrast, there are five cysteines in poplar IspS amino acid sequence has five cysteines, as shown in the homology model of FIG. 6 upon which the kudzu cysteines are superimposed. Several of the cysteines are apparently conserved between the poplar and kudzu IspS sequences indicating that these positions are important in stabilizing the structure, activity and/or other protein function. The remaining cysteines (nonconserved residues 57, 291, 421 and 446) in kudzu were mutated to serine as described herein.

I. Mutagenesis

The QUIKCHANGE® Multi-Site Directed Mutagenesis Kit (Stratagene) was used as per the manufacturer's directions. The following primers were utilized for mutagenesis:

```
C57S-F
                                     (SEQ ID NO: 10)
5'-CTGGAGGAAGAAGTTCGC TCCATGATCAACCGTGTAGAC;

C291S-F
                                     (SEQ ID NO: 11)
5'-CGCCAGACCCGCAGTTTGGTGAA TCTCGCAAAGCTGTTACTAAAAT
G;

C421S-F
                                     (SEQ ID NO: 12)
5'-CGCCGTCTTACTTTTCCGTA TCCCAGCAGCAGGAAGACATC;

C446S-F
                                     (SEQ ID NO: 13)
5'-CATGGTCTGGTGCGTTCTAGC TCCGTTATCTTCCGCCTGTGC;
and C421S-R
                                     (SEQ ID NO: 14)
5'-GATGTCTTCCTGCTGCTG GGATACGGAAAAGTAAGACGGCG.
```

The plasmid pTrcKudzu(kan) described in Example 1 was used as template DNA. The primers C57S-F, C291S-F, C421S-F, and C446-F were combined in a single reaction (100 pmol). Template DNA was added (~200 nanograms) and 0.5 μl of Quiksolution was added to the recommended volumes of enzyme and buffer. The PCR reaction was carried out in an Eppendorf PCR machine using an annealing temperature of 55° C. and an extension time of 12 minutes for 30 cycles. Other parameters of the cycle were as indicated in the instructions. The PCR mix was treated with DpnI for 4 hours at 37° C. (2×1 μl for 2 h each) and then 5 μl of the reaction were transformed into E. coli Top10 (Invitrogen) chemically competent cells and plated on Luria agar containing kanamycin (50 μg/ml). After overnight incubation at 37° C., several colonies were picked and inoculated into 5 ml of Luria Broth containing kanamycin (50 μg/ml). The plasmids were isolated using the QIAprep Spin Miniprep kit (Qiagen), and the IspS genes were sequenced in their entirety. Various single and combinations of mutations were made as indicated in the Table 5-1 below.

TABLE 5-1

BL21(λDE3) Cells Transformed with Mutated pTrcKudzu Plasmids*

| Strain* | C57S | C291S | C421S | C446S |
|---|---|---|---|---|
| C1 | + | + | | |
| C2 | | + | | + |
| C4 | + | + | | + |
| C6 | + | | | + |
| C11 | | | | + |
| C20 | | | + | |
| C6-4 | + | | + | + |

All the variant plasmids were transformed into chemically competent BL21(λDE3) cells (Novagen). In a second reaction pTrcKudzu(kan) and plasmid DNA isolated from C6 were used as templates in a QUIKCHANGE® site directed mutagenesis kit (Stratagene) single site reaction with C421S-F and C421S-R primers. After confirmation by sequencing, two additional strains were obtained.

II. Cell Growth and Isoprene Production

Figure 7:
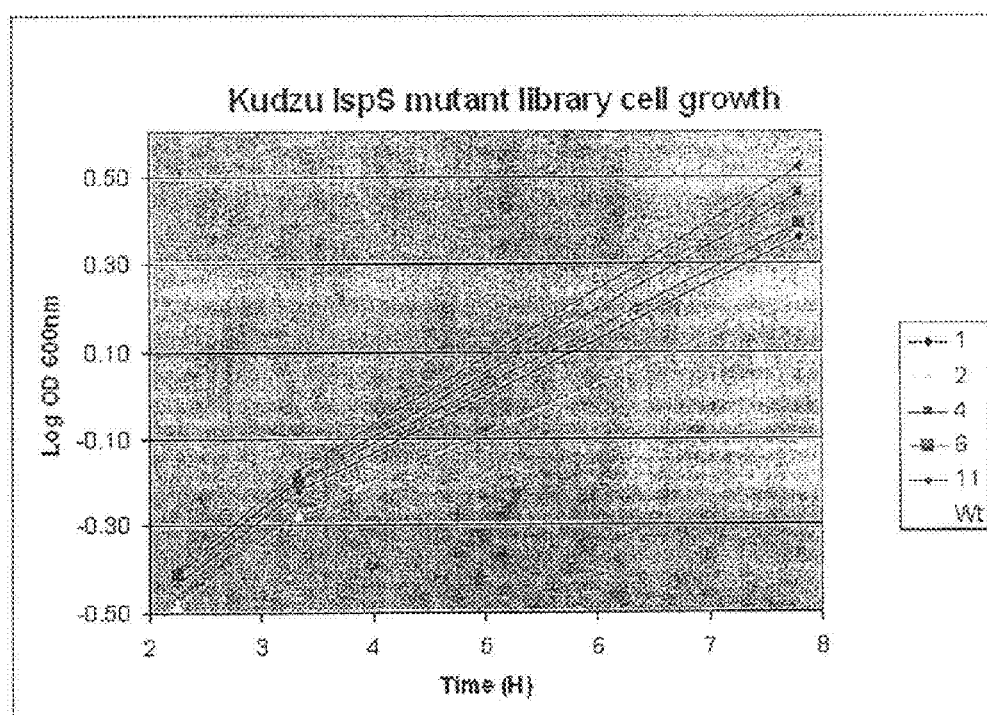
FIG. 7 provides a graph showing the growth curves of the kudzu IspS cysteine mutants of Example 5.

Cells were grown in 5 ml tubes containing Luria Broth supplemented with 50 mg/L kanamycin at 30° C. overnight with agitation. These cultures were diluted into TM3 broth supplemented with 10 g/L glucose and 50 mg/L kanamycin. The culture volume was 25 ml in a 250 ml baffled Bellco Delong flask in which cells were grown at 30° C. with agitation (225 rpm). Samples were taken aseptically, as indicated, for optical density measurements at $A_{600}$. The results are shown in FIG. 7. The cultures were induced at 3.33 hrs with 200 µM IPTG and allowed to continue growth until harvest at 7.8 hr. The cultures were centrifuged at 10,000×g for 10 min, the supernatants decanted and the cell pellets frozen at −80° C. overnight.

Figure 8:
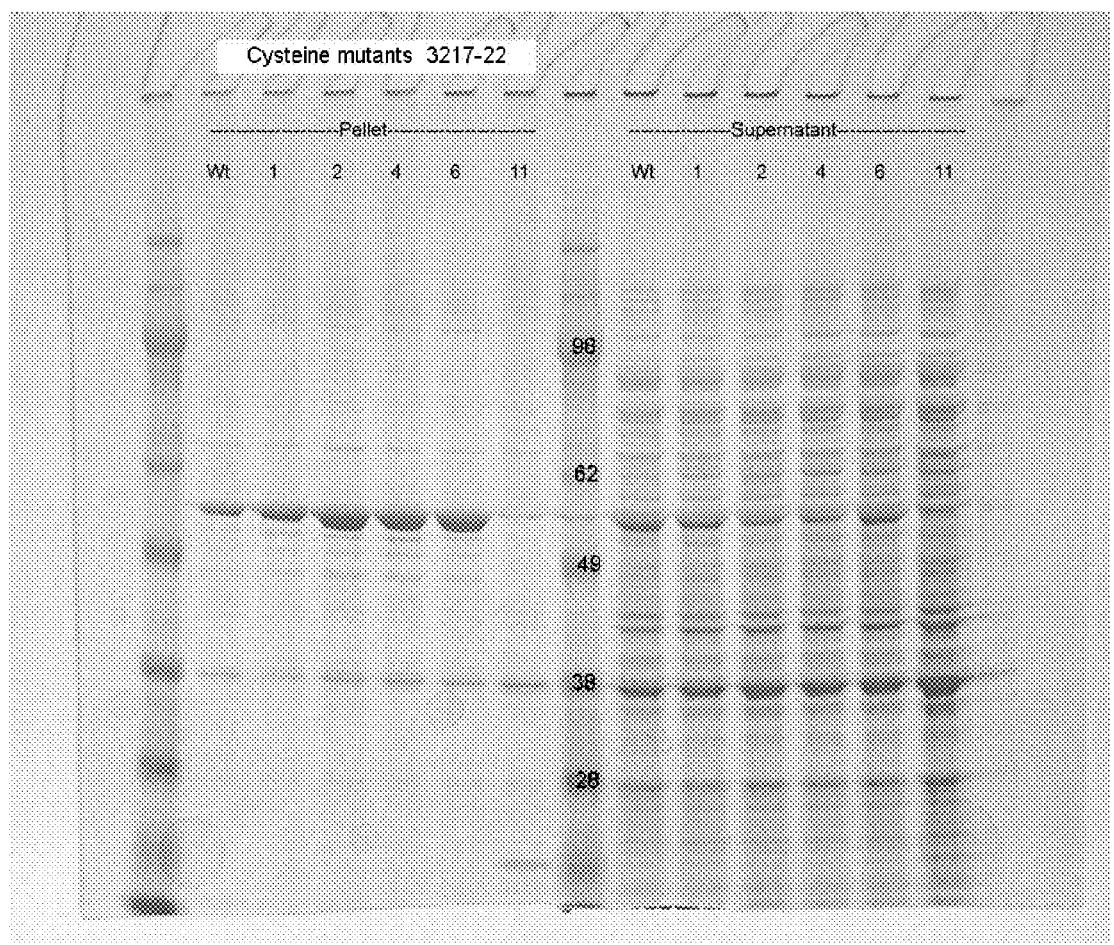
FIG. 8 shows an SDS-PAGE analysis of kudzu IspS cysteine mutants from lysed cells. Pellet and supernatant fractions were prepared by centrifugation.

Frozen cell pellets were thawed and resuspended in 2 ml PEB (50 mM Tris-HCl, pH 8.0, 20 mM MgCl, 2 mM dithiothreitol, and 50% [v/v] glycerol). Cells were lysed by French pressure cell disruption, one pass, at 20,000 psi. The lysate was centrifuged for 15 min at 10,000×g. The supernatants were decanted and the pellets resuspended in 2 ml PEB. The pellets and supernatants were analyzed by SDS-PAGE, 4-12% NuPage gels (Invitrogen), run in MES buffer under reducing conditions. The molecular weight standard was See-Blue2 (Invitrogen). The results are shown in FIG. 8. The IspS protein concentrations were estimated using the BCA assay (Pierce) using BSA as standard (Table 5-2).

III. Assays for Isoprene Synthase Activity and Solubility

Briefly the activity of the supernatants was measured by reaction with DMAPP, and the isoprene evolved was quantified by GC/MS.

Headspace Assay. A sample of 200 µl of the desired culture is inoculated into 2 ml CTC headspace vials (Agilent vial Catalog No. 5188 2753, and cap Catalog No. 5188 2759). The cap was screwed on tightly and the vials were incubated at 37° C. with shaking at 250 rpm. After 30 minutes the vials were removed from the incubator and cooled briefly with ambient tap water. The vials were placed into the CombiPal Headspace auto sampler for analysis by GC-MS. The analysis was performed using an Agilent 6890 GC/MS system interfaced with a CTC Analytics CombiPAL autosampler operating in headspace mode. An Agilent HP-5MS GC/MS column (30 m×0.25 mm; 0.25 µm film thickness) was used for separation of analytes. The sampler was set up to inject 500 µL of headspace gas. The GC/MS method utilized helium as the carrier gas at a flow of 1 ml/min. The injection port was held at 250° C. with a split ratio of 50:1. The oven temperature was held at 37° C. for the 2 min duration of the analysis. The Agilent 5793N mass selective detector was run in single ion monitoring (SIM) mode on m/z 67. The detector was switched off from 1.4 to 1.7 minutes to allow the elution of permanent gases. Under these conditions isoprene(2-methyl-1,3-butadiene) was observed to elute at 1.78 minutes. A calibration table was used to quantify the absolute amount of isoprene and was found to be linear from 1 µg/L to 200 µg/L. The limit of detection was estimated to be 50-100 ng/L using this method.

DMAPP Assay. An aliquot of 95 µl of the supernatant fraction from the centrifuged French Pressure cell lysate was added to the headspace vials. A 5 µL aliquot of 8 mM DMAPP in 100 mM potassium phosphate buffer, pH 8.2 was added, the vials sealed and allowed to incubate at room temperature for 30 min. The amount of isoprene produced was measured by GC/MS as described above and reported in Table 5-2.

TABLE 5-2

Isoprene Synthase Activity from Crude Extracts of Cysteine Mutants

| Supernatant | Activity (mU/ml) | Protein (mg/ml) | Specific Activity (mU/mgP) |
|---|---|---|---|
| Wt | 59.0 | 2.48 | 23.79 |
| C1 | 5.3 | 2.64 | 2.01 |
| C2 | 0.2 | 3.52 | 0.06 |
| C4 | 0.5 | 3.22 | 0.16 |
| C6 | 9.0 | 3.32 | 2.71 |
| C11 | 0.1 | 4.26 | 0.03 |

The values shown in Table 5-2 are averages of reactions with two different concentrations of extract. All proteins containing any of the cysteine mutations resulted in severe diminution of enzyme activity and an apparent decrease of soluble protein as judged by a relative increase in the proportion of protein in the insoluble (pellet) fraction.

Example 6

Mutation of Residues in Poplar Isoprene Synthase

Alignment of the amino acid sequences of kudzu and poplar isoprene synthases with other synthases was done using Vector Nti (Invitrogen). The aligned sequences included: beta-ocimene synthase *Lotus corniculatus* (AAT86042); putative terpene synthetase *Medficago trunculata* (AAV36465); hypothetical protein *Vitis vinifera* (can65805); hypothetical protein *Vitis vinifera* (CAN62729); pinene synthase *Quercus ilex* (CAK55186); IspS *Pueraria montana* (kudzu) Sharkey (AAQ84170); monoterpene synthase *Eucaliptus globulus* (BAF02832); IspS *Populus nigra* Fortunati (CAL69918); IspS *Populus tremuloides* Sharkey (AAQ16588); IspS *Populus alba* (BAD98243); and IspS *Populus alba* x *tremula* Zimmer (CAC35696). The sequence from the database of *Populus alba* x *tremula* (CAC35696) exhibited different amino acids at positions 272 and 497 that were otherwise highly conserved. Additionally based on analysis of the homology model of poplar IspS, position 453 was identified as a third candidate for mutagenesis.

I. Mutagenesis

The QUIKCHANGE® Multi-Site Directed Mutagenesis kit (Stratagene) was used as per the manufacturer's directions to introduce the following mutations singly and in combination into the *Populus alba* x *tremula* IspS sequence (SEQ ID NO:7): K272R; C497W; and N453D. The following primers were utilized for mutagenesis:

```
Poplar K272R
                                          (SEQ ID NO: 17)
5'-ccaaactgcacttcg ctcgtgaccgcctgattgag;

Poplar N453D
                                          (SEQ ID NO: 18)
5'-atctttcgcctgtgcgacgacctggcaagc;
and Poplar C497W
                                          (SEQ ID NO: 19)
5'-tgaatctgatcgacgaaacctggaagaaaatgaacaaagaaaaac.
```

The following primer,
Poplar InSeq,
5'-gagaaaatcggtaaggaactgg (SEQ ID NO: 8)
was used for sequencing.

Mutagenesis was done according to the manufacturer's directions, with all three mutagenesis primers being added to a single reaction mix (100 ng each) with pTrcPoplar as the template DNA (100 ng). Addition of 0.5 µl of Quik Solution aided the mutagenesis reaction. The suggested PCR cycle was run with an annealing temperature of 55° C. and an extension time of 12 min. Other parameters were as indicated in the instructions. The PCR mix was digested with DpnI for 4 hrs at 37° C. (1 µl each×2 h) and then 5 µl of the reaction was transformed into E. coli Top10 chemically competent cells (Invitrogen). Several colonies were selected and grown up in 5 ml of Luria Broth (LB) containing carbenicillin (50 µg/ml). Plasmids were isolated using the Qiagen QIAprep spin miniprep kit and sent for sequencing using forward and reverse primers that hybridized to the vector, as well as the Poplar InSeq primer.

The resulting variants of pTrcPoplar were obtained: pTrcPoplar K272R, pTrcPoplar K272R/N453D; pTrcPoplar K272R/N453D/C497W; and pTrcPoplar 272R/497W. These plasmids were transformed into BL21(λDE3)pLysS chemically competent cells (Novagen) for analysis. The variants were analyzed for headspace activity (production of isoprene from whole cells), solubility, and specific activity.

II. Cell Growth and Isoprene Production

The variants, the parent Poplar strain, and the strain containing pTrcKudzu were grown overnight at 37° C. in 5 ml of Luria Bertani medium containing either carbenicillin (50 µg/ml-Poplar strains) or kanamycin (50 µg/ml-Kudzu strain). These cultures were diluted into TM3 broth to an $OD_{600}$ of 0.05, supplemented with 10 g/L glucose and either 50 µg/ml carbenicillin (Poplar mutants and wild type) or 50 mg/L kanamycin (BL21/pTrcKudzu). The recipe for TM3 broth is as follows: $K_2HPO_4$ (13.6 g/l) $KH_2PO_4$ (13.6 g/l), $MgSO_4*7H_2O$ (2 g/l) Citric Acid Monohydrate (2 g/L) Ferric Ammonium Citrate (0.3 g/L) $(NH_4)_2SO_4$ (3.2 g/L) yeast extract (0.2 g/L) 1 ml of 1000× Trace Elements solution, pH adjusted to 6.8 with ammonium hydroxide qs to volume with sterile $diH_2O$ and filter sterilized with a 0.22 micron filter. The recipe for 1000× Trace Elements solution is as follows: Citric Acids*$H_2O$ (40 g/L), $MnSO_4*H_2O$ (30 g/L), NaCl (10 g/L), $FeSO_4*7H_2O$ (1 g/L), $CoCl_2*6H_2O$ (1 g/L), $ZnSO*7H_2O$ (1 g/L), $CuSO_4*5H_2O$ (100 mg/L), $H_3BO_3$ (100 mg/L), $NaMoO_4*2H_2O$ (100 mg/L). Each component was dissolved one at a time in $diH_2O$, pH adjusted to 3.0 with HCl/NaOH, qs to volume and filter sterilized with a 0.22 micron filter.

The diluted culture volume was 25 ml in a 250 ml baffled Bellco Delong flask for growth at 30° C. with agitation (225 rpm). Samples were taken aseptically, as indicated, for optical density measurements at $A_{600}$. Two sets of cultures were set up, one for induction with 0.2 mM IPTG and one that remained un-induced. After 3 hours of growth at 30° C. with shaking at 200 rpm ($OD_{600}$~0.5), one set of the cultures was induced with 0.2 mM IPTG and incubated for a further 3 h at 30° C. with shaking at 200 rpm, the un-induced set was further incubated for the same amount of time. The $OD_{600}$ was determined for all cultures prior to the induction time (3 h post inoculation) and at the time of the measurement of isoprene by the Headspace assay (3 h post-induction, total of 6 h of growth). The cell cultures were centrifuged at 7000×g for 15 minutes in a Sorvall superspeed centrifuge to pellet the cells. The supernatant was removed and the cell pellet frozen for use in an in vitro assay for isoprene synthase activity. Results of the growth and headspace assays are shown in the following tables.

TABLE 6-1

Growth of E. coli Strains Expressing Poplar IspS Variants ($OD_{600}$ values)

| Strain | Pre-induction (after 3 h growth) | Post-induction (3 h with IPTG) | Non-induced (after 6 h growth) |
|---|---|---|---|
| pTrcPoplar K272R | 0.49 | 3.3 | 4.7 |
| pTrcPoplar K272R/N453D | 0.48 | 3.7 | 4.8 |
| pTrcPoplar K272R/N453D/C497W | 0.41 | 3.1 | 5.1 |
| pTrcPoplar K272R/497W H2 | 0.45 | 0.8 | 0.97 |
| pTrcPoplar WT | 0.49 | 3.5 | 4.7 |
| pTrcKudzu WT | 0.44 | 3.3 | 4.2 |

TABLE 6-2

Production of Isoprene by E. coli Strains Expressing Poplar IspS Variants (µg/L)

| Strain | Pre-induction (after 3 h growth) | Post-induction (3 h with IPTG) | Non-induced (after 6 h growth) |
|---|---|---|---|
| pTrcPoplar K272R | n/a | 0 | 0 |
| pTrcPoplar K272R/N453D | n/a | 0 | 0 |
| pTrcPoplar K272R/N453D/C497W | n/a | 0 | 0 |
| pTrcPoplar K272R/497W H2 | n/a | 0 | 0 |
| pTrcPoplar WT | n/a | 0 | 0 |
| pTrcKudzu WT | n/a | 1.3 | 0.29 |

Surprisingly, the strain expressing the kudzu IspS demonstrated any measurable isoprene production. This is unexpected given that kinetic properties of the poplar enzymes were reported in the literature to be superior to those of kudzu enzymes. In particular, the prior art describes the specific activity (U/mg) and $K_m$ (µM) of recombinant kudzu IspS to be 0.075 and 7,700 respectively, native aspen IspS to be 0.5 and 8,000 respectively, and recombinant poplar IspS to be 0.16 and 9,000 respectively (Silver and Fall, J Biol Chem, 270: 13010-1316, 1995; Miller et al., Planta, 213:483-487, 2001; and Sharkey et al., Plant Physiology, 137:700-712, 2005). The published $K_m$ values for the three enzymes are all quite high and within range of each other, but the specific activity for kudzu isoprene synthase is significantly worse than that of the other two isoprene synthases.

III. Assays for Isoprene Synthase Activity and Solubility

By using the DMAPP assay, the activity of isoprene synthase can be measured directly as DMAPP is the direct substrate for the enzyme. The cell pellets of the poplar parent and mutant strains, as well as the wild type kudzu were thawed and resuspended in 2 ml PEB (50 mM Tris-HCl, pH 8.0, 20 mM MgCl, 2 mM dithiothreitol, and 50% [v/v] glycerol). Cells were lysed by French pressure cell disruption, one pass, at 20,000 psi. The lysate (1 ml) was then centrifuged in a microfuge for 20 min at 20,000 rpm at 4° C. The supernatant was removed and the pellet resuspended in 1 ml of PEB. The supernatant and pellet samples were analyzed by SDS-PAGE, and DMAPP assay, while the total protein content was determined by BCA.

TABLE 6-3

DMAPP Assay of Isoprene Production from the
Supernatant of the Centrifuged Cell Lysate

| Strain | OD600 (prior to lysis) | Total Protein (mg/ml) | Isoprene/ Total Protein |
|---|---|---|---|
| Induced | | | |
| pTrcPoplar K272R | 3.3 | 1.70 | 0.03 |
| pTrcPoplar K272R/N453D | 3.6 | 1.3 | 0.08 |
| pTrcPoplar K272R/N453D/C497W | 3.1 | 1.10 | 0.08 |
| pTrcPoplar K272R/497W H2 | 0.803 | 0.80 | 0.11 |
| pTrcPoplar WT | 3.5 | 1.30 | 0.06 |
| pTrcKudzu WT | 3.3 | 1.50 | 11.15 |
| Uninduced | | | |
| pTrcPoplar K272R | 4.7 | 1.7 | 0.26 |
| pTrcPoplar K272R/N453D | 4.8 | 1.8 | 0.07 |
| pTrcPoplar K272R/N453D/C497W | 5.2 | 1.9 | 0.02 |
| pTrcPoplar K272R/497W H2 | 0.969 | 1.0 | 0.17 |
| pTrcPoplar WT | 4.6 | 1.7 | 0.05 |
| pTrcKudzu WT | 4.2 | 1.9 | 1.62 |

Production was normalized to total cell lysate supernatant protein.

TABLE 6-4

DMAPP Assay of Isoprene Production from the Pellet
of the Centrifuged Cell Lysate

| Strain | OD600 (prior to lysis) | Total Protein (mg/ml) | Isoprene/ Total Protein |
|---|---|---|---|
| Induced | | | |
| pTrcPoplar K272R | 3.3 | 1.02 | 0.118 |
| pTrcPoplar K272R/N453D | 3.6 | 1.36 | 0.000 |
| pTrcPoplar K272R/N453D/C497W | 3.1 | 1.49 | 0.040 |
| pTrcPoplar K272R/C497W H2 | 0.80 | 1.38 | 0.043 |
| pTrcPoplar WT | 3.5 | 1.57 | 0.050 |
| pTrcKudzu WT | 3.3 | 1.47 | 0.040 |
| Uninduced | | | |
| pTrcPoplar K272R | 4.7 | 1.40 | 0.170 |
| pTrcPoplar K272R/N453D | 4.8 | 1.53 | 0.120 |
| pTrcPoplar K272R/N453D/C497W | 5.2 | 1.42 | 0.131 |
| pTrcPoplar K272R/C497W H2 | 0.97 | 1.55 | 0.080 |
| pTrcPoplar WT | 4.6 | 1.38 | 0.120 |
| pTrcKudzu WT | 4.2 | 1.55 | 0.120 |

Production was normalized to total cell lysate pellet protein.

The poplar variant K272R/C497W showed a 1.8× increase in activity as compared to the wild type in the supernatant fraction of the induced cultures. Likewise, the poplar variants K272R and K272R/C497W showed a 5.2× and 3.4× increase in activity as compared to the wild type in the supernatant fraction of the uninduced cultures. Moreover the poplar variant K272R showed a 2× increase in activity as compared to wild type in the pellet of the induced cultures. However, the most striking result was that the kudzu IspS is more active than the poplar IspS employed herein (185×). In the above tables, H2 is the name of the clone designated pTrcPoplar K272R/C497W H2.

Example 7

Subcloning of Kudzu Isoprene Synthase

Figure 9:
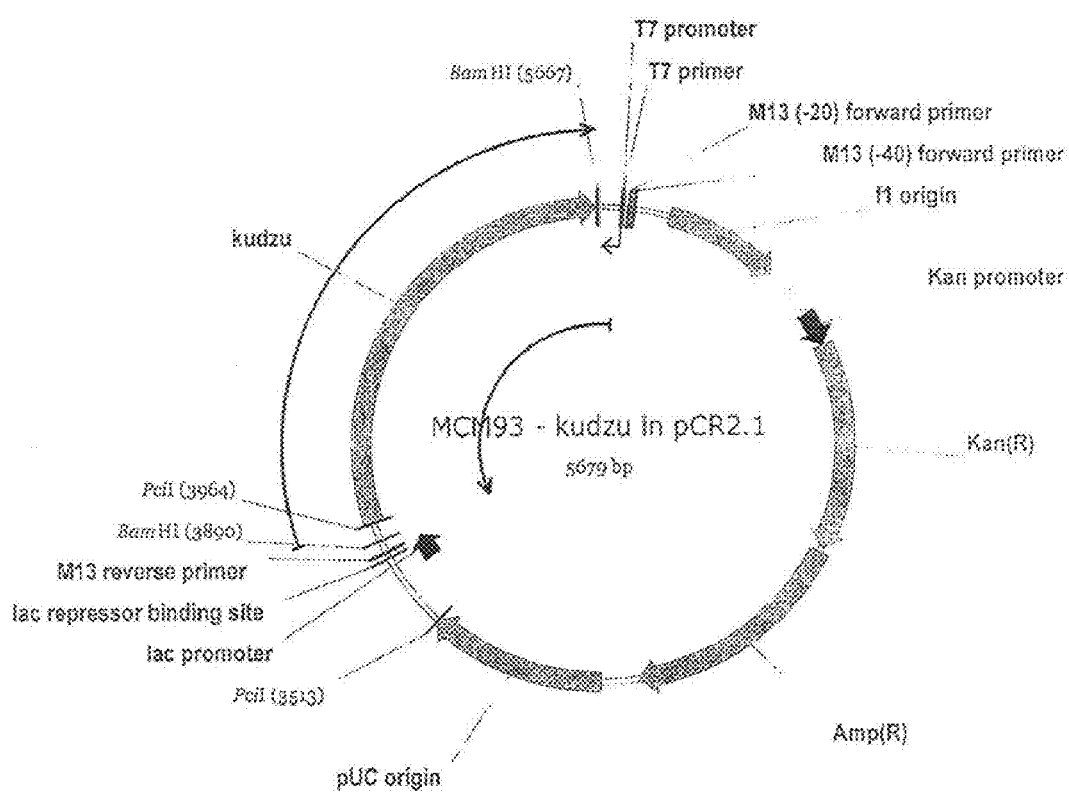
FIG. 9 provides a map of plasmid MCM93 (pCR2.1-Kudzu).

In this Example, methods used in the construction of kudzu isoprene synthase (IspS) SELs are described. To create an expression vector for construction of site evaluation libraries (SEL), the kudzu isoprene synthase gene was subcloned into the pET24d vector (Novagen) from the pCR2.1 vector (Invitrogen). The kudzu IspS gene was amplified from pTrcKudzu template DNA using primers MCM50 5'-GATCATGCAT TCGCCCTTAG GAGGTAAAAA AACATGTGTG CGAC-CTCTTC TCAATTTACT (SEQ ID NO:20); and MCM53 5'-CGGTCGACGG ATCCCTGCAG TTAGACATAC ATCAGCTG (SEQ ID NO:21). PCR reactions were carried out using Taq DNA Polymerase (Invitrogen), and the resulting PCR product was cloned into pCR2.1-TOPO TA cloning vector (Invitrogen), and transformed into E. coli Top10 chemically competent cells (Invitrogen). Transformants were plated on L agar containing carbenicillin (50 µg/ml) and incubated overnight at 37° C. Five ml Luria Broth cultures containing carbenicillin 50 µg/ml were inoculated with single transformants and grown overnight at 37° C. Five colonies were screened for the correct insert by sequencing of plasmid DNA isolated from 1 ml of liquid culture (Luria Broth) and purified using the QIAprep Spin Mini-prep Kit (Qiagen). The resulting plasmid, designated MCM93, contains the kudzu IspS coding sequence in a pCR2.1 backbone (FIG. 9). The sequence of MCM93 (SEQ ID NO:22) is shown in FIG. 10.

Figure 11:
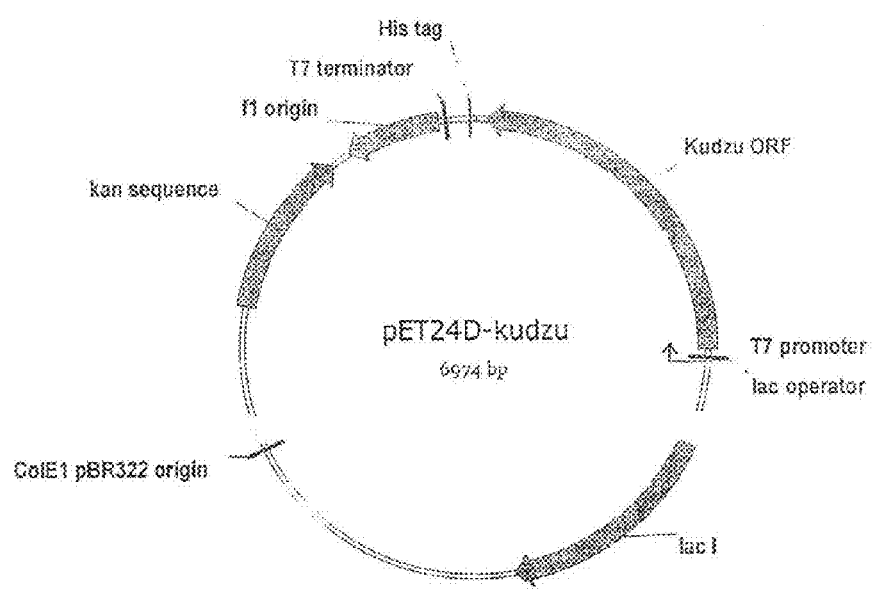
FIG. 11 provides a map of pET24D-Kudzu.

The kudzu coding sequence was removed by restriction endonuclease digestion with PciI and BamH1 (Roche) and gel purified using the QIAquick Gel Extraction kit (Qiagen). The pET24d vector DNA was digested with NcoI and BamHI (Roche), treated with shrimp alkaline phosphatase (Roche), and purified using the QIAprep Spin Mini-prep Kit (Qiagen). The kudzu IspS fragment was ligated to the NcoI/BamH1 digested pET24d using the Rapid DNA Ligation Kit (Roche) at a 5:1 fragment to vector ratio in a total volume of 20 µl. A portion of the ligation mixture (5 µl) was transformed into E. coli Top10 chemically competent cells and plated on L agar containing kanamycin (50 µg/ml). The correct transformant was confirmed by sequencing and transformed into chemically competent BL21(λDE3)pLysS cells (Novagen). A single colony was selected after overnight growth at 37° C. on L agar containing kanamycin (50 µg/ml). A map of the resulting plasmid designated as pET24D-Kudzu is shown in FIG. 11. The sequence of pET24D-Kudzu (SEQ ID NO:23) is shown in FIG. 12. IspS Activity was confirmed using the headspace assay as described in Example 5).

Example 8

Construction of Isoprene Synthase Site Evaluation Libraries (SELs)

In order to improve the kinetic parameters of a plant IspS SELs are prepared at sites selected from homology models of both the kudzu and the poplar IspS enzymes. While it is predicted from the homology models that engineering at the indicated sites would improve both enzymes, in this embodiment, kudzu SELs are described. Kudzu IspS surface sites of interest include but are not limited to: 26 L, 30 E, 31 F, 33 Q, 35 L, 36 E, 37 N, 39 L, 40 K, 41 V, 43 K, 44 L, 61 R, 62 V, 63 D, 65 Q, 87 K, 94 E, 95 N, 99 L, 100 D, 105 N, 137 K, 138 E, 143 G, 144 E, 182 N, 184 L, 185 K, 187 G, 189 N, 190 T, 225 P, 226 H, 247 K, 257 T, 258 E, 259 M, 266 D, 334 N, 353 D, 357 S, 358 I, 361 E, 389 N, 392 I, 393 I, 398 K, 401 E, 421 C, 423 Q, 424 Q, 425 E, 426 D, 430 H, 432 L, 433 R, 434 S, 437 D, 443 R, 462 L, 463 E, 476 H, 478 N, 479 D, 485 Q, 508 D, 513 P, 515 A, 532 Q, 533 Y, 537 L, 538 G, 539 R, 542 Y, 543 A, and 557 P. Kudzu IspS active site positions of interest include but are not limited to: 24 P, 25 N, 309 Y, 310 D, 377 L, 381 F, 384 E, 399 Y, 402 N, 403 A, 406 S, 407 S, 409 G, 411 A, 413 L, 449 F, 456 A, 457 T, 458 S, 458 S, 459 A, 460 A, 461 E, 462 L, 463 E, 464 R, 465 G, 466 E, 467 T, 468 T, 469 N, 523 M, 527 S, and 531 Y. Additional kudzu IspS active site positions of interest include but are not limited to: 20 A, 21 N, 22 Y, 23 Q, 271 R, 278 W, 299 F, 302 V, and 408 S. Each library SEL contains clones, maximally including 20 different variants. For example, kudzu isoprene synthase SEL 531 contains variants in which the DNA triplet coding for tyrosine at position 531 of the mature kudzu enzyme is replaced by another DNA triplet encoding: alanine, aspartic acid, cysteine, glutamic acid, phenylalanine, glycine, histidine, isoleucine, lysine, leucine, methionine, asparagine, proline, glutamine, arginine, serine, threonine, valine, or tryptophan. Briefly, DNA triplets of specific positions in the DNA coding strand of the mature IspS are replaced. The mutated IspS nucleic acids are subsequently ligated to a suitable expression vector and used to transform suitable host cells.

Site evaluation libraries are created either by ordering synthetic constructs (e.g., DNA2.0) or by ordering primers with the "nns" sequence in place of the codon to be mutated. The primers are then be used to mutate the gene to produce an SEL at the indicated site using commercially available mutagenesis kits (e.g., Stratagene) as has been described (e.g., WO0507682A2). The mutated codons are identified by sequence analysis. The site libraries are arrayed in 96 well master plates, and frozen for later use. Cultures are grown from the master plates and prepared for screening.

The desired end products are IspS enzymes that function optimally in a host metabolically engineered to maximize carbon flow through IspS. To this end several stages of screening are used to ensure that correct parameters are being addressed. Exemplary screens include but are not limited to: expression, DMAPP feeding for production of HG, microreactor, protein determination, and headspace assays. Expression screen: One example of a method to analyze the level of protein expression is as follows. Soluble and insoluble fractions of cell lysates (obtained from lysed cell cultures) are prepared by centrifugation. The resulting supernatants and pellets are analyzed by SDS-PAGE. The percent soluble protein is determined by densitometry analysis of the protein present in the supernatant versus the pellet.

In an exemplary embodiment, kudzu site evaluation libraries are constructed in the pET24D expression vector. The pET24D-Kudzu vector, containing the kudzu isoprene synthase gene, serves as the template DNA.

Materials:
pET24D-Kudzu vector (~50 ng/µl)
Kudzu IS site-directed mutagenic primers (Integrated DNA Technologies)
QUIKCHANGE® Multi Site-Directed Mutagenesis Kit (Stratagene)
MJ Research PTC-200 Peltier Thermal Cylcer (Bio-Rad Laboratories)
One Shot TOP10 competent cells (Invitrogen)
QIAprep Spin Miniprep Kit (Qiagen)
BL21(λDE3) pLysS competent cells (Invitrogen)
Luria Broth (LB) agar plates Methods:
The method of mutagenesis was based on the codon-specific mutation approach, in which the creation of all possible mutations in a specific DNA triplet was performed using a single forward primer with a length of 25 to 45 nucleotides, enclosing a specific designed triple DNA sequence NNS (N=A, C, T or G and S=C or G) corresponding with the sequence of the codon to be mutated. This method results in the random incorporation of nucleotides at a specific pET24D-kudzu codon of interest. Table 8-1 lists the oligonucleotide primers used for mutagenesis, with the number in the primer name corresponding with the codon position in the mature kudzu isoprene synthase enzyme sequence. All oligonucleotide primers were synthesized (Integrated DNA Technologies) on a 100 nmole scale and PAGE purified.

TABLE 8-1

Kudzu IspS Codon-Specific Mutation Primers

| Name | SEQ ID | Primer Sequence |
| --- | --- | --- |
| IS_A20 | NO: 24 | CATAATTCCCGTCGTTCCNNSAACTATCAGCCAAAC CTG |
| IS_N21 | NO: 25 | CATAATTCCCGTCGTTCCGCANNSTATCAGCCAAAC CTGTG |
| IS_Y22 | NO: 26 | CCCGTCGTTCCGCAAACNNSCAGCCAAACCTGTGGA ATTTC |
| IS_Q23 | NO: 27 | GTCGTTCCGCAAACTATNNSCCAAACCTGTGGAATT TC |
| IS_R271 | NO: 28 | CTGGATTTTGTACGCGACNNSCTGATGGAAGTTTAT TTC |
| IS_W278 | NO: 29 | CTGATGGAAGTTTATTTCNNSGCACTGGGTATGGCG CC |
| IS_F299 | NO: 30 | CAAAGCTGTTACTAAAATGNNSGGTCTGGTGACGAT CATC |
| IS_V302 | NO: 31 | CTAAAATGTTTGGTCTGNNSACGATCATCGATGACG TG |
| IS_S408 | NO: 32 | GAAAACGCCAGCGTTTCCTCCNNSGGTGTAGCGCTG CTGGC |

A PCR reaction was set up in a 0.5 ml thin-walled PCR tube following the manufacturer's protocol for the QUIKCHANGE® Multi Site-Directed Mutagenesis Kit (Stratagene): 1 µl pET24 Kudzu vector (50 ng/µl); 1 µl Kudzu IS site-directed forward mutagenic primer (10 µM); 2.5 µl 10× QUIKCHANGE® Multi Reaction buffer; 1 µl dNTP Mix, 1 µl QUIKCHANGE® Multi enzyme blend (2.5 U/µl); and 18.5 µl distilled autoclaved water to provide a 25 µl total reaction mix. The pET24 Kudzu SELs were amplified using the following conditions: 95° C., for 1 min ($1^{st}$ cycle only), followed by 95° C. for 1 min, 55° C. for 1 min, 65° C. for 12 min, and repeat cycling 29 times. Then the reaction mixture was subjected to DpnI digestion (supplied with QUIKCHANGE® Multi Site-Directed Mutagenesis Kit) by addition of 1.5 µl DpnI restriction enzyme to each tube, and incubated at 37° C. for 2 hours to digest the parental pET24D-kudzu vector. The DpnI-treated PCR reaction was then transformed into One Shot TOP10 competent cells (Invitrogen), plated onto LB agar plates containing 50 µg/ml kanamycin, and incubated overnight at 37° C. The next day, 96 random colonies were picked and sequenced to identify a minimum of 15 of the possible 19 amino acid variants. Upon identification of the site-directed variants, each variant clone was then inoculated in a 5 ml tube of LB+50 µg/ml kanamycin and grown overnight at 37° C. with shaking (250 rpm). The following day plasmid DNA was purified using the QIAprep Spin Miniprep Kit (Qiagen). The variants were then transformed into One Shot BL21(λDE3) pLysS competent cells (Invitrogen) for protein expression screening, plated on LB agar plates containing 50 µg/ml kanamycin and 30 µg/ml chloramphenicol and incubated overnight at 37° C.

An alternative method for producing pET24D-Kudzu SELs in *E. coli* BL21(λDE3) pLysS cells was also successfully employed. The TOP10 competent cell transformants obtained from the DpnI-treated PCR reaction described above were harvested by applying 3 ml of LB media to the top of the agar and resuspending the cells by scraping with a sterile plate spreader. The 3 ml of pooled, resuspended cells were then used to inoculate a 25 ml shake flask containing LB+50 µg/ml kanamycin. The pooled culture was then grown overnight at 37° C. with shaking (250 rpm). The following day plasmid DNA was purified from the pooled cultures using the QIAprep Spin Miniprep Kit (Qiagen). The pooled plasmid DNA was then transformed into One Shot BL21(λDE3) pLysS competent cells for protein expression screening as described above.

To make a master plate, the correct constructs are arrayed in quadruplicate in 96 well plates. One colony of the correct sequence is used to inoculate 4 wells and the plates are grown for several hours to overnight at 37° C. in LB containing 50 µg/ml kanamycin with shaking (200 rpm). Sterile glycerol is added to the cultures to a final concentration of 15% (for a final total volume of 150-200 µl/well). The plates are then sealed using BREATHE-EASIER (EMS Catalog No. 70536-20) membranes and stored at −80° C.

Example 9

Production and Purification of Isoprene Synthase Inclusion Bodies

Figure 13:
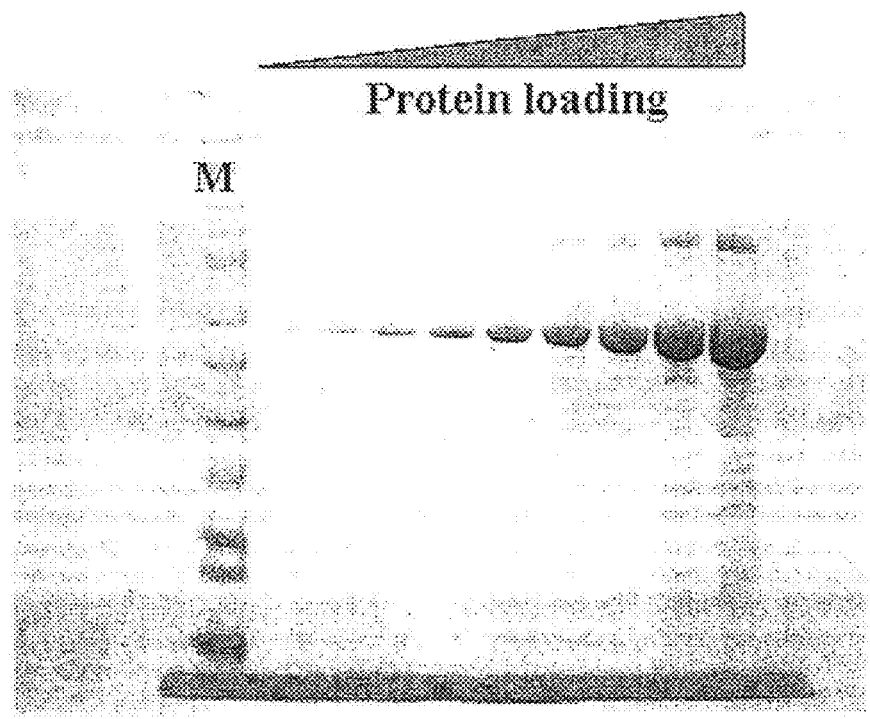
FIG. 13 shows an SDS-PAGE analysis of kudzu isoprene synthase-containing inclusion bodies. Lane M contains molecular weight markers, while the other lanes contain increasing amounts of the purified inclusion body preparation. The kudzu isoprene synthase was estimated to have a purity of >90%.

Inclusion bodies containing kudzu isoprene synthase were formed when the enzyme is overexpressed in the presence of the chaperone GroELS in the strain BL21(λDE3). Briefly pETNHisKudzu (U.S. Application No. 61/013,574, herein incorporated by reference) was subcloned into pGro7 (Takara Catalog No. 3340) according to the manufacturer's instructions. A 500 mL of culture was grown essentially as described (Whittington et al., Proc Natl Acad Sci USA, 99:15375-15380, 2002). Despite the presence of chaperone and low temperature of cultivation the culture yielded predominantly inclusion bodies and only low levels of soluble active protein. The inclusion bodies were harvested using the IFOLD Protein Refolding System (Novagen Catalog No. 71552-3) according to the manufacturer's instructions. This procedure led to a high yield (>50 mg) of recombinant kudzu isoprene synthase. The purity of the inclusion body is shown in FIG. 13. This preparation was used for the production of rabbit polyclonal anti-isoprene synthase antisera (Invitrogen).

Example 10

High Throughput Biochemical Screen of Isoprene Synthase Variants

This example describes high throughput methods for the determination of isoprene synthase activity. Libraries of BL21(λDE3)pLysS *E. coli* host cells capable of expressing isoprene synthase variants are arrayed in 96-well plates and stored frozen at −80° C. as 15% glycerol stocks as described above in Example 8. To analyze a plate of up to 96 variants, a replica stamp of the glycerol stock master plate is made with a 96-pin MULTI-BLOT floating pin tool (V&P Scientific Catalog No. VP 408AF) onto Luria broth agar containing appropriate antibiotic(s) (e.g., 30 µg/mL chloramphenicol, 50 µg/mL kanamycin). The replica plate is incubated over night at 30° C. to allow growth of bacterial patches. Using the same floating pin replicator a 96-square deep well plate containing 250 µL of TM3 medium supplemented with 0.08% Biospringer yeast extract and 1% glucose plus antibiotics (30 µg/mL chloramphenicol, 50 µg/mL kanamycin) is inoculated from the agar plate and incubated overnight at 30° C. The recipe for TM3 broth is as follows: $K_2HPO_4$ (13.6 g/l) $KH_2PO_4$ (13.6 µg/l), $MgSO_4*7H_2O$ (2 g/l) Citric Acid Monohydrate (2 g/L) Ferric Ammonium Citrate (0.3 g/L) $(NH_4)_2SO_4$ (3.2 g/L) yeast extract (0.2 g/L) 1 ml of 1000× Trace Elements solution, pH adjusted to 6.8 with ammonium hydroxide qs to volume with sterile $diH_2O$ and filter sterilized with a 0.22 micron filter. The recipe for 1000× Trace Elements solution is as follows: Citric Acids*$H_2O$ (40 g/L), $MnSO_4*H_2O$ (30 g/L), NaCl (10 g/L), $FeSO_4*7H_2O$ (1 g/L), $CoCl_2*6H_2O$ (1 g/L), $ZnSO*7H_2O$ (1 g/L), $CuSO_4*5H_2O$ (100 mg/L), $H_3BO_3$ (100 mg/L), $NaMoO_4*2H_2O$ (100 mg/L). Each component was dissolved one at a time in $diH_2O$, pH adjusted to 3.0 with HCl/NaOH, qs to volume and filter sterilized with a 0.22 micron filter. The overnight cultures are diluted with the same medium to an $OD_{600}$ of 0.05 and grown in another 96-square deep well plate (Thomson Instrument, Catalog No. 951652C), with each well containing 600 µL of the dilution. The dilutions are grown at 30° C. with shaking to an $OD_{600}$ of 0.8 and are then induced with IPTG added to a concentration of 400 µM. The plate is grown for 5 hours and $OD_{600}$ is determined for quality control and normalization.

A volume of 400 µL of culture is transferred into a new 96-well plate (Perkin Elmer, Catalog No. 6008290) and cells are harvested by centrifugation in a Beckman Coulter Allegra 6R centrifuge at 2500×g. The pellet is resuspended in 200 µL of hypotonic buffer (5 mM $MgCL_2$, 5 mM Tris HCl, 5 mM DTT pH 8.0) and the plate is frozen at −80° C. for a minimum time of 60 min. Cell lysate is prepared by thawing the plate and adding 32 µL of isoprene synthase DMAPP assay buffer (57mM Tris HCl, 19 mM $MgCl_2$, 74 µg/mL DNase I (Sigma Catalog No. DN-25), 2.63×10$^5$ U/mL of READYLYSE lysozyme solution (Epicentre Catalog No. R1802M), and 5 mg/mL of molecular biology grade BSA. The plate is incubated with shaking at 25° C. for 30 min and then placed on ice. For isoprene production, an 80 µL aliquot of lysate is transferred to a 96-deep well glass plate (Zinsser Catalog No. 3600600) and 20 µL of a 10 mM DMAPP solution in 100 mM $KHPO_4$, pH 8.2 (Cayman Chemical Catalog No. 63180) is added. The plate is sealed with an aluminum plate seal (Beckman Coultor Catalog No. 538619) and incubated with shaking at 30° C. of 60 minutes. The enzymatic reactions are terminated by heating the glass block (70° C. for 5 min). The headspace of each well is quantitatively analyzed as described in Example 5.

Figure 14A:
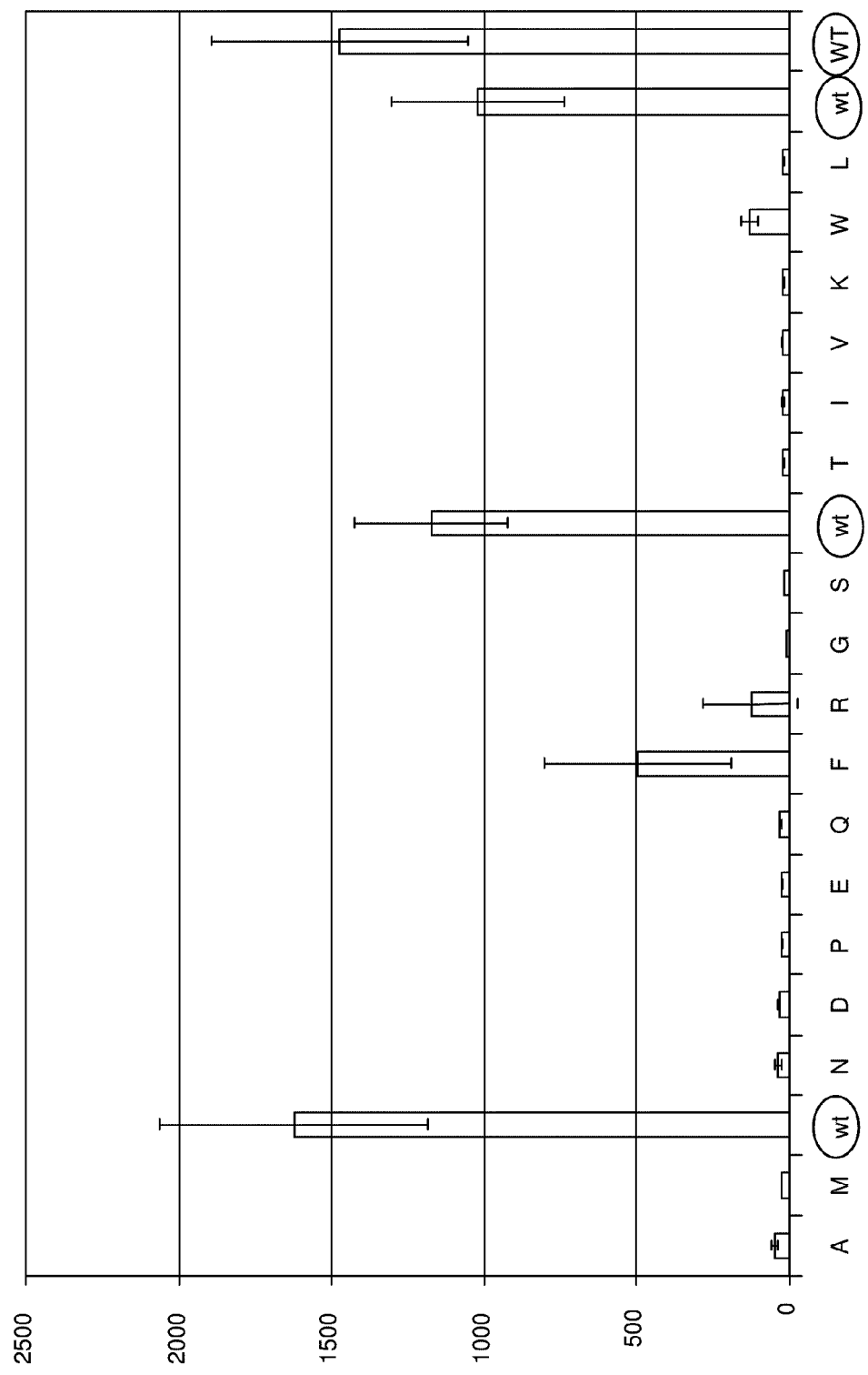
FIG. 14 provides graphs showing isoprene synthase activity of kudzu site evaluation library (SEL) members for positions Y22, A20 and S408. Most members show highly decreased activity, while conservative substitutions show a lesser decrease in activity. Panel A shows assay results for the Y22 library members in comparison with independent wild type samples (circled WT). Panel B shows assay results for the A20 library members in comparison to wild type samples (circled WT). Panel C shows assay results for the S408 library members, indicating that member S408D has 1.5 to 2-fold higher activity than the average of the wild type controls.
Figure 14B:
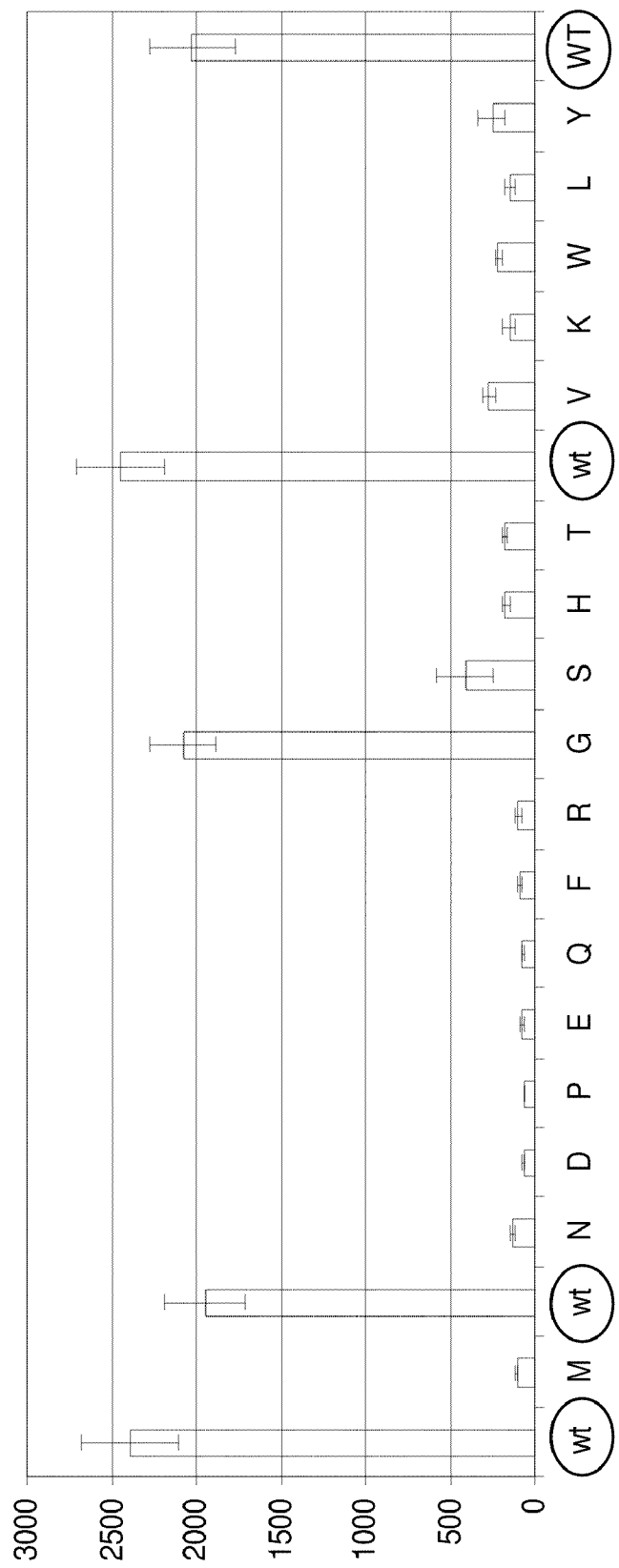
Figure 14C:
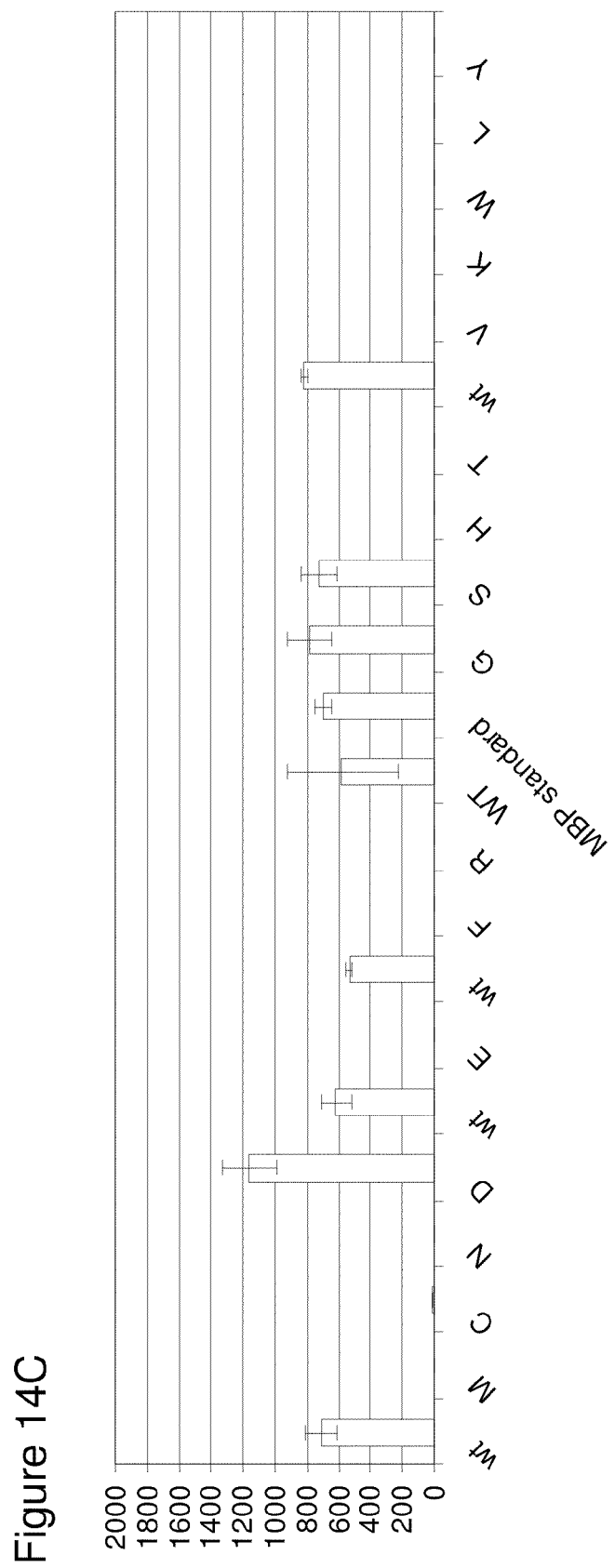

To determine protein concentration 5 µL or more of lysate is run on precast gels (Invitrogen Catalog No. NP0301BOX) for western blot analysis after transfer to a nitrocellulose membrane (Invitrogen Catalog No. LC2000). The primary antibody employed is an anti-isoprene synthase antibody of Example 9. Primary antibody binding is followed by development with a secondary antibody labeled with Alexa Fluor 488 (Invitrogen Catalog No. A-11008) to permit quantitative signal determination. The western blot procedure was carried out as described by Invitrogen. The fluorescence signal was recorded with a Molecular Dynamics STORM instrument using the blue filter setting and quantitatively analyzed with the Molecular Dynamics IMAGEQUANT image analysis software package. Specific activity of the library members was calculated from the ratio of the amount of isoprene produced divided by either the $A_{600}$ of the induction cultures or the isoprene synthase protein concentration determined by western blot. Isoprene synthase protein standard was calibrated by standard gel densitometry with BSA stained with Coomassie brilliant blue R250 serving as primary standard. Increased, decreased, or no change in specific activity of the entire library was tabulated for further analysis. FIG. 14 provides graphs showing isoprene synthase activity of kudzu site evaluation library (SEL) members for positions Y22, A20, and S408. Most members show highly decreased activity relative to wild type, while conservative substitutions show a lesser decrease in activity. Activity of variant A20G approximates that of the wild type kudzu enzyme, indicating that it is a candidate partner for a combinatorial mutant. Interestingly, variant S408D of library S408 showed an increase in activity compared to wild type thus providing another candidate partner for a combinatorial mutant.

Example 11

Isoprene Synthase Truncations

This example describes the identification of the amino acid sequence of the protein in the lower band of the doublet seen in purified poplar IspS preparations (see FIG. 21). A series of N-terminally truncated IspS molecules based on putative cleavage sites identified by mass spectrometry was also generated. A shorter N-terminal truncation of IspS (the "MEA" truncation in pDu39, see below) was also generated, to examine the effect of further truncation on IspS activity (Williams D C, McGarvey D J, Katahira E J, Croteau R (1998) Biochemistry 37:12213-12220).

I. Construction of an N-Terminally 6XHis-Tagged IspS (in pDu27) for Protein Purification:

The full length *P. alba* IspS from the template *P. alba* pET24a (FIGS. 19 and 20) was prepared by PCR. The following PCR reaction was prepared: 1 µl (Template)-*P. alba* pET24a, 5 µl 10× PfuUltraII Fusion buffer, 1 µl dNTP's (10 mM), 1 µl primer (50 µM) primer F-(MCM219), 1 µl primer (50 µM) primer R-(MCM182), 41 µl diH$_2$O and 1 µl of PfuUltra II Fusion DNA Polymerase (Stratagene). PCR cycling parameters were as follows: 95° C. 1 min., 95° C. 1 min, 55° C. 20 sec., 72° C. 27 sec. for 29 cycles followed by 72° C. 3 min and 4° C. until cool, using an Eppendorf Mastercycler. The PCR product was gel extracted and purified, using 0.8% E-gel (Invitrogen) and Qiagen QIAquick Gel Extraction and QIAprep Spin Miniprep kits, according to the manufacturer's recommended protocol. A 3 µl aliquot of purified product was ligated to the pET200D/TOPO vector (Invitrogen), according to the manufacturer's protocol. The reaction was incubated for 5 minutes at room temperature, and the 6 µl topoisomerase mixture was then transformed into *E. coli* Top10 chemically competent cells (Invitrogen) according to the manufacturer's protocol. Transformants were selected for on LB plates containing kanamycin (50 µg/ml) (Kan50), and incubated at 37° C. overnight. Five colonies were picked and screened using PuReTaq Ready-To-Go PCR Beads (Amersham) using the T7 Forward and MCM182 primers. Clones harboring inserts of the correct size were further verified by sequencing using the T7 Forward and T7 Reverse primers (Quintara Biosciences). One construct, pDu27 (FIGS. 16-18), was chosen for further study. A 1 µl aliquot of the plasmid preparation was transformed into BL21(λDE3) pLysS (Invitrogen) according to the manufacturer's protocol. Transformants were selected for on LB plates containing Kan50+ and chloramphenicol (35 µg/ml) (Cm35) and incubated at 37° C. overnight. The resulting strain was used for expression and purification of N-terminally 6XHis-tagged *P. alba* IspS.

II. Purification of 6XHis-Tagged IspS
Expression of 6XHis-Tagged IspS

N-terminally 6XHis-tagged IspS was expressed and purified from strain MD08-99. The growth procedure is suitable for histidine tagged enzymes expressed in BL21(λDE3) pLysS cells. A 10 ml of overnight culture was prepared for each 1 L of planned growth. The appropriate antibiotics (50 mg/ml kanamycin, 50 mg/ml chloramphenicol, and/or 50 mg/ml Carbenecillin) was added to 10 ml of LB medium in a 25 ml flask and was inoculated with 1 colony from a fresh plate of cells or directly from glycerol frozen cell stock. Cultures were grown at 30° C. overnight with shaking at ~220 rpm. Day cultures were prepared in 1 liter of LB medium with appropriate antibiotics for each culture. Each 1 L day culture was inoculated with 10 ml of overnight culture and grown at 30-37° C. with shaking at ~220 rpm until the $OD_{600}$ reached ~0.4-0.6. Day cultures were then induced with 400 µM IPTG and allowed to continue growing at 30° C. with shaking at 220 rpm for ~5-6 hours. Cells were then harvested by centrifugation at 10,000×g for 10 min, 4° C. Following Harvest, cells were used directly or stored at −80° C. until ready to process.

Purification of 6XHis-Tagged IspS

For purification of histidine tagged enzymes from BL21 (λDE3)pLysS cells, cells were gently resuspended in fresh Lysis buffer (Lysis buffer: Ni wash buffer+0.5 mM PMSF, 0.01% Tween-20, 1 mg/ml lysozyme, 0.2 mg/ml DNaseI; Ni wash buffer: 50 mM NaH$_2$PO$_4$, 300 mM NaCl, 20 mM Imidazole, pH 8.0). Approximately 40-50 ml of lysis buffer was used per 1L of cell pellet. Cells were then incubated on ice for approximately 30 min. The cell suspension was then lysed fully by passing 2-3 times through a french pressure cell (large french press cell at 1200 psi/High setting) until lysate started to look clear. A sample of the lysate was saved for activity assay and gel analysis (~100 µl). The lysate was then clarified by centrifuging the lysate at 30,000×g for 30 min, 4° C. in a Sorvall Discovery 90SE ultracentrifuge. The supernatant was removed and retained. A sample of the "clarified lysate" was saved for activity assay and gel analysis (~100 µl).

The clarified lysate was run over HisTrap HP columns (GE Healthcare) using a gradient from 0-100% Ni buffer B. Samples were then analyzed by SDS-PAGE gel (4-12% gel NUPAGE, Invitrogen) according to manufacturer's directions. Desired fractions were concentrated on spin filters (Vivaspin-20, Sartoris,) and then desalted over a HiPrep 26/10 Desalting column (GE heathcare) packed with Sephadex G25 resin. The G-25 buffer consisted of 50 mM HEPES, 50 mM NaCl, and 1 mM DTT, pH 7.4. The desired sample was then purified over a HiTrap Q HP column (GE) using a gradient elution from 0% Q seph buffer A to 100% Q seph buffer B (Q seph buffer A: 50 mM Tris, 0.05 M NaCl, 1 mM DTT, pH 7.6 and Q seph buffer B: 50 mM Tris, 1.0 M NaCl, 1 mM DTT, pH 7.6). Fractions containing the desired protein were analyzed and concentrated. Sample buffer was then exchanged into 50 mM HEPES, 50 mM NaCL, pH 7.4 with 1 mM DTT by passing the sample over a Hi Prep 26/10 Desalting column (GE heathcare) packed with Sephadex G25 resin. A final polishing step of Gel filtration was used when necessary. The sample was passed through a Hi Load 26/60 Superdex 200 prep grade (GE) in gel fitration buffer: (50 mM HEPES, 150 mM NaCl, 1 mM DTT, pH 7.4). Fractions were then analyzed and concentrated. The samples were then stored at −80° C. For preparation for analysis of the band, the sample is run on an SDS-PAGE gel (4-12% NUPAGE gel, Invitrogen), stained and the desired band excised and processed as described below.

III. Mass Spectrometry of Isoprene Synthase

Sample Preparation

An In-Gel Digestion and LCQ-Deca Mass Spectrometry Procedure was utilized (Modified Rosenfeld in-gel Digest Protocol) (Rosenfeld et al, Anal. Biochem. (1992) 203, 173-179; Hellman et al, Anal Biochem, (1995) 224, 451-455). The purified sample of Isoprene synthase was run on a 4-12% SDS-PAGE (NUPAGE, Invitrogen) and stained with Coomassie Brilliant Blue R-250 (Thermo Scientific) or SimplyBlue Safe Stain (Invitrogen). Band(s) of interest were excised from the gel and destained. Each gel slice was diced into small pieces ~1 mm×1 mm and placed into 0.65 mL "slick" (siliconized) tubes from PGC Scientific. Approximately 100 µL of 25 mM $NH_4HCO_3$/50% $ACN/H_2O$ was added to each tube and vortexed for 10 min. Supernatants were extracted and discarded. These steps were repeated twice. Then gel pieces were then run in a Savant SpeedVac to dryness (~20 to 30 min).

Samples were then reduced and alkylated. For reduction, 25 µL (or enough to cover) of 10 mM DTT in 25 mM $NH_4HCO_3$ (prepared fresh) were added to dried gels. Tubes were then vortexed and spun briefly. Reactions were incubated at 50° C. for 1 hour. For alkylation, supernatants were removed and 25 µL or more of 55 mM iodoacetamide (IAA) in 25 mM $NH_4HCO_3$ were added to the gel. Reaction tubes were vortexed and spun briefly again. Reactions were allowed in dark for 1 hour at room temperature. Supernatants were removed and gels were washed with ~100 µL of 25 mM $NH_4HCO_3$/50% $ACN/H_2O$, by vortexing for 10 min and briefly spinning. Supernatant were removed and the wash step was repeated once. Gel pieces were then dried in a SpeedVac (~15-30 min).

Digestion buffer was prepared by adding 400 µL of 0.1% n-octyl B-D-glucopyranosidase water to 100 uL of 8M Urea. 400 uL of this digestion buffer was added to 20 ug of freshly prepared Trypsin. 0.05 µg/µL of sequencing-grade Trypsin was prepared from one vial of 20 µg sequencing grade trypsin (Promega) that was dissolved into 400 uL of 1.6 M Urea solution. Trypsin enzyme solution was added enough to cover gel pieces. Tubes were covered with parafilm and incubated at 37° C. overnight (16-20 hrs). It was ensured that there is a little extra buffer above the gel.

Peptides were extracted from gels by briefly vortexing and spinning the digest. The digest solution was transferred with gel loading tips into a 0.65 mL siliconized tube. 50 µL (enough to cover) of 50% $ACN/0.1\%$ $FA/H_2O$ were added to the gel pieces and samples were vortexed for 10 min, spun, and then sonicated for five min. Extracted peptides were pooled together in one tube. Extraction steps were repeated two to three more times until the gel pieces became white in appearance and shrank in size. Extracted digests were vortexed, spun and dried in a SpeedVac to a volume of 55 µL. In cases where the volume was less than 55 µL, enough 0.1% FA was added to make up a final volume of 55 µL.

Mass Spectrometry

The sample was injected onto a Thermofinnigan (San Jose, Calif.) LCQ-Deca electrospray ionization (ESI) ion-trap mass spectrometer. A Vydac C18 column (5µ, 300 A, 0.2×150 mm, Michrom Bioresources, Auburn, Calif.) was used with a flow rate of 200 µL/min. The injection volume was 50 uL, and was filtered through an on-line trapping cartridge (Peptide CapTrap, Michrom Bioresources, Auburn, Calif.) before loading onto the column. Separation of the in-gel digest was performed with the following gradient (Solvent A: 0.1% trifluoroacetic acid in H2O (J. T. Baker, Phillipsburg, N.J.), Solvent B: 0.08% trifluoroacetic acid in acetonitrile (J. T. Baker, Phillipsburg, N.J.)):

TABLE 11-1

Gradient Table

| min | A % | B % |
|---|---|---|
| 0 | 0.00 | 100 | 0 |
| 1 | 10.00 | 86 | 14 |
| 2 | 16.00 | 81 | 19 |
| 3 | 20.00 | 78 | 22 |
| 4 | 21.00 | 77 | 23 |
| 5 | 22.00 | 75 | 25 |
| 6 | 24.00 | 73 | 27 |
| 7 | 32.00 | 69 | 31 |
| 8 | 34.00 | 66 | 34 |
| 9 | 37.00 | 64 | 36 |
| 10 | 47.00 | 60 | 40 |
| 11 | 50.00 | 30 | 70 |
| 12 | 55.00 | 100 | 0 |
| 13 | 60.00 | 100 | 0 |
| 14 | 65.00 | 100 | 0 |
| 15 | | 100 | 0 |

Mass Spectrometry Results

An aliquot of 6.4 µg of protein was loaded into 5 lanes on a 4-12% bis-tris NUPAGE gel (Invitrogen), MOPS buffer, 50 min run. As described above, the gel was stained for 2 minutes, and then de-stained for 15 minutes. The gel was washed in $H_2O$, then all bands were excised, cut into small pieces, and destained. Gel pieces were reduced and alkyated with DTT/IAA for 1 hour each at 52° C. and RT, respectively. Trypsin was added for an overnight digestion. Extracted peptides were run on the LCQ-Deca. FIGS. 21 and 22 show the results for the mass spectrometry analysis. The lower doublet band (in FIG. 21) is identified as IspS. FIG. 22 shows that N-terminal truncations were observed after amino acids 39, 40, 42, and 44 (according to the peptide sequence of the N-terminally His-tagged IspS protein in pDu27). The C-terminus of IspS is intact.

IV. Construction of N-Terminally Truncated IspS Variants:

All truncated constructs without affinity tags were generated using the QuickChange Site-directed Mutagenesis kit (Stratagene) using the template P. alba pET24a for PCR amplification. Approximately 50 ng of template DNA was used for amplification (with an Eppendorf Mastercycler Gradient PCR Machine) of the mutagenized PCR product with the Forward (For) and Reverse (Rev) primer pairs that correspond to each relevant truncation (QC MSV For and QC MSV Rev, for example, see Table 11-2). The following PCR reaction mixtures were used: 1 µl P. alba pET24a, 5 µl 10× PfuUltra HF buffer, 1 l dNTP's, 1 ul (50 µM) primer-For (e.g. QC MSV For), 1 µl (50 µM) primer-Rev (e.g. QC MSV Rev), 2 µl DMSO, 39 µl di$H_2O$, 1 µl PfuUltra HF Polymerase (Stratagene). The following PCR cycling parameters were used: 95° C. 1 min, 95° C. 30 sec., 55° C. 1 min., 68° C. 7.3 min. for one cycle followed by 95° C. 30 sec., 55° C. 1 min., 68° C. 7.3 min for a total of 18 cycles and then followed by 4° C. The PCR products were treated with 1-2 µl of DpnI (Roche) for 1-3 hour at 37° C. A 5 µl aliquot of the DpnI treated products was visualized on a 0.8% E-gel (Invitrogen). A 1 µl aliquot of each product was transformed into chemically competent E. coli Top10 cells (Invitrogen) according to the manufacturer's protocol. Transformants were selected for on LB medium containing kanamycin at a concentration of 50 μg/ml (Kan50), and incubated overnight at 37° C. Five colonies of each transformation were selected and grown to stationary phase in 3 ml liquid LB Kan50. Plasmids were purified using a Qiagen miniprep kit according to the manufacturer's recommended protocol. Purified plasmids were sequenced (by Quintara Biosciences) with T7 Forward and Reverse primers, and confirmed for their respective truncation. The resulting plasmids (pDU39 through pDU43, see Table 11-4, FIGS. 23-34) were transformed into chemically competent E. coli BL21(λDE3) pLysS (Invitrogen) according to the manufacturer's recommended protocol. Table X describes the strains used for expression of truncated IspS enzymes.

Constructs with affinity (6XHis) and proteolysis (TEV, Tobacco Etch Virus) tags were generated using P. alba pET24a as a template for PCR reactions. PCR reaction mixtures were prepared as follows: 1 ul (P. alba pET24a), 5 ul 10× PfuUltraII Fusion buffer, 1 ul dNTP's (10 mM), 1 ul primer (50 μM) Alba FL-NdeI-For or Alba TRC (MEA)-NdeI-F, 1 ul primer (50 uM) Alba FLTRC (+) TEV-R, 41 ul diH$_2$O and 1 ul of PfuUltra II Fusion DNA Polymerase from Stratagene. PCR cycling parameters were as follows: 95° C. 1 min., 95° C. 30 sec., 55° C. 20 sec., 72° C. 25 sec. for one cycle and then repeating 95° C. 30 sec., 55° C. 20 sec., 72° C. 25 sec. for an additional 28 cycles, followed by 72° C. 3 min and then 4° C. After amplification and verification of the correct molecular weight of the product by visualization on 0.8% E-gel (Invitrogen), PCR products were digested with restriction enzymes NdeI and XhoI (Roche) for 2 hours at 37° C., and then gel purified using the Qiaquick Gel Purification system (Qiagen) according to the manufacturer's recommended protocol. 3 μl of purified product was ligated to pET-24a (Invitrogen) that was digested with NdeI and XhoI (Roche), gel purified and dephosphorylated (using SAP, shrimp alkaline phosphatase) (Promega) according to the manufacturer's recommended protocols. T4 ligase (NEB) was used for the ligation reaction, which was incubated overnight at 16° C. The ligation reaction was dialyzed into water for 30 min., and 2 μl of the reaction were used to electroporate MCM331 (see below) competent cells. Cells were allowed to recover at 30° C. for 2 hours, and then selected on Kan50 with 5 mM (R)-(−)-Mevalonolactone (MVA) (Sigma) spread onto the plate. Positive transformants were inoculated into 3 ml of liquid LB Kan50, and plasmids were isolated using the QIAPrep Spin miniprep kit (Qiagen). Inserts were verified by restriction digestion using NdeI and XhoI (Roche) and positive clones were sequenced (Quintara Biosciences) with T7 promoter and T7 terminator sequencing primers. 1 μl of each plasmid (see Table 11-4 for plasmid description and FIGS. 35-39) was transformed into chemically competent E. coli BL21(λDE3) pLysS (Invitrogen) according to the manufacturer's recommended protocol. Transformants were selected on LB Kan50+Cm35 (Chloramphenicol 35 ug/ml) plates and incubated at 37° C. See Table 11-5 for a description of all expression strains.

Strain MCM331 was prepared as follows. A synthetic operon containing mevalonate kinase, mevalonate phosphate kinase, mevalonate pyrophosphate decarboxylase, and the IPP isomerase was integrated into the chromosome of E. coli. If desired, expression may be altered by integrating different promoters 5' of the operon.

i) Target Vector Construction

The attTn7 site was selected for integration. Regions of homology upstream (attTn7 up) (primers MCM78 and MCM79) and downstream (attTn7 down) (primers MCM88 and MCM89) were amplified by PCR from MG1655 cells. A 50 μL reaction with 1 μL 10 μM primers, 3 μL ddH$_2$O, 45 μL Invitrogen Platinum PCR Supermix High Fidelity, and a scraped colony of MG1655 was denatured for 2:00 at 94° C., cycled 25 times (2:00 at 94° C., 0:30 at 50° C., and 1:00 at 68° C.), extended for 7:00 at 72° C., and cooled to 4° C. This resulting DNA was cloned into pCR2.1 (Invitrogen) according to the manufacturer's instructions, resulting in plasmids MCM278 (attTn7 up) and MCM252 (attTn7 down). The 832 bp ApaI-PvuI fragment digested and gel purified from MCM252 was cloned into ApaI-PvuI digested and gel purified plasmid pR6K, creating plasmid MCM276. The 825 bp PstI-NotI fragment digested and gel purified from MCM278 was cloned into PstI-NotI digested and gel purified MCM276, creating plasmid MCM281.

ii) Cloning of Lower Pathway and Promoter

MVK-PMK-MVD-IDI genes were amplified from pTrcK-KDyIkIS with primers MCM104 and MCM105 using Roche Expand Long PCR System according to the manufacturer's instructions. This product was digested with NotI and ApaI and cloned into MCM281 which had been digested with NotI and ApaI and gel purified. Primers MCM120 and MCM127 were used to amplify CMR cassette from the GeneBridges FRT-gb2-Cm-FRT template DNA using Stratagene Pfu Ultra II. A PCR program of denaturing at 95° C. for 4:00, 5 cycles of 95° C. for 0:20, 55° C. for 0:20, 72° C. for 2:00, 25 cycles of 95° C. for 0:20, 58° C. for 0:20, 72° C. for 2:00, 72° C. for 10:00, and then cooling to 4° C. was used with four 50 uL PCR reactions containing 1 uL ~10 ng/μL template, 1 μL each primer, 1.25 μL 10 mM dNTPs, 5 μL 10× buffer, 1 μL enzyme, and 39.75 μL ddH$_2$0. Reactions were pooled, purified on a Qiagen PCR cleanup column, and used to electroporate water-washed Pir1 cells containing plasmid MCM296. Electroporation was carried out in 2 mM cuvettes at 2.5V and 200 ohms. Electroporation reactions were recovered in LB for 3 hr at 30° C. Transformant MCM330 was selected on LA with CMP5, Kan50.

iii) Integration into E. coli Chromosome

Miniprepped DNA (Qiaquick Spin kit) from MCM330 was digested with SnaBI and used to electroporate BL21(DE3) (Novagen) or MG1655 containing GeneBridges plasmid pRedET Carb. Cells were grown at 30° C. to ~OD1 then induced with 0.4% L-arabinose at 37° C. for 1.5 hours. These cells were washed three times in 4 C ddH$_2$O before electroporation with 2 μL of DNA. Integrants were selected on L agar with containing chloramphenicol (5 μg/ml) and subsequently confirmed to not grow on L agar+Kanamycin (50 μg/ml). BL21 integrant MCM331 and MG1655 integrant MCM333 were frozen.

TABLE 11-2

| | Primers |
|---|---|
| MCM219 | caccatgcgttgtagcgtgtcca (SEQ ID NO: 33) |
| MCM182 | gggcccgtttaaactttaactagactctgcagtt agcgttcaaacggcagaa (SEQ ID NO: 34) |
| QC MSV For | gaaggagatatacatatgagcgtgtccaccgaaa atg (SEQ ID NO: 35) |
| QC MSV Rev | cattttcggtggacacgctcatatgtatatctcc ttc (SEQ ID NO: 36) |

TABLE 11-2-continued

Primers

| | |
|---|---|
| QC MVS For | gaaggagatatacatatggtgtccaccgaaaatg tgtc (SEQ ID NO: 37) |
| QC MVS Rev | gacacattttcggtggacaccatatgtatatctc cttc (SEQ ID NO: 38) |
| QC MTE For | gaaggagatatacatatgaccgaaaatgtgtctt tcac (SEQ ID NO: 39) |
| QC MTE Rev | gtgaaagacacattttcggtcatatgtatatctc cttc (SEQ ID NO: 40) |
| QC MNV For | gaaggagatatacatatgaatgtgtctttcaccg aaac (SEQ ID NO: 41) |
| QC MNV Rev | gtttcggtgaaagacacattcatatgtatatctc cttc (SEQ ID NO: 42) |
| QC MEA For | gaaggagatatacatatggaagctcgtcgttctg cg (SEQ ID NO: 43) |
| QC MEA Rev | cgcagaacgacgagcttccatatgtatatctcct tc (SEQ ID NO: 44) |
| Alba FL-NdeI-For | gaaggagatatacatatgcgttgtagcgtg (SEQ ID NO: 45) |
| Alba FLTRC (+) TEV-R | cccgcgcttactcgaggccctgaaaatacaggtt ttcgcgttcaaacggcagaatcggtt (SEQ ID NO: 46) |
| AlbaTRC (MEA)- NdeI-F | gaaactgaaacccatatggaagctcgtcgttctg c (SEQ ID NO: 47) |

TABLE 11-3

Primers for construction of strain MCM331

| | | |
|---|---|---|
| MCM78 | attTn7 up rev for integration construct | gcatgctcgagcggccgcTTTT AATCAAACATCCTGCCAACTC (SEQ ID NO: 48) |
| MCM79 | attTn7 down rev for integration construct | gatcgaagggcgatcgTGTCAC AGTCTGGCGAAACCG (SEQ ID NO: 49) |
| MCM88 | attTn7 up forw for integration construct | ctgaattctgcagatatcTGTT TTTCCACTCTTCGTTCACTTT (SEQ ID NO: 50) |
| MCM89 | attTn7 down forw for integration construct | tctagagggccCAAGAAAAATG CCCCGCTTACG (SEQ ID NO: 51) |
| MCM104 | GI1.2 promoter MVK | Gatcgcggccgcgcccttgacg atgccacatcctgagcaaAtaa ttcaaccactaattgtgagcgg ataacacaaggaggAaacagct atgtcattaccgttcttaactt c (SEQ ID NO: 52) |
| MCM105 | aspA terminator-yIDI | Gatcgggcccaagaaaaaagg cacgtcatctgacgtgcCTttt ttatttgtagacgcgttgttat agcattcta (SEQ ID NO: 53) |

TABLE 11-3-continued

Primers for construction of strain MCM331

| | | |
|---|---|---|
| MCM120 | Forward of attTn7: attTn7 homology, GB marker homology | aaagtagccgaagatgacggtt tgtcacatggagttggcaggat gtttgattaaaagcAATTAACC CTCACTAAAGGGCGG (SEQ ID NO: 54) |
| MCM127 | Rev complement of 1.2 GI: GB marker homology (extra long), promoter, RBS, ATG | AGAGTGTTCACCAAAAATAATA ACCTTTCCCGGTGCAgaaGtta agaacggtaatgacatagctgt ttcctccttgtgttAtccgctc acaattagtggttgaattattt gctcaggatgtggcatcgtcaa gggcTAATACGACTCACTATAG GGCTCG (SEQ ID NO: 55) |

TABLE 11-4

Plasmids for expression of IspS variants

| | |
|---|---|
| MD09-161 | pET24a-P. alba FL C-Term (+) TEV, His tag/MCM331 |
| MD09-163 | pET24a-P. alba TRC (MEA) C-Term (+) TEV, His tag/MCM331 |
| pDu27 | Alba-FL-pET200/D-TOPO |
| pDu39 | Mtg pET24a-P. alba-MEA/Top10 (Untagged) |
| pDu40 | Mtg pET24a-P. alba-MNV/Top10 (Untagged) |
| pDu41 | Mtg pET24a-P. alba-MSV/Top10 (Untagged) |
| pDu42 | Mtg pET24a-P. alba-MTE/Top10 (Untagged) |
| pDu43 | Mtg pET24a-P. alba-MVS/Top10 (Untagged) |

TABLE 11-5

Strains for expression of IspS variants

| | |
|---|---|
| MD08-99 | Alba-FL-pET200/D-TOPO (pDu27) in BL21 (λDE3) pLysS |
| MD09-165 | BL21 (λDE3) pLysS, pET24a-P. alba FL C-Term (+) TEV, His tag |
| MD09-167 | BL21 (λDE3) pLysS, pET24a-P. alba TRC (MEA) C-Term (+) TEV, His tag |
| MD09-173 | BL21 (λDE3) pLysS, pET24a-P. alba (MEA) Untagged (pDu39) |
| MD09-174 | BL21 (λDE3) pLysS, pET24a-P. alba (MNV) Untagged (pDu40) |
| MD09-175 | BL21 (λDE3) pLysS, pET24a-P. alba (MSV) Untagged (pDu41) |
| MD09-176 | BL21 (λDE3) pLysS, pET24a-P. alba (MTE) Untagged (pDu42) |
| MD09-177 | BL21 (λDE3) pLysS, pET24a-P. alba (MVS) Untagged (pDu43) |

V. Biochemical Analysis of IspS Truncations

The relative activity of the various N-terminally truncated IspS enzymes was determined by DMAPP assay. The strains described above were analyzed via DMAPP assay in a 96-well plate. All strains were assayed in quadruplicate. The "Full Length" variant refers to the IspS enzyme expressed in BL21(λDE3) pLysS (Invitrogen) from the P. alba pET24a plasmid.

TABLE 11-6

DMAPP Assay of N-terminal Truncations

| Variant | Activity Data | | | Avg $OD_{600}$ | OD Normalized |
|---|---|---|---|---|---|
| | Average | Std Dev | % CV | | |
| MD09-173 | 1125.6 | 93.7 | 8.3 | 5.2 | 217.6 |
| MD09-174 | 118.6 | 8.0 | 6.7 | 5.2 | 22.8 |

TABLE 11-6-continued

DMAPP Assay of N-terminal Truncations

| Variant | Activity Data | | | Avg OD₆₀₀ | OD Normalized |
|---|---|---|---|---|---|
| | Average | Std Dev | % CV | | |
| MD09-175 | 1064.6 | 71.7 | 6.7 | 4.9 | 219.0 |
| MD09-176 | 1179.1 | 64.7 | 5.5 | 4.9 | 238.7 |
| MD09-177 | 831.7 | 89.6 | 10.8 | 4.9 | 168.2 |
| Full Length | 805.8 | 65.1 | 8.1 | 5.0 | 161.3 |

Results: Table X shows that when normalized for $OD_{600}$, strains MD09-173 (with plasmid pDu39), MD09-175 (pDu41), MD09-176 (pDu42), and MD09-177 (pDu43) all displayed higher DMAPP activity than the "Full Length" wild type IspS enzyme (in strain BL21(λDE3) pLysS with *P. alba* pET24a).

VI. Detailed Kinetic Analysis of the "MEA" Truncation in IspS

The relative specific activity was determined and the kinetics of "N-terminally truncated" *P. alba* isoprene synthases were examined compared to "Full length" *P. alba* isoprene synthases. Four strains expressing four different constructs were used in this analysis: BL21(λDE3) pLysS with *P. alba* pET24a; MD09-173; MD09-165; and MD09-167 (Strains described above in detail). These strains express "full length" *P. alba* IspS, "truncated" *P. alba* IspS (the MEA truncation), "full length" C-terminally TEV and His-tagged *P. alba* IspS, and "truncated" C-terminally TEV and His-tagged *P. alba* IspS, respectively. In the experiments described below, "truncated" refers specifically to the MEA variant of *P. alba* IspS.

All strains were inoculated into LB containing 30 mg/L chloramphenicol(Cm) and 50 mg/L kanamycin and grown overnight in 2 mL culture tubes at 37° C. The overnight cultures were diluted 1:100 in 25 mL of LB broth containing 30 mg/L chloramphenicol(Cm) and 50 mg/L kanamycin the following morning and grown at 37° C. until OD~0.5. Each strain was grown in triplicate. The cultures were then induced with 400 uM IPTG and incubated at 30° C. for 4 hours. 20 mL of each culture were centrifuged at 3000×g for 20 min. and the supernatant was discarded. The pellets were frozen at −80° C. overnight. Pellets were resuspended in 2 mL of a buffer containing 100 mM Tris, 100 mM NaCl, 0.25 mg/mL lysozyme and 0.25 mg/mL DNAase, pH 8. Cell suspensions were french pressed at 20,000 psi twice and the lysate was then centrifuged at 14000×g for 20 minutes to yield cell free extract that was used for kinetic studies and protein concentration determination.

To measure specific activity, 5 μL of cell free extract from each strain was incubated with 5 mM DMAPP, 50 mM $MgCl_2$ in a buffer containing 100 mM Tris and 100 mM NaCl (pH 8) to a final volume of 100 μL for 15 min. at 30° C. in gas tight 2 mL vials. Reactions were terminated with the addition of 100 μL of 500 uM EDTA, pH 8. Samples were analyzed by GC-MS to determine the concentration of isoprene in the headspace of the vials.

To determine $k_{cat}$ and $K_M$, 5 uL of cell free extract from each strain was incubated with DMAPP at concentrations ranging from 0.625 to 40 mM DMAPP in a buffer containing 100 mM Tris, 50 mM $MgCl_2$ and 100 mM NaCl (pH 8) to a final volume of 100 μL for 15 min. at 30° C. in gas tight 2 mL vials. Reactions were terminated with the addition of 100 μL of 500 mM EDTA, pH 8. Samples were analyzed by GC-MS to determine the concentration of isoprene in the headspace of the vials. Data were analyzed using Kaleidagraph and fit to following equation for uncompetitive substrate inhibition:

rate/E=$k_{cat}$*S/($K_M$+S*(1+S/$K_i$)). All data were run in triplicate with the exception of MD09-167 with 2.5 mM DMAPP which was run in duplicate.

Cell free extract was run on a Caliper microfluidic electrophoresis instrument (Caliper Life Sciences, Hopkinton, Mass., USA) in order to quantify the amount of isoprene synthase in each sample. The microfluidic chip and protein samples were prepared according to the manufacturer's instructions (LabChip® HT Protein Express, P/N 760301). Culture lysates were prepared in 96-well mictrotiter plates by adding 50 mM Tris pH 8.0 containing 0.1% Tween 20, 0.1 mg/ml lysozyme, 1.0 ug/ml DNAse at room temperature for 30 minutes, followed by centrifugation. Supernatants were then transferred to another 96 well plate and stored at −20° C. until use, when they were thawed at room temperature for 30 minutes. After shaking briefly, the 2 μl of each culture sample was transferred to a 96-well PCR plate (Bio-Rad, Hercules, Calif., USA) containing 7 μl samples buffer (Caliper) followed by heating the plate to 90° C. for 5 minutes on a thermostatically controlled plate heater. The plate was allowed to cool before adding 35 μl water to each sample. The plate was then placed in the instrument along with a protein standard supplied and calibrated by the manufacturer. The instrument functions by mixing the sample with a fluorescent dye that attaches non-covalently to the proteins, followed by electrophoresis through a gel matrix. As the proteins move past a focal point in the chip, the fluorescence signal is recorded and the protein concentration is determined by quantitating the signal relative to the signal generated by a calibrated set of protein standards.

TABLE 11-7

$k_{cat}$ and $K_M$ and specific activity values for isoprene synthases

| Isoprene Synthase | $k_{cat}$ ± S.D. ($s^{-1}$) | $K_M$ ± S.D. (mM) | $K_i$ ± S.D. (mM) | S.A. (nmol/mg/min) |
|---|---|---|---|---|
| Full Length | 0.72 ± 0.09 | 2.4 ± 0.3 | 15.7 ± 0.2 | 420 ± 60 |
| Truncated | 1.5 ± 0.2 | 1.8 ± 0.2 | 9.8 ± 0.9 | 800 ± 100 |
| MD09-165 | 0.8 ± 0.1 | 2.4 ± 0.5 | 19 ± 4 | 440 ± 80 |
| MD09-167 | 1.1 ± 0.3 | 2 ± 1 | 8.7 ± 0.9 | 610 ± 60 |

Parameters were determined by fitting the following uncompetitive substrate inhibition equation to data obtained for rate/[E] vs. [DMAPP]:

$$\frac{rate}{[E]} = \frac{k_{cat}*[S]}{K_M + [S]*\left(1 + \frac{[S]}{K_i}\right)}$$

The specific activities (S.A.) were calculated for reactions containing 5 mM DMAPP, 50 mM $MgCl_2$, 100 mM Tris, 100 mM NaCl, and 2.5-4.5 μg isoprene synthase from the supernatant of whole cell lysate. Reactions were performed at 30° C. for 15 minutes in triplicate using independently grown cultures.

Results/Discussion:

The specific activity of each protein was determined (FIG. 40 and Table 11-7). The specific activity of truncated isoprene synthase was approximately 2-fold greater than the specific activity of full length isoprene synthase. The C-terminally His-tagged full length isoprene synthase yielded approximately the same specific activity as the full length isoprene synthase. The C-terminally His-tagged truncated isoprene synthase gave a specific activity that was less than the non-tagged truncated isoprene synthase, but greater than the specific activity of both full length isoprene synthases.

The rate of conversion of DMAPP to isoprene was analyzed over a range of DMAPP concentrations in order to determine the $k_{cat}$ and $K_M$ parameters of the enzymes (FIGS. 41 and 42 and Table 11-7). The enzymes all exhibited rate profiles consistent with uncompetitive substrate inhibition by DMAPP. The $K_i$ for the full length constructs was greater than the $K_i$ for truncated constructs as determined by altering $K_i$ and observing the best fit (R-value) to the data (data not shown). All data has been fit to a $K_i$ of 10 mM in the figures in this document. The $K_M$s of truncated isoprene synthase decreased relative to the full length isoprene synthases. Therefore, as the substrate concentration decreases the ratio between the isoprene synthase activity of the truncated isoprene synthase to the full length isoprene synthase will increase (FIG. 43). The $k_{cats}$ of truncated isoprene synthases increased relative to the full length isoprene synthases. This results in greater isoprene synthase activity for the truncated isoprene synthases than the full length isoprene synthases at all substrate concentrations (FIG. 43). The ratio of the isoprene synthase activity of the truncated isoprene synthase to the full length isoprene synthase at varying DMAPP levels was determined (FIG. 43).

Conclusions: "Truncated" isoprene synthases exhibit increased $k_{cat}$ values and decreased $K_M$ values with respect to the catalysis of the conversion of DMAPP to isoprene compared to "full length" isoprene synthases. The specific activity of "truncated" isoprene synthases is increased relative to the specific activity of "full length" isoprene synthases. The most active isoprene synthase was non-tagged truncated isoprene synthase "MEA" variant (in strain MD09-173). The truncated isoprene synthase may increase the isoprene synthase activity in organisms used for production of isoprene compared to the full length isoprene synthase.

Example 12

Isoprene Synthase Enrichment—Relief of DMAPP Toxicity

This example identifies residue changes within IspS that confer better activity to the enzyme through kinetic improvement, increased expression, increased solubility, or any other means by which DMAPP is more effectively converted to isoprene by Isoprene Synthase. This procedure allows for the relief of cytotoxic intracellular levels of DMAPP by expression of improved IspS variants. In a population of cells expressing a heterogeneous mixture of IspS variants, the best enzymes should allow for better growth of their host strain, and should be enriched in the mixed population.

I. Strain Construction

Construction of Strains MCM518-521 and 528-531 in which Lambda promoters drive integrated mKKDyI was as follows. Primers MCM120 and MCM224 (Table 12-1) were used to amplify the resistance cassette from the GeneBridges FRT-gb2-Cm-FRT template using Stratagene Herculase II Fusion kit according to the manufacturer's protocol. Four 50 µL reactions were cycled as follows: 95° C., 2 min; (95° C., 20 sec, 55° C., 20 sec, 72° C., 1 min) for 30 cycles; 72° C., 3 min; and 4° C. until cool. The four reactions were pooled and purified on a Qiagen PCR column according to the manufacturer's protocol and eluted with 60 µL EB at 55° C.

Plasmid pRedET-carb (GeneBridges) was electroporated into MCM446. Transformants were recovered by shaking for one hour in SOC (Invitrogen) at 30° C. and then selected on LB containing carbenicillin (50 µg/ml) (carb50) plates at 30° C. overnight. A carbenicillin resistant colony was frozen as MCM508 (Table 12-2).

Strain MCM508 was grown from a fresh streak in 5 mL LB/carb50 at 30° C. to an $OD_{600}$ of ~0.5. 40 mM L-arabinose was added and culture was incubated at 37° C. for 1.5 hrs. Cells were harvested and electroporated with 3 µL of purified amplicons as previously, and then recovered in 500 µL SOC at 37° C. for 1.5-3 hrs. Transformants were selected on LB/kan10 plates at 37° C.

Recombination of the amplicon at the target locus was confirmed by PCR with primers GB-DW and MCM208. The resulting amplicons were sequenced to identify four clones with the sequences below. Carbenicillin-sensitive clones were frozen as strains MCM518-521.

MCM518-521 were restreaked on LB kan10 plates and grown overnight at 37° C.

Strains MCM518-521 were cultured in LB/kan10 at 37° C. and then electrotransformed with plasmid pCP20 (Datsenko K A, Wanner B L. One-step inactivation of chromosomal genes in Escherichia coli K-12 using PCR products. Proc Natl Acad Sci USA. Jun. 6, 2000;97(12):6640-5). Cells were recovered in 500 µL SOC, shaking at 30° C. for 1 hour. Transformants were selected on LB/carb50 plates at 30° C. overnight. The following morning a colony from each transformation was grown at 30° C. in liquid LB/carb50 until visibly turbid. The culture was then shifted to 37° C. for at least 3 hrs. Cells were streaked from this culture onto LB plates and grown overnight at 37° C.

The following day colonies were patched to LB, LB/carb50 and LB/kan10. Clones that grew on neither carb50 nor kan10 and were cultured in liquid LB from the patch on LB and frozen as MCM528-531.

DNA Sequences

These assemblies include the new promoters inserted on the chromosome in strains MCM518-521, as well as the very beginning of the mMVK ORF. Upstream of these assemblies is sequence from the GeneBridges FRT-gb2-Cm-FRT cassette. Downstream is the remainder of the mMVK ORF and then the rest of the lower MVA pathway integron from strain MCM508.

MCM518

(SEQ ID NO: 56)

aaagaccgaccaagcgacgtctgagagctccctggcgaattcggtaccaa taaaagagctttatttcatgatctgtgtgttggttttgtgtgcggcgc ggaagttcctattctctagaaagtataggaacttcctcgagccctatagt gagtcgtattaaattcatataaaaaacatacagataaccatctgcggtga taaattatctctggcggtgttgacataaataccactggcggtgatactga gcacatcagcaggacgcactgaccaccatgaaggtgcaaaggaggtaaaa aaacatggtatcctgttctgcgccgggtaagatttacctgttcggtgaac acgccgtagtttatgcgaaactgcaattgcgtgtgcggtggaactgcgt acccgtgttcgcgcggaactcaatgactctatcactattcagagc

MCM519

(SEQ ID NO: 57)

aaagaccgaccaagcgacgtctgagagctccctggcgaattcggtaccaa taaaagagctttatttcatgatctgtgtgttggttttgtgtgcggcgc ggaagttcctattctctagaaagtataggaacttcctcgagccctatagt

```
gagtcgtattaaattcatataaaaaacatacagataaccatctgcggtga taaattatctctggcggtgttgacctaaataccactggcggtgatactga gcacatcagcaggacgcactgaccaccatgaaggtgcaaaggaggtaaaa aaacatggtatcctgttctgcgccgggtaagatttacctgttcggtgaac acgccgtagtttatggcgaaactgcaattgcgtgtgcggtggaactgcgt acccgtgttcgcgcggaactcaatgactctatcactattcagagc MCM520
                                       (SEQ ID NO: 58)
aaagaccgaccaagcgacgtctgagagctccctggcgaattcggtaccaa taaaagagctttattttcatgatctgtgtgttggttttttgtgtgcggcgc ggaagttcctattctctagaaagtataggaacttcctcgagccctatagt gagtcgtattaaattcatataaaaaacatacagataaccatctgcggtga taaattatctctggcggtgttgacctaaataccactggcggtgatactga gcacatcagcaggacgcactgaccaccatgaaggtgcaaaggtaaaaaaa catggtatcctgttctgcgccgggtaagatttacctgttcggtgaacacg ccgtagtttatggcgaaactgcaattgcgtgtgcggtggaactgcgtacc cgtgttcgcgcggaactcaatgactctatcactattcagagc MCM521 (in strains MCM531 and MD09-171)
                                       (SEQ ID NO: 59)
aaagaccgaccaagcgacgtctgagagctccctggcgaattcggtaccaa taaaagagctttattttcatgatctgtgtgttggttttttgtgtgcggcgc ggaagttcctattctctagaaagtataggaacttcctcgagccctatagt gagtcgtattaaattcatataaaaaacatacagataaccatctgcggtga taaattatctctggcggtgttgacgtaaataccactggcggtgatactga gcacatcagcaggacgcactgaccaccatgaaggtgcaaaggaggtaaaa aaacatggtatcctgttctgcgccgggtaagatttacctgttcggtgaac acgccgtagtttatggcgaaactgcaattgcgtgtgcggtggaactgcgt acccgtgttcgcgcggaactcaatgactctatcactattcagagc
```

The neo-PL.2-mKKDyI (from MCM521) was transduced into BL21(λDE3) to generate strain MD09-171. A P1 lysate of MCM521 was made and transduced into BL21(λDE3) according to standard molecular biology techniques (Miller, A Short Course in Bacterial Genetics). Transductants were selected on Kan20 LB medium plates. Positive colonies were further verified by PCR to confirm the presence of PL.2-mKKDyI in the BL21(λDE3) strain. 1 µl of pCP20 plasmid was then transformed into this strain and selected for on LB+Carb50 and incubated at 30° C. Positive transformants were subsequently streaked on an LB plate and incubated at 37° C. for loss of the pCP20 plasmid. To confirm the loss of the neomycin (kanamycin) resistance marker, colonies that grew at 37° C. were patched onto LB Kan20, LB Carb50, and plain LB plates. The strains with integrated PL.2 mKKDyI without the kanamycin resistance marker that have lost pCP20 should be sensitive to kanamycin and carbenicillin. 4 KanS CarbS were used to check by PCR for the presence of mKKDyI in BL21(λDE3) with the parental BL21(λDE3) strain as a control. Once PCR confirmed the presence of mKKDyI, the resulting strain was transformed with 1 µl of the pLysS plasmid (Invitrogen). The resulting strain, MD09-171, was used for the enrichment experiments described below.

TABLE 12-1

Primers used for strain construction

| | |
|---|---|
| MCM120 | aaagtagccgaagatgacggtttgtcacatggagttggcaggat gtttgattaaaagcaattaaccctcactaaagggcgg (SEQ ID NO: 60) |
| MCM208 | gctctgaatagtgatagagtca (SEQ ID NO: 61) |
| MCM224 | taaatcttacccggcgcagaacaggataccatgttttttacct cctttgcaccttcatggtggtcagtgcgtcctgctgatgtgctc agtatcaccgccagtggtatttangtcaacaccgccagagataa tttatcaccgcagatggttatctgtatgtttttttatatgaattt aatacgactcactataggcgctcg (SEQ ID NO: 62) |
| GB-DW | aaagaccgaccaagcgacgtctga (SEQ ID NO: 63) |
| MCM161 | caccatggtatcctgttctgcg (SEQ ID NO: 64) |
| MCM162 | ttaatctactttcagaccttgc (SEQ ID NO: 65) |
| MCM143 | aggaggtggtctcaaatgactgccgacaacaatagta (SEQ ID NO:66) |
| MCM144 | aggaggtggtctcagcgctctgcagttatagcattctatgaatt tgcctg (SEQ ID NO:67) |

TABLE 12-2

Strains

| Strain | Description | Parent |
|---|---|---|
| MCM508 | BL21 gil.6-mKKDyI + predet.-carb | MCM446 |
| MCM518 | BL21 neo-PL.6-mKKDyI, clone10 | MCM508 |
| MCM519 | BL21 neo-PL.0-mKKDyI, clone11 | MCM508 |
| MCM520 | BL21 neo-PL.0-mKKDyI (bad RBS in front of mMVK), clone13 | MCM508 |
| MCM521 | BL21 neo-PL.2-mKKDyI, clone15 | MCM508 |
| MCM528 | BL21 PL.6-mKKDyI, loopedout | MCM518 |
| MCM529 | BL21 PL.0-mKKDyI, loopedout | MCM519 |
| MCM530 | BL21 PL.0-mKKDyI (bad RBS in front of mMVK), loopedout | MCM520 |
| MCM531 | BL21 PL.2-mKKDyI, loopedout | MCM521 |
| MD09-171 | BL21 (λDE3) PL.2-mKKDyI, loopedout + pLysS | MCM521 |

II. Growth Inhibition of MCM531 by Mevalonic Acid

An overnight culture of MCM531 (see strain description) was back-diluted to an $OD_{600}$ of 0.05 (this corresponds to an $OD_{600}$ of approx 0.005 in a 96-well plate reader) (SpectraMax M2, Molecular Devices). The diluted culture was then aliquotted into separate wells in a 96-well deep-well plate into standard TM3 medium (13.6 g $K_2PO_4$, 13.6 g $KH_2PO_4$, 2.0 g $MgSO_4*7H_2O$) supplemented with 1% glucose and 0.8 g/L Biospringer yeast extract (1% Yeast extract final))with 0, 1, 5, 10, 15 or 20 mM MVA added. FIG. 44 shows the growth curve of MCM531 in the various concentrations of MVA. Each MVA concentration was assayed in quadruplicate, error bars were negligible. FIG. 44 shows that MCM531 was severely inhibited for growth at concentrations of 5 mM MVA and higher.

III. Mutagenesis of IspS and Selection/Enrichment Assay

To generate a randomly mutagenized IspS open reading frame, the GeneMorph II EZ Clone domain mutagenesis kit (Stratagene) was used according to the manufacturer's recommended protocol. Specific primers to amplify the template (Pdu39 (pET24a-P. alba (MEA))) are described below (Table 12-3, pET24 Megaprime Forward and Reverse). To achieve the desired mutation frequency, the protocol outlined in the GeneMorph II kit was followed. To generate 2 to 3 residue changes per molecule, approximately 150 ng of starting template DNA was used for the initial PCR reaction. More or less template was used to generate IspS enzymes with either fewer or more residue changes, respectively. The resulting mutant "megaprimers" were then used to amplify the rest of the plasmid according to the manufacturer's recommended protocol.

The final PCR product from the GeneMorph II kit was treated with DpnI according to the manufacturer's recommended protocol. Prior to transformation into E. coli, it was necessary to desalt the PCR reaction by microdialysis. Typically, approximately 20 µl of the PCR reaction was subjected to microdialysis and used for electroporation into strain MD09-171 (Table 12-2) by standard molecular biology procedures. After electroporation, cells were recovered for 2 hours at 30° C., and then plated onto LB medium Kan50 Cm35. The entire transformation volume was plated to recover all mutations generated by the mutagenesis procedure.

For enrichment, all transformants were scraped and pooled together. An aliquot from each pool was frozen for storage in the −80. Prior to the enrichment, strains (control or experimental pools) were inoculated directly into LB with Kan50 and grown for a few hours, to minimize the loss of pool heterogeneity. After this recovery period, cells were diluted into liquid TM3 medium (described above) with Kan50, 5 mM MVA, and 200 µM IPTG. (The exact dilution was determined empirically for each pool/source of medium/control reaction). Cultures were then placed in the shaking incubator at 34° C. until an $OD_{600}$ of no more than 5. At this point, plasmids were purified from 1 ml of the "enriched" culture via miniprep protocol (Qiagen). This plasmid preparation was then transformed into electrocompetent MD09-171 cells as described above. The transformed cells were recovered for 2 hours in LB medium without antibiotics, and then subjected to a subsequent round of enrichment by dilution into TM3 with Kan50, 5 mM MVA and 200 µM IPTG as described above. This culture was placed into the shaking incubator at 34° C. until it reached an $OD_{600}$ of no more than 5, as described above. Plasmids were then purified, retransformed and subjected to further rounds of "enrichment." The enrichment process continued for 5 or 6 rounds of selection, plasmid purification, and retransformation. The process continued until the culture was homogeneous, i.e. contained only one variant of IspS by sequencing analysis.

After the last round of enrichment, the plasmid pool was transformed into chemically competent E. coli Top10 cells (Invitrogen) per the manufacturer's recommended protocol, recovered, plated onto LB medium with Kan50, and sent for complete sequencing (Quintara Biosciences) for comparison to the wild type sequence of P. alba IspS. Primers used for sequencing are described below.

TABLE 12-3

Primers used for IspS mutagenesis and sequencing

| | |
|---|---|
| pET24 Megaprime Forward | gtttaactttaagaaggagatataca t |
| pET24 Megaprime Reverse | gagctcgaattcggatcctta |
| alba sequencing reverse | ctcgtacaggctcaggatag |
| alba sequencing reverse2 | ttacgtcccaacgctcaact |

TABLE 12-3-continued

Primers used for IspS mutagenesis and sequencing

| | |
|---|---|
| EWL1000 | gcactgtctttccgtctgctgc |
| QB 1493 | cttcggcaacgcatggaaat |

IV. Individual Residue Changes Identified by Enrichment/DMAPP Toxicity Relief:

Plasmids isolated from selection/enrichment were fully sequenced. The following residue changes were confirmed by sequencing (Quintara Biosciences). The residue numbering corresponds to the P. alba "Full Length" sequence (in P. alba pET24a; SEQ ID NO:120), where the starting methionine is amino acid number 1. Identified residue changes included: V10M, F12S, T15A, E18G, V58I, V58F, L70Q, L70V, L70T, T71P, V79L, E89D, G94A, S119F, F120L, G127R, E175V, T212I, S257A, R262G, A266G, F280L, N297K, F305L, L319M, E323K, A328T, D342E, A359T, K366N, E368D, L374M, S396T, V418S, K438N, H440R, T442I, T442A, I449V, A469S, K500R, K505Q, G507S, S509N, F511Y, and N532K.

Combinations of Residue Changes (in a single IspS enzyme) Identified by Enrichment/DMAPP Toxicity Relief: G127R/F511Y, L70Q/G94A/R262G/F305L, F12S/T15A/E18G/N297K, S396T/T442I, V10M/E323K, F120L/A266G, K438N/K500R, V79L/S509N, E175V/S257A/E368D/A469S, T71P/L374M, F280L/H440R, E89D/H440R, V58F/A328T/N532K, S119F/D342E/I449V, and K366N/G507S.

Example 13

Construction of Site Saturation Libraries (SSLs) and Biochemical Analysis of the L70R Variant This example includes an examination of possible amino acid substitutions at sites identified by the selection/enrichment procedure described above and other sites of potential interest (active site, conserved between Poplar species) for their effect on solubility, expression, and activity of IspS.

I. Strain Construction

Residues identified by the selection/enrichment procedure (L70, G94, R262, F305) described above were chosen for analysis. In addition, residues that are putatively involved in substrate binding (F303, V3065, F385, S412, Q416, F450), and residues that are different between the various Poplar species (e.g. V418, T442) were chosen for further analysis (numbering corresponds to the "full length" amino acid sequence of P. alba IspS). To generate a randomized pool of amino acid substitutions (the Site Saturation Library, SSL), pDu39 (see description above) was subjected to Quick-Change (Stratagene) mutagenesis with the QC primers indicated below (Table 13-1), according to the manufacturer's recommended protocol. The PCR Reaction was prepared as follows:

1 µl pDu39, 5 µl 10× PfuUltra HF buffer, 1 µl dNTP's, 1 µl (50 µM) primer-For (e.g. QC L69 F), 1 µl (50 uM) primer-Rev (e.g. QC L69 R), 2 µl DMSO, 39 µl diH2O, and 1 µl PfuUltra HF Polymerase (Stratagene). The PCR cycling parameters for QuickChange were as follows: 95° C. 1 min, 95° C. 30 sec., 55° C. 1 min., 68° C. 7.3 min. for one cycle followed by 95° C. 30 sec., 55° C. 1 min., 68° C. 7.3 min for 17 more cycles. The temperature was then reduced to 4° C. Incorporation of the bases NNK at the codon for the residues described above allows for the insertion of codons that represent all 20 possible amino acids at the given site. 1 µl of the resulting pools of mutagenized PCR products was DpnI treated (described above), and transformed into chemically competent E. coli Top10 cells (Invitrogen) according to the manufacturer's recommended protocol. Entire transformation reactions were recovered in 1 ml LB medium without antibiotics at 37° C. for 1 hour and plated onto LB Kan50. The next day, all transformants were scraped off of the LB plates, mixed thoroughly, and plasmids were purified via miniprep (Qiagen). Pools of plasmids were then transformed into chemically competent BL21(λDE3)pLysS cells (Invitrogen) according to the manufacturer's protocol. The transformation reactions were recovered in 1 ml LB medium at 37° C. for 1 hour and then plated onto LB Kan50 Cm35 at dilutions sufficient to generate separation of positive colonies. After overnight incubation at 37° C., individual colonies were inoculated into individual wells in a 96-well deep-well microtiter plate (VWR) containing 500 ul of liquid LB Kan50 Cm35 each. In eight wells (typically column 12, A through H) strain MD09-173 (see above) or BL21(λDE3)pLysS with P. alba pET24a (Full Length) was inoculated as a control for the DMAPP assay. The microtiter plates were then sealed with a semi-permeable membrane (Breathe-Easier, Diversified Biotech), and incubated overnight at 30° C. in a shaking incubator (Vertiga). The next day, 100 μl samples from each well within a 96-well plate were mixed with 50 μl of 50% glycerol in a new 200 ul 96-well plate, and frozen at −80° C. until further analysis. This plate was then used for the DMAPP assay described below.

TABLE 13-1

Primers used for mutagenesis

| | | |
|---|---|---|
| QC L70F | gaaaaagcagaatttnnkaccctgctggaactg | (SEQ ID NO: 68) |
| QC L70R | cagttccagcagggtmnnaaattctgcttttc | (SEQ ID NO: 69) |
| QC G94F | gagtctgatatccgtnnkgcgctggatcgcttc | (SEQ ID NO: 70) |
| QC G94R | gaagcgatccagcgcmnnacggatatcagactc | (SEQ ID NO: 71) |
| QC R262F | tcccgttggtggcgtnnkgtgggtctggcgacc | (SEQ ID NO: 72) |
| QC R262R | ggtcgccagacccacmnnacgccaccaacggga | (SEQ ID NO: 73) |
| QC F303F | tccgtcgcaaaaatgnnktctttcgtaaccatt | (SEQ ID NO: 74) |
| QC F303R | aatggttacgaaagamnncattttgcgacgga | (SEQ ID NO: 75) |
| QC F305F | gcaaaaatgttttctnnkgtaaccattatcgac | (SEQ ID NO: 76) |
| QC F305R | gtcgataatggttacmnnagaaaacattttgc | (SEQ ID NO: 77) |
| QC V306F | aaaatgttttctttcnnkaccattatcgacgat | (SEQ ID NO: 78) |
| QC V306R | atcgtcgataatggtmnngaaagaaaacatttt | (SEQ ID NO: 79) |
| QC F385F | gacctgtgcaacgctnnkctgcaagaagccaag | (SEQ ID NO: 80) |
| QC F385R | cttggcttcttgcagmnnagcgttgcacaggtc | (SEQ ID NO: 81) |

TABLE 13-1-continued

Primers used for mutagenesis

| | | |
|---|---|---|
| QC S412F | gcatggaaatcctctnnkggcccgctgcaactg | (SEQ ID NO: 82) |
| QC S412R | cagttgcagcgggccmnnagaggatttccatgc | (SEQ ID NO: 83) |
| QC Q416F | tcttctggcccgctgnnkctggtgttcgcttac | (SEQ ID NO: 84) |
| QC Q416R | gtaagcgaacaccagmnncagcgggccagaaga | (SEQ ID NO: 85) |
| QC V418F | ggcccgctgcaactgnnkttcgcttacttcgct | (SEQ ID NO: 86) |
| QC V418R | agcgaagtaagcgaamnncagttgcagcgggcc | (SEQ ID NO: 87) |
| QC T442F | caaaaataccatgacnnkatctctcgtccttcc | (SEQ ID NO: 88) |
| QC T442R | ggaaggacgagagatmnngtcatggtattttg | (SEQ ID NO: 89) |
| QC F450F | cgtccttcccatatcnnkcgtctgtgcaatgac | (SEQ ID NO: 90) |
| QC F450R | gtcattgcacagacgmnngatatgggaaggacg | (SEQ ID NO: 91) |

II. Generation of a "Winner" Plate for Secondary Assay and Identification of L70R as a Variant with Increased Specific Activity Variants that displayed increased specific isoprene production when compared to wild type were chosen for further analysis. FIG. 45 shows a typical data set of an SSL plate for an individual residue, in this case L70. From this particular plate, the samples in wells C3 (27), D3 (39), and E3 (51) were chosen for further analysis. Other variants at different residues (listed above) that showed increased isoprene productivity, when subjected to DMAPP analysis, were isolated from their original SSL plates stored at −80° C. (described above), and re-arrayed onto a new "winner" plate for secondary screening. Two wells containing MD09-173 were included as controls. All variants were sequenced (Quintara Biosciences) and subjected to the DMAPP assay as described above. See Table 13-2 for sequencing results. For the DMAPP assay, a single growth of each variant was assayed, and therefore a single lysate generated, but in quadruplicate to generate statistically significant data. Samples were assayed at the $OD_{600}$ indicated in Table 13-2. Protein analysis was performed on all lysates using the Western Breeze Western blot kit (Invitrogen) followed by fluorescence detection on a Storm860 (see below)

III. DMAPP Assay—Growth, Lysis and Isoprene Measurement

A patch plate was prepared from a glycerol stock plate using a VP-Scientific Replication Tool patch LB Agar CM35/Kan50 large patch plate from overnight glycerol stock Plate. Cultures were incubated at 30° C. overnight (20 to 24 hr). Plates were stored at 4° C. for up to a week.

An overnight growth plate was prepared from 500 mL of LB CM35/Kan50 media. 300 μL/well of LB CM35/Kan50 media were dispensed into deep 96 well plate. Using the V&S Replication Tool, the patch inoculum was transferred to a deep 96 well plate. Media was inoculated by dipping the tool then shaking the pin within the well. The overnight growth plate was sealed with a Breathe-Easier Sealing Membrane.

The plate was incubated at 30° C. overnight in a Vertiga Shaking Incubator at 800 rpm for 16 to 18 hours.

A deep 96 well day growth plate was prepared by dispensing 588 μL/well of LB CM35/Kan50 media. The overnight growth plate was removed from the incubator and cultures were diluted 50-fold. 12 μL of overnight culture was transferred to a day growth plate containing 588 μL/well of supplemented LB media. The overnight growth plate was sealed with a new Breathe-Easier Sealing Membrane and was incubated at 34° C. and 800 rpm for 2.25 hr in the Vertiga Shaking Incubator.

To induce the expression of IspS, thawed 12 mM IPTG was poured into 50 mL or 100 mL sterile reservoir and dispensed 20 μL/well into each 600 μL/well culture. Overnight growth plate was resealed with Breathe-Easier Sealing Membrane and incubated at 34° C. and 800 rpm for 4 hours in the Vertiga Shaking Incubator.

To harvest cell, 200 μL of induced culture was transferred to 450 μL Nunc storage plate. The plate was centrifuged at 3300 rpm for 20 min at 4° C. in a low speed benchtop centrifuge. 180 μL supernatant was removed with a pipettor and discarded. The plate was sealed with an aluminum foil membrane, covered with a plastic plate lid and stored frozen at −80° C.

The $OD_{600}$ of the plates were read. 150 μL 1×PBS was dispensed into a 96 well Costar Read Plate (#9017). 50 μL of culture sample was then transferred to the read plate. The $OD_{600}$ reading was then taken with a Spectramax Plate Reader.

Lysis: The harvest plate was defrosted in a room temperature water bath for 4 min and then incubated in Thermomixer at 25° C. at 1200 rpm for 1 min. Lysis buffer was dispensed at 80 μL/well to 20 μL/well of harvest cells. 1.25× Lysis Working Stock buffer was prepared from 6.25 ml 1M Tris pH 8, 625 μl 10% Tween 20, 312.5 μl 0.2 M PMSF, 462.5 μl 10 mg/ml DNAse I (Sigma), 1.25 ml 1 M $MgCl_2$, 132.5 μl 25000 U/μl Lysozyme (Epicentre Technologies) and 40.968 ml $dIH_2O$. Plates were incubated on a Thermomixer at 25° C. and 1200 rpm for 30 min. 1× Lysis Buffer stock was prepared by diluting 19 ml of 1.25× Lysis Working stock with 4.75 ml $dIH_2O$.

DMAPP Working Stock was prepared as follows.

IV. Western Blot of Isoprene Synthase with Fluorescence Labeled Secondary Antibody.

Samples were prepared and run on NativePAGE™ Novex® Bis-Tris Gels (Invitrogen) according to the manufacturer's protocol. After completion of the run the gels were immediately transferred to Nitrocellulose membranes using the XCell II™ Blot Module (Invitrogen) according to the manufacturer's recommended protocol. After transfer, the membrane was placed in 15 ml of the appropriate Blocking Solution (Ultra filtered Water 31.5 ml, Blocker/Diluent (Part A) 9 ml, Blocker/Diluent (Part B) 4.5 ml) in the covered, plastic dish provided in the kit and incubated for 30 minutes on a rotary shaker set at 1 revolution/sec. The Blocking Solution was decanted and the membrane rinsed 2 times with 20 ml of water for 5 minutes. The membrane was incubated with 15 ml of Primary Antibody (Ab) Solution (24 μl of primary Ab in 15 ml Blocking solution) for 1 hour, followed by washing 3 times 5 minutes with 20 ml of 1× Antibody Wash Solution. The membrane was then incubated in 15 ml of Secondary Antibody Solution (15 ul secondary Ab (Alexa Fluor 488 goat anti-rabbit IgG (H+L, Invitrogen)) in 15 of blocking solution) for 30 minutes. The membrane was washed 3 times at 5 minutes with 20 ml of Antibody Wash, and rinsed two times 2 minutes with 20 ml of water. The membrane was dried between paper towels and stored at room temperature for further detection. The fluorescent bands were detected and quantified using the Storm 860 Molecular Imager (GMI, Inc).

V. Results:

Table 13-2 shows all of the relevant data for each variant assayed: sequencing results, residue change, average isoprene production, protein concentration, and average specific activity (of all 4 replicates). FIG. 46 shows the graphical representation of the data shown in Table 13-2. Specific activity was calculated by multiplying the isoprene produced (μg/l) by 0.0414 and then dividing by protein concentration (mg/ml). This conversion factor (0.0414) accounts for the total headspace volume in a sealed 2 ml GC vial (1.9 ml), the lysate volume (15 ul), the duration of the DMAPP assay (45 min), and the molecular weight of isoprene. Thus, specific activity values are given in nmol isoprene/mg Isps/min.

The data in Table 13-2 and the graph in FIG. 46 show that of all variants analyzed, all three L70R variants displayed Dimethylallyl Pyrophosphate (triammonium salt) 25 mg (Cayman Chemicals, Cat No. 63180)

| final | total vol | diluent | stock vol | stock | dilution | Reagent | Units | Plate(s) |
|---|---|---|---|---|---|---|---|---|
| 30 | 840 | 840 | solid | 25000 | 1 | DMAPP | mg/mL | 1 |
| 3 | 2500 | 2250 | 250 | 30 | 10 | DMAPP | mg/mL | 1 |

The Diluent was 0.1 M Potassium Phosphate. 200 uL/well was dispensed for transfer to sample wells and was stored on ice.

DMAPP Reaction: 1× Lysis Buffer was dispensed at 65 μL/well. 15 μL/well of lysate was transferred to the respective sample wells in a 96 Deep well Zinsser Glass Block. DMAPP reagent was dispensed at 20 μL/well. The glass block was sealed with an aluminum foil membrane and incubated at 25° C. at 450 rpm for 45 min. The reaction was stopped by transferring the Glass Block to a 70° C. water bath and incubating for 6 min. GC Analysis was performed as previously described.

higher specific activity than wild type. To analyze the L70R variants further, the specific activity values for all 3 isolates (4 replicates of each) were averaged and compared to the controls (2 isolates, 4 replicates each). Therefore, there were 12 measurements for the L70R variant, and 8 for wild type. These data are shown below in Table 13-3. When corrected for protein, the L70R variants displayed a 25% increase in activity over MD09-173 (the MEA truncation). FIG. 47 shows the average specific activity for all L70R variants compared to MEA. Error bars show one standard deviation. The two data sets for L70R and the MEA control were subjected to a Student's T-Test for statistical analysis, which yielded a P-value of $6.0011 \times 10^{-5}$.

TABLE 13-2

Sequencing Results, Isoprene Production, Protein concentration, and Specific Activity for all residues in the Winner Plate

| Residue | WT codon | Mutant codon | Amino acid change | OD600 | Avg. Isoprene produced (4 replicates) | Std. Dev. (isoprene) | Protein concentration (mg/ml) | Avg. Specific Activity (4 replicates) | Std. Dev. (Specific Activity) |
|---|---|---|---|---|---|---|---|---|---|
| L70 | CTG | TGG | W | 2.6488 | 663.00 | 18.64 | 0.139 | 198.020 | 5.566 |
| L70 | CTG | CGG | R | 3.4944 | 1235.72 | 48.82 | 0.127 | 401.451 | 15.860 |
| L70 | CTG | CGT | R | 3.32416 | 944.77 | 19.15 | 0.121 | 323.523 | 6.539 |
| L70 | CTG | CGT | R | 3.37232 | 947.11 | 17.74 | 0.106 | 371.375 | 6.957 |
| L70 | CTG | TGG | W | 2.83584 | 774.49 | 32.60 | 0.129 | 248.925 | 10.477 |
| G94 | GGT | GAG | E | 3.304 | 1070.41 | 20.52 | 0.144 | 307.731 | 5.898 |
| G94 | GGT | GGG | G | 3.40816 | 982.64 | 27.37 | 0.133 | 306.891 | 8.549 |
| R262 | CGT | CGT | R | 3.01616 | 861.08 | 29.13 | 0.116 | 307.227 | 10.395 |
| R262 | CGT | CGG | R | 3.31744 | 965.44 | 19.25 | 0.136 | 294.311 | 5.868 |
| F305 | TTC | TTT | F | 2.90864 | 788.46 | 15.15 | 0.119 | 274.297 | 5.270 |
| F305 | TTC | CTG | L | 2.7776 | 626.70 | 22.91 | 0.141 | 183.823 | 6.719 |
| WT1 | | | | 3.71392 | 991.65 | 35.78 | 0.144 | 285.216 | 10.292 |
| F305 | TTC | TTC | F | 2.604 | 694.03 | 35.93 | 0.118 | 244.488 | 12.658 |
| V306 | GTA | GTA | V | 3.33648 | 912.56 | 38.76 | nd | nd | nd |
| V306 | GTA | GTA | V | 3.17632 | 892.97 | 56.10 | 0.137 | 269.415 | 16.927 |
| F385 | TTC | TTC | F | 2.89184 | 721.24 | 29.36 | 0.134 | 223.380 | 9.094 |
| Q416 | CAA | CAG | Q | 3.00272 | 953.07 | 57.38 | 0.149 | 264.718 | 15.938 |
| V418 | GTG | ATG | M | 2.14144 | 767.25 | 27.94 | 0.164 | 194.099 | 7.067 |
| V418 | GTG | ACG | T | 3.24688 | 973.57 | 75.08 | 0.192 | 209.801 | 16.179 |
| V418 | GTG | ACG | T | 3.13264 | 936.98 | 68.50 | 0.171 | 226.197 | 16.536 |
| T442 | ACC | GTA | V | 3.07552 | 951.64 | 38.06 | 0.154 | 255.496 | 10.217 |
| F450 | TTC | TTC | F | 2.93328 | 911.44 | 50.88 | 0.126 | 299.018 | 16.691 |
| V418 | GTG | ACG | T | 3.08896 | 1057.71 | 46.28 | 0.183 | 238.887 | 10.454 |
| WT2 | | | | 3.37568 | 960.25 | 58.16 | 0.131 | 304.346 | 18.434 |

Note that sequence of all plasmids is identical to Pdu39 (see above) with the exception of the indicated codon. The L70R variants are highlighted in gray.

TABLE 13-3

Average Specific Activity of all L70R variants relative to the MEA control.

| Variant Average | Specific Activity | Standard Deviation |
|---|---|---|
| L70R | 365.116 | 35.31977 |
| WT (the MEA control) | 294.7809 | 17.19228 |

See FIG. 47 for bar graph.

Example 14

Truncations of *P. alba*, *P. tremuloides*, *P. trichocharpa*, and Kudzu Isoprene Synthases This example describes the generation of a series of truncations in the IspS enzymes of *P. alba*, *P. tremuloides*, *P. trichocharpa*, and Kudzu and to determine their effect on activity.

I. Strain Construction

All isoprene synthase genes were codon optimized for *E. coli*, synthesized, and cloned into pET24a by DNA2.0 (Menlo Park, Calif.). All truncated constructs were generated using the QuickChange Site-Directed Mutagensis kit (Stratagene) using the previously described templates *P. alba* pET24a (for plasmids pDu47-3 through -7, FIGS. 48, 49, 51-60), *P. tremuloides* pET24a (plasmid pDu48, FIGS. 49C, 61 and 62), *P. trichocharpa* pET24a (pDu49, FIGS. 50A, 63, 64), or pET24d-Kudzu (pDu50 and 50-4, FIGS. 50B, 50C, 65-68) for PCR amplification. Approximately 50 ng of template DNA was used for amplification (with an Eppendorf Mastercycler Gradient PCR Machine) of the PCR product with the Forward (For) and Reverse (Rev) primer pairs that correspond to each relevant truncation (QC Trunc -3 F and QC Trunc -3 R, for example, see Table 14-1). PCR reactions mixtures were as follows: 1 µl *P. alba* pET24a (or other template), 5 µl 10× PfuUltra HF buffer, 1 µl dNTP's (10 mM), 1 µl (50 uM) primer-For, 1 µl (50 µM) primer-Rev, 1.5 µl DMSO, 39.5 µl diH$_2$O and 1 µl PfuUltra HF Polymerase.

PCR cycle parameters were as follows: (95° C. 1 min., 95° C. 1 min., 55° C. 1 min., 68° C. 7.30 min.) for 18 cycles then 4° C. until cool using an Eppendorf Mastercycler Gradient Machine. The PCR products were treated with 1-2 µl of DpnI (Roche) for 1-3 hour at 37° C. 5 µl of the DpnI treated products were visualized on a 0.8% E-gel (Invitrogen). 1 µl of each product was transformed into chemically competent *E. coli* Top10 cells (Invitrogen) (according to the manufacturer's protocol). Transformants were selected for on LB medium containing kanamycin at a concentration of 50 µg/ml (Kan50), and incubated overnight at 37° C. Five colonies of each transformation were selected and grown to stationary phase in 3 ml liquid LB Kan50. Plasmids were purified using a QIAPrep Spin miniprep kit (Qiagen) according to the manufacturer's recommended protocol. Purified plasmids were sequenced (by Quintara Biosciences) with T7 Forward and Reverse primers, compared to the parental sequence, and confirmed for their respective truncation. The resulting plasmids (pDu47-3 through pDu50-4, see Table 14-2) were transformed into chemically competent *E. coli* BL21(DE3) pLysS (Invitrogen) according to the manufacturer's recommended protocol. Table 14-3 describes the strains used for expression of truncated IspS enzymes.

After overnight incubation at 37° C., individual colonies were inoculated into individual wells in a 96-well deep-well microtiter plate (VWR) containing 500 µl of liquid LB Kan50 CM35 each. Microtiter plates were then sealed with a semi-permeable membrane (Breathe-Easier, Diversified Biotech), and incubated overnight at 30° C. in a shaking incubator (Vertiga). The next day, 100 µl samples from each well within a 96-well plate were mixed with 50 µl of 50% glycerol in a new 200 µl 96-well plate, and frozen at −80° C. until further analysis. This plate was then used for the DMAPP assay as described in Example 13. Table 14-4 shows the average specific productivity of all samples, and FIG. 69 shows the graphical representation of the same data.

DMAPP activity and protein quantitation was determined as described in Example 13.

Specific activity was calculated by multiplying the isoprene produced (μg/l) by 0.00776 and then dividing by protein concentration (mg/ml). This conversion factor (0.00776) accounts for the total headspace volume in a sealed 2 ml GC vial (1.9 ml), the lysate volume (80 μl), the duration of the DMAPP assay (45 min), and the molecular weight of isoprene. Thus, specific activity values are given in nmol isoprene/mg IspS/min.

TABLE 14-1

| Primers | | |
|---|---|---|
| QC Trunc-3 F | gaaggagatatacatatgaccgaagctcgtcgt | (SEQ ID NO: 92) |
| QC Trunc-3 R | acgacgagcttcggtcatatgtatatctccttc | (SEQ ID NO: 93) |
| QC Trunc-4 F | gaaggagatatacatatggaaaccgaagctcgt | (SEQ ID NO: 94) |
| QC Trunc-4 R | acgagcttcggtttccatatgtatatctccttc | (SEQ ID NO: 95) |
| QC Trunc-5 F | gaaggagatatacatatgactgaaaccgaagct | (SEQ ID NO: 96) |
| QC Trunc-5 R | agcttcggtttcagtcatatgtatatctccttc | (SEQ ID NO: 97) |
| QC Trunc-6 F | gaaggagatatacatatggaaactgaaaccgaa | (SEQ ID NO: 98) |
| QC Trunc-6 R | ttcggtttcagtttccatatgtatatctccttc | (SEQ ID NO: 99) |
| QC Trunc-7 F | gaaggagatatacatatgaccgaaactgaaac | (SEQ ID NO: 100) |
| QC Trunc-7 F | ggtttcagtttcggtcatatgtatatctccttc | (SEQ ID NO: 101) |
| QC Kudzu MEA F | agaaggagatataccatggaagctcgtcgttccgcaaac | (SEQ ID NO: 102) |

TABLE 14-1-continued

| Primers | | |
|---|---|---|
| QC Kudzu MEA R | gtttgcggaacgacgagcttccatggtatatctccttct | (SEQ ID NO: 103) |
| QC Kudzu-4 F | agaaggagatataccatggagcataattcccgt | (SEQ ID NO: 104) |
| QC Kudzu-4 R | acgggaattatgctccatggtatatctccttct | (SEQ ID NO: 105) |
| QC Trem/Trich-2 F | gaaggagatatacatatggaaacgcgtcgttct | (SEQ ID NO: 106) |
| QC Trem/Trich-2 R | agaacgacgcgtttccatatgtatatctccttc | (SEQ ID NO: 107) |

TABLE 14-2

| Plasmids | |
|---|---|
| pDu47-3 | Mtg pET24a-*P. alba* TRC (-3) |
| pDu47-4 | Mtg pET24a-*P. alba* TRC (-4) |
| pDu47-5 | Mtg pET24a-*P. alba* TRC (-5) |
| pDu47-6 | Mtg pET24a-*P. alba* TRC (-6) |
| pDu47-7 | Mtg pET24a-*P. alba* TRC (-7) |
| pDu48 | Mtg pET24a-*P. tremu* TRC (MET) |
| pDu49 | Mtg pET24a-*P. tricho* TRC (MET) |
| pDu50 | Mtg pET24d-Kudzu TRC (MEA) |
| pDu50-4 | Mtg pET24d-Kudzu TRC (-4) |

TABLE 14-3

| Strains | |
|---|---|
| MD09-197-3 | BL21(DE3)pLysS, pDu47-3 |
| MD09-197-4 | BL21(DE3)pLysS, pDu47-4 |
| MD09-197-5 | BL21(DE3)pLysS, pDu47-5 |
| MD09-197-6 | BL21(DE3)pLysS, pDu47-6 |
| MD09-197-7 | BL21(DE3)pLysS, pDu47-7 |
| MD09-198 | BL21(DE3)pLysS, pDu48 |
| MD09-199 | BL21(DE3)pLysS, pDu49 |
| MD09-200 | BL21(DE3)pLysS, pDu50 |
| MD09-200-4 | BL21(DE3)pLysS, pDu50-4 |

TABLE 14-4

Specific Productivity of Variants listed above

| | | Isoprene Produced (μg/l) | | | $OD_{600}$ | | OD |
|---|---|---|---|---|---|---|---|
| Sample | Sample | Average | Std Dev | % CV | Raw | xDF xCF | Norm |
| IspS N terminal Truncation Variants | MD09-197-3 | 3381 | 154 | 5 | 0.3060 | 3.4 | 986.6 |
| | MD09-197-4 | 3000 | 206 | 7 | 0.3160 | 3.5 | 847.7 |
| | MD09-197-5 | 2932 | 266 | 9 | 0.3200 | 3.6 | 818.2 |
| | MD09-197-6 | 2450 | 217 | 9 | 0.3040 | 3.4 | 719.4 |
| | MD09-197-7 | 2285 | 397 | 17 | 0.3020 | 3.4 | 675.5 |
| | MD09-198 | 1916 | 106 | 6 | 0.3330 | 3.7 | 513.6 |
| | MD09-199 | 2031 | 108 | 5 | 0.2140 | 2.4 | 847.6 |
| | MD09-200 | 141 | 8 | 6 | 0.3700 | 4.1 | 34.0 |
| | MD09-200-4 | 1829 | 197 | 11 | 0.2760 | 3.1 | 591.5 |
| | MD09-173 | 2414 | 201 | 8 | 0.3400 | 3.8 | 633.9 |
| | MD09-176 | 2826 | 354 | 13 | 0.3260 | 3.7 | 773.9 |
| | BL21 DE3 pLysS + *P alba* pET24a | 2175 | 117 | 5 | 0.2990 | 3.3 | 649.6 |

A second experiment was conducted with the strains outlined in Table 14-5. Control was BL21 DE3 pLysS with *P. alba* pET24a (full length *P. alba* IspS).

TABLE 14-5

Strains

| | |
|---|---|
| MD09-197-3 | BL21(DE3)pLysS, pDu47-3 |
| MD09-197-4 | BL21(DE3)pLysS, pDu47-4 |
| MD09-197-5 | BL21(DE3)pLysS, pDu47-5 |
| MD09-197-6 | BL21(DE3)pLysS, pDu47-6 |
| MD09-197-7 | BL21(DE3)pLysS, pDu47-7 |
| MD09-198 | BL21(DE3)pLysS, pDu48 |
| MD09-199 | BL21(DE3)pLysS, pDu49 |
| MD09-173 | BL21(DE3)pLysS, pET24a-*P. alba* (MEA) Untagged (pDu39) |
| MD09-174 | BL21(DE3)pLysS, pET24a-*P. alba* (MNV) Untagged (pDu40) |
| MD09-175 | BL21(DE3)pLysS, pET24a-*P. alba* (MSV) Untagged (pDu41) |
| MD09-176 | BL21(DE3)pLysS, pET24a-*P. alba* (MTE) Untagged (pDu42) |
| MD09-177 | BL21(DE3)pLysS, pET24a-*P. alba* (MVS) Untagged (pDu43) |
| MD09-197-3 | BL21(DE3)pLysS, pDu47-3 |
| MD09-197-4 | BL21(DE3)pLysS, pDu47-4 |

Results

All truncations of *P. alba* IspS and two from *P. tremuloides* and *P. trichocharpa* were assayed in parallel to compare their relevant specific activities via DMAPP assay and quantitative Western blot. At least two samples per variant were assayed for isoprene production and amount of IspS in mg/ml. Variant MD09-174 produced little isoprene and expressed little protein, yet displayed high specific activity. High specific activities were also displayed by MD09-173, MD09-176, and MD09-197-3 (see Table 14-6 and FIG. 70). The highest levels of protein (µg) in 3 µg total protein were displayed by MD09-176 and MD09-197-3, indicating that these variants are more effectively expressed in the *E. coli* BL21 DE3 host strain.

TABLE 14-6

Specific Activity of truncations.

| Strain | Average Specific Activity | Standard Deviation | Average ug IspS/ 3 µg total protein |
|---|---|---|---|
| *P. alba* FL | 240.16239 | 31.0423851 | 0.198 |
| MD09-175 | 331.8755329 | 8.958408319 | 0.188 |
| MD09-177 | 340.1959506 | 39.72104203 | 0.150 |
| MD09-176 | 363.516921 | 3.376026129 | 0.202 |
| MD09-174 | 452.7792122 | 27.71567075 | 0.018 |
| MD09-197-7 | 279.2042431 | 23.82331163 | 0.158 |
| MD09-197-6 | 309.8357305 | 7.903564316 | 0.164 |
| MD09-197-5 | 293.22592 | 20.97161876 | 0.165 |
| MD09-197-4 | 321.3926574 | 56.13760028 | 0.186 |
| MD09-197-3 | 333.0604155 | 45.92710529 | 0.207 |
| MD09-173 | 368.4597405 | 37.80631246 | 0.159 |
| MD09-198 | 297.6476631 | 56.81405985 | 0.154 |
| MD09-199 | 256.7342861 | 8.239697653 | 0.216 |

Example 15

Constructs for Three-Dimensional Structure Determination

I. Construction of pMAL-C4X Kudzu

A synthetic gene, coding for isoprene synthase (IspS) of the Kudzu vine (*Pueraria lobata*) and codon-optimized for *E. coli*, was purchased from DNA2.0 (Menlo Park, Calif.) and provided as plasmid p9795 (FIGS. 71 and 72). The insert was removed by digestion with BspLU11I/PstI, gel-purified, and religated into NcoI/PstI-digested pTrcHis2B (Invitrogen, Carlsbad, Calif.). The resulting plasmid was named pTrcKudzu (FIG. 73: map of pTrcKudzu). The stop codon in the insert is before the PstI site, which results in a construct in which the His-Tag is not attached to the IspS protein.

A PCR reaction was performed to amplify the *E. coli* codon-optimized Kudzu gene using plasmid pTrcKudzu as the DNA template, primers EL-959 and EL-960, 10 mM dNTP (Roche, Indianapolis, Ind.), and Pfu Ultra II Fusion DNA polymerase (Stratagene, La Jolla, Calif.) according to manufacturer's protocol. PCR conditions were as follows: 95° C. for 2 min (first cycle only), 95° C. for 25 sec, 60° C. for 25 sec, 72° C. for 30 sec, repeat for 28 cycles, with final extension at 72° C. for 1 min. The PCR product was then purified using the QIAquick PCR Purification Kit (Qiagen Inc, Valencia, Calif.).

The Kudzu PCR product (1 µg) was digested using EcoRI and HindIII restriction endonucleases (Roche) according to manufacturer's protocol. The digest was incubated 37° C. for 30 minutes to minimize digestion of the internal EcoRI site that is present in the Kudzu gene. The digested PCR fragment was then purified using the QIAquick PCR Purification Kit. The vector pMAL-C4X (0.5 µg) (New England Biolabs, Ipswich, Mass.; FIGS. 75 and 76) was digested using EcoRI and HindIII restriction endonucleases (Roche) according to manufacturer's protocol. The digested vector was then gel purified using the QIAquick Gel Extraction Kit (Qiagen Inc). A DNA ligation reaction was performed using T4 DNA ligase (New England Biolabs) with a 5:1 ratio of digested Kudzu PCR product to digested pMAL-C4X vector according to manufacturer's protocol. An aliquot of the ligation reaction was then transformed into TOP10 chemically competent cells (Invitrogen Corp). Transformants were selected on LA+50 µg/µl carbenicillin plates.

Screening of transformants containing the Kudzu gene was performed by picking colonies and performing PCR with primers EL-957 and EL-966 using PuReTaq Ready-To-Go PCR beads (GE Healthcare, Piscataway, N.J.) according to manufacturer's protocol. PCR conditions were as follows: 95° C. for 2 min (first cycle only), 95° C. for 30 sec, 50° C. for 30 sec, 72° C. for 40 sec, repeat for 28 cycles, with final extension at 72° C. for 1 min. PCR products were analyzed on a 2% E-gel (Invitrogen Corp) looking for a 600 bp fragment. Colonies containing the correct sized PCR product insert were submitted for DNA sequencing using primers EL-950, EL-951, EL-953, and EL-957. DNA sequencing confirmed the construction of plasmid pMAL-C4X Kudzu (FIGS. 77-79).

TABLE 15-1

Primer sequences

| Primer name | Primer sequence |
|---|---|
| EL-950 | CGGTGAACTGAAAGGTGACGTCC (SEQ ID NO: 108) |
| EL-951 | GGACGTTAACGCTATTAACACCCTG (SEQ ID NO: 109) |
| EL-953 | CACATCGTCGATCAGCTCCAGC (SEQ ID NO: 110) |
| EL-957 | GGTCGTCAGACTGTCGATGAAGCC (SEQ ID NO: 111) |

TABLE 15-1-continued

Primer sequences

| Primer name | Primer sequence |
|---|---|
| EL-959 | GCTTATGAATTCTGTGCGACCTCTTCTCAATTTACTCAG (SEQ ID NO: 112) |
| EL-960 | GCTTATAAGCTTAGACATACATCAGCTGGTTAATCGGG (SEQ ID NO: 113) |
| EL-966 | CTCCTCCAGCAGGTTCTCACC (SEQ ID NO: 114) |

Plasmid pMAL-C4X Kudzu was transformed into One-Shot BL21(λDE3) chemically competent cells (Invitrogen Corp). Expression strain transformants were selected on LA+50 mg/ml carbenicillin plates.

II. IspS Variants for Crystal Structure Trials

This example describes methods to generate affinity tagged isoprene synthase (IspS) enzymes for expression, purification and crystallization.

Strain Construction

For constructs in the pET200D-TOPO vector (Invitrogen), PCR products of the IspS enzymes from *P. alba, P. tremuloides*, and *P. trichocharpa* were gel extracted and purified (Qiagen), using 0.8% E-gel (Invitrogen), according to the manufacturer's recommended protocol. PCR reactions for pET200 constructs are as follows: Reaction mixture was 1 μl (Templates)-pET24a-*P. alba*, 5 μl 10× PfuUltraII Fusion buffer, 1 μl dNTP's (10 mM), 1 μl primer (50 uM) primer F-(MCM219 or 218), 1 μl primer (50 uM) primer R-(MCM182), 41 μl diH2O and 1 μl of PfuUltra II Fusion DNA Polymerase from Stratagene; Cycle Parameter were 95° C. 1 min., 95° C. 1 min, 55° C. 20 sec., 72° C. 27 sec. for 29 cycles followed by 72° C. for 3 min and then 4° C. until cool, using an Eppendorf Mastercycler. Similar reactions were performed for *P. tremuloides, P. trichocarpa*, and Kudzu. 3 μl of purified product was then ligated to the pET200D/TOPO vector (Invitrogen), according to the manufacturer's protocol. The reaction was incubated for 5 minutes at room temperature, and the 6 μl topoisomerase mixture was then transformed into *E. coli* Top10 chemically competent cells (Invitrogen) according to the manufacturer's protocol. Transformants were selected for on LB Kan50, and incubated at 37° C. overnight. Five colonies per construct were chosen and screened using PuReTaq Ready-To-Go PCR Beads (Amersham) using the T7 Forward and MCM182 primers (Table 15-2). Clones harboring inserts of the correct size were further verified by plasmid miniprep using the QIAPrep Spin Miniprep kit (Qiagen) followed by sequencing using the T7 Forward and T7 Reverse primers (Quintara Biosciences). One fully sequenced construct for each IspS variant (see below for details and sequence/FIGS. 79-90), was chosen for further study. 1 μl of each plasmid was transformed into BL21(λDE3) pLysS (Invitrogen) according to the manufacturer's protocol. Transformants were selected for on LB medium with Kan50+Cm35 and incubated at 37° C. overnight. The resulting strains were used for expression and purification of various IspS enzymes for crystallography studies.

Construction of N-terminally 6His-tagged IspS plasmids, strains and purification is described in Example 11.

TABLE 15-2

Primers

| | |
|---|---|
| MCM219 | caccatgcgttgtagcgtgtcca (SEQ ID NO: 114) |
| MCM182 | gggcccgtttaaactttaactagactctgcagttagcgttcaa acggcagaa (SEQ ID NO: 115) |
| MCM218 | caccatgcgtcgttctgcgaactac (SEQ ID NO: 116) |

TABLE 15-3

Plasmids

| | |
|---|---|
| *P. alba* pET24a | pET24a with "full length" IspS from *P. alba* |
| *P. trichocharpa* pET24a | pET24a with "full length" IspS from *P. trichocharpa* |
| *P. tremuloides* pET24a | pET24a with "full length" IspS from *P. tremuloides* |
| MBP-Kudzu | |
| pDu27 | *P. alba*FL-pET200/Top 10 |
| pDu30 | *P. alba*TRC-pET200/Top 10 |
| pDu31 | *P. trem*TRC-pET200/Top 10 |
| pDu32 | *P. trich*TRC-pET200/Top 10 |
| MD09-161 | pET24a-*P. alba* FL C-Term (+) TEV, His tag/MCM331 |
| MD09-163 | pET24a-*P. alba* TRC (MEA) C-Term (+) TEV, His tag/MCM331 |

TABLE 15-4

Strains

| | |
|---|---|
| MBP-Kudzu | |
| MD08-99 | BL21 DE3 pLys + pDu27 |
| MD08-100 | BL21 DE3 pLys + pDu30 |
| MD08-102 | BL21 DE3 pLys + pDu31 |
| MD08-104 | BL21 DE3 pLys + pDu32 |
| MD09-165 | BL21(DE3)pLysS, pET24a-*P. alba* FL C-Term (+) TEV, His tag |
| MD09-167 | BL21(DE3) pLysS, pET24a-*P. alba* TRC (MEA) C-Term (+) TEV, His tag |

III. Digestion of TEV (Tobacco Etch Virus) or EK (Enterokinase)-tagged Enzymes

TEV Cleavage (IspS from Strains MD09-165 and MD09-167)

Strains MD09-165 and MD09-167 are described in Example 11. For digestion, enzymes were purified through a Ni charged sepharose (GE Healthcare) and desalted into 50 mM HEPES, 50 mM NaCl pH 7.4 buffer containing 1 mM DTT. Digestion was performed with TurboTEV Protease from Eton Bioscience Inc. One unit of TurboTEV per 10 μg of purified protein was used. The digest was performed at 4° C. overnight. Samples were passed through another Ni column equilibrated in the Ni buffer to remove uncleaved enzyme, tag, TurboTEV protease (that is also tagged) and impurities. The Ni column pass though and washes were analyzed using SDS-PAGE gel (NUPAGE, Invitrogen) and DMAPP activity assays. Samples containing pure enzyme were pooled and desalted into 50 mM NaCl pH 7.4 buffer containing 1 mM DTT and stored at −80° C.

EK Cleavage (IspS from Strains MD08-102 and MD08-104)

For digestion enzymes were purified through a Ni charged sepharose (GE Healthcare) and desalted into 50 mM HEPES, 50 mM NaCl pH 7.4 buffer containing 1 mM DTT.

Digestion was performed with EKMax (E180-02) (Invitrogen) using 1 unit of EKMax per 20 µg of purified protein at 4° C. overnight. Samples were passed over EK Away resin (Invitrogen) to remove excess enterokinase. Samples were batched onto Ni charged sepharose resin (equilibrated in the Ni wash buffer) and incubated for 30 min at 4° C., with occasional inverting. This removed uncleaved enzyme, tag, and impurities. The Ni column pass through and washes were analyzed using SDS-PAGE gel (4-12% NUPAGE, Invitrogen) and DMAPP activity assays. Samples containing pure enzyme were pooled and desalted into 50 mM HEPES, 50 mM NaCl pH 7.4 buffer containing 1 mM DTT and stored at −80° C.

IV. Purification of MBP-IspS

Construction of pMAL-C4X Kudzu for the expression of MBP-Kudzu isoprene synthase is described above. MBP-Kudzu isoprene synthase production from *E. coli* grown in batch culture at the 15-L scale.

Medium Recipe (Per Liter Fermentation Medium)

$K_2HPO_4$ 7.5 g, $MgSO_4*7H_2O$ 2 g, citric acid monohydrate 2 g, ferric ammonium citrate 0.3 g, yeast extract 0.5 g, 1000× Modified Trace Metal Solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution

Citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO*7H_2O$ 1 g, $CuSO_4*5H_2O$ 100 mg, $H_3BO_3$ 100 mg, $NaMoO_4*2H_2O$ 100 mg. Each component is dissolved one at a time in $diH_2O$, pH to 3.0 with HCl/NaOH, then q.s. to volume and filter sterilized with 0.22 micron filter.

Fermentation was performed in a 15-L bioreactor with BL21 (DE3) *E. coli* cells containing the pMAL-C4X plasmid expressing a maltose binding protein (MBP)-Kudzu isoprene synthase fusion molecule. This experiment was carried out to produce isoprene synthase at the desired fermentation pH 7.0 and temperature 30° C. A frozen vial of the *E. coli* strain was thawed and inoculated into tryptone-yeast extract medium. After the inoculum grew to OD 1.0, measured at 550 nm ($OD_{550}$), 120 mL was used to inoculate a 15-L bioreactor bringing the initial volume to 9-L.

Expression of the desired molecule was achieved by adding isopropyl-beta-D-1-thiogalactopyranoside (IPTG). The IPTG concentration was brought to 1 mM when the $OD_{550}$ reached a value of 10. Cells containing the desired product were harvested 3 hrs after IPTG addition.

MBP-IspS Purification

The broth was centrifuged for 15 min at 10000×g. The pellet was collected and frozen at −80° C. until further purification. Cells were resuspended in MBP-Bind Buffer (5% glycerol, 20 mM Tris pH 7.4, 200 mM NaCl, 2 mM DTT, 1 mg/ml lysozyme) and passed through the french press three times at 20000 psi. The lysate was then ultracentrifuged at 100000×g for 1 hour to yield a relatively clear solution. The supernatant was pipetted from the top of the tube without disturbing the gelatinous material on the bottom of the centrifuge tube. Gel filtration was performed on the supernatant using a Superdex-200 26/60 column (GE healthcare). The column was developed using MBP-Bind buffer at a flow rate of 3 mL/min at 23° C. Fractions were tested for DMAPP activity as described below. Active fractions were pooled and loaded onto 25 mL amylose resin (New England Biolabs). The column was washed with 10 column volumes MBP-Bind buffer and the protein was then eluted with 2 column volumes of MBP-Bind buffer containing 10 mM maltose to yield >90% pure MBP-IspS.

V. DMAPP Assay

The following reaction mixture was used for the DMAPP assay: 25 µL lysate mixture, 5 µL $MgCl_2$ (1 M), 5 µL DMAPP (100 mM), and 65 µL 100 mM Tris pH 8, 100 mM NaCl for a total volume of 100 µL. The reaction is performed at 30° C. for 15 minutes in a gas tight 1.8 mL GC tube. Reactions are terminated by the addition of 100 µL 500 mM EDTA (pH 8). The amount of isoprene produced was measured by GC/MS as described above.

Example 16

Three-dimensional Structure of IspS

Seven constructs of plant isoprene synthase (IspS) were prepared to generate crystals suitable for x-ray diffraction. These were: a construct containing N-terminal histidine-tagged maltose binding protein and kudzu IspS (MBP-kudzu), full-length *P. alba* IspS with N-terminal histidine-tag (MD08-99), *P. alba* IspS with the first nineteen N-terminal residues removed (MD08-100), this construct also had the N-terminal his-tag removed after purification. Full-length, untagged *P. alba* IspS (strain RM11608-2). A truncated *P. alba* IspS construct featuring two additional residues before the twin-arginine motif was generated (MD09-167). *P. tricharpa* IspS was generated, which contains both an N-terminal his-tag and N-terminal truncation (MD08-104), and another construct composed of IspS from *P. tremuloides* was generated with an N-terminal his-tag and N-terminal truncation (MD08-102). Construction of strains expressing various isoprene synthases are described above.

Each construct was purified and a concentrated protein solution was then prepared for surveying possible crystallization conditions. Each construct was purified independently and surveyed as described below. All in-house crystallization screens were set up using the hanging drop vapor diffusion method. At a minimum, each construct was surveyed using the following commercial screens: the Crystal Screen from Hampton Research (Aliso Viejo, Calif.) and the JCSG+ Suite from Qiagen (Valencia, Calif.).

Purified MBP-kudzu using was set up using the following commercial screens: the Crystal Screen from Hampton Research and the JCSG+ Suite from. Additionally, purified MBP-kudzu was sent to the Hauptman-Woodward Institute (Buffalo, N.Y.) for high-throughput screening, where no fewer than 1536 conditions were surveyed. The purified MBP-kudzu fusion precipitated out of solution in the majority of conditions, and no protein crystals were observed.

The next construct used for crystallization screening was MD08-99 (full-length *P. alba* IspS with N-terminal histidine-tag). MD08-99 was purified and the histidine-tag was removed. The same three initial crystallization screens were performed as for MBP-kudzu. The Hampton Research Crystal Screen and Qiagen JCSG+ Suite were each performed at multiple protein concentrations. Small needle-like crystals were observed in some Hampton Research Crystal Screen conditions. Further attempts to improve the crystals involved co-crystallization with the IspS inhibitor sodium ibandronate (Sigma-Aldrich, St Louis, Mo.). Taken together, an additional 288 crystallization conditions were attempted with variations of pH, concentration, and crystallization reagents. The nine best crystals were then prepared for data collection and tested in-house on a Rigaku RU200 rotating anode generator and R-AXIS IV++, and they either did not diffract x-rays or were salt crystals.

The first nineteen N-terminal residues of *P. alba* IspS were removed to produce construct MD08-100. This construct had the N-terminal histidine-tag removed after purification. In house crystallization screens were performed using the Hampton Research Crystal Screen and Qiagen JCSG+ Suite, each with multiple protein concentrations. Initial crystal hits included hexagonal plates that diffracted to 16 Å resolution, and small rods that diffracted to 5 Å resolution using the in-house x-ray generator. In an attempt to improve the crystals, MD08-100 was co-crystallized with either sodium ibandronate or sodium pyrophosphate (Sigma-Aldrich, St Louis, Mo.), both of which are inhibitors of the IspS activity. Neither inhibitor resulted in improved crystals or improved diffraction. An additional 168 crystallization conditions were attempted with variations of pH, concentration, and crystallization reagents. The twenty-one most promising MD08-100 crystals were screened for diffraction, with the best resolution obtained being 5 Å.

Full-length, untagged *P. alba* IspS (strain RM11608-2) from a fermentation run was purified. An initial screen was set up using the Hampton Research Crystal Screen, and crystals were observed in four different conditions. All four crystals were tested for diffraction in-house, with three being salt crystals and one not diffracting.

A truncated *P. alba* IspS construct featuring two additional residues before the twin-arginine motif was generated (MD09-167). This construct contains a C-terminal histidine-tag, and crystallization experiments were set up with the tag either cleaved or not cleaved, at varying protein concentrations, and with or without sodium pyrophosphate. Initial crystallization screens were done as per MBP-kudzu. Crystals from this construct were observed in numerous conditions; optimization included 528 variations of pH, precipitating agents, concentrations, and inhibitors. From the optimization experiments, fifteen different MD09-167 crystals were screened in-house for diffraction. In an effort to improve the resolution, various crystal freezing conditions were tested, with the effect of improving the diffraction limits from 10 Å to 6.5 Å.

A new construct containing *P. tricharpa* IspS was generated, which contains both an N-terminal histidine-tag and an N-terminal truncation (MD08-104). Purified MD08-104 with cleaved histidine-tag was surveyed using the Hampton Research Crystal Screen and the Qiagen JCSG+ suite. This construct generated heavier precipitate than the *P. alba* IspS constructs. Very small needles were observed, with none of the crystals being suitable for diffraction.

Another construct composed of IspS from *P. tremuloides* was generated with an N-terminal histidine-tag and an N-terminal truncation (MD08-102). Purified MD08-102 with and without cleaved histidine-tag was set up using the Hampton Research Crystal Screen and the Qiagen JCSG+ Suite at varying protein concentrations. Rod and plate-like crystals were observed in some conditions and an additional 120 experiments were performed to improve the crystals by varying pH, concentration, and crystallization reagents. From the optimization experiments, ten crystals were tested in-house, with the initial best diffraction reaching 5 Å. Upon further modification of the freezing conditions of the crystals, a crystal was found that diffracted to 3.3 Å from the non-cleaved histidine-tagged protein. This crystal was grown by mixing 2 µL of protein (10 mg/ml, with 30 mM $MgCl_2$) with 2 µL of precipitant solution [10% (wt/vol) polyethylene glycol 8000, 0.1 M HEPES, pH 7.5, 8% ethylene glycol] and equilibrated against 500 µL of precipitant. A cluster of rod-shaped crystals appeared after three weeks. The crystals belong to the tetragonal space group P43212, and have unit cell dimensions a=154.2, b=154.2, c=142.7.

In-house x-ray diffraction data were collected under a nitrogen stream at 100 K using a Rigaku RU200 generator and R-AXIS IV++ detector. Before flash-freezing the crystal in liquid nitrogen, it was cryoprotected by swiping it through a solution containing 10% (wt/vol) polyethylene glycol 8000, 0.1 M HEPES, pH 7.5, and 25% ethylene glycol. Data were integrated using Mosflm (Leslie, A. (1998) J. of Appl. Crystallography 30, 1036-1040) and scaled using SCALA (Collaborative Computational Project, N. (1994) Acta Crystallographica Section D 50, 760-763). The data were then phased by molecular replacement using MrBUMP (Keegan, R. M., and Winn, M. D. (2007) Acta Crystallographica Section D 63, 447-457; Vagin, A., and Teplyakov, A. (1997) J. of Appl. Crystallography 30, 1022-1025), with a monomer of limonene synthase (Protein Data Bank ID 2ONH)(Berman, H., et al. (2007) Nucl. Acids Res. 35, D301-303) as the starting model. The crystal contains one dimer in the asymmetric unit with a solvent content of 66%.

A 3.05 Å data set from the same crystal was then collected using beamline 11-1 of the Stanford Synchrotron Radiation Laboratory. These data were also processed using Mosflm and SCALA. Data collection and refinement statistics are given in Table 16-1.

Refinement with Refmac5 (Collaborative Computational Project, N. (1994) Acta Crystallographica Section D 50, 760-763) was used with iterative manual rebuilding steps using the visualization program Coot (Emsley, P., and Cowtan, K. (2004) Acta Crystallographica Section D 60, 2126-2132). During refinement, the geometry of the protein was checked using Molprobity (Davis, I. W., et al. (2007) Nucl. Acids Res., gkm216).

The fold of poplar IspS is similar to bornyl diphosphate synthase (Whittington, D. A., et al. (2002) Proc. Natl Acad. Sci. USA 99, 15375-15380), limonene synthase (Hyatt, D. C., et al. (2007) Proc. Natl Acad. Sci. USA 104, 5360-5365), and tobacco 5-epi-aristolochene synthase (Starks, C. M., et al. (1997) Science 277, 1815-1820). The structure consists of two helical domains, a C-terminal domain containing the active site and N-terminal domain (FIGS. 90 and 91). Coordinates are provided in Table 16-7.

TABLE 16-1

| Data Collection and Refinement Statistics | |
|---|---|
| Data Collection | |
| Space Group | $P4_32_12$ |
| Cell dimensions | |
| a, b, c (Å) | 154.2, 154.2, 142.7 |
| α, β, γ, (°) | 90.0, 90.0, 90.0 |
| Resolution (Å) | 37.8-3.05 |
| $R_{merge}$ | 16.4 (72.9)$^a$ |
| <I/σI> | 10.3 (2.6) |
| Completeness (%) | 99.8 (100) |
| Redundancy | 7.3 (7.4) |
| Refinement | |
| Resolution (Å) | 37.8-3.05 |
| No. measured reflections | 248741 |
| No. Unique reflections | 34201 |
| $R_{work}$ | 21.1 |
| $R_{free}$ | 27.1 |

TABLE 16-1-continued

Data Collection and Refinement Statistics

| | |
|---|---|
| rmsd bonds, (Å) | 0.011 |
| rmsd angles, (°) | 1.28 |
| No. of Atoms | |
| Protein, ions[b] | 8331 |
| Water | 18 |

Flexible Loops

The unique and unexpected discovery coming from the determination of the three dimensional structure of isoprene synthase is that several crucial loops forming the active site are flexible. The discovery can be immediately seen when the known structure of other terpene synthases are compared with the structure of isoprene synthase (FIG. 94). Overall, the structures are highly conserved in the conformation of secondary structure and connectivity loops. (In this example of the *Poplar tremuloides* IspS from construct *P. trem*TRC-pET200, the numbering convention is such that the first number of the complete sequence containing the tag is −35, with the first residue of IspS being 1.) However, three segments, forming a considerable portion of the substrate binding pocket, notably the truncated N-terminus, along with two loops comprised of residues 438-453 (Loop I) and residues 512-527 (Loop II) are seen to diverge (FIGS. 95 to 97). This has been attributed to the absence of substrate complexed with the enzyme in our structure determination.

In comparing the enzyme with BdpS, for example, we find that the loops corresponding to residues 498-513 and 573-587 are composed of the same number of residues and have a homologous, but not identical amino sequence in these regions. We expect that the related terpene synthases will be found to display similar flexibility in the segments as these structure become more thoroughly studied. The residues in terpene synthases corresponding to these variable loop regions are enumerated in Table 16-2.

TABLE 16-2

Residues corresponding to variable loops in terpene synthases

| | Poplar IspS | LS | BdpS | TEAS |
|---|---|---|---|---|
| N-term I | Met 1 | Met 57 | Ile 54 | Val 14 |
| | Arg 2 | Arg 58 | Arg 55 | Arg 15 |
| | Arg 3 | Arg 59 | Arg 56 | Pro 16 |
| | Ser 4 | Ser 60 | Ser 57 | Val 17 |
| | Ala 5 | Gly 61 | Gly 58 | Ala 18 |
| | Asn 6 | Asn 62 | Asn 59 | Asp 19 |
| | Tyr 7 | Tyr 63 | Tyr 60 | Phe 20 |
| | Glu 8 | Asn 64 | Gln 61 | Ser 21 |
| | Pro 9 | Pro 65 | Pro 62 | Pro 22 |
| | Asn 10 | Ser 66 | Ala 63 | Ser 23 |
| | Ser 11 | Arg 67 | Leu 64 | Leu 24 |
| | Trp 12 | Trp 68 | Trp 65 | Trp 25 |
| | Asp 13 | Asp 69 | Asp 66 | Gly 26 |
| | Tyr 14 | Val 70 | Ser 67 | Asp 27 |
| | Asp 15 | Asn 71 | Asn 68 | Gln 28 |
| | Tyr 16 | Phe 72 | Tyr 69 | Phe 29 |
| N-term II | Leu 17 | Ile 73 | Ile 70 | Leu 30 |
| | Leu 18 | Gln 74 | Gln 71 | Ser 31 |
| | Ser 19 | Ser 75 | Ser 72 | Phe 32 |
| | Ser 20 | Leu 76 | Leu 73 | Ser 34 |
| | Asp 21 | Leu 77 | Asn 74 | Ile 35 |
| | Thr 22 | Ser 78 | Thr 75 | Asp 36 |
| | Asp 23 | Asp 79 | Pro 76 | Asn 37 |
| | Glu 24 | Tyr 80 | Tyr 77 | Gln 38 |
| | Ser 25 | Lys 81 | Thr 78 | Val 39 |
| | Ile 26 | Glu 82 | Glu 79 | Ala 40 |
| | Glu 27 | Asp 83 | Glu 80 | Glu 41 |
| | Val 28 | Lys 84 | Arg 81 | Lys 42 |
| Loop I | Leu 438 | Leu 498 | Leu 498 | Thr 446 |
| | Ala 439 | Gly 499 | Gly 499 | Ala 447 |
| | Ser 440 | Thr 500 | Thr 500 | The 448 |
| | Ala 441 | Ser 501 | Ser 502 | Tyr 449 |
| | Ser 442 | Val 502 | Tyr 503 | Glu 450 |
| | Ala 443 | Glu 503 | Phe 504 | Val 451 |
| | Glu 444 | Glu 504 | Glu 505 | Glu 452 |
| | Ile 445 | Val 505 | Leu 506 | Lys 453 |
| | Ala 446 | Ser 506 | Ala 507 | Ser 454 |
| | Arg 447 | Arg 507 | Arg 508 | Arg 455 |
| | Gly 448 | Gly 508 | Gly 509 | Gly 456 |
| | Glu 449 | Asp 509 | Asp 510 | Gln 457 |
| | Thr 450 | Val 510 | Val 511 | Ile 458 |
| | Ala 451 | Pro 511 | Pro 512 | Ala 459 |
| | Asn 452 | Lys 512 | Lys 513 | Thr 460 |
| | Ser 453 | Ser 513 | Thr 514 | Gly 461 |
| Loop II | Tyr 512 | Tyr 576 | Tyr 573 | Tyr 520 |
| | | | | Ile 521 |
| | His 513 | His 577 | Leu 574 | His 522 |
| | Asn 514 | Asn 578 | His 575 | Asn 523 |
| | Gly 515 | Gly 579 | Gly 576 | Leu 524 |
| | Asp 516 | Asp 580 | Asp 577 | Asp 525 |
| | Ala 517 | Gly 581 | Gly 578 | Gly 526 |
| | His 518 | His 582 | Phe 579 | Tyr 527 |
| | Thr 519 | Gly 583 | Gly 580 | The 528 |
| | Ser 520 | Thr 584 | Val 581 | His 529 |
| | Pro 521 | Gln 585 | Gln 582 | Pro 530 |
| | Asp 522 | His 585 | His 583 | Glu 531 |
| | Glu 523 | Pro 586 | Ser 584 | Lys 532 |
| | Leu 524 | Ile 587 | Lys 585 | Val 533 |
| | Thr 525 | Ile 588 | Thr 586 | Lue 534 |
| | Arg 526 | His 589 | Tyr 587 | Lys 535 |

This important finding can be exploited for the engineering of improved isoprene synthase in a straightforward manner. It would be desirable to exploit the flexibility to enhance enzyme performance by making substitutions in the amino aids forming these segments to facilitate the transitions the enzyme must undergo in the steps of binding substrate and allowing rearrangement of substrate in different kinetic steps that are postulated to occur during enzymatic de-phosphorylation and for electron transfer to convert DMAPP to isoprene.

The structure provides the new insight that these loops can be present in at least two conformations: the "open" form in the absence of substrate, as we have see in the uncomplexed structure of the isoprene synthase, and a "closed," or active form when the substrate is bound. It would therefore also be beneficial to modify residues coming in contact with the loops in the active form as described in Table 16-3.

TABLE 16-3

Residues coming within 5 angstroms of flexible elements

| | P trem IspS | 1N1B | 2ONG | 5EAS[e] |
|---|---|---|---|---|
| N-term neigbors | L17, L18, S19, S20, S239, R243, F253, A254, R255, D256, R257, I259, E260, D293, Y295, D296, V297, Y298, G299, T300, E303, Y325, L374, Y375, elements of loop I, elements of loop II, V529, L530, T534 | 70I, 71Q, 72S, 73L, 298S, 302S, 312F, 313V, 314R, 315D, 316R, 318V, 319E, 352D, 354Y, 355D, 356V, 357Y, 358G, 359T, 362E, 384Y, 433Y, 434H, elements of loop I, elements of loop II, 589I, 590A, 594F | I73, Q74, S75, L76, F299, R303, F313, A314, R315, A316, R317, V319, E320, D353, Y355, D356, V357, Y358, G359, T360, E363, Y385, F434, Y435, elements of loop I, elements of loop II, M590, T591, F595 | L30, S31, F32, S33, S248, K252, Y262, A263, R264, D265, R266, V268, E269, D302, F304, D305, A306, Y307, G308, T309, E312, Y334, F383, I384, elements of loop I, elements of loop II, I538, I538, V543 |
| Loop I neighbors | Elements of N-term, D293, Y295, V297, E370, A371, W373, L374, S378, T379, P380, F382, Y385, F386, R433, L434 C435, N436, D437, V454, S455, C456, Y457, M458, T469, V472, I476, Y512, elements of loop II | Elements of N-term, 352D, 354Y, 356V, 429E, 430A, 432W, 433Y, 437Y, 438T, 439P, 441L, 444Y, 445L, 493R, 494L, 495P, 496D, 497D, 514I, 515Q, 516C, 517Y, 518M, 529V, 532V, 536I, 572Y, elements of loop II | Elements of N-term, D353, Y355, V357, E430, A431, W433, F434, H438, K439, P440, L442, Y445, L446, R493, L494, A495, D496, D497, L514, Q515, C516, Y517, M518, R529, V532, I536, Y573, elements of loop II | Elements of N-term, D304, F304, A306, E379, S380, W382, F383, Y387, T388, P389, V391, Y394, L395, R441, V442, I443, D444, D445, I462, E463, C464, C465, M466, M477, F480, A484, Y520, elements of loop II |
| Loop II neighbors | Elements of N-terminus, E187, L188, R255, R257, F270, E271, Q273, Y274, F285, V288, A439, S440, S442, S508, H509, C510, T511, Y512, R528, V529, L530, S531, V532 | Elements of N-terminus, 246D, 247L, 314R, 316R, 329E, 330S, 332F, 333W, 344I, 348I, 499G, 500T, 503Y, 568A, 569Q, 570F, 571I, 572Y, 588H, 589I, 590A, 591G, 592L | Elements of N-terminus, D247, I248, R315, R317, E330, P331, Q333, H334, N345, I347, G499, T500, V502, A569, Q570, L571, M572, Y573, Q589, M590, T591, R592, T593 | Elements of N-terminus, E195, Q196, R264, R266, F279, E280, Q282, Y283, I294, I297, A447, T448, E450, V516, E517, V518, T519, Y520, H537, I538, I539, N540, L541 |

Selection of Sites for Improvement of Plant Isoprene Synthase

The isoprene synthases of plants were expected to be homologous to the terpene synthases. The three-dimensional structures of three homologous terpene synthases have been determined: *Salvia officinalis* bornyl diphosphate synthase (BdpS; pdb entry 1N1B), *Mentha spicata* limonene synthase (LS; pdb entry 2ONG), and tobacco 5-epi-aristolochene synthase (TEAS; pdb entry 5EAS). These enzymes share only 33% homology but their tertiary structure is conserved. Sequence identity is shown in Table 16-4, and structural homology between the structures is shown in Table 16-5. In addition, the structures of intermediate complexes with all three related enzymes have shown that not only tertiary folding, but also detailed interactions in the active sites of these enzymes are highly conserved.

TABLE 16-4

Percent Identity of Terpene Cyclases.

| | P trem IspS | 1N1B | 2ONG | 5EAS[e] |
|---|---|---|---|---|
| P alba IspS[a] | 98.6 | 40.7 | 41.3 | 33.2 |
| P trem IspS[b] | | 41.0 | 41.4 | 33.2 |
| 1N1B[c] | | | 51.4 | 33.8 |
| 2ONG[d] | | | | 33.3 |

[a]Polar alba isoprene synthase
[b]Polar tremuloides isoprene synthase
[c]bornyl diphosphate synthase
[d]limonene synthase
[e]5-epi-aristolochene synthase

TABLE 16-5

Structural Alignment of Terpene Synthases

| | 1N1B[b] | 2ONG[c] | 5EAS[d] |
|---|---|---|---|
| P trem IspS[a] | 1.40 (465)[e] | 1.29 (468) | 1.62 (458) |
| 1N1B | | 1.27 (520) | 1.97 (476) |
| 2ONG | | | 1.83 (477) |

[a]Polar tremuloides isoprene synthase
[b]bornyl diphosphate synthase
[c]limonene synthase
[d]5-epi-aristolochene synthase
[e]Root mean square deviation in Å for Cα atoms, with the number of aligned residues in parenthesis In this example of the *Poplar tremuloides* IspS from construct *P. trem*TRC-pET200, the numbering convention is such that the first number of the complete sequence containing the tag is −35, with the first residue of IspS being 1.

A comparison of the active site from the structure of BdpS and the structure of poplar IspS indicates that the active site involved in metal ion binding and phosphate recognition is conserved. In particular, Arg 255, Asp 292, Asp 296, Glu 370, Arg 433 and Asn 436 of poplar IspS were observed to overlap equivalent residues in BdpS. The positioning of an intermediate of the BdpS was also compared with the poplar IspS structure. Based on this it was possible to identify the analogous binding region and the approach direction that dimethylallyl pyrophosphate would require in order to bind and react with the poplar IspS enzyme.

Based on the structure of poplar IspS, sites in the poplar IspS were identified as candidates for mutagenesis to produce variant IspS enzymes with improved performance. Briefly, sites were selected in the IspS that might alter the interaction of the metal binding, diphosphate recognition, DMAPP chain binding and/or the approach to the active site.

I. Diphosphate/Metal Binding Sites

The side chains of amino acid residues in the poplar IspS that are found in proximity to the metal and diphosphate binding side chains were identified. These residues include Asp 293, Tyr 385, Ser 392, and Asp 437. Engineering of these sites may result in increased enzyme activity.

II. Substrate Access Loops

The substrate access loops of poplar IspS are in regions that deviate from the BdpS structure. In the BdpS structure the residues create a cover over the active site. It is likely that upon substrate binding the structure of poplar IspS will form a similar structure. As such the residues in these loops, including residues 440-453 and 512-524, may be in a position to alter the activity of the poplar IspS. In the poplar IspS enzyme, residues 440-453 have the sequence SASAEIARGETANS and residues 512-526 have the sequence YHNGDAHTSPDEL.

III. Isoprenyl Binding Site

The complex of BdpS and the product of the reaction, bornyl diphosphate (PDB entry 1N24), was used to identify residues in the poplar IspS structure that with protein engineering may be used modulate substrate specificity and/or reaction rate (altered on and off rates of substrate and product). These residues include Ser 261, Trp 264, Phe 285, Thr 289, Ser 393, Ser 394, Phe 432, and Try 512.

TABLE 16-6

Candidate mutagenesis sites.

| | Poplar IspS |
|---|---|
| DPP/Metal Binding Sites | Asp 293 |
| | Tyr 385 |
| | Ser 392 |
| | Asp 437 |
| Substrate Access Loop I | Ser 440 |
| | Ala 441 |
| | Ser 442 |
| | Ala 443 |
| | Glu 444 |
| | Ile 445 |
| | Ala 446 |
| | Arg 447 |
| | Gly 448 |
| | Glu 449 |
| | Thr 450 |
| | Ala 451 |
| | Asn 452 |
| | Ser 453 |
| Substate Access Loop II | Tyr 512 |
| | His 513 |
| | Asn 514 |
| | Gly 515 |
| | Asp 516 |
| | Ala 517 |
| | His 518 |
| | Thr 519 |
| | Ser 520 |
| | Pro 521 |
| | Asp 522 |
| | Glu 523 |
| | Leu 524 |
| Isoprenyl Binding Site | Ser 261 |
| | Trp 264 |
| | Phe 285 |
| | Thr 289 |
| | Ser 393 |
| | Ser 394 |
| | Phe 432 |
| | Tyr 512 |

TABLE 16-7

Coordinates of *P. tremuloides* IspS

```
HEADER ---                    XX-XXX-XX xxxx
COMPND ---
REMARK   3
REMARK   3 REFINEMENT.
REMARK   3   PROGRAM     : REFMAC 5.5.0088
REMARK   3   AUTHORS     : MURSHUDOV, VAGIN, DODSON
REMARK   3
REMARK   3    REFINEMENT TARGET: MAXIMUM LIKELIHOOD
REMARK   3
REMARK   3  DATA USED IN REFINEMENT.
REMARK   3   RESOLUTION RANGE HIGH (ANGSTROMS): 3.05
REMARK   3   RESOLUTION RANGE LOW  (ANGSTROMS): 110.17
REMARK   3   DATA CUTOFF       (SIGMA(F)): NONE
REMARK   3   COMPLETENESS FOR RANGE    (%): 99.67
REMARK   3   NUMBER OF REFLECTIONS        : 32446
REMARK   3
REMARK   3  FIT TO DATA USED IN REFINEMENT.
REMARK   3   CROSS-VALIDATION METHOD          : THROUGHOUT
REMARK   3   FREE R VALUE TEST SET SELECTION: RANDOM
REMARK   3   R VALUE     (WORKING + TEST SET): .21396
REMARK   3   R VALUE           (WORKING SET): .21092
REMARK   3   FREE R VALUE           : .27112
REMARK   3   FREE R VALUE TEST SET SIZE (%): 5.1
REMARK   3   FREE R VALUE TEST SET COUNT    : 1727
REMARK   3
REMARK   3  FIT IN THE HIGHEST RESOLUTION BIN.
REMARK   3   TOTAL NUMBER OF BINS USED    :    20
REMARK   3   BIN RESOLUTION RANGE HIGH    :    3.050
REMARK   3   BIN RESOLUTION RANGE LOW     :    3.129
REMARK   3   REFLECTION IN BIN (WORKING SET):   2359
REMARK   3   BIN COMPLETENESS (WORKING + TEST) (%):   100.00
REMARK   3   BIN R VALUE       (WORKING SET):   .288
REMARK   3   BIN FREE R VALUE SET COUNT   :   127
```

TABLE 16-7-continued

Coordinates of *P. tremuloides* IspS

```
REMARK   3   BIN FREE R VALUE        :   .352
REMARK   3
REMARK   3   NUMBER OF NON-HYDROGEN ATOMS USED IN REFINEMENT.
REMARK   3     ALL ATOMS           :     8349
REMARK   3
REMARK   3   B VALUES.
REMARK   3    FROM WILSON PLOT       (A**2): NULL
REMARK   3    MEAN B VALUE       (OVERALL, A**2): 24.592
REMARK   3    OVERALL ANISOTROPIC B VALUE.
REMARK   3     B11 (A**2):     .41
REMARK   3     B22 (A**2):     .41
REMARK   3     B33 (A**2):    -.81
REMARK   3     B12 (A**2):     .00
REMARK   3     B13 (A**2):     .00
REMARK   3     B23 (A**2):     .00
REMARK   3
REMARK   3   ESTIMATED OVERALL COORDINATE ERROR.
REMARK   3    ESU BASED ON R VALUE       (A): NULL
REMARK   3    ESU BASED ON FREE R VALUE       (A): .427
REMARK   3    ESU BASED ON MAXIMUM LIKELIHOOD       (A): .327
REMARK   3    ESU FOR B VALUES BASED ON MAXIMUM LIKELIHOOD (A**2): 39.836
REMARK   3
REMARK   3   CORRELATION COEFFICIENTS.
REMARK   3    CORRELATION COEFFICIENT FO-FC      : .916
REMARK   3    CORRELATION COEFFICIENT FO-FC FREE: .868
REMARK   3
REMARK   3   RMS DEVIATIONS FROM IDEAL VALUES      COUNT      RMS      WEIGHT
REMARK   3    BOND LENGTHS REFINED ATOMS      (A): 8495; .011; .022
REMARK   3    BOND LENGTHS OTHERS          (A): 5804; .001; .020
REMARK   3    BOND ANGLES REFINED ATOMS (DEGREES): 11476; 1.279; 1.953
REMARK   3    BOND ANGLES OTHERS         (DEGREES): 14093; .882; 3.000
REMARK   3    TORSION ANGLES, PERIOD 1    (DEGREES): 1020; 7.002; 5.000
REMARK   3    TORSION ANGLES, PERIOD 2    (DEGREES): 435; 35.412; 24.299
REMARK   3    TORSION ANGLES, PERIOD 3    (DEGREES): 1525; 18.250; 15.000
REMARK   3    TORSION ANGLES, PERIOD 4    (DEGREES): 58; 16.811; 15.000
REMARK   3    CHIRAL-CENTER RESTRAINTS       (A**3): 1266; .070; .200
REMARK   3    GENERAL PLANES REFINED ATOMS     (A): 9416; .005; .020
REMARK   3    GENERAL PLANES OTHERS         (A): 1780; .001; .020
REMARK   3
REMARK   3   ISOTROPIC THERMAL FACTOR RESTRAINTS.    COUNT      RMS      WEIGHT
REMARK   3    MAIN-CHAIN BOND REFINED ATOMS (A**2): 5104; .514; 1.500
REMARK   3    MAIN-CHAIN BOND OTHER ATOMS      (A**2): 2068; .059; 1.500
REMARK   3    MAIN-CHAIN ANGLE REFINED ATOMS (A**2): 8204; 1.000; 2.000
REMARK   3    SIDE-CHAIN BOND REFINED ATOMS (A**2): 3391; 1.218; 3.000
REMARK   3    SIDE-CHAIN ANGLE REFINED ATOMS (A**2): 3272; 2.157; 4.500
REMARK   3
REMARK   3   NCS RESTRAINTS STATISTICS
REMARK   3    NUMBER OF DIFFERENT NCS GROUPS:     1
REMARK   3
REMARK   3   NCS GROUP NUMBER          : 1
REMARK   3     CHAIN NAMES        : A B
REMARK   3     NUMBER OF COMPONENTS NCS GROUP:    1
REMARK   3      COMPONENT C SSSEQI TO C SSSEQI CODE
REMARK   3        1    A    17    A    541    6
REMARK   3        1    B    17    B    541    6
REMARK   3       GROUP CHAIN       COUNT RMS      WEIGHT
REMARK   3   LOOSE POSITIONAL 1 1 (A): 7038; .37; 5.00
REMARK   3   LOOSE THERMAL 1 1 (A**2): 7038; 1.09; 10.00
REMARK   3
REMARK   3   TWIN DETAILS
REMARK   3    NUMBER OF TWIN DOMAINS: NULL
REMARK   3
REMARK   3
REMARK   3   TLS DETAILS
REMARK   3    NUMBER OF TLS GROUPS: 8
REMARK   3    ATOM RECORD CONTAINS RESIDUAL B FACTORS ONLY
REMARK   3
REMARK   3   TLS GROUP:    1
REMARK   3    NUMBER OF COMPONENTS GROUP:     1
REMARK   3    COMPONENTS     C SSSEQI TO C SSSEQI
REMARK   3    RESIDUE RANGE: A     17     A     219
REMARK   3    ORIGIN FOR THE GROUP (A): -64.7667 37.6643      -.0896
REMARK   3    T TENSOR
REMARK   3     T11     .0648 T22     .0357
REMARK   3     T33     .0787 T12     .0200
REMARK   3     T13     .0129 T23     -.0089
REMARK   3    L TENSOR
REMARK   3     L11     3.7204 L22     1.5111
```

TABLE 16-7-continued

Coordinates of *P. tremuloides* IspS

```
REMARK   3     L33     2.6701 L12      .5715
REMARK   3     L13      .6692 L23     -.9699
REMARK   3     S TENSOR
REMARK   3     S11      .0562 S12      .0478 S13     -.1976
REMARK   3     S21     -.1702 S22     -.0055 S23      .1376
REMARK   3     S31      .0900 S32     -.2188 S33     -.0507
REMARK   3
REMARK   3   TLS GROUP: 2
REMARK   3    NUMBER OF COMPONENTS GROUP: 1
REMARK   3    COMPONENTS      C SSSEQI TO C SSSEQI
REMARK   3    RESIDUE RANGE: A     220     A      287
REMARK   3    ORIGIN FOR THE GROUP (A): -59.5787 8.4529    -.7693
REMARK   3    T TENSOR
REMARK   3     T11      .1615 T22      .0645
REMARK   3     T33      .1539 T12     -.0314
REMARK   3     T13     -.0461 T23      .0198
REMARK   3     L TENSOR
REMARK   3     L11     2.4192 L22     4.6709
REMARK   3     L33      .7709 L12    -3.2943
REMARK   3     L13     -.1814 L23     -.0705
REMARK   3     S TENSOR
REMARK   3     S11      .0055 S12     -.0699 S13     -.2073
REMARK   3     S21     -.1805 S22      .0996 S23      .3781
REMARK   3     S31      .2596 S32      .0887 S33     -.1051
REMARK   3
REMARK   3   TLS GROUP: 3
REMARK   3    NUMBER OF COMPONENTS GROUP: 1
REMARK   3    COMPONENTS      C SSSEQI TO C SSSEQI
REMARK   3    RESIDUE RANGE: A     288     A      374
REMARK   3    ORIGIN FOR THE GROUP (A): -40.1866 1.6932     .5805
REMARK   3    T TENSOR
REMARK   3     T11      .1149 T22      .1003
REMARK   3     T33      .1629 T12      .0153
REMARK   3     T13      .0224 T23      .0164
REMARK   3     L TENSOR
REMARK   3     L11      .2271 L22      .7399
REMARK   3     L33     4.8529 L12      .3413
REMARK   3     L13      .4755 L23     -.1746
REMARK   3     S TENSOR
REMARK   3     S11     -.0449 S12     -.0288 S13     -.1131
REMARK   3     S21     -.1346 S22     -.0665 S23     -.2749
REMARK   3     S31     -.0040 S32      .1558 S33      .1114
REMARK   3
REMARK   3   TLS GROUP: 4
REMARK   3    NUMBER OF COMPONENTS GROUP: 1
REMARK   3    COMPONENTS      C SSSEQI TO C SSSEQI
REMARK   3    RESIDUE RANGE: A     375     A      541
REMARK   3    ORIGIN FOR THE GROUP (A): -47.2220 21.5399 6.9217
REMARK   3    T TENSOR
REMARK   3     T11      .1551 T22      .1194
REMARK   3     T33      .1485 T12     -.0666
REMARK   3     T13      .0275 T23      .0272
REMARK   3     L TENSOR
REMARK   3     L11     2.2352 L22     2.1698
REMARK   3     L33     2.3370 L12     -.4501
REMARK   3     L13     2.2662 L23     -.1852
REMARK   3     S TENSOR
REMARK   3     S11      .0233 S12     -.3041 S13     -.0323
REMARK   3     S21      .3375 S22      .0236 S23      .0121
REMARK   3     S31      .0592 S32     -.2979 S33     -.0469
REMARK   3
REMARK   3   TLS GROUP: 5
REMARK   3    NUMBER OF COMPONENTS GROUP: 1
REMARK   3    COMPONENTS      C SSSEQI TO C SSSEQI
REMARK   3    RESIDUE RANGE: B      17     B      219
REMARK   3    ORIGIN FOR THE GROUP (A): -73.9834 -39.9016 -18.5783
REMARK   3    T TENSOR
REMARK   3     T11      .0658 T22      .1153
REMARK   3     T33      .1251 T12     -.0621
REMARK   3     T13     -.0164 T23     -.0098
REMARK   3     L TENSOR
REMARK   3     L11     4.6230 L22     1.7260
REMARK   3     L33     3.8816 L12     -.4202
REMARK   3     L13    -1.8646 L23     -.9046
REMARK   3     S TENSOR
REMARK   3     S11     -.0685 S12      .0375 S13     -.0003
REMARK   3     S21      .1931 S22      .0510 S23     -.0097
REMARK   3     S31      .0317 S32     -.2047 S33      .0175
```

TABLE 16-7-continued

Coordinates of *P. tremuloides* IspS

| | | | | | | | | | | | |
|---|---|---|---|---|---|---|---|---|---|---|---|
| REMARK | 3 | | | | | | | | | | |
| REMARK | 3 | TLS GROUP: 6 | | | | | | | | | |
| REMARK | 3 | NUMBER OF COMPONENTS GROUP: 1 | | | | | | | | | |
| REMARK | 3 | COMPONENTS | | C SSSEQI TO C SSSEQI | | | | | | | |
| REMARK | 3 | RESIDUE RANGE: B | | 220 | B | 287 | | | | | |
| REMARK | 3 | ORIGIN FOR THE GROUP (A): −62.1586 −12.7634 −18.1912 | | | | | | | | | |
| REMARK | 3 | T TENSOR | | | | | | | | | |
| REMARK | 3 | T11 | .1825 T22 | | .0804 | | | | | | |
| REMARK | 3 | T33 | .1512 T12 | | .0549 | | | | | | |
| REMARK | 3 | T13 | .0773 T23 | | .0208 | | | | | | |
| REMARK | 3 | L TENSOR | | | | | | | | | |
| REMARK | 3 | L11 | 5.4421 L22 | | 4.0606 | | | | | | |
| REMARK | 3 | L33 | 1.5369 L12 | | 4.6706 | | | | | | |
| REMARK | 3 | L13 | −2.0058 L23 | | −1.5537 | | | | | | |
| REMARK | 3 | S TENSOR | | | | | | | | | |
| REMARK | 3 | S11 | .1622 S12 | | .0431 S13 | | .3257 | | | | |
| REMARK | 3 | S21 | .1755 S22 | | .0292 S23 | | .2977 | | | | |
| REMARK | 3 | S31 | −.1910 S32 | | −.0506 S33 | | −.1914 | | | | |
| REMARK | 3 | | | | | | | | | | |
| REMARK | 3 | TLS GROUP: 7 | | | | | | | | | |
| REMARK | 3 | NUMBER OF COMPONENTS GROUP: 1 | | | | | | | | | |
| REMARK | 3 | COMPONENTS | | C SSSEQI TO C SSSEQI | | | | | | | |
| REMARK | 3 | RESIDUE RANGE: B | | 288 | B | 374 | | | | | |
| REMARK | 3 | ORIGIN FOR THE GROUP (A): −41.6930 −10.8250 −19.6636 | | | | | | | | | |
| REMARK | 3 | T TENSOR | | | | | | | | | |
| REMARK | 3 | T11 | .1424 T22 | | .0604 | | | | | | |
| REMARK | 3 | T33 | .1153 T12 | | .0184 | | | | | | |
| REMARK | 3 | T13 | .0146 T23 | | .0276 | | | | | | |
| REMARK | 3 | L TENSOR | | | | | | | | | |
| REMARK | 3 | L11 | .6426 L22 | | .8163 | | | | | | |
| REMARK | 3 | L33 | 2.3437 L12 | | −.1831 | | | | | | |
| REMARK | 3 | L13 | −.5246 L23 | | .4917 | | | | | | |
| REMARK | 3 | S TENSOR | | | | | | | | | |
| REMARK | 3 | S11 | .0592 S12 | | −.0206 S13 | | .0071 | | | | |
| REMARK | 3 | S21 | .0906 S22 | | −.0229 S23 | | −.1585 | | | | |
| REMARK | 3 | S31 | −.0355 S32 | | .0262 S33 | | −.0363 | | | | |
| REMARK | 3 | | | | | | | | | | |
| REMARK | 3 | TLS GROUP: 8 | | | | | | | | | |
| REMARK | 3 | NUMBER OF COMPONENTS GROUP: 1 | | | | | | | | | |
| REMARK | 3 | COMPONENTS | | C SSSEQI TO C SSSEQI | | | | | | | |
| REMARK | 3 | RESIDUE RANGE: B | | 375 | B | 541 | | | | | |
| REMARK | 3 | ORIGIN FOR THE GROUP (A): −53.4886 −28.3212 −26.0670 | | | | | | | | | |
| REMARK | 3 | T TENSOR | | | | | | | | | |
| REMARK | 3 | T11 | .1107 T22 | | .1220 | | | | | | |
| REMARK | 3 | T33 | .1514 T12 | | .0692 | | | | | | |
| REMARK | 3 | T13 | −.0073 T23 | | .0518 | | | | | | |
| REMARK | 3 | L TENSOR | | | | | | | | | |
| REMARK | 3 | L11 | 2.6766 L22 | | 1.8433 | | | | | | |
| REMARK | 3 | L33 | 2.6389 L12 | | .1130 | | | | | | |
| REMARK | 3 | L13 | −2.4696 L23 | | .6986 | | | | | | |
| REMARK | 3 | S TENSOR | | | | | | | | | |
| REMARK | 3 | S11 | .1115 S12 | | .3882 S13 | | .0569 | | | | |
| REMARK | 3 | S21 | −.0725 S22 | | −.0724 S23 | | .1450 | | | | |
| REMARK | 3 | S31 | −.1453 S32 | | −.4044 S33 | | −.0392 | | | | |
| REMARK | 3 | | | | | | | | | | |
| REMARK | 3 | | | | | | | | | | |
| REMARK | 3 | BULK SOLVENT MODELLING. | | | | | | | | | |
| REMARK | 3 | METHOD USED: MASK | | | | | | | | | |
| REMARK | 3 | PARAMETERS FOR MASK CALCULATION | | | | | | | | | |
| REMARK | 3 | VDW PROBE RADIUS: 1.40 | | | | | | | | | |
| REMARK | 3 | ION PROBE RADIUS: .80 | | | | | | | | | |
| REMARK | 3 | SHRINKAGE RADIUS: .80 | | | | | | | | | |
| REMARK | 3 | | | | | | | | | | |
| REMARK | 3 | OTHER REFINEMENT REMARKS: | | | | | | | | | |
| REMARK | 3 | HYDROGENS HAVE BEEN ADDED IN THE RIDING POSITIONS | | | | | | | | | |
| REMARK | 3 | U VALUES | | : RESIDUAL ONLY | | | | | | | |
| REMARK | 3 | | | | | | | | | | |
| CISPEP | 1 ALA A 446 | | ARG A 447 | | | .00 | | | | | |
| CISPEP | 2 GLY A 515 | | ASP A 516 | | | .00 | | | | | |
| CISPEP | 3 THR B 22 | | ASP B 23 | | .00 | | | | | | |
| CISPEP | 4 ALA B 446 | | ARG B 447 | | | .00 | | | | | |
| CISPEP | 5 GLY B 515 | | ASP B 516 | | | .00 | | | | | |
| CRYST1 | 155.800 155.800 143.690 90.00 90.00 90.00 P 43 21 2 | | | | | | | | | | |
| SCALE1 | .006418 .000000 .000000 | | | .00000 | | | | | | | |
| SCALE2 | .000000 .006418 .000000 | | | .00000 | | | | | | | |
| SCALE3 | .000000 .000000 .006959 | | | .00000 | | | | | | | |
| ATOM | 1 | N | LEU | A | 17 | −63.930 | 24.416 | −19.202 | 1.00 | 30.90 | N |
| ATOM | 2 | CA | LEU | A | 17 | −64.132 | 23.019 | −19.731 | 1.00 | 31.43 | C |

TABLE 16-7-continued

Coordinates of *P. tremuloides* IspS

| | | | | | | | | | | | |
|---|---|---|---|---|---|---|---|---|---|---|---|
| ATOM | 4 | CB | LEU | A | 17 | −63.308 | 22.800 | −21.021 | 1.00 | 31.35 | C |
| ATOM | 7 | CG | LEU | A | 17 | −64.002 | 23.016 | −22.386 | 1.00 | 31.95 | C |
| ATOM | 9 | CD1 | LEU | A | 17 | −62.989 | 23.068 | −23.550 | 1.00 | 31.88 | C |
| ATOM | 13 | CD2 | LEU | A | 17 | −65.052 | 21.915 | −22.676 | 1.00 | 31.95 | C |
| ATOM | 17 | C | LEU | A | 17 | −63.783 | 21.952 | −18.660 | 1.00 | 31.39 | C |
| ATOM | 18 | O | LEU | A | 17 | −63.142 | 22.291 | −17.651 | 1.00 | 31.61 | O |
| ATOM | 22 | N | LEU | A | 18 | −64.216 | 20.693 | −18.877 | 1.00 | 31.11 | N |
| ATOM | 23 | CA | LEU | A | 18 | −63.986 | 19.529 | −17.957 | 1.00 | 30.78 | C |
| ATOM | 25 | CB | LEU | A | 18 | −62.503 | 19.072 | −17.935 | 1.00 | 30.97 | C |
| ATOM | 28 | CG | LEU | A | 18 | −61.303 | 19.949 | −17.496 | 1.00 | 31.10 | C |
| ATOM | 30 | CD1 | LEU | A | 18 | −61.406 | 20.430 | −16.064 | 1.00 | 30.71 | C |
| ATOM | 34 | CD2 | LEU | A | 18 | −59.977 | 19.173 | −17.703 | 1.00 | 31.87 | C |
| ATOM | 38 | C | LEU | A | 18 | −64.531 | 19.665 | −16.522 | 1.00 | 30.38 | C |
| ATOM | 39 | O | LEU | A | 18 | −64.837 | 18.667 | −15.883 | 1.00 | 29.86 | O |
| ATOM | 41 | N | SER | A | 19 | −64.587 | 20.900 | −16.023 | 1.00 | 30.45 | N |
| ATOM | 42 | CA | SER | A | 19 | −65.335 | 21.276 | −14.815 | 1.00 | 30.37 | C |
| ATOM | 44 | CB | SER | A | 19 | −64.604 | 22.417 | −14.026 | 1.00 | 30.02 | C |
| ATOM | 47 | OG | SER | A | 19 | −64.881 | 23.741 | −14.489 | 1.00 | 28.00 | O |
| ATOM | 49 | C | SER | A | 19 | −66.784 | 21.654 | −15.218 | 1.00 | 31.03 | C |
| ATOM | 50 | O | SER | A | 19 | −67.666 | 21.711 | −14.367 | 1.00 | 30.95 | O |
| ATOM | 52 | N | SER | A | 20 | −67.023 | 21.880 | −16.519 | 1.00 | 31.85 | N |
| ATOM | 53 | CA | SER | A | 20 | −68.355 | 22.247 | −17.051 | 1.00 | 32.37 | C |
| ATOM | 55 | CB | SER | A | 20 | −68.291 | 22.507 | −18.579 | 1.00 | 32.39 | C |
| ATOM | 58 | OG | SER | A | 20 | −67.387 | 23.542 | −18.931 | 1.00 | 31.77 | O |
| ATOM | 60 | C | SER | A | 20 | −69.357 | 21.124 | −16.744 | 1.00 | 33.04 | C |
| ATOM | 61 | O | SER | A | 20 | −69.076 | 20.254 | −15.922 | 1.00 | 33.08 | O |
| ATOM | 63 | N | ASP | A | 21 | −70.522 | 21.136 | −17.393 | 1.00 | 33.88 | N |
| ATOM | 64 | CA | ASP | A | 21 | −71.512 | 20.069 | −17.206 | 1.00 | 34.48 | C |
| ATOM | 66 | CB | ASP | A | 21 | −72.907 | 20.655 | −17.127 | 1.00 | 34.59 | C |
| ATOM | 69 | CG | ASP | A | 21 | −73.022 | 21.661 | −16.006 | 1.00 | 35.54 | C |
| ATOM | 70 | OD1 | ASP | A | 21 | −72.041 | 21.836 | −15.251 | 1.00 | 35.31 | O |
| ATOM | 71 | OD2 | ASP | A | 21 | −74.082 | 22.289 | −15.870 | 1.00 | 38.72 | O |
| ATOM | 72 | C | ASP | A | 21 | −71.409 | 18.975 | −18.260 | 1.00 | 34.94 | C |
| ATOM | 73 | O | ASP | A | 21 | −72.134 | 18.947 | −19.269 | 1.00 | 34.58 | O |
| ATOM | 75 | N | THR | A | 22 | −70.457 | 18.086 | −17.989 | 1.00 | 35.66 | N |
| ATOM | 76 | CA | THR | A | 22 | −70.340 | 16.799 | −18.657 | 1.00 | 36.27 | C |
| ATOM | 78 | CB | THR | A | 22 | −68.895 | 16.576 | −19.168 | 1.00 | 36.30 | C |
| ATOM | 80 | OG1 | THR | A | 22 | −67.968 | 17.278 | −18.322 | 1.00 | 36.04 | O |
| ATOM | 82 | CG2 | THR | A | 22 | −68.755 | 17.088 | −20.604 | 1.00 | 36.11 | C |
| ATOM | 86 | C | THR | A | 22 | −70.792 | 15.714 | −17.648 | 1.00 | 36.83 | C |
| ATOM | 87 | O | THR | A | 22 | −69.968 | 15.022 | −17.035 | 1.00 | 37.05 | O |
| ATOM | 89 | N | ASP | A | 23 | −72.121 | 15.599 | −17.494 | 1.00 | 37.27 | N |
| ATOM | 90 | CA | ASP | A | 23 | −72.790 | 14.802 | −16.441 | 1.00 | 37.25 | C |
| ATOM | 92 | CB | ASP | A | 23 | −72.962 | 15.659 | −15.167 | 1.00 | 37.17 | C |
| ATOM | 95 | CG | ASP | A | 23 | −71.625 | 16.081 | −14.549 | 1.00 | 37.74 | C |
| ATOM | 96 | OD1 | ASP | A | 23 | −70.714 | 15.241 | −14.436 | 1.00 | 38.88 | O |
| ATOM | 97 | OD2 | ASP | A | 23 | −71.472 | 17.256 | −14.164 | 1.00 | 38.91 | O |
| ATOM | 98 | C | ASP | A | 23 | −74.172 | 14.351 | −16.956 | 1.00 | 37.18 | C |
| ATOM | 99 | O | ASP | A | 23 | −75.137 | 15.112 | −16.846 | 1.00 | 37.10 | O |
| ATOM | 101 | N | GLU | A | 24 | −74.280 | 13.134 | −17.501 | 1.00 | 37.23 | N |
| ATOM | 102 | CA | GLU | A | 24 | −75.406 | 12.815 | −18.410 | 1.00 | 37.58 | C |
| ATOM | 104 | CB | GLU | A | 24 | −74.941 | 13.007 | −19.865 | 1.00 | 37.77 | C |
| ATOM | 107 | CG | GLU | A | 24 | −74.424 | 14.417 | −20.239 | 1.00 | 37.98 | C |
| ATOM | 110 | CD | GLU | A | 24 | −74.121 | 14.556 | −21.746 | 1.00 | 38.35 | C |
| ATOM | 111 | OE1 | GLU | A | 24 | −74.284 | 13.564 | −22.503 | 1.00 | 38.12 | O |
| ATOM | 112 | OE2 | GLU | A | 24 | −73.721 | 15.661 | −22.174 | 1.00 | 38.18 | O |
| ATOM | 113 | C | GLU | A | 24 | −76.139 | 11.440 | −18.323 | 1.00 | 37.79 | C |
| ATOM | 114 | O | GLU | A | 24 | −77.323 | 11.397 | −17.960 | 1.00 | 37.90 | O |
| ATOM | 116 | N | SER | A | 25 | −75.462 | 10.345 | −18.696 | 1.00 | 37.92 | N |
| ATOM | 117 | CA | SER | A | 25 | −76.140 | 9.070 | −19.048 | 1.00 | 38.09 | C |
| ATOM | 119 | CB | SER | A | 25 | −75.167 | 8.076 | −19.723 | 1.00 | 38.11 | C |
| ATOM | 122 | OG | SER | A | 25 | −74.503 | 7.239 | −18.787 | 1.00 | 38.02 | O |
| ATOM | 124 | C | SER | A | 25 | −76.917 | 8.374 | −17.907 | 1.00 | 38.42 | C |
| ATOM | 125 | O | SER | A | 25 | −76.635 | 8.581 | −16.724 | 1.00 | 38.15 | O |
| ATOM | 127 | N | ILE | A | 26 | −77.861 | 7.511 | −18.312 | 1.00 | 39.00 | N |
| ATOM | 128 | CA | ILE | A | 26 | −78.993 | 7.042 | −17.476 | 1.00 | 39.30 | C |
| ATOM | 130 | CB | ILE | A | 26 | −78.594 | 5.965 | −16.429 | 1.00 | 39.34 | C |
| ATOM | 132 | CG1 | ILE | A | 26 | −77.892 | 4.791 | −17.120 | 1.00 | 39.37 | C |
| ATOM | 135 | CD1 | ILE | A | 26 | −77.766 | 3.531 | −16.253 | 1.00 | 39.46 | C |
| ATOM | 139 | CG2 | ILE | A | 26 | −79.836 | 5.423 | −15.714 | 1.00 | 39.29 | C |
| ATOM | 143 | C | ILE | A | 26 | −79.716 | 8.260 | −16.852 | 1.00 | 39.66 | C |
| ATOM | 144 | O | ILE | A | 26 | −79.274 | 8.831 | −15.838 | 1.00 | 39.49 | O |
| ATOM | 146 | N | GLU | A | 27 | −80.837 | 8.623 | −17.486 | 1.00 | 39.99 | N |
| ATOM | 147 | CA | GLU | A | 27 | −81.450 | 9.965 | −17.383 | 1.00 | 40.11 | C |
| ATOM | 149 | CB | GLU | A | 27 | −82.395 | 10.183 | −18.587 | 1.00 | 40.19 | C |
| ATOM | 152 | CG | GLU | A | 27 | −81.632 | 10.311 | −19.904 | 1.00 | 40.60 | C |
| ATOM | 155 | CD | GLU | A | 27 | −82.528 | 10.434 | −21.116 | 1.00 | 41.06 | C |
| ATOM | 156 | OE1 | GLU | A | 27 | −83.328 | 9.502 | −21.367 | 1.00 | 41.10 | O |

TABLE 16-7-continued

Coordinates of *P. tremuloides* IspS

| ATOM | 157 | OE2 | GLU | A | 27 | −82.409 | 11.458 | −21.830 | 1.00 | 41.36 | O |
|---|---|---|---|---|---|---|---|---|---|---|---|
| ATOM | 158 | C | GLU | A | 27 | −82.144 | 10.264 | −16.042 | 1.00 | 40.02 | C |
| ATOM | 159 | O | GLU | A | 27 | −81.977 | 9.518 | −15.071 | 1.00 | 40.01 | O |
| ATOM | 161 | N | VAL | A | 28 | −82.899 | 11.370 | −16.005 | 1.00 | 39.84 | N |
| ATOM | 162 | CA | VAL | A | 28 | −83.463 | 11.960 | −14.779 | 1.00 | 39.65 | C |
| ATOM | 164 | CB | VAL | A | 28 | −83.884 | 10.905 | −13.694 | 1.00 | 39.78 | C |
| ATOM | 166 | CG1 | VAL | A | 28 | −84.472 | 11.596 | −12.456 | 1.00 | 39.87 | C |
| ATOM | 170 | CG2 | VAL | A | 28 | −84.887 | 9.880 | −14.274 | 1.00 | 39.49 | C |
| ATOM | 174 | C | VAL | A | 28 | −82.469 | 12.980 | −14.206 | 1.00 | 39.46 | C |
| ATOM | 175 | O | VAL | A | 28 | −82.798 | 13.717 | −13.270 | 1.00 | 39.38 | O |
| ATOM | 177 | N | HIS | A | 29 | −81.264 | 13.025 | −14.786 | 1.00 | 39.30 | N |
| ATOM | 178 | CA | HIS | A | 29 | −80.236 | 14.006 | −14.412 | 1.00 | 39.23 | C |
| ATOM | 180 | CB | HIS | A | 29 | −78.866 | 13.344 | −14.186 | 1.00 | 39.45 | C |
| ATOM | 183 | CG | HIS | A | 29 | −78.910 | 12.139 | −13.296 | 1.00 | 41.29 | C |
| ATOM | 184 | ND1 | HIS | A | 29 | −78.407 | 12.140 | −12.007 | 1.00 | 42.51 | N |
| ATOM | 186 | CE1 | HIS | A | 29 | −78.585 | 10.942 | −11.472 | 1.00 | 43.37 | C |
| ATOM | 188 | NE2 | HIS | A | 29 | −79.181 | 10.164 | −12.365 | 1.00 | 43.18 | N |
| ATOM | 190 | CD2 | HIS | A | 29 | −79.393 | 10.888 | −13.515 | 1.00 | 42.55 | C |
| ATOM | 192 | C | HIS | A | 29 | −80.090 | 15.110 | −15.464 | 1.00 | 38.60 | C |
| ATOM | 193 | O | HIS | A | 29 | −79.049 | 15.774 | −15.499 | 1.00 | 38.61 | O |
| ATOM | 195 | N | LYS | A | 30 | −81.110 | 15.320 | −16.311 | 1.00 | 37.87 | N |
| ATOM | 196 | CA | LYS | A | 30 | −81.265 | 16.610 | −17.001 | 1.00 | 37.22 | C |
| ATOM | 198 | CB | LYS | A | 30 | −82.283 | 16.542 | −18.140 | 1.00 | 37.09 | C |
| ATOM | 201 | CG | LYS | A | 30 | −81.764 | 15.794 | −19.360 | 1.00 | 37.00 | C |
| ATOM | 204 | CD | LYS | A | 30 | −82.831 | 15.653 | −20.457 | 1.00 | 36.89 | C |
| ATOM | 207 | CE | LYS | A | 30 | −82.413 | 14.637 | −21.531 | 1.00 | 36.48 | C |
| ATOM | 210 | NZ | LYS | A | 30 | −83.422 | 14.458 | −22.611 | 1.00 | 35.46 | N |
| ATOM | 214 | C | LYS | A | 30 | −81.648 | 17.649 | −15.938 | 1.00 | 36.88 | C |
| ATOM | 215 | O | LYS | A | 30 | −82.516 | 18.499 | −16.136 | 1.00 | 36.71 | O |
| ATOM | 217 | N | ASP | A | 31 | −80.982 | 17.506 | −14.788 | 1.00 | 36.58 | N |
| ATOM | 218 | CA | ASP | A | 31 | −80.895 | 18.476 | −13.720 | 1.00 | 36.18 | C |
| ATOM | 220 | CB | ASP | A | 31 | −80.518 | 17.751 | −12.396 | 1.00 | 36.20 | C |
| ATOM | 223 | CG | ASP | A | 31 | −79.863 | 18.669 | −11.342 | 1.00 | 36.65 | C |
| ATOM | 224 | OD1 | ASP | A | 31 | −80.055 | 19.901 | −11.390 | 1.00 | 38.17 | O |
| ATOM | 225 | OD2 | ASP | A | 31 | −79.147 | 18.150 | −10.449 | 1.00 | 35.46 | O |
| ATOM | 226 | C | ASP | A | 31 | −79.811 | 19.426 | −14.226 | 1.00 | 35.74 | C |
| ATOM | 227 | O | ASP | A | 31 | −78.628 | 19.279 | −13.918 | 1.00 | 35.44 | O |
| ATOM | 229 | N | LYS | A | 32 | −80.220 | 20.343 | −15.096 | 1.00 | 35.30 | N |
| ATOM | 230 | CA | LYS | A | 32 | −79.360 | 21.449 | −15.507 | 1.00 | 34.69 | C |
| ATOM | 232 | CB | LYS | A | 32 | −78.698 | 21.188 | −16.849 | 1.00 | 34.63 | C |
| ATOM | 235 | CG | LYS | A | 32 | −77.699 | 20.042 | −16.765 | 1.00 | 34.51 | C |
| ATOM | 238 | CD | LYS | A | 32 | −76.953 | 19.853 | −18.078 | 1.00 | 34.48 | C |
| ATOM | 241 | CE | LYS | A | 32 | −76.859 | 18.387 | −18.503 | 1.00 | 33.77 | C |
| ATOM | 244 | NZ | LYS | A | 32 | −77.002 | 18.244 | −19.985 | 1.00 | 32.92 | N |
| ATOM | 248 | C | LYS | A | 32 | −80.162 | 22.745 | −15.459 | 1.00 | 34.01 | C |
| ATOM | 249 | O | LYS | A | 32 | −80.468 | 23.380 | −16.473 | 1.00 | 33.41 | O |
| ATOM | 251 | N | ALA | A | 33 | −80.540 | 23.051 | −14.219 | 1.00 | 33.21 | N |
| ATOM | 252 | CA | ALA | A | 33 | −80.785 | 24.381 | −13.766 | 1.00 | 32.60 | C |
| ATOM | 254 | CB | ALA | A | 33 | −81.619 | 24.347 | −12.484 | 1.00 | 32.28 | C |
| ATOM | 258 | C | ALA | A | 33 | −79.411 | 25.031 | −13.524 | 1.00 | 32.31 | C |
| ATOM | 259 | O | ALA | A | 33 | −79.335 | 26.081 | −12.901 | 1.00 | 32.80 | O |
| ATOM | 261 | N | LYS | A | 34 | −78.323 | 24.389 | −13.968 | 1.00 | 31.70 | N |
| ATOM | 262 | CA | LYS | A | 34 | −77.035 | 25.071 | −14.186 | 1.00 | 31.12 | C |
| ATOM | 264 | CB | LYS | A | 34 | −75.863 | 24.089 | −14.128 | 1.00 | 31.23 | C |
| ATOM | 267 | CG | LYS | A | 34 | −75.118 | 24.077 | −12.791 | 1.00 | 31.76 | C |
| ATOM | 270 | CD | LYS | A | 34 | −73.584 | 24.412 | −12.921 | 1.00 | 31.49 | C |
| ATOM | 273 | CE | LYS | A | 34 | −72.685 | 23.269 | −12.506 | 1.00 | 30.50 | C |
| ATOM | 276 | NZ | LYS | A | 34 | −72.951 | 22.090 | −13.348 | 1.00 | 29.53 | N |
| ATOM | 280 | C | LYS | A | 34 | −77.024 | 25.884 | −15.518 | 1.00 | 30.50 | C |
| ATOM | 281 | O | LYS | A | 34 | −76.977 | 25.353 | −16.625 | 1.00 | 29.82 | O |
| ATOM | 283 | N | LYS | A | 35 | −76.927 | 27.191 | −15.337 | 1.00 | 29.97 | N |
| ATOM | 284 | CA | LYS | A | 35 | −77.632 | 28.233 | −16.098 | 1.00 | 29.41 | C |
| ATOM | 286 | CB | LYS | A | 35 | −78.852 | 27.704 | −16.867 | 1.00 | 29.53 | C |
| ATOM | 289 | CG | LYS | A | 35 | −80.166 | 27.594 | −16.077 | 1.00 | 30.18 | C |
| ATOM | 292 | CD | LYS | A | 35 | −81.030 | 28.858 | −16.203 | 1.00 | 31.25 | C |
| ATOM | 295 | CE | LYS | A | 35 | −82.375 | 28.721 | −15.486 | 1.00 | 31.85 | C |
| ATOM | 298 | NZ | LYS | A | 35 | −83.298 | 29.865 | −15.783 | 1.00 | 31.73 | N |
| ATOM | 302 | C | LYS | A | 35 | −78.053 | 29.277 | −15.026 | 1.00 | 28.53 | C |
| ATOM | 303 | O | LYS | A | 35 | −78.246 | 30.460 | −15.307 | 1.00 | 28.53 | O |
| ATOM | 305 | N | LEU | A | 36 | −78.225 | 28.791 | −13.796 | 1.00 | 27.29 | N |
| ATOM | 306 | CA | LEU | A | 36 | −77.998 | 29.576 | −12.594 | 1.00 | 26.21 | C |
| ATOM | 308 | CB | LEU | A | 36 | −78.088 | 28.679 | −11.364 | 1.00 | 25.76 | C |
| ATOM | 311 | CG | LEU | A | 36 | −79.468 | 28.350 | −10.832 | 1.00 | 24.08 | C |
| ATOM | 313 | CD1 | LEU | A | 36 | −79.376 | 27.233 | −9.836 | 1.00 | 22.16 | C |
| ATOM | 317 | CD2 | LEU | A | 36 | −80.051 | 29.586 | −10.213 | 1.00 | 23.45 | C |
| ATOM | 321 | C | LEU | A | 36 | −76.587 | 30.137 | −12.665 | 1.00 | 25.93 | C |
| ATOM | 322 | O | LEU | A | 36 | −76.290 | 31.221 | −12.137 | 1.00 | 26.11 | O |
| ATOM | 324 | N | GLU | A | 37 | −75.714 | 29.332 | −13.260 | 1.00 | 25.24 | N |

TABLE 16-7-continued

Coordinates of *P. tremuloides* IspS

| ATOM | 325 | CA | GLU | A | 37 | −74.381 | 29.739 | −13.650 | 1.00 | 24.85 | C |
| ATOM | 327 | CB | GLU | A | 37 | −73.678 | 28.566 | −14.313 | 1.00 | 24.74 | C |
| ATOM | 330 | CG | GLU | A | 37 | −72.182 | 28.667 | −14.285 | 1.00 | 23.93 | C |
| ATOM | 333 | CD | GLU | A | 37 | −71.519 | 27.490 | −14.937 | 1.00 | 22.32 | C |
| ATOM | 334 | OE1 | GLU | A | 37 | −72.203 | 26.738 | −15.657 | 1.00 | 20.57 | O |
| ATOM | 335 | OE2 | GLU | A | 37 | −70.303 | 27.322 | −14.728 | 1.00 | 22.27 | O |
| ATOM | 336 | C | GLU | A | 37 | −74.391 | 30.927 | −14.600 | 1.00 | 24.69 | C |
| ATOM | 337 | O | GLU | A | 37 | −73.666 | 31.891 | −14.389 | 1.00 | 24.49 | O |
| ATOM | 339 | N | ALA | A | 38 | −75.203 | 30.850 | −15.650 | 1.00 | 24.68 | N |
| ATOM | 340 | CA | ALA | A | 38 | −75.352 | 31.960 | −16.599 | 1.00 | 24.87 | C |
| ATOM | 342 | CB | ALA | A | 38 | −76.453 | 31.656 | −17.609 | 1.00 | 24.53 | C |
| ATOM | 346 | C | ALA | A | 38 | −75.643 | 33.278 | −15.880 | 1.00 | 25.08 | C |
| ATOM | 347 | O | ALA | A | 38 | −75.009 | 34.295 | −16.135 | 1.00 | 25.21 | O |
| ATOM | 349 | N | GLU | A | 39 | −76.591 | 33.228 | −14.956 | 1.00 | 25.35 | N |
| ATOM | 350 | CA | GLU | A | 39 | −77.050 | 34.400 | −14.219 | 1.00 | 25.51 | C |
| ATOM | 352 | CB | GLU | A | 39 | −78.283 | 34.014 | −13.396 | 1.00 | 25.95 | C |
| ATOM | 355 | CG | GLU | A | 39 | −79.302 | 35.119 | −13.136 | 1.00 | 27.03 | C |
| ATOM | 358 | CD | GLU | A | 39 | −80.715 | 34.557 | −12.906 | 1.00 | 28.70 | C |
| ATOM | 359 | OE1 | GLU | A | 39 | −81.006 | 33.416 | −13.346 | 1.00 | 27.40 | O |
| ATOM | 360 | OE2 | GLU | A | 39 | −81.540 | 35.266 | −12.289 | 1.00 | 31.12 | O |
| ATOM | 361 | C | GLU | A | 39 | −75.970 | 34.966 | −13.306 | 1.00 | 25.11 | C |
| ATOM | 362 | O | GLU | A | 39 | −75.870 | 36.167 | −13.164 | 1.00 | 25.28 | O |
| ATOM | 364 | N | VAL | A | 40 | −75.182 | 34.107 | −12.672 | 1.00 | 24.86 | N |
| ATOM | 365 | CA | VAL | A | 40 | −74.079 | 34.568 | −11.824 | 1.00 | 24.69 | C |
| ATOM | 367 | CB | VAL | A | 40 | −73.511 | 33.420 | −10.952 | 1.00 | 24.56 | C |
| ATOM | 369 | CG1 | VAL | A | 40 | −72.239 | 33.857 | −10.240 | 1.00 | 23.69 | C |
| ATOM | 373 | CG2 | VAL | A | 40 | −74.553 | 32.955 | −9.955 | 1.00 | 24.68 | C |
| ATOM | 377 | C | VAL | A | 40 | −72.971 | 35.148 | −12.698 | 1.00 | 24.76 | C |
| ATOM | 378 | O | VAL | A | 40 | −72.337 | 36.139 | −12.362 | 1.00 | 24.16 | O |
| ATOM | 380 | N | ARG | A | 41 | −72.744 | 34.506 | −13.831 | 1.00 | 25.25 | N |
| ATOM | 381 | CA | ARG | A | 41 | −71.727 | 34.948 | −14.769 | 1.00 | 25.66 | C |
| ATOM | 383 | CB | ARG | A | 41 | −71.576 | 33.927 | −15.896 | 1.00 | 25.88 | C |
| ATOM | 386 | CG | ARG | A | 41 | −70.726 | 34.385 | −17.062 | 1.00 | 27.04 | C |
| ATOM | 389 | CD | ARG | A | 41 | −71.519 | 35.178 | −18.095 | 1.00 | 27.90 | C |
| ATOM | 392 | NE | ARG | A | 41 | −70.653 | 35.635 | −19.180 | 1.00 | 29.20 | N |
| ATOM | 394 | CZ | ARG | A | 41 | −70.946 | 36.615 | −20.034 | 1.00 | 29.94 | C |
| ATOM | 395 | NH1 | ARG | A | 41 | −70.077 | 36.945 | −20.980 | 1.00 | 29.86 | N |
| ATOM | 398 | NH2 | ARG | A | 41 | −72.096 | 37.273 | −19.957 | 1.00 | 30.54 | N |
| ATOM | 401 | C | ARG | A | 41 | −72.104 | 36.301 | −15.335 | 1.00 | 25.60 | C |
| ATOM | 402 | O | ARG | A | 41 | −71.237 | 37.113 | −15.612 | 1.00 | 25.77 | O |
| ATOM | 404 | N | ARG | A | 42 | −73.400 | 36.521 | −15.537 | 1.00 | 25.50 | N |
| ATOM | 405 | CA | ARG | A | 42 | −73.900 | 37.810 | −15.979 | 1.00 | 25.39 | C |
| ATOM | 407 | CB | ARG | A | 42 | −75.389 | 37.723 | −16.313 | 1.00 | 25.09 | C |
| ATOM | 410 | CG | ARG | A | 42 | −76.077 | 39.062 | −16.445 | 1.00 | 23.84 | C |
| ATOM | 413 | CD | ARG | A | 42 | −77.459 | 38.906 | −16.980 | 1.00 | 22.37 | C |
| ATOM | 416 | NE | ARG | A | 42 | −78.448 | 38.554 | −15.965 | 1.00 | 21.69 | N |
| ATOM | 418 | CZ | ARG | A | 42 | −79.705 | 38.206 | −16.248 | 1.00 | 22.99 | C |
| ATOM | 419 | NH1 | ARG | A | 42 | −80.122 | 38.146 | −17.517 | 1.00 | 24.16 | N |
| ATOM | 422 | NH2 | ARG | A | 42 | −80.557 | 37.900 | −15.275 | 1.00 | 22.94 | N |
| ATOM | 425 | C | ARG | A | 42 | −73.666 | 38.889 | −14.925 | 1.00 | 26.00 | C |
| ATOM | 426 | O | ARG | A | 42 | −73.173 | 39.959 | −15.244 | 1.00 | 26.17 | O |
| ATOM | 428 | N | GLU | A | 43 | −74.014 | 38.621 | −13.673 | 1.00 | 26.66 | N |
| ATOM | 429 | CA | GLU | A | 43 | −73.930 | 39.662 | −12.650 | 1.00 | 27.47 | C |
| ATOM | 431 | CB | GLU | A | 43 | −74.749 | 39.304 | −11.401 | 1.00 | 27.97 | C |
| ATOM | 434 | CG | GLU | A | 43 | −76.274 | 39.266 | −11.661 | 1.00 | 31.05 | C |
| ATOM | 437 | CD | GLU | A | 43 | −76.869 | 40.636 | −12.063 | 1.00 | 34.68 | C |
| ATOM | 438 | OE1 | GLU | A | 43 | −76.804 | 41.571 | −11.222 | 1.00 | 37.63 | O |
| ATOM | 439 | OE2 | GLU | A | 43 | −77.398 | 40.773 | −13.205 | 1.00 | 34.52 | O |
| ATOM | 440 | C | GLU | A | 43 | −72.494 | 40.035 | −12.275 | 1.00 | 27.15 | C |
| ATOM | 441 | O | GLU | A | 43 | −72.292 | 41.118 | −11.716 | 1.00 | 27.49 | O |
| ATOM | 443 | N | ILE | A | 44 | −71.517 | 39.166 | −12.588 | 1.00 | 26.57 | N |
| ATOM | 444 | CA | ILE | A | 44 | −70.090 | 39.456 | −12.334 | 1.00 | 25.80 | C |
| ATOM | 446 | CB | ILE | A | 44 | −69.206 | 38.187 | −12.187 | 1.00 | 25.52 | C |
| ATOM | 448 | CG1 | ILE | A | 44 | −69.624 | 37.320 | −11.010 | 1.00 | 24.69 | C |
| ATOM | 451 | CD1 | ILE | A | 44 | −68.828 | 36.061 | −10.899 | 1.00 | 23.08 | C |
| ATOM | 455 | CG2 | ILE | A | 44 | −67.790 | 38.581 | −11.916 | 1.00 | 25.73 | C |
| ATOM | 459 | C | ILE | A | 44 | −69.522 | 40.286 | −13.472 | 1.00 | 25.40 | C |
| ATOM | 460 | O | ILE | A | 44 | −68.745 | 41.211 | −13.236 | 1.00 | 25.26 | O |
| ATOM | 462 | N | ASN | A | 45 | −69.912 | 39.945 | −14.700 | 1.00 | 25.14 | N |
| ATOM | 463 | CA | ASN | A | 45 | −69.480 | 40.669 | −15.906 | 1.00 | 25.02 | C |
| ATOM | 465 | CB | ASN | A | 45 | −69.696 | 39.813 | −17.151 | 1.00 | 24.69 | C |
| ATOM | 468 | CG | ASN | A | 45 | −68.662 | 38.735 | −17.302 | 1.00 | 24.01 | C |
| ATOM | 469 | OD1 | ASN | A | 45 | −67.470 | 39.013 | −17.395 | 1.00 | 23.81 | O |
| ATOM | 470 | ND2 | ASN | A | 45 | −69.111 | 37.490 | −17.344 | 1.00 | 23.28 | N |
| ATOM | 473 | C | ASN | A | 45 | −70.177 | 42.014 | −16.114 | 1.00 | 25.52 | C |
| ATOM | 474 | O | ASN | A | 45 | −69.704 | 42.836 | −16.890 | 1.00 | 25.40 | O |
| ATOM | 476 | N | ASN | A | 46 | −71.308 | 42.210 | −15.437 | 1.00 | 26.33 | N |
| ATOM | 477 | CA | ASN | A | 46 | −72.085 | 43.453 | −15.468 | 1.00 | 26.72 | C |

TABLE 16-7-continued

Coordinates of *P. tremuloides* IspS

| ATOM | 479 | CB | ASN | A | 46 | −73.102 | 43.404 | −14.322 | 1.00 | 26.31 | C |
|------|-----|-----|-----|---|----|---------|--------|---------|------|-------|---|
| ATOM | 482 | CG | ASN | A | 46 | −73.935 | 44.641 | −14.209 | 1.00 | 24.24 | C |
| ATOM | 483 | OD1 | ASN | A | 46 | −73.948 | 45.472 | −15.091 | 1.00 | 22.38 | O |
| ATOM | 484 | ND2 | ASN | A | 46 | −74.645 | 44.766 | −13.106 | 1.00 | 21.64 | N |
| ATOM | 487 | C | ASN | A | 46 | −71.185 | 44.680 | −15.349 | 1.00 | 28.11 | C |
| ATOM | 488 | O | ASN | A | 46 | −70.603 | 44.933 | −14.304 | 1.00 | 28.16 | O |
| ATOM | 490 | N | GLU | A | 47 | −71.084 | 45.441 | −16.433 | 1.00 | 29.93 | N |
| ATOM | 491 | CA | GLU | A | 47 | −70.128 | 46.558 | −16.544 | 1.00 | 31.30 | C |
| ATOM | 493 | CB | GLU | A | 47 | −69.933 | 46.969 | −18.013 | 1.00 | 31.28 | C |
| ATOM | 496 | CG | GLU | A | 47 | −69.737 | 45.795 | −19.020 | 1.00 | 32.37 | C |
| ATOM | 499 | CD | GLU | A | 47 | −71.060 | 45.127 | −19.545 | 1.00 | 32.69 | C |
| ATOM | 500 | OE1 | GLU | A | 47 | −72.055 | 45.833 | −19.816 | 1.00 | 32.16 | O |
| ATOM | 501 | OE2 | GLU | A | 47 | −71.087 | 43.880 | −19.699 | 1.00 | 32.41 | O |
| ATOM | 502 | C | GLU | A | 47 | −70.582 | 47.774 | −15.729 | 1.00 | 32.47 | C |
| ATOM | 503 | O | GLU | A | 47 | −69.760 | 48.525 | −15.230 | 1.00 | 32.86 | O |
| ATOM | 505 | N | LYS | A | 48 | −71.898 | 47.945 | −15.585 | 1.00 | 33.93 | N |
| ATOM | 506 | CA | LYS | A | 48 | −72.491 | 49.075 | −14.861 | 1.00 | 34.85 | C |
| ATOM | 508 | CB | LYS | A | 48 | −73.660 | 49.672 | −15.684 | 1.00 | 35.08 | C |
| ATOM | 511 | CG | LYS | A | 48 | −73.221 | 50.119 | −17.126 | 1.00 | 36.58 | C |
| ATOM | 514 | CD | LYS | A | 48 | −74.035 | 51.277 | −17.751 | 1.00 | 37.93 | C |
| ATOM | 517 | CE | LYS | A | 48 | −75.353 | 50.799 | −18.415 | 1.00 | 39.02 | C |
| ATOM | 520 | NZ | LYS | A | 48 | −75.159 | 49.990 | −19.669 | 1.00 | 39.11 | N |
| ATOM | 524 | C | LYS | A | 48 | −72.926 | 48.632 | −13.465 | 1.00 | 35.26 | C |
| ATOM | 525 | O | LYS | A | 48 | −74.011 | 48.954 | −13.015 | 1.00 | 35.04 | O |
| ATOM | 527 | N | ALA | A | 49 | −72.051 | 47.890 | −12.790 | 1.00 | 36.29 | N |
| ATOM | 528 | CA | ALA | A | 49 | −72.321 | 47.348 | −11.456 | 1.00 | 37.18 | C |
| ATOM | 530 | CB | ALA | A | 49 | −71.828 | 45.923 | −11.353 | 1.00 | 37.20 | C |
| ATOM | 534 | C | ALA | A | 49 | −71.618 | 48.191 | −10.418 | 1.00 | 37.88 | C |
| ATOM | 535 | O | ALA | A | 49 | −70.480 | 48.610 | −10.638 | 1.00 | 38.17 | O |
| ATOM | 537 | N | GLU | A | 50 | −72.278 | 48.404 | −9.280 | 1.00 | 38.53 | N |
| ATOM | 538 | CA | GLU | A | 50 | −71.730 | 49.242 | −8.213 | 1.00 | 39.08 | C |
| ATOM | 540 | CB | GLU | A | 50 | −72.790 | 49.545 | −7.146 | 1.00 | 39.43 | C |
| ATOM | 543 | CG | GLU | A | 50 | −72.708 | 50.953 | −6.600 | 1.00 | 40.86 | C |
| ATOM | 546 | CD | GLU | A | 50 | −73.089 | 52.010 | −7.639 | 1.00 | 42.77 | C |
| ATOM | 547 | OE1 | GLU | A | 50 | −74.225 | 52.530 | −7.570 | 1.00 | 45.07 | O |
| ATOM | 548 | OE2 | GLU | A | 50 | −72.265 | 52.320 | −8.530 | 1.00 | 43.35 | O |
| ATOM | 549 | C | GLU | A | 50 | −70.560 | 48.521 | −7.600 | 1.00 | 38.89 | C |
| ATOM | 550 | O | GLU | A | 50 | −70.699 | 47.378 | −7.201 | 1.00 | 39.05 | O |
| ATOM | 552 | N | PHE | A | 51 | −69.411 | 49.181 | −7.536 | 1.00 | 38.99 | N |
| ATOM | 553 | CA | PHE | A | 51 | −68.161 | 48.502 | −7.196 | 1.00 | 39.52 | C |
| ATOM | 555 | CB | PHE | A | 51 | −67.000 | 49.494 | −7.098 | 1.00 | 40.05 | C |
| ATOM | 558 | CG | PHE | A | 51 | −66.460 | 49.948 | −8.431 | 1.00 | 42.80 | C |
| ATOM | 559 | CD1 | PHE | A | 51 | −66.135 | 49.014 | −9.435 | 1.00 | 45.21 | C |
| ATOM | 561 | CE1 | PHE | A | 51 | −65.612 | 49.425 | −10.675 | 1.00 | 46.12 | C |
| ATOM | 563 | CZ | PHE | A | 51 | −65.403 | 50.790 | −10.917 | 1.00 | 47.21 | C |
| ATOM | 565 | CE2 | PHE | A | 51 | −65.726 | 51.741 | −9.913 | 1.00 | 46.72 | C |
| ATOM | 567 | CD2 | PHE | A | 51 | −66.247 | 51.310 | −8.679 | 1.00 | 45.05 | C |
| ATOM | 569 | C | PHE | A | 51 | −68.223 | 47.687 | −5.905 | 1.00 | 39.05 | C |
| ATOM | 570 | O | PHE | A | 51 | −67.897 | 46.506 | −5.900 | 1.00 | 39.28 | O |
| ATOM | 572 | N | LEU | A | 52 | −68.648 | 48.307 | −4.813 | 1.00 | 38.42 | N |
| ATOM | 573 | CA | LEU | A | 52 | −68.709 | 47.610 | −3.528 | 1.00 | 37.94 | C |
| ATOM | 575 | CB | LEU | A | 52 | −69.084 | 48.594 | −2.413 | 1.00 | 38.53 | C |
| ATOM | 578 | CG | LEU | A | 52 | −68.057 | 49.726 | −2.181 | 1.00 | 40.46 | C |
| ATOM | 580 | CD1 | LEU | A | 52 | −68.691 | 51.101 | −1.787 | 1.00 | 41.88 | C |
| ATOM | 584 | CD2 | LEU | A | 52 | −67.020 | 49.274 | −1.141 | 1.00 | 41.83 | C |
| ATOM | 588 | C | LEU | A | 52 | −69.667 | 46.406 | −3.532 | 1.00 | 36.72 | C |
| ATOM | 589 | O | LEU | A | 52 | −69.517 | 45.494 | −2.724 | 1.00 | 36.84 | O |
| ATOM | 591 | N | THR | A | 53 | −70.649 | 46.398 | −4.431 | 1.00 | 35.37 | N |
| ATOM | 592 | CA | THR | A | 53 | −71.545 | 45.247 | −4.569 | 1.00 | 34.11 | C |
| ATOM | 594 | CB | THR | A | 53 | −72.867 | 45.594 | −5.277 | 1.00 | 33.87 | C |
| ATOM | 596 | OG1 | THR | A | 53 | −73.339 | 46.863 | −4.828 | 1.00 | 33.49 | O |
| ATOM | 598 | CG2 | THR | A | 53 | −73.917 | 44.535 | −4.983 | 1.00 | 33.70 | C |
| ATOM | 602 | C | THR | A | 53 | −70.853 | 44.148 | −5.359 | 1.00 | 33.04 | C |
| ATOM | 603 | O | THR | A | 53 | −70.893 | 42.977 | −4.973 | 1.00 | 32.90 | O |
| ATOM | 605 | N | LEU | A | 54 | −70.228 | 44.528 | −6.467 | 1.00 | 31.76 | N |
| ATOM | 606 | CA | LEU | A | 54 | −69.469 | 43.578 | −7.286 | 1.00 | 31.13 | C |
| ATOM | 608 | CB | LEU | A | 54 | −68.721 | 44.308 | −8.392 | 1.00 | 30.92 | C |
| ATOM | 611 | CG | LEU | A | 54 | −68.028 | 43.437 | −9.424 | 1.00 | 30.27 | C |
| ATOM | 613 | CD1 | LEU | A | 54 | −69.034 | 42.769 | −10.310 | 1.00 | 29.56 | C |
| ATOM | 617 | CD2 | LEU | A | 54 | −67.108 | 44.306 | −10.242 | 1.00 | 31.15 | C |
| ATOM | 621 | C | LEU | A | 54 | −68.466 | 42.808 | −6.443 | 1.00 | 30.60 | C |
| ATOM | 622 | O | LEU | A | 54 | −68.378 | 41.587 | −6.543 | 1.00 | 30.30 | O |
| ATOM | 624 | N | LEU | A | 55 | −67.725 | 43.551 | −5.618 | 1.00 | 30.09 | N |
| ATOM | 625 | CA | LEU | A | 55 | −66.730 | 43.000 | −4.695 | 1.00 | 29.47 | C |
| ATOM | 627 | CB | LEU | A | 55 | −66.006 | 44.126 | −3.944 | 1.00 | 29.44 | C |
| ATOM | 630 | CG | LEU | A | 55 | −65.069 | 45.017 | −4.781 | 1.00 | 29.74 | C |
| ATOM | 632 | CD1 | LEU | A | 55 | −64.609 | 46.255 | −4.003 | 1.00 | 29.43 | C |
| ATOM | 636 | CD2 | LEU | A | 55 | −63.859 | 44.234 | −5.286 | 1.00 | 29.64 | C |

TABLE 16-7-continued

Coordinates of *P. tremuloides* IspS

| ATOM | 640 | C | LEU | A | 55 | −67.340 | 42.024 | −3.696 | 1.00 | 28.87 | C |
|---|---|---|---|---|---|---|---|---|---|---|---|
| ATOM | 641 | O | LEU | A | 55 | −66.746 | 40.991 | −3.383 | 1.00 | 28.98 | O |
| ATOM | 643 | N | GLU | A | 56 | −68.525 | 42.330 | −3.198 | 1.00 | 28.01 | N |
| ATOM | 644 | CA | GLU | A | 56 | −69.160 | 41.419 | −2.256 | 1.00 | 27.64 | C |
| ATOM | 646 | CB | GLU | A | 56 | −70.172 | 42.173 | −1.395 | 1.00 | 28.19 | C |
| ATOM | 649 | CG | GLU | A | 56 | −69.497 | 43.167 | −.459 | 1.00 | 29.75 | C |
| ATOM | 652 | CD | GLU | A | 56 | −70.457 | 43.858 | .478 | 1.00 | 33.04 | C |
| ATOM | 653 | OE1 | GLU | A | 56 | −71.667 | 43.538 | .481 | 1.00 | 34.46 | O |
| ATOM | 654 | OE2 | GLU | A | 56 | −69.988 | 44.737 | 1.226 | 1.00 | 36.78 | O |
| ATOM | 655 | C | GLU | A | 56 | −69.776 | 40.200 | −2.945 | 1.00 | 26.37 | C |
| ATOM | 656 | O | GLU | A | 56 | −69.914 | 39.146 | −2.333 | 1.00 | 26.02 | O |
| ATOM | 658 | N | LEU | A | 57 | −70.134 | 40.347 | −4.218 | 1.00 | 25.30 | N |
| ATOM | 659 | CA | LEU | A | 57 | −70.569 | 39.212 | −5.036 | 1.00 | 24.17 | C |
| ATOM | 661 | CB | LEU | A | 57 | −71.125 | 39.680 | −6.382 | 1.00 | 23.71 | C |
| ATOM | 664 | CG | LEU | A | 57 | −71.417 | 38.568 | −7.390 | 1.00 | 22.27 | C |
| ATOM | 666 | CD1 | LEU | A | 57 | −72.515 | 37.675 | −6.858 | 1.00 | 19.31 | C |
| ATOM | 670 | CD2 | LEU | A | 57 | −71.752 | 39.167 | −8.768 | 1.00 | 20.30 | C |
| ATOM | 674 | C | LEU | A | 57 | −69.404 | 38.267 | −5.284 | 1.00 | 23.69 | C |
| ATOM | 675 | O | LEU | A | 57 | −69.547 | 37.051 | −5.136 | 1.00 | 23.83 | O |
| ATOM | 677 | N | ILE | A | 58 | −68.261 | 38.822 | −5.682 | 1.00 | 22.82 | N |
| ATOM | 678 | CA | ILE | A | 58 | −67.070 | 38.019 | −5.925 | 1.00 | 22.39 | C |
| ATOM | 680 | CB | ILE | A | 58 | −65.884 | 38.899 | −6.355 | 1.00 | 22.21 | C |
| ATOM | 682 | CG1 | ILE | A | 58 | −66.088 | 39.386 | −7.792 | 1.00 | 21.83 | C |
| ATOM | 685 | CD1 | ILE | A | 58 | −65.002 | 40.314 | −8.320 | 1.00 | 20.43 | C |
| ATOM | 689 | CG2 | ILE | A | 58 | −64.565 | 38.131 | −6.245 | 1.00 | 22.64 | C |
| ATOM | 693 | C | ILE | A | 58 | −66.719 | 37.227 | −4.662 | 1.00 | 22.35 | C |
| ATOM | 694 | O | ILE | A | 58 | −66.520 | 36.002 | −4.706 | 1.00 | 21.95 | O |
| ATOM | 696 | N | ASP | A | 59 | −66.676 | 37.951 | −3.543 | 1.00 | 22.32 | N |
| ATOM | 697 | CA | ASP | A | 59 | −66.396 | 37.396 | −2.215 | 1.00 | 22.26 | C |
| ATOM | 699 | CB | ASP | A | 59 | −66.570 | 38.500 | −1.171 | 1.00 | 22.67 | C |
| ATOM | 702 | CG | ASP | A | 59 | −66.126 | 38.092 | .213 | 1.00 | 23.91 | C |
| ATOM | 703 | OD1 | ASP | A | 59 | −65.271 | 37.182 | .338 | 1.00 | 23.77 | O |
| ATOM | 704 | OD2 | ASP | A | 59 | −66.641 | 38.718 | 1.178 | 1.00 | 27.12 | O |
| ATOM | 705 | C | ASP | A | 59 | −67.304 | 36.216 | −1.901 | 1.00 | 21.79 | C |
| ATOM | 706 | O | ASP | A | 59 | −66.828 | 35.102 | −1.668 | 1.00 | 21.71 | O |
| ATOM | 708 | N | ASN | A | 60 | −68.610 | 36.466 | −1.926 | 1.00 | 21.51 | N |
| ATOM | 709 | CA | ASN | A | 60 | −69.619 | 35.418 | −1.759 | 1.00 | 21.28 | C |
| ATOM | 711 | CB | ASN | A | 60 | −71.012 | 36.006 | −1.958 | 1.00 | 21.25 | C |
| ATOM | 714 | CG | ASN | A | 60 | −71.476 | 36.827 | −.776 | 1.00 | 21.82 | C |
| ATOM | 715 | OD1 | ASN | A | 60 | −71.067 | 36.598 | .364 | 1.00 | 20.81 | O |
| ATOM | 716 | ND2 | ASN | A | 60 | −72.361 | 37.783 | −1.043 | 1.00 | 23.63 | N |
| ATOM | 719 | C | ASN | A | 60 | −69.445 | 34.240 | −2.725 | 1.00 | 21.22 | C |
| ATOM | 720 | O | ASN | A | 60 | −69.444 | 33.053 | −2.303 | 1.00 | 20.95 | O |
| ATOM | 722 | N | VAL | A | 61 | −69.308 | 34.566 | −4.018 | 1.00 | 20.83 | N |
| ATOM | 723 | CA | VAL | A | 61 | −69.147 | 33.536 | −5.043 | 1.00 | 20.57 | C |
| ATOM | 725 | CB | VAL | A | 61 | −68.915 | 34.122 | −6.466 | 1.00 | 20.53 | C |
| ATOM | 727 | CG1 | VAL | A | 61 | −68.382 | 33.042 | −7.430 | 1.00 | 19.44 | C |
| ATOM | 731 | CG2 | VAL | A | 61 | −70.190 | 34.758 | −7.006 | 1.00 | 19.75 | C |
| ATOM | 735 | C | VAL | A | 61 | −67.981 | 32.646 | −4.644 | 1.00 | 20.62 | C |
| ATOM | 736 | O | VAL | A | 61 | −68.080 | 31.431 | −4.699 | 1.00 | 20.56 | O |
| ATOM | 738 | N | GLN | A | 62 | −66.888 | 33.255 | −4.209 | 1.00 | 20.76 | N |
| ATOM | 739 | CA | GLN | A | 62 | −65.703 | 32.481 | −3.898 | 1.00 | 21.18 | C |
| ATOM | 741 | CB | GLN | A | 62 | −64.461 | 33.379 | −3.824 | 1.00 | 21.39 | C |
| ATOM | 744 | CG | GLN | A | 62 | −64.007 | 33.920 | −5.165 | 1.00 | 21.64 | C |
| ATOM | 747 | CD | GLN | A | 62 | −62.608 | 34.512 | −5.135 | 1.00 | 22.04 | C |
| ATOM | 748 | OE1 | GLN | A | 62 | −61.890 | 34.483 | −6.145 | 1.00 | 23.18 | O |
| ATOM | 749 | NE2 | GLN | A | 62 | −62.217 | 35.062 | −3.989 | 1.00 | 20.39 | N |
| ATOM | 752 | C | GLN | A | 62 | −65.891 | 31.681 | −2.607 | 1.00 | 21.09 | C |
| ATOM | 753 | O | GLN | A | 62 | −65.544 | 30.485 | −2.554 | 1.00 | 21.30 | O |
| ATOM | 755 | N | ARG | A | 63 | −66.448 | 32.325 | −1.583 | 1.00 | 20.63 | N |
| ATOM | 756 | CA | ARG | A | 63 | −66.590 | 31.677 | −.273 | 1.00 | 20.54 | C |
| ATOM | 758 | CB | ARG | A | 63 | −67.025 | 32.686 | .786 | 1.00 | 20.57 | C |
| ATOM | 761 | CG | ARG | A | 63 | −66.031 | 33.823 | .930 | 1.00 | 22.55 | C |
| ATOM | 764 | CD | ARG | A | 63 | −66.214 | 34.632 | 2.179 | 1.00 | 24.93 | C |
| ATOM | 767 | NE | ARG | A | 63 | −66.123 | 33.781 | 3.355 | 1.00 | 27.75 | N |
| ATOM | 769 | CZ | ARG | A | 63 | −66.496 | 34.151 | 4.573 | 1.00 | 30.24 | C |
| ATOM | 770 | NH1 | ARG | A | 63 | −66.971 | 35.385 | 4.782 | 1.00 | 31.79 | N |
| ATOM | 773 | NH2 | ARG | A | 63 | −66.399 | 33.285 | 5.581 | 1.00 | 30.07 | N |
| ATOM | 776 | C | ARG | A | 63 | −67.557 | 30.499 | −.338 | 1.00 | 19.81 | C |
| ATOM | 777 | O | ARG | A | 63 | −67.283 | 29.431 | .209 | 1.00 | 19.67 | O |
| ATOM | 779 | N | LEU | A | 64 | −68.661 | 30.684 | −1.057 | 1.00 | 19.04 | N |
| ATOM | 780 | CA | LEU | A | 64 | −69.636 | 29.617 | −1.246 | 1.00 | 18.44 | C |
| ATOM | 782 | CB | LEU | A | 64 | −70.865 | 30.167 | −1.954 | 1.00 | 18.59 | C |
| ATOM | 785 | CG | LEU | A | 64 | −71.662 | 31.170 | −1.140 | 1.00 | 18.32 | C |
| ATOM | 787 | CD1 | LEU | A | 64 | −72.669 | 31.852 | −2.034 | 1.00 | 18.10 | C |
| ATOM | 791 | CD2 | LEU | A | 64 | −72.334 | 30.444 | .004 | 1.00 | 18.29 | C |
| ATOM | 795 | C | LEU | A | 64 | −69.089 | 28.436 | −2.037 | 1.00 | 17.80 | C |
| ATOM | 796 | O | LEU | A | 64 | −69.802 | 27.453 | −2.252 | 1.00 | 17.79 | O |

TABLE 16-7-continued

Coordinates of *P. tremuloides* IspS

| ATOM | 798 | N | GLY | A | 65 | −67.850 | 28.573 | −2.515 | 1.00 | 17.07 | N |
| --- | --- | --- | --- | --- | --- | --- | --- | --- | --- | --- | --- |
| ATOM | 799 | CA | GLY | A | 65 | −67.084 | 27.480 | −3.081 | 1.00 | 16.27 | C |
| ATOM | 802 | C | GLY | A | 65 | −67.137 | 27.406 | −4.588 | 1.00 | 15.77 | C |
| ATOM | 803 | O | GLY | A | 65 | −66.893 | 26.347 | −5.154 | 1.00 | 15.78 | O |
| ATOM | 805 | N | LEU | A | 66 | −67.439 | 28.521 | −5.246 | 1.00 | 15.24 | N |
| ATOM | 806 | CA | LEU | A | 66 | −67.621 | 28.537 | −6.701 | 1.00 | 14.93 | C |
| ATOM | 808 | CB | LEU | A | 66 | −68.977 | 29.146 | −7.021 | 1.00 | 14.84 | C |
| ATOM | 811 | CG | LEU | A | 66 | −70.204 | 28.334 | −6.619 | 1.00 | 13.97 | C |
| ATOM | 813 | CD1 | LEU | A | 66 | −71.391 | 29.260 | −6.650 | 1.00 | 13.74 | C |
| ATOM | 817 | CD2 | LEU | A | 66 | −70.415 | 27.125 | −7.534 | 1.00 | 11.22 | C |
| ATOM | 821 | C | LEU | A | 66 | −66.533 | 29.314 | −7.454 | 1.00 | 15.09 | C |
| ATOM | 822 | O | LEU | A | 66 | −66.621 | 29.497 | −8.678 | 1.00 | 14.81 | O |
| ATOM | 824 | N | GLY | A | 67 | −65.510 | 29.758 | −6.720 | 1.00 | 15.21 | N |
| ATOM | 825 | CA | GLY | A | 67 | −64.404 | 30.526 | −7.280 | 1.00 | 14.98 | C |
| ATOM | 828 | C | GLY | A | 67 | −63.873 | 29.952 | −8.569 | 1.00 | 14.60 | C |
| ATOM | 829 | O | GLY | A | 67 | −63.891 | 30.619 | −9.579 | 1.00 | 14.63 | O |
| ATOM | 831 | N | TYR | A | 68 | −63.419 | 28.706 | −8.523 | 1.00 | 14.57 | N |
| ATOM | 832 | CA | TYR | A | 68 | −62.831 | 28.029 | −9.688 | 1.00 | 14.72 | C |
| ATOM | 834 | CB | TYR | A | 68 | −62.608 | 26.539 | −9.372 | 1.00 | 14.73 | C |
| ATOM | 837 | CG | TYR | A | 68 | −63.858 | 25.689 | −9.330 | 1.00 | 12.47 | C |
| ATOM | 838 | CD1 | TYR | A | 68 | −64.163 | 24.826 | −10.366 | 1.00 | 10.68 | C |
| ATOM | 840 | CE1 | TYR | A | 68 | −65.310 | 24.043 | −10.340 | 1.00 | 10.55 | C |
| ATOM | 842 | CZ | TYR | A | 68 | −66.163 | 24.119 | −9.258 | 1.00 | 10.41 | C |
| ATOM | 843 | OH | TYR | A | 68 | −67.311 | 23.349 | −9.212 | 1.00 | 6.97 | O |
| ATOM | 845 | CE2 | TYR | A | 68 | −65.864 | 24.979 | −8.210 | 1.00 | 11.44 | C |
| ATOM | 847 | CD2 | TYR | A | 68 | −64.722 | 25.750 | −8.252 | 1.00 | 11.29 | C |
| ATOM | 849 | C | TYR | A | 68 | −63.648 | 28.141 | −10.980 | 1.00 | 15.31 | C |
| ATOM | 850 | O | TYR | A | 68 | −63.106 | 28.230 | −12.083 | 1.00 | 15.01 | O |
| ATOM | 852 | N | ARG | A | 69 | −64.959 | 28.136 | −10.816 | 1.00 | 16.03 | N |
| ATOM | 853 | CA | ARG | A | 69 | −65.884 | 28.083 | −11.922 | 1.00 | 16.67 | C |
| ATOM | 855 | CB | ARG | A | 69 | −67.224 | 27.649 | −11.348 | 1.00 | 16.58 | C |
| ATOM | 858 | CG | ARG | A | 69 | −68.332 | 27.445 | −12.335 | 1.00 | 16.07 | C |
| ATOM | 861 | CD | ARG | A | 69 | −69.378 | 26.578 | −11.701 | 1.00 | 14.26 | C |
| ATOM | 864 | NE | ARG | A | 69 | −68.915 | 25.205 | −11.677 | 1.00 | 12.82 | N |
| ATOM | 866 | CZ | ARG | A | 69 | −69.063 | 24.346 | −12.676 | 1.00 | 12.42 | C |
| ATOM | 867 | NH1 | ARG | A | 69 | −69.676 | 24.694 | −13.792 | 1.00 | 12.27 | N |
| ATOM | 870 | NH2 | ARG | A | 69 | −68.601 | 23.119 | −12.553 | 1.00 | 13.23 | N |
| ATOM | 873 | C | ARG | A | 69 | −66.010 | 29.409 | −12.692 | 1.00 | 17.62 | C |
| ATOM | 874 | O | ARG | A | 69 | −66.281 | 29.401 | −13.892 | 1.00 | 17.10 | O |
| ATOM | 876 | N | PHE | A | 70 | −65.811 | 30.529 | −11.985 | 1.00 | 19.11 | N |
| ATOM | 877 | CA | PHE | A | 70 | −65.936 | 31.891 | −12.530 | 1.00 | 19.96 | C |
| ATOM | 879 | CB | PHE | A | 70 | −67.024 | 32.666 | −11.763 | 1.00 | 19.89 | C |
| ATOM | 882 | CG | PHE | A | 70 | −68.365 | 32.010 | −11.784 | 1.00 | 18.68 | C |
| ATOM | 883 | CD1 | PHE | A | 70 | −69.158 | 32.082 | −12.903 | 1.00 | 18.05 | C |
| ATOM | 885 | CE1 | PHE | A | 70 | −70.376 | 31.452 | −12.938 | 1.00 | 18.03 | C |
| ATOM | 887 | CZ | PHE | A | 70 | −70.825 | 30.754 | −11.851 | 1.00 | 17.26 | C |
| ATOM | 889 | CE2 | PHE | A | 70 | −70.051 | 30.672 | −10.736 | 1.00 | 17.60 | C |
| ATOM | 891 | CD2 | PHE | A | 70 | −68.822 | 31.300 | −10.700 | 1.00 | 17.86 | C |
| ATOM | 893 | C | PHE | A | 70 | −64.627 | 32.661 | −12.400 | 1.00 | 21.34 | C |
| ATOM | 894 | O | PHE | A | 70 | −64.629 | 33.862 | −12.171 | 1.00 | 21.25 | O |
| ATOM | 896 | N | GLU | A | 71 | −63.501 | 31.977 | −12.541 | 1.00 | 23.19 | N |
| ATOM | 897 | CA | GLU | A | 71 | −62.211 | 32.591 | −12.214 | 1.00 | 24.60 | C |
| ATOM | 899 | CB | GLU | A | 71 | −61.127 | 31.524 | −12.073 | 1.00 | 25.03 | C |
| ATOM | 902 | CG | GLU | A | 71 | −59.717 | 32.059 | −11.861 | 1.00 | 27.10 | C |
| ATOM | 905 | CD | GLU | A | 71 | −58.712 | 30.949 | −11.549 | 1.00 | 30.10 | C |
| ATOM | 906 | OE1 | GLU | A | 71 | −59.084 | 30.007 | −10.796 | 1.00 | 32.05 | O |
| ATOM | 907 | OE2 | GLU | A | 71 | −57.558 | 31.027 | −12.051 | 1.00 | 30.50 | O |
| ATOM | 908 | C | GLU | A | 71 | −61.809 | 33.644 | −13.241 | 1.00 | 25.23 | C |
| ATOM | 909 | O | GLU | A | 71 | −61.362 | 34.717 | −12.862 | 1.00 | 25.54 | O |
| ATOM | 911 | N | SER | A | 72 | −61.979 | 33.345 | −14.530 | 1.00 | 25.91 | N |
| ATOM | 912 | CA | SER | A | 72 | −61.641 | 34.294 | −15.588 | 1.00 | 26.37 | C |
| ATOM | 914 | CB | SER | A | 72 | −61.656 | 33.606 | −16.941 | 1.00 | 26.32 | C |
| ATOM | 917 | OG | SER | A | 72 | −62.985 | 33.278 | −17.291 | 1.00 | 27.28 | O |
| ATOM | 919 | C | SER | A | 72 | −62.609 | 35.476 | −15.608 | 1.00 | 26.84 | C |
| ATOM | 920 | O | SER | A | 72 | −62.197 | 36.601 | −15.852 | 1.00 | 27.02 | O |
| ATOM | 922 | N | ASP | A | 73 | −63.893 | 35.214 | −15.361 | 1.00 | 27.45 | N |
| ATOM | 923 | CA | ASP | A | 73 | −64.895 | 36.277 | −15.246 | 1.00 | 27.87 | C |
| ATOM | 925 | CB | ASP | A | 73 | −66.289 | 35.705 | −14.968 | 1.00 | 27.99 | C |
| ATOM | 928 | CG | ASP | A | 73 | −66.842 | 34.913 | −16.140 | 1.00 | 29.49 | C |
| ATOM | 929 | OD1 | ASP | A | 73 | −67.215 | 35.530 | −17.155 | 1.00 | 30.90 | O |
| ATOM | 930 | OD2 | ASP | A | 73 | −66.916 | 33.667 | −16.054 | 1.00 | 31.85 | O |
| ATOM | 931 | C | ASP | A | 73 | −64.518 | 37.221 | −14.121 | 1.00 | 27.86 | C |
| ATOM | 932 | O | ASP | A | 73 | −64.598 | 38.435 | −14.286 | 1.00 | 28.05 | O |
| ATOM | 934 | N | ILE | A | 74 | −64.118 | 36.652 | −12.985 | 1.00 | 27.88 | N |
| ATOM | 935 | CA | ILE | A | 74 | −63.698 | 37.422 | −11.821 | 1.00 | 27.98 | C |
| ATOM | 937 | CB | ILE | A | 74 | −63.348 | 36.521 | −10.637 | 1.00 | 27.71 | C |
| ATOM | 939 | CG1 | ILE | A | 74 | −64.607 | 36.007 | −9.960 | 1.00 | 27.60 | C |
| ATOM | 942 | CD1 | ILE | A | 74 | −64.355 | 34.846 | −9.023 | 1.00 | 27.67 | C |

TABLE 16-7-continued

Coordinates of *P. tremuloides* IspS

| ATOM | 946 | CG2 | ILE | A | 74 | −62.551 | 37.272 | −9.621 | 1.00 | 26.82 | C |
|---|---|---|---|---|---|---|---|---|---|---|---|
| ATOM | 950 | C | ILE | A | 74 | −62.472 | 38.252 | −12.133 | 1.00 | 28.80 | C |
| ATOM | 951 | O | ILE | A | 74 | −62.475 | 39.453 | −11.917 | 1.00 | 29.00 | O |
| ATOM | 953 | N | ARG | A | 75 | −61.415 | 37.616 | −12.628 | 1.00 | 29.80 | N |
| ATOM | 954 | CA | ARG | A | 75 | −60.197 | 38.341 | −12.968 | 1.00 | 30.79 | C |
| ATOM | 956 | CB | ARG | A | 75 | −59.286 | 37.507 | −13.841 | 1.00 | 31.33 | C |
| ATOM | 959 | CG | ARG | A | 75 | −58.506 | 36.441 | −13.115 | 1.00 | 34.25 | C |
| ATOM | 962 | CD | ARG | A | 75 | −57.286 | 36.009 | −13.929 | 1.00 | 37.53 | C |
| ATOM | 965 | NE | ARG | A | 75 | −56.238 | 37.019 | −13.799 | 1.00 | 40.89 | N |
| ATOM | 967 | CZ | ARG | A | 75 | −54.934 | 36.807 | −13.967 | 1.00 | 44.24 | C |
| ATOM | 968 | NH1 | ARG | A | 75 | −54.459 | 35.602 | −14.294 | 1.00 | 45.02 | N |
| ATOM | 971 | NH2 | ARG | A | 75 | −54.089 | 37.821 | −13.796 | 1.00 | 45.88 | N |
| ATOM | 974 | C | ARG | A | 75 | −60.548 | 39.596 | −13.727 | 1.00 | 30.95 | C |
| ATOM | 975 | O | ARG | A | 75 | −60.163 | 40.685 | −13.336 | 1.00 | 31.27 | O |
| ATOM | 977 | N | ARG | A | 76 | −61.293 | 39.435 | −14.815 | 1.00 | 31.31 | N |
| ATOM | 978 | CA | ARG | A | 76 | −61.712 | 40.567 | −15.638 | 1.00 | 31.62 | C |
| ATOM | 980 | CB | ARG | A | 76 | −62.593 | 40.106 | −16.794 | 1.00 | 31.97 | C |
| ATOM | 983 | CG | ARG | A | 76 | −61.833 | 39.392 | −17.895 | 1.00 | 32.91 | C |
| ATOM | 986 | CD | ARG | A | 76 | −62.615 | 39.453 | −19.205 | 1.00 | 34.43 | C |
| ATOM | 989 | NE | ARG | A | 76 | −63.925 | 38.803 | −19.128 | 1.00 | 35.66 | N |
| ATOM | 991 | CZ | ARG | A | 76 | −64.115 | 37.480 | −19.106 | 1.00 | 37.15 | C |
| ATOM | 992 | NH1 | ARG | A | 76 | −63.085 | 36.632 | −19.129 | 1.00 | 37.93 | N |
| ATOM | 995 | NH2 | ARG | A | 76 | −65.347 | 36.992 | −19.048 | 1.00 | 37.64 | N |
| ATOM | 998 | C | ARG | A | 76 | −62.453 | 41.629 | −14.849 | 1.00 | 31.41 | C |
| ATOM | 999 | O | ARG | A | 76 | −62.144 | 42.798 | −14.966 | 1.00 | 31.35 | O |
| ATOM | 1001 | N | ALA | A | 77 | −63.437 | 41.230 | −14.058 | 1.00 | 31.53 | N |
| ATOM | 1002 | CA | ALA | A | 77 | −64.136 | 42.177 | −13.211 | 1.00 | 31.73 | C |
| ATOM | 1004 | CB | ALA | A | 77 | −65.074 | 41.468 | −12.275 | 1.00 | 31.69 | C |
| ATOM | 1008 | C | ALA | A | 77 | −63.107 | 42.950 | −12.423 | 1.00 | 32.23 | C |
| ATOM | 1009 | O | ALA | A | 77 | −63.116 | 44.176 | −12.411 | 1.00 | 32.42 | O |
| ATOM | 1011 | N | LEU | A | 78 | −62.198 | 42.223 | −11.786 | 1.00 | 32.95 | N |
| ATOM | 1012 | CA | LEU | A | 78 | −61.168 | 42.838 | −10.963 | 1.00 | 33.51 | C |
| ATOM | 1014 | CB | LEU | A | 78 | −60.319 | 41.775 | −10.265 | 1.00 | 33.10 | C |
| ATOM | 1017 | CG | LEU | A | 78 | −60.959 | 41.077 | −9.081 | 1.00 | 32.30 | C |
| ATOM | 1019 | CD1 | LEU | A | 78 | −59.960 | 40.104 | −8.472 | 1.00 | 30.80 | C |
| ATOM | 1023 | CD2 | LEU | A | 78 | −61.438 | 42.117 | −8.056 | 1.00 | 31.89 | C |
| ATOM | 1027 | C | LEU | A | 78 | −60.249 | 43.752 | −11.753 | 1.00 | 34.70 | C |
| ATOM | 1028 | O | LEU | A | 78 | −59.790 | 44.753 | −11.214 | 1.00 | 35.18 | O |
| ATOM | 1030 | N | ASP | A | 79 | −59.955 | 43.404 | −13.007 | 1.00 | 35.91 | N |
| ATOM | 1031 | CA | ASP | A | 79 | −59.054 | 44.205 | −13.828 | 1.00 | 36.89 | C |
| ATOM | 1033 | CB | ASP | A | 79 | −58.637 | 43.452 | −15.083 | 1.00 | 37.06 | C |
| ATOM | 1036 | CG | ASP | A | 79 | −57.518 | 44.150 | −15.821 | 1.00 | 38.41 | C |
| ATOM | 1037 | OD1 | ASP | A | 79 | −57.800 | 45.080 | −16.615 | 1.00 | 39.85 | O |
| ATOM | 1038 | OD2 | ASP | A | 79 | −56.347 | 43.775 | −15.592 | 1.00 | 40.78 | O |
| ATOM | 1039 | C | ASP | A | 79 | −59.721 | 45.505 | −14.220 | 1.00 | 37.75 | C |
| ATOM | 1040 | O | ASP | A | 79 | −59.105 | 46.568 | −14.177 | 1.00 | 37.82 | O |
| ATOM | 1042 | N | ARG | A | 80 | −60.984 | 45.401 | −14.615 | 1.00 | 38.99 | N |
| ATOM | 1043 | CA | ARG | A | 80 | −61.814 | 46.558 | −14.923 | 1.00 | 39.88 | C |
| ATOM | 1045 | CB | ARG | A | 80 | −63.191 | 46.106 | −15.427 | 1.00 | 40.41 | C |
| ATOM | 1048 | CG | ARG | A | 80 | −64.025 | 47.183 | −16.122 | 1.00 | 42.77 | C |
| ATOM | 1051 | CD | ARG | A | 80 | −65.347 | 46.624 | −16.718 | 1.00 | 45.79 | C |
| ATOM | 1054 | NE | ARG | A | 80 | −66.107 | 45.799 | −15.765 | 1.00 | 48.55 | N |
| ATOM | 1056 | CZ | ARG | A | 80 | −66.136 | 44.457 | −15.742 | 1.00 | 50.37 | C |
| ATOM | 1057 | NH1 | ARG | A | 80 | −65.450 | 43.724 | −16.636 | 1.00 | 49.78 | N |
| ATOM | 1060 | NH2 | ARG | A | 80 | −66.868 | 43.835 | −14.805 | 1.00 | 50.77 | N |
| ATOM | 1063 | C | ARG | A | 80 | −61.946 | 47.409 | −13.668 | 1.00 | 39.80 | C |
| ATOM | 1064 | O | ARG | A | 80 | −61.840 | 48.630 | −13.742 | 1.00 | 40.37 | O |
| ATOM | 1066 | N | PHE | A | 81 | −62.136 | 46.771 | −12.516 | 1.00 | 39.62 | N |
| ATOM | 1067 | CA | PHE | A | 81 | −62.216 | 47.505 | −11.245 | 1.00 | 39.61 | C |
| ATOM | 1069 | CB | PHE | A | 81 | −62.392 | 46.561 | −10.053 | 1.00 | 39.74 | C |
| ATOM | 1072 | CG | PHE | A | 81 | −62.282 | 47.247 | −8.712 | 1.00 | 38.81 | C |
| ATOM | 1073 | CD1 | PHE | A | 81 | −63.238 | 48.153 | −8.315 | 1.00 | 39.03 | C |
| ATOM | 1075 | CE1 | PHE | A | 81 | −63.153 | 48.787 | −7.100 | 1.00 | 39.69 | C |
| ATOM | 1077 | CZ | PHE | A | 81 | −62.095 | 48.515 | −6.261 | 1.00 | 39.54 | C |
| ATOM | 1079 | CE2 | PHE | A | 81 | −61.134 | 47.608 | −6.647 | 1.00 | 38.66 | C |
| ATOM | 1081 | CD2 | PHE | A | 81 | −61.228 | 46.986 | −7.865 | 1.00 | 38.27 | C |
| ATOM | 1083 | C | PHE | A | 81 | −61.006 | 48.378 | −10.970 | 1.00 | 39.58 | C |
| ATOM | 1084 | O | PHE | A | 81 | −61.165 | 49.535 | −10.581 | 1.00 | 39.76 | O |
| ATOM | 1086 | N | VAL | A | 82 | −59.810 | 47.817 | −11.142 | 1.00 | 39.50 | N |
| ATOM | 1087 | CA | VAL | A | 82 | −58.575 | 48.562 | −10.892 | 1.00 | 39.47 | C |
| ATOM | 1089 | CB | VAL | A | 82 | −57.314 | 47.659 | −10.977 | 1.00 | 39.37 | C |
| ATOM | 1091 | CG1 | VAL | A | 82 | −56.108 | 48.426 | −11.521 | 1.00 | 39.06 | C |
| ATOM | 1095 | CG2 | VAL | A | 82 | −57.009 | 47.079 | −9.614 | 1.00 | 39.23 | C |
| ATOM | 1099 | C | VAL | A | 82 | −58.457 | 49.755 | −11.833 | 1.00 | 39.54 | C |
| ATOM | 1100 | O | VAL | A | 82 | −58.222 | 50.884 | −11.378 | 1.00 | 39.45 | O |
| ATOM | 1102 | N | SER | A | 83 | −58.678 | 49.513 | −13.126 | 1.00 | 39.65 | N |
| ATOM | 1103 | CA | SER | A | 83 | −58.469 | 50.535 | −14.157 | 1.00 | 39.82 | C |
| ATOM | 1105 | CB | SER | A | 83 | −58.196 | 49.880 | −15.526 | 1.00 | 39.84 | C |

TABLE 16-7-continued

Coordinates of *P. tremuloides* IspS

| ATOM | 1108 | OG | SER | A | 83 | −59.138 | 48.870 | −15.829 | 1.00 | 40.00 | O |
| ATOM | 1110 | C | SER | A | 83 | −59.617 | 51.561 | −14.219 | 1.00 | 39.62 | C |
| ATOM | 1111 | O | SER | A | 83 | −60.149 | 51.853 | −15.286 | 1.00 | 39.59 | O |
| ATOM | 1113 | N | SER | A | 84 | −59.957 | 52.108 | −13.052 | 1.00 | 39.44 | N |
| ATOM | 1114 | CA | SER | A | 84 | −60.926 | 53.197 | −12.910 | 1.00 | 39.13 | C |
| ATOM | 1116 | CB | SER | A | 84 | −62.238 | 52.834 | −13.618 | 1.00 | 39.03 | C |
| ATOM | 1119 | OG | SER | A | 84 | −62.620 | 51.505 | −13.325 | 1.00 | 37.97 | O |
| ATOM | 1121 | C | SER | A | 84 | −61.243 | 53.580 | −11.446 | 1.00 | 39.17 | C |
| ATOM | 1122 | O | SER | A | 84 | −62.189 | 54.341 | −11.230 | 1.00 | 39.58 | O |
| ATOM | 1124 | N | GLY | A | 85 | −60.482 | 53.077 | −10.457 | 1.00 | 38.74 | N |
| ATOM | 1125 | CA | GLY | A | 85 | −60.795 | 53.282 | −9.024 | 1.00 | 38.26 | C |
| ATOM | 1128 | C | GLY | A | 85 | −61.724 | 52.238 | −8.413 | 1.00 | 37.79 | C |
| ATOM | 1129 | O | GLY | A | 85 | −61.529 | 51.799 | −7.273 | 1.00 | 36.84 | O |
| ATOM | 1131 | N | SER | A | 94 | −63.557 | 54.187 | 1.994 | 1.00 | 28.27 | N |
| ATOM | 1132 | CA | SER | A | 94 | −64.069 | 52.892 | 2.476 | 1.00 | 28.03 | C |
| ATOM | 1134 | CB | SER | A | 94 | −64.856 | 52.225 | 1.359 | 1.00 | 27.84 | C |
| ATOM | 1137 | OG | SER | A | 94 | −65.234 | 50.921 | 1.743 | 1.00 | 28.20 | O |
| ATOM | 1139 | C | SER | A | 94 | −62.992 | 51.910 | 2.934 | 1.00 | 27.83 | C |
| ATOM | 1140 | O | SER | A | 94 | −62.339 | 51.325 | 2.090 | 1.00 | 28.15 | O |
| ATOM | 1142 | N | LEU | A | 95 | −62.815 | 51.705 | 4.245 | 1.00 | 27.70 | N |
| ATOM | 1143 | CA | LEU | A | 95 | −61.813 | 50.728 | 4.751 | 1.00 | 27.59 | C |
| ATOM | 1145 | CB | LEU | A | 95 | −61.692 | 50.747 | 6.282 | 1.00 | 27.49 | C |
| ATOM | 1148 | CG | LEU | A | 95 | −60.871 | 49.596 | 6.909 | 1.00 | 27.47 | C |
| ATOM | 1150 | CD1 | LEU | A | 95 | −59.400 | 49.900 | 6.902 | 1.00 | 27.70 | C |
| ATOM | 1154 | CD2 | LEU | A | 95 | −61.292 | 49.274 | 8.329 | 1.00 | 27.50 | C |
| ATOM | 1158 | C | LEU | A | 95 | −62.173 | 49.314 | 4.318 | 1.00 | 27.71 | C |
| ATOM | 1159 | O | LEU | A | 95 | −61.303 | 48.537 | 3.914 | 1.00 | 27.73 | O |
| ATOM | 1161 | N | HIS | A | 96 | −63.461 | 48.989 | 4.437 | 1.00 | 27.74 | N |
| ATOM | 1162 | CA | HIS | A | 96 | −64.003 | 47.715 | 3.977 | 1.00 | 27.54 | C |
| ATOM | 1164 | CB | HIS | A | 96 | −65.497 | 47.680 | 4.230 | 1.00 | 27.57 | C |
| ATOM | 1167 | CG | HIS | A | 96 | −66.161 | 46.482 | 3.654 | 1.00 | 28.65 | C |
| ATOM | 1168 | ND1 | HIS | A | 96 | −65.790 | 45.201 | 3.988 | 1.00 | 30.59 | N |
| ATOM | 1170 | CE1 | HIS | A | 96 | −66.540 | 44.341 | 3.325 | 1.00 | 31.88 | C |
| ATOM | 1172 | NE2 | HIS | A | 96 | −67.384 | 45.021 | 2.570 | 1.00 | 32.06 | N |
| ATOM | 1174 | CD2 | HIS | A | 96 | −67.166 | 46.364 | 2.758 | 1.00 | 30.47 | C |
| ATOM | 1176 | C | HIS | A | 96 | −63.705 | 47.450 | 2.492 | 1.00 | 27.09 | C |
| ATOM | 1177 | O | HIS | A | 96 | −63.128 | 46.425 | 2.150 | 1.00 | 27.18 | O |
| ATOM | 1179 | N | GLY | A | 97 | −64.079 | 48.386 | 1.625 | 1.00 | 26.55 | N |
| ATOM | 1180 | CA | GLY | A | 97 | −63.760 | 48.300 | .205 | 1.00 | 26.26 | C |
| ATOM | 1183 | C | GLY | A | 97 | −62.277 | 48.112 | −.088 | 1.00 | 26.23 | C |
| ATOM | 1184 | O | GLY | A | 97 | −61.918 | 47.334 | −.974 | 1.00 | 26.39 | O |
| ATOM | 1186 | N | THR | A | 98 | −61.415 | 48.815 | .653 | 1.00 | 25.83 | N |
| ATOM | 1187 | CA | THR | A | 98 | −59.967 | 48.755 | .435 | 1.00 | 25.36 | C |
| ATOM | 1189 | CB | THR | A | 98 | −59.204 | 49.847 | 1.215 | 1.00 | 25.07 | C |
| ATOM | 1191 | OG1 | THR | A | 98 | −59.796 | 51.123 | .980 | 1.00 | 23.62 | O |
| ATOM | 1193 | CG2 | THR | A | 98 | −57.755 | 49.905 | .780 | 1.00 | 24.88 | C |
| ATOM | 1197 | C | THR | A | 98 | −59.416 | 47.389 | .845 | 1.00 | 25.69 | C |
| ATOM | 1198 | O | THR | A | 98 | −58.622 | 46.802 | .111 | 1.00 | 25.66 | O |
| ATOM | 1200 | N | ALA | A | 99 | −59.847 | 46.890 | 2.008 | 1.00 | 25.95 | N |
| ATOM | 1201 | CA | ALA | A | 99 | −59.468 | 45.540 | 2.495 | 1.00 | 25.93 | C |
| ATOM | 1203 | CB | ALA | A | 99 | −59.945 | 45.330 | 3.929 | 1.00 | 25.82 | C |
| ATOM | 1207 | C | ALA | A | 99 | −59.984 | 44.404 | 1.595 | 1.00 | 25.64 | C |
| ATOM | 1208 | O | ALA | A | 99 | −59.204 | 43.599 | 1.102 | 1.00 | 25.38 | O |
| ATOM | 1210 | N | LEU | A | 100 | −61.290 | 44.348 | 1.371 | 1.00 | 25.46 | N |
| ATOM | 1211 | CA | LEU | A | 100 | −61.856 | 43.335 | .474 | 1.00 | 25.55 | C |
| ATOM | 1213 | CB | LEU | A | 100 | −63.361 | 43.540 | .326 | 1.00 | 25.37 | C |
| ATOM | 1216 | CG | LEU | A | 100 | −64.118 | 42.464 | −.443 | 1.00 | 25.41 | C |
| ATOM | 1218 | CD1 | LEU | A | 100 | −64.038 | 41.115 | .281 | 1.00 | 26.01 | C |
| ATOM | 1222 | CD2 | LEU | A | 100 | −65.555 | 42.893 | −.639 | 1.00 | 25.19 | C |
| ATOM | 1226 | C | LEU | A | 100 | −61.196 | 43.353 | −.919 | 1.00 | 25.70 | C |
| ATOM | 1227 | O | LEU | A | 100 | −60.819 | 42.301 | −1.469 | 1.00 | 25.36 | O |
| ATOM | 1229 | N | SER | A | 101 | −61.064 | 44.550 | −1.489 | 1.00 | 25.77 | N |
| ATOM | 1230 | CA | SER | A | 101 | −60.434 | 44.688 | −2.805 | 1.00 | 25.67 | C |
| ATOM | 1232 | CB | SER | A | 101 | −60.629 | 46.098 | −3.375 | 1.00 | 25.83 | C |
| ATOM | 1235 | OG | SER | A | 101 | −59.840 | 47.064 | −2.688 | 1.00 | 26.98 | O |
| ATOM | 1237 | C | SER | A | 101 | −58.947 | 44.336 | −2.756 | 1.00 | 25.01 | C |
| ATOM | 1238 | O | SER | A | 101 | −58.427 | 43.705 | −3.672 | 1.00 | 24.94 | O |
| ATOM | 1240 | N | PHE | A | 102 | −58.270 | 44.737 | −1.687 | 1.00 | 24.30 | N |
| ATOM | 1241 | CA | PHE | A | 102 | −56.852 | 44.436 | −1.560 | 1.00 | 23.99 | C |
| ATOM | 1243 | CB | PHE | A | 102 | −56.295 | 44.963 | −.229 | 1.00 | 23.84 | C |
| ATOM | 1246 | CG | PHE | A | 102 | −54.860 | 44.606 | .027 | 1.00 | 23.24 | C |
| ATOM | 1247 | CD1 | PHE | A | 102 | −53.849 | 45.504 | −.259 | 1.00 | 23.56 | C |
| ATOM | 1249 | CE1 | PHE | A | 102 | −52.507 | 45.182 | −.007 | 1.00 | 24.50 | C |
| ATOM | 1251 | CZ | PHE | A | 102 | −52.175 | 43.941 | .540 | 1.00 | 24.27 | C |
| ATOM | 1253 | CE2 | PHE | A | 102 | −53.180 | 43.042 | .834 | 1.00 | 23.95 | C |
| ATOM | 1255 | CD2 | PHE | A | 102 | −54.520 | 43.376 | .576 | 1.00 | 23.45 | C |
| ATOM | 1257 | C | PHE | A | 102 | −56.673 | 42.928 | −1.679 | 1.00 | 23.65 | C |
| ATOM | 1258 | O | PHE | A | 102 | −55.890 | 42.442 | −2.501 | 1.00 | 23.55 | O |

TABLE 16-7-continued

| | | | | | | | | | | | |
|---|---|---|---|---|---|---|---|---|---|---|---|
| ATOM | 1260 | N | ARG | A | 103 | −57.443 | 42.202 | −.880 | 1.00 | 23.20 | N |
| ATOM | 1261 | CA | ARG | A | 103 | −57.298 | 40.765 | −.764 | 1.00 | 22.84 | C |
| ATOM | 1263 | CB | ARG | A | 103 | −58.250 | 40.231 | .291 | 1.00 | 23.01 | C |
| ATOM | 1266 | CG | ARG | A | 103 | −58.054 | 38.774 | .597 | 1.00 | 23.93 | C |
| ATOM | 1269 | CD | ARG | A | 103 | −58.703 | 38.376 | 1.937 | 1.00 | 23.84 | C |
| ATOM | 1272 | NE | ARG | A | 103 | −60.150 | 38.538 | 1.919 | 1.00 | 22.36 | N |
| ATOM | 1274 | CZ | ARG | A | 103 | −60.982 | 37.763 | 1.240 | 1.00 | 20.62 | C |
| ATOM | 1275 | NH1 | ARG | A | 103 | −60.512 | 36.773 | .490 | 1.00 | 20.19 | N |
| ATOM | 1278 | NH2 | ARG | A | 103 | −62.288 | 38.003 | 1.293 | 1.00 | 20.32 | N |
| ATOM | 1281 | C | ARG | A | 103 | −57.602 | 40.117 | −2.082 | 1.00 | 22.34 | C |
| ATOM | 1282 | O | ARG | A | 103 | −56.826 | 39.303 | −2.576 | 1.00 | 22.37 | O |
| ATOM | 1284 | N | LEU | A | 104 | −58.729 | 40.496 | −2.667 | 1.00 | 21.98 | N |
| ATOM | 1285 | CA | LEU | A | 104 | −59.129 | 39.926 | −3.951 | 1.00 | 21.60 | C |
| ATOM | 1287 | CB | LEU | A | 104 | −60.503 | 40.442 | −4.378 | 1.00 | 21.23 | C |
| ATOM | 1290 | CG | LEU | A | 104 | −61.590 | 39.832 | −3.522 | 1.00 | 20.30 | C |
| ATOM | 1292 | CD1 | LEU | A | 104 | −62.949 | 40.401 | −3.856 | 1.00 | 19.53 | C |
| ATOM | 1296 | CD2 | LEU | A | 104 | −61.554 | 38.344 | −3.725 | 1.00 | 19.71 | C |
| ATOM | 1300 | C | LEU | A | 104 | −58.101 | 40.198 | −5.040 | 1.00 | 21.48 | C |
| ATOM | 1301 | O | LEU | A | 104 | −57.743 | 39.294 | −5.780 | 1.00 | 21.62 | O |
| ATOM | 1303 | N | LEU | A | 105 | −57.623 | 41.432 | −5.139 | 1.00 | 21.14 | N |
| ATOM | 1304 | CA | LEU | A | 105 | −56.655 | 41.747 | −6.173 | 1.00 | 21.05 | C |
| ATOM | 1306 | CB | LEU | A | 105 | −56.352 | 43.248 | −6.205 | 1.00 | 20.94 | C |
| ATOM | 1309 | CG | LEU | A | 105 | −57.465 | 44.165 | −6.732 | 1.00 | 20.06 | C |
| ATOM | 1311 | CD1 | LEU | A | 105 | −57.060 | 45.617 | −6.580 | 1.00 | 17.92 | C |
| ATOM | 1315 | CD2 | LEU | A | 105 | −57.804 | 43.857 | −8.174 | 1.00 | 19.18 | C |
| ATOM | 1319 | C | LEU | A | 105 | −55.372 | 40.908 | −5.997 | 1.00 | 21.32 | C |
| ATOM | 1320 | O | LEU | A | 105 | −54.840 | 40.357 | −6.976 | 1.00 | 21.37 | O |
| ATOM | 1322 | N | ARG | A | 106 | −54.893 | 40.777 | −4.763 | 1.00 | 21.25 | N |
| ATOM | 1323 | CA | ARG | A | 106 | −53.678 | 40.003 | −4.528 | 1.00 | 21.33 | C |
| ATOM | 1325 | CB | ARG | A | 106 | −53.151 | 40.211 | −3.117 | 1.00 | 21.53 | C |
| ATOM | 1328 | CG | ARG | A | 106 | −51.772 | 39.588 | −2.917 | 1.00 | 22.60 | C |
| ATOM | 1331 | CD | ARG | A | 106 | −51.098 | 40.091 | −1.666 | 1.00 | 23.60 | C |
| ATOM | 1334 | NE | ARG | A | 106 | −50.374 | 41.330 | −1.897 | 1.00 | 24.60 | N |
| ATOM | 1336 | CZ | ARG | A | 106 | −49.606 | 41.916 | −.989 | 1.00 | 26.54 | C |
| ATOM | 1337 | NH1 | ARG | A | 106 | −49.469 | 41.380 | .225 | 1.00 | 26.98 | N |
| ATOM | 1340 | NH2 | ARG | A | 106 | −48.967 | 43.041 | −1.295 | 1.00 | 27.19 | N |
| ATOM | 1343 | C | ARG | A | 106 | −53.888 | 38.517 | −4.767 | 1.00 | 21.19 | C |
| ATOM | 1344 | O | ARG | A | 106 | −52.998 | 37.821 | −5.278 | 1.00 | 21.18 | O |
| ATOM | 1346 | N | GLN | A | 107 | −55.061 | 38.028 | −4.378 | 1.00 | 21.09 | N |
| ATOM | 1347 | CA | GLN | A | 107 | −55.425 | 36.635 | −4.618 | 1.00 | 20.76 | C |
| ATOM | 1349 | CB | GLN | A | 107 | −56.861 | 36.378 | −4.168 | 1.00 | 20.51 | C |
| ATOM | 1352 | CG | GLN | A | 107 | −57.329 | 34.941 | −4.327 | 1.00 | 19.68 | C |
| ATOM | 1355 | CD | GLN | A | 107 | −58.790 | 34.772 | −4.010 | 1.00 | 18.26 | C |
| ATOM | 1356 | OE1 | GLN | A | 107 | −59.395 | 35.591 | −3.334 | 1.00 | 17.44 | O |
| ATOM | 1357 | NE2 | GLN | A | 107 | −59.366 | 33.698 | −4.497 | 1.00 | 18.48 | N |
| ATOM | 1360 | C | GLN | A | 107 | −55.304 | 36.306 | −6.094 | 1.00 | 20.93 | C |
| ATOM | 1361 | O | GLN | A | 107 | −54.917 | 35.212 | −6.447 | 1.00 | 21.45 | O |
| ATOM | 1363 | N | HIS | A | 108 | −55.642 | 37.260 | −6.951 | 1.00 | 21.09 | N |
| ATOM | 1364 | CA | HIS | A | 108 | −55.686 | 37.030 | −8.379 | 1.00 | 21.28 | C |
| ATOM | 1366 | CB | HIS | A | 108 | −57.024 | 37.541 | −8.913 | 1.00 | 21.02 | C |
| ATOM | 1369 | CG | HIS | A | 108 | −58.182 | 36.706 | −8.478 | 1.00 | 19.70 | C |
| ATOM | 1370 | ND1 | HIS | A | 108 | −58.637 | 35.632 | −9.210 | 1.00 | 19.91 | N |
| ATOM | 1372 | CE1 | HIS | A | 108 | −59.641 | 35.060 | −8.571 | 1.00 | 19.27 | C |
| ATOM | 1374 | NE2 | HIS | A | 108 | −59.851 | 35.720 | −7.449 | 1.00 | 18.10 | N |
| ATOM | 1376 | CD2 | HIS | A | 108 | −58.950 | 36.753 | −7.367 | 1.00 | 18.98 | C |
| ATOM | 1378 | C | HIS | A | 108 | −54.456 | 37.621 | −9.108 | 1.00 | 22.21 | C |
| ATOM | 1379 | O | HIS | A | 108 | −54.505 | 37.980 | −10.304 | 1.00 | 21.80 | O |
| ATOM | 1381 | N | GLY | A | 109 | −53.345 | 37.686 | −8.375 | 1.00 | 23.19 | N |
| ATOM | 1382 | CA | GLY | A | 109 | −52.055 | 38.007 | −8.956 | 1.00 | 24.17 | C |
| ATOM | 1385 | C | GLY | A | 109 | −51.813 | 39.470 | −9.275 | 1.00 | 25.25 | C |
| ATOM | 1386 | O | GLY | A | 109 | −50.767 | 39.802 | −9.845 | 1.00 | 25.26 | O |
| ATOM | 1388 | N | PHE | A | 110 | −52.755 | 40.349 | −8.917 | 1.00 | 26.42 | N |
| ATOM | 1389 | CA | PHE | A | 110 | −52.575 | 41.783 | −9.154 | 1.00 | 27.33 | C |
| ATOM | 1391 | CB | PHE | A | 110 | −53.895 | 42.546 | −9.067 | 1.00 | 27.36 | C |
| ATOM | 1394 | CG | PHE | A | 110 | −54.838 | 42.250 | −10.193 | 1.00 | 27.83 | C |
| ATOM | 1395 | CD1 | PHE | A | 110 | −54.633 | 42.801 | −11.439 | 1.00 | 28.69 | C |
| ATOM | 1397 | CE1 | PHE | A | 110 | −55.490 | 42.529 | −12.488 | 1.00 | 28.91 | C |
| ATOM | 1399 | CZ | PHE | A | 110 | −56.568 | 41.702 | −12.295 | 1.00 | 28.85 | C |
| ATOM | 1401 | CE2 | PHE | A | 110 | −56.787 | 41.146 | −11.060 | 1.00 | 28.67 | C |
| ATOM | 1403 | CD2 | PHE | A | 110 | −55.923 | 41.418 | −10.013 | 1.00 | 28.39 | C |
| ATOM | 1405 | C | PHE | A | 110 | −51.582 | 42.369 | −8.163 | 1.00 | 28.25 | C |
| ATOM | 1406 | O | PHE | A | 110 | −51.449 | 41.890 | −7.024 | 1.00 | 28.71 | O |
| ATOM | 1408 | N | GLU | A | 111 | −50.886 | 43.411 | −8.607 | 1.00 | 29.05 | N |
| ATOM | 1409 | CA | GLU | A | 111 | −49.951 | 44.142 | −7.760 | 1.00 | 29.66 | C |
| ATOM | 1411 | CB | GLU | A | 111 | −48.902 | 44.803 | −8.648 | 1.00 | 30.37 | C |
| ATOM | 1414 | CG | GLU | A | 111 | −47.750 | 45.509 | −7.947 | 1.00 | 33.30 | C |
| ATOM | 1417 | CD | GLU | A | 111 | −46.916 | 46.342 | −8.946 | 1.00 | 38.00 | C |
| ATOM | 1418 | OE1 | GLU | A | 111 | −46.312 | 45.750 | −9.885 | 1.00 | 39.60 | O |

TABLE 16-7-continued

Coordinates of *P. tremuloides* IspS

| ATOM | 1419 | OE2 | GLU | A | 111 | −46.886 | 47.594 | −8.802 | 1.00 | 40.87 | O |
|---|---|---|---|---|---|---|---|---|---|---|---|
| ATOM | 1420 | C | GLU | A | 111 | −50.724 | 45.184 | −6.935 | 1.00 | 28.98 | C |
| ATOM | 1421 | O | GLU | A | 111 | −51.293 | 46.123 | −7.495 | 1.00 | 28.45 | O |
| ATOM | 1423 | N | VAL | A | 112 | −50.787 | 44.961 | −5.618 | 1.00 | 28.47 | N |
| ATOM | 1424 | CA | VAL | A | 112 | −51.284 | 45.950 | −4.655 | 1.00 | 28.09 | C |
| ATOM | 1426 | CB | VAL | A | 112 | −52.564 | 45.501 | −3.908 | 1.00 | 27.76 | C |
| ATOM | 1428 | CG1 | VAL | A | 112 | −53.745 | 45.466 | −4.836 | 1.00 | 27.38 | C |
| ATOM | 1432 | CG2 | VAL | A | 112 | −52.360 | 44.167 | −3.252 | 1.00 | 27.80 | C |
| ATOM | 1436 | C | VAL | A | 112 | −50.193 | 46.199 | −3.631 | 1.00 | 28.15 | C |
| ATOM | 1437 | O | VAL | A | 112 | −49.339 | 45.354 | −3.436 | 1.00 | 27.90 | O |
| ATOM | 1439 | N | SER | A | 113 | −50.241 | 47.354 | −2.974 | 1.00 | 28.54 | N |
| ATOM | 1440 | CA | SER | A | 113 | −49.194 | 47.782 | −2.047 | 1.00 | 28.93 | C |
| ATOM | 1442 | CB | SER | A | 113 | −48.563 | 49.064 | −2.564 | 1.00 | 29.12 | C |
| ATOM | 1445 | OG | SER | A | 113 | −47.692 | 49.644 | −1.619 | 1.00 | 29.57 | O |
| ATOM | 1447 | C | SER | A | 113 | −49.780 | 48.041 | −.685 | 1.00 | 29.13 | C |
| ATOM | 1448 | O | SER | A | 113 | −50.937 | 48.426 | −.581 | 1.00 | 28.90 | O |
| ATOM | 1450 | N | GLN | A | 114 | −48.985 | 47.857 | .367 | 1.00 | 29.84 | N |
| ATOM | 1451 | CA | GLN | A | 114 | −49.524 | 48.019 | 1.736 | 1.00 | 30.40 | C |
| ATOM | 1453 | CB | GLN | A | 114 | −48.568 | 47.507 | 2.830 | 1.00 | 30.34 | C |
| ATOM | 1456 | CG | GLN | A | 114 | −47.199 | 48.159 | 2.844 | 1.00 | 30.61 | C |
| ATOM | 1459 | CD | GLN | A | 114 | −46.456 | 47.928 | 4.147 | 1.00 | 30.77 | C |
| ATOM | 1460 | OE1 | GLN | A | 114 | −46.876 | 47.129 | 4.982 | 1.00 | 31.92 | O |
| ATOM | 1461 | NE2 | GLN | A | 114 | −45.341 | 48.624 | 4.324 | 1.00 | 30.02 | N |
| ATOM | 1464 | C | GLN | A | 114 | −49.939 | 49.440 | 2.068 | 1.00 | 30.62 | C |
| ATOM | 1465 | O | GLN | A | 114 | −50.573 | 49.644 | 3.094 | 1.00 | 30.73 | O |
| ATOM | 1467 | N | GLU | A | 115 | −49.592 | 50.407 | 1.216 | 1.00 | 30.94 | N |
| ATOM | 1468 | CA | GLU | A | 115 | −49.963 | 51.794 | 1.458 | 1.00 | 31.45 | C |
| ATOM | 1470 | CB | GLU | A | 115 | −48.881 | 52.777 | .975 | 1.00 | 31.86 | C |
| ATOM | 1473 | CG | GLU | A | 115 | −48.489 | 52.723 | −.509 | 1.00 | 33.48 | C |
| ATOM | 1476 | CD | GLU | A | 115 | −47.006 | 53.100 | −.759 | 1.00 | 36.13 | C |
| ATOM | 1477 | OE1 | GLU | A | 115 | −46.106 | 52.668 | .022 | 1.00 | 38.72 | O |
| ATOM | 1478 | OE2 | GLU | A | 115 | −46.741 | 53.811 | −1.754 | 1.00 | 35.70 | O |
| ATOM | 1479 | C | GLU | A | 115 | −51.338 | 52.125 | .895 | 1.00 | 31.45 | C |
| ATOM | 1480 | O | GLU | A | 115 | −51.716 | 53.283 | .808 | 1.00 | 31.80 | O |
| ATOM | 1482 | N | ALA | A | 116 | −52.108 | 51.105 | .549 | 1.00 | 31.58 | N |
| ATOM | 1483 | CA | ALA | A | 116 | −53.524 | 51.286 | .284 | 1.00 | 31.67 | C |
| ATOM | 1485 | CB | ALA | A | 116 | −54.071 | 50.092 | −.461 | 1.00 | 31.62 | C |
| ATOM | 1489 | C | ALA | A | 116 | −54.273 | 51.473 | 1.596 | 1.00 | 31.88 | C |
| ATOM | 1490 | O | ALA | A | 116 | −55.428 | 51.874 | 1.604 | 1.00 | 31.82 | O |
| ATOM | 1492 | N | PHE | A | 117 | −53.608 | 51.161 | 2.702 | 1.00 | 32.39 | N |
| ATOM | 1493 | CA | PHE | A | 117 | −54.193 | 51.271 | 4.030 | 1.00 | 32.87 | C |
| ATOM | 1495 | CB | PHE | A | 117 | −53.884 | 50.003 | 4.856 | 1.00 | 32.79 | C |
| ATOM | 1498 | CG | PHE | A | 117 | −54.539 | 48.758 | 4.323 | 1.00 | 31.03 | C |
| ATOM | 1499 | CD1 | PHE | A | 117 | −53.782 | 47.749 | 3.760 | 1.00 | 28.79 | C |
| ATOM | 1501 | CE1 | PHE | A | 117 | −54.379 | 46.620 | 3.265 | 1.00 | 28.36 | C |
| ATOM | 1503 | CZ | PHE | A | 117 | −55.754 | 46.489 | 3.316 | 1.00 | 29.50 | C |
| ATOM | 1505 | CE2 | PHE | A | 117 | −56.527 | 47.493 | 3.872 | 1.00 | 29.91 | C |
| ATOM | 1507 | CD2 | PHE | A | 117 | −55.917 | 48.613 | 4.375 | 1.00 | 30.09 | C |
| ATOM | 1509 | C | PHE | A | 117 | −53.683 | 52.493 | 4.773 | 1.00 | 33.71 | C |
| ATOM | 1510 | O | PHE | A | 117 | −54.012 | 52.678 | 5.937 | 1.00 | 33.61 | O |
| ATOM | 1512 | N | SER | A | 118 | −52.886 | 53.325 | 4.107 | 1.00 | 35.09 | N |
| ATOM | 1513 | CA | SER | A | 118 | −52.186 | 54.429 | 4.779 | 1.00 | 36.12 | C |
| ATOM | 1515 | CB | SER | A | 118 | −51.073 | 54.990 | 3.895 | 1.00 | 36.09 | C |
| ATOM | 1518 | OG | SER | A | 118 | −51.607 | 55.747 | 2.820 | 1.00 | 35.96 | O |
| ATOM | 1520 | C | SER | A | 118 | −53.134 | 55.552 | 5.184 | 1.00 | 37.17 | C |
| ATOM | 1521 | O | SER | A | 118 | −52.873 | 56.255 | 6.166 | 1.00 | 37.22 | O |
| ATOM | 1523 | N | GLY | A | 119 | −54.231 | 55.705 | 4.436 | 1.00 | 38.40 | N |
| ATOM | 1524 | CA | GLY | A | 119 | −55.227 | 56.735 | 4.708 | 1.00 | 39.47 | C |
| ATOM | 1527 | C | GLY | A | 119 | −56.255 | 56.398 | 5.778 | 1.00 | 40.62 | C |
| ATOM | 1528 | O | GLY | A | 119 | −57.259 | 57.086 | 5.877 | 1.00 | 40.74 | O |
| ATOM | 1530 | N | PHE | A | 120 | −56.024 | 55.344 | 6.563 | 1.00 | 42.13 | N |
| ATOM | 1531 | CA | PHE | A | 120 | −56.906 | 54.971 | 7.684 | 1.00 | 43.27 | C |
| ATOM | 1533 | CB | PHE | A | 120 | −57.510 | 53.586 | 7.455 | 1.00 | 43.21 | C |
| ATOM | 1536 | CG | PHE | A | 120 | −58.176 | 53.439 | 6.134 | 1.00 | 42.36 | C |
| ATOM | 1537 | CD1 | PHE | A | 120 | −59.418 | 54.006 | 5.911 | 1.00 | 41.23 | C |
| ATOM | 1539 | CE1 | PHE | A | 120 | −60.035 | 53.880 | 4.691 | 1.00 | 40.87 | C |
| ATOM | 1541 | CZ | PHE | A | 120 | −59.414 | 53.182 | 3.675 | 1.00 | 41.03 | C |
| ATOM | 1543 | CE2 | PHE | A | 120 | −58.167 | 52.618 | 3.883 | 1.00 | 40.92 | C |
| ATOM | 1545 | CD2 | PHE | A | 120 | −57.556 | 52.746 | 5.106 | 1.00 | 41.30 | C |
| ATOM | 1547 | C | PHE | A | 120 | −56.179 | 54.952 | 9.019 | 1.00 | 44.71 | C |
| ATOM | 1548 | O | PHE | A | 120 | −56.732 | 54.489 | 10.025 | 1.00 | 44.80 | O |
| ATOM | 1550 | N | LYS | A | 121 | −54.939 | 55.430 | 9.021 | 1.00 | 46.38 | N |
| ATOM | 1551 | CA | LYS | A | 121 | −54.153 | 55.519 | 10.235 | 1.00 | 47.81 | C |
| ATOM | 1553 | CB | LYS | A | 121 | −52.722 | 55.050 | 9.957 | 1.00 | 47.86 | C |
| ATOM | 1556 | CG | LYS | A | 121 | −52.648 | 53.537 | 9.648 | 1.00 | 48.24 | C |
| ATOM | 1559 | CD | LYS | A | 121 | −51.417 | 53.119 | 8.823 | 1.00 | 49.41 | C |
| ATOM | 1562 | CE | LYS | A | 121 | −50.095 | 53.142 | 9.621 | 1.00 | 49.88 | C |
| ATOM | 1565 | NZ | LYS | A | 121 | −49.944 | 52.005 | 10.584 | 1.00 | 49.89 | N |

TABLE 16-7-continued

Coordinates of *P. tremuloides* IspS

| ATOM | 1569 | C   | LYS | A | 121 | −54.257 | 56.964 | 10.735 | 1.00 | 49.00 | C |
|------|------|-----|-----|---|-----|---------|--------|--------|------|-------|---|
| ATOM | 1570 | O   | LYS | A | 121 | −54.712 | 57.839 | 10.000 | 1.00 | 49.11 | O |
| ATOM | 1572 | N   | ASP | A | 122 | −53.899 | 57.206 | 11.995 | 1.00 | 50.51 | N |
| ATOM | 1573 | CA  | ASP | A | 122 | −54.078 | 58.537 | 12.596 | 1.00 | 51.46 | C |
| ATOM | 1575 | CB  | ASP | A | 122 | −54.604 | 58.443 | 14.050 | 1.00 | 51.29 | C |
| ATOM | 1578 | CG  | ASP | A | 122 | −53.570 | 57.919 | 15.036 | 1.00 | 50.73 | C |
| ATOM | 1579 | OD1 | ASP | A | 122 | −52.353 | 58.025 | 14.777 | 1.00 | 49.90 | O |
| ATOM | 1580 | OD2 | ASP | A | 122 | −53.988 | 57.398 | 16.088 | 1.00 | 49.66 | O |
| ATOM | 1581 | C   | ASP | A | 122 | −52.792 | 59.358 | 12.502 | 1.00 | 52.60 | C |
| ATOM | 1582 | O   | ASP | A | 122 | −51.830 | 58.953 | 11.835 | 1.00 | 52.65 | O |
| ATOM | 1584 | N   | GLN | A | 123 | −52.802 | 60.512 | 13.172 | 1.00 | 53.88 | N |
| ATOM | 1585 | CA  | GLN | A | 123 | −51.680 | 61.456 | 13.195 | 1.00 | 54.66 | C |
| ATOM | 1587 | CB  | GLN | A | 123 | −51.993 | 62.594 | 14.178 | 1.00 | 55.01 | C |
| ATOM | 1590 | CG  | GLN | A | 123 | −53.249 | 63.442 | 13.831 | 1.00 | 56.15 | C |
| ATOM | 1593 | CD  | GLN | A | 123 | −52.943 | 64.736 | 13.064 | 1.00 | 57.64 | C |
| ATOM | 1594 | OE1 | GLN | A | 123 | −51.779 | 65.102 | 12.859 | 1.00 | 59.10 | O |
| ATOM | 1595 | NE2 | GLN | A | 123 | −54.001 | 65.438 | 12.652 | 1.00 | 57.63 | N |
| ATOM | 1598 | C   | GLN | A | 123 | −50.365 | 60.772 | 13.591 | 1.00 | 54.87 | C |
| ATOM | 1599 | O   | GLN | A | 123 | −49.309 | 61.078 | 13.034 | 1.00 | 54.67 | O |
| ATOM | 1601 | N   | ASN | A | 124 | −50.458 | 59.834 | 14.538 | 1.00 | 55.21 | N |
| ATOM | 1602 | CA  | ASN | A | 124 | −49.300 | 59.137 | 15.109 | 1.00 | 55.39 | C |
| ATOM | 1604 | CB  | ASN | A | 124 | −49.421 | 59.122 | 16.637 | 1.00 | 55.52 | C |
| ATOM | 1607 | CG  | ASN | A | 124 | −49.833 | 60.478 | 17.202 | 1.00 | 55.98 | C |
| ATOM | 1608 | OD1 | ASN | A | 124 | −49.093 | 61.460 | 17.091 | 1.00 | 56.93 | O |
| ATOM | 1609 | ND2 | ASN | A | 124 | −51.026 | 60.540 | 17.797 | 1.00 | 55.99 | N |
| ATOM | 1612 | C   | ASN | A | 124 | −49.116 | 57.705 | 14.589 | 1.00 | 55.27 | C |
| ATOM | 1613 | O   | ASN | A | 124 | −48.530 | 56.864 | 15.271 | 1.00 | 55.18 | O |
| ATOM | 1615 | N   | GLY | A | 125 | −49.626 | 57.430 | 13.391 | 1.00 | 55.18 | N |
| ATOM | 1616 | CA  | GLY | A | 125 | −49.311 | 56.190 | 12.672 | 1.00 | 55.08 | C |
| ATOM | 1619 | C   | GLY | A | 125 | −49.994 | 54.897 | 13.119 | 1.00 | 54.90 | C |
| ATOM | 1620 | O   | GLY | A | 125 | −49.543 | 53.806 | 12.750 | 1.00 | 55.24 | O |
| ATOM | 1622 | N   | ASN | A | 126 | −51.072 | 55.008 | 13.900 | 1.00 | 54.23 | N |
| ATOM | 1623 | CA  | ASN | A | 126 | −51.871 | 53.853 | 14.329 | 1.00 | 53.39 | C |
| ATOM | 1625 | CB  | ASN | A | 126 | −51.927 | 53.782 | 15.852 | 1.00 | 53.27 | C |
| ATOM | 1628 | CG  | ASN | A | 126 | −50.596 | 53.425 | 16.466 | 1.00 | 52.81 | C |
| ATOM | 1629 | OD1 | ASN | A | 126 | −49.636 | 53.113 | 15.764 | 1.00 | 52.29 | O |
| ATOM | 1630 | ND2 | ASN | A | 126 | −50.532 | 53.460 | 17.789 | 1.00 | 52.53 | N |
| ATOM | 1633 | C   | ASN | A | 126 | −53.274 | 53.978 | 13.771 | 1.00 | 52.82 | C |
| ATOM | 1634 | O   | ASN | A | 126 | −53.724 | 55.081 | 13.494 | 1.00 | 52.69 | O |
| ATOM | 1636 | N   | PHE | A | 127 | −53.968 | 52.857 | 13.607 | 1.00 | 52.17 | N |
| ATOM | 1637 | CA  | PHE | A | 127 | −55.287 | 52.875 | 12.962 | 1.00 | 51.56 | C |
| ATOM | 1639 | CB  | PHE | A | 127 | −55.805 | 51.451 | 12.721 | 1.00 | 51.35 | C |
| ATOM | 1642 | CG  | PHE | A | 127 | −55.119 | 50.730 | 11.587 | 1.00 | 50.06 | C |
| ATOM | 1643 | CD1 | PHE | A | 127 | −54.068 | 49.856 | 11.831 | 1.00 | 48.90 | C |
| ATOM | 1645 | CE1 | PHE | A | 127 | −53.437 | 49.187 | 10.789 | 1.00 | 47.59 | C |
| ATOM | 1647 | CZ  | PHE | A | 127 | −53.857 | 49.383 | 9.495  | 1.00 | 47.40 | C |
| ATOM | 1649 | CE2 | PHE | A | 127 | −54.906 | 50.244 | 9.234  | 1.00 | 47.96 | C |
| ATOM | 1651 | CD2 | PHE | A | 127 | −55.533 | 50.915 | 10.276 | 1.00 | 48.85 | C |
| ATOM | 1653 | C   | PHE | A | 127 | −56.303 | 53.690 | 13.776 | 1.00 | 51.35 | C |
| ATOM | 1654 | O   | PHE | A | 127 | −56.347 | 53.594 | 15.002 | 1.00 | 51.09 | O |
| ATOM | 1656 | N   | LEU | A | 128 | −57.100 | 54.500 | 13.083 | 1.00 | 51.15 | N |
| ATOM | 1657 | CA  | LEU | A | 128 | −58.143 | 55.280 | 13.727 | 1.00 | 51.09 | C |
| ATOM | 1659 | CB  | LEU | A | 128 | −59.039 | 55.979 | 12.694 | 1.00 | 51.17 | C |
| ATOM | 1662 | CG  | LEU | A | 128 | −58.463 | 57.046 | 11.746 | 1.00 | 51.31 | C |
| ATOM | 1664 | CD1 | LEU | A | 128 | −59.571 | 57.628 | 10.855 | 1.00 | 50.76 | C |
| ATOM | 1668 | CD2 | LEU | A | 128 | −57.762 | 58.157 | 12.508 | 1.00 | 50.98 | C |
| ATOM | 1672 | C   | LEU | A | 128 | −58.996 | 54.353 | 14.581 | 1.00 | 51.06 | C |
| ATOM | 1673 | O   | LEU | A | 128 | −59.573 | 53.393 | 14.078 | 1.00 | 50.94 | O |
| ATOM | 1675 | N   | GLU | A | 129 | −59.053 | 54.637 | 15.879 | 1.00 | 51.12 | N |
| ATOM | 1676 | CA  | GLU | A | 129 | −59.916 | 53.913 | 16.808 | 1.00 | 50.99 | C |
| ATOM | 1678 | CB  | GLU | A | 129 | −60.019 | 54.665 | 18.132 | 1.00 | 51.14 | C |
| ATOM | 1681 | CG  | GLU | A | 129 | −58.850 | 54.431 | 19.049 | 1.00 | 52.04 | C |
| ATOM | 1684 | CD  | GLU | A | 129 | −58.903 | 53.069 | 19.697 | 1.00 | 53.22 | C |
| ATOM | 1685 | OE1 | GLU | A | 129 | −58.040 | 52.219 | 19.376 | 1.00 | 54.19 | O |
| ATOM | 1686 | OE2 | GLU | A | 129 | −59.823 | 52.848 | 20.516 | 1.00 | 53.51 | O |
| ATOM | 1687 | C   | GLU | A | 129 | −61.314 | 53.712 | 16.260 | 1.00 | 50.66 | C |
| ATOM | 1688 | O   | GLU | A | 129 | −61.791 | 52.587 | 16.200 | 1.00 | 50.83 | O |
| ATOM | 1690 | N   | ASN | A | 130 | −61.960 | 54.799 | 15.839 | 1.00 | 50.28 | N |
| ATOM | 1691 | CA  | ASN | A | 130 | −63.389 | 54.765 | 15.486 | 1.00 | 50.03 | C |
| ATOM | 1693 | CB  | ASN | A | 130 | −63.910 | 56.182 | 15.193 | 1.00 | 50.09 | C |
| ATOM | 1696 | CG  | ASN | A | 130 | −63.286 | 56.805 | 13.960 | 1.00 | 50.37 | C |
| ATOM | 1697 | OD1 | ASN | A | 130 | −62.504 | 56.177 | 13.249 | 1.00 | 51.44 | O |
| ATOM | 1698 | ND2 | ASN | A | 130 | −63.634 | 58.056 | 13.701 | 1.00 | 50.27 | N |
| ATOM | 1701 | C   | ASN | A | 130 | −63.804 | 53.782 | 14.369 | 1.00 | 49.56 | C |
| ATOM | 1702 | O   | ASN | A | 130 | −64.993 | 53.581 | 14.131 | 1.00 | 49.44 | O |
| ATOM | 1704 | N   | LEU | A | 131 | −62.828 | 53.175 | 13.699 | 1.00 | 49.21 | N |
| ATOM | 1705 | CA  | LEU | A | 131 | −63.087 | 52.103 | 12.729 | 1.00 | 48.78 | C |
| ATOM | 1707 | CB  | LEU | A | 131 | −61.846 | 51.832 | 11.875 | 1.00 | 48.64 | C |

TABLE 16-7-continued

Coordinates of *P. tremuloides* IspS

| ATOM | 1710 | CG | LEU | A | 131 | −61.445 | 52.939 | 10.898 | 1.00 | 48.26 | C |
|---|---|---|---|---|---|---|---|---|---|---|---|
| ATOM | 1712 | CD1 | LEU | A | 131 | −60.029 | 52.709 | 10.375 | 1.00 | 47.76 | C |
| ATOM | 1716 | CD2 | LEU | A | 131 | −62.441 | 53.039 | 9.754 | 1.00 | 47.32 | C |
| ATOM | 1720 | C | LEU | A | 131 | −63.516 | 50.798 | 13.394 | 1.00 | 48.58 | C |
| ATOM | 1721 | O | LEU | A | 131 | −64.093 | 49.939 | 12.731 | 1.00 | 48.64 | O |
| ATOM | 1723 | N | LYS | A | 132 | −63.225 | 50.645 | 14.689 | 1.00 | 48.23 | N |
| ATOM | 1724 | CA | LYS | A | 132 | −63.650 | 49.474 | 15.465 | 1.00 | 47.80 | C |
| ATOM | 1726 | CB | LYS | A | 132 | −63.156 | 49.587 | 16.913 | 1.00 | 47.71 | C |
| ATOM | 1729 | CG | LYS | A | 132 | −63.930 | 50.615 | 17.728 | 1.00 | 47.80 | C |
| ATOM | 1732 | CD | LYS | A | 132 | −63.430 | 50.779 | 19.153 | 1.00 | 47.75 | C |
| ATOM | 1735 | CE | LYS | A | 132 | −64.438 | 51.577 | 19.982 | 1.00 | 47.22 | C |
| ATOM | 1738 | NZ | LYS | A | 132 | −63.769 | 52.364 | 21.033 | 1.00 | 46.65 | N |
| ATOM | 1742 | C | LYS | A | 132 | −65.182 | 49.308 | 15.446 | 1.00 | 47.56 | C |
| ATOM | 1743 | O | LYS | A | 132 | −65.696 | 48.204 | 15.616 | 1.00 | 47.76 | O |
| ATOM | 1745 | N | GLU | A | 133 | −65.901 | 50.413 | 15.249 | 1.00 | 47.18 | N |
| ATOM | 1746 | CA | GLU | A | 133 | −67.371 | 50.412 | 15.191 | 1.00 | 46.79 | C |
| ATOM | 1748 | CB | GLU | A | 133 | −67.898 | 51.850 | 15.337 | 1.00 | 46.95 | C |
| ATOM | 1751 | CG | GLU | A | 133 | −67.840 | 52.376 | 16.776 | 1.00 | 47.56 | C |
| ATOM | 1754 | CD | GLU | A | 133 | −67.613 | 53.886 | 16.863 | 1.00 | 48.41 | C |
| ATOM | 1755 | OE1 | GLU | A | 133 | −68.247 | 54.648 | 16.093 | 1.00 | 47.67 | O |
| ATOM | 1756 | OE2 | GLU | A | 133 | −66.798 | 54.304 | 17.721 | 1.00 | 48.92 | O |
| ATOM | 1757 | C | GLU | A | 133 | −67.949 | 49.770 | 13.918 | 1.00 | 46.10 | C |
| ATOM | 1758 | O | GLU | A | 133 | −69.140 | 49.446 | 13.874 | 1.00 | 46.11 | O |
| ATOM | 1760 | N | ASP | A | 134 | −67.103 | 49.601 | 12.896 | 1.00 | 45.11 | N |
| ATOM | 1761 | CA | ASP | A | 134 | −67.477 | 48.995 | 11.608 | 1.00 | 44.06 | C |
| ATOM | 1763 | CB | ASP | A | 134 | −66.934 | 49.868 | 10.474 | 1.00 | 43.97 | C |
| ATOM | 1766 | CG | ASP | A | 134 | −67.380 | 49.411 | 9.104 | 1.00 | 44.08 | C |
| ATOM | 1767 | OD1 | ASP | A | 134 | −68.072 | 48.373 | 8.972 | 1.00 | 43.42 | O |
| ATOM | 1768 | OD2 | ASP | A | 134 | −67.020 | 50.116 | 8.141 | 1.00 | 44.84 | O |
| ATOM | 1769 | C | ASP | A | 134 | −66.910 | 47.570 | 11.526 | 1.00 | 43.12 | C |
| ATOM | 1770 | O | ASP | A | 134 | −65.788 | 47.357 | 11.080 | 1.00 | 43.19 | O |
| ATOM | 1772 | N | ILE | A | 135 | −67.708 | 46.594 | 11.944 | 1.00 | 41.85 | N |
| ATOM | 1773 | CA | ILE | A | 135 | −67.216 | 45.247 | 12.216 | 1.00 | 40.75 | C |
| ATOM | 1775 | CB | ILE | A | 135 | −68.183 | 44.507 | 13.170 | 1.00 | 40.80 | C |
| ATOM | 1777 | CG1 | ILE | A | 135 | −68.227 | 45.226 | 14.524 | 1.00 | 41.21 | C |
| ATOM | 1780 | CD1 | ILE | A | 135 | −69.353 | 46.283 | 14.633 | 1.00 | 42.86 | C |
| ATOM | 1784 | CG2 | ILE | A | 135 | −67.776 | 43.063 | 13.373 | 1.00 | 40.88 | C |
| ATOM | 1788 | C | ILE | A | 135 | −66.980 | 44.457 | 10.933 | 1.00 | 39.67 | C |
| ATOM | 1789 | O | ILE | A | 135 | −66.166 | 43.537 | 10.901 | 1.00 | 39.37 | O |
| ATOM | 1791 | N | LYS | A | 136 | −67.690 | 44.828 | 9.877 | 1.00 | 38.62 | N |
| ATOM | 1792 | CA | LYS | A | 136 | −67.465 | 44.256 | 8.554 | 1.00 | 37.88 | C |
| ATOM | 1794 | CB | LYS | A | 136 | −68.525 | 44.749 | 7.561 | 1.00 | 38.33 | C |
| ATOM | 1797 | CG | LYS | A | 136 | −69.955 | 44.342 | 7.879 | 1.00 | 40.17 | C |
| ATOM | 1800 | CD | LYS | A | 136 | −70.486 | 43.262 | 6.911 | 1.00 | 42.97 | C |
| ATOM | 1803 | CE | LYS | A | 136 | −71.624 | 42.389 | 7.536 | 1.00 | 44.00 | C |
| ATOM | 1806 | NZ | LYS | A | 136 | −72.950 | 43.086 | 7.726 | 1.00 | 43.82 | N |
| ATOM | 1810 | C | LYS | A | 136 | −66.097 | 44.687 | 8.047 | 1.00 | 36.38 | C |
| ATOM | 1811 | O | LYS | A | 136 | −65.399 | 43.914 | 7.388 | 1.00 | 36.24 | O |
| ATOM | 1813 | N | ALA | A | 137 | −65.728 | 45.931 | 8.341 | 1.00 | 34.51 | N |
| ATOM | 1814 | CA | ALA | A | 137 | −64.463 | 46.474 | 7.876 | 1.00 | 33.41 | C |
| ATOM | 1816 | CB | ALA | A | 137 | −64.432 | 47.981 | 8.058 | 1.00 | 33.43 | C |
| ATOM | 1820 | C | ALA | A | 137 | −63.291 | 45.827 | 8.600 | 1.00 | 32.30 | C |
| ATOM | 1821 | O | ALA | A | 137 | −62.288 | 45.481 | 7.995 | 1.00 | 31.89 | O |
| ATOM | 1823 | N | ILE | A | 138 | −63.437 | 45.662 | 9.905 | 1.00 | 31.41 | N |
| ATOM | 1824 | CA | ILE | A | 138 | −62.395 | 45.074 | 10.737 | 1.00 | 30.60 | C |
| ATOM | 1826 | CB | ILE | A | 138 | −62.770 | 45.131 | 12.238 | 1.00 | 30.20 | C |
| ATOM | 1828 | CG1 | ILE | A | 138 | −62.914 | 46.576 | 12.689 | 1.00 | 29.92 | C |
| ATOM | 1831 | CD1 | ILE | A | 138 | −61.681 | 47.414 | 12.417 | 1.00 | 30.50 | C |
| ATOM | 1835 | CG2 | ILE | A | 138 | −61.706 | 44.470 | 13.085 | 1.00 | 29.73 | C |
| ATOM | 1839 | C | ILE | A | 138 | −62.140 | 43.631 | 10.320 | 1.00 | 30.34 | C |
| ATOM | 1840 | O | ILE | A | 138 | −60.972 | 43.203 | 10.212 | 1.00 | 30.65 | O |
| ATOM | 1842 | N | LEU | A | 139 | −63.227 | 42.884 | 10.098 | 1.00 | 29.69 | N |
| ATOM | 1843 | CA | LEU | A | 139 | −63.134 | 41.523 | 9.562 | 1.00 | 29.23 | C |
| ATOM | 1845 | CB | LEU | A | 139 | −64.517 | 40.917 | 9.332 | 1.00 | 28.92 | C |
| ATOM | 1848 | CG | LEU | A | 139 | −65.066 | 40.185 | 10.545 | 1.00 | 29.06 | C |
| ATOM | 1850 | CD1 | LEU | A | 139 | −66.541 | 39.875 | 10.352 | 1.00 | 28.20 | C |
| ATOM | 1854 | CD2 | LEU | A | 139 | −64.250 | 38.922 | 10.813 | 1.00 | 28.59 | C |
| ATOM | 1858 | C | LEU | A | 139 | −62.382 | 41.546 | 8.247 | 1.00 | 29.00 | C |
| ATOM | 1859 | O | LEU | A | 139 | −61.444 | 40.773 | 8.035 | 1.00 | 29.50 | O |
| ATOM | 1861 | N | SER | A | 140 | −62.790 | 42.458 | 7.372 | 1.00 | 28.14 | N |
| ATOM | 1862 | CA | SER | A | 140 | −62.222 | 42.526 | 6.054 | 1.00 | 27.40 | C |
| ATOM | 1864 | CB | SER | A | 140 | −62.912 | 43.619 | 5.260 | 1.00 | 27.35 | C |
| ATOM | 1867 | OG | SER | A | 140 | −63.310 | 43.103 | 4.015 | 1.00 | 28.43 | O |
| ATOM | 1869 | C | SER | A | 140 | −60.720 | 42.777 | 6.123 | 1.00 | 26.77 | C |
| ATOM | 1870 | O | SER | A | 140 | −59.975 | 42.269 | 5.298 | 1.00 | 27.29 | O |
| ATOM | 1872 | N | LEU | A | 141 | −60.285 | 43.563 | 7.105 | 1.00 | 25.89 | N |
| ATOM | 1873 | CA | LEU | A | 141 | −58.872 | 43.897 | 7.283 | 1.00 | 25.20 | C |
| ATOM | 1875 | CB | LEU | A | 141 | −58.717 | 45.164 | 8.155 | 1.00 | 25.00 | C |

TABLE 16-7-continued

Coordinates of *P. tremuloides* IspS

| ATOM | 1878 | CG | LEU | A | 141 | −57.298 | 45.670 | 8.489 | 1.00 | 24.35 | C |
|---|---|---|---|---|---|---|---|---|---|---|---|
| ATOM | 1880 | CD1 | LEU | A | 141 | −56.497 | 45.974 | 7.232 | 1.00 | 22.75 | C |
| ATOM | 1884 | CD2 | LEU | A | 141 | −57.329 | 46.893 | 9.385 | 1.00 | 22.81 | C |
| ATOM | 1888 | C | LEU | A | 141 | −58.140 | 42.721 | 7.920 | 1.00 | 24.92 | C |
| ATOM | 1889 | O | LEU | A | 141 | −57.034 | 42.380 | 7.521 | 1.00 | 24.77 | O |
| ATOM | 1891 | N | TYR | A | 142 | −58.751 | 42.101 | 8.921 | 1.00 | 24.51 | N |
| ATOM | 1892 | CA | TYR | A | 142 | −58.163 | 40.913 | 9.514 | 1.00 | 24.36 | C |
| ATOM | 1894 | CB | TYR | A | 142 | −59.120 | 40.325 | 10.538 | 1.00 | 24.18 | C |
| ATOM | 1897 | CG | TYR | A | 142 | −58.774 | 38.941 | 11.046 | 1.00 | 23.72 | C |
| ATOM | 1898 | CD1 | TYR | A | 142 | −57.878 | 38.763 | 12.091 | 1.00 | 22.97 | C |
| ATOM | 1900 | CE1 | TYR | A | 142 | −57.593 | 37.500 | 12.582 | 1.00 | 24.25 | C |
| ATOM | 1902 | CZ | TYR | A | 142 | −58.229 | 36.386 | 12.030 | 1.00 | 25.75 | C |
| ATOM | 1903 | OH | TYR | A | 142 | −57.967 | 35.100 | 12.500 | 1.00 | 26.97 | O |
| ATOM | 1905 | CE2 | TYR | A | 142 | −59.120 | 36.551 | 10.988 | 1.00 | 25.02 | C |
| ATOM | 1907 | CD2 | TYR | A | 142 | −59.390 | 37.820 | 10.511 | 1.00 | 24.01 | C |
| ATOM | 1909 | C | TYR | A | 142 | −57.877 | 39.896 | 8.423 | 1.00 | 24.39 | C |
| ATOM | 1910 | O | TYR | A | 142 | −56.822 | 39.276 | 8.380 | 1.00 | 24.19 | O |
| ATOM | 1912 | N | GLU | A | 143 | −58.841 | 39.760 | 7.527 | 1.00 | 24.59 | N |
| ATOM | 1913 | CA | GLU | A | 143 | −58.820 | 38.728 | 6.521 | 1.00 | 24.70 | C |
| ATOM | 1915 | CB | GLU | A | 143 | −60.194 | 38.636 | 5.853 | 1.00 | 24.69 | C |
| ATOM | 1918 | CG | GLU | A | 143 | −60.651 | 37.219 | 5.547 | 1.00 | 27.21 | C |
| ATOM | 1921 | CD | GLU | A | 143 | −61.127 | 36.426 | 6.774 | 1.00 | 30.20 | C |
| ATOM | 1922 | OE1 | GLU | A | 143 | −60.261 | 35.776 | 7.393 | 1.00 | 33.40 | O |
| ATOM | 1923 | OE2 | GLU | A | 143 | −62.351 | 36.421 | 7.097 | 1.00 | 30.50 | O |
| ATOM | 1924 | C | GLU | A | 143 | −57.701 | 39.010 | 5.518 | 1.00 | 24.08 | C |
| ATOM | 1925 | O | GLU | A | 143 | −56.984 | 38.090 | 5.126 | 1.00 | 24.53 | O |
| ATOM | 1927 | N | ALA | A | 144 | −57.537 | 40.281 | 5.147 | 1.00 | 23.30 | N |
| ATOM | 1928 | CA | ALA | A | 144 | −56.515 | 40.715 | 4.173 | 1.00 | 22.79 | C |
| ATOM | 1930 | CB | ALA | A | 144 | −56.787 | 42.154 | 3.740 | 1.00 | 22.49 | C |
| ATOM | 1934 | C | ALA | A | 144 | −55.073 | 40.598 | 4.701 | 1.00 | 22.42 | C |
| ATOM | 1935 | O | ALA | A | 144 | −54.128 | 40.380 | 3.935 | 1.00 | 22.36 | O |
| ATOM | 1937 | N | SER | A | 145 | −54.909 | 40.713 | 6.012 | 1.00 | 21.80 | N |
| ATOM | 1938 | CA | SER | A | 145 | −53.593 | 40.822 | 6.600 | 1.00 | 21.36 | C |
| ATOM | 1940 | CB | SER | A | 145 | −53.726 | 41.170 | 8.066 | 1.00 | 21.21 | C |
| ATOM | 1943 | OG | SER | A | 145 | −54.337 | 40.100 | 8.753 | 1.00 | 21.59 | O |
| ATOM | 1945 | C | SER | A | 145 | −52.797 | 39.537 | 6.476 | 1.00 | 21.30 | C |
| ATOM | 1946 | O | SER | A | 145 | −51.571 | 39.533 | 6.701 | 1.00 | 21.50 | O |
| ATOM | 1948 | N | PHE | A | 146 | −53.488 | 38.439 | 6.154 | 1.00 | 21.00 | N |
| ATOM | 1949 | CA | PHE | A | 146 | −52.827 | 37.127 | 6.030 | 1.00 | 20.41 | C |
| ATOM | 1951 | CB | PHE | A | 146 | −53.796 | 35.979 | 6.338 | 1.00 | 20.20 | C |
| ATOM | 1954 | CG | PHE | A | 146 | −54.130 | 35.873 | 7.798 | 1.00 | 19.91 | C |
| ATOM | 1955 | CD1 | PHE | A | 146 | −53.382 | 35.087 | 8.637 | 1.00 | 20.48 | C |
| ATOM | 1957 | CE1 | PHE | A | 146 | −53.679 | 35.012 | 9.992 | 1.00 | 20.59 | C |
| ATOM | 1959 | CZ | PHE | A | 146 | −54.731 | 35.740 | 10.508 | 1.00 | 19.15 | C |
| ATOM | 1961 | CE2 | PHE | A | 146 | −55.464 | 36.536 | 9.691 | 1.00 | 19.10 | C |
| ATOM | 1963 | CD2 | PHE | A | 146 | −55.155 | 36.615 | 8.343 | 1.00 | 20.16 | C |
| ATOM | 1965 | C | PHE | A | 146 | −52.174 | 36.964 | 4.680 | 1.00 | 19.76 | C |
| ATOM | 1966 | O | PHE | A | 146 | −51.305 | 36.116 | 4.523 | 1.00 | 19.46 | O |
| ATOM | 1968 | N | LEU | A | 147 | −52.550 | 37.819 | 3.729 | 1.00 | 19.34 | N |
| ATOM | 1969 | CA | LEU | A | 147 | −51.933 | 37.804 | 2.402 | 1.00 | 19.13 | C |
| ATOM | 1971 | CB | LEU | A | 147 | −52.905 | 38.367 | 1.347 | 1.00 | 18.67 | C |
| ATOM | 1974 | CG | LEU | A | 147 | −53.964 | 37.334 | .919 | 1.00 | 18.11 | C |
| ATOM | 1976 | CD1 | LEU | A | 147 | −55.090 | 37.248 | 1.961 | 1.00 | 15.10 | C |
| ATOM | 1980 | CD2 | LEU | A | 147 | −54.494 | 37.609 | −.499 | 1.00 | 16.50 | C |
| ATOM | 1984 | C | LEU | A | 147 | −50.582 | 38.525 | 2.369 | 1.00 | 19.10 | C |
| ATOM | 1985 | O | LEU | A | 147 | −49.992 | 38.715 | 1.311 | 1.00 | 19.44 | O |
| ATOM | 1987 | N | ALA | A | 148 | −50.075 | 38.882 | 3.542 | 1.00 | 19.13 | N |
| ATOM | 1988 | CA | ALA | A | 148 | −48.967 | 39.806 | 3.664 | 1.00 | 18.84 | C |
| ATOM | 1990 | CB | ALA | A | 148 | −48.762 | 40.167 | 5.117 | 1.00 | 18.78 | C |
| ATOM | 1994 | C | ALA | A | 148 | −47.723 | 39.184 | 3.113 | 1.00 | 18.85 | C |
| ATOM | 1995 | O | ALA | A | 148 | −47.548 | 37.975 | 3.206 | 1.00 | 18.80 | O |
| ATOM | 1997 | N | LEU | A | 149 | −46.869 | 40.013 | 2.523 | 1.00 | 19.08 | N |
| ATOM | 1998 | CA | LEU | A | 149 | −45.507 | 39.601 | 2.215 | 1.00 | 19.32 | C |
| ATOM | 2000 | CB | LEU | A | 149 | −45.056 | 40.145 | .863 | 1.00 | 19.14 | C |
| ATOM | 2003 | CG | LEU | A | 149 | −45.819 | 39.650 | −.364 | 1.00 | 19.16 | C |
| ATOM | 2005 | CD1 | LEU | A | 149 | −45.036 | 39.929 | −1.645 | 1.00 | 18.43 | C |
| ATOM | 2009 | CD2 | LEU | A | 149 | −46.089 | 38.175 | −.259 | 1.00 | 20.09 | C |
| ATOM | 2013 | C | LEU | A | 149 | −44.527 | 40.029 | 3.304 | 1.00 | 19.60 | C |
| ATOM | 2014 | O | LEU | A | 149 | −44.797 | 40.916 | 4.113 | 1.00 | 19.20 | O |
| ATOM | 2016 | N | GLU | A | 150 | −43.384 | 39.361 | 3.309 | 1.00 | 20.42 | N |
| ATOM | 2017 | CA | GLU | A | 150 | −42.286 | 39.674 | 4.215 | 1.00 | 21.03 | C |
| ATOM | 2019 | CB | GLU | A | 150 | −41.098 | 38.741 | 3.948 | 1.00 | 21.03 | C |
| ATOM | 2022 | CG | GLU | A | 150 | −40.491 | 38.176 | 5.205 | 1.00 | 22.23 | C |
| ATOM | 2025 | CD | GLU | A | 150 | −39.433 | 37.117 | 4.941 | 1.00 | 24.34 | C |
| ATOM | 2026 | OE1 | GLU | A | 150 | −39.189 | 36.786 | 3.753 | 1.00 | 24.53 | O |
| ATOM | 2027 | OE2 | GLU | A | 150 | −38.843 | 36.625 | 5.940 | 1.00 | 25.82 | O |
| ATOM | 2028 | C | GLU | A | 150 | −41.887 | 41.130 | 4.011 | 1.00 | 21.29 | C |
| ATOM | 2029 | O | GLU | A | 150 | −41.619 | 41.544 | 2.885 | 1.00 | 21.13 | O |

TABLE 16-7-continued

Coordinates of *P. tremuloides* IspS

| ATOM | 2031 | N | GLY | A | 151 | −41.893 | 41.903 | 5.094 | 1.00 | 21.89 | N |
|---|---|---|---|---|---|---|---|---|---|---|---|
| ATOM | 2032 | CA | GLY | A | 151 | −41.636 | 43.341 | 5.030 | 1.00 | 22.25 | C |
| ATOM | 2035 | C | GLY | A | 151 | −42.871 | 44.221 | 5.152 | 1.00 | 22.67 | C |
| ATOM | 2036 | O | GLY | A | 151 | −42.757 | 45.397 | 5.462 | 1.00 | 22.84 | O |
| ATOM | 2038 | N | GLU | A | 152 | −44.055 | 43.669 | 4.918 | 1.00 | 23.19 | N |
| ATOM | 2039 | CA | GLU | A | 152 | −45.263 | 44.474 | 4.937 | 1.00 | 23.76 | C |
| ATOM | 2041 | CB | GLU | A | 152 | −46.350 | 43.813 | 4.100 | 1.00 | 23.79 | C |
| ATOM | 2044 | CG | GLU | A | 152 | −46.037 | 43.890 | 2.615 | 1.00 | 23.98 | C |
| ATOM | 2047 | CD | GLU | A | 152 | −47.147 | 43.368 | 1.749 | 1.00 | 23.72 | C |
| ATOM | 2048 | OE1 | GLU | A | 152 | −47.226 | 43.771 | .574 | 1.00 | 22.11 | O |
| ATOM | 2049 | OE2 | GLU | A | 152 | −47.939 | 42.542 | 2.241 | 1.00 | 25.41 | O |
| ATOM | 2050 | C | GLU | A | 152 | −45.722 | 44.719 | 6.365 | 1.00 | 24.47 | C |
| ATOM | 2051 | O | GLU | A | 152 | −46.586 | 44.006 | 6.906 | 1.00 | 24.70 | O |
| ATOM | 2053 | N | ASN | A | 153 | −45.134 | 45.744 | 6.969 | 1.00 | 25.00 | N |
| ATOM | 2054 | CA | ASN | A | 153 | −45.287 | 45.978 | 8.404 | 1.00 | 25.59 | C |
| ATOM | 2056 | CB | ASN | A | 153 | −44.221 | 46.957 | 8.902 | 1.00 | 25.55 | C |
| ATOM | 2059 | CG | ASN | A | 153 | −44.386 | 48.331 | 8.308 | 1.00 | 25.57 | C |
| ATOM | 2060 | OD1 | ASN | A | 153 | −44.114 | 48.557 | 7.128 | 1.00 | 24.52 | O |
| ATOM | 2061 | ND2 | ASN | A | 153 | −44.867 | 49.256 | 9.117 | 1.00 | 27.05 | N |
| ATOM | 2064 | C | ASN | A | 153 | −46.679 | 46.486 | 8.772 | 1.00 | 25.92 | C |
| ATOM | 2065 | O | ASN | A | 153 | −47.172 | 46.238 | 9.872 | 1.00 | 26.02 | O |
| ATOM | 2067 | N | ILE | A | 154 | −47.310 | 47.197 | 7.847 | 1.00 | 26.35 | N |
| ATOM | 2068 | CA | ILE | A | 154 | −48.638 | 47.751 | 8.082 | 1.00 | 26.57 | C |
| ATOM | 2070 | CB | ILE | A | 154 | −49.013 | 48.779 | 7.007 | 1.00 | 26.45 | C |
| ATOM | 2072 | CG1 | ILE | A | 154 | −48.159 | 50.023 | 7.164 | 1.00 | 26.36 | C |
| ATOM | 2075 | CD1 | ILE | A | 154 | −48.060 | 50.790 | 5.883 | 1.00 | 27.92 | C |
| ATOM | 2079 | CG2 | ILE | A | 154 | −50.467 | 49.152 | 7.089 | 1.00 | 26.25 | C |
| ATOM | 2083 | C | ILE | A | 154 | −49.674 | 46.643 | 8.111 | 1.00 | 26.96 | C |
| ATOM | 2084 | O | ILE | A | 154 | −50.650 | 46.741 | 8.851 | 1.00 | 27.12 | O |
| ATOM | 2086 | N | LEU | A | 155 | −49.467 | 45.588 | 7.320 | 1.00 | 27.35 | N |
| ATOM | 2087 | CA | LEU | A | 155 | −50.422 | 44.475 | 7.304 | 1.00 | 27.76 | C |
| ATOM | 2089 | CB | LEU | A | 155 | −50.238 | 43.594 | 6.067 | 1.00 | 27.73 | C |
| ATOM | 2092 | CG | LEU | A | 155 | −51.090 | 43.990 | 4.875 | 1.00 | 27.31 | C |
| ATOM | 2094 | CD1 | LEU | A | 155 | −50.980 | 45.456 | 4.683 | 1.00 | 28.13 | C |
| ATOM | 2098 | CD2 | LEU | A | 155 | −50.633 | 43.262 | 3.623 | 1.00 | 27.79 | C |
| ATOM | 2102 | C | LEU | A | 155 | −50.340 | 43.642 | 8.582 | 1.00 | 28.22 | C |
| ATOM | 2103 | O | LEU | A | 155 | −51.361 | 43.237 | 9.112 | 1.00 | 27.95 | O |
| ATOM | 2105 | N | ASP | A | 156 | −49.128 | 43.395 | 9.068 | 1.00 | 28.95 | N |
| ATOM | 2106 | CA | ASP | A | 156 | −48.944 | 42.723 | 10.348 | 1.00 | 29.71 | C |
| ATOM | 2108 | CB | ASP | A | 156 | −47.450 | 42.461 | 10.639 | 1.00 | 30.23 | C |
| ATOM | 2111 | CG | ASP | A | 156 | −46.938 | 41.125 | 10.027 | 1.00 | 32.82 | C |
| ATOM | 2112 | OD1 | ASP | A | 156 | −47.765 | 40.240 | 9.658 | 1.00 | 36.27 | O |
| ATOM | 2113 | OD2 | ASP | A | 156 | −45.700 | 40.961 | 9.923 | 1.00 | 34.48 | O |
| ATOM | 2114 | C | ASP | A | 156 | −49.570 | 43.539 | 11.469 | 1.00 | 29.66 | C |
| ATOM | 2115 | O | ASP | A | 156 | −50.109 | 42.969 | 12.425 | 1.00 | 29.81 | O |
| ATOM | 2117 | N | GLU | A | 157 | −49.514 | 44.866 | 11.345 | 1.00 | 29.69 | N |
| ATOM | 2118 | CA | GLU | A | 157 | −50.129 | 45.768 | 12.329 | 1.00 | 29.57 | C |
| ATOM | 2120 | CB | GLU | A | 157 | −49.581 | 47.186 | 12.178 | 1.00 | 29.71 | C |
| ATOM | 2123 | CG | GLU | A | 157 | −48.164 | 47.326 | 12.712 | 1.00 | 30.53 | C |
| ATOM | 2126 | CD | GLU | A | 157 | −47.455 | 48.544 | 12.169 | 1.00 | 31.96 | C |
| ATOM | 2127 | OE1 | GLU | A | 157 | −48.167 | 49.491 | 11.741 | 1.00 | 33.56 | O |
| ATOM | 2128 | OE2 | GLU | A | 157 | −46.195 | 48.546 | 12.166 | 1.00 | 31.54 | O |
| ATOM | 2129 | C | GLU | A | 157 | −51.649 | 45.771 | 12.230 | 1.00 | 29.16 | C |
| ATOM | 2130 | O | GLU | A | 157 | −52.330 | 45.819 | 13.241 | 1.00 | 29.00 | O |
| ATOM | 2132 | N | ALA | A | 158 | −52.172 | 45.716 | 11.010 | 1.00 | 28.86 | N |
| ATOM | 2133 | CA | ALA | A | 158 | −53.606 | 45.570 | 10.792 | 1.00 | 28.79 | C |
| ATOM | 2135 | CB | ALA | A | 158 | −53.893 | 45.456 | 9.301 | 1.00 | 28.44 | C |
| ATOM | 2139 | C | ALA | A | 158 | −54.171 | 44.352 | 11.536 | 1.00 | 28.93 | C |
| ATOM | 2140 | O | ALA | A | 158 | −55.265 | 44.402 | 12.098 | 1.00 | 28.77 | O |
| ATOM | 2142 | N | LYS | A | 159 | −53.416 | 43.260 | 11.528 | 1.00 | 29.19 | N |
| ATOM | 2143 | CA | LYS | A | 159 | −53.849 | 42.022 | 12.143 | 1.00 | 29.57 | C |
| ATOM | 2145 | CB | LYS | A | 159 | −52.929 | 40.880 | 11.710 | 1.00 | 29.62 | C |
| ATOM | 2148 | CG | LYS | A | 159 | −53.297 | 39.513 | 12.258 | 1.00 | 30.27 | C |
| ATOM | 2151 | CD | LYS | A | 159 | −52.765 | 38.365 | 11.387 | 1.00 | 31.78 | C |
| ATOM | 2154 | CE | LYS | A | 159 | −51.259 | 38.132 | 11.525 | 1.00 | 33.15 | C |
| ATOM | 2157 | NZ | LYS | A | 159 | −50.911 | 36.696 | 11.248 | 1.00 | 33.88 | N |
| ATOM | 2161 | C | LYS | A | 159 | −53.866 | 42.160 | 13.670 | 1.00 | 29.99 | C |
| ATOM | 2162 | O | LYS | A | 159 | −54.767 | 41.642 | 14.332 | 1.00 | 30.29 | O |
| ATOM | 2164 | N | VAL | A | 160 | −52.886 | 42.862 | 14.236 | 1.00 | 30.07 | N |
| ATOM | 2165 | CA | VAL | A | 160 | −52.840 | 43.047 | 15.696 | 1.00 | 30.03 | C |
| ATOM | 2167 | CB | VAL | A | 160 | −51.520 | 43.691 | 16.162 | 1.00 | 29.88 | C |
| ATOM | 2169 | CG1 | VAL | A | 160 | −51.515 | 43.863 | 17.671 | 1.00 | 28.94 | C |
| ATOM | 2173 | CG2 | VAL | A | 160 | −50.341 | 42.848 | 15.707 | 1.00 | 30.23 | C |
| ATOM | 2177 | C | VAL | A | 160 | −53.996 | 43.925 | 16.149 | 1.00 | 30.05 | C |
| ATOM | 2178 | O | VAL | A | 160 | −54.544 | 43.752 | 17.234 | 1.00 | 30.31 | O |
| ATOM | 2180 | N | PHE | A | 161 | −54.355 | 44.862 | 15.290 | 1.00 | 30.08 | N |
| ATOM | 2181 | CA | PHE | A | 161 | −55.407 | 45.808 | 15.558 | 1.00 | 30.09 | C |
| ATOM | 2183 | CB | PHE | A | 161 | −55.255 | 46.993 | 14.598 | 1.00 | 29.92 | C |

TABLE 16-7-continued

Coordinates of *P. tremuloides* IspS

| ATOM | 2186 | CG | PHE | A | 161 | −56.370 | 47.974 | 14.654 | 1.00 | 28.52 | C |
| --- | --- | --- | --- | --- | --- | --- | --- | --- | --- | --- | --- |
| ATOM | 2187 | CD1 | PHE | A | 161 | −56.347 | 49.005 | 15.554 | 1.00 | 27.92 | C |
| ATOM | 2189 | CE1 | PHE | A | 161 | −57.361 | 49.903 | 15.600 | 1.00 | 28.06 | C |
| ATOM | 2191 | CZ | PHE | A | 161 | −58.411 | 49.783 | 14.733 | 1.00 | 28.76 | C |
| ATOM | 2193 | CE2 | PHE | A | 161 | −58.441 | 48.757 | 13.826 | 1.00 | 28.31 | C |
| ATOM | 2195 | CD2 | PHE | A | 161 | −57.429 | 47.869 | 13.789 | 1.00 | 28.16 | C |
| ATOM | 2197 | C | PHE | A | 161 | −56.746 | 45.123 | 15.388 | 1.00 | 30.55 | C |
| ATOM | 2198 | O | PHE | A | 161 | −57.598 | 45.203 | 16.258 | 1.00 | 30.53 | O |
| ATOM | 2200 | N | ALA | A | 162 | −56.930 | 44.438 | 14.271 | 1.00 | 31.34 | N |
| ATOM | 2201 | CA | ALA | A | 162 | −58.193 | 43.770 | 14.023 | 1.00 | 32.26 | C |
| ATOM | 2203 | CB | ALA | A | 162 | −58.217 | 43.139 | 12.643 | 1.00 | 32.31 | C |
| ATOM | 2207 | C | ALA | A | 162 | −58.500 | 42.734 | 15.118 | 1.00 | 33.09 | C |
| ATOM | 2208 | O | ALA | A | 162 | −59.557 | 42.814 | 15.735 | 1.00 | 33.83 | O |
| ATOM | 2210 | N | ILE | A | 163 | −57.587 | 41.799 | 15.393 | 1.00 | 33.59 | N |
| ATOM | 2211 | CA | ILE | A | 163 | −57.826 | 40.799 | 16.438 | 1.00 | 34.02 | C |
| ATOM | 2213 | CB | ILE | A | 163 | −56.597 | 39.907 | 16.745 | 1.00 | 33.98 | C |
| ATOM | 2215 | CG1 | ILE | A | 163 | −56.235 | 39.008 | 15.566 | 1.00 | 34.37 | C |
| ATOM | 2218 | CD1 | ILE | A | 163 | −54.878 | 38.317 | 15.722 | 1.00 | 34.38 | C |
| ATOM | 2222 | CG2 | ILE | A | 163 | −56.883 | 38.995 | 17.919 | 1.00 | 33.38 | C |
| ATOM | 2226 | C | ILE | A | 163 | −58.225 | 41.472 | 17.744 | 1.00 | 34.75 | C |
| ATOM | 2227 | O | ILE | A | 163 | −59.189 | 41.064 | 18.373 | 1.00 | 35.03 | O |
| ATOM | 2229 | N | SER | A | 164 | −57.501 | 42.504 | 18.156 | 1.00 | 35.76 | N |
| ATOM | 2230 | CA | SER | A | 164 | −57.763 | 43.117 | 19.463 | 1.00 | 36.59 | C |
| ATOM | 2232 | CB | SER | A | 164 | −56.828 | 44.293 | 19.735 | 1.00 | 36.59 | C |
| ATOM | 2235 | OG | SER | A | 164 | −57.350 | 45.485 | 19.164 | 1.00 | 36.46 | O |
| ATOM | 2237 | C | SER | A | 164 | −59.196 | 43.611 | 19.556 | 1.00 | 37.42 | C |
| ATOM | 2238 | O | SER | A | 164 | −59.860 | 43.420 | 20.571 | 1.00 | 37.38 | O |
| ATOM | 2240 | N | HIS | A | 165 | −59.661 | 44.251 | 18.486 | 1.00 | 38.51 | N |
| ATOM | 2241 | CA | HIS | A | 165 | −60.990 | 44.851 | 18.467 | 1.00 | 39.40 | C |
| ATOM | 2243 | CB | HIS | A | 165 | −61.008 | 46.097 | 17.574 | 1.00 | 39.76 | C |
| ATOM | 2246 | CG | HIS | A | 165 | −60.467 | 47.323 | 18.251 | 1.00 | 42.06 | C |
| ATOM | 2247 | ND1 | HIS | A | 165 | −59.205 | 47.821 | 18.000 | 1.00 | 44.21 | N |
| ATOM | 2249 | CE1 | HIS | A | 165 | −58.998 | 48.893 | 18.748 | 1.00 | 45.04 | C |
| ATOM | 2251 | NE2 | HIS | A | 165 | −60.080 | 49.106 | 19.478 | 1.00 | 44.99 | N |
| ATOM | 2253 | CD2 | HIS | A | 165 | −61.011 | 48.135 | 19.192 | 1.00 | 43.76 | C |
| ATOM | 2255 | C | HIS | A | 165 | −62.078 | 43.872 | 18.060 | 1.00 | 39.38 | C |
| ATOM | 2256 | O | HIS | A | 165 | −63.248 | 44.244 | 18.067 | 1.00 | 39.43 | O |
| ATOM | 2258 | N | LEU | A | 166 | −61.683 | 42.632 | 17.745 | 1.00 | 39.54 | N |
| ATOM | 2259 | CA | LEU | A | 166 | −62.589 | 41.550 | 17.326 | 1.00 | 39.55 | C |
| ATOM | 2261 | CB | LEU | A | 166 | −62.001 | 40.766 | 16.154 | 1.00 | 39.28 | C |
| ATOM | 2264 | CG | LEU | A | 166 | −62.156 | 41.339 | 14.752 | 1.00 | 38.23 | C |
| ATOM | 2266 | CD1 | LEU | A | 166 | −61.361 | 40.501 | 13.805 | 1.00 | 37.53 | C |
| ATOM | 2270 | CD2 | LEU | A | 166 | −63.594 | 41.367 | 14.332 | 1.00 | 37.21 | C |
| ATOM | 2274 | C | LEU | A | 166 | −62.842 | 40.555 | 18.438 | 1.00 | 40.08 | C |
| ATOM | 2275 | O | LEU | A | 166 | −63.991 | 40.220 | 18.733 | 1.00 | 40.42 | O |
| ATOM | 2277 | N | LYS | A | 167 | −61.766 | 40.074 | 19.052 | 1.00 | 40.58 | N |
| ATOM | 2278 | CA | LYS | A | 167 | −61.875 | 39.090 | 20.133 | 1.00 | 41.09 | C |
| ATOM | 2280 | CB | LYS | A | 167 | −60.491 | 38.632 | 20.595 | 1.00 | 41.13 | C |
| ATOM | 2283 | CG | LYS | A | 167 | −59.897 | 39.399 | 21.768 | 1.00 | 42.16 | C |
| ATOM | 2286 | CD | LYS | A | 167 | −58.421 | 39.035 | 22.013 | 1.00 | 44.45 | C |
| ATOM | 2289 | CE | LYS | A | 167 | −58.070 | 37.561 | 21.654 | 1.00 | 45.56 | C |
| ATOM | 2292 | NZ | LYS | A | 167 | −56.610 | 37.237 | 21.798 | 1.00 | 46.20 | N |
| ATOM | 2296 | C | LYS | A | 167 | −62.678 | 39.584 | 21.337 | 1.00 | 41.23 | C |
| ATOM | 2297 | O | LYS | A | 167 | −62.994 | 38.793 | 22.215 | 1.00 | 41.47 | O |
| ATOM | 2299 | N | GLU | A | 168 | −62.995 | 40.884 | 21.352 | 1.00 | 41.49 | N |
| ATOM | 2300 | CA | GLU | A | 168 | −63.704 | 41.583 | 22.437 | 1.00 | 41.42 | C |
| ATOM | 2302 | CB | GLU | A | 168 | −65.201 | 41.730 | 22.100 | 1.00 | 41.27 | C |
| ATOM | 2305 | CG | GLU | A | 168 | −65.995 | 40.424 | 22.016 | 1.00 | 41.01 | C |
| ATOM | 2308 | CD | GLU | A | 168 | −66.928 | 40.328 | 20.787 | 1.00 | 40.84 | C |
| ATOM | 2309 | OE1 | GLU | A | 168 | −66.701 | 41.040 | 19.770 | 1.00 | 39.82 | O |
| ATOM | 2310 | OE2 | GLU | A | 168 | −67.884 | 39.509 | 20.845 | 1.00 | 39.04 | O |
| ATOM | 2311 | C | GLU | A | 168 | −63.484 | 41.004 | 23.843 | 1.00 | 41.66 | C |
| ATOM | 2312 | O | GLU | A | 168 | −62.435 | 41.231 | 24.469 | 1.00 | 41.46 | O |
| ATOM | 2314 | N | GLU | A | 172 | −71.668 | 38.961 | 21.192 | 1.00 | 55.65 | N |
| ATOM | 2315 | CA | GLU | A | 172 | −73.052 | 39.153 | 20.721 | 1.00 | 56.00 | C |
| ATOM | 2317 | CB | GLU | A | 172 | −73.876 | 37.880 | 20.937 | 1.00 | 56.27 | C |
| ATOM | 2320 | CG | GLU | A | 172 | −73.198 | 36.620 | 20.390 | 1.00 | 57.12 | C |
| ATOM | 2323 | CD | GLU | A | 172 | −74.056 | 35.363 | 20.516 | 1.00 | 58.18 | C |
| ATOM | 2324 | OE1 | GLU | A | 172 | −75.300 | 35.480 | 20.622 | 1.00 | 58.84 | O |
| ATOM | 2325 | OE2 | GLU | A | 172 | −73.480 | 34.249 | 20.498 | 1.00 | 58.98 | O |
| ATOM | 2326 | C | GLU | A | 172 | −73.766 | 40.386 | 21.334 | 1.00 | 55.70 | C |
| ATOM | 2327 | O | GLU | A | 172 | −74.956 | 40.347 | 21.688 | 1.00 | 54.95 | O |
| ATOM | 2329 | N | LYS | A | 173 | −72.987 | 41.458 | 21.486 | 1.00 | 55.58 | N |
| ATOM | 2330 | CA | LYS | A | 173 | −73.496 | 42.831 | 21.466 | 1.00 | 55.43 | C |
| ATOM | 2332 | CB | LYS | A | 173 | −72.649 | 43.741 | 22.357 | 1.00 | 55.51 | C |
| ATOM | 2335 | CG | LYS | A | 173 | −72.527 | 43.223 | 23.793 | 1.00 | 56.07 | C |
| ATOM | 2338 | CD | LYS | A | 173 | −72.803 | 44.291 | 24.868 | 1.00 | 55.87 | C |
| ATOM | 2341 | CE | LYS | A | 173 | −73.111 | 43.642 | 26.221 | 1.00 | 55.20 | C |

TABLE 16-7-continued

Coordinates of *P. tremuloides* IspS

| | | | | | | | | | | |
|---|---|---|---|---|---|---|---|---|---|---|
| ATOM | 2344 | NZ | LYS | A | 173 | −72.893 | 44.576 | 27.348 | 1.00 | 54.63 | N |
| ATOM | 2348 | C | LYS | A | 173 | −73.449 | 43.297 | 20.009 | 1.00 | 55.01 | C |
| ATOM | 2349 | O | LYS | A | 173 | −74.091 | 44.274 | 19.625 | 1.00 | 54.97 | O |
| ATOM | 2351 | N | ILE | A | 174 | −72.647 | 42.581 | 19.223 | 1.00 | 54.57 | N |
| ATOM | 2352 | CA | ILE | A | 174 | −72.713 | 42.550 | 17.767 | 1.00 | 54.22 | C |
| ATOM | 2354 | CB | ILE | A | 174 | −71.429 | 41.845 | 17.227 | 1.00 | 54.21 | C |
| ATOM | 2356 | CG1 | ILE | A | 174 | −70.196 | 42.724 | 17.474 | 1.00 | 54.73 | C |
| ATOM | 2359 | CD1 | ILE | A | 174 | −68.858 | 41.949 | 17.553 | 1.00 | 55.78 | C |
| ATOM | 2363 | CG2 | ILE | A | 174 | −71.532 | 41.504 | 15.759 | 1.00 | 54.06 | C |
| ATOM | 2367 | C | ILE | A | 174 | −73.957 | 41.744 | 17.384 | 1.00 | 53.88 | C |
| ATOM | 2368 | O | ILE | A | 174 | −74.587 | 41.134 | 18.250 | 1.00 | 53.83 | O |
| ATOM | 2370 | N | GLY | A | 175 | −74.332 | 41.747 | 16.107 | 1.00 | 53.59 | N |
| ATOM | 2371 | CA | GLY | A | 175 | −75.351 | 40.817 | 15.613 | 1.00 | 53.51 | C |
| ATOM | 2374 | C | GLY | A | 175 | −75.130 | 39.395 | 16.126 | 1.00 | 53.43 | C |
| ATOM | 2375 | O | GLY | A | 175 | −74.119 | 39.105 | 16.760 | 1.00 | 53.80 | O |
| ATOM | 2377 | N | LYS | A | 176 | −76.070 | 38.495 | 15.861 | 1.00 | 53.10 | N |
| ATOM | 2378 | CA | LYS | A | 176 | −75.926 | 37.098 | 16.286 | 1.00 | 52.68 | C |
| ATOM | 2380 | CB | LYS | A | 176 | −77.291 | 36.522 | 16.677 | 1.00 | 52.99 | C |
| ATOM | 2383 | CG | LYS | A | 176 | −78.003 | 37.387 | 17.746 | 1.00 | 54.12 | C |
| ATOM | 2386 | CD | LYS | A | 176 | −79.201 | 36.697 | 18.436 | 1.00 | 54.57 | C |
| ATOM | 2389 | CE | LYS | A | 176 | −79.503 | 37.369 | 19.792 | 1.00 | 54.79 | C |
| ATOM | 2392 | NZ | LYS | A | 176 | −80.458 | 36.598 | 20.653 | 1.00 | 55.20 | N |
| ATOM | 2396 | C | LYS | A | 176 | −75.246 | 36.267 | 15.196 | 1.00 | 51.83 | C |
| ATOM | 2397 | O | LYS | A | 176 | −74.393 | 35.433 | 15.486 | 1.00 | 51.69 | O |
| ATOM | 2399 | N | GLU | A | 177 | −75.609 | 36.520 | 13.940 | 1.00 | 50.90 | N |
| ATOM | 2400 | CA | GLU | A | 177 | −74.975 | 35.854 | 12.800 | 1.00 | 50.19 | C |
| ATOM | 2402 | CB | GLU | A | 177 | −75.792 | 36.062 | 11.507 | 1.00 | 50.41 | C |
| ATOM | 2405 | CG | GLU | A | 177 | −75.506 | 37.368 | 10.735 | 1.00 | 51.03 | C |
| ATOM | 2408 | CD | GLU | A | 177 | −76.403 | 37.572 | 9.507 | 1.00 | 52.17 | C |
| ATOM | 2409 | OE1 | GLU | A | 177 | −75.955 | 38.276 | 8.569 | 1.00 | 52.63 | O |
| ATOM | 2410 | OE2 | GLU | A | 177 | −77.546 | 37.048 | 9.479 | 1.00 | 52.03 | O |
| ATOM | 2411 | C | GLU | A | 177 | −73.549 | 36.369 | 12.607 | 1.00 | 49.10 | C |
| ATOM | 2412 | O | GLU | A | 177 | −72.626 | 35.597 | 12.321 | 1.00 | 49.53 | O |
| ATOM | 2414 | N | LEU | A | 178 | −73.388 | 37.681 | 12.770 | 1.00 | 47.39 | N |
| ATOM | 2415 | CA | LEU | A | 178 | −72.110 | 38.371 | 12.575 | 1.00 | 45.63 | C |
| ATOM | 2417 | CB | LEU | A | 178 | −72.352 | 39.877 | 12.615 | 1.00 | 45.59 | C |
| ATOM | 2420 | CG | LEU | A | 178 | −71.280 | 40.809 | 12.085 | 1.00 | 45.45 | C |
| ATOM | 2422 | CD1 | LEU | A | 178 | −70.969 | 40.515 | 10.620 | 1.00 | 45.45 | C |
| ATOM | 2426 | CD2 | LEU | A | 178 | −71.765 | 42.233 | 12.279 | 1.00 | 44.63 | C |
| ATOM | 2430 | C | LEU | A | 178 | −71.095 | 37.979 | 13.634 | 1.00 | 44.06 | C |
| ATOM | 2431 | O | LEU | A | 178 | −69.902 | 38.012 | 13.387 | 1.00 | 43.70 | O |
| ATOM | 2433 | N | ALA | A | 179 | −71.586 | 37.611 | 14.810 | 1.00 | 42.54 | N |
| ATOM | 2434 | CA | ALA | A | 179 | −70.753 | 37.041 | 15.847 | 1.00 | 41.66 | C |
| ATOM | 2436 | CB | ALA | A | 179 | −71.545 | 36.884 | 17.122 | 1.00 | 41.69 | C |
| ATOM | 2440 | C | ALA | A | 179 | −70.193 | 35.695 | 15.416 | 1.00 | 40.75 | C |
| ATOM | 2441 | O | ALA | A | 179 | −69.078 | 35.351 | 15.769 | 1.00 | 40.61 | O |
| ATOM | 2443 | N | GLU | A | 180 | −70.974 | 34.931 | 14.664 | 1.00 | 39.88 | N |
| ATOM | 2444 | CA | GLU | A | 180 | −70.518 | 33.639 | 14.143 | 1.00 | 39.40 | C |
| ATOM | 2446 | CB | GLU | A | 180 | −71.710 | 32.781 | 13.718 | 1.00 | 39.74 | C |
| ATOM | 2449 | CG | GLU | A | 180 | −72.650 | 32.415 | 14.865 | 1.00 | 40.88 | C |
| ATOM | 2452 | CD | GLU | A | 180 | −73.913 | 31.710 | 14.398 | 1.00 | 42.02 | C |
| ATOM | 2453 | OE1 | GLU | A | 180 | −74.380 | 32.022 | 13.271 | 1.00 | 43.05 | O |
| ATOM | 2454 | OE2 | GLU | A | 180 | −74.437 | 30.857 | 15.166 | 1.00 | 41.93 | O |
| ATOM | 2455 | C | GLU | A | 180 | −69.565 | 33.805 | 12.960 | 1.00 | 38.29 | C |
| ATOM | 2456 | O | GLU | A | 180 | −68.739 | 32.940 | 12.699 | 1.00 | 38.23 | O |
| ATOM | 2458 | N | GLN | A | 181 | −69.704 | 34.911 | 12.240 | 1.00 | 36.92 | N |
| ATOM | 2459 | CA | GLN | A | 181 | −68.748 | 35.299 | 11.223 | 1.00 | 35.74 | C |
| ATOM | 2461 | CB | GLN | A | 181 | −69.272 | 36.516 | 10.463 | 1.00 | 35.94 | C |
| ATOM | 2464 | CG | GLN | A | 181 | −68.931 | 36.537 | 8.975 | 1.00 | 36.93 | C |
| ATOM | 2467 | CD | GLN | A | 181 | −69.693 | 35.492 | 8.176 | 1.00 | 37.72 | C |
| ATOM | 2468 | OE1 | GLN | A | 181 | −70.769 | 35.067 | 8.567 | 1.00 | 38.78 | O |
| ATOM | 2469 | NE2 | GLN | A | 181 | −69.139 | 35.083 | 7.050 | 1.00 | 38.11 | N |
| ATOM | 2472 | C | GLN | A | 181 | −67.406 | 35.632 | 11.881 | 1.00 | 34.64 | C |
| ATOM | 2473 | O | GLN | A | 181 | −66.348 | 35.411 | 11.294 | 1.00 | 34.73 | O |
| ATOM | 2475 | N | VAL | A | 182 | −67.448 | 36.158 | 13.102 | 1.00 | 33.29 | N |
| ATOM | 2476 | CA | VAL | A | 182 | −66.224 | 36.488 | 13.842 | 1.00 | 32.28 | C |
| ATOM | 2478 | CB | VAL | A | 182 | −66.433 | 37.653 | 14.855 | 1.00 | 32.10 | C |
| ATOM | 2480 | CG1 | VAL | A | 182 | −66.328 | 38.991 | 14.166 | 1.00 | 31.51 | C |
| ATOM | 2484 | CG2 | VAL | A | 182 | −65.420 | 37.594 | 15.957 | 1.00 | 31.69 | C |
| ATOM | 2488 | C | VAL | A | 182 | −65.613 | 35.298 | 14.575 | 1.00 | 31.49 | C |
| ATOM | 2489 | O | VAL | A | 182 | −64.396 | 35.230 | 14.668 | 1.00 | 31.43 | O |
| ATOM | 2491 | N | SER | A | 183 | −66.422 | 34.378 | 15.106 | 1.00 | 30.56 | N |
| ATOM | 2492 | CA | SER | A | 183 | −65.860 | 33.174 | 15.744 | 1.00 | 30.16 | C |
| ATOM | 2494 | CB | SER | A | 183 | −66.926 | 32.253 | 16.327 | 1.00 | 30.29 | C |
| ATOM | 2497 | OG | SER | A | 183 | −67.796 | 32.934 | 17.214 | 1.00 | 32.35 | O |
| ATOM | 2499 | C | SER | A | 183 | −65.111 | 32.403 | 14.692 | 1.00 | 29.30 | C |
| ATOM | 2500 | O | SER | A | 183 | −63.974 | 31.981 | 14.903 | 1.00 | 29.32 | O |
| ATOM | 2502 | N | HIS | A | 184 | −65.768 | 32.252 | 13.546 | 1.00 | 28.24 | N |

TABLE 16-7-continued

Coordinates of *P. tremuloides* IspS

| ATOM | 2503 | CA | HIS | A | 184 | −65.215 | 31.578 | 12.379 | 1.00 | 27.36 | C |
| --- | --- | --- | --- | --- | --- | --- | --- | --- | --- | --- | --- |
| ATOM | 2505 | CB | HIS | A | 184 | −66.245 | 31.653 | 11.254 | 1.00 | 27.41 | C |
| ATOM | 2508 | CG | HIS | A | 184 | −65.930 | 30.807 | 10.064 | 1.00 | 26.90 | C |
| ATOM | 2509 | ND1 | HIS | A | 184 | −65.484 | 29.511 | 10.166 | 1.00 | 27.76 | N |
| ATOM | 2511 | CE1 | HIS | A | 184 | −65.321 | 29.009 | 8.955 | 1.00 | 27.47 | C |
| ATOM | 2513 | NE2 | HIS | A | 184 | −65.661 | 29.929 | 8.075 | 1.00 | 26.52 | N |
| ATOM | 2515 | CD2 | HIS | A | 184 | −66.059 | 31.058 | 8.742 | 1.00 | 26.61 | C |
| ATOM | 2517 | C | HIS | A | 184 | −63.898 | 32.200 | 11.940 | 1.00 | 26.69 | C |
| ATOM | 2518 | O | HIS | A | 184 | −62.881 | 31.525 | 11.862 | 1.00 | 26.44 | O |
| ATOM | 2520 | N | ALA | A | 185 | −63.909 | 33.498 | 11.675 | 1.00 | 26.11 | N |
| ATOM | 2521 | CA | ALA | A | 185 | −62.711 | 34.176 | 11.205 | 1.00 | 25.63 | C |
| ATOM | 2523 | CB | ALA | A | 185 | −62.970 | 35.627 | 11.109 | 1.00 | 25.74 | C |
| ATOM | 2527 | C | ALA | A | 185 | −61.552 | 33.917 | 12.153 | 1.00 | 25.33 | C |
| ATOM | 2528 | O | ALA | A | 185 | −60.451 | 33.572 | 11.725 | 1.00 | 25.79 | O |
| ATOM | 2530 | N | LEU | A | 186 | −61.814 | 34.066 | 13.450 | 1.00 | 24.77 | N |
| ATOM | 2531 | CA | LEU | A | 186 | −60.776 | 33.940 | 14.470 | 1.00 | 24.05 | C |
| ATOM | 2533 | CB | LEU | A | 186 | −61.256 | 34.498 | 15.814 | 1.00 | 23.63 | C |
| ATOM | 2536 | CG | LEU | A | 186 | −61.516 | 36.012 | 15.903 | 1.00 | 22.51 | C |
| ATOM | 2538 | CD1 | LEU | A | 186 | −62.057 | 36.399 | 17.266 | 1.00 | 20.79 | C |
| ATOM | 2542 | CD2 | LEU | A | 186 | −60.273 | 36.793 | 15.613 | 1.00 | 21.13 | C |
| ATOM | 2546 | C | LEU | A | 186 | −60.316 | 32.497 | 14.613 | 1.00 | 24.02 | C |
| ATOM | 2547 | O | LEU | A | 186 | −59.169 | 32.250 | 14.943 | 1.00 | 24.27 | O |
| ATOM | 2549 | N | GLU | A | 187 | −61.201 | 31.543 | 14.347 | 1.00 | 23.88 | N |
| ATOM | 2550 | CA | GLU | A | 187 | −60.836 | 30.117 | 14.348 | 1.00 | 23.53 | C |
| ATOM | 2552 | CB | GLU | A | 187 | −62.029 | 29.270 | 13.919 | 1.00 | 23.66 | C |
| ATOM | 2555 | CG | GLU | A | 187 | −61.945 | 27.828 | 14.316 | 1.00 | 25.26 | C |
| ATOM | 2558 | CD | GLU | A | 187 | −63.049 | 26.971 | 13.693 | 1.00 | 28.04 | C |
| ATOM | 2559 | OE1 | GLU | A | 187 | −63.672 | 27.393 | 12.681 | 1.00 | 28.67 | O |
| ATOM | 2560 | OE2 | GLU | A | 187 | −63.288 | 25.858 | 14.225 | 1.00 | 29.72 | O |
| ATOM | 2561 | C | GLU | A | 187 | −59.686 | 29.838 | 13.395 | 1.00 | 22.92 | C |
| ATOM | 2562 | O | GLU | A | 187 | −58.765 | 29.091 | 13.729 | 1.00 | 22.53 | O |
| ATOM | 2564 | N | LEU | A | 188 | −59.763 | 30.446 | 12.209 | 1.00 | 22.46 | N |
| ATOM | 2565 | CA | LEU | A | 188 | −58.799 | 30.246 | 11.121 | 1.00 | 22.07 | C |
| ATOM | 2567 | CB | LEU | A | 188 | −58.802 | 28.794 | 10.635 | 1.00 | 22.11 | C |
| ATOM | 2570 | CG | LEU | A | 188 | −57.876 | 28.362 | 9.493 | 1.00 | 22.17 | C |
| ATOM | 2572 | CD1 | LEU | A | 188 | −56.456 | 28.051 | 9.961 | 1.00 | 21.62 | C |
| ATOM | 2576 | CD2 | LEU | A | 188 | −58.464 | 27.134 | 8.822 | 1.00 | 22.40 | C |
| ATOM | 2580 | C | LEU | A | 188 | −59.237 | 31.137 | 9.985 | 1.00 | 21.69 | C |
| ATOM | 2581 | O | LEU | A | 188 | −60.380 | 31.075 | 9.563 | 1.00 | 21.53 | O |
| ATOM | 2583 | N | PRO | A | 189 | −58.333 | 31.973 | 9.474 | 1.00 | 21.46 | N |
| ATOM | 2584 | CA | PRO | A | 189 | −58.745 | 32.935 | 8.472 | 1.00 | 21.18 | C |
| ATOM | 2586 | CB | PRO | A | 189 | −57.592 | 33.936 | 8.486 | 1.00 | 21.03 | C |
| ATOM | 2589 | CG | PRO | A | 189 | −56.423 | 33.118 | 8.757 | 1.00 | 21.21 | C |
| ATOM | 2592 | CD | PRO | A | 189 | −56.873 | 31.992 | 9.668 | 1.00 | 21.61 | C |
| ATOM | 2595 | C | PRO | A | 189 | −58.946 | 32.314 | 7.076 | 1.00 | 20.96 | C |
| ATOM | 2596 | O | PRO | A | 189 | −58.418 | 31.247 | 6.793 | 1.00 | 21.02 | O |
| ATOM | 2597 | N | LEU | A | 190 | −59.714 | 32.994 | 6.226 | 1.00 | 20.89 | N |
| ATOM | 2598 | CA | LEU | A | 190 | −60.018 | 32.533 | 4.867 | 1.00 | 20.74 | C |
| ATOM | 2600 | CB | LEU | A | 190 | −60.597 | 33.690 | 4.053 | 1.00 | 20.76 | C |
| ATOM | 2603 | CG | LEU | A | 190 | −62.090 | 33.924 | 4.259 | 1.00 | 21.35 | C |
| ATOM | 2605 | CD1 | LEU | A | 190 | −62.537 | 35.196 | 3.578 | 1.00 | 20.54 | C |
| ATOM | 2609 | CD2 | LEU | A | 190 | −62.889 | 32.712 | 3.720 | 1.00 | 23.39 | C |
| ATOM | 2613 | C | LEU | A | 190 | −58.814 | 31.971 | 4.112 | 1.00 | 20.35 | C |
| ATOM | 2614 | O | LEU | A | 190 | −58.859 | 30.871 | 3.546 | 1.00 | 20.08 | O |
| ATOM | 2616 | N | HIS | A | 191 | −57.734 | 32.746 | 4.132 | 1.00 | 19.81 | N |
| ATOM | 2617 | CA | HIS | A | 191 | −56.537 | 32.448 | 3.364 | 1.00 | 18.89 | C |
| ATOM | 2619 | CB | HIS | A | 191 | −55.548 | 33.592 | 3.536 | 1.00 | 18.92 | C |
| ATOM | 2622 | CG | HIS | A | 191 | −54.372 | 33.520 | 2.623 | 1.00 | 18.51 | C |
| ATOM | 2623 | ND1 | HIS | A | 191 | −54.482 | 33.647 | 1.258 | 1.00 | 18.08 | N |
| ATOM | 2625 | CE1 | HIS | A | 191 | −53.281 | 33.544 | .718 | 1.00 | 18.96 | C |
| ATOM | 2627 | NE2 | HIS | A | 191 | −52.397 | 33.371 | 1.684 | 1.00 | 17.01 | N |
| ATOM | 2629 | CD2 | HIS | A | 191 | −53.054 | 33.355 | 2.884 | 1.00 | 17.94 | C |
| ATOM | 2631 | C | HIS | A | 191 | −55.889 | 31.142 | 3.759 | 1.00 | 18.32 | C |
| ATOM | 2632 | O | HIS | A | 191 | −55.217 | 30.531 | 2.942 | 1.00 | 17.98 | O |
| ATOM | 2634 | N | ARG | A | 192 | −56.093 | 30.719 | 5.006 | 1.00 | 18.06 | N |
| ATOM | 2635 | CA | ARG | A | 192 | −55.502 | 29.480 | 5.523 | 1.00 | 17.99 | C |
| ATOM | 2637 | CB | ARG | A | 192 | −54.940 | 29.722 | 6.909 | 1.00 | 17.77 | C |
| ATOM | 2640 | CG | ARG | A | 192 | −53.822 | 30.683 | 6.881 | 1.00 | 18.47 | C |
| ATOM | 2643 | CD | ARG | A | 192 | −53.082 | 30.748 | 8.196 | 1.00 | 19.80 | C |
| ATOM | 2646 | NE | ARG | A | 192 | −52.174 | 31.900 | 8.224 | 1.00 | 20.33 | N |
| ATOM | 2648 | CZ | ARG | A | 192 | −51.176 | 32.048 | 9.077 | 1.00 | 20.10 | C |
| ATOM | 2649 | NH1 | ARG | A | 192 | −50.928 | 31.113 | 9.972 | 1.00 | 21.72 | N |
| ATOM | 2652 | NH2 | ARG | A | 192 | −50.407 | 33.119 | 9.019 | 1.00 | 20.79 | N |
| ATOM | 2655 | C | ARG | A | 192 | −56.477 | 28.311 | 5.590 | 1.00 | 18.00 | C |
| ATOM | 2656 | O | ARG | A | 192 | −56.067 | 27.170 | 5.871 | 1.00 | 18.21 | O |
| ATOM | 2658 | N | ARG | A | 193 | −57.758 | 28.588 | 5.335 | 1.00 | 17.59 | N |
| ATOM | 2659 | CA | ARG | A | 193 | −58.779 | 27.563 | 5.382 | 1.00 | 17.16 | C |
| ATOM | 2661 | CB | ARG | A | 193 | −60.141 | 28.164 | 5.741 | 1.00 | 17.45 | C |

TABLE 16-7-continued

Coordinates of *P. tremuloides* IspS

| ATOM | 2664 | CG | ARG | A | 193 | −61.109 | 27.132 | 6.322 | 1.00 | 18.70 | C |
|---|---|---|---|---|---|---|---|---|---|---|---|
| ATOM | 2667 | CD | ARG | A | 193 | −62.479 | 27.682 | 6.686 | 1.00 | 20.20 | C |
| ATOM | 2670 | NE | ARG | A | 193 | −62.423 | 28.682 | 7.751 | 1.00 | 22.59 | N |
| ATOM | 2672 | CZ | ARG | A | 193 | −62.386 | 28.435 | 9.067 | 1.00 | 24.12 | C |
| ATOM | 2673 | NH1 | ARG | A | 193 | −62.395 | 27.198 | 9.575 | 1.00 | 22.66 | N |
| ATOM | 2676 | NH2 | ARG | A | 193 | −62.348 | 29.469 | 9.898 | 1.00 | 26.36 | N |
| ATOM | 2679 | C | ARG | A | 193 | −58.871 | 26.842 | 4.058 | 1.00 | 16.63 | C |
| ATOM | 2680 | O | ARG | A | 193 | −58.861 | 27.461 | 3.005 | 1.00 | 15.93 | O |
| ATOM | 2682 | N | THR | A | 194 | −58.955 | 25.518 | 4.149 | 1.00 | 16.72 | N |
| ATOM | 2683 | CA | THR | A | 194 | −59.332 | 24.638 | 3.051 | 1.00 | 16.88 | C |
| ATOM | 2685 | CB | THR | A | 194 | −59.520 | 23.250 | 3.592 | 1.00 | 16.43 | C |
| ATOM | 2687 | OG1 | THR | A | 194 | −58.252 | 22.605 | 3.583 | 1.00 | 17.74 | O |
| ATOM | 2689 | CG2 | THR | A | 194 | −60.454 | 22.441 | 2.754 | 1.00 | 18.43 | C |
| ATOM | 2693 | C | THR | A | 194 | −60.607 | 25.112 | 2.384 | 1.00 | 17.28 | C |
| ATOM | 2694 | O | THR | A | 194 | −61.441 | 25.734 | 3.022 | 1.00 | 17.44 | O |
| ATOM | 2696 | N | GLN | A | 195 | −60.765 | 24.855 | 1.091 | 1.00 | 18.05 | N |
| ATOM | 2697 | CA | GLN | A | 195 | −61.925 | 25.402 | .397 | 1.00 | 18.76 | C |
| ATOM | 2699 | CB | GLN | A | 195 | −61.768 | 25.381 | −1.114 | 1.00 | 18.87 | C |
| ATOM | 2702 | CG | GLN | A | 195 | −63.145 | 25.523 | −1.761 | 1.00 | 20.75 | C |
| ATOM | 2705 | CD | GLN | A | 195 | −63.095 | 25.922 | −3.179 | 1.00 | 23.41 | C |
| ATOM | 2706 | OE1 | GLN | A | 195 | −62.031 | 26.088 | −3.733 | 1.00 | 27.07 | O |
| ATOM | 2707 | NE2 | GLN | A | 195 | −64.248 | 26.090 | −3.791 | 1.00 | 25.02 | N |
| ATOM | 2710 | C | GLN | A | 195 | −63.243 | 24.704 | .765 | 1.00 | 18.93 | C |
| ATOM | 2711 | O | GLN | A | 195 | −64.169 | 25.333 | 1.291 | 1.00 | 19.42 | O |
| ATOM | 2713 | N | ARG | A | 196 | −63.345 | 23.418 | .443 | 1.00 | 18.90 | N |
| ATOM | 2714 | CA | ARG | A | 196 | −64.577 | 22.685 | .663 | 1.00 | 18.68 | C |
| ATOM | 2716 | CB | ARG | A | 196 | −64.356 | 21.186 | .454 | 1.00 | 18.53 | C |
| ATOM | 2719 | CG | ARG | A | 196 | −64.851 | 20.644 | −.888 | 1.00 | 18.31 | C |
| ATOM | 2722 | CD | ARG | A | 196 | −64.705 | 21.622 | −2.037 | 1.00 | 17.93 | C |
| ATOM | 2725 | NE | ARG | A | 196 | −65.930 | 21.720 | −2.834 | 1.00 | 18.52 | N |
| ATOM | 2727 | CZ | ARG | A | 196 | −66.480 | 22.857 | −3.256 | 1.00 | 18.63 | C |
| ATOM | 2728 | NH1 | ARG | A | 196 | −65.938 | 24.014 | −2.937 | 1.00 | 19.84 | N |
| ATOM | 2731 | NH2 | ARG | A | 196 | −67.582 | 22.844 | −3.999 | 1.00 | 18.53 | N |
| ATOM | 2734 | C | ARG | A | 196 | −65.070 | 22.982 | 2.061 | 1.00 | 19.02 | C |
| ATOM | 2735 | O | ARG | A | 196 | −66.276 | 23.085 | 2.284 | 1.00 | 19.30 | O |
| ATOM | 2737 | N | LEU | A | 197 | −64.127 | 23.152 | 2.990 | 1.00 | 19.09 | N |
| ATOM | 2738 | CA | LEU | A | 197 | −64.444 | 23.432 | 4.379 | 1.00 | 19.19 | C |
| ATOM | 2740 | CB | LEU | A | 197 | −63.203 | 23.346 | 5.262 | 1.00 | 19.14 | C |
| ATOM | 2743 | CG | LEU | A | 197 | −63.135 | 22.097 | 6.130 | 1.00 | 19.99 | C |
| ATOM | 2745 | CD1 | LEU | A | 197 | −64.476 | 21.899 | 6.811 | 1.00 | 21.56 | C |
| ATOM | 2749 | CD2 | LEU | A | 197 | −62.016 | 22.198 | 7.161 | 1.00 | 20.06 | C |
| ATOM | 2753 | C | LEU | A | 197 | −65.071 | 24.781 | 4.553 | 1.00 | 19.52 | C |
| ATOM | 2754 | O | LEU | A | 197 | −66.052 | 24.902 | 5.252 | 1.00 | 19.85 | O |
| ATOM | 2756 | N | GLU | A | 198 | −64.488 | 25.803 | 3.941 | 1.00 | 20.11 | N |
| ATOM | 2757 | CA | GLU | A | 198 | −65.051 | 27.147 | 3.986 | 1.00 | 20.47 | C |
| ATOM | 2759 | CB | GLU | A | 198 | −64.079 | 28.156 | 3.385 | 1.00 | 20.84 | C |
| ATOM | 2762 | CG | GLU | A | 198 | −64.659 | 29.539 | 3.069 | 1.00 | 22.30 | C |
| ATOM | 2765 | CD | GLU | A | 198 | −65.206 | 30.260 | 4.283 | 1.00 | 24.40 | C |
| ATOM | 2766 | OE1 | GLU | A | 198 | −64.852 | 29.894 | 5.418 | 1.00 | 25.34 | O |
| ATOM | 2767 | OE2 | GLU | A | 198 | −65.991 | 31.217 | 4.106 | 1.00 | 26.83 | O |
| ATOM | 2768 | C | GLU | A | 198 | −66.360 | 27.186 | 3.226 | 1.00 | 20.57 | C |
| ATOM | 2769 | O | GLU | A | 198 | −67.212 | 28.009 | 3.529 | 1.00 | 20.65 | O |
| ATOM | 2771 | N | ALA | A | 199 | −66.519 | 26.298 | 2.240 | 1.00 | 20.76 | N |
| ATOM | 2772 | CA | ALA | A | 199 | −67.751 | 26.229 | 1.452 | 1.00 | 20.52 | C |
| ATOM | 2774 | CB | ALA | A | 199 | −67.521 | 25.492 | .166 | 1.00 | 20.44 | C |
| ATOM | 2778 | C | ALA | A | 199 | −68.907 | 25.611 | 2.232 | 1.00 | 20.55 | C |
| ATOM | 2779 | O | ALA | A | 199 | −69.988 | 26.158 | 2.202 | 1.00 | 20.17 | O |
| ATOM | 2781 | N | VAL | A | 200 | −68.701 | 24.493 | 2.933 | 1.00 | 21.10 | N |
| ATOM | 2782 | CA | VAL | A | 200 | −69.791 | 23.935 | 3.774 | 1.00 | 21.51 | C |
| ATOM | 2784 | CB | VAL | A | 200 | −69.509 | 22.576 | 4.485 | 1.00 | 21.18 | C |
| ATOM | 2786 | CG1 | VAL | A | 200 | −69.618 | 21.460 | 3.525 | 1.00 | 21.27 | C |
| ATOM | 2790 | CG2 | VAL | A | 200 | −68.161 | 22.569 | 5.200 | 1.00 | 21.23 | C |
| ATOM | 2794 | C | VAL | A | 200 | −70.170 | 24.905 | 4.860 | 1.00 | 21.99 | C |
| ATOM | 2795 | O | VAL | A | 200 | −71.338 | 25.022 | 5.186 | 1.00 | 22.99 | O |
| ATOM | 2797 | N | TRP | A | 201 | −69.204 | 25.590 | 5.440 | 1.00 | 22.10 | N |
| ATOM | 2798 | CA | TRP | A | 201 | −69.551 | 26.565 | 6.433 | 1.00 | 22.58 | C |
| ATOM | 2800 | CB | TRP | A | 201 | −68.315 | 27.144 | 7.121 | 1.00 | 22.92 | C |
| ATOM | 2803 | CG | TRP | A | 201 | −68.667 | 27.957 | 8.310 | 1.00 | 23.65 | C |
| ATOM | 2804 | CD1 | TRP | A | 201 | −68.758 | 27.520 | 9.588 | 1.00 | 25.08 | C |
| ATOM | 2806 | NE1 | TRP | A | 201 | −69.127 | 28.549 | 10.417 | 1.00 | 26.35 | N |
| ATOM | 2808 | CE2 | TRP | A | 201 | −69.290 | 29.683 | 9.669 | 1.00 | 25.48 | C |
| ATOM | 2809 | CD2 | TRP | A | 201 | −69.010 | 29.344 | 8.332 | 1.00 | 24.77 | C |
| ATOM | 2810 | CE3 | TRP | A | 201 | −69.095 | 30.336 | 7.355 | 1.00 | 24.92 | C |
| ATOM | 2812 | CZ3 | TRP | A | 201 | −69.450 | 31.616 | 7.739 | 1.00 | 24.96 | C |
| ATOM | 2814 | CH2 | TRP | A | 201 | −69.720 | 31.918 | 9.078 | 1.00 | 25.08 | C |
| ATOM | 2816 | CZ2 | TRP | A | 201 | −69.648 | 30.968 | 10.056 | 1.00 | 24.68 | C |
| ATOM | 2818 | C | TRP | A | 201 | −70.351 | 27.662 | 5.758 | 1.00 | 22.71 | C |
| ATOM | 2819 | O | TRP | A | 201 | −71.482 | 27.921 | 6.140 | 1.00 | 22.76 | O |

TABLE 16-7-continued

Coordinates of *P. tremuloides* IspS

| ATOM | 2821 | N | SER | A | 202 | −69.776 | 28.272 | 4.727 | 1.00 | 23.04 | N |
| ATOM | 2822 | CA | SER | A | 202 | −70.335 | 29.500 | 4.165 | 1.00 | 23.29 | C |
| ATOM | 2824 | CB | SER | A | 202 | −69.304 | 30.205 | 3.290 | 1.00 | 23.20 | C |
| ATOM | 2827 | OG | SER | A | 202 | −68.306 | 30.807 | 4.111 | 1.00 | 23.07 | O |
| ATOM | 2829 | C | SER | A | 202 | −71.666 | 29.341 | 3.432 | 1.00 | 23.66 | C |
| ATOM | 2830 | O | SER | A | 202 | −72.392 | 30.310 | 3.265 | 1.00 | 23.38 | O |
| ATOM | 2832 | N | ILE | A | 203 | −71.996 | 28.124 | 3.016 | 1.00 | 24.49 | N |
| ATOM | 2833 | CA | ILE | A | 203 | −73.321 | 27.859 | 2.460 | 1.00 | 25.07 | C |
| ATOM | 2835 | CB | ILE | A | 203 | −73.391 | 26.530 | 1.653 | 1.00 | 24.74 | C |
| ATOM | 2837 | CG1 | ILE | A | 203 | −72.494 | 26.587 | .423 | 1.00 | 24.36 | C |
| ATOM | 2840 | CD1 | ILE | A | 203 | −72.344 | 25.255 | −.281 | 1.00 | 23.81 | C |
| ATOM | 2844 | CG2 | ILE | A | 203 | −74.795 | 26.292 | 1.156 | 1.00 | 24.45 | C |
| ATOM | 2848 | C | ILE | A | 203 | −74.338 | 27.858 | 3.607 | 1.00 | 25.91 | C |
| ATOM | 2849 | O | ILE | A | 203 | −75.350 | 28.554 | 3.546 | 1.00 | 26.26 | O |
| ATOM | 2851 | N | GLU | A | 204 | −74.051 | 27.104 | 4.662 | 1.00 | 26.69 | N |
| ATOM | 2852 | CA | GLU | A | 204 | −74.929 | 27.053 | 5.824 | 1.00 | 27.40 | C |
| ATOM | 2854 | CB | GLU | A | 204 | −74.286 | 26.217 | 6.931 | 1.00 | 27.65 | C |
| ATOM | 2857 | CG | GLU | A | 204 | −75.132 | 26.032 | 8.183 | 1.00 | 29.02 | C |
| ATOM | 2860 | CD | GLU | A | 204 | −76.530 | 25.491 | 7.903 | 1.00 | 30.44 | C |
| ATOM | 2861 | OE1 | GLU | A | 204 | −76.746 | 24.858 | 6.844 | 1.00 | 31.22 | O |
| ATOM | 2862 | OE2 | GLU | A | 204 | −77.417 | 25.703 | 8.753 | 1.00 | 31.96 | O |
| ATOM | 2863 | C | GLU | A | 204 | −75.258 | 28.451 | 6.342 | 1.00 | 27.61 | C |
| ATOM | 2864 | O | GLU | A | 204 | −76.409 | 28.778 | 6.526 | 1.00 | 27.78 | O |
| ATOM | 2866 | N | ALA | A | 205 | −74.240 | 29.274 | 6.547 | 1.00 | 28.15 | N |
| ATOM | 2867 | CA | ALA | A | 205 | −74.416 | 30.637 | 7.050 | 1.00 | 28.41 | C |
| ATOM | 2869 | CB | ALA | A | 205 | −73.062 | 31.285 | 7.274 | 1.00 | 28.41 | C |
| ATOM | 2873 | C | ALA | A | 205 | −75.234 | 31.520 | 6.136 | 1.00 | 28.84 | C |
| ATOM | 2874 | O | ALA | A | 205 | −76.050 | 32.302 | 6.610 | 1.00 | 28.54 | O |
| ATOM | 2876 | N | TYR | A | 206 | −74.978 | 31.408 | 4.832 | 1.00 | 29.84 | N |
| ATOM | 2877 | CA | TYR | A | 206 | −75.581 | 32.281 | 3.805 | 1.00 | 30.41 | C |
| ATOM | 2879 | CB | TYR | A | 206 | −74.801 | 32.170 | 2.493 | 1.00 | 30.20 | C |
| ATOM | 2882 | CG | TYR | A | 206 | −75.180 | 33.173 | 1.425 | 1.00 | 29.62 | C |
| ATOM | 2883 | CD1 | TYR | A | 206 | −74.721 | 34.482 | 1.484 | 1.00 | 30.32 | C |
| ATOM | 2885 | CE1 | TYR | A | 206 | −75.047 | 35.412 | .489 | 1.00 | 29.70 | C |
| ATOM | 2887 | CZ | TYR | A | 206 | −75.830 | 35.028 | −.578 | 1.00 | 28.41 | C |
| ATOM | 2888 | OH | TYR | A | 206 | −76.155 | 35.956 | −1.548 | 1.00 | 26.74 | O |
| ATOM | 2890 | CE2 | TYR | A | 206 | −76.291 | 33.724 | −.659 | 1.00 | 28.16 | C |
| ATOM | 2892 | CD2 | TYR | A | 206 | −75.958 | 32.806 | .335 | 1.00 | 28.39 | C |
| ATOM | 2894 | C | TYR | A | 206 | −77.038 | 31.918 | 3.561 | 1.00 | 31.15 | C |
| ATOM | 2895 | O | TYR | A | 206 | −77.858 | 32.781 | 3.268 | 1.00 | 31.30 | O |
| ATOM | 2897 | N | ARG | A | 207 | −77.341 | 30.631 | 3.676 | 1.00 | 32.05 | N |
| ATOM | 2898 | CA | ARG | A | 207 | −78.691 | 30.128 | 3.555 | 1.00 | 32.81 | C |
| ATOM | 2900 | CB | ARG | A | 207 | −78.684 | 28.623 | 3.813 | 1.00 | 32.86 | C |
| ATOM | 2903 | CG | ARG | A | 207 | −80.028 | 27.941 | 3.673 | 1.00 | 34.01 | C |
| ATOM | 2906 | CD | ARG | A | 207 | −80.066 | 26.632 | 4.450 | 1.00 | 35.11 | C |
| ATOM | 2909 | NE | ARG | A | 207 | −79.096 | 25.669 | 3.939 | 1.00 | 35.35 | N |
| ATOM | 2911 | CZ | ARG | A | 207 | −79.353 | 24.737 | 3.022 | 1.00 | 36.00 | C |
| ATOM | 2912 | NH1 | ARG | A | 207 | −80.562 | 24.611 | 2.478 | 1.00 | 35.55 | N |
| ATOM | 2915 | NH2 | ARG | A | 207 | −78.381 | 23.918 | 2.640 | 1.00 | 37.05 | N |
| ATOM | 2918 | C | ARG | A | 207 | −79.609 | 30.826 | 4.550 | 1.00 | 33.57 | C |
| ATOM | 2919 | O | ARG | A | 207 | −80.783 | 31.003 | 4.263 | 1.00 | 33.82 | O |
| ATOM | 2921 | N | LYS | A | 208 | −79.064 | 31.223 | 5.707 | 1.00 | 34.58 | N |
| ATOM | 2922 | CA | LYS | A | 208 | −79.835 | 31.830 | 6.812 | 1.00 | 35.21 | C |
| ATOM | 2924 | CB | LYS | A | 208 | −79.137 | 31.599 | 8.159 | 1.00 | 35.05 | C |
| ATOM | 2927 | CG | LYS | A | 208 | −78.847 | 30.147 | 8.496 | 1.00 | 34.78 | C |
| ATOM | 2930 | CD | LYS | A | 208 | −78.583 | 29.974 | 9.980 | 1.00 | 34.44 | C |
| ATOM | 2933 | CE | LYS | A | 208 | −77.992 | 28.619 | 10.309 | 1.00 | 34.16 | C |
| ATOM | 2936 | NZ | LYS | A | 208 | −76.540 | 28.693 | 10.572 | 1.00 | 33.81 | N |
| ATOM | 2940 | C | LYS | A | 208 | −80.075 | 33.333 | 6.663 | 1.00 | 36.06 | C |
| ATOM | 2941 | O | LYS | A | 208 | −81.032 | 33.857 | 7.226 | 1.00 | 36.19 | O |
| ATOM | 2943 | N | LYS | A | 209 | −79.197 | 34.032 | 5.946 | 1.00 | 36.93 | N |
| ATOM | 2944 | CA | LYS | A | 209 | −79.412 | 35.445 | 5.652 | 1.00 | 37.77 | C |
| ATOM | 2946 | CB | LYS | A | 209 | −78.284 | 35.998 | 4.779 | 1.00 | 38.18 | C |
| ATOM | 2949 | CG | LYS | A | 209 | −76.928 | 36.134 | 5.458 | 1.00 | 39.90 | C |
| ATOM | 2952 | CD | LYS | A | 209 | −75.982 | 37.023 | 4.621 | 1.00 | 42.39 | C |
| ATOM | 2955 | CE | LYS | A | 209 | −74.531 | 37.016 | 5.169 | 1.00 | 44.21 | C |
| ATOM | 2958 | NZ | LYS | A | 209 | −74.350 | 37.688 | 6.509 | 1.00 | 44.75 | N |
| ATOM | 2962 | C | LYS | A | 209 | −80.738 | 35.600 | 4.911 | 1.00 | 37.89 | C |
| ATOM | 2963 | O | LYS | A | 209 | −81.049 | 34.785 | 4.036 | 1.00 | 38.20 | O |
| ATOM | 2965 | N | GLU | A | 210 | −81.518 | 36.632 | 5.243 | 1.00 | 37.87 | N |
| ATOM | 2966 | CA | GLU | A | 210 | −82.847 | 36.797 | 4.630 | 1.00 | 37.72 | C |
| ATOM | 2968 | CB | GLU | A | 210 | −83.821 | 37.578 | 5.549 | 1.00 | 38.19 | C |
| ATOM | 2971 | CG | GLU | A | 210 | −83.850 | 39.130 | 5.404 | 1.00 | 39.68 | C |
| ATOM | 2974 | CD | GLU | A | 210 | −85.270 | 39.736 | 5.534 | 1.00 | 41.27 | C |
| ATOM | 2975 | OE1 | GLU | A | 210 | −86.172 | 39.100 | 6.136 | 1.00 | 41.67 | O |
| ATOM | 2976 | OE2 | GLU | A | 210 | −85.482 | 40.859 | 5.019 | 1.00 | 42.17 | O |
| ATOM | 2977 | C | GLU | A | 210 | −82.760 | 37.394 | 3.219 | 1.00 | 36.68 | C |
| ATOM | 2978 | O | GLU | A | 210 | −83.605 | 37.103 | 2.371 | 1.00 | 36.39 | O |

TABLE 16-7-continued

Coordinates of *P. tremuloides* IspS

| ATOM | 2980 | N | ASP | A | 211 | −81.725 | 38.198 | 2.969 | 1.00 | 35.65 | N |
|---|---|---|---|---|---|---|---|---|---|---|---|
| ATOM | 2981 | CA | ASP | A | 211 | −81.481 | 38.777 | 1.632 | 1.00 | 34.94 | C |
| ATOM | 2983 | CB | ASP | A | 211 | −81.064 | 40.257 | 1.740 | 1.00 | 35.22 | C |
| ATOM | 2986 | CG | ASP | A | 211 | −79.811 | 40.477 | 2.599 | 1.00 | 35.84 | C |
| ATOM | 2987 | OD1 | ASP | A | 211 | −79.379 | 39.557 | 3.341 | 1.00 | 35.60 | O |
| ATOM | 2988 | OD2 | ASP | A | 211 | −79.276 | 41.606 | 2.536 | 1.00 | 36.73 | O |
| ATOM | 2989 | C | ASP | A | 211 | −80.451 | 37.989 | .811 | 1.00 | 33.73 | C |
| ATOM | 2990 | O | ASP | A | 211 | −79.753 | 38.556 | −.021 | 1.00 | 33.40 | O |
| ATOM | 2992 | N | ALA | A | 212 | −80.366 | 36.682 | 1.057 | 1.00 | 32.53 | N |
| ATOM | 2993 | CA | ALA | A | 212 | −79.506 | 35.783 | .293 | 1.00 | 31.40 | C |
| ATOM | 2995 | CB | ALA | A | 212 | −79.569 | 34.382 | .889 | 1.00 | 30.79 | C |
| ATOM | 2999 | C | ALA | A | 212 | −79.940 | 35.762 | −1.176 | 1.00 | 30.60 | C |
| ATOM | 3000 | O | ALA | A | 212 | −81.124 | 35.594 | −1.467 | 1.00 | 30.37 | O |
| ATOM | 3002 | N | ASN | A | 213 | −79.000 | 35.967 | −2.097 | 1.00 | 29.71 | N |
| ATOM | 3003 | CA | ASN | A | 213 | −79.304 | 35.809 | −3.520 | 1.00 | 29.27 | C |
| ATOM | 3005 | CB | ASN | A | 213 | −78.144 | 36.315 | −4.402 | 1.00 | 29.30 | C |
| ATOM | 3008 | CG | ASN | A | 213 | −78.442 | 36.217 | −5.911 | 1.00 | 29.07 | C |
| ATOM | 3009 | OD1 | ASN | A | 213 | −78.437 | 37.215 | −6.624 | 1.00 | 29.38 | O |
| ATOM | 3010 | ND2 | ASN | A | 213 | −78.691 | 35.015 | −6.389 | 1.00 | 28.37 | N |
| ATOM | 3013 | C | ASN | A | 213 | −79.634 | 34.328 | −3.785 | 1.00 | 28.81 | C |
| ATOM | 3014 | O | ASN | A | 213 | −78.784 | 33.455 | −3.658 | 1.00 | 29.04 | O |
| ATOM | 3016 | N | GLN | A | 214 | −80.880 | 34.053 | −4.145 | 1.00 | 28.04 | N |
| ATOM | 3017 | CA | GLN | A | 214 | −81.376 | 32.692 | −4.191 | 1.00 | 27.32 | C |
| ATOM | 3019 | CB | GLN | A | 214 | −82.906 | 32.700 | −4.178 | 1.00 | 27.47 | C |
| ATOM | 3022 | CG | GLN | A | 214 | −83.505 | 33.269 | −2.889 | 1.00 | 27.68 | C |
| ATOM | 3025 | CD | GLN | A | 214 | −83.294 | 32.359 | −1.688 | 1.00 | 27.54 | C |
| ATOM | 3026 | OE1 | GLN | A | 214 | −83.940 | 31.320 | −1.571 | 1.00 | 28.19 | O |
| ATOM | 3027 | NE2 | GLN | A | 214 | −82.392 | 32.748 | −.790 | 1.00 | 26.90 | N |
| ATOM | 3030 | C | GLN | A | 214 | −80.858 | 31.902 | −5.385 | 1.00 | 26.71 | C |
| ATOM | 3031 | O | GLN | A | 214 | −80.863 | 30.668 | −5.355 | 1.00 | 26.91 | O |
| ATOM | 3033 | N | VAL | A | 215 | −80.439 | 32.600 | −6.442 | 1.00 | 25.81 | N |
| ATOM | 3034 | CA | VAL | A | 215 | −79.789 | 31.947 | −7.588 | 1.00 | 24.88 | C |
| ATOM | 3036 | CB | VAL | A | 215 | −79.651 | 32.894 | −8.808 | 1.00 | 24.81 | C |
| ATOM | 3038 | CG1 | VAL | A | 215 | −78.459 | 32.483 | −9.680 | 1.00 | 24.94 | C |
| ATOM | 3042 | CG2 | VAL | A | 215 | −80.935 | 32.907 | −9.620 | 1.00 | 23.74 | C |
| ATOM | 3046 | C | VAL | A | 215 | −78.415 | 31.427 | −7.176 | 1.00 | 24.18 | C |
| ATOM | 3047 | O | VAL | A | 215 | −78.073 | 30.282 | −7.430 | 1.00 | 23.74 | O |
| ATOM | 3049 | N | LEU | A | 216 | −77.650 | 32.283 | −6.510 | 1.00 | 23.78 | N |
| ATOM | 3050 | CA | LEU | A | 216 | −76.299 | 31.961 | −6.036 | 1.00 | 23.33 | C |
| ATOM | 3052 | CB | LEU | A | 216 | −75.680 | 33.195 | −5.373 | 1.00 | 23.10 | C |
| ATOM | 3055 | CG | LEU | A | 216 | −74.194 | 33.192 | −5.059 | 1.00 | 22.91 | C |
| ATOM | 3057 | CD1 | LEU | A | 216 | −73.383 | 32.962 | −6.312 | 1.00 | 22.88 | C |
| ATOM | 3061 | CD2 | LEU | A | 216 | −73.826 | 34.518 | −4.424 | 1.00 | 22.03 | C |
| ATOM | 3065 | C | LEU | A | 216 | −76.333 | 30.797 | −5.050 | 1.00 | 22.92 | C |
| ATOM | 3066 | O | LEU | A | 216 | −75.598 | 29.826 | −5.201 | 1.00 | 23.38 | O |
| ATOM | 3068 | N | LEU | A | 217 | −77.214 | 30.890 | −4.060 | 1.00 | 22.09 | N |
| ATOM | 3069 | CA | LEU | A | 217 | −77.367 | 29.851 | −3.054 | 1.00 | 21.14 | C |
| ATOM | 3071 | CB | LEU | A | 217 | −78.488 | 30.225 | −2.090 | 1.00 | 21.11 | C |
| ATOM | 3074 | CG | LEU | A | 217 | −78.782 | 29.236 | −.961 | 1.00 | 21.08 | C |
| ATOM | 3076 | CD1 | LEU | A | 217 | −77.703 | 29.267 | .101 | 1.00 | 19.87 | C |
| ATOM | 3080 | CD2 | LEU | A | 217 | −80.146 | 29.535 | −.360 | 1.00 | 21.46 | C |
| ATOM | 3084 | C | LEU | A | 217 | −77.682 | 28.517 | −3.685 | 1.00 | 20.38 | C |
| ATOM | 3085 | O | LEU | A | 217 | −77.133 | 27.508 | −3.286 | 1.00 | 20.04 | O |
| ATOM | 3087 | N | GLU | A | 218 | −78.579 | 28.512 | −4.661 | 1.00 | 19.97 | N |
| ATOM | 3088 | CA | GLU | A | 218 | −79.027 | 27.260 | −5.273 | 1.00 | 19.72 | C |
| ATOM | 3090 | CB | GLU | A | 218 | −80.220 | 27.499 | −6.212 | 1.00 | 19.87 | C |
| ATOM | 3093 | CG | GLU | A | 218 | −81.005 | 26.228 | −6.627 | 1.00 | 21.03 | C |
| ATOM | 3096 | CD | GLU | A | 218 | −82.303 | 26.535 | −7.424 | 1.00 | 22.59 | C |
| ATOM | 3097 | OE1 | GLU | A | 218 | −82.643 | 27.730 | −7.619 | 1.00 | 23.61 | O |
| ATOM | 3098 | OE2 | GLU | A | 218 | −82.983 | 25.578 | −7.863 | 1.00 | 22.31 | O |
| ATOM | 3099 | C | GLU | A | 218 | −77.854 | 26.613 | −6.009 | 1.00 | 19.03 | C |
| ATOM | 3100 | O | GLU | A | 218 | −77.522 | 25.452 | −5.764 | 1.00 | 18.97 | O |
| ATOM | 3102 | N | LEU | A | 219 | −77.203 | 27.381 | −6.878 | 1.00 | 18.06 | N |
| ATOM | 3103 | CA | LEU | A | 219 | −76.012 | 26.907 | −7.573 | 1.00 | 17.15 | C |
| ATOM | 3105 | CB | LEU | A | 219 | −75.439 | 28.029 | −8.418 | 1.00 | 16.75 | C |
| ATOM | 3108 | CG | LEU | A | 219 | −74.196 | 27.717 | −9.231 | 1.00 | 16.01 | C |
| ATOM | 3110 | CD1 | LEU | A | 219 | −74.511 | 26.832 | −10.404 | 1.00 | 12.99 | C |
| ATOM | 3114 | CD2 | LEU | A | 219 | −73.577 | 29.028 | −9.675 | 1.00 | 16.20 | C |
| ATOM | 3118 | C | LEU | A | 219 | −74.973 | 26.409 | −6.570 | 1.00 | 16.75 | C |
| ATOM | 3119 | O | LEU | A | 219 | −74.377 | 25.355 | −6.757 | 1.00 | 16.47 | O |
| ATOM | 3121 | N | ALA | A | 220 | −74.786 | 27.169 | −5.496 | 1.00 | 16.40 | N |
| ATOM | 3122 | CA | ALA | A | 220 | −73.858 | 26.808 | −4.422 | 1.00 | 16.15 | C |
| ATOM | 3124 | CB | ALA | A | 220 | −73.906 | 27.830 | −3.302 | 1.00 | 16.13 | C |
| ATOM | 3128 | C | ALA | A | 220 | −74.137 | 25.436 | −3.862 | 1.00 | 16.03 | C |
| ATOM | 3129 | O | ALA | A | 220 | −73.253 | 24.603 | −3.799 | 1.00 | 16.30 | O |
| ATOM | 3131 | N | ILE | A | 221 | −75.371 | 25.201 | −3.447 | 1.00 | 16.24 | N |
| ATOM | 3132 | CA | ILE | A | 221 | −75.731 | 23.916 | −2.857 | 1.00 | 16.33 | C |
| ATOM | 3134 | CB | ILE | A | 221 | −77.203 | 23.895 | −2.352 | 1.00 | 15.94 | C |

TABLE 16-7-continued

Coordinates of *P. tremuloides* IspS

| ATOM | 3136 | CG1 | ILE | A | 221 | −77.410 | 24.879 | −1.203 | 1.00 | 15.36 | C |
|---|---|---|---|---|---|---|---|---|---|---|---|
| ATOM | 3139 | CD1 | ILE | A | 221 | −78.842 | 25.234 | −.962 | 1.00 | 14.49 | C |
| ATOM | 3143 | CG2 | ILE | A | 221 | −77.571 | 22.537 | −1.836 | 1.00 | 15.18 | C |
| ATOM | 3147 | C | ILE | A | 221 | −75.509 | 22.841 | −3.911 | 1.00 | 17.06 | C |
| ATOM | 3148 | O | ILE | A | 221 | −74.899 | 21.819 | −3.653 | 1.00 | 16.51 | O |
| ATOM | 3150 | N | LEU | A | 222 | −75.981 | 23.138 | −5.117 | 1.00 | 18.53 | N |
| ATOM | 3151 | CA | LEU | A | 222 | −76.006 | 22.207 | −6.243 | 1.00 | 19.25 | C |
| ATOM | 3153 | CB | LEU | A | 222 | −76.657 | 22.891 | −7.445 | 1.00 | 19.18 | C |
| ATOM | 3156 | CG | LEU | A | 222 | −77.037 | 21.972 | −8.597 | 1.00 | 19.65 | C |
| ATOM | 3158 | CD1 | LEU | A | 222 | −78.318 | 22.489 | −9.268 | 1.00 | 19.24 | C |
| ATOM | 3162 | CD2 | LEU | A | 222 | −75.869 | 21.788 | −9.597 | 1.00 | 18.75 | C |
| ATOM | 3166 | C | LEU | A | 222 | −74.618 | 21.751 | −6.630 | 1.00 | 20.07 | C |
| ATOM | 3167 | O | LEU | A | 222 | −74.381 | 20.558 | −6.778 | 1.00 | 20.55 | O |
| ATOM | 3169 | N | ASP | A | 223 | −73.710 | 22.711 | −6.797 | 1.00 | 20.92 | N |
| ATOM | 3170 | CA | ASP | A | 223 | −72.330 | 22.427 | −7.189 | 1.00 | 21.43 | C |
| ATOM | 3172 | CB | ASP | A | 223 | −71.621 | 23.723 | −7.585 | 1.00 | 21.63 | C |
| ATOM | 3175 | CG | ASP | A | 223 | −70.202 | 23.495 | −8.070 | 1.00 | 22.51 | C |
| ATOM | 3176 | OD1 | ASP | A | 223 | −69.296 | 23.282 | −7.225 | 1.00 | 24.67 | O |
| ATOM | 3177 | OD2 | ASP | A | 223 | −69.990 | 23.544 | −9.296 | 1.00 | 22.73 | O |
| ATOM | 3178 | C | ASP | A | 223 | −71.573 | 21.722 | −6.060 | 1.00 | 21.79 | C |
| ATOM | 3179 | O | ASP | A | 223 | −70.843 | 20.764 | −6.313 | 1.00 | 21.73 | O |
| ATOM | 3181 | N | TYR | A | 224 | −71.755 | 22.182 | −4.820 | 1.00 | 22.14 | N |
| ATOM | 3182 | CA | TYR | A | 224 | −71.120 | 21.529 | −3.686 | 1.00 | 22.22 | C |
| ATOM | 3184 | CB | TYR | A | 224 | −71.462 | 22.190 | −2.355 | 1.00 | 22.38 | C |
| ATOM | 3187 | CG | TYR | A | 224 | −70.673 | 21.542 | −1.249 | 1.00 | 22.65 | C |
| ATOM | 3188 | CD1 | TYR | A | 224 | −69.356 | 21.864 | −1.053 | 1.00 | 22.59 | C |
| ATOM | 3190 | CE1 | TYR | A | 224 | −68.622 | 21.258 | −.098 | 1.00 | 23.38 | C |
| ATOM | 3192 | CZ | TYR | A | 224 | −69.177 | 20.288 | .670 | 1.00 | 23.22 | C |
| ATOM | 3193 | OH | TYR | A | 224 | −68.402 | 19.684 | 1.620 | 1.00 | 23.93 | O |
| ATOM | 3195 | CE2 | TYR | A | 224 | −70.483 | 19.931 | .500 | 1.00 | 23.36 | C |
| ATOM | 3197 | CD2 | TYR | A | 224 | −71.221 | 20.547 | −.464 | 1.00 | 23.41 | C |
| ATOM | 3199 | C | TYR | A | 224 | −71.485 | 20.065 | −3.605 | 1.00 | 22.52 | C |
| ATOM | 3200 | O | TYR | A | 224 | −70.641 | 19.233 | −3.311 | 1.00 | 22.93 | O |
| ATOM | 3202 | N | ASN | A | 225 | −72.742 | 19.749 | −3.856 | 1.00 | 22.94 | N |
| ATOM | 3203 | CA | ASN | A | 225 | −73.187 | 18.374 | −3.801 | 1.00 | 23.44 | C |
| ATOM | 3205 | CB | ASN | A | 225 | −74.706 | 18.310 | −3.729 | 1.00 | 23.34 | C |
| ATOM | 3208 | CG | ASN | A | 225 | −75.210 | 18.579 | −2.352 | 1.00 | 22.62 | C |
| ATOM | 3209 | OD1 | ASN | A | 225 | −74.749 | 17.977 | −1.407 | 1.00 | 23.33 | O |
| ATOM | 3210 | ND2 | ASN | A | 225 | −76.146 | 19.494 | −2.223 | 1.00 | 22.52 | N |
| ATOM | 3213 | C | ASN | A | 225 | −72.694 | 17.523 | −4.959 | 1.00 | 24.26 | C |
| ATOM | 3214 | O | ASN | A | 225 | −72.408 | 16.328 | −4.767 | 1.00 | 24.88 | O |
| ATOM | 3216 | N | MET | A | 226 | −72.607 | 18.119 | −6.150 | 1.00 | 24.67 | N |
| ATOM | 3217 | CA | MET | A | 226 | −72.167 | 17.395 | −7.349 | 1.00 | 24.95 | C |
| ATOM | 3219 | CB | MET | A | 226 | −72.421 | 18.237 | −8.594 | 1.00 | 25.37 | C |
| ATOM | 3222 | CG | MET | A | 226 | −71.785 | 17.713 | −9.873 | 1.00 | 27.23 | C |
| ATOM | 3225 | SD | MET | A | 226 | −70.837 | 19.010 | −10.708 | 1.00 | 31.73 | S |
| ATOM | 3226 | CE | MET | A | 226 | −72.185 | 20.000 | −11.367 | 1.00 | 31.30 | C |
| ATOM | 3230 | C | MET | A | 226 | −70.688 | 17.045 | −7.247 | 1.00 | 24.70 | C |
| ATOM | 3231 | O | MET | A | 226 | −70.291 | 15.929 | −7.568 | 1.00 | 24.91 | O |
| ATOM | 3233 | N | ILE | A | 227 | −69.873 | 17.995 | −6.799 | 1.00 | 24.43 | N |
| ATOM | 3234 | CA | ILE | A | 227 | −68.456 | 17.726 | −6.598 | 1.00 | 24.18 | C |
| ATOM | 3236 | CB | ILE | A | 227 | −67.656 | 18.971 | −6.154 | 1.00 | 24.15 | C |
| ATOM | 3238 | CG1 | ILE | A | 227 | −67.628 | 20.021 | −7.253 | 1.00 | 23.64 | C |
| ATOM | 3241 | CD1 | ILE | A | 227 | −66.853 | 21.246 | −6.880 | 1.00 | 23.11 | C |
| ATOM | 3245 | CG2 | ILE | A | 227 | −66.229 | 18.603 | −5.827 | 1.00 | 24.36 | C |
| ATOM | 3249 | C | ILE | A | 227 | −68.329 | 16.645 | −5.546 | 1.00 | 23.98 | C |
| ATOM | 3250 | O | ILE | A | 227 | −67.609 | 15.689 | −5.747 | 1.00 | 24.35 | O |
| ATOM | 3252 | N | GLN | A | 228 | −69.048 | 16.779 | −4.439 | 1.00 | 23.79 | N |
| ATOM | 3253 | CA | GLN | A | 228 | −69.020 | 15.754 | −3.382 | 1.00 | 23.66 | C |
| ATOM | 3255 | CB | GLN | A | 228 | −70.077 | 16.010 | −2.305 | 1.00 | 23.64 | C |
| ATOM | 3258 | CG | GLN | A | 228 | −69.972 | 15.049 | −1.145 | 1.00 | 22.91 | C |
| ATOM | 3261 | CD | GLN | A | 228 | −70.891 | 15.417 | −.033 | 1.00 | 23.26 | C |
| ATOM | 3262 | OE1 | GLN | A | 228 | −72.082 | 15.098 | −.069 | 1.00 | 25.64 | O |
| ATOM | 3263 | NE2 | GLN | A | 228 | −70.357 | 16.083 | .978 | 1.00 | 21.77 | N |
| ATOM | 3266 | C | GLN | A | 228 | −69.243 | 14.349 | −3.893 | 1.00 | 23.54 | C |
| ATOM | 3267 | O | GLN | A | 228 | −68.664 | 13.412 | −3.357 | 1.00 | 23.59 | O |
| ATOM | 3269 | N | SER | A | 229 | −70.105 | 14.194 | −4.893 | 1.00 | 23.27 | N |
| ATOM | 3270 | CA | SER | A | 229 | −70.394 | 12.868 | −5.406 | 1.00 | 23.35 | C |
| ATOM | 3272 | CB | SER | A | 229 | −71.753 | 12.812 | −6.095 | 1.00 | 23.31 | C |
| ATOM | 3275 | OG | SER | A | 229 | −71.836 | 13.823 | −7.060 | 1.00 | 24.31 | O |
| ATOM | 3277 | C | SER | A | 229 | −69.287 | 12.394 | −6.331 | 1.00 | 23.19 | C |
| ATOM | 3278 | O | SER | A | 229 | −69.130 | 11.194 | −6.512 | 1.00 | 23.44 | O |
| ATOM | 3280 | N | VAL | A | 230 | −68.512 | 13.306 | −6.914 | 1.00 | 23.14 | N |
| ATOM | 3281 | CA | VAL | A | 230 | −67.269 | 12.874 | −7.552 | 1.00 | 23.00 | C |
| ATOM | 3283 | CB | VAL | A | 230 | −66.469 | 13.998 | −8.253 | 1.00 | 22.75 | C |
| ATOM | 3285 | CG1 | VAL | A | 230 | −65.091 | 13.470 | −8.667 | 1.00 | 21.87 | C |
| ATOM | 3289 | CG2 | VAL | A | 230 | −67.222 | 14.539 | −9.459 | 1.00 | 21.74 | C |
| ATOM | 3293 | C | VAL | A | 230 | −66.417 | 12.268 | −6.452 | 1.00 | 23.35 | C |

TABLE 16-7-continued

Coordinates of *P. tremuloides* IspS

| ATOM | 3294 | O | VAL | A | 230 | −65.917 | 11.173 | −6.589 | 1.00 | 23.68 | O |
| ATOM | 3296 | N | TYR | A | 231 | −66.284 | 12.968 | −5.340 | 1.00 | 23.96 | N |
| ATOM | 3297 | CA | TYR | A | 231 | −65.414 | 12.509 | −4.274 | 1.00 | 24.60 | C |
| ATOM | 3299 | CB | TYR | A | 231 | −65.486 | 13.426 | −3.051 | 1.00 | 24.69 | C |
| ATOM | 3302 | CG | TYR | A | 231 | −64.963 | 14.837 | −3.211 | 1.00 | 24.11 | C |
| ATOM | 3303 | CD1 | TYR | A | 231 | −64.071 | 15.190 | −4.214 | 1.00 | 24.31 | C |
| ATOM | 3305 | CE1 | TYR | A | 231 | −63.592 | 16.491 | −4.322 | 1.00 | 24.63 | C |
| ATOM | 3307 | CZ | TYR | A | 231 | −63.994 | 17.441 | −3.406 | 1.00 | 25.13 | C |
| ATOM | 3308 | OH | TYR | A | 231 | −63.554 | 18.754 | −3.456 | 1.00 | 24.64 | O |
| ATOM | 3310 | CE2 | TYR | A | 231 | −64.863 | 17.086 | −2.402 | 1.00 | 25.76 | C |
| ATOM | 3312 | CD2 | TYR | A | 231 | −65.329 | 15.800 | −2.308 | 1.00 | 24.28 | C |
| ATOM | 3314 | C | TYR | A | 231 | −65.785 | 11.111 | −3.833 | 1.00 | 25.26 | C |
| ATOM | 3315 | O | TYR | A | 231 | −64.917 | 10.315 | −3.488 | 1.00 | 25.44 | O |
| ATOM | 3317 | N | GLN | A | 232 | −67.079 | 10.819 | −3.833 | 1.00 | 26.04 | N |
| ATOM | 3318 | CA | GLN | A | 232 | −67.566 | 9.532 | −3.362 | 1.00 | 26.57 | C |
| ATOM | 3320 | CB | GLN | A | 232 | −69.060 | 9.621 | −3.057 | 1.00 | 26.44 | C |
| ATOM | 3323 | CG | GLN | A | 232 | −69.339 | 10.397 | −1.778 | 1.00 | 26.25 | C |
| ATOM | 3326 | CD | GLN | A | 232 | −70.786 | 10.819 | −1.630 | 1.00 | 26.53 | C |
| ATOM | 3327 | OE1 | GLN | A | 232 | −71.667 | 10.305 | −2.318 | 1.00 | 27.77 | O |
| ATOM | 3328 | NE2 | GLN | A | 232 | −71.040 | 11.759 | −.723 | 1.00 | 25.51 | N |
| ATOM | 3331 | C | GLN | A | 232 | −67.238 | 8.414 | −4.351 | 1.00 | 27.44 | C |
| ATOM | 3332 | O | GLN | A | 232 | −66.852 | 7.319 | −3.935 | 1.00 | 27.33 | O |
| ATOM | 3334 | N | ARG | A | 233 | −67.373 | 8.691 | −5.649 | 1.00 | 28.66 | N |
| ATOM | 3335 | CA | ARG | A | 233 | −66.905 | 7.768 | −6.685 | 1.00 | 29.86 | C |
| ATOM | 3337 | CB | ARG | A | 233 | −67.212 | 8.292 | −8.090 | 1.00 | 30.08 | C |
| ATOM | 3340 | CG | ARG | A | 233 | −66.378 | 7.634 | −9.179 | 1.00 | 32.80 | C |
| ATOM | 3343 | CD | ARG | A | 233 | −66.913 | 7.923 | −10.572 | 1.00 | 36.74 | C |
| ATOM | 3346 | NE | ARG | A | 233 | −66.962 | 9.363 | −10.860 | 1.00 | 40.33 | N |
| ATOM | 3348 | CZ | ARG | A | 233 | −68.069 | 10.119 | −10.891 | 1.00 | 43.12 | C |
| ATOM | 3349 | NH1 | ARG | A | 233 | −69.276 | 9.600 | −10.655 | 1.00 | 44.55 | N |
| ATOM | 3352 | NH2 | ARG | A | 233 | −67.971 | 11.418 | −11.169 | 1.00 | 43.38 | N |
| ATOM | 3355 | C | ARG | A | 233 | −65.401 | 7.518 | −6.514 | 1.00 | 30.34 | C |
| ATOM | 3356 | O | ARG | A | 233 | −64.962 | 6.374 | −6.412 | 1.00 | 30.55 | O |
| ATOM | 3358 | N | ASP | A | 234 | −64.621 | 8.591 | −6.461 | 1.00 | 31.00 | N |
| ATOM | 3359 | CA | ASP | A | 234 | −63.187 | 8.487 | −6.205 | 1.00 | 31.48 | C |
| ATOM | 3361 | CB | ASP | A | 234 | −62.594 | 9.870 | −5.942 | 1.00 | 31.56 | C |
| ATOM | 3364 | CG | ASP | A | 234 | −62.573 | 10.741 | −7.167 | 1.00 | 32.78 | C |
| ATOM | 3365 | OD1 | ASP | A | 234 | −62.911 | 10.249 | −8.276 | 1.00 | 34.25 | O |
| ATOM | 3366 | OD2 | ASP | A | 234 | −62.215 | 11.930 | −7.011 | 1.00 | 34.81 | O |
| ATOM | 3367 | C | ASP | A | 234 | −62.885 | 7.596 | −5.010 | 1.00 | 31.70 | C |
| ATOM | 3368 | O | ASP | A | 234 | −61.985 | 6.780 | −5.053 | 1.00 | 31.56 | O |
| ATOM | 3370 | N | LEU | A | 235 | −63.647 | 7.766 | −3.943 | 1.00 | 32.43 | N |
| ATOM | 3371 | CA | LEU | A | 235 | −63.366 | 7.102 | −2.685 | 1.00 | 33.04 | C |
| ATOM | 3373 | CB | LEU | A | 235 | −64.072 | 7.833 | −1.553 | 1.00 | 32.57 | C |
| ATOM | 3376 | CG | LEU | A | 235 | −63.884 | 7.252 | −.167 | 1.00 | 30.85 | C |
| ATOM | 3378 | CD1 | LEU | A | 235 | −62.428 | 7.261 | .174 | 1.00 | 28.78 | C |
| ATOM | 3382 | CD2 | LEU | A | 235 | −64.703 | 8.050 | .823 | 1.00 | 29.93 | C |
| ATOM | 3386 | C | LEU | A | 235 | −63.789 | 5.637 | −2.686 | 1.00 | 34.69 | C |
| ATOM | 3387 | O | LEU | A | 235 | −63.123 | 4.812 | −2.065 | 1.00 | 35.29 | O |
| ATOM | 3389 | N | ARG | A | 236 | −64.893 | 5.299 | −3.354 | 1.00 | 36.09 | N |
| ATOM | 3390 | CA | ARG | A | 236 | −65.290 | 3.893 | −3.458 | 1.00 | 37.26 | C |
| ATOM | 3392 | CB | ARG | A | 236 | −66.672 | 3.736 | −4.103 | 1.00 | 37.64 | C |
| ATOM | 3395 | CG | ARG | A | 236 | −67.839 | 4.000 | −3.157 | 1.00 | 39.15 | C |
| ATOM | 3398 | CD | ARG | A | 236 | −69.162 | 3.528 | −3.741 | 1.00 | 40.25 | C |
| ATOM | 3401 | NE | ARG | A | 236 | −69.385 | 4.046 | −5.095 | 1.00 | 41.64 | N |
| ATOM | 3403 | CZ | ARG | A | 236 | −69.837 | 5.269 | −5.392 | 1.00 | 42.54 | C |
| ATOM | 3404 | NH1 | ARG | A | 236 | −70.115 | 6.147 | −4.430 | 1.00 | 42.18 | N |
| ATOM | 3407 | NH2 | ARG | A | 236 | −70.012 | 5.621 | −6.668 | 1.00 | 43.04 | N |
| ATOM | 3410 | C | ARG | A | 236 | −64.266 | 3.108 | −4.262 | 1.00 | 37.81 | C |
| ATOM | 3411 | O | ARG | A | 236 | −64.104 | 1.912 | −4.060 | 1.00 | 38.07 | O |
| ATOM | 3413 | N | GLU | A | 237 | −63.584 | 3.801 | −5.168 | 1.00 | 38.69 | N |
| ATOM | 3414 | CA | GLU | A | 237 | −62.639 | 3.189 | −6.102 | 1.00 | 39.45 | C |
| ATOM | 3416 | CB | GLU | A | 237 | −62.452 | 4.108 | −7.338 | 1.00 | 40.25 | C |
| ATOM | 3419 | CG | GLU | A | 237 | −62.268 | 3.387 | −8.710 | 1.00 | 43.02 | C |
| ATOM | 3422 | CD | GLU | A | 237 | −60.835 | 3.458 | −9.287 | 1.00 | 46.64 | C |
| ATOM | 3423 | OE1 | GLU | A | 237 | −60.093 | 4.440 | −8.997 | 1.00 | 48.03 | O |
| ATOM | 3424 | OE2 | GLU | A | 237 | −60.466 | 2.519 | −10.047 | 1.00 | 48.35 | O |
| ATOM | 3425 | C | GLU | A | 237 | −61.310 | 2.905 | −5.408 | 1.00 | 38.70 | C |
| ATOM | 3426 | O | GLU | A | 237 | −60.832 | 1.782 | −5.440 | 1.00 | 38.33 | O |
| ATOM | 3428 | N | THR | A | 238 | −60.726 | 3.908 | −4.764 | 1.00 | 38.40 | N |
| ATOM | 3429 | CA | THR | A | 238 | −59.504 | 3.669 | −4.009 | 1.00 | 38.74 | C |
| ATOM | 3431 | CB | THR | A | 238 | −58.710 | 4.965 | −3.593 | 1.00 | 38.78 | C |
| ATOM | 3433 | OG1 | THR | A | 238 | −59.294 | 5.583 | −2.444 | 1.00 | 38.38 | O |
| ATOM | 3435 | CG2 | THR | A | 238 | −58.612 | 5.963 | −4.743 | 1.00 | 38.94 | C |
| ATOM | 3439 | C | THR | A | 238 | −59.802 | 2.834 | −2.773 | 1.00 | 39.05 | C |
| ATOM | 3440 | O | THR | A | 238 | −58.886 | 2.294 | −2.153 | 1.00 | 39.17 | O |
| ATOM | 3442 | N | SER | A | 239 | −61.076 | 2.717 | −2.408 | 1.00 | 39.34 | N |
| ATOM | 3443 | CA | SER | A | 239 | −61.443 | 1.841 | −1.304 | 1.00 | 39.47 | C |

TABLE 16-7-continued

Coordinates of *P. tremuloides* IspS

| ATOM | 3445 | CB | SER | A | 239 | −62.844 | 2.149 | −.792 | 1.00 | 39.34 | C |
|---|---|---|---|---|---|---|---|---|---|---|---|
| ATOM | 3448 | OG | SER | A | 239 | −63.087 | 1.428 | .396 | 1.00 | 39.94 | O |
| ATOM | 3450 | C | SER | A | 239 | −61.313 | .367 | −1.699 | 1.00 | 39.53 | C |
| ATOM | 3451 | O | SER | A | 239 | −60.834 | −.439 | −.900 | 1.00 | 39.53 | O |
| ATOM | 3453 | N | ARG | A | 240 | −61.728 | .021 | −2.921 | 1.00 | 39.69 | N |
| ATOM | 3454 | CA | ARG | A | 240 | −61.559 | −1.341 | −3.439 | 1.00 | 39.79 | C |
| ATOM | 3456 | CB | ARG | A | 240 | −62.105 | −1.492 | −4.867 | 1.00 | 40.34 | C |
| ATOM | 3459 | CG | ARG | A | 240 | −63.624 | −1.715 | −4.947 | 1.00 | 43.03 | C |
| ATOM | 3462 | CD | ARG | A | 240 | −64.104 | −2.125 | −6.364 | 1.00 | 46.66 | C |
| ATOM | 3465 | NE | ARG | A | 240 | −63.780 | −1.136 | −7.416 | 1.00 | 50.46 | N |
| ATOM | 3467 | CZ | ARG | A | 240 | −64.535 | −.082 | −7.775 | 1.00 | 53.13 | C |
| ATOM | 3468 | NH1 | ARG | A | 240 | −64.112 | .732 | −8.749 | 1.00 | 53.13 | N |
| ATOM | 3471 | NH2 | ARG | A | 240 | −65.707 | .178 | −7.178 | 1.00 | 54.02 | N |
| ATOM | 3474 | C | ARG | A | 240 | −60.089 | −1.704 | −3.414 | 1.00 | 38.94 | C |
| ATOM | 3475 | O | ARG | A | 240 | −59.732 | −2.795 | −2.978 | 1.00 | 39.09 | O |
| ATOM | 3477 | N | TRP | A | 241 | −59.246 | −.775 | −3.862 | 1.00 | 37.92 | N |
| ATOM | 3478 | CA | TRP | A | 241 | −57.787 | −.947 | −3.842 | 1.00 | 36.93 | C |
| ATOM | 3480 | CB | TRP | A | 241 | −57.099 | .318 | −4.388 | 1.00 | 36.57 | C |
| ATOM | 3483 | CG | TRP | A | 241 | −55.624 | .333 | −4.209 | 1.00 | 34.71 | C |
| ATOM | 3484 | CD1 | TRP | A | 241 | −54.702 | −.312 | −4.969 | 1.00 | 33.50 | C |
| ATOM | 3486 | NE1 | TRP | A | 241 | −53.441 | −.068 | −4.482 | 1.00 | 32.62 | N |
| ATOM | 3488 | CE2 | TRP | A | 241 | −53.538 | .747 | −3.392 | 1.00 | 31.16 | C |
| ATOM | 3489 | CD2 | TRP | A | 241 | −54.896 | 1.022 | −3.191 | 1.00 | 32.61 | C |
| ATOM | 3490 | CE3 | TRP | A | 241 | −55.268 | 1.837 | −2.117 | 1.00 | 32.63 | C |
| ATOM | 3492 | CZ3 | TRP | A | 241 | −54.293 | 2.345 | −1.307 | 1.00 | 31.31 | C |
| ATOM | 3494 | CH2 | TRP | A | 241 | −52.956 | 2.053 | −1.537 | 1.00 | 31.81 | C |
| ATOM | 3496 | CZ2 | TRP | A | 241 | −52.560 | 1.252 | −2.577 | 1.00 | 31.18 | C |
| ATOM | 3498 | C | TRP | A | 241 | −57.263 | −1.274 | −2.444 | 1.00 | 36.67 | C |
| ATOM | 3499 | O | TRP | A | 241 | −56.540 | −2.247 | −2.252 | 1.00 | 36.32 | O |
| ATOM | 3501 | N | TRP | A | 242 | −57.647 | −.460 | −1.471 | 1.00 | 36.59 | N |
| ATOM | 3502 | CA | TRP | A | 242 | −57.150 | −.593 | −.100 | 1.00 | 36.80 | C |
| ATOM | 3504 | CB | TRP | A | 242 | −57.694 | .582 | .734 | 1.00 | 36.47 | C |
| ATOM | 3507 | CG | TRP | A | 242 | −57.113 | .754 | 2.107 | 1.00 | 35.59 | C |
| ATOM | 3508 | CD1 | TRP | A | 242 | −57.806 | .831 | 3.270 | 1.00 | 35.14 | C |
| ATOM | 3510 | NE1 | TRP | A | 242 | −56.950 | .999 | 4.328 | 1.00 | 34.47 | N |
| ATOM | 3512 | CE2 | TRP | A | 242 | −55.667 | 1.032 | 3.859 | 1.00 | 34.64 | C |
| ATOM | 3513 | CD2 | TRP | A | 242 | −55.728 | .884 | 2.461 | 1.00 | 35.26 | C |
| ATOM | 3514 | CE3 | TRP | A | 242 | −54.531 | .882 | 1.732 | 1.00 | 35.22 | C |
| ATOM | 3516 | CZ3 | TRP | A | 242 | −53.342 | 1.024 | 2.409 | 1.00 | 34.30 | C |
| ATOM | 3518 | CH2 | TRP | A | 242 | −53.318 | 1.169 | 3.799 | 1.00 | 34.70 | C |
| ATOM | 3520 | CZ2 | TRP | A | 242 | −54.467 | 1.173 | 4.542 | 1.00 | 34.63 | C |
| ATOM | 3522 | C | TRP | A | 242 | −57.482 | −1.975 | .524 | 1.00 | 37.34 | C |
| ATOM | 3523 | O | TRP | A | 242 | −56.628 | −2.623 | 1.126 | 1.00 | 36.53 | O |
| ATOM | 3525 | N | ARG | A | 243 | −58.720 | −2.421 | .348 | 1.00 | 38.54 | N |
| ATOM | 3526 | CA | ARG | A | 243 | −59.149 | −3.734 | .822 | 1.00 | 39.71 | C |
| ATOM | 3528 | CB | ARG | A | 243 | −60.669 | −3.896 | .687 | 1.00 | 40.10 | C |
| ATOM | 3531 | CG | ARG | A | 243 | −61.495 | −3.134 | 1.747 | 1.00 | 42.18 | C |
| ATOM | 3534 | CD | ARG | A | 243 | −62.826 | −2.623 | 1.169 | 1.00 | 45.18 | C |
| ATOM | 3537 | NE | ARG | A | 243 | −63.506 | −3.656 | .369 | 1.00 | 48.22 | N |
| ATOM | 3539 | CZ | ARG | A | 243 | −64.374 | −3.431 | −.629 | 1.00 | 49.95 | C |
| ATOM | 3540 | NH1 | ARG | A | 243 | −64.717 | −2.182 | −.991 | 1.00 | 50.13 | N |
| ATOM | 3543 | NH2 | ARG | A | 243 | −64.911 | −4.477 | −1.273 | 1.00 | 49.77 | N |
| ATOM | 3546 | C | ARG | A | 243 | −58.438 | −4.852 | .068 | 1.00 | 40.08 | C |
| ATOM | 3547 | O | ARG | A | 243 | −58.084 | −5.870 | .665 | 1.00 | 40.45 | O |
| ATOM | 3549 | N | ARG | A | 244 | −58.236 | −4.663 | −1.236 | 1.00 | 40.42 | N |
| ATOM | 3550 | CA | ARG | A | 244 | −57.499 | −5.621 | −2.063 | 1.00 | 40.65 | C |
| ATOM | 3552 | CB | ARG | A | 244 | −57.370 | −5.100 | −3.503 | 1.00 | 41.29 | C |
| ATOM | 3555 | CG | ARG | A | 244 | −56.939 | −6.126 | −4.560 | 1.00 | 43.27 | C |
| ATOM | 3558 | CD | ARG | A | 244 | −58.090 | −7.062 | −4.952 | 1.00 | 46.01 | C |
| ATOM | 3561 | NE | ARG | A | 244 | −57.595 | −8.337 | −5.485 | 1.00 | 48.77 | N |
| ATOM | 3563 | CZ | ARG | A | 244 | −57.075 | −9.332 | −4.752 | 1.00 | 51.17 | C |
| ATOM | 3564 | NH1 | ARG | A | 244 | −56.968 | −9.234 | −3.422 | 1.00 | 51.63 | N |
| ATOM | 3567 | NH2 | ARG | A | 244 | −56.656 | −10.448 | −5.353 | 1.00 | 52.11 | N |
| ATOM | 3570 | C | ARG | A | 244 | −56.120 | −5.861 | −1.465 | 1.00 | 40.12 | C |
| ATOM | 3571 | O | ARG | A | 244 | −55.728 | −7.000 | −1.235 | 1.00 | 39.96 | O |
| ATOM | 3573 | N | VAL | A | 245 | −55.399 | −4.778 | −1.201 | 1.00 | 39.78 | N |
| ATOM | 3574 | CA | VAL | A | 245 | −54.099 | −4.858 | −.543 | 1.00 | 39.68 | C |
| ATOM | 3576 | CB | VAL | A | 245 | −53.430 | −3.458 | −.437 | 1.00 | 39.70 | C |
| ATOM | 3578 | CG1 | VAL | A | 245 | −53.133 | −2.914 | −1.824 | 1.00 | 39.54 | C |
| ATOM | 3582 | CG2 | VAL | A | 245 | −52.145 | −3.507 | .395 | 1.00 | 39.41 | C |
| ATOM | 3586 | C | VAL | A | 245 | −54.262 | −5.472 | .841 | 1.00 | 39.73 | C |
| ATOM | 3587 | O | VAL | A | 245 | −53.455 | −6.291 | 1.253 | 1.00 | 39.53 | O |
| ATOM | 3589 | N | GLY | A | 246 | −55.312 | −5.051 | 1.544 | 1.00 | 40.11 | N |
| ATOM | 3590 | CA | GLY | A | 246 | −55.705 | −5.617 | 2.839 | 1.00 | 40.35 | C |
| ATOM | 3593 | C | GLY | A | 246 | −54.621 | −5.648 | 3.894 | 1.00 | 40.58 | C |
| ATOM | 3594 | O | GLY | A | 246 | −54.396 | −6.676 | 4.510 | 1.00 | 40.68 | O |
| ATOM | 3596 | N | LEU | A | 247 | −53.963 | −4.522 | 4.129 | 1.00 | 41.15 | N |
| ATOM | 3597 | CA | LEU | A | 247 | −52.778 | −4.519 | 4.982 | 1.00 | 41.71 | C |

TABLE 16-7-continued

| | | | | | | | | | | | |
|---|---|---|---|---|---|---|---|---|---|---|---|
| ATOM | 3599 | CB | LEU | A | 247 | −51.808 | −3.422 | 4.537 | 1.00 | 41.60 | C |
| ATOM | 3602 | CG | LEU | A | 247 | −50.334 | −3.815 | 4.441 | 1.00 | 40.83 | C |
| ATOM | 3604 | CD1 | LEU | A | 247 | −50.158 | −5.014 | 3.539 | 1.00 | 40.54 | C |
| ATOM | 3608 | CD2 | LEU | A | 247 | −49.534 | −2.644 | 3.918 | 1.00 | 39.92 | C |
| ATOM | 3612 | C | LEU | A | 247 | −53.136 | −4.385 | 6.471 | 1.00 | 42.60 | C |
| ATOM | 3613 | O | LEU | A | 247 | −52.588 | −5.111 | 7.313 | 1.00 | 42.06 | O |
| ATOM | 3615 | N | ALA | A | 248 | −54.064 | −3.475 | 6.788 | 1.00 | 43.75 | N |
| ATOM | 3616 | CA | ALA | A | 248 | −54.603 | −3.352 | 8.162 | 1.00 | 44.52 | C |
| ATOM | 3618 | CB | ALA | A | 248 | −55.712 | −2.296 | 8.210 | 1.00 | 44.31 | C |
| ATOM | 3622 | C | ALA | A | 248 | −55.129 | −4.706 | 8.695 | 1.00 | 45.10 | C |
| ATOM | 3623 | O | ALA | A | 248 | −54.969 | −5.041 | 9.875 | 1.00 | 44.96 | O |
| ATOM | 3625 | N | THR | A | 249 | −55.742 | −5.477 | 7.802 | 1.00 | 45.91 | N |
| ATOM | 3626 | CA | THR | A | 249 | −56.328 | −6.768 | 8.154 | 1.00 | 46.50 | C |
| ATOM | 3628 | CB | THR | A | 249 | −57.303 | −7.277 | 7.041 | 1.00 | 46.48 | C |
| ATOM | 3630 | OG1 | THR | A | 249 | −56.583 | −8.039 | 6.063 | 1.00 | 46.20 | O |
| ATOM | 3632 | CG2 | THR | A | 249 | −58.033 | −6.102 | 6.350 | 1.00 | 46.70 | C |
| ATOM | 3636 | C | THR | A | 249 | −55.257 | −7.840 | 8.447 | 1.00 | 47.06 | C |
| ATOM | 3637 | O | THR | A | 249 | −55.531 | −8.813 | 9.159 | 1.00 | 47.22 | O |
| ATOM | 3639 | N | LYS | A | 250 | −54.049 | −7.661 | 7.905 | 1.00 | 47.52 | N |
| ATOM | 3640 | CA | LYS | A | 250 | −52.952 | −8.620 | 8.096 | 1.00 | 47.91 | C |
| ATOM | 3642 | CB | LYS | A | 250 | −52.319 | −8.976 | 6.744 | 1.00 | 48.09 | C |
| ATOM | 3645 | CG | LYS | A | 250 | −52.911 | −10.229 | 6.088 | 1.00 | 48.91 | C |
| ATOM | 3648 | CD | LYS | A | 250 | −52.210 | −11.510 | 6.585 | 1.00 | 49.88 | C |
| ATOM | 3651 | CE | LYS | A | 250 | −53.066 | −12.760 | 6.349 | 1.00 | 50.12 | C |
| ATOM | 3654 | NZ | LYS | A | 250 | −52.385 | −14.011 | 6.791 | 1.00 | 49.99 | N |
| ATOM | 3658 | C | LYS | A | 250 | −51.880 | −8.129 | 9.078 | 1.00 | 48.13 | C |
| ATOM | 3659 | O | LYS | A | 250 | −51.252 | −8.939 | 9.759 | 1.00 | 47.89 | O |
| ATOM | 3661 | N | LEU | A | 251 | −51.667 | −6.812 | 9.134 | 1.00 | 48.63 | N |
| ATOM | 3662 | CA | LEU | A | 251 | −50.758 | −6.187 | 10.114 | 1.00 | 48.83 | C |
| ATOM | 3664 | CB | LEU | A | 251 | −49.981 | −5.020 | 9.485 | 1.00 | 48.74 | C |
| ATOM | 3667 | CG | LEU | A | 251 | −48.569 | −5.296 | 8.960 | 1.00 | 48.51 | C |
| ATOM | 3669 | CD1 | LEU | A | 251 | −48.472 | −6.594 | 8.174 | 1.00 | 47.96 | C |
| ATOM | 3673 | CD2 | LEU | A | 251 | −48.102 | −4.115 | 8.116 | 1.00 | 48.76 | C |
| ATOM | 3677 | C | LEU | A | 251 | −51.559 | −5.703 | 11.324 | 1.00 | 49.17 | C |
| ATOM | 3678 | O | LEU | A | 251 | −52.176 | −4.632 | 11.304 | 1.00 | 49.28 | O |
| ATOM | 3680 | N | HIS | A | 252 | −51.521 | −6.486 | 12.393 | 1.00 | 49.53 | N |
| ATOM | 3681 | CA | HIS | A | 252 | −52.470 | −6.322 | 13.494 | 1.00 | 50.02 | C |
| ATOM | 3683 | CB | HIS | A | 252 | −52.598 | −7.647 | 14.266 | 1.00 | 50.42 | C |
| ATOM | 3686 | CG | HIS | A | 252 | −52.860 | −8.834 | 13.380 | 1.00 | 52.23 | C |
| ATOM | 3687 | ND1 | HIS | A | 252 | −54.032 | −8.989 | 12.667 | 1.00 | 53.75 | N |
| ATOM | 3689 | CE1 | HIS | A | 252 | −53.978 | −10.113 | 11.973 | 1.00 | 54.43 | C |
| ATOM | 3691 | NE2 | HIS | A | 252 | −52.810 | −10.689 | 12.201 | 1.00 | 54.52 | N |
| ATOM | 3693 | CD2 | HIS | A | 252 | −52.090 | −9.910 | 13.077 | 1.00 | 53.70 | C |
| ATOM | 3695 | C | HIS | A | 252 | −52.161 | −5.147 | 14.441 | 1.00 | 49.64 | C |
| ATOM | 3696 | O | HIS | A | 252 | −52.951 | −4.849 | 15.336 | 1.00 | 49.61 | O |
| ATOM | 3698 | N | PHE | A | 253 | −51.027 | −4.483 | 14.229 | 1.00 | 49.37 | N |
| ATOM | 3699 | CA | PHE | A | 253 | −50.652 | −3.273 | 14.973 | 1.00 | 49.15 | C |
| ATOM | 3701 | CB | PHE | A | 253 | −49.144 | −3.273 | 15.260 | 1.00 | 49.07 | C |
| ATOM | 3704 | CG | PHE | A | 253 | −48.307 | −3.112 | 14.025 | 1.00 | 48.30 | C |
| ATOM | 3705 | CD1 | PHE | A | 253 | −48.028 | −1.851 | 13.518 | 1.00 | 48.10 | C |
| ATOM | 3707 | CE1 | PHE | A | 253 | −47.290 | −1.702 | 12.349 | 1.00 | 48.21 | C |
| ATOM | 3709 | CZ | PHE | A | 253 | −46.825 | −2.825 | 11.675 | 1.00 | 47.88 | C |
| ATOM | 3711 | CE2 | PHE | A | 253 | −47.101 | −4.090 | 12.175 | 1.00 | 47.66 | C |
| ATOM | 3713 | CD2 | PHE | A | 253 | −47.842 | −4.226 | 13.338 | 1.00 | 47.74 | C |
| ATOM | 3715 | C | PHE | A | 253 | −50.974 | −2.006 | 14.176 | 1.00 | 49.31 | C |
| ATOM | 3716 | O | PHE | A | 253 | −50.846 | −.893 | 14.702 | 1.00 | 49.01 | O |
| ATOM | 3718 | N | ALA | A | 254 | −51.365 | −2.185 | 12.910 | 1.00 | 49.48 | N |
| ATOM | 3719 | CA | ALA | A | 254 | −51.412 | −1.095 | 11.931 | 1.00 | 49.63 | C |
| ATOM | 3721 | CB | ALA | A | 254 | −51.344 | −1.663 | 10.524 | 1.00 | 49.64 | C |
| ATOM | 3725 | C | ALA | A | 254 | −52.650 | −.224 | 12.061 | 1.00 | 49.77 | C |
| ATOM | 3726 | O | ALA | A | 254 | −53.761 | −.735 | 12.219 | 1.00 | 49.86 | O |
| ATOM | 3728 | N | ARG | A | 255 | −52.452 | 1.090 | 11.975 | 1.00 | 49.93 | N |
| ATOM | 3729 | CA | ARG | A | 255 | −53.562 | 2.042 | 11.908 | 1.00 | 50.27 | C |
| ATOM | 3731 | CB | ARG | A | 255 | −53.094 | 3.468 | 12.237 | 1.00 | 50.43 | C |
| ATOM | 3734 | CG | ARG | A | 255 | −52.678 | 3.736 | 13.696 | 1.00 | 50.82 | C |
| ATOM | 3737 | CD | ARG | A | 255 | −52.242 | 5.211 | 13.887 | 1.00 | 51.32 | C |
| ATOM | 3740 | NE | ARG | A | 255 | −51.003 | 5.522 | 13.155 | 1.00 | 51.81 | N |
| ATOM | 3742 | CZ | ARG | A | 255 | −50.571 | 6.746 | 12.829 | 1.00 | 51.67 | C |
| ATOM | 3743 | NH1 | ARG | A | 255 | −51.264 | 7.839 | 13.146 | 1.00 | 51.63 | N |
| ATOM | 3746 | NH2 | ARG | A | 255 | −49.427 | 6.877 | 12.162 | 1.00 | 51.52 | N |
| ATOM | 3749 | C | ARG | A | 255 | −54.160 | 2.040 | 10.497 | 1.00 | 50.32 | C |
| ATOM | 3750 | O | ARG | A | 255 | −53.416 | 2.081 | 9.504 | 1.00 | 50.35 | O |
| ATOM | 3752 | N | ASP | A | 256 | −55.492 | 2.005 | 10.412 | 1.00 | 50.17 | N |
| ATOM | 3753 | CA | ASP | A | 256 | −56.190 | 2.090 | 9.128 | 1.00 | 50.18 | C |
| ATOM | 3755 | CB | ASP | A | 256 | −57.259 | 1.009 | 9.037 | 1.00 | 50.37 | C |
| ATOM | 3758 | CG | ASP | A | 256 | −58.095 | 1.130 | 7.780 | 1.00 | 50.96 | C |
| ATOM | 3759 | OD1 | ASP | A | 256 | −59.252 | 1.601 | 7.881 | 1.00 | 52.00 | O |
| ATOM | 3760 | OD2 | ASP | A | 256 | −57.581 | .787 | 6.693 | 1.00 | 50.94 | O |

TABLE 16-7-continued

Coordinates of *P. tremuloides* IspS

| ATOM | 3761 | C | ASP | A | 256 | −56.838 | 3.470 | 8.945 | 1.00 | 49.85 | C |
| --- | --- | --- | --- | --- | --- | --- | --- | --- | --- | --- | --- |
| ATOM | 3762 | O | ASP | A | 256 | −57.812 | 3.804 | 9.624 | 1.00 | 50.13 | O |
| ATOM | 3764 | N | ARG | A | 257 | −56.315 | 4.263 | 8.013 | 1.00 | 49.11 | N |
| ATOM | 3765 | CA | ARG | A | 257 | −56.712 | 5.665 | 7.913 | 1.00 | 48.59 | C |
| ATOM | 3767 | CB | ARG | A | 257 | −55.622 | 6.553 | 8.529 | 1.00 | 48.79 | C |
| ATOM | 3770 | CG | ARG | A | 257 | −55.318 | 6.275 | 10.006 | 1.00 | 49.85 | C |
| ATOM | 3773 | CD | ARG | A | 257 | −56.538 | 6.480 | 10.908 | 1.00 | 51.01 | C |
| ATOM | 3776 | NE | ARG | A | 257 | −56.198 | 7.274 | 12.089 | 1.00 | 51.80 | N |
| ATOM | 3778 | CZ | ARG | A | 257 | −55.779 | 6.791 | 13.260 | 1.00 | 52.00 | C |
| ATOM | 3779 | NH1 | ARG | A | 257 | −55.643 | 5.486 | 13.468 | 1.00 | 51.64 | N |
| ATOM | 3782 | NH2 | ARG | A | 257 | −55.501 | 7.638 | 14.245 | 1.00 | 52.62 | N |
| ATOM | 3785 | C | ARG | A | 257 | −56.988 | 6.112 | 6.477 | 1.00 | 47.58 | C |
| ATOM | 3786 | O | ARG | A | 257 | −56.476 | 7.144 | 6.031 | 1.00 | 47.40 | O |
| ATOM | 3788 | N | LEU | A | 258 | −57.814 | 5.352 | 5.761 | 1.00 | 46.18 | N |
| ATOM | 3789 | CA | LEU | A | 258 | −58.094 | 5.672 | 4.358 | 1.00 | 44.78 | C |
| ATOM | 3791 | CB | LEU | A | 258 | −58.777 | 4.508 | 3.629 | 1.00 | 44.57 | C |
| ATOM | 3794 | CG | LEU | A | 258 | −58.917 | 4.731 | 2.121 | 1.00 | 43.79 | C |
| ATOM | 3796 | CD1 | LEU | A | 258 | −57.557 | 4.661 | 1.478 | 1.00 | 43.89 | C |
| ATOM | 3800 | CD2 | LEU | A | 258 | −59.850 | 3.733 | 1.492 | 1.00 | 42.88 | C |
| ATOM | 3804 | C | LEU | A | 258 | −58.970 | 6.907 | 4.259 | 1.00 | 43.52 | C |
| ATOM | 3805 | O | LEU | A | 258 | −58.643 | 7.849 | 3.545 | 1.00 | 43.42 | O |
| ATOM | 3807 | N | ILE | A | 259 | −60.080 | 6.895 | 4.983 | 1.00 | 41.98 | N |
| ATOM | 3808 | CA | ILE | A | 259 | −61.072 | 7.948 | 4.843 | 1.00 | 40.89 | C |
| ATOM | 3810 | CB | ILE | A | 259 | −62.349 | 7.703 | 5.693 | 1.00 | 41.02 | C |
| ATOM | 3812 | CG1 | ILE | A | 259 | −62.846 | 6.248 | 5.570 | 1.00 | 41.82 | C |
| ATOM | 3815 | CD1 | ILE | A | 259 | −64.029 | 5.872 | 6.508 | 1.00 | 42.29 | C |
| ATOM | 3819 | CG2 | ILE | A | 259 | −63.446 | 8.662 | 5.262 | 1.00 | 40.47 | C |
| ATOM | 3823 | C | ILE | A | 259 | −60.424 | 9.253 | 5.273 | 1.00 | 39.74 | C |
| ATOM | 3824 | O | ILE | A | 259 | −60.607 | 10.291 | 4.635 | 1.00 | 39.25 | O |
| ATOM | 3826 | N | GLU | A | 260 | −59.650 | 9.191 | 6.355 | 1.00 | 38.46 | N |
| ATOM | 3827 | CA | GLU | A | 260 | −58.951 | 10.366 | 6.846 | 1.00 | 37.44 | C |
| ATOM | 3829 | CB | GLU | A | 260 | −58.183 | 10.072 | 8.140 | 1.00 | 37.74 | C |
| ATOM | 3832 | CG | GLU | A | 260 | −59.041 | 9.934 | 9.393 | 1.00 | 38.71 | C |
| ATOM | 3835 | CD | GLU | A | 260 | −59.469 | 8.501 | 9.693 | 1.00 | 41.00 | C |
| ATOM | 3836 | OE1 | GLU | A | 260 | −59.273 | 7.594 | 8.842 | 1.00 | 42.70 | O |
| ATOM | 3837 | OE2 | GLU | A | 260 | −60.012 | 8.281 | 10.800 | 1.00 | 42.43 | O |
| ATOM | 3838 | C | GLU | A | 260 | −57.995 | 10.841 | 5.764 | 1.00 | 35.94 | C |
| ATOM | 3839 | O | GLU | A | 260 | −57.981 | 12.020 | 5.418 | 1.00 | 36.10 | O |
| ATOM | 3841 | N | SER | A | 261 | −57.222 | 9.908 | 5.212 | 1.00 | 34.02 | N |
| ATOM | 3842 | CA | SER | A | 261 | −56.263 | 10.229 | 4.152 | 1.00 | 32.47 | C |
| ATOM | 3844 | CB | SER | A | 261 | −55.407 | 9.015 | 3.774 | 1.00 | 32.51 | C |
| ATOM | 3847 | OG | SER | A | 261 | −54.253 | 8.940 | 4.584 | 1.00 | 33.14 | O |
| ATOM | 3849 | C | SER | A | 261 | −56.894 | 10.764 | 2.889 | 1.00 | 30.82 | C |
| ATOM | 3850 | O | SER | A | 261 | −56.199 | 11.306 | 2.062 | 1.00 | 30.79 | O |
| ATOM | 3852 | N | PHE | A | 262 | −58.194 | 10.589 | 2.713 | 1.00 | 29.25 | N |
| ATOM | 3853 | CA | PHE | A | 262 | −58.861 | 11.091 | 1.514 | 1.00 | 27.98 | C |
| ATOM | 3855 | CB | PHE | A | 262 | −60.011 | 10.185 | 1.119 | 1.00 | 27.57 | C |
| ATOM | 3858 | CG | PHE | A | 262 | −60.473 | 10.423 | −.251 | 1.00 | 26.11 | C |
| ATOM | 3859 | CD1 | PHE | A | 262 | −59.763 | 9.914 | −1.318 | 1.00 | 25.14 | C |
| ATOM | 3861 | CE1 | PHE | A | 262 | −60.169 | 10.147 | −2.605 | 1.00 | 24.32 | C |
| ATOM | 3863 | CZ | PHE | A | 262 | −61.284 | 10.917 | −2.840 | 1.00 | 24.36 | C |
| ATOM | 3865 | CE2 | PHE | A | 262 | −61.987 | 11.445 | −1.785 | 1.00 | 25.23 | C |
| ATOM | 3867 | CD2 | PHE | A | 262 | −61.575 | 11.201 | −.492 | 1.00 | 25.61 | C |
| ATOM | 3869 | C | PHE | A | 262 | −59.394 | 12.507 | 1.707 | 1.00 | 27.29 | C |
| ATOM | 3870 | O | PHE | A | 262 | −59.275 | 13.359 | .821 | 1.00 | 27.39 | O |
| ATOM | 3872 | N | TYR | A | 263 | −60.025 | 12.723 | 2.856 | 1.00 | 26.19 | N |
| ATOM | 3873 | CA | TYR | A | 263 | −60.415 | 14.052 | 3.310 | 1.00 | 25.22 | C |
| ATOM | 3875 | CB | TYR | A | 263 | −60.975 | 13.942 | 4.735 | 1.00 | 25.21 | C |
| ATOM | 3878 | CG | TYR | A | 263 | −61.037 | 15.199 | 5.578 | 1.00 | 25.37 | C |
| ATOM | 3879 | CD1 | TYR | A | 263 | −62.020 | 16.152 | 5.385 | 1.00 | 24.95 | C |
| ATOM | 3881 | CE1 | TYR | A | 263 | −62.084 | 17.282 | 6.197 | 1.00 | 26.54 | C |
| ATOM | 3883 | CZ | TYR | A | 263 | −61.158 | 17.455 | 7.229 | 1.00 | 27.44 | C |
| ATOM | 3884 | OH | TYR | A | 263 | −61.186 | 18.567 | 8.059 | 1.00 | 28.97 | O |
| ATOM | 3886 | CE2 | TYR | A | 263 | −60.185 | 16.512 | 7.438 | 1.00 | 27.10 | C |
| ATOM | 3888 | CD2 | TYR | A | 263 | −60.136 | 15.390 | 6.626 | 1.00 | 26.91 | C |
| ATOM | 3890 | C | TYR | A | 263 | −59.190 | 14.946 | 3.238 | 1.00 | 24.29 | C |
| ATOM | 3891 | O | TYR | A | 263 | −59.267 | 16.077 | 2.757 | 1.00 | 24.13 | O |
| ATOM | 3893 | N | TRP | A | 264 | −58.055 | 14.415 | 3.682 | 1.00 | 23.01 | N |
| ATOM | 3894 | CA | TRP | A | 264 | −56.789 | 15.121 | 3.567 | 1.00 | 22.32 | C |
| ATOM | 3896 | CB | TRP | A | 264 | −55.642 | 14.261 | 4.119 | 1.00 | 22.26 | C |
| ATOM | 3899 | CG | TRP | A | 264 | −54.326 | 14.874 | 3.860 | 1.00 | 22.16 | C |
| ATOM | 3900 | CD1 | TRP | A | 264 | −53.614 | 14.821 | 2.699 | 1.00 | 22.68 | C |
| ATOM | 3902 | NE1 | TRP | A | 264 | −52.456 | 15.538 | 2.818 | 1.00 | 23.08 | N |
| ATOM | 3904 | CE2 | TRP | A | 264 | −52.407 | 16.083 | 4.072 | 1.00 | 23.07 | C |
| ATOM | 3905 | CD2 | TRP | A | 264 | −53.579 | 15.686 | 4.753 | 1.00 | 22.18 | C |
| ATOM | 3906 | CE3 | TRP | A | 264 | −53.782 | 16.119 | 6.066 | 1.00 | 22.57 | C |
| ATOM | 3908 | CZ3 | TRP | A | 264 | −52.824 | 16.925 | 6.657 | 1.00 | 23.43 | C |
| ATOM | 3910 | CH2 | TRP | A | 264 | −51.656 | 17.297 | 5.955 | 1.00 | 24.14 | C |

TABLE 16-7-continued

Coordinates of *P. tremuloides* IspS

| ATOM | 3912 | CZ2 | TRP | A | 264 | −51.433 | 16.886 | 4.663 | 1.00 | 23.64 | C |
|------|------|-----|-----|---|-----|---------|--------|-------|------|-------|---|
| ATOM | 3914 | C | TRP | A | 264 | −56.485 | 15.523 | 2.112 | 1.00 | 21.50 | C |
| ATOM | 3915 | O | TRP | A | 264 | −56.179 | 16.682 | 1.820 | 1.00 | 21.29 | O |
| ATOM | 3917 | N | ALA | A | 265 | −56.561 | 14.547 | 1.213 | 1.00 | 20.41 | N |
| ATOM | 3918 | CA | ALA | A | 265 | −56.242 | 14.760 | −.187 | 1.00 | 19.63 | C |
| ATOM | 3920 | CB | ALA | A | 265 | −56.298 | 13.437 | −.953 | 1.00 | 19.39 | C |
| ATOM | 3924 | C | ALA | A | 265 | −57.176 | 15.792 | −.798 | 1.00 | 19.07 | C |
| ATOM | 3925 | O | ALA | A | 265 | −56.760 | 16.573 | −1.633 | 1.00 | 18.99 | O |
| ATOM | 3927 | N | VAL | A | 266 | −58.431 | 15.814 | −.359 | 1.00 | 18.78 | N |
| ATOM | 3928 | CA | VAL | A | 266 | −59.396 | 16.828 | −.818 | 1.00 | 18.56 | C |
| ATOM | 3930 | CB | VAL | A | 266 | −60.839 | 16.541 | −.278 | 1.00 | 18.41 | C |
| ATOM | 3932 | CG1 | VAL | A | 266 | −61.405 | 15.298 | −.935 | 1.00 | 18.88 | C |
| ATOM | 3936 | CG2 | VAL | A | 266 | −61.780 | 17.709 | −.505 | 1.00 | 17.21 | C |
| ATOM | 3940 | C | VAL | A | 266 | −58.947 | 18.257 | −.450 | 1.00 | 18.43 | C |
| ATOM | 3941 | O | VAL | A | 266 | −59.250 | 19.200 | −1.171 | 1.00 | 18.83 | O |
| ATOM | 3943 | N | GLY | A | 267 | −58.230 | 18.411 | .663 | 1.00 | 17.96 | N |
| ATOM | 3944 | CA | GLY | A | 267 | −57.714 | 19.712 | 1.067 | 1.00 | 17.45 | C |
| ATOM | 3947 | C | GLY | A | 267 | −56.687 | 20.180 | .070 | 1.00 | 17.20 | C |
| ATOM | 3948 | O | GLY | A | 267 | −56.574 | 21.365 | −.215 | 1.00 | 17.41 | O |
| ATOM | 3950 | N | VAL | A | 268 | −55.959 | 19.219 | −.480 | 1.00 | 16.88 | N |
| ATOM | 3951 | CA | VAL | A | 268 | −54.822 | 19.487 | −1.319 | 1.00 | 16.62 | C |
| ATOM | 3953 | CB | VAL | A | 268 | −53.833 | 18.300 | −1.290 | 1.00 | 16.19 | C |
| ATOM | 3955 | CG1 | VAL | A | 268 | −52.691 | 18.536 | −2.240 | 1.00 | 15.50 | C |
| ATOM | 3959 | CG2 | VAL | A | 268 | −53.310 | 18.121 | .103 | 1.00 | 15.30 | C |
| ATOM | 3963 | C | VAL | A | 268 | −55.262 | 19.788 | −2.736 | 1.00 | 17.15 | C |
| ATOM | 3964 | O | VAL | A | 268 | −54.748 | 20.710 | −3.350 | 1.00 | 17.12 | O |
| ATOM | 3966 | N | ALA | A | 269 | −56.217 | 19.014 | −3.243 | 1.00 | 17.99 | N |
| ATOM | 3967 | CA | ALA | A | 269 | −56.688 | 19.158 | −4.622 | 1.00 | 18.79 | C |
| ATOM | 3969 | CB | ALA | A | 269 | −55.958 | 18.183 | −5.551 | 1.00 | 18.26 | C |
| ATOM | 3973 | C | ALA | A | 269 | −58.196 | 18.938 | −4.672 | 1.00 | 19.70 | C |
| ATOM | 3974 | O | ALA | A | 269 | −58.665 | 17.834 | −4.958 | 1.00 | 19.50 | O |
| ATOM | 3976 | N | PHE | A | 270 | −58.945 | 20.011 | −4.417 | 1.00 | 21.09 | N |
| ATOM | 3977 | CA | PHE | A | 270 | −60.393 | 19.910 | −4.211 | 1.00 | 22.32 | C |
| ATOM | 3979 | CB | PHE | A | 270 | −60.925 | 21.108 | −3.404 | 1.00 | 22.49 | C |
| ATOM | 3982 | CG | PHE | A | 270 | −61.193 | 22.321 | −4.246 | 1.00 | 23.31 | C |
| ATOM | 3983 | CD1 | PHE | A | 270 | −62.423 | 22.483 | −4.883 | 1.00 | 24.16 | C |
| ATOM | 3985 | CE1 | PHE | A | 270 | −62.662 | 23.569 | −5.683 | 1.00 | 23.84 | C |
| ATOM | 3987 | CZ | PHE | A | 270 | −61.675 | 24.497 | −5.871 | 1.00 | 23.93 | C |
| ATOM | 3989 | CE2 | PHE | A | 270 | −60.448 | 24.349 | −5.242 | 1.00 | 23.33 | C |
| ATOM | 3991 | CD2 | PHE | A | 270 | −60.213 | 23.268 | −4.443 | 1.00 | 23.11 | C |
| ATOM | 3993 | C | PHE | A | 270 | −61.173 | 19.820 | −5.515 | 1.00 | 23.21 | C |
| ATOM | 3994 | O | PHE | A | 270 | −62.142 | 19.069 | −5.599 | 1.00 | 23.48 | O |
| ATOM | 3996 | N | GLU | A | 271 | −60.771 | 20.599 | −6.522 | 1.00 | 24.16 | N |
| ATOM | 3997 | CA | GLU | A | 271 | −61.595 | 20.744 | −7.741 | 1.00 | 25.01 | C |
| ATOM | 3999 | CB | GLU | A | 271 | −61.065 | 21.863 | −8.655 | 1.00 | 25.19 | C |
| ATOM | 4002 | CG | GLU | A | 271 | −59.563 | 21.909 | −8.794 | 1.00 | 27.45 | C |
| ATOM | 4005 | CD | GLU | A | 271 | −58.857 | 22.910 | −7.857 | 1.00 | 30.03 | C |
| ATOM | 4006 | OE1 | GLU | A | 271 | −58.905 | 24.145 | −8.147 | 1.00 | 29.41 | O |
| ATOM | 4007 | OE2 | GLU | A | 271 | −58.227 | 22.431 | −6.865 | 1.00 | 30.71 | O |
| ATOM | 4008 | C | GLU | A | 271 | −61.799 | 19.391 | −8.484 | 1.00 | 24.95 | C |
| ATOM | 4009 | O | GLU | A | 271 | −60.972 | 18.480 | −8.352 | 1.00 | 25.70 | O |
| ATOM | 4011 | N | PRO | A | 272 | −62.918 | 19.242 | −9.224 | 1.00 | 24.59 | N |
| ATOM | 4012 | CA | PRO | A | 272 | −63.399 | 17.915 | −9.656 | 1.00 | 24.38 | C |
| ATOM | 4014 | CB | PRO | A | 272 | −64.675 | 18.243 | −10.430 | 1.00 | 24.25 | C |
| ATOM | 4017 | CG | PRO | A | 272 | −65.105 | 19.536 | −9.869 | 1.00 | 24.53 | C |
| ATOM | 4020 | CD | PRO | A | 272 | −63.855 | 20.295 | −9.639 | 1.00 | 24.42 | C |
| ATOM | 4023 | C | PRO | A | 272 | −62.475 | 17.111 | −10.549 | 1.00 | 24.29 | C |
| ATOM | 4024 | O | PRO | A | 272 | −62.406 | 15.886 | −10.410 | 1.00 | 24.45 | O |
| ATOM | 4025 | N | GLN | A | 273 | −61.777 | 17.781 | −11.462 | 1.00 | 24.13 | N |
| ATOM | 4026 | CA | GLN | A | 273 | −60.998 | 17.064 | −12.461 | 1.00 | 24.13 | C |
| ATOM | 4028 | CB | GLN | A | 273 | −60.523 | 17.983 | −13.567 | 1.00 | 23.84 | C |
| ATOM | 4031 | CG | GLN | A | 273 | −59.556 | 19.041 | −13.117 | 1.00 | 24.37 | C |
| ATOM | 4034 | CD | GLN | A | 273 | −60.222 | 20.360 | −12.775 | 1.00 | 25.22 | C |
| ATOM | 4035 | OE1 | GLN | A | 273 | −61.392 | 20.412 | −12.367 | 1.00 | 25.71 | O |
| ATOM | 4036 | NE2 | GLN | A | 273 | −59.468 | 21.441 | −12.932 | 1.00 | 24.95 | N |
| ATOM | 4039 | C | GLN | A | 273 | −59.808 | 16.327 | −11.877 | 1.00 | 24.33 | C |
| ATOM | 4040 | O | GLN | A | 273 | −59.224 | 15.486 | −12.555 | 1.00 | 24.91 | O |
| ATOM | 4042 | N | TYR | A | 274 | −59.462 | 16.607 | −10.626 | 1.00 | 24.27 | N |
| ATOM | 4043 | CA | TYR | A | 274 | −58.211 | 16.119 | −10.067 | 1.00 | 24.38 | C |
| ATOM | 4045 | CB | TYR | A | 274 | −57.639 | 17.180 | −9.138 | 1.00 | 24.36 | C |
| ATOM | 4048 | CG | TYR | A | 274 | −57.066 | 18.398 | −9.819 | 1.00 | 24.35 | C |
| ATOM | 4049 | CD1 | TYR | A | 274 | −56.249 | 18.291 | −10.935 | 1.00 | 24.13 | C |
| ATOM | 4051 | CE1 | TYR | A | 274 | −55.716 | 19.409 | −11.542 | 1.00 | 23.75 | C |
| ATOM | 4053 | CZ | TYR | A | 274 | −55.968 | 20.646 | −11.019 | 1.00 | 24.14 | C |
| ATOM | 4054 | OH | TYR | A | 274 | −55.431 | 21.762 | −11.597 | 1.00 | 24.45 | O |
| ATOM | 4056 | CE2 | TYR | A | 274 | −56.755 | 20.780 | −9.903 | 1.00 | 24.92 | C |
| ATOM | 4058 | CD2 | TYR | A | 274 | −57.297 | 19.658 | −9.308 | 1.00 | 24.74 | C |
| ATOM | 4060 | C | TYR | A | 274 | −58.319 | 14.796 | −9.310 | 1.00 | 24.63 | C |

TABLE 16-7-continued

Coordinates of *P. tremuloides* IspS

| ATOM | 4061 | O | TYR | A | 274 | −57.681 | 14.613 | −8.276 | 1.00 | 24.47 | O |
|---|---|---|---|---|---|---|---|---|---|---|---|
| ATOM | 4063 | N | SER | A | 275 | −59.097 | 13.852 | −9.821 | 1.00 | 25.00 | N |
| ATOM | 4064 | CA | SER | A | 275 | −59.254 | 12.575 | −9.116 | 1.00 | 25.11 | C |
| ATOM | 4066 | CB | SER | A | 275 | −60.244 | 11.664 | −9.842 | 1.00 | 25.14 | C |
| ATOM | 4069 | OG | SER | A | 275 | −61.537 | 12.252 | −9.852 | 1.00 | 25.96 | O |
| ATOM | 4071 | C | SER | A | 275 | −57.907 | 11.885 | −8.963 | 1.00 | 24.94 | C |
| ATOM | 4072 | O | SER | A | 275 | −57.544 | 11.439 | −7.877 | 1.00 | 24.57 | O |
| ATOM | 4074 | N | ASP | A | 276 | −57.149 | 11.822 | −10.052 | 1.00 | 25.01 | N |
| ATOM | 4075 | CA | ASP | A | 276 | −55.840 | 11.187 | −9.990 | 1.00 | 24.92 | C |
| ATOM | 4077 | CB | ASP | A | 276 | −55.102 | 11.257 | −11.324 | 1.00 | 25.02 | C |
| ATOM | 4080 | CG | ASP | A | 276 | −55.827 | 10.495 | −12.407 | 1.00 | 26.27 | C |
| ATOM | 4081 | OD1 | ASP | A | 276 | −56.372 | 9.411 | −12.080 | 1.00 | 26.65 | O |
| ATOM | 4082 | OD2 | ASP | A | 276 | −55.880 | 10.991 | −13.563 | 1.00 | 28.21 | O |
| ATOM | 4083 | C | ASP | A | 276 | −55.026 | 11.798 | −8.881 | 1.00 | 24.30 | C |
| ATOM | 4084 | O | ASP | A | 276 | −54.454 | 11.064 | −8.099 | 1.00 | 24.64 | O |
| ATOM | 4086 | N | CYS | A | 277 | −55.005 | 13.124 | −8.772 | 1.00 | 23.61 | N |
| ATOM | 4087 | CA | CYS | A | 277 | −54.210 | 13.746 | −7.715 | 1.00 | 22.91 | C |
| ATOM | 4089 | CB | CYS | A | 277 | −54.262 | 15.268 | −7.748 | 1.00 | 22.83 | C |
| ATOM | 4092 | SG | CYS | A | 277 | −53.048 | 15.994 | −6.615 | 1.00 | 22.43 | S |
| ATOM | 4094 | C | CYS | A | 277 | −54.653 | 13.251 | −6.357 | 1.00 | 22.39 | C |
| ATOM | 4095 | O | CYS | A | 277 | −53.822 | 12.833 | −5.559 | 1.00 | 22.23 | O |
| ATOM | 4097 | N | ARG | A | 278 | −55.962 | 13.262 | −6.115 | 1.00 | 22.01 | N |
| ATOM | 4098 | CA | ARG | A | 278 | −56.519 | 12.813 | −4.829 | 1.00 | 21.40 | C |
| ATOM | 4100 | CB | ARG | A | 278 | −58.021 | 13.053 | −4.753 | 1.00 | 21.07 | C |
| ATOM | 4103 | CG | ARG | A | 278 | −58.382 | 14.509 | −4.754 | 1.00 | 20.39 | C |
| ATOM | 4106 | CD | ARG | A | 278 | −59.852 | 14.698 | −4.527 | 1.00 | 20.05 | C |
| ATOM | 4109 | NE | ARG | A | 278 | −60.683 | 14.331 | −5.675 | 1.00 | 18.86 | N |
| ATOM | 4111 | CZ | ARG | A | 278 | −60.993 | 15.144 | −6.679 | 1.00 | 18.58 | C |
| ATOM | 4112 | NH1 | ARG | A | 278 | −60.530 | 16.391 | −6.730 | 1.00 | 18.45 | N |
| ATOM | 4115 | NH2 | ARG | A | 278 | −61.775 | 14.702 | −7.647 | 1.00 | 19.04 | N |
| ATOM | 4118 | C | ARG | A | 278 | −56.224 | 11.358 | −4.530 | 1.00 | 21.12 | C |
| ATOM | 4119 | O | ARG | A | 278 | −55.804 | 11.050 | −3.434 | 1.00 | 21.59 | O |
| ATOM | 4121 | N | ASN | A | 279 | −56.412 | 10.467 | −5.493 | 1.00 | 20.94 | N |
| ATOM | 4122 | CA | ASN | A | 279 | −56.168 | 9.044 | −5.243 | 1.00 | 21.08 | C |
| ATOM | 4124 | CB | ASN | A | 279 | −56.672 | 8.182 | −6.401 | 1.00 | 21.54 | C |
| ATOM | 4127 | CG | ASN | A | 279 | −58.199 | 8.346 | −6.642 | 1.00 | 23.94 | C |
| ATOM | 4128 | OD1 | ASN | A | 279 | −58.920 | 8.941 | −5.823 | 1.00 | 26.47 | O |
| ATOM | 4129 | ND2 | ASN | A | 279 | −58.685 | 7.825 | −7.769 | 1.00 | 25.52 | N |
| ATOM | 4132 | C | ASN | A | 279 | −54.699 | 8.798 | −4.972 | 1.00 | 20.30 | C |
| ATOM | 4133 | O | ASN | A | 279 | −54.337 | 8.200 | −3.977 | 1.00 | 19.95 | O |
| ATOM | 4135 | N | SER | A | 280 | −53.851 | 9.297 | −5.856 | 1.00 | 20.02 | N |
| ATOM | 4136 | CA | SER | A | 280 | −52.409 | 9.335 | −5.612 | 1.00 | 19.32 | C |
| ATOM | 4138 | CB | SER | A | 280 | −51.725 | 10.304 | −6.580 | 1.00 | 19.35 | C |
| ATOM | 4141 | OG | SER | A | 280 | −50.624 | 9.705 | −7.212 | 1.00 | 19.77 | O |
| ATOM | 4143 | C | SER | A | 280 | −52.122 | 9.745 | −4.166 | 1.00 | 18.55 | C |
| ATOM | 4144 | O | SER | A | 280 | −51.514 | 8.976 | −3.436 | 1.00 | 18.98 | O |
| ATOM | 4146 | N | VAL | A | 281 | −52.580 | 10.923 | −3.743 | 1.00 | 17.45 | N |
| ATOM | 4147 | CA | VAL | A | 281 | −52.235 | 11.444 | −2.416 | 1.00 | 17.01 | C |
| ATOM | 4149 | CB | VAL | A | 281 | −52.650 | 12.934 | −2.235 | 1.00 | 17.20 | C |
| ATOM | 4151 | CG1 | VAL | A | 281 | −52.492 | 13.376 | −.787 | 1.00 | 16.76 | C |
| ATOM | 4155 | CG2 | VAL | A | 281 | −51.826 | 13.847 | −3.128 | 1.00 | 17.13 | C |
| ATOM | 4159 | C | VAL | A | 281 | −52.861 | 10.607 | −1.301 | 1.00 | 16.82 | C |
| ATOM | 4160 | O | VAL | A | 281 | −52.217 | 10.314 | −.289 | 1.00 | 16.81 | O |
| ATOM | 4162 | N | ALA | A | 282 | −54.118 | 10.225 | −1.481 | 1.00 | 16.55 | N |
| ATOM | 4163 | CA | ALA | A | 282 | −54.774 | 9.304 | −.559 | 1.00 | 16.31 | C |
| ATOM | 4165 | CB | ALA | A | 282 | −56.174 | 8.951 | −1.060 | 1.00 | 16.08 | C |
| ATOM | 4169 | C | ALA | A | 282 | −53.946 | 8.036 | −.355 | 1.00 | 16.31 | C |
| ATOM | 4170 | O | ALA | A | 282 | −53.671 | 7.653 | .762 | 1.00 | 16.16 | O |
| ATOM | 4172 | N | LYS | A | 283 | −53.539 | 7.395 | −1.443 | 1.00 | 16.92 | N |
| ATOM | 4173 | CA | LYS | A | 283 | −52.773 | 6.139 | −1.368 | 1.00 | 17.39 | C |
| ATOM | 4175 | CB | LYS | A | 283 | −52.454 | 5.596 | −2.773 | 1.00 | 17.31 | C |
| ATOM | 4178 | CG | LYS | A | 283 | −53.680 | 5.066 | −3.519 | 1.00 | 17.85 | C |
| ATOM | 4181 | CD | LYS | A | 283 | −53.389 | 4.527 | −4.941 | 1.00 | 18.98 | C |
| ATOM | 4184 | CE | LYS | A | 283 | −54.709 | 4.275 | −5.718 | 1.00 | 19.79 | C |
| ATOM | 4187 | NZ | LYS | A | 283 | −54.695 | 3.091 | −6.625 | 1.00 | 20.11 | N |
| ATOM | 4191 | C | LYS | A | 283 | −51.483 | 6.338 | −.591 | 1.00 | 17.82 | C |
| ATOM | 4192 | O | LYS | A | 283 | −51.170 | 5.577 | .331 | 1.00 | 17.37 | O |
| ATOM | 4194 | N | MET | A | 284 | −50.744 | 7.381 | −.964 | 1.00 | 18.49 | N |
| ATOM | 4195 | CA | MET | A | 284 | −49.434 | 7.622 | −.373 | 1.00 | 18.82 | C |
| ATOM | 4197 | CB | MET | A | 284 | −48.688 | 8.795 | −1.047 | 1.00 | 18.84 | C |
| ATOM | 4200 | CG | MET | A | 284 | −48.118 | 8.506 | −2.444 | 1.00 | 18.47 | C |
| ATOM | 4203 | SD | MET | A | 284 | −47.540 | 6.819 | −2.718 | 1.00 | 19.50 | S |
| ATOM | 4204 | CE | MET | A | 284 | −49.088 | 5.982 | −3.094 | 1.00 | 19.36 | C |
| ATOM | 4208 | C | MET | A | 284 | −49.575 | 7.848 | 1.115 | 1.00 | 18.95 | C |
| ATOM | 4209 | O | MET | A | 284 | −48.901 | 7.166 | 1.892 | 1.00 | 19.29 | O |
| ATOM | 4211 | N | PHE | A | 285 | −50.465 | 8.762 | 1.507 | 1.00 | 18.94 | N |
| ATOM | 4212 | CA | PHE | A | 285 | −50.671 | 9.082 | 2.930 | 1.00 | 19.26 | C |
| ATOM | 4214 | CB | PHE | A | 285 | −51.714 | 10.185 | 3.073 | 1.00 | 19.72 | C |

TABLE 16-7-continued

Coordinates of *P. tremuloides* IspS

| ATOM | 4217 | CG | PHE | A | 285 | −51.575 | 11.016 | 4.328 | 1.00 | 21.97 | C |
|---|---|---|---|---|---|---|---|---|---|---|---|
| ATOM | 4218 | CD1 | PHE | A | 285 | −50.335 | 11.202 | 4.954 | 1.00 | 24.49 | C |
| ATOM | 4220 | CE1 | PHE | A | 285 | −50.209 | 11.996 | 6.086 | 1.00 | 25.11 | C |
| ATOM | 4222 | CZ | PHE | A | 285 | −51.321 | 12.634 | 6.597 | 1.00 | 26.40 | C |
| ATOM | 4224 | CE2 | PHE | A | 285 | −52.566 | 12.470 | 5.977 | 1.00 | 26.44 | C |
| ATOM | 4226 | CD2 | PHE | A | 285 | −52.678 | 11.670 | 4.846 | 1.00 | 24.55 | C |
| ATOM | 4228 | C | PHE | A | 285 | −51.097 | 7.879 | 3.770 | 1.00 | 18.74 | C |
| ATOM | 4229 | O | PHE | A | 285 | −50.700 | 7.729 | 4.924 | 1.00 | 18.31 | O |
| ATOM | 4231 | N | SER | A | 286 | −51.903 | 7.019 | 3.169 | 1.00 | 18.49 | N |
| ATOM | 4232 | CA | SER | A | 286 | −52.281 | 5.772 | 3.791 | 1.00 | 18.38 | C |
| ATOM | 4234 | CB | SER | A | 286 | −53.302 | 5.065 | 2.926 | 1.00 | 18.45 | C |
| ATOM | 4237 | OG | SER | A | 286 | −54.389 | 5.949 | 2.687 | 1.00 | 19.82 | O |
| ATOM | 4239 | C | SER | A | 286 | −51.070 | 4.888 | 4.048 | 1.00 | 18.08 | C |
| ATOM | 4240 | O | SER | A | 286 | −50.931 | 4.376 | 5.146 | 1.00 | 18.18 | O |
| ATOM | 4242 | N | PHE | A | 287 | −50.195 | 4.714 | 3.054 | 1.00 | 17.72 | N |
| ATOM | 4243 | CA | PHE | A | 287 | −48.911 | 4.024 | 3.279 | 1.00 | 17.23 | C |
| ATOM | 4245 | CB | PHE | A | 287 | −48.133 | 3.801 | 1.977 | 1.00 | 17.09 | C |
| ATOM | 4248 | CG | PHE | A | 287 | −48.513 | 2.555 | 1.258 | 1.00 | 17.26 | C |
| ATOM | 4249 | CD1 | PHE | A | 287 | −48.220 | 1.315 | 1.802 | 1.00 | 18.31 | C |
| ATOM | 4251 | CE1 | PHE | A | 287 | −48.583 | .129 | 1.131 | 1.00 | 18.47 | C |
| ATOM | 4253 | CZ | PHE | A | 287 | −49.237 | .198 | −.091 | 1.00 | 17.88 | C |
| ATOM | 4255 | CE2 | PHE | A | 287 | −49.530 | 1.441 | −.642 | 1.00 | 17.57 | C |
| ATOM | 4257 | CD2 | PHE | A | 287 | −49.168 | 2.608 | .031 | 1.00 | 17.79 | C |
| ATOM | 4259 | C | PHE | A | 287 | −48.022 | 4.787 | 4.277 | 1.00 | 16.92 | C |
| ATOM | 4260 | O | PHE | A | 287 | −47.369 | 4.173 | 5.143 | 1.00 | 17.18 | O |
| ATOM | 4262 | N | VAL | A | 288 | −47.989 | 6.113 | 4.174 | 1.00 | 16.00 | N |
| ATOM | 4263 | CA | VAL | A | 288 | −47.148 | 6.883 | 5.080 | 1.00 | 15.45 | C |
| ATOM | 4265 | CB | VAL | A | 288 | −47.289 | 8.399 | 4.863 | 1.00 | 15.21 | C |
| ATOM | 4267 | CG1 | VAL | A | 288 | −46.433 | 9.162 | 5.852 | 1.00 | 14.24 | C |
| ATOM | 4271 | CG2 | VAL | A | 288 | −46.898 | 8.757 | 3.450 | 1.00 | 14.46 | C |
| ATOM | 4275 | C | VAL | A | 288 | −47.479 | 6.499 | 6.527 | 1.00 | 15.46 | C |
| ATOM | 4276 | O | VAL | A | 288 | −46.590 | 6.160 | 7.299 | 1.00 | 14.79 | O |
| ATOM | 4278 | N | THR | A | 289 | −48.759 | 6.494 | 6.880 | 1.00 | 15.62 | N |
| ATOM | 4279 | CA | THR | A | 289 | −49.110 | 6.272 | 8.274 | 1.00 | 16.09 | C |
| ATOM | 4281 | CB | THR | A | 289 | −50.602 | 6.557 | 8.588 | 1.00 | 15.72 | C |
| ATOM | 4283 | OG1 | THR | A | 289 | −51.422 | 5.827 | 7.708 | 1.00 | 16.52 | O |
| ATOM | 4285 | CG2 | THR | A | 289 | −50.927 | 8.007 | 8.371 | 1.00 | 16.56 | C |
| ATOM | 4289 | C | THR | A | 289 | −48.677 | 4.879 | 8.727 | 1.00 | 16.34 | C |
| ATOM | 4290 | O | THR | A | 289 | −48.234 | 4.707 | 9.881 | 1.00 | 16.68 | O |
| ATOM | 4292 | N | ILE | A | 290 | −48.737 | 3.904 | 7.820 | 1.00 | 16.29 | N |
| ATOM | 4293 | CA | ILE | A | 290 | −48.347 | 2.538 | 8.166 | 1.00 | 16.56 | C |
| ATOM | 4295 | CB | ILE | A | 290 | −48.734 | 1.516 | 7.096 | 1.00 | 16.48 | C |
| ATOM | 4297 | CG1 | ILE | A | 290 | −50.247 | 1.440 | 6.944 | 1.00 | 16.91 | C |
| ATOM | 4300 | CD1 | ILE | A | 290 | −50.677 | .564 | 5.811 | 1.00 | 16.52 | C |
| ATOM | 4304 | CG2 | ILE | A | 290 | −48.262 | .145 | 7.488 | 1.00 | 16.52 | C |
| ATOM | 4308 | C | ILE | A | 290 | −46.842 | 2.456 | 8.402 | 1.00 | 16.94 | C |
| ATOM | 4309 | O | ILE | A | 290 | −46.404 | 1.968 | 9.443 | 1.00 | 17.06 | O |
| ATOM | 4311 | N | ILE | A | 291 | −46.048 | 2.942 | 7.451 | 1.00 | 17.22 | N |
| ATOM | 4312 | CA | ILE | A | 291 | −44.595 | 2.969 | 7.640 | 1.00 | 17.20 | C |
| ATOM | 4314 | CB | ILE | A | 291 | −43.842 | 3.534 | 6.405 | 1.00 | 17.32 | C |
| ATOM | 4316 | CG1 | ILE | A | 291 | −44.172 | 2.744 | 5.125 | 1.00 | 17.61 | C |
| ATOM | 4319 | CD1 | ILE | A | 291 | −44.004 | 1.265 | 5.250 | 1.00 | 18.21 | C |
| ATOM | 4323 | CG2 | ILE | A | 291 | −42.336 | 3.550 | 6.637 | 1.00 | 16.64 | C |
| ATOM | 4327 | C | ILE | A | 291 | −44.262 | 3.794 | 8.886 | 1.00 | 17.36 | C |
| ATOM | 4328 | O | ILE | A | 291 | −43.420 | 3.413 | 9.670 | 1.00 | 17.06 | O |
| ATOM | 4330 | N | ASP | A | 292 | −44.950 | 4.906 | 9.093 | 1.00 | 18.12 | N |
| ATOM | 4331 | CA | ASP | A | 292 | −44.627 | 5.755 | 10.227 | 1.00 | 18.83 | C |
| ATOM | 4333 | CB | ASP | A | 292 | −45.511 | 7.017 | 10.285 | 1.00 | 19.22 | C |
| ATOM | 4336 | CG | ASP | A | 292 | −45.185 | 7.920 | 11.485 | 1.00 | 19.93 | C |
| ATOM | 4337 | OD1 | ASP | A | 292 | −44.062 | 8.460 | 11.544 | 1.00 | 21.80 | O |
| ATOM | 4338 | OD2 | ASP | A | 292 | −46.048 | 8.080 | 12.375 | 1.00 | 20.46 | O |
| ATOM | 4339 | C | ASP | A | 292 | −44.745 | 4.947 | 11.509 | 1.00 | 18.96 | C |
| ATOM | 4340 | O | ASP | A | 292 | −43.902 | 5.094 | 12.394 | 1.00 | 19.05 | O |
| ATOM | 4342 | N | ASP | A | 293 | −45.774 | 4.097 | 11.610 | 1.00 | 19.05 | N |
| ATOM | 4343 | CA | ASP | A | 293 | −45.951 | 3.273 | 12.817 | 1.00 | 18.99 | C |
| ATOM | 4345 | CB | ASP | A | 293 | −47.237 | 2.443 | 12.790 | 1.00 | 18.95 | C |
| ATOM | 4348 | CG | ASP | A | 293 | −48.496 | 3.272 | 12.921 | 1.00 | 19.27 | C |
| ATOM | 4349 | OD1 | ASP | A | 293 | −48.483 | 4.361 | 13.523 | 1.00 | 21.51 | O |
| ATOM | 4350 | OD2 | ASP | A | 293 | −49.536 | 2.812 | 12.421 | 1.00 | 19.61 | O |
| ATOM | 4351 | C | ASP | A | 293 | −44.783 | 2.322 | 12.935 | 1.00 | 19.07 | C |
| ATOM | 4352 | O | ASP | A | 293 | −44.244 | 2.135 | 14.024 | 1.00 | 19.35 | O |
| ATOM | 4354 | N | ILE | A | 294 | −44.390 | 1.730 | 11.805 | 1.00 | 19.10 | N |
| ATOM | 4355 | CA | ILE | A | 294 | −43.320 | .727 | 11.786 | 1.00 | 19.04 | C |
| ATOM | 4357 | CB | ILE | A | 294 | −43.137 | .109 | 10.386 | 1.00 | 18.49 | C |
| ATOM | 4359 | CG1 | ILE | A | 294 | −44.343 | −.754 | 10.038 | 1.00 | 17.60 | C |
| ATOM | 4362 | CD1 | ILE | A | 294 | −44.204 | −1.504 | 8.752 | 1.00 | 16.77 | C |
| ATOM | 4366 | CG2 | ILE | A | 294 | −41.895 | −.745 | 10.348 | 1.00 | 18.77 | C |
| ATOM | 4370 | C | ILE | A | 294 | −41.974 | 1.273 | 12.298 | 1.00 | 19.55 | C |

TABLE 16-7-continued

| | | | | | | Coordinates of *P. tremuloides* IspS | | | | | |
|---|---|---|---|---|---|---|---|---|---|---|---|
| ATOM | 4371 | O | ILE | A | 294 | −41.234 | .550 | 12.974 | 1.00 | 19.75 | O |
| ATOM | 4373 | N | TYR | A | 295 | −41.649 | 2.525 | 11.983 | 1.00 | 19.75 | N |
| ATOM | 4374 | CA | TYR | A | 295 | −40.411 | 3.103 | 12.476 | 1.00 | 19.91 | C |
| ATOM | 4376 | CB | TYR | A | 295 | −39.856 | 4.178 | 11.542 | 1.00 | 19.66 | C |
| ATOM | 4379 | CG | TYR | A | 295 | −39.206 | 3.695 | 10.245 | 1.00 | 18.19 | C |
| ATOM | 4380 | CD1 | TYR | A | 295 | −37.821 | 3.727 | 10.075 | 1.00 | 16.19 | C |
| ATOM | 4382 | CE1 | TYR | A | 295 | −37.222 | 3.331 | 8.882 | 1.00 | 14.68 | C |
| ATOM | 4384 | CZ | TYR | A | 295 | −38.004 | 2.906 | 7.828 | 1.00 | 15.04 | C |
| ATOM | 4385 | OH | TYR | A | 295 | −37.428 | 2.485 | 6.631 | 1.00 | 12.25 | O |
| ATOM | 4387 | CE2 | TYR | A | 295 | −39.383 | 2.871 | 7.975 | 1.00 | 16.48 | C |
| ATOM | 4389 | CD2 | TYR | A | 295 | −39.975 | 3.271 | 9.172 | 1.00 | 17.01 | C |
| ATOM | 4391 | C | TYR | A | 295 | −40.647 | 3.677 | 13.858 | 1.00 | 20.73 | C |
| ATOM | 4392 | O | TYR | A | 295 | −39.749 | 3.635 | 14.717 | 1.00 | 21.64 | O |
| ATOM | 4394 | N | ASP | A | 296 | −41.843 | 4.200 | 14.103 | 1.00 | 21.38 | N |
| ATOM | 4395 | CA | ASP | A | 296 | −42.100 | 4.865 | 15.391 | 1.00 | 22.20 | C |
| ATOM | 4397 | CB | ASP | A | 296 | −43.421 | 5.644 | 15.391 | 1.00 | 22.69 | C |
| ATOM | 4400 | CG | ASP | A | 296 | −43.567 | 6.548 | 16.607 | 1.00 | 23.85 | C |
| ATOM | 4401 | OD1 | ASP | A | 296 | −42.568 | 7.179 | 17.014 | 1.00 | 25.49 | O |
| ATOM | 4402 | OD2 | ASP | A | 296 | −44.689 | 6.648 | 17.145 | 1.00 | 26.12 | O |
| ATOM | 4403 | C | ASP | A | 296 | −42.106 | 3.890 | 16.549 | 1.00 | 22.10 | C |
| ATOM | 4404 | O | ASP | A | 296 | −41.376 | 4.082 | 17.506 | 1.00 | 22.14 | O |
| ATOM | 4406 | N | VAL | A | 297 | −42.900 | 2.828 | 16.435 | 1.00 | 22.25 | N |
| ATOM | 4407 | CA | VAL | A | 297 | −43.163 | 1.937 | 17.570 | 1.00 | 22.22 | C |
| ATOM | 4409 | CB | VAL | A | 297 | −44.635 | 2.116 | 18.057 | 1.00 | 22.07 | C |
| ATOM | 4411 | CG1 | VAL | A | 297 | −44.958 | 3.587 | 18.215 | 1.00 | 21.63 | C |
| ATOM | 4415 | CG2 | VAL | A | 297 | −45.618 | 1.459 | 17.099 | 1.00 | 20.76 | C |
| ATOM | 4419 | C | VAL | A | 297 | −42.861 | .422 | 17.373 | 1.00 | 22.49 | C |
| ATOM | 4420 | O | VAL | A | 297 | −42.517 | −.255 | 18.343 | 1.00 | 22.40 | O |
| ATOM | 4422 | N | TYR | A | 298 | −42.990 | −.117 | 16.157 | 1.00 | 22.69 | N |
| ATOM | 4423 | CA | TYR | A | 298 | −43.065 | −1.579 | 15.993 | 1.00 | 22.90 | C |
| ATOM | 4425 | CB | TYR | A | 298 | −44.089 | −1.974 | 14.934 | 1.00 | 22.77 | C |
| ATOM | 4428 | CG | TYR | A | 298 | −44.341 | −3.469 | 14.932 | 1.00 | 23.74 | C |
| ATOM | 4429 | CD1 | TYR | A | 298 | −45.249 | −4.043 | 15.819 | 1.00 | 25.72 | C |
| ATOM | 4431 | CE1 | TYR | A | 298 | −45.484 | −5.435 | 15.833 | 1.00 | 26.12 | C |
| ATOM | 4433 | CZ | TYR | A | 298 | −44.798 | −6.247 | 14.954 | 1.00 | 25.59 | C |
| ATOM | 4434 | OH | TYR | A | 298 | −45.027 | −7.593 | 14.970 | 1.00 | 25.33 | O |
| ATOM | 4436 | CE2 | TYR | A | 298 | −43.890 | −5.702 | 14.062 | 1.00 | 24.79 | C |
| ATOM | 4438 | CD2 | TYR | A | 298 | −43.661 | −4.317 | 14.061 | 1.00 | 24.20 | C |
| ATOM | 4440 | C | TYR | A | 298 | −41.750 | −2.258 | 15.649 | 1.00 | 23.02 | C |
| ATOM | 4441 | O | TYR | A | 298 | −41.387 | −3.257 | 16.256 | 1.00 | 22.80 | O |
| ATOM | 4443 | N | GLY | A | 299 | −41.069 | −1.747 | 14.634 | 1.00 | 23.47 | N |
| ATOM | 4444 | CA | GLY | A | 299 | −39.839 | −2.361 | 14.149 | 1.00 | 23.36 | C |
| ATOM | 4447 | C | GLY | A | 299 | −38.631 | −1.978 | 14.984 | 1.00 | 23.27 | C |
| ATOM | 4448 | O | GLY | A | 299 | −38.532 | −.858 | 15.501 | 1.00 | 23.35 | O |
| ATOM | 4450 | N | THR | A | 300 | −37.702 | −2.918 | 15.098 | 1.00 | 23.11 | N |
| ATOM | 4451 | CA | THR | A | 300 | −36.459 | −2.682 | 15.797 | 1.00 | 22.90 | C |
| ATOM | 4453 | CB | THR | A | 300 | −35.869 | −3.957 | 16.386 | 1.00 | 22.83 | C |
| ATOM | 4455 | OG1 | THR | A | 300 | −35.328 | −4.756 | 15.328 | 1.00 | 22.61 | O |
| ATOM | 4457 | CG2 | THR | A | 300 | −36.928 | −4.732 | 17.162 | 1.00 | 22.18 | C |
| ATOM | 4461 | C | THR | A | 300 | −35.482 | −2.120 | 14.796 | 1.00 | 23.00 | C |
| ATOM | 4462 | O | THR | A | 300 | −35.606 | −2.364 | 13.602 | 1.00 | 23.13 | O |
| ATOM | 4464 | N | LEU | A | 301 | −34.496 | −1.394 | 15.309 | 1.00 | 23.07 | N |
| ATOM | 4465 | CA | LEU | A | 301 | −33.596 | −.572 | 14.498 | 1.00 | 22.84 | C |
| ATOM | 4467 | CB | LEU | A | 301 | −32.515 | .007 | 15.403 | 1.00 | 22.80 | C |
| ATOM | 4470 | CG | LEU | A | 301 | −31.965 | 1.412 | 15.182 | 1.00 | 22.39 | C |
| ATOM | 4472 | CD1 | LEU | A | 301 | −32.983 | 2.365 | 14.587 | 1.00 | 22.44 | C |
| ATOM | 4476 | CD2 | LEU | A | 301 | −31.482 | 1.919 | 16.536 | 1.00 | 22.19 | C |
| ATOM | 4480 | C | LEU | A | 301 | −32.964 | −1.358 | 13.361 | 1.00 | 22.95 | C |
| ATOM | 4481 | O | LEU | A | 301 | −32.910 | −.888 | 12.232 | 1.00 | 22.50 | O |
| ATOM | 4483 | N | ASP | A | 302 | −32.511 | −2.569 | 13.673 | 1.00 | 23.35 | N |
| ATOM | 4484 | CA | ASP | A | 302 | −31.929 | −3.469 | 12.670 | 1.00 | 23.65 | C |
| ATOM | 4486 | CB | ASP | A | 302 | −31.332 | −4.747 | 13.328 | 1.00 | 24.12 | C |
| ATOM | 4489 | CG | ASP | A | 302 | −29.984 | −4.498 | 14.057 | 1.00 | 25.23 | C |
| ATOM | 4490 | OD1 | ASP | A | 302 | −29.003 | −4.051 | 13.409 | 1.00 | 26.43 | O |
| ATOM | 4491 | OD2 | ASP | A | 302 | −29.896 | −4.780 | 15.277 | 1.00 | 26.92 | O |
| ATOM | 4492 | C | ASP | A | 302 | −32.945 | −3.859 | 11.581 | 1.00 | 23.11 | C |
| ATOM | 4493 | O | ASP | A | 302 | −32.544 | −4.086 | 10.445 | 1.00 | 23.05 | O |
| ATOM | 4495 | N | GLU | A | 303 | −34.235 | −3.965 | 11.927 | 1.00 | 22.63 | N |
| ATOM | 4496 | CA | GLU | A | 303 | −35.295 | −4.248 | 10.931 | 1.00 | 22.40 | C |
| ATOM | 4498 | CB | GLU | A | 303 | −36.625 | −4.675 | 11.589 | 1.00 | 22.20 | C |
| ATOM | 4501 | CG | GLU | A | 303 | −36.537 | −5.956 | 12.426 | 1.00 | 22.66 | C |
| ATOM | 4504 | CD | GLU | A | 303 | −37.832 | −6.341 | 13.159 | 1.00 | 22.69 | C |
| ATOM | 4505 | OE1 | GLU | A | 303 | −38.614 | −5.449 | 13.568 | 1.00 | 22.23 | O |
| ATOM | 4506 | OE2 | GLU | A | 303 | −38.051 | −7.558 | 13.338 | 1.00 | 21.64 | O |
| ATOM | 4507 | C | GLU | A | 303 | −35.533 | −3.017 | 10.067 | 1.00 | 22.35 | C |
| ATOM | 4508 | O | GLU | A | 303 | −35.658 | −3.105 | 8.841 | 1.00 | 22.27 | O |
| ATOM | 4510 | N | LEU | A | 304 | −35.597 | −1.866 | 10.724 | 1.00 | 22.34 | N |
| ATOM | 4511 | CA | LEU | A | 304 | −35.776 | −.607 | 10.040 | 1.00 | 22.26 | C |

TABLE 16-7-continued

Coordinates of *P. tremuloides* IspS

| ATOM | 4513 | CB | LEU | A | 304 | −35.861 | .537 | 11.052 | 1.00 | 22.49 | C |
|---|---|---|---|---|---|---|---|---|---|---|---|
| ATOM | 4516 | CG | LEU | A | 304 | −37.089 | .517 | 11.973 | 1.00 | 23.05 | C |
| ATOM | 4518 | CD1 | LEU | A | 304 | −37.109 | 1.708 | 12.932 | 1.00 | 23.46 | C |
| ATOM | 4522 | CD2 | LEU | A | 304 | −38.353 | .511 | 11.142 | 1.00 | 23.96 | C |
| ATOM | 4526 | C | LEU | A | 304 | −34.634 | −.383 | 9.063 | 1.00 | 22.09 | C |
| ATOM | 4527 | O | LEU | A | 304 | −34.873 | .094 | 7.969 | 1.00 | 22.32 | O |
| ATOM | 4529 | N | GLU | A | 305 | −33.408 | −.740 | 9.450 | 1.00 | 21.91 | N |
| ATOM | 4530 | CA | GLU | A | 305 | −32.259 | −.685 | 8.541 | 1.00 | 21.93 | C |
| ATOM | 4532 | CB | GLU | A | 305 | −30.988 | −1.194 | 9.219 | 1.00 | 22.35 | C |
| ATOM | 4535 | CG | GLU | A | 305 | −30.363 | −.258 | 10.249 | 1.00 | 24.12 | C |
| ATOM | 4538 | CD | GLU | A | 305 | −29.751 | 1.002 | 9.649 | 1.00 | 26.11 | C |
| ATOM | 4539 | OE1 | GLU | A | 305 | −29.275 | 1.846 | 10.454 | 1.00 | 25.68 | O |
| ATOM | 4540 | OE2 | GLU | A | 305 | −29.756 | 1.146 | 8.391 | 1.00 | 27.67 | O |
| ATOM | 4541 | C | GLU | A | 305 | −32.475 | −1.524 | 7.295 | 1.00 | 21.54 | C |
| ATOM | 4542 | O | GLU | A | 305 | −32.010 | −1.162 | 6.220 | 1.00 | 21.75 | O |
| ATOM | 4544 | N | LEU | A | 306 | −33.155 | −2.660 | 7.448 | 1.00 | 21.21 | N |
| ATOM | 4545 | CA | LEU | A | 306 | −33.459 | −3.557 | 6.316 | 1.00 | 20.66 | C |
| ATOM | 4547 | CB | LEU | A | 306 | −33.880 | −4.956 | 6.795 | 1.00 | 20.26 | C |
| ATOM | 4550 | CG | LEU | A | 306 | −32.725 | −5.854 | 7.220 | 1.00 | 19.57 | C |
| ATOM | 4552 | CD1 | LEU | A | 306 | −33.261 | −7.150 | 7.777 | 1.00 | 20.18 | C |
| ATOM | 4556 | CD2 | LEU | A | 306 | −31.791 | −6.120 | 6.061 | 1.00 | 18.29 | C |
| ATOM | 4560 | C | LEU | A | 306 | −34.535 | −2.967 | 5.416 | 1.00 | 20.23 | C |
| ATOM | 4561 | O | LEU | A | 306 | −34.412 | −2.966 | 4.197 | 1.00 | 19.97 | O |
| ATOM | 4563 | N | PHE | A | 307 | −35.588 | −2.457 | 6.023 | 1.00 | 19.99 | N |
| ATOM | 4564 | CA | PHE | A | 307 | −36.635 | −1.861 | 5.237 | 1.00 | 20.00 | C |
| ATOM | 4566 | CB | PHE | A | 307 | −37.771 | −1.388 | 6.118 | 1.00 | 20.08 | C |
| ATOM | 4569 | CG | PHE | A | 307 | −39.011 | −1.115 | 5.370 | 1.00 | 19.05 | C |
| ATOM | 4570 | CD1 | PHE | A | 307 | −39.895 | −2.118 | 5.119 | 1.00 | 18.77 | C |
| ATOM | 4572 | CE1 | PHE | A | 307 | −41.037 | −1.873 | 4.421 | 1.00 | 20.07 | C |
| ATOM | 4574 | CZ | PHE | A | 307 | −41.296 | −.621 | 3.959 | 1.00 | 19.63 | C |
| ATOM | 4576 | CE2 | PHE | A | 307 | −40.411 | .391 | 4.199 | 1.00 | 19.27 | C |
| ATOM | 4578 | CD2 | PHE | A | 307 | −39.278 | .142 | 4.900 | 1.00 | 19.17 | C |
| ATOM | 4580 | C | PHE | A | 307 | −36.087 | −.695 | 4.447 | 1.00 | 20.25 | C |
| ATOM | 4581 | O | PHE | A | 307 | −36.356 | −.589 | 3.242 | 1.00 | 20.08 | O |
| ATOM | 4583 | N | THR | A | 308 | −35.325 | .167 | 5.137 | 1.00 | 20.51 | N |
| ATOM | 4584 | CA | THR | A | 308 | −34.737 | 1.379 | 4.538 | 1.00 | 20.60 | C |
| ATOM | 4586 | CB | THR | A | 308 | −33.860 | 2.177 | 5.541 | 1.00 | 20.41 | C |
| ATOM | 4588 | OG1 | THR | A | 308 | −34.672 | 2.661 | 6.611 | 1.00 | 20.05 | O |
| ATOM | 4590 | CG2 | THR | A | 308 | −33.198 | 3.376 | 4.864 | 1.00 | 20.38 | C |
| ATOM | 4594 | C | THR | A | 308 | −33.895 | 1.009 | 3.331 | 1.00 | 20.82 | C |
| ATOM | 4595 | O | THR | A | 308 | −34.057 | 1.571 | 2.243 | 1.00 | 20.45 | O |
| ATOM | 4597 | N | ASP | A | 309 | −33.020 | .031 | 3.522 | 1.00 | 21.32 | N |
| ATOM | 4598 | CA | ASP | A | 309 | −32.138 | −.399 | 2.449 | 1.00 | 21.88 | C |
| ATOM | 4600 | CB | ASP | A | 309 | −31.042 | −1.324 | 2.971 | 1.00 | 22.44 | C |
| ATOM | 4603 | CG | ASP | A | 309 | −30.164 | −1.847 | 1.857 | 1.00 | 25.69 | C |
| ATOM | 4604 | OD1 | ASP | A | 309 | −29.599 | −1.010 | 1.089 | 1.00 | 28.02 | O |
| ATOM | 4605 | OD2 | ASP | A | 309 | −30.076 | −3.100 | 1.730 | 1.00 | 30.59 | O |
| ATOM | 4606 | C | ASP | A | 309 | −32.928 | −1.085 | 1.357 | 1.00 | 21.17 | C |
| ATOM | 4607 | O | ASP | A | 309 | −32.601 | −.948 | .188 | 1.00 | 20.95 | O |
| ATOM | 4609 | N | ALA | A | 310 | −33.965 | −1.818 | 1.757 | 1.00 | 20.99 | N |
| ATOM | 4610 | CA | ALA | A | 310 | −34.885 | −2.474 | .828 | 1.00 | 20.91 | C |
| ATOM | 4612 | CB | ALA | A | 310 | −35.931 | −3.244 | 1.591 | 1.00 | 20.77 | C |
| ATOM | 4616 | C | ALA | A | 310 | −35.567 | −1.501 | −.123 | 1.00 | 21.08 | C |
| ATOM | 4617 | O | ALA | A | 310 | −35.745 | −1.816 | −1.305 | 1.00 | 20.76 | O |
| ATOM | 4619 | N | VAL | A | 311 | −35.958 | −.334 | .402 | 1.00 | 21.51 | N |
| ATOM | 4620 | CA | VAL | A | 311 | −36.594 | .719 | −.396 | 1.00 | 21.50 | C |
| ATOM | 4622 | CB | VAL | A | 311 | −37.424 | 1.715 | .477 | 1.00 | 21.73 | C |
| ATOM | 4624 | CG1 | VAL | A | 311 | −38.724 | 1.076 | .941 | 1.00 | 21.01 | C |
| ATOM | 4628 | CG2 | VAL | A | 311 | −37.765 | 2.993 | −.292 | 1.00 | 21.88 | C |
| ATOM | 4632 | C | VAL | A | 311 | −35.553 | 1.445 | −1.230 | 1.00 | 21.67 | C |
| ATOM | 4633 | O | VAL | A | 311 | −35.811 | 1.728 | −2.389 | 1.00 | 21.71 | O |
| ATOM | 4635 | N | GLU | A | 312 | −34.381 | 1.724 | −.663 | 1.00 | 22.25 | N |
| ATOM | 4636 | CA | GLU | A | 312 | −33.248 | 2.284 | −1.443 | 1.00 | 23.00 | C |
| ATOM | 4638 | CB | GLU | A | 312 | −31.951 | 2.331 | −.608 | 1.00 | 23.36 | C |
| ATOM | 4641 | CG | GLU | A | 312 | −31.897 | 3.383 | .511 | 1.00 | 24.72 | C |
| ATOM | 4644 | CD | GLU | A | 312 | −30.526 | 3.469 | 1.189 | 1.00 | 27.09 | C |
| ATOM | 4645 | OE1 | GLU | A | 312 | −30.083 | 4.608 | 1.458 | 1.00 | 30.07 | O |
| ATOM | 4646 | OE2 | GLU | A | 312 | −29.885 | 2.418 | 1.454 | 1.00 | 27.86 | O |
| ATOM | 4647 | C | GLU | A | 312 | −32.954 | 1.498 | −2.731 | 1.00 | 23.13 | C |
| ATOM | 4648 | O | GLU | A | 312 | −32.851 | 2.064 | −3.803 | 1.00 | 22.88 | O |
| ATOM | 4650 | N | ARG | A | 313 | −32.819 | .188 | −2.615 | 1.00 | 23.74 | N |
| ATOM | 4651 | CA | ARG | A | 313 | −32.400 | −.628 | −3.743 | 1.00 | 24.46 | C |
| ATOM | 4653 | CB | ARG | A | 313 | −31.758 | −1.916 | −3.232 | 1.00 | 25.01 | C |
| ATOM | 4656 | CG | ARG | A | 313 | −30.421 | −1.667 | −2.481 | 1.00 | 27.74 | C |
| ATOM | 4659 | CD | ARG | A | 313 | −29.715 | −2.963 | −2.072 | 1.00 | 31.41 | C |
| ATOM | 4662 | NE | ARG | A | 313 | −30.675 | −3.921 | −1.499 | 1.00 | 34.94 | N |
| ATOM | 4664 | CZ | ARG | A | 313 | −31.203 | −4.974 | −2.138 | 1.00 | 37.87 | C |
| ATOM | 4665 | NH1 | ARG | A | 313 | −30.861 | −5.282 | −3.402 | 1.00 | 38.35 | N |

TABLE 16-7-continued

| | | | | | | | | | | | |
|---|---|---|---|---|---|---|---|---|---|---|---|
| colspan="12" | Coordinates of *P. tremuloides* IspS |
| ATOM | 4668 | NH2 | ARG | A | 313 | −32.079 | −5.746 | −1.495 | 1.00 | 38.82 | N |
| ATOM | 4671 | C | ARG | A | 313 | −33.523 | −.914 | −4.739 | 1.00 | 24.27 | C |
| ATOM | 4672 | O | ARG | A | 313 | −33.257 | −1.178 | −5.898 | 1.00 | 24.17 | O |
| ATOM | 4674 | N | TRP | A | 314 | −34.770 | −.873 | −4.282 | 1.00 | 24.59 | N |
| ATOM | 4675 | CA | TRP | A | 314 | −35.939 | −1.042 | −5.142 | 1.00 | 24.66 | C |
| ATOM | 4677 | CB | TRP | A | 314 | −36.175 | .234 | −5.961 | 1.00 | 24.39 | C |
| ATOM | 4680 | CG | TRP | A | 314 | −37.575 | .382 | −6.386 | 1.00 | 22.61 | C |
| ATOM | 4681 | CD1 | TRP | A | 314 | −38.073 | .204 | −7.635 | 1.00 | 21.66 | C |
| ATOM | 4683 | NE1 | TRP | A | 314 | −39.429 | .403 | −7.634 | 1.00 | 21.42 | N |
| ATOM | 4685 | CE2 | TRP | A | 314 | −39.829 | .707 | −6.360 | 1.00 | 20.99 | C |
| ATOM | 4686 | CD2 | TRP | A | 314 | −38.683 | .701 | −5.550 | 1.00 | 21.41 | C |
| ATOM | 4687 | CE3 | TRP | A | 314 | −38.817 | .991 | −4.191 | 1.00 | 21.48 | C |
| ATOM | 4689 | CZ3 | TRP | A | 314 | −40.080 | 1.277 | −3.693 | 1.00 | 21.38 | C |
| ATOM | 4691 | CH2 | TRP | A | 314 | −41.204 | 1.269 | −4.523 | 1.00 | 20.84 | C |
| ATOM | 4693 | CZ2 | TRP | A | 314 | −41.099 | .985 | −5.857 | 1.00 | 20.87 | C |
| ATOM | 4695 | C | TRP | A | 314 | −35.831 | −2.286 | −6.038 | 1.00 | 25.65 | C |
| ATOM | 4696 | O | TRP | A | 314 | −36.069 | −2.238 | −7.259 | 1.00 | 25.69 | O |
| ATOM | 4698 | N | ASP | A | 315 | −35.480 | −3.400 | −5.404 | 1.00 | 26.79 | N |
| ATOM | 4699 | CA | ASP | A | 315 | −35.253 | −4.667 | −6.087 | 1.00 | 28.01 | C |
| ATOM | 4701 | CB | ASP | A | 315 | −33.801 | −5.097 | −5.890 | 1.00 | 28.07 | C |
| ATOM | 4704 | CG | ASP | A | 315 | −33.553 | −6.536 | −6.296 | 1.00 | 29.92 | C |
| ATOM | 4705 | OD1 | ASP | A | 315 | −34.262 | −7.026 | −7.197 | 1.00 | 32.58 | O |
| ATOM | 4706 | OD2 | ASP | A | 315 | −32.648 | −7.194 | −5.722 | 1.00 | 32.73 | O |
| ATOM | 4707 | C | ASP | A | 315 | −36.202 | −5.710 | −5.518 | 1.00 | 28.91 | C |
| ATOM | 4708 | O | ASP | A | 315 | −36.019 | −6.163 | −4.399 | 1.00 | 29.17 | O |
| ATOM | 4710 | N | VAL | A | 316 | −37.218 | −6.091 | −6.283 | 1.00 | 30.25 | N |
| ATOM | 4711 | CA | VAL | A | 316 | −38.233 | −7.012 | −5.778 | 1.00 | 31.47 | C |
| ATOM | 4713 | CB | VAL | A | 316 | −39.396 | −7.156 | −6.755 | 1.00 | 31.56 | C |
| ATOM | 4715 | CG1 | VAL | A | 316 | −40.668 | −7.590 | −6.027 | 1.00 | 30.99 | C |
| ATOM | 4719 | CG2 | VAL | A | 316 | −39.033 | −8.141 | −7.862 | 1.00 | 31.84 | C |
| ATOM | 4723 | C | VAL | A | 316 | −37.663 | −8.405 | −5.540 | 1.00 | 32.86 | C |
| ATOM | 4724 | O | VAL | A | 316 | −38.170 | −9.153 | −4.708 | 1.00 | 32.99 | O |
| ATOM | 4726 | N | ASN | A | 317 | −36.607 | −8.750 | −6.278 | 1.00 | 34.55 | N |
| ATOM | 4727 | CA | ASN | A | 317 | −35.940 | −10.060 | −6.160 | 1.00 | 35.53 | C |
| ATOM | 4729 | CB | ASN | A | 317 | −35.013 | −10.298 | −7.367 | 1.00 | 35.68 | C |
| ATOM | 4732 | CG | ASN | A | 317 | −35.752 | −10.264 | −8.713 | 1.00 | 35.92 | C |
| ATOM | 4733 | OD1 | ASN | A | 317 | −36.634 | −11.092 | −8.971 | 1.00 | 36.95 | O |
| ATOM | 4734 | ND2 | ASN | A | 317 | −35.368 | −9.323 | −9.585 | 1.00 | 34.17 | N |
| ATOM | 4737 | C | ASN | A | 317 | −35.126 | −10.225 | −4.871 | 1.00 | 36.40 | C |
| ATOM | 4738 | O | ASN | A | 317 | −34.385 | −11.195 | −4.747 | 1.00 | 36.47 | O |
| ATOM | 4740 | N | ALA | A | 318 | −35.239 | −9.265 | −3.944 | 1.00 | 37.52 | N |
| ATOM | 4741 | CA | ALA | A | 318 | −34.614 | −9.335 | −2.613 | 1.00 | 38.45 | C |
| ATOM | 4743 | CB | ALA | A | 318 | −33.371 | −8.465 | −2.557 | 1.00 | 38.43 | C |
| ATOM | 4747 | C | ALA | A | 318 | −35.631 | −8.902 | −1.554 | 1.00 | 39.28 | C |
| ATOM | 4748 | O | ALA | A | 318 | −35.361 | −8.094 | −.662 | 1.00 | 39.55 | O |
| ATOM | 4750 | N | ILE | A | 319 | −36.823 | −9.456 | −1.698 | 1.00 | 40.17 | N |
| ATOM | 4751 | CA | ILE | A | 319 | −37.905 | −9.310 | −.740 | 1.00 | 40.49 | C |
| ATOM | 4753 | CB | ILE | A | 319 | −39.275 | −9.588 | −1.469 | 1.00 | 40.64 | C |
| ATOM | 4755 | CG1 | ILE | A | 319 | −40.473 | −9.078 | −.683 | 1.00 | 40.88 | C |
| ATOM | 4758 | CD1 | ILE | A | 319 | −41.799 | −9.535 | −1.280 | 1.00 | 40.86 | C |
| ATOM | 4762 | CG2 | ILE | A | 319 | −39.460 | −11.082 | −1.801 | 1.00 | 40.50 | C |
| ATOM | 4766 | C | ILE | A | 319 | −37.656 | −10.319 | .393 | 1.00 | 40.69 | C |
| ATOM | 4767 | O | ILE | A | 319 | −38.136 | −10.138 | 1.504 | 1.00 | 40.88 | O |
| ATOM | 4769 | N | ASN | A | 320 | −36.886 | −11.374 | .104 | 1.00 | 40.79 | N |
| ATOM | 4770 | CA | ASN | A | 320 | −36.689 | −12.483 | 1.049 | 1.00 | 40.64 | C |
| ATOM | 4772 | CB | ASN | A | 320 | −36.240 | −13.761 | .314 | 1.00 | 40.73 | C |
| ATOM | 4775 | CG | ASN | A | 320 | −37.370 | −14.422 | −.468 | 1.00 | 40.98 | C |
| ATOM | 4776 | OD1 | ASN | A | 320 | −38.556 | −14.309 | −.119 | 1.00 | 40.77 | O |
| ATOM | 4777 | ND2 | ASN | A | 320 | −37.001 | −15.131 | −1.529 | 1.00 | 41.31 | N |
| ATOM | 4780 | C | ASN | A | 320 | −35.711 | −12.175 | 2.169 | 1.00 | 40.16 | C |
| ATOM | 4781 | O | ASN | A | 320 | −35.546 | −12.978 | 3.077 | 1.00 | 40.15 | O |
| ATOM | 4783 | N | ASP | A | 321 | −35.067 | −11.017 | 2.101 | 1.00 | 39.66 | N |
| ATOM | 4784 | CA | ASP | A | 321 | −34.111 | −10.615 | 3.126 | 1.00 | 39.51 | C |
| ATOM | 4786 | CB | ASP | A | 321 | −33.114 | −9.571 | 2.575 | 1.00 | 40.17 | C |
| ATOM | 4789 | CG | ASP | A | 321 | −32.595 | −9.904 | 1.152 | 1.00 | 42.12 | C |
| ATOM | 4790 | OD1 | ASP | A | 321 | −32.425 | −11.115 | .820 | 1.00 | 44.15 | O |
| ATOM | 4791 | OD2 | ASP | A | 321 | −32.354 | −8.934 | .375 | 1.00 | 43.28 | O |
| ATOM | 4792 | C | ASP | A | 321 | −34.851 | −10.030 | 4.337 | 1.00 | 38.27 | C |
| ATOM | 4793 | O | ASP | A | 321 | −34.304 | −9.987 | 5.443 | 1.00 | 38.15 | O |
| ATOM | 4795 | N | LEU | A | 322 | −36.089 | −9.583 | 4.108 | 1.00 | 36.72 | N |
| ATOM | 4796 | CA | LEU | A | 322 | −36.887 | −8.875 | 5.104 | 1.00 | 35.38 | C |
| ATOM | 4798 | CB | LEU | A | 322 | −37.894 | −7.942 | 4.422 | 1.00 | 35.15 | C |
| ATOM | 4801 | CG | LEU | A | 322 | −37.370 | −6.840 | 3.503 | 1.00 | 34.83 | C |
| ATOM | 4803 | CD1 | LEU | A | 322 | −38.479 | −6.286 | 2.626 | 1.00 | 34.45 | C |
| ATOM | 4807 | CD2 | LEU | A | 322 | −36.742 | −5.740 | 4.316 | 1.00 | 34.89 | C |
| ATOM | 4811 | C | LEU | A | 322 | −37.683 | −9.834 | 5.963 | 1.00 | 34.57 | C |
| ATOM | 4812 | O | LEU | A | 322 | −37.975 | −10.933 | 5.527 | 1.00 | 34.27 | O |
| ATOM | 4814 | N | PRO | A | 323 | −38.039 | −9.402 | 7.189 | 1.00 | 33.93 | N |

TABLE 16-7-continued

Coordinates of *P. tremuloides* IspS

| ATOM | 4815 | CA | PRO | A | 323 | −39.070 | −9.917 | 8.067 | 1.00 | 33.49 | C |
|---|---|---|---|---|---|---|---|---|---|---|---|
| ATOM | 4817 | CB | PRO | A | 323 | −39.151 | −8.840 | 9.141 | 1.00 | 33.31 | C |
| ATOM | 4820 | CG | PRO | A | 323 | −37.791 | −8.419 | 9.311 | 1.00 | 33.67 | C |
| ATOM | 4823 | CD | PRO | A | 323 | −37.154 | −8.496 | 7.941 | 1.00 | 34.20 | C |
| ATOM | 4826 | C | PRO | A | 323 | −40.429 | −10.036 | 7.425 | 1.00 | 33.33 | C |
| ATOM | 4827 | O | PRO | A | 323 | −40.776 | −9.232 | 6.579 | 1.00 | 33.35 | O |
| ATOM | 4828 | N | ASP | A | 324 | −41.209 | −11.005 | 7.891 | 1.00 | 33.37 | N |
| ATOM | 4829 | CA | ASP | A | 324 | −42.511 | −11.329 | 7.313 | 1.00 | 33.36 | C |
| ATOM | 4831 | CB | ASP | A | 324 | −43.137 | −12.542 | 8.037 | 1.00 | 33.59 | C |
| ATOM | 4834 | CG | ASP | A | 324 | −42.496 | −13.881 | 7.619 | 1.00 | 34.18 | C |
| ATOM | 4835 | OD1 | ASP | A | 324 | −41.885 | −13.915 | 6.518 | 1.00 | 36.44 | O |
| ATOM | 4836 | OD2 | ASP | A | 324 | −42.607 | −14.887 | 8.371 | 1.00 | 32.19 | O |
| ATOM | 4837 | C | ASP | A | 324 | −43.484 | −10.149 | 7.289 | 1.00 | 32.90 | C |
| ATOM | 4838 | O | ASP | A | 324 | −44.108 | −9.885 | 6.255 | 1.00 | 33.36 | O |
| ATOM | 4840 | N | TYR | A | 325 | −43.606 | −9.423 | 8.392 | 1.00 | 32.10 | N |
| ATOM | 4841 | CA | TYR | A | 325 | −44.515 | −8.279 | 8.400 | 1.00 | 31.65 | C |
| ATOM | 4843 | CB | TYR | A | 325 | −44.718 | −7.726 | 9.815 | 1.00 | 31.68 | C |
| ATOM | 4846 | CG | TYR | A | 325 | −43.618 | −6.846 | 10.352 | 1.00 | 31.35 | C |
| ATOM | 4847 | CD1 | TYR | A | 325 | −42.507 | −7.389 | 10.992 | 1.00 | 31.31 | C |
| ATOM | 4849 | CE1 | TYR | A | 325 | −41.497 | −6.574 | 11.504 | 1.00 | 31.46 | C |
| ATOM | 4851 | CZ | TYR | A | 325 | −41.613 | −5.192 | 11.392 | 1.00 | 32.41 | C |
| ATOM | 4852 | OH | TYR | A | 325 | −40.637 | −4.336 | 11.893 | 1.00 | 32.78 | O |
| ATOM | 4854 | CE2 | TYR | A | 325 | −42.723 | −4.644 | 10.769 | 1.00 | 32.17 | C |
| ATOM | 4856 | CD2 | TYR | A | 325 | −43.713 | −5.470 | 10.261 | 1.00 | 31.47 | C |
| ATOM | 4858 | C | TYR | A | 325 | −44.094 | −7.179 | 7.424 | 1.00 | 31.17 | C |
| ATOM | 4859 | O | TYR | A | 325 | −44.947 | −6.458 | 6.920 | 1.00 | 31.09 | O |
| ATOM | 4861 | N | MET | A | 326 | −42.796 | −7.068 | 7.145 | 1.00 | 30.73 | N |
| ATOM | 4862 | CA | MET | A | 326 | −42.277 | −6.036 | 6.225 | 1.00 | 30.49 | C |
| ATOM | 4864 | CB | MET | A | 326 | −40.832 | −5.702 | 6.565 | 1.00 | 30.16 | C |
| ATOM | 4867 | CG | MET | A | 326 | −40.725 | −4.918 | 7.830 | 1.00 | 29.57 | C |
| ATOM | 4870 | SD | MET | A | 326 | −39.057 | −4.376 | 8.166 | 1.00 | 28.39 | S |
| ATOM | 4871 | CE | MET | A | 326 | −39.407 | −2.787 | 8.933 | 1.00 | 26.18 | C |
| ATOM | 4875 | C | MET | A | 326 | −42.371 | −6.418 | 4.748 | 1.00 | 30.59 | C |
| ATOM | 4876 | O | MET | A | 326 | −42.786 | −5.603 | 3.920 | 1.00 | 30.48 | O |
| ATOM | 4878 | N | LYS | A | 327 | −41.936 | −7.643 | 4.438 | 1.00 | 30.68 | N |
| ATOM | 4879 | CA | LYS | A | 327 | −42.170 | −8.299 | 3.143 | 1.00 | 30.56 | C |
| ATOM | 4881 | CB | LYS | A | 327 | −42.267 | −9.830 | 3.326 | 1.00 | 30.84 | C |
| ATOM | 4884 | CG | LYS | A | 327 | −41.052 | −10.607 | 2.844 | 1.00 | 32.35 | C |
| ATOM | 4887 | CD | LYS | A | 327 | −40.990 | −12.019 | 3.412 | 1.00 | 34.43 | C |
| ATOM | 4890 | CE | LYS | A | 327 | −40.221 | −12.941 | 2.462 | 1.00 | 35.77 | C |
| ATOM | 4893 | NZ | LYS | A | 327 | −39.691 | −14.162 | 3.150 | 1.00 | 37.20 | N |
| ATOM | 4897 | C | LYS | A | 327 | −43.453 | −7.811 | 2.515 | 1.00 | 29.89 | C |
| ATOM | 4898 | O | LYS | A | 327 | −43.447 | −7.220 | 1.436 | 1.00 | 29.85 | O |
| ATOM | 4900 | N | LEU | A | 328 | −44.544 | −8.046 | 3.230 | 1.00 | 29.10 | N |
| ATOM | 4901 | CA | LEU | A | 328 | −45.871 | −7.781 | 2.730 | 1.00 | 28.77 | C |
| ATOM | 4903 | CB | LEU | A | 328 | −46.899 | −8.336 | 3.709 | 1.00 | 28.81 | C |
| ATOM | 4906 | CG | LEU | A | 328 | −48.349 | −8.364 | 3.257 | 1.00 | 28.82 | C |
| ATOM | 4908 | CD1 | LEU | A | 328 | −48.519 | −9.260 | 2.046 | 1.00 | 29.09 | C |
| ATOM | 4912 | CD2 | LEU | A | 328 | −49.202 | −8.845 | 4.411 | 1.00 | 29.16 | C |
| ATOM | 4916 | C | LEU | A | 328 | −46.057 | −6.291 | 2.564 | 1.00 | 28.61 | C |
| ATOM | 4917 | O | LEU | A | 328 | −46.582 | −5.828 | 1.554 | 1.00 | 29.00 | O |
| ATOM | 4919 | N | CYS | A | 329 | −45.612 | −5.532 | 3.557 | 1.00 | 28.24 | N |
| ATOM | 4920 | CA | CYS | A | 329 | −45.737 | −4.086 | 3.504 | 1.00 | 27.95 | C |
| ATOM | 4922 | CB | CYS | A | 329 | −45.311 | −3.459 | 4.834 | 1.00 | 28.21 | C |
| ATOM | 4925 | SG | CYS | A | 329 | −45.280 | −1.630 | 4.817 | 1.00 | 32.39 | S |
| ATOM | 4927 | C | CYS | A | 329 | −44.921 | −3.541 | 2.327 | 1.00 | 26.34 | C |
| ATOM | 4928 | O | CYS | A | 329 | −45.459 | −2.853 | 1.475 | 1.00 | 26.23 | O |
| ATOM | 4930 | N | PHE | A | 330 | −43.642 | −3.882 | 2.269 | 1.00 | 24.82 | N |
| ATOM | 4931 | CA | PHE | A | 330 | −42.790 | −3.514 | 1.130 | 1.00 | 23.82 | C |
| ATOM | 4933 | CB | PHE | A | 330 | −41.397 | −4.137 | 1.283 | 1.00 | 23.64 | C |
| ATOM | 4936 | CG | PHE | A | 330 | −40.492 | −3.873 | .117 | 1.00 | 22.63 | C |
| ATOM | 4937 | CD1 | PHE | A | 330 | −39.845 | −2.658 | −.008 | 1.00 | 21.68 | C |
| ATOM | 4939 | CE1 | PHE | A | 330 | −39.020 | −2.393 | −1.082 | 1.00 | 21.07 | C |
| ATOM | 4941 | CZ | PHE | A | 330 | −38.829 | −3.343 | −2.046 | 1.00 | 22.00 | C |
| ATOM | 4943 | CE2 | PHE | A | 330 | −39.474 | −4.568 | −1.944 | 1.00 | 22.60 | C |
| ATOM | 4945 | CD2 | PHE | A | 330 | −40.309 | −4.824 | −.865 | 1.00 | 22.36 | C |
| ATOM | 4947 | C | PHE | A | 330 | −43.348 | −3.863 | −.281 | 1.00 | 22.99 | C |
| ATOM | 4948 | O | PHE | A | 330 | −43.350 | −3.012 | −1.182 | 1.00 | 22.98 | O |
| ATOM | 4950 | N | LEU | A | 331 | −43.789 | −5.101 | −.492 | 1.00 | 21.65 | N |
| ATOM | 4951 | CA | LEU | A | 331 | −44.306 | −5.484 | −1.816 | 1.00 | 20.74 | C |
| ATOM | 4953 | CB | LEU | A | 331 | −44.573 | −6.990 | −1.912 | 1.00 | 20.57 | C |
| ATOM | 4956 | CG | LEU | A | 331 | −44.959 | −7.575 | −3.277 | 1.00 | 19.82 | C |
| ATOM | 4958 | CD1 | LEU | A | 331 | −43.936 | −7.246 | −4.329 | 1.00 | 19.00 | C |
| ATOM | 4962 | CD2 | LEU | A | 331 | −45.128 | −9.092 | −3.165 | 1.00 | 19.11 | C |
| ATOM | 4966 | C | LEU | A | 331 | −45.568 | −4.710 | −2.159 | 1.00 | 19.98 | C |
| ATOM | 4967 | O | LEU | A | 331 | −45.753 | −4.324 | −3.300 | 1.00 | 20.15 | O |
| ATOM | 4969 | N | ALA | A | 332 | −46.431 | −4.495 | −1.172 | 1.00 | 19.09 | N |
| ATOM | 4970 | CA | ALA | A | 332 | −47.619 | −3.675 | −1.353 | 1.00 | 18.46 | C |

TABLE 16-7-continued

Coordinates of *P. tremuloides* IspS

| ATOM | 4972 | CB | ALA | A | 332 | −48.406 | −3.587 | −.045 | 1.00 | 18.20 | C |
|---|---|---|---|---|---|---|---|---|---|---|---|
| ATOM | 4976 | C | ALA | A | 332 | −47.248 | −2.279 | −1.856 | 1.00 | 17.91 | C |
| ATOM | 4977 | O | ALA | A | 332 | −47.890 | −1.745 | −2.744 | 1.00 | 17.98 | O |
| ATOM | 4979 | N | LEU | A | 333 | −46.197 | −1.706 | −1.295 | 1.00 | 17.62 | N |
| ATOM | 4980 | CA | LEU | A | 333 | −45.753 | −.353 | −1.637 | 1.00 | 17.60 | C |
| ATOM | 4982 | CB | LEU | A | 333 | −44.725 | .132 | −.598 | 1.00 | 17.59 | C |
| ATOM | 4985 | CG | LEU | A | 333 | −44.122 | 1.533 | −.761 | 1.00 | 17.16 | C |
| ATOM | 4987 | CD1 | LEU | A | 333 | −45.166 | 2.629 | −.554 | 1.00 | 16.99 | C |
| ATOM | 4991 | CD2 | LEU | A | 333 | −42.979 | 1.704 | .200 | 1.00 | 15.89 | C |
| ATOM | 4995 | C | LEU | A | 333 | −45.100 | −.320 | −3.005 | 1.00 | 17.70 | C |
| ATOM | 4996 | O | LEU | A | 333 | −45.321 | .603 | −3.795 | 1.00 | 17.86 | O |
| ATOM | 4998 | N | TYR | A | 334 | −44.248 | −1.319 | −3.234 | 1.00 | 17.63 | N |
| ATOM | 4999 | CA | TYR | A | 334 | −43.542 | −1.531 | −4.489 | 1.00 | 17.44 | C |
| ATOM | 5001 | CB | TYR | A | 334 | −42.893 | −2.908 | −4.444 | 1.00 | 17.50 | C |
| ATOM | 5004 | CG | TYR | A | 334 | −41.897 | −3.169 | −5.523 | 1.00 | 18.03 | C |
| ATOM | 5005 | CD1 | TYR | A | 334 | −40.698 | −2.473 | −5.569 | 1.00 | 18.83 | C |
| ATOM | 5007 | CE1 | TYR | A | 334 | −39.764 | −2.725 | −6.542 | 1.00 | 18.13 | C |
| ATOM | 5009 | CZ | TYR | A | 334 | −40.016 | −3.678 | −7.478 | 1.00 | 18.78 | C |
| ATOM | 5010 | OH | TYR | A | 334 | −39.096 | −3.929 | −8.439 | 1.00 | 21.71 | O |
| ATOM | 5012 | CE2 | TYR | A | 334 | −41.180 | −4.391 | −7.462 | 1.00 | 19.74 | C |
| ATOM | 5014 | CD2 | TYR | A | 334 | −42.118 | −4.139 | −6.472 | 1.00 | 19.59 | C |
| ATOM | 5016 | C | TYR | A | 334 | −44.500 | −1.497 | −5.649 | 1.00 | 17.43 | C |
| ATOM | 5017 | O | TYR | A | 334 | −44.264 | −.803 | −6.636 | 1.00 | 17.64 | O |
| ATOM | 5019 | N | ASN | A | 335 | −45.589 | −2.253 | −5.504 | 1.00 | 17.30 | N |
| ATOM | 5020 | CA | ASN | A | 335 | −46.574 | −2.448 | −6.553 | 1.00 | 17.23 | C |
| ATOM | 5022 | CB | ASN | A | 335 | −47.544 | −3.551 | −6.166 | 1.00 | 17.32 | C |
| ATOM | 5025 | CG | ASN | A | 335 | −46.952 | −4.920 | −6.332 | 1.00 | 18.16 | C |
| ATOM | 5026 | OD1 | ASN | A | 335 | −45.913 | −5.090 | −6.989 | 1.00 | 18.99 | O |
| ATOM | 5027 | ND2 | ASN | A | 335 | −47.616 | −5.921 | −5.749 | 1.00 | 18.49 | N |
| ATOM | 5030 | C | ASN | A | 335 | −47.365 | −1.218 | −6.812 | 1.00 | 17.12 | C |
| ATOM | 5031 | O | ASN | A | 335 | −47.613 | −.852 | −7.965 | 1.00 | 17.36 | O |
| ATOM | 5033 | N | THR | A | 336 | −47.789 | −.602 | −5.722 | 1.00 | 17.20 | N |
| ATOM | 5034 | CA | THR | A | 336 | −48.601 | .593 | −5.779 | 1.00 | 17.36 | C |
| ATOM | 5036 | CB | THR | A | 336 | −48.888 | 1.104 | −4.381 | 1.00 | 17.20 | C |
| ATOM | 5038 | OG1 | THR | A | 336 | −49.611 | .103 | −3.657 | 1.00 | 16.26 | O |
| ATOM | 5040 | CG2 | THR | A | 336 | −49.688 | 2.384 | −4.452 | 1.00 | 17.18 | C |
| ATOM | 5044 | C | THR | A | 336 | −47.893 | 1.691 | −6.550 | 1.00 | 17.84 | C |
| ATOM | 5045 | O | THR | A | 336 | −48.511 | 2.388 | −7.360 | 1.00 | 18.07 | O |
| ATOM | 5047 | N | ILE | A | 337 | −46.595 | 1.831 | −6.298 | 1.00 | 18.14 | N |
| ATOM | 5048 | CA | ILE | A | 337 | −45.817 | 2.904 | −6.895 | 1.00 | 18.50 | C |
| ATOM | 5050 | CB | ILE | A | 337 | −44.584 | 3.209 | −6.066 | 1.00 | 18.31 | C |
| ATOM | 5052 | CG1 | ILE | A | 337 | −45.014 | 3.997 | −4.837 | 1.00 | 18.58 | C |
| ATOM | 5055 | CD1 | ILE | A | 337 | −44.043 | 3.866 | −3.735 | 1.00 | 20.66 | C |
| ATOM | 5059 | CG2 | ILE | A | 337 | −43.570 | 3.988 | −6.867 | 1.00 | 16.98 | C |
| ATOM | 5063 | C | ILE | A | 337 | −45.447 | 2.548 | −8.314 | 1.00 | 19.29 | C |
| ATOM | 5064 | O | ILE | A | 337 | −45.556 | 3.387 | −9.214 | 1.00 | 19.17 | O |
| ATOM | 5066 | N | ASN | A | 338 | −45.033 | 1.299 | −8.513 | 1.00 | 20.16 | N |
| ATOM | 5067 | CA | ASN | A | 338 | −44.861 | .767 | −9.864 | 1.00 | 20.93 | C |
| ATOM | 5069 | CB | ASN | A | 338 | −44.409 | −.695 | −9.830 | 1.00 | 21.07 | C |
| ATOM | 5072 | CG | ASN | A | 338 | −42.953 | −.845 | −9.439 | 1.00 | 21.61 | C |
| ATOM | 5073 | OD1 | ASN | A | 338 | −42.232 | .143 | −9.308 | 1.00 | 22.40 | O |
| ATOM | 5074 | ND2 | ASN | A | 338 | −42.509 | −2.086 | −9.260 | 1.00 | 21.92 | N |
| ATOM | 5077 | C | ASN | A | 338 | −46.123 | .914 | −10.719 | 1.00 | 21.44 | C |
| ATOM | 5078 | O | ASN | A | 338 | −46.022 | 1.202 | −11.904 | 1.00 | 21.25 | O |
| ATOM | 5080 | N | GLU | A | 339 | −47.303 | .747 | −10.128 | 1.00 | 22.21 | N |
| ATOM | 5081 | CA | GLU | A | 339 | −48.532 | 1.000 | −10.880 | 1.00 | 23.31 | C |
| ATOM | 5083 | CB | GLU | A | 339 | −49.768 | .464 | −10.164 | 1.00 | 24.13 | C |
| ATOM | 5086 | CG | GLU | A | 339 | −50.146 | −.936 | −10.660 | 1.00 | 28.69 | C |
| ATOM | 5089 | CD | GLU | A | 339 | −50.939 | −1.740 | −9.638 | 1.00 | 35.06 | C |
| ATOM | 5090 | OE1 | GLU | A | 339 | −51.899 | −1.136 | −9.067 | 1.00 | 39.51 | O |
| ATOM | 5091 | OE2 | GLU | A | 339 | −50.596 | −2.952 | −9.414 | 1.00 | 36.64 | O |
| ATOM | 5092 | C | GLU | A | 339 | −48.725 | 2.463 | −11.269 | 1.00 | 22.71 | C |
| ATOM | 5093 | O | GLU | A | 339 | −49.215 | 2.743 | −12.372 | 1.00 | 22.48 | O |
| ATOM | 5095 | N | ILE | A | 340 | −48.339 | 3.390 | −10.390 | 1.00 | 22.19 | N |
| ATOM | 5096 | CA | ILE | A | 340 | −48.406 | 4.813 | −10.734 | 1.00 | 21.64 | C |
| ATOM | 5098 | CB | ILE | A | 340 | −48.135 | 5.739 | −9.538 | 1.00 | 21.33 | C |
| ATOM | 5100 | CG1 | ILE | A | 340 | −49.229 | 5.596 | −8.482 | 1.00 | 21.29 | C |
| ATOM | 5103 | CD1 | ILE | A | 340 | −48.925 | 6.306 | −7.150 | 1.00 | 20.00 | C |
| ATOM | 5107 | CG2 | ILE | A | 340 | −48.091 | 7.177 | −9.982 | 1.00 | 20.28 | C |
| ATOM | 5111 | C | ILE | A | 340 | −47.414 | 5.128 | −11.861 | 1.00 | 21.78 | C |
| ATOM | 5112 | O | ILE | A | 340 | −47.786 | 5.826 | −12.818 | 1.00 | 22.13 | O |
| ATOM | 5114 | N | ALA | A | 341 | −46.179 | 4.609 | −11.771 | 1.00 | 21.34 | N |
| ATOM | 5115 | CA | ALA | A | 341 | −45.147 | 4.892 | −12.787 | 1.00 | 21.03 | C |
| ATOM | 5117 | CB | ALA | A | 341 | −43.837 | 4.268 | −12.406 | 1.00 | 20.55 | C |
| ATOM | 5121 | C | ALA | A | 341 | −45.592 | 4.426 | −14.183 | 1.00 | 21.32 | C |
| ATOM | 5122 | O | ALA | A | 341 | −45.228 | 5.036 | −15.217 | 1.00 | 21.11 | O |
| ATOM | 5124 | N | TYR | A | 342 | −46.393 | 3.355 | −14.196 | 1.00 | 21.45 | N |
| ATOM | 5125 | CA | TYR | A | 342 | −47.008 | 2.861 | −15.414 | 1.00 | 21.41 | C |

TABLE 16-7-continued

Coordinates of *P. tremuloides* IspS

| ATOM | 5127 | CB | TYR | A | 342 | −47.627 | 1.468 | −15.208 | 1.00 | 21.31 | C |
|---|---|---|---|---|---|---|---|---|---|---|---|
| ATOM | 5130 | CG | TYR | A | 342 | −48.336 | .957 | −16.450 | 1.00 | 19.60 | C |
| ATOM | 5131 | CD1 | TYR | A | 342 | −47.613 | .463 | −17.521 | 1.00 | 16.69 | C |
| ATOM | 5133 | CE1 | TYR | A | 342 | −48.231 | .032 | −18.643 | 1.00 | 15.50 | C |
| ATOM | 5135 | CZ | TYR | A | 342 | −49.595 | .085 | −18.728 | 1.00 | 15.88 | C |
| ATOM | 5136 | OH | TYR | A | 342 | −50.196 | −.352 | −19.877 | 1.00 | 16.46 | O |
| ATOM | 5138 | CE2 | TYR | A | 342 | −50.352 | .558 | −17.681 | 1.00 | 16.50 | C |
| ATOM | 5140 | CD2 | TYR | A | 342 | −49.725 | .997 | −16.556 | 1.00 | 18.17 | C |
| ATOM | 5142 | C | TYR | A | 342 | −48.064 | 3.830 | −15.899 | 1.00 | 22.08 | C |
| ATOM | 5143 | O | TYR | A | 342 | −48.094 | 4.169 | −17.048 | 1.00 | 22.07 | O |
| ATOM | 5145 | N | ASP | A | 343 | −48.942 | 4.283 | −15.032 | 1.00 | 23.41 | N |
| ATOM | 5146 | CA | ASP | A | 343 | −49.970 | 5.211 | −15.481 | 1.00 | 24.66 | C |
| ATOM | 5148 | CB | ASP | A | 343 | −50.851 | 5.674 | −14.318 | 1.00 | 25.10 | C |
| ATOM | 5151 | CG | ASP | A | 343 | −51.720 | 4.552 | −13.732 | 1.00 | 26.06 | C |
| ATOM | 5152 | OD1 | ASP | A | 343 | −52.107 | 3.613 | −14.477 | 1.00 | 26.39 | O |
| ATOM | 5153 | OD2 | ASP | A | 343 | −52.032 | 4.642 | −12.516 | 1.00 | 27.29 | O |
| ATOM | 5154 | C | ASP | A | 343 | −49.316 | 6.420 | −16.142 | 1.00 | 25.22 | C |
| ATOM | 5155 | O | ASP | A | 343 | −49.755 | 6.874 | −17.192 | 1.00 | 25.47 | O |
| ATOM | 5157 | N | ASN | A | 344 | −48.260 | 6.936 | −15.528 | 1.00 | 25.87 | N |
| ATOM | 5158 | CA | ASN | A | 344 | −47.508 | 8.042 | −16.127 | 1.00 | 26.41 | C |
| ATOM | 5160 | CB | ASN | A | 344 | −46.498 | 8.605 | −15.134 | 1.00 | 26.56 | C |
| ATOM | 5163 | CG | ASN | A | 344 | −47.152 | 9.407 | −14.073 | 1.00 | 26.95 | C |
| ATOM | 5164 | OD1 | ASN | A | 344 | −47.495 | 10.568 | −14.296 | 1.00 | 29.13 | O |
| ATOM | 5165 | ND2 | ASN | A | 344 | −47.367 | 8.799 | −12.916 | 1.00 | 26.36 | N |
| ATOM | 5168 | C | ASN | A | 344 | −46.785 | 7.674 | −17.416 | 1.00 | 26.53 | C |
| ATOM | 5169 | O | ASN | A | 344 | −46.658 | 8.508 | −18.304 | 1.00 | 26.74 | O |
| ATOM | 5171 | N | LEU | A | 345 | −46.280 | 6.448 | −17.510 | 1.00 | 26.56 | N |
| ATOM | 5172 | CA | LEU | A | 345 | −45.634 | 6.019 | −18.739 | 1.00 | 26.37 | C |
| ATOM | 5174 | CB | LEU | A | 345 | −44.890 | 4.693 | −18.550 | 1.00 | 26.32 | C |
| ATOM | 5177 | CG | LEU | A | 345 | −43.995 | 4.339 | −19.750 | 1.00 | 25.96 | C |
| ATOM | 5179 | CD1 | LEU | A | 345 | −42.706 | 5.133 | −19.665 | 1.00 | 25.07 | C |
| ATOM | 5183 | CD2 | LEU | A | 345 | −43.724 | 2.835 | −19.874 | 1.00 | 24.75 | C |
| ATOM | 5187 | C | LEU | A | 345 | −46.679 | 5.908 | −19.856 | 1.00 | 26.38 | C |
| ATOM | 5188 | O | LEU | A | 345 | −46.435 | 6.335 | −20.966 | 1.00 | 26.52 | O |
| ATOM | 5190 | N | LYS | A | 346 | −47.839 | 5.340 | −19.563 | 1.00 | 26.59 | N |
| ATOM | 5191 | CA | LYS | A | 346 | −48.880 | 5.176 | −20.572 | 1.00 | 26.89 | C |
| ATOM | 5193 | CB | LYS | A | 346 | −50.065 | 4.367 | −20.011 | 1.00 | 26.80 | C |
| ATOM | 5196 | CG | LYS | A | 346 | −51.073 | 3.931 | −21.062 | 1.00 | 26.26 | C |
| ATOM | 5199 | CD | LYS | A | 346 | −52.210 | 3.080 | −20.517 | 1.00 | 26.15 | C |
| ATOM | 5202 | CE | LYS | A | 346 | −53.227 | 3.849 | −19.689 | 1.00 | 26.40 | C |
| ATOM | 5205 | NZ | LYS | A | 346 | −53.136 | 3.506 | −18.223 | 1.00 | 27.67 | N |
| ATOM | 5209 | C | LYS | A | 346 | −49.372 | 6.537 | −21.071 | 1.00 | 27.52 | C |
| ATOM | 5210 | O | LYS | A | 346 | −49.562 | 6.742 | −22.272 | 1.00 | 27.57 | O |
| ATOM | 5212 | N | ASP | A | 347 | −49.567 | 7.472 | −20.148 | 1.00 | 28.10 | N |
| ATOM | 5213 | CA | ASP | A | 347 | −50.309 | 8.689 | −20.465 | 1.00 | 28.58 | C |
| ATOM | 5215 | CB | ASP | A | 347 | −51.305 | 9.017 | −19.329 | 1.00 | 28.85 | C |
| ATOM | 5218 | CG | ASP | A | 347 | −52.426 | 7.950 | −19.197 | 1.00 | 30.01 | C |
| ATOM | 5219 | OD1 | ASP | A | 347 | −52.827 | 7.349 | −20.223 | 1.00 | 30.51 | O |
| ATOM | 5220 | OD2 | ASP | A | 347 | −52.910 | 7.704 | −18.069 | 1.00 | 32.61 | O |
| ATOM | 5221 | C | ASP | A | 347 | −49.407 | 9.871 | −20.804 | 1.00 | 28.22 | C |
| ATOM | 5222 | O | ASP | A | 347 | −49.778 | 10.710 | −21.611 | 1.00 | 28.39 | O |
| ATOM | 5224 | N | LYS | A | 348 | −48.228 | 9.930 | −20.206 | 1.00 | 28.03 | N |
| ATOM | 5225 | CA | LYS | A | 348 | −47.301 | 11.021 | −20.467 | 1.00 | 28.01 | C |
| ATOM | 5227 | CB | LYS | A | 348 | −46.785 | 11.648 | −19.164 | 1.00 | 28.39 | C |
| ATOM | 5230 | CG | LYS | A | 348 | −47.834 | 12.305 | −18.257 | 1.00 | 30.18 | C |
| ATOM | 5233 | CD | LYS | A | 348 | −47.143 | 12.898 | −17.003 | 1.00 | 32.40 | C |
| ATOM | 5236 | CE | LYS | A | 348 | −48.124 | 13.121 | −15.874 | 1.00 | 33.59 | C |
| ATOM | 5239 | NZ | LYS | A | 348 | −49.319 | 13.878 | −16.341 | 1.00 | 35.48 | N |
| ATOM | 5243 | C | LYS | A | 348 | −46.107 | 10.551 | −21.260 | 1.00 | 27.25 | C |
| ATOM | 5244 | O | LYS | A | 348 | −45.241 | 11.345 | −21.566 | 1.00 | 27.60 | O |
| ATOM | 5246 | N | GLY | A | 349 | −46.036 | 9.271 | −21.583 | 1.00 | 26.47 | N |
| ATOM | 5247 | CA | GLY | A | 349 | −44.863 | 8.742 | −22.261 | 1.00 | 26.01 | C |
| ATOM | 5250 | C | GLY | A | 349 | −43.559 | 9.109 | −21.587 | 1.00 | 25.67 | C |
| ATOM | 5251 | O | GLY | A | 349 | −42.613 | 9.472 | −22.250 | 1.00 | 25.85 | O |
| ATOM | 5253 | N | GLU | A | 350 | −43.498 | 9.032 | −20.269 | 1.00 | 25.55 | N |
| ATOM | 5254 | CA | GLU | A | 350 | −42.272 | 9.374 | −19.555 | 1.00 | 25.76 | C |
| ATOM | 5256 | CB | GLU | A | 350 | −42.332 | 10.814 | −19.021 | 1.00 | 26.34 | C |
| ATOM | 5259 | CG | GLU | A | 350 | −42.179 | 11.928 | −20.106 | 1.00 | 29.04 | C |
| ATOM | 5262 | CD | GLU | A | 350 | −40.745 | 12.101 | −20.598 | 1.00 | 32.08 | C |
| ATOM | 5263 | OE1 | GLU | A | 350 | −39.853 | 12.170 | −19.716 | 1.00 | 35.46 | O |
| ATOM | 5264 | OE2 | GLU | A | 350 | −40.516 | 12.174 | −21.839 | 1.00 | 31.64 | O |
| ATOM | 5265 | C | GLU | A | 350 | −42.084 | 8.414 | −18.400 | 1.00 | 24.87 | C |
| ATOM | 5266 | O | GLU | A | 350 | −43.067 | 8.046 | −17.760 | 1.00 | 25.16 | O |
| ATOM | 5268 | N | ASN | A | 351 | −40.833 | 8.009 | −18.145 | 1.00 | 23.71 | N |
| ATOM | 5269 | CA | ASN | A | 351 | −40.494 | 7.189 | −16.980 | 1.00 | 22.88 | C |
| ATOM | 5271 | CB | ASN | A | 351 | −39.351 | 6.229 | −17.287 | 1.00 | 22.88 | C |
| ATOM | 5274 | CG | ASN | A | 351 | −39.141 | 5.215 | −16.184 | 1.00 | 22.98 | C |
| ATOM | 5275 | OD1 | ASN | A | 351 | −39.006 | 5.584 | −15.035 | 1.00 | 22.68 | O |

TABLE 16-7-continued

| | | | | | | | | | | |
|---|---|---|---|---|---|---|---|---|---|---|
| ATOM | 5276 | ND2 | ASN | A | 351 | −39.139 | 3.924 | −16.529 | 1.00 | 24.38 | N |
| ATOM | 5279 | C | ASN | A | 351 | −40.126 | 8.058 | −15.786 | 1.00 | 22.40 | C |
| ATOM | 5280 | O | ASN | A | 351 | −39.097 | 8.741 | −15.785 | 1.00 | 22.66 | O |
| ATOM | 5282 | N | ILE | A | 352 | −40.965 | 8.021 | −14.760 | 1.00 | 21.55 | N |
| ATOM | 5283 | CA | ILE | A | 352 | −40.770 | 8.860 | −13.591 | 1.00 | 20.75 | C |
| ATOM | 5285 | CB | ILE | A | 352 | −42.002 | 9.788 | −13.360 | 1.00 | 20.95 | C |
| ATOM | 5287 | CG1 | ILE | A | 352 | −43.263 | 8.970 | −13.022 | 1.00 | 20.82 | C |
| ATOM | 5290 | CD1 | ILE | A | 352 | −44.237 | 9.698 | −12.122 | 1.00 | 20.21 | C |
| ATOM | 5294 | CG2 | ILE | A | 352 | −42.266 | 10.669 | −14.582 | 1.00 | 19.85 | C |
| ATOM | 5298 | C | ILE | A | 352 | −40.516 | 8.016 | −12.339 | 1.00 | 20.37 | C |
| ATOM | 5299 | O | ILE | A | 352 | −40.574 | 8.513 | −11.224 | 1.00 | 20.55 | O |
| ATOM | 5301 | N | LEU | A | 353 | −40.236 | 6.733 | −12.519 | 1.00 | 19.98 | N |
| ATOM | 5302 | CA | LEU | A | 353 | −40.061 | 5.828 | −11.387 | 1.00 | 19.42 | C |
| ATOM | 5304 | CB | LEU | A | 353 | −39.894 | 4.392 | −11.870 | 1.00 | 19.27 | C |
| ATOM | 5307 | CG | LEU | A | 353 | −39.989 | 3.318 | −10.799 | 1.00 | 19.01 | C |
| ATOM | 5309 | CD1 | LEU | A | 353 | −41.164 | 3.574 | −9.867 | 1.00 | 18.35 | C |
| ATOM | 5313 | CD2 | LEU | A | 353 | −40.085 | 1.938 | −11.468 | 1.00 | 18.74 | C |
| ATOM | 5317 | C | LEU | A | 353 | −38.890 | 6.240 | −10.523 | 1.00 | 19.11 | C |
| ATOM | 5318 | O | LEU | A | 353 | −39.022 | 6.319 | −9.314 | 1.00 | 18.96 | O |
| ATOM | 5320 | N | PRO | A | 354 | −37.746 | 6.549 | −11.142 | 1.00 | 19.06 | N |
| ATOM | 5321 | CA | PRO | A | 354 | −36.631 | 7.069 | −10.367 | 1.00 | 19.29 | C |
| ATOM | 5323 | CB | PRO | A | 354 | −35.749 | 7.717 | −11.438 | 1.00 | 19.25 | C |
| ATOM | 5326 | CG | PRO | A | 354 | −35.997 | 6.942 | −12.638 | 1.00 | 19.08 | C |
| ATOM | 5329 | CD | PRO | A | 354 | −37.409 | 6.472 | −12.572 | 1.00 | 19.00 | C |
| ATOM | 5332 | C | PRO | A | 354 | −37.024 | 8.122 | −9.328 | 1.00 | 19.33 | C |
| ATOM | 5333 | O | PRO | A | 354 | −36.534 | 8.057 | −8.193 | 1.00 | 19.73 | O |
| ATOM | 5334 | N | TYR | A | 355 | −37.891 | 9.063 | −9.721 | 1.00 | 18.83 | N |
| ATOM | 5335 | CA | TYR | A | 355 | −38.206 | 10.221 | −8.898 | 1.00 | 18.79 | C |
| ATOM | 5337 | CB | TYR | A | 355 | −38.836 | 11.359 | −9.707 | 1.00 | 19.10 | C |
| ATOM | 5340 | CG | TYR | A | 355 | −38.142 | 11.708 | −11.009 | 1.00 | 20.15 | C |
| ATOM | 5341 | CD1 | TYR | A | 355 | −36.940 | 12.403 | −11.027 | 1.00 | 20.78 | C |
| ATOM | 5343 | CE1 | TYR | A | 355 | −36.321 | 12.719 | −12.232 | 1.00 | 22.19 | C |
| ATOM | 5345 | CZ | TYR | A | 355 | −36.918 | 12.347 | −13.438 | 1.00 | 22.19 | C |
| ATOM | 5346 | OH | TYR | A | 355 | −36.341 | 12.660 | −14.657 | 1.00 | 23.29 | O |
| ATOM | 5348 | CE2 | TYR | A | 355 | −38.113 | 11.677 | −13.430 | 1.00 | 21.62 | C |
| ATOM | 5350 | CD2 | TYR | A | 355 | −38.720 | 11.371 | −12.227 | 1.00 | 21.05 | C |
| ATOM | 5352 | C | TYR | A | 355 | −39.155 | 9.864 | −7.777 | 1.00 | 18.43 | C |
| ATOM | 5353 | O | TYR | A | 355 | −39.081 | 10.460 | −6.709 | 1.00 | 18.61 | O |
| ATOM | 5355 | N | LEU | A | 356 | −40.058 | 8.917 | −8.023 | 1.00 | 17.92 | N |
| ATOM | 5356 | CA | LEU | A | 356 | −40.993 | 8.467 | −6.994 | 1.00 | 17.38 | C |
| ATOM | 5358 | CB | LEU | A | 356 | −42.136 | 7.658 | −7.597 | 1.00 | 17.17 | C |
| ATOM | 5361 | CG | LEU | A | 356 | −42.956 | 8.366 | −8.682 | 1.00 | 17.56 | C |
| ATOM | 5363 | CD1 | LEU | A | 356 | −43.933 | 7.419 | −9.371 | 1.00 | 17.47 | C |
| ATOM | 5367 | CD2 | LEU | A | 356 | −43.698 | 9.548 | −8.112 | 1.00 | 18.08 | C |
| ATOM | 5371 | C | LEU | A | 356 | −40.241 | 7.623 | −5.978 | 1.00 | 17.10 | C |
| ATOM | 5372 | O | LEU | A | 356 | −40.332 | 7.859 | −4.783 | 1.00 | 17.62 | O |
| ATOM | 5374 | N | THR | A | 357 | −39.464 | 6.656 | −6.442 | 1.00 | 16.64 | N |
| ATOM | 5375 | CA | THR | A | 357 | −38.775 | 5.769 | −5.513 | 1.00 | 16.18 | C |
| ATOM | 5377 | CB | THR | A | 357 | −38.104 | 4.554 | −6.213 | 1.00 | 16.04 | C |
| ATOM | 5379 | OG1 | THR | A | 357 | −37.092 | 4.996 | −7.123 | 1.00 | 15.93 | O |
| ATOM | 5381 | CG2 | THR | A | 357 | −39.142 | 3.732 | −6.962 | 1.00 | 14.99 | C |
| ATOM | 5385 | C | THR | A | 357 | −37.764 | 6.544 | −4.686 | 1.00 | 16.16 | C |
| ATOM | 5386 | O | THR | A | 357 | −37.599 | 6.278 | −3.506 | 1.00 | 16.07 | O |
| ATOM | 5388 | N | LYS | A | 358 | −37.107 | 7.524 | −5.291 | 1.00 | 16.20 | N |
| ATOM | 5389 | CA | LYS | A | 358 | −36.186 | 8.365 | −4.543 | 1.00 | 16.46 | C |
| ATOM | 5391 | CB | LYS | A | 358 | −35.518 | 9.386 | −5.453 | 1.00 | 16.80 | C |
| ATOM | 5394 | CG | LYS | A | 358 | −34.612 | 10.388 | −4.741 | 1.00 | 18.30 | C |
| ATOM | 5397 | CD | LYS | A | 358 | −33.352 | 9.738 | −4.168 | 1.00 | 20.21 | C |
| ATOM | 5400 | CE | LYS | A | 358 | −32.335 | 10.811 | −3.768 | 1.00 | 21.96 | C |
| ATOM | 5403 | NZ | LYS | A | 358 | −31.163 | 10.275 | −3.019 | 1.00 | 22.95 | N |
| ATOM | 5407 | C | LYS | A | 358 | −36.936 | 9.083 | −3.440 | 1.00 | 16.26 | C |
| ATOM | 5408 | O | LYS | A | 358 | −36.448 | 9.161 | −2.320 | 1.00 | 16.15 | O |
| ATOM | 5410 | N | ALA | A | 359 | −38.126 | 9.593 | −3.763 | 1.00 | 16.11 | N |
| ATOM | 5411 | CA | ALA | A | 359 | −38.937 | 10.332 | −2.798 | 1.00 | 16.10 | C |
| ATOM | 5413 | CB | ALA | A | 359 | −40.221 | 10.768 | −3.406 | 1.00 | 15.71 | C |
| ATOM | 5417 | C | ALA | A | 359 | −39.215 | 9.476 | −1.588 | 1.00 | 16.52 | C |
| ATOM | 5418 | O | ALA | A | 359 | −39.247 | 9.970 | −.442 | 1.00 | 16.82 | O |
| ATOM | 5420 | N | TRP | A | 360 | −39.398 | 8.187 | −1.843 | 1.00 | 16.79 | N |
| ATOM | 5421 | CA | TRP | A | 360 | −39.704 | 7.247 | −.780 | 1.00 | 17.25 | C |
| ATOM | 5423 | CB | TRP | A | 360 | −40.390 | 6.006 | −1.352 | 1.00 | 17.41 | C |
| ATOM | 5426 | CG | TRP | A | 360 | −41.852 | 6.129 | −1.318 | 1.00 | 17.06 | C |
| ATOM | 5427 | CD1 | TRP | A | 360 | −42.664 | 6.451 | −2.346 | 1.00 | 17.94 | C |
| ATOM | 5429 | NE1 | TRP | A | 360 | −43.967 | 6.489 | −1.926 | 1.00 | 18.03 | N |
| ATOM | 5431 | CE2 | TRP | A | 360 | −44.002 | 6.193 | −.592 | 1.00 | 17.72 | C |
| ATOM | 5432 | CD2 | TRP | A | 360 | −42.684 | 5.965 | −.179 | 1.00 | 16.60 | C |
| ATOM | 5433 | CE3 | TRP | A | 360 | −42.441 | 5.654 | 1.155 | 1.00 | 16.65 | C |
| ATOM | 5435 | CZ3 | TRP | A | 360 | −43.508 | 5.573 | 2.022 | 1.00 | 16.91 | C |
| ATOM | 5437 | CH2 | TRP | A | 360 | −44.811 | 5.807 | 1.586 | 1.00 | 17.82 | C |

TABLE 16-7-continued

| | | | | | | | | | | | |
|---|---|---|---|---|---|---|---|---|---|---|---|
| ATOM | 5439 | CZ2 | TRP | A | 360 | −45.080 | 6.114 | .282 | 1.00 | 18.49 | C |
| ATOM | 5441 | C | TRP | A | 360 | −38.490 | 6.865 | .073 | 1.00 | 17.52 | C |
| ATOM | 5442 | O | TRP | A | 360 | −38.603 | 6.767 | 1.297 | 1.00 | 17.38 | O |
| ATOM | 5444 | N | ALA | A | 361 | −37.344 | 6.651 | −.568 | 1.00 | 17.82 | N |
| ATOM | 5445 | CA | ALA | A | 361 | −36.122 | 6.336 | .157 | 1.00 | 18.11 | C |
| ATOM | 5447 | CB | ALA | A | 361 | −34.982 | 6.050 | −.805 | 1.00 | 17.92 | C |
| ATOM | 5451 | C | ALA | A | 361 | −35.781 | 7.507 | 1.063 | 1.00 | 18.52 | C |
| ATOM | 5452 | O | ALA | A | 361 | −35.434 | 7.327 | 2.229 | 1.00 | 18.48 | O |
| ATOM | 5454 | N | ASP | A | 362 | −35.911 | 8.711 | .521 | 1.00 | 19.16 | N |
| ATOM | 5455 | CA | ASP | A | 362 | −35.627 | 9.925 | 1.276 | 1.00 | 19.90 | C |
| ATOM | 5457 | CB | ASP | A | 362 | −35.797 | 11.167 | .387 | 1.00 | 20.39 | C |
| ATOM | 5460 | CG | ASP | A | 362 | −34.596 | 11.424 | −.530 | 1.00 | 21.84 | C |
| ATOM | 5461 | OD1 | ASP | A | 362 | −33.630 | 10.625 | −.561 | 1.00 | 22.88 | O |
| ATOM | 5462 | OD2 | ASP | A | 362 | −34.630 | 12.453 | −1.231 | 1.00 | 24.83 | O |
| ATOM | 5463 | C | ASP | A | 362 | −36.532 | 10.039 | 2.510 | 1.00 | 19.91 | C |
| ATOM | 5464 | O | ASP | A | 362 | −36.074 | 10.427 | 3.591 | 1.00 | 19.76 | O |
| ATOM | 5466 | N | LEU | A | 363 | −37.813 | 9.707 | 2.346 | 1.00 | 19.95 | N |
| ATOM | 5467 | CA | LEU | A | 363 | −38.747 | 9.688 | 3.478 | 1.00 | 19.85 | C |
| ATOM | 5469 | CB | LEU | A | 363 | −40.175 | 9.415 | 3.006 | 1.00 | 19.70 | C |
| ATOM | 5472 | CG | LEU | A | 363 | −41.219 | 9.293 | 4.123 | 1.00 | 18.58 | C |
| ATOM | 5474 | CD1 | LEU | A | 363 | −41.189 | 10.551 | 4.965 | 1.00 | 18.37 | C |
| ATOM | 5478 | CD2 | LEU | A | 363 | −42.597 | 9.073 | 3.551 | 1.00 | 16.43 | C |
| ATOM | 5482 | C | LEU | A | 363 | −38.368 | 8.613 | 4.488 | 1.00 | 20.24 | C |
| ATOM | 5483 | O | LEU | A | 363 | −38.314 | 8.875 | 5.691 | 1.00 | 20.52 | O |
| ATOM | 5485 | N | CYS | A | 364 | −38.129 | 7.397 | 3.997 | 1.00 | 20.29 | N |
| ATOM | 5486 | CA | CYS | A | 364 | −37.741 | 6.308 | 4.874 | 1.00 | 20.39 | C |
| ATOM | 5488 | CB | CYS | A | 364 | −37.595 | 4.985 | 4.111 | 1.00 | 20.37 | C |
| ATOM | 5491 | SG | CYS | A | 364 | −39.208 | 4.201 | 3.666 | 1.00 | 20.69 | S |
| ATOM | 5493 | C | CYS | A | 364 | −36.467 | 6.683 | 5.646 | 1.00 | 20.59 | C |
| ATOM | 5494 | O | CYS | A | 364 | −36.386 | 6.445 | 6.863 | 1.00 | 20.82 | O |
| ATOM | 5496 | N | ASN | A | 365 | −35.495 | 7.314 | 4.980 | 1.00 | 20.35 | N |
| ATOM | 5497 | CA | ASN | A | 365 | −34.282 | 7.716 | 5.697 | 1.00 | 20.14 | C |
| ATOM | 5499 | CB | ASN | A | 365 | −33.188 | 8.203 | 4.754 | 1.00 | 20.18 | C |
| ATOM | 5502 | CG | ASN | A | 365 | −32.359 | 7.064 | 4.184 | 1.00 | 20.55 | C |
| ATOM | 5503 | OD1 | ASN | A | 365 | −31.706 | 6.316 | 4.925 | 1.00 | 20.40 | O |
| ATOM | 5504 | ND2 | ASN | A | 365 | −32.365 | 6.938 | 2.854 | 1.00 | 21.25 | N |
| ATOM | 5507 | C | ASN | A | 365 | −34.590 | 8.746 | 6.779 | 1.00 | 19.92 | C |
| ATOM | 5508 | O | ASN | A | 365 | −33.997 | 8.685 | 7.857 | 1.00 | 19.94 | O |
| ATOM | 5510 | N | ALA | A | 366 | −35.531 | 9.658 | 6.507 | 1.00 | 19.58 | N |
| ATOM | 5511 | CA | ALA | A | 366 | −36.036 | 10.578 | 7.537 | 1.00 | 19.39 | C |
| ATOM | 5513 | CB | ALA | A | 366 | −37.083 | 11.507 | 6.971 | 1.00 | 18.79 | C |
| ATOM | 5517 | C | ALA | A | 366 | −36.597 | 9.784 | 8.730 | 1.00 | 19.75 | C |
| ATOM | 5518 | O | ALA | A | 366 | −36.215 | 10.049 | 9.891 | 1.00 | 19.53 | O |
| ATOM | 5520 | N | PHE | A | 367 | −37.460 | 8.797 | 8.447 | 1.00 | 19.69 | N |
| ATOM | 5521 | CA | PHE | A | 367 | −37.985 | 7.925 | 9.502 | 1.00 | 20.11 | C |
| ATOM | 5523 | CB | PHE | A | 367 | −38.952 | 6.857 | 8.967 | 1.00 | 20.47 | C |
| ATOM | 5526 | CG | PHE | A | 367 | −40.293 | 7.370 | 8.494 | 1.00 | 21.35 | C |
| ATOM | 5527 | CD1 | PHE | A | 367 | −40.985 | 8.347 | 9.180 | 1.00 | 21.54 | C |
| ATOM | 5529 | CE1 | PHE | A | 367 | −42.224 | 8.775 | 8.732 | 1.00 | 21.47 | C |
| ATOM | 5531 | CZ | PHE | A | 367 | −42.798 | 8.213 | 7.612 | 1.00 | 21.87 | C |
| ATOM | 5533 | CE2 | PHE | A | 367 | −42.135 | 7.230 | 6.924 | 1.00 | 22.60 | C |
| ATOM | 5535 | CD2 | PHE | A | 367 | −40.894 | 6.798 | 7.373 | 1.00 | 22.90 | C |
| ATOM | 5537 | C | PHE | A | 367 | −36.871 | 7.179 | 10.252 | 1.00 | 20.12 | C |
| ATOM | 5538 | O | PHE | A | 367 | −36.940 | 7.009 | 11.476 | 1.00 | 19.88 | O |
| ATOM | 5540 | N | LEU | A | 368 | −35.868 | 6.696 | 9.516 | 1.00 | 20.30 | N |
| ATOM | 5541 | CA | LEU | A | 368 | −34.775 | 5.931 | 10.133 | 1.00 | 20.19 | C |
| ATOM | 5543 | CB | LEU | A | 368 | −33.783 | 5.413 | 9.085 | 1.00 | 20.08 | C |
| ATOM | 5546 | CG | LEU | A | 368 | −32.743 | 4.363 | 9.514 | 1.00 | 19.30 | C |
| ATOM | 5548 | CD1 | LEU | A | 368 | −33.384 | 3.227 | 10.260 | 1.00 | 18.66 | C |
| ATOM | 5552 | CD2 | LEU | A | 368 | −31.968 | 3.807 | 8.319 | 1.00 | 18.16 | C |
| ATOM | 5556 | C | LEU | A | 368 | −34.063 | 6.812 | 11.128 | 1.00 | 20.41 | C |
| ATOM | 5557 | O | LEU | A | 368 | −33.842 | 6.407 | 12.257 | 1.00 | 20.01 | O |
| ATOM | 5559 | N | GLN | A | 369 | −33.751 | 8.036 | 10.711 | 1.00 | 20.89 | N |
| ATOM | 5560 | CA | GLN | A | 369 | −33.037 | 8.970 | 11.564 | 1.00 | 21.49 | C |
| ATOM | 5562 | CB | GLN | A | 369 | −32.782 | 10.280 | 10.832 | 1.00 | 21.58 | C |
| ATOM | 5565 | CG | GLN | A | 369 | −32.071 | 11.359 | 11.677 | 1.00 | 21.20 | C |
| ATOM | 5568 | CD | GLN | A | 369 | −30.639 | 11.006 | 11.976 | 1.00 | 20.04 | C |
| ATOM | 5569 | OE1 | GLN | A | 369 | −30.282 | 10.650 | 13.108 | 1.00 | 19.10 | O |
| ATOM | 5570 | NE2 | GLN | A | 369 | −29.803 | 11.095 | 10.956 | 1.00 | 18.75 | N |
| ATOM | 5573 | C | GLN | A | 369 | −33.763 | 9.265 | 12.870 | 1.00 | 22.21 | C |
| ATOM | 5574 | O | GLN | A | 369 | −33.122 | 9.343 | 13.909 | 1.00 | 22.41 | O |
| ATOM | 5576 | N | GLU | A | 370 | −35.080 | 9.455 | 12.822 | 1.00 | 23.05 | N |
| ATOM | 5577 | CA | GLU | A | 370 | −35.856 | 9.718 | 14.046 | 1.00 | 23.71 | C |
| ATOM | 5579 | CB | GLU | A | 370 | −37.329 | 10.041 | 13.726 | 1.00 | 24.04 | C |
| ATOM | 5582 | CG | GLU | A | 370 | −37.484 | 11.293 | 12.862 | 1.00 | 26.84 | C |
| ATOM | 5585 | CD | GLU | A | 370 | −38.897 | 11.910 | 12.834 | 1.00 | 30.36 | C |
| ATOM | 5586 | OE1 | GLU | A | 370 | −39.886 | 11.161 | 12.586 | 1.00 | 31.90 | O |
| ATOM | 5587 | OE2 | GLU | A | 370 | −38.992 | 13.164 | 13.014 | 1.00 | 31.62 | O |

TABLE 16-7-continued

Coordinates of *P. tremuloides* IspS

| ATOM | 5588 | C | GLU | A | 370 | −35.755 | 8.523 | 14.994 | 1.00 | 23.60 | C |
|---|---|---|---|---|---|---|---|---|---|---|---|
| ATOM | 5589 | O | GLU | A | 370 | −35.534 | 8.689 | 16.199 | 1.00 | 23.33 | O |
| ATOM | 5591 | N | ALA | A | 371 | −35.904 | 7.322 | 14.435 | 1.00 | 23.72 | N |
| ATOM | 5592 | CA | ALA | A | 371 | −35.771 | 6.091 | 15.201 | 1.00 | 23.91 | C |
| ATOM | 5594 | CB | ALA | A | 371 | −35.991 | 4.868 | 14.312 | 1.00 | 23.76 | C |
| ATOM | 5598 | C | ALA | A | 371 | −34.392 | 6.051 | 15.840 | 1.00 | 24.20 | C |
| ATOM | 5599 | O | ALA | A | 371 | −34.277 | 5.804 | 17.035 | 1.00 | 24.54 | O |
| ATOM | 5601 | N | LYS | A | 372 | −33.355 | 6.333 | 15.049 | 1.00 | 24.38 | N |
| ATOM | 5602 | CA | LYS | A | 372 | −31.979 | 6.273 | 15.530 | 1.00 | 24.39 | C |
| ATOM | 5604 | CB | LYS | A | 372 | −30.970 | 6.466 | 14.393 | 1.00 | 24.43 | C |
| ATOM | 5607 | CG | LYS | A | 372 | −30.623 | 5.164 | 13.645 | 1.00 | 25.20 | C |
| ATOM | 5610 | CD | LYS | A | 372 | −29.188 | 5.149 | 13.069 | 1.00 | 26.09 | C |
| ATOM | 5613 | CE | LYS | A | 372 | −29.114 | 5.437 | 11.557 | 1.00 | 27.01 | C |
| ATOM | 5616 | NZ | LYS | A | 372 | −29.002 | 4.200 | 10.709 | 1.00 | 26.82 | N |
| ATOM | 5620 | C | LYS | A | 372 | −31.717 | 7.268 | 16.645 | 1.00 | 24.59 | C |
| ATOM | 5621 | O | LYS | A | 372 | −31.096 | 6.908 | 17.627 | 1.00 | 25.13 | O |
| ATOM | 5623 | N | TRP | A | 373 | −32.181 | 8.507 | 16.520 | 1.00 | 24.78 | N |
| ATOM | 5624 | CA | TRP | A | 373 | −32.006 | 9.473 | 17.610 | 1.00 | 24.90 | C |
| ATOM | 5626 | CB | TRP | A | 373 | −32.565 | 10.863 | 17.266 | 1.00 | 24.75 | C |
| ATOM | 5629 | CG | TRP | A | 373 | −31.701 | 11.677 | 16.338 | 1.00 | 23.59 | C |
| ATOM | 5630 | CD1 | TRP | A | 373 | −30.344 | 11.663 | 16.259 | 1.00 | 22.38 | C |
| ATOM | 5632 | NE1 | TRP | A | 373 | −29.915 | 12.539 | 15.298 | 1.00 | 21.59 | N |
| ATOM | 5634 | CE2 | TRP | A | 373 | −30.999 | 13.162 | 14.744 | 1.00 | 21.69 | C |
| ATOM | 5635 | CD2 | TRP | A | 373 | −32.147 | 12.644 | 15.376 | 1.00 | 22.41 | C |
| ATOM | 5636 | CE3 | TRP | A | 373 | −33.409 | 13.110 | 14.976 | 1.00 | 21.98 | C |
| ATOM | 5638 | CZ3 | TRP | A | 373 | −33.480 | 14.072 | 13.979 | 1.00 | 22.08 | C |
| ATOM | 5640 | CH2 | TRP | A | 373 | −32.313 | 14.567 | 13.366 | 1.00 | 22.31 | C |
| ATOM | 5642 | CZ2 | TRP | A | 373 | −31.067 | 14.124 | 13.736 | 1.00 | 21.87 | C |
| ATOM | 5644 | C | TRP | A | 373 | −32.678 | 8.970 | 18.881 | 1.00 | 25.53 | C |
| ATOM | 5645 | O | TRP | A | 373 | −32.101 | 9.072 | 19.972 | 1.00 | 25.99 | O |
| ATOM | 5647 | N | LEU | A | 374 | −33.881 | 8.420 | 18.739 | 1.00 | 25.84 | N |
| ATOM | 5648 | CA | LEU | A | 374 | −34.667 | 7.980 | 19.893 | 1.00 | 26.29 | C |
| ATOM | 5650 | CB | LEU | A | 374 | −36.070 | 7.562 | 19.443 | 1.00 | 26.32 | C |
| ATOM | 5653 | CG | LEU | A | 374 | −37.227 | 7.646 | 20.444 | 1.00 | 26.39 | C |
| ATOM | 5655 | CD1 | LEU | A | 374 | −38.456 | 8.286 | 19.761 | 1.00 | 26.95 | C |
| ATOM | 5659 | CD2 | LEU | A | 374 | −37.583 | 6.281 | 21.050 | 1.00 | 26.24 | C |
| ATOM | 5663 | C | LEU | A | 374 | −33.982 | 6.824 | 20.623 | 1.00 | 26.77 | C |
| ATOM | 5664 | O | LEU | A | 374 | −33.995 | 6.758 | 21.860 | 1.00 | 26.95 | O |
| ATOM | 5666 | N | TYR | A | 375 | −33.383 | 5.919 | 19.854 | 1.00 | 27.23 | N |
| ATOM | 5667 | CA | TYR | A | 375 | −32.706 | 4.761 | 20.425 | 1.00 | 27.74 | C |
| ATOM | 5669 | CB | TYR | A | 375 | −32.195 | 3.814 | 19.328 | 1.00 | 27.78 | C |
| ATOM | 5672 | CG | TYR | A | 375 | −31.526 | 2.556 | 19.848 | 1.00 | 28.74 | C |
| ATOM | 5673 | CD1 | TYR | A | 375 | −32.264 | 1.394 | 20.090 | 1.00 | 29.61 | C |
| ATOM | 5675 | CE1 | TYR | A | 375 | −31.652 | .232 | 20.573 | 1.00 | 29.89 | C |
| ATOM | 5677 | CZ | TYR | A | 375 | −30.287 | .226 | 20.817 | 1.00 | 30.15 | C |
| ATOM | 5678 | OH | TYR | A | 375 | −29.676 | −.917 | 21.286 | 1.00 | 30.57 | O |
| ATOM | 5680 | CE2 | TYR | A | 375 | −29.530 | 1.367 | 20.579 | 1.00 | 30.05 | C |
| ATOM | 5682 | CD2 | TYR | A | 375 | −30.152 | 2.522 | 20.096 | 1.00 | 29.74 | C |
| ATOM | 5684 | C | TYR | A | 375 | −31.553 | 5.248 | 21.275 | 1.00 | 27.97 | C |
| ATOM | 5685 | O | TYR | A | 375 | −31.404 | 4.837 | 22.422 | 1.00 | 28.00 | O |
| ATOM | 5687 | N | ASN | A | 376 | −30.763 | 6.158 | 20.719 | 1.00 | 28.32 | N |
| ATOM | 5688 | CA | ASN | A | 376 | −29.531 | 6.590 | 21.368 | 1.00 | 28.71 | C |
| ATOM | 5690 | CB | ASN | A | 376 | −28.569 | 7.161 | 20.329 | 1.00 | 28.60 | C |
| ATOM | 5693 | CG | ASN | A | 376 | −28.215 | 6.159 | 19.255 | 1.00 | 28.32 | C |
| ATOM | 5694 | OD1 | ASN | A | 376 | −27.961 | 4.977 | 19.527 | 1.00 | 25.72 | O |
| ATOM | 5695 | ND2 | ASN | A | 376 | −28.195 | 6.631 | 18.015 | 1.00 | 29.29 | N |
| ATOM | 5698 | C | ASN | A | 376 | −29.728 | 7.617 | 22.484 | 1.00 | 29.05 | C |
| ATOM | 5699 | O | ASN | A | 376 | −28.752 | 8.021 | 23.136 | 1.00 | 29.03 | O |
| ATOM | 5701 | N | LYS | A | 377 | −30.977 | 8.021 | 22.716 | 1.00 | 29.16 | N |
| ATOM | 5702 | CA | LYS | A | 377 | −31.254 | 9.178 | 23.549 | 1.00 | 29.27 | C |
| ATOM | 5704 | CB | LYS | A | 377 | −31.051 | 8.879 | 25.050 | 1.00 | 29.52 | C |
| ATOM | 5707 | CG | LYS | A | 377 | −32.202 | 8.112 | 25.723 | 1.00 | 30.36 | C |
| ATOM | 5710 | CD | LYS | A | 377 | −32.202 | 6.638 | 25.340 | 1.00 | 31.54 | C |
| ATOM | 5713 | CE | LYS | A | 377 | −33.322 | 5.862 | 26.031 | 1.00 | 32.30 | C |
| ATOM | 5716 | NZ | LYS | A | 377 | −33.559 | 4.509 | 25.411 | 1.00 | 32.13 | N |
| ATOM | 5720 | C | LYS | A | 377 | −30.337 | 10.299 | 23.080 | 1.00 | 28.92 | C |
| ATOM | 5721 | O | LYS | A | 377 | −29.590 | 10.867 | 23.875 | 1.00 | 28.94 | O |
| ATOM | 5723 | N | SER | A | 378 | −30.377 | 10.575 | 21.776 | 1.00 | 28.52 | N |
| ATOM | 5724 | CA | SER | A | 378 | −29.652 | 11.700 | 21.201 | 1.00 | 28.30 | C |
| ATOM | 5726 | CB | SER | A | 378 | −29.623 | 11.620 | 19.678 | 1.00 | 28.33 | C |
| ATOM | 5729 | OG | SER | A | 378 | −28.919 | 10.482 | 19.237 | 1.00 | 29.36 | O |
| ATOM | 5731 | C | SER | A | 378 | −30.355 | 12.977 | 21.594 | 1.00 | 27.97 | C |
| ATOM | 5732 | O | SER | A | 378 | −31.483 | 12.947 | 22.108 | 1.00 | 27.91 | O |
| ATOM | 5734 | N | THR | A | 379 | −29.684 | 14.098 | 21.344 | 1.00 | 27.60 | N |
| ATOM | 5735 | CA | THR | A | 379 | −30.257 | 15.422 | 21.581 | 1.00 | 27.24 | C |
| ATOM | 5737 | CB | THR | A | 379 | −29.929 | 15.950 | 23.002 | 1.00 | 27.23 | C |
| ATOM | 5739 | OG1 | THR | A | 379 | −28.512 | 16.102 | 23.158 | 1.00 | 26.85 | O |
| ATOM | 5741 | CG2 | THR | A | 379 | −30.467 | 15.007 | 24.067 | 1.00 | 27.48 | C |

TABLE 16-7-continued

Coordinates of *P. tremuloides* IspS

| ATOM | 5745 | C | THR | A | 379 | −29.738 | 16.414 | 20.548 | 1.00 | 26.83 | C |
| --- | --- | --- | --- | --- | --- | --- | --- | --- | --- | --- | --- |
| ATOM | 5746 | O | THR | A | 379 | −28.834 | 17.190 | 20.844 | 1.00 | 26.69 | O |
| ATOM | 5748 | N | PRO | A | 380 | −30.305 | 16.390 | 19.331 | 1.00 | 26.56 | N |
| ATOM | 5749 | CA | PRO | A | 380 | −29.884 | 17.315 | 18.278 | 1.00 | 26.52 | C |
| ATOM | 5751 | CB | PRO | A | 380 | −30.380 | 16.648 | 16.992 | 1.00 | 26.46 | C |
| ATOM | 5754 | CG | PRO | A | 380 | −31.281 | 15.533 | 17.408 | 1.00 | 26.41 | C |
| ATOM | 5757 | CD | PRO | A | 380 | −31.395 | 15.508 | 18.887 | 1.00 | 26.53 | C |
| ATOM | 5760 | C | PRO | A | 380 | −30.469 | 18.728 | 18.386 | 1.00 | 26.55 | C |
| ATOM | 5761 | O | PRO | A | 380 | −31.472 | 18.966 | 19.063 | 1.00 | 26.69 | O |
| ATOM | 5762 | N | THR | A | 381 | −29.840 | 19.661 | 17.692 | 1.00 | 26.51 | N |
| ATOM | 5763 | CA | THR | A | 381 | −30.299 | 21.034 | 17.699 | 1.00 | 26.51 | C |
| ATOM | 5765 | CB | THR | A | 381 | −29.261 | 21.955 | 17.033 | 1.00 | 26.99 | C |
| ATOM | 5767 | OG1 | THR | A | 381 | −28.919 | 21.431 | 15.732 | 1.00 | 27.65 | O |
| ATOM | 5769 | CG2 | THR | A | 381 | −28.003 | 22.082 | 17.930 | 1.00 | 26.41 | C |
| ATOM | 5773 | C | THR | A | 381 | −31.635 | 21.167 | 16.970 | 1.00 | 26.06 | C |
| ATOM | 5774 | O | THR | A | 381 | −31.972 | 20.347 | 16.112 | 1.00 | 26.03 | O |
| ATOM | 5776 | N | PHE | A | 382 | −32.386 | 22.218 | 17.294 | 1.00 | 25.52 | N |
| ATOM | 5777 | CA | PHE | A | 382 | −33.681 | 22.436 | 16.654 | 1.00 | 24.83 | C |
| ATOM | 5779 | CB | PHE | A | 382 | −34.284 | 23.793 | 17.011 | 1.00 | 24.53 | C |
| ATOM | 5782 | CG | PHE | A | 382 | −35.495 | 24.113 | 16.211 | 1.00 | 23.77 | C |
| ATOM | 5783 | CD1 | PHE | A | 382 | −36.745 | 23.715 | 16.637 | 1.00 | 24.50 | C |
| ATOM | 5785 | CE1 | PHE | A | 382 | −37.873 | 23.977 | 15.878 | 1.00 | 24.49 | C |
| ATOM | 5787 | CZ | PHE | A | 382 | −37.744 | 24.630 | 14.673 | 1.00 | 24.41 | C |
| ATOM | 5789 | CE2 | PHE | A | 382 | −36.490 | 25.014 | 14.235 | 1.00 | 23.88 | C |
| ATOM | 5791 | CD2 | PHE | A | 382 | −35.381 | 24.752 | 14.999 | 1.00 | 23.29 | C |
| ATOM | 5793 | C | PHE | A | 382 | −33.542 | 22.342 | 15.150 | 1.00 | 24.49 | C |
| ATOM | 5794 | O | PHE | A | 382 | −34.361 | 21.731 | 14.485 | 1.00 | 24.32 | O |
| ATOM | 5796 | N | ASP | A | 383 | −32.498 | 22.969 | 14.627 | 1.00 | 24.42 | N |
| ATOM | 5797 | CA | ASP | A | 383 | −32.257 | 23.005 | 13.190 | 1.00 | 24.19 | C |
| ATOM | 5799 | CB | ASP | A | 383 | −31.101 | 23.966 | 12.867 | 1.00 | 24.21 | C |
| ATOM | 5802 | CG | ASP | A | 383 | −31.473 | 25.423 | 13.050 | 1.00 | 23.72 | C |
| ATOM | 5803 | OD1 | ASP | A | 383 | −32.634 | 25.794 | 12.837 | 1.00 | 25.60 | O |
| ATOM | 5804 | OD2 | ASP | A | 383 | −30.594 | 26.220 | 13.383 | 1.00 | 24.03 | O |
| ATOM | 5805 | C | ASP | A | 383 | −31.982 | 21.612 | 12.599 | 1.00 | 24.06 | C |
| ATOM | 5806 | O | ASP | A | 383 | −32.393 | 21.342 | 11.473 | 1.00 | 24.00 | O |
| ATOM | 5808 | N | ASP | A | 384 | −31.298 | 20.739 | 13.336 | 1.00 | 23.78 | N |
| ATOM | 5809 | CA | ASP | A | 384 | −31.078 | 19.379 | 12.848 | 1.00 | 24.11 | C |
| ATOM | 5811 | CB | ASP | A | 384 | −29.981 | 18.651 | 13.632 | 1.00 | 24.54 | C |
| ATOM | 5814 | CG | ASP | A | 384 | −28.573 | 19.009 | 13.159 | 1.00 | 26.32 | C |
| ATOM | 5815 | OD1 | ASP | A | 384 | −28.441 | 19.852 | 12.232 | 1.00 | 28.55 | O |
| ATOM | 5816 | OD2 | ASP | A | 384 | −27.599 | 18.451 | 13.728 | 1.00 | 27.18 | O |
| ATOM | 5817 | C | ASP | A | 384 | −32.351 | 18.550 | 12.905 | 1.00 | 23.83 | C |
| ATOM | 5818 | O | ASP | A | 384 | −32.670 | 17.825 | 11.955 | 1.00 | 24.24 | O |
| ATOM | 5820 | N | TYR | A | 385 | −33.070 | 18.637 | 14.017 | 1.00 | 23.31 | N |
| ATOM | 5821 | CA | TYR | A | 385 | −34.294 | 17.861 | 14.179 | 1.00 | 22.89 | C |
| ATOM | 5823 | CB | TYR | A | 385 | −34.833 | 17.979 | 15.608 | 1.00 | 22.86 | C |
| ATOM | 5826 | CG | TYR | A | 385 | −36.144 | 17.245 | 15.807 | 1.00 | 22.65 | C |
| ATOM | 5827 | CD1 | TYR | A | 385 | −36.163 | 15.868 | 16.030 | 1.00 | 22.36 | C |
| ATOM | 5829 | CE1 | TYR | A | 385 | −37.351 | 15.189 | 16.206 | 1.00 | 22.77 | C |
| ATOM | 5831 | CZ | TYR | A | 385 | −38.545 | 15.887 | 16.146 | 1.00 | 23.54 | C |
| ATOM | 5832 | OH | TYR | A | 385 | −39.733 | 15.212 | 16.309 | 1.00 | 24.38 | O |
| ATOM | 5834 | CE2 | TYR | A | 385 | −38.554 | 17.258 | 15.913 | 1.00 | 22.76 | C |
| ATOM | 5836 | CD2 | TYR | A | 385 | −37.360 | 17.923 | 15.744 | 1.00 | 22.12 | C |
| ATOM | 5838 | C | TYR | A | 385 | −35.375 | 18.299 | 13.190 | 1.00 | 22.55 | C |
| ATOM | 5839 | O | TYR | A | 385 | −36.050 | 17.467 | 12.584 | 1.00 | 22.85 | O |
| ATOM | 5841 | N | PHE | A | 386 | −35.537 | 19.609 | 13.042 | 1.00 | 22.08 | N |
| ATOM | 5842 | CA | PHE | A | 386 | −36.626 | 20.155 | 12.248 | 1.00 | 21.62 | C |
| ATOM | 5844 | CB | PHE | A | 386 | −36.857 | 21.628 | 12.568 | 1.00 | 21.73 | C |
| ATOM | 5847 | CG | PHE | A | 386 | −38.033 | 22.209 | 11.851 | 1.00 | 21.54 | C |
| ATOM | 5848 | CD1 | PHE | A | 386 | −39.311 | 21.933 | 12.273 | 1.00 | 21.29 | C |
| ATOM | 5850 | CE1 | PHE | A | 386 | −40.380 | 22.444 | 11.623 | 1.00 | 22.11 | C |
| ATOM | 5852 | CZ | PHE | A | 386 | −40.193 | 23.240 | 10.517 | 1.00 | 23.28 | C |
| ATOM | 5854 | CE2 | PHE | A | 386 | −38.920 | 23.502 | 10.069 | 1.00 | 23.10 | C |
| ATOM | 5856 | CD2 | PHE | A | 386 | −37.853 | 22.989 | 10.737 | 1.00 | 22.15 | C |
| ATOM | 5858 | C | PHE | A | 386 | −36.369 | 19.987 | 10.769 | 1.00 | 21.09 | C |
| ATOM | 5859 | O | PHE | A | 386 | −37.278 | 19.700 | 10.006 | 1.00 | 20.91 | O |
| ATOM | 5861 | N | GLY | A | 387 | −35.127 | 20.177 | 10.362 | 1.00 | 20.68 | N |
| ATOM | 5862 | CA | GLY | A | 387 | −34.747 | 19.917 | 8.985 | 1.00 | 20.43 | C |
| ATOM | 5865 | C | GLY | A | 387 | −35.151 | 18.521 | 8.544 | 1.00 | 19.95 | C |
| ATOM | 5866 | O | GLY | A | 387 | −35.553 | 18.327 | 7.398 | 1.00 | 20.24 | O |
| ATOM | 5868 | N | ASN | A | 388 | −35.032 | 17.554 | 9.451 | 1.00 | 19.12 | N |
| ATOM | 5869 | CA | ASN | A | 388 | −35.451 | 16.182 | 9.202 | 1.00 | 18.73 | C |
| ATOM | 5871 | CB | ASN | A | 388 | −34.744 | 15.272 | 10.205 | 1.00 | 18.90 | C |
| ATOM | 5874 | CG | ASN | A | 388 | −34.863 | 13.795 | 9.871 | 1.00 | 18.35 | C |
| ATOM | 5875 | OD1 | ASN | A | 388 | −34.163 | 13.284 | 8.993 | 1.00 | 17.24 | O |
| ATOM | 5876 | ND2 | ASN | A | 388 | −35.714 | 13.092 | 10.614 | 1.00 | 17.01 | N |
| ATOM | 5879 | C | ASN | A | 388 | −36.968 | 16.033 | 9.350 | 1.00 | 18.65 | C |
| ATOM | 5880 | O | ASN | A | 388 | −37.624 | 15.370 | 8.551 | 1.00 | 18.82 | O |

TABLE 16-7-continued

Coordinates of *P. tremuloides* IspS

| ATOM | 5882 | N | ALA | A | 389 | −37.527 | 16.670 | 10.371 | 1.00 | 18.38 | N |
|---|---|---|---|---|---|---|---|---|---|---|---|
| ATOM | 5883 | CA | ALA | A | 389 | −38.926 | 16.477 | 10.728 | 1.00 | 18.02 | C |
| ATOM | 5885 | CB | ALA | A | 389 | −39.203 | 17.107 | 12.084 | 1.00 | 17.83 | C |
| ATOM | 5889 | C | ALA | A | 389 | −39.949 | 16.966 | 9.700 | 1.00 | 17.90 | C |
| ATOM | 5890 | O | ALA | A | 389 | −41.095 | 16.544 | 9.760 | 1.00 | 17.74 | O |
| ATOM | 5892 | N | TRP | A | 390 | −39.585 | 17.860 | 8.783 | 1.00 | 18.11 | N |
| ATOM | 5893 | CA | TRP | A | 390 | −40.543 | 18.254 | 7.731 | 1.00 | 18.46 | C |
| ATOM | 5895 | CB | TRP | A | 390 | −40.459 | 19.737 | 7.329 | 1.00 | 18.59 | C |
| ATOM | 5898 | CG | TRP | A | 390 | −39.143 | 20.224 | 6.821 | 1.00 | 19.26 | C |
| ATOM | 5899 | CD1 | TRP | A | 390 | −38.224 | 20.947 | 7.519 | 1.00 | 20.64 | C |
| ATOM | 5901 | NE1 | TRP | A | 390 | −37.138 | 21.224 | 6.729 | 1.00 | 20.62 | N |
| ATOM | 5903 | CE2 | TRP | A | 390 | −37.352 | 20.694 | 5.485 | 1.00 | 19.57 | C |
| ATOM | 5904 | CD2 | TRP | A | 390 | −38.607 | 20.066 | 5.504 | 1.00 | 19.15 | C |
| ATOM | 5905 | CE3 | TRP | A | 390 | −39.060 | 19.448 | 4.344 | 1.00 | 20.13 | C |
| ATOM | 5907 | CZ3 | TRP | A | 390 | −38.254 | 19.477 | 3.224 | 1.00 | 20.27 | C |
| ATOM | 5909 | CH2 | TRP | A | 390 | −37.017 | 20.110 | 3.239 | 1.00 | 19.38 | C |
| ATOM | 5911 | CZ2 | TRP | A | 390 | −36.549 | 20.724 | 4.356 | 1.00 | 19.49 | C |
| ATOM | 5913 | C | TRP | A | 390 | −40.407 | 17.343 | 6.527 | 1.00 | 18.73 | C |
| ATOM | 5914 | O | TRP | A | 390 | −41.369 | 17.143 | 5.788 | 1.00 | 18.32 | O |
| ATOM | 5916 | N | LYS | A | 391 | −39.200 | 16.806 | 6.336 | 1.00 | 19.30 | N |
| ATOM | 5917 | CA | LYS | A | 391 | −38.969 | 15.692 | 5.404 | 1.00 | 19.70 | C |
| ATOM | 5919 | CB | LYS | A | 391 | −37.459 | 15.392 | 5.244 | 1.00 | 19.92 | C |
| ATOM | 5922 | CG | LYS | A | 391 | −36.812 | 15.953 | 3.935 | 1.00 | 22.08 | C |
| ATOM | 5925 | CD | LYS | A | 391 | −35.257 | 16.217 | 4.040 | 1.00 | 23.92 | C |
| ATOM | 5928 | CE | LYS | A | 391 | −34.918 | 17.698 | 4.426 | 1.00 | 24.43 | C |
| ATOM | 5931 | NZ | LYS | A | 391 | −33.699 | 17.901 | 5.307 | 1.00 | 23.23 | N |
| ATOM | 5935 | C | LYS | A | 391 | −39.731 | 14.441 | 5.861 | 1.00 | 19.46 | C |
| ATOM | 5936 | O | LYS | A | 391 | −40.284 | 13.709 | 5.032 | 1.00 | 20.07 | O |
| ATOM | 5938 | N | SER | A | 392 | −39.793 | 14.202 | 7.170 | 1.00 | 18.95 | N |
| ATOM | 5939 | CA | SER | A | 392 | −40.455 | 12.998 | 7.666 | 1.00 | 18.63 | C |
| ATOM | 5941 | CB | SER | A | 392 | −39.850 | 12.508 | 9.000 | 1.00 | 18.75 | C |
| ATOM | 5944 | OG | SER | A | 392 | −40.314 | 13.230 | 10.126 | 1.00 | 18.94 | O |
| ATOM | 5946 | C | SER | A | 392 | −41.964 | 13.152 | 7.771 | 1.00 | 18.20 | C |
| ATOM | 5947 | O | SER | A | 392 | −42.654 | 12.182 | 8.031 | 1.00 | 18.12 | O |
| ATOM | 5949 | N | SER | A | 393 | −42.477 | 14.360 | 7.567 | 1.00 | 18.07 | N |
| ATOM | 5950 | CA | SER | A | 393 | −43.929 | 14.591 | 7.556 | 1.00 | 18.02 | C |
| ATOM | 5952 | CB | SER | A | 393 | −44.229 | 16.078 | 7.504 | 1.00 | 18.08 | C |
| ATOM | 5955 | OG | SER | A | 393 | −43.995 | 16.558 | 6.192 | 1.00 | 18.01 | O |
| ATOM | 5957 | C | SER | A | 393 | −44.594 | 13.971 | 6.340 | 1.00 | 17.87 | C |
| ATOM | 5958 | O | SER | A | 393 | −45.778 | 13.661 | 6.372 | 1.00 | 18.03 | O |
| ATOM | 5960 | N | SER | A | 394 | −43.823 | 13.841 | 5.264 | 1.00 | 17.69 | N |
| ATOM | 5961 | CA | SER | A | 394 | −44.284 | 13.306 | 3.989 | 1.00 | 17.59 | C |
| ATOM | 5963 | CB | SER | A | 394 | −45.329 | 12.180 | 4.149 | 1.00 | 17.61 | C |
| ATOM | 5966 | OG | SER | A | 394 | −46.648 | 12.681 | 4.294 | 1.00 | 17.18 | O |
| ATOM | 5968 | C | SER | A | 394 | −44.828 | 14.415 | 3.115 | 1.00 | 17.42 | C |
| ATOM | 5969 | O | SER | A | 394 | −45.345 | 14.146 | 2.024 | 1.00 | 17.31 | O |
| ATOM | 5971 | N | GLY | A | 395 | −44.711 | 15.654 | 3.592 | 1.00 | 17.23 | N |
| ATOM | 5972 | CA | GLY | A | 395 | −45.088 | 16.827 | 2.807 | 1.00 | 17.26 | C |
| ATOM | 5975 | C | GLY | A | 395 | −44.478 | 16.749 | 1.415 | 1.00 | 17.29 | C |
| ATOM | 5976 | O | GLY | A | 395 | −45.203 | 16.653 | .413 | 1.00 | 18.06 | O |
| ATOM | 5978 | N | PRO | A | 396 | −43.145 | 16.754 | 1.331 | 1.00 | 16.72 | N |
| ATOM | 5979 | CA | PRO | A | 396 | −42.582 | 16.610 | .006 | 1.00 | 16.40 | C |
| ATOM | 5981 | CB | PRO | A | 396 | −41.080 | 16.549 | .259 | 1.00 | 16.62 | C |
| ATOM | 5984 | CG | PRO | A | 396 | −40.903 | 16.749 | 1.775 | 1.00 | 17.11 | C |
| ATOM | 5987 | CD | PRO | A | 396 | −42.157 | 17.252 | 2.296 | 1.00 | 16.87 | C |
| ATOM | 5990 | C | PRO | A | 396 | −43.053 | 15.374 | −.748 | 1.00 | 15.89 | C |
| ATOM | 5991 | O | PRO | A | 396 | −43.501 | 15.498 | −1.894 | 1.00 | 15.90 | O |
| ATOM | 5992 | N | LEU | A | 397 | −42.973 | 14.197 | −.135 | 1.00 | 15.27 | N |
| ATOM | 5993 | CA | LEU | A | 397 | −43.287 | 12.976 | −.886 | 1.00 | 14.57 | C |
| ATOM | 5995 | CB | LEU | A | 397 | −43.332 | 11.733 | −.008 | 1.00 | 14.36 | C |
| ATOM | 5998 | CG | LEU | A | 397 | −43.541 | 10.431 | −.781 | 1.00 | 14.02 | C |
| ATOM | 6000 | CD1 | LEU | A | 397 | −42.690 | 9.348 | −.206 | 1.00 | 15.04 | C |
| ATOM | 6004 | CD2 | LEU | A | 397 | −44.985 | 9.976 | −.805 | 1.00 | 13.75 | C |
| ATOM | 6008 | C | LEU | A | 397 | −44.618 | 13.182 | −1.542 | 1.00 | 14.39 | C |
| ATOM | 6009 | O | LEU | A | 397 | −44.736 | 12.999 | −2.745 | 1.00 | 14.57 | O |
| ATOM | 6011 | N | GLN | A | 398 | −45.604 | 13.607 | −.751 | 1.00 | 14.08 | N |
| ATOM | 6012 | CA | GLN | A | 398 | −46.962 | 13.828 | −1.245 | 1.00 | 13.91 | C |
| ATOM | 6014 | CB | GLN | A | 398 | −47.860 | 14.363 | −.136 | 1.00 | 13.99 | C |
| ATOM | 6017 | CG | GLN | A | 398 | −48.274 | 13.321 | .909 | 1.00 | 14.01 | C |
| ATOM | 6020 | CD | GLN | A | 398 | −49.189 | 13.902 | 1.983 | 1.00 | 13.41 | C |
| ATOM | 6021 | OE1 | GLN | A | 398 | −49.941 | 14.847 | 1.740 | 1.00 | 14.65 | O |
| ATOM | 6022 | NE2 | GLN | A | 398 | −49.122 | 13.344 | 3.168 | 1.00 | 12.17 | N |
| ATOM | 6025 | C | GLN | A | 398 | −47.015 | 14.800 | −2.403 | 1.00 | 13.84 | C |
| ATOM | 6026 | O | GLN | A | 398 | −47.677 | 14.547 | −3.396 | 1.00 | 13.46 | O |
| ATOM | 6028 | N | LEU | A | 399 | −46.319 | 15.922 | −2.272 | 1.00 | 14.11 | N |
| ATOM | 6029 | CA | LEU | A | 399 | −46.359 | 16.942 | −3.315 | 1.00 | 14.37 | C |
| ATOM | 6031 | CB | LEU | A | 399 | −45.900 | 18.282 | −2.756 | 1.00 | 14.26 | C |
| ATOM | 6034 | CG | LEU | A | 399 | −46.882 | 18.830 | −1.704 | 1.00 | 14.44 | C |

TABLE 16-7-continued

Coordinates of *P. tremuloides* IspS

| ATOM | 6036 | CD1 | LEU | A | 399 | −46.250 | 19.960 | −.919 | 1.00 | 16.43 | C |
|---|---|---|---|---|---|---|---|---|---|---|---|
| ATOM | 6040 | CD2 | LEU | A | 399 | −48.191 | 19.304 | −2.317 | 1.00 | 12.20 | C |
| ATOM | 6044 | C | LEU | A | 399 | −45.582 | 16.525 | −4.578 | 1.00 | 14.68 | C |
| ATOM | 6045 | O | LEU | A | 399 | −46.043 | 16.784 | −5.687 | 1.00 | 14.70 | O |
| ATOM | 6047 | N | ILE | A | 400 | −44.443 | 15.844 | −4.419 | 1.00 | 14.92 | N |
| ATOM | 6048 | CA | ILE | A | 400 | −43.748 | 15.221 | −5.564 | 1.00 | 15.08 | C |
| ATOM | 6050 | CB | ILE | A | 400 | −42.549 | 14.355 | −5.129 | 1.00 | 15.35 | C |
| ATOM | 6052 | CG1 | ILE | A | 400 | −41.406 | 15.254 | −4.611 | 1.00 | 16.83 | C |
| ATOM | 6055 | CD1 | ILE | A | 400 | −40.234 | 14.490 | −3.958 | 1.00 | 17.18 | C |
| ATOM | 6059 | CG2 | ILE | A | 400 | −42.060 | 13.486 | −6.292 | 1.00 | 14.03 | C |
| ATOM | 6063 | C | ILE | A | 400 | −44.682 | 14.329 | −6.358 | 1.00 | 15.08 | C |
| ATOM | 6064 | O | ILE | A | 400 | −44.672 | 14.362 | −7.574 | 1.00 | 15.18 | O |
| ATOM | 6066 | N | PHE | A | 401 | −45.474 | 13.524 | −5.650 | 1.00 | 15.16 | N |
| ATOM | 6067 | CA | PHE | A | 401 | −46.501 | 12.674 | −6.258 | 1.00 | 14.90 | C |
| ATOM | 6069 | CB | PHE | A | 401 | −47.052 | 11.663 | −5.240 | 1.00 | 14.51 | C |
| ATOM | 6072 | CG | PHE | A | 401 | −46.294 | 10.378 | −5.201 | 1.00 | 12.92 | C |
| ATOM | 6073 | CD1 | PHE | A | 401 | −46.727 | 9.282 | −5.931 | 1.00 | 11.98 | C |
| ATOM | 6075 | CE1 | PHE | A | 401 | −46.032 | 8.093 | −5.917 | 1.00 | 11.20 | C |
| ATOM | 6077 | CZ | PHE | A | 401 | −44.881 | 7.985 | −5.165 | 1.00 | 12.03 | C |
| ATOM | 6079 | CE2 | PHE | A | 401 | −44.431 | 9.078 | −4.428 | 1.00 | 11.98 | C |
| ATOM | 6081 | CD2 | PHE | A | 401 | −45.143 | 10.263 | −4.453 | 1.00 | 12.09 | C |
| ATOM | 6083 | C | PHE | A | 401 | −47.641 | 13.509 | −6.806 | 1.00 | 15.39 | C |
| ATOM | 6084 | O | PHE | A | 401 | −48.183 | 13.215 | −7.858 | 1.00 | 15.51 | O |
| ATOM | 6086 | N | ALA | A | 402 | −48.022 | 14.545 | −6.080 | 1.00 | 16.15 | N |
| ATOM | 6087 | CA | ALA | A | 402 | −49.110 | 15.393 | −6.525 | 1.00 | 16.90 | C |
| ATOM | 6089 | CB | ALA | A | 402 | −49.391 | 16.473 | −5.505 | 1.00 | 16.99 | C |
| ATOM | 6093 | C | ALA | A | 402 | −48.722 | 16.003 | −7.856 | 1.00 | 17.50 | C |
| ATOM | 6094 | O | ALA | A | 402 | −49.549 | 16.100 | −8.770 | 1.00 | 17.48 | O |
| ATOM | 6096 | N | TYR | A | 403 | −47.444 | 16.367 | −7.963 | 1.00 | 18.28 | N |
| ATOM | 6097 | CA | TYR | A | 403 | −46.916 | 17.046 | −9.142 | 1.00 | 18.94 | C |
| ATOM | 6099 | CB | TYR | A | 403 | −45.412 | 17.252 | −9.043 | 1.00 | 19.03 | C |
| ATOM | 6102 | CG | TYR | A | 403 | −44.823 | 17.801 | −10.314 | 1.00 | 19.79 | C |
| ATOM | 6103 | CD1 | TYR | A | 403 | −44.973 | 19.138 | −10.652 | 1.00 | 20.80 | C |
| ATOM | 6105 | CE1 | TYR | A | 403 | −44.436 | 19.643 | −11.827 | 1.00 | 20.73 | C |
| ATOM | 6107 | CZ | TYR | A | 403 | −43.759 | 18.804 | −12.674 | 1.00 | 21.16 | C |
| ATOM | 6108 | OH | TYR | A | 403 | −43.231 | 19.283 | −13.836 | 1.00 | 22.98 | O |
| ATOM | 6110 | CE2 | TYR | A | 403 | −43.608 | 17.476 | −12.370 | 1.00 | 21.23 | C |
| ATOM | 6112 | CD2 | TYR | A | 403 | −44.137 | 16.980 | −11.195 | 1.00 | 20.93 | C |
| ATOM | 6114 | C | TYR | A | 403 | −47.198 | 16.293 | −10.413 | 1.00 | 19.39 | C |
| ATOM | 6115 | O | TYR | A | 403 | −47.567 | 16.904 | −11.422 | 1.00 | 19.57 | O |
| ATOM | 6117 | N | PHE | A | 404 | −47.023 | 14.976 | −10.376 | 1.00 | 19.74 | N |
| ATOM | 6118 | CA | PHE | A | 404 | −47.239 | 14.177 | −11.573 | 1.00 | 20.35 | C |
| ATOM | 6120 | CB | PHE | A | 404 | −46.533 | 12.841 | −11.466 | 1.00 | 19.96 | C |
| ATOM | 6123 | CG | PHE | A | 404 | −45.048 | 12.971 | −11.387 | 1.00 | 18.81 | C |
| ATOM | 6124 | CD1 | PHE | A | 404 | −44.292 | 13.115 | −12.528 | 1.00 | 17.42 | C |
| ATOM | 6126 | CE1 | PHE | A | 404 | −42.935 | 13.239 | −12.457 | 1.00 | 17.24 | C |
| ATOM | 6128 | CZ | PHE | A | 404 | −42.312 | 13.237 | −11.237 | 1.00 | 17.40 | C |
| ATOM | 6130 | CE2 | PHE | A | 404 | −43.056 | 13.106 | −10.093 | 1.00 | 17.72 | C |
| ATOM | 6132 | CD2 | PHE | A | 404 | −44.413 | 12.975 | −10.170 | 1.00 | 17.93 | C |
| ATOM | 6134 | C | PHE | A | 404 | −48.713 | 13.994 | −11.894 | 1.00 | 21.59 | C |
| ATOM | 6135 | O | PHE | A | 404 | −49.072 | 13.717 | −13.046 | 1.00 | 21.71 | O |
| ATOM | 6137 | N | ALA | A | 405 | −49.572 | 14.169 | −10.896 | 1.00 | 22.87 | N |
| ATOM | 6138 | CA | ALA | A | 405 | −50.990 | 13.939 | −11.099 | 1.00 | 24.06 | C |
| ATOM | 6140 | CB | ALA | A | 405 | −51.604 | 13.408 | −9.833 | 1.00 | 24.15 | C |
| ATOM | 6144 | C | ALA | A | 405 | −51.724 | 15.192 | −11.556 | 1.00 | 25.21 | C |
| ATOM | 6145 | O | ALA | A | 405 | −52.876 | 15.114 | −11.939 | 1.00 | 25.51 | O |
| ATOM | 6147 | N | VAL | A | 406 | −51.056 | 16.336 | −11.530 | 1.00 | 26.52 | N |
| ATOM | 6148 | CA | VAL | A | 406 | −51.713 | 17.617 | −11.759 | 1.00 | 27.68 | C |
| ATOM | 6150 | CB | VAL | A | 406 | −51.694 | 18.406 | −10.434 | 1.00 | 27.60 | C |
| ATOM | 6152 | CG1 | VAL | A | 406 | −51.654 | 19.913 | −10.663 | 1.00 | 28.07 | C |
| ATOM | 6156 | CG2 | VAL | A | 406 | −52.883 | 18.009 | −9.596 | 1.00 | 27.41 | C |
| ATOM | 6160 | C | VAL | A | 406 | −51.097 | 18.429 | −12.925 | 1.00 | 29.10 | C |
| ATOM | 6161 | O | VAL | A | 406 | −51.810 | 19.104 | −13.678 | 1.00 | 28.53 | O |
| ATOM | 6163 | N | VAL | A | 407 | −49.772 | 18.356 | −13.059 | 1.00 | 30.90 | N |
| ATOM | 6164 | CA | VAL | A | 407 | −49.052 | 19.003 | −14.151 | 1.00 | 32.15 | C |
| ATOM | 6166 | CB | VAL | A | 407 | −47.574 | 19.228 | −13.777 | 1.00 | 32.25 | C |
| ATOM | 6168 | CG1 | VAL | A | 407 | −46.770 | 19.780 | −14.964 | 1.00 | 32.22 | C |
| ATOM | 6172 | CG2 | VAL | A | 407 | −47.490 | 20.154 | −12.583 | 1.00 | 32.25 | C |
| ATOM | 6176 | C | VAL | A | 407 | −49.134 | 18.160 | −15.421 | 1.00 | 33.36 | C |
| ATOM | 6177 | O | VAL | A | 407 | −48.688 | 17.009 | −15.454 | 1.00 | 33.40 | O |
| ATOM | 6179 | N | GLN | A | 408 | −49.693 | 18.767 | −16.463 | 1.00 | 34.93 | N |
| ATOM | 6180 | CA | GLN | A | 408 | −49.930 | 18.102 | −17.749 | 1.00 | 36.16 | C |
| ATOM | 6182 | CB | GLN | A | 408 | −50.779 | 19.016 | −18.638 | 1.00 | 36.63 | C |
| ATOM | 6185 | CG | GLN | A | 408 | −51.625 | 18.270 | −19.672 | 1.00 | 38.95 | C |
| ATOM | 6188 | CD | GLN | A | 408 | −52.991 | 18.930 | −19.887 | 1.00 | 41.80 | C |
| ATOM | 6189 | OE1 | GLN | A | 408 | −53.739 | 19.150 | −18.921 | 1.00 | 43.40 | O |
| ATOM | 6190 | NE2 | GLN | A | 408 | −53.323 | 19.244 | −21.151 | 1.00 | 41.68 | N |
| ATOM | 6193 | C | GLN | A | 408 | −48.630 | 17.725 | −18.470 | 1.00 | 36.22 | C |

TABLE 16-7-continued

| | | | | | | | | | | | |
|---|---|---|---|---|---|---|---|---|---|---|---|
| colspan="12" | Coordinates of *P. tremuloides* IspS |
| ATOM | 6194 | O | GLN | A | 408 | −48.456 | 16.588 | −18.920 | 1.00 | 35.86 | O |
| ATOM | 6196 | N | ASN | A | 409 | −47.726 | 18.694 | −18.578 | 1.00 | 36.64 | N |
| ATOM | 6197 | CA | ASN | A | 409 | −46.400 | 18.441 | −19.136 | 1.00 | 36.85 | C |
| ATOM | 6199 | CB | ASN | A | 409 | −46.134 | 19.306 | −20.373 | 1.00 | 36.73 | C |
| ATOM | 6202 | CG | ASN | A | 409 | −46.808 | 18.752 | −21.604 | 1.00 | 36.19 | C |
| ATOM | 6203 | OD1 | ASN | A | 409 | −46.178 | 18.072 | −22.420 | 1.00 | 35.00 | O |
| ATOM | 6204 | ND2 | ASN | A | 409 | −48.110 | 18.994 | −21.720 | 1.00 | 34.99 | N |
| ATOM | 6207 | C | ASN | A | 409 | −45.312 | 18.613 | −18.095 | 1.00 | 36.96 | C |
| ATOM | 6208 | O | ASN | A | 409 | −45.032 | 19.720 | −17.618 | 1.00 | 36.81 | O |
| ATOM | 6210 | N | ILE | A | 410 | −44.713 | 17.488 | −17.734 | 1.00 | 37.10 | N |
| ATOM | 6211 | CA | ILE | A | 410 | −43.625 | 17.508 | −16.792 | 1.00 | 37.27 | C |
| ATOM | 6213 | CB | ILE | A | 410 | −43.265 | 16.092 | −16.295 | 1.00 | 37.38 | C |
| ATOM | 6215 | CG1 | ILE | A | 410 | −42.745 | 15.209 | −17.426 | 1.00 | 37.84 | C |
| ATOM | 6218 | CD1 | ILE | A | 410 | −42.416 | 13.824 | −16.985 | 1.00 | 38.96 | C |
| ATOM | 6222 | CG2 | ILE | A | 410 | −44.491 | 15.437 | −15.676 | 1.00 | 37.67 | C |
| ATOM | 6226 | C | ILE | A | 410 | −42.467 | 18.179 | −17.492 | 1.00 | 37.12 | C |
| ATOM | 6227 | O | ILE | A | 410 | −42.150 | 17.839 | −18.617 | 1.00 | 36.87 | O |
| ATOM | 6229 | N | LYS | A | 411 | −41.896 | 19.187 | −16.851 | 1.00 | 37.38 | N |
| ATOM | 6230 | CA | LYS | A | 411 | −40.680 | 19.813 | −17.332 | 1.00 | 37.73 | C |
| ATOM | 6232 | CB | LYS | A | 411 | −40.756 | 21.332 | −17.171 | 1.00 | 38.15 | C |
| ATOM | 6235 | CG | LYS | A | 411 | −41.979 | 21.962 | −17.837 | 1.00 | 39.89 | C |
| ATOM | 6238 | CD | LYS | A | 411 | −41.797 | 23.463 | −18.080 | 1.00 | 42.48 | C |
| ATOM | 6241 | CE | LYS | A | 411 | −43.029 | 24.069 | −18.795 | 1.00 | 44.22 | C |
| ATOM | 6244 | NZ | LYS | A | 411 | −42.977 | 25.576 | −18.904 | 1.00 | 45.31 | N |
| ATOM | 6248 | C | LYS | A | 411 | −39.562 | 19.244 | −16.489 | 1.00 | 37.38 | C |
| ATOM | 6249 | O | LYS | A | 411 | −39.721 | 19.112 | −15.281 | 1.00 | 37.28 | O |
| ATOM | 6251 | N | LYS | A | 412 | −38.445 | 18.886 | −17.122 | 1.00 | 37.24 | N |
| ATOM | 6252 | CA | LYS | A | 412 | −37.333 | 18.243 | −16.413 | 1.00 | 36.95 | C |
| ATOM | 6254 | CB | LYS | A | 412 | −36.286 | 17.701 | −17.384 | 1.00 | 37.14 | C |
| ATOM | 6257 | CG | LYS | A | 412 | −35.233 | 16.818 | −16.720 | 1.00 | 37.89 | C |
| ATOM | 6260 | CD | LYS | A | 412 | −34.334 | 16.125 | −17.757 | 1.00 | 39.54 | C |
| ATOM | 6263 | CE | LYS | A | 412 | −33.263 | 17.068 | −18.348 | 1.00 | 40.08 | C |
| ATOM | 6266 | NZ | LYS | A | 412 | −32.161 | 17.399 | −17.376 | 1.00 | 40.16 | N |
| ATOM | 6270 | C | LYS | A | 412 | −36.664 | 19.177 | −15.419 | 1.00 | 36.42 | C |
| ATOM | 6271 | O | LYS | A | 412 | −36.246 | 18.728 | −14.357 | 1.00 | 36.56 | O |
| ATOM | 6273 | N | GLU | A | 413 | −36.570 | 20.466 | −15.744 | 1.00 | 35.77 | N |
| ATOM | 6274 | CA | GLU | A | 413 | −35.948 | 21.423 | −14.820 | 1.00 | 35.38 | C |
| ATOM | 6276 | CB | GLU | A | 413 | −35.688 | 22.792 | −15.489 | 1.00 | 35.73 | C |
| ATOM | 6279 | CG | GLU | A | 413 | −36.510 | 24.013 | −14.973 | 1.00 | 37.10 | C |
| ATOM | 6282 | CD | GLU | A | 413 | −35.621 | 25.235 | −14.633 | 1.00 | 38.51 | C |
| ATOM | 6283 | OE1 | GLU | A | 413 | −34.778 | 25.125 | −13.714 | 1.00 | 39.24 | O |
| ATOM | 6284 | OE2 | GLU | A | 413 | −35.768 | 26.306 | −15.266 | 1.00 | 39.04 | O |
| ATOM | 6285 | C | GLU | A | 413 | −36.760 | 21.551 | −13.522 | 1.00 | 34.43 | C |
| ATOM | 6286 | O | GLU | A | 413 | −36.196 | 21.801 | −12.460 | 1.00 | 34.34 | O |
| ATOM | 6288 | N | GLU | A | 414 | −38.074 | 21.360 | −13.616 | 1.00 | 33.45 | N |
| ATOM | 6289 | CA | GLU | A | 414 | −38.956 | 21.407 | −12.452 | 1.00 | 32.80 | C |
| ATOM | 6291 | CB | GLU | A | 414 | −40.435 | 21.425 | −12.864 | 1.00 | 32.83 | C |
| ATOM | 6294 | CG | GLU | A | 414 | −40.923 | 22.736 | −13.478 | 1.00 | 33.15 | C |
| ATOM | 6297 | CD | GLU | A | 414 | −42.360 | 22.668 | −14.003 | 1.00 | 33.82 | C |
| ATOM | 6298 | OE1 | GLU | A | 414 | −42.876 | 21.560 | −14.231 | 1.00 | 35.31 | O |
| ATOM | 6299 | OE2 | GLU | A | 414 | −42.985 | 23.727 | −14.204 | 1.00 | 33.98 | O |
| ATOM | 6300 | C | GLU | A | 414 | −38.715 | 20.222 | −11.536 | 1.00 | 32.18 | C |
| ATOM | 6301 | O | GLU | A | 414 | −38.407 | 20.409 | −10.372 | 1.00 | 32.25 | O |
| ATOM | 6303 | N | ILE | A | 415 | −38.863 | 19.002 | −12.044 | 1.00 | 31.63 | N |
| ATOM | 6304 | CA | ILE | A | 415 | −38.725 | 17.819 | −11.181 | 1.00 | 31.28 | C |
| ATOM | 6306 | CB | ILE | A | 415 | −39.131 | 16.472 | −11.852 | 1.00 | 31.14 | C |
| ATOM | 6308 | CG1 | ILE | A | 415 | −38.349 | 16.204 | −13.133 | 1.00 | 31.13 | C |
| ATOM | 6311 | CD1 | ILE | A | 415 | −38.786 | 14.926 | −13.836 | 1.00 | 30.72 | C |
| ATOM | 6315 | CG2 | ILE | A | 415 | −40.611 | 16.454 | −12.160 | 1.00 | 31.12 | C |
| ATOM | 6319 | C | ILE | A | 415 | −37.316 | 17.705 | −10.636 | 1.00 | 31.08 | C |
| ATOM | 6320 | O | ILE | A | 415 | −37.105 | 17.188 | −9.539 | 1.00 | 31.22 | O |
| ATOM | 6322 | N | GLU | A | 416 | −36.345 | 18.208 | −11.381 | 1.00 | 30.67 | N |
| ATOM | 6323 | CA | GLU | A | 416 | −34.998 | 18.270 | −10.850 | 1.00 | 30.55 | C |
| ATOM | 6325 | CB | GLU | A | 416 | −34.011 | 18.654 | −11.955 | 1.00 | 30.91 | C |
| ATOM | 6328 | CG | GLU | A | 416 | −32.654 | 17.967 | −11.845 | 1.00 | 32.55 | C |
| ATOM | 6331 | CD | GLU | A | 416 | −31.802 | 18.130 | −13.109 | 1.00 | 34.91 | C |
| ATOM | 6332 | OE1 | GLU | A | 416 | −32.337 | 18.563 | −14.161 | 1.00 | 35.53 | O |
| ATOM | 6333 | OE2 | GLU | A | 416 | −30.590 | 17.816 | −13.052 | 1.00 | 36.45 | O |
| ATOM | 6334 | C | GLU | A | 416 | −34.962 | 19.249 | −9.650 | 1.00 | 29.74 | C |
| ATOM | 6335 | O | GLU | A | 416 | −34.143 | 19.097 | −8.738 | 1.00 | 29.73 | O |
| ATOM | 6337 | N | ASN | A | 417 | −35.864 | 20.234 | −9.652 | 1.00 | 28.69 | N |
| ATOM | 6338 | CA | ASN | A | 417 | −36.060 | 21.134 | −8.503 | 1.00 | 27.92 | C |
| ATOM | 6340 | CB | ASN | A | 417 | −36.632 | 22.477 | −8.963 | 1.00 | 27.75 | C |
| ATOM | 6343 | CG | ASN | A | 417 | −35.572 | 23.532 | −9.095 | 1.00 | 26.84 | C |
| ATOM | 6344 | OD1 | ASN | A | 417 | −35.160 | 24.132 | −8.105 | 1.00 | 24.88 | O |
| ATOM | 6345 | ND2 | ASN | A | 417 | −35.117 | 23.765 | −10.318 | 1.00 | 26.28 | N |
| ATOM | 6348 | C | ASN | A | 417 | −36.917 | 20.580 | −7.356 | 1.00 | 27.41 | C |
| ATOM | 6349 | O | ASN | A | 417 | −36.650 | 20.838 | −6.187 | 1.00 | 27.15 | O |

TABLE 16-7-continued

Coordinates of *P. tremuloides* IspS

| ATOM | 6351 | N | LEU | A | 418 | −37.955 | 19.834 | −7.675 | 1.00 | 27.09 | N |
| ATOM | 6352 | CA | LEU | A | 418 | −38.694 | 19.156 | −6.628 | 1.00 | 27.02 | C |
| ATOM | 6354 | CB | LEU | A | 418 | −39.921 | 18.423 | −7.200 | 1.00 | 26.95 | C |
| ATOM | 6357 | CG | LEU | A | 418 | −41.030 | 19.284 | −7.826 | 1.00 | 25.97 | C |
| ATOM | 6359 | CD1 | LEU | A | 418 | −42.127 | 18.429 | −8.447 | 1.00 | 24.88 | C |
| ATOM | 6363 | CD2 | LEU | A | 418 | −41.623 | 20.226 | −6.803 | 1.00 | 24.50 | C |
| ATOM | 6367 | C | LEU | A | 418 | −37.763 | 18.196 | −5.860 | 1.00 | 27.26 | C |
| ATOM | 6368 | O | LEU | A | 418 | −37.834 | 18.123 | −4.644 | 1.00 | 27.07 | O |
| ATOM | 6370 | N | GLN | A | 419 | −36.873 | 17.494 | −6.561 | 1.00 | 27.67 | N |
| ATOM | 6371 | CA | GLN | A | 419 | −35.924 | 16.575 | −5.909 | 1.00 | 28.28 | C |
| ATOM | 6373 | CB | GLN | A | 419 | −35.155 | 15.758 | −6.945 | 1.00 | 28.36 | C |
| ATOM | 6376 | CG | GLN | A | 419 | −35.747 | 14.375 | −7.146 | 1.00 | 29.43 | C |
| ATOM | 6379 | CD | GLN | A | 419 | −35.052 | 13.573 | −8.215 | 1.00 | 29.76 | C |
| ATOM | 6380 | OE1 | GLN | A | 419 | −34.355 | 14.112 | −9.066 | 1.00 | 29.93 | O |
| ATOM | 6381 | NE2 | GLN | A | 419 | −35.252 | 12.270 | −8.184 | 1.00 | 31.33 | N |
| ATOM | 6384 | C | GLN | A | 419 | −34.922 | 17.219 | −4.947 | 1.00 | 28.73 | C |
| ATOM | 6385 | O | GLN | A | 419 | −34.540 | 16.608 | −3.952 | 1.00 | 28.90 | O |
| ATOM | 6387 | N | LYS | A | 420 | −34.490 | 18.440 | −5.240 | 1.00 | 29.27 | N |
| ATOM | 6388 | CA | LYS | A | 420 | −33.608 | 19.166 | −4.335 | 1.00 | 29.81 | C |
| ATOM | 6390 | CB | LYS | A | 420 | −32.758 | 20.163 | −5.129 | 1.00 | 30.24 | C |
| ATOM | 6393 | CG | LYS | A | 420 | −31.592 | 19.513 | −5.867 | 1.00 | 31.75 | C |
| ATOM | 6396 | CD | LYS | A | 420 | −31.259 | 20.217 | −7.183 | 1.00 | 34.14 | C |
| ATOM | 6399 | CE | LYS | A | 420 | −30.140 | 19.463 | −7.953 | 1.00 | 36.21 | C |
| ATOM | 6402 | NZ | LYS | A | 420 | −30.073 | 19.759 | −9.439 | 1.00 | 36.76 | N |
| ATOM | 6406 | C | LYS | A | 420 | −34.375 | 19.872 | −3.204 | 1.00 | 29.98 | C |
| ATOM | 6407 | O | LYS | A | 420 | −33.759 | 20.547 | −2.384 | 1.00 | 30.44 | O |
| ATOM | 6409 | N | TYR | A | 421 | −35.706 | 19.694 | −3.162 | 1.00 | 30.07 | N |
| ATOM | 6410 | CA | TYR | A | 421 | −36.646 | 20.309 | −2.171 | 1.00 | 29.73 | C |
| ATOM | 6412 | CB | TYR | A | 421 | −36.298 | 19.949 | −.712 | 1.00 | 29.59 | C |
| ATOM | 6415 | CG | TYR | A | 421 | −36.386 | 18.468 | −.470 | 1.00 | 30.57 | C |
| ATOM | 6416 | CD1 | TYR | A | 421 | −37.582 | 17.785 | −.643 | 1.00 | 30.87 | C |
| ATOM | 6418 | CE1 | TYR | A | 421 | −37.665 | 16.414 | −.448 | 1.00 | 31.28 | C |
| ATOM | 6420 | CZ | TYR | A | 421 | −36.549 | 15.705 | −.068 | 1.00 | 31.90 | C |
| ATOM | 6421 | OH | TYR | A | 421 | −36.620 | 14.347 | .124 | 1.00 | 32.43 | O |
| ATOM | 6423 | CE2 | TYR | A | 421 | −35.355 | 16.354 | .119 | 1.00 | 32.68 | C |
| ATOM | 6425 | CD2 | TYR | A | 421 | −35.274 | 17.736 | −.095 | 1.00 | 32.42 | C |
| ATOM | 6427 | C | TYR | A | 421 | −36.850 | 21.816 | −2.347 | 1.00 | 29.24 | C |
| ATOM | 6428 | O | TYR | A | 421 | −36.709 | 22.590 | −1.401 | 1.00 | 29.26 | O |
| ATOM | 6430 | N | HIS | A | 422 | −37.219 | 22.214 | −3.563 | 1.00 | 28.65 | N |
| ATOM | 6431 | CA | HIS | A | 422 | −37.540 | 23.604 | −3.859 | 1.00 | 28.26 | C |
| ATOM | 6433 | CB | HIS | A | 422 | −38.150 | 23.715 | −5.256 | 1.00 | 28.33 | C |
| ATOM | 6436 | CG | HIS | A | 422 | −38.299 | 25.124 | −5.748 | 1.00 | 28.44 | C |
| ATOM | 6437 | ND1 | HIS | A | 422 | −37.225 | 25.904 | −6.106 | 1.00 | 28.97 | N |
| ATOM | 6439 | CE1 | HIS | A | 422 | −37.660 | 27.082 | −6.520 | 1.00 | 29.40 | C |
| ATOM | 6441 | NE2 | HIS | A | 422 | −38.977 | 27.090 | −6.443 | 1.00 | 28.14 | N |
| ATOM | 6443 | CD2 | HIS | A | 422 | −39.399 | 25.879 | −5.965 | 1.00 | 27.76 | C |
| ATOM | 6445 | C | HIS | A | 422 | −38.511 | 24.147 | −2.816 | 1.00 | 27.74 | C |
| ATOM | 6446 | O | HIS | A | 422 | −39.357 | 23.408 | −2.310 | 1.00 | 27.53 | O |
| ATOM | 6448 | N | ASP | A | 423 | −38.384 | 25.437 | −2.505 | 1.00 | 27.12 | N |
| ATOM | 6449 | CA | ASP | A | 423 | −39.186 | 26.072 | −1.454 | 1.00 | 26.63 | C |
| ATOM | 6451 | CB | ASP | A | 423 | −38.877 | 27.575 | −1.349 | 1.00 | 27.05 | C |
| ATOM | 6454 | CG | ASP | A | 423 | −37.456 | 27.875 | −.851 | 1.00 | 28.35 | C |
| ATOM | 6455 | OD1 | ASP | A | 423 | −36.951 | 27.121 | .018 | 1.00 | 30.99 | O |
| ATOM | 6456 | OD2 | ASP | A | 423 | −36.860 | 28.884 | −1.322 | 1.00 | 27.89 | O |
| ATOM | 6457 | C | ASP | A | 423 | −40.689 | 25.883 | −1.698 | 1.00 | 25.71 | C |
| ATOM | 6458 | O | ASP | A | 423 | −41.487 | 25.831 | −.749 | 1.00 | 26.26 | O |
| ATOM | 6460 | N | ILE | A | 424 | −41.075 | 25.781 | −2.966 | 1.00 | 24.01 | N |
| ATOM | 6461 | CA | ILE | A | 424 | −42.479 | 25.596 | −3.327 | 1.00 | 22.72 | C |
| ATOM | 6463 | CB | ILE | A | 424 | −42.639 | 25.391 | −4.843 | 1.00 | 22.40 | C |
| ATOM | 6465 | CG1 | ILE | A | 424 | −44.029 | 25.668 | −5.318 | 1.00 | 21.78 | C |
| ATOM | 6468 | CD1 | ILE | A | 424 | −44.086 | 25.499 | −6.793 | 1.00 | 22.22 | C |
| ATOM | 6472 | CG2 | ILE | A | 424 | −42.340 | 23.985 | −5.255 | 1.00 | 22.87 | C |
| ATOM | 6476 | C | ILE | A | 424 | −43.103 | 24.442 | −2.562 | 1.00 | 21.91 | C |
| ATOM | 6477 | O | ILE | A | 424 | −44.238 | 24.574 | −2.115 | 1.00 | 21.73 | O |
| ATOM | 6479 | N | ILE | A | 425 | −42.365 | 23.334 | −2.399 | 1.00 | 21.23 | N |
| ATOM | 6480 | CA | ILE | A | 425 | −42.853 | 22.173 | −1.634 | 1.00 | 20.73 | C |
| ATOM | 6482 | CB | ILE | A | 425 | −42.622 | 20.820 | −2.330 | 1.00 | 20.10 | C |
| ATOM | 6484 | CG1 | ILE | A | 425 | −41.158 | 20.409 | −2.290 | 1.00 | 18.72 | C |
| ATOM | 6487 | CD1 | ILE | A | 425 | −40.923 | 19.075 | −2.948 | 1.00 | 18.27 | C |
| ATOM | 6491 | CG2 | ILE | A | 425 | −43.146 | 20.840 | −3.741 | 1.00 | 19.57 | C |
| ATOM | 6495 | C | ILE | A | 425 | −42.252 | 22.060 | −.242 | 1.00 | 21.21 | C |
| ATOM | 6496 | O | ILE | A | 425 | −42.810 | 21.370 | .613 | 1.00 | 21.30 | O |
| ATOM | 6498 | N | SER | A | 426 | −41.129 | 22.721 | −.002 | 1.00 | 21.56 | N |
| ATOM | 6499 | CA | SER | A | 426 | −40.492 | 22.620 | 1.299 | 1.00 | 22.23 | C |
| ATOM | 6501 | CB | SER | A | 426 | −39.043 | 23.082 | 1.234 | 1.00 | 22.36 | C |
| ATOM | 6504 | OG | SER | A | 426 | −38.977 | 24.501 | 1.342 | 1.00 | 24.09 | O |
| ATOM | 6506 | C | SER | A | 426 | −41.242 | 23.460 | 2.334 | 1.00 | 22.39 | C |
| ATOM | 6507 | O | SER | A | 426 | −41.390 | 23.051 | 3.491 | 1.00 | 22.95 | O |

TABLE 16-7-continued

Coordinates of P. tremuloides IspS

| | | | | | | | | | | | |
|---|---|---|---|---|---|---|---|---|---|---|---|
| ATOM | 6509 | N | ARG | A | 427 | −41.701 | 24.643 | 1.937 | 1.00 | 22.08 | N |
| ATOM | 6510 | CA | ARG | A | 427 | −42.332 | 25.541 | 2.905 | 1.00 | 21.87 | C |
| ATOM | 6512 | CB | ARG | A | 427 | −42.466 | 26.955 | 2.345 | 1.00 | 21.99 | C |
| ATOM | 6515 | CG | ARG | A | 427 | −41.170 | 27.696 | 2.493 | 1.00 | 23.36 | C |
| ATOM | 6518 | CD | ARG | A | 427 | −40.954 | 28.727 | 1.433 | 1.00 | 26.07 | C |
| ATOM | 6521 | NE | ARG | A | 427 | −39.680 | 29.407 | 1.667 | 1.00 | 28.18 | N |
| ATOM | 6523 | CZ | ARG | A | 427 | −39.127 | 30.298 | .844 | 1.00 | 29.21 | C |
| ATOM | 6524 | NH1 | ARG | A | 427 | −39.723 | 30.633 | −.298 | 1.00 | 28.60 | N |
| ATOM | 6527 | NH2 | ARG | A | 427 | −37.962 | 30.854 | 1.173 | 1.00 | 30.48 | N |
| ATOM | 6530 | C | ARG | A | 427 | −43.651 | 25.003 | 3.434 | 1.00 | 21.21 | C |
| ATOM | 6531 | O | ARG | A | 427 | −43.817 | 24.891 | 4.645 | 1.00 | 21.11 | O |
| ATOM | 6533 | N | PRO | A | 428 | −44.573 | 24.622 | 2.541 | 1.00 | 20.52 | N |
| ATOM | 6534 | CA | PRO | A | 428 | −45.789 | 23.999 | 3.040 | 1.00 | 20.27 | C |
| ATOM | 6536 | CB | PRO | A | 428 | −46.410 | 23.369 | 1.791 | 1.00 | 20.44 | C |
| ATOM | 6539 | CG | PRO | A | 428 | −45.864 | 24.119 | .666 | 1.00 | 20.63 | C |
| ATOM | 6542 | CD | PRO | A | 428 | −44.521 | 24.644 | 1.074 | 1.00 | 20.54 | C |
| ATOM | 6545 | C | PRO | A | 428 | −45.450 | 22.917 | 4.050 | 1.00 | 19.75 | C |
| ATOM | 6546 | O | PRO | A | 428 | −46.089 | 22.834 | 5.095 | 1.00 | 19.77 | O |
| ATOM | 6547 | N | SER | A | 429 | −44.424 | 22.123 | 3.747 | 1.00 | 18.97 | N |
| ATOM | 6548 | CA | SER | A | 429 | −44.008 | 21.045 | 4.636 | 1.00 | 18.45 | C |
| ATOM | 6550 | CB | SER | A | 429 | −42.954 | 20.180 | 3.972 | 1.00 | 18.35 | C |
| ATOM | 6553 | OG | SER | A | 429 | −43.452 | 19.716 | 2.733 | 1.00 | 19.12 | O |
| ATOM | 6555 | C | SER | A | 429 | −43.519 | 21.525 | 5.985 | 1.00 | 17.97 | C |
| ATOM | 6556 | O | SER | A | 429 | −43.733 | 20.846 | 6.968 | 1.00 | 17.88 | O |
| ATOM | 6558 | N | HIS | A | 430 | −42.879 | 22.689 | 6.053 | 1.00 | 17.73 | N |
| ATOM | 6559 | CA | HIS | A | 430 | −42.593 | 23.289 | 7.359 | 1.00 | 17.71 | C |
| ATOM | 6561 | CB | HIS | A | 430 | −41.937 | 24.668 | 7.241 | 1.00 | 17.97 | C |
| ATOM | 6564 | CG | HIS | A | 430 | −40.558 | 24.663 | 6.651 | 1.00 | 18.87 | C |
| ATOM | 6565 | ND1 | HIS | A | 430 | −39.940 | 23.524 | 6.186 | 1.00 | 19.85 | N |
| ATOM | 6567 | CE1 | HIS | A | 430 | −38.746 | 23.836 | 5.709 | 1.00 | 19.43 | C |
| ATOM | 6569 | NE2 | HIS | A | 430 | −38.573 | 25.137 | 5.838 | 1.00 | 19.06 | N |
| ATOM | 6571 | CD2 | HIS | A | 430 | −39.693 | 25.681 | 6.418 | 1.00 | 19.32 | C |
| ATOM | 6573 | C | HIS | A | 430 | −43.914 | 23.444 | 8.131 | 1.00 | 17.31 | C |
| ATOM | 6574 | O | HIS | A | 430 | −44.023 | 23.013 | 9.287 | 1.00 | 17.06 | O |
| ATOM | 6576 | N | ILE | A | 431 | −44.913 | 24.050 | 7.475 | 1.00 | 16.74 | N |
| ATOM | 6577 | CA | ILE | A | 431 | −46.218 | 24.304 | 8.091 | 1.00 | 16.15 | C |
| ATOM | 6579 | CB | ILE | A | 431 | −47.174 | 25.057 | 7.174 | 1.00 | 16.18 | C |
| ATOM | 6581 | CG1 | ILE | A | 431 | −46.613 | 26.428 | 6.801 | 1.00 | 17.05 | C |
| ATOM | 6584 | CD1 | ILE | A | 431 | −46.441 | 27.352 | 7.994 | 1.00 | 18.34 | C |
| ATOM | 6588 | CG2 | ILE | A | 431 | −48.496 | 25.263 | 7.860 | 1.00 | 15.28 | C |
| ATOM | 6592 | C | ILE | A | 431 | −46.899 | 23.021 | 8.476 | 1.00 | 15.75 | C |
| ATOM | 6593 | O | ILE | A | 431 | −47.624 | 22.980 | 9.445 | 1.00 | 15.95 | O |
| ATOM | 6595 | N | PHE | A | 432 | −46.663 | 21.969 | 7.714 | 1.00 | 15.59 | N |
| ATOM | 6596 | CA | PHE | A | 432 | −47.192 | 20.652 | 8.041 | 1.00 | 15.52 | C |
| ATOM | 6598 | CB | PHE | A | 432 | −46.837 | 19.683 | 6.913 | 1.00 | 15.23 | C |
| ATOM | 6601 | CG | PHE | A | 432 | −47.451 | 18.318 | 7.031 | 1.00 | 15.98 | C |
| ATOM | 6602 | CD1 | PHE | A | 432 | −48.324 | 17.972 | 8.052 | 1.00 | 16.55 | C |
| ATOM | 6604 | CE1 | PHE | A | 432 | −48.867 | 16.700 | 8.102 | 1.00 | 16.04 | C |
| ATOM | 6606 | CZ | PHE | A | 432 | −48.559 | 15.774 | 7.130 | 1.00 | 15.29 | C |
| ATOM | 6608 | CE2 | PHE | A | 432 | −47.718 | 16.107 | 6.114 | 1.00 | 15.37 | C |
| ATOM | 6610 | CD2 | PHE | A | 432 | −47.172 | 17.364 | 6.061 | 1.00 | 16.74 | C |
| ATOM | 6612 | C | PHE | A | 432 | −46.640 | 20.191 | 9.392 | 1.00 | 15.54 | C |
| ATOM | 6613 | O | PHE | A | 432 | −47.383 | 20.006 | 10.343 | 1.00 | 15.37 | O |
| ATOM | 6615 | N | ARG | A | 433 | −45.328 | 20.041 | 9.483 | 1.00 | 15.98 | N |
| ATOM | 6616 | CA | ARG | A | 433 | −44.695 | 19.542 | 10.709 | 1.00 | 16.20 | C |
| ATOM | 6618 | CB | ARG | A | 433 | −43.176 | 19.476 | 10.526 | 1.00 | 15.85 | C |
| ATOM | 6621 | CG | ARG | A | 433 | −42.411 | 19.183 | 11.804 | 1.00 | 16.11 | C |
| ATOM | 6624 | CD | ARG | A | 433 | −42.848 | 17.890 | 12.489 | 1.00 | 15.70 | C |
| ATOM | 6627 | NE | ARG | A | 433 | −42.811 | 16.747 | 11.588 | 1.00 | 15.64 | N |
| ATOM | 6629 | CZ | ARG | A | 433 | −43.377 | 15.571 | 11.838 | 1.00 | 16.27 | C |
| ATOM | 6630 | NH1 | ARG | A | 433 | −44.029 | 15.359 | 12.965 | 1.00 | 16.82 | N |
| ATOM | 6633 | NH2 | ARG | A | 433 | −43.302 | 14.598 | 10.948 | 1.00 | 16.96 | N |
| ATOM | 6636 | C | ARG | A | 433 | −45.029 | 20.411 | 11.935 | 1.00 | 16.46 | C |
| ATOM | 6637 | O | ARG | A | 433 | −45.296 | 19.890 | 13.031 | 1.00 | 16.31 | O |
| ATOM | 6639 | N | LEU | A | 434 | −45.006 | 21.731 | 11.724 | 1.00 | 16.47 | N |
| ATOM | 6640 | CA | LEU | A | 434 | −45.123 | 22.701 | 12.800 | 1.00 | 15.98 | C |
| ATOM | 6642 | CB | LEU | A | 434 | −44.771 | 24.114 | 12.303 | 1.00 | 15.83 | C |
| ATOM | 6645 | CG | LEU | A | 434 | −43.287 | 24.486 | 12.218 | 1.00 | 14.95 | C |
| ATOM | 6647 | CD1 | LEU | A | 434 | −43.130 | 25.918 | 11.826 | 1.00 | 15.09 | C |
| ATOM | 6651 | CD2 | LEU | A | 434 | −42.600 | 24.281 | 13.536 | 1.00 | 14.37 | C |
| ATOM | 6655 | C | LEU | A | 434 | −46.517 | 22.660 | 13.387 | 1.00 | 16.19 | C |
| ATOM | 6656 | O | LEU | A | 434 | −46.669 | 22.564 | 14.604 | 1.00 | 15.92 | O |
| ATOM | 6658 | N | CYS | A | 435 | −47.529 | 22.715 | 12.520 | 1.00 | 16.78 | N |
| ATOM | 6659 | CA | CYS | A | 435 | −48.936 | 22.591 | 12.940 | 1.00 | 17.48 | C |
| ATOM | 6661 | CB | CYS | A | 435 | −49.870 | 22.617 | 11.726 | 1.00 | 17.54 | C |
| ATOM | 6664 | SG | CYS | A | 435 | −50.110 | 24.233 | 10.985 | 1.00 | 18.80 | S |
| ATOM | 6666 | C | CYS | A | 435 | −49.192 | 21.296 | 13.708 | 1.00 | 17.84 | C |
| ATOM | 6667 | O | CYS | A | 435 | −50.043 | 21.250 | 14.597 | 1.00 | 17.92 | O |

TABLE 16-7-continued

| | | | | | | | | | | |
|---|---|---|---|---|---|---|---|---|---|---|
| ATOM | 6669 | N | ASN | A | 436 | −48.446 | 20.257 | 13.333 | 1.00 | 18.24 | N |
| ATOM | 6670 | CA | ASN | A | 436 | −48.603 | 18.913 | 13.846 | 1.00 | 18.50 | C |
| ATOM | 6672 | CB | ASN | A | 436 | −47.936 | 17.949 | 12.867 | 1.00 | 18.63 | C |
| ATOM | 6675 | CG | ASN | A | 436 | −48.156 | 16.487 | 13.213 | 1.00 | 18.58 | C |
| ATOM | 6676 | OD1 | ASN | A | 436 | −48.810 | 16.129 | 14.185 | 1.00 | 18.80 | O |
| ATOM | 6677 | ND2 | ASN | A | 436 | −47.588 | 15.633 | 12.398 | 1.00 | 19.29 | N |
| ATOM | 6680 | C | ASN | A | 436 | −47.975 | 18.755 | 15.210 | 1.00 | 18.83 | C |
| ATOM | 6681 | O | ASN | A | 436 | −48.551 | 18.153 | 16.115 | 1.00 | 19.00 | O |
| ATOM | 6683 | N | ASP | A | 437 | −46.763 | 19.255 | 15.351 | 1.00 | 19.29 | N |
| ATOM | 6684 | CA | ASP | A | 437 | −46.097 | 19.179 | 16.634 | 1.00 | 19.62 | C |
| ATOM | 6686 | CB | ASP | A | 437 | −44.615 | 19.522 | 16.510 | 1.00 | 19.45 | C |
| ATOM | 6689 | CG | ASP | A | 437 | −43.849 | 18.480 | 15.734 | 1.00 | 19.36 | C |
| ATOM | 6690 | OD1 | ASP | A | 437 | −44.491 | 17.586 | 15.158 | 1.00 | 19.89 | O |
| ATOM | 6691 | OD2 | ASP | A | 437 | −42.608 | 18.543 | 15.699 | 1.00 | 19.86 | O |
| ATOM | 6692 | C | ASP | A | 437 | −46.799 | 20.106 | 17.597 | 1.00 | 20.01 | C |
| ATOM | 6693 | O | ASP | A | 437 | −46.916 | 19.790 | 18.779 | 1.00 | 20.30 | O |
| ATOM | 6695 | N | LEU | A | 438 | −47.288 | 21.233 | 17.092 | 1.00 | 20.40 | N |
| ATOM | 6696 | CA | LEU | A | 438 | −47.996 | 22.174 | 17.940 | 1.00 | 21.03 | C |
| ATOM | 6698 | CB | LEU | A | 438 | −48.510 | 23.363 | 17.126 | 1.00 | 21.01 | C |
| ATOM | 6701 | CG | LEU | A | 438 | −47.575 | 24.565 | 17.078 | 1.00 | 20.32 | C |
| ATOM | 6703 | CD1 | LEU | A | 438 | −47.938 | 25.524 | 15.952 | 1.00 | 19.14 | C |
| ATOM | 6707 | CD2 | LEU | A | 438 | −47.611 | 25.263 | 18.415 | 1.00 | 19.73 | C |
| ATOM | 6711 | C | LEU | A | 438 | −49.153 | 21.496 | 18.679 | 1.00 | 21.81 | C |
| ATOM | 6712 | O | LEU | A | 438 | −49.277 | 21.633 | 19.902 | 1.00 | 21.55 | O |
| ATOM | 6714 | N | ALA | A | 439 | −49.973 | 20.754 | 17.932 | 1.00 | 22.76 | N |
| ATOM | 6715 | CA | ALA | A | 439 | −51.138 | 20.055 | 18.486 | 1.00 | 23.58 | C |
| ATOM | 6717 | CB | ALA | A | 439 | −51.905 | 19.360 | 17.386 | 1.00 | 23.57 | C |
| ATOM | 6721 | C | ALA | A | 439 | −50.746 | 19.042 | 19.542 | 1.00 | 24.47 | C |
| ATOM | 6722 | O | ALA | A | 439 | −51.386 | 18.951 | 20.575 | 1.00 | 24.63 | O |
| ATOM | 6724 | N | SER | A | 440 | −49.685 | 18.291 | 19.276 | 1.00 | 25.78 | N |
| ATOM | 6725 | CA | SER | A | 440 | −49.242 | 17.227 | 20.168 | 1.00 | 26.84 | C |
| ATOM | 6727 | CB | SER | A | 440 | −48.566 | 16.130 | 19.353 | 1.00 | 26.92 | C |
| ATOM | 6730 | OG | SER | A | 440 | −47.321 | 16.582 | 18.859 | 1.00 | 27.46 | O |
| ATOM | 6732 | C | SER | A | 440 | −48.270 | 17.691 | 21.244 | 1.00 | 27.68 | C |
| ATOM | 6733 | O | SER | A | 440 | −47.934 | 16.923 | 22.132 | 1.00 | 28.00 | O |
| ATOM | 6735 | N | ALA | A | 441 | −47.822 | 18.935 | 21.174 | 1.00 | 28.83 | N |
| ATOM | 6736 | CA | ALA | A | 441 | −46.760 | 19.419 | 22.056 | 1.00 | 29.73 | C |
| ATOM | 6738 | CB | ALA | A | 441 | −46.529 | 20.910 | 21.841 | 1.00 | 29.84 | C |
| ATOM | 6742 | C | ALA | A | 441 | −46.982 | 19.132 | 23.539 | 1.00 | 30.57 | C |
| ATOM | 6743 | O | ALA | A | 441 | −46.306 | 18.274 | 24.093 | 1.00 | 30.50 | O |
| ATOM | 6745 | N | SER | A | 442 | −47.929 | 19.827 | 24.172 | 1.00 | 31.90 | N |
| ATOM | 6746 | CA | SER | A | 442 | −47.999 | 19.862 | 25.654 | 1.00 | 32.95 | C |
| ATOM | 6748 | CB | SER | A | 442 | −49.043 | 20.870 | 26.169 | 1.00 | 32.91 | C |
| ATOM | 6751 | OG | SER | A | 442 | −50.331 | 20.614 | 25.650 | 1.00 | 33.50 | O |
| ATOM | 6753 | C | SER | A | 442 | −48.219 | 18.497 | 26.289 | 1.00 | 33.69 | C |
| ATOM | 6754 | O | SER | A | 442 | −47.754 | 18.246 | 27.397 | 1.00 | 33.59 | O |
| ATOM | 6756 | N | ALA | A | 443 | −48.922 | 17.623 | 25.578 | 1.00 | 34.93 | N |
| ATOM | 6757 | CA | ALA | A | 443 | −49.050 | 16.231 | 25.980 | 1.00 | 35.81 | C |
| ATOM | 6759 | CB | ALA | A | 443 | −49.981 | 15.488 | 25.030 | 1.00 | 35.72 | C |
| ATOM | 6763 | C | ALA | A | 443 | −47.663 | 15.580 | 25.996 | 1.00 | 36.71 | C |
| ATOM | 6764 | O | ALA | A | 443 | −47.198 | 15.115 | 27.047 | 1.00 | 36.94 | O |
| ATOM | 6766 | N | GLU | A | 444 | −46.999 | 15.567 | 24.838 | 1.00 | 37.47 | N |
| ATOM | 6767 | CA | GLU | A | 444 | −45.688 | 14.930 | 24.718 | 1.00 | 37.93 | C |
| ATOM | 6769 | CB | GLU | A | 444 | −45.164 | 14.996 | 23.277 | 1.00 | 37.99 | C |
| ATOM | 6772 | CG | GLU | A | 444 | −45.952 | 14.100 | 22.326 | 1.00 | 39.24 | C |
| ATOM | 6775 | CD | GLU | A | 444 | −45.419 | 14.080 | 20.886 | 1.00 | 41.03 | C |
| ATOM | 6776 | OE1 | GLU | A | 444 | −44.612 | 14.958 | 20.510 | 1.00 | 42.16 | O |
| ATOM | 6777 | OE2 | GLU | A | 444 | −45.827 | 13.178 | 20.119 | 1.00 | 42.36 | O |
| ATOM | 6778 | C | GLU | A | 444 | −44.694 | 15.534 | 25.708 | 1.00 | 38.09 | C |
| ATOM | 6779 | O | GLU | A | 444 | −43.924 | 14.803 | 26.324 | 1.00 | 38.17 | O |
| ATOM | 6781 | N | ILE | A | 445 | −44.739 | 16.851 | 25.889 | 1.00 | 38.41 | N |
| ATOM | 6782 | CA | ILE | A | 445 | −43.829 | 17.530 | 26.814 | 1.00 | 38.75 | C |
| ATOM | 6784 | CB | ILE | A | 445 | −43.802 | 19.065 | 26.587 | 1.00 | 38.69 | C |
| ATOM | 6786 | CG1 | ILE | A | 445 | −43.314 | 19.396 | 25.170 | 1.00 | 38.18 | C |
| ATOM | 6789 | CD1 | ILE | A | 445 | −43.702 | 20.775 | 24.712 | 1.00 | 37.58 | C |
| ATOM | 6793 | CG2 | ILE | A | 445 | −42.909 | 19.753 | 27.617 | 1.00 | 38.26 | C |
| ATOM | 6797 | C | ILE | A | 445 | −44.243 | 17.194 | 28.246 | 1.00 | 39.35 | C |
| ATOM | 6798 | O | ILE | A | 445 | −45.039 | 17.901 | 28.870 | 1.00 | 39.44 | O |
| ATOM | 6800 | N | ALA | A | 446 | −43.696 | 16.092 | 28.750 | 1.00 | 40.02 | N |
| ATOM | 6801 | CA | ALA | A | 446 | −44.082 | 15.540 | 30.045 | 1.00 | 40.51 | C |
| ATOM | 6803 | CB | ALA | A | 446 | −43.815 | 16.552 | 31.170 | 1.00 | 40.55 | C |
| ATOM | 6807 | C | ALA | A | 446 | −45.559 | 15.130 | 30.029 | 1.00 | 40.86 | C |
| ATOM | 6808 | O | ALA | A | 446 | −46.407 | 16.021 | 30.121 | 1.00 | 40.77 | O |
| ATOM | 6810 | N | ARG | A | 447 | −45.925 | 13.842 | 29.899 | 1.00 | 41.31 | N |
| ATOM | 6811 | CA | ARG | A | 447 | −45.072 | 12.633 | 29.691 | 1.00 | 41.58 | C |
| ATOM | 6813 | CB | ARG | A | 447 | −45.272 | 12.092 | 28.258 | 1.00 | 41.84 | C |
| ATOM | 6816 | CG | ARG | A | 447 | −46.667 | 11.495 | 27.991 | 1.00 | 42.69 | C |
| ATOM | 6819 | CD | ARG | A | 447 | −46.778 | 10.901 | 26.582 | 1.00 | 43.92 | C |

TABLE 16-7-continued

| | | | | | | | | | | | |
|---|---|---|---|---|---|---|---|---|---|---|---|
| ATOM | 6822 | NE | ARG | A | 447 | −47.764 | 11.589 | 25.744 | 1.00 | 45.34 | N |
| ATOM | 6824 | CZ | ARG | A | 447 | −47.887 | 11.435 | 24.420 | 1.00 | 46.56 | C |
| ATOM | 6825 | NH1 | ARG | A | 447 | −47.077 | 10.623 | 23.742 | 1.00 | 46.71 | N |
| ATOM | 6828 | NH2 | ARG | A | 447 | −48.828 | 12.107 | 23.757 | 1.00 | 46.97 | N |
| ATOM | 6831 | C | ARG | A | 447 | −43.581 | 12.728 | 30.054 | 1.00 | 41.38 | C |
| ATOM | 6832 | O | ARG | A | 447 | −43.231 | 12.747 | 31.238 | 1.00 | 41.92 | O |
| ATOM | 6834 | N | GLY | A | 448 | −42.710 | 12.736 | 29.051 | 1.00 | 40.88 | N |
| ATOM | 6835 | CA | GLY | A | 448 | −41.312 | 13.128 | 29.234 | 1.00 | 40.44 | C |
| ATOM | 6838 | C | GLY | A | 448 | −40.579 | 13.316 | 27.915 | 1.00 | 40.08 | C |
| ATOM | 6839 | O | GLY | A | 448 | −39.364 | 13.488 | 27.901 | 1.00 | 40.05 | O |
| ATOM | 6841 | N | GLU | A | 449 | −41.323 | 13.332 | 26.809 | 1.00 | 39.56 | N |
| ATOM | 6842 | CA | GLU | A | 449 | −40.750 | 13.132 | 25.486 | 1.00 | 39.19 | C |
| ATOM | 6844 | CB | GLU | A | 449 | −41.827 | 12.668 | 24.502 | 1.00 | 39.52 | C |
| ATOM | 6847 | CG | GLU | A | 449 | −42.403 | 11.290 | 24.810 | 1.00 | 40.61 | C |
| ATOM | 6850 | CD | GLU | A | 449 | −43.348 | 10.782 | 23.715 | 1.00 | 42.21 | C |
| ATOM | 6851 | OE1 | GLU | A | 449 | −43.068 | 11.019 | 22.503 | 1.00 | 41.83 | O |
| ATOM | 6852 | OE2 | GLU | A | 449 | −44.368 | 10.141 | 24.082 | 1.00 | 42.41 | O |
| ATOM | 6853 | C | GLU | A | 449 | −40.037 | 14.365 | 24.921 | 1.00 | 38.34 | C |
| ATOM | 6854 | O | GLU | A | 449 | −40.511 | 15.497 | 25.031 | 1.00 | 38.01 | O |
| ATOM | 6856 | N | THR | A | 450 | −38.904 | 14.106 | 24.279 | 1.00 | 37.37 | N |
| ATOM | 6857 | CA | THR | A | 450 | −38.047 | 15.138 | 23.726 | 1.00 | 36.37 | C |
| ATOM | 6859 | CB | THR | A | 450 | −36.607 | 14.985 | 24.285 | 1.00 | 36.39 | C |
| ATOM | 6861 | OG1 | THR | A | 450 | −35.846 | 16.153 | 23.982 | 1.00 | 36.63 | O |
| ATOM | 6863 | CG2 | THR | A | 450 | −35.888 | 13.749 | 23.706 | 1.00 | 36.52 | C |
| ATOM | 6867 | C | THR | A | 450 | −38.013 | 15.100 | 22.190 | 1.00 | 35.36 | C |
| ATOM | 6868 | O | THR | A | 450 | −37.175 | 15.764 | 21.583 | 1.00 | 35.43 | O |
| ATOM | 6870 | N | ALA | A | 451 | −38.917 | 14.338 | 21.563 | 1.00 | 33.98 | N |
| ATOM | 6871 | CA | ALA | A | 451 | −38.920 | 14.182 | 20.096 | 1.00 | 32.81 | C |
| ATOM | 6873 | CB | ALA | A | 451 | −39.030 | 12.708 | 19.708 | 1.00 | 32.99 | C |
| ATOM | 6877 | C | ALA | A | 451 | −40.043 | 14.987 | 19.459 | 1.00 | 31.46 | C |
| ATOM | 6878 | O | ALA | A | 451 | −41.050 | 14.432 | 18.996 | 1.00 | 31.06 | O |
| ATOM | 6880 | N | ASN | A | 452 | −39.848 | 16.302 | 19.432 | 1.00 | 29.88 | N |
| ATOM | 6881 | CA | ASN | A | 452 | −40.881 | 17.225 | 18.973 | 1.00 | 28.81 | C |
| ATOM | 6883 | CB | ASN | A | 452 | −41.957 | 17.329 | 20.051 | 1.00 | 28.57 | C |
| ATOM | 6886 | CG | ASN | A | 452 | −42.969 | 18.380 | 19.757 | 1.00 | 28.30 | C |
| ATOM | 6887 | OD1 | ASN | A | 452 | −42.622 | 19.517 | 19.468 | 1.00 | 29.35 | O |
| ATOM | 6888 | ND2 | ASN | A | 452 | −44.236 | 18.018 | 19.836 | 1.00 | 28.36 | N |
| ATOM | 6891 | C | ASN | A | 452 | −40.285 | 18.590 | 18.641 | 1.00 | 27.76 | C |
| ATOM | 6892 | O | ASN | A | 452 | −39.365 | 19.018 | 19.296 | 1.00 | 28.04 | O |
| ATOM | 6894 | N | SER | A | 453 | −40.807 | 19.269 | 17.630 | 1.00 | 26.77 | N |
| ATOM | 6895 | CA | SER | A | 453 | −40.226 | 20.533 | 17.182 | 1.00 | 26.38 | C |
| ATOM | 6897 | CB | SER | A | 453 | −40.912 | 21.015 | 15.903 | 1.00 | 26.40 | C |
| ATOM | 6900 | OG | SER | A | 453 | −40.796 | 20.044 | 14.876 | 1.00 | 25.79 | O |
| ATOM | 6902 | C | SER | A | 453 | −40.253 | 21.643 | 18.233 | 1.00 | 26.12 | C |
| ATOM | 6903 | O | SER | A | 453 | −39.280 | 22.361 | 18.385 | 1.00 | 25.97 | O |
| ATOM | 6905 | N | VAL | A | 454 | −41.368 | 21.784 | 18.942 | 1.00 | 26.15 | N |
| ATOM | 6906 | CA | VAL | A | 454 | −41.518 | 22.780 | 20.022 | 1.00 | 26.21 | C |
| ATOM | 6908 | CB | VAL | A | 454 | −42.975 | 22.818 | 20.532 | 1.00 | 26.04 | C |
| ATOM | 6910 | CG1 | VAL | A | 454 | −43.122 | 23.787 | 21.694 | 1.00 | 25.24 | C |
| ATOM | 6914 | CG2 | VAL | A | 454 | −43.913 | 23.190 | 19.401 | 1.00 | 26.32 | C |
| ATOM | 6918 | C | VAL | A | 454 | −40.617 | 22.451 | 21.211 | 1.00 | 26.63 | C |
| ATOM | 6919 | O | VAL | A | 454 | −40.173 | 23.328 | 21.959 | 1.00 | 26.53 | O |
| ATOM | 6921 | N | SER | A | 455 | −40.374 | 21.160 | 21.380 | 1.00 | 27.21 | N |
| ATOM | 6922 | CA | SER | A | 455 | −39.541 | 20.651 | 22.437 | 1.00 | 27.60 | C |
| ATOM | 6924 | CB | SER | A | 455 | −39.677 | 19.141 | 22.490 | 1.00 | 27.31 | C |
| ATOM | 6927 | OG | SER | A | 455 | −38.922 | 18.625 | 23.545 | 1.00 | 28.13 | O |
| ATOM | 6929 | C | SER | A | 455 | −38.096 | 21.045 | 22.181 | 1.00 | 28.29 | C |
| ATOM | 6930 | O | SER | A | 455 | −37.445 | 21.628 | 23.043 | 1.00 | 28.63 | O |
| ATOM | 6932 | N | CYS | A | 456 | −37.599 | 20.748 | 20.988 | 1.00 | 29.04 | N |
| ATOM | 6933 | CA | CYS | A | 456 | −36.219 | 21.082 | 20.640 | 1.00 | 29.65 | C |
| ATOM | 6935 | CB | CYS | A | 456 | −35.868 | 20.535 | 19.256 | 1.00 | 29.52 | C |
| ATOM | 6938 | SG | CYS | A | 456 | −35.959 | 18.734 | 19.163 | 1.00 | 29.71 | S |
| ATOM | 6940 | C | CYS | A | 456 | −35.955 | 22.589 | 20.710 | 1.00 | 30.26 | C |
| ATOM | 6941 | O | CYS | A | 456 | −34.887 | 23.007 | 21.162 | 1.00 | 30.49 | O |
| ATOM | 6943 | N | TYR | A | 457 | −36.924 | 23.399 | 20.283 | 1.00 | 30.88 | N |
| ATOM | 6944 | CA | TYR | A | 457 | −36.767 | 24.850 | 20.308 | 1.00 | 31.45 | C |
| ATOM | 6946 | CB | TYR | A | 457 | −37.967 | 25.557 | 19.648 | 1.00 | 31.55 | C |
| ATOM | 6949 | CG | TYR | A | 457 | −37.691 | 26.991 | 19.178 | 1.00 | 32.09 | C |
| ATOM | 6950 | CD1 | TYR | A | 457 | −37.378 | 27.269 | 17.843 | 1.00 | 31.69 | C |
| ATOM | 6952 | CE1 | TYR | A | 457 | −37.128 | 28.569 | 17.418 | 1.00 | 31.73 | C |
| ATOM | 6954 | CZ | TYR | A | 457 | −37.186 | 29.613 | 18.328 | 1.00 | 32.84 | C |
| ATOM | 6955 | OH | TYR | A | 457 | −36.945 | 30.917 | 17.927 | 1.00 | 33.81 | O |
| ATOM | 6957 | CE2 | TYR | A | 457 | −37.492 | 29.364 | 19.658 | 1.00 | 32.72 | C |
| ATOM | 6959 | CD2 | TYR | A | 457 | −37.746 | 28.064 | 20.074 | 1.00 | 32.44 | C |
| ATOM | 6961 | C | TYR | A | 457 | −36.571 | 25.295 | 21.758 | 1.00 | 31.99 | C |
| ATOM | 6962 | O | TYR | A | 457 | −35.648 | 26.053 | 22.052 | 1.00 | 31.98 | O |
| ATOM | 6964 | N | MET | A | 458 | −37.419 | 24.799 | 22.661 | 1.00 | 32.76 | N |
| ATOM | 6965 | CA | MET | A | 458 | −37.211 | 24.987 | 24.105 | 1.00 | 33.37 | C |

TABLE 16-7-continued

| | | | | | | | | | | | |
|---|---|---|---|---|---|---|---|---|---|---|---|
| ATOM | 6967 | CB | MET | A | 458 | −38.151 | 24.097 | 24.921 | 1.00 | 33.43 | C |
| ATOM | 6970 | CG | MET | A | 458 | −39.570 | 24.593 | 25.059 | 1.00 | 33.70 | C |
| ATOM | 6973 | SD | MET | A | 458 | −40.641 | 23.312 | 25.737 | 1.00 | 34.59 | S |
| ATOM | 6974 | CE | MET | A | 458 | −39.709 | 22.763 | 27.179 | 1.00 | 34.71 | C |
| ATOM | 6978 | C | MET | A | 458 | −35.784 | 24.641 | 24.517 | 1.00 | 33.78 | C |
| ATOM | 6979 | O | MET | A | 458 | −35.101 | 25.437 | 25.151 | 1.00 | 33.73 | O |
| ATOM | 6981 | N | ARG | A | 459 | −35.347 | 23.445 | 24.145 | 1.00 | 34.46 | N |
| ATOM | 6982 | CA | ARG | A | 459 | −34.051 | 22.926 | 24.581 | 1.00 | 35.15 | C |
| ATOM | 6984 | CB | ARG | A | 459 | −33.876 | 21.447 | 24.171 | 1.00 | 35.68 | C |
| ATOM | 6987 | CG | ARG | A | 459 | −32.494 | 20.864 | 24.500 | 1.00 | 37.23 | C |
| ATOM | 6990 | CD | ARG | A | 459 | −32.491 | 19.345 | 24.752 | 1.00 | 39.80 | C |
| ATOM | 6993 | NE | ARG | A | 459 | −33.140 | 18.538 | 23.711 | 1.00 | 42.88 | N |
| ATOM | 6995 | CZ | ARG | A | 459 | −32.704 | 18.407 | 22.453 | 1.00 | 45.43 | C |
| ATOM | 6996 | NH1 | ARG | A | 459 | −31.615 | 19.062 | 22.035 | 1.00 | 47.50 | N |
| ATOM | 6999 | NH2 | ARG | A | 459 | −33.366 | 17.629 | 21.595 | 1.00 | 44.77 | N |
| ATOM | 7002 | C | ARG | A | 459 | −32.878 | 23.749 | 24.072 | 1.00 | 34.92 | C |
| ATOM | 7003 | O | ARG | A | 459 | −32.007 | 24.109 | 24.849 | 1.00 | 35.06 | O |
| ATOM | 7005 | N | THR | A | 460 | −32.854 | 24.047 | 22.778 | 1.00 | 34.96 | N |
| ATOM | 7006 | CA | THR | A | 460 | −31.674 | 24.678 | 22.163 | 1.00 | 34.91 | C |
| ATOM | 7008 | CB | THR | A | 460 | −31.494 | 24.263 | 20.680 | 1.00 | 34.88 | C |
| ATOM | 7010 | OG1 | THR | A | 460 | −32.330 | 25.067 | 19.841 | 1.00 | 34.39 | O |
| ATOM | 7012 | CG2 | THR | A | 460 | −31.825 | 22.776 | 20.488 | 1.00 | 35.44 | C |
| ATOM | 7016 | C | THR | A | 460 | −31.672 | 26.210 | 22.258 | 1.00 | 34.78 | C |
| ATOM | 7017 | O | THR | A | 460 | −30.673 | 26.837 | 21.911 | 1.00 | 34.92 | O |
| ATOM | 7019 | N | LYS | A | 461 | −32.781 | 26.806 | 22.701 | 1.00 | 34.41 | N |
| ATOM | 7020 | CA | LYS | A | 461 | −32.811 | 28.231 | 23.039 | 1.00 | 34.25 | C |
| ATOM | 7022 | CB | LYS | A | 461 | −33.921 | 28.947 | 22.265 | 1.00 | 34.56 | C |
| ATOM | 7025 | CG | LYS | A | 461 | −33.717 | 28.986 | 20.750 | 1.00 | 35.84 | C |
| ATOM | 7028 | CD | LYS | A | 461 | −32.519 | 29.859 | 20.347 | 1.00 | 37.64 | C |
| ATOM | 7031 | CE | LYS | A | 461 | −32.232 | 29.804 | 18.838 | 1.00 | 38.44 | C |
| ATOM | 7034 | NZ | LYS | A | 461 | −33.141 | 30.671 | 18.027 | 1.00 | 38.31 | N |
| ATOM | 7038 | C | LYS | A | 461 | −32.974 | 28.476 | 24.544 | 1.00 | 33.73 | C |
| ATOM | 7039 | O | LYS | A | 461 | −32.994 | 29.626 | 24.983 | 1.00 | 33.23 | O |
| ATOM | 7041 | N | GLY | A | 462 | −33.078 | 27.395 | 25.321 | 1.00 | 33.48 | N |
| ATOM | 7042 | CA | GLY | A | 462 | −33.173 | 27.464 | 26.784 | 1.00 | 33.23 | C |
| ATOM | 7045 | C | GLY | A | 462 | −34.332 | 28.320 | 27.239 | 1.00 | 32.95 | C |
| ATOM | 7046 | O | GLY | A | 462 | −34.144 | 29.258 | 28.004 | 1.00 | 33.17 | O |
| ATOM | 7048 | N | ILE | A | 463 | −35.528 | 28.000 | 26.757 | 1.00 | 32.52 | N |
| ATOM | 7049 | CA | ILE | A | 463 | −36.694 | 28.843 | 26.971 | 1.00 | 32.32 | C |
| ATOM | 7051 | CB | ILE | A | 463 | −37.006 | 29.724 | 25.734 | 1.00 | 32.47 | C |
| ATOM | 7053 | CG1 | ILE | A | 463 | −37.152 | 28.866 | 24.463 | 1.00 | 32.41 | C |
| ATOM | 7056 | CD1 | ILE | A | 463 | −37.359 | 29.675 | 23.191 | 1.00 | 32.02 | C |
| ATOM | 7060 | CG2 | ILE | A | 463 | −35.937 | 30.810 | 25.571 | 1.00 | 32.44 | C |
| ATOM | 7064 | C | ILE | A | 463 | −37.902 | 28.006 | 27.309 | 1.00 | 32.15 | C |
| ATOM | 7065 | O | ILE | A | 463 | −37.886 | 26.799 | 27.145 | 1.00 | 32.01 | O |
| ATOM | 7067 | N | SER | A | 464 | −38.950 | 28.670 | 27.780 | 1.00 | 32.27 | N |
| ATOM | 7068 | CA | SER | A | 464 | −40.163 | 28.006 | 28.239 | 1.00 | 32.52 | C |
| ATOM | 7070 | CB | SER | A | 464 | −40.964 | 28.974 | 29.110 | 1.00 | 32.65 | C |
| ATOM | 7073 | OG | SER | A | 464 | −41.112 | 30.224 | 28.457 | 1.00 | 32.69 | O |
| ATOM | 7075 | C | SER | A | 464 | −41.036 | 27.522 | 27.079 | 1.00 | 32.53 | C |
| ATOM | 7076 | O | SER | A | 464 | −40.968 | 28.069 | 25.986 | 1.00 | 32.62 | O |
| ATOM | 7078 | N | GLU | A | 465 | −41.857 | 26.500 | 27.332 | 1.00 | 32.47 | N |
| ATOM | 7079 | CA | GLU | A | 465 | −42.836 | 26.010 | 26.353 | 1.00 | 32.33 | C |
| ATOM | 7081 | CB | GLU | A | 465 | −43.689 | 24.868 | 26.935 | 1.00 | 32.34 | C |
| ATOM | 7084 | CG | GLU | A | 465 | −44.756 | 24.312 | 25.974 | 1.00 | 32.37 | C |
| ATOM | 7087 | CD | GLU | A | 465 | −45.675 | 23.279 | 26.611 | 1.00 | 32.47 | C |
| ATOM | 7088 | OE1 | GLU | A | 465 | −45.297 | 22.659 | 27.630 | 1.00 | 31.63 | O |
| ATOM | 7089 | OE2 | GLU | A | 465 | −46.785 | 23.086 | 26.074 | 1.00 | 32.77 | O |
| ATOM | 7090 | C | GLU | A | 465 | −43.758 | 27.124 | 25.864 | 1.00 | 32.33 | C |
| ATOM | 7091 | O | GLU | A | 465 | −44.078 | 27.183 | 24.676 | 1.00 | 32.60 | O |
| ATOM | 7093 | N | GLU | A | 466 | −44.196 | 28.001 | 26.767 | 1.00 | 32.08 | N |
| ATOM | 7094 | CA | GLU | A | 466 | −45.085 | 29.097 | 26.380 | 1.00 | 31.79 | C |
| ATOM | 7096 | CB | GLU | A | 466 | −45.606 | 29.832 | 27.624 | 1.00 | 31.91 | C |
| ATOM | 7099 | CG | GLU | A | 466 | −46.503 | 31.041 | 27.304 | 1.00 | 32.82 | C |
| ATOM | 7102 | CD | GLU | A | 466 | −47.426 | 31.472 | 28.452 | 1.00 | 33.67 | C |
| ATOM | 7103 | OE1 | GLU | A | 466 | −47.519 | 30.756 | 29.478 | 1.00 | 35.09 | O |
| ATOM | 7104 | OE2 | GLU | A | 466 | −48.077 | 32.533 | 28.312 | 1.00 | 33.12 | O |
| ATOM | 7105 | C | GLU | A | 466 | −44.392 | 30.052 | 25.386 | 1.00 | 31.13 | C |
| ATOM | 7106 | O | GLU | A | 466 | −45.032 | 30.603 | 24.492 | 1.00 | 30.87 | O |
| ATOM | 7108 | N | LEU | A | 467 | −43.077 | 30.194 | 25.531 | 1.00 | 30.57 | N |
| ATOM | 7109 | CA | LEU | A | 467 | −42.265 | 31.102 | 24.708 | 1.00 | 30.18 | C |
| ATOM | 7111 | CB | LEU | A | 467 | −41.055 | 31.604 | 25.524 | 1.00 | 30.38 | C |
| ATOM | 7114 | CG | LEU | A | 467 | −40.674 | 33.087 | 25.463 | 1.00 | 30.39 | C |
| ATOM | 7116 | CD1 | LEU | A | 467 | −41.608 | 33.900 | 26.362 | 1.00 | 30.23 | C |
| ATOM | 7120 | CD2 | LEU | A | 467 | −39.214 | 33.308 | 25.872 | 1.00 | 30.31 | C |
| ATOM | 7124 | C | LEU | A | 467 | −41.773 | 30.401 | 23.439 | 1.00 | 29.47 | C |
| ATOM | 7125 | O | LEU | A | 467 | −41.660 | 31.010 | 22.382 | 1.00 | 29.17 | O |
| ATOM | 7127 | N | ALA | A | 468 | −41.445 | 29.121 | 23.562 | 1.00 | 28.93 | N |

TABLE 16-7-continued

Coordinates of *P. tremuloides* IspS

| ATOM | 7128 | CA | ALA | A | 468 | −41.095 | 28.310 | 22.404 | 1.00 | 28.45 | C |
| --- | --- | --- | --- | --- | --- | --- | --- | --- | --- | --- | --- |
| ATOM | 7130 | CB | ALA | A | 468 | −40.613 | 26.935 | 22.830 | 1.00 | 28.10 | C |
| ATOM | 7134 | C | ALA | A | 468 | −42.306 | 28.193 | 21.494 | 1.00 | 28.08 | C |
| ATOM | 7135 | O | ALA | A | 468 | −42.179 | 28.321 | 20.285 | 1.00 | 28.24 | O |
| ATOM | 7137 | N | THR | A | 469 | −43.479 | 27.964 | 22.080 | 1.00 | 27.58 | N |
| ATOM | 7138 | CA | THR | A | 469 | −44.719 | 27.870 | 21.322 | 1.00 | 27.26 | C |
| ATOM | 7140 | CB | THR | A | 469 | −45.928 | 27.710 | 22.261 | 1.00 | 27.28 | C |
| ATOM | 7142 | OG1 | THR | A | 469 | −46.063 | 26.330 | 22.627 | 1.00 | 27.55 | O |
| ATOM | 7144 | CG2 | THR | A | 469 | −47.222 | 28.185 | 21.597 | 1.00 | 27.34 | C |
| ATOM | 7148 | C | THR | A | 469 | −44.916 | 29.099 | 20.449 | 1.00 | 27.10 | C |
| ATOM | 7149 | O | THR | A | 469 | −45.176 | 28.989 | 19.250 | 1.00 | 27.11 | O |
| ATOM | 7151 | N | GLU | A | 470 | −44.774 | 30.267 | 21.061 | 1.00 | 26.88 | N |
| ATOM | 7152 | CA | GLU | A | 470 | −44.944 | 31.542 | 20.376 | 1.00 | 26.84 | C |
| ATOM | 7154 | CB | GLU | A | 470 | −44.832 | 32.663 | 21.400 | 1.00 | 27.07 | C |
| ATOM | 7157 | CG | GLU | A | 470 | −45.357 | 34.003 | 20.958 | 1.00 | 28.47 | C |
| ATOM | 7160 | CD | GLU | A | 470 | −45.140 | 35.087 | 22.008 | 1.00 | 30.51 | C |
| ATOM | 7161 | OE1 | GLU | A | 470 | −45.029 | 34.775 | 23.221 | 1.00 | 31.53 | O |
| ATOM | 7162 | OE2 | GLU | A | 470 | −45.083 | 36.269 | 21.608 | 1.00 | 32.59 | O |
| ATOM | 7163 | C | GLU | A | 470 | −43.926 | 31.750 | 19.239 | 1.00 | 26.48 | C |
| ATOM | 7164 | O | GLU | A | 470 | −44.261 | 32.296 | 18.184 | 1.00 | 26.29 | O |
| ATOM | 7166 | N | SER | A | 471 | −42.686 | 31.316 | 19.452 | 1.00 | 26.12 | N |
| ATOM | 7167 | CA | SER | A | 471 | −41.660 | 31.386 | 18.408 | 1.00 | 25.85 | C |
| ATOM | 7169 | CB | SER | A | 471 | −40.296 | 30.933 | 18.941 | 1.00 | 25.96 | C |
| ATOM | 7172 | OG | SER | A | 471 | −39.656 | 31.939 | 19.711 | 1.00 | 26.53 | O |
| ATOM | 7174 | C | SER | A | 471 | −42.036 | 30.529 | 17.208 | 1.00 | 25.35 | C |
| ATOM | 7175 | O | SER | A | 471 | −41.761 | 30.899 | 16.067 | 1.00 | 25.43 | O |
| ATOM | 7177 | N | VAL | A | 472 | −42.653 | 29.381 | 17.482 | 1.00 | 24.95 | N |
| ATOM | 7178 | CA | VAL | A | 472 | −43.097 | 28.451 | 16.438 | 1.00 | 24.65 | C |
| ATOM | 7180 | CB | VAL | A | 472 | −43.485 | 27.055 | 17.024 | 1.00 | 24.57 | C |
| ATOM | 7182 | CG1 | VAL | A | 472 | −44.257 | 26.222 | 16.016 | 1.00 | 23.23 | C |
| ATOM | 7186 | CG2 | VAL | A | 472 | −42.232 | 26.309 | 17.494 | 1.00 | 23.83 | C |
| ATOM | 7190 | C | VAL | A | 472 | −44.252 | 29.039 | 15.631 | 1.00 | 24.71 | C |
| ATOM | 7191 | O | VAL | A | 472 | −44.369 | 28.776 | 14.440 | 1.00 | 24.63 | O |
| ATOM | 7193 | N | MET | A | 473 | −45.073 | 29.866 | 16.269 | 1.00 | 24.79 | N |
| ATOM | 7194 | CA | MET | A | 473 | −46.143 | 30.591 | 15.565 | 1.00 | 24.94 | C |
| ATOM | 7196 | CB | MET | A | 473 | −47.059 | 31.266 | 16.576 | 1.00 | 25.11 | C |
| ATOM | 7199 | CG | MET | A | 473 | −47.683 | 30.335 | 17.560 | 1.00 | 25.11 | C |
| ATOM | 7202 | SD | MET | A | 473 | −48.967 | 29.391 | 16.780 | 1.00 | 25.35 | S |
| ATOM | 7203 | CE | MET | A | 473 | −50.064 | 29.163 | 18.189 | 1.00 | 26.11 | C |
| ATOM | 7207 | C | MET | A | 473 | −45.613 | 31.672 | 14.605 | 1.00 | 24.86 | C |
| ATOM | 7208 | O | MET | A | 473 | −46.132 | 31.849 | 13.513 | 1.00 | 24.57 | O |
| ATOM | 7210 | N | ASN | A | 474 | −44.589 | 32.405 | 15.032 | 1.00 | 24.89 | N |
| ATOM | 7211 | CA | ASN | A | 474 | −43.951 | 33.383 | 14.166 | 1.00 | 25.00 | C |
| ATOM | 7213 | CB | ASN | A | 474 | −43.009 | 34.278 | 14.966 | 1.00 | 25.12 | C |
| ATOM | 7216 | CG | ASN | A | 474 | −43.700 | 34.966 | 16.127 | 1.00 | 25.77 | C |
| ATOM | 7217 | OD1 | ASN | A | 474 | −43.058 | 35.312 | 17.114 | 1.00 | 26.96 | O |
| ATOM | 7218 | ND2 | ASN | A | 474 | −45.015 | 35.163 | 16.021 | 1.00 | 26.31 | N |
| ATOM | 7221 | C | ASN | A | 474 | −43.195 | 32.707 | 13.024 | 1.00 | 24.84 | C |
| ATOM | 7222 | O | ASN | A | 474 | −42.979 | 33.313 | 11.973 | 1.00 | 25.07 | O |
| ATOM | 7224 | N | LEU | A | 475 | −42.792 | 31.455 | 13.227 | 1.00 | 24.46 | N |
| ATOM | 7225 | CA | LEU | A | 475 | −42.218 | 30.671 | 12.142 | 1.00 | 24.06 | C |
| ATOM | 7227 | CB | LEU | A | 475 | −41.596 | 29.367 | 12.653 | 1.00 | 24.27 | C |
| ATOM | 7230 | CG | LEU | A | 475 | −40.307 | 29.072 | 11.886 | 1.00 | 25.08 | C |
| ATOM | 7232 | CD1 | LEU | A | 475 | −39.207 | 30.000 | 12.419 | 1.00 | 25.89 | C |
| ATOM | 7236 | CD2 | LEU | A | 475 | −39.887 | 27.622 | 11.985 | 1.00 | 25.33 | C |
| ATOM | 7240 | C | LEU | A | 475 | −43.278 | 30.365 | 11.085 | 1.00 | 23.26 | C |
| ATOM | 7241 | O | LEU | A | 475 | −43.018 | 30.479 | 9.884 | 1.00 | 22.90 | O |
| ATOM | 7243 | N | ILE | A | 476 | −44.471 | 29.978 | 11.534 | 1.00 | 22.53 | N |
| ATOM | 7244 | CA | ILE | A | 476 | −45.544 | 29.632 | 10.606 | 1.00 | 21.93 | C |
| ATOM | 7246 | CB | ILE | A | 476 | −46.773 | 29.017 | 11.308 | 1.00 | 21.58 | C |
| ATOM | 7248 | CG1 | ILE | A | 476 | −46.499 | 27.550 | 11.664 | 1.00 | 21.32 | C |
| ATOM | 7251 | CD1 | ILE | A | 476 | −47.552 | 26.902 | 12.598 | 1.00 | 20.33 | C |
| ATOM | 7255 | CG2 | ILE | A | 476 | −47.994 | 29.104 | 10.428 | 1.00 | 20.46 | C |
| ATOM | 7259 | C | ILE | A | 476 | −45.926 | 30.887 | 9.853 | 1.00 | 22.07 | C |
| ATOM | 7260 | O | ILE | A | 476 | −46.007 | 30.869 | 8.626 | 1.00 | 22.47 | O |
| ATOM | 7262 | N | ASP | A | 477 | −46.122 | 31.982 | 10.584 | 1.00 | 21.81 | N |
| ATOM | 7263 | CA | ASP | A | 477 | −46.483 | 33.245 | 9.970 | 1.00 | 21.56 | C |
| ATOM | 7265 | CB | ASP | A | 477 | −46.643 | 34.337 | 11.032 | 1.00 | 21.89 | C |
| ATOM | 7268 | CG | ASP | A | 477 | −47.962 | 34.217 | 11.817 | 1.00 | 23.39 | C |
| ATOM | 7269 | OD1 | ASP | A | 477 | −48.854 | 33.441 | 11.375 | 1.00 | 24.41 | O |
| ATOM | 7270 | OD2 | ASP | A | 477 | −48.103 | 34.902 | 12.875 | 1.00 | 23.80 | O |
| ATOM | 7271 | C | ASP | A | 477 | −45.425 | 33.626 | 8.947 | 1.00 | 21.06 | C |
| ATOM | 7272 | O | ASP | A | 477 | −45.759 | 33.913 | 7.795 | 1.00 | 20.78 | O |
| ATOM | 7274 | N | GLU | A | 478 | −44.156 | 33.591 | 9.361 | 1.00 | 20.63 | N |
| ATOM | 7275 | CA | GLU | A | 478 | −43.027 | 33.919 | 8.467 | 1.00 | 20.45 | C |
| ATOM | 7277 | CB | GLU | A | 478 | −41.680 | 33.793 | 9.200 | 1.00 | 20.66 | C |
| ATOM | 7280 | CG | GLU | A | 478 | −40.422 | 34.044 | 8.339 | 1.00 | 22.27 | C |
| ATOM | 7283 | CD | GLU | A | 478 | −39.107 | 33.579 | 9.018 | 1.00 | 24.72 | C |

TABLE 16-7-continued

Coordinates of *P. tremuloides* IspS

| ATOM | 7284 | OE1 | GLU | A | 478 | −38.553 | 34.367 | 9.817 | 1.00 | 26.19 | O |
|---|---|---|---|---|---|---|---|---|---|---|---|
| ATOM | 7285 | OE2 | GLU | A | 478 | −38.619 | 32.442 | 8.745 | 1.00 | 25.66 | O |
| ATOM | 7286 | C | GLU | A | 478 | −43.041 | 33.042 | 7.217 | 1.00 | 19.54 | C |
| ATOM | 7287 | O | GLU | A | 478 | −42.879 | 33.544 | 6.102 | 1.00 | 19.02 | O |
| ATOM | 7289 | N | THR | A | 479 | −43.250 | 31.743 | 7.413 | 1.00 | 18.76 | N |
| ATOM | 7290 | CA | THR | A | 479 | −43.358 | 30.808 | 6.294 | 1.00 | 18.45 | C |
| ATOM | 7292 | CB | THR | A | 479 | −43.503 | 29.339 | 6.774 | 1.00 | 18.26 | C |
| ATOM | 7294 | OG1 | THR | A | 479 | −42.334 | 28.955 | 7.494 | 1.00 | 17.30 | O |
| ATOM | 7296 | CG2 | THR | A | 479 | −43.669 | 28.394 | 5.592 | 1.00 | 17.93 | C |
| ATOM | 7300 | C | THR | A | 479 | −44.504 | 31.173 | 5.314 | 1.00 | 18.39 | C |
| ATOM | 7301 | O | THR | A | 479 | −44.280 | 31.200 | 4.103 | 1.00 | 18.58 | O |
| ATOM | 7303 | N | TRP | A | 480 | −45.709 | 31.457 | 5.818 | 1.00 | 17.85 | N |
| ATOM | 7304 | CA | TRP | A | 480 | −46.801 | 31.909 | 4.942 | 1.00 | 17.44 | C |
| ATOM | 7306 | CB | TRP | A | 480 | −48.086 | 32.225 | 5.728 | 1.00 | 17.67 | C |
| ATOM | 7309 | CG | TRP | A | 480 | −48.969 | 31.042 | 5.888 | 1.00 | 17.09 | C |
| ATOM | 7310 | CD1 | TRP | A | 480 | −48.996 | 30.195 | 6.936 | 1.00 | 16.76 | C |
| ATOM | 7312 | NE1 | TRP | A | 480 | −49.914 | 29.216 | 6.724 | 1.00 | 17.08 | N |
| ATOM | 7314 | CE2 | TRP | A | 480 | −50.501 | 29.410 | 5.507 | 1.00 | 17.86 | C |
| ATOM | 7315 | CD2 | TRP | A | 480 | −49.930 | 30.559 | 4.954 | 1.00 | 17.15 | C |
| ATOM | 7316 | CE3 | TRP | A | 480 | −50.356 | 30.980 | 3.696 | 1.00 | 18.31 | C |
| ATOM | 7318 | CZ3 | TRP | A | 480 | −51.337 | 30.244 | 3.039 | 1.00 | 19.10 | C |
| ATOM | 7320 | CH2 | TRP | A | 480 | −51.897 | 29.107 | 3.622 | 1.00 | 18.83 | C |
| ATOM | 7322 | CZ2 | TRP | A | 480 | −51.493 | 28.673 | 4.855 | 1.00 | 18.86 | C |
| ATOM | 7324 | C | TRP | A | 480 | −46.426 | 33.124 | 4.097 | 1.00 | 17.10 | C |
| ATOM | 7325 | O | TRP | A | 480 | −46.824 | 33.215 | 2.943 | 1.00 | 17.22 | O |
| ATOM | 7327 | N | LYS | A | 481 | −45.675 | 34.062 | 4.659 | 1.00 | 16.60 | N |
| ATOM | 7328 | CA | LYS | A | 481 | −45.275 | 35.215 | 3.886 | 1.00 | 16.23 | C |
| ATOM | 7330 | CB | LYS | A | 481 | −44.566 | 36.243 | 4.747 | 1.00 | 16.42 | C |
| ATOM | 7333 | CG | LYS | A | 481 | −45.417 | 36.954 | 5.769 | 1.00 | 16.42 | C |
| ATOM | 7336 | CD | LYS | A | 481 | −44.555 | 37.979 | 6.505 | 1.00 | 16.40 | C |
| ATOM | 7339 | CE | LYS | A | 481 | −45.199 | 38.504 | 7.782 | 1.00 | 16.66 | C |
| ATOM | 7342 | NZ | LYS | A | 481 | −44.184 | 38.717 | 8.846 | 1.00 | 16.72 | N |
| ATOM | 7346 | C | LYS | A | 481 | −44.357 | 34.782 | 2.767 | 1.00 | 15.94 | C |
| ATOM | 7347 | O | LYS | A | 481 | −44.451 | 35.291 | 1.674 | 1.00 | 16.09 | O |
| ATOM | 7349 | N | LYS | A | 482 | −43.461 | 33.849 | 3.034 | 1.00 | 15.98 | N |
| ATOM | 7350 | CA | LYS | A | 482 | −42.559 | 33.369 | 1.996 | 1.00 | 16.30 | C |
| ATOM | 7352 | CB | LYS | A | 482 | −41.409 | 32.563 | 2.594 | 1.00 | 16.51 | C |
| ATOM | 7355 | CG | LYS | A | 482 | −40.354 | 33.445 | 3.286 | 1.00 | 17.46 | C |
| ATOM | 7358 | CD | LYS | A | 482 | −39.486 | 32.647 | 4.241 | 1.00 | 18.48 | C |
| ATOM | 7361 | CE | LYS | A | 482 | −38.625 | 33.548 | 5.096 | 1.00 | 18.94 | C |
| ATOM | 7364 | NZ | LYS | A | 482 | −37.865 | 32.773 | 6.129 | 1.00 | 20.40 | N |
| ATOM | 7368 | C | LYS | A | 482 | −43.296 | 32.561 | .938 | 1.00 | 16.40 | C |
| ATOM | 7369 | O | LYS | A | 482 | −42.941 | 32.614 | −.229 | 1.00 | 16.85 | O |
| ATOM | 7371 | N | MET | A | 483 | −44.328 | 31.824 | 1.332 | 1.00 | 16.57 | N |
| ATOM | 7372 | CA | MET | A | 483 | −45.149 | 31.100 | .366 | 1.00 | 16.67 | C |
| ATOM | 7374 | CB | MET | A | 483 | −46.128 | 30.156 | 1.057 | 1.00 | 16.55 | C |
| ATOM | 7377 | CG | MET | A | 483 | −45.496 | 28.923 | 1.675 | 1.00 | 16.50 | C |
| ATOM | 7380 | SD | MET | A | 483 | −46.715 | 27.684 | 2.194 | 1.00 | 17.39 | S |
| ATOM | 7381 | CE | MET | A | 483 | −47.937 | 28.704 | 3.025 | 1.00 | 17.27 | C |
| ATOM | 7385 | C | MET | A | 483 | −45.928 | 32.069 | −.495 | 1.00 | 17.06 | C |
| ATOM | 7386 | O | MET | A | 483 | −46.027 | 31.867 | −1.688 | 1.00 | 17.17 | O |
| ATOM | 7388 | N | ASN | A | 484 | −46.483 | 33.110 | .118 | 1.00 | 17.72 | N |
| ATOM | 7389 | CA | ASN | A | 484 | −47.305 | 34.093 | −.587 | 1.00 | 18.35 | C |
| ATOM | 7391 | CB | ASN | A | 484 | −47.861 | 35.129 | .397 | 1.00 | 18.26 | C |
| ATOM | 7394 | CG | ASN | A | 484 | −48.994 | 34.601 | 1.248 | 1.00 | 17.35 | C |
| ATOM | 7395 | OD1 | ASN | A | 484 | −49.597 | 33.577 | .934 | 1.00 | 17.54 | O |
| ATOM | 7396 | ND2 | ASN | A | 484 | −49.304 | 35.317 | 2.331 | 1.00 | 14.10 | N |
| ATOM | 7399 | C | ASN | A | 484 | −46.541 | 34.839 | −1.677 | 1.00 | 19.51 | C |
| ATOM | 7400 | O | ASN | A | 484 | −47.123 | 35.250 | −2.685 | 1.00 | 19.49 | O |
| ATOM | 7402 | N | LYS | A | 485 | −45.243 | 35.035 | −1.463 | 1.00 | 20.86 | N |
| ATOM | 7403 | CA | LYS | A | 485 | −44.394 | 35.681 | −2.456 | 1.00 | 22.12 | C |
| ATOM | 7405 | CB | LYS | A | 485 | −43.070 | 36.092 | −1.823 | 1.00 | 22.08 | C |
| ATOM | 7408 | CG | LYS | A | 485 | −42.229 | 37.060 | −2.641 | 1.00 | 23.09 | C |
| ATOM | 7411 | CD | LYS | A | 485 | −40.783 | 37.072 | −2.109 | 1.00 | 25.38 | C |
| ATOM | 7414 | CE | LYS | A | 485 | −40.098 | 38.460 | −2.135 | 1.00 | 26.12 | C |
| ATOM | 7417 | NZ | LYS | A | 485 | −38.943 | 38.555 | −3.086 | 1.00 | 26.61 | N |
| ATOM | 7421 | C | LYS | A | 485 | −44.164 | 34.743 | −3.656 | 1.00 | 23.36 | C |
| ATOM | 7422 | O | LYS | A | 485 | −44.120 | 35.191 | −4.802 | 1.00 | 23.00 | O |
| ATOM | 7424 | N | GLU | A | 486 | −44.027 | 33.442 | −3.400 | 1.00 | 24.99 | N |
| ATOM | 7425 | CA | GLU | A | 486 | −43.902 | 32.479 | −4.491 | 1.00 | 26.35 | C |
| ATOM | 7427 | CB | GLU | A | 486 | −43.627 | 31.061 | −3.978 | 1.00 | 26.55 | C |
| ATOM | 7430 | CG | GLU | A | 486 | −42.985 | 30.130 | −5.033 | 1.00 | 28.29 | C |
| ATOM | 7433 | CD | GLU | A | 486 | −41.466 | 30.324 | −5.191 | 1.00 | 31.11 | C |
| ATOM | 7434 | OE1 | GLU | A | 486 | −40.981 | 30.466 | −6.341 | 1.00 | 32.07 | O |
| ATOM | 7435 | OE2 | GLU | A | 486 | −40.744 | 30.335 | −4.159 | 1.00 | 33.04 | O |
| ATOM | 7436 | C | GLU | A | 486 | −45.157 | 32.501 | −5.362 | 1.00 | 27.13 | C |
| ATOM | 7437 | O | GLU | A | 486 | −45.064 | 32.618 | −6.583 | 1.00 | 27.57 | O |
| ATOM | 7439 | N | LYS | A | 487 | −46.325 | 32.422 | −4.739 | 1.00 | 28.12 | N |

TABLE 16-7-continued

Coordinates of *P. tremuloides* IspS

| ATOM | 7440 | CA  | LYS | A | 487 | −47.582 | 32.378 | −5.485  | 1.00 | 29.12 | C |
| ---- | ---- | --- | --- | - | --- | ------- | ------ | ------- | ---- | ----- | - |
| ATOM | 7442 | CB  | LYS | A | 487 | −48.788 | 32.260 | −4.542  | 1.00 | 29.21 | C |
| ATOM | 7445 | CG  | LYS | A | 487 | −50.167 | 32.296 | −5.235  | 1.00 | 28.57 | C |
| ATOM | 7448 | CD  | LYS | A | 487 | −50.403 | 31.040 | −6.036  | 1.00 | 27.91 | C |
| ATOM | 7451 | CE  | LYS | A | 487 | −51.615 | 31.141 | −6.936  | 1.00 | 28.38 | C |
| ATOM | 7454 | NZ  | LYS | A | 487 | −52.874 | 31.460 | −6.211  | 1.00 | 28.03 | N |
| ATOM | 7458 | C   | LYS | A | 487 | −47.756 | 33.603 | −6.352  | 1.00 | 30.18 | C |
| ATOM | 7459 | O   | LYS | A | 487 | −48.308 | 33.514 | −7.446  | 1.00 | 30.21 | O |
| ATOM | 7461 | N   | LEU | A | 488 | −47.295 | 34.743 | −5.844  | 1.00 | 31.64 | N |
| ATOM | 7462 | CA  | LEU | A | 488 | −47.422 | 36.026 | −6.532  | 1.00 | 32.65 | C |
| ATOM | 7464 | CB  | LEU | A | 488 | −47.426 | 37.144 | −5.494  | 1.00 | 32.43 | C |
| ATOM | 7467 | CG  | LEU | A | 488 | −48.091 | 38.446 | −5.907  | 1.00 | 32.50 | C |
| ATOM | 7469 | CD1 | LEU | A | 488 | −49.593 | 38.288 | −5.943  | 1.00 | 32.66 | C |
| ATOM | 7473 | CD2 | LEU | A | 488 | −47.707 | 39.554 | −4.943  | 1.00 | 33.38 | C |
| ATOM | 7477 | C   | LEU | A | 488 | −46.286 | 36.242 | −7.542  | 1.00 | 33.99 | C |
| ATOM | 7478 | O   | LEU | A | 488 | −46.536 | 36.539 | −8.705  | 1.00 | 33.72 | O |
| ATOM | 7480 | N   | GLY | A | 489 | −45.046 | 36.045 | −7.091  | 1.00 | 35.85 | N |
| ATOM | 7481 | CA  | GLY | A | 489 | −43.845 | 36.361 | −7.874  | 1.00 | 37.37 | C |
| ATOM | 7484 | C   | GLY | A | 489 | −43.278 | 35.221 | −8.709  | 1.00 | 38.76 | C |
| ATOM | 7485 | O   | GLY | A | 489 | −42.414 | 34.467 | −8.250  | 1.00 | 39.06 | O |
| ATOM | 7487 | N   | GLY | A | 490 | −43.760 | 35.119 | −9.947  | 1.00 | 40.26 | N |
| ATOM | 7488 | CA  | GLY | A | 490 | −43.285 | 34.130 | −10.927 | 1.00 | 41.03 | C |
| ATOM | 7491 | C   | GLY | A | 490 | −42.193 | 33.194 | −10.436 | 1.00 | 41.61 | C |
| ATOM | 7492 | O   | GLY | A | 490 | −41.010 | 33.547 | −10.423 | 1.00 | 41.62 | O |
| ATOM | 7494 | N   | SER | A | 491 | −42.590 | 31.996 | −10.023 | 1.00 | 42.17 | N |
| ATOM | 7495 | CA  | SER | A | 491 | −41.619 | 30.962 | −9.662  | 1.00 | 42.54 | C |
| ATOM | 7497 | CB  | SER | A | 491 | −42.279 | 29.909 | −8.741  | 1.00 | 42.63 | C |
| ATOM | 7500 | OG  | SER | A | 491 | −43.451 | 29.345 | −9.294  | 1.00 | 42.44 | O |
| ATOM | 7502 | C   | SER | A | 491 | −41.032 | 30.349 | −10.952 | 1.00 | 42.50 | C |
| ATOM | 7503 | O   | SER | A | 491 | −41.117 | 30.961 | −12.030 | 1.00 | 42.57 | O |
| ATOM | 7505 | N   | LEU | A | 492 | −40.405 | 29.177 | −10.843 | 1.00 | 42.18 | N |
| ATOM | 7506 | CA  | LEU | A | 492 | −40.185 | 28.333 | −12.021 | 1.00 | 41.96 | C |
| ATOM | 7508 | CB  | LEU | A | 492 | −39.110 | 27.270 | −11.782 | 1.00 | 42.39 | C |
| ATOM | 7511 | CG  | LEU | A | 492 | −37.695 | 27.671 | −11.353 | 1.00 | 44.21 | C |
| ATOM | 7513 | CD1 | LEU | A | 492 | −36.783 | 26.438 | −11.498 | 1.00 | 45.26 | C |
| ATOM | 7517 | CD2 | LEU | A | 492 | −37.120 | 28.896 | −12.129 | 1.00 | 45.51 | C |
| ATOM | 7521 | C   | LEU | A | 492 | −41.479 | 27.610 | −12.356 | 1.00 | 40.88 | C |
| ATOM | 7522 | O   | LEU | A | 492 | −41.713 | 27.244 | −13.504 | 1.00 | 40.78 | O |
| ATOM | 7524 | N   | PHE | A | 493 | −42.308 | 27.409 | −11.339 | 1.00 | 39.61 | N |
| ATOM | 7525 | CA  | PHE | A | 493 | −43.500 | 26.595 | −11.460 | 1.00 | 38.85 | C |
| ATOM | 7527 | CB  | PHE | A | 493 | −43.783 | 25.911 | −10.124 | 1.00 | 38.62 | C |
| ATOM | 7530 | CG  | PHE | A | 493 | −42.725 | 24.937 | −9.713  | 1.00 | 37.16 | C |
| ATOM | 7531 | CD1 | PHE | A | 493 | −42.901 | 23.587 | −9.916  | 1.00 | 35.26 | C |
| ATOM | 7533 | CE1 | PHE | A | 493 | −41.934 | 22.698 | −9.546  | 1.00 | 34.86 | C |
| ATOM | 7535 | CZ  | PHE | A | 493 | −40.769 | 23.143 | −8.966  | 1.00 | 35.09 | C |
| ATOM | 7537 | CE2 | PHE | A | 493 | −40.574 | 24.482 | −8.759  | 1.00 | 35.45 | C |
| ATOM | 7539 | CD2 | PHE | A | 493 | −41.549 | 25.374 | −9.130  | 1.00 | 36.36 | C |
| ATOM | 7541 | C   | PHE | A | 493 | −44.714 | 27.412 | −11.890 | 1.00 | 38.62 | C |
| ATOM | 7542 | O   | PHE | A | 493 | −44.756 | 28.621 | −11.702 | 1.00 | 38.86 | O |
| ATOM | 7544 | N   | ALA | A | 494 | −45.698 | 26.731 | −12.469 | 1.00 | 38.32 | N |
| ATOM | 7545 | CA  | ALA | A | 494 | −46.977 | 27.337 | −12.843 | 1.00 | 38.09 | C |
| ATOM | 7547 | CB  | ALA | A | 494 | −47.658 | 26.486 | −13.906 | 1.00 | 38.17 | C |
| ATOM | 7551 | C   | ALA | A | 494 | −47.891 | 27.479 | −11.623 | 1.00 | 37.76 | C |
| ATOM | 7552 | O   | ALA | A | 494 | −48.039 | 26.541 | −10.845 | 1.00 | 38.15 | O |
| ATOM | 7554 | N   | LYS | A | 495 | −48.541 | 28.629 | −11.484 | 1.00 | 37.15 | N |
| ATOM | 7555 | CA  | LYS | A | 495 | −49.321 | 28.947 | −10.270 | 1.00 | 36.53 | C |
| ATOM | 7557 | CB  | LYS | A | 495 | −50.116 | 30.258 | −10.477 | 1.00 | 36.90 | C |
| ATOM | 7560 | CG  | LYS | A | 495 | −49.235 | 31.524 | −10.582 | 1.00 | 37.72 | C |
| ATOM | 7563 | CD  | LYS | A | 495 | −50.061 | 32.826 | −10.585 | 1.00 | 38.87 | C |
| ATOM | 7566 | CE  | LYS | A | 495 | −49.140 | 34.065 | −10.665 | 1.00 | 39.78 | C |
| ATOM | 7569 | NZ  | LYS | A | 495 | −49.786 | 35.369 | −10.282 | 1.00 | 39.78 | N |
| ATOM | 7573 | C   | LYS | A | 495 | −50.238 | 27.809 | −9.724  | 1.00 | 35.25 | C |
| ATOM | 7574 | O   | LYS | A | 495 | −50.261 | 27.563 | −8.523  | 1.00 | 34.91 | O |
| ATOM | 7576 | N   | PRO | A | 496 | −50.978 | 27.107 | −10.599 | 1.00 | 33.76 | N |
| ATOM | 7577 | CA  | PRO | A | 496 | −51.846 | 26.015 | −10.162 | 1.00 | 32.74 | C |
| ATOM | 7579 | CB  | PRO | A | 496 | −52.222 | 25.340 | −11.474 | 1.00 | 32.99 | C |
| ATOM | 7582 | CG  | PRO | A | 496 | −52.337 | 26.470 | −12.385 | 1.00 | 33.75 | C |
| ATOM | 7585 | CD  | PRO | A | 496 | −51.196 | 27.400 | −12.022 | 1.00 | 33.83 | C |
| ATOM | 7588 | C   | PRO | A | 496 | −51.194 | 24.998 | −9.267  | 1.00 | 31.24 | C |
| ATOM | 7589 | O   | PRO | A | 496 | −51.822 | 24.522 | −8.331  | 1.00 | 31.54 | O |
| ATOM | 7590 | N   | PHE | A | 497 | −49.954 | 24.642 | −9.566  | 1.00 | 29.40 | N |
| ATOM | 7591 | CA  | PHE | A | 497 | −49.229 | 23.726 | −8.708  | 1.00 | 27.76 | C |
| ATOM | 7593 | CB  | PHE | A | 497 | −48.162 | 22.948 | −9.474  | 1.00 | 27.62 | C |
| ATOM | 7596 | CG  | PHE | A | 497 | −47.351 | 22.040 | −8.597  | 1.00 | 26.33 | C |
| ATOM | 7597 | CD1 | PHE | A | 497 | −47.944 | 20.969 | −7.974  | 1.00 | 24.96 | C |
| ATOM | 7599 | CE1 | PHE | A | 497 | −47.218 | 20.151 | −7.156  | 1.00 | 25.04 | C |
| ATOM | 7601 | CZ  | PHE | A | 497 | −45.875 | 20.396 | −6.940  | 1.00 | 24.79 | C |
| ATOM | 7603 | CE2 | PHE | A | 497 | −45.274 | 21.457 | −7.549  | 1.00 | 24.73 | C |

TABLE 16-7-continued

Coordinates of *P. tremuloides* IspS

| ATOM | 7605 | CD2 | PHE | A | 497 | −46.010 | 22.282 | −8.366 | 1.00 | 25.48 | C |
|---|---|---|---|---|---|---|---|---|---|---|---|
| ATOM | 7607 | C | PHE | A | 497 | −48.592 | 24.407 | −7.494 | 1.00 | 26.59 | C |
| ATOM | 7608 | O | PHE | A | 497 | −48.361 | 23.738 | −6.500 | 1.00 | 26.77 | O |
| ATOM | 7610 | N | VAL | A | 498 | −48.291 | 25.704 | −7.535 | 1.00 | 24.83 | N |
| ATOM | 7611 | CA | VAL | A | 498 | −47.869 | 26.338 | −6.289 | 1.00 | 23.86 | C |
| ATOM | 7613 | CB | VAL | A | 498 | −47.181 | 27.722 | −6.455 | 1.00 | 23.47 | C |
| ATOM | 7615 | CG1 | VAL | A | 498 | −48.163 | 28.755 | −6.759 | 1.00 | 24.57 | C |
| ATOM | 7619 | CG2 | VAL | A | 498 | −46.151 | 27.690 | −7.551 | 1.00 | 23.54 | C |
| ATOM | 7623 | C | VAL | A | 498 | −49.094 | 26.396 | −5.355 | 1.00 | 22.97 | C |
| ATOM | 7624 | O | VAL | A | 498 | −48.978 | 26.130 | −4.161 | 1.00 | 23.39 | O |
| ATOM | 7626 | N | GLU | A | 499 | −50.268 | 26.687 | −5.903 | 1.00 | 21.68 | N |
| ATOM | 7627 | CA | GLU | A | 499 | −51.473 | 26.719 | −5.106 | 1.00 | 20.84 | C |
| ATOM | 7629 | CB | GLU | A | 499 | −52.677 | 27.136 | −5.930 | 1.00 | 20.99 | C |
| ATOM | 7632 | CG | GLU | A | 499 | −53.957 | 27.352 | −5.099 | 1.00 | 21.25 | C |
| ATOM | 7635 | CD | GLU | A | 499 | −53.930 | 28.630 | −4.265 | 1.00 | 21.77 | C |
| ATOM | 7636 | OE1 | GLU | A | 499 | −52.982 | 29.448 | −4.383 | 1.00 | 20.74 | O |
| ATOM | 7637 | OE2 | GLU | A | 499 | −54.876 | 28.812 | −3.476 | 1.00 | 22.76 | O |
| ATOM | 7638 | C | GLU | A | 499 | −51.766 | 25.371 | −4.497 | 1.00 | 20.35 | C |
| ATOM | 7639 | O | GLU | A | 499 | −52.137 | 25.308 | −3.318 | 1.00 | 20.78 | O |
| ATOM | 7641 | N | THR | A | 500 | −51.629 | 24.286 | −5.264 | 1.00 | 19.40 | N |
| ATOM | 7642 | CA | THR | A | 500 | −51.894 | 22.970 | −4.667 | 1.00 | 18.94 | C |
| ATOM | 7644 | CB | THR | A | 500 | −51.993 | 21.782 | −5.683 | 1.00 | 18.96 | C |
| ATOM | 7646 | OG1 | THR | A | 500 | −50.708 | 21.475 | −6.202 | 1.00 | 19.44 | O |
| ATOM | 7648 | CG2 | THR | A | 500 | −52.991 | 22.071 | −6.835 | 1.00 | 18.75 | C |
| ATOM | 7652 | C | THR | A | 500 | −50.895 | 22.674 | −3.526 | 1.00 | 18.20 | C |
| ATOM | 7653 | O | THR | A | 500 | −51.280 | 22.100 | −2.519 | 1.00 | 17.68 | O |
| ATOM | 7655 | N | ALA | A | 501 | −49.646 | 23.119 | −3.666 | 1.00 | 17.49 | N |
| ATOM | 7656 | CA | ALA | A | 501 | −48.663 | 23.021 | −2.593 | 1.00 | 17.18 | C |
| ATOM | 7658 | CB | ALA | A | 501 | −47.348 | 23.563 | −3.051 | 1.00 | 16.98 | C |
| ATOM | 7662 | C | ALA | A | 501 | −49.120 | 23.770 | −1.338 | 1.00 | 17.38 | C |
| ATOM | 7663 | O | ALA | A | 501 | −49.098 | 23.219 | −.230 | 1.00 | 17.45 | O |
| ATOM | 7665 | N | ILE | A | 502 | −49.517 | 25.031 | −1.508 | 1.00 | 17.29 | N |
| ATOM | 7666 | CA | ILE | A | 502 | −49.971 | 25.857 | −.386 | 1.00 | 17.07 | C |
| ATOM | 7668 | CB | ILE | A | 502 | −50.353 | 27.304 | −.846 | 1.00 | 17.09 | C |
| ATOM | 7670 | CG1 | ILE | A | 502 | −49.092 | 28.069 | −1.286 | 1.00 | 17.17 | C |
| ATOM | 7673 | CD1 | ILE | A | 502 | −49.345 | 29.345 | −2.116 | 1.00 | 16.25 | C |
| ATOM | 7677 | CG2 | ILE | A | 502 | −51.110 | 28.076 | .265 | 1.00 | 16.14 | C |
| ATOM | 7681 | C | ILE | A | 502 | −51.155 | 25.168 | .285 | 1.00 | 17.24 | C |
| ATOM | 7682 | O | ILE | A | 502 | −51.265 | 25.163 | 1.516 | 1.00 | 17.03 | O |
| ATOM | 7684 | N | ASN | A | 503 | −52.022 | 24.559 | −.522 | 1.00 | 17.32 | N |
| ATOM | 7685 | CA | ASN | A | 503 | −53.167 | 23.823 | .022 | 1.00 | 17.75 | C |
| ATOM | 7687 | CB | ASN | A | 503 | −53.986 | 23.221 | −1.121 | 1.00 | 17.70 | C |
| ATOM | 7690 | CG | ASN | A | 503 | −54.760 | 24.261 | −1.888 | 1.00 | 18.41 | C |
| ATOM | 7691 | OD1 | ASN | A | 503 | −55.058 | 25.334 | −1.382 | 1.00 | 18.94 | O |
| ATOM | 7692 | ND2 | ASN | A | 503 | −55.107 | 23.939 | −3.119 | 1.00 | 20.42 | N |
| ATOM | 7695 | C | ASN | A | 503 | −52.803 | 22.727 | 1.075 | 1.00 | 17.74 | C |
| ATOM | 7696 | O | ASN | A | 503 | −53.619 | 22.387 | 1.949 | 1.00 | 17.96 | O |
| ATOM | 7698 | N | LEU | A | 504 | −51.589 | 22.185 | .993 | 1.00 | 17.23 | N |
| ATOM | 7699 | CA | LEU | A | 504 | −51.105 | 21.249 | 1.994 | 1.00 | 17.10 | C |
| ATOM | 7701 | CB | LEU | A | 504 | −49.745 | 20.686 | 1.583 | 1.00 | 17.28 | C |
| ATOM | 7704 | CG | LEU | A | 504 | −49.213 | 19.528 | 2.426 | 1.00 | 17.29 | C |
| ATOM | 7706 | CD1 | LEU | A | 504 | −49.570 | 18.196 | 1.762 | 1.00 | 17.22 | C |
| ATOM | 7710 | CD2 | LEU | A | 504 | −47.708 | 19.686 | 2.616 | 1.00 | 16.83 | C |
| ATOM | 7714 | C | LEU | A | 504 | −50.971 | 21.939 | 3.347 | 1.00 | 16.97 | C |
| ATOM | 7715 | O | LEU | A | 504 | −51.237 | 21.330 | 4.379 | 1.00 | 16.84 | O |
| ATOM | 7717 | N | ALA | A | 505 | −50.535 | 23.201 | 3.330 | 1.00 | 16.90 | N |
| ATOM | 7718 | CA | ALA | A | 505 | −50.433 | 24.015 | 4.540 | 1.00 | 16.68 | C |
| ATOM | 7720 | CB | ALA | A | 505 | −49.739 | 25.309 | 4.243 | 1.00 | 16.54 | C |
| ATOM | 7724 | C | ALA | A | 505 | −51.826 | 24.281 | 5.074 | 1.00 | 16.77 | C |
| ATOM | 7725 | O | ALA | A | 505 | −52.087 | 24.123 | 6.266 | 1.00 | 16.80 | O |
| ATOM | 7727 | N | ARG | A | 506 | −52.726 | 24.664 | 4.172 | 1.00 | 16.82 | N |
| ATOM | 7728 | CA | ARG | A | 506 | −54.128 | 24.875 | 4.521 | 1.00 | 16.84 | C |
| ATOM | 7730 | CB | ARG | A | 506 | −54.944 | 25.274 | 3.286 | 1.00 | 16.86 | C |
| ATOM | 7733 | CG | ARG | A | 506 | −54.649 | 26.661 | 2.795 | 1.00 | 16.27 | C |
| ATOM | 7736 | CD | ARG | A | 506 | −55.586 | 27.090 | 1.726 | 1.00 | 15.26 | C |
| ATOM | 7739 | NE | ARG | A | 506 | −55.240 | 28.436 | 1.273 | 1.00 | 15.31 | N |
| ATOM | 7741 | CZ | ARG | A | 506 | −54.744 | 28.758 | .082 | 1.00 | 14.28 | C |
| ATOM | 7742 | NH1 | ARG | A | 506 | −54.519 | 27.856 | −.856 | 1.00 | 14.12 | N |
| ATOM | 7745 | NH2 | ARG | A | 506 | −54.471 | 30.018 | −.176 | 1.00 | 15.94 | N |
| ATOM | 7748 | C | ARG | A | 506 | −54.732 | 23.631 | 5.122 | 1.00 | 16.96 | C |
| ATOM | 7749 | O | ARG | A | 506 | −55.480 | 23.707 | 6.089 | 1.00 | 16.71 | O |
| ATOM | 7751 | N | GLN | A | 507 | −54.415 | 22.481 | 4.542 | 1.00 | 17.37 | N |
| ATOM | 7752 | CA | GLN | A | 507 | −54.962 | 21.233 | 5.048 | 1.00 | 17.87 | C |
| ATOM | 7754 | CB | GLN | A | 507 | −54.712 | 20.075 | 4.087 | 1.00 | 17.80 | C |
| ATOM | 7757 | CG | GLN | A | 507 | −55.293 | 18.740 | 4.571 | 1.00 | 17.24 | C |
| ATOM | 7760 | CD | GLN | A | 507 | −56.777 | 18.805 | 4.860 | 1.00 | 16.23 | C |
| ATOM | 7761 | OE1 | GLN | A | 507 | −57.506 | 19.585 | 4.250 | 1.00 | 16.66 | O |
| ATOM | 7762 | NE2 | GLN | A | 507 | −57.233 | 17.980 | 5.790 | 1.00 | 14.96 | N |

TABLE 16-7-continued

Coordinates of *P. tremuloides* IspS

| ATOM | 7765 | C | GLN | A | 507 | −54.401 | 20.890 | 6.423 | 1.00 | 18.28 | C |
|---|---|---|---|---|---|---|---|---|---|---|---|
| ATOM | 7766 | O | GLN | A | 507 | −55.148 | 20.419 | 7.287 | 1.00 | 18.53 | O |
| ATOM | 7768 | N | SER | A | 508 | −53.096 | 21.113 | 6.609 | 1.00 | 18.50 | N |
| ATOM | 7769 | CA | SER | A | 508 | −52.435 | 20.924 | 7.908 | 1.00 | 18.54 | C |
| ATOM | 7771 | CB | SER | A | 508 | −50.979 | 21.385 | 7.856 | 1.00 | 18.40 | C |
| ATOM | 7774 | OG | SER | A | 508 | −50.259 | 20.694 | 6.857 | 1.00 | 18.51 | O |
| ATOM | 7776 | C | SER | A | 508 | −53.147 | 21.752 | 8.942 | 1.00 | 18.78 | C |
| ATOM | 7777 | O | SER | A | 508 | −53.535 | 21.278 | 10.006 | 1.00 | 18.33 | O |
| ATOM | 7779 | N | HIS | A | 509 | −53.324 | 23.014 | 8.599 | 1.00 | 19.37 | N |
| ATOM | 7780 | CA | HIS | A | 509 | −54.014 | 23.922 | 9.466 | 1.00 | 19.92 | C |
| ATOM | 7782 | CB | HIS | A | 509 | −54.126 | 25.295 | 8.818 | 1.00 | 20.07 | C |
| ATOM | 7785 | CG | HIS | A | 509 | −53.000 | 26.188 | 9.174 | 1.00 | 19.82 | C |
| ATOM | 7786 | ND1 | HIS | A | 509 | −52.079 | 26.631 | 8.255 | 1.00 | 19.73 | N |
| ATOM | 7788 | CE1 | HIS | A | 509 | −51.187 | 27.383 | 8.866 | 1.00 | 20.25 | C |
| ATOM | 7790 | NE2 | HIS | A | 509 | −51.485 | 27.426 | 10.149 | 1.00 | 21.66 | N |
| ATOM | 7792 | CD2 | HIS | A | 509 | −52.615 | 26.682 | 10.368 | 1.00 | 20.98 | C |
| ATOM | 7794 | C | HIS | A | 509 | −55.389 | 23.448 | 9.839 | 1.00 | 20.41 | C |
| ATOM | 7795 | O | HIS | A | 509 | −55.821 | 23.694 | 10.934 | 1.00 | 20.22 | O |
| ATOM | 7797 | N | CYS | A | 510 | −56.093 | 22.808 | 8.918 | 1.00 | 21.33 | N |
| ATOM | 7798 | CA | CYS | A | 510 | −57.470 | 22.396 | 9.189 | 1.00 | 22.03 | C |
| ATOM | 7800 | CB | CYS | A | 510 | −58.278 | 22.383 | 7.894 | 1.00 | 21.90 | C |
| ATOM | 7803 | SG | CYS | A | 510 | −58.522 | 24.055 | 7.270 | 1.00 | 21.93 | 5 |
| ATOM | 7805 | C | CYS | A | 510 | −57.527 | 21.054 | 9.908 | 1.00 | 22.60 | C |
| ATOM | 7806 | O | CYS | A | 510 | −58.423 | 20.822 | 10.706 | 1.00 | 22.23 | O |
| ATOM | 7808 | N | THR | A | 511 | −56.553 | 20.194 | 9.627 | 1.00 | 23.67 | N |
| ATOM | 7809 | CA | THR | A | 511 | −56.421 | 18.920 | 10.305 | 1.00 | 24.81 | C |
| ATOM | 7811 | CB | THR | A | 511 | −55.437 | 18.000 | 9.565 | 1.00 | 24.70 | C |
| ATOM | 7813 | OG1 | THR | A | 511 | −56.071 | 17.485 | 8.394 | 1.00 | 24.45 | O |
| ATOM | 7815 | CG2 | THR | A | 511 | −55.003 | 16.844 | 10.448 | 1.00 | 24.23 | C |
| ATOM | 7819 | C | THR | A | 511 | −55.965 | 19.086 | 11.756 | 1.00 | 26.22 | C |
| ATOM | 7820 | O | THR | A | 511 | −56.685 | 18.717 | 12.679 | 1.00 | 26.12 | O |
| ATOM | 7822 | N | TYR | A | 512 | −54.775 | 19.643 | 11.959 | 1.00 | 28.08 | N |
| ATOM | 7823 | CA | TYR | A | 512 | −54.177 | 19.657 | 13.298 | 1.00 | 29.63 | C |
| ATOM | 7825 | CB | TYR | A | 512 | −52.663 | 19.783 | 13.238 | 1.00 | 29.67 | C |
| ATOM | 7828 | CG | TYR | A | 512 | −52.117 | 18.579 | 12.560 | 1.00 | 29.56 | C |
| ATOM | 7829 | CD1 | TYR | A | 512 | −51.965 | 17.395 | 13.246 | 1.00 | 29.66 | C |
| ATOM | 7831 | CE1 | TYR | A | 512 | −51.507 | 16.273 | 12.614 | 1.00 | 30.94 | C |
| ATOM | 7833 | CZ | TYR | A | 512 | −51.217 | 16.326 | 11.263 | 1.00 | 32.04 | C |
| ATOM | 7834 | OH | TYR | A | 512 | −50.757 | 15.209 | 10.608 | 1.00 | 33.78 | O |
| ATOM | 7836 | CE2 | TYR | A | 512 | −51.390 | 17.492 | 10.557 | 1.00 | 31.29 | C |
| ATOM | 7838 | CD2 | TYR | A | 512 | −51.847 | 18.600 | 11.205 | 1.00 | 30.53 | C |
| ATOM | 7840 | C | TYR | A | 512 | −54.812 | 20.676 | 14.206 | 1.00 | 31.11 | C |
| ATOM | 7841 | O | TYR | A | 512 | −55.494 | 20.277 | 15.139 | 1.00 | 31.34 | O |
| ATOM | 7843 | N | HIS | A | 513 | −54.583 | 21.969 | 13.966 | 1.00 | 32.89 | N |
| ATOM | 7844 | CA | HIS | A | 513 | −55.505 | 23.023 | 14.442 | 1.00 | 34.48 | C |
| ATOM | 7846 | CB | HIS | A | 513 | −56.372 | 23.461 | 13.225 | 1.00 | 35.13 | C |
| ATOM | 7849 | CG | HIS | A | 513 | −57.704 | 24.108 | 13.529 | 1.00 | 37.10 | C |
| ATOM | 7850 | ND1 | HIS | A | 513 | −58.265 | 25.040 | 12.678 | 1.00 | 38.69 | N |
| ATOM | 7852 | CE1 | HIS | A | 513 | −59.442 | 25.416 | 13.151 | 1.00 | 39.23 | C |
| ATOM | 7854 | NE2 | HIS | A | 513 | −59.678 | 24.751 | 14.268 | 1.00 | 38.18 | N |
| ATOM | 7856 | CD2 | HIS | A | 513 | −58.615 | 23.915 | 14.519 | 1.00 | 38.17 | C |
| ATOM | 7858 | C | HIS | A | 513 | −56.337 | 22.503 | 15.610 | 1.00 | 35.00 | C |
| ATOM | 7859 | O | HIS | A | 513 | −56.302 | 23.074 | 16.712 | 1.00 | 35.48 | O |
| ATOM | 7861 | N | ASN | A | 514 | −57.079 | 21.419 | 15.351 | 1.00 | 35.23 | N |
| ATOM | 7862 | CA | ASN | A | 514 | −57.934 | 20.768 | 16.347 | 1.00 | 35.46 | C |
| ATOM | 7864 | CB | ASN | A | 514 | −58.342 | 19.343 | 15.903 | 1.00 | 35.39 | C |
| ATOM | 7867 | CG | ASN | A | 514 | −59.383 | 19.345 | 14.786 | 1.00 | 34.01 | C |
| ATOM | 7868 | OD1 | ASN | A | 514 | −59.336 | 20.185 | 13.896 | 1.00 | 33.36 | O |
| ATOM | 7869 | ND2 | ASN | A | 514 | −60.315 | 18.406 | 14.833 | 1.00 | 31.13 | N |
| ATOM | 7872 | C | ASN | A | 514 | −57.464 | 20.751 | 17.818 | 1.00 | 36.15 | C |
| ATOM | 7873 | O | ASN | A | 514 | −56.397 | 20.211 | 18.153 | 1.00 | 36.13 | O |
| ATOM | 7875 | N | GLY | A | 515 | −58.277 | 21.430 | 18.640 | 1.00 | 36.95 | N |
| ATOM | 7876 | CA | GLY | A | 515 | −58.427 | 21.235 | 20.079 | 1.00 | 37.43 | C |
| ATOM | 7879 | C | GLY | A | 515 | −59.724 | 20.470 | 20.381 | 1.00 | 38.18 | C |
| ATOM | 7880 | O | GLY | A | 515 | −59.636 | 19.418 | 21.021 | 1.00 | 38.57 | O |
| ATOM | 7882 | N | ASP | A | 516 | −60.930 | 20.921 | 19.969 | 1.00 | 38.73 | N |
| ATOM | 7883 | CA | ASP | A | 516 | −61.249 | 22.194 | 19.293 | 1.00 | 39.26 | C |
| ATOM | 7885 | CB | ASP | A | 516 | −61.607 | 21.904 | 17.845 | 1.00 | 39.51 | C |
| ATOM | 7888 | CG | ASP | A | 516 | −60.523 | 22.291 | 16.894 | 1.00 | 42.32 | C |
| ATOM | 7889 | OD1 | ASP | A | 516 | −59.613 | 23.084 | 17.286 | 1.00 | 45.56 | O |
| ATOM | 7890 | OD2 | ASP | A | 516 | −60.578 | 21.797 | 15.740 | 1.00 | 45.52 | O |
| ATOM | 7891 | C | ASP | A | 516 | −62.466 | 22.913 | 19.884 | 1.00 | 39.38 | C |
| ATOM | 7892 | O | ASP | A | 516 | −63.032 | 22.454 | 20.880 | 1.00 | 39.74 | O |
| ATOM | 7894 | N | ALA | A | 517 | −62.850 | 24.038 | 19.259 | 1.00 | 39.40 | N |
| ATOM | 7895 | CA | ALA | A | 517 | −64.140 | 24.752 | 19.481 | 1.00 | 39.50 | C |
| ATOM | 7897 | CB | ALA | A | 517 | −65.117 | 24.403 | 18.333 | 1.00 | 39.27 | C |
| ATOM | 7901 | C | ALA | A | 517 | −64.837 | 24.566 | 20.863 | 1.00 | 39.90 | C |
| ATOM | 7902 | O | ALA | A | 517 | −64.173 | 24.428 | 21.899 | 1.00 | 39.89 | O |

TABLE 16-7-continued

Coordinates of *P. tremuloides* IspS

| ATOM | 7904 | N | HIS | A | 518 | −66.175 | 24.617 | 20.876 | 1.00 | 40.33 | N |
|---|---|---|---|---|---|---|---|---|---|---|---|
| ATOM | 7905 | CA | HIS | A | 518 | −66.973 | 24.112 | 22.016 | 1.00 | 40.73 | C |
| ATOM | 7907 | CB | HIS | A | 518 | −68.091 | 25.092 | 22.396 | 1.00 | 41.22 | C |
| ATOM | 7910 | CG | HIS | A | 518 | −67.578 | 26.419 | 22.866 | 1.00 | 43.58 | C |
| ATOM | 7911 | ND1 | HIS | A | 518 | −67.426 | 26.725 | 24.207 | 1.00 | 45.88 | N |
| ATOM | 7913 | CE1 | HIS | A | 518 | −66.938 | 27.950 | 24.320 | 1.00 | 46.42 | C |
| ATOM | 7915 | NE2 | HIS | A | 518 | −66.760 | 28.446 | 23.102 | 1.00 | 46.25 | N |
| ATOM | 7917 | CD2 | HIS | A | 518 | −67.145 | 27.506 | 22.174 | 1.00 | 45.24 | C |
| ATOM | 7919 | C | HIS | A | 518 | −67.526 | 22.725 | 21.655 | 1.00 | 40.17 | C |
| ATOM | 7920 | O | HIS | A | 518 | −68.738 | 22.501 | 21.571 | 1.00 | 40.02 | O |
| ATOM | 7922 | N | THR | A | 519 | −66.581 | 21.812 | 21.448 | 1.00 | 39.64 | N |
| ATOM | 7923 | CA | THR | A | 519 | −66.808 | 20.466 | 20.918 | 1.00 | 39.16 | C |
| ATOM | 7925 | CB | THR | A | 519 | −67.414 | 20.469 | 19.453 | 1.00 | 39.16 | C |
| ATOM | 7927 | OG1 | THR | A | 519 | −66.847 | 21.529 | 18.665 | 1.00 | 39.04 | O |
| ATOM | 7929 | CG2 | THR | A | 519 | −68.942 | 20.633 | 19.480 | 1.00 | 38.82 | C |
| ATOM | 7933 | C | THR | A | 519 | −65.428 | 19.771 | 20.978 | 1.00 | 38.85 | C |
| ATOM | 7934 | O | THR | A | 519 | −64.391 | 20.433 | 20.878 | 1.00 | 38.66 | O |
| ATOM | 7936 | N | SER | A | 520 | −65.407 | 18.455 | 21.170 | 1.00 | 38.37 | N |
| ATOM | 7937 | CA | SER | A | 520 | −64.160 | 17.745 | 21.500 | 1.00 | 38.08 | C |
| ATOM | 7939 | CB | SER | A | 520 | −64.514 | 16.320 | 21.931 | 1.00 | 38.06 | C |
| ATOM | 7942 | OG | SER | A | 520 | −64.560 | 15.475 | 20.805 | 1.00 | 38.66 | O |
| ATOM | 7944 | C | SER | A | 520 | −63.136 | 17.771 | 20.327 | 1.00 | 37.86 | C |
| ATOM | 7945 | O | SER | A | 520 | −63.420 | 18.369 | 19.289 | 1.00 | 37.50 | O |
| ATOM | 7947 | N | PRO | A | 521 | −61.948 | 17.122 | 20.482 | 1.00 | 37.98 | N |
| ATOM | 7948 | CA | PRO | A | 521 | −60.944 | 17.170 | 19.379 | 1.00 | 37.92 | C |
| ATOM | 7950 | CB | PRO | A | 521 | −59.674 | 16.527 | 19.987 | 1.00 | 37.87 | C |
| ATOM | 7953 | CG | PRO | A | 521 | −60.091 | 15.919 | 21.330 | 1.00 | 38.28 | C |
| ATOM | 7956 | CD | PRO | A | 521 | −61.577 | 16.137 | 21.526 | 1.00 | 38.13 | C |
| ATOM | 7959 | C | PRO | A | 521 | −61.432 | 16.446 | 18.110 | 1.00 | 37.96 | C |
| ATOM | 7960 | O | PRO | A | 521 | −61.769 | 17.118 | 17.140 | 1.00 | 38.09 | O |
| ATOM | 7961 | N | ASP | A | 522 | −61.483 | 15.108 | 18.107 | 1.00 | 38.07 | N |
| ATOM | 7962 | CA | ASP | A | 522 | −62.351 | 14.393 | 17.161 | 1.00 | 38.14 | C |
| ATOM | 7964 | CB | ASP | A | 522 | −62.132 | 12.877 | 17.204 | 1.00 | 38.31 | C |
| ATOM | 7967 | CG | ASP | A | 522 | −60.769 | 12.456 | 16.640 | 1.00 | 39.45 | C |
| ATOM | 7968 | OD1 | ASP | A | 522 | −60.160 | 13.200 | 15.827 | 1.00 | 39.72 | O |
| ATOM | 7969 | OD2 | ASP | A | 522 | −60.302 | 11.361 | 17.025 | 1.00 | 41.59 | O |
| ATOM | 7970 | C | ASP | A | 522 | −63.760 | 14.780 | 17.591 | 1.00 | 37.92 | C |
| ATOM | 7971 | O | ASP | A | 522 | −63.908 | 15.608 | 18.474 | 1.00 | 38.01 | O |
| ATOM | 7973 | N | GLU | A | 523 | −64.799 | 14.239 | 16.974 | 1.00 | 37.79 | N |
| ATOM | 7974 | CA | GLU | A | 523 | −66.150 | 14.818 | 17.121 | 1.00 | 37.83 | C |
| ATOM | 7976 | CB | GLU | A | 523 | −66.618 | 14.919 | 18.591 | 1.00 | 37.85 | C |
| ATOM | 7979 | CG | GLU | A | 523 | −66.346 | 13.678 | 19.483 | 1.00 | 39.40 | C |
| ATOM | 7982 | CD | GLU | A | 523 | −66.916 | 13.802 | 20.931 | 1.00 | 41.49 | C |
| ATOM | 7983 | OE1 | GLU | A | 523 | −67.714 | 14.737 | 21.207 | 1.00 | 42.81 | O |
| ATOM | 7984 | OE2 | GLU | A | 523 | −66.566 | 12.957 | 21.800 | 1.00 | 42.04 | O |
| ATOM | 7985 | C | GLU | A | 523 | −66.242 | 16.203 | 16.430 | 1.00 | 37.51 | C |
| ATOM | 7986 | O | GLU | A | 523 | −67.338 | 16.751 | 16.283 | 1.00 | 37.70 | O |
| ATOM | 7988 | N | LEU | A | 524 | −65.097 | 16.775 | 16.043 | 1.00 | 37.03 | N |
| ATOM | 7989 | CA | LEU | A | 524 | −65.044 | 17.863 | 15.067 | 1.00 | 36.58 | C |
| ATOM | 7991 | CB | LEU | A | 524 | −64.174 | 19.022 | 15.559 | 1.00 | 36.56 | C |
| ATOM | 7994 | CG | LEU | A | 524 | −63.963 | 20.225 | 14.624 | 1.00 | 36.35 | C |
| ATOM | 7996 | CD1 | LEU | A | 524 | −63.400 | 21.376 | 15.418 | 1.00 | 35.74 | C |
| ATOM | 8000 | CD2 | LEU | A | 524 | −65.242 | 20.681 | 13.910 | 1.00 | 36.53 | C |
| ATOM | 8004 | C | LEU | A | 524 | −64.478 | 17.287 | 13.782 | 1.00 | 36.20 | C |
| ATOM | 8005 | O | LEU | A | 524 | −65.106 | 17.363 | 12.733 | 1.00 | 36.14 | O |
| ATOM | 8007 | N | THR | A | 525 | −63.298 | 16.686 | 13.869 | 1.00 | 35.83 | N |
| ATOM | 8008 | CA | THR | A | 525 | −62.756 | 15.935 | 12.748 | 1.00 | 35.66 | C |
| ATOM | 8010 | CB | THR | A | 525 | −61.585 | 15.015 | 13.173 | 1.00 | 35.48 | C |
| ATOM | 8012 | OG1 | THR | A | 525 | −60.776 | 15.678 | 14.152 | 1.00 | 35.55 | O |
| ATOM | 8014 | CG2 | THR | A | 525 | −60.720 | 14.641 | 11.978 | 1.00 | 34.73 | C |
| ATOM | 8018 | C | THR | A | 525 | −63.875 | 15.098 | 12.123 | 1.00 | 35.89 | C |
| ATOM | 8019 | O | THR | A | 525 | −64.040 | 15.095 | 10.909 | 1.00 | 35.98 | O |
| ATOM | 8021 | N | ARG | A | 526 | −64.667 | 14.420 | 12.954 | 1.00 | 36.06 | N |
| ATOM | 8022 | CA | ARG | A | 526 | −65.739 | 13.574 | 12.448 | 1.00 | 36.18 | C |
| ATOM | 8024 | CB | ARG | A | 526 | −66.340 | 12.718 | 13.555 | 1.00 | 36.56 | C |
| ATOM | 8027 | CG | ARG | A | 526 | −67.416 | 11.754 | 13.054 | 1.00 | 38.35 | C |
| ATOM | 8030 | CD | ARG | A | 526 | −67.781 | 10.702 | 14.092 | 1.00 | 41.00 | C |
| ATOM | 8033 | NE | ARG | A | 526 | −67.740 | 11.207 | 15.470 | 1.00 | 43.08 | N |
| ATOM | 8035 | CZ | ARG | A | 526 | −68.637 | 12.033 | 16.024 | 1.00 | 44.51 | C |
| ATOM | 8036 | NH1 | ARG | A | 526 | −69.681 | 12.500 | 15.336 | 1.00 | 44.46 | N |
| ATOM | 8039 | NH2 | ARG | A | 526 | −68.476 | 12.406 | 17.288 | 1.00 | 45.02 | N |
| ATOM | 8042 | C | ARG | A | 526 | −66.834 | 14.384 | 11.774 | 1.00 | 35.68 | C |
| ATOM | 8043 | O | ARG | A | 526 | −67.253 | 14.035 | 10.675 | 1.00 | 35.84 | O |
| ATOM | 8045 | N | LYS | A | 527 | −67.309 | 15.447 | 12.424 | 1.00 | 35.06 | N |
| ATOM | 8046 | CA | LYS | A | 527 | −68.285 | 16.343 | 11.780 | 1.00 | 34.61 | C |
| ATOM | 8048 | CB | LYS | A | 527 | −68.680 | 17.528 | 12.683 | 1.00 | 34.74 | C |
| ATOM | 8051 | CG | LYS | A | 527 | −69.818 | 17.225 | 13.651 | 1.00 | 35.40 | C |
| ATOM | 8054 | CD | LYS | A | 527 | −70.301 | 18.452 | 14.441 | 1.00 | 35.99 | C |

TABLE 16-7-continued

Coordinates of *P. tremuloides* IspS

| ATOM | 8057 | CE | LYS | A | 527 | −71.280 | 18.021 | 15.556 | 1.00 | 36.42 | C |
|---|---|---|---|---|---|---|---|---|---|---|---|
| ATOM | 8060 | NZ | LYS | A | 527 | −71.652 | 19.095 | 16.530 | 1.00 | 36.31 | N |
| ATOM | 8064 | C | LYS | A | 527 | −67.723 | 16.860 | 10.457 | 1.00 | 33.77 | C |
| ATOM | 8065 | O | LYS | A | 527 | −68.377 | 16.763 | 9.423 | 1.00 | 33.75 | O |
| ATOM | 8067 | N | ARG | A | 528 | −66.501 | 17.388 | 10.499 | 1.00 | 32.71 | N |
| ATOM | 8068 | CA | ARG | A | 528 | −65.840 | 17.929 | 9.310 | 1.00 | 31.79 | C |
| ATOM | 8070 | CB | ARG | A | 528 | −64.425 | 18.464 | 9.644 | 1.00 | 31.74 | C |
| ATOM | 8073 | CG | ARG | A | 528 | −64.419 | 19.844 | 10.330 | 1.00 | 30.90 | C |
| ATOM | 8076 | CD | ARG | A | 528 | −63.021 | 20.439 | 10.527 | 1.00 | 29.75 | C |
| ATOM | 8079 | NE | ARG | A | 528 | −63.098 | 21.745 | 11.190 | 1.00 | 29.55 | N |
| ATOM | 8081 | CZ | ARG | A | 528 | −62.056 | 22.513 | 11.528 | 1.00 | 29.96 | C |
| ATOM | 8082 | NH1 | ARG | A | 528 | −60.801 | 22.145 | 11.284 | 1.00 | 29.74 | N |
| ATOM | 8085 | NH2 | ARG | A | 528 | −62.269 | 23.677 | 12.130 | 1.00 | 30.71 | N |
| ATOM | 8088 | C | ARG | A | 528 | −65.796 | 16.904 | 8.172 | 1.00 | 30.99 | C |
| ATOM | 8089 | O | ARG | A | 528 | −66.226 | 17.206 | 7.068 | 1.00 | 30.97 | O |
| ATOM | 8091 | N | VAL | A | 529 | −65.313 | 15.694 | 8.450 | 1.00 | 30.12 | N |
| ATOM | 8092 | CA | VAL | A | 529 | −65.239 | 14.631 | 7.438 | 1.00 | 29.43 | C |
| ATOM | 8094 | CB | VAL | A | 529 | −64.557 | 13.354 | 7.972 | 1.00 | 29.39 | C |
| ATOM | 8096 | CG1 | VAL | A | 529 | −64.785 | 12.187 | 7.023 | 1.00 | 28.89 | C |
| ATOM | 8100 | CG2 | VAL | A | 529 | −63.062 | 13.589 | 8.186 | 1.00 | 29.44 | C |
| ATOM | 8104 | C | VAL | A | 529 | −66.609 | 14.243 | 6.887 | 1.00 | 28.95 | C |
| ATOM | 8105 | O | VAL | A | 529 | −66.755 | 14.016 | 5.690 | 1.00 | 29.09 | O |
| ATOM | 8107 | N | LEU | A | 530 | −67.615 | 14.153 | 7.744 | 1.00 | 28.18 | N |
| ATOM | 8108 | CA | LEU | A | 530 | −68.956 | 13.874 | 7.246 | 1.00 | 27.72 | C |
| ATOM | 8110 | CB | LEU | A | 530 | −69.971 | 13.715 | 8.395 | 1.00 | 27.75 | C |
| ATOM | 8113 | CG | LEU | A | 530 | −70.334 | 12.274 | 8.775 | 1.00 | 27.36 | C |
| ATOM | 8115 | CD1 | LEU | A | 530 | −69.096 | 11.415 | 9.050 | 1.00 | 26.86 | C |
| ATOM | 8119 | CD2 | LEU | A | 530 | −71.273 | 12.279 | 9.968 | 1.00 | 27.14 | C |
| ATOM | 8123 | C | LEU | A | 530 | −69.401 | 14.963 | 6.256 | 1.00 | 27.16 | C |
| ATOM | 8124 | O | LEU | A | 530 | −69.861 | 14.652 | 5.161 | 1.00 | 27.42 | O |
| ATOM | 8126 | N | SER | A | 531 | −69.230 | 16.229 | 6.635 | 1.00 | 26.21 | N |
| ATOM | 8127 | CA | SER | A | 531 | −69.730 | 17.359 | 5.853 | 1.00 | 25.12 | C |
| ATOM | 8129 | CB | SER | A | 531 | −69.519 | 18.657 | 6.618 | 1.00 | 25.01 | C |
| ATOM | 8132 | OG | SER | A | 531 | −68.167 | 18.791 | 6.985 | 1.00 | 23.94 | O |
| ATOM | 8134 | C | SER | A | 531 | −69.055 | 17.476 | 4.507 | 1.00 | 24.48 | C |
| ATOM | 8135 | O | SER | A | 531 | −69.687 | 17.886 | 3.538 | 1.00 | 24.14 | O |
| ATOM | 8137 | N | VAL | A | 532 | −67.774 | 17.115 | 4.461 | 1.00 | 23.89 | N |
| ATOM | 8138 | CA | VAL | A | 532 | −66.962 | 17.226 | 3.246 | 1.00 | 23.53 | C |
| ATOM | 8140 | CB | VAL | A | 532 | −65.470 | 17.437 | 3.575 | 1.00 | 23.09 | C |
| ATOM | 8142 | CG1 | VAL | A | 532 | −64.633 | 17.355 | 2.348 | 1.00 | 22.32 | C |
| ATOM | 8146 | CG2 | VAL | A | 532 | −65.268 | 18.773 | 4.198 | 1.00 | 23.07 | C |
| ATOM | 8150 | C | VAL | A | 532 | −67.100 | 16.028 | 2.316 | 1.00 | 23.67 | C |
| ATOM | 8151 | O | VAL | A | 532 | −67.137 | 16.209 | 1.099 | 1.00 | 23.58 | O |
| ATOM | 8153 | N | ILE | A | 533 | −67.187 | 14.824 | 2.886 | 1.00 | 23.85 | N |
| ATOM | 8154 | CA | ILE | A | 533 | −67.172 | 13.578 | 2.107 | 1.00 | 24.08 | C |
| ATOM | 8156 | CB | ILE | A | 533 | −66.172 | 12.555 | 2.691 | 1.00 | 24.10 | C |
| ATOM | 8158 | CG1 | ILE | A | 533 | −64.745 | 13.079 | 2.631 | 1.00 | 23.47 | C |
| ATOM | 8161 | CD1 | ILE | A | 533 | −64.178 | 13.083 | 1.255 | 1.00 | 23.42 | C |
| ATOM | 8165 | CG2 | ILE | A | 533 | −66.254 | 11.231 | 1.932 | 1.00 | 24.56 | C |
| ATOM | 8169 | C | ILE | A | 533 | −68.522 | 12.859 | 1.990 | 1.00 | 24.27 | C |
| ATOM | 8170 | O | ILE | A | 533 | −68.991 | 12.620 | .887 | 1.00 | 24.34 | O |
| ATOM | 8172 | N | THR | A | 534 | −69.133 | 12.487 | 3.111 | 1.00 | 24.57 | N |
| ATOM | 8173 | CA | THR | A | 534 | −70.279 | 11.564 | 3.072 | 1.00 | 24.92 | C |
| ATOM | 8175 | CB | THR | A | 534 | −70.200 | 10.522 | 4.207 | 1.00 | 24.93 | C |
| ATOM | 8177 | OG1 | THR | A | 534 | −70.491 | 11.149 | 5.458 | 1.00 | 25.28 | O |
| ATOM | 8179 | CG2 | THR | A | 534 | −68.804 | 9.885 | 4.257 | 1.00 | 24.75 | C |
| ATOM | 8183 | C | THR | A | 534 | −71.673 | 12.209 | 3.083 | 1.00 | 25.00 | C |
| ATOM | 8184 | O | THR | A | 534 | −72.601 | 11.646 | 2.522 | 1.00 | 24.94 | O |
| ATOM | 8186 | N | GLU | A | 535 | −71.821 | 13.374 | 3.708 | 1.00 | 25.26 | N |
| ATOM | 8187 | CA | GLU | A | 535 | −73.132 | 14.024 | 3.833 | 1.00 | 25.34 | C |
| ATOM | 8189 | CB | GLU | A | 535 | −73.333 | 14.523 | 5.255 | 1.00 | 25.44 | C |
| ATOM | 8192 | CG | GLU | A | 535 | −73.753 | 13.424 | 6.196 | 1.00 | 25.80 | C |
| ATOM | 8195 | CD | GLU | A | 535 | −74.307 | 13.963 | 7.468 | 1.00 | 25.72 | C |
| ATOM | 8196 | OE1 | GLU | A | 535 | −75.375 | 13.487 | 7.881 | 1.00 | 24.50 | O |
| ATOM | 8197 | OE2 | GLU | A | 535 | −73.678 | 14.877 | 8.039 | 1.00 | 27.03 | O |
| ATOM | 8198 | C | GLU | A | 535 | −73.363 | 15.179 | 2.859 | 1.00 | 25.26 | C |
| ATOM | 8199 | O | GLU | A | 535 | −72.686 | 16.206 | 2.939 | 1.00 | 25.02 | O |
| ATOM | 8201 | N | PRO | A | 536 | −74.351 | 15.030 | 1.959 | 1.00 | 25.25 | N |
| ATOM | 8202 | CA | PRO | A | 536 | −74.655 | 16.111 | 1.050 | 1.00 | 25.18 | C |
| ATOM | 8204 | CB | PRO | A | 536 | −75.661 | 15.484 | .076 | 1.00 | 25.15 | C |
| ATOM | 8207 | CG | PRO | A | 536 | −75.825 | 14.077 | .476 | 1.00 | 24.98 | C |
| ATOM | 8210 | CD | PRO | A | 536 | −75.363 | 13.965 | 1.868 | 1.00 | 25.26 | C |
| ATOM | 8213 | C | PRO | A | 536 | −75.289 | 17.265 | 1.801 | 1.00 | 25.30 | C |
| ATOM | 8214 | O | PRO | A | 536 | −75.826 | 17.070 | 2.883 | 1.00 | 25.57 | O |
| ATOM | 8215 | N | ILE | A | 537 | −75.213 | 18.458 | 1.230 | 1.00 | 25.36 | N |
| ATOM | 8216 | CA | ILE | A | 537 | −75.807 | 19.638 | 1.827 | 1.00 | 25.34 | C |
| ATOM | 8218 | CB | ILE | A | 537 | −75.201 | 20.918 | 1.221 | 1.00 | 25.14 | C |
| ATOM | 8220 | CG1 | ILE | A | 537 | −73.787 | 21.131 | 1.744 | 1.00 | 24.32 | C |

TABLE 16-7-continued

Coordinates of *P. tremuloides* IspS

| ATOM | 8223 | CD1 | ILE | A | 537 | −73.228 | 22.472 | 1.406 | 1.00 | 23.22 | C |
|---|---|---|---|---|---|---|---|---|---|---|---|
| ATOM | 8227 | CG2 | ILE | A | 537 | −76.030 | 22.131 | 1.569 | 1.00 | 25.54 | C |
| ATOM | 8231 | C | ILE | A | 537 | −77.313 | 19.603 | 1.611 | 1.00 | 25.67 | C |
| ATOM | 8232 | O | ILE | A | 537 | −77.786 | 19.132 | .579 | 1.00 | 25.47 | O |
| ATOM | 8234 | N | LEU | A | 538 | −78.071 | 20.088 | 2.586 | 1.00 | 26.22 | N |
| ATOM | 8235 | CA | LEU | A | 538 | −79.514 | 20.051 | 2.467 | 1.00 | 26.65 | C |
| ATOM | 8237 | CB | LEU | A | 538 | −80.213 | 20.525 | 3.749 | 1.00 | 26.78 | C |
| ATOM | 8240 | CG | LEU | A | 538 | −80.162 | 19.609 | 4.989 | 1.00 | 26.64 | C |
| ATOM | 8242 | CD1 | LEU | A | 538 | −81.218 | 20.033 | 6.007 | 1.00 | 26.16 | C |
| ATOM | 8246 | CD2 | LEU | A | 538 | −80.346 | 18.138 | 4.633 | 1.00 | 26.12 | C |
| ATOM | 8250 | C | LEU | A | 538 | −79.925 | 20.881 | 1.262 | 1.00 | 27.08 | C |
| ATOM | 8253 | N | PRO | A | 539 | −80.786 | 20.306 | .414 | 1.00 | 28.03 | N |
| ATOM | 8254 | CA | PRO | A | 539 | −81.117 | 20.855 | −.888 | 1.00 | 28.44 | C |
| ATOM | 8256 | CB | PRO | A | 539 | −82.093 | 19.828 | −1.449 | 1.00 | 28.40 | C |
| ATOM | 8259 | CG | PR0 | A | 539 | −82.793 | 19.328 | −.253 | 1.00 | 28.30 | C |
| ATOM | 8262 | CD | PRO | A | 539 | −81.720 | 19.228 | .787 | 1.00 | 28.11 | C |
| ATOM | 8265 | C | PRO | A | 539 | −81.813 | 22.194 | −.804 | 1.00 | 28.89 | C |
| ATOM | 8266 | O | PRO | A | 539 | −82.396 | 22.535 | .226 | 1.00 | 28.97 | O |
| ATOM | 8267 | N | PHE | A | 540 | −81.774 | 22.932 | −1.906 | 1.00 | 29.32 | N |
| ATOM | 8268 | CA | PHE | A | 540 | −82.380 | 24.245 | −1.962 | 1.00 | 29.50 | C |
| ATOM | 8270 | CB | PHE | A | 540 | −82.146 | 24.874 | −3.326 | 1.00 | 29.56 | C |
| ATOM | 8273 | CG | PHE | A | 540 | −82.757 | 26.227 | −3.463 | 1.00 | 29.75 | C |
| ATOM | 8274 | CD1 | PHE | A | 540 | −83.874 | 26.429 | −4.255 | 1.00 | 29.47 | C |
| ATOM | 8276 | CE1 | PHE | A | 540 | −84.441 | 27.681 | −4.364 | 1.00 | 29.46 | C |
| ATOM | 8278 | CZ | PHE | A | 540 | −83.901 | 28.743 | −3.674 | 1.00 | 29.81 | C |
| ATOM | 8280 | CE2 | PHE | A | 540 | −82.791 | 28.553 | −2.877 | 1.00 | 30.21 | C |
| ATOM | 8282 | CD2 | PHE | A | 540 | −82.229 | 27.300 | −2.770 | 1.00 | 30.17 | C |
| ATOM | 8284 | C | PHE | A | 540 | −83.865 | 24.129 | −1.722 | 1.00 | 29.66 | C |
| ATOM | 8285 | O | PHE | A | 540 | −84.568 | 23.551 | −2.545 | 1.00 | 29.66 | O |
| ATOM | 8287 | N | GLU | A | 541 | −84.337 | 24.673 | −.601 | 1.00 | 29.90 | N |
| ATOM | 8288 | CA | GLU | A | 541 | −85.761 | 24.605 | −.233 | 1.00 | 30.06 | C |
| ATOM | 8290 | CB | GLU | A | 541 | −85.951 | 23.724 | 1.017 | 1.00 | 30.15 | C |
| ATOM | 8293 | CG | GLU | A | 541 | −87.411 | 23.361 | 1.367 | 1.00 | 30.64 | C |
| ATOM | 8296 | CD | GLU | A | 541 | −88.091 | 24.351 | 2.322 | 1.00 | 31.35 | C |
| ATOM | 8297 | OE1 | GLU | A | 541 | −87.468 | 25.370 | 2.680 | 1.00 | 32.67 | O |
| ATOM | 8298 | OE2 | GLU | A | 541 | −89.254 | 24.114 | 2.719 | 1.00 | 30.48 | O |
| ATOM | 8299 | C | GLU | A | 541 | −86.315 | 26.011 | −.010 | 1.00 | 29.89 | C |
| ATOM | 8300 | O | GLU | A | 541 | −86.835 | 26.636 | −.936 | 1.00 | 29.71 | O |
| ATOM | 8302 | N | LEU | B | 17 | −69.666 | −25.325 | 2.227 | 1.00 | 33.20 | N |
| ATOM | 8303 | CA | LEU | B | 17 | −69.356 | −25.417 | .755 | 1.00 | 33.49 | C |
| ATOM | 8305 | CB | LEU | B | 17 | −70.240 | −26.475 | .048 | 1.00 | 33.44 | C |
| ATOM | 8308 | CG | LEU | B | 17 | −70.077 | −27.986 | .328 | 1.00 | 33.60 | C |
| ATOM | 8310 | CD1 | LEU | B | 17 | −71.285 | −28.778 | −.217 | 1.00 | 32.76 | C |
| ATOM | 8314 | CD2 | LEU | B | 17 | −68.763 | −28.553 | −.230 | 1.00 | 33.21 | C |
| ATOM | 8318 | C | LEU | B | 17 | −69.513 | −24.044 | .055 | 1.00 | 33.54 | C |
| ATOM | 8319 | O | LEU | B | 17 | −70.550 | −23.380 | .195 | 1.00 | 33.77 | O |
| ATOM | 8323 | N | LEU | B | 18 | −68.481 | −23.637 | −.696 | 1.00 | 33.44 | N |
| ATOM | 8324 | CA | LEU | B | 18 | −68.476 | −22.362 | −1.454 | 1.00 | 33.07 | C |
| ATOM | 8326 | CB | LEU | B | 18 | −67.029 | −21.960 | −1.840 | 1.00 | 33.21 | C |
| ATOM | 8329 | CG | LEU | B | 18 | −66.065 | −21.488 | −.721 | 1.00 | 34.06 | C |
| ATOM | 8331 | CD1 | LEU | B | 18 | −64.607 | −21.351 | −1.235 | 1.00 | 34.51 | C |
| ATOM | 8335 | CD2 | LEU | B | 18 | −66.516 | −20.164 | −.061 | 1.00 | 33.43 | C |
| ATOM | 8339 | C | LEU | B | 18 | −69.379 | −22.400 | −2.714 | 1.00 | 32.37 | C |
| ATOM | 8340 | O | LEU | B | 18 | −69.710 | −21.355 | −3.274 | 1.00 | 32.29 | O |
| ATOM | 8342 | N | SER | B | 19 | −69.765 | −23.597 | −3.153 | 1.00 | 31.62 | N |
| ATOM | 8343 | CA | SER | B | 19 | −70.711 | −23.749 | −4.253 | 1.00 | 31.16 | C |
| ATOM | 8345 | CB | SER | B | 19 | −70.443 | −25.067 | −5.033 | 1.00 | 31.09 | C |
| ATOM | 8348 | OG | SER | B | 19 | −70.977 | −26.243 | −4.421 | 1.00 | 29.36 | O |
| ATOM | 8350 | C | SER | B | 19 | −72.168 | −23.663 | −3.759 | 1.00 | 31.45 | C |
| ATOM | 8351 | O | SER | B | 19 | −73.076 | −23.432 | −4.551 | 1.00 | 31.13 | O |
| ATOM | 8353 | N | SER | B | 20 | −72.386 | −23.824 | −2.451 | 1.00 | 31.91 | N |
| ATOM | 8354 | CA | SER | B | 20 | −73.749 | −23.900 | −1.879 | 1.00 | 32.34 | C |
| ATOM | 8356 | CB | SER | B | 20 | −73.706 | −24.122 | −.357 | 1.00 | 32.35 | C |
| ATOM | 8359 | OG | SER | B | 20 | −73.393 | −25.473 | −.055 | 1.00 | 32.34 | O |
| ATOM | 8361 | C | SER | B | 20 | −74.601 | −22.670 | −2.204 | 1.00 | 32.69 | C |
| ATOM | 8362 | O | SER | B | 20 | −74.072 | −21.600 | −2.487 | 1.00 | 32.89 | O |
| ATOM | 8364 | N | ASP | B | 21 | −75.921 | −22.831 | −2.119 | 1.00 | 33.13 | N |
| ATOM | 8365 | CA | ASP | B | 21 | −76.874 | −21.901 | −2.745 | 1.00 | 33.40 | C |
| ATOM | 8367 | CB | ASP | B | 21 | −78.179 | −22.628 | −3.045 | 1.00 | 33.64 | C |
| ATOM | 8370 | CG | ASP | B | 21 | −77.943 | −23.883 | −3.828 | 1.00 | 35.35 | C |
| ATOM | 8371 | OD1 | ASP | B | 21 | −77.031 | −23.866 | −4.684 | 1.00 | 38.26 | O |
| ATOM | 8372 | OD2 | ASP | B | 21 | −78.631 | −24.890 | −3.590 | 1.00 | 37.55 | O |
| ATOM | 8373 | C | ASP | B | 21 | −77.141 | −20.649 | −1.940 | 1.00 | 33.23 | C |
| ATOM | 8374 | O | ASP | B | 21 | −78.039 | −20.616 | −1.106 | 1.00 | 32.91 | O |
| ATOM | 8376 | N | THR | B | 22 | −76.348 | −19.621 | −2.229 | 1.00 | 33.46 | N |
| ATOM | 8377 | CA | THR | B | 22 | −76.443 | −18.307 | −1.593 | 1.00 | 33.79 | C |
| ATOM | 8379 | CB | THR | B | 22 | −76.460 | −18.378 | −.016 | 1.00 | 33.74 | C |
| ATOM | 8381 | OG1 | THR | B | 22 | −75.426 | −19.250 | .460 | 1.00 | 32.97 | O |

TABLE 16-7-continued

Coordinates of *P. tremuloides* IspS

| ATOM | 8383 | CG2 | THR | B | 22 | −77.805 | −18.838 | .535 | 1.00 | 33.55 | C |
|---|---|---|---|---|---|---|---|---|---|---|---|
| ATOM | 8387 | C | THR | B | 22 | −75.217 | −17.479 | −2.018 | 1.00 | 34.24 | C |
| ATOM | 8388 | O | THR | B | 22 | −74.102 | −17.988 | −1.892 | 1.00 | 33.95 | O |
| ATOM | 8390 | N | ASP | B | 23 | −75.361 | −16.248 | −2.543 | 1.00 | 34.99 | N |
| ATOM | 8391 | CA | ASP | B | 23 | −76.603 | −15.620 | −3.103 | 1.00 | 35.61 | C |
| ATOM | 8393 | CB | ASP | B | 23 | −77.242 | −16.538 | −4.170 | 1.00 | 35.51 | C |
| ATOM | 8396 | CG | ASP | B | 23 | −76.196 | −17.236 | −5.034 | 1.00 | 36.08 | C |
| ATOM | 8397 | OD1 | ASP | B | 23 | −75.084 | −16.685 | −5.194 | 1.00 | 35.58 | O |
| ATOM | 8398 | OD2 | ASP | B | 23 | −76.473 | −18.344 | −5.541 | 1.00 | 37.65 | O |
| ATOM | 8399 | C | ASP | B | 23 | −77.662 | −15.083 | −2.097 | 1.00 | 36.10 | C |
| ATOM | 8400 | O | ASP | B | 23 | −78.644 | −15.770 | −1.799 | 1.00 | 36.13 | O |
| ATOM | 8402 | N | GLU | B | 24 | −77.487 | −13.845 | −1.616 | 1.00 | 36.74 | N |
| ATOM | 8403 | CA | GLU | B | 24 | −78.358 | −13.316 | −.543 | 1.00 | 37.59 | C |
| ATOM | 8405 | CB | GLU | B | 24 | −77.765 | −13.666 | .838 | 1.00 | 37.88 | C |
| ATOM | 8408 | CG | GLU | B | 24 | −77.624 | −15.173 | 1.120 | 1.00 | 38.51 | C |
| ATOM | 8411 | CD | GLU | B | 24 | −77.314 | −15.510 | 2.588 | 1.00 | 39.48 | C |
| ATOM | 8412 | OE1 | GLU | B | 24 | −77.171 | −14.581 | 3.434 | 1.00 | 39.60 | O |
| ATOM | 8413 | OE2 | GLU | B | 24 | −77.221 | −16.725 | 2.884 | 1.00 | 39.51 | O |
| ATOM | 8414 | C | GLU | B | 24 | −78.730 | −11.809 | −.559 | 1.00 | 38.11 | C |
| ATOM | 8415 | O | GLU | B | 24 | −79.840 | −11.453 | −.972 | 1.00 | 38.20 | O |
| ATOM | 8417 | N | SER | B | 25 | −77.825 | −10.941 | −.089 | 1.00 | 38.70 | N |
| ATOM | 8418 | CA | SER | B | 25 | −78.192 | −9.560 | .312 | 1.00 | 39.21 | C |
| ATOM | 8420 | CB | SER | B | 25 | −76.995 | −8.783 | .916 | 1.00 | 39.29 | C |
| ATOM | 8423 | OG | SER | B | 25 | −76.267 | −8.037 | −.056 | 1.00 | 39.40 | O |
| ATOM | 8425 | C | SER | B | 25 | −78.853 | −8.738 | −.802 | 1.00 | 39.69 | C |
| ATOM | 8426 | O | SER | B | 25 | −78.707 | −9.050 | −1.995 | 1.00 | 39.75 | O |
| ATOM | 8428 | N | ILE | B | 26 | −79.544 | −7.670 | −.378 | 1.00 | 40.21 | N |
| ATOM | 8429 | CA | ILE | B | 26 | −80.554 | −6.962 | −1.189 | 1.00 | 40.55 | C |
| ATOM | 8431 | CB | ILE | B | 26 | −79.925 | −6.082 | −2.319 | 1.00 | 40.66 | C |
| ATOM | 8433 | CG1 | ILE | B | 26 | −79.083 | −4.951 | −1.700 | 1.00 | 40.73 | C |
| ATOM | 8436 | CD1 | ILE | B | 26 | −78.596 | −3.877 | −2.698 | 1.00 | 40.68 | C |
| ATOM | 8440 | CG2 | ILE | B | 26 | −81.018 | −5.475 | −3.203 | 1.00 | 40.88 | C |
| ATOM | 8444 | C | ILE | B | 26 | −81.575 | −7.999 | −1.714 | 1.00 | 40.72 | C |
| ATOM | 8445 | O | ILE | B | 26 | −81.311 | −8.710 | −2.690 | 1.00 | 40.80 | O |
| ATOM | 8447 | N | GLU | B | 27 | −82.729 | −8.070 | −1.037 | 1.00 | 40.86 | N |
| ATOM | 8448 | CA | GLU | B | 27 | −83.694 | −9.190 | −1.160 | 1.00 | 40.88 | C |
| ATOM | 8450 | CB | GLU | B | 27 | −84.782 | −9.060 | −.061 | 1.00 | 40.95 | C |
| ATOM | 8453 | CG | GLU | B | 27 | −84.235 | −9.257 | 1.379 | 1.00 | 41.28 | C |
| ATOM | 8456 | CD | GLU | B | 27 | −85.123 | −8.657 | 2.484 | 1.00 | 41.74 | C |
| ATOM | 8457 | OE1 | GLU | B | 27 | −85.593 | −7.504 | 2.344 | 1.00 | 41.14 | O |
| ATOM | 8458 | OE2 | GLU | B | 27 | −85.332 | −9.337 | 3.514 | 1.00 | 42.36 | O |
| ATOM | 8459 | C | GLU | B | 27 | −84.290 | −9.355 | −2.587 | 1.00 | 40.75 | C |
| ATOM | 8460 | O | GLU | B | 27 | −83.664 | −8.936 | −3.569 | 1.00 | 40.88 | O |
| ATOM | 8462 | N | VAL | B | 28 | −85.461 | −9.994 | −2.712 | 1.00 | 40.40 | N |
| ATOM | 8463 | CA | VAL | B | 28 | −86.033 | −10.361 | −4.027 | 1.00 | 39.97 | C |
| ATOM | 8465 | CB | VAL | B | 28 | −86.034 | −9.157 | −5.053 | 1.00 | 40.03 | C |
| ATOM | 8467 | CG1 | VAL | B | 28 | −86.494 | −9.600 | −6.444 | 1.00 | 39.63 | C |
| ATOM | 8471 | CG2 | VAL | B | 28 | −86.900 | −7.994 | −4.525 | 1.00 | 39.86 | C |
| ATOM | 8475 | C | VAL | B | 28 | −85.335 | −11.600 | −4.625 | 1.00 | 39.63 | C |
| ATOM | 8476 | O | VAL | B | 28 | −85.858 | −12.204 | −5.567 | 1.00 | 39.63 | O |
| ATOM | 8478 | N | HIS | B | 29 | −84.175 | −11.980 | −4.069 | 1.00 | 39.21 | N |
| ATOM | 8479 | CA | HIS | B | 29 | −83.431 | −13.177 | −4.504 | 1.00 | 38.81 | C |
| ATOM | 8481 | CB | HIS | B | 29 | −81.914 | −12.913 | −4.665 | 1.00 | 38.97 | C |
| ATOM | 8484 | CG | HIS | B | 29 | −81.571 | −11.721 | −5.512 | 1.00 | 39.99 | C |
| ATOM | 8485 | ND1 | HIS | B | 29 | −81.181 | −11.825 | −6.834 | 1.00 | 40.79 | N |
| ATOM | 8487 | CE1 | HIS | B | 29 | −80.931 | −10.615 | −7.312 | 1.00 | 40.76 | C |
| ATOM | 8489 | NE2 | HIS | B | 29 | −81.134 | −9.734 | −6.346 | 1.00 | 40.27 | N |
| ATOM | 8491 | CD2 | HIS | B | 29 | −81.525 | −10.400 | −5.209 | 1.00 | 40.17 | C |
| ATOM | 8493 | C | HIS | B | 29 | −83.611 | −14.340 | −3.523 | 1.00 | 38.05 | C |
| ATOM | 8494 | O | HIS | B | 29 | −82.782 | −15.259 | −3.526 | 1.00 | 38.02 | O |
| ATOM | 8496 | N | LYS | B | 30 | −84.667 | −14.321 | −2.694 | 1.00 | 37.06 | N |
| ATOM | 8497 | CA | LYS | B | 30 | −85.107 | −15.559 | −2.022 | 1.00 | 36.33 | C |
| ATOM | 8499 | CB | LYS | B | 30 | −86.056 | −15.286 | −.836 | 1.00 | 36.27 | C |
| ATOM | 8502 | CG | LYS | B | 30 | −85.352 | −14.818 | .461 | 1.00 | 36.09 | C |
| ATOM | 8505 | CD | LYS | B | 30 | −86.355 | −14.599 | 1.612 | 1.00 | 36.03 | C |
| ATOM | 8508 | CE | LYS | B | 30 | −85.811 | −13.659 | 2.701 | 1.00 | 36.24 | C |
| ATOM | 8511 | NZ | LYS | B | 30 | −86.802 | −13.356 | 3.789 | 1.00 | 35.65 | N |
| ATOM | 8515 | C | LYS | B | 30 | −85.710 | −16.510 | −3.094 | 1.00 | 35.69 | C |
| ATOM | 8516 | O | LYS | B | 30 | −86.706 | −17.205 | −2.879 | 1.00 | 35.35 | O |
| ATOM | 8518 | N | ASP | B | 31 | −85.075 | −16.484 | −4.268 | 1.00 | 35.13 | N |
| ATOM | 8519 | CA | ASP | B | 31 | −85.145 | −17.519 | −5.282 | 1.00 | 34.64 | C |
| ATOM | 8521 | CB | ASP | B | 31 | −84.592 | −16.962 | −6.623 | 1.00 | 34.60 | C |
| ATOM | 8524 | CG | ASP | B | 31 | −84.419 | −18.032 | −7.725 | 1.00 | 34.24 | C |
| ATOM | 8525 | OD1 | ASP | B | 31 | −84.914 | −19.165 | −7.570 | 1.00 | 34.58 | O |
| ATOM | 8526 | OD2 | ASP | B | 31 | −83.776 | −17.732 | −8.761 | 1.00 | 31.56 | O |
| ATOM | 8527 | C | ASP | B | 31 | −84.304 | −18.675 | −4.721 | 1.00 | 34.31 | C |
| ATOM | 8528 | O | ASP | B | 31 | −83.122 | −18.838 | −5.038 | 1.00 | 34.03 | O |
| ATOM | 8530 | N | LYS | B | 32 | −84.917 | −19.429 | −3.813 | 1.00 | 33.94 | N |

TABLE 16-7-continued

Coordinates of *P. tremuloides* IspS

| ATOM | 8531 | CA | LYS | B | 32 | −84.380 | −20.710 | −3.369 | 1.00 | 33.36 | C |
|---|---|---|---|---|---|---|---|---|---|---|---|
| ATOM | 8533 | CB | LYS | B | 32 | −83.772 | −20.607 | −1.973 | 1.00 | 33.45 | C |
| ATOM | 8536 | CG | LYS | B | 32 | −82.540 | −19.693 | −1.951 | 1.00 | 33.56 | C |
| ATOM | 8539 | CD | LYS | B | 32 | −82.025 | −19.455 | −.532 | 1.00 | 34.17 | C |
| ATOM | 8542 | CE | LYS | B | 32 | −81.671 | −17.987 | −.283 | 1.00 | 34.16 | C |
| ATOM | 8545 | NZ | LYS | B | 32 | −80.746 | −17.437 | −1.311 | 1.00 | 34.07 | N |
| ATOM | 8549 | C | LYS | B | 32 | −85.490 | −21.764 | −3.499 | 1.00 | 32.57 | C |
| ATOM | 8550 | O | LYS | B | 32 | −85.908 | −22.412 | −2.538 | 1.00 | 32.10 | O |
| ATOM | 8552 | N | ALA | B | 33 | −85.976 | −21.859 | −4.738 | 1.00 | 31.66 | N |
| ATOM | 8553 | CA | ALA | B | 33 | −86.576 | −23.055 | −5.259 | 1.00 | 30.94 | C |
| ATOM | 8555 | CB | ALA | B | 33 | −87.247 | −22.773 | −6.597 | 1.00 | 30.47 | C |
| ATOM | 8559 | C | ALA | B | 33 | −85.442 | −24.081 | −5.403 | 1.00 | 30.55 | C |
| ATOM | 8560 | O | ALA | B | 33 | −85.684 | −25.230 | −5.751 | 1.00 | 31.12 | O |
| ATOM | 8562 | N | LYS | B | 34 | −84.200 | −23.660 | −5.161 | 1.00 | 29.73 | N |
| ATOM | 8563 | CA | LYS | B | 34 | −83.107 | −24.585 | −4.839 | 1.00 | 29.09 | C |
| ATOM | 8565 | CB | LYS | B | 34 | −81.776 | −23.817 | −4.865 | 1.00 | 29.30 | C |
| ATOM | 8568 | CG | LYS | B | 34 | −80.678 | −24.474 | −5.726 | 1.00 | 29.76 | C |
| ATOM | 8571 | CD | LYS | B | 34 | −79.633 | −23.458 | −6.283 | 1.00 | 28.74 | C |
| ATOM | 8574 | CE | LYS | B | 34 | −78.417 | −24.186 | −6.890 | 1.00 | 27.56 | C |
| ATOM | 8577 | NZ | LYS | B | 34 | −78.745 | −25.174 | −7.935 | 1.00 | 26.16 | N |
| ATOM | 8581 | C | LYS | B | 34 | −83.376 | −25.320 | −3.472 | 1.00 | 28.37 | C |
| ATOM | 8582 | O | LYS | B | 34 | −83.254 | −24.755 | −2.374 | 1.00 | 27.82 | O |
| ATOM | 8584 | N | LYS | B | 35 | −83.635 | −26.620 | −3.604 | 1.00 | 27.53 | N |
| ATOM | 8585 | CA | LYS | B | 35 | −84.629 | −27.429 | −2.851 | 1.00 | 26.77 | C |
| ATOM | 8587 | CB | LYS | B | 35 | −85.729 | −26.602 | −2.170 | 1.00 | 26.81 | C |
| ATOM | 8590 | CG | LYS | B | 35 | −87.089 | −26.520 | −2.907 | 1.00 | 27.05 | C |
| ATOM | 8593 | CD | LYS | B | 35 | −88.096 | −27.604 | −2.452 | 1.00 | 27.41 | C |
| ATOM | 8596 | CE | LYS | B | 35 | −89.394 | −27.636 | −3.300 | 1.00 | 27.21 | C |
| ATOM | 8599 | NZ | LYS | B | 35 | −90.501 | −26.792 | −2.762 | 1.00 | 26.28 | N |
| ATOM | 8603 | C | LYS | B | 35 | −85.257 | −28.357 | −3.920 | 1.00 | 26.03 | C |
| ATOM | 8604 | O | LYS | B | 35 | −85.853 | −29.386 | −3.626 | 1.00 | 26.00 | O |
| ATOM | 8606 | N | LEU | B | 36 | −85.171 | −27.909 | −5.168 | 1.00 | 24.98 | N |
| ATOM | 8607 | CA | LEU | B | 36 | −85.095 | −28.783 | −6.319 | 1.00 | 24.02 | C |
| ATOM | 8609 | CB | LEU | B | 36 | −85.004 | −27.930 | −7.594 | 1.00 | 23.83 | C |
| ATOM | 8612 | CG | LEU | B | 36 | −86.208 | −27.103 | −8.062 | 1.00 | 22.23 | C |
| ATOM | 8614 | CD1 | LEU | B | 36 | −85.762 | −25.873 | −8.802 | 1.00 | 19.93 | C |
| ATOM | 8618 | CD2 | LEU | B | 36 | −87.092 | −27.930 | −8.951 | 1.00 | 22.11 | C |
| ATOM | 8622 | C | LEU | B | 36 | −83.834 | −29.659 | −6.185 | 1.00 | 23.58 | C |
| ATOM | 8623 | O | LEU | B | 36 | −83.840 | −30.842 | −6.508 | 1.00 | 23.38 | O |
| ATOM | 8625 | N | GLU | B | 37 | −82.742 | −29.046 | −5.739 | 1.00 | 23.18 | N |
| ATOM | 8626 | CA | GLU | B | 37 | −81.510 | −29.753 | −5.396 | 1.00 | 22.88 | C |
| ATOM | 8628 | CB | GLU | B | 37 | −80.466 | −28.766 | −4.855 | 1.00 | 22.76 | C |
| ATOM | 8631 | CG | GLU | B | 37 | −79.038 | −29.297 | −4.874 | 1.00 | 22.24 | C |
| ATOM | 8634 | CD | GLU | B | 37 | −78.085 | −28.505 | −4.009 | 1.00 | 21.06 | C |
| ATOM | 8635 | OE1 | GLU | B | 37 | −78.368 | −27.331 | −3.737 | 1.00 | 19.65 | O |
| ATOM | 8636 | OE2 | GLU | B | 37 | −77.037 | −29.059 | −3.615 | 1.00 | 20.62 | O |
| ATOM | 8637 | C | GLU | B | 37 | −81.748 | −30.856 | −4.364 | 1.00 | 22.95 | C |
| ATOM | 8638 | O | GLU | B | 37 | −81.164 | −31.933 | −4.458 | 1.00 | 22.99 | O |
| ATOM | 8640 | N | ALA | B | 38 | −82.591 | −30.575 | −3.372 | 1.00 | 23.02 | N |
| ATOM | 8641 | CA | ALA | B | 38 | −82.973 | −31.565 | −2.364 | 1.00 | 22.93 | C |
| ATOM | 8643 | CB | ALA | B | 38 | −83.966 | −30.959 | −1.374 | 1.00 | 22.73 | C |
| ATOM | 8647 | C | ALA | B | 38 | −83.580 | −32.778 | −3.044 | 1.00 | 23.05 | C |
| ATOM | 8648 | O | ALA | B | 38 | −83.170 | −33.909 | −2.813 | 1.00 | 22.52 | O |
| ATOM | 8650 | N | GLU | B | 39 | −84.546 | −32.506 | −3.912 | 1.00 | 23.66 | N |
| ATOM | 8651 | CA | GLU | B | 39 | −85.273 | −33.534 | −4.642 | 1.00 | 24.08 | C |
| ATOM | 8653 | CB | GLU | B | 39 | −86.403 | −32.891 | −5.453 | 1.00 | 24.28 | C |
| ATOM | 8656 | CG | GLU | B | 39 | −87.405 | −33.869 | −6.075 | 1.00 | 25.14 | C |
| ATOM | 8659 | CD | GLU | B | 39 | −88.773 | −33.227 | −6.341 | 1.00 | 26.43 | C |
| ATOM | 8660 | OE1 | GLU | B | 39 | −89.232 | −32.381 | −5.519 | 1.00 | 25.90 | O |
| ATOM | 8661 | OE2 | GLU | B | 39 | −89.387 | −33.584 | −7.375 | 1.00 | 26.99 | O |
| ATOM | 8662 | C | GLU | B | 39 | −84.362 | −34.359 | −5.545 | 1.00 | 24.18 | C |
| ATOM | 8663 | O | GLU | B | 39 | −84.483 | −35.579 | −5.575 | 1.00 | 24.32 | O |
| ATOM | 8665 | N | VAL | B | 40 | −83.450 | −33.710 | −6.269 | 1.00 | 24.43 | N |
| ATOM | 8666 | CA | VAL | B | 40 | −82.533 | −34.437 | −7.153 | 1.00 | 24.59 | C |
| ATOM | 8668 | CB | VAL | B | 40 | −81.734 | −33.496 | −8.087 | 1.00 | 24.65 | C |
| ATOM | 8670 | CG1 | VAL | B | 40 | −80.611 | −34.258 | −8.792 | 1.00 | 24.14 | C |
| ATOM | 8674 | CG2 | VAL | B | 40 | −82.662 | −32.852 | −9.106 | 1.00 | 23.89 | C |
| ATOM | 8678 | C | VAL | B | 40 | −81.592 | −35.304 | −6.328 | 1.00 | 24.99 | C |
| ATOM | 8679 | O | VAL | B | 40 | −81.265 | −36.407 | −6.717 | 1.00 | 24.77 | O |
| ATOM | 8681 | N | ARG | B | 41 | −81.184 | −34.811 | −5.171 | 1.00 | 25.79 | N |
| ATOM | 8682 | CA | ARG | B | 41 | −80.387 | −35.613 | −4.248 | 1.00 | 26.75 | C |
| ATOM | 8684 | CB | ARG | B | 41 | −80.032 | −34.823 | −2.998 | 1.00 | 27.38 | C |
| ATOM | 8687 | CG | ARG | B | 41 | −78.568 | −34.777 | −2.757 | 1.00 | 30.18 | C |
| ATOM | 8690 | CD | ARG | B | 41 | −78.281 | −34.610 | −1.273 | 1.00 | 34.43 | C |
| ATOM | 8693 | NE | ARG | B | 41 | −76.896 | −34.198 | −1.016 | 1.00 | 37.07 | N |
| ATOM | 8695 | CZ | ARG | B | 41 | −76.350 | −33.045 | −1.416 | 1.00 | 38.54 | C |
| ATOM | 8696 | NH1 | ARG | B | 41 | −75.083 | −32.797 | −1.112 | 1.00 | 40.04 | N |
| ATOM | 8699 | NH2 | ARG | B | 41 | −77.037 | −32.145 | −2.128 | 1.00 | 38.45 | N |

TABLE 16-7-continued

Coordinates of *P. tremuloides* IspS

| ATOM | 8702 | C | ARG | B | 41 | −81.081 | −36.860 | −3.762 | 1.00 | 26.60 | C |
|---|---|---|---|---|---|---|---|---|---|---|---|
| ATOM | 8703 | O | ARG | B | 41 | −80.446 | −37.894 | −3.627 | 1.00 | 26.89 | O |
| ATOM | 8705 | N | ARG | B | 42 | −82.363 | −36.733 | −3.423 | 1.00 | 26.41 | N |
| ATOM | 8706 | CA | ARG | B | 42 | −83.159 | −37.870 | −3.002 | 1.00 | 26.09 | C |
| ATOM | 8708 | CB | ARG | B | 42 | −84.588 | −37.452 | −2.674 | 1.00 | 25.99 | C |
| ATOM | 8711 | CG | ARG | B | 42 | −85.426 | −38.562 | −2.049 | 1.00 | 25.45 | C |
| ATOM | 8714 | CD | ARG | B | 42 | −86.783 | −38.078 | −1.645 | 1.00 | 24.26 | C |
| ATOM | 8717 | NE | ARG | B | 42 | −87.549 | −37.602 | −2.794 | 1.00 | 23.73 | N |
| ATOM | 8719 | CZ | ARG | B | 42 | −88.547 | −36.722 | −2.717 | 1.00 | 24.51 | C |
| ATOM | 8720 | NH1 | ARG | B | 42 | −88.912 | −36.195 | −1.545 | 1.00 | 24.99 | N |
| ATOM | 8723 | NH2 | ARG | B | 42 | −89.185 | −36.354 | −3.816 | 1.00 | 24.46 | N |
| ATOM | 8726 | C | ARG | B | 42 | −83.167 | −38.894 | −4.118 | 1.00 | 26.28 | C |
| ATOM | 8727 | O | ARG | B | 42 | −82.864 | −40.054 | −3.888 | 1.00 | 26.39 | O |
| ATOM | 8729 | N | GLU | B | 43 | −83.476 | −38.460 | −5.334 | 1.00 | 26.52 | N |
| ATOM | 8730 | CA | GLU | B | 43 | −83.476 | −39.370 | −6.479 | 1.00 | 27.00 | C |
| ATOM | 8732 | CB | GLU | B | 43 | −83.982 | −38.676 | −7.753 | 1.00 | 27.50 | C |
| ATOM | 8735 | CG | GLU | B | 43 | −85.469 | −38.275 | −7.699 | 1.00 | 29.78 | C |
| ATOM | 8738 | CD | GLU | B | 43 | −86.342 | −39.301 | −6.974 | 1.00 | 32.52 | C |
| ATOM | 8739 | OE1 | GLU | B | 43 | −86.388 | −40.455 | −7.445 | 1.00 | 35.06 | O |
| ATOM | 8740 | OE2 | GLU | B | 43 | −86.966 | −38.963 | −5.936 | 1.00 | 33.80 | O |
| ATOM | 8741 | C | GLU | B | 43 | −82.147 | −40.059 | −6.769 | 1.00 | 26.37 | C |
| ATOM | 8742 | O | GLU | B | 43 | −82.162 | −41.126 | −7.355 | 1.00 | 26.63 | O |
| ATOM | 8744 | N | ILE | B | 44 | −81.018 | −39.472 | −6.373 | 1.00 | 25.85 | N |
| ATOM | 8745 | CA | ILE | B | 44 | −79.717 | −40.126 | −6.555 | 1.00 | 25.55 | C |
| ATOM | 8747 | CB | ILE | B | 44 | −78.547 | −39.121 | −6.692 | 1.00 | 25.26 | C |
| ATOM | 8749 | CG1 | ILE | B | 44 | −78.706 | −38.273 | −7.953 | 1.00 | 24.47 | C |
| ATOM | 8752 | CD1 | ILE | B | 44 | −77.690 | −37.163 | −8.114 | 1.00 | 23.21 | C |
| ATOM | 8756 | CG2 | ILE | B | 44 | −77.207 | −39.863 | −6.778 | 1.00 | 25.35 | C |
| ATOM | 8760 | C | ILE | B | 44 | −79.404 | −41.109 | −5.428 | 1.00 | 25.84 | C |
| ATOM | 8761 | O | ILE | B | 44 | −78.925 | −42.208 | −5.698 | 1.00 | 25.97 | O |
| ATOM | 8763 | N | ASN | B | 45 | −79.663 | −40.708 | −4.177 | 1.00 | 26.25 | N |
| ATOM | 8764 | CA | ASN | B | 45 | −79.403 | −41.542 | −2.983 | 1.00 | 26.34 | C |
| ATOM | 8766 | CB | ASN | B | 45 | −79.284 | −40.681 | −1.719 | 1.00 | 26.01 | C |
| ATOM | 8769 | CG | ASN | B | 45 | −78.072 | −39.789 | −1.723 | 1.00 | 24.65 | C |
| ATOM | 8770 | OD1 | ASN | B | 45 | −76.957 | −40.226 | −1.434 | 1.00 | 22.47 | O |
| ATOM | 8771 | ND2 | ASN | B | 45 | −78.288 | −38.516 | −2.009 | 1.00 | 23.36 | N |
| ATOM | 8774 | C | ASN | B | 45 | −80.488 | −42.586 | −2.731 | 1.00 | 27.18 | C |
| ATOM | 8775 | O | ASN | B | 45 | −80.374 | −43.390 | −1.806 | 1.00 | 27.30 | O |
| ATOM | 8777 | N | ASN | B | 46 | −81.553 | −42.541 | −3.527 | 1.00 | 28.17 | N |
| ATOM | 8778 | CA | ASN | B | 46 | −82.619 | −43.536 | −3.489 | 1.00 | 29.02 | C |
| ATOM | 8780 | CB | ASN | B | 46 | −83.558 | −43.289 | −4.665 | 1.00 | 29.05 | C |
| ATOM | 8783 | CG | ASN | B | 46 | −84.615 | −44.345 | −4.806 | 1.00 | 28.82 | C |
| ATOM | 8784 | OD1 | ASN | B | 46 | −84.861 | −45.132 | −3.895 | 1.00 | 28.14 | O |
| ATOM | 8785 | ND2 | ASN | B | 46 | −85.255 | −44.369 | −5.968 | 1.00 | 29.67 | N |
| ATOM | 8788 | C | ASN | B | 46 | −82.076 | −44.958 | −3.549 | 1.00 | 30.14 | C |
| ATOM | 8789 | O | ASN | B | 46 | −81.566 | −45.408 | −4.581 | 1.00 | 30.30 | O |
| ATOM | 8791 | N | GLU | B | 47 | −82.218 | −45.674 | −2.446 | 1.00 | 31.36 | N |
| ATOM | 8792 | CA | GLU | B | 47 | −81.575 | −46.968 | −2.295 | 1.00 | 32.61 | C |
| ATOM | 8794 | CB | GLU | B | 47 | −81.617 | −47.430 | −.823 | 1.00 | 33.09 | C |
| ATOM | 8797 | CG | GLU | B | 47 | −80.974 | −46.466 | .218 | 1.00 | 34.19 | C |
| ATOM | 8800 | CD | GLU | B | 47 | −81.919 | −45.337 | .721 | 1.00 | 34.57 | C |
| ATOM | 8801 | OE1 | GLU | B | 47 | −82.911 | −45.012 | .029 | 1.00 | 34.53 | O |
| ATOM | 8802 | OE2 | GLU | B | 47 | −81.652 | −44.762 | 1.805 | 1.00 | 34.30 | O |
| ATOM | 8803 | C | GLU | B | 47 | −82.205 | −48.046 | −3.172 | 1.00 | 33.18 | C |
| ATOM | 8804 | O | GLU | B | 47 | −81.604 | −49.088 | −3.370 | 1.00 | 33.44 | O |
| ATOM | 8806 | N | LYS | B | 48 | −83.408 | −47.808 | −3.692 | 1.00 | 34.11 | N |
| ATOM | 8807 | CA | LYS | B | 48 | −84.164 | −48.853 | −4.396 | 1.00 | 34.85 | C |
| ATOM | 8809 | CB | LYS | B | 48 | −85.379 | −49.254 | −3.542 | 1.00 | 35.09 | C |
| ATOM | 8812 | CG | LYS | B | 48 | −85.003 | −49.723 | −2.127 | 1.00 | 36.00 | C |
| ATOM | 8815 | CD | LYS | B | 48 | −86.174 | −50.338 | −1.350 | 1.00 | 37.13 | C |
| ATOM | 8818 | CE | LYS | B | 48 | −87.312 | −49.340 | −1.094 | 1.00 | 37.90 | C |
| ATOM | 8821 | NZ | LYS | B | 48 | −86.908 | −48.161 | −.272 | 1.00 | 38.31 | N |
| ATOM | 8825 | C | LYS | B | 48 | −84.586 | −48.487 | −5.835 | 1.00 | 35.13 | C |
| ATOM | 8826 | O | LYS | B | 48 | −85.544 | −49.030 | −6.361 | 1.00 | 34.60 | O |
| ATOM | 8828 | N | ALA | B | 49 | −83.858 | −47.576 | −6.474 | 1.00 | 36.09 | N |
| ATOM | 8829 | CA | ALA | B | 49 | −84.093 | −47.261 | −7.886 | 1.00 | 36.87 | C |
| ATOM | 8831 | CB | ALA | B | 49 | −83.550 | −45.880 | −8.238 | 1.00 | 36.73 | C |
| ATOM | 8835 | C | ALA | B | 49 | −83.406 | −48.325 | −8.714 | 1.00 | 37.56 | C |
| ATOM | 8836 | O | ALA | B | 49 | −82.315 | −48.761 | −8.363 | 1.00 | 37.62 | O |
| ATOM | 8838 | N | GLU | B | 50 | −84.028 | −48.754 | −9.807 | 1.00 | 38.54 | N |
| ATOM | 8839 | CA | GLU | B | 50 | −83.399 | −49.772 | −10.652 | 1.00 | 39.40 | C |
| ATOM | 8841 | CB | GLU | B | 50 | −84.380 | −50.384 | −11.673 | 1.00 | 39.71 | C |
| ATOM | 8844 | CG | GLU | B | 50 | −83.959 | −51.808 | −12.179 | 1.00 | 41.33 | C |
| ATOM | 8847 | CD | GLU | B | 50 | −83.733 | −52.860 | −11.039 | 1.00 | 42.88 | C |
| ATOM | 8848 | OE1 | GLU | B | 50 | −84.683 | −53.628 | −10.718 | 1.00 | 42.94 | O |
| ATOM | 8849 | OE2 | GLU | B | 50 | −82.603 | −52.921 | −10.472 | 1.00 | 42.96 | O |
| ATOM | 8850 | C | GLU | B | 50 | −82.171 | −49.163 | −11.330 | 1.00 | 39.43 | C |
| ATOM | 8851 | O | GLU | B | 50 | −82.211 | −48.017 | −11.791 | 1.00 | 39.66 | O |

TABLE 16-7-continued

Coordinates of *P. tremuloides* IspS

| ATOM | 8853 | N | PHE | B | 51 | −81.084 | −49.929 | −11.376 | 1.00 | 39.32 | N |
|------|------|------|-----|---|----|---------|---------|---------|------|-------|---|
| ATOM | 8854 | CA | PHE | B | 51 | −79.763 | −49.360 | −11.636 | 1.00 | 39.32 | C |
| ATOM | 8856 | CB | PHE | B | 51 | −78.675 | −50.429 | −11.476 | 1.00 | 39.62 | C |
| ATOM | 8859 | CG | PHE | B | 51 | −78.470 | −50.889 | −10.032 | 1.00 | 41.82 | C |
| ATOM | 8860 | CD1 | PHE | B | 51 | −78.093 | −49.978 | −9.032 | 1.00 | 42.93 | C |
| ATOM | 8862 | CE1 | PHE | B | 51 | −77.892 | −50.391 | −7.705 | 1.00 | 43.30 | C |
| ATOM | 8864 | CZ | PHE | B | 51 | −78.059 | −51.729 | −7.359 | 1.00 | 44.33 | C |
| ATOM | 8866 | CE2 | PHE | B | 51 | −78.430 | −52.659 | −8.341 | 1.00 | 44.75 | C |
| ATOM | 8868 | CD2 | PHE | B | 51 | −78.633 | −52.234 | −9.677 | 1.00 | 44.06 | C |
| ATOM | 8870 | C | PHE | B | 51 | −79.646 | −48.625 | −12.976 | 1.00 | 38.57 | C |
| ATOM | 8871 | O | PHE | B | 51 | −79.045 | −47.564 | −13.046 | 1.00 | 38.50 | O |
| ATOM | 8873 | N | LEU | B | 52 | −80.262 | −49.155 | −14.024 | 1.00 | 37.99 | N |
| ATOM | 8874 | CA | LEU | B | 52 | −80.176 | −48.539 | −15.351 | 1.00 | 37.42 | C |
| ATOM | 8876 | CB | LEU | B | 52 | −80.774 | −49.476 | −16.399 | 1.00 | 37.66 | C |
| ATOM | 8879 | CG | LEU | B | 52 | −80.502 | −49.168 | −17.876 | 1.00 | 38.39 | C |
| ATOM | 8881 | CD1 | LEU | B | 52 | −80.171 | −50.452 | −18.652 | 1.00 | 38.46 | C |
| ATOM | 8885 | CD2 | LEU | B | 52 | −81.703 | −48.432 | −18.500 | 1.00 | 39.23 | C |
| ATOM | 8889 | C | LEU | B | 52 | −80.824 | −47.143 | −15.431 | 1.00 | 36.69 | C |
| ATOM | 8890 | O | LEU | B | 52 | −80.383 | −46.312 | −16.224 | 1.00 | 36.59 | O |
| ATOM | 8892 | N | THR | B | 53 | −81.859 | −46.879 | −14.625 | 1.00 | 35.87 | N |
| ATOM | 8893 | CA | THR | B | 53 | −82.409 | −45.510 | −14.513 | 1.00 | 34.91 | C |
| ATOM | 8895 | CB | THR | B | 53 | −83.784 | −45.421 | −13.805 | 1.00 | 34.72 | C |
| ATOM | 8897 | OG1 | THR | B | 53 | −84.724 | −46.269 | −14.455 | 1.00 | 34.04 | O |
| ATOM | 8899 | CG2 | THR | B | 53 | −84.316 | −43.981 | −13.855 | 1.00 | 34.81 | C |
| ATOM | 8903 | C | THR | B | 53 | −81.454 | −44.642 | −13.722 | 1.00 | 34.05 | C |
| ATOM | 8904 | O | THR | B | 53 | −81.170 | −43.513 | −14.121 | 1.00 | 34.16 | O |
| ATOM | 8906 | N | LEU | B | 54 | −80.987 | −45.167 | −12.593 | 1.00 | 32.84 | N |
| ATOM | 8907 | CA | LEU | B | 54 | −80.027 | −44.461 | −11.772 | 1.00 | 32.16 | C |
| ATOM | 8909 | CB | LEU | B | 54 | −79.506 | −45.354 | −10.662 | 1.00 | 32.27 | C |
| ATOM | 8912 | CG | LEU | B | 54 | −78.521 | −44.702 | −9.698 | 1.00 | 32.56 | C |
| ATOM | 8914 | CD1 | LEU | B | 54 | −79.275 | −43.760 | −8.769 | 1.00 | 32.38 | C |
| ATOM | 8918 | CD2 | LEU | B | 54 | −77.755 | −45.789 | −8.917 | 1.00 | 33.29 | C |
| ATOM | 8922 | C | LEU | B | 54 | −78.870 | −44.006 | −12.634 | 1.00 | 31.50 | C |
| ATOM | 8923 | O | LEU | B | 54 | −78.509 | −42.840 | −12.607 | 1.00 | 31.98 | O |
| ATOM | 8925 | N | LEU | B | 55 | −78.297 | −44.914 | −13.418 | 1.00 | 30.43 | N |
| ATOM | 8926 | CA | LEU | B | 55 | −77.220 | −44.540 | −14.333 | 1.00 | 29.36 | C |
| ATOM | 8928 | CB | LEU | B | 55 | −76.765 | −45.733 | −15.173 | 1.00 | 29.23 | C |
| ATOM | 8931 | CG | LEU | B | 55 | −76.157 | −46.902 | −14.391 | 1.00 | 28.60 | C |
| ATOM | 8933 | CD1 | LEU | B | 55 | −75.697 | −48.004 | −15.348 | 1.00 | 27.60 | C |
| ATOM | 8937 | CD2 | LEU | B | 55 | −75.020 | −46.440 | −13.469 | 1.00 | 27.20 | C |
| ATOM | 8941 | C | LEU | B | 55 | −77.678 | −43.406 | −15.230 | 1.00 | 28.60 | C |
| ATOM | 8942 | O | LEU | B | 55 | −77.063 | −42.365 | −15.267 | 1.00 | 28.17 | O |
| ATOM | 8944 | N | GLU | B | 56 | −78.786 | −43.594 | −15.919 | 1.00 | 28.23 | N |
| ATOM | 8945 | CA | GLU | B | 56 | −79.326 | −42.530 | −16.759 | 1.00 | 28.64 | C |
| ATOM | 8947 | CB | GLU | B | 56 | −80.567 | −43.031 | −17.524 | 1.00 | 29.27 | C |
| ATOM | 8950 | CG | GLU | B | 56 | −80.229 | −43.783 | −18.829 | 1.00 | 31.73 | C |
| ATOM | 8953 | CD | GLU | B | 56 | −81.265 | −44.860 | −19.206 | 1.00 | 35.52 | C |
| ATOM | 8954 | OE1 | GLU | B | 56 | −82.474 | −44.693 | −18.889 | 1.00 | 36.97 | O |
| ATOM | 8955 | OE2 | GLU | B | 56 | −80.856 | −45.877 | −19.825 | 1.00 | 37.55 | O |
| ATOM | 8956 | C | GLU | B | 56 | −79.632 | −41.203 | −15.995 | 1.00 | 27.77 | C |
| ATOM | 8957 | O | GLU | B | 56 | −79.561 | −40.103 | −16.582 | 1.00 | 27.84 | O |
| ATOM | 8959 | N | LEU | B | 57 | −79.976 | −41.303 | −14.710 | 1.00 | 26.29 | N |
| ATOM | 8960 | CA | LEU | B | 57 | −80.158 | −40.120 | −13.895 | 1.00 | 25.06 | C |
| ATOM | 8962 | CB | LEU | B | 57 | −80.724 | −40.462 | −12.514 | 1.00 | 24.83 | C |
| ATOM | 8965 | CG | LEU | B | 57 | −80.952 | −39.298 | −11.544 | 1.00 | 23.72 | C |
| ATOM | 8967 | CD1 | LEU | B | 57 | −81.909 | −38.278 | −12.117 | 1.00 | 21.43 | C |
| ATOM | 8971 | CD2 | LEU | B | 57 | −81.477 | −39.830 | −10.227 | 1.00 | 22.41 | C |
| ATOM | 8975 | C | LEU | B | 57 | −78.801 | −39.459 | −13.780 | 1.00 | 24.40 | C |
| ATOM | 8976 | O | LEU | B | 57 | −78.591 | −38.373 | −14.306 | 1.00 | 24.70 | O |
| ATOM | 8978 | N | ILE | B | 58 | −77.855 | −40.133 | −13.144 | 1.00 | 23.56 | N |
| ATOM | 8979 | CA | ILE | B | 58 | −76.509 | −39.574 | −12.991 | 1.00 | 22.91 | C |
| ATOM | 8981 | CB | ILE | B | 58 | −75.454 | −40.635 | −12.599 | 1.00 | 22.49 | C |
| ATOM | 8983 | CG1 | ILE | B | 58 | −75.753 | −41.251 | −11.235 | 1.00 | 22.09 | C |
| ATOM | 8986 | CD1 | ILE | B | 58 | −74.936 | −42.464 | −10.926 | 1.00 | 20.88 | C |
| ATOM | 8990 | CG2 | ILE | B | 58 | −74.103 | −39.992 | −12.534 | 1.00 | 22.63 | C |
| ATOM | 8994 | C | ILE | B | 58 | −76.062 | −38.927 | −14.302 | 1.00 | 22.64 | C |
| ATOM | 8995 | O | ILE | B | 58 | −75.603 | −37.796 | −14.315 | 1.00 | 22.38 | O |
| ATOM | 8997 | N | ASP | B | 59 | −76.228 | −39.646 | −15.404 | 1.00 | 22.56 | N |
| ATOM | 8998 | CA | ASP | B | 59 | −75.715 | −39.196 | −16.684 | 1.00 | 22.76 | C |
| ATOM | 9000 | CB | ASP | B | 59 | −75.926 | −40.269 | −17.757 | 1.00 | 22.93 | C |
| ATOM | 9003 | CG | ASP | B | 59 | −75.274 | −39.904 | −19.088 | 1.00 | 24.58 | C |
| ATOM | 9004 | OD1 | ASP | B | 59 | −74.157 | −39.322 | −19.081 | 1.00 | 25.70 | O |
| ATOM | 9005 | OD2 | ASP | B | 59 | −75.897 | −40.186 | −20.142 | 1.00 | 27.51 | O |
| ATOM | 9006 | C | ASP | B | 59 | −76.343 | −37.863 | −17.104 | 1.00 | 22.40 | C |
| ATOM | 9007 | O | ASP | B | 59 | −75.634 | −36.939 | −17.520 | 1.00 | 22.40 | O |
| ATOM | 9009 | N | ASN | B | 60 | −77.662 | −37.767 | −16.991 | 1.00 | 21.91 | N |
| ATOM | 9010 | CA | ASN | B | 60 | −78.349 | −36.500 | −17.217 | 1.00 | 21.70 | C |
| ATOM | 9012 | CB | ASN | B | 60 | −79.867 | −36.674 | −17.088 | 1.00 | 22.12 | C |

TABLE 16-7-continued

Coordinates of *P. tremuloides* IspS

| ATOM | 9015 | CG | ASN | B | 60 | −80.477 | −37.390 | −18.268 | 1.00 | 22.76 | C |
|---|---|---|---|---|---|---|---|---|---|---|---|
| ATOM | 9016 | OD1 | ASN | B | 60 | −80.027 | −37.233 | −19.393 | 1.00 | 24.28 | O |
| ATOM | 9017 | ND2 | ASN | B | 60 | −81.515 | −38.172 | −18.017 | 1.00 | 24.36 | N |
| ATOM | 9020 | C | ASN | B | 60 | −77.898 | −35.427 | −16.234 | 1.00 | 21.17 | C |
| ATOM | 9021 | O | ASN | B | 60 | −77.700 | −34.273 | −16.614 | 1.00 | 20.85 | O |
| ATOM | 9023 | N | VAL | B | 61 | −77.745 | −35.805 | −14.968 | 1.00 | 20.60 | N |
| ATOM | 9024 | CA | VAL | B | 61 | −77.382 | −34.841 | −13.942 | 1.00 | 20.48 | C |
| ATOM | 9026 | CB | VAL | B | 61 | −77.277 | −35.490 | −12.551 | 1.00 | 20.26 | C |
| ATOM | 9028 | CG1 | VAL | B | 61 | −76.585 | −34.562 | −11.565 | 1.00 | 19.92 | C |
| ATOM | 9032 | CG2 | VAL | B | 61 | −78.668 | −35.857 | −12.049 | 1.00 | 20.66 | C |
| ATOM | 9036 | C | VAL | B | 61 | −76.068 | −34.208 | −14.335 | 1.00 | 20.66 | C |
| ATOM | 9037 | O | VAL | B | 61 | −75.871 | −32.998 | −14.182 | 1.00 | 20.74 | O |
| ATOM | 9039 | N | GLN | B | 62 | −75.187 | −35.048 | −14.875 | 1.00 | 20.92 | N |
| ATOM | 9040 | CA | GLN | B | 62 | −73.854 | −34.636 | −15.285 | 1.00 | 20.69 | C |
| ATOM | 9042 | CB | GLN | B | 62 | −72.917 | −35.847 | −15.404 | 1.00 | 20.77 | C |
| ATOM | 9045 | CG | GLN | B | 62 | −72.456 | −36.369 | −14.035 | 1.00 | 20.91 | C |
| ATOM | 9048 | CD | GLN | B | 62 | −71.328 | −37.383 | −14.112 | 1.00 | 20.75 | C |
| ATOM | 9049 | OE1 | GLN | B | 62 | −70.512 | −37.498 | −13.192 | 1.00 | 20.93 | O |
| ATOM | 9050 | NE2 | GLN | B | 62 | −71.291 | −38.135 | −15.195 | 1.00 | 20.39 | N |
| ATOM | 9053 | C | GLN | B | 62 | −73.900 | −33.834 | −16.567 | 1.00 | 20.32 | C |
| ATOM | 9054 | O | GLN | B | 62 | −73.410 | −32.712 | −16.569 | 1.00 | 20.79 | O |
| ATOM | 9056 | N | ARG | B | 63 | −74.512 | −34.373 | −17.625 | 1.00 | 19.87 | N |
| ATOM | 9057 | CA | ARG | B | 63 | −74.520 | −33.696 | −18.940 | 1.00 | 19.81 | C |
| ATOM | 9059 | CB | ARG | B | 63 | −75.240 | −34.536 | −20.013 | 1.00 | 19.75 | C |
| ATOM | 9062 | CG | ARG | B | 63 | −74.492 | −35.846 | −20.345 | 1.00 | 21.69 | C |
| ATOM | 9065 | CD | ARG | B | 63 | −75.158 | −36.786 | −21.368 | 1.00 | 24.89 | C |
| ATOM | 9068 | NE | ARG | B | 63 | −74.674 | −36.558 | −22.741 | 1.00 | 29.32 | N |
| ATOM | 9070 | CZ | ARG | B | 63 | −75.323 | −35.878 | −23.702 | 1.00 | 33.71 | C |
| ATOM | 9071 | NH1 | ARG | B | 63 | −76.537 | −35.345 | −23.510 | 1.00 | 36.67 | N |
| ATOM | 9074 | NH2 | ARG | B | 63 | −74.761 | −35.736 | −24.894 | 1.00 | 34.58 | N |
| ATOM | 9077 | C | ARG | B | 63 | −75.099 | −32.276 | −18.822 | 1.00 | 19.39 | C |
| ATOM | 9078 | O | ARG | B | 63 | −74.553 | −31.310 | −19.395 | 1.00 | 19.63 | O |
| ATOM | 9080 | N | LEU | B | 64 | −76.155 | −32.148 | −18.017 | 1.00 | 18.62 | N |
| ATOM | 9081 | CA | LEU | B | 64 | −76.811 | −30.856 | −17.753 | 1.00 | 17.96 | C |
| ATOM | 9083 | CB | LEU | B | 64 | −78.136 | −31.077 | −17.008 | 1.00 | 17.97 | C |
| ATOM | 9086 | CG | LEU | B | 64 | −79.264 | −31.737 | −17.809 | 1.00 | 17.08 | C |
| ATOM | 9088 | CD1 | LEU | B | 64 | −80.276 | −32.354 | −16.879 | 1.00 | 15.15 | C |
| ATOM | 9092 | CD2 | LEU | B | 64 | −79.904 | −30.734 | −18.737 | 1.00 | 15.30 | C |
| ATOM | 9096 | C | LEU | B | 64 | −75.975 | −29.847 | −16.966 | 1.00 | 17.39 | C |
| ATOM | 9097 | O | LEU | B | 64 | −76.370 | −28.685 | −16.825 | 1.00 | 17.38 | O |
| ATOM | 9099 | N | GLY | B | 65 | −74.848 | −30.286 | −16.432 | 1.00 | 16.73 | N |
| ATOM | 9100 | CA | GLY | B | 65 | −73.917 | −29.374 | −15.818 | 1.00 | 16.65 | C |
| ATOM | 9103 | C | GLY | B | 65 | −74.077 | −29.249 | −14.319 | 1.00 | 16.68 | C |
| ATOM | 9104 | O | GLY | B | 65 | −73.565 | −28.302 | −13.718 | 1.00 | 16.79 | O |
| ATOM | 9106 | N | LEU | B | 66 | −74.758 | −30.209 | −13.702 | 1.00 | 16.60 | N |
| ATOM | 9107 | CA | LEU | B | 66 | −74.978 | −30.177 | −12.264 | 1.00 | 16.58 | C |
| ATOM | 9109 | CB | LEU | B | 66 | −76.465 | −30.389 | −11.957 | 1.00 | 16.35 | C |
| ATOM | 9112 | CG | LEU | B | 66 | −77.363 | −29.187 | −12.234 | 1.00 | 15.57 | C |
| ATOM | 9114 | CD1 | LEU | B | 66 | −78.828 | −29.602 | −12.163 | 1.00 | 15.26 | C |
| ATOM | 9118 | CD2 | LEU | B | 66 | −77.063 | −28.051 | −11.270 | 1.00 | 13.66 | C |
| ATOM | 9122 | C | LEU | B | 66 | −74.129 | −31.203 | −11.513 | 1.00 | 16.94 | C |
| ATOM | 9123 | O | LEU | B | 66 | −74.152 | −31.251 | −10.279 | 1.00 | 17.50 | O |
| ATOM | 9125 | N | GLY | B | 67 | −73.373 | −32.017 | −12.236 | 1.00 | 17.03 | N |
| ATOM | 9126 | CA | GLY | B | 67 | −72.541 | −33.036 | −11.602 | 1.00 | 17.13 | C |
| ATOM | 9129 | C | GLY | B | 67 | −71.642 | −32.557 | −10.461 | 1.00 | 17.08 | C |
| ATOM | 9130 | O | GLY | B | 67 | −71.378 | −33.317 | −9.522 | 1.00 | 17.33 | O |
| ATOM | 9132 | N | TYR | B | 68 | −71.159 | −31.316 | −10.541 | 1.00 | 16.83 | N |
| ATOM | 9133 | CA | TYR | B | 68 | −70.217 | −30.804 | −9.552 | 1.00 | 16.64 | C |
| ATOM | 9135 | CB | TYR | B | 68 | −69.654 | −29.437 | −9.951 | 1.00 | 16.25 | C |
| ATOM | 9138 | CG | TYR | B | 68 | −70.609 | −28.273 | −9.802 | 1.00 | 13.51 | C |
| ATOM | 9139 | CD1 | TYR | B | 68 | −70.521 | −27.411 | −8.738 | 1.00 | 10.49 | C |
| ATOM | 9141 | CE1 | TYR | B | 68 | −71.407 | −26.342 | −8.608 | 1.00 | 10.25 | C |
| ATOM | 9143 | CZ | TYR | B | 68 | −72.382 | −26.135 | −9.555 | 1.00 | 9.74 | C |
| ATOM | 9144 | OH | TYR | B | 68 | −73.253 | −25.086 | −9.450 | 1.00 | 7.62 | O |
| ATOM | 9146 | CE2 | TYR | B | 68 | −72.484 | −26.978 | −10.625 | 1.00 | 11.14 | C |
| ATOM | 9148 | CD2 | TYR | B | 68 | −71.603 | −28.037 | −10.748 | 1.00 | 12.56 | C |
| ATOM | 9150 | C | TYR | B | 68 | −70.828 | −30.700 | −8.172 | 1.00 | 17.79 | C |
| ATOM | 9151 | O | TYR | B | 68 | −70.107 | −30.811 | −7.182 | 1.00 | 18.00 | O |
| ATOM | 9153 | N | ARG | B | 69 | −72.146 | −30.485 | −8.090 | 1.00 | 18.85 | N |
| ATOM | 9154 | CA | ARG | B | 69 | −72.784 | −30.269 | −6.789 | 1.00 | 19.46 | C |
| ATOM | 9156 | CB | ARG | B | 69 | −73.708 | −29.047 | −6.819 | 1.00 | 19.23 | C |
| ATOM | 9159 | CG | ARG | B | 69 | −75.030 | −29.219 | −7.509 | 1.00 | 18.83 | C |
| ATOM | 9162 | CD | ARG | B | 69 | −76.053 | −28.192 | −6.985 | 1.00 | 17.73 | C |
| ATOM | 9165 | NE | ARG | B | 69 | −75.642 | −26.830 | −7.297 | 1.00 | 16.01 | N |
| ATOM | 9167 | CZ | ARG | B | 69 | −75.330 | −25.889 | −6.417 | 1.00 | 14.68 | C |
| ATOM | 9168 | NH1 | ARG | B | 69 | −75.400 | −26.093 | −5.112 | 1.00 | 14.99 | N |
| ATOM | 9171 | NH2 | ARG | B | 69 | −74.959 | −24.707 | −6.861 | 1.00 | 15.04 | N |
| ATOM | 9174 | C | ARG | B | 69 | −73.490 | −31.489 | −6.234 | 1.00 | 20.50 | C |

TABLE 16-7-continued

Coordinates of *P. tremuloides* IspS

| ATOM | 9175 | O | ARG | B | 69 | −74.084 | −31.418 | −5.163 | 1.00 | 20.67 | O |
|---|---|---|---|---|---|---|---|---|---|---|---|
| ATOM | 9177 | N | PHE | B | 70 | −73.416 | −32.677 | −6.959 | 1.00 | 22.04 | N |
| ATOM | 9178 | CA | PHE | B | 70 | −73.853 | −33.917 | −6.450 | 1.00 | 23.03 | C |
| ATOM | 9180 | CB | PHE | B | 70 | −75.081 | −34.428 | −7.211 | 1.00 | 22.94 | C |
| ATOM | 9183 | CG | PHE | B | 70 | −76.236 | −33.503 | −7.157 | 1.00 | 21.78 | C |
| ATOM | 9184 | CD1 | PHE | B | 70 | −77.024 | −33.441 | −6.028 | 1.00 | 20.54 | C |
| ATOM | 9186 | CE1 | PHE | B | 70 | −78.076 | −32.571 | −5.959 | 1.00 | 20.32 | C |
| ATOM | 9188 | CZ | PHE | B | 70 | −78.353 | −31.752 | −7.025 | 1.00 | 20.73 | C |
| ATOM | 9190 | CE2 | PHE | B | 70 | −77.564 | −31.796 | −8.160 | 1.00 | 21.24 | C |
| ATOM | 9192 | CD2 | PHE | B | 70 | −76.511 | −32.665 | −8.220 | 1.00 | 21.22 | C |
| ATOM | 9194 | C | PHE | B | 70 | −72.765 | −34.962 | −6.570 | 1.00 | 24.33 | C |
| ATOM | 9195 | O | PHE | B | 70 | −73.069 | −36.142 | −6.614 | 1.00 | 24.56 | O |
| ATOM | 9197 | N | GLU | B | 71 | −71.500 | −34.547 | −6.624 | 1.00 | 26.01 | N |
| ATOM | 9198 | CA | GLU | B | 71 | −70.413 | −35.506 | −6.804 | 1.00 | 27.04 | C |
| ATOM | 9200 | CB | GLU | B | 71 | −69.042 | −34.824 | −6.885 | 1.00 | 27.48 | C |
| ATOM | 9203 | CG | GLU | B | 71 | −67.851 | −35.816 | −6.794 | 1.00 | 28.94 | C |
| ATOM | 9206 | CD | GLU | B | 71 | −66.491 | −35.192 | −7.081 | 1.00 | 30.38 | C |
| ATOM | 9207 | OE1 | GLU | B | 71 | −66.398 | −34.192 | −7.835 | 1.00 | 30.52 | O |
| ATOM | 9208 | OE2 | GLU | B | 71 | −65.501 | −35.730 | −6.544 | 1.00 | 32.16 | O |
| ATOM | 9209 | C | GLU | B | 71 | −70.436 | −36.531 | −5.680 | 1.00 | 27.46 | C |
| ATOM | 9210 | O | GLU | B | 71 | −70.449 | −37.723 | −5.937 | 1.00 | 27.67 | O |
| ATOM | 9212 | N | SER | B | 72 | −70.464 | −36.087 | −4.435 | 1.00 | 28.04 | N |
| ATOM | 9213 | CA | SER | B | 72 | −70.381 | −37.044 | −3.348 | 1.00 | 28.86 | C |
| ATOM | 9215 | CB | SER | B | 72 | −70.388 | −36.340 | −1.983 | 1.00 | 29.09 | C |
| ATOM | 9218 | OG | SER | B | 72 | −71.649 | −35.751 | −1.687 | 1.00 | 30.21 | O |
| ATOM | 9220 | C | SER | B | 72 | −71.519 | −38.058 | −3.481 | 1.00 | 29.30 | C |
| ATOM | 9221 | O | SER | B | 72 | −71.304 | −39.265 | −3.384 | 1.00 | 29.24 | O |
| ATOM | 9223 | N | ASP | B | 73 | −72.719 | −37.560 | −3.756 | 1.00 | 30.03 | N |
| ATOM | 9224 | CA | ASP | B | 73 | −73.897 | −38.417 | −3.874 | 1.00 | 30.63 | C |
| ATOM | 9226 | CB | ASP | B | 73 | −75.184 | −37.598 | −4.116 | 1.00 | 30.74 | C |
| ATOM | 9229 | CG | ASP | B | 73 | −75.419 | −36.509 | −3.052 | 1.00 | 31.84 | C |
| ATOM | 9230 | OD1 | ASP | B | 73 | −75.562 | −36.830 | −1.841 | 1.00 | 31.70 | O |
| ATOM | 9231 | OD2 | ASP | B | 73 | −75.473 | −35.317 | −3.443 | 1.00 | 33.81 | O |
| ATOM | 9232 | C | ASP | B | 73 | −73.722 | −39.443 | −4.994 | 1.00 | 30.81 | C |
| ATOM | 9233 | O | ASP | B | 73 | −74.130 | −40.590 | −4.835 | 1.00 | 31.39 | O |
| ATOM | 9235 | N | ILE | B | 74 | −73.122 | −39.031 | −6.112 | 1.00 | 30.96 | N |
| ATOM | 9236 | CA | ILE | B | 74 | −72.917 | −39.912 | −7.282 | 1.00 | 31.04 | C |
| ATOM | 9238 | CB | ILE | B | 74 | −72.461 | −39.114 | −8.524 | 1.00 | 30.88 | C |
| ATOM | 9240 | CG1 | ILE | B | 74 | −73.585 | −38.213 | −9.018 | 1.00 | 30.99 | C |
| ATOM | 9243 | CD1 | ILE | B | 74 | −73.105 | −37.120 | −9.923 | 1.00 | 31.54 | C |
| ATOM | 9247 | CG2 | ILE | B | 74 | −72.052 | −40.035 | −9.642 | 1.00 | 29.85 | C |
| ATOM | 9251 | C | ILE | B | 74 | −71.885 | −41.005 | −6.999 | 1.00 | 31.45 | C |
| ATOM | 9252 | O | ILE | B | 74 | −72.098 | −42.165 | −7.347 | 1.00 | 31.31 | O |
| ATOM | 9254 | N | ARG | B | 75 | −70.768 | −40.628 | −6.380 | 1.00 | 31.93 | N |
| ATOM | 9255 | CA | ARG | B | 75 | −69.778 | −41.601 | −5.947 | 1.00 | 32.38 | C |
| ATOM | 9257 | CB | ARG | B | 75 | −68.629 | −40.959 | −5.137 | 1.00 | 32.87 | C |
| ATOM | 9260 | CG | ARG | B | 75 | −67.310 | −40.751 | −5.915 | 1.00 | 35.01 | C |
| ATOM | 9263 | CD | ARG | B | 75 | −66.089 | −40.489 | −5.003 | 1.00 | 37.62 | C |
| ATOM | 9266 | NE | ARG | B | 75 | −65.260 | −41.687 | −4.783 | 1.00 | 41.03 | N |
| ATOM | 9268 | CZ | ARG | B | 75 | −64.461 | −42.253 | −5.700 | 1.00 | 44.29 | C |
| ATOM | 9269 | NH1 | ARG | B | 75 | −64.385 | −41.751 | −6.931 | 1.00 | 46.22 | N |
| ATOM | 9272 | NH2 | ARG | B | 75 | −63.741 | −43.341 | −5.404 | 1.00 | 44.30 | N |
| ATOM | 9275 | C | ARG | B | 75 | −70.478 | −42.673 | −5.126 | 1.00 | 32.18 | C |
| ATOM | 9276 | O | ARG | B | 75 | −70.307 | −43.849 | −5.398 | 1.00 | 32.19 | O |
| ATOM | 9278 | N | ARG | B | 76 | −71.280 | −42.275 | −4.143 | 1.00 | 32.21 | N |
| ATOM | 9279 | CA | ARG | B | 76 | −71.975 | −43.256 | −3.307 | 1.00 | 32.61 | C |
| ATOM | 9281 | CB | ARG | B | 76 | −72.737 | −42.582 | −2.162 | 1.00 | 32.75 | C |
| ATOM | 9284 | CG | ARG | B | 76 | −71.880 | −42.320 | −.929 | 1.00 | 33.44 | C |
| ATOM | 9287 | CD | ARG | B | 76 | −72.720 | −42.046 | .334 | 1.00 | 34.16 | C |
| ATOM | 9290 | NE | ARG | B | 76 | −73.797 | −41.074 | .124 | 1.00 | 34.53 | N |
| ATOM | 9292 | CZ | ARG | B | 76 | −73.627 | −39.765 | −.063 | 1.00 | 34.38 | C |
| ATOM | 9293 | NH1 | ARG | B | 76 | −72.414 | −39.219 | −.092 | 1.00 | 34.34 | N |
| ATOM | 9296 | NH2 | ARG | B | 76 | −74.689 | −38.993 | −.241 | 1.00 | 34.71 | N |
| ATOM | 9299 | C | ARG | B | 76 | −72.918 | −44.159 | −4.112 | 1.00 | 32.81 | C |
| ATOM | 9300 | O | ARG | B | 76 | −72.863 | −45.379 | −3.995 | 1.00 | 32.86 | O |
| ATOM | 9302 | N | ALA | B | 77 | −73.780 | −43.559 | −4.923 | 1.00 | 33.10 | N |
| ATOM | 9303 | CA | ALA | B | 77 | −74.655 | −44.307 | −5.813 | 1.00 | 33.27 | C |
| ATOM | 9305 | CB | ALA | B | 77 | −75.321 | −43.366 | −6.770 | 1.00 | 33.26 | C |
| ATOM | 9309 | C | ALA | B | 77 | −73.884 | −45.370 | −6.578 | 1.00 | 33.80 | C |
| ATOM | 9310 | O | ALA | B | 77 | −74.235 | −46.542 | −6.559 | 1.00 | 33.75 | O |
| ATOM | 9312 | N | LEU | B | 78 | −72.816 | −44.952 | −7.242 | 1.00 | 34.77 | N |
| ATOM | 9313 | CA | LEU | B | 78 | −71.987 | −45.868 | −8.019 | 1.00 | 35.41 | C |
| ATOM | 9315 | CB | LEU | B | 78 | −70.845 | −45.109 | −8.702 | 1.00 | 35.01 | C |
| ATOM | 9318 | CG | LEU | B | 78 | −71.220 | −44.092 | −9.782 | 1.00 | 34.37 | C |
| ATOM | 9320 | CD1 | LEU | B | 78 | −69.945 | −43.502 | −10.381 | 1.00 | 33.93 | C |
| ATOM | 9324 | CD2 | LEU | B | 78 | −72.109 | −44.692 | −10.873 | 1.00 | 32.94 | C |
| ATOM | 9328 | C | LEU | B | 78 | −71.409 | −46.974 | −7.142 | 1.00 | 36.50 | C |
| ATOM | 9329 | O | LEU | B | 78 | −71.336 | −48.124 | −7.552 | 1.00 | 36.87 | O |

TABLE 16-7-continued

Coordinates of *P. tremuloides* IspS

| ATOM | 9331 | N   | ASP | B | 79 | −71.005 | −46.619 | −5.931  | 1.00 | 37.74 | N |
|------|------|-----|-----|---|----|---------|---------|---------|------|-------|---|
| ATOM | 9332 | CA  | ASP | B | 79 | −70.308 | −47.545 | −5.056  | 1.00 | 38.74 | C |
| ATOM | 9334 | CB  | ASP | B | 79 | −69.787 | −46.810 | −3.819  | 1.00 | 38.99 | C |
| ATOM | 9337 | CG  | ASP | B | 79 | −68.499 | −47.386 | −3.313  | 1.00 | 40.08 | C |
| ATOM | 9338 | OD1 | ASP | B | 79 | −68.494 | −48.591 | −2.976  | 1.00 | 42.32 | O |
| ATOM | 9339 | OD2 | ASP | B | 79 | −67.494 | −46.638 | −3.261  | 1.00 | 41.24 | O |
| ATOM | 9340 | C   | ASP | B | 79 | −71.207 | −48.705 | −4.645  | 1.00 | 39.42 | C |
| ATOM | 9341 | O   | ASP | B | 79 | −70.736 | −49.835 | −4.505  | 1.00 | 39.58 | O |
| ATOM | 9343 | N   | ARG | B | 80 | −72.495 | −48.424 | −4.450  | 1.00 | 40.26 | N |
| ATOM | 9344 | CA  | ARG | B | 80 | −73.471 | −49.470 | −4.143  | 1.00 | 40.92 | C |
| ATOM | 9346 | CB  | ARG | B | 80 | −74.823 | −48.881 | −3.716  | 1.00 | 41.46 | C |
| ATOM | 9349 | CG  | ARG | B | 80 | −74.871 | −48.247 | −2.308  | 1.00 | 42.87 | C |
| ATOM | 9352 | CD  | ARG | B | 80 | −76.316 | −47.826 | −1.936  | 1.00 | 44.62 | C |
| ATOM | 9355 | NE  | ARG | B | 80 | −76.946 | −46.968 | −2.949  | 1.00 | 45.87 | N |
| ATOM | 9357 | CZ  | ARG | B | 80 | −76.741 | −45.651 | −3.089  | 1.00 | 46.82 | C |
| ATOM | 9358 | NH1 | ARG | B | 80 | −75.905 | −44.989 | −2.282  | 1.00 | 46.27 | N |
| ATOM | 9361 | NH2 | ARG | B | 80 | −77.378 | −44.988 | −4.059  | 1.00 | 47.22 | N |
| ATOM | 9364 | C   | ARG | B | 80 | −73.667 | −50.341 | −5.371  | 1.00 | 40.77 | C |
| ATOM | 9365 | O   | ARG | B | 80 | −73.642 | −51.563 | −5.275  | 1.00 | 41.06 | O |
| ATOM | 9367 | N   | PHE | B | 81 | −73.863 | −49.705 | −6.520  | 1.00 | 40.56 | N |
| ATOM | 9368 | CA  | PHE | B | 81 | −73.986 | −50.418 | −7.787  | 1.00 | 40.59 | C |
| ATOM | 9370 | CB  | PHE | B | 81 | −73.984 | −49.426 | −8.956  | 1.00 | 40.73 | C |
| ATOM | 9373 | CG  | PHE | B | 81 | −73.898 | −50.063 | −10.323 | 1.00 | 40.84 | C |
| ATOM | 9374 | CD1 | PHE | B | 81 | −75.000 | −50.668 | −10.893 | 1.00 | 41.39 | C |
| ATOM | 9376 | CE1 | PHE | B | 81 | −74.925 | −51.236 | −12.167 | 1.00 | 41.67 | C |
| ATOM | 9378 | CZ  | PHE | B | 81 | −73.741 | −51.191 | −12.877 | 1.00 | 41.33 | C |
| ATOM | 9380 | CE2 | PHE | B | 81 | −72.638 | −50.580 | −12.326 | 1.00 | 41.19 | C |
| ATOM | 9382 | CD2 | PHE | B | 81 | −72.720 | −50.012 | −11.057 | 1.00 | 41.39 | C |
| ATOM | 9384 | C   | PHE | B | 81 | −72.871 | −51.441 | −7.953  | 1.00 | 40.47 | C |
| ATOM | 9385 | O   | PHE | B | 81 | −73.134 | −52.583 | −8.311  | 1.00 | 40.85 | O |
| ATOM | 9387 | N   | VAL | B | 82 | −71.633 | −51.051 | −7.683  | 1.00 | 40.26 | N |
| ATOM | 9388 | CA  | VAL | B | 82 | −70.522 | −51.986 | −7.821  | 1.00 | 40.24 | C |
| ATOM | 9390 | CB  | VAL | B | 82 | −69.173 | −51.386 | −7.379  | 1.00 | 40.28 | C |
| ATOM | 9392 | CG1 | VAL | B | 82 | −68.164 | −52.493 | −7.063  | 1.00 | 39.98 | C |
| ATOM | 9396 | CG2 | VAL | B | 82 | −68.644 | −50.462 | −8.451  | 1.00 | 40.09 | C |
| ATOM | 9400 | C   | VAL | B | 82 | −70.788 | −53.230 | −7.005  | 1.00 | 40.16 | C |
| ATOM | 9401 | O   | VAL | B | 82 | −70.880 | −54.313 | −7.559  | 1.00 | 40.13 | O |
| ATOM | 9403 | N   | SER | B | 83 | −70.953 | −53.056 | −5.698  | 1.00 | 40.26 | N |
| ATOM | 9404 | CA  | SER | B | 83 | −71.070 | −54.174 | −4.749  | 1.00 | 40.43 | C |
| ATOM | 9406 | CB  | SER | B | 83 | −70.797 | −53.666 | −3.331  | 1.00 | 40.54 | C |
| ATOM | 9409 | OG  | SER | B | 83 | −71.256 | −52.330 | −3.191  | 1.00 | 40.89 | O |
| ATOM | 9411 | C   | SER | B | 83 | −72.415 | −54.912 | −4.831  | 1.00 | 40.34 | C |
| ATOM | 9412 | O   | SER | B | 83 | −73.137 | −55.046 | −3.845  | 1.00 | 39.99 | O |
| ATOM | 9414 | N   | SER | B | 84 | −72.698 | −55.400 | −6.038  | 1.00 | 40.57 | N |
| ATOM | 9415 | CA  | SER | B | 84 | −73.902 | −56.154 | −6.411  | 1.00 | 40.63 | C |
| ATOM | 9417 | CB  | SER | B | 84 | −75.154 | −55.679 | −5.651  | 1.00 | 40.56 | C |
| ATOM | 9420 | OG  | SER | B | 84 | −75.292 | −54.268 | −5.663  | 1.00 | 39.82 | O |
| ATOM | 9422 | C   | SER | B | 84 | −74.104 | −56.026 | −7.940  | 1.00 | 40.85 | C |
| ATOM | 9423 | O   | SER | B | 84 | −75.104 | −55.462 | −8.395  | 1.00 | 41.24 | O |
| ATOM | 9425 | N   | GLY | B | 85 | −73.136 | −56.524 | −8.720  | 1.00 | 40.75 | N |
| ATOM | 9426 | CA  | GLY | B | 85 | −73.201 | −56.506 | −10.191 | 1.00 | 40.64 | C |
| ATOM | 9429 | C   | GLY | B | 85 | −73.225 | −55.120 | −10.815 | 1.00 | 40.64 | C |
| ATOM | 9430 | O   | GLY | B | 85 | −74.133 | −54.794 | −11.590 | 1.00 | 40.32 | O |
| ATOM | 9432 | N   | THR | B | 93 | −74.847 | −57.360 | −18.759 | 1.00 | 36.30 | N |
| ATOM | 9433 | CA  | THR | B | 93 | −75.593 | −58.129 | −19.774 | 1.00 | 35.99 | C |
| ATOM | 9435 | CB  | THR | B | 93 | −76.251 | −59.379 | −19.152 | 1.00 | 35.87 | C |
| ATOM | 9437 | OG1 | THR | B | 93 | −76.347 | −60.389 | −20.158 | 1.00 | 35.64 | O |
| ATOM | 9439 | CG2 | THR | B | 93 | −77.646 | −59.062 | −18.548 | 1.00 | 34.95 | C |
| ATOM | 9443 | C   | THR | B | 93 | −76.625 | −57.274 | −20.583 | 1.00 | 35.90 | C |
| ATOM | 9444 | O   | THR | B | 93 | −77.764 | −57.688 | −20.843 | 1.00 | 35.74 | O |
| ATOM | 9446 | N   | SER | B | 94 | −76.175 | −56.076 | −20.963 | 1.00 | 35.58 | N |
| ATOM | 9447 | CA  | SER | B | 94 | −76.874 | −55.150 | −21.866 | 1.00 | 34.97 | C |
| ATOM | 9449 | CB  | SER | B | 94 | −78.074 | −54.472 | −21.190 | 1.00 | 35.06 | C |
| ATOM | 9452 | OG  | SER | B | 94 | −77.702 | −53.260 | −20.541 | 1.00 | 34.37 | O |
| ATOM | 9454 | C   | SER | B | 94 | −75.831 | −54.097 | −22.232 | 1.00 | 34.39 | C |
| ATOM | 9455 | O   | SER | B | 94 | −75.212 | −53.518 | −21.341 | 1.00 | 34.11 | O |
| ATOM | 9457 | N   | LEU | B | 95 | −75.619 | −53.864 | −23.522 | 1.00 | 33.77 | N |
| ATOM | 9458 | CA  | LEU | B | 95 | −74.490 | −53.045 | −23.952 | 1.00 | 33.33 | C |
| ATOM | 9460 | CB  | LEU | B | 95 | −74.373 | −53.010 | −25.475 | 1.00 | 33.30 | C |
| ATOM | 9463 | CG  | LEU | B | 95 | −73.154 | −52.246 | −26.006 | 1.00 | 33.27 | C |
| ATOM | 9465 | CD1 | LEU | B | 95 | −71.909 | −52.455 | −25.137 | 1.00 | 32.89 | C |
| ATOM | 9469 | CD2 | LEU | B | 95 | −72.864 | −52.649 | −27.438 | 1.00 | 33.19 | C |
| ATOM | 9473 | C   | LEU | B | 95 | −74.551 | −51.623 | −23.413 | 1.00 | 33.00 | C |
| ATOM | 9474 | O   | LEU | B | 95 | −73.588 | −51.151 | −22.809 | 1.00 | 32.83 | O |
| ATOM | 9476 | N   | HIS | B | 96 | −75.678 | −50.949 | −23.633 | 1.00 | 32.64 | N |
| ATOM | 9477 | CA  | HIS | B | 96 | −75.853 | −49.576 | −23.171 | 1.00 | 32.39 | C |
| ATOM | 9479 | CB  | HIS | B | 96 | −77.246 | −49.069 | −23.527 | 1.00 | 32.64 | C |
| ATOM | 9482 | CG  | HIS | B | 96 | −77.528 | −47.689 | −23.025 | 1.00 | 34.16 | C |

TABLE 16-7-continued

Coordinates of *P. tremuloides* IspS

| ATOM | 9483 | ND1 | HIS | B | 96 | −76.565 | −46.703 | −22.981 | 1.00 | 36.21 | N |
|------|------|-----|-----|---|----|---------|---------|---------|------|-------|---|
| ATOM | 9485 | CE1 | HIS | B | 96 | −77.096 | −45.594 | −22.496 | 1.00 | 36.92 | C |
| ATOM | 9487 | NE2 | HIS | B | 96 | −78.371 | −45.827 | −22.227 | 1.00 | 37.06 | N |
| ATOM | 9489 | CD2 | HIS | B | 96 | −78.664 | −47.130 | −22.548 | 1.00 | 35.43 | C |
| ATOM | 9491 | C   | HIS | B | 96 | −75.612 | −49.445 | −21.665 | 1.00 | 31.78 | C |
| ATOM | 9492 | O   | HIS | B | 96 | −74.936 | −48.523 | −21.215 | 1.00 | 31.95 | O |
| ATOM | 9494 | N   | GLY | B | 97 | −76.156 | −50.372 | −20.887 | 1.00 | 31.10 | N |
| ATOM | 9495 | CA  | GLY | B | 97 | −75.907 | −50.396 | −19.446 | 1.00 | 30.52 | C |
| ATOM | 9498 | C   | GLY | B | 97 | −74.434 | −50.532 | −19.085 | 1.00 | 29.95 | C |
| ATOM | 9499 | O   | GLY | B | 97 | −73.936 | −49.797 | −18.241 | 1.00 | 30.21 | O |
| ATOM | 9501 | N   | THR | B | 98 | −73.740 | −51.470 | −19.726 | 1.00 | 29.15 | N |
| ATOM | 9502 | CA  | THR | B | 98 | −72.314 | −51.690 | −19.490 | 1.00 | 28.55 | C |
| ATOM | 9504 | CB  | THR | B | 98 | −71.803 | −52.955 | −20.248 | 1.00 | 28.48 | C |
| ATOM | 9506 | OG1 | THR | B | 98 | −72.678 | −54.066 | −19.997 | 1.00 | 28.41 | O |
| ATOM | 9508 | CG2 | THR | B | 98 | −70.405 | −53.331 | −19.816 | 1.00 | 27.74 | C |
| ATOM | 9512 | C   | THR | B | 98 | −71.492 | −50.452 | −19.894 | 1.00 | 28.31 | C |
| ATOM | 9513 | O   | THR | B | 98 | −70.658 | −49.979 | −19.127 | 1.00 | 28.13 | O |
| ATOM | 9515 | N   | ALA | B | 99 | −71.750 | −49.910 | −21.080 | 1.00 | 28.04 | N |
| ATOM | 9516 | CA  | ALA | B | 99 | −70.984 | −48.758 | −21.578 | 1.00 | 27.88 | C |
| ATOM | 9518 | CB  | ALA | B | 99 | −71.387 | −48.406 | −23.014 | 1.00 | 27.78 | C |
| ATOM | 9522 | C   | ALA | B | 99 | −71.127 | −47.538 | −20.684 | 1.00 | 27.62 | C |
| ATOM | 9523 | O   | ALA | B | 99 | −70.135 | −46.885 | −20.361 | 1.00 | 27.84 | O |
| ATOM | 9525 | N   | LEU | B | 100 | −72.357 | −47.233 | −20.290 | 1.00 | 27.20 | N |
| ATOM | 9526 | CA  | LEU | B | 100 | −72.613 | −46.088 | −19.422 | 1.00 | 27.08 | C |
| ATOM | 9528 | CB  | LEU | B | 100 | −74.122 | −45.900 | −19.230 | 1.00 | 26.95 | C |
| ATOM | 9531 | CG  | LEU | B | 100 | −74.560 | −44.715 | −18.367 | 1.00 | 26.27 | C |
| ATOM | 9533 | CD1 | LEU | B | 100 | −73.753 | −43.478 | −18.734 | 1.00 | 26.19 | C |
| ATOM | 9537 | CD2 | LEU | B | 100 | −76.052 | −44.445 | −18.504 | 1.00 | 25.20 | C |
| ATOM | 9541 | C   | LEU | B | 100 | −71.928 | −46.221 | −18.046 | 1.00 | 27.23 | C |
| ATOM | 9542 | O   | LEU | B | 100 | −71.368 | −45.243 | −17.523 | 1.00 | 27.16 | O |
| ATOM | 9544 | N   | SER | B | 101 | −71.980 | −47.429 | −17.472 | 1.00 | 27.00 | N |
| ATOM | 9545 | CA  | SER | B | 101 | −71.475 | −47.682 | −16.117 | 1.00 | 26.63 | C |
| ATOM | 9547 | CB  | SER | B | 101 | −72.039 | −48.992 | −15.568 | 1.00 | 26.49 | C |
| ATOM | 9550 | OG  | SER | B | 101 | −71.758 | −50.063 | −16.442 | 1.00 | 26.38 | O |
| ATOM | 9552 | C   | SER | B | 101 | −69.956 | −47.740 | −16.090 | 1.00 | 26.47 | C |
| ATOM | 9553 | O   | SER | B | 101 | −69.326 | −47.324 | −15.121 | 1.00 | 26.35 | O |
| ATOM | 9555 | N   | PHE | B | 102 | −69.381 | −48.288 | −17.154 | 1.00 | 26.29 | N |
| ATOM | 9556 | CA  | PHE | B | 102 | −67.934 | −48.332 | −17.322 | 1.00 | 25.91 | C |
| ATOM | 9558 | CB  | PHE | B | 102 | −67.588 | −49.005 | −18.652 | 1.00 | 25.96 | C |
| ATOM | 9561 | CG  | PHE | B | 102 | −66.133 | −49.020 | −18.958 | 1.00 | 25.81 | C |
| ATOM | 9562 | CD1 | PHE | B | 102 | −65.360 | −50.115 | −18.633 | 1.00 | 25.96 | C |
| ATOM | 9564 | CE1 | PHE | B | 102 | −63.999 | −50.122 | −18.909 | 1.00 | 26.94 | C |
| ATOM | 9566 | CZ  | PHE | B | 102 | −63.403 | −49.026 | −19.519 | 1.00 | 26.27 | C |
| ATOM | 9568 | CE2 | PHE | B | 102 | −64.174 | −47.930 | −19.848 | 1.00 | 26.19 | C |
| ATOM | 9570 | CD2 | PHE | B | 102 | −65.531 | −47.933 | −19.573 | 1.00 | 26.04 | C |
| ATOM | 9572 | C   | PHE | B | 102 | −67.416 | −46.911 | −17.315 | 1.00 | 25.56 | C |
| ATOM | 9573 | O   | PHE | B | 102 | −66.486 | −46.564 | −16.568 | 1.00 | 25.37 | O |
| ATOM | 9575 | N   | ARG | B | 103 | −68.050 | −46.095 | −18.152 | 1.00 | 25.20 | N |
| ATOM | 9576 | CA  | ARG | B | 103 | −67.663 | −44.696 | −18.322 | 1.00 | 25.09 | C |
| ATOM | 9578 | CB  | ARG | B | 103 | −68.510 | −44.026 | −19.400 | 1.00 | 25.12 | C |
| ATOM | 9581 | CG  | ARG | B | 103 | −68.194 | −42.561 | −19.572 | 1.00 | 25.41 | C |
| ATOM | 9584 | CD  | ARG | B | 103 | −68.744 | −42.035 | −20.889 | 1.00 | 26.68 | C |
| ATOM | 9587 | NE  | ARG | B | 103 | −70.197 | −41.843 | −20.877 | 1.00 | 27.49 | N |
| ATOM | 9589 | CZ  | ARG | B | 103 | −70.826 | −40.851 | −20.246 | 1.00 | 26.56 | C |
| ATOM | 9590 | NH1 | ARG | B | 103 | −70.139 | −39.963 | −19.531 | 1.00 | 27.11 | N |
| ATOM | 9593 | NH2 | ARG | B | 103 | −72.148 | −40.759 | −20.310 | 1.00 | 25.20 | N |
| ATOM | 9596 | C   | ARG | B | 103 | −67.785 | −43.898 | −17.033 | 1.00 | 24.61 | C |
| ATOM | 9597 | O   | ARG | B | 103 | −66.865 | −43.168 | −16.659 | 1.00 | 24.67 | O |
| ATOM | 9599 | N   | LEU | B | 104 | −68.927 | −44.013 | −16.371 | 1.00 | 23.79 | N |
| ATOM | 9600 | CA  | LEU | B | 104 | −69.125 | −43.263 | −15.148 | 1.00 | 23.23 | C |
| ATOM | 9602 | CB  | LEU | B | 104 | −70.591 | −43.342 | −14.693 | 1.00 | 23.01 | C |
| ATOM | 9605 | CG  | LEU | B | 104 | −71.607 | −42.620 | −15.584 | 1.00 | 21.36 | C |
| ATOM | 9607 | CD1 | LEU | B | 104 | −73.002 | −42.860 | −15.067 | 1.00 | 19.31 | C |
| ATOM | 9611 | CD2 | LEU | B | 104 | −71.310 | −41.157 | −15.633 | 1.00 | 19.57 | C |
| ATOM | 9615 | C   | LEU | B | 104 | −68.156 | −43.781 | −14.071 | 1.00 | 23.15 | C |
| ATOM | 9616 | O   | LEU | B | 104 | −67.445 | −43.007 | −13.423 | 1.00 | 23.40 | O |
| ATOM | 9618 | N   | LEU | B | 105 | −68.106 | −45.091 | −13.894 | 1.00 | 22.79 | N |
| ATOM | 9619 | CA  | LEU | B | 105 | −67.203 | −45.659 | −12.916 | 1.00 | 22.40 | C |
| ATOM | 9621 | CB  | LEU | B | 105 | −67.303 | −47.178 | −12.912 | 1.00 | 22.42 | C |
| ATOM | 9624 | CG  | LEU | B | 105 | −68.505 | −47.709 | −12.163 | 1.00 | 21.82 | C |
| ATOM | 9626 | CD1 | LEU | B | 105 | −68.810 | −49.120 | −12.591 | 1.00 | 21.95 | C |
| ATOM | 9630 | CD2 | LEU | B | 105 | −68.201 | −47.648 | −10.692 | 1.00 | 22.14 | C |
| ATOM | 9634 | C   | LEU | B | 105 | −65.767 | −45.239 | −13.196 | 1.00 | 22.33 | C |
| ATOM | 9635 | O   | LEU | B | 105 | −65.049 | −44.823 | −12.275 | 1.00 | 22.13 | O |
| ATOM | 9637 | N   | ARG | B | 106 | −65.331 | −45.342 | −14.451 | 1.00 | 22.08 | N |
| ATOM | 9638 | CA  | ARG | B | 106 | −63.953 | −44.973 | −14.730 | 1.00 | 22.20 | C |
| ATOM | 9640 | CB  | ARG | B | 106 | −63.521 | −45.266 | −16.151 | 1.00 | 22.33 | C |
| ATOM | 9643 | CG  | ARG | B | 106 | −62.075 | −44.827 | −16.329 | 1.00 | 23.60 | C |

TABLE 16-7-continued

Coordinates of *P. tremuloides* IspS

| ATOM | 9646 | CD | ARG | B | 106 | −61.383 | −45.445 | −17.513 | 1.00 | 24.71 | C |
|---|---|---|---|---|---|---|---|---|---|---|---|
| ATOM | 9649 | NE | ARG | B | 106 | −61.078 | −46.852 | −17.319 | 1.00 | 24.66 | N |
| ATOM | 9651 | CZ | ARG | B | 106 | −60.418 | −47.582 | −18.206 | 1.00 | 25.75 | C |
| ATOM | 9652 | NH1 | ARG | B | 106 | −59.995 | −47.028 | −19.337 | 1.00 | 26.41 | N |
| ATOM | 9655 | NH2 | ARG | B | 106 | −60.182 | −48.866 | −17.971 | 1.00 | 26.54 | N |
| ATOM | 9658 | C | ARG | B | 106 | −63.732 | −43.504 | −14.438 | 1.00 | 21.75 | C |
| ATOM | 9659 | O | ARG | B | 106 | −62.801 | −43.145 | −13.725 | 1.00 | 21.50 | O |
| ATOM | 9661 | N | GLN | B | 107 | −64.609 | −42.680 | −15.003 | 1.00 | 21.69 | N |
| ATOM | 9662 | CA | GLN | B | 107 | −64.630 | −41.239 | −14.794 | 1.00 | 21.64 | C |
| ATOM | 9664 | CB | GLN | B | 107 | −65.964 | −40.664 | −15.261 | 1.00 | 21.71 | C |
| ATOM | 9667 | CG | GLN | B | 107 | −66.169 | −39.178 | −14.929 | 1.00 | 21.97 | C |
| ATOM | 9670 | CD | GLN | B | 107 | −67.588 | −38.723 | −15.172 | 1.00 | 21.54 | C |
| ATOM | 9671 | OE1 | GLN | B | 107 | −68.355 | −39.365 | −15.906 | 1.00 | 20.08 | O |
| ATOM | 9672 | NE2 | GLN | B | 107 | −67.948 | −37.600 | −14.556 | 1.00 | 21.45 | N |
| ATOM | 9675 | C | GLN | B | 107 | −64.454 | −40.850 | −13.352 | 1.00 | 21.70 | C |
| ATOM | 9676 | O | GLN | B | 107 | −63.776 | −39.865 | −13.078 | 1.00 | 22.14 | O |
| ATOM | 9678 | N | HIS | B | 108 | −65.091 | −41.599 | −12.450 | 1.00 | 21.53 | N |
| ATOM | 9679 | CA | HIS | B | 108 | −65.049 | −41.326 | −11.019 | 1.00 | 21.63 | C |
| ATOM | 9681 | CB | HIS | B | 108 | −66.447 | −41.535 | −10.429 | 1.00 | 21.47 | C |
| ATOM | 9684 | CG | HIS | B | 108 | −67.416 | −40.445 | −10.752 | 1.00 | 20.91 | C |
| ATOM | 9685 | ND1 | HIS | B | 108 | −67.541 | −39.315 | −9.976 | 1.00 | 20.66 | N |
| ATOM | 9687 | CE1 | HIS | B | 108 | −68.476 | −38.535 | −10.490 | 1.00 | 20.90 | C |
| ATOM | 9689 | NE2 | HIS | B | 108 | −68.966 | −39.118 | −11.567 | 1.00 | 19.67 | N |
| ATOM | 9691 | CD2 | HIS | B | 108 | −68.326 | −40.320 | −11.747 | 1.00 | 20.76 | C |
| ATOM | 9693 | C | HIS | B | 108 | −64.024 | −42.209 | −10.269 | 1.00 | 22.22 | C |
| ATOM | 9694 | O | HIS | B | 108 | −64.220 | −42.553 | −9.104 | 1.00 | 22.17 | O |
| ATOM | 9696 | N | GLY | B | 109 | −62.950 | −42.613 | −10.933 | 1.00 | 22.91 | N |
| ATOM | 9697 | CA | GLY | B | 109 | −61.846 | −43.288 | −10.245 | 1.00 | 23.85 | C |
| ATOM | 9700 | C | GLY | B | 109 | −61.986 | −44.748 | −9.800 | 1.00 | 24.50 | C |
| ATOM | 9701 | O | GLY | B | 109 | −61.053 | −45.306 | −9.189 | 1.00 | 24.12 | O |
| ATOM | 9703 | N | PHE | B | 110 | −63.128 | −45.371 | −10.094 | 1.00 | 25.16 | N |
| ATOM | 9704 | CA | PHE | B | 110 | −63.309 | −46.791 | −9.800 | 1.00 | 25.67 | C |
| ATOM | 9706 | CB | PHE | B | 110 | −64.782 | −47.187 | −9.891 | 1.00 | 25.80 | C |
| ATOM | 9709 | CG | PHE | B | 110 | −65.625 | −46.656 | −8.772 | 1.00 | 26.12 | C |
| ATOM | 9710 | CD1 | PHE | B | 110 | −65.564 | −47.230 | −7.510 | 1.00 | 27.13 | C |
| ATOM | 9712 | CE1 | PHE | B | 110 | −66.353 | −46.751 | −6.468 | 1.00 | 27.42 | C |
| ATOM | 9714 | CZ | PHE | B | 110 | −67.215 | −45.691 | −6.692 | 1.00 | 26.93 | C |
| ATOM | 9716 | CE2 | PHE | B | 110 | −67.284 | −45.119 | −7.954 | 1.00 | 26.49 | C |
| ATOM | 9718 | CD2 | PHE | B | 110 | −66.494 | −45.601 | −8.981 | 1.00 | 25.96 | C |
| ATOM | 9720 | C | PHE | B | 110 | −62.505 | −47.615 | −10.793 | 1.00 | 25.92 | C |
| ATOM | 9721 | O | PHE | B | 110 | −62.232 | −47.157 | −11.898 | 1.00 | 26.41 | O |
| ATOM | 9723 | N | GLU | B | 111 | −62.134 | −48.832 | −10.406 | 1.00 | 26.06 | N |
| ATOM | 9724 | CA | GLU | B | 111 | −61.403 | −49.724 | −11.304 | 1.00 | 26.17 | C |
| ATOM | 9726 | CB | GLU | B | 111 | −60.444 | −50.609 | −10.511 | 1.00 | 26.50 | C |
| ATOM | 9729 | CG | GLU | B | 111 | −59.372 | −51.272 | −11.374 | 1.00 | 28.11 | C |
| ATOM | 9732 | CD | GLU | B | 111 | −58.607 | −52.377 | −10.646 | 1.00 | 30.70 | C |
| ATOM | 9733 | OE1 | GLU | B | 111 | −58.660 | −52.436 | −9.390 | 1.00 | 31.99 | O |
| ATOM | 9734 | OE2 | GLU | B | 111 | −57.948 | −53.190 | −11.338 | 1.00 | 32.09 | O |
| ATOM | 9735 | C | GLU | B | 111 | −62.355 | −50.598 | −12.130 | 1.00 | 25.60 | C |
| ATOM | 9736 | O | GLU | B | 111 | −63.116 | −51.388 | −11.585 | 1.00 | 25.48 | O |
| ATOM | 9738 | N | VAL | B | 112 | −62.314 | −50.439 | −13.447 | 1.00 | 25.24 | N |
| ATOM | 9739 | CA | VAL | B | 112 | −63.026 | −51.331 | −14.357 | 1.00 | 24.90 | C |
| ATOM | 9741 | CB | VAL | B | 112 | −64.308 | −50.712 | −14.908 | 1.00 | 24.92 | C |
| ATOM | 9743 | CG1 | VAL | B | 112 | −65.268 | −50.437 | −13.771 | 1.00 | 25.26 | C |
| ATOM | 9747 | CG2 | VAL | B | 112 | −63.999 | −49.450 | −15.706 | 1.00 | 24.77 | C |
| ATOM | 9751 | C | VAL | B | 112 | −62.144 | −51.701 | −15.522 | 1.00 | 24.66 | C |
| ATOM | 9752 | O | VAL | B | 112 | −61.217 | −50.964 | −15.862 | 1.00 | 23.80 | O |
| ATOM | 9754 | N | SER | B | 113 | −62.467 | −52.842 | −16.132 | 1.00 | 24.88 | N |
| ATOM | 9755 | CA | SER | B | 113 | −61.604 | −53.494 | −17.109 | 1.00 | 25.21 | C |
| ATOM | 9757 | CB | SER | B | 113 | −61.286 | −54.913 | −16.654 | 1.00 | 24.94 | C |
| ATOM | 9760 | OG | SER | B | 113 | −60.357 | −55.523 | −17.528 | 1.00 | 24.31 | O |
| ATOM | 9762 | C | SER | B | 113 | −62.233 | −53.532 | −18.492 | 1.00 | 25.88 | C |
| ATOM | 9763 | O | SER | B | 113 | −63.446 | −53.651 | −18.630 | 1.00 | 25.86 | O |
| ATOM | 9765 | N | GLN | B | 114 | −61.406 | −53.438 | −19.526 | 1.00 | 26.92 | N |
| ATOM | 9766 | CA | GLN | B | 114 | −61.928 | −53.491 | −20.880 | 1.00 | 27.83 | C |
| ATOM | 9768 | CB | GLN | B | 114 | −60.846 | −53.194 | −21.917 | 1.00 | 27.75 | C |
| ATOM | 9771 | CG | GLN | B | 114 | −59.559 | −53.952 | −21.726 | 1.00 | 28.05 | C |
| ATOM | 9774 | CD | GLN | B | 114 | −58.739 | −54.077 | −23.007 | 1.00 | 28.39 | C |
| ATOM | 9775 | OE1 | GLN | B | 114 | −59.086 | −53.515 | −24.051 | 1.00 | 29.05 | O |
| ATOM | 9776 | NE2 | GLN | B | 114 | −57.637 | −54.808 | −22.925 | 1.00 | 27.62 | N |
| ATOM | 9779 | C | GLN | B | 114 | −62.615 | −54.827 | −21.158 | 1.00 | 28.78 | C |
| ATOM | 9780 | O | GLN | B | 114 | −63.484 | −54.905 | −22.022 | 1.00 | 29.10 | O |
| ATOM | 9782 | N | GLU | B | 115 | −62.248 | −55.861 | −20.401 | 1.00 | 29.99 | N |
| ATOM | 9783 | CA | GLU | B | 115 | −62.888 | −57.181 | −20.505 | 1.00 | 30.89 | C |
| ATOM | 9785 | CB | GLU | B | 115 | −62.252 | −58.202 | −19.549 | 1.00 | 31.10 | C |
| ATOM | 9788 | CG | GLU | B | 115 | −60.740 | −58.394 | −19.697 | 1.00 | 32.35 | C |
| ATOM | 9791 | CD | GLU | B | 115 | −60.320 | −58.796 | −21.106 | 1.00 | 34.20 | C |
| ATOM | 9792 | OE1 | GLU | B | 115 | −60.965 | −59.699 | −21.688 | 1.00 | 34.94 | O |

TABLE 16-7-continued

Coordinates of *P. tremuloides* IspS

| ATOM | 9793 | OE2 | GLU | B | 115 | −59.348 | −58.201 | −21.634 | 1.00 | 35.60 | O |
|---|---|---|---|---|---|---|---|---|---|---|---|
| ATOM | 9794 | C | GLU | B | 115 | −64.380 | −57.120 | −20.224 | 1.00 | 31.26 | C |
| ATOM | 9795 | O | GLU | B | 115 | −65.125 | −57.971 | −20.691 | 1.00 | 31.54 | O |
| ATOM | 9797 | N | ALA | B | 116 | −64.825 | −56.127 | −19.465 | 1.00 | 31.91 | N |
| ATOM | 9798 | CA | ALA | B | 116 | −66.255 | −55.937 | −19.259 | 1.00 | 32.69 | C |
| ATOM | 9800 | CB | ALA | B | 116 | −66.521 | −54.648 | −18.513 | 1.00 | 32.62 | C |
| ATOM | 9804 | C | ALA | B | 116 | −66.999 | −55.950 | −20.597 | 1.00 | 33.33 | C |
| ATOM | 9805 | O | ALA | B | 116 | −68.156 | −56.364 | −20.668 | 1.00 | 33.26 | O |
| ATOM | 9807 | N | PHE | B | 117 | −66.316 | −55.521 | −21.655 | 1.00 | 34.16 | N |
| ATOM | 9808 | CA | PHE | B | 117 | −66.889 | −55.498 | −22.996 | 1.00 | 34.98 | C |
| ATOM | 9810 | CB | PHE | B | 117 | −66.310 | −54.314 | −23.766 | 1.00 | 35.02 | C |
| ATOM | 9813 | CG | PHE | B | 117 | −66.868 | −52.997 | −23.345 | 1.00 | 35.06 | C |
| ATOM | 9814 | CD1 | PHE | B | 117 | −66.061 | −52.046 | −22.729 | 1.00 | 35.33 | C |
| ATOM | 9816 | CE1 | PHE | B | 117 | −66.576 | −50.825 | −22.342 | 1.00 | 35.16 | C |
| ATOM | 9818 | CZ | PHE | B | 117 | −67.907 | −50.544 | −22.570 | 1.00 | 35.37 | C |
| ATOM | 9820 | CE2 | PHE | B | 117 | −68.723 | −51.488 | −23.187 | 1.00 | 35.28 | C |
| ATOM | 9822 | CD2 | PHE | B | 117 | −68.201 | −52.701 | −23.571 | 1.00 | 34.68 | C |
| ATOM | 9824 | C | PHE | B | 117 | −66.676 | −56.766 | −23.830 | 1.00 | 35.86 | C |
| ATOM | 9825 | O | PHE | B | 117 | −66.934 | −56.755 | −25.037 | 1.00 | 35.91 | O |
| ATOM | 9827 | N | SER | B | 118 | −66.215 | −57.853 | −23.212 | 1.00 | 36.98 | N |
| ATOM | 9828 | CA | SER | B | 118 | −65.924 | −59.086 | −23.960 | 1.00 | 37.76 | C |
| ATOM | 9830 | CB | SER | B | 118 | −64.836 | −59.907 | −23.262 | 1.00 | 37.73 | C |
| ATOM | 9833 | OG | SER | B | 118 | −65.272 | −60.346 | −21.987 | 1.00 | 37.77 | O |
| ATOM | 9835 | C | SER | B | 118 | −67.178 | −59.939 | −24.215 | 1.00 | 38.48 | C |
| ATOM | 9836 | O | SER | B | 118 | −67.207 | −60.724 | −25.157 | 1.00 | 38.42 | O |
| ATOM | 9838 | N | GLY | B | 119 | −68.221 | −59.765 | −23.407 | 1.00 | 39.51 | N |
| ATOM | 9839 | CA | GLY | B | 119 | −69.481 | −60.473 | −23.629 | 1.00 | 40.51 | C |
| ATOM | 9842 | C | GLY | B | 119 | −70.287 | −60.034 | −24.848 | 1.00 | 41.51 | C |
| ATOM | 9843 | O | GLY | B | 119 | −71.444 | −60.433 | −25.002 | 1.00 | 41.53 | O |
| ATOM | 9845 | N | PHE | B | 120 | −69.688 | −59.210 | −25.709 | 1.00 | 42.79 | N |
| ATOM | 9846 | CA | PHE | B | 120 | −70.382 | −58.621 | −26.864 | 1.00 | 43.81 | C |
| ATOM | 9848 | CB | PHE | B | 120 | −70.643 | −57.121 | −26.601 | 1.00 | 43.76 | C |
| ATOM | 9851 | CG | PHE | B | 120 | −71.367 | −56.853 | −25.293 | 1.00 | 43.65 | C |
| ATOM | 9852 | CD1 | PHE | B | 120 | −72.762 | −56.874 | −25.230 | 1.00 | 43.48 | C |
| ATOM | 9854 | CE1 | PHE | B | 120 | −73.437 | −56.650 | −24.023 | 1.00 | 43.03 | C |
| ATOM | 9856 | CZ | PHE | B | 120 | −72.717 | −56.413 | −22.865 | 1.00 | 43.09 | C |
| ATOM | 9858 | CE2 | PHE | B | 120 | −71.323 | −56.397 | −22.909 | 1.00 | 43.38 | C |
| ATOM | 9860 | CD2 | PHE | B | 120 | −70.655 | −56.619 | −24.120 | 1.00 | 43.41 | C |
| ATOM | 9862 | C | PHE | B | 120 | −69.607 | −58.832 | −28.175 | 1.00 | 44.81 | C |
| ATOM | 9863 | O | PHE | B | 120 | −69.930 | −58.238 | −29.205 | 1.00 | 44.65 | O |
| ATOM | 9865 | N | LYS | B | 121 | −68.602 | −59.705 | −28.126 | 1.00 | 46.19 | N |
| ATOM | 9866 | CA | LYS | B | 121 | −67.757 | −60.004 | −29.272 | 1.00 | 47.31 | C |
| ATOM | 9868 | CB | LYS | B | 121 | −66.275 | −59.928 | −28.870 | 1.00 | 47.47 | C |
| ATOM | 9871 | CG | LYS | B | 121 | −65.743 | −58.495 | −28.637 | 1.00 | 48.13 | C |
| ATOM | 9874 | CD | LYS | B | 121 | −64.532 | −58.439 | −27.675 | 1.00 | 48.89 | C |
| ATOM | 9877 | CE | LYS | B | 121 | −63.261 | −59.094 | −28.241 | 1.00 | 49.20 | C |
| ATOM | 9880 | NZ | LYS | B | 121 | −62.541 | −58.232 | −29.218 | 1.00 | 49.04 | N |
| ATOM | 9884 | C | LYS | B | 121 | −68.096 | −61.400 | −29.810 | 1.00 | 48.15 | C |
| ATOM | 9885 | O | LYS | B | 121 | −68.199 | −62.361 | −29.043 | 1.00 | 48.36 | O |
| ATOM | 9887 | N | ASP | B | 122 | −68.270 | −61.510 | −31.126 | 1.00 | 49.04 | N |
| ATOM | 9888 | CA | ASP | B | 122 | −68.611 | −62.788 | −31.754 | 1.00 | 49.60 | C |
| ATOM | 9890 | CB | ASP | B | 122 | −69.070 | −62.596 | −33.217 | 1.00 | 49.52 | C |
| ATOM | 9893 | CG | ASP | B | 122 | −67.989 | −62.015 | −34.126 | 1.00 | 49.18 | C |
| ATOM | 9894 | OD1 | ASP | B | 122 | −66.792 | −62.306 | −33.938 | 1.00 | 48.96 | O |
| ATOM | 9895 | OD2 | ASP | B | 122 | −68.351 | −61.268 | −35.057 | 1.00 | 48.82 | O |
| ATOM | 9896 | C | ASP | B | 122 | −67.455 | −63.785 | −31.651 | 1.00 | 50.31 | C |
| ATOM | 9897 | O | ASP | B | 122 | −66.369 | −63.441 | −31.171 | 1.00 | 50.33 | O |
| ATOM | 9899 | N | GLN | B | 123 | −67.705 | −65.014 | −32.098 | 1.00 | 51.05 | N |
| ATOM | 9900 | CA | GLN | B | 123 | −66.716 | −66.095 | −32.057 | 1.00 | 51.61 | C |
| ATOM | 9902 | CB | GLN | B | 123 | −67.263 | −67.330 | −32.785 | 1.00 | 51.82 | C |
| ATOM | 9905 | CG | GLN | B | 123 | −68.483 | −67.986 | −32.117 | 1.00 | 52.32 | C |
| ATOM | 9908 | CD | GLN | B | 123 | −68.117 | −69.137 | −31.184 | 1.00 | 52.64 | C |
| ATOM | 9909 | OE1 | GLN | B | 123 | −67.146 | −69.062 | −30.432 | 1.00 | 53.02 | O |
| ATOM | 9910 | NE2 | GLN | B | 123 | −68.904 | −70.207 | −31.230 | 1.00 | 52.04 | N |
| ATOM | 9913 | C | GLN | B | 123 | −65.358 | −65.694 | −32.659 | 1.00 | 51.78 | C |
| ATOM | 9914 | O | GLN | B | 123 | −64.309 | −66.000 | −32.090 | 1.00 | 51.67 | O |
| ATOM | 9916 | N | ASN | B | 124 | −65.388 | −65.004 | −33.799 | 1.00 | 52.05 | N |
| ATOM | 9917 | CA | ASN | B | 124 | −64.166 | −64.547 | −34.473 | 1.00 | 52.25 | C |
| ATOM | 9919 | CB | ASN | B | 124 | −64.486 | −64.042 | −35.884 | 1.00 | 52.25 | C |
| ATOM | 9922 | CG | ASN | B | 124 | −64.911 | −65.158 | −36.819 | 1.00 | 51.88 | C |
| ATOM | 9923 | OD1 | ASN | B | 124 | −65.918 | −65.825 | −36.592 | 1.00 | 51.43 | O |
| ATOM | 9924 | ND2 | ASN | B | 124 | −64.144 | −65.364 | −37.880 | 1.00 | 51.23 | N |
| ATOM | 9927 | C | ASN | B | 124 | −63.382 | −63.466 | −33.716 | 1.00 | 52.43 | C |
| ATOM | 9928 | O | ASN | B | 124 | −62.189 | −63.287 | −33.959 | 1.00 | 52.33 | O |
| ATOM | 9930 | N | GLY | B | 125 | −64.051 | −62.747 | −32.815 | 1.00 | 52.66 | N |
| ATOM | 9931 | CA | GLY | B | 125 | −63.396 | −61.745 | −31.968 | 1.00 | 52.68 | C |
| ATOM | 9934 | C | GLY | B | 125 | −63.916 | −60.329 | −32.135 | 1.00 | 52.63 | C |
| ATOM | 9935 | O | GLY | B | 125 | −63.539 | −59.447 | −31.367 | 1.00 | 52.57 | O |

TABLE 16-7-continued

Coordinates of *P. tremuloides* IspS

| ATOM | 9937 | N | ASN | B | 126 | −64.782 | −60.117 | −33.129 | 1.00 | 52.54 | N |
|---|---|---|---|---|---|---|---|---|---|---|---|
| ATOM | 9938 | CA | ASN | B | 126 | −65.343 | −58.793 | −33.443 | 1.00 | 52.41 | C |
| ATOM | 9940 | CB | ASN | B | 126 | −65.575 | −58.671 | −34.949 | 1.00 | 52.40 | C |
| ATOM | 9943 | CG | ASN | B | 126 | −64.322 | −58.951 | −35.751 | 1.00 | 52.64 | C |
| ATOM | 9944 | OD1 | ASN | B | 126 | −63.426 | −59.665 | −35.297 | 1.00 | 52.77 | O |
| ATOM | 9945 | ND2 | ASN | B | 126 | −64.249 | −58.390 | −36.952 | 1.00 | 53.00 | N |
| ATOM | 9948 | C | ASN | B | 126 | −66.656 | −58.524 | −32.712 | 1.00 | 52.10 | C |
| ATOM | 9949 | O | ASN | B | 126 | −67.253 | −59.432 | −32.153 | 1.00 | 52.27 | O |
| ATOM | 9951 | N | PHE | B | 127 | −67.111 | −57.279 | −32.724 | 1.00 | 51.61 | N |
| ATOM | 9952 | CA | PHE | B | 127 | −68.362 | −56.936 | −32.055 | 1.00 | 51.23 | C |
| ATOM | 9954 | CB | PHE | B | 127 | −68.506 | −55.416 | −31.905 | 1.00 | 51.21 | C |
| ATOM | 9957 | CG | PHE | B | 127 | −67.702 | −54.848 | −30.770 | 1.00 | 50.58 | C |
| ATOM | 9958 | CD1 | PHE | B | 127 | −66.513 | −54.192 | −31.003 | 1.00 | 50.15 | C |
| ATOM | 9960 | CE1 | PHE | B | 127 | −65.777 | −53.686 | −29.948 | 1.00 | 50.15 | C |
| ATOM | 9962 | CZ | PHE | B | 127 | −66.225 | −53.839 | −28.647 | 1.00 | 49.71 | C |
| ATOM | 9964 | CE2 | PHE | B | 127 | −67.399 | −54.496 | −28.405 | 1.00 | 49.50 | C |
| ATOM | 9966 | CD2 | PHE | B | 127 | −68.132 | −54.999 | −29.459 | 1.00 | 49.99 | C |
| ATOM | 9968 | C | PHE | B | 127 | −69.537 | −57.505 | −32.821 | 1.00 | 50.99 | C |
| ATOM | 9969 | O | PHE | B | 127 | −69.468 | −57.641 | −34.040 | 1.00 | 50.92 | O |
| ATOM | 9971 | N | LEU | B | 128 | −70.609 | −57.840 | −32.106 | 1.00 | 50.83 | N |
| ATOM | 9972 | CA | LEU | B | 128 | −71.799 | −58.422 | −32.731 | 1.00 | 50.76 | C |
| ATOM | 9974 | CB | LEU | B | 128 | −72.780 | −58.953 | −31.669 | 1.00 | 50.80 | C |
| ATOM | 9977 | CG | LEU | B | 128 | −72.341 | −60.098 | −30.734 | 1.00 | 50.91 | C |
| ATOM | 9979 | CD1 | LEU | B | 128 | −73.483 | −60.532 | −29.813 | 1.00 | 50.61 | C |
| ATOM | 9983 | CD2 | LEU | B | 128 | −71.818 | −61.303 | −31.497 | 1.00 | 50.79 | C |
| ATOM | 9987 | C | LEU | B | 128 | −72.500 | −57.407 | −33.646 | 1.00 | 50.55 | C |
| ATOM | 9988 | O | LEU | B | 128 | −73.105 | −56.455 | −33.171 | 1.00 | 50.34 | O |
| ATOM | 9990 | N | GLU | B | 129 | −72.402 | −57.628 | −34.957 | 1.00 | 50.50 | N |
| ATOM | 9991 | CA | GLU | B | 129 | −73.038 | −56.783 | −35.982 | 1.00 | 50.48 | C |
| ATOM | 9993 | CB | GLU | B | 129 | −73.150 | −57.551 | −37.310 | 1.00 | 50.68 | C |
| ATOM | 9996 | CG | GLU | B | 129 | −72.262 | −57.024 | −38.434 | 1.00 | 51.36 | C |
| ATOM | 9999 | CD | GLU | B | 129 | −72.799 | −55.745 | −39.060 | 1.00 | 51.88 | C |
| ATOM | 10000 | OE1 | GLU | B | 129 | −72.110 | −54.707 | −38.961 | 1.00 | 52.72 | O |
| ATOM | 10001 | OE2 | GLU | B | 129 | −73.906 | −55.773 | −39.643 | 1.00 | 51.58 | O |
| ATOM | 10002 | C | GLU | B | 129 | −74.428 | −56.264 | −35.629 | 1.00 | 50.25 | C |
| ATOM | 10003 | O | GLU | B | 129 | −74.737 | −55.110 | −35.899 | 1.00 | 50.18 | O |
| ATOM | 10005 | N | ASN | B | 130 | −75.263 | −57.125 | −35.047 | 1.00 | 50.06 | N |
| ATOM | 10006 | CA | ASN | B | 130 | −76.678 | −56.806 | −34.785 | 1.00 | 49.71 | C |
| ATOM | 10008 | CB | ASN | B | 130 | −77.477 | −58.100 | −34.550 | 1.00 | 49.69 | C |
| ATOM | 10011 | CG | ASN | B | 130 | −77.053 | −58.837 | −33.291 | 1.00 | 49.39 | C |
| ATOM | 10012 | OD1 | ASN | B | 130 | −76.357 | −59.848 | −33.361 | 1.00 | 48.74 | O |
| ATOM | 10013 | ND2 | ASN | B | 130 | −77.468 | −58.329 | −32.134 | 1.00 | 48.99 | N |
| ATOM | 10016 | C | ASN | B | 130 | −76.934 | −55.800 | −33.646 | 1.00 | 49.37 | C |
| ATOM | 10017 | O | ASN | B | 130 | −78.083 | −55.456 | −33.366 | 1.00 | 49.29 | O |
| ATOM | 10019 | N | LEU | B | 131 | −75.868 | −55.336 | −32.996 | 1.00 | 48.98 | N |
| ATOM | 10020 | CA | LEU | B | 131 | −75.957 | −54.279 | −31.988 | 1.00 | 48.56 | C |
| ATOM | 10022 | CB | LEU | B | 131 | −74.797 | −54.392 | −30.991 | 1.00 | 48.44 | C |
| ATOM | 10025 | CG | LEU | B | 131 | −74.759 | −55.671 | −30.148 | 1.00 | 48.19 | C |
| ATOM | 10027 | CD1 | LEU | B | 131 | −73.382 | −55.852 | −29.523 | 1.00 | 47.23 | C |
| ATOM | 10031 | CD2 | LEU | B | 131 | −75.861 | −55.670 | −29.083 | 1.00 | 47.77 | C |
| ATOM | 10035 | C | LEU | B | 131 | −75.968 | −52.875 | −32.604 | 1.00 | 48.29 | C |
| ATOM | 10036 | O | LEU | B | 131 | −76.022 | −51.895 | −31.874 | 1.00 | 48.44 | O |
| ATOM | 10038 | N | LYS | B | 132 | −75.927 | −52.771 | −33.934 | 1.00 | 47.95 | N |
| ATOM | 10039 | CA | LYS | B | 132 | −76.020 | −51.471 | −34.621 | 1.00 | 47.64 | C |
| ATOM | 10041 | CB | LYS | B | 132 | −75.548 | −51.590 | −36.080 | 1.00 | 47.63 | C |
| ATOM | 10044 | CG | LYS | B | 132 | −76.595 | −52.235 | −36.998 | 1.00 | 48.19 | C |
| ATOM | 10047 | CD | LYS | B | 132 | −76.111 | −52.483 | −38.429 | 1.00 | 48.16 | C |
| ATOM | 10050 | CE | LYS | B | 132 | −77.239 | −53.040 | −39.290 | 1.00 | 47.23 | C |
| ATOM | 10053 | NZ | LYS | B | 132 | −76.725 | −53.936 | −40.331 | 1.00 | 47.01 | N |
| ATOM | 10057 | C | LYS | B | 132 | −77.449 | −50.907 | −34.597 | 1.00 | 47.13 | C |
| ATOM | 10058 | O | LYS | B | 132 | −77.683 | −49.772 | −35.005 | 1.00 | 46.87 | O |
| ATOM | 10060 | N | GLU | B | 133 | −78.403 | −51.716 | −34.149 | 1.00 | 46.77 | N |
| ATOM | 10061 | CA | GLU | B | 133 | −79.806 | −51.315 | −34.107 | 1.00 | 46.49 | C |
| ATOM | 10063 | CB | GLU | B | 133 | −80.691 | −52.458 | −34.622 | 1.00 | 46.56 | C |
| ATOM | 10066 | CG | GLU | B | 133 | −80.732 | −52.515 | −36.155 | 1.00 | 47.01 | C |
| ATOM | 10069 | CD | GLU | B | 133 | −80.737 | −53.926 | −36.715 | 1.00 | 47.40 | C |
| ATOM | 10070 | OE1 | GLU | B | 133 | −81.500 | −54.775 | −36.206 | 1.00 | 47.97 | O |
| ATOM | 10071 | OE2 | GLU | B | 133 | −79.983 | −54.177 | −37.679 | 1.00 | 47.22 | O |
| ATOM | 10072 | C | GLU | B | 133 | −80.260 | −50.830 | −32.723 | 1.00 | 45.92 | C |
| ATOM | 10073 | O | GLU | B | 133 | −81.369 | −50.308 | −32.600 | 1.00 | 46.14 | O |
| ATOM | 10075 | N | ASP | B | 134 | −79.424 | −51.002 | −31.691 | 1.00 | 44.98 | N |
| ATOM | 10076 | CA | ASP | B | 134 | −79.611 | −50.277 | −30.428 | 1.00 | 44.14 | C |
| ATOM | 10078 | CB | ASP | B | 134 | −79.375 | −51.162 | −29.197 | 1.00 | 43.95 | C |
| ATOM | 10081 | CG | ASP | B | 134 | −79.646 | −50.419 | −27.883 | 1.00 | 43.57 | C |
| ATOM | 10082 | OD1 | ASP | B | 134 | −80.014 | −49.230 | −27.919 | 1.00 | 42.21 | O |
| ATOM | 10083 | OD2 | ASP | B | 134 | −79.488 | −51.011 | −26.802 | 1.00 | 43.69 | O |
| ATOM | 10084 | C | ASP | B | 134 | −78.662 | −49.073 | −30.426 | 1.00 | 43.47 | C |
| ATOM | 10085 | O | ASP | B | 134 | −77.478 | −49.196 | −30.104 | 1.00 | 43.55 | O |

TABLE 16-7-continued

Coordinates of *P. tremuloides* IspS

| ATOM | 10087 | N | ILE | B | 135 | −79.198 | −47.908 | −30.776 | 1.00 | 42.47 | N |
|---|---|---|---|---|---|---|---|---|---|---|---|
| ATOM | 10088 | CA | ILE | B | 135 | −78.375 | −46.739 | −31.033 | 1.00 | 41.65 | C |
| ATOM | 10090 | CB | ILE | B | 135 | −79.080 | −45.783 | −32.012 | 1.00 | 41.45 | C |
| ATOM | 10092 | CG1 | ILE | B | 135 | −78.877 | −46.313 | −33.434 | 1.00 | 41.74 | C |
| ATOM | 10095 | CD1 | ILE | B | 135 | −79.174 | −45.331 | −34.540 | 1.00 | 42.77 | C |
| ATOM | 10099 | CG2 | ILE | B | 135 | −78.533 | −44.391 | −31.905 | 1.00 | 41.68 | C |
| ATOM | 10103 | C | ILE | B | 135 | −77.901 | −46.059 | −29.746 | 1.00 | 41.14 | C |
| ATOM | 10104 | O | ILE | B | 135 | −76.752 | −45.624 | −29.676 | 1.00 | 41.11 | O |
| ATOM | 10106 | N | LYS | B | 136 | −78.742 | −45.998 | −28.714 | 1.00 | 40.53 | N |
| ATOM | 10107 | CA | LYS | B | 136 | −78.281 | −45.480 | −27.409 | 1.00 | 40.10 | C |
| ATOM | 10109 | CB | LYS | B | 136 | −79.431 | −45.361 | −26.375 | 1.00 | 40.40 | C |
| ATOM | 10112 | CG | LYS | B | 136 | −79.910 | −46.697 | −25.786 | 1.00 | 42.49 | C |
| ATOM | 10115 | CD | LYS | B | 136 | −81.002 | −46.574 | −24.698 | 1.00 | 44.79 | C |
| ATOM | 10118 | CE | LYS | B | 136 | −81.599 | −47.994 | −24.363 | 1.00 | 46.03 | C |
| ATOM | 10121 | NZ | LYS | B | 136 | −82.231 | −48.149 | −22.994 | 1.00 | 46.23 | N |
| ATOM | 10125 | C | LYS | B | 136 | −77.104 | −46.327 | −26.863 | 1.00 | 38.85 | C |
| ATOM | 10126 | O | LYS | B | 136 | −76.246 | −45.806 | −26.143 | 1.00 | 38.91 | O |
| ATOM | 10128 | N | ALA | B | 137 | −77.062 | −47.617 | −27.219 | 1.00 | 37.27 | N |
| ATOM | 10129 | CA | ALA | B | 137 | −75.935 | −48.486 | −26.864 | 1.00 | 35.88 | C |
| ATOM | 10131 | CB | ALA | B | 137 | −76.255 | −49.952 | −27.116 | 1.00 | 35.69 | C |
| ATOM | 10135 | C | ALA | B | 137 | −74.708 | −48.085 | −27.645 | 1.00 | 34.63 | C |
| ATOM | 10136 | O | ALA | B | 137 | −73.647 | −47.894 | −27.055 | 1.00 | 34.70 | O |
| ATOM | 10138 | N | ILE | B | 138 | −74.845 | −47.946 | −28.965 | 1.00 | 33.12 | N |
| ATOM | 10139 | CA | ILE | B | 138 | −73.693 | −47.597 | −29.805 | 1.00 | 31.97 | C |
| ATOM | 10141 | CB | ILE | B | 138 | −74.020 | −47.572 | −31.296 | 1.00 | 31.50 | C |
| ATOM | 10143 | CG1 | ILE | B | 138 | −74.433 | −48.955 | −31.774 | 1.00 | 31.28 | C |
| ATOM | 10146 | CD1 | ILE | B | 138 | −73.460 | −50.052 | −31.417 | 1.00 | 30.86 | C |
| ATOM | 10150 | CG2 | ILE | B | 138 | −72.819 | −47.138 | −32.073 | 1.00 | 30.61 | C |
| ATOM | 10154 | C | ILE | B | 138 | −73.124 | −46.245 | −29.413 | 1.00 | 31.57 | C |
| ATOM | 10155 | O | ILE | B | 138 | −71.909 | −46.090 | −29.305 | 1.00 | 31.77 | O |
| ATOM | 10157 | N | LEU | B | 139 | −73.997 | −45.268 | −29.192 | 1.00 | 30.92 | N |
| ATOM | 10158 | CA | LEU | B | 139 | −73.555 | −43.962 | −28.713 | 1.00 | 30.29 | C |
| ATOM | 10160 | CB | LEU | B | 139 | −74.732 | −43.000 | −28.530 | 1.00 | 30.13 | C |
| ATOM | 10163 | CG | LEU | B | 139 | −74.778 | −41.890 | −29.574 | 1.00 | 29.96 | C |
| ATOM | 10165 | CD1 | LEU | B | 139 | −73.496 | −41.060 | −29.508 | 1.00 | 28.26 | C |
| ATOM | 10169 | CD2 | LEU | B | 139 | −76.022 | −41.019 | −29.397 | 1.00 | 29.48 | C |
| ATOM | 10173 | C | LEU | B | 139 | −72.835 | −44.136 | −27.397 | 1.00 | 29.95 | C |
| ATOM | 10174 | O | LEU | B | 139 | −71.709 | −43.687 | −27.232 | 1.00 | 30.45 | O |
| ATOM | 10176 | N | SER | B | 140 | −73.492 | −44.807 | −26.463 | 1.00 | 29.33 | N |
| ATOM | 10177 | CA | SER | B | 140 | −72.916 | −45.061 | −25.150 | 1.00 | 28.84 | C |
| ATOM | 10179 | CB | SER | B | 140 | −73.900 | −45.878 | −24.298 | 1.00 | 28.93 | C |
| ATOM | 10182 | OG | SER | B | 140 | −73.527 | −45.870 | −22.930 | 1.00 | 30.33 | O |
| ATOM | 10184 | C | SER | B | 140 | −71.555 | −45.770 | −25.243 | 1.00 | 27.78 | C |
| ATOM | 10185 | O | SER | B | 140 | −70.637 | −45.454 | −24.489 | 1.00 | 27.46 | O |
| ATOM | 10187 | N | LEU | B | 141 | −71.432 | −46.719 | −26.167 | 1.00 | 26.82 | N |
| ATOM | 10188 | CA | LEU | B | 141 | −70.178 | −47.433 | −26.348 | 1.00 | 26.34 | C |
| ATOM | 10190 | CB | LEU | B | 141 | −70.366 | −48.658 | −27.256 | 1.00 | 26.16 | C |
| ATOM | 10193 | CG | LEU | B | 141 | −69.098 | −49.472 | −27.584 | 1.00 | 26.09 | C |
| ATOM | 10195 | CD1 | LEU | B | 141 | −68.355 | −49.960 | −26.330 | 1.00 | 24.64 | C |
| ATOM | 10199 | CD2 | LEU | B | 141 | −69.455 | −50.643 | −28.481 | 1.00 | 25.94 | C |
| ATOM | 10203 | C | LEU | B | 141 | −69.124 | −46.476 | −26.914 | 1.00 | 25.89 | C |
| ATOM | 10204 | O | LEU | B | 141 | −68.025 | −46.346 | −26.366 | 1.00 | 25.77 | O |
| ATOM | 10206 | N | TYR | B | 142 | −69.471 | −45.809 | −28.008 | 1.00 | 25.41 | N |
| ATOM | 10207 | CA | TYR | B | 142 | −68.609 | −44.804 | −28.610 | 1.00 | 25.03 | C |
| ATOM | 10209 | CB | TYR | B | 142 | −69.399 | −43.982 | −29.617 | 1.00 | 24.80 | C |
| ATOM | 10212 | CG | TYR | B | 142 | −68.736 | −42.695 | −30.043 | 1.00 | 24.47 | C |
| ATOM | 10213 | CD1 | TYR | B | 142 | −67.761 | −42.686 | −31.029 | 1.00 | 24.18 | C |
| ATOM | 10215 | CE1 | TYR | B | 142 | −67.166 | −41.516 | −31.438 | 1.00 | 24.70 | C |
| ATOM | 10217 | CZ | TYR | B | 142 | −67.548 | −40.315 | −30.871 | 1.00 | 25.80 | C |
| ATOM | 10218 | OH | TYR | B | 142 | −66.940 | −39.129 | −31.279 | 1.00 | 27.63 | O |
| ATOM | 10220 | CE2 | TYR | B | 142 | −68.522 | −40.299 | −29.890 | 1.00 | 25.57 | C |
| ATOM | 10222 | CD2 | TYR | B | 142 | −69.110 | −41.485 | −29.485 | 1.00 | 24.73 | C |
| ATOM | 10224 | C | TYR | B | 142 | −68.095 | −43.883 | −27.537 | 1.00 | 25.17 | C |
| ATOM | 10225 | O | TYR | B | 142 | −66.886 | −43.732 | −27.360 | 1.00 | 25.40 | O |
| ATOM | 10227 | N | GLU | B | 143 | −69.038 | −43.293 | −26.807 | 1.00 | 25.12 | N |
| ATOM | 10228 | CA | GLU | B | 143 | −68.744 | −42.256 | −25.828 | 1.00 | 25.10 | C |
| ATOM | 10230 | CB | GLU | B | 143 | −70.046 | −41.726 | −25.226 | 1.00 | 25.33 | C |
| ATOM | 10233 | CG | GLU | B | 143 | −70.006 | −40.244 | −24.849 | 1.00 | 27.57 | C |
| ATOM | 10236 | CD | GLU | B | 143 | −70.321 | −39.313 | −26.023 | 1.00 | 30.43 | C |
| ATOM | 10237 | OE1 | GLU | B | 143 | −69.343 | −38.764 | −26.583 | 1.00 | 32.89 | O |
| ATOM | 10238 | OE2 | GLU | B | 143 | −71.526 | −39.130 | −26.377 | 1.00 | 30.86 | O |
| ATOM | 10239 | C | GLU | B | 143 | −67.794 | −42.746 | −24.729 | 1.00 | 24.43 | C |
| ATOM | 10240 | O | GLU | B | 143 | −67.026 | −41.959 | −24.179 | 1.00 | 24.06 | O |
| ATOM | 10242 | N | ALA | B | 144 | −67.840 | −44.050 | −24.449 | 1.00 | 24.01 | N |
| ATOM | 10243 | CA | ALA | B | 144 | −67.033 | −44.681 | −23.399 | 1.00 | 23.74 | C |
| ATOM | 10245 | CB | ALA | B | 144 | −67.726 | −45.943 | −22.883 | 1.00 | 23.48 | C |
| ATOM | 10249 | C | ALA | B | 144 | −65.631 | −45.025 | −23.864 | 1.00 | 23.57 | C |
| ATOM | 10250 | O | ALA | B | 144 | −64.720 | −45.171 | −23.060 | 1.00 | 23.69 | O |

TABLE 16-7-continued

Coordinates of *P. tremuloides* IspS

| ATOM | 10252 | N | SER | B | 145 | −65.455 | −45.168 | −25.165 | 1.00 | 23.45 | N |
|---|---|---|---|---|---|---|---|---|---|---|---|
| ATOM | 10253 | CA | SER | B | 145 | −64.168 | −45.568 | −25.701 | 1.00 | 23.44 | C |
| ATOM | 10255 | CB | SER | B | 145 | −64.300 | −45.856 | −27.214 | 1.00 | 23.63 | C |
| ATOM | 10258 | OG | SER | B | 145 | −64.822 | −44.748 | −27.952 | 1.00 | 24.24 | O |
| ATOM | 10260 | C | SER | B | 145 | −63.065 | −44.520 | −25.416 | 1.00 | 23.24 | C |
| ATOM | 10261 | O | SER | B | 145 | −61.877 | −44.848 | −25.288 | 1.00 | 23.25 | O |
| ATOM | 10263 | N | PHE | B | 146 | −63.454 | −43.257 | −25.285 | 1.00 | 22.92 | N |
| ATOM | 10264 | CA | PHE | B | 146 | −62.464 | −42.189 | −25.170 | 1.00 | 22.35 | C |
| ATOM | 10266 | CB | PHE | B | 146 | −63.090 | −40.837 | −25.478 | 1.00 | 22.09 | C |
| ATOM | 10269 | CG | PHE | B | 146 | −63.505 | −40.717 | −26.911 | 1.00 | 22.40 | C |
| ATOM | 10270 | CD1 | PHE | B | 146 | −62.619 | −40.229 | −27.868 | 1.00 | 21.98 | C |
| ATOM | 10272 | CE1 | PHE | B | 146 | −62.985 | −40.156 | −29.201 | 1.00 | 21.80 | C |
| ATOM | 10274 | CZ | PHE | B | 146 | −64.241 | −40.579 | −29.594 | 1.00 | 21.91 | C |
| ATOM | 10276 | CE2 | PHE | B | 146 | −65.123 | −41.098 | −28.649 | 1.00 | 22.29 | C |
| ATOM | 10278 | CD2 | PHE | B | 146 | −64.751 | −41.170 | −27.323 | 1.00 | 22.34 | C |
| ATOM | 10280 | C | PHE | B | 146 | −61.762 | −42.208 | −23.837 | 1.00 | 21.91 | C |
| ATOM | 10281 | O | PHE | B | 146 | −60.669 | −41.683 | −23.733 | 1.00 | 22.30 | O |
| ATOM | 10283 | N | LEU | B | 147 | −62.361 | −42.864 | −22.841 | 1.00 | 21.27 | N |
| ATOM | 10284 | CA | LEU | B | 147 | −61.727 | −43.050 | −21.535 | 1.00 | 20.49 | C |
| ATOM | 10286 | CB | LEU | B | 147 | −62.791 | −43.333 | −20.478 | 1.00 | 20.14 | C |
| ATOM | 10289 | CG | LEU | B | 147 | −63.609 | −42.109 | −20.102 | 1.00 | 18.87 | C |
| ATOM | 10291 | CD1 | LEU | B | 147 | −64.813 | −42.020 | −20.959 | 1.00 | 15.94 | C |
| ATOM | 10295 | CD2 | LEU | B | 147 | −63.988 | −42.189 | −18.642 | 1.00 | 18.62 | C |
| ATOM | 10299 | C | LEU | B | 147 | −60.678 | −44.163 | −21.498 | 1.00 | 20.41 | C |
| ATOM | 10300 | O | LEU | B | 147 | −60.243 | −44.552 | −20.415 | 1.00 | 20.44 | O |
| ATOM | 10302 | N | ALA | B | 148 | −60.268 | −44.664 | −22.662 | 1.00 | 20.28 | N |
| ATOM | 10303 | CA | ALA | B | 148 | −59.330 | −45.784 | −22.745 | 1.00 | 20.33 | C |
| ATOM | 10305 | CB | ALA | B | 148 | −59.188 | −46.231 | −24.194 | 1.00 | 20.15 | C |
| ATOM | 10309 | C | ALA | B | 148 | −57.952 | −45.462 | −22.170 | 1.00 | 20.54 | C |
| ATOM | 10310 | O | ALA | B | 148 | −57.435 | −44.366 | −22.341 | 1.00 | 20.23 | O |
| ATOM | 10312 | N | LEU | B | 149 | −57.366 | −46.435 | −21.486 | 1.00 | 21.19 | N |
| ATOM | 10313 | CA | LEU | B | 149 | −55.969 | −46.354 | −21.067 | 1.00 | 22.02 | C |
| ATOM | 10315 | CB | LEU | B | 149 | −55.768 | −47.073 | −19.725 | 1.00 | 21.90 | C |
| ATOM | 10318 | CG | LEU | B | 149 | −56.541 | −46.496 | −18.523 | 1.00 | 21.50 | C |
| ATOM | 10320 | CD1 | LEU | B | 149 | −55.979 | −47.006 | −17.223 | 1.00 | 20.96 | C |
| ATOM | 10324 | CD2 | LEU | B | 149 | −56.520 | −44.974 | −18.505 | 1.00 | 20.95 | C |
| ATOM | 10328 | C | LEU | B | 149 | −55.054 | −46.930 | −22.159 | 1.00 | 22.84 | C |
| ATOM | 10329 | O | LEU | B | 149 | −55.507 | −47.678 | −23.017 | 1.00 | 22.91 | O |
| ATOM | 10331 | N | GLU | B | 150 | −53.781 | −46.550 | −22.163 | 1.00 | 23.93 | N |
| ATOM | 10332 | CA | GLU | B | 150 | −52.858 | −47.071 | −23.174 | 1.00 | 25.03 | C |
| ATOM | 10334 | CB | GLU | B | 150 | −51.472 | −46.431 | −23.012 | 1.00 | 25.41 | C |
| ATOM | 10337 | CG | GLU | B | 150 | −50.530 | −46.608 | −24.213 | 1.00 | 27.44 | C |
| ATOM | 10340 | CD | GLU | B | 150 | −49.132 | −45.987 | −23.992 | 1.00 | 30.04 | C |
| ATOM | 10341 | OE1 | GLU | B | 150 | −48.925 | −45.330 | −22.943 | 1.00 | 31.41 | O |
| ATOM | 10342 | OE2 | GLU | B | 150 | −48.242 | −46.161 | −24.867 | 1.00 | 30.34 | O |
| ATOM | 10343 | C | GLU | B | 150 | −52.787 | −48.600 | −23.024 | 1.00 | 25.36 | C |
| ATOM | 10344 | O | GLU | B | 150 | −52.613 | −49.098 | −21.911 | 1.00 | 25.58 | O |
| ATOM | 10346 | N | GLY | B | 151 | −52.968 | −49.337 | −24.122 | 1.00 | 25.79 | N |
| ATOM | 10347 | CA | GLY | B | 151 | −52.959 | −50.816 | −24.086 | 1.00 | 26.11 | C |
| ATOM | 10350 | C | GLY | B | 151 | −54.323 | −51.522 | −24.047 | 1.00 | 26.44 | C |
| ATOM | 10351 | O | GLY | B | 151 | −54.393 | −52.747 | −24.135 | 1.00 | 26.91 | O |
| ATOM | 10353 | N | GLU | B | 152 | −55.407 | −50.768 | −23.899 | 1.00 | 26.58 | N |
| ATOM | 10354 | CA | GLU | B | 152 | −56.757 | −51.319 | −23.971 | 1.00 | 26.57 | C |
| ATOM | 10356 | CB | GLU | B | 152 | −57.697 | −50.531 | −23.065 | 1.00 | 26.74 | C |
| ATOM | 10359 | CG | GLU | B | 152 | −57.291 | −50.595 | −21.596 | 1.00 | 27.63 | C |
| ATOM | 10362 | CD | GLU | B | 152 | −58.271 | −49.893 | −20.668 | 1.00 | 28.86 | C |
| ATOM | 10363 | OE1 | GLU | B | 152 | −58.239 | −50.192 | −19.449 | 1.00 | 28.80 | O |
| ATOM | 10364 | OE2 | GLU | B | 152 | −59.066 | −49.044 | −21.154 | 1.00 | 29.26 | O |
| ATOM | 10365 | C | GLU | B | 152 | −57.254 | −51.303 | −25.415 | 1.00 | 26.53 | C |
| ATOM | 10366 | O | GLU | B | 152 | −57.937 | −50.381 | −25.869 | 1.00 | 26.00 | O |
| ATOM | 10368 | N | ASN | B | 153 | −56.888 | −52.354 | −26.127 | 1.00 | 26.77 | N |
| ATOM | 10369 | CA | ASN | B | 153 | −57.189 | −52.498 | −27.545 | 1.00 | 27.05 | C |
| ATOM | 10371 | CB | ASN | B | 153 | −56.345 | −53.640 | −28.104 | 1.00 | 27.12 | C |
| ATOM | 10374 | CG | ASN | B | 153 | −56.770 | −54.992 | −27.549 | 1.00 | 27.81 | C |
| ATOM | 10375 | OD1 | ASN | B | 153 | −56.540 | −55.307 | −26.379 | 1.00 | 27.65 | O |
| ATOM | 10376 | ND2 | ASN | B | 153 | −57.426 | −55.782 | −28.382 | 1.00 | 29.43 | N |
| ATOM | 10379 | C | ASN | B | 153 | −58.659 | −52.788 | −27.873 | 1.00 | 27.09 | C |
| ATOM | 10380 | O | ASN | B | 153 | −59.053 | −52.658 | −29.029 | 1.00 | 27.11 | O |
| ATOM | 10382 | N | ILE | B | 154 | −59.448 | −53.223 | −26.884 | 1.00 | 27.17 | N |
| ATOM | 10383 | CA | ILE | B | 154 | −60.865 | −53.544 | −27.100 | 1.00 | 27.11 | C |
| ATOM | 10385 | CB | ILE | B | 154 | −61.454 | −54.369 | −25.956 | 1.00 | 26.99 | C |
| ATOM | 10387 | CG1 | ILE | B | 154 | −60.811 | −55.750 | −25.907 | 1.00 | 27.16 | C |
| ATOM | 10390 | CD1 | ILE | B | 154 | −61.309 | −56.622 | −24.746 | 1.00 | 27.41 | C |
| ATOM | 10394 | CG2 | ILE | B | 154 | −62.953 | −54.519 | −26.124 | 1.00 | 26.65 | C |
| ATOM | 10398 | C | ILE | B | 154 | −61.704 | −52.284 | −27.229 | 1.00 | 27.43 | C |
| ATOM | 10399 | O | ILE | B | 154 | −62.718 | −52.279 | −27.939 | 1.00 | 27.39 | O |
| ATOM | 10401 | N | LEU | B | 155 | −61.296 | −51.226 | −26.522 | 1.00 | 27.76 | N |
| ATOM | 10402 | CA | LEU | B | 155 | −61.964 | −49.918 | −26.609 | 1.00 | 27.75 | C |

TABLE 16-7-continued

Coordinates of *P. tremuloides* IspS

| ATOM | 10404 | CB  | LEU | B | 155 | −61.578 | −49.024 | −25.430 | 1.00 | 27.31 | C |
| ATOM | 10407 | CG  | LEU | B | 155 | −61.968 | −49.544 | −24.052 | 1.00 | 26.64 | C |
| ATOM | 10409 | CD1 | LEU | B | 155 | −61.444 | −48.631 | −22.981 | 1.00 | 25.82 | C |
| ATOM | 10413 | CD2 | LEU | B | 155 | −63.465 | −49.674 | −23.944 | 1.00 | 26.45 | C |
| ATOM | 10417 | C   | LEU | B | 155 | −61.620 | −49.226 | −27.924 | 1.00 | 28.32 | C |
| ATOM | 10418 | O   | LEU | B | 155 | −62.499 | −48.672 | −28.583 | 1.00 | 28.72 | O |
| ATOM | 10420 | N   | ASP | B | 156 | −60.348 | −49.264 | −28.309 | 1.00 | 28.84 | N |
| ATOM | 10421 | CA  | ASP | B | 156 | −59.934 | −48.737 | −29.601 | 1.00 | 29.43 | C |
| ATOM | 10423 | CB  | ASP | B | 156 | −58.423 | −48.928 | −29.823 | 1.00 | 29.92 | C |
| ATOM | 10426 | CG  | ASP | B | 156 | −57.566 | −47.912 | −29.045 | 1.00 | 31.35 | C |
| ATOM | 10427 | OD1 | ASP | B | 156 | −57.803 | −46.680 | −29.162 | 1.00 | 33.23 | O |
| ATOM | 10428 | OD2 | ASP | B | 156 | −56.640 | −48.351 | −28.324 | 1.00 | 33.08 | O |
| ATOM | 10429 | C   | ASP | B | 156 | −60.719 | −49.411 | −30.717 | 1.00 | 29.36 | C |
| ATOM | 10430 | O   | ASP | B | 156 | −61.075 | −48.768 | −31.697 | 1.00 | 29.33 | O |
| ATOM | 10432 | N   | GLU | B | 157 | −60.981 | −50.705 | −30.558 | 1.00 | 29.63 | N |
| ATOM | 10433 | CA  | GLU | B | 157 | −61.845 | −51.457 | −31.479 | 1.00 | 29.98 | C |
| ATOM | 10435 | CB  | GLU | B | 157 | −61.729 | −52.971 | −31.234 | 1.00 | 30.30 | C |
| ATOM | 10438 | CG  | GLU | B | 157 | −60.664 | −53.647 | −32.087 | 1.00 | 31.79 | C |
| ATOM | 10441 | CD  | GLU | B | 157 | −60.075 | −54.901 | −31.439 | 1.00 | 33.87 | C |
| ATOM | 10442 | OE1 | GLU | B | 157 | −60.793 | −55.560 | −30.640 | 1.00 | 35.07 | O |
| ATOM | 10443 | OE2 | GLU | B | 157 | −58.894 | −55.223 | −31.743 | 1.00 | 33.70 | O |
| ATOM | 10444 | C   | GLU | B | 157 | −63.304 | −51.030 | −31.349 | 1.00 | 29.53 | C |
| ATOM | 10445 | O   | GLU | B | 157 | −63.999 | −50.878 | −32.351 | 1.00 | 29.53 | O |
| ATOM | 10447 | N   | ALA | B | 158 | −63.758 | −50.853 | −30.112 | 1.00 | 29.11 | N |
| ATOM | 10448 | CA  | ALA | B | 158 | −65.104 | −50.370 | −29.840 | 1.00 | 28.87 | C |
| ATOM | 10450 | CB  | ALA | B | 158 | −65.307 | −50.195 | −28.351 | 1.00 | 28.82 | C |
| ATOM | 10454 | C   | ALA | B | 158 | −65.383 | −49.065 | −30.567 | 1.00 | 28.73 | C |
| ATOM | 10455 | O   | ALA | B | 158 | −66.485 | −48.857 | −31.065 | 1.00 | 28.80 | O |
| ATOM | 10457 | N   | LYS | B | 159 | −64.385 | −48.197 | −30.642 | 1.00 | 28.65 | N |
| ATOM | 10458 | CA  | LYS | B | 159 | −64.553 | −46.910 | −31.296 | 1.00 | 28.98 | C |
| ATOM | 10460 | CB  | LYS | B | 159 | −63.439 | −45.950 | −30.857 | 1.00 | 29.16 | C |
| ATOM | 10463 | CG  | LYS | B | 159 | −63.558 | −44.536 | −31.426 | 1.00 | 29.82 | C |
| ATOM | 10466 | CD  | LYS | B | 159 | −62.812 | −43.493 | −30.592 | 1.00 | 30.96 | C |
| ATOM | 10469 | CE  | LYS | B | 159 | −61.295 | −43.610 | −30.691 | 1.00 | 31.57 | C |
| ATOM | 10472 | NZ  | LYS | B | 159 | −60.630 | −42.426 | −30.079 | 1.00 | 31.49 | N |
| ATOM | 10476 | C   | LYS | B | 159 | −64.594 | −47.041 | −32.826 | 1.00 | 29.08 | C |
| ATOM | 10477 | O   | LYS | B | 159 | −65.385 | −46.372 | −33.486 | 1.00 | 28.73 | O |
| ATOM | 10479 | N   | VAL | B | 160 | −63.736 | −47.891 | −33.386 | 1.00 | 29.53 | N |
| ATOM | 10480 | CA  | VAL | B | 160 | −63.686 | −48.087 | −34.836 | 1.00 | 29.89 | C |
| ATOM | 10482 | CB  | VAL | B | 160 | −62.466 | −48.971 | −35.282 | 1.00 | 29.93 | C |
| ATOM | 10484 | CG1 | VAL | B | 160 | −62.576 | −49.375 | −36.756 | 1.00 | 29.58 | C |
| ATOM | 10488 | CG2 | VAL | B | 160 | −61.152 | −48.244 | −35.040 | 1.00 | 29.41 | C |
| ATOM | 10492 | C   | VAL | B | 160 | −65.001 | −48.723 | −35.263 | 1.00 | 30.32 | C |
| ATOM | 10493 | O   | VAL | B | 160 | −65.507 | −48.459 | −36.362 | 1.00 | 30.41 | O |
| ATOM | 10495 | N   | PHE | B | 161 | −65.558 | −49.540 | −34.371 | 1.00 | 30.83 | N |
| ATOM | 10496 | CA  | PHE | B | 161 | −66.854 | −50.178 | −34.599 | 1.00 | 31.34 | C |
| ATOM | 10498 | CB  | PHE | B | 161 | −67.090 | −51.321 | −33.599 | 1.00 | 31.34 | C |
| ATOM | 10501 | CG  | PHE | B | 161 | −68.492 | −51.834 | −33.603 | 1.00 | 31.09 | C |
| ATOM | 10502 | CD1 | PHE | B | 161 | −68.940 | −52.636 | −34.633 | 1.00 | 31.61 | C |
| ATOM | 10504 | CE1 | PHE | B | 161 | −70.249 | −53.098 | −34.649 | 1.00 | 31.48 | C |
| ATOM | 10506 | CZ  | PHE | B | 161 | −71.114 | −52.748 | −33.628 | 1.00 | 30.76 | C |
| ATOM | 10508 | CE2 | PHE | B | 161 | −70.677 | −51.944 | −32.606 | 1.00 | 30.19 | C |
| ATOM | 10510 | CD2 | PHE | B | 161 | −69.378 | −51.486 | −32.597 | 1.00 | 30.70 | C |
| ATOM | 10512 | C   | PHE | B | 161 | −67.992 | −49.173 | −34.504 | 1.00 | 31.65 | C |
| ATOM | 10513 | O   | PHE | B | 161 | −68.785 | −49.038 | −35.432 | 1.00 | 31.62 | O |
| ATOM | 10515 | N   | ALA | B | 162 | −68.068 | −48.483 | −33.373 | 1.00 | 32.26 | N |
| ATOM | 10516 | CA  | ALA | B | 162 | −69.135 | −47.519 | −33.129 | 1.00 | 32.84 | C |
| ATOM | 10518 | CB  | ALA | B | 162 | −68.948 | −46.854 | −31.778 | 1.00 | 32.66 | C |
| ATOM | 10522 | C   | ALA | B | 162 | −69.224 | −46.474 | −34.245 | 1.00 | 33.40 | C |
| ATOM | 10523 | O   | ALA | B | 162 | −70.229 | −46.408 | −34.937 | 1.00 | 33.45 | O |
| ATOM | 10525 | N   | ILE | B | 163 | −68.164 | −45.697 | −34.444 | 1.00 | 34.38 | N |
| ATOM | 10526 | CA  | ILE | B | 163 | −68.166 | −44.610 | −35.439 | 1.00 | 35.23 | C |
| ATOM | 10528 | CB  | ILE | B | 163 | −66.734 | −44.062 | −35.733 | 1.00 | 35.18 | C |
| ATOM | 10530 | CG1 | ILE | B | 163 | −66.092 | −43.457 | −34.488 | 1.00 | 35.21 | C |
| ATOM | 10533 | CD1 | ILE | B | 163 | −64.620 | −43.171 | −34.663 | 1.00 | 35.96 | C |
| ATOM | 10537 | CG2 | ILE | B | 163 | −66.778 | −42.977 | −36.799 | 1.00 | 34.72 | C |
| ATOM | 10541 | C   | ILE | B | 163 | −68.778 | −45.052 | −36.766 | 1.00 | 36.18 | C |
| ATOM | 10542 | O   | ILE | B | 163 | −69.588 | −44.335 | −37.360 | 1.00 | 35.87 | O |
| ATOM | 10544 | N   | SER | B | 164 | −68.379 | −46.240 | −37.217 | 1.00 | 37.67 | N |
| ATOM | 10545 | CA  | SER | B | 164 | −68.761 | −46.752 | −38.539 | 1.00 | 38.74 | C |
| ATOM | 10547 | CB  | SER | B | 164 | −68.104 | −48.117 | −38.815 | 1.00 | 38.80 | C |
| ATOM | 10550 | OG  | SER | B | 164 | −68.733 | −49.158 | −38.077 | 1.00 | 39.07 | O |
| ATOM | 10552 | C   | SER | B | 164 | −70.277 | −46.861 | −38.699 | 1.00 | 39.51 | C |
| ATOM | 10553 | O   | SER | B | 164 | −70.820 | −46.494 | −39.737 | 1.00 | 39.96 | O |
| ATOM | 10555 | N   | HIS | B | 165 | −70.962 | −47.363 | −37.680 | 1.00 | 40.28 | N |
| ATOM | 10556 | CA  | HIS | B | 165 | −72.410 | −47.485 | −37.767 | 1.00 | 41.07 | C |
| ATOM | 10558 | CB  | HIS | B | 165 | −72.911 | −48.686 | −36.957 | 1.00 | 41.38 | C |
| ATOM | 10561 | CG  | HIS | B | 165 | −72.571 | −50.005 | −37.587 | 1.00 | 42.65 | C |

TABLE 16-7-continued

| | | | | Coordinates of *P. tremuloides* IspS | | | | | | |
|---|---|---|---|---|---|---|---|---|---|---|
| ATOM | 10562 | ND1 | HIS | B | 165 | −71.647 | −50.875 | −37.046 | 1.00 | 43.54 | N |
| ATOM | 10564 | CE1 | HIS | B | 165 | −71.535 | −51.938 | −37.825 | 1.00 | 43.54 | C |
| ATOM | 10566 | NE2 | HIS | B | 165 | −72.346 | −51.785 | −38.858 | 1.00 | 43.25 | N |
| ATOM | 10568 | CD2 | HIS | B | 165 | −73.001 | −50.582 | −38.737 | 1.00 | 43.31 | C |
| ATOM | 10570 | C | HIS | B | 165 | −73.125 | −46.193 | −37.380 | 1.00 | 41.21 | C |
| ATOM | 10571 | O | HIS | B | 165 | −74.257 | −45.980 | −37.805 | 1.00 | 41.53 | O |
| ATOM | 10573 | N | LEU | B | 166 | −72.459 | −45.326 | −36.614 | 1.00 | 41.32 | N |
| ATOM | 10574 | CA | LEU | B | 166 | −73.042 | −44.039 | −36.201 | 1.00 | 41.31 | C |
| ATOM | 10576 | CB | LEU | B | 166 | −72.317 | −43.460 | −34.973 | 1.00 | 41.14 | C |
| ATOM | 10579 | CG | LEU | B | 166 | −72.732 | −43.975 | −33.589 | 1.00 | 40.03 | C |
| ATOM | 10581 | CD1 | LEU | B | 166 | −71.673 | −43.634 | −32.579 | 1.00 | 38.86 | C |
| ATOM | 10585 | CD2 | LEU | B | 166 | −74.077 | −43.421 | −33.151 | 1.00 | 38.52 | C |
| ATOM | 10589 | C | LEU | B | 166 | −73.045 | −42.992 | −37.313 | 1.00 | 41.80 | C |
| ATOM | 10590 | O | LEU | B | 166 | −74.006 | −42.230 | −37.442 | 1.00 | 41.73 | O |
| ATOM | 10592 | N | LYS | B | 167 | −71.982 | −42.947 | −38.116 | 1.00 | 42.47 | N |
| ATOM | 10593 | CA | LYS | B | 167 | −71.847 | −41.891 | −39.137 | 1.00 | 43.00 | C |
| ATOM | 10595 | CB | LYS | B | 167 | −70.416 | −41.822 | −39.702 | 1.00 | 43.12 | C |
| ATOM | 10598 | CG | LYS | B | 167 | −69.937 | −43.068 | −40.450 | 1.00 | 44.12 | C |
| ATOM | 10601 | CD | LYS | B | 167 | −69.138 | −42.725 | −41.736 | 1.00 | 45.36 | C |
| ATOM | 10604 | CE | LYS | B | 167 | −67.898 | −41.842 | −41.483 | 1.00 | 45.65 | C |
| ATOM | 10607 | NZ | LYS | B | 167 | −67.267 | −41.400 | −42.762 | 1.00 | 44.94 | N |
| ATOM | 10611 | C | LYS | B | 167 | −72.873 | −41.950 | −40.283 | 1.00 | 42.99 | C |
| ATOM | 10612 | O | LYS | B | 167 | −72.826 | −41.124 | −41.182 | 1.00 | 42.95 | O |
| ATOM | 10614 | N | GLU | B | 168 | −73.791 | −42.912 | −40.244 | 1.00 | 43.23 | N |
| ATOM | 10615 | CA | GLU | B | 168 | −74.928 | −42.940 | −41.167 | 1.00 | 43.44 | C |
| ATOM | 10617 | CB | GLU | B | 168 | −74.652 | −43.969 | −42.272 | 1.00 | 43.58 | C |
| ATOM | 10620 | CG | GLU | B | 168 | −73.918 | −43.363 | −43.501 | 1.00 | 44.36 | C |
| ATOM | 10623 | CD | GLU | B | 168 | −72.618 | −44.082 | −43.895 | 1.00 | 44.53 | C |
| ATOM | 10624 | OE1 | GLU | B | 168 | −71.853 | −44.494 | −42.992 | 1.00 | 44.71 | O |
| ATOM | 10625 | OE2 | GLU | B | 168 | −72.351 | −44.197 | −45.115 | 1.00 | 43.31 | O |
| ATOM | 10626 | C | GLU | B | 168 | −76.263 | −43.214 | −40.442 | 1.00 | 43.24 | C |
| ATOM | 10627 | O | GLU | B | 168 | −76.932 | −42.291 | −39.942 | 1.00 | 42.54 | O |
| ATOM | 10629 | N | GLY | B | 175 | −83.548 | −42.037 | −36.239 | 1.00 | 49.43 | N |
| ATOM | 10630 | CA | GLY | B | 175 | −84.473 | −41.266 | −35.416 | 1.00 | 49.54 | C |
| ATOM | 10633 | C | GLY | B | 175 | −84.709 | −39.884 | −36.001 | 1.00 | 49.76 | C |
| ATOM | 10634 | O | GLY | B | 175 | −84.828 | −39.741 | −37.220 | 1.00 | 49.70 | O |
| ATOM | 10636 | N | LYS | B | 176 | −84.766 | −38.870 | −35.131 | 1.00 | 49.95 | N |
| ATOM | 10637 | CA | LYS | B | 176 | −85.014 | −37.468 | −35.534 | 1.00 | 50.05 | C |
| ATOM | 10639 | CB | LYS | B | 176 | −86.522 | −37.225 | −35.730 | 1.00 | 50.27 | C |
| ATOM | 10642 | CG | LYS | B | 176 | −87.301 | −36.813 | −34.460 | 1.00 | 51.33 | C |
| ATOM | 10645 | CD | LYS | B | 176 | −88.553 | −37.658 | −34.202 | 1.00 | 52.21 | C |
| ATOM | 10648 | CE | LYS | B | 176 | −88.841 | −37.754 | −32.695 | 1.00 | 52.36 | C |
| ATOM | 10651 | NZ | LYS | B | 176 | −90.029 | −38.607 | −32.422 | 1.00 | 52.15 | N |
| ATOM | 10655 | C | LYS | B | 176 | −84.427 | −36.432 | −34.554 | 1.00 | 49.75 | C |
| ATOM | 10656 | O | LYS | B | 176 | −83.990 | −35.370 | −34.972 | 1.00 | 49.88 | O |
| ATOM | 10658 | N | GLU | B | 177 | −84.473 | −36.729 | −33.254 | 1.00 | 49.46 | N |
| ATOM | 10659 | CA | GLU | B | 177 | −83.769 | −35.959 | −32.221 | 1.00 | 48.92 | C |
| ATOM | 10661 | CB | GLU | B | 177 | −84.628 | −35.813 | −30.946 | 1.00 | 49.03 | C |
| ATOM | 10664 | CG | GLU | B | 177 | −84.196 | −36.691 | −29.732 | 1.00 | 49.60 | C |
| ATOM | 10667 | CD | GLU | B | 177 | −85.278 | −36.871 | −28.662 | 1.00 | 50.10 | C |
| ATOM | 10668 | OE1 | GLU | B | 177 | −84.998 | −37.576 | −27.670 | 1.00 | 49.78 | O |
| ATOM | 10669 | OE2 | GLU | B | 177 | −86.401 | −36.336 | −28.808 | 1.00 | 50.78 | O |
| ATOM | 10670 | C | GLU | B | 177 | −82.469 | −36.703 | −31.924 | 1.00 | 48.19 | C |
| ATOM | 10671 | O | GLU | B | 177 | −81.421 | −36.085 | −31.721 | 1.00 | 48.68 | O |
| ATOM | 10673 | N | LEU | B | 178 | −82.557 | −38.037 | −31.900 | 1.00 | 46.98 | N |
| ATOM | 10674 | CA | LEU | B | 178 | −81.398 | −38.924 | −31.817 | 1.00 | 45.91 | C |
| ATOM | 10676 | CB | LEU | B | 178 | −81.838 | −40.387 | −31.945 | 1.00 | 45.70 | C |
| ATOM | 10679 | CG | LEU | B | 178 | −81.111 | −41.408 | −31.074 | 1.00 | 45.24 | C |
| ATOM | 10681 | CD1 | LEU | B | 178 | −81.498 | −41.225 | −29.609 | 1.00 | 44.88 | C |
| ATOM | 10685 | CD2 | LEU | B | 178 | −81.413 | −42.826 | −31.539 | 1.00 | 44.19 | C |
| ATOM | 10689 | C | LEU | B | 178 | −80.423 | −38.571 | −32.934 | 1.00 | 45.27 | C |
| ATOM | 10690 | O | LEU | B | 178 | −79.211 | −38.624 | −32.759 | 1.00 | 44.99 | O |
| ATOM | 10692 | N | ALA | B | 179 | −80.970 | −38.203 | −34.088 | 1.00 | 44.75 | N |
| ATOM | 10693 | CA | ALA | B | 179 | −80.174 | −37.661 | −35.181 | 1.00 | 44.24 | C |
| ATOM | 10695 | CB | ALA | B | 179 | −81.088 | −37.069 | −36.231 | 1.00 | 44.30 | C |
| ATOM | 10699 | C | ALA | B | 179 | −79.192 | −36.602 | −34.683 | 1.00 | 43.65 | C |
| ATOM | 10700 | O | ALA | B | 179 | −78.028 | −36.604 | −35.061 | 1.00 | 43.56 | O |
| ATOM | 10702 | N | GLU | B | 180 | −79.675 | −35.707 | −33.827 | 1.00 | 43.01 | N |
| ATOM | 10703 | CA | GLU | B | 180 | −78.863 | −34.610 | −33.311 | 1.00 | 42.49 | C |
| ATOM | 10705 | CB | GLU | B | 180 | −79.749 | −33.477 | −32.789 | 1.00 | 42.85 | C |
| ATOM | 10708 | CG | GLU | B | 180 | −80.574 | −32.800 | −33.881 | 1.00 | 44.23 | C |
| ATOM | 10711 | CD | GLU | B | 180 | −80.991 | −31.382 | −33.519 | 1.00 | 45.80 | C |
| ATOM | 10712 | OE1 | GLU | B | 180 | −80.098 | −30.580 | −33.156 | 1.00 | 46.69 | O |
| ATOM | 10713 | OE2 | GLU | B | 180 | −82.203 | −31.065 | −33.610 | 1.00 | 46.71 | O |
| ATOM | 10714 | C | GLU | B | 180 | −77.944 | −35.075 | −32.210 | 1.00 | 41.39 | C |
| ATOM | 10715 | O | GLU | B | 180 | −76.843 | −34.562 | −32.071 | 1.00 | 41.27 | O |
| ATOM | 10717 | N | GLN | B | 181 | −78.404 | −36.035 | −31.419 | 1.00 | 40.20 | N |
| ATOM | 10718 | CA | GLN | B | 181 | −77.570 | −36.632 | −30.394 | 1.00 | 39.45 | C |

TABLE 16-7-continued

Coordinates of *P. tremuloides* IspS

| ATOM | 10720 | CB | GLN | B | 181 | −78.280 | −37.809 | −29.736 | 1.00 | 39.88 | C |
|---|---|---|---|---|---|---|---|---|---|---|---|
| ATOM | 10723 | CG | GLN | B | 181 | −78.005 | −37.959 | −28.249 | 1.00 | 41.64 | C |
| ATOM | 10726 | CD | GLN | B | 181 | −78.873 | −37.036 | −27.404 | 1.00 | 44.00 | C |
| ATOM | 10727 | OE1 | GLN | B | 181 | −80.109 | −36.992 | −27.581 | 1.00 | 45.65 | O |
| ATOM | 10728 | NE2 | GLN | B | 181 | −78.235 | −36.291 | −26.474 | 1.00 | 43.41 | N |
| ATOM | 10731 | C | GLN | B | 181 | −76.270 | −37.120 | −31.003 | 1.00 | 38.28 | C |
| ATOM | 10732 | O | GLN | B | 181 | −75.203 | −36.767 | −30.523 | 1.00 | 38.27 | O |
| ATOM | 10734 | N | VAL | B | 182 | −76.358 | −37.911 | −32.072 | 1.00 | 37.05 | N |
| ATOM | 10735 | CA | VAL | B | 182 | −75.160 | −38.515 | −32.675 | 1.00 | 36.20 | C |
| ATOM | 10737 | CB | VAL | B | 182 | −75.486 | −39.661 | −33.681 | 1.00 | 36.11 | C |
| ATOM | 10739 | CG1 | VAL | B | 182 | −76.493 | −40.641 | −33.080 | 1.00 | 36.13 | C |
| ATOM | 10743 | CG2 | VAL | B | 182 | −75.977 | −39.106 | −35.004 | 1.00 | 36.06 | C |
| ATOM | 10747 | C | VAL | B | 182 | −74.238 | −37.495 | −33.364 | 1.00 | 35.44 | C |
| ATOM | 10748 | O | VAL | B | 182 | −73.012 | −37.682 | −33.375 | 1.00 | 35.19 | O |
| ATOM | 10750 | N | SER | B | 183 | −74.811 | −36.432 | −33.936 | 1.00 | 34.41 | N |
| ATOM | 10751 | CA | SER | B | 183 | −73.998 | −35.416 | −34.630 | 1.00 | 33.74 | C |
| ATOM | 10753 | CB | SER | B | 183 | −74.858 | −34.438 | −35.422 | 1.00 | 33.58 | C |
| ATOM | 10756 | OG | SER | B | 183 | −76.003 | −35.085 | −35.925 | 1.00 | 34.52 | O |
| ATOM | 10758 | C | SER | B | 183 | −73.184 | −34.644 | −33.625 | 1.00 | 32.88 | C |
| ATOM | 10759 | O | SER | B | 183 | −72.055 | −34.251 | −33.906 | 1.00 | 33.25 | O |
| ATOM | 10761 | N | HIS | B | 184 | −73.788 | −34.427 | −32.461 | 1.00 | 31.83 | N |
| ATOM | 10762 | CA | HIS | B | 184 | −73.150 | −33.787 | −31.326 | 1.00 | 30.98 | C |
| ATOM | 10764 | CB | HIS | B | 184 | −74.188 | −33.627 | −30.212 | 1.00 | 31.14 | C |
| ATOM | 10767 | CG | HIS | B | 184 | −73.710 | −32.849 | −29.030 | 1.00 | 31.91 | C |
| ATOM | 10768 | ND1 | HIS | B | 184 | −73.326 | −31.527 | −29.114 | 1.00 | 33.18 | N |
| ATOM | 10770 | CE1 | HIS | B | 184 | −72.960 | −31.107 | −27.914 | 1.00 | 33.10 | C |
| ATOM | 10772 | NE2 | HIS | B | 184 | −73.106 | −32.102 | −27.056 | 1.00 | 31.85 | N |
| ATOM | 10774 | CD2 | HIS | B | 184 | −73.583 | −33.200 | −27.727 | 1.00 | 31.86 | C |
| ATOM | 10776 | C | HIS | B | 184 | −71.968 | −34.632 | −30.865 | 1.00 | 30.13 | C |
| ATOM | 10777 | O | HIS | B | 184 | −70.863 | −34.122 | −30.709 | 1.00 | 29.95 | O |
| ATOM | 10779 | N | ALA | B | 185 | −72.194 | −35.931 | −30.683 | 1.00 | 29.27 | N |
| ATOM | 10780 | CA | ALA | B | 185 | −71.123 | −36.856 | −30.281 | 1.00 | 28.64 | C |
| ATOM | 10782 | CB | ALA | B | 185 | −71.689 | −38.233 | −29.986 | 1.00 | 28.44 | C |
| ATOM | 10786 | C | ALA | B | 185 | −70.017 | −36.965 | −31.330 | 1.00 | 28.08 | C |
| ATOM | 10787 | O | ALA | B | 185 | −68.839 | −37.043 | −30.992 | 1.00 | 28.26 | O |
| ATOM | 10789 | N | LEU | B | 186 | −70.394 | −36.984 | −32.602 | 1.00 | 27.40 | N |
| ATOM | 10790 | CA | LEU | B | 186 | −69.412 | −37.101 | −33.674 | 1.00 | 26.84 | C |
| ATOM | 10792 | CB | LEU | B | 186 | −70.088 | −37.481 | −35.000 | 1.00 | 26.75 | C |
| ATOM | 10795 | CG | LEU | B | 186 | −70.085 | −38.983 | −35.320 | 1.00 | 26.70 | C |
| ATOM | 10797 | CD1 | LEU | B | 186 | −70.214 | −39.868 | −34.075 | 1.00 | 27.07 | C |
| ATOM | 10801 | CD2 | LEU | B | 186 | −71.179 | −39.306 | −36.303 | 1.00 | 26.29 | C |
| ATOM | 10805 | C | LEU | B | 186 | −68.594 | −35.822 | −33.815 | 1.00 | 26.45 | C |
| ATOM | 10806 | O | LEU | B | 186 | −67.449 | −35.875 | −34.237 | 1.00 | 26.48 | O |
| ATOM | 10808 | N | GLU | B | 187 | −69.186 | −34.685 | −33.454 | 1.00 | 25.93 | N |
| ATOM | 10809 | CA | GLU | B | 187 | −68.479 | −33.406 | −33.403 | 1.00 | 25.57 | C |
| ATOM | 10811 | CB | GLU | B | 187 | −69.447 | −32.310 | −32.962 | 1.00 | 25.61 | C |
| ATOM | 10814 | CG | GLU | B | 187 | −69.035 | −30.899 | −33.325 | 1.00 | 26.29 | C |
| ATOM | 10817 | CD | GLU | B | 187 | −69.930 | −29.857 | −32.671 | 1.00 | 27.10 | C |
| ATOM | 10818 | OE1 | GLU | B | 187 | −70.312 | −30.057 | −31.487 | 1.00 | 26.51 | O |
| ATOM | 10819 | OE2 | GLU | B | 187 | −70.251 | −28.846 | −33.344 | 1.00 | 27.54 | O |
| ATOM | 10820 | C | GLU | B | 187 | −67.307 | −33.490 | −32.418 | 1.00 | 25.13 | C |
| ATOM | 10821 | O | GLU | B | 187 | −66.155 | −33.165 | −32.749 | 1.00 | 24.85 | O |
| ATOM | 10823 | N | LEU | B | 188 | −67.625 | −33.938 | −31.204 | 1.00 | 24.58 | N |
| ATOM | 10824 | CA | LEU | B | 188 | −66.644 | −34.137 | −30.148 | 1.00 | 24.06 | C |
| ATOM | 10826 | CB | LEU | B | 188 | −66.343 | −32.817 | −29.451 | 1.00 | 24.12 | C |
| ATOM | 10829 | CG | LEU | B | 188 | −65.042 | −32.714 | −28.670 | 1.00 | 23.61 | C |
| ATOM | 10831 | CD1 | LEU | B | 188 | −63.895 | −32.872 | −29.629 | 1.00 | 23.12 | C |
| ATOM | 10835 | CD2 | LEU | B | 188 | −64.976 | −31.368 | −27.964 | 1.00 | 23.18 | C |
| ATOM | 10839 | C | LEU | B | 188 | −67.248 | −35.087 | −29.140 | 1.00 | 23.70 | C |
| ATOM | 10840 | O | LEU | B | 188 | −68.392 | −34.901 | −28.743 | 1.00 | 23.68 | O |
| ATOM | 10842 | N | PRO | B | 189 | −66.493 | −36.106 | −28.713 | 1.00 | 23.34 | N |
| ATOM | 10843 | CA | PRO | B | 189 | −67.031 | −36.983 | −27.692 | 1.00 | 23.08 | C |
| ATOM | 10845 | CB | PRO | B | 189 | −66.018 | −38.115 | −27.638 | 1.00 | 22.96 | C |
| ATOM | 10848 | CG | PRO | B | 189 | −64.743 | −37.452 | −27.940 | 1.00 | 23.22 | C |
| ATOM | 10851 | CD | PRO | B | 189 | −65.059 | −36.350 | −28.929 | 1.00 | 23.54 | C |
| ATOM | 10854 | C | PRO | B | 189 | −67.053 | −36.229 | −26.387 | 1.00 | 22.86 | C |
| ATOM | 10855 | O | PRO | B | 189 | −66.284 | −35.285 | −26.215 | 1.00 | 23.03 | O |
| ATOM | 10856 | N | LEU | B | 190 | −67.912 | −36.628 | −25.465 | 1.00 | 22.56 | N |
| ATOM | 10857 | CA | LEU | B | 190 | −68.152 | −35.773 | −24.323 | 1.00 | 22.41 | C |
| ATOM | 10859 | CB | LEU | B | 190 | −69.567 | −35.970 | −23.766 | 1.00 | 23.04 | C |
| ATOM | 10862 | CG | LEU | B | 190 | −69.853 | −37.136 | −22.848 | 1.00 | 23.41 | C |
| ATOM | 10864 | CD1 | LEU | B | 190 | −69.303 | −36.733 | −21.481 | 1.00 | 25.02 | C |
| ATOM | 10868 | CD2 | LEU | B | 190 | −71.342 | −37.411 | −22.820 | 1.00 | 21.69 | C |
| ATOM | 10872 | C | LEU | B | 190 | −67.065 | −35.899 | −23.266 | 1.00 | 21.56 | C |
| ATOM | 10873 | O | LEU | B | 190 | −66.860 | −34.976 | −22.477 | 1.00 | 21.67 | O |
| ATOM | 10875 | N | HIS | B | 191 | −66.320 | −36.998 | −23.283 | 1.00 | 20.39 | N |
| ATOM | 10876 | CA | HIS | B | 191 | −65.089 | −37.037 | −22.490 | 1.00 | 19.40 | C |
| ATOM | 10878 | CB | HIS | B | 191 | −64.399 | −38.393 | −22.597 | 1.00 | 19.19 | C |

TABLE 16-7-continued

Coordinates of *P. tremuloides* IspS

| ATOM | 10881 | CG | HIS | B | 191 | −63.222 | −38.530 | −21.689 | 1.00 | 19.32 | C |
|---|---|---|---|---|---|---|---|---|---|---|---|
| ATOM | 10882 | ND1 | HIS | B | 191 | −63.347 | −38.562 | −20.317 | 1.00 | 20.95 | N |
| ATOM | 10884 | CE1 | HIS | B | 191 | −62.145 | −38.659 | −19.771 | 1.00 | 21.15 | C |
| ATOM | 10886 | NE2 | HIS | B | 191 | −61.245 | −38.689 | −20.741 | 1.00 | 19.36 | N |
| ATOM | 10888 | CD2 | HIS | B | 191 | −61.893 | −38.604 | −21.948 | 1.00 | 19.49 | C |
| ATOM | 10890 | C | HIS | B | 191 | −64.094 | −35.913 | −22.841 | 1.00 | 18.62 | C |
| ATOM | 10891 | O | HIS | B | 191 | −63.150 | −35.677 | −22.085 | 1.00 | 18.59 | O |
| ATOM | 10893 | N | ARG | B | 192 | −64.307 | −35.216 | −23.957 | 1.00 | 17.72 | N |
| ATOM | 10894 | CA | ARG | B | 192 | −63.394 | −34.150 | −24.394 | 1.00 | 17.57 | C |
| ATOM | 10896 | CB | ARG | B | 192 | −62.838 | −34.504 | −25.773 | 1.00 | 17.81 | C |
| ATOM | 10899 | CG | ARG | B | 192 | −61.971 | −35.736 | −25.781 | 1.00 | 18.59 | C |
| ATOM | 10902 | CD | ARG | B | 192 | −61.484 | −36.067 | −27.181 | 1.00 | 20.10 | C |
| ATOM | 10905 | NE | ARG | B | 192 | −60.462 | −37.116 | −27.165 | 1.00 | 21.62 | N |
| ATOM | 10907 | CZ | ARG | B | 192 | −59.919 | −37.648 | −28.254 | 1.00 | 22.77 | C |
| ATOM | 10908 | NH1 | ARG | B | 192 | −60.304 | −37.248 | −29.454 | 1.00 | 24.20 | N |
| ATOM | 10911 | NH2 | ARG | B | 192 | −58.987 | −38.581 | −28.149 | 1.00 | 23.37 | N |
| ATOM | 10914 | C | ARG | B | 192 | −63.983 | −32.726 | −24.440 | 1.00 | 17.01 | C |
| ATOM | 10915 | O | ARG | B | 192 | −63.242 | −31.739 | −24.526 | 1.00 | 15.78 | O |
| ATOM | 10917 | N | ARG | B | 193 | −65.309 | −32.634 | −24.392 | 1.00 | 17.01 | N |
| ATOM | 10918 | CA | ARG | B | 193 | −66.015 | −31.350 | −24.453 | 1.00 | 16.99 | C |
| ATOM | 10920 | CB | ARG | B | 193 | −67.476 | −31.582 | −24.892 | 1.00 | 17.29 | C |
| ATOM | 10923 | CG | ARG | B | 193 | −68.192 | −30.318 | −25.377 | 1.00 | 18.42 | C |
| ATOM | 10926 | CD | ARG | B | 193 | −69.664 | −30.559 | −25.646 | 1.00 | 19.63 | C |
| ATOM | 10929 | NE | ARG | B | 193 | −69.912 | −31.592 | −26.648 | 1.00 | 21.16 | N |
| ATOM | 10931 | CZ | ARG | B | 193 | −69.868 | −31.398 | −27.971 | 1.00 | 23.56 | C |
| ATOM | 10932 | NH1 | ARG | B | 193 | −69.575 | −30.210 | −28.496 | 1.00 | 23.37 | N |
| ATOM | 10935 | NH2 | ARG | B | 193 | −70.112 | −32.413 | −28.789 | 1.00 | 25.37 | N |
| ATOM | 10938 | C | ARG | B | 193 | −65.974 | −30.658 | −23.087 | 1.00 | 16.46 | C |
| ATOM | 10939 | O | ARG | B | 193 | −66.040 | −31.323 | −22.034 | 1.00 | 16.47 | O |
| ATOM | 10941 | N | THR | B | 194 | −65.864 | −29.335 | −23.078 | 1.00 | 15.84 | N |
| ATOM | 10942 | CA | THR | B | 194 | −65.886 | −28.629 | −21.799 | 1.00 | 15.67 | C |
| ATOM | 10944 | CB | THR | B | 194 | −65.354 | −27.199 | −21.884 | 1.00 | 15.48 | C |
| ATOM | 10946 | OG1 | THR | B | 194 | −66.077 | −26.478 | −22.882 | 1.00 | 15.55 | O |
| ATOM | 10948 | CG2 | THR | B | 194 | −63.877 | −27.189 | −22.211 | 1.00 | 14.65 | C |
| ATOM | 10952 | C | THR | B | 194 | −67.310 | −28.613 | −21.270 | 1.00 | 15.79 | C |
| ATOM | 10953 | O | THR | B | 194 | −68.264 | −28.652 | −22.030 | 1.00 | 15.73 | O |
| ATOM | 10955 | N | GLN | B | 195 | −67.444 | −28.557 | −19.957 | 1.00 | 16.20 | N |
| ATOM | 10956 | CA | GLN | B | 195 | −68.737 | −28.711 | −19.328 | 1.00 | 16.84 | C |
| ATOM | 10958 | CB | GLN | B | 195 | −68.601 | −28.781 | −17.816 | 1.00 | 17.07 | C |
| ATOM | 10961 | CG | GLN | B | 195 | −69.921 | −28.440 | −17.153 | 1.00 | 18.86 | C |
| ATOM | 10964 | CD | GLN | B | 195 | −69.999 | −28.875 | −15.746 | 1.00 | 20.95 | C |
| ATOM | 10965 | OE1 | GLN | B | 195 | −69.099 | −29.511 | −15.245 | 1.00 | 24.63 | O |
| ATOM | 10966 | NE2 | GLN | B | 195 | −71.071 | −28.529 | −15.082 | 1.00 | 22.36 | N |
| ATOM | 10969 | C | GLN | B | 195 | −69.757 | −27.623 | −19.669 | 1.00 | 16.93 | C |
| ATOM | 10970 | O | GLN | B | 195 | −70.858 | −27.931 | −20.136 | 1.00 | 16.98 | O |
| ATOM | 10972 | N | ARG | B | 196 | −69.430 | −26.366 | −19.386 | 1.00 | 16.92 | N |
| ATOM | 10973 | CA | ARG | B | 196 | −70.358 | −25.301 | −19.685 | 1.00 | 17.06 | C |
| ATOM | 10975 | CB | ARG | B | 196 | −69.719 | −23.932 | −19.459 | 1.00 | 17.00 | C |
| ATOM | 10978 | CG | ARG | B | 196 | −70.095 | −23.289 | −18.120 | 1.00 | 17.09 | C |
| ATOM | 10981 | CD | ARG | B | 196 | −70.283 | −24.320 | −16.995 | 1.00 | 17.56 | C |
| ATOM | 10984 | NE | ARG | B | 196 | −71.452 | −24.043 | −16.146 | 1.00 | 17.64 | N |
| ATOM | 10986 | CZ | ARG | B | 196 | −72.289 | −24.965 | −15.664 | 1.00 | 17.93 | C |
| ATOM | 10987 | NH1 | ARG | B | 196 | −72.136 | −26.244 | −15.966 | 1.00 | 17.72 | N |
| ATOM | 10990 | NH2 | ARG | B | 196 | −73.305 | −24.611 | −14.878 | 1.00 | 18.27 | N |
| ATOM | 10993 | C | ARG | B | 196 | −70.881 | −25.481 | −21.098 | 1.00 | 17.42 | C |
| ATOM | 10994 | O | ARG | B | 196 | −72.079 | −25.519 | −21.317 | 1.00 | 17.66 | O |
| ATOM | 10996 | N | LEU | B | 197 | −69.984 | −25.676 | −22.044 | 1.00 | 18.04 | N |
| ATOM | 10997 | CA | LEU | B | 197 | −70.379 | −25.925 | −23.425 | 1.00 | 18.51 | C |
| ATOM | 10999 | CB | LEU | B | 197 | −69.133 | −26.085 | −24.289 | 1.00 | 18.52 | C |
| ATOM | 11002 | CG | LEU | B | 197 | −68.998 | −25.185 | −25.508 | 1.00 | 18.06 | C |
| ATOM | 11004 | CD1 | LEU | B | 197 | −68.209 | −23.932 | −25.205 | 1.00 | 15.52 | C |
| ATOM | 11008 | CD2 | LEU | B | 197 | −68.293 | −26.002 | −26.574 | 1.00 | 20.21 | C |
| ATOM | 11012 | C | LEU | B | 197 | −71.290 | −27.163 | −23.580 | 1.00 | 19.14 | C |
| ATOM | 11013 | O | LEU | B | 197 | −72.226 | −27.150 | −24.372 | 1.00 | 19.52 | O |
| ATOM | 11015 | N | GLU | B | 198 | −71.030 | −28.235 | −22.842 | 1.00 | 19.72 | N |
| ATOM | 11016 | CA | GLU | B | 198 | −71.918 | −29.396 | −22.909 | 1.00 | 20.43 | C |
| ATOM | 11018 | CB | GLU | B | 198 | −71.272 | −30.631 | −22.270 | 1.00 | 20.65 | C |
| ATOM | 11021 | CG | GLU | B | 198 | −72.176 | −31.880 | −22.172 | 1.00 | 22.51 | C |
| ATOM | 11024 | CD | GLU | B | 198 | −72.635 | −32.460 | −23.522 | 1.00 | 25.57 | C |
| ATOM | 11025 | OE1 | GLU | B | 198 | −72.315 | −31.896 | −24.581 | 1.00 | 28.90 | O |
| ATOM | 11026 | OE2 | GLU | B | 198 | −73.326 | −33.506 | −23.540 | 1.00 | 28.09 | O |
| ATOM | 11027 | C | GLU | B | 198 | −73.271 | −29.101 | −22.259 | 1.00 | 20.72 | C |
| ATOM | 11028 | O | GLU | B | 198 | −74.281 | −29.693 | −22.644 | 1.00 | 20.82 | O |
| ATOM | 11030 | N | ALA | B | 199 | −73.282 | −28.199 | −21.270 | 1.00 | 20.86 | N |
| ATOM | 11031 | CA | ALA | B | 199 | −74.508 | −27.814 | −20.565 | 1.00 | 20.66 | C |
| ATOM | 11033 | CB | ALA | B | 199 | −74.176 | −27.013 | −19.326 | 1.00 | 20.36 | C |
| ATOM | 11037 | C | ALA | B | 199 | −75.472 | −27.033 | −21.461 | 1.00 | 20.84 | C |
| ATOM | 11038 | O | ALA | B | 199 | −76.644 | −27.404 | −21.590 | 1.00 | 20.84 | O |

TABLE 16-7-continued

| | | | | | | | | | | |
|---|---|---|---|---|---|---|---|---|---|---|
| ATOM | 11040 | N | VAL | B | 200 | −75.002 | −25.961 | −22.092 | 1.00 | 21.12 | N |
| ATOM | 11041 | CA | VAL | B | 200 | −75.903 | −25.177 | −22.942 | 1.00 | 21.60 | C |
| ATOM | 11043 | CB | VAL | B | 200 | −75.215 | −24.042 | −23.701 | 1.00 | 21.30 | C |
| ATOM | 11045 | CG1 | VAL | B | 200 | −74.660 | −23.055 | −22.738 | 1.00 | 21.26 | C |
| ATOM | 11049 | CG2 | VAL | B | 200 | −74.135 | −24.575 | −24.626 | 1.00 | 21.28 | C |
| ATOM | 11053 | C | VAL | B | 200 | −76.603 | −26.077 | −23.944 | 1.00 | 22.32 | C |
| ATOM | 11054 | O | VAL | B | 200 | −77.791 | −25.908 | −24.218 | 1.00 | 22.32 | O |
| ATOM | 11056 | N | TRP | B | 201 | −75.872 | −27.047 | −24.472 | 1.00 | 23.16 | N |
| ATOM | 11057 | CA | TRP | B | 201 | −76.441 | −27.946 | −25.454 | 1.00 | 24.02 | C |
| ATOM | 11059 | CB | TRP | B | 201 | −75.348 | −28.718 | −26.195 | 1.00 | 24.36 | C |
| ATOM | 11062 | CG | TRP | B | 201 | −75.898 | −29.510 | −27.331 | 1.00 | 24.84 | C |
| ATOM | 11063 | CD1 | TRP | B | 201 | −76.060 | −29.092 | −28.613 | 1.00 | 25.41 | C |
| ATOM | 11065 | NE1 | TRP | B | 201 | −76.599 | −30.094 | −29.374 | 1.00 | 25.61 | N |
| ATOM | 11067 | CE2 | TRP | B | 201 | −76.807 | −31.184 | −28.579 | 1.00 | 25.34 | C |
| ATOM | 11068 | CD2 | TRP | B | 201 | −76.374 | −30.847 | −27.279 | 1.00 | 25.56 | C |
| ATOM | 11069 | CE3 | TRP | B | 201 | −76.466 | −31.800 | −26.264 | 1.00 | 27.13 | C |
| ATOM | 11071 | CZ3 | TRP | B | 201 | −76.989 | −33.046 | −26.574 | 1.00 | 28.66 | C |
| ATOM | 11073 | CH2 | TRP | B | 201 | −77.419 | −33.347 | −27.885 | 1.00 | 28.01 | C |
| ATOM | 11075 | CZ2 | TRP | B | 201 | −77.332 | −32.425 | −28.894 | 1.00 | 26.09 | C |
| ATOM | 11077 | C | TRP | B | 201 | −77.411 | −28.938 | −24.833 | 1.00 | 24.22 | C |
| ATOM | 11078 | O | TRP | B | 201 | −78.473 | −29.172 | −25.383 | 1.00 | 24.83 | O |
| ATOM | 11080 | N | SER | B | 202 | −77.034 | −29.541 | −23.715 | 1.00 | 24.39 | N |
| ATOM | 11081 | CA | SER | B | 202 | −77.818 | −30.626 | −23.144 | 1.00 | 24.50 | C |
| ATOM | 11083 | CB | SER | B | 202 | −76.968 | −31.455 | −22.184 | 1.00 | 24.42 | C |
| ATOM | 11086 | OG | SER | B | 202 | −75.848 | −32.021 | −22.848 | 1.00 | 23.80 | O |
| ATOM | 11088 | C | SER | B | 202 | −79.067 | −30.099 | −22.441 | 1.00 | 24.98 | C |
| ATOM | 11089 | O | SER | B | 202 | −80.057 | −30.816 | −22.324 | 1.00 | 24.73 | O |
| ATOM | 11091 | N | ILE | B | 203 | −79.032 | −28.849 | −21.982 | 1.00 | 25.60 | N |
| ATOM | 11092 | CA | ILE | B | 203 | −80.219 | −28.255 | −21.372 | 1.00 | 25.98 | C |
| ATOM | 11094 | CB | ILE | B | 203 | −79.908 | −26.967 | −20.591 | 1.00 | 25.85 | C |
| ATOM | 11096 | CG1 | ILE | B | 203 | −79.086 | −27.326 | −19.348 | 1.00 | 25.76 | C |
| ATOM | 11099 | CD1 | ILE | B | 203 | −78.779 | −26.159 | −18.431 | 1.00 | 26.28 | C |
| ATOM | 11103 | CG2 | ILE | B | 203 | −81.212 | −26.253 | −20.206 | 1.00 | 24.51 | C |
| ATOM | 11107 | C | ILE | B | 203 | −81.280 | −28.016 | −22.443 | 1.00 | 26.67 | C |
| ATOM | 11108 | O | ILE | B | 203 | −82.428 | −28.398 | −22.260 | 1.00 | 26.96 | O |
| ATOM | 11110 | N | GLU | B | 204 | −80.879 | −27.412 | −23.563 | 1.00 | 27.30 | N |
| ATOM | 11111 | CA | GLU | B | 204 | −81.758 | −27.205 | −24.720 | 1.00 | 27.49 | C |
| ATOM | 11113 | CB | GLU | B | 204 | −81.036 | −26.384 | −25.804 | 1.00 | 27.67 | C |
| ATOM | 11116 | CG | GLU | B | 204 | −81.849 | −26.077 | −27.073 | 1.00 | 28.50 | C |
| ATOM | 11119 | CD | GLU | B | 204 | −82.987 | −25.072 | −26.855 | 1.00 | 29.81 | C |
| ATOM | 11120 | OE1 | GLU | B | 204 | −83.158 | −24.600 | −25.711 | 1.00 | 31.40 | O |
| ATOM | 11121 | OE2 | GLU | B | 204 | −83.710 | −24.750 | −27.832 | 1.00 | 29.57 | O |
| ATOM | 11122 | C | GLU | B | 204 | −82.201 | −28.542 | −25.287 | 1.00 | 27.52 | C |
| ATOM | 11123 | O | GLU | B | 204 | −83.321 | −28.667 | −25.738 | 1.00 | 27.67 | O |
| ATOM | 11125 | N | ALA | B | 205 | −81.326 | −29.539 | −25.266 | 1.00 | 27.74 | N |
| ATOM | 11126 | CA | ALA | B | 205 | −81.684 | −30.872 | −25.728 | 1.00 | 28.09 | C |
| ATOM | 11128 | CB | ALA | B | 205 | −80.472 | −31.789 | −25.726 | 1.00 | 27.75 | C |
| ATOM | 11132 | C | ALA | B | 205 | −82.771 | −31.448 | −24.839 | 1.00 | 28.81 | C |
| ATOM | 11133 | O | ALA | B | 205 | −83.811 | −31.877 | −25.325 | 1.00 | 28.90 | O |
| ATOM | 11135 | N | TYR | B | 206 | −82.517 | −31.433 | −23.531 | 1.00 | 29.72 | N |
| ATOM | 11136 | CA | TYR | B | 206 | −83.408 | −32.020 | −22.527 | 1.00 | 30.30 | C |
| ATOM | 11138 | CB | TYR | B | 206 | −82.760 | −31.915 | −21.149 | 1.00 | 30.24 | C |
| ATOM | 11141 | CG | TYR | B | 206 | −83.276 | −32.889 | −20.127 | 1.00 | 29.79 | C |
| ATOM | 11142 | CD1 | TYR | B | 206 | −83.055 | −34.245 | −20.286 | 1.00 | 30.71 | C |
| ATOM | 11144 | CE1 | TYR | B | 206 | −83.498 | −35.161 | −19.360 | 1.00 | 30.78 | C |
| ATOM | 11146 | CZ | TYR | B | 206 | −84.159 | −34.731 | −18.238 | 1.00 | 30.03 | C |
| ATOM | 11147 | OH | TYR | B | 206 | −84.582 | −35.684 | −17.343 | 1.00 | 30.51 | O |
| ATOM | 11149 | CE2 | TYR | B | 206 | −84.394 | −33.379 | −18.042 | 1.00 | 29.42 | C |
| ATOM | 11151 | CD2 | TYR | B | 206 | −83.945 | −32.463 | −18.989 | 1.00 | 29.05 | C |
| ATOM | 11153 | C | TYR | B | 206 | −84.744 | −31.308 | −22.467 | 1.00 | 31.19 | C |
| ATOM | 11154 | O | TYR | B | 206 | −85.790 | −31.930 | −22.311 | 1.00 | 31.44 | O |
| ATOM | 11156 | N | ARG | B | 207 | −84.683 | −29.988 | −22.558 | 1.00 | 32.21 | N |
| ATOM | 11157 | CA | ARG | B | 207 | −85.853 | −29.128 | −22.521 | 1.00 | 33.04 | C |
| ATOM | 11159 | CB | ARG | B | 207 | −85.394 | −27.700 | −22.843 | 1.00 | 32.86 | C |
| ATOM | 11162 | CG | ARG | B | 207 | −86.441 | −26.637 | −22.846 | 1.00 | 32.82 | C |
| ATOM | 11165 | CD | ARG | B | 207 | −85.905 | −25.360 | −23.462 | 1.00 | 32.76 | C |
| ATOM | 11168 | NE | ARG | B | 207 | −85.148 | −24.561 | −22.504 | 1.00 | 32.80 | N |
| ATOM | 11170 | CZ | ARG | B | 207 | −85.676 | −23.709 | −21.628 | 1.00 | 33.40 | C |
| ATOM | 11171 | NH1 | ARG | B | 207 | −86.989 | −23.526 | −21.555 | 1.00 | 34.29 | N |
| ATOM | 11174 | NH2 | ARG | B | 207 | −84.884 | −23.030 | −20.808 | 1.00 | 33.89 | N |
| ATOM | 11177 | C | ARG | B | 207 | −86.971 | −29.606 | −23.478 | 1.00 | 34.14 | C |
| ATOM | 11178 | O | ARG | B | 207 | −88.144 | −29.521 | −23.128 | 1.00 | 34.34 | O |
| ATOM | 11180 | N | LYS | B | 208 | −86.607 | −30.137 | −24.652 | 1.00 | 35.32 | N |
| ATOM | 11181 | CA | LYS | B | 208 | −87.581 | −30.535 | −25.688 | 1.00 | 36.16 | C |
| ATOM | 11183 | CB | LYS | B | 208 | −86.960 | −30.468 | −27.090 | 1.00 | 36.01 | C |
| ATOM | 11186 | CG | LYS | B | 208 | −86.126 | −29.234 | −27.368 | 1.00 | 35.85 | C |
| ATOM | 11189 | CD | LYS | B | 208 | −85.934 | −29.023 | −28.861 | 1.00 | 35.98 | C |
| ATOM | 11192 | CE | LYS | B | 208 | −84.774 | −28.086 | −29.186 | 1.00 | 35.63 | C |

TABLE 16-7-continued

Coordinates of *P. tremuloides* IspS

| ATOM | 11195 | NZ | LYS | B | 208 | −83.566 | −28.843 | −29.596 | 1.00 | 35.17 | N |
|---|---|---|---|---|---|---|---|---|---|---|---|
| ATOM | 11199 | C | LYS | B | 208 | −88.166 | −31.937 | −25.490 | 1.00 | 37.25 | C |
| ATOM | 11200 | O | LYS | B | 208 | −89.212 | −32.250 | −26.054 | 1.00 | 37.50 | O |
| ATOM | 11202 | N | LYS | B | 209 | −87.484 | −32.788 | −24.730 | 1.00 | 38.58 | N |
| ATOM | 11203 | CA | LYS | B | 209 | −88.026 | −34.106 | −24.383 | 1.00 | 39.89 | C |
| ATOM | 11205 | CB | LYS | B | 209 | −87.013 | −34.923 | −23.578 | 1.00 | 40.23 | C |
| ATOM | 11208 | CG | LYS | B | 209 | −85.914 | −35.604 | −24.373 | 1.00 | 41.47 | C |
| ATOM | 11211 | CD | LYS | B | 209 | −84.858 | −36.178 | −23.417 | 1.00 | 43.71 | C |
| ATOM | 11214 | CE | LYS | B | 209 | −84.448 | −37.612 | −23.764 | 1.00 | 45.15 | C |
| ATOM | 11217 | NZ | LYS | B | 209 | −85.390 | −38.621 | −23.163 | 1.00 | 45.73 | N |
| ATOM | 11221 | C | LYS | B | 209 | −89.288 | −33.950 | −23.530 | 1.00 | 40.51 | C |
| ATOM | 11222 | O | LYS | B | 209 | −89.230 | −33.367 | −22.441 | 1.00 | 40.84 | O |
| ATOM | 11224 | N | GLU | B | 210 | −90.418 | −34.477 | −24.000 | 1.00 | 40.92 | N |
| ATOM | 11225 | CA | GLU | B | 210 | −91.652 | −34.386 | −23.223 | 1.00 | 41.27 | C |
| ATOM | 11227 | CB | GLU | B | 210 | −92.855 | −34.935 | −23.998 | 1.00 | 41.77 | C |
| ATOM | 11230 | CG | GLU | B | 210 | −92.822 | −36.446 | −24.265 | 1.00 | 43.47 | C |
| ATOM | 11233 | CD | GLU | B | 210 | −94.049 | −36.922 | −25.032 | 1.00 | 45.23 | C |
| ATOM | 11234 | OE1 | GLU | B | 210 | −95.188 | −36.590 | −24.612 | 1.00 | 45.02 | O |
| ATOM | 11235 | OE2 | GLU | B | 210 | −93.863 | −37.629 | −26.053 | 1.00 | 46.74 | O |
| ATOM | 11236 | C | GLU | B | 210 | −91.494 | −35.121 | −21.895 | 1.00 | 40.71 | C |
| ATOM | 11237 | O | GLU | B | 210 | −91.996 | −34.667 | −20.864 | 1.00 | 40.99 | O |
| ATOM | 11239 | N | ASP | B | 211 | −90.773 | −36.240 | −21.924 | 1.00 | 39.76 | N |
| ATOM | 11240 | CA | ASP | B | 211 | −90.533 | −37.050 | −20.721 | 1.00 | 38.96 | C |
| ATOM | 11242 | CB | ASP | B | 211 | −90.151 | −38.476 | −21.123 | 1.00 | 39.10 | C |
| ATOM | 11245 | CG | ASP | B | 211 | −89.101 | −38.499 | −22.212 | 1.00 | 40.26 | C |
| ATOM | 11246 | OD1 | ASP | B | 211 | −89.327 | −37.827 | −23.254 | 1.00 | 41.25 | O |
| ATOM | 11247 | OD2 | ASP | B | 211 | −88.055 | −39.160 | −22.020 | 1.00 | 41.66 | O |
| ATOM | 11248 | C | ASP | B | 211 | −89.440 | −36.468 | −19.826 | 1.00 | 37.75 | C |
| ATOM | 11249 | O | ASP | B | 211 | −89.009 | −37.131 | −18.892 | 1.00 | 37.62 | O |
| ATOM | 11251 | N | ALA | B | 212 | −88.989 | −35.245 | −20.115 | 1.00 | 36.47 | N |
| ATOM | 11252 | CA | ALA | B | 212 | −87.941 | −34.587 | −19.335 | 1.00 | 35.36 | C |
| ATOM | 11254 | CB | ALA | B | 212 | −87.516 | −33.294 | −20.011 | 1.00 | 35.23 | C |
| ATOM | 11258 | C | ALA | B | 212 | −88.423 | −34.307 | −17.920 | 1.00 | 34.40 | C |
| ATOM | 11259 | O | ALA | B | 212 | −89.559 | −33.870 | −17.728 | 1.00 | 34.42 | O |
| ATOM | 11261 | N | ASN | B | 213 | −87.565 | −34.574 | −16.937 | 1.00 | 33.24 | N |
| ATOM | 11262 | CA | ASN | B | 213 | −87.890 | −34.333 | −15.533 | 1.00 | 32.67 | C |
| ATOM | 11264 | CB | ASN | B | 213 | −86.840 | −34.986 | −14.623 | 1.00 | 32.58 | C |
| ATOM | 11267 | CG | ASN | B | 213 | −87.204 | −34.912 | −13.152 | 1.00 | 32.67 | C |
| ATOM | 11268 | OD1 | ASN | B | 213 | −87.891 | −33.994 | −12.722 | 1.00 | 32.62 | O |
| ATOM | 11269 | ND2 | ASN | B | 213 | −86.734 | −35.882 | −12.371 | 1.00 | 33.18 | N |
| ATOM | 11272 | C | ASN | B | 213 | −87.990 | −32.825 | −15.266 | 1.00 | 32.19 | C |
| ATOM | 11273 | O | ASN | B | 213 | −87.010 | −32.092 | −15.376 | 1.00 | 32.38 | O |
| ATOM | 11275 | N | GLN | B | 214 | −89.182 | −32.356 | −14.923 | 1.00 | 31.48 | N |
| ATOM | 11276 | CA | GLN | B | 214 | −89.389 | −30.924 | −14.756 | 1.00 | 30.85 | C |
| ATOM | 11278 | CB | GLN | B | 214 | −90.889 | −30.581 | −14.693 | 1.00 | 30.82 | C |
| ATOM | 11281 | CG | GLN | B | 214 | −91.684 | −30.869 | −16.002 | 1.00 | 30.80 | C |
| ATOM | 11284 | CD | GLN | B | 214 | −90.990 | −30.378 | −17.291 | 1.00 | 29.69 | C |
| ATOM | 11285 | OE1 | GLN | B | 214 | −90.893 | −29.174 | −17.543 | 1.00 | 29.07 | O |
| ATOM | 11286 | NE2 | GLN | B | 214 | −90.526 | −31.321 | −18.113 | 1.00 | 27.71 | N |
| ATOM | 11289 | C | GLN | B | 214 | −88.638 | −30.369 | −13.543 | 1.00 | 30.37 | C |
| ATOM | 11290 | O | GLN | B | 214 | −88.263 | −29.200 | −13.533 | 1.00 | 30.80 | O |
| ATOM | 11292 | N | VAL | B | 215 | −88.393 | −31.200 | −12.532 | 1.00 | 29.54 | N |
| ATOM | 11293 | CA | VAL | B | 215 | −87.566 | −30.779 | −11.395 | 1.00 | 28.56 | C |
| ATOM | 11295 | CB | VAL | B | 215 | −87.564 | −31.818 | −10.260 | 1.00 | 28.64 | C |
| ATOM | 11297 | CG1 | VAL | B | 215 | −86.758 | −31.299 | −9.075 | 1.00 | 27.94 | C |
| ATOM | 11301 | CG2 | VAL | B | 215 | −88.999 | −32.167 | −9.856 | 1.00 | 28.26 | C |
| ATOM | 11305 | C | VAL | B | 215 | −86.124 | −30.545 | −11.845 | 1.00 | 27.63 | C |
| ATOM | 11306 | O | VAL | B | 215 | −85.566 | −29.472 | −11.615 | 1.00 | 27.58 | O |
| ATOM | 11308 | N | LEU | B | 216 | −85.546 | −31.548 | −12.504 | 1.00 | 26.37 | N |
| ATOM | 11309 | CA | LEU | B | 216 | −84.143 | −31.509 | −12.930 | 1.00 | 25.47 | C |
| ATOM | 11311 | CB | LEU | B | 216 | −83.714 | −32.866 | −13.490 | 1.00 | 25.46 | C |
| ATOM | 11314 | CG | LEU | B | 216 | −82.274 | −32.995 | −13.979 | 1.00 | 24.97 | C |
| ATOM | 11316 | CD1 | LEU | B | 216 | −81.289 | −32.640 | −12.883 | 1.00 | 24.62 | C |
| ATOM | 11320 | CD2 | LEU | B | 216 | −82.042 | −34.407 | −14.472 | 1.00 | 24.55 | C |
| ATOM | 11324 | C | LEU | B | 216 | −83.861 | −30.447 | −13.972 | 1.00 | 24.68 | C |
| ATOM | 11325 | O | LEU | B | 216 | −82.819 | −29.820 | −13.929 | 1.00 | 24.91 | O |
| ATOM | 11327 | N | LEU | B | 217 | −84.776 | −30.269 | −14.916 | 1.00 | 23.79 | N |
| ATOM | 11328 | CA | LEU | B | 217 | −84.625 | −29.260 | −15.960 | 1.00 | 23.13 | C |
| ATOM | 11330 | CB | LEU | B | 217 | −85.765 | −29.384 | −16.972 | 1.00 | 23.36 | C |
| ATOM | 11333 | CG | LEU | B | 217 | −85.808 | −28.374 | −18.123 | 1.00 | 23.18 | C |
| ATOM | 11335 | CD1 | LEU | B | 217 | −84.462 | −28.268 | −18.796 | 1.00 | 22.69 | C |
| ATOM | 11339 | CD2 | LEU | B | 217 | −86.861 | −28.786 | −19.126 | 1.00 | 23.38 | C |
| ATOM | 11343 | C | LEU | B | 217 | −84.631 | −27.853 | −15.383 | 1.00 | 22.51 | C |
| ATOM | 11344 | O | LEU | B | 217 | −83.903 | −26.973 | −15.855 | 1.00 | 22.08 | O |
| ATOM | 11346 | N | GLU | B | 218 | −85.481 | −27.647 | −14.375 | 1.00 | 21.84 | N |
| ATOM | 11347 | CA | GLU | B | 218 | −85.619 | −26.339 | −13.725 | 1.00 | 21.26 | C |
| ATOM | 11349 | CB | GLU | B | 218 | −86.813 | −26.341 | −12.768 | 1.00 | 21.27 | C |
| ATOM | 11352 | CG | GLU | B | 218 | −87.206 | −24.956 | −12.246 | 1.00 | 21.35 | C |

TABLE 16-7-continued

Coordinates of *P. tremuloides* IspS

| ATOM | 11355 | CD | GLU | B | 218 | −88.501 | −24.964 | −11.441 | 1.00 | 20.89 | C |
|---|---|---|---|---|---|---|---|---|---|---|---|
| ATOM | 11356 | OE1 | GLU | B | 218 | −89.097 | −26.052 | −11.263 | 1.00 | 20.47 | O |
| ATOM | 11357 | OE2 | GLU | B | 218 | −88.915 | −23.874 | −10.986 | 1.00 | 20.15 | O |
| ATOM | 11358 | C | GLU | B | 218 | −84.348 | −26.001 | −12.969 | 1.00 | 20.58 | C |
| ATOM | 11359 | O | GLU | B | 218 | −83.877 | −24.865 | −12.982 | 1.00 | 20.31 | O |
| ATOM | 11361 | N | LEU | B | 219 | −83.802 | −27.015 | −12.312 | 1.00 | 19.87 | N |
| ATOM | 11362 | CA | LEU | B | 219 | −82.559 | −26.885 | −11.592 | 1.00 | 19.12 | C |
| ATOM | 11364 | CB | LEU | B | 219 | −82.310 | −28.132 | −10.746 | 1.00 | 18.58 | C |
| ATOM | 11367 | CG | LEU | B | 219 | −81.159 | −28.054 | −9.762 | 1.00 | 17.07 | C |
| ATOM | 11369 | CD1 | LEU | B | 219 | −81.321 | −26.847 | −8.872 | 1.00 | 16.10 | C |
| ATOM | 11373 | CD2 | LEU | B | 219 | −81.107 | −29.311 | −8.954 | 1.00 | 15.22 | C |
| ATOM | 11377 | C | LEU | B | 219 | −81.443 | −26.675 | −12.599 | 1.00 | 19.16 | C |
| ATOM | 11378 | O | LEU | B | 219 | −80.684 | −25.721 | −12.478 | 1.00 | 19.42 | O |
| ATOM | 11380 | N | ALA | B | 220 | −81.368 | −27.546 | −13.606 | 1.00 | 19.04 | N |
| ATOM | 11381 | CA | ALA | B | 220 | −80.356 | −27.431 | −14.669 | 1.00 | 19.04 | C |
| ATOM | 11383 | CB | ALA | B | 220 | −80.648 | −28.398 | −15.817 | 1.00 | 18.64 | C |
| ATOM | 11387 | C | ALA | B | 220 | −80.257 | −26.004 | −15.196 | 1.00 | 19.06 | C |
| ATOM | 11388 | O | ALA | B | 220 | −79.159 | −25.472 | −15.321 | 1.00 | 19.08 | O |
| ATOM | 11390 | N | ILE | B | 221 | −81.410 | −25.390 | −15.475 | 1.00 | 19.19 | N |
| ATOM | 11391 | CA | ILE | B | 221 | −81.473 | −24.016 | −15.963 | 1.00 | 19.22 | C |
| ATOM | 11393 | CB | ILE | B | 221 | −82.898 | −23.638 | −16.423 | 1.00 | 19.03 | C |
| ATOM | 11395 | CG1 | ILE | B | 221 | −83.229 | −24.323 | −17.755 | 1.00 | 18.52 | C |
| ATOM | 11398 | CD1 | ILE | B | 221 | −84.687 | −24.645 | −17.928 | 1.00 | 17.52 | C |
| ATOM | 11402 | CG2 | ILE | B | 221 | −83.024 | −22.121 | −16.564 | 1.00 | 18.03 | C |
| ATOM | 11406 | C | ILE | B | 221 | −81.030 | −23.013 | −14.906 | 1.00 | 19.62 | C |
| ATOM | 11407 | O | ILE | B | 221 | −80.137 | −22.190 | −15.136 | 1.00 | 19.53 | O |
| ATOM | 11409 | N | LEU | B | 222 | −81.666 | −23.096 | −13.745 | 1.00 | 20.27 | N |
| ATOM | 11410 | CA | LEU | B | 222 | −81.412 | −22.161 | −12.654 | 1.00 | 20.63 | C |
| ATOM | 11412 | CB | LEU | B | 222 | −82.203 | −22.561 | −11.412 | 1.00 | 20.50 | C |
| ATOM | 11415 | CG | LEU | B | 222 | −82.195 | −21.523 | −10.296 | 1.00 | 20.76 | C |
| ATOM | 11417 | CD1 | LEU | B | 222 | −83.439 | −21.675 | −9.431 | 1.00 | 21.02 | C |
| ATOM | 11421 | CD2 | LEU | B | 222 | −80.924 | −21.625 | −9.453 | 1.00 | 20.21 | C |
| ATOM | 11425 | C | LEU | B | 222 | −79.925 | −22.089 | −12.341 | 1.00 | 20.98 | C |
| ATOM | 11426 | O | LEU | B | 222 | −79.337 | −21.011 | −12.381 | 1.00 | 21.40 | O |
| ATOM | 11428 | N | ASP | B | 223 | −79.319 | −23.240 | −12.064 | 1.00 | 21.24 | N |
| ATOM | 11429 | CA | ASP | B | 223 | −77.907 | −23.298 | −11.709 | 1.00 | 21.48 | C |
| ATOM | 11431 | CB | ASP | B | 223 | −77.509 | −24.724 | −11.314 | 1.00 | 21.66 | C |
| ATOM | 11434 | CG | ASP | B | 223 | −76.168 | −24.792 | −10.589 | 1.00 | 22.70 | C |
| ATOM | 11435 | OD1 | ASP | B | 223 | −75.095 | −24.775 | −11.244 | 1.00 | 24.25 | O |
| ATOM | 11436 | OD2 | ASP | B | 223 | −76.190 | −24.893 | −9.349 | 1.00 | 24.85 | O |
| ATOM | 11437 | C | ASP | B | 223 | −77.017 | −22.768 | −12.835 | 1.00 | 21.64 | C |
| ATOM | 11438 | O | ASP | B | 223 | −76.035 | −22.104 | −12.548 | 1.00 | 21.66 | O |
| ATOM | 11440 | N | TYR | B | 224 | −77.361 | −23.023 | −14.100 | 1.00 | 22.07 | N |
| ATOM | 11441 | CA | TYR | B | 224 | −76.517 | −22.561 | −15.218 | 1.00 | 22.47 | C |
| ATOM | 11443 | CB | TYR | B | 224 | −76.980 | −23.111 | −16.589 | 1.00 | 22.35 | C |
| ATOM | 11446 | CG | TYR | B | 224 | −76.032 | −22.733 | −17.724 | 1.00 | 22.25 | C |
| ATOM | 11447 | CD1 | TYR | B | 224 | −75.002 | −23.576 | −18.116 | 1.00 | 21.46 | C |
| ATOM | 11449 | CE1 | TYR | B | 224 | −74.126 | −23.216 | −19.135 | 1.00 | 21.43 | C |
| ATOM | 11451 | CZ | TYR | B | 224 | −74.260 | −21.991 | −19.761 | 1.00 | 21.62 | C |
| ATOM | 11452 | OH | TYR | B | 224 | −73.387 | −21.618 | −20.760 | 1.00 | 20.46 | O |
| ATOM | 11454 | CE2 | TYR | B | 224 | −75.270 | −21.132 | −19.387 | 1.00 | 22.04 | C |
| ATOM | 11456 | CD2 | TYR | B | 224 | −76.144 | −21.500 | −18.373 | 1.00 | 22.73 | C |
| ATOM | 11458 | C | TYR | B | 224 | −76.414 | −21.023 | −15.262 | 1.00 | 23.06 | C |
| ATOM | 11459 | O | TYR | B | 224 | −75.323 | −20.467 | −15.507 | 1.00 | 22.89 | O |
| ATOM | 11461 | N | ASN | B | 225 | −77.543 | −20.350 | −15.027 | 1.00 | 23.66 | N |
| ATOM | 11462 | CA | ASN | B | 225 | −77.593 | −18.884 | −15.072 | 1.00 | 24.16 | C |
| ATOM | 11464 | CB | ASN | B | 225 | −79.040 | −18.367 | −15.107 | 1.00 | 24.12 | C |
| ATOM | 11467 | CG | ASN | B | 225 | −79.778 | −18.761 | −16.365 | 1.00 | 23.89 | C |
| ATOM | 11468 | OD1 | ASN | B | 225 | −79.182 | −18.877 | −17.437 | 1.00 | 24.33 | O |
| ATOM | 11469 | ND2 | ASN | B | 225 | −81.088 | −18.965 | −16.244 | 1.00 | 22.05 | N |
| ATOM | 11472 | C | ASN | B | 225 | −76.880 | −18.265 | −13.881 | 1.00 | 24.73 | C |
| ATOM | 11473 | O | ASN | B | 225 | −76.195 | −17.247 | −14.027 | 1.00 | 25.09 | O |
| ATOM | 11475 | N | MET | B | 226 | −77.067 | −18.864 | −12.703 | 1.00 | 25.15 | N |
| ATOM | 11476 | CA | MET | B | 226 | −76.423 | −18.390 | −11.479 | 1.00 | 25.53 | C |
| ATOM | 11478 | CB | MET | B | 226 | −76.806 | −19.278 | −10.282 | 1.00 | 26.11 | C |
| ATOM | 11481 | CG | MET | B | 226 | −75.905 | −19.169 | −9.023 | 1.00 | 27.59 | C |
| ATOM | 11484 | SD | MET | B | 226 | −75.676 | −20.788 | −8.214 | 1.00 | 30.67 | S |
| ATOM | 11485 | CE | MET | B | 226 | −77.308 | −21.005 | −7.476 | 1.00 | 29.78 | C |
| ATOM | 11489 | C | MET | B | 226 | −74.920 | −18.380 | −11.692 | 1.00 | 25.16 | C |
| ATOM | 11490 | O | MET | B | 226 | −74.258 | −17.387 | −11.391 | 1.00 | 25.10 | O |
| ATOM | 11492 | N | ILE | B | 227 | −74.388 | −19.473 | −12.239 | 1.00 | 24.88 | N |
| ATOM | 11493 | CA | ILE | B | 227 | −72.944 | −19.564 | −12.501 | 1.00 | 24.70 | C |
| ATOM | 11495 | CB | ILE | B | 227 | −72.476 | −20.994 | −12.882 | 1.00 | 24.45 | C |
| ATOM | 11497 | CG1 | ILE | B | 227 | −72.656 | −21.947 | −11.695 | 1.00 | 23.80 | C |
| ATOM | 11500 | CD1 | ILE | B | 227 | −72.094 | −23.332 | −11.885 | 1.00 | 21.97 | C |
| ATOM | 11504 | CG2 | ILE | B | 227 | −71.030 | −20.969 | −13.266 | 1.00 | 24.90 | C |
| ATOM | 11508 | C | ILE | B | 227 | −72.529 | −18.550 | −13.566 | 1.00 | 24.45 | C |
| ATOM | 11509 | O | ILE | B | 227 | −71.578 | −17.810 | −13.373 | 1.00 | 24.42 | O |

TABLE 16-7-continued

Coordinates of *P. tremuloides* IspS

| ATOM | 11511 | N   | GLN | B | 228 | −73.264 | −18.484 | −14.668 | 1.00 | 24.31 | N |
| ATOM | 11512 | CA  | GLN | B | 228 | −73.038 | −17.414 | −15.639 | 1.00 | 24.19 | C |
| ATOM | 11514 | CB  | GLN | B | 228 | −74.143 | −17.363 | −16.688 | 1.00 | 24.02 | C |
| ATOM | 11517 | CG  | GLN | B | 228 | −73.788 | −16.488 | −17.864 | 1.00 | 23.42 | C |
| ATOM | 11520 | CD  | GLN | B | 228 | −74.807 | −16.567 | −18.983 | 1.00 | 23.70 | C |
| ATOM | 11521 | OE1 | GLN | B | 228 | −75.790 | −15.813 | −19.015 | 1.00 | 24.07 | O |
| ATOM | 11522 | NE2 | GLN | B | 228 | −74.564 | −17.465 | −19.927 | 1.00 | 23.49 | N |
| ATOM | 11525 | C   | GLN | B | 228 | −72.913 | −16.037 | −14.987 | 1.00 | 24.37 | C |
| ATOM | 11526 | O   | GLN | B | 228 | −72.145 | −15.210 | −15.470 | 1.00 | 24.45 | O |
| ATOM | 11528 | N   | SER | B | 229 | −73.653 | −15.776 | −13.909 | 1.00 | 24.45 | N |
| ATOM | 11529 | CA  | SER | B | 229 | −73.578 | −14.459 | −13.264 | 1.00 | 24.76 | C |
| ATOM | 11531 | CB  | SER | B | 229 | −74.815 | −14.163 | −12.397 | 1.00 | 24.84 | C |
| ATOM | 11534 | OG  | SER | B | 229 | −74.711 | −14.718 | −11.096 | 1.00 | 25.81 | O |
| ATOM | 11536 | C   | SER | B | 229 | −72.270 | −14.279 | −12.469 | 1.00 | 24.64 | C |
| ATOM | 11537 | O   | SER | B | 229 | −71.726 | −13.172 | −12.408 | 1.00 | 24.95 | O |
| ATOM | 11539 | N   | VAL | B | 230 | −71.751 | −15.350 | −11.878 | 1.00 | 24.20 | N |
| ATOM | 11540 | CA  | VAL | B | 230 | −70.415 | −15.277 | −11.299 | 1.00 | 23.99 | C |
| ATOM | 11542 | CB  | VAL | B | 230 | −70.006 | −16.581 | −10.574 | 1.00 | 23.92 | C |
| ATOM | 11544 | CG1 | VAL | B | 230 | −68.546 | −16.510 | −10.105 | 1.00 | 23.71 | C |
| ATOM | 11548 | CG2 | VAL | B | 230 | −70.923 | −16.853 | −9.409  | 1.00 | 23.52 | C |
| ATOM | 11552 | C   | VAL | B | 230 | −69.386 | −14.966 | −12.400 | 1.00 | 24.12 | C |
| ATOM | 11553 | O   | VAL | B | 230 | −68.397 | −14.291 | −12.136 | 1.00 | 24.01 | O |
| ATOM | 11555 | N   | TYR | B | 231 | −69.612 | −15.461 | −13.621 | 1.00 | 24.30 | N |
| ATOM | 11556 | CA  | TYR | B | 231 | −68.672 | −15.235 | −14.728 | 1.00 | 24.53 | C |
| ATOM | 11558 | CB  | TYR | B | 231 | −68.997 | −16.104 | −15.946 | 1.00 | 24.08 | C |
| ATOM | 11561 | CG  | TYR | B | 231 | −68.892 | −17.605 | −15.754 | 1.00 | 23.29 | C |
| ATOM | 11562 | CD1 | TYR | B | 231 | −68.173 | −18.168 | −14.706 | 1.00 | 23.08 | C |
| ATOM | 11564 | CE1 | TYR | B | 231 | −68.073 | −19.547 | −14.565 | 1.00 | 22.01 | C |
| ATOM | 11566 | CZ  | TYR | B | 231 | −68.685 | −20.369 | −15.479 | 1.00 | 21.16 | C |
| ATOM | 11567 | OH  | TYR | B | 231 | −68.607 | −21.746 | −15.353 | 1.00 | 20.18 | O |
| ATOM | 11569 | CE2 | TYR | B | 231 | −69.387 | −19.825 | −16.523 | 1.00 | 21.64 | C |
| ATOM | 11571 | CD2 | TYR | B | 231 | −69.476 | −18.464 | −16.662 | 1.00 | 22.15 | C |
| ATOM | 11573 | C   | TYR | B | 231 | −68.658 | −13.772 | −15.166 | 1.00 | 25.37 | C |
| ATOM | 11574 | O   | TYR | B | 231 | −67.602 | −13.221 | −15.528 | 1.00 | 25.25 | O |
| ATOM | 11576 | N   | GLN | B | 232 | −69.832 | −13.148 | −15.129 | 1.00 | 26.11 | N |
| ATOM | 11577 | CA  | GLN | B | 232 | −69.978 | −11.797 | −15.622 | 1.00 | 26.68 | C |
| ATOM | 11579 | CB  | GLN | B | 232 | −71.430 | −11.541 | −15.995 | 1.00 | 26.45 | C |
| ATOM | 11582 | CG  | GLN | B | 232 | −71.883 | −12.385 | −17.176 | 1.00 | 25.67 | C |
| ATOM | 11585 | CD  | GLN | B | 232 | −73.388 | −12.394 | −17.381 | 1.00 | 24.91 | C |
| ATOM | 11586 | OE1 | GLN | B | 232 | −74.140 | −11.761 | −16.637 | 1.00 | 24.81 | O |
| ATOM | 11587 | NE2 | GLN | B | 232 | −73.834 | −13.113 | −18.407 | 1.00 | 23.39 | N |
| ATOM | 11590 | C   | GLN | B | 232 | −69.445 | −10.802 | −14.593 | 1.00 | 27.90 | C |
| ATOM | 11591 | O   | GLN | B | 232 | −68.909 | −9.752  | −14.958 | 1.00 | 27.96 | O |
| ATOM | 11593 | N   | ARG | B | 233 | −69.572 | −11.145 | −13.312 | 1.00 | 29.35 | N |
| ATOM | 11594 | CA  | ARG | B | 233 | −68.908 | −10.396 | −12.241 | 1.00 | 30.59 | C |
| ATOM | 11596 | CB  | ARG | B | 233 | −69.490 | −10.775 | −10.867 | 1.00 | 30.99 | C |
| ATOM | 11599 | CG  | ARG | B | 233 | −68.824 | −10.114 | −9.661  | 1.00 | 32.72 | C |
| ATOM | 11602 | CD  | ARG | B | 233 | −69.695 | −10.210 | −8.391  | 1.00 | 35.70 | C |
| ATOM | 11605 | NE  | ARG | B | 233 | −70.162 | −11.578 | −8.086  | 1.00 | 38.29 | N |
| ATOM | 11607 | CZ  | ARG | B | 233 | −71.403 | −12.053 | −8.276  | 1.00 | 39.65 | C |
| ATOM | 11608 | NH1 | ARG | B | 233 | −72.367 | −11.287 | −8.787  | 1.00 | 40.23 | N |
| ATOM | 11611 | NH2 | ARG | B | 233 | −71.687 | −13.320 | −7.949  | 1.00 | 39.61 | N |
| ATOM | 11614 | C   | ARG | B | 233 | −67.390 | −10.632 | −12.303 | 1.00 | 31.10 | C |
| ATOM | 11615 | O   | ARG | B | 233 | −66.615 | −9.693  | −12.181 | 1.00 | 31.19 | O |
| ATOM | 11617 | N   | ASP | B | 234 | −66.954 | −11.868 | −12.517 | 1.00 | 31.91 | N |
| ATOM | 11618 | CA  | ASP | B | 234 | −65.530 | −12.102 | −12.750 | 1.00 | 32.63 | C |
| ATOM | 11620 | CB  | ASP | B | 234 | −65.220 | −13.566 | −13.090 | 1.00 | 32.53 | C |
| ATOM | 11623 | CG  | ASP | B | 234 | −65.336 | −14.493 | −11.894 | 1.00 | 32.90 | C |
| ATOM | 11624 | OD1 | ASP | B | 234 | −65.477 | −14.028 | −10.746 | 1.00 | 33.06 | O |
| ATOM | 11625 | OD2 | ASP | B | 234 | −65.293 | −15.713 | −12.107 | 1.00 | 34.22 | O |
| ATOM | 11626 | C   | ASP | B | 234 | −65.058 | −11.206 | −13.886 | 1.00 | 33.10 | C |
| ATOM | 11627 | O   | ASP | B | 234 | −64.097 | −10.458 | −13.723 | 1.00 | 33.55 | O |
| ATOM | 11629 | N   | LEU | B | 235 | −65.753 | −11.256 | −15.017 | 1.00 | 33.49 | N |
| ATOM | 11630 | CA  | LEU | B | 235 | −65.311 | −10.550 | −16.216 | 1.00 | 34.06 | C |
| ATOM | 11632 | CB  | LEU | B | 235 | −66.139 | −10.996 | −17.422 | 1.00 | 33.80 | C |
| ATOM | 11635 | CG  | LEU | B | 235 | −65.769 | −10.403 | −18.775 | 1.00 | 32.13 | C |
| ATOM | 11637 | CD1 | LEU | B | 235 | −64.303 | −10.679 | −19.050 | 1.00 | 30.94 | C |
| ATOM | 11641 | CD2 | LEU | B | 235 | −66.670 | −10.959 | −19.870 | 1.00 | 29.93 | C |
| ATOM | 11645 | C   | LEU | B | 235 | −65.345 | −9.023  | −16.103 | 1.00 | 35.40 | C |
| ATOM | 11646 | O   | LEU | B | 235 | −64.500 | −8.352  | −16.682 | 1.00 | 35.61 | O |
| ATOM | 11648 | N   | ARG | B | 236 | −66.327 | −8.473  | −15.386 | 1.00 | 36.92 | N |
| ATOM | 11649 | CA  | ARG | B | 236 | −66.380 | −7.019  | −15.137 | 1.00 | 38.06 | C |
| ATOM | 11651 | CB  | ARG | B | 236 | −67.650 | −6.607  | −14.367 | 1.00 | 38.43 | C |
| ATOM | 11654 | CG  | ARG | B | 236 | −68.882 | −6.321  | −15.230 | 1.00 | 39.58 | C |
| ATOM | 11657 | CD  | ARG | B | 236 | −69.958 | −5.520  | −14.459 | 1.00 | 40.93 | C |
| ATOM | 11660 | NE  | ARG | B | 236 | −70.383 | −6.149  | −13.199 | 1.00 | 41.74 | N |
| ATOM | 11662 | CZ  | ARG | B | 236 | −71.208 | −7.195  | −13.095 | 1.00 | 42.20 | C |
| ATOM | 11663 | NH1 | ARG | B | 236 | −71.719 | −7.784  | −14.175 | 1.00 | 41.61 | N |

TABLE 16-7-continued

Coordinates of *P. tremuloides* IspS

| | | | | | | | | | | | |
|---|---|---|---|---|---|---|---|---|---|---|---|
| ATOM | 11666 | NH2 | ARG | B | 236 | −71.517 | −7.672 | −11.892 | 1.00 | 42.99 | N |
| ATOM | 11669 | C | ARG | B | 236 | −65.170 | −6.550 | −14.343 | 1.00 | 38.57 | C |
| ATOM | 11670 | O | ARG | B | 236 | −64.593 | −5.524 | −14.665 | 1.00 | 38.61 | O |
| ATOM | 11672 | N | GLU | B | 237 | −64.822 | −7.292 | −13.291 | 1.00 | 39.42 | N |
| ATOM | 11673 | CA | GLU | B | 237 | −63.625 | −7.017 | −12.480 | 1.00 | 40.18 | C |
| ATOM | 11675 | CB | GLU | B | 237 | −63.471 | −8.033 | −11.317 | 1.00 | 40.67 | C |
| ATOM | 11678 | CG | GLU | B | 237 | −64.336 | −7.750 | −10.057 | 1.00 | 42.61 | C |
| ATOM | 11681 | CD | GLU | B | 237 | −64.258 | −8.858 | −8.961 | 1.00 | 45.07 | C |
| ATOM | 11682 | OE1 | GLU | B | 237 | −64.051 | −10.066 | −9.282 | 1.00 | 46.74 | O |
| ATOM | 11683 | OE2 | GLU | B | 237 | −64.436 | −8.511 | −7.764 | 1.00 | 45.87 | O |
| ATOM | 11684 | C | GLU | B | 237 | −62.352 | −7.024 | −13.344 | 1.00 | 39.93 | C |
| ATOM | 11685 | O | GLU | B | 237 | −61.593 | −6.050 | −13.332 | 1.00 | 39.96 | O |
| ATOM | 11687 | N | THR | B | 238 | −62.123 | −8.104 | −14.095 | 1.00 | 39.56 | N |
| ATOM | 11688 | CA | THR | B | 238 | −60.900 | −8.200 | −14.895 | 1.00 | 39.42 | C |
| ATOM | 11690 | CB | THR | B | 238 | −60.492 | −9.666 | −15.268 | 1.00 | 39.39 | C |
| ATOM | 11692 | OG1 | THR | B | 238 | −61.222 | −10.123 | −16.413 | 1.00 | 39.37 | O |
| ATOM | 11694 | CG2 | THR | B | 238 | −60.683 | −10.612 | −14.095 | 1.00 | 38.73 | C |
| ATOM | 11698 | C | THR | B | 238 | −60.961 | −7.326 | −16.156 | 1.00 | 39.48 | C |
| ATOM | 11699 | O | THR | B | 238 | −59.930 | −7.062 | −16.761 | 1.00 | 39.48 | O |
| ATOM | 11701 | N | SER | B | 239 | −62.149 | −6.871 | −16.549 | 1.00 | 39.62 | N |
| ATOM | 11702 | CA | SER | B | 239 | −62.264 | −5.882 | −17.631 | 1.00 | 39.63 | C |
| ATOM | 11704 | CB | SER | B | 239 | −63.689 | −5.810 | −18.172 | 1.00 | 39.56 | C |
| ATOM | 11707 | OG | SER | B | 239 | −63.945 | −6.917 | −19.010 | 1.00 | 38.96 | O |
| ATOM | 11709 | C | SER | B | 239 | −61.796 | −4.496 | −17.181 | 1.00 | 39.99 | C |
| ATOM | 11710 | O | SER | B | 239 | −61.108 | −3.807 | −17.933 | 1.00 | 40.10 | O |
| ATOM | 11712 | N | ARG | B | 240 | −62.168 | −4.088 | −15.965 | 1.00 | 40.35 | N |
| ATOM | 11713 | CA | ARG | B | 240 | −61.624 | −2.864 | −15.363 | 1.00 | 40.68 | C |
| ATOM | 11715 | CB | ARG | B | 240 | −62.025 | −2.712 | −13.881 | 1.00 | 41.26 | C |
| ATOM | 11718 | CG | ARG | B | 240 | −63.231 | −1.782 | −13.621 | 1.00 | 43.86 | C |
| ATOM | 11721 | CD | ARG | B | 240 | −63.334 | −1.375 | −12.130 | 1.00 | 47.07 | C |
| ATOM | 11724 | NE | ARG | B | 240 | −63.365 | −2.537 | −11.222 | 1.00 | 50.14 | N |
| ATOM | 11726 | CZ | ARG | B | 240 | −64.462 | −3.077 | −10.671 | 1.00 | 52.32 | C |
| ATOM | 11727 | NH1 | ARG | B | 240 | −64.342 | −4.141 | −9.875 | 1.00 | 53.16 | N |
| ATOM | 11730 | NH2 | ARG | B | 240 | −65.677 | −2.577 | −10.899 | 1.00 | 53.18 | N |
| ATOM | 11733 | C | ARG | B | 240 | −60.113 | −2.914 | −15.464 | 1.00 | 39.91 | C |
| ATOM | 11734 | O | ARG | B | 240 | −59.490 | −2.000 | −15.988 | 1.00 | 39.86 | O |
| ATOM | 11736 | N | TRP | B | 241 | −59.541 | −4.002 | −14.962 | 1.00 | 39.14 | N |
| ATOM | 11737 | CA | TRP | B | 241 | −58.105 | −4.217 | −15.004 | 1.00 | 38.37 | C |
| ATOM | 11739 | CB | TRP | B | 241 | −57.773 | −5.635 | −14.521 | 1.00 | 38.17 | C |
| ATOM | 11742 | CG | TRP | B | 241 | −56.373 | −6.005 | −14.773 | 1.00 | 36.58 | C |
| ATOM | 11743 | CD1 | TRP | B | 241 | −55.290 | −5.668 | −14.022 | 1.00 | 36.32 | C |
| ATOM | 11745 | NE1 | TRP | B | 241 | −54.152 | −6.176 | −14.587 | 1.00 | 35.63 | N |
| ATOM | 11747 | CE2 | TRP | B | 241 | −54.494 | −6.846 | −15.731 | 1.00 | 34.31 | C |
| ATOM | 11748 | CD2 | TRP | B | 241 | −55.883 | −6.757 | −15.874 | 1.00 | 33.99 | C |
| ATOM | 11749 | CE3 | TRP | B | 241 | −56.484 | −7.357 | −16.977 | 1.00 | 33.28 | C |
| ATOM | 11751 | CZ3 | TRP | B | 241 | −55.691 | −8.034 | −17.883 | 1.00 | 32.79 | C |
| ATOM | 11753 | CH2 | TRP | B | 241 | −54.313 | −8.101 | −17.720 | 1.00 | 33.06 | C |
| ATOM | 11755 | CZ2 | TRP | B | 241 | −53.697 | −7.515 | −16.648 | 1.00 | 34.16 | C |
| ATOM | 11757 | C | TRP | B | 241 | −57.561 | −3.999 | −16.409 | 1.00 | 38.25 | C |
| ATOM | 11758 | O | TRP | B | 241 | −56.607 | −3.252 | −16.603 | 1.00 | 38.13 | O |
| ATOM | 11760 | N | TRP | B | 242 | −58.186 | −4.644 | −17.386 | 1.00 | 38.21 | N |
| ATOM | 11761 | CA | TRP | B | 242 | −57.695 | −4.628 | −18.765 | 1.00 | 38.27 | C |
| ATOM | 11763 | CB | TRP | B | 242 | −58.479 | −5.640 | −19.609 | 1.00 | 38.31 | C |
| ATOM | 11766 | CG | TRP | B | 242 | −57.948 | −5.872 | −20.990 | 1.00 | 38.61 | C |
| ATOM | 11767 | CD1 | TRP | B | 242 | −58.642 | −5.754 | −22.156 | 1.00 | 39.11 | C |
| ATOM | 11769 | NE1 | TRP | B | 242 | −57.828 | −6.046 | −23.224 | 1.00 | 39.31 | N |
| ATOM | 11771 | CE2 | TRP | B | 242 | −56.582 | −6.363 | −22.759 | 1.00 | 38.95 | C |
| ATOM | 11772 | CD2 | TRP | B | 242 | −56.617 | −6.263 | −21.356 | 1.00 | 38.66 | C |
| ATOM | 11773 | CE3 | TRP | B | 242 | −55.454 | −6.528 | −20.637 | 1.00 | 38.98 | C |
| ATOM | 11775 | CZ3 | TRP | B | 242 | −54.314 | −6.886 | −21.326 | 1.00 | 39.20 | C |
| ATOM | 11777 | CH2 | TRP | B | 242 | −54.313 | −6.985 | −22.716 | 1.00 | 39.12 | C |
| ATOM | 11779 | CZ2 | TRP | B | 242 | −55.434 | −6.724 | −23.451 | 1.00 | 39.22 | C |
| ATOM | 11781 | C | TRP | B | 242 | −57.739 | −3.241 | −19.400 | 1.00 | 38.27 | C |
| ATOM | 11782 | O | TRP | B | 242 | −56.814 | −2.873 | −20.108 | 1.00 | 37.81 | O |
| ATOM | 11784 | N | ARG | B | 243 | −58.809 | −2.489 | −19.140 | 1.00 | 38.79 | N |
| ATOM | 11785 | CA | ARG | B | 243 | −58.936 | −1.097 | −19.607 | 1.00 | 39.37 | C |
| ATOM | 11787 | CB | ARG | B | 243 | −60.351 | −.552 | −19.346 | 1.00 | 39.66 | C |
| ATOM | 11790 | CG | ARG | B | 243 | −61.324 | −.792 | −20.520 | 1.00 | 41.96 | C |
| ATOM | 11793 | CD | ARG | B | 243 | −62.687 | −1.338 | −20.085 | 1.00 | 44.82 | C |
| ATOM | 11796 | NE | ARG | B | 243 | −63.461 | −.380 | −19.296 | 1.00 | 47.15 | N |
| ATOM | 11798 | CZ | ARG | B | 243 | −64.389 | −.704 | −18.386 | 1.00 | 49.26 | C |
| ATOM | 11799 | NH1 | ARG | B | 243 | −64.685 | −1.976 | −18.109 | 1.00 | 49.18 | N |
| ATOM | 11802 | NH2 | ARG | B | 243 | −65.028 | .262 | −17.729 | 1.00 | 50.40 | N |
| ATOM | 11805 | C | ARG | B | 243 | −57.890 | −.183 | −18.980 | 1.00 | 39.28 | C |
| ATOM | 11806 | O | ARG | B | 243 | −57.246 | .577 | −19.681 | 1.00 | 39.40 | O |
| ATOM | 11808 | N | ARG | B | 244 | −57.724 | −.282 | −17.665 | 1.00 | 39.52 | N |
| ATOM | 11809 | CA | ARG | B | 244 | −56.734 | .489 | −16.888 | 1.00 | 39.61 | C |
| ATOM | 11811 | CB | ARG | B | 244 | −56.774 | .041 | −15.409 | 1.00 | 40.25 | C |

TABLE 16-7-continued

| | | | | | | | | | | |
|---|---|---|---|---|---|---|---|---|---|---|
| ATOM | 11814 | CG | ARG | B | 244 | −56.115 | .971 | −14.383 | 1.00 | 42.01 | C |
| ATOM | 11817 | CD | ARG | B | 244 | −57.029 | 2.154 | −14.017 | 1.00 | 44.39 | C |
| ATOM | 11820 | NE | ARG | B | 244 | −56.391 | 3.115 | −13.103 | 1.00 | 46.36 | N |
| ATOM | 11822 | CZ | ARG | B | 244 | −55.434 | 3.984 | −13.441 | 1.00 | 48.06 | C |
| ATOM | 11823 | NH1 | ARG | B | 244 | −54.951 | 4.043 | −14.686 | 1.00 | 48.90 | N |
| ATOM | 11826 | NH2 | ARG | B | 244 | −54.947 | 4.805 | −12.519 | 1.00 | 48.82 | N |
| ATOM | 11829 | C | ARG | B | 244 | −55.323 | .322 | −17.437 | 1.00 | 38.83 | C |
| ATOM | 11830 | O | ARG | B | 244 | −54.594 | 1.300 | −17.567 | 1.00 | 38.39 | O |
| ATOM | 11832 | N | VAL | B | 245 | −54.953 | −.922 | −17.738 | 1.00 | 38.52 | N |
| ATOM | 11833 | CA | VAL | B | 245 | −53.694 | −1.241 | −18.437 | 1.00 | 38.43 | C |
| ATOM | 11835 | CB | VAL | B | 245 | −53.491 | −2.760 | −18.614 | 1.00 | 38.31 | C |
| ATOM | 11837 | CG1 | VAL | B | 245 | −53.247 | −3.426 | −17.283 | 1.00 | 37.77 | C |
| ATOM | 11841 | CG2 | VAL | B | 245 | −52.344 | −3.036 | −19.561 | 1.00 | 37.66 | C |
| ATOM | 11845 | C | VAL | B | 245 | −53.650 | −.638 | −19.832 | 1.00 | 38.68 | C |
| ATOM | 11846 | O | VAL | B | 245 | −52.615 | −.153 | −20.247 | 1.00 | 38.57 | O |
| ATOM | 11848 | N | GLY | B | 246 | −54.765 | −.724 | −20.559 | 1.00 | 39.26 | N |
| ATOM | 11849 | CA | GLY | B | 246 | −54.974 | −.012 | −21.834 | 1.00 | 39.62 | C |
| ATOM | 11852 | C | GLY | B | 246 | −53.962 | −.262 | −22.942 | 1.00 | 40.08 | C |
| ATOM | 11853 | O | GLY | B | 246 | −53.617 | .650 | −23.700 | 1.00 | 39.89 | O |
| ATOM | 11855 | N | LEU | B | 247 | −53.502 | −1.500 | −23.062 | 1.00 | 40.75 | N |
| ATOM | 11856 | CA | LEU | B | 247 | −52.347 | −1.778 | −23.905 | 1.00 | 41.34 | C |
| ATOM | 11858 | CB | LEU | B | 247 | −51.655 | −3.065 | −23.459 | 1.00 | 41.15 | C |
| ATOM | 11861 | CG | LEU | B | 247 | −50.132 | −3.026 | −23.298 | 1.00 | 40.49 | C |
| ATOM | 11863 | CD1 | LEU | B | 247 | −49.622 | −1.769 | −22.605 | 1.00 | 39.50 | C |
| ATOM | 11867 | CD2 | LEU | B | 247 | −49.695 | −4.242 | −22.526 | 1.00 | 39.98 | C |
| ATOM | 11871 | C | LEU | B | 247 | −52.744 | −1.836 | −25.370 | 1.00 | 42.50 | C |
| ATOM | 11872 | O | LEU | B | 247 | −52.005 | −1.358 | −26.225 | 1.00 | 42.33 | O |
| ATOM | 11874 | N | ALA | B | 248 | −53.925 | −2.390 | −25.654 | 1.00 | 44.14 | N |
| ATOM | 11875 | CA | ALA | B | 248 | −54.439 | −2.494 | −27.041 | 1.00 | 45.16 | C |
| ATOM | 11877 | CB | ALA | B | 248 | −55.705 | −3.347 | −27.087 | 1.00 | 45.15 | C |
| ATOM | 11881 | C | ALA | B | 248 | −54.692 | −1.140 | −27.739 | 1.00 | 45.98 | C |
| ATOM | 11882 | O | ALA | B | 248 | −54.604 | −1.053 | −28.971 | 1.00 | 46.37 | O |
| ATOM | 11884 | N | THR | B | 249 | −55.004 | −.095 | −26.975 | 1.00 | 46.64 | N |
| ATOM | 11885 | CA | THR | B | 249 | −55.142 | 1.234 | −27.570 | 1.00 | 47.25 | C |
| ATOM | 11887 | CB | THR | B | 249 | −55.905 | 2.253 | −26.655 | 1.00 | 47.44 | C |
| ATOM | 11889 | OG1 | THR | B | 249 | −55.001 | 2.845 | −25.706 | 1.00 | 47.52 | O |
| ATOM | 11891 | CG2 | THR | B | 249 | −57.104 | 1.592 | −25.928 | 1.00 | 47.44 | C |
| ATOM | 11895 | C | THR | B | 249 | −53.756 | 1.793 | −27.931 | 1.00 | 47.59 | C |
| ATOM | 11896 | O | THR | B | 249 | −53.553 | 2.279 | −29.049 | 1.00 | 48.07 | O |
| ATOM | 11898 | N | LYS | B | 250 | −52.808 | 1.710 | −26.995 | 1.00 | 47.67 | N |
| ATOM | 11899 | CA | LYS | B | 250 | −51.469 | 2.299 | −27.185 | 1.00 | 47.68 | C |
| ATOM | 11901 | CB | LYS | B | 250 | −50.793 | 2.553 | −25.833 | 1.00 | 47.68 | C |
| ATOM | 11904 | CG | LYS | B | 250 | −51.428 | 3.673 | −24.999 | 1.00 | 47.77 | C |
| ATOM | 11907 | CD | LYS | B | 250 | −51.142 | 5.086 | −25.552 | 1.00 | 47.59 | C |
| ATOM | 11910 | CE | LYS | B | 250 | −49.676 | 5.496 | −25.441 | 1.00 | 46.75 | C |
| ATOM | 11913 | NZ | LYS | B | 250 | −49.479 | 6.878 | −25.948 | 1.00 | 46.49 | N |
| ATOM | 11917 | C | LYS | B | 250 | −50.541 | 1.465 | −28.082 | 1.00 | 47.72 | C |
| ATOM | 11918 | O | LYS | B | 250 | −49.591 | 1.988 | −28.663 | 1.00 | 47.54 | O |
| ATOM | 11920 | N | LEU | B | 251 | −50.804 | .169 | −28.184 | 1.00 | 47.82 | N |
| ATOM | 11921 | CA | LEU | B | 251 | −50.072 | −.675 | −29.118 | 1.00 | 47.96 | C |
| ATOM | 11923 | CB | LEU | B | 251 | −49.584 | −1.970 | −28.447 | 1.00 | 48.04 | C |
| ATOM | 11926 | CG | LEU | B | 251 | −48.109 | −2.064 | −28.033 | 1.00 | 47.39 | C |
| ATOM | 11928 | CD1 | LEU | B | 251 | −47.659 | −.881 | −27.186 | 1.00 | 46.47 | C |
| ATOM | 11932 | CD2 | LEU | B | 251 | −47.894 | −3.376 | −27.304 | 1.00 | 46.78 | C |
| ATOM | 11936 | C | LEU | B | 251 | −50.985 | −.964 | −30.306 | 1.00 | 48.19 | C |
| ATOM | 11937 | O | LEU | B | 251 | −51.975 | −1.693 | −30.194 | 1.00 | 48.38 | O |
| ATOM | 11939 | N | HIS | B | 252 | −50.627 | −.396 | −31.449 | 1.00 | 48.42 | N |
| ATOM | 11940 | CA | HIS | B | 252 | −51.521 | −.329 | −32.601 | 1.00 | 48.62 | C |
| ATOM | 11942 | CB | HIS | B | 252 | −51.110 | .850 | −33.492 | 1.00 | 48.99 | C |
| ATOM | 11945 | CG | HIS | B | 252 | −51.000 | 2.145 | −32.742 | 1.00 | 50.56 | C |
| ATOM | 11946 | ND1 | HIS | B | 252 | −52.095 | 2.935 | −32.453 | 1.00 | 52.11 | N |
| ATOM | 11948 | CE1 | HIS | B | 252 | −51.704 | 3.993 | −31.766 | 1.00 | 52.68 | C |
| ATOM | 11950 | NE2 | HIS | B | 252 | −50.397 | 3.912 | −31.585 | 1.00 | 52.86 | N |
| ATOM | 11952 | CD2 | HIS | B | 252 | −49.932 | 2.764 | −32.181 | 1.00 | 51.68 | C |
| ATOM | 11954 | C | HIS | B | 252 | −51.582 | −1.636 | −33.383 | 1.00 | 48.14 | C |
| ATOM | 11955 | O | HIS | B | 252 | −52.615 | −1.975 | −33.935 | 1.00 | 48.02 | O |
| ATOM | 11957 | N | PHE | B | 253 | −50.481 | −2.372 | −33.405 | 1.00 | 48.10 | N |
| ATOM | 11958 | CA | PHE | B | 253 | −50.422 | −3.702 | −34.044 | 1.00 | 48.18 | C |
| ATOM | 11960 | CB | PHE | B | 253 | −48.965 | −4.070 | −34.375 | 1.00 | 48.16 | C |
| ATOM | 11963 | CG | PHE | B | 253 | −48.119 | −4.311 | −33.163 | 1.00 | 47.85 | C |
| ATOM | 11964 | CD1 | PHE | B | 253 | −47.900 | −5.596 | −32.702 | 1.00 | 48.56 | C |
| ATOM | 11966 | CE1 | PHE | B | 253 | −47.140 | −5.812 | −31.576 | 1.00 | 48.98 | C |
| ATOM | 11968 | CZ | PHE | B | 253 | −46.602 | −4.729 | −30.895 | 1.00 | 48.50 | C |
| ATOM | 11970 | CE2 | PHE | B | 253 | −46.817 | −3.454 | −31.349 | 1.00 | 47.40 | C |
| ATOM | 11972 | CD2 | PHE | B | 253 | −47.569 | −3.249 | −32.465 | 1.00 | 47.22 | C |
| ATOM | 11974 | C | PHE | B | 253 | −51.038 | −4.819 | −33.185 | 1.00 | 48.30 | C |
| ATOM | 11975 | O | PHE | B | 253 | −51.344 | −5.903 | −33.691 | 1.00 | 47.63 | O |
| ATOM | 11977 | N | ALA | B | 254 | −51.204 | −4.541 | −31.888 | 1.00 | 48.86 | N |

TABLE 16-7-continued

| | | | | | | | | | | | |
|---|---|---|---|---|---|---|---|---|---|---|---|
| colspan="12" | Coordinates of *P. tremuloides* IspS |

| ATOM | 11978 | CA | ALA | B | 254 | −51.653 | −5.531 | −30.903 | 1.00 | 49.13 | C |
| ATOM | 11980 | CB | ALA | B | 254 | −51.290 | −5.071 | −29.494 | 1.00 | 49.02 | C |
| ATOM | 11984 | C | ALA | B | 254 | −53.153 | −5.806 | −30.982 | 1.00 | 49.46 | C |
| ATOM | 11985 | O | ALA | B | 254 | −53.967 | −4.870 | −31.011 | 1.00 | 49.50 | O |
| ATOM | 11987 | N | ARG | B | 255 | −53.501 | −7.097 | −31.006 | 1.00 | 49.75 | N |
| ATOM | 11988 | CA | ARG | B | 255 | −54.896 | −7.549 | −30.918 | 1.00 | 49.89 | C |
| ATOM | 11990 | CB | ARG | B | 255 | −55.028 | −9.051 | −31.245 | 1.00 | 49.94 | C |
| ATOM | 11993 | CG | ARG | B | 255 | −54.839 | −9.439 | −32.724 | 1.00 | 49.93 | C |
| ATOM | 11996 | CD | ARG | B | 255 | −54.709 | −10.967 | −32.904 | 1.00 | 49.79 | C |
| ATOM | 11999 | NE | ARG | B | 255 | −53.527 | −11.505 | −32.219 | 1.00 | 50.11 | N |
| ATOM | 12001 | CZ | ARG | B | 255 | −53.276 | −12.801 | −32.010 | 1.00 | 50.54 | C |
| ATOM | 12002 | NH1 | ARG | B | 255 | −54.117 | −13.736 | −32.439 | 1.00 | 51.36 | N |
| ATOM | 12005 | NH2 | ARG | B | 255 | −52.175 | −13.172 | −31.360 | 1.00 | 50.21 | N |
| ATOM | 12008 | C | ARG | B | 255 | −55.425 | −7.308 | −29.511 | 1.00 | 49.83 | C |
| ATOM | 12009 | O | ARG | B | 255 | −54.666 | −6.975 | −28.599 | 1.00 | 49.95 | O |
| ATOM | 12011 | N | ASP | B | 256 | −56.736 | −7.463 | −29.350 | 1.00 | 49.72 | N |
| ATOM | 12012 | CA | ASP | B | 256 | −57.360 | −7.483 | −28.034 | 1.00 | 49.55 | C |
| ATOM | 12014 | CB | ASP | B | 256 | −58.183 | −6.222 | −27.812 | 1.00 | 49.52 | C |
| ATOM | 12017 | CG | ASP | B | 256 | −59.134 | −6.362 | −26.654 | 1.00 | 50.30 | C |
| ATOM | 12018 | OD1 | ASP | B | 256 | −60.310 | −5.944 | −26.780 | 1.00 | 50.45 | O |
| ATOM | 12019 | OD2 | ASP | B | 256 | −58.702 | −6.926 | −25.622 | 1.00 | 51.68 | O |
| ATOM | 12020 | C | ASP | B | 256 | −58.254 | −8.721 | −27.931 | 1.00 | 49.15 | C |
| ATOM | 12021 | O | ASP | B | 256 | −59.159 | −8.901 | −28.737 | 1.00 | 49.28 | O |
| ATOM | 12023 | N | ARG | B | 257 | −57.998 | −9.565 | −26.937 | 1.00 | 48.61 | N |
| ATOM | 12024 | CA | ARG | B | 257 | −58.743 | −10.809 | −26.765 | 1.00 | 48.20 | C |
| ATOM | 12026 | CB | ARG | B | 257 | −57.949 | −11.984 | −27.373 | 1.00 | 48.41 | C |
| ATOM | 12029 | CG | ARG | B | 257 | −57.505 | −11.799 | −28.821 | 1.00 | 49.37 | C |
| ATOM | 12032 | CD | ARG | B | 257 | −58.693 | −11.636 | −29.784 | 1.00 | 50.80 | C |
| ATOM | 12035 | NE | ARG | B | 257 | −58.908 | −12.814 | −30.627 | 1.00 | 52.11 | N |
| ATOM | 12037 | CZ | ARG | B | 257 | −58.678 | −12.876 | −31.944 | 1.00 | 52.99 | C |
| ATOM | 12038 | NH1 | ARG | B | 257 | −58.214 | −11.820 | −32.623 | 1.00 | 52.37 | N |
| ATOM | 12041 | NH2 | ARG | B | 257 | −58.918 | −14.016 | −32.596 | 1.00 | 52.97 | N |
| ATOM | 12044 | C | ARG | B | 257 | −59.032 | −11.089 | −25.280 | 1.00 | 47.32 | C |
| ATOM | 12045 | O | ARG | B | 257 | −58.579 | −12.101 | −24.735 | 1.00 | 47.46 | O |
| ATOM | 12047 | N | LEU | B | 258 | −59.770 | −10.201 | −24.616 | 1.00 | 45.94 | N |
| ATOM | 12048 | CA | LEU | B | 258 | −60.108 | −10.430 | −23.205 | 1.00 | 44.67 | C |
| ATOM | 12050 | CB | LEU | B | 258 | −60.332 | −9.130 | −22.438 | 1.00 | 44.61 | C |
| ATOM | 12053 | CG | LEU | B | 258 | −60.422 | −9.323 | −20.920 | 1.00 | 43.83 | C |
| ATOM | 12055 | CD1 | LEU | B | 258 | −59.045 | −9.552 | −20.339 | 1.00 | 43.48 | C |
| ATOM | 12059 | CD2 | LEU | B | 258 | −61.073 | −8.139 | −20.262 | 1.00 | 43.85 | C |
| ATOM | 12063 | C | LEU | B | 258 | −61.347 | −11.286 | −23.090 | 1.00 | 43.49 | C |
| ATOM | 12064 | O | LEU | B | 258 | −61.375 | −12.220 | −22.295 | 1.00 | 43.84 | O |
| ATOM | 12066 | N | ILE | B | 259 | −62.364 | −10.968 | −23.883 | 1.00 | 41.92 | N |
| ATOM | 12067 | CA | ILE | B | 259 | −63.617 | −11.711 | −23.841 | 1.00 | 40.80 | C |
| ATOM | 12069 | CB | ILE | B | 259 | −64.718 | −11.132 | −24.783 | 1.00 | 41.05 | C |
| ATOM | 12071 | CG1 | ILE | B | 259 | −64.852 | −9.598 | −24.653 | 1.00 | 41.61 | C |
| ATOM | 12074 | CD1 | ILE | B | 259 | −65.200 | −8.874 | −25.985 | 1.00 | 42.16 | C |
| ATOM | 12078 | CG2 | ILE | B | 259 | −66.065 | −11.816 | −24.496 | 1.00 | 40.46 | C |
| ATOM | 12082 | C | ILE | B | 259 | −63.319 | −13.151 | −24.250 | 1.00 | 39.50 | C |
| ATOM | 12083 | O | ILE | B | 259 | −63.782 | −14.082 | −23.598 | 1.00 | 39.30 | O |
| ATOM | 12085 | N | GLU | B | 260 | −62.524 | −13.318 | −25.316 | 1.00 | 37.99 | N |
| ATOM | 12086 | CA | GLU | B | 260 | −62.120 | −14.652 | −25.812 | 1.00 | 36.60 | C |
| ATOM | 12088 | CB | GLU | B | 260 | −61.329 | −14.574 | −27.142 | 1.00 | 36.75 | C |
| ATOM | 12091 | CG | GLU | B | 260 | −62.167 | −14.319 | −28.425 | 1.00 | 37.79 | C |
| ATOM | 12094 | CD | GLU | B | 260 | −62.134 | −12.851 | −28.905 | 1.00 | 39.47 | C |
| ATOM | 12095 | OE1 | GLU | B | 260 | −62.207 | −11.923 | −28.055 | 1.00 | 39.97 | O |
| ATOM | 12096 | OE2 | GLU | B | 260 | −62.033 | −12.628 | −30.139 | 1.00 | 40.31 | O |
| ATOM | 12097 | C | GLU | B | 260 | −61.282 | −15.381 | −24.770 | 1.00 | 34.83 | C |
| ATOM | 12098 | O | GLU | B | 260 | −61.465 | −16.568 | −24.544 | 1.00 | 34.69 | O |
| ATOM | 12100 | N | SER | B | 261 | −60.365 | −14.669 | −24.131 | 1.00 | 32.89 | N |
| ATOM | 12101 | CA | SER | B | 261 | −59.508 | −15.292 | −23.139 | 1.00 | 31.48 | C |
| ATOM | 12103 | CB | SER | B | 261 | −58.341 | −14.376 | −22.768 | 1.00 | 31.55 | C |
| ATOM | 12106 | OG | SER | B | 261 | −57.298 | −14.493 | −23.728 | 1.00 | 31.75 | O |
| ATOM | 12108 | C | SER | B | 261 | −60.294 | −15.716 | −21.900 | 1.00 | 30.04 | C |
| ATOM | 12109 | O | SER | B | 261 | −59.921 | −16.674 | −21.208 | 1.00 | 29.70 | O |
| ATOM | 12111 | N | PHE | B | 262 | −61.389 | −15.021 | −21.618 | 1.00 | 28.25 | N |
| ATOM | 12112 | CA | PHE | B | 262 | −62.203 | −15.404 | −20.480 | 1.00 | 26.75 | C |
| ATOM | 12114 | CB | PHE | B | 262 | −63.111 | −14.278 | −20.009 | 1.00 | 26.36 | C |
| ATOM | 12117 | CG | PHE | B | 262 | −63.532 | −14.453 | −18.603 | 1.00 | 24.33 | C |
| ATOM | 12118 | CD1 | PHE | B | 262 | −62.697 | −14.092 | −17.584 | 1.00 | 22.66 | C |
| ATOM | 12120 | CE1 | PHE | B | 262 | −63.047 | −14.283 | −16.301 | 1.00 | 22.65 | C |
| ATOM | 12122 | CZ | PHE | B | 262 | −64.245 | −14.873 | −16.007 | 1.00 | 23.93 | C |
| ATOM | 12124 | CE2 | PHE | B | 262 | −65.076 | −15.267 | −17.010 | 1.00 | 24.08 | C |
| ATOM | 12126 | CD2 | PHE | B | 262 | −64.711 | −15.067 | −18.304 | 1.00 | 23.96 | C |
| ATOM | 12128 | C | PHE | B | 262 | −63.017 | −16.660 | −20.751 | 1.00 | 26.02 | C |
| ATOM | 12129 | O | PHE | B | 262 | −63.074 | −17.546 | −19.909 | 1.00 | 26.32 | O |
| ATOM | 12131 | N | TYR | B | 263 | −63.652 | −16.732 | −21.915 | 1.00 | 24.98 | N |
| ATOM | 12132 | CA | TYR | B | 263 | −64.299 | −17.969 | −22.396 | 1.00 | 24.14 | C |

TABLE 16-7-continued

Coordinates of *P. tremuloides* IspS

| ATOM | 12134 | CB | TYR | B | 263 | −64.701 | −17.756 | −23.853 | 1.00 | 24.00 | C |
|------|-------|-----|-----|---|-----|---------|---------|---------|------|-------|---|
| ATOM | 12137 | CG | TYR | B | 263 | −65.080 | −18.961 | −24.667 | 1.00 | 24.32 | C |
| ATOM | 12138 | CD1 | TYR | B | 263 | −66.302 | −19.604 | −24.489 | 1.00 | 25.03 | C |
| ATOM | 12140 | CE1 | TYR | B | 263 | −66.666 | −20.694 | −25.285 | 1.00 | 25.81 | C |
| ATOM | 12142 | CZ | TYR | B | 263 | −65.798 | −21.132 | −26.287 | 1.00 | 27.06 | C |
| ATOM | 12143 | OH | TYR | B | 263 | −66.106 | −22.191 | −27.123 | 1.00 | 27.14 | O |
| ATOM | 12145 | CE2 | TYR | B | 263 | −64.590 | −20.489 | −26.479 | 1.00 | 26.80 | C |
| ATOM | 12147 | CD2 | TYR | B | 263 | −64.250 | −19.404 | −25.680 | 1.00 | 25.65 | C |
| ATOM | 12149 | C | TYR | B | 263 | −63.351 | −19.162 | −22.256 | 1.00 | 23.35 | C |
| ATOM | 12150 | O | TYR | B | 263 | −63.712 | −20.219 | −21.740 | 1.00 | 22.80 | O |
| ATOM | 12152 | N | TRP | B | 264 | −62.119 | −18.955 | −22.702 | 1.00 | 22.64 | N |
| ATOM | 12153 | CA | TRP | B | 264 | −61.047 | −19.918 | −22.523 | 1.00 | 21.95 | C |
| ATOM | 12155 | CB | TRP | B | 264 | −59.737 | −19.334 | −23.061 | 1.00 | 21.84 | C |
| ATOM | 12158 | CG | TRP | B | 264 | −58.603 | −20.278 | −22.964 | 1.00 | 22.90 | C |
| ATOM | 12159 | CD1 | TRP | B | 264 | −57.700 | −20.387 | −21.943 | 1.00 | 23.98 | C |
| ATOM | 12161 | NE1 | TRP | B | 264 | −56.800 | −21.386 | −22.214 | 1.00 | 23.95 | N |
| ATOM | 12163 | CE2 | TRP | B | 264 | −57.124 | −21.949 | −23.417 | 1.00 | 23.51 | C |
| ATOM | 12164 | CD2 | TRP | B | 264 | −58.252 | −21.273 | −23.915 | 1.00 | 23.40 | C |
| ATOM | 12165 | CE3 | TRP | B | 264 | −58.776 | −21.652 | −25.147 | 1.00 | 23.68 | C |
| ATOM | 12167 | CZ3 | TRP | B | 264 | −58.178 | −22.669 | −25.826 | 1.00 | 24.44 | C |
| ATOM | 12169 | CH2 | TRP | B | 264 | −57.060 | −23.324 | −25.310 | 1.00 | 24.97 | C |
| ATOM | 12171 | CZ2 | TRP | B | 264 | −56.521 | −22.978 | −24.103 | 1.00 | 24.44 | C |
| ATOM | 12173 | C | TRP | B | 264 | −60.897 | −20.326 | −21.050 | 1.00 | 21.11 | C |
| ATOM | 12174 | O | TRP | B | 264 | −60.768 | −21.511 | −20.748 | 1.00 | 20.98 | O |
| ATOM | 12176 | N | ALA | B | 265 | −60.916 | −19.344 | −20.147 | 1.00 | 20.17 | N |
| ATOM | 12177 | CA | ALA | B | 265 | −60.774 | −19.602 | −18.712 | 1.00 | 19.36 | C |
| ATOM | 12179 | CB | ALA | B | 265 | −60.621 | −18.305 | −17.944 | 1.00 | 19.30 | C |
| ATOM | 12183 | C | ALA | B | 265 | −61.947 | −20.397 | −18.171 | 1.00 | 18.63 | C |
| ATOM | 12184 | O | ALA | B | 265 | −61.763 | −21.349 | −17.434 | 1.00 | 18.64 | O |
| ATOM | 12186 | N | VAL | B | 266 | −63.159 | −20.034 | −18.557 | 1.00 | 18.11 | N |
| ATOM | 12187 | CA | VAL | B | 266 | −64.335 | −20.758 | −18.075 | 1.00 | 17.60 | C |
| ATOM | 12189 | CB | VAL | B | 266 | −65.652 | −20.221 | −18.675 | 1.00 | 17.38 | C |
| ATOM | 12191 | CG1 | VAL | B | 266 | −65.902 | −18.803 | −18.199 | 1.00 | 17.09 | C |
| ATOM | 12195 | CG2 | VAL | B | 266 | −66.817 | −21.120 | −18.312 | 1.00 | 15.40 | C |
| ATOM | 12199 | C | VAL | B | 266 | −64.221 | −22.246 | −18.376 | 1.00 | 17.67 | C |
| ATOM | 12200 | O | VAL | B | 266 | −64.766 | −23.058 | −17.647 | 1.00 | 18.27 | O |
| ATOM | 12202 | N | GLY | B | 267 | −63.516 | −22.607 | −19.444 | 1.00 | 17.43 | N |
| ATOM | 12203 | CA | GLY | B | 267 | −63.316 | −24.013 | −19.789 | 1.00 | 16.98 | C |
| ATOM | 12206 | C | GLY | B | 267 | −62.253 | −24.683 | −18.947 | 1.00 | 16.55 | C |
| ATOM | 12207 | O | GLY | B | 267 | −62.360 | −25.859 | −18.609 | 1.00 | 16.37 | O |
| ATOM | 12209 | N | VAL | B | 268 | −61.215 | −23.939 | −18.608 | 1.00 | 16.30 | N |
| ATOM | 12210 | CA | VAL | B | 268 | −60.160 | −24.500 | −17.794 | 1.00 | 16.23 | C |
| ATOM | 12212 | CB | VAL | B | 268 | −58.893 | −23.651 | −17.840 | 1.00 | 15.68 | C |
| ATOM | 12214 | CG1 | VAL | B | 268 | −57.857 | −24.194 | −16.894 | 1.00 | 15.01 | C |
| ATOM | 12218 | CG2 | VAL | B | 268 | −58.361 | −23.674 | −19.235 | 1.00 | 15.01 | C |
| ATOM | 12222 | C | VAL | B | 268 | −60.654 | −24.718 | −16.374 | 1.00 | 16.86 | C |
| ATOM | 12223 | O | VAL | B | 268 | −60.421 | −25.784 | −15.813 | 1.00 | 16.93 | O |
| ATOM | 12225 | N | ALA | B | 269 | −61.362 | −23.733 | −15.817 | 1.00 | 17.64 | N |
| ATOM | 12226 | CA | ALA | B | 269 | −61.911 | −23.838 | −14.461 | 1.00 | 18.46 | C |
| ATOM | 12228 | CB | ALA | B | 269 | −60.958 | −23.215 | −13.472 | 1.00 | 18.15 | C |
| ATOM | 12232 | C | ALA | B | 269 | −63.312 | −23.213 | −14.340 | 1.00 | 19.34 | C |
| ATOM | 12233 | O | ALA | B | 269 | −63.448 | −22.030 | −14.047 | 1.00 | 19.78 | O |
| ATOM | 12235 | N | PHE | B | 270 | −64.347 | −24.028 | −14.529 | 1.00 | 20.34 | N |
| ATOM | 12236 | CA | PHE | B | 270 | −65.724 | −23.535 | −14.631 | 1.00 | 21.21 | C |
| ATOM | 12238 | CB | PHE | B | 270 | −66.564 | −24.483 | −15.482 | 1.00 | 21.34 | C |
| ATOM | 12241 | CG | PHE | B | 270 | −67.083 | −25.667 | −14.718 | 1.00 | 22.46 | C |
| ATOM | 12242 | CD1 | PHE | B | 270 | −68.294 | −25.596 | −14.039 | 1.00 | 23.19 | C |
| ATOM | 12244 | CE1 | PHE | B | 270 | −68.756 | −26.672 | −13.315 | 1.00 | 23.27 | C |
| ATOM | 12246 | CZ | PHE | B | 270 | −68.003 | −27.836 | −13.258 | 1.00 | 23.35 | C |
| ATOM | 12248 | CE2 | PHE | B | 270 | −66.794 | −27.918 | −13.932 | 1.00 | 22.73 | C |
| ATOM | 12250 | CD2 | PHE | B | 270 | −66.340 | −26.843 | −14.646 | 1.00 | 22.88 | C |
| ATOM | 12252 | C | PHE | B | 270 | −66.464 | −23.366 | −13.316 | 1.00 | 21.98 | C |
| ATOM | 12253 | O | PHE | B | 270 | −67.408 | −22.583 | −13.268 | 1.00 | 21.93 | O |
| ATOM | 12255 | N | GLU | B | 271 | −66.102 | −24.126 | −12.275 | 1.00 | 23.01 | N |
| ATOM | 12256 | CA | GLU | B | 271 | −66.929 | −24.142 | −11.037 | 1.00 | 23.99 | C |
| ATOM | 12258 | CB | GLU | B | 271 | −66.679 | −25.353 | −10.113 | 1.00 | 24.25 | C |
| ATOM | 12261 | CG | GLU | B | 271 | −65.286 | −25.877 | −10.092 | 1.00 | 26.22 | C |
| ATOM | 12264 | CD | GLU | B | 271 | −65.013 | −26.914 | −11.183 | 1.00 | 29.01 | C |
| ATOM | 12265 | OE1 | GLU | B | 271 | −65.563 | −28.032 | −11.090 | 1.00 | 31.36 | O |
| ATOM | 12266 | OE2 | GLU | B | 271 | −64.232 | −26.622 | −12.121 | 1.00 | 30.98 | O |
| ATOM | 12267 | C | GLU | B | 271 | −66.795 | −22.831 | −10.281 | 1.00 | 23.90 | C |
| ATOM | 12268 | O | GLU | B | 271 | −65.702 | −22.296 | −10.181 | 1.00 | 24.29 | O |
| ATOM | 12270 | N | PRO | B | 272 | −67.913 | −22.316 | −9.745 | 1.00 | 24.09 | N |
| ATOM | 12271 | CA | PRO | B | 272 | −68.005 | −20.885 | −9.428 | 1.00 | 24.11 | C |
| ATOM | 12273 | CB | PRO | B | 272 | −69.380 | −20.751 | −8.751 | 1.00 | 24.03 | C |
| ATOM | 12276 | CG | PRO | B | 272 | −70.083 | −22.069 | −8.997 | 1.00 | 24.12 | C |
| ATOM | 12279 | CD | PRO | B | 272 | −69.013 | −23.083 | −9.132 | 1.00 | 23.99 | C |
| ATOM | 12282 | C | PRO | B | 272 | −66.900 | −20.386 | −8.501 | 1.00 | 24.28 | C |

TABLE 16-7-continued

Coordinates of *P. tremuloides* IspS

| ATOM | 12283 | O | PRO | B | 272 | −66.421 | −19.261 | −8.676 | 1.00 | 24.40 | O |
|---|---|---|---|---|---|---|---|---|---|---|---|
| ATOM | 12284 | N | GLN | B | 273 | −66.480 | −21.222 | −7.547 | 1.00 | 24.20 | N |
| ATOM | 12285 | CA | GLN | B | 273 | −65.500 | −20.809 | −6.551 | 1.00 | 24.20 | C |
| ATOM | 12287 | CB | GLN | B | 273 | −65.437 | −21.840 | −5.426 | 1.00 | 24.42 | C |
| ATOM | 12290 | CG | GLN | B | 273 | −64.750 | −23.176 | −5.775 | 1.00 | 25.17 | C |
| ATOM | 12293 | CD | GLN | B | 273 | −65.717 | −24.334 | −6.007 | 1.00 | 26.13 | C |
| ATOM | 12294 | OE1 | GLN | B | 273 | −66.857 | −24.141 | −6.453 | 1.00 | 27.46 | O |
| ATOM | 12295 | NE2 | GLN | B | 273 | −65.251 | −25.554 | −5.721 | 1.00 | 25.05 | N |
| ATOM | 12298 | C | GLN | B | 273 | −64.086 | −20.546 | −7.088 | 1.00 | 24.27 | C |
| ATOM | 12299 | O | GLN | B | 273 | −63.221 | −20.151 | −6.329 | 1.00 | 24.32 | O |
| ATOM | 12301 | N | TYR | B | 274 | −63.842 | −20.759 | −8.380 | 1.00 | 24.59 | N |
| ATOM | 12302 | CA | TYR | B | 274 | −62.509 | −20.551 | −8.962 | 1.00 | 24.85 | C |
| ATOM | 12304 | CB | TYR | B | 274 | −62.129 | −21.724 | −9.880 | 1.00 | 24.62 | C |
| ATOM | 12307 | CG | TYR | B | 274 | −62.009 | −23.054 | −9.184 | 1.00 | 24.35 | C |
| ATOM | 12308 | CD1 | TYR | B | 274 | −61.395 | −23.169 | −7.946 | 1.00 | 24.62 | C |
| ATOM | 12310 | CE1 | TYR | B | 274 | −61.280 | −24.391 | −7.314 | 1.00 | 25.10 | C |
| ATOM | 12312 | CZ | TYR | B | 274 | −61.771 | −25.525 | −7.920 | 1.00 | 24.92 | C |
| ATOM | 12313 | OH | TYR | B | 274 | −61.661 | −26.748 | −7.299 | 1.00 | 24.73 | O |
| ATOM | 12315 | CE2 | TYR | B | 274 | −62.366 | −25.437 | −9.150 | 1.00 | 24.76 | C |
| ATOM | 12317 | CD2 | TYR | B | 274 | −62.477 | −24.203 | −9.779 | 1.00 | 24.70 | C |
| ATOM | 12319 | C | TYR | B | 274 | −62.409 | −19.235 | −9.745 | 1.00 | 25.27 | C |
| ATOM | 12320 | O | TYR | B | 274 | −61.956 | −19.210 | −10.895 | 1.00 | 25.42 | O |
| ATOM | 12322 | N | SER | B | 275 | −62.808 | −18.134 | −9.121 | 1.00 | 25.40 | N |
| ATOM | 12323 | CA | SER | B | 275 | −62.755 | −16.849 | −9.802 | 1.00 | 25.43 | C |
| ATOM | 12325 | CB | SER | B | 275 | −63.615 | −15.814 | −9.071 | 1.00 | 25.53 | C |
| ATOM | 12328 | OG | SER | B | 275 | −65.006 | −16.068 | −9.291 | 1.00 | 25.52 | O |
| ATOM | 12330 | C | SER | B | 275 | −61.300 | −16.403 | −9.948 | 1.00 | 25.36 | C |
| ATOM | 12331 | O | SER | B | 275 | −60.885 | −15.903 | −10.996 | 1.00 | 25.17 | O |
| ATOM | 12333 | N | ASP | B | 276 | −60.517 | −16.617 | −8.901 | 1.00 | 25.41 | N |
| ATOM | 12334 | CA | ASP | B | 276 | −59.095 | −16.353 | −8.979 | 1.00 | 25.42 | C |
| ATOM | 12336 | CB | ASP | B | 276 | −58.390 | −16.794 | −7.712 | 1.00 | 25.44 | C |
| ATOM | 12339 | CG | ASP | B | 276 | −58.728 | −15.925 | −6.558 | 1.00 | 26.32 | C |
| ATOM | 12340 | OD1 | ASP | B | 276 | −59.302 | −14.857 | −6.818 | 1.00 | 27.50 | O |
| ATOM | 12341 | OD2 | ASP | B | 276 | −58.442 | −16.299 | −5.398 | 1.00 | 30.16 | O |
| ATOM | 12342 | C | ASP | B | 276 | −58.495 | −17.069 | −10.157 | 1.00 | 25.20 | C |
| ATOM | 12343 | O | ASP | B | 276 | −57.745 | −16.461 | −10.929 | 1.00 | 25.66 | O |
| ATOM | 12345 | N | CYS | B | 277 | −58.814 | −18.353 | −10.305 | 1.00 | 24.60 | N |
| ATOM | 12346 | CA | CYS | B | 277 | −58.228 | −19.110 | −11.391 | 1.00 | 24.30 | C |
| ATOM | 12348 | CB | CYS | B | 277 | −58.684 | −20.561 | −11.392 | 1.00 | 24.28 | C |
| ATOM | 12351 | SG | CYS | B | 277 | −57.737 | −21.574 | −12.569 | 1.00 | 23.82 | S |
| ATOM | 12353 | C | CYS | B | 277 | −58.593 | −18.448 | −12.698 | 1.00 | 24.09 | C |
| ATOM | 12354 | O | CYS | B | 277 | −57.727 | −18.013 | −13.450 | 1.00 | 23.87 | O |
| ATOM | 12356 | N | ARG | B | 278 | −59.893 | −18.329 | −12.933 | 1.00 | 24.22 | N |
| ATOM | 12357 | CA | ARG | B | 278 | −60.400 | −17.746 | −14.171 | 1.00 | 23.98 | C |
| ATOM | 12359 | CB | ARG | B | 278 | −61.917 | −17.556 | −14.123 | 1.00 | 23.93 | C |
| ATOM | 12362 | CG | ARG | B | 278 | −62.662 | −18.871 | −14.283 | 1.00 | 24.07 | C |
| ATOM | 12365 | CD | ARG | B | 278 | −64.132 | −18.670 | −14.607 | 1.00 | 24.48 | C |
| ATOM | 12368 | NE | ARG | B | 278 | −64.874 | −18.141 | −13.472 | 1.00 | 23.75 | N |
| ATOM | 12370 | CZ | ARG | B | 278 | −65.254 | −18.856 | −12.419 | 1.00 | 23.72 | C |
| ATOM | 12371 | NH1 | ARG | B | 278 | −64.973 | −20.149 | −12.326 | 1.00 | 22.86 | N |
| ATOM | 12374 | NH2 | ARG | B | 278 | −65.927 | −18.262 | −11.443 | 1.00 | 25.08 | N |
| ATOM | 12377 | C | ARG | B | 278 | −59.701 | −16.453 | −14.491 | 1.00 | 23.56 | C |
| ATOM | 12378 | O | ARG | B | 278 | −59.296 | −16.265 | −15.628 | 1.00 | 23.87 | O |
| ATOM | 12380 | N | ASN | B | 279 | −59.512 | −15.593 | −13.495 | 1.00 | 23.24 | N |
| ATOM | 12381 | CA | ASN | B | 279 | −58.854 | −14.301 | −13.734 | 1.00 | 23.48 | C |
| ATOM | 12383 | CB | ASN | B | 279 | −59.055 | −13.340 | −12.574 | 1.00 | 24.05 | C |
| ATOM | 12386 | CG | ASN | B | 279 | −60.510 | −13.017 | −12.346 | 1.00 | 26.58 | C |
| ATOM | 12387 | OD1 | ASN | B | 279 | −61.378 | −13.310 | −13.189 | 1.00 | 28.96 | O |
| ATOM | 12388 | ND2 | ASN | B | 279 | −60.799 | −12.416 | −11.194 | 1.00 | 30.30 | N |
| ATOM | 12391 | C | ASN | B | 279 | −57.376 | −14.404 | −14.027 | 1.00 | 22.58 | C |
| ATOM | 12392 | O | ASN | B | 279 | −56.903 | −13.749 | −14.941 | 1.00 | 22.73 | O |
| ATOM | 12394 | N | SER | B | 280 | −56.648 | −15.205 | −13.251 | 1.00 | 21.62 | N |
| ATOM | 12395 | CA | SER | B | 280 | −55.243 | −15.483 | −13.550 | 1.00 | 20.73 | C |
| ATOM | 12397 | CB | SER | B | 280 | −54.696 | −16.597 | −12.659 | 1.00 | 20.85 | C |
| ATOM | 12400 | OG | SER | B | 280 | −53.805 | −16.099 | −11.683 | 1.00 | 21.55 | O |
| ATOM | 12402 | C | SER | B | 280 | −55.091 | −15.896 | −15.004 | 1.00 | 20.04 | C |
| ATOM | 12403 | O | SER | B | 280 | −54.293 | −15.312 | −15.738 | 1.00 | 19.87 | O |
| ATOM | 12405 | N | VAL | B | 281 | −55.875 | −16.893 | −15.413 | 1.00 | 19.24 | N |
| ATOM | 12406 | CA | VAL | B | 281 | −55.720 | −17.491 | −16.720 | 1.00 | 18.77 | C |
| ATOM | 12408 | CB | VAL | B | 281 | −56.482 | −18.834 | −16.815 | 1.00 | 18.74 | C |
| ATOM | 12410 | CG1 | VAL | B | 281 | −56.467 | −19.404 | −18.251 | 1.00 | 18.34 | C |
| ATOM | 12414 | CG2 | VAL | B | 281 | −55.863 | −19.844 | −15.848 | 1.00 | 18.13 | C |
| ATOM | 12418 | C | VAL | B | 281 | −56.142 | −16.486 | −17.787 | 1.00 | 18.89 | C |
| ATOM | 12419 | O | VAL | B | 281 | −55.483 | −16.364 | −18.832 | 1.00 | 18.75 | O |
| ATOM | 12421 | N | ALA | B | 282 | −57.210 | −15.739 | −17.505 | 1.00 | 18.85 | N |
| ATOM | 12422 | CA | ALA | B | 282 | −57.709 | −14.723 | −18.439 | 1.00 | 18.80 | C |
| ATOM | 12424 | CB | ALA | B | 282 | −59.051 | −14.191 | −17.991 | 1.00 | 18.32 | C |
| ATOM | 12428 | C | ALA | B | 282 | −56.718 | −13.576 | −18.615 | 1.00 | 18.94 | C |

TABLE 16-7-continued

Coordinates of *P. tremuloides* IspS

| ATOM | 12429 | O   | ALA | B | 282 | −56.582 | −13.021 | −19.700 | 1.00 | 19.16 | O |
| ---- | ----- | --- | --- | - | --- | ------- | ------- | ------- | ---- | ----- | - |
| ATOM | 12431 | N   | LYS | B | 283 | −56.022 | −13.211 | −17.553 | 1.00 | 19.24 | N |
| ATOM | 12432 | CA  | LYS | B | 283 | −55.037 | −12.145 | −17.658 | 1.00 | 19.62 | C |
| ATOM | 12434 | CB  | LYS | B | 283 | −54.649 | −11.615 | −16.276 | 1.00 | 19.68 | C |
| ATOM | 12437 | CG  | LYS | B | 283 | −55.779 | −10.923 | −15.518 | 1.00 | 19.95 | C |
| ATOM | 12440 | CD  | LYS | B | 283 | −55.265 | −10.398 | −14.196 | 1.00 | 21.72 | C |
| ATOM | 12443 | CE  | LYS | B | 283 | −56.364 | −10.236 | −13.164 | 1.00 | 23.83 | C |
| ATOM | 12446 | NZ  | LYS | B | 283 | −56.129 | −9.003  | −12.351 | 1.00 | 24.72 | N |
| ATOM | 12450 | C   | LYS | B | 283 | −53.802 | −12.643 | −18.396 | 1.00 | 19.77 | C |
| ATOM | 12451 | O   | LYS | B | 283 | −53.237 | −11.929 | −19.208 | 1.00 | 20.05 | O |
| ATOM | 12453 | N   | MET | B | 284 | −53.387 | −13.871 | −18.117 | 1.00 | 19.88 | N |
| ATOM | 12454 | CA  | MET | B | 284 | −52.136 | −14.367 | −18.652 | 1.00 | 19.90 | C |
| ATOM | 12456 | CB  | MET | B | 284 | −51.719 | −15.676 | −17.960 | 1.00 | 20.08 | C |
| ATOM | 12459 | CG  | MET | B | 284 | −51.125 | −15.505 | −16.560 | 1.00 | 20.62 | C |
| ATOM | 12462 | SD  | MET | B | 284 | −49.782 | −14.295 | −16.485 | 1.00 | 23.69 | S |
| ATOM | 12463 | CE  | MET | B | 284 | −50.600 | −12.872 | −15.754 | 1.00 | 23.82 | C |
| ATOM | 12467 | C   | MET | B | 284 | −52.257 | −14.572 | −20.145 | 1.00 | 19.82 | C |
| ATOM | 12468 | O   | MET | B | 284 | −51.326 | −14.269 | −20.889 | 1.00 | 20.21 | O |
| ATOM | 12470 | N   | PHE | B | 285 | −53.401 | −15.088 | −20.579 | 1.00 | 19.72 | N |
| ATOM | 12471 | CA  | PHE | B | 285 | −53.620 | −15.428 | −21.986 | 1.00 | 19.66 | C |
| ATOM | 12473 | CB  | PHE | B | 285 | −54.863 | −16.324 | −22.114 | 1.00 | 20.09 | C |
| ATOM | 12476 | CG  | PHE | B | 285 | −54.986 | −17.077 | −23.427 | 1.00 | 21.18 | C |
| ATOM | 12477 | CD1 | PHE | B | 285 | −53.877 | −17.362 | −24.232 | 1.00 | 22.86 | C |
| ATOM | 12479 | CE1 | PHE | B | 285 | −54.013 | −18.070 | −25.424 | 1.00 | 22.58 | C |
| ATOM | 12481 | CZ  | PHE | B | 285 | −55.254 | −18.518 | −25.806 | 1.00 | 23.49 | C |
| ATOM | 12483 | CE2 | PHE | B | 285 | −56.365 | −18.254 | −25.002 | 1.00 | 23.36 | C |
| ATOM | 12485 | CD2 | PHE | B | 285 | −56.222 | −17.551 | −23.823 | 1.00 | 21.76 | C |
| ATOM | 12487 | C   | PHE | B | 285 | −53.781 | −14.148 | −22.781 | 1.00 | 19.18 | C |
| ATOM | 12488 | O   | PHE | B | 285 | −53.333 | −14.046 | −23.914 | 1.00 | 18.98 | O |
| ATOM | 12490 | N   | SER | B | 286 | −54.410 | −13.161 | −22.164 | 1.00 | 18.92 | N |
| ATOM | 12491 | CA  | SER | B | 286 | −54.488 | −11.843 | −22.753 | 1.00 | 19.15 | C |
| ATOM | 12493 | CB  | SER | B | 286 | −55.292 | −10.894 | −21.863 | 1.00 | 19.38 | C |
| ATOM | 12496 | OG  | SER | B | 286 | −56.684 | −11.180 | −21.957 | 1.00 | 20.24 | O |
| ATOM | 12498 | C   | SER | B | 286 | −53.106 | −11.267 | −23.032 | 1.00 | 18.91 | C |
| ATOM | 12499 | O   | SER | B | 286 | −52.894 | −10.668 | −24.087 | 1.00 | 19.48 | O |
| ATOM | 12501 | N   | PHE | B | 287 | −52.172 | −11.446 | −22.102 | 1.00 | 18.48 | N |
| ATOM | 12502 | CA  | PHE | B | 287 | −50.768 | −11.065 | −22.339 | 1.00 | 18.30 | C |
| ATOM | 12504 | CB  | PHE | B | 287 | −49.958 | −11.035 | −21.044 | 1.00 | 18.27 | C |
| ATOM | 12507 | CG  | PHE | B | 287 | −50.040 | −9.740  | −20.324 | 1.00 | 18.59 | C |
| ATOM | 12508 | CD1 | PHE | B | 287 | −49.375 | −8.624  | −20.813 | 1.00 | 20.02 | C |
| ATOM | 12510 | CE1 | PHE | B | 287 | −49.456 | −7.410  | −20.152 | 1.00 | 20.57 | C |
| ATOM | 12512 | CZ  | PHE | B | 287 | −50.208 | −7.308  | −18.985 | 1.00 | 20.02 | C |
| ATOM | 12514 | CE2 | PHE | B | 287 | −50.869 | −8.417  | −18.503 | 1.00 | 19.78 | C |
| ATOM | 12516 | CD2 | PHE | B | 287 | −50.781 | −9.623  | −19.164 | 1.00 | 19.05 | C |
| ATOM | 12518 | C   | PHE | B | 287 | −50.067 | −11.978 | −23.339 | 1.00 | 18.01 | C |
| ATOM | 12519 | O   | PHE | B | 287 | −49.374 | −11.498 | −24.229 | 1.00 | 18.00 | O |
| ATOM | 12521 | N   | VAL | B | 288 | −50.236 | −13.286 | −23.194 | 1.00 | 17.69 | N |
| ATOM | 12522 | CA  | VAL | B | 288 | −49.720 | −14.206 | −24.197 | 1.00 | 17.66 | C |
| ATOM | 12524 | CB  | VAL | B | 288 | −50.168 | −15.649 | −23.930 | 1.00 | 17.37 | C |
| ATOM | 12526 | CG1 | VAL | B | 288 | −49.937 | −16.529 | −25.134 | 1.00 | 16.24 | C |
| ATOM | 12530 | CG2 | VAL | B | 288 | −49.414 | −16.185 | −22.758 | 1.00 | 17.21 | C |
| ATOM | 12534 | C   | VAL | B | 288 | −50.081 | −13.761 | −25.633 | 1.00 | 18.08 | C |
| ATOM | 12535 | O   | VAL | B | 288 | −49.207 | −13.710 | −26.492 | 1.00 | 18.08 | O |
| ATOM | 12537 | N   | THR | B | 289 | −51.327 | −13.396 | −25.895 | 1.00 | 18.42 | N |
| ATOM | 12538 | CA  | THR | B | 289 | −51.683 | −13.001 | −27.256 | 1.00 | 19.33 | C |
| ATOM | 12540 | CB  | THR | B | 289 | −53.171 | −12.736 | −27.401 | 1.00 | 19.35 | C |
| ATOM | 12542 | OG1 | THR | B | 289 | −53.573 | −11.895 | −26.321 | 1.00 | 21.59 | O |
| ATOM | 12544 | CG2 | THR | B | 289 | −53.973 | −14.046 | −27.350 | 1.00 | 19.09 | C |
| ATOM | 12548 | C   | THR | B | 289 | −50.901 | −11.766 | −27.723 | 1.00 | 19.71 | C |
| ATOM | 12549 | O   | THR | B | 289 | −50.469 | −11.707 | −28.891 | 1.00 | 19.88 | O |
| ATOM | 12551 | N   | ILE | B | 290 | −50.689 | −10.796 | −26.829 | 1.00 | 19.94 | N |
| ATOM | 12552 | CA  | ILE | B | 290 | −49.943 | −9.585  | −27.225 | 1.00 | 20.39 | C |
| ATOM | 12554 | CB  | ILE | B | 290 | −50.069 | −8.410  | −26.221 | 1.00 | 20.50 | C |
| ATOM | 12556 | CG1 | ILE | B | 290 | −51.510 | −8.137  | −25.823 | 1.00 | 21.25 | C |
| ATOM | 12559 | CD1 | ILE | B | 290 | −51.650 | −6.854  | −25.002 | 1.00 | 21.58 | C |
| ATOM | 12563 | CG2 | ILE | B | 290 | −49.546 | −7.134  | −26.853 | 1.00 | 20.39 | C |
| ATOM | 12567 | C   | ILE | B | 290 | −48.434 | −9.840  | −27.438 | 1.00 | 20.45 | C |
| ATOM | 12568 | O   | ILE | B | 290 | −47.853 | −9.317  | −28.393 | 1.00 | 20.76 | O |
| ATOM | 12570 | N   | ILE | B | 291 | −47.808 | −10.616 | −26.546 | 1.00 | 20.21 | N |
| ATOM | 12571 | CA  | ILE | B | 291 | −46.375 | −10.869 | −26.618 | 1.00 | 19.87 | C |
| ATOM | 12573 | CB  | ILE | B | 291 | −45.840 | −11.603 | −25.407 | 1.00 | 19.79 | C |
| ATOM | 12575 | CG1 | ILE | B | 291 | −46.205 | −10.879 | −24.102 | 1.00 | 19.71 | C |
| ATOM | 12578 | CD1 | ILE | B | 291 | −45.326 | −9.734  | −23.748 | 1.00 | 19.77 | C |
| ATOM | 12582 | CG2 | ILE | B | 291 | −44.336 | −11.747 | −25.516 | 1.00 | 18.91 | C |
| ATOM | 12586 | C   | ILE | B | 291 | −46.134 | −11.735 | −27.825 | 1.00 | 20.44 | C |
| ATOM | 12587 | O   | ILE | B | 291 | −45.233 | −11.481 | −28.600 | 1.00 | 20.35 | O |
| ATOM | 12589 | N   | ASP | B | 292 | −46.965 | −12.751 | −28.005 | 1.00 | 21.33 | N |
| ATOM | 12590 | CA  | ASP | B | 292 | −46.915 | −13.563 | −29.228 | 1.00 | 22.13 | C |

TABLE 16-7-continued

Coordinates of *P. tremuloides* IspS

| ATOM | 12592 | CB | ASP | B | 292 | −48.120 | −14.508 | −29.316 | 1.00 | 22.40 | C |
|------|-------|-----|-----|---|-----|---------|---------|---------|------|-------|---|
| ATOM | 12595 | CG | ASP | B | 292 | −47.847 | −15.741 | −30.160 | 1.00 | 23.47 | C |
| ATOM | 12596 | OD1 | ASP | B | 292 | −46.852 | −15.765 | −30.923 | 1.00 | 24.83 | O |
| ATOM | 12597 | OD2 | ASP | B | 292 | −48.637 | −16.707 | −30.038 | 1.00 | 25.22 | O |
| ATOM | 12598 | C | ASP | B | 292 | −46.856 | −12.716 | −30.507 | 1.00 | 22.28 | C |
| ATOM | 12599 | O | ASP | B | 292 | −46.088 | −13.033 | −31.399 | 1.00 | 22.73 | O |
| ATOM | 12601 | N | ASP | B | 293 | −47.656 | −11.658 | −30.611 | 1.00 | 22.22 | N |
| ATOM | 12602 | CA | ASP | B | 293 | −47.630 | −10.828 | −31.822 | 1.00 | 22.43 | C |
| ATOM | 12604 | CB | ASP | B | 293 | −48.840 | −9.894 | −31.885 | 1.00 | 23.03 | C |
| ATOM | 12607 | CG | ASP | B | 293 | −50.157 | −10.644 | −31.959 | 1.00 | 24.69 | C |
| ATOM | 12608 | OD1 | ASP | B | 293 | −50.113 | −11.900 | −32.025 | 1.00 | 28.66 | O |
| ATOM | 12609 | OD2 | ASP | B | 293 | −51.231 | −9.986 | −31.930 | 1.00 | 23.57 | O |
| ATOM | 12610 | C | ASP | B | 293 | −46.354 | −9.997 | −31.921 | 1.00 | 21.94 | C |
| ATOM | 12611 | O | ASP | B | 293 | −45.898 | −9.674 | −33.019 | 1.00 | 22.31 | O |
| ATOM | 12613 | N | ILE | B | 294 | −45.783 | −9.643 | −30.780 | 1.00 | 21.05 | N |
| ATOM | 12614 | CA | ILE | B | 294 | −44.513 | −8.941 | −30.770 | 1.00 | 20.53 | C |
| ATOM | 12616 | CB | ILE | B | 294 | −44.166 | −8.448 | −29.344 | 1.00 | 20.42 | C |
| ATOM | 12618 | CG1 | ILE | B | 294 | −45.150 | −7.349 | −28.945 | 1.00 | 19.66 | C |
| ATOM | 12621 | CD1 | ILE | B | 294 | −45.057 | −6.956 | −27.536 | 1.00 | 18.81 | C |
| ATOM | 12625 | CG2 | ILE | B | 294 | −42.726 | −7.924 | −29.253 | 1.00 | 19.99 | C |
| ATOM | 12629 | C | ILE | B | 294 | −43.416 | −9.845 | −31.343 | 1.00 | 20.44 | C |
| ATOM | 12630 | O | ILE | B | 294 | −42.650 | −9.431 | −32.205 | 1.00 | 20.17 | O |
| ATOM | 12632 | N | TYR | B | 295 | −43.355 | −11.088 | −30.886 | 1.00 | 20.65 | N |
| ATOM | 12633 | CA | TYR | B | 295 | −42.313 | −12.008 | −31.353 | 1.00 | 20.76 | C |
| ATOM | 12635 | CB | TYR | B | 295 | −42.145 | −13.198 | −30.412 | 1.00 | 20.29 | C |
| ATOM | 12638 | CG | TYR | B | 295 | −41.393 | −12.926 | −29.129 | 1.00 | 17.92 | C |
| ATOM | 12639 | CD1 | TYR | B | 295 | −40.117 | −13.409 | −28.936 | 1.00 | 17.62 | C |
| ATOM | 12641 | CE1 | TYR | B | 295 | −39.427 | −13.195 | −27.747 | 1.00 | 17.12 | C |
| ATOM | 12643 | CZ | TYR | B | 295 | −40.022 | −12.493 | −26.730 | 1.00 | 16.61 | C |
| ATOM | 12644 | OH | TYR | B | 295 | −39.357 | −12.281 | −25.528 | 1.00 | 14.46 | O |
| ATOM | 12646 | CE2 | TYR | B | 295 | −41.296 | −12.008 | −26.911 | 1.00 | 16.82 | C |
| ATOM | 12648 | CD2 | TYR | B | 295 | −41.972 | −12.235 | −28.102 | 1.00 | 16.39 | C |
| ATOM | 12650 | C | TYR | B | 295 | −42.619 | −12.519 | −32.749 | 1.00 | 21.65 | C |
| ATOM | 12651 | O | TYR | B | 295 | −41.698 | −12.751 | −33.540 | 1.00 | 22.13 | O |
| ATOM | 12653 | N | ASP | B | 296 | −43.905 | −12.677 | −33.049 | 1.00 | 22.47 | N |
| ATOM | 12654 | CA | ASP | B | 296 | −44.327 | −13.316 | −34.285 | 1.00 | 23.52 | C |
| ATOM | 12656 | CB | ASP | B | 296 | −45.761 | −13.851 | −34.185 | 1.00 | 23.99 | C |
| ATOM | 12659 | CG | ASP | B | 296 | −46.134 | −14.744 | −35.369 | 1.00 | 26.22 | C |
| ATOM | 12660 | OD1 | ASP | B | 296 | −45.508 | −15.832 | −35.538 | 1.00 | 27.70 | O |
| ATOM | 12661 | OD2 | ASP | B | 296 | −47.052 | −14.348 | −36.128 | 1.00 | 28.78 | O |
| ATOM | 12662 | C | ASP | B | 296 | −44.228 | −12.392 | −35.478 | 1.00 | 23.68 | C |
| ATOM | 12663 | O | ASP | B | 296 | −43.673 | −12.784 | −36.502 | 1.00 | 24.01 | O |
| ATOM | 12665 | N | VAL | B | 297 | −44.765 | −11.178 | −35.364 | 1.00 | 23.90 | N |
| ATOM | 12666 | CA | VAL | B | 297 | −44.801 | −10.273 | −36.524 | 1.00 | 23.99 | C |
| ATOM | 12668 | CB | VAL | B | 297 | −46.251 | −10.003 | −36.973 | 1.00 | 23.87 | C |
| ATOM | 12670 | CG1 | VAL | B | 297 | −46.949 | −11.310 | −37.197 | 1.00 | 23.75 | C |
| ATOM | 12674 | CG2 | VAL | B | 297 | −47.002 | −9.136 | −35.966 | 1.00 | 23.05 | C |
| ATOM | 12678 | C | VAL | B | 297 | −44.060 | −8.940 | −36.383 | 1.00 | 24.27 | C |
| ATOM | 12679 | O | VAL | B | 297 | −43.485 | −8.465 | −37.342 | 1.00 | 23.84 | O |
| ATOM | 12681 | N | TYR | B | 298 | −44.058 | −8.347 | −35.199 | 1.00 | 24.87 | N |
| ATOM | 12682 | CA | TYR | B | 298 | −43.760 | −6.926 | −35.078 | 1.00 | 25.67 | C |
| ATOM | 12684 | CB | TYR | B | 298 | −44.656 | −6.294 | −34.010 | 1.00 | 26.06 | C |
| ATOM | 12687 | CG | TYR | B | 298 | −44.520 | −4.789 | −33.932 | 1.00 | 27.95 | C |
| ATOM | 12688 | CD1 | TYR | B | 298 | −45.097 | −3.968 | −34.901 | 1.00 | 29.74 | C |
| ATOM | 12690 | CE1 | TYR | B | 298 | −44.982 | −2.574 | −34.843 | 1.00 | 29.93 | C |
| ATOM | 12692 | CZ | TYR | B | 298 | −44.282 | −1.991 | −33.806 | 1.00 | 29.96 | C |
| ATOM | 12693 | OH | TYR | B | 298 | −44.165 | −.631 | −33.746 | 1.00 | 30.01 | O |
| ATOM | 12695 | CE2 | TYR | B | 298 | −43.697 | −2.777 | −32.829 | 1.00 | 30.39 | C |
| ATOM | 12697 | CD2 | TYR | B | 298 | −43.811 | −4.181 | −32.899 | 1.00 | 29.96 | C |
| ATOM | 12699 | C | TYR | B | 298 | −42.318 | −6.592 | −34.755 | 1.00 | 25.76 | C |
| ATOM | 12700 | O | TYR | B | 298 | −41.696 | −5.830 | −35.470 | 1.00 | 26.54 | O |
| ATOM | 12702 | N | GLY | B | 299 | −41.798 | −7.111 | −33.653 | 1.00 | 25.89 | N |
| ATOM | 12703 | CA | GLY | B | 299 | −40.473 | −6.706 | −33.167 | 1.00 | 25.78 | C |
| ATOM | 12706 | C | GLY | B | 299 | −39.346 | −7.341 | −33.951 | 1.00 | 25.52 | C |
| ATOM | 12707 | O | GLY | B | 299 | −39.513 | −8.410 | −34.525 | 1.00 | 26.04 | O |
| ATOM | 12709 | N | THR | B | 300 | −38.196 | −6.685 | −33.990 | 1.00 | 25.32 | N |
| ATOM | 12710 | CA | THR | B | 300 | −37.063 | −7.237 | −34.716 | 1.00 | 25.16 | C |
| ATOM | 12712 | CB | THR | B | 300 | −36.088 | −6.164 | −35.295 | 1.00 | 25.08 | C |
| ATOM | 12714 | OG1 | THR | B | 300 | −35.191 | −5.710 | −34.281 | 1.00 | 25.07 | O |
| ATOM | 12716 | CG2 | THR | B | 300 | −36.833 | −4.978 | −35.875 | 1.00 | 25.08 | C |
| ATOM | 12720 | C | THR | B | 300 | −36.324 | −8.139 | −33.771 | 1.00 | 25.13 | C |
| ATOM | 12721 | O | THR | B | 300 | −36.335 | −7.950 | −32.570 | 1.00 | 25.28 | O |
| ATOM | 12723 | N | LEU | B | 301 | −35.662 | −9.129 | −34.332 | 1.00 | 25.50 | N |
| ATOM | 12724 | CA | LEU | B | 301 | −34.918 | −10.093 | −33.538 | 1.00 | 25.42 | C |
| ATOM | 12726 | CB | LEU | B | 301 | −34.148 | −11.020 | −34.479 | 1.00 | 25.17 | C |
| ATOM | 12729 | CG | LEU | B | 301 | −33.624 | −12.338 | −33.941 | 1.00 | 24.95 | C |
| ATOM | 12731 | CD1 | LEU | B | 301 | −34.715 | −13.233 | −33.437 | 1.00 | 24.42 | C |
| ATOM | 12735 | CD2 | LEU | B | 301 | −32.900 | −12.998 | −35.080 | 1.00 | 26.50 | C |

TABLE 16-7-continued

Coordinates of *P. tremuloides* IspS

| ATOM | 12739 | C   | LEU | B | 301 | −33.995 | −9.425  | −32.485 | 1.00 | 25.54 | C |
|------|-------|-----|-----|---|-----|---------|---------|---------|------|-------|---|
| ATOM | 12740 | O   | LEU | B | 301 | −33.843 | −9.959  | −31.394 | 1.00 | 25.35 | O |
| ATOM | 12742 | N   | ASP | B | 302 | −33.417 | −8.257  | −32.782 | 1.00 | 25.68 | N |
| ATOM | 12743 | CA  | ASP | B | 302 | −32.598 | −7.550  | −31.774 | 1.00 | 26.02 | C |
| ATOM | 12745 | CB  | ASP | B | 302 | −31.800 | −6.377  | −32.378 | 1.00 | 26.37 | C |
| ATOM | 12748 | CG  | ASP | B | 302 | −30.563 | −6.833  | −33.167 | 1.00 | 28.27 | C |
| ATOM | 12749 | OD1 | ASP | B | 302 | −29.508 | −6.156  | −33.048 | 1.00 | 29.05 | O |
| ATOM | 12750 | OD2 | ASP | B | 302 | −30.652 | −7.852  | −33.910 | 1.00 | 31.04 | O |
| ATOM | 12751 | C   | ASP | B | 302 | −33.472 | −7.037  | −30.630 | 1.00 | 25.69 | C |
| ATOM | 12752 | O   | ASP | B | 302 | −33.110 | −7.142  | −29.447 | 1.00 | 25.90 | O |
| ATOM | 12754 | N   | GLU | B | 303 | −34.622 | −6.473  | −30.993 | 1.00 | 25.04 | N |
| ATOM | 12755 | CA  | GLU | B | 303 | −35.600 | −6.029  | −30.011 | 1.00 | 24.33 | C |
| ATOM | 12757 | CB  | GLU | B | 303 | −36.783 | −5.346  | −30.697 | 1.00 | 24.20 | C |
| ATOM | 12760 | CG  | GLU | B | 303 | −36.399 | −4.109  | −31.466 | 1.00 | 24.23 | C |
| ATOM | 12763 | CD  | GLU | B | 303 | −37.589 | −3.382  | −32.063 | 1.00 | 24.23 | C |
| ATOM | 12764 | OE1 | GLU | B | 303 | −38.496 | −4.065  | −32.604 | 1.00 | 22.66 | O |
| ATOM | 12765 | OE2 | GLU | B | 303 | −37.592 | −2.121  | −31.995 | 1.00 | 23.93 | O |
| ATOM | 12766 | C   | GLU | B | 303 | −36.103 | −7.212  | −29.193 | 1.00 | 23.87 | C |
| ATOM | 12767 | O   | GLU | B | 303 | −36.396 | −7.058  | −28.011 | 1.00 | 23.59 | O |
| ATOM | 12769 | N   | LEU | B | 304 | −36.204 | −8.383  | −29.825 | 1.00 | 23.39 | N |
| ATOM | 12770 | CA  | LEU | B | 304 | −36.766 | −9.570  | −29.166 | 1.00 | 23.23 | C |
| ATOM | 12772 | CB  | LEU | B | 304 | −37.180 | −10.624 | −30.208 | 1.00 | 22.83 | C |
| ATOM | 12775 | CG  | LEU | B | 304 | −38.381 | −10.217 | −31.074 | 1.00 | 22.06 | C |
| ATOM | 12777 | CD1 | LEU | B | 304 | −38.822 | −11.321 | −32.037 | 1.00 | 20.11 | C |
| ATOM | 12781 | CD2 | LEU | B | 304 | −39.551 | −9.800  | −30.163 | 1.00 | 21.94 | C |
| ATOM | 12785 | C   | LEU | B | 304 | −35.810 | −10.147 | −28.106 | 1.00 | 23.37 | C |
| ATOM | 12786 | O   | LEU | B | 304 | −36.248 | −10.785 | −27.141 | 1.00 | 23.22 | O |
| ATOM | 12788 | N   | GLU | B | 305 | −34.514 | −9.892  | −28.283 | 1.00 | 23.30 | N |
| ATOM | 12789 | CA  | GLU | B | 305 | −33.512 | −10.308 | −27.324 | 1.00 | 23.18 | C |
| ATOM | 12791 | CB  | GLU | B | 305 | −32.114 | −10.176 | −27.899 | 1.00 | 23.58 | C |
| ATOM | 12794 | CG  | GLU | B | 305 | −31.832 | −11.142 | −29.047 | 1.00 | 25.27 | C |
| ATOM | 12797 | CD  | GLU | B | 305 | −31.306 | −12.488 | −28.585 | 1.00 | 27.91 | C |
| ATOM | 12798 | OE1 | GLU | B | 305 | −30.946 | −13.303 | −29.470 | 1.00 | 29.87 | O |
| ATOM | 12799 | OE2 | GLU | B | 305 | −31.244 | −12.728 | −27.351 | 1.00 | 29.28 | O |
| ATOM | 12800 | C   | GLU | B | 305 | −33.633 | −9.440  | −26.104 | 1.00 | 22.52 | C |
| ATOM | 12801 | O   | GLU | B | 305 | −33.793 | −9.956  | −25.005 | 1.00 | 23.39 | O |
| ATOM | 12803 | N   | LEU | B | 306 | −33.576 | −8.124  | −26.274 | 1.00 | 21.51 | N |
| ATOM | 12804 | CA  | LEU | B | 306 | −33.715 | −7.224  | −25.114 | 1.00 | 20.70 | C |
| ATOM | 12806 | CB  | LEU | B | 306 | −33.899 | −5.764  | −25.544 | 1.00 | 20.59 | C |
| ATOM | 12809 | CG  | LEU | B | 306 | −32.769 | −5.065  | −26.293 | 1.00 | 20.12 | C |
| ATOM | 12811 | CD1 | LEU | B | 306 | −32.992 | −3.576  | −26.203 | 1.00 | 19.89 | C |
| ATOM | 12815 | CD2 | LEU | B | 306 | −31.402 | −5.437  | −25.739 | 1.00 | 19.81 | C |
| ATOM | 12819 | C   | LEU | B | 306 | −34.896 | −7.645  | −24.237 | 1.00 | 19.91 | C |
| ATOM | 12820 | O   | LEU | B | 306 | −34.771 | −7.778  | −23.031 | 1.00 | 19.53 | O |
| ATOM | 12822 | N   | PHE | B | 307 | −36.030 | −7.883  | −24.872 | 1.00 | 19.48 | N |
| ATOM | 12823 | CA  | PHE | B | 307 | −37.231 | −8.267  | −24.170 | 1.00 | 19.36 | C |
| ATOM | 12825 | CB  | PHE | B | 307 | −38.400 | −8.406  | −25.138 | 1.00 | 19.54 | C |
| ATOM | 12828 | CG  | PHE | B | 307 | −39.729 | −8.296  | −24.482 | 1.00 | 19.66 | C |
| ATOM | 12829 | CD1 | PHE | B | 307 | −40.365 | −7.079  | −24.400 | 1.00 | 21.03 | C |
| ATOM | 12831 | CE1 | PHE | B | 307 | −41.590 | −6.968  | −23.787 | 1.00 | 21.62 | C |
| ATOM | 12833 | CZ  | PHE | B | 307 | −42.182 | −8.072  | −23.248 | 1.00 | 20.25 | C |
| ATOM | 12835 | CE2 | PHE | B | 307 | −41.553 | −9.292  | −23.329 | 1.00 | 20.07 | C |
| ATOM | 12837 | CD2 | PHE | B | 307 | −40.338 | −9.400  | −23.939 | 1.00 | 19.62 | C |
| ATOM | 12839 | C   | PHE | B | 307 | −37.039 | −9.577  | −23.443 | 1.00 | 19.22 | C |
| ATOM | 12840 | O   | PHE | B | 307 | −37.354 | −9.684  | −22.260 | 1.00 | 19.50 | O |
| ATOM | 12842 | N   | THR | B | 308 | −36.532 | −10.583 | −24.143 | 1.00 | 18.96 | N |
| ATOM | 12843 | CA  | THR | B | 308 | −36.321 | −11.874 | −23.511 | 1.00 | 18.84 | C |
| ATOM | 12845 | CB  | THR | B | 308 | −35.774 | −12.879 | −24.490 | 1.00 | 18.62 | C |
| ATOM | 12847 | OG1 | THR | B | 308 | −36.687 | −12.988 | −25.579 | 1.00 | 18.88 | O |
| ATOM | 12849 | CG2 | THR | B | 308 | −35.626 | −14.228 | −23.833 | 1.00 | 18.74 | C |
| ATOM | 12853 | C   | THR | B | 308 | −35.384 | −11.737 | −22.317 | 1.00 | 19.04 | C |
| ATOM | 12854 | O   | THR | B | 308 | −35.686 | −12.244 | −21.233 | 1.00 | 18.69 | O |
| ATOM | 12856 | N   | ASP | B | 309 | −34.264 | −11.031 | −22.511 | 1.00 | 19.36 | N |
| ATOM | 12857 | CA  | ASP | B | 309 | −33.335 | −10.751 | −21.421 | 1.00 | 19.65 | C |
| ATOM | 12859 | CB  | ASP | B | 309 | −32.121 | −9.983  | −21.942 | 1.00 | 19.92 | C |
| ATOM | 12862 | CG  | ASP | B | 309 | −31.171 | −9.536  | −20.814 | 1.00 | 23.51 | C |
| ATOM | 12863 | OD1 | ASP | B | 309 | −30.520 | −10.412 | −20.175 | 1.00 | 27.27 | O |
| ATOM | 12864 | OD2 | ASP | B | 309 | −31.076 | −8.299  | −20.561 | 1.00 | 27.40 | O |
| ATOM | 12865 | C   | ASP | B | 309 | −34.048 | −9.977  | −20.295 | 1.00 | 19.08 | C |
| ATOM | 12866 | O   | ASP | B | 309 | −33.912 | −10.308 | −19.124 | 1.00 | 18.55 | O |
| ATOM | 12868 | N   | ALA | B | 310 | −34.836 | −8.975  | −20.665 | 1.00 | 18.93 | N |
| ATOM | 12869 | CA  | ALA | B | 310 | −35.546 | −8.151  | −19.688 | 1.00 | 19.12 | C |
| ATOM | 12871 | CB  | ALA | B | 310 | −36.346 | −7.062  | −20.380 | 1.00 | 18.79 | C |
| ATOM | 12875 | C   | ALA | B | 310 | −36.462 | −8.965  | −18.784 | 1.00 | 19.36 | C |
| ATOM | 12876 | O   | ALA | B | 310 | −36.560 | −8.696  | −17.577 | 1.00 | 19.58 | O |
| ATOM | 12878 | N   | VAL | B | 311 | −37.143 | −9.942  | −19.370 | 1.00 | 19.61 | N |
| ATOM | 12879 | CA  | VAL | B | 311 | −37.996 | −10.845 | −18.611 | 1.00 | 19.68 | C |
| ATOM | 12881 | CB  | VAL | B | 311 | −38.867 | −11.682 | −19.555 | 1.00 | 19.46 | C |

TABLE 16-7-continued

Coordinates of *P. tremuloides* IspS

| ATOM | 12883 | CG1 | VAL | B | 311 | −39.948 | −10.825 | −20.123 | 1.00 | 18.49 | C |
|---|---|---|---|---|---|---|---|---|---|---|---|
| ATOM | 12887 | CG2 | VAL | B | 311 | −39.469 | −12.863 | −18.843 | 1.00 | 19.31 | C |
| ATOM | 12891 | C | VAL | B | 311 | −37.161 | −11.726 | −17.673 | 1.00 | 20.46 | C |
| ATOM | 12892 | O | VAL | B | 311 | −37.479 | −11.843 | −16.494 | 1.00 | 20.25 | O |
| ATOM | 12894 | N | GLU | B | 312 | −36.085 | −12.317 | −18.189 | 1.00 | 21.67 | N |
| ATOM | 12895 | CA | GLU | B | 312 | −35.198 | −13.168 | −17.384 | 1.00 | 22.65 | C |
| ATOM | 12897 | CB | GLU | B | 312 | −34.056 | −13.708 | −18.239 | 1.00 | 23.03 | C |
| ATOM | 12900 | CG | GLU | B | 312 | −34.454 | −14.764 | −19.261 | 1.00 | 24.88 | C |
| ATOM | 12903 | CD | GLU | B | 312 | −33.335 | −15.077 | −20.267 | 1.00 | 27.34 | C |
| ATOM | 12904 | OE1 | GLU | B | 312 | −33.485 | −16.057 | −21.028 | 1.00 | 29.07 | O |
| ATOM | 12905 | OE2 | GLU | B | 312 | −32.316 | −14.342 | −20.313 | 1.00 | 28.63 | O |
| ATOM | 12906 | C | GLU | B | 312 | −34.598 | −12.443 | −16.167 | 1.00 | 23.09 | C |
| ATOM | 12907 | O | GLU | B | 312 | −34.506 | −13.007 | −15.082 | 1.00 | 23.04 | O |
| ATOM | 12909 | N | ARG | B | 313 | −34.186 | −11.199 | −16.335 | 1.00 | 23.67 | N |
| ATOM | 12910 | CA | ARG | B | 313 | −33.590 | −10.486 | −15.222 | 1.00 | 24.60 | C |
| ATOM | 12912 | CB | ARG | B | 313 | −32.609 | −9.436 | −15.735 | 1.00 | 25.26 | C |
| ATOM | 12915 | CG | ARG | B | 313 | −31.333 | −10.030 | −16.398 | 1.00 | 27.83 | C |
| ATOM | 12918 | CD | ARG | B | 313 | −30.289 | −8.943 | −16.754 | 1.00 | 31.87 | C |
| ATOM | 12921 | NE | ARG | B | 313 | −30.922 | −7.793 | −17.430 | 1.00 | 35.71 | N |
| ATOM | 12923 | CZ | ARG | B | 313 | −31.341 | −6.661 | −16.837 | 1.00 | 38.42 | C |
| ATOM | 12924 | NH1 | ARG | B | 313 | −31.189 | −6.452 | −15.522 | 1.00 | 39.15 | N |
| ATOM | 12927 | NH2 | ARG | B | 313 | −31.919 | −5.711 | −17.576 | 1.00 | 39.25 | N |
| ATOM | 12930 | C | ARG | B | 313 | −34.638 | −9.879 | −14.280 | 1.00 | 24.67 | C |
| ATOM | 12931 | O | ARG | B | 313 | −34.359 | −9.645 | −13.117 | 1.00 | 24.09 | O |
| ATOM | 12933 | N | TRP | B | 314 | −35.843 | −9.635 | −14.781 | 1.00 | 25.60 | N |
| ATOM | 12934 | CA | TRP | B | 314 | −36.971 | −9.180 | −13.951 | 1.00 | 26.20 | C |
| ATOM | 12936 | CB | TRP | B | 314 | −37.488 | −10.339 | −13.097 | 1.00 | 25.90 | C |
| ATOM | 12939 | CG | TRP | B | 314 | −38.912 | −10.184 | −12.662 | 1.00 | 23.93 | C |
| ATOM | 12940 | CD1 | TRP | B | 314 | −39.355 | −9.854 | −11.424 | 1.00 | 22.76 | C |
| ATOM | 12942 | NE1 | TRP | B | 314 | −40.727 | −9.804 | −11.412 | 1.00 | 21.93 | N |
| ATOM | 12944 | CE2 | TRP | B | 314 | −41.189 | −10.107 | −12.659 | 1.00 | 20.38 | C |
| ATOM | 12945 | CD2 | TRP | B | 314 | −40.074 | −10.352 | −13.473 | 1.00 | 21.17 | C |
| ATOM | 12946 | CE3 | TRP | B | 314 | −40.277 | −10.684 | −14.811 | 1.00 | 20.19 | C |
| ATOM | 12948 | CZ3 | TRP | B | 314 | −41.549 | −10.766 | −15.280 | 1.00 | 19.79 | C |
| ATOM | 12950 | CH2 | TRP | B | 314 | −42.640 | −10.512 | −14.445 | 1.00 | 21.00 | C |
| ATOM | 12952 | CZ2 | TRP | B | 314 | −42.474 | −10.179 | −13.130 | 1.00 | 20.60 | C |
| ATOM | 12954 | C | TRP | B | 314 | −36.620 | −7.966 | −13.076 | 1.00 | 27.57 | C |
| ATOM | 12955 | O | TRP | B | 314 | −36.890 | −7.935 | −11.870 | 1.00 | 27.56 | O |
| ATOM | 12957 | N | ASP | B | 315 | −36.039 | −6.959 | −13.718 | 1.00 | 29.12 | N |
| ATOM | 12958 | CA | ASP | B | 315 | −35.452 | −5.822 | −13.027 | 1.00 | 30.46 | C |
| ATOM | 12960 | CB | ASP | B | 315 | −33.935 | −5.796 | −13.315 | 1.00 | 30.84 | C |
| ATOM | 12963 | CG | ASP | B | 315 | −33.227 | −4.551 | −12.772 | 1.00 | 32.75 | C |
| ATOM | 12964 | OD1 | ASP | B | 315 | −33.747 | −3.904 | −11.830 | 1.00 | 35.67 | O |
| ATOM | 12965 | OD2 | ASP | B | 315 | −32.128 | −4.222 | −13.295 | 1.00 | 34.91 | O |
| ATOM | 12966 | C | ASP | B | 315 | −36.157 | −4.592 | −13.557 | 1.00 | 31.10 | C |
| ATOM | 12967 | O | ASP | B | 315 | −35.888 | −4.157 | −14.674 | 1.00 | 31.35 | O |
| ATOM | 12969 | N | VAL | B | 316 | −37.088 | −4.044 | −12.781 | 1.00 | 32.06 | N |
| ATOM | 12970 | CA | VAL | B | 316 | −37.864 | −2.896 | −13.262 | 1.00 | 32.65 | C |
| ATOM | 12972 | CB | VAL | B | 316 | −39.016 | −2.510 | −12.334 | 1.00 | 32.45 | C |
| ATOM | 12974 | CG1 | VAL | B | 316 | −39.911 | −1.499 | −13.012 | 1.00 | 32.15 | C |
| ATOM | 12978 | CG2 | VAL | B | 316 | −38.490 | −1.960 | −11.040 | 1.00 | 32.91 | C |
| ATOM | 12982 | C | VAL | B | 316 | −36.964 | −1.692 | −13.442 | 1.00 | 33.43 | C |
| ATOM | 12983 | O | VAL | B | 316 | −37.228 | −.854 | −14.294 | 1.00 | 33.74 | O |
| ATOM | 12985 | N | ASN | B | 317 | −35.881 | −1.628 | −12.663 | 1.00 | 34.29 | N |
| ATOM | 12986 | CA | ASN | B | 317 | −34.937 | −.510 | −12.730 | 1.00 | 34.63 | C |
| ATOM | 12988 | CB | ASN | B | 317 | −33.995 | −.526 | −11.505 | 1.00 | 34.50 | C |
| ATOM | 12991 | CG | ASN | B | 317 | −34.692 | −.084 | −10.201 | 1.00 | 34.08 | C |
| ATOM | 12992 | OD1 | ASN | B | 317 | −35.198 | 1.042 | −10.104 | 1.00 | 33.72 | O |
| ATOM | 12993 | ND2 | ASN | B | 317 | −34.690 | −.961 | −9.193 | 1.00 | 31.22 | N |
| ATOM | 12996 | C | ASN | B | 317 | −34.124 | −.481 | −14.029 | 1.00 | 35.21 | C |
| ATOM | 12997 | O | ASN | B | 317 | −33.196 | .296 | −14.127 | 1.00 | 35.52 | O |
| ATOM | 12999 | N | ALA | B | 318 | −34.470 | −1.318 | −15.013 | 1.00 | 35.89 | N |
| ATOM | 13000 | CA | ALA | B | 318 | −33.757 | −1.382 | −16.299 | 1.00 | 36.48 | C |
| ATOM | 13002 | CB | ALA | B | 318 | −32.727 | −2.508 | −16.253 | 1.00 | 36.49 | C |
| ATOM | 13006 | C | ALA | B | 318 | −34.695 | −1.525 | −17.534 | 1.00 | 37.02 | C |
| ATOM | 13007 | O | ALA | B | 318 | −34.297 | −1.984 | −18.616 | 1.00 | 36.52 | O |
| ATOM | 13009 | N | ILE | B | 319 | −35.952 | −1.137 | −17.339 | 1.00 | 37.76 | N |
| ATOM | 13010 | CA | ILE | B | 319 | −36.848 | −.733 | −18.424 | 1.00 | 38.08 | C |
| ATOM | 13012 | CB | ILE | B | 319 | −37.926 | .247 | −17.893 | 1.00 | 38.11 | C |
| ATOM | 13014 | CG1 | ILE | B | 319 | −39.110 | −.495 | −17.293 | 1.00 | 38.08 | C |
| ATOM | 13017 | CD1 | ILE | B | 319 | −40.068 | .451 | −16.596 | 1.00 | 38.27 | C |
| ATOM | 13021 | CG2 | ILE | B | 319 | −38.408 | 1.189 | −18.996 | 1.00 | 37.84 | C |
| ATOM | 13025 | C | ILE | B | 319 | −36.134 | .053 | −19.516 | 1.00 | 38.29 | C |
| ATOM | 13026 | O | ILE | B | 319 | −36.192 | −.324 | −20.677 | 1.00 | 38.68 | O |
| ATOM | 13028 | N | ASN | B | 320 | −35.460 | 1.141 | −19.125 | 1.00 | 38.36 | N |
| ATOM | 13029 | CA | ASN | B | 320 | −34.977 | 2.168 | −20.074 | 1.00 | 38.17 | C |
| ATOM | 13031 | CB | ASN | B | 320 | −34.278 | 3.331 | −19.331 | 1.00 | 38.16 | C |
| ATOM | 13034 | CG | ASN | B | 320 | −35.258 | 4.207 | −18.514 | 1.00 | 37.87 | C |

TABLE 16-7-continued

Coordinates of *P. tremuloides* IspS

| ATOM | 13035 | OD1 | ASN | B | 320 | −36.366 | 4.542 | −18.955 | 1.00 | 36.50 | O |
|---|---|---|---|---|---|---|---|---|---|---|---|
| ATOM | 13036 | ND2 | ASN | B | 320 | −34.827 | 4.589 | −17.322 | 1.00 | 38.12 | N |
| ATOM | 13039 | C | ASN | B | 320 | −34.082 | 1.643 | −21.206 | 1.00 | 37.78 | C |
| ATOM | 13040 | O | ASN | B | 320 | −33.856 | 2.332 | −22.181 | 1.00 | 37.76 | O |
| ATOM | 13042 | N | ASP | B | 321 | −33.600 | .416 | −21.083 | 1.00 | 37.46 | N |
| ATOM | 13043 | CA | ASP | B | 321 | −32.852 | −.224 | −22.162 | 1.00 | 37.25 | C |
| ATOM | 13045 | CB | ASP | B | 321 | −32.091 | −1.467 | −21.629 | 1.00 | 37.83 | C |
| ATOM | 13048 | CG | ASP | B | 321 | −31.351 | −1.207 | −20.285 | 1.00 | 39.33 | C |
| ATOM | 13049 | OD1 | ASP | B | 321 | −31.247 | −.021 | −19.871 | 1.00 | 40.72 | O |
| ATOM | 13050 | OD2 | ASP | B | 321 | −30.887 | −2.199 | −19.648 | 1.00 | 39.62 | O |
| ATOM | 13051 | C | ASP | B | 321 | −33.764 | −.636 | −23.339 | 1.00 | 35.99 | C |
| ATOM | 13052 | O | ASP | B | 321 | −33.273 | −.904 | −24.436 | 1.00 | 35.87 | O |
| ATOM | 13054 | N | LEU | B | 322 | −35.076 | −.674 | −23.111 | 1.00 | 34.66 | N |
| ATOM | 13055 | CA | LEU | B | 322 | −36.024 | −1.263 | −24.061 | 1.00 | 33.77 | C |
| ATOM | 13057 | CB | LEU | B | 322 | −37.180 | −1.961 | −23.327 | 1.00 | 33.65 | C |
| ATOM | 13060 | CG | LEU | B | 322 | −36.994 | −3.260 | −22.544 | 1.00 | 32.41 | C |
| ATOM | 13062 | CD1 | LEU | B | 322 | −38.223 | −3.482 | −21.693 | 1.00 | 31.54 | C |
| ATOM | 13066 | CD2 | LEU | B | 322 | −36.769 | −4.432 | −23.460 | 1.00 | 30.73 | C |
| ATOM | 13070 | C | LEU | B | 322 | −36.670 | −.243 | −24.982 | 1.00 | 33.32 | C |
| ATOM | 13071 | O | LEU | B | 322 | −36.910 | .893 | −24.570 | 1.00 | 33.37 | O |
| ATOM | 13073 | N | PRO | B | 323 | −37.005 | −.667 | −26.218 | 1.00 | 32.72 | N |
| ATOM | 13074 | CA | PRO | B | 323 | −37.856 | .068 | −27.126 | 1.00 | 32.42 | C |
| ATOM | 13076 | CB | PRO | B | 323 | −38.239 | −.985 | −28.158 | 1.00 | 32.28 | C |
| ATOM | 13079 | CG | PRO | B | 323 | −37.098 | −1.849 | −28.231 | 1.00 | 32.46 | C |
| ATOM | 13082 | CD | PRO | B | 323 | −36.498 | −1.891 | −26.857 | 1.00 | 32.79 | C |
| ATOM | 13085 | C | PRO | B | 323 | −39.115 | .576 | −26.453 | 1.00 | 32.50 | C |
| ATOM | 13086 | O | PRO | B | 323 | −39.655 | −.083 | −25.550 | 1.00 | 32.46 | O |
| ATOM | 13087 | N | ASP | B | 324 | −39.590 | 1.725 | −26.923 | 1.00 | 32.44 | N |
| ATOM | 13088 | CA | ASP | B | 324 | −40.729 | 2.387 | −26.318 | 1.00 | 32.44 | C |
| ATOM | 13090 | CB | ASP | B | 324 | −41.059 | 3.678 | −27.071 | 1.00 | 32.91 | C |
| ATOM | 13093 | CG | ASP | B | 324 | −40.241 | 4.873 | −26.576 | 1.00 | 34.17 | C |
| ATOM | 13094 | OD1 | ASP | B | 324 | −39.507 | 4.728 | −25.562 | 1.00 | 35.83 | O |
| ATOM | 13095 | OD2 | ASP | B | 324 | −40.351 | 5.960 | −27.196 | 1.00 | 35.42 | O |
| ATOM | 13096 | C | ASP | B | 324 | −41.967 | 1.504 | −26.186 | 1.00 | 31.78 | C |
| ATOM | 13097 | O | ASP | B | 324 | −42.546 | 1.440 | −25.102 | 1.00 | 31.77 | O |
| ATOM | 13099 | N | TYR | B | 325 | −42.368 | .821 | −27.258 | 1.00 | 30.99 | N |
| ATOM | 13100 | CA | TYR | B | 325 | −43.519 | −.086 | −27.167 | 1.00 | 30.49 | C |
| ATOM | 13102 | CB | TYR | B | 325 | −43.941 | −.640 | −28.536 | 1.00 | 30.28 | C |
| ATOM | 13105 | CG | TYR | B | 325 | −43.027 | −1.688 | −29.134 | 1.00 | 30.25 | C |
| ATOM | 13106 | CD1 | TYR | B | 325 | −41.917 | −1.332 | −29.893 | 1.00 | 29.81 | C |
| ATOM | 13108 | CE1 | TYR | B | 325 | −41.089 | −2.300 | −30.449 | 1.00 | 29.74 | C |
| ATOM | 13110 | CZ | TYR | B | 325 | −41.371 | −3.643 | −30.258 | 1.00 | 30.22 | C |
| ATOM | 13111 | OH | TYR | B | 325 | −40.565 | −4.625 | −30.805 | 1.00 | 31.28 | O |
| ATOM | 13113 | CE2 | TYR | B | 325 | −42.466 | −4.015 | −29.519 | 1.00 | 30.23 | C |
| ATOM | 13115 | CD2 | TYR | B | 325 | −43.288 | −3.038 | −28.963 | 1.00 | 30.49 | C |
| ATOM | 13117 | C | TYR | B | 325 | −43.284 | −1.221 | −26.168 | 1.00 | 30.14 | C |
| ATOM | 13118 | O | TYR | B | 325 | −44.219 | −1.638 | −25.483 | 1.00 | 30.19 | O |
| ATOM | 13120 | N | MET | B | 326 | −42.048 | −1.700 | −26.060 | 1.00 | 29.74 | N |
| ATOM | 13121 | CA | MET | B | 326 | −41.755 | −2.820 | −25.155 | 1.00 | 29.82 | C |
| ATOM | 13123 | CB | MET | B | 326 | −40.461 | −3.541 | −25.549 | 1.00 | 29.69 | C |
| ATOM | 13126 | CG | MET | B | 326 | −40.650 | −4.510 | −26.686 | 1.00 | 28.83 | C |
| ATOM | 13129 | SD | MET | B | 326 | −39.123 | −5.272 | −27.204 | 1.00 | 26.99 | S |
| ATOM | 13130 | CE | MET | B | 326 | −39.761 | −6.499 | −28.328 | 1.00 | 29.13 | C |
| ATOM | 13134 | C | MET | B | 326 | −41.696 | −2.402 | −23.683 | 1.00 | 29.92 | C |
| ATOM | 13135 | O | MET | B | 326 | −42.032 | −3.204 | −22.801 | 1.00 | 29.75 | O |
| ATOM | 13137 | N | LYS | B | 327 | −41.251 | −1.166 | −23.429 | 1.00 | 29.68 | N |
| ATOM | 13138 | CA | LYS | B | 327 | −41.318 | −.578 | −22.088 | 1.00 | 29.46 | C |
| ATOM | 13140 | CB | LYS | B | 327 | −41.016 | .921 | −22.114 | 1.00 | 29.93 | C |
| ATOM | 13143 | CG | LYS | B | 327 | −39.572 | 1.305 | −21.951 | 1.00 | 31.63 | C |
| ATOM | 13146 | CD | LYS | B | 327 | −39.410 | 2.803 | −22.249 | 1.00 | 34.93 | C |
| ATOM | 13149 | CE | LYS | B | 327 | −37.986 | 3.291 | −22.021 | 1.00 | 36.86 | C |
| ATOM | 13152 | NZ | LYS | B | 327 | −37.642 | 4.436 | −22.917 | 1.00 | 37.83 | N |
| ATOM | 13156 | C | LYS | B | 327 | −42.708 | −.752 | −21.531 | 1.00 | 28.46 | C |
| ATOM | 13157 | O | LYS | B | 327 | −42.879 | −1.314 | −20.461 | 1.00 | 28.54 | O |
| ATOM | 13159 | N | LEU | B | 328 | −43.696 | −.258 | −22.268 | 1.00 | 27.39 | N |
| ATOM | 13160 | CA | LEU | B | 328 | −45.056 | −.216 | −21.785 | 1.00 | 26.79 | C |
| ATOM | 13162 | CB | LEU | B | 328 | −45.946 | .519 | −22.773 | 1.00 | 26.68 | C |
| ATOM | 13165 | CG | LEU | B | 328 | −47.265 | 1.034 | −22.212 | 1.00 | 26.00 | C |
| ATOM | 13167 | CD1 | LEU | B | 328 | −47.010 | 1.964 | −21.036 | 1.00 | 24.88 | C |
| ATOM | 13171 | CD2 | LEU | B | 328 | −48.051 | 1.740 | −23.308 | 1.00 | 24.55 | C |
| ATOM | 13175 | C | LEU | B | 328 | −45.560 | −1.628 | −21.587 | 1.00 | 26.70 | C |
| ATOM | 13176 | O | LEU | B | 328 | −46.110 | −1.983 | −20.543 | 1.00 | 27.03 | O |
| ATOM | 13178 | N | CYS | B | 329 | −45.341 | −2.453 | −22.591 | 1.00 | 26.39 | N |
| ATOM | 13179 | CA | CYS | B | 329 | −45.750 | −3.843 | −22.524 | 1.00 | 26.12 | C |
| ATOM | 13181 | CB | CYS | B | 329 | −45.382 | −4.526 | −23.838 | 1.00 | 26.47 | C |
| ATOM | 13184 | SG | CYS | B | 329 | −45.857 | −6.236 | −23.880 | 1.00 | 30.60 | S |
| ATOM | 13186 | C | CYS | B | 329 | −45.124 | −4.568 | −21.319 | 1.00 | 24.45 | C |
| ATOM | 13187 | O | CYS | B | 329 | −45.829 | −5.105 | −20.486 | 1.00 | 23.93 | O |

TABLE 16-7-continued

Coordinates of *P. tremuloides* IspS

| ATOM | 13189 | N | PHE | B | 330 | −43.801 | −4.553 | −21.228 | 1.00 | 23.30 | N |
|---|---|---|---|---|---|---|---|---|---|---|---|
| ATOM | 13190 | CA | PHE | B | 330 | −43.087 | −5.220 | −20.141 | 1.00 | 22.47 | C |
| ATOM | 13192 | CB | PHE | B | 330 | −41.575 | −5.019 | −20.267 | 1.00 | 22.42 | C |
| ATOM | 13195 | CG | PHE | B | 330 | −40.800 | −5.518 | −19.076 | 1.00 | 22.37 | C |
| ATOM | 13196 | CD1 | PHE | B | 330 | −40.502 | −6.864 | −18.940 | 1.00 | 22.47 | C |
| ATOM | 13198 | CE1 | PHE | B | 330 | −39.799 | −7.339 | −17.836 | 1.00 | 21.64 | C |
| ATOM | 13200 | CZ | PHE | B | 330 | −39.379 | −6.472 | −16.866 | 1.00 | 21.50 | C |
| ATOM | 13202 | CE2 | PHE | B | 330 | −39.659 | −5.122 | −16.983 | 1.00 | 21.92 | C |
| ATOM | 13204 | CD2 | PHE | B | 330 | −40.374 | −4.648 | −18.084 | 1.00 | 22.29 | C |
| ATOM | 13206 | C | PHE | B | 330 | −43.524 | −4.739 | −18.765 | 1.00 | 21.87 | C |
| ATOM | 13207 | O | PHE | B | 330 | −43.779 | −5.552 | −17.875 | 1.00 | 21.98 | O |
| ATOM | 13209 | N | LEU | B | 331 | −43.594 | −3.427 | −18.573 | 1.00 | 20.88 | N |
| ATOM | 13210 | CA | LEU | B | 331 | −43.997 | −2.894 | −17.276 | 1.00 | 20.25 | C |
| ATOM | 13212 | CB | LEU | B | 331 | −43.927 | −1.354 | −17.257 | 1.00 | 20.06 | C |
| ATOM | 13215 | CG | LEU | B | 331 | −44.124 | −.628 | −15.912 | 1.00 | 19.21 | C |
| ATOM | 13217 | CD1 | LEU | B | 331 | −43.542 | −1.408 | −14.737 | 1.00 | 18.78 | C |
| ATOM | 13221 | CD2 | LEU | B | 331 | −43.555 | .770 | −15.957 | 1.00 | 15.75 | C |
| ATOM | 13225 | C | LEU | B | 331 | −45.398 | −3.408 | −16.902 | 1.00 | 19.99 | C |
| ATOM | 13226 | O | LEU | B | 331 | −45.606 | −3.860 | −15.771 | 1.00 | 19.67 | O |
| ATOM | 13228 | N | ALA | B | 332 | −46.336 | −3.373 | −17.860 | 1.00 | 19.56 | N |
| ATOM | 13229 | CA | ALA | B | 332 | −47.695 | −3.882 | −17.629 | 1.00 | 19.24 | C |
| ATOM | 13231 | CB | ALA | B | 332 | −48.528 | −3.802 | −18.891 | 1.00 | 18.58 | C |
| ATOM | 13235 | C | ALA | B | 332 | −47.637 | −5.321 | −17.108 | 1.00 | 19.23 | C |
| ATOM | 13236 | O | ALA | B | 332 | −48.235 | −5.650 | −16.079 | 1.00 | 19.18 | O |
| ATOM | 13238 | N | LEU | B | 333 | −46.891 | −6.162 | −17.816 | 1.00 | 19.16 | N |
| ATOM | 13239 | CA | LEU | B | 333 | −46.727 | −7.554 | −17.438 | 1.00 | 19.08 | C |
| ATOM | 13241 | CB | LEU | B | 333 | −45.830 | −8.260 | −18.462 | 1.00 | 18.97 | C |
| ATOM | 13244 | CG | LEU | B | 333 | −45.511 | −9.758 | −18.307 | 1.00 | 19.18 | C |
| ATOM | 13246 | CD1 | LEU | B | 333 | −46.779 | −10.611 | −18.121 | 1.00 | 18.09 | C |
| ATOM | 13250 | CD2 | LEU | B | 333 | −44.676 | −10.262 | −19.499 | 1.00 | 17.17 | C |
| ATOM | 13254 | C | LEU | B | 333 | −46.111 | −7.616 | −16.042 | 1.00 | 19.16 | C |
| ATOM | 13255 | O | LEU | B | 333 | −46.629 | −8.279 | −15.137 | 1.00 | 18.97 | O |
| ATOM | 13257 | N | TYR | B | 334 | −45.013 | −6.887 | −15.884 | 1.00 | 19.23 | N |
| ATOM | 13258 | CA | TYR | B | 334 | −44.212 | −6.906 | −14.664 | 1.00 | 19.33 | C |
| ATOM | 13260 | CB | TYR | B | 334 | −43.092 | −5.873 | −14.785 | 1.00 | 19.43 | C |
| ATOM | 13263 | CG | TYR | B | 334 | −42.190 | −5.748 | −13.596 | 1.00 | 19.44 | C |
| ATOM | 13264 | CD1 | TYR | B | 334 | −41.006 | −6.464 | −13.524 | 1.00 | 20.60 | C |
| ATOM | 13266 | CE1 | TYR | B | 334 | −40.148 | −6.347 | −12.442 | 1.00 | 20.77 | C |
| ATOM | 13268 | CZ | TYR | B | 334 | −40.474 | −5.503 | −11.417 | 1.00 | 21.51 | C |
| ATOM | 13269 | OH | TYR | B | 334 | −39.628 | −5.387 | −10.353 | 1.00 | 21.42 | O |
| ATOM | 13271 | CE2 | TYR | B | 334 | −41.646 | −4.768 | −11.466 | 1.00 | 22.15 | C |
| ATOM | 13273 | CD2 | TYR | B | 334 | −42.495 | −4.892 | −12.565 | 1.00 | 20.55 | C |
| ATOM | 13275 | C | TYR | B | 334 | −45.065 | −6.614 | −13.443 | 1.00 | 19.37 | C |
| ATOM | 13276 | O | TYR | B | 334 | −44.980 | −7.337 | −12.441 | 1.00 | 19.94 | O |
| ATOM | 13278 | N | ASN | B | 335 | −45.888 | −5.565 | −13.527 | 1.00 | 18.83 | N |
| ATOM | 13279 | CA | ASN | B | 335 | −46.784 | −5.236 | −12.443 | 1.00 | 18.37 | C |
| ATOM | 13281 | CB | ASN | B | 335 | −47.452 | −3.896 | −12.675 | 1.00 | 18.52 | C |
| ATOM | 13284 | CG | ASN | B | 335 | −46.493 | −2.742 | −12.518 | 1.00 | 19.27 | C |
| ATOM | 13285 | OD1 | ASN | B | 335 | −45.421 | −2.906 | −11.953 | 1.00 | 21.25 | O |
| ATOM | 13286 | ND2 | ASN | B | 335 | −46.872 | −1.566 | −13.022 | 1.00 | 19.24 | N |
| ATOM | 13289 | C | ASN | B | 335 | −47.812 | −6.333 | −12.291 | 1.00 | 18.22 | C |
| ATOM | 13290 | O | ASN | B | 335 | −47.966 | −6.891 | −11.207 | 1.00 | 18.53 | O |
| ATOM | 13292 | N | THR | B | 336 | −48.481 | −6.697 | −13.379 | 1.00 | 17.95 | N |
| ATOM | 13293 | CA | THR | B | 336 | −49.525 | −7.728 | −13.301 | 1.00 | 17.61 | C |
| ATOM | 13295 | CB | THR | B | 336 | −49.980 | −8.204 | −14.676 | 1.00 | 17.36 | C |
| ATOM | 13297 | OG1 | THR | B | 336 | −50.249 | −7.065 | −15.500 | 1.00 | 17.02 | O |
| ATOM | 13299 | CG2 | THR | B | 336 | −51.228 | −9.044 | −14.551 | 1.00 | 16.07 | C |
| ATOM | 13303 | C | THR | B | 336 | −49.065 | −8.941 | −12.501 | 1.00 | 17.75 | C |
| ATOM | 13304 | O | THR | B | 336 | −49.788 | −9.429 | −11.621 | 1.00 | 18.09 | O |
| ATOM | 13306 | N | ILE | B | 337 | −47.859 | −9.411 | −12.785 | 1.00 | 17.69 | N |
| ATOM | 13307 | CA | ILE | B | 337 | −47.384 | −10.630 | −12.165 | 1.00 | 17.74 | C |
| ATOM | 13309 | CB | ILE | B | 337 | −46.228 | −11.245 | −12.949 | 1.00 | 17.40 | C |
| ATOM | 13311 | CG1 | ILE | B | 337 | −46.795 | −11.865 | −14.227 | 1.00 | 18.44 | C |
| ATOM | 13314 | CD1 | ILE | B | 337 | −45.767 | −12.192 | −15.300 | 1.00 | 19.26 | C |
| ATOM | 13318 | CG2 | ILE | B | 337 | −45.568 | −12.320 | −12.152 | 1.00 | 16.25 | C |
| ATOM | 13322 | C | ILE | B | 337 | −47.053 | −10.395 | −10.699 | 1.00 | 18.32 | C |
| ATOM | 13323 | O | ILE | B | 337 | −47.497 | −11.175 | −9.838 | 1.00 | 18.06 | O |
| ATOM | 13325 | N | ASN | B | 338 | −46.321 | −9.311 | −10.404 | 1.00 | 18.89 | N |
| ATOM | 13326 | CA | ASN | B | 338 | −45.985 | −8.978 | −9.007 | 1.00 | 19.49 | C |
| ATOM | 13328 | CB | ASN | B | 338 | −45.189 | −7.690 | −8.917 | 1.00 | 19.43 | C |
| ATOM | 13331 | CG | ASN | B | 338 | −43.789 | −7.836 | −9.444 | 1.00 | 20.83 | C |
| ATOM | 13332 | OD1 | ASN | B | 338 | −43.292 | −8.954 | −9.634 | 1.00 | 21.52 | O |
| ATOM | 13333 | ND2 | ASN | B | 338 | −43.124 | −6.697 | −9.676 | 1.00 | 22.32 | N |
| ATOM | 13336 | C | ASN | B | 338 | −47.229 | −8.835 | −8.146 | 1.00 | 20.05 | C |
| ATOM | 13337 | O | ASN | B | 338 | −47.182 | −9.055 | −6.953 | 1.00 | 19.81 | O |
| ATOM | 13339 | N | GLU | B | 339 | −48.337 | −8.459 | −8.770 | 1.00 | 20.81 | N |
| ATOM | 13340 | CA | GLU | B | 339 | −49.589 | −8.347 | −8.086 | 1.00 | 21.81 | C |
| ATOM | 13342 | CB | GLU | B | 339 | −50.563 | −7.544 | −8.933 | 1.00 | 22.69 | C |

TABLE 16-7-continued

Coordinates of *P. tremuloides* IspS

| ATOM | 13345 | CG | GLU | B | 339 | −51.240 | −6.422 | −8.148 | 1.00 | 27.28 | C |
|---|---|---|---|---|---|---|---|---|---|---|---|
| ATOM | 13348 | CD | GLU | B | 339 | −52.571 | −5.959 | −8.768 | 1.00 | 32.79 | C |
| ATOM | 13349 | OE1 | GLU | B | 339 | −52.761 | −4.713 | −8.897 | 1.00 | 36.20 | O |
| ATOM | 13350 | OE2 | GLU | B | 339 | −53.416 | −6.837 | −9.114 | 1.00 | 34.35 | O |
| ATOM | 13351 | C | GLU | B | 339 | −50.170 | −9.732 | −7.762 | 1.00 | 21.59 | C |
| ATOM | 13352 | O | GLU | B | 339 | −50.690 | −9.946 | −6.666 | 1.00 | 21.38 | O |
| ATOM | 13354 | N | ILE | B | 340 | −50.094 | −10.676 | −8.700 | 1.00 | 21.48 | N |
| ATOM | 13355 | CA | ILE | B | 340 | −50.486 | −12.049 | −8.384 | 1.00 | 21.27 | C |
| ATOM | 13357 | CB | ILE | B | 340 | −50.437 | −12.990 | −9.603 | 1.00 | 21.17 | C |
| ATOM | 13359 | CG1 | ILE | B | 340 | −51.478 | −12.589 | −10.643 | 1.00 | 20.99 | C |
| ATOM | 13362 | CD1 | ILE | B | 340 | −51.245 | −13.202 | −12.017 | 1.00 | 19.72 | C |
| ATOM | 13366 | CG2 | ILE | B | 340 | −50.702 | −14.444 | −9.177 | 1.00 | 21.09 | C |
| ATOM | 13370 | C | ILE | B | 340 | −49.557 | −12.585 | −7.278 | 1.00 | 21.40 | C |
| ATOM | 13371 | O | ILE | B | 340 | −50.023 | −13.238 | −6.334 | 1.00 | 21.74 | O |
| ATOM | 13373 | N | ALA | B | 341 | −48.256 | −12.301 | −7.380 | 1.00 | 20.90 | N |
| ATOM | 13374 | CA | ALA | B | 341 | −47.312 | −12.721 | −6.349 | 1.00 | 20.62 | C |
| ATOM | 13376 | CB | ALA | B | 341 | −45.922 | −12.260 | −6.694 | 1.00 | 20.53 | C |
| ATOM | 13380 | C | ALA | B | 341 | −47.720 | −12.195 | −4.969 | 1.00 | 20.59 | C |
| ATOM | 13381 | O | ALA | B | 341 | −47.606 | −12.901 | −3.950 | 1.00 | 20.57 | O |
| ATOM | 13383 | N | TYR | B | 342 | −48.208 | −10.958 | −4.949 | 1.00 | 20.62 | N |
| ATOM | 13384 | CA | TYR | B | 342 | −48.600 | −10.303 | −3.707 | 1.00 | 20.59 | C |
| ATOM | 13386 | CB | TYR | B | 342 | −48.790 | −8.792 | −3.907 | 1.00 | 20.05 | C |
| ATOM | 13389 | CG | TYR | B | 342 | −49.309 | −8.143 | −2.674 | 1.00 | 18.29 | C |
| ATOM | 13390 | CD1 | TYR | B | 342 | −48.443 | −7.683 | −1.698 | 1.00 | 17.62 | C |
| ATOM | 13392 | CE1 | TYR | B | 342 | −48.914 | −7.111 | −.518 | 1.00 | 17.91 | C |
| ATOM | 13394 | CZ | TYR | B | 342 | −50.285 | −7.005 | −.298 | 1.00 | 18.18 | C |
| ATOM | 13395 | OH | TYR | B | 342 | −50.763 | −6.433 | .877 | 1.00 | 16.00 | O |
| ATOM | 13397 | CE2 | TYR | B | 342 | −51.169 | −7.467 | −1.275 | 1.00 | 18.10 | C |
| ATOM | 13399 | CD2 | TYR | B | 342 | −50.670 | −8.037 | −2.450 | 1.00 | 17.67 | C |
| ATOM | 13401 | C | TYR | B | 342 | −49.863 | −10.928 | −3.118 | 1.00 | 21.48 | C |
| ATOM | 13402 | O | TYR | B | 342 | −49.960 | −11.089 | −1.913 | 1.00 | 20.91 | O |
| ATOM | 13404 | N | ASP | B | 343 | −50.832 | −11.273 | −3.959 | 1.00 | 22.93 | N |
| ATOM | 13405 | CA | ASP | B | 343 | −52.048 | −11.925 | −3.470 | 1.00 | 24.30 | C |
| ATOM | 13407 | CB | ASP | B | 343 | −53.010 | −12.282 | −4.608 | 1.00 | 24.59 | C |
| ATOM | 13410 | CG | ASP | B | 343 | −53.577 | −11.060 | −5.334 | 1.00 | 26.66 | C |
| ATOM | 13411 | OD1 | ASP | B | 343 | −53.619 | −9.936 | −4.756 | 1.00 | 28.24 | O |
| ATOM | 13412 | OD2 | ASP | B | 343 | −54.004 | −11.247 | −6.506 | 1.00 | 29.56 | O |
| ATOM | 13413 | C | ASP | B | 343 | −51.660 | −13.208 | −2.761 | 1.00 | 24.97 | C |
| ATOM | 13414 | O | ASP | B | 343 | −52.128 | −13.495 | −1.658 | 1.00 | 24.95 | O |
| ATOM | 13416 | N | ASN | B | 344 | −50.792 | −13.973 | −3.413 | 1.00 | 25.90 | N |
| ATOM | 13417 | CA | ASN | B | 344 | −50.322 | −15.252 | −2.884 | 1.00 | 26.59 | C |
| ATOM | 13419 | CB | ASN | B | 344 | −49.623 | −16.043 | −3.978 | 1.00 | 26.74 | C |
| ATOM | 13422 | CG | ASN | B | 344 | −50.594 | −16.639 | −4.933 | 1.00 | 28.21 | C |
| ATOM | 13423 | OD1 | ASN | B | 344 | −51.080 | −17.737 | −4.688 | 1.00 | 32.10 | O |
| ATOM | 13424 | ND2 | ASN | B | 344 | −50.923 | −15.916 | −6.016 | 1.00 | 28.40 | N |
| ATOM | 13427 | C | ASN | B | 344 | −49.421 | −15.146 | −1.655 | 1.00 | 26.78 | C |
| ATOM | 13428 | O | ASN | B | 344 | −49.424 | −16.053 | −.821 | 1.00 | 27.06 | O |
| ATOM | 13430 | N | LEU | B | 345 | −48.647 | −14.067 | −1.533 | 1.00 | 26.74 | N |
| ATOM | 13431 | CA | LEU | B | 345 | −47.970 | −13.793 | −.261 | 1.00 | 26.59 | C |
| ATOM | 13433 | CB | LEU | B | 345 | −47.005 | −12.618 | −.396 | 1.00 | 26.25 | C |
| ATOM | 13436 | CG | LEU | B | 345 | −46.046 | −12.376 | .764 | 1.00 | 24.65 | C |
| ATOM | 13438 | CD1 | LEU | B | 345 | −45.258 | −13.621 | 1.115 | 1.00 | 22.50 | C |
| ATOM | 13442 | CD2 | LEU | B | 345 | −45.119 | −11.251 | .387 | 1.00 | 23.54 | C |
| ATOM | 13446 | C | LEU | B | 345 | −49.004 | −13.503 | .840 | 1.00 | 27.00 | C |
| ATOM | 13447 | O | LEU | B | 345 | −48.903 | −14.014 | 1.947 | 1.00 | 26.93 | O |
| ATOM | 13449 | N | LYS | B | 346 | −50.008 | −12.697 | .518 | 1.00 | 27.54 | N |
| ATOM | 13450 | CA | LYS | B | 346 | −51.012 | −12.300 | 1.491 | 1.00 | 27.96 | C |
| ATOM | 13452 | CB | LYS | B | 346 | −51.998 | −11.288 | .889 | 1.00 | 28.13 | C |
| ATOM | 13455 | CG | LYS | B | 346 | −52.822 | −10.527 | 1.926 | 1.00 | 28.70 | C |
| ATOM | 13458 | CD | LYS | B | 346 | −53.781 | −9.526 | 1.281 | 1.00 | 29.73 | C |
| ATOM | 13461 | CE | LYS | B | 346 | −55.205 | −10.063 | 1.133 | 1.00 | 31.17 | C |
| ATOM | 13464 | NZ | LYS | B | 346 | −55.839 | −9.661 | −.171 | 1.00 | 32.83 | N |
| ATOM | 13468 | C | LYS | B | 346 | −51.788 | −13.498 | 1.984 | 1.00 | 28.31 | C |
| ATOM | 13469 | O | LYS | B | 346 | −52.074 | −13.600 | 3.177 | 1.00 | 28.52 | O |
| ATOM | 13471 | N | ASP | B | 347 | −52.149 | −14.396 | 1.075 | 1.00 | 28.56 | N |
| ATOM | 13472 | CA | ASP | B | 347 | −53.102 | −15.441 | 1.427 | 1.00 | 29.11 | C |
| ATOM | 13474 | CB | ASP | B | 347 | −54.068 | −15.736 | .268 | 1.00 | 29.50 | C |
| ATOM | 13477 | CG | ASP | B | 347 | −54.902 | −14.500 | −.150 | 1.00 | 31.04 | C |
| ATOM | 13478 | OD1 | ASP | B | 347 | −54.961 | −13.500 | .616 | 1.00 | 31.35 | O |
| ATOM | 13479 | OD2 | ASP | B | 347 | −55.496 | −14.534 | −1.261 | 1.00 | 33.39 | O |
| ATOM | 13480 | C | ASP | B | 347 | −52.403 | −16.699 | 1.891 | 1.00 | 28.79 | C |
| ATOM | 13481 | O | ASP | B | 347 | −52.824 | −17.321 | 2.854 | 1.00 | 29.02 | O |
| ATOM | 13483 | N | LYS | B | 348 | −51.326 | −17.068 | 1.222 | 1.00 | 28.74 | N |
| ATOM | 13484 | CA | LYS | B | 348 | −50.612 | −18.293 | 1.564 | 1.00 | 28.84 | C |
| ATOM | 13486 | CB | LYS | B | 348 | −50.290 | −19.101 | .299 | 1.00 | 29.24 | C |
| ATOM | 13489 | CG | LYS | B | 348 | −51.513 | −19.470 | −.576 | 1.00 | 30.97 | C |
| ATOM | 13492 | CD | LYS | B | 348 | −51.051 | −20.300 | −1.803 | 1.00 | 33.66 | C |
| ATOM | 13495 | CE | LYS | B | 348 | −52.033 | −20.244 | −2.989 | 1.00 | 34.52 | C |

TABLE 16-7-continued

Coordinates of *P. tremuloides* IspS

| ATOM | 13498 | NZ | LYS | B | 348 | −53.445 | −20.542 | −2.607 | 1.00 | 35.61 | N |
|---|---|---|---|---|---|---|---|---|---|---|---|
| ATOM | 13502 | C | LYS | B | 348 | −49.330 | −18.029 | 2.358 | 1.00 | 27.97 | C |
| ATOM | 13503 | O | LYS | B | 348 | −48.763 | −18.948 | 2.925 | 1.00 | 27.88 | O |
| ATOM | 13505 | N | GLY | B | 349 | −48.874 | −16.785 | 2.403 | 1.00 | 27.21 | N |
| ATOM | 13506 | CA | GLY | B | 349 | −47.625 | −16.473 | 3.075 | 1.00 | 26.87 | C |
| ATOM | 13509 | C | GLY | B | 349 | −46.437 | −17.227 | 2.514 | 1.00 | 26.71 | C |
| ATOM | 13510 | O | GLY | B | 349 | −45.576 | −17.669 | 3.271 | 1.00 | 26.65 | O |
| ATOM | 13512 | N | GLU | B | 350 | −46.409 | −17.390 | 1.191 | 1.00 | 26.61 | N |
| ATOM | 13513 | CA | GLU | B | 350 | −45.263 | −17.953 | .470 | 1.00 | 26.43 | C |
| ATOM | 13515 | CB | GLU | B | 350 | −45.624 | −19.310 | −.128 | 1.00 | 26.85 | C |
| ATOM | 13518 | CG | GLU | B | 350 | −45.685 | −20.453 | .888 | 1.00 | 29.63 | C |
| ATOM | 13521 | CD | GLU | B | 350 | −44.304 | −21.036 | 1.227 | 1.00 | 34.21 | C |
| ATOM | 13522 | OE1 | GLU | B | 350 | −43.417 | −21.045 | .328 | 1.00 | 36.93 | O |
| ATOM | 13523 | OE2 | GLU | B | 350 | −44.106 | −21.498 | 2.384 | 1.00 | 35.89 | O |
| ATOM | 13524 | C | GLU | B | 350 | −44.900 | −16.981 | −.637 | 1.00 | 25.49 | C |
| ATOM | 13525 | O | GLU | B | 350 | −45.774 | −16.312 | −1.181 | 1.00 | 25.35 | O |
| ATOM | 13527 | N | ASN | B | 351 | −43.616 | −16.866 | −.955 | 1.00 | 24.74 | N |
| ATOM | 13528 | CA | ASN | B | 351 | −43.206 | −16.046 | −2.090 | 1.00 | 24.47 | C |
| ATOM | 13530 | CB | ASN | B | 351 | −41.851 | −15.369 | −1.867 | 1.00 | 24.94 | C |
| ATOM | 13533 | CG | ASN | B | 351 | −41.428 | −14.489 | −3.062 | 1.00 | 26.98 | C |
| ATOM | 13534 | OD1 | ASN | B | 351 | −41.976 | −14.605 | −4.170 | 1.00 | 28.96 | O |
| ATOM | 13535 | ND2 | ASN | B | 351 | −40.457 | −13.601 | −2.834 | 1.00 | 29.55 | N |
| ATOM | 13538 | C | ASN | B | 351 | −43.095 | −16.918 | −3.303 | 1.00 | 23.33 | C |
| ATOM | 13539 | O | ASN | B | 351 | −42.120 | −17.641 | −3.429 | 1.00 | 23.47 | O |
| ATOM | 13541 | N | ILE | B | 352 | −44.060 | −16.823 | −4.208 | 1.00 | 22.09 | N |
| ATOM | 13542 | CA | ILE | B | 352 | −44.048 | −17.644 | −5.410 | 1.00 | 21.22 | C |
| ATOM | 13544 | CB | ILE | B | 352 | −45.452 | −18.213 | −5.675 | 1.00 | 21.23 | C |
| ATOM | 13546 | CG1 | ILE | B | 352 | −46.464 | −17.080 | −5.913 | 1.00 | 21.11 | C |
| ATOM | 13549 | CD1 | ILE | B | 352 | −47.346 | −17.305 | −7.126 | 1.00 | 20.33 | C |
| ATOM | 13553 | CG2 | ILE | B | 352 | −45.875 | −19.116 | −4.519 | 1.00 | 19.79 | C |
| ATOM | 13557 | C | ILE | B | 352 | −43.508 | −16.947 | −6.689 | 1.00 | 20.88 | C |
| ATOM | 13558 | O | ILE | B | 352 | −43.486 | −17.553 | −7.758 | 1.00 | 20.76 | O |
| ATOM | 13560 | N | LEU | B | 353 | −43.030 | −15.705 | −6.574 | 1.00 | 20.44 | N |
| ATOM | 13561 | CA | LEU | B | 353 | −42.603 | −14.907 | −7.750 | 1.00 | 19.84 | C |
| ATOM | 13563 | CB | LEU | B | 353 | −42.055 | −13.527 | −7.325 | 1.00 | 19.67 | C |
| ATOM | 13566 | CG | LEU | B | 353 | −42.003 | −12.339 | −8.311 | 1.00 | 18.47 | C |
| ATOM | 13568 | CD1 | LEU | B | 353 | −43.306 | −12.083 | −9.008 | 1.00 | 17.03 | C |
| ATOM | 13572 | CD2 | LEU | B | 353 | −41.604 | −11.064 | −7.597 | 1.00 | 17.08 | C |
| ATOM | 13576 | C | LEU | B | 353 | −41.587 | −15.628 | −8.633 | 1.00 | 19.81 | C |
| ATOM | 13577 | O | LEU | B | 353 | −41.720 | −15.596 | −9.851 | 1.00 | 19.55 | O |
| ATOM | 13579 | N | PRO | B | 354 | −40.578 | −16.299 | −8.024 | 1.00 | 20.01 | N |
| ATOM | 13580 | CA | PRO | B | 354 | −39.571 | −17.010 | −8.822 | 1.00 | 19.73 | C |
| ATOM | 13582 | CB | PRO | B | 354 | −38.781 | −17.796 | −7.779 | 1.00 | 19.55 | C |
| ATOM | 13585 | CG | PRO | B | 354 | −38.928 | −17.037 | −6.542 | 1.00 | 19.61 | C |
| ATOM | 13588 | CD | PRO | B | 354 | −40.289 | −16.413 | −6.578 | 1.00 | 19.90 | C |
| ATOM | 13591 | C | PRO | B | 354 | −40.187 | −17.971 | −9.804 | 1.00 | 19.87 | C |
| ATOM | 13592 | O | PRO | B | 354 | −39.693 | −18.103 | −10.918 | 1.00 | 20.08 | O |
| ATOM | 13593 | N | TYR | B | 355 | −41.264 | −18.636 | −9.387 | 1.00 | 20.14 | N |
| ATOM | 13594 | CA | TYR | B | 355 | −41.909 | −19.665 | −10.216 | 1.00 | 20.24 | C |
| ATOM | 13596 | CB | TYR | B | 355 | −42.878 | −20.520 | −9.394 | 1.00 | 20.40 | C |
| ATOM | 13599 | CG | TYR | B | 355 | −42.189 | −21.153 | −8.214 | 1.00 | 21.82 | C |
| ATOM | 13600 | CD1 | TYR | B | 355 | −41.119 | −21.999 | −8.412 | 1.00 | 22.86 | C |
| ATOM | 13602 | CE1 | TYR | B | 355 | −40.457 | −22.564 | −7.353 | 1.00 | 25.07 | C |
| ATOM | 13604 | CZ | TYR | B | 355 | −40.850 | −22.285 | −6.053 | 1.00 | 25.58 | C |
| ATOM | 13605 | OH | TYR | B | 355 | −40.153 | −22.887 | −5.020 | 1.00 | 27.33 | O |
| ATOM | 13607 | CE2 | TYR | B | 355 | −41.918 | −21.433 | −5.815 | 1.00 | 23.93 | C |
| ATOM | 13609 | CD2 | TYR | B | 355 | −42.577 | −20.867 | −6.900 | 1.00 | 23.10 | C |
| ATOM | 13611 | C | TYR | B | 355 | −42.625 | −19.001 | −11.361 | 1.00 | 19.67 | C |
| ATOM | 13612 | O | TYR | B | 355 | −42.455 | −19.405 | −12.510 | 1.00 | 19.75 | O |
| ATOM | 13614 | N | LEU | B | 356 | −43.385 | −17.954 | −11.030 | 1.00 | 18.97 | N |
| ATOM | 13615 | CA | LEU | B | 356 | −44.180 | −17.205 | −12.004 | 1.00 | 18.26 | C |
| ATOM | 13617 | CB | LEU | B | 356 | −45.039 | −16.157 | −11.293 | 1.00 | 18.03 | C |
| ATOM | 13620 | CG | LEU | B | 356 | −46.056 | −16.727 | −10.312 | 1.00 | 18.13 | C |
| ATOM | 13622 | CD1 | LEU | B | 356 | −46.691 | −15.613 | −9.500 | 1.00 | 19.37 | C |
| ATOM | 13626 | CD2 | LEU | B | 356 | −47.106 | −17.521 | −11.046 | 1.00 | 17.93 | C |
| ATOM | 13630 | C | LEU | B | 356 | −43.298 | −16.536 | −13.056 | 1.00 | 17.76 | C |
| ATOM | 13631 | O | LEU | B | 356 | −43.598 | −16.567 | −14.259 | 1.00 | 16.93 | O |
| ATOM | 13633 | N | THR | B | 357 | −42.201 | −15.949 | −12.600 | 1.00 | 17.56 | N |
| ATOM | 13634 | CA | THR | B | 357 | −41.335 | −15.215 | −13.501 | 1.00 | 17.63 | C |
| ATOM | 13636 | CB | THR | B | 357 | −40.438 | −14.236 | −12.759 | 1.00 | 17.69 | C |
| ATOM | 13638 | OG1 | THR | B | 357 | −39.530 | −14.974 | −11.934 | 1.00 | 18.39 | O |
| ATOM | 13640 | CG2 | THR | B | 357 | −41.288 | −13.242 | −11.927 | 1.00 | 16.47 | C |
| ATOM | 13644 | C | THR | B | 357 | −40.477 | −16.145 | −14.356 | 1.00 | 17.55 | C |
| ATOM | 13645 | O | THR | B | 357 | −40.154 | −15.793 | −15.498 | 1.00 | 17.17 | O |
| ATOM | 13647 | N | LYS | B | 358 | −40.127 | −17.321 | −13.824 | 1.00 | 17.37 | N |
| ATOM | 13648 | CA | LYS | B | 358 | −39.462 | −18.337 | −14.649 | 1.00 | 17.55 | C |
| ATOM | 13650 | CB | LYS | B | 358 | −39.030 | −19.542 | −13.827 | 1.00 | 17.87 | C |
| ATOM | 13653 | CG | LYS | B | 358 | −38.450 | −20.718 | −14.640 | 1.00 | 18.75 | C |

TABLE 16-7-continued

Coordinates of *P. tremuloides* IspS

| | | | | | | | | | | | |
|---|---|---|---|---|---|---|---|---|---|---|---|
| ATOM | 13656 | CD | LYS | B | 358 | −37.013 | −20.497 | −15.112 | 1.00 | 20.18 | C |
| ATOM | 13659 | CE | LYS | B | 358 | −36.361 | −21.843 | −15.457 | 1.00 | 21.49 | C |
| ATOM | 13662 | NZ | LYS | B | 358 | −35.189 | −21.702 | −16.361 | 1.00 | 22.89 | N |
| ATOM | 13666 | C | LYS | B | 358 | −40.403 | −18.777 | −15.754 | 1.00 | 17.43 | C |
| ATOM | 13667 | O | LYS | B | 358 | −40.031 | −18.775 | −16.926 | 1.00 | 17.52 | O |
| ATOM | 13669 | N | ALA | B | 359 | −41.633 | −19.120 | −15.384 | 1.00 | 17.42 | N |
| ATOM | 13670 | CA | ALA | B | 359 | −42.654 | −19.471 | −16.359 | 1.00 | 17.52 | C |
| ATOM | 13672 | CB | ALA | B | 359 | −44.011 | −19.434 | −15.738 | 1.00 | 17.16 | C |
| ATOM | 13676 | C | ALA | B | 359 | −42.585 | −18.521 | −17.531 | 1.00 | 18.18 | C |
| ATOM | 13677 | O | ALA | B | 359 | −42.513 | −18.956 | −18.675 | 1.00 | 18.50 | O |
| ATOM | 13679 | N | TRP | B | 360 | −42.556 | −17.223 | −17.245 | 1.00 | 19.14 | N |
| ATOM | 13680 | CA | TRP | B | 360 | −42.526 | −16.206 | −18.301 | 1.00 | 19.77 | C |
| ATOM | 13682 | CB | TRP | B | 360 | −42.922 | −14.837 | −17.746 | 1.00 | 20.15 | C |
| ATOM | 13685 | CG | TRP | B | 360 | −44.377 | −14.653 | −17.813 | 1.00 | 20.50 | C |
| ATOM | 13686 | CD1 | TRP | B | 360 | −45.259 | −14.729 | −16.788 | 1.00 | 22.15 | C |
| ATOM | 13688 | NE1 | TRP | B | 360 | −46.536 | −14.533 | −17.248 | 1.00 | 22.84 | N |
| ATOM | 13690 | CE2 | TRP | B | 360 | −46.487 | −14.348 | −18.603 | 1.00 | 21.68 | C |
| ATOM | 13691 | CD2 | TRP | B | 360 | −45.134 | −14.418 | −18.987 | 1.00 | 20.85 | C |
| ATOM | 13692 | CE3 | TRP | B | 360 | −44.802 | −14.253 | −20.334 | 1.00 | 21.21 | C |
| ATOM | 13694 | CZ3 | TRP | B | 360 | −45.821 | −14.025 | −21.245 | 1.00 | 20.75 | C |
| ATOM | 13696 | CH2 | TRP | B | 360 | −47.166 | −13.961 | −20.827 | 1.00 | 21.21 | C |
| ATOM | 13698 | CZ2 | TRP | B | 360 | −47.515 | −14.123 | −19.516 | 1.00 | 20.97 | C |
| ATOM | 13700 | C | TRP | B | 360 | −41.215 | −16.110 | −19.081 | 1.00 | 19.96 | C |
| ATOM | 13701 | O | TRP | B | 360 | −41.242 | −15.791 | −20.271 | 1.00 | 19.94 | O |
| ATOM | 13703 | N | ALA | B | 361 | −40.089 | −16.368 | −18.420 | 1.00 | 20.14 | N |
| ATOM | 13704 | CA | ALA | B | 361 | −38.790 | −16.437 | −19.102 | 1.00 | 20.41 | C |
| ATOM | 13706 | CB | ALA | B | 361 | −37.676 | −16.581 | −18.102 | 1.00 | 20.67 | C |
| ATOM | 13710 | C | ALA | B | 361 | −38.763 | −17.618 | −20.041 | 1.00 | 20.55 | C |
| ATOM | 13711 | O | ALA | B | 361 | −38.330 | −17.510 | −21.187 | 1.00 | 20.76 | O |
| ATOM | 13713 | N | ASP | B | 362 | −39.230 | −18.749 | −19.534 | 1.00 | 20.57 | N |
| ATOM | 13714 | CA | ASP | B | 362 | −39.360 | −19.965 | −20.326 | 1.00 | 20.97 | C |
| ATOM | 13716 | CB | ASP | B | 362 | −39.984 | −21.082 | −19.470 | 1.00 | 21.39 | C |
| ATOM | 13719 | CG | ASP | B | 362 | −38.938 | −21.902 | −18.693 | 1.00 | 22.80 | C |
| ATOM | 13720 | OD1 | ASP | B | 362 | −38.836 | −23.109 | −18.970 | 1.00 | 28.57 | O |
| ATOM | 13721 | OD2 | ASP | B | 362 | −38.210 | −21.384 | −17.825 | 1.00 | 22.78 | O |
| ATOM | 13722 | C | ASP | B | 362 | −40.179 | −19.748 | −21.618 | 1.00 | 20.66 | C |
| ATOM | 13723 | O | ASP | B | 362 | −39.740 | −20.141 | −22.701 | 1.00 | 20.69 | O |
| ATOM | 13725 | N | LEU | B | 363 | −41.346 | −19.110 | −21.501 | 1.00 | 20.22 | N |
| ATOM | 13726 | CA | LEU | B | 363 | −42.245 | −18.885 | −22.648 | 1.00 | 19.82 | C |
| ATOM | 13728 | CB | LEU | B | 363 | −43.592 | −18.327 | −22.164 | 1.00 | 19.11 | C |
| ATOM | 13731 | CG | LEU | B | 363 | −44.644 | −17.945 | −23.209 | 1.00 | 17.02 | C |
| ATOM | 13733 | CD1 | LEU | B | 363 | −44.829 | −19.033 | −24.214 | 1.00 | 16.20 | C |
| ATOM | 13737 | CD2 | LEU | B | 363 | −45.979 | −17.618 | −22.586 | 1.00 | 14.21 | C |
| ATOM | 13741 | C | LEU | B | 363 | −41.633 | −17.950 | −23.706 | 1.00 | 20.76 | C |
| ATOM | 13742 | O | LEU | B | 363 | −41.656 | −18.235 | −24.910 | 1.00 | 21.00 | O |
| ATOM | 13744 | N | CYS | B | 364 | −41.088 | −16.826 | −23.253 | 1.00 | 21.42 | N |
| ATOM | 13745 | CA | CYS | B | 364 | −40.427 | −15.884 | −24.147 | 1.00 | 21.67 | C |
| ATOM | 13747 | CB | CYS | B | 364 | −39.969 | −14.639 | −23.376 | 1.00 | 21.86 | C |
| ATOM | 13750 | SG | CYS | B | 364 | −41.327 | −13.638 | −22.722 | 1.00 | 23.36 | S |
| ATOM | 13752 | C | CYS | B | 364 | −39.229 | −16.547 | −24.835 | 1.00 | 21.52 | C |
| ATOM | 13753 | O | CYS | B | 364 | −39.010 | −16.323 | −26.037 | 1.00 | 21.67 | O |
| ATOM | 13755 | N | ASN | B | 365 | −38.454 | −17.352 | −24.095 | 1.00 | 20.83 | N |
| ATOM | 13756 | CA | ASN | B | 365 | −37.306 | −18.025 | −24.713 | 1.00 | 20.65 | C |
| ATOM | 13758 | CB | ASN | B | 365 | −36.425 | −18.756 | −23.691 | 1.00 | 20.74 | C |
| ATOM | 13761 | CG | ASN | B | 365 | −35.330 | −17.865 | −23.100 | 1.00 | 20.53 | C |
| ATOM | 13762 | OD1 | ASN | B | 365 | −34.553 | −17.229 | −23.830 | 1.00 | 18.26 | O |
| ATOM | 13763 | ND2 | ASN | B | 365 | −35.252 | −17.841 | −21.763 | 1.00 | 20.69 | N |
| ATOM | 13766 | C | ASN | B | 365 | −37.756 | −18.987 | −25.811 | 1.00 | 20.43 | C |
| ATOM | 13767 | O | ASN | B | 365 | −36.998 | −19.253 | −26.759 | 1.00 | 20.11 | O |
| ATOM | 13769 | N | ALA | B | 366 | −38.987 | −19.492 | −25.667 | 1.00 | 20.01 | N |
| ATOM | 13770 | CA | ALA | B | 366 | −39.618 | −20.340 | −26.665 | 1.00 | 19.70 | C |
| ATOM | 13772 | CB | ALA | B | 366 | −40.766 | −21.113 | −26.045 | 1.00 | 19.53 | C |
| ATOM | 13776 | C | ALA | B | 366 | −40.099 | −19.494 | −27.838 | 1.00 | 19.74 | C |
| ATOM | 13777 | O | ALA | B | 366 | −39.846 | −19.824 | −28.989 | 1.00 | 19.61 | O |
| ATOM | 13779 | N | PHE | B | 367 | −40.791 | −18.399 | −27.553 | 1.00 | 19.99 | N |
| ATOM | 13780 | CA | PHE | B | 367 | −41.138 | −17.446 | −28.606 | 1.00 | 20.36 | C |
| ATOM | 13782 | CB | PHE | B | 367 | −41.805 | −16.194 | −28.026 | 1.00 | 20.62 | C |
| ATOM | 13785 | CG | PHE | B | 367 | −43.200 | −16.403 | −27.537 | 1.00 | 21.75 | C |
| ATOM | 13786 | CD1 | PHE | B | 367 | −44.136 | −17.071 | −28.315 | 1.00 | 23.00 | C |
| ATOM | 13788 | CE1 | PHE | B | 367 | −45.435 | −17.242 | −27.874 | 1.00 | 23.60 | C |
| ATOM | 13790 | CZ | PHE | B | 367 | −45.819 | −16.731 | −26.648 | 1.00 | 23.64 | C |
| ATOM | 13792 | CE2 | PHE | B | 367 | −44.901 | −16.049 | −25.871 | 1.00 | 23.56 | C |
| ATOM | 13794 | CD2 | PHE | B | 367 | −43.599 | −15.883 | −26.316 | 1.00 | 22.91 | C |
| ATOM | 13796 | C | PHE | B | 367 | −39.906 | −16.986 | −29.393 | 1.00 | 20.19 | C |
| ATOM | 13797 | O | PHE | B | 367 | −39.934 | −16.903 | −30.615 | 1.00 | 19.98 | O |
| ATOM | 13799 | N | LEU | B | 368 | −38.839 | −16.659 | −28.675 | 1.00 | 20.24 | N |
| ATOM | 13800 | CA | LEU | B | 368 | −37.629 | −16.161 | −29.298 | 1.00 | 20.31 | C |
| ATOM | 13802 | CB | LEU | B | 368 | −36.569 | −15.900 | −28.232 | 1.00 | 20.27 | C |

TABLE 16-7-continued

Coordinates of *P. tremuloides* IspS

| ATOM | 13805 | CG | LEU | B | 368 | −35.235 | −15.313 | −28.694 | 1.00 | 20.12 | C |
|---|---|---|---|---|---|---|---|---|---|---|---|
| ATOM | 13807 | CD1 | LEU | B | 368 | −35.417 | −14.069 | −29.592 | 1.00 | 20.05 | C |
| ATOM | 13811 | CD2 | LEU | B | 368 | −34.409 | −14.987 | −27.465 | 1.00 | 18.60 | C |
| ATOM | 13815 | C | LEU | B | 368 | −37.122 | −17.179 | −30.295 | 1.00 | 20.53 | C |
| ATOM | 13816 | O | LEU | B | 368 | −36.844 | −16.844 | −31.446 | 1.00 | 20.49 | O |
| ATOM | 13818 | N | GLN | B | 369 | −37.032 | −18.426 | −29.832 | 1.00 | 20.80 | N |
| ATOM | 13819 | CA | GLN | B | 369 | −36.565 | −19.557 | −30.638 | 1.00 | 20.90 | C |
| ATOM | 13821 | CB | GLN | B | 369 | −36.614 | −20.857 | −29.815 | 1.00 | 20.98 | C |
| ATOM | 13824 | CG | GLN | B | 369 | −36.343 | −22.159 | −30.576 | 1.00 | 20.75 | C |
| ATOM | 13827 | CD | GLN | B | 369 | −34.946 | −22.238 | −31.126 | 1.00 | 20.29 | C |
| ATOM | 13828 | OE1 | GLN | B | 369 | −34.718 | −21.984 | −32.305 | 1.00 | 20.17 | O |
| ATOM | 13829 | NE2 | GLN | B | 369 | −33.996 | −22.581 | −30.272 | 1.00 | 20.33 | N |
| ATOM | 13832 | C | GLN | B | 369 | −37.365 | −19.718 | −31.910 | 1.00 | 21.04 | C |
| ATOM | 13833 | O | GLN | B | 369 | −36.803 | −20.097 | −32.929 | 1.00 | 20.82 | O |
| ATOM | 13835 | N | GLU | B | 370 | −38.668 | −19.453 | −31.863 | 1.00 | 21.80 | N |
| ATOM | 13836 | CA | GLU | B | 370 | −39.480 | −19.512 | −33.087 | 1.00 | 22.73 | C |
| ATOM | 13838 | CB | GLU | B | 370 | −40.996 | −19.518 | −32.801 | 1.00 | 23.18 | C |
| ATOM | 13841 | CG | GLU | B | 370 | −41.449 | −20.608 | −31.809 | 1.00 | 25.92 | C |
| ATOM | 13844 | CD | GLU | B | 370 | −42.927 | −21.064 | −31.957 | 1.00 | 29.74 | C |
| ATOM | 13845 | OE1 | GLU | B | 370 | −43.840 | −20.191 | −32.101 | 1.00 | 30.13 | O |
| ATOM | 13846 | OE2 | GLU | B | 370 | −43.156 | −22.316 | −31.892 | 1.00 | 31.94 | O |
| ATOM | 13847 | C | GLU | B | 370 | −39.079 | −18.358 | −34.016 | 1.00 | 22.62 | C |
| ATOM | 13848 | O | GLU | B | 370 | −38.933 | −18.565 | −35.221 | 1.00 | 22.53 | O |
| ATOM | 13850 | N | ALA | B | 371 | −38.864 | −17.166 | −33.456 | 1.00 | 22.65 | N |
| ATOM | 13851 | CA | ALA | B | 371 | −38.427 | −16.023 | −34.254 | 1.00 | 22.95 | C |
| ATOM | 13853 | CB | ALA | B | 371 | −38.375 | −14.753 | −33.424 | 1.00 | 22.97 | C |
| ATOM | 13857 | C | ALA | B | 371 | −37.070 | −16.296 | −34.891 | 1.00 | 23.13 | C |
| ATOM | 13858 | O | ALA | B | 371 | −36.900 | −16.063 | −36.091 | 1.00 | 23.38 | O |
| ATOM | 13860 | N | LYS | B | 372 | −36.113 | −16.804 | −34.107 | 1.00 | 23.15 | N |
| ATOM | 13861 | CA | LYS | B | 372 | −34.776 | −17.102 | −34.640 | 1.00 | 23.10 | C |
| ATOM | 13863 | CB | LYS | B | 372 | −33.808 | −17.633 | −33.575 | 1.00 | 22.85 | C |
| ATOM | 13866 | CG | LYS | B | 372 | −33.414 | −16.616 | −32.514 | 1.00 | 24.28 | C |
| ATOM | 13869 | CD | LYS | B | 372 | −31.973 | −16.806 | −31.969 | 1.00 | 26.34 | C |
| ATOM | 13872 | CE | LYS | B | 372 | −31.919 | −17.407 | −30.544 | 1.00 | 27.84 | C |
| ATOM | 13875 | NZ | LYS | B | 372 | −31.673 | −16.405 | −29.458 | 1.00 | 27.93 | N |
| ATOM | 13879 | C | LYS | B | 372 | −34.887 | −18.093 | −35.790 | 1.00 | 23.16 | C |
| ATOM | 13880 | O | LYS | B | 372 | −34.231 | −17.920 | −36.804 | 1.00 | 23.73 | O |
| ATOM | 13882 | N | TRP | B | 373 | −35.720 | −19.122 | −35.658 | 1.00 | 23.11 | N |
| ATOM | 13883 | CA | TRP | B | 373 | −35.844 | −20.094 | −36.742 | 1.00 | 22.99 | C |
| ATOM | 13885 | CB | TRP | B | 373 | −36.746 | −21.274 | −36.370 | 1.00 | 22.71 | C |
| ATOM | 13888 | CG | TRP | B | 373 | −36.081 | −22.343 | −35.562 | 1.00 | 20.71 | C |
| ATOM | 13889 | CD1 | TRP | B | 373 | −34.770 | −22.740 | −35.623 | 1.00 | 19.89 | C |
| ATOM | 13891 | NE1 | TRP | B | 373 | −34.540 | −23.757 | −34.734 | 1.00 | 19.05 | N |
| ATOM | 13893 | CE2 | TRP | B | 373 | −35.715 | −24.050 | −34.090 | 1.00 | 18.91 | C |
| ATOM | 13894 | CD2 | TRP | B | 373 | −36.707 | −23.184 | −34.599 | 1.00 | 18.41 | C |
| ATOM | 13895 | CE3 | TRP | B | 373 | −38.007 | −23.288 | −34.105 | 1.00 | 15.66 | C |
| ATOM | 13897 | CZ3 | TRP | B | 373 | −38.271 | −24.216 | −33.130 | 1.00 | 15.41 | C |
| ATOM | 13899 | CH2 | TRP | B | 373 | −37.276 | −25.069 | −32.647 | 1.00 | 16.33 | C |
| ATOM | 13901 | CZ2 | TRP | B | 373 | −35.994 | −25.005 | −33.112 | 1.00 | 17.53 | C |
| ATOM | 13903 | C | TRP | B | 373 | −36.374 | −19.416 | −37.991 | 1.00 | 23.59 | C |
| ATOM | 13904 | O | TRP | B | 373 | −35.878 | −19.653 | −39.096 | 1.00 | 23.60 | O |
| ATOM | 13906 | N | LEU | B | 374 | −37.374 | −18.559 | −37.801 | 1.00 | 24.32 | N |
| ATOM | 13907 | CA | LEU | B | 374 | −38.008 | −17.859 | −38.915 | 1.00 | 24.66 | C |
| ATOM | 13909 | CB | LEU | B | 374 | −39.181 | −17.019 | −38.428 | 1.00 | 24.85 | C |
| ATOM | 13912 | CG | LEU | B | 374 | −40.112 | −16.449 | −39.496 | 1.00 | 25.45 | C |
| ATOM | 13914 | CD1 | LEU | B | 374 | −41.002 | −17.535 | −40.070 | 1.00 | 24.83 | C |
| ATOM | 13918 | CD2 | LEU | B | 374 | −40.959 | −15.293 | −38.885 | 1.00 | 26.92 | C |
| ATOM | 13922 | C | LEU | B | 374 | −37.009 | −16.975 | −39.618 | 1.00 | 24.64 | C |
| ATOM | 13923 | O | LEU | B | 374 | −36.934 | −16.992 | −40.830 | 1.00 | 24.33 | O |
| ATOM | 13925 | N | TYR | B | 375 | −36.232 | −16.220 | −38.850 | 1.00 | 25.09 | N |
| ATOM | 13926 | CA | TYR | B | 375 | −35.283 | −15.274 | −39.433 | 1.00 | 25.71 | C |
| ATOM | 13928 | CB | TYR | B | 375 | −34.534 | −14.479 | −38.349 | 1.00 | 25.91 | C |
| ATOM | 13931 | CG | TYR | B | 375 | −33.536 | −13.468 | −38.892 | 1.00 | 27.11 | C |
| ATOM | 13932 | CD1 | TYR | B | 375 | −33.950 | −12.200 | −39.305 | 1.00 | 27.98 | C |
| ATOM | 13934 | CE1 | TYR | B | 375 | −33.039 | −11.271 | −39.811 | 1.00 | 28.61 | C |
| ATOM | 13936 | CZ | TYR | B | 375 | −31.693 | −11.605 | −39.904 | 1.00 | 29.13 | C |
| ATOM | 13937 | OH | TYR | B | 375 | −30.790 | −10.685 | −40.397 | 1.00 | 29.83 | O |
| ATOM | 13939 | CE2 | TYR | B | 375 | −31.256 | −12.863 | −39.501 | 1.00 | 28.79 | C |
| ATOM | 13941 | CD2 | TYR | B | 375 | −32.177 | −13.783 | −38.995 | 1.00 | 28.03 | C |
| ATOM | 13943 | C | TYR | B | 375 | −34.305 | −16.036 | −40.301 | 1.00 | 25.64 | C |
| ATOM | 13944 | O | TYR | B | 375 | −34.201 | −15.788 | −41.503 | 1.00 | 25.74 | O |
| ATOM | 13946 | N | ASN | B | 376 | −33.635 | −17.000 | −39.685 | 1.00 | 25.73 | N |
| ATOM | 13947 | CA | ASN | B | 376 | −32.599 | −17.777 | −40.346 | 1.00 | 25.78 | C |
| ATOM | 13949 | CB | ASN | B | 376 | −31.739 | −18.497 | −39.303 | 1.00 | 25.73 | C |
| ATOM | 13952 | CG | ASN | B | 376 | −31.155 | −17.565 | −38.273 | 1.00 | 25.13 | C |
| ATOM | 13953 | OD1 | ASN | B | 376 | −30.491 | −16.590 | −38.601 | 1.00 | 25.53 | O |
| ATOM | 13954 | ND2 | ASN | B | 376 | −31.389 | −17.874 | −37.013 | 1.00 | 24.64 | N |
| ATOM | 13957 | C | ASN | B | 376 | −33.126 | −18.824 | −41.332 | 1.00 | 26.04 | C |

TABLE 16-7-continued

Coordinates of *P. tremuloides* IspS

| ATOM | 13958 | O   | ASN | B | 376 | −32.343 | −19.644 | −41.807 | 1.00 | 26.36 | O |
|------|-------|-----|-----|---|-----|---------|---------|---------|------|-------|---|
| ATOM | 13960 | N   | LYS | B | 377 | −34.428 | −18.824 | −41.632 | 1.00 | 26.16 | N |
| ATOM | 13961 | CA  | LYS | B | 377 | −35.012 | −19.811 | −42.552 | 1.00 | 26.27 | C |
| ATOM | 13963 | CB  | LYS | B | 377 | −34.575 | −19.538 | −44.010 | 1.00 | 26.51 | C |
| ATOM | 13966 | CG  | LYS | B | 377 | −35.470 | −18.561 | −44.802 | 1.00 | 28.01 | C |
| ATOM | 13969 | CD  | LYS | B | 377 | −34.629 | −17.592 | −45.667 | 1.00 | 29.99 | C |
| ATOM | 13972 | CE  | LYS | B | 377 | −35.493 | −16.605 | −46.465 | 1.00 | 31.02 | C |
| ATOM | 13975 | NZ  | LYS | B | 377 | −36.420 | −15.819 | −45.589 | 1.00 | 32.17 | N |
| ATOM | 13979 | C   | LYS | B | 377 | −34.647 | −21.243 | −42.150 | 1.00 | 25.93 | C |
| ATOM | 13980 | O   | LYS | B | 377 | −34.380 | −22.084 | −43.003 | 1.00 | 25.82 | O |
| ATOM | 13982 | N   | SER | B | 378 | −34.637 | −21.522 | −40.852 | 1.00 | 25.65 | N |
| ATOM | 13983 | CA  | SER | B | 378 | −34.324 | −22.860 | −40.385 | 1.00 | 25.54 | C |
| ATOM | 13985 | CB  | SER | B | 378 | −34.132 | −22.877 | −38.882 | 1.00 | 25.41 | C |
| ATOM | 13988 | OG  | SER | B | 378 | −32.905 | −22.269 | −38.570 | 1.00 | 25.67 | O |
| ATOM | 13990 | C   | SER | B | 378 | −35.412 | −23.838 | −40.790 | 1.00 | 25.62 | C |
| ATOM | 13991 | O   | SER | B | 378 | −36.495 | −23.435 | −41.199 | 1.00 | 25.70 | O |
| ATOM | 13993 | N   | THR | B | 379 | −35.108 | −25.129 | −40.690 | 1.00 | 25.66 | N |
| ATOM | 13994 | CA  | THR | B | 379 | −36.038 | −26.175 | −41.097 | 1.00 | 25.55 | C |
| ATOM | 13996 | CB  | THR | B | 379 | −35.788 | −26.635 | −42.546 | 1.00 | 25.59 | C |
| ATOM | 13998 | OG1 | THR | B | 379 | −34.391 | −26.899 | −42.736 | 1.00 | 25.46 | O |
| ATOM | 14000 | CG2 | THR | B | 379 | −36.255 | −25.574 | −43.528 | 1.00 | 25.88 | C |
| ATOM | 14004 | C   | THR | B | 379 | −35.886 | −27.348 | −40.160 | 1.00 | 25.45 | C |
| ATOM | 14005 | O   | THR | B | 379 | −35.372 | −28.393 | −40.548 | 1.00 | 25.70 | O |
| ATOM | 14007 | N   | PRO | B | 380 | −36.335 | −27.179 | −38.915 | 1.00 | 25.37 | N |
| ATOM | 14008 | CA  | PRO | B | 380 | −36.144 | −28.182 | −37.876 | 1.00 | 25.22 | C |
| ATOM | 14010 | CB  | PRO | B | 380 | −36.500 | −27.437 | −36.583 | 1.00 | 25.19 | C |
| ATOM | 14013 | CG  | PRO | B | 380 | −36.643 | −26.021 | −36.955 | 1.00 | 25.83 | C |
| ATOM | 14016 | CD  | PRO | B | 380 | −37.025 | −25.998 | −38.390 | 1.00 | 25.71 | C |
| ATOM | 14019 | C   | PRO | B | 380 | −37.052 | −29.379 | −38.009 | 1.00 | 24.82 | C |
| ATOM | 14020 | O   | PRO | B | 380 | −38.143 | −29.280 | −38.575 | 1.00 | 24.84 | O |
| ATOM | 14021 | N   | THR | B | 381 | −36.607 | −30.493 | −37.436 | 1.00 | 24.42 | N |
| ATOM | 14022 | CA  | THR | B | 381 | −37.386 | −31.712 | −37.429 | 1.00 | 23.99 | C |
| ATOM | 14024 | CB  | THR | B | 381 | −36.614 | −32.873 | −36.789 | 1.00 | 23.99 | C |
| ATOM | 14026 | OG1 | THR | B | 381 | −36.339 | −32.575 | −35.418 | 1.00 | 24.02 | O |
| ATOM | 14028 | CG2 | THR | B | 381 | −35.302 | −33.117 | −37.524 | 1.00 | 23.76 | C |
| ATOM | 14032 | C   | THR | B | 381 | −38.649 | −31.461 | −36.636 | 1.00 | 23.78 | C |
| ATOM | 14033 | O   | THR | B | 381 | −38.700 | −30.548 | −35.813 | 1.00 | 23.89 | O |
| ATOM | 14035 | N   | PHE | B | 382 | −39.672 | −32.267 | −36.889 | 1.00 | 23.53 | N |
| ATOM | 14036 | CA  | PHE | B | 382 | −40.905 | −32.204 | −36.105 | 1.00 | 22.97 | C |
| ATOM | 14038 | CB  | PHE | B | 382 | −41.870 | −33.305 | −36.527 | 1.00 | 22.89 | C |
| ATOM | 14041 | CG  | PHE | B | 382 | −43.079 | −33.394 | −35.655 | 1.00 | 22.26 | C |
| ATOM | 14042 | CD1 | PHE | B | 382 | −44.189 | −32.601 | −35.910 | 1.00 | 21.65 | C |
| ATOM | 14044 | CE1 | PHE | B | 382 | −45.300 | −32.672 | −35.099 | 1.00 | 20.87 | C |
| ATOM | 14046 | CZ  | PHE | B | 382 | −45.310 | −33.534 | −34.016 | 1.00 | 20.36 | C |
| ATOM | 14048 | CE2 | PHE | B | 382 | −44.204 | −34.317 | −33.744 | 1.00 | 20.52 | C |
| ATOM | 14050 | CD2 | PHE | B | 382 | −43.098 | −34.243 | −34.556 | 1.00 | 21.17 | C |
| ATOM | 14052 | C   | PHE | B | 382 | −40.677 | −32.329 | −34.605 | 1.00 | 22.69 | C |
| ATOM | 14053 | O   | PHE | B | 382 | −41.341 | −31.657 | −33.834 | 1.00 | 22.44 | O |
| ATOM | 14055 | N   | ASP | B | 383 | −39.764 | −33.205 | −34.191 | 1.00 | 22.52 | N |
| ATOM | 14056 | CA  | ASP | B | 383 | −39.491 | −33.375 | −32.765 | 1.00 | 22.50 | C |
| ATOM | 14058 | CB  | ASP | B | 383 | −38.531 | −34.525 | −32.527 | 1.00 | 22.43 | C |
| ATOM | 14061 | CG  | ASP | B | 383 | −39.174 | −35.863 | −32.711 | 1.00 | 22.71 | C |
| ATOM | 14062 | OD1 | ASP | B | 383 | −40.359 | −35.945 | −33.074 | 1.00 | 22.89 | O |
| ATOM | 14063 | OD2 | ASP | B | 383 | −38.470 | −36.856 | −32.492 | 1.00 | 25.17 | O |
| ATOM | 14064 | C   | ASP | B | 383 | −38.954 | −32.116 | −32.091 | 1.00 | 22.43 | C |
| ATOM | 14065 | O   | ASP | B | 383 | −39.438 | −31.758 | −31.014 | 1.00 | 22.40 | O |
| ATOM | 14067 | N   | ASP | B | 384 | −37.966 | −31.464 | −32.713 | 1.00 | 22.37 | N |
| ATOM | 14068 | CA  | ASP | B | 384 | −37.422 | −30.191 | −32.213 | 1.00 | 22.61 | C |
| ATOM | 14070 | CB  | ASP | B | 384 | −36.317 | −29.648 | −33.124 | 1.00 | 22.82 | C |
| ATOM | 14073 | CG  | ASP | B | 384 | −34.963 | −30.208 | −32.807 | 1.00 | 23.40 | C |
| ATOM | 14074 | OD1 | ASP | B | 384 | −34.847 | −30.973 | −31.832 | 1.00 | 25.33 | O |
| ATOM | 14075 | OD2 | ASP | B | 384 | −34.009 | −29.891 | −33.545 | 1.00 | 24.26 | O |
| ATOM | 14076 | C   | ASP | B | 384 | −38.482 | −29.113 | −32.130 | 1.00 | 22.56 | C |
| ATOM | 14077 | O   | ASP | B | 384 | −38.598 | −28.429 | −31.108 | 1.00 | 22.48 | O |
| ATOM | 14079 | N   | TYR | B | 385 | −39.227 | −28.963 | −33.227 | 1.00 | 22.36 | N |
| ATOM | 14080 | CA  | TYR | B | 385 | −40.170 | −27.870 | −33.402 | 1.00 | 22.18 | C |
| ATOM | 14082 | CB  | TYR | B | 385 | −40.738 | −27.867 | −34.812 | 1.00 | 22.05 | C |
| ATOM | 14085 | CG  | TYR | B | 385 | −41.818 | −26.834 | −35.019 | 1.00 | 22.60 | C |
| ATOM | 14086 | CD1 | TYR | B | 385 | −41.493 | −25.553 | −35.437 | 1.00 | 23.64 | C |
| ATOM | 14088 | CE1 | TYR | B | 385 | −42.462 | −24.580 | −35.630 | 1.00 | 25.00 | C |
| ATOM | 14090 | CZ  | TYR | B | 385 | −43.788 | −24.882 | −35.410 | 1.00 | 26.86 | C |
| ATOM | 14091 | OH  | TYR | B | 385 | −44.734 | −23.883 | −35.622 | 1.00 | 28.48 | O |
| ATOM | 14093 | CE2 | TYR | B | 385 | −44.149 | −26.171 | −34.980 | 1.00 | 25.95 | C |
| ATOM | 14095 | CD2 | TYR | B | 385 | −43.158 | −27.133 | −34.790 | 1.00 | 23.94 | C |
| ATOM | 14097 | C   | TYR | B | 385 | −41.319 | −27.986 | −32.446 | 1.00 | 22.13 | C |
| ATOM | 14098 | O   | TYR | B | 385 | −41.703 | −27.017 | −31.808 | 1.00 | 22.95 | O |
| ATOM | 14100 | N   | PHE | B | 386 | −41.899 | −29.169 | −32.380 | 1.00 | 21.80 | N |
| ATOM | 14101 | CA  | PHE | B | 386 | −43.048 | −29.394 | −31.525 | 1.00 | 21.62 | C |

TABLE 16-7-continued

Coordinates of *P. tremuloides* IspS

| ATOM | 14103 | CB | PHE | B | 386 | −43.624 | −30.795 | −31.768 | 1.00 | 21.73 | C |
|---|---|---|---|---|---|---|---|---|---|---|---|
| ATOM | 14106 | CG | PHE | B | 386 | −44.834 | −31.104 | −30.952 | 1.00 | 21.27 | C |
| ATOM | 14107 | CD1 | PHE | B | 386 | −46.034 | −30.447 | −31.196 | 1.00 | 22.55 | C |
| ATOM | 14109 | CE1 | PHE | B | 386 | −47.164 | −30.732 | −30.448 | 1.00 | 23.14 | C |
| ATOM | 14111 | CZ | PHE | B | 386 | −47.095 | −31.699 | −29.446 | 1.00 | 23.20 | C |
| ATOM | 14113 | CE2 | PHE | B | 386 | −45.896 | −32.358 | −29.208 | 1.00 | 21.57 | C |
| ATOM | 14115 | CD2 | PHE | B | 386 | −44.781 | −32.057 | −29.959 | 1.00 | 20.29 | C |
| ATOM | 14117 | C | PHE | B | 386 | −42.630 | −29.226 | −30.073 | 1.00 | 21.34 | C |
| ATOM | 14118 | O | PHE | B | 386 | −43.353 | −28.639 | −29.284 | 1.00 | 21.44 | O |
| ATOM | 14120 | N | GLY | B | 387 | −41.447 | −29.725 | −29.736 | 1.00 | 20.84 | N |
| ATOM | 14121 | CA | GLY | B | 387 | −40.935 | −29.618 | −28.387 | 1.00 | 20.57 | C |
| ATOM | 14124 | C | GLY | B | 387 | −40.854 | −28.186 | −27.916 | 1.00 | 20.26 | C |
| ATOM | 14125 | O | GLY | B | 387 | −40.930 | −27.908 | −26.724 | 1.00 | 20.86 | O |
| ATOM | 14127 | N | ASN | B | 388 | −40.691 | −27.268 | −28.852 | 1.00 | 19.81 | N |
| ATOM | 14128 | CA | ASN | B | 388 | −40.758 | −25.853 | −28.536 | 1.00 | 19.51 | C |
| ATOM | 14130 | CB | ASN | B | 388 | −39.877 | −25.086 | −29.508 | 1.00 | 19.42 | C |
| ATOM | 14133 | CG | ASN | B | 388 | −39.593 | −23.700 | −29.045 | 1.00 | 19.26 | C |
| ATOM | 14134 | OD1 | ASN | B | 388 | −38.916 | −23.513 | −28.038 | 1.00 | 18.93 | O |
| ATOM | 14135 | ND2 | ASN | B | 388 | −40.105 | −22.709 | −29.774 | 1.00 | 17.99 | N |
| ATOM | 14138 | C | ASN | B | 388 | −42.200 | −25.320 | −28.604 | 1.00 | 19.41 | C |
| ATOM | 14139 | O | ASN | B | 388 | −42.591 | −24.447 | −27.833 | 1.00 | 19.58 | O |
| ATOM | 14141 | N | ALA | B | 389 | −42.989 | −25.848 | −29.532 | 1.00 | 19.11 | N |
| ATOM | 14142 | CA | ALA | B | 389 | −44.313 | −25.307 | −29.808 | 1.00 | 18.87 | C |
| ATOM | 14144 | CB | ALA | B | 389 | −44.897 | −25.949 | −31.060 | 1.00 | 18.87 | C |
| ATOM | 14148 | C | ALA | B | 389 | −45.264 | −25.460 | −28.634 | 1.00 | 18.51 | C |
| ATOM | 14149 | O | ALA | B | 389 | −45.916 | −24.511 | −28.262 | 1.00 | 18.33 | O |
| ATOM | 14151 | N | TRP | B | 390 | −45.344 | −26.652 | −28.054 | 1.00 | 18.73 | N |
| ATOM | 14152 | CA | TRP | B | 390 | −46.258 | −26.887 | −26.935 | 1.00 | 18.74 | C |
| ATOM | 14154 | CB | TRP | B | 390 | −46.389 | −28.377 | −26.569 | 1.00 | 18.75 | C |
| ATOM | 14157 | CG | TRP | B | 390 | −45.166 | −29.122 | −26.019 | 1.00 | 18.46 | C |
| ATOM | 14158 | CD1 | TRP | B | 390 | −44.390 | −30.001 | −26.705 | 1.00 | 18.75 | C |
| ATOM | 14160 | NE1 | TRP | B | 390 | −43.417 | −30.519 | −25.897 | 1.00 | 17.56 | N |
| ATOM | 14162 | CE2 | TRP | B | 390 | −43.559 | −30.005 | −24.642 | 1.00 | 16.67 | C |
| ATOM | 14163 | CD2 | TRP | B | 390 | −44.661 | −29.124 | −24.674 | 1.00 | 17.50 | C |
| ATOM | 14164 | CE3 | TRP | B | 390 | −45.008 | −28.448 | −23.505 | 1.00 | 18.38 | C |
| ATOM | 14166 | CZ3 | TRP | B | 390 | −44.251 | −28.685 | −22.347 | 1.00 | 18.34 | C |
| ATOM | 14168 | CH2 | TRP | B | 390 | −43.164 | −29.573 | −22.361 | 1.00 | 16.75 | C |
| ATOM | 14170 | CZ2 | TRP | B | 390 | −42.805 | −30.234 | −23.495 | 1.00 | 15.75 | C |
| ATOM | 14172 | C | TRP | B | 390 | −45.861 | −26.066 | −25.727 | 1.00 | 18.91 | C |
| ATOM | 14173 | O | TRP | B | 390 | −46.707 | −25.691 | −24.919 | 1.00 | 19.02 | O |
| ATOM | 14175 | N | LYS | B | 391 | −44.570 | −25.787 | −25.612 | 1.00 | 18.95 | N |
| ATOM | 14176 | CA | LYS | B | 391 | −44.085 | −24.810 | −24.643 | 1.00 | 18.85 | C |
| ATOM | 14178 | CB | LYS | B | 391 | −42.544 | −24.888 | −24.508 | 1.00 | 19.52 | C |
| ATOM | 14181 | CG | LYS | B | 391 | −42.023 | −25.373 | −23.143 | 1.00 | 21.17 | C |
| ATOM | 14184 | CD | LYS | B | 391 | −40.516 | −25.689 | −23.191 | 1.00 | 22.87 | C |
| ATOM | 14187 | CE | LYS | B | 391 | −40.251 | −27.159 | −23.508 | 1.00 | 23.91 | C |
| ATOM | 14190 | NZ | LYS | B | 391 | −38.938 | −27.354 | −24.191 | 1.00 | 25.44 | N |
| ATOM | 14194 | C | LYS | B | 391 | −44.537 | −23.400 | −25.032 | 1.00 | 17.57 | C |
| ATOM | 14195 | O | LYS | B | 391 | −44.937 | −22.629 | −24.180 | 1.00 | 17.66 | O |
| ATOM | 14197 | N | SER | B | 392 | −44.490 | −23.068 | −26.314 | 1.00 | 16.65 | N |
| ATOM | 14198 | CA | SER | B | 392 | −44.879 | −21.718 | −26.764 | 1.00 | 16.27 | C |
| ATOM | 14200 | CB | SER | B | 392 | −44.241 | −21.375 | −28.119 | 1.00 | 16.22 | C |
| ATOM | 14203 | OG | SER | B | 392 | −44.937 | −21.969 | −29.207 | 1.00 | 15.94 | O |
| ATOM | 14205 | C | SER | B | 392 | −46.384 | −21.504 | −26.866 | 1.00 | 15.87 | C |
| ATOM | 14206 | O | SER | B | 392 | −46.825 | −20.395 | −27.093 | 1.00 | 15.56 | O |
| ATOM | 14208 | N | SER | B | 393 | −47.167 | −22.568 | −26.724 | 1.00 | 15.92 | N |
| ATOM | 14209 | CA | SER | B | 393 | −48.629 | −22.474 | −26.718 | 1.00 | 15.80 | C |
| ATOM | 14211 | CB | SER | B | 393 | −49.240 | −23.867 | −26.630 | 1.00 | 15.78 | C |
| ATOM | 14214 | OG | SER | B | 393 | −49.025 | −24.426 | −25.348 | 1.00 | 15.00 | O |
| ATOM | 14216 | C | SER | B | 393 | −49.097 | −21.646 | −25.533 | 1.00 | 15.94 | C |
| ATOM | 14217 | O | SER | B | 393 | −50.115 | −20.948 | −25.599 | 1.00 | 15.60 | O |
| ATOM | 14219 | N | SER | B | 394 | −48.296 | −21.740 | −24.471 | 1.00 | 16.14 | N |
| ATOM | 14220 | CA | SER | B | 394 | −48.487 | −21.091 | −23.177 | 1.00 | 16.31 | C |
| ATOM | 14222 | CB | SER | B | 394 | −49.062 | −19.662 | −23.271 | 1.00 | 16.18 | C |
| ATOM | 14225 | OG | SER | B | 394 | −50.472 | −19.649 | −23.358 | 1.00 | 16.57 | O |
| ATOM | 14227 | C | SER | B | 394 | −49.316 | −22.006 | −22.297 | 1.00 | 16.34 | C |
| ATOM | 14228 | O | SER | B | 394 | −49.822 | −21.595 | −21.261 | 1.00 | 16.47 | O |
| ATOM | 14230 | N | GLY | B | 395 | −49.403 | −23.268 | −22.702 | 1.00 | 16.55 | N |
| ATOM | 14231 | CA | GLY | B | 395 | −50.103 | −24.282 | −21.927 | 1.00 | 16.79 | C |
| ATOM | 14234 | C | GLY | B | 395 | −49.543 | −24.391 | −20.534 | 1.00 | 16.80 | C |
| ATOM | 14235 | O | GLY | B | 395 | −50.222 | −24.083 | −19.556 | 1.00 | 16.74 | O |
| ATOM | 14237 | N | PRO | B | 396 | −48.291 | −24.824 | −20.430 | 1.00 | 17.07 | N |
| ATOM | 14238 | CA | PRO | B | 396 | −47.698 | −24.930 | −19.103 | 1.00 | 17.18 | C |
| ATOM | 14240 | CB | PRO | B | 396 | −46.273 | −25.399 | −19.386 | 1.00 | 17.09 | C |
| ATOM | 14243 | CG | PRO | B | 396 | −46.087 | −25.237 | −20.874 | 1.00 | 17.77 | C |
| ATOM | 14246 | CD | PRO | B | 396 | −47.424 | −25.390 | −21.470 | 1.00 | 17.20 | C |
| ATOM | 14249 | C | PRO | B | 396 | −47.707 | −23.615 | −18.313 | 1.00 | 17.17 | C |
| ATOM | 14250 | O | PRO | B | 396 | −47.921 | −23.644 | −17.089 | 1.00 | 17.10 | O |

TABLE 16-7-continued

| | | | | | | | | | | | |
|---|---|---|---|---|---|---|---|---|---|---|---|
| colspan="12" | Coordinates of *P. tremuloides* IspS |

| | | | | | | | | | | | |
|---|---|---|---|---|---|---|---|---|---|---|---|
| ATOM | 14251 | N | LEU | B | 397 | −47.499 | −22.475 | −18.983 | 1.00 | 17.04 | N |
| ATOM | 14252 | CA | LEU | B | 397 | −47.513 | −21.183 | −18.261 | 1.00 | 16.77 | C |
| ATOM | 14254 | CB | LEU | B | 397 | −47.116 | −19.969 | −19.135 | 1.00 | 16.84 | C |
| ATOM | 14257 | CG | LEU | B | 397 | −47.145 | −18.576 | −18.458 | 1.00 | 16.91 | C |
| ATOM | 14259 | CD1 | LEU | B | 397 | −46.577 | −18.641 | −17.096 | 1.00 | 18.36 | C |
| ATOM | 14263 | CD2 | LEU | B | 397 | −46.373 | −17.515 | −19.196 | 1.00 | 16.88 | C |
| ATOM | 14267 | C | LEU | B | 397 | −48.894 | −20.988 | −17.682 | 1.00 | 16.24 | C |
| ATOM | 14268 | O | LEU | B | 397 | −49.051 | −20.710 | −16.494 | 1.00 | 16.09 | O |
| ATOM | 14270 | N | GLN | B | 398 | −49.902 | −21.173 | −18.515 | 1.00 | 15.72 | N |
| ATOM | 14271 | CA | GLN | B | 398 | −51.262 | −21.093 | −18.024 | 1.00 | 15.49 | C |
| ATOM | 14273 | CB | GLN | B | 398 | −52.267 | −21.387 | −19.120 | 1.00 | 15.51 | C |
| ATOM | 14276 | CG | GLN | B | 398 | −52.371 | −20.275 | −20.118 | 1.00 | 16.12 | C |
| ATOM | 14279 | CD | GLN | B | 398 | −53.436 | −20.545 | −21.114 | 1.00 | 17.86 | C |
| ATOM | 14280 | OE1 | GLN | B | 398 | −54.509 | −21.028 | −20.757 | 1.00 | 20.99 | O |
| ATOM | 14281 | NE2 | GLN | B | 398 | −53.170 | −20.239 | −22.374 | 1.00 | 18.31 | N |
| ATOM | 14284 | C | GLN | B | 398 | −51.471 | −22.040 | −16.873 | 1.00 | 15.03 | C |
| ATOM | 14285 | O | GLN | B | 398 | −51.974 | −21.638 | −15.843 | 1.00 | 15.21 | O |
| ATOM | 14287 | N | LEU | B | 399 | −51.065 | −23.291 | −17.022 | 1.00 | 14.72 | N |
| ATOM | 14288 | CA | LEU | B | 399 | −51.361 | −24.254 | −15.978 | 1.00 | 14.65 | C |
| ATOM | 14290 | CB | LEU | B | 399 | −51.201 | −25.688 | −16.475 | 1.00 | 14.44 | C |
| ATOM | 14293 | CG | LEU | B | 399 | −52.250 | −26.191 | −17.478 | 1.00 | 14.28 | C |
| ATOM | 14295 | CD1 | LEU | B | 399 | −51.907 | −27.633 | −17.846 | 1.00 | 15.50 | C |
| ATOM | 14299 | CD2 | LEU | B | 399 | −53.713 | −26.077 | −16.986 | 1.00 | 10.96 | C |
| ATOM | 14303 | C | LEU | B | 399 | −50.554 | −23.995 | −14.704 | 1.00 | 14.88 | C |
| ATOM | 14304 | O | LEU | B | 399 | −51.100 | −24.161 | −13.618 | 1.00 | 15.21 | O |
| ATOM | 14306 | N | ILE | B | 400 | −49.291 | −23.562 | −14.810 | 1.00 | 14.91 | N |
| ATOM | 14307 | CA | ILE | B | 400 | −48.532 | −23.174 | −13.607 | 1.00 | 14.89 | C |
| ATOM | 14309 | CB | ILE | B | 400 | −47.158 | −22.574 | −13.907 | 1.00 | 15.19 | C |
| ATOM | 14311 | CG1 | ILE | B | 400 | −46.189 | −23.674 | −14.353 | 1.00 | 16.76 | C |
| ATOM | 14314 | CD1 | ILE | B | 400 | −44.777 | −23.162 | −14.716 | 1.00 | 18.19 | C |
| ATOM | 14318 | CG2 | ILE | B | 400 | −46.603 | −21.906 | −12.665 | 1.00 | 13.65 | C |
| ATOM | 14322 | C | ILE | B | 400 | −49.288 | −22.137 | −12.819 | 1.00 | 14.77 | C |
| ATOM | 14323 | O | ILE | B | 400 | −49.485 | −22.302 | −11.632 | 1.00 | 15.36 | O |
| ATOM | 14325 | N | PHE | B | 401 | −49.717 | −21.071 | −13.486 | 1.00 | 14.59 | N |
| ATOM | 14326 | CA | PHE | B | 401 | −50.491 | −20.001 | −12.844 | 1.00 | 14.22 | C |
| ATOM | 14328 | CB | PHE | B | 401 | −50.825 | −18.900 | −13.845 | 1.00 | 14.12 | C |
| ATOM | 14331 | CG | PHE | B | 401 | −49.803 | −17.790 | −13.872 | 1.00 | 13.83 | C |
| ATOM | 14332 | CD1 | PHE | B | 401 | −50.012 | −16.623 | −13.173 | 1.00 | 12.77 | C |
| ATOM | 14334 | CE1 | PHE | B | 401 | −49.074 | −15.629 | −13.189 | 1.00 | 13.09 | C |
| ATOM | 14336 | CZ | PHE | B | 401 | −47.906 | −15.781 | −13.902 | 1.00 | 12.96 | C |
| ATOM | 14338 | CE2 | PHE | B | 401 | −47.684 | −16.928 | −14.592 | 1.00 | 12.86 | C |
| ATOM | 14340 | CD2 | PHE | B | 401 | −48.622 | −17.932 | −14.574 | 1.00 | 13.30 | C |
| ATOM | 14342 | C | PHE | B | 401 | −51.765 | −20.478 | −12.212 | 1.00 | 14.26 | C |
| ATOM | 14343 | O | PHE | B | 401 | −52.184 | −19.944 | −11.207 | 1.00 | 13.90 | O |
| ATOM | 14345 | N | ALA | B | 402 | −52.377 | −21.480 | −12.828 | 1.00 | 15.09 | N |
| ATOM | 14346 | CA | ALA | B | 402 | −53.641 | −22.054 | −12.364 | 1.00 | 15.76 | C |
| ATOM | 14348 | CB | ALA | B | 402 | −54.264 | −22.899 | −13.454 | 1.00 | 15.57 | C |
| ATOM | 14352 | C | ALA | B | 402 | −53.417 | −22.896 | −11.129 | 1.00 | 16.63 | C |
| ATOM | 14353 | O | ALA | B | 402 | −54.284 | −22.970 | −10.259 | 1.00 | 17.00 | O |
| ATOM | 14355 | N | TYR | B | 403 | −52.253 | −23.544 | −11.060 | 1.00 | 17.50 | N |
| ATOM | 14356 | CA | TYR | B | 403 | −51.885 | −24.317 | −9.894 | 1.00 | 17.86 | C |
| ATOM | 14358 | CB | TYR | B | 403 | −50.486 | −24.911 | −10.038 | 1.00 | 17.73 | C |
| ATOM | 14361 | CG | TYR | B | 403 | −50.006 | −25.576 | −8.764 | 1.00 | 18.24 | C |
| ATOM | 14362 | CD1 | TYR | B | 403 | −50.401 | −26.867 | −8.436 | 1.00 | 18.12 | C |
| ATOM | 14364 | CE1 | TYR | B | 403 | −49.971 | −27.476 | −7.273 | 1.00 | 18.07 | C |
| ATOM | 14366 | CZ | TYR | B | 403 | −49.145 | −26.790 | −6.409 | 1.00 | 18.62 | C |
| ATOM | 14367 | OH | TYR | B | 403 | −48.727 | −27.383 | −5.244 | 1.00 | 17.70 | O |
| ATOM | 14369 | CE2 | TYR | B | 403 | −48.748 | −25.499 | −6.703 | 1.00 | 18.93 | C |
| ATOM | 14371 | CD2 | TYR | B | 403 | −49.177 | −24.901 | −7.876 | 1.00 | 18.88 | C |
| ATOM | 14373 | C | TYR | B | 403 | −51.966 | −23.461 | −8.630 | 1.00 | 18.48 | C |
| ATOM | 14374 | O | TYR | B | 403 | −52.494 | −23.908 | −7.616 | 1.00 | 18.66 | O |
| ATOM | 14376 | N | PHE | B | 404 | −51.468 | −22.232 | −8.682 | 1.00 | 18.91 | N |
| ATOM | 14377 | CA | PHE | B | 404 | −51.400 | −21.430 | −7.468 | 1.00 | 19.53 | C |
| ATOM | 14379 | CB | PHE | B | 404 | −50.395 | −20.325 | −7.644 | 1.00 | 19.35 | C |
| ATOM | 14382 | CG | PHE | B | 404 | −49.014 | −20.808 | −7.799 | 1.00 | 18.79 | C |
| ATOM | 14383 | CD1 | PHE | B | 404 | −48.311 | −21.246 | −6.701 | 1.00 | 17.67 | C |
| ATOM | 14385 | CE1 | PHE | B | 404 | −47.001 | −21.683 | −6.832 | 1.00 | 18.44 | C |
| ATOM | 14387 | CZ | PHE | B | 404 | −46.384 | −21.688 | −8.078 | 1.00 | 18.44 | C |
| ATOM | 14389 | CE2 | PHE | B | 404 | −47.083 | −21.245 | −9.190 | 1.00 | 18.79 | C |
| ATOM | 14391 | CD2 | PHE | B | 404 | −48.396 | −20.805 | −9.047 | 1.00 | 18.90 | C |
| ATOM | 14393 | C | PHE | B | 404 | −52.733 | −20.817 | −7.072 | 1.00 | 20.49 | C |
| ATOM | 14394 | O | PHE | B | 404 | −52.925 | −20.389 | −5.924 | 1.00 | 19.95 | O |
| ATOM | 14396 | N | ALA | B | 405 | −53.636 | −20.756 | −8.043 | 1.00 | 21.92 | N |
| ATOM | 14397 | CA | ALA | B | 405 | −54.918 | −20.106 | −7.872 | 1.00 | 23.09 | C |
| ATOM | 14399 | CB | ALA | B | 405 | −55.333 | −19.426 | −9.167 | 1.00 | 23.15 | C |
| ATOM | 14403 | C | ALA | B | 405 | −55.959 | −21.113 | −7.446 | 1.00 | 24.23 | C |
| ATOM | 14404 | O | ALA | B | 405 | −57.003 | −20.726 | −6.925 | 1.00 | 24.33 | O |
| ATOM | 14406 | N | VAL | B | 406 | −55.657 | −22.399 | −7.662 | 1.00 | 25.80 | N |

TABLE 16-7-continued

Coordinates of *P. tremuloides* IspS

| ATOM | 14407 | CA | VAL | B | 406 | −56.569 | −23.511 | −7.355 | 1.00 | 26.88 | C |
|------|-------|-----|-----|---|-----|---------|---------|--------|------|-------|---|
| ATOM | 14409 | CB | VAL | B | 406 | −56.640 | −24.514 | −8.512 | 1.00 | 26.64 | C |
| ATOM | 14411 | CG1 | VAL | B | 406 | −57.132 | −25.854 | −8.012 | 1.00 | 27.24 | C |
| ATOM | 14415 | CG2 | VAL | B | 406 | −57.547 | −23.986 | −9.593 | 1.00 | 26.45 | C |
| ATOM | 14419 | C | VAL | B | 406 | −56.161 | −24.266 | −6.094 | 1.00 | 27.91 | C |
| ATOM | 14420 | O | VAL | B | 406 | −56.932 | −24.345 | −5.155 | 1.00 | 28.28 | O |
| ATOM | 14422 | N | VAL | B | 407 | −54.954 | −24.825 | −6.087 | 1.00 | 29.25 | N |
| ATOM | 14423 | CA | VAL | B | 407 | −54.443 | −25.573 | −4.941 | 1.00 | 30.16 | C |
| ATOM | 14425 | CB | VAL | B | 407 | −53.128 | −26.276 | −5.279 | 1.00 | 30.04 | C |
| ATOM | 14427 | CG1 | VAL | B | 407 | −52.482 | −26.831 | −4.032 | 1.00 | 30.42 | C |
| ATOM | 14431 | CG2 | VAL | B | 407 | −53.378 | −27.376 | −6.280 | 1.00 | 30.14 | C |
| ATOM | 14435 | C | VAL | B | 407 | −54.208 | −24.646 | −3.755 | 1.00 | 31.34 | C |
| ATOM | 14436 | O | VAL | B | 407 | −53.535 | −23.618 | −3.876 | 1.00 | 31.46 | O |
| ATOM | 14438 | N | GLN | B | 408 | −54.753 | −25.032 | −2.604 | 1.00 | 32.63 | N |
| ATOM | 14439 | CA | GLN | B | 408 | −54.727 | −24.191 | −1.417 | 1.00 | 33.51 | C |
| ATOM | 14441 | CB | GLN | B | 408 | −55.891 | −24.572 | −.514 | 1.00 | 33.84 | C |
| ATOM | 14444 | CG | GLN | B | 408 | −56.161 | −23.548 | .577 | 1.00 | 35.49 | C |
| ATOM | 14447 | CD | GLN | B | 408 | −57.623 | −23.161 | .656 | 1.00 | 37.61 | C |
| ATOM | 14448 | OE1 | GLN | B | 408 | −58.519 | −24.006 | .501 | 1.00 | 38.23 | O |
| ATOM | 14449 | NE2 | GLN | B | 408 | −57.876 | −21.874 | .893 | 1.00 | 38.64 | N |
| ATOM | 14452 | C | GLN | B | 408 | −53.399 | −24.274 | −.647 | 1.00 | 33.72 | C |
| ATOM | 14453 | O | GLN | B | 408 | −52.852 | −23.253 | −.204 | 1.00 | 33.52 | O |
| ATOM | 14455 | N | ASN | B | 409 | −52.889 | −25.491 | −.490 | 1.00 | 33.95 | N |
| ATOM | 14456 | CA | ASN | B | 409 | −51.642 | −25.707 | .226 | 1.00 | 34.16 | C |
| ATOM | 14458 | CB | ASN | B | 409 | −51.865 | −26.665 | 1.391 | 1.00 | 34.25 | C |
| ATOM | 14461 | CG | ASN | B | 409 | −52.756 | −26.069 | 2.459 | 1.00 | 34.39 | C |
| ATOM | 14462 | OD1 | ASN | B | 409 | −52.269 | −25.577 | 3.480 | 1.00 | 34.40 | O |
| ATOM | 14463 | ND2 | ASN | B | 409 | −54.070 | −26.089 | 2.222 | 1.00 | 34.12 | N |
| ATOM | 14466 | C | ASN | B | 409 | −50.582 | −26.244 | −.709 | 1.00 | 34.12 | C |
| ATOM | 14467 | O | ASN | B | 409 | −50.578 | −27.422 | −1.046 | 1.00 | 34.41 | O |
| ATOM | 14469 | N | ILE | B | 410 | −49.681 | −25.369 | −1.127 | 1.00 | 34.07 | N |
| ATOM | 14470 | CA | ILE | B | 410 | −48.699 | −25.718 | −2.138 | 1.00 | 34.08 | C |
| ATOM | 14472 | CB | ILE | B | 410 | −48.138 | −24.455 | −2.840 | 1.00 | 34.15 | C |
| ATOM | 14474 | CG1 | ILE | B | 410 | −47.274 | −23.610 | −1.891 | 1.00 | 34.26 | C |
| ATOM | 14477 | CD1 | ILE | B | 410 | −47.216 | −22.139 | −2.249 | 1.00 | 34.10 | C |
| ATOM | 14481 | CG2 | ILE | B | 410 | −49.290 | −23.634 | −3.404 | 1.00 | 34.49 | C |
| ATOM | 14485 | C | ILE | B | 410 | −47.586 | −26.553 | −1.533 | 1.00 | 33.93 | C |
| ATOM | 14486 | O | ILE | B | 410 | −47.181 | −26.317 | −.405 | 1.00 | 33.80 | O |
| ATOM | 14488 | N | LYS | B | 411 | −47.123 | −27.546 | −2.285 | 1.00 | 34.12 | N |
| ATOM | 14489 | CA | LYS | B | 411 | −46.012 | −28.395 | −1.874 | 1.00 | 34.45 | C |
| ATOM | 14491 | CB | LYS | B | 411 | −46.414 | −29.873 | −1.907 | 1.00 | 34.67 | C |
| ATOM | 14494 | CG | LYS | B | 411 | −47.850 | −30.130 | −1.460 | 1.00 | 35.79 | C |
| ATOM | 14497 | CD | LYS | B | 411 | −48.102 | −31.586 | −1.052 | 1.00 | 37.60 | C |
| ATOM | 14500 | CE | LYS | B | 411 | −49.450 | −31.728 | −.309 | 1.00 | 38.80 | C |
| ATOM | 14503 | NZ | LYS | B | 411 | −49.568 | −32.992 | .488 | 1.00 | 39.20 | N |
| ATOM | 14507 | C | LYS | B | 411 | −44.843 | −28.132 | −2.810 | 1.00 | 34.33 | C |
| ATOM | 14508 | O | LYS | B | 411 | −45.038 | −27.956 | −4.006 | 1.00 | 34.14 | O |
| ATOM | 14510 | N | LYS | B | 412 | −43.631 | −28.102 | −2.265 | 1.00 | 34.50 | N |
| ATOM | 14511 | CA | LYS | B | 412 | −42.460 | −27.688 | −3.042 | 1.00 | 34.69 | C |
| ATOM | 14513 | CB | LYS | B | 412 | −41.242 | −27.398 | −2.154 | 1.00 | 35.13 | C |
| ATOM | 14516 | CG | LYS | B | 412 | −41.205 | −25.960 | −1.613 | 1.00 | 36.90 | C |
| ATOM | 14519 | CD | LYS | B | 412 | −40.079 | −25.749 | −.588 | 1.00 | 38.57 | C |
| ATOM | 14522 | CE | LYS | B | 412 | −40.546 | −24.852 | .555 | 1.00 | 39.55 | C |
| ATOM | 14525 | NZ | LYS | B | 412 | −39.491 | −24.644 | 1.587 | 1.00 | 40.83 | N |
| ATOM | 14529 | C | LYS | B | 412 | −42.075 | −28.687 | −4.103 | 1.00 | 34.13 | C |
| ATOM | 14530 | O | LYS | B | 412 | −41.468 | −28.308 | −5.093 | 1.00 | 34.21 | O |
| ATOM | 14532 | N | GLU | B | 413 | −42.408 | −29.958 | −3.910 | 1.00 | 33.54 | N |
| ATOM | 14533 | CA | GLU | B | 413 | −42.095 | −30.949 | −4.933 | 1.00 | 33.19 | C |
| ATOM | 14535 | CB | GLU | B | 413 | −41.886 | −32.335 | −4.330 | 1.00 | 33.44 | C |
| ATOM | 14538 | CG | GLU | B | 413 | −43.127 | −33.037 | −3.807 | 1.00 | 34.37 | C |
| ATOM | 14541 | CD | GLU | B | 413 | −42.834 | −34.490 | −3.499 | 1.00 | 35.56 | C |
| ATOM | 14542 | OE1 | GLU | B | 413 | −42.662 | −35.264 | −4.471 | 1.00 | 35.30 | O |
| ATOM | 14543 | OE2 | GLU | B | 413 | −42.751 | −34.847 | −2.297 | 1.00 | 36.69 | O |
| ATOM | 14544 | C | GLU | B | 413 | −43.157 | −30.965 | −6.029 | 1.00 | 32.47 | C |
| ATOM | 14545 | O | GLU | B | 413 | −42.846 | −31.232 | −7.193 | 1.00 | 32.28 | O |
| ATOM | 14547 | N | GLU | B | 414 | −44.403 | −30.676 | −5.652 | 1.00 | 31.58 | N |
| ATOM | 14548 | CA | GLU | B | 414 | −45.482 | −30.512 | −6.614 | 1.00 | 30.99 | C |
| ATOM | 14550 | CB | GLU | B | 414 | −46.781 | −30.101 | −5.927 | 1.00 | 30.98 | C |
| ATOM | 14553 | CG | GLU | B | 414 | −47.732 | −31.245 | −5.642 | 1.00 | 31.82 | C |
| ATOM | 14556 | CD | GLU | B | 414 | −49.100 | −30.774 | −5.138 | 1.00 | 34.29 | C |
| ATOM | 14557 | OE1 | GLU | B | 414 | −49.258 | −29.581 | −4.777 | 1.00 | 35.53 | O |
| ATOM | 14558 | OE2 | GLU | B | 414 | −50.036 | −31.603 | −5.101 | 1.00 | 36.44 | O |
| ATOM | 14559 | C | GLU | B | 414 | −45.104 | −29.455 | −7.628 | 1.00 | 30.59 | C |
| ATOM | 14560 | O | GLU | B | 414 | −45.169 | −29.687 | −8.828 | 1.00 | 30.37 | O |
| ATOM | 14562 | N | ILE | B | 415 | −44.684 | −28.295 | −7.140 | 1.00 | 30.49 | N |
| ATOM | 14563 | CA | ILE | B | 415 | −44.367 | −27.177 | −8.028 | 1.00 | 30.40 | C |
| ATOM | 14565 | CB | ILE | B | 415 | −44.412 | −25.797 | −7.320 | 1.00 | 30.40 | C |
| ATOM | 14567 | CG1 | ILE | B | 415 | −43.235 | −25.589 | −6.388 | 1.00 | 30.36 | C |

TABLE 16-7-continued

Coordinates of *P. tremuloides* IspS

| ATOM | 14570 | CD1 | ILE | B | 415 | −43.373 | −24.313 | −5.611 | 1.00 | 31.01 | C |
|---|---|---|---|---|---|---|---|---|---|---|---|
| ATOM | 14574 | CG2 | ILE | B | 415 | −45.686 | −25.644 | −6.523 | 1.00 | 30.85 | C |
| ATOM | 14578 | C | ILE | B | 415 | −43.037 | −27.347 | −8.730 | 1.00 | 30.12 | C |
| ATOM | 14579 | O | ILE | B | 415 | −42.870 | −26.865 | −9.840 | 1.00 | 30.42 | O |
| ATOM | 14581 | N | GLU | B | 416 | −42.095 | −28.030 | −8.099 | 1.00 | 29.75 | N |
| ATOM | 14582 | CA | GLU | B | 416 | −40.799 | −28.249 | −8.719 | 1.00 | 29.70 | C |
| ATOM | 14584 | CB | GLU | B | 416 | −39.825 | −28.777 | −7.690 | 1.00 | 30.02 | C |
| ATOM | 14587 | CG | GLU | B | 416 | −38.386 | −28.426 | −7.948 | 1.00 | 31.20 | C |
| ATOM | 14590 | CD | GLU | B | 416 | −37.523 | −28.839 | −6.776 | 1.00 | 32.91 | C |
| ATOM | 14591 | OE1 | GLU | B | 416 | −38.008 | −28.723 | −5.632 | 1.00 | 32.37 | O |
| ATOM | 14592 | OE2 | GLU | B | 416 | −36.377 | −29.294 | −6.994 | 1.00 | 35.31 | O |
| ATOM | 14593 | C | GLU | B | 416 | −40.917 | −29.222 | −9.890 | 1.00 | 29.24 | C |
| ATOM | 14594 | O | GLU | B | 416 | −40.121 | −29.177 | −10.835 | 1.00 | 28.86 | O |
| ATOM | 14596 | N | ASN | B | 417 | −41.915 | −30.097 | −9.819 | 1.00 | 28.81 | N |
| ATOM | 14597 | CA | ASN | B | 417 | −42.252 | −30.960 | −10.941 | 1.00 | 28.66 | C |
| ATOM | 14599 | CB | ASN | B | 417 | −43.165 | −32.105 | −10.503 | 1.00 | 28.72 | C |
| ATOM | 14602 | CG | ASN | B | 417 | −42.379 | −33.285 | −9.973 | 1.00 | 29.78 | C |
| ATOM | 14603 | OD1 | ASN | B | 417 | −41.887 | −34.108 | −10.744 | 1.00 | 30.39 | O |
| ATOM | 14604 | ND2 | ASN | B | 417 | −42.223 | −33.358 | −8.653 | 1.00 | 31.45 | N |
| ATOM | 14607 | C | ASN | B | 417 | −42.888 | −30.183 | −12.067 | 1.00 | 28.32 | C |
| ATOM | 14608 | O | ASN | B | 417 | −42.611 | −30.456 | −13.232 | 1.00 | 27.95 | O |
| ATOM | 14610 | N | LEU | B | 418 | −43.740 | −29.217 | −11.713 | 1.00 | 28.23 | N |
| ATOM | 14611 | CA | LEU | B | 418 | −44.349 | −28.313 | −12.697 | 1.00 | 27.92 | C |
| ATOM | 14613 | CB | LEU | B | 418 | −45.298 | −27.320 | −12.023 | 1.00 | 27.48 | C |
| ATOM | 14616 | CG | LEU | B | 418 | −46.636 | −27.896 | −11.553 | 1.00 | 27.02 | C |
| ATOM | 14618 | CD1 | LEU | B | 418 | −47.393 | −26.882 | −10.691 | 1.00 | 26.70 | C |
| ATOM | 14622 | CD2 | LEU | B | 418 | −47.499 | −28.355 | −12.720 | 1.00 | 25.90 | C |
| ATOM | 14626 | C | LEU | B | 418 | −43.275 | −27.567 | −13.491 | 1.00 | 28.20 | C |
| ATOM | 14627 | O | LEU | B | 418 | −43.310 | −27.541 | −14.733 | 1.00 | 27.90 | O |
| ATOM | 14629 | N | GLN | B | 419 | −42.308 | −26.995 | −12.770 | 1.00 | 28.43 | N |
| ATOM | 14630 | CA | GLN | B | 419 | −41.170 | −26.315 | −13.395 | 1.00 | 28.72 | C |
| ATOM | 14632 | CB | GLN | B | 419 | −40.223 | −25.746 | −12.347 | 1.00 | 28.81 | C |
| ATOM | 14635 | CG | GLN | B | 419 | −40.592 | −24.332 | −11.946 | 1.00 | 30.14 | C |
| ATOM | 14638 | CD | GLN | B | 419 | −39.535 | −23.671 | −11.092 | 1.00 | 32.05 | C |
| ATOM | 14639 | OE1 | GLN | B | 419 | −39.246 | −22.477 | −11.257 | 1.00 | 33.88 | O |
| ATOM | 14640 | NE2 | GLN | B | 419 | −38.948 | −24.437 | −10.170 | 1.00 | 31.84 | N |
| ATOM | 14643 | C | GLN | B | 419 | −40.390 | −27.179 | −14.370 | 1.00 | 28.83 | C |
| ATOM | 14644 | O | GLN | B | 419 | −39.922 | −26.668 | −15.386 | 1.00 | 28.72 | O |
| ATOM | 14646 | N | LYS | B | 420 | −40.265 | −28.475 | −14.067 | 1.00 | 29.21 | N |
| ATOM | 14647 | CA | LYS | B | 420 | −39.613 | −29.451 | −14.968 | 1.00 | 29.26 | C |
| ATOM | 14649 | CB | LYS | B | 420 | −38.924 | −30.555 | −14.143 | 1.00 | 29.42 | C |
| ATOM | 14652 | CG | LYS | B | 420 | −37.800 | −30.052 | −13.207 | 1.00 | 30.58 | C |
| ATOM | 14655 | CD | LYS | B | 420 | −37.373 | −31.113 | −12.151 | 1.00 | 32.35 | C |
| ATOM | 14658 | CE | LYS | B | 420 | −36.572 | −30.506 | −10.955 | 1.00 | 33.05 | C |
| ATOM | 14661 | NZ | LYS | B | 420 | −36.520 | −31.368 | −9.702 | 1.00 | 32.62 | N |
| ATOM | 14665 | C | LYS | B | 420 | −40.579 | −30.057 | −16.021 | 1.00 | 28.96 | C |
| ATOM | 14666 | O | LYS | B | 420 | −40.216 | −30.965 | −16.753 | 1.00 | 28.66 | O |
| ATOM | 14668 | N | TYR | B | 421 | −41.804 | −29.543 | −16.088 | 1.00 | 29.01 | N |
| ATOM | 14669 | CA | TYR | B | 421 | −42.777 | −29.893 | −17.134 | 1.00 | 29.16 | C |
| ATOM | 14671 | CB | TYR | B | 421 | −42.209 | −29.602 | −18.534 | 1.00 | 29.48 | C |
| ATOM | 14674 | CG | TYR | B | 421 | −41.968 | −28.127 | −18.773 | 1.00 | 31.04 | C |
| ATOM | 14675 | CD1 | TYR | B | 421 | −43.018 | −27.219 | −18.716 | 1.00 | 32.54 | C |
| ATOM | 14677 | CE1 | TYR | B | 421 | −42.815 | −25.878 | −18.914 | 1.00 | 33.35 | C |
| ATOM | 14679 | CZ | TYR | B | 421 | −41.556 | −25.413 | −19.193 | 1.00 | 34.56 | C |
| ATOM | 14680 | OH | TYR | B | 421 | −41.377 | −24.066 | −19.384 | 1.00 | 37.99 | O |
| ATOM | 14682 | CE2 | TYR | B | 421 | −40.490 | −26.278 | −19.267 | 1.00 | 33.56 | C |
| ATOM | 14684 | CD2 | TYR | B | 421 | −40.702 | −27.638 | −19.051 | 1.00 | 32.75 | C |
| ATOM | 14686 | C | TYR | B | 421 | −43.345 | −31.311 | −17.042 | 1.00 | 28.60 | C |
| ATOM | 14687 | O | TYR | B | 421 | −43.395 | −32.046 | −18.025 | 1.00 | 28.49 | O |
| ATOM | 14689 | N | HIS | B | 422 | −43.808 | −31.662 | −15.846 | 1.00 | 28.18 | N |
| ATOM | 14690 | CA | HIS | B | 422 | −44.507 | −32.919 | −15.594 | 1.00 | 27.66 | C |
| ATOM | 14692 | CB | HIS | B | 422 | −45.082 | −32.914 | −14.180 | 1.00 | 27.73 | C |
| ATOM | 14695 | CG | HIS | B | 422 | −45.500 | −34.264 | −13.685 | 1.00 | 28.14 | C |
| ATOM | 14696 | ND1 | HIS | B | 422 | −44.597 | −35.195 | −13.217 | 1.00 | 29.15 | N |
| ATOM | 14698 | CE1 | HIS | B | 422 | −45.247 | −36.277 | −12.829 | 1.00 | 29.50 | C |
| ATOM | 14700 | NE2 | HIS | B | 422 | −46.539 | −36.078 | −13.022 | 1.00 | 28.69 | N |
| ATOM | 14702 | CD2 | HIS | B | 422 | −46.724 | −34.827 | −13.552 | 1.00 | 27.24 | C |
| ATOM | 14704 | C | HIS | B | 422 | −45.650 | −33.164 | −16.575 | 1.00 | 27.29 | C |
| ATOM | 14705 | O | HIS | B | 422 | −46.463 | −32.269 | −16.853 | 1.00 | 26.86 | O |
| ATOM | 14707 | N | ASP | B | 423 | −45.712 | −34.402 | −17.060 | 1.00 | 26.96 | N |
| ATOM | 14708 | CA | ASP | B | 423 | −46.772 | −34.883 | −17.952 | 1.00 | 26.78 | C |
| ATOM | 14710 | CB | ASP | B | 423 | −46.792 | −36.413 | −17.939 | 1.00 | 27.01 | C |
| ATOM | 14713 | CG | ASP | B | 423 | −45.594 | −37.018 | −18.646 | 1.00 | 28.21 | C |
| ATOM | 14714 | OD1 | ASP | B | 423 | −45.100 | −36.378 | −19.602 | 1.00 | 31.33 | O |
| ATOM | 14715 | OD2 | ASP | B | 423 | −45.153 | −38.130 | −18.262 | 1.00 | 28.39 | O |
| ATOM | 14716 | C | ASP | B | 423 | −48.187 | −34.383 | −17.651 | 1.00 | 26.21 | C |
| ATOM | 14717 | O | ASP | B | 423 | −49.015 | −34.336 | −18.556 | 1.00 | 26.75 | O |
| ATOM | 14719 | N | ILE | B | 424 | −48.463 | −34.042 | −16.391 | 1.00 | 25.11 | N |

TABLE 16-7-continued

Coordinates of *P. tremuloides* IspS

| ATOM | 14720 | CA | ILE | B | 424 | −49.773 | −33.553 | −15.956 | 1.00 | 23.82 | C |
|------|-------|-----|-----|---|-----|---------|---------|---------|------|-------|---|
| ATOM | 14722 | CB | ILE | B | 424 | −49.798 | −33.310 | −14.439 | 1.00 | 23.67 | C |
| ATOM | 14724 | CG1 | ILE | B | 424 | −51.196 | −32.990 | −13.938 | 1.00 | 22.97 | C |
| ATOM | 14727 | CD1 | ILE | B | 424 | −51.220 | −32.693 | −12.465 | 1.00 | 22.06 | C |
| ATOM | 14731 | CG2 | ILE | B | 424 | −48.859 | −32.171 | −14.065 | 1.00 | 24.35 | C |
| ATOM | 14735 | C | ILE | B | 424 | −50.102 | −32.265 | −16.669 | 1.00 | 23.08 | C |
| ATOM | 14736 | O | ILE | B | 424 | −51.265 | −32.025 | −17.023 | 1.00 | 22.99 | O |
| ATOM | 14738 | N | ILE | B | 425 | −49.082 | −31.436 | −16.886 | 1.00 | 22.22 | N |
| ATOM | 14739 | CA | ILE | B | 425 | −49.282 | −30.199 | −17.633 | 1.00 | 21.61 | C |
| ATOM | 14741 | CB | ILE | B | 425 | −48.796 | −28.959 | −16.848 | 1.00 | 21.18 | C |
| ATOM | 14743 | CG1 | ILE | B | 425 | −47.279 | −28.853 | −16.804 | 1.00 | 19.47 | C |
| ATOM | 14746 | CD1 | ILE | B | 425 | −46.850 | −27.581 | −16.140 | 1.00 | 18.00 | C |
| ATOM | 14750 | CG2 | ILE | B | 425 | −49.357 | −28.977 | −15.428 | 1.00 | 20.75 | C |
| ATOM | 14754 | C | ILE | B | 425 | −48.665 | −30.255 | −19.033 | 1.00 | 21.73 | C |
| ATOM | 14755 | O | ILE | B | 425 | −49.100 | −29.523 | −19.912 | 1.00 | 21.75 | O |
| ATOM | 14757 | N | SER | B | 426 | −47.686 | −31.134 | −19.258 | 1.00 | 21.74 | N |
| ATOM | 14758 | CA | SER | B | 426 | −47.016 | −31.174 | −20.560 | 1.00 | 21.53 | C |
| ATOM | 14760 | CB | SER | B | 426 | −45.639 | −31.876 | −20.516 | 1.00 | 21.66 | C |
| ATOM | 14763 | OG | SER | B | 426 | −45.724 | −33.281 | −20.405 | 1.00 | 22.19 | O |
| ATOM | 14765 | C | SER | B | 426 | −47.922 | −31.798 | −21.582 | 1.00 | 21.19 | C |
| ATOM | 14766 | O | SER | B | 426 | −47.950 | −31.358 | −22.721 | 1.00 | 21.37 | O |
| ATOM | 14768 | N | ARG | B | 427 | −48.692 | −32.800 | −21.177 | 1.00 | 20.91 | N |
| ATOM | 14769 | CA | ARG | B | 427 | −49.532 | −33.504 | −22.143 | 1.00 | 20.78 | C |
| ATOM | 14771 | CB | ARG | B | 427 | −50.038 | −34.840 | −21.616 | 1.00 | 20.94 | C |
| ATOM | 14774 | CG | ARG | B | 427 | −49.006 | −35.887 | −21.874 | 1.00 | 22.76 | C |
| ATOM | 14777 | CD | ARG | B | 427 | −49.158 | −37.101 | −21.025 | 1.00 | 26.75 | C |
| ATOM | 14780 | NE | ARG | B | 427 | −47.960 | −37.927 | −21.185 | 1.00 | 29.36 | N |
| ATOM | 14782 | CZ | ARG | B | 427 | −47.574 | −38.887 | −20.352 | 1.00 | 30.25 | C |
| ATOM | 14783 | NH1 | ARG | B | 427 | −48.293 | −39.179 | −19.266 | 1.00 | 30.27 | N |
| ATOM | 14786 | NH2 | ARG | B | 427 | −46.447 | −39.547 | −20.611 | 1.00 | 31.25 | N |
| ATOM | 14789 | C | ARG | B | 427 | −50.646 | −32.650 | −22.668 | 1.00 | 20.07 | C |
| ATOM | 14790 | O | ARG | B | 427 | −50.724 | −32.466 | −23.866 | 1.00 | 20.13 | O |
| ATOM | 14792 | N | PRO | B | 428 | −51.482 | −32.091 | −21.786 | 1.00 | 19.38 | N |
| ATOM | 14793 | CA | PRO | B | 428 | −52.533 | −31.202 | −22.264 | 1.00 | 19.05 | C |
| ATOM | 14795 | CB | PRO | B | 428 | −53.046 | −30.547 | −20.990 | 1.00 | 19.13 | C |
| ATOM | 14798 | CG | PRO | B | 428 | −52.696 | −31.476 | −19.918 | 1.00 | 19.55 | C |
| ATOM | 14801 | CD | PRO | B | 428 | −51.443 | −32.161 | −20.319 | 1.00 | 19.20 | C |
| ATOM | 14804 | C | PRO | B | 428 | −52.016 | −30.135 | −23.227 | 1.00 | 18.84 | C |
| ATOM | 14805 | O | PRO | B | 428 | −52.688 | −29.802 | −24.205 | 1.00 | 18.73 | O |
| ATOM | 14806 | N | SER | B | 429 | −50.828 | −29.608 | −22.964 | 1.00 | 18.57 | N |
| ATOM | 14807 | CA | SER | B | 429 | −50.208 | −28.679 | −23.899 | 1.00 | 18.64 | C |
| ATOM | 14809 | CB | SER | B | 429 | −48.960 | −28.086 | −23.291 | 1.00 | 18.46 | C |
| ATOM | 14812 | OG | SER | B | 429 | −49.141 | −27.980 | −21.911 | 1.00 | 19.08 | O |
| ATOM | 14814 | C | SER | B | 429 | −49.877 | −29.315 | −25.260 | 1.00 | 18.52 | C |
| ATOM | 14815 | O | SER | B | 429 | −49.886 | −28.633 | −26.276 | 1.00 | 19.02 | O |
| ATOM | 14817 | N | HIS | B | 430 | −49.579 | −30.606 | −25.297 | 1.00 | 18.29 | N |
| ATOM | 14818 | CA | HIS | B | 430 | −49.457 | −31.273 | −26.583 | 1.00 | 18.25 | C |
| ATOM | 14820 | CB | HIS | B | 430 | −49.085 | −32.765 | −26.467 | 1.00 | 18.40 | C |
| ATOM | 14823 | CG | HIS | B | 430 | −47.753 | −33.024 | −25.806 | 1.00 | 19.41 | C |
| ATOM | 14824 | ND1 | HIS | B | 430 | −46.776 | −32.055 | −25.657 | 1.00 | 19.55 | N |
| ATOM | 14826 | CE1 | HIS | B | 430 | −45.729 | −32.576 | −25.043 | 1.00 | 17.77 | C |
| ATOM | 14828 | NE2 | HIS | B | 430 | −45.981 | −33.849 | −24.800 | 1.00 | 18.52 | N |
| ATOM | 14830 | CD2 | HIS | B | 430 | −47.232 | −34.160 | −25.277 | 1.00 | 19.19 | C |
| ATOM | 14832 | C | HIS | B | 430 | −50.789 | −31.105 | −27.306 | 1.00 | 17.93 | C |
| ATOM | 14833 | O | HIS | B | 430 | −50.816 | −30.599 | −28.417 | 1.00 | 18.54 | O |
| ATOM | 14835 | N | ILE | B | 431 | −51.897 | −31.479 | −26.665 | 1.00 | 17.34 | N |
| ATOM | 14836 | CA | ILE | B | 431 | −53.217 | −31.372 | −27.301 | 1.00 | 16.58 | C |
| ATOM | 14838 | CB | ILE | B | 431 | −54.400 | −31.738 | −26.375 | 1.00 | 16.53 | C |
| ATOM | 14840 | CG1 | ILE | B | 431 | −54.225 | −33.123 | −25.728 | 1.00 | 16.06 | C |
| ATOM | 14843 | CD1 | ILE | B | 431 | −54.069 | −34.212 | −26.698 | 1.00 | 16.05 | C |
| ATOM | 14847 | CG2 | ILE | B | 431 | −55.701 | −31.666 | −27.149 | 1.00 | 15.49 | C |
| ATOM | 14851 | C | ILE | B | 431 | −53.431 | −29.949 | −27.748 | 1.00 | 16.35 | C |
| ATOM | 14852 | O | ILE | B | 431 | −53.856 | −29.712 | −28.860 | 1.00 | 16.74 | O |
| ATOM | 14854 | N | PHE | B | 432 | −53.110 | −29.003 | −26.881 | 1.00 | 16.15 | N |
| ATOM | 14855 | CA | PHE | B | 432 | −53.353 | −27.577 | −27.145 | 1.00 | 16.19 | C |
| ATOM | 14857 | CB | PHE | B | 432 | −52.811 | −26.776 | −25.956 | 1.00 | 16.36 | C |
| ATOM | 14860 | CG | PHE | B | 432 | −53.007 | −25.295 | −26.043 | 1.00 | 16.54 | C |
| ATOM | 14861 | CD1 | PHE | B | 432 | −53.869 | −24.708 | −26.946 | 1.00 | 16.55 | C |
| ATOM | 14863 | CE1 | PHE | B | 432 | −54.007 | −23.334 | −26.974 | 1.00 | 17.89 | C |
| ATOM | 14865 | CZ | PHE | B | 432 | −53.305 | −22.538 | −26.080 | 1.00 | 17.96 | C |
| ATOM | 14867 | CE2 | PHE | B | 432 | −52.461 | −23.114 | −25.169 | 1.00 | 17.30 | C |
| ATOM | 14869 | CD2 | PHE | B | 432 | −52.323 | −24.482 | −25.151 | 1.00 | 17.54 | C |
| ATOM | 14871 | C | PHE | B | 432 | −52.726 | −27.104 | −28.452 | 1.00 | 15.93 | C |
| ATOM | 14872 | O | PHE | B | 432 | −53.398 | −26.525 | −29.303 | 1.00 | 15.63 | O |
| ATOM | 14874 | N | ARG | B | 433 | −51.438 | −27.387 | −28.594 | 1.00 | 15.79 | N |
| ATOM | 14875 | CA | ARG | B | 433 | −50.674 | −27.044 | −29.778 | 1.00 | 15.74 | C |
| ATOM | 14877 | CB | ARG | B | 433 | −49.196 | −27.279 | −29.470 | 1.00 | 15.68 | C |
| ATOM | 14880 | CG | ARG | B | 433 | −48.259 | −27.218 | −30.665 | 1.00 | 16.39 | C |

TABLE 16-7-continued

Coordinates of *P. tremuloides* IspS

| ATOM | 14883 | CD | ARG | B | 433 | −48.348 | −25.919 | −31.388 | 1.00 | 16.27 | C |
| --- | --- | --- | --- | --- | --- | --- | --- | --- | --- | --- | --- |
| ATOM | 14886 | NE | ARG | B | 433 | −47.969 | −24.850 | −30.492 | 1.00 | 17.34 | N |
| ATOM | 14888 | CZ | ARG | B | 433 | −48.210 | −23.565 | −30.703 | 1.00 | 17.89 | C |
| ATOM | 14889 | NH1 | ARG | B | 433 | −48.834 | −23.142 | −31.803 | 1.00 | 16.79 | N |
| ATOM | 14892 | NH2 | ARG | B | 433 | −47.805 | −22.701 | −29.792 | 1.00 | 18.53 | N |
| ATOM | 14895 | C | ARG | B | 433 | −51.114 | −27.852 | −31.011 | 1.00 | 15.85 | C |
| ATOM | 14896 | O | ARG | B | 433 | −51.197 | −27.328 | −32.120 | 1.00 | 15.40 | O |
| ATOM | 14898 | N | LEU | B | 434 | −51.381 | −29.134 | −30.813 | 1.00 | 16.18 | N |
| ATOM | 14899 | CA | LEU | B | 434 | −51.794 | −29.986 | −31.902 | 1.00 | 16.58 | C |
| ATOM | 14901 | CB | LEU | B | 434 | −51.802 | −31.453 | −31.468 | 1.00 | 16.79 | C |
| ATOM | 14904 | CG | LEU | B | 434 | −50.408 | −32.055 | −31.232 | 1.00 | 17.49 | C |
| ATOM | 14906 | CD1 | LEU | B | 434 | −50.486 | −33.548 | −30.864 | 1.00 | 16.63 | C |
| ATOM | 14910 | CD2 | LEU | B | 434 | −49.511 | −31.836 | −32.467 | 1.00 | 18.00 | C |
| ATOM | 14914 | C | LEU | B | 434 | −53.158 | −29.559 | −32.423 | 1.00 | 17.07 | C |
| ATOM | 14915 | O | LEU | B | 434 | −53.333 | −29.442 | −33.633 | 1.00 | 17.44 | O |
| ATOM | 14917 | N | CYS | B | 435 | −54.118 | −29.308 | −31.532 | 1.00 | 17.23 | N |
| ATOM | 14918 | CA | CYS | B | 435 | −55.419 | −28.778 | −31.947 | 1.00 | 17.44 | C |
| ATOM | 14920 | CB | CYS | B | 435 | −56.301 | −28.529 | −30.746 | 1.00 | 17.38 | C |
| ATOM | 14923 | SG | CYS | B | 435 | −56.825 | −29.993 | −29.971 | 1.00 | 17.90 | S |
| ATOM | 14925 | C | CYS | B | 435 | −55.295 | −27.460 | −32.696 | 1.00 | 17.78 | C |
| ATOM | 14926 | O | CYS | B | 435 | −55.978 | −27.232 | −33.701 | 1.00 | 17.44 | O |
| ATOM | 14928 | N | ASN | B | 436 | −54.442 | −26.585 | −32.178 | 1.00 | 18.31 | N |
| ATOM | 14929 | CA | ASN | B | 436 | −54.248 | −25.267 | −32.769 | 1.00 | 19.14 | C |
| ATOM | 14931 | CB | ASN | B | 436 | −53.392 | −24.394 | −31.844 | 1.00 | 19.31 | C |
| ATOM | 14934 | CG | ASN | B | 436 | −52.984 | −23.068 | −32.478 | 1.00 | 20.07 | C |
| ATOM | 14935 | OD1 | ASN | B | 436 | −53.456 | −22.686 | −33.555 | 1.00 | 22.72 | O |
| ATOM | 14936 | ND2 | ASN | B | 436 | −52.099 | −22.356 | −31.800 | 1.00 | 20.90 | N |
| ATOM | 14939 | C | ASN | B | 436 | −53.615 | −25.345 | −34.157 | 1.00 | 19.51 | C |
| ATOM | 14940 | O | ASN | B | 436 | −54.173 | −24.840 | −35.131 | 1.00 | 19.79 | O |
| ATOM | 14942 | N | ASP | B | 437 | −52.446 | −25.965 | −34.245 | 1.00 | 19.85 | N |
| ATOM | 14943 | CA | ASP | B | 437 | −51.754 | −26.058 | −35.517 | 1.00 | 20.01 | C |
| ATOM | 14945 | CB | ASP | B | 437 | −50.340 | −26.638 | −35.331 | 1.00 | 20.00 | C |
| ATOM | 14948 | CG | ASP | B | 437 | −49.397 | −25.675 | −34.557 | 1.00 | 21.23 | C |
| ATOM | 14949 | OD1 | ASP | B | 437 | −49.902 | −24.749 | −33.877 | 1.00 | 22.90 | O |
| ATOM | 14950 | OD2 | ASP | B | 437 | −48.149 | −25.821 | −34.632 | 1.00 | 22.18 | O |
| ATOM | 14951 | C | ASP | B | 437 | −52.629 | −26.838 | −36.512 | 1.00 | 20.00 | C |
| ATOM | 14952 | O | ASP | B | 437 | −52.678 | −26.491 | −37.695 | 1.00 | 20.02 | O |
| ATOM | 14954 | N | LEU | B | 438 | −53.372 | −27.836 | −36.021 | 1.00 | 20.02 | N |
| ATOM | 14955 | CA | LEU | B | 438 | −54.352 | −28.558 | −36.858 | 1.00 | 20.18 | C |
| ATOM | 14957 | CB | LEU | B | 438 | −55.144 | −29.593 | −36.049 | 1.00 | 19.88 | C |
| ATOM | 14960 | CG | LEU | B | 438 | −54.699 | −31.050 | −36.142 | 1.00 | 18.97 | C |
| ATOM | 14962 | CD1 | LEU | B | 438 | −55.537 | −31.869 | −35.200 | 1.00 | 18.86 | C |
| ATOM | 14966 | CD2 | LEU | B | 438 | −54.818 | −31.585 | −37.550 | 1.00 | 16.23 | C |
| ATOM | 14970 | C | LEU | B | 438 | −55.358 | −27.644 | −37.564 | 1.00 | 20.60 | C |
| ATOM | 14971 | O | LEU | B | 438 | −55.717 | −27.889 | −38.712 | 1.00 | 20.30 | O |
| ATOM | 14973 | N | ALA | B | 439 | −55.825 | −26.620 | −36.853 | 1.00 | 21.39 | N |
| ATOM | 14974 | CA | ALA | B | 439 | −56.802 | −25.654 | −37.377 | 1.00 | 21.96 | C |
| ATOM | 14976 | CB | ALA | B | 439 | −57.306 | −24.741 | −36.242 | 1.00 | 21.77 | C |
| ATOM | 14980 | C | ALA | B | 439 | −56.214 | −24.805 | −38.494 | 1.00 | 22.47 | C |
| ATOM | 14981 | O | ALA | B | 439 | −56.850 | −24.559 | −39.517 | 1.00 | 22.13 | O |
| ATOM | 14983 | N | SER | B | 440 | −54.983 | −24.370 | −38.282 | 1.00 | 23.40 | N |
| ATOM | 14984 | CA | SER | B | 440 | −54.337 | −23.428 | −39.169 | 1.00 | 24.40 | C |
| ATOM | 14986 | CB | SER | B | 440 | −53.423 | −22.529 | −38.342 | 1.00 | 24.44 | C |
| ATOM | 14989 | OG | SER | B | 440 | −52.994 | −23.206 | −37.166 | 1.00 | 25.19 | O |
| ATOM | 14991 | C | SER | B | 440 | −53.544 | −24.103 | −40.289 | 1.00 | 25.15 | C |
| ATOM | 14992 | O | SER | B | 440 | −53.093 | −23.424 | −41.210 | 1.00 | 25.24 | O |
| ATOM | 14994 | N | ALA | B | 441 | −53.392 | −25.428 | −40.222 | 1.00 | 25.99 | N |
| ATOM | 14995 | CA | ALA | B | 441 | −52.488 | −26.160 | −41.119 | 1.00 | 26.53 | C |
| ATOM | 14997 | CB | ALA | B | 441 | −52.532 | −27.655 | −40.830 | 1.00 | 26.26 | C |
| ATOM | 15001 | C | ALA | B | 441 | −52.726 | −25.903 | −42.608 | 1.00 | 27.31 | C |
| ATOM | 15002 | O | ALA | B | 441 | −51.811 | −25.489 | −43.310 | 1.00 | 27.26 | O |
| ATOM | 15004 | N | SER | B | 442 | −53.940 | −26.134 | −43.098 | 1.00 | 28.45 | N |
| ATOM | 15005 | CA | SER | B | 442 | −54.138 | −26.138 | −44.545 | 1.00 | 29.47 | C |
| ATOM | 15007 | CB | SER | B | 442 | −55.477 | −26.769 | −44.936 | 1.00 | 29.40 | C |
| ATOM | 15010 | OG | SER | B | 442 | −56.454 | −25.784 | −45.181 | 1.00 | 30.36 | O |
| ATOM | 15012 | C | SER | B | 442 | −53.966 | −24.731 | −45.125 | 1.00 | 30.22 | C |
| ATOM | 15013 | O | SER | B | 442 | −53.304 | −24.562 | −46.139 | 1.00 | 30.26 | O |
| ATOM | 15015 | N | ALA | B | 443 | −54.537 | −23.729 | −44.467 | 1.00 | 31.38 | N |
| ATOM | 15016 | CA | ALA | B | 443 | −54.308 | −22.333 | −44.835 | 1.00 | 32.22 | C |
| ATOM | 15018 | CB | ALA | B | 443 | −55.057 | −21.410 | −43.893 | 1.00 | 32.28 | C |
| ATOM | 15022 | C | ALA | B | 443 | −52.820 | −21.992 | −44.818 | 1.00 | 33.12 | C |
| ATOM | 15023 | O | ALA | B | 443 | −52.302 | −21.419 | −45.766 | 1.00 | 33.24 | O |
| ATOM | 15025 | N | GLU | B | 444 | −52.136 | −22.351 | −43.736 | 1.00 | 34.43 | N |
| ATOM | 15026 | CA | GLU | B | 444 | −50.711 | −22.033 | −43.582 | 1.00 | 35.35 | C |
| ATOM | 15028 | CB | GLU | B | 444 | −50.237 | −22.271 | −42.134 | 1.00 | 35.46 | C |
| ATOM | 15031 | CG | GLU | B | 444 | −50.757 | −21.227 | −41.126 | 1.00 | 36.42 | C |
| ATOM | 15034 | CD | GLU | B | 444 | −50.178 | −21.376 | −39.708 | 1.00 | 37.82 | C |
| ATOM | 15035 | OE1 | GLU | B | 444 | −49.965 | −22.506 | −39.224 | 1.00 | 37.92 | O |

TABLE 16-7-continued

Coordinates of *P. tremuloides* IspS

| ATOM | 15036 | OE2 | GLU | B | 444 | −49.955 | −20.344 | −39.049 | 1.00 | 40.09 | O |
|---|---|---|---|---|---|---|---|---|---|---|---|
| ATOM | 15037 | C | GLU | B | 444 | −49.840 | −22.794 | −44.594 | 1.00 | 35.87 | C |
| ATOM | 15038 | O | GLU | B | 444 | −48.870 | −22.239 | −45.107 | 1.00 | 35.85 | O |
| ATOM | 15040 | N | ILE | B | 445 | −50.193 | −24.048 | −44.883 | 1.00 | 36.63 | N |
| ATOM | 15041 | CA | ILE | B | 445 | −49.517 | −24.837 | −45.928 | 1.00 | 37.21 | C |
| ATOM | 15043 | CB | ILE | B | 445 | −49.854 | −26.366 | −45.832 | 1.00 | 37.15 | C |
| ATOM | 15045 | CG1 | ILE | B | 445 | −49.181 | −26.991 | −44.609 | 1.00 | 36.85 | C |
| ATOM | 15048 | CD1 | ILE | B | 445 | −49.867 | −28.244 | −44.102 | 1.00 | 36.62 | C |
| ATOM | 15052 | CG2 | ILE | B | 445 | −49.416 | −27.120 | −47.093 | 1.00 | 36.66 | C |
| ATOM | 15056 | C | ILE | B | 445 | −49.933 | −24.289 | −47.290 | 1.00 | 37.88 | C |
| ATOM | 15057 | O | ILE | B | 445 | −50.926 | −24.733 | −47.874 | 1.00 | 38.20 | O |
| ATOM | 15059 | N | ALA | B | 446 | −49.175 | −23.314 | −47.785 | 1.00 | 38.56 | N |
| ATOM | 15060 | CA | ALA | B | 446 | −49.544 | −22.575 | −48.992 | 1.00 | 39.03 | C |
| ATOM | 15062 | CB | ALA | B | 446 | −49.833 | −23.522 | −50.169 | 1.00 | 39.19 | C |
| ATOM | 15066 | C | ALA | B | 446 | −50.768 | −21.740 | −48.685 | 1.00 | 39.42 | C |
| ATOM | 15067 | O | ALA | B | 446 | −51.866 | −22.288 | −48.742 | 1.00 | 39.26 | O |
| ATOM | 15069 | N | ARG | B | 447 | −50.650 | −20.443 | −48.361 | 1.00 | 40.06 | N |
| ATOM | 15070 | CA | ARG | B | 447 | −49.426 | −19.589 | −48.361 | 1.00 | 40.54 | C |
| ATOM | 15072 | CB | ARG | B | 447 | −49.276 | −18.901 | −46.986 | 1.00 | 40.70 | C |
| ATOM | 15075 | CG | ARG | B | 447 | −50.121 | −17.634 | −46.836 | 1.00 | 41.82 | C |
| ATOM | 15078 | CD | ARG | B | 447 | −50.292 | −17.234 | −45.377 | 1.00 | 42.99 | C |
| ATOM | 15081 | NE | ARG | B | 447 | −51.628 | −17.546 | −44.864 | 1.00 | 44.22 | N |
| ATOM | 15083 | CZ | ARG | B | 447 | −51.924 | −17.766 | −43.580 | 1.00 | 46.00 | C |
| ATOM | 15084 | NH1 | ARG | B | 447 | −50.977 | −17.730 | −42.633 | 1.00 | 46.34 | N |
| ATOM | 15087 | NH2 | ARG | B | 447 | −53.184 | −18.039 | −43.236 | 1.00 | 46.39 | N |
| ATOM | 15090 | C | ARG | B | 447 | −48.095 | −20.208 | −48.837 | 1.00 | 40.35 | C |
| ATOM | 15091 | O | ARG | B | 447 | −47.897 | −20.403 | −50.038 | 1.00 | 40.95 | O |
| ATOM | 15093 | N | GLY | B | 448 | −47.170 | −20.442 | −47.918 | 1.00 | 39.87 | N |
| ATOM | 15094 | CA | GLY | B | 448 | −46.020 | −21.306 | −48.162 | 1.00 | 39.52 | C |
| ATOM | 15097 | C | GLY | B | 448 | −45.258 | −21.517 | −46.865 | 1.00 | 39.26 | C |
| ATOM | 15098 | O | GLY | B | 448 | −44.071 | −21.842 | −46.885 | 1.00 | 39.15 | O |
| ATOM | 15100 | N | GLU | B | 449 | −45.966 | −21.344 | −45.742 | 1.00 | 38.85 | N |
| ATOM | 15101 | CA | GLU | B | 449 | −45.365 | −21.215 | −44.426 | 1.00 | 38.45 | C |
| ATOM | 15103 | CB | GLU | B | 449 | −46.288 | −20.472 | −43.444 | 1.00 | 38.76 | C |
| ATOM | 15106 | CG | GLU | B | 449 | −46.346 | −18.943 | −43.636 | 1.00 | 40.34 | C |
| ATOM | 15109 | CD | GLU | B | 449 | −47.486 | −18.257 | −42.839 | 1.00 | 42.09 | C |
| ATOM | 15110 | OE1 | GLU | B | 449 | −47.897 | −18.787 | −41.780 | 1.00 | 43.23 | O |
| ATOM | 15111 | OE2 | GLU | B | 449 | −47.972 | −17.184 | −43.274 | 1.00 | 42.13 | O |
| ATOM | 15112 | C | GLU | B | 449 | −45.073 | −22.600 | −43.906 | 1.00 | 37.54 | C |
| ATOM | 15113 | O | GLU | B | 449 | −45.810 | −23.553 | −44.167 | 1.00 | 37.34 | O |
| ATOM | 15115 | N | THR | B | 450 | −43.986 | −22.688 | −43.159 | 1.00 | 36.47 | N |
| ATOM | 15116 | CA | THR | B | 450 | −43.459 | −23.950 | −42.702 | 1.00 | 35.65 | C |
| ATOM | 15118 | CB | THR | B | 450 | −42.017 | −24.105 | −43.245 | 1.00 | 35.81 | C |
| ATOM | 15120 | OG1 | THR | B | 450 | −41.593 | −25.465 | −43.109 | 1.00 | 37.67 | O |
| ATOM | 15122 | CG2 | THR | B | 450 | −41.029 | −23.152 | −42.538 | 1.00 | 36.21 | C |
| ATOM | 15126 | C | THR | B | 450 | −43.528 | −24.084 | −41.166 | 1.00 | 34.22 | C |
| ATOM | 15127 | O | THR | B | 450 | −43.165 | −25.127 | −40.619 | 1.00 | 34.00 | O |
| ATOM | 15129 | N | ALA | B | 451 | −44.024 | −23.034 | −40.495 | 1.00 | 32.69 | N |
| ATOM | 15130 | CA | ALA | B | 451 | −44.144 | −22.974 | −39.026 | 1.00 | 31.28 | C |
| ATOM | 15132 | CB | ALA | B | 451 | −43.952 | −21.546 | −38.545 | 1.00 | 31.06 | C |
| ATOM | 15136 | C | ALA | B | 451 | −45.495 | −23.500 | −38.547 | 1.00 | 29.97 | C |
| ATOM | 15137 | O | ALA | B | 451 | −46.337 | −22.735 | −38.082 | 1.00 | 30.08 | O |
| ATOM | 15139 | N | ASN | B | 452 | −45.690 | −24.809 | −38.656 | 1.00 | 28.19 | N |
| ATOM | 15140 | CA | ASN | B | 452 | −46.935 | −25.444 | −38.272 | 1.00 | 26.73 | C |
| ATOM | 15142 | CB | ASN | B | 452 | −47.929 | −25.339 | −39.422 | 1.00 | 26.45 | C |
| ATOM | 15145 | CG | ASN | B | 452 | −49.311 | −25.832 | −39.057 | 1.00 | 25.38 | C |
| ATOM | 15146 | OD1 | ASN | B | 452 | −49.608 | −27.004 | −39.195 | 1.00 | 24.57 | O |
| ATOM | 15147 | ND2 | ASN | B | 452 | −50.171 | −24.928 | −38.618 | 1.00 | 24.44 | N |
| ATOM | 15150 | C | ASN | B | 452 | −46.631 | −26.889 | −37.952 | 1.00 | 26.05 | C |
| ATOM | 15151 | O | ASN | B | 452 | −45.930 | −27.544 | −38.695 | 1.00 | 26.21 | O |
| ATOM | 15153 | N | SER | B | 453 | −47.131 | −27.388 | −36.834 | 1.00 | 25.30 | N |
| ATOM | 15154 | CA | SER | B | 453 | −46.843 | −28.760 | −36.432 | 1.00 | 24.72 | C |
| ATOM | 15156 | CB | SER | B | 453 | −47.638 | −29.139 | −35.174 | 1.00 | 24.81 | C |
| ATOM | 15159 | OG | SER | B | 453 | −47.143 | −28.455 | −34.031 | 1.00 | 24.36 | O |
| ATOM | 15161 | C | SER | B | 453 | −47.111 | −29.770 | −37.543 | 1.00 | 24.12 | C |
| ATOM | 15162 | O | SER | B | 453 | −46.325 | −30.679 | −37.743 | 1.00 | 24.33 | O |
| ATOM | 15164 | N | VAL | B | 454 | −48.202 | −29.606 | −38.272 | 1.00 | 23.57 | N |
| ATOM | 15165 | CA | VAL | B | 454 | −48.546 | −30.541 | −39.328 | 1.00 | 23.27 | C |
| ATOM | 15167 | CB | VAL | B | 454 | −50.001 | −30.361 | −39.795 | 1.00 | 23.06 | C |
| ATOM | 15169 | CG1 | VAL | B | 454 | −50.363 | −31.385 | −40.829 | 1.00 | 22.41 | C |
| ATOM | 15173 | CG2 | VAL | B | 454 | −50.946 | −30.489 | −38.622 | 1.00 | 22.80 | C |
| ATOM | 15177 | C | VAL | B | 454 | −47.581 | −30.473 | −40.521 | 1.00 | 23.83 | C |
| ATOM | 15178 | O | VAL | B | 454 | −47.370 | −31.493 | −41.175 | 1.00 | 24.48 | O |
| ATOM | 15180 | N | SER | B | 455 | −46.981 | −29.309 | −40.803 | 1.00 | 23.99 | N |
| ATOM | 15181 | CA | SER | B | 455 | −45.978 | −29.198 | −41.881 | 1.00 | 24.22 | C |
| ATOM | 15183 | CB | SER | B | 455 | −45.577 | −27.767 | −42.111 | 1.00 | 24.02 | C |
| ATOM | 15186 | OG | SER | B | 455 | −46.655 | −27.098 | −42.689 | 1.00 | 25.57 | O |
| ATOM | 15188 | C | SER | B | 455 | −44.708 | −29.949 | −41.582 | 1.00 | 24.65 | C |

TABLE 16-7-continued

Coordinates of P. tremuloides IspS

| ATOM | 15189 | O | SER | B | 455 | −44.211 | −30.700 | −42.417 | 1.00 | 25.23 | O |
|---|---|---|---|---|---|---|---|---|---|---|---|
| ATOM | 15191 | N | CYS | B | 456 | −44.151 | −29.700 | −40.405 | 1.00 | 24.82 | N |
| ATOM | 15192 | CA | CYS | B | 456 | −43.024 | −30.462 | −39.935 | 1.00 | 24.81 | C |
| ATOM | 15194 | CB | CYS | B | 456 | −42.765 | −30.170 | −38.470 | 1.00 | 24.92 | C |
| ATOM | 15197 | SG | CYS | B | 456 | −42.139 | −28.541 | −38.190 | 1.00 | 25.18 | S |
| ATOM | 15199 | C | CYS | B | 456 | −43.304 | −31.938 | −40.124 | 1.00 | 24.84 | C |
| ATOM | 15200 | O | CYS | B | 456 | −42.507 | −32.634 | −40.728 | 1.00 | 25.34 | O |
| ATOM | 15202 | N | TYR | B | 457 | −44.442 | −32.421 | −39.644 | 1.00 | 24.75 | N |
| ATOM | 15203 | CA | TYR | B | 457 | −44.735 | −33.838 | −39.778 | 1.00 | 24.85 | C |
| ATOM | 15205 | CB | TYR | B | 457 | −46.069 | −34.197 | −39.142 | 1.00 | 24.64 | C |
| ATOM | 15208 | CG | TYR | B | 457 | −46.057 | −35.537 | −38.451 | 1.00 | 24.00 | C |
| ATOM | 15209 | CD1 | TYR | B | 457 | −45.846 | −35.635 | −37.083 | 1.00 | 24.19 | C |
| ATOM | 15211 | CE1 | TYR | B | 457 | −45.848 | −36.873 | −36.436 | 1.00 | 23.72 | C |
| ATOM | 15213 | CZ | TYR | B | 457 | −46.059 | −38.025 | −37.170 | 1.00 | 23.27 | C |
| ATOM | 15214 | OH | TYR | B | 457 | −46.063 | −39.244 | −36.554 | 1.00 | 22.94 | O |
| ATOM | 15216 | CE2 | TYR | B | 457 | −46.268 | −37.961 | −38.528 | 1.00 | 23.68 | C |
| ATOM | 15218 | CD2 | TYR | B | 457 | −46.265 | −36.711 | −39.163 | 1.00 | 24.16 | C |
| ATOM | 15220 | C | TYR | B | 457 | −44.676 | −34.267 | −41.251 | 1.00 | 25.30 | C |
| ATOM | 15221 | O | TYR | B | 457 | −43.965 | −35.208 | −41.584 | 1.00 | 24.94 | O |
| ATOM | 15223 | N | MET | B | 458 | −45.388 | −33.569 | −42.134 | 1.00 | 26.02 | N |
| ATOM | 15224 | CA | MET | B | 458 | −45.207 | −33.775 | −43.585 | 1.00 | 26.76 | C |
| ATOM | 15226 | CB | MET | B | 458 | −45.913 | −32.685 | −44.407 | 1.00 | 26.84 | C |
| ATOM | 15229 | CG | MET | B | 458 | −47.419 | −32.720 | −44.429 | 1.00 | 27.32 | C |
| ATOM | 15232 | SD | MET | B | 458 | −48.092 | −31.238 | −45.229 | 1.00 | 27.76 | S |
| ATOM | 15233 | CE | MET | B | 458 | −47.283 | −31.311 | −46.830 | 1.00 | 26.95 | C |
| ATOM | 15237 | C | MET | B | 458 | −43.723 | −33.759 | −43.996 | 1.00 | 27.06 | C |
| ATOM | 15238 | O | MET | B | 458 | −43.192 | −34.746 | −44.485 | 1.00 | 26.94 | O |
| ATOM | 15240 | N | ARG | B | 459 | −43.069 | −32.624 | −43.800 | 1.00 | 27.58 | N |
| ATOM | 15241 | CA | ARG | B | 459 | −41.720 | −32.419 | −44.289 | 1.00 | 28.38 | C |
| ATOM | 15243 | CB | ARG | B | 459 | −41.313 | −30.965 | −44.041 | 1.00 | 28.96 | C |
| ATOM | 15246 | CG | ARG | B | 459 | −39.862 | −30.642 | −44.328 | 1.00 | 31.93 | C |
| ATOM | 15249 | CD | ARG | B | 459 | −39.656 | −29.139 | −44.480 | 1.00 | 36.88 | C |
| ATOM | 15252 | NE | ARG | B | 459 | −40.318 | −28.349 | −43.427 | 1.00 | 41.70 | N |
| ATOM | 15254 | CZ | ARG | B | 459 | −39.890 | −28.241 | −42.161 | 1.00 | 45.68 | C |
| ATOM | 15255 | NH1 | ARG | B | 459 | −38.795 | −28.899 | −41.751 | 1.00 | 48.08 | N |
| ATOM | 15258 | NH2 | ARG | B | 459 | −40.566 | −27.489 | −41.284 | 1.00 | 45.92 | N |
| ATOM | 15261 | C | ARG | B | 459 | −40.717 | −33.401 | −43.672 | 1.00 | 28.03 | C |
| ATOM | 15262 | O | ARG | B | 459 | −39.829 | −33.881 | −44.356 | 1.00 | 28.13 | O |
| ATOM | 15264 | N | THR | B | 460 | −40.882 | −33.711 | −42.393 | 1.00 | 27.88 | N |
| ATOM | 15265 | CA | THR | B | 460 | −40.002 | −34.635 | −41.664 | 1.00 | 27.75 | C |
| ATOM | 15267 | CB | THR | B | 460 | −40.240 | −34.502 | −40.134 | 1.00 | 27.79 | C |
| ATOM | 15269 | OG1 | THR | B | 460 | −39.805 | −33.209 | −39.689 | 1.00 | 27.98 | O |
| ATOM | 15271 | CG2 | THR | B | 460 | −39.519 | −35.589 | −39.356 | 1.00 | 27.46 | C |
| ATOM | 15275 | C | THR | B | 460 | −40.171 | −36.114 | −42.045 | 1.00 | 27.72 | C |
| ATOM | 15276 | O | THR | B | 460 | −39.211 | −36.857 | −42.069 | 1.00 | 27.60 | O |
| ATOM | 15278 | N | LYS | B | 461 | −41.398 | −36.538 | −42.313 | 1.00 | 28.05 | N |
| ATOM | 15279 | CA | LYS | B | 461 | −41.701 | −37.929 | −42.649 | 1.00 | 28.25 | C |
| ATOM | 15281 | CB | LYS | B | 461 | −42.972 | −38.381 | −41.914 | 1.00 | 28.32 | C |
| ATOM | 15284 | CG | LYS | B | 461 | −42.767 | −38.763 | −40.453 | 1.00 | 28.57 | C |
| ATOM | 15287 | CD | LYS | B | 461 | −42.569 | −40.271 | −40.299 | 1.00 | 29.79 | C |
| ATOM | 15290 | CE | LYS | B | 461 | −41.913 | −40.651 | −38.970 | 1.00 | 30.32 | C |
| ATOM | 15293 | NZ | LYS | B | 461 | −42.651 | −40.184 | −37.749 | 1.00 | 30.60 | N |
| ATOM | 15297 | C | LYS | B | 461 | −41.876 | −38.139 | −44.155 | 1.00 | 28.50 | C |
| ATOM | 15298 | O | LYS | B | 461 | −42.071 | −39.269 | −44.598 | 1.00 | 28.58 | O |
| ATOM | 15300 | N | GLY | B | 462 | −41.818 | −37.057 | −44.933 | 1.00 | 28.79 | N |
| ATOM | 15301 | CA | GLY | B | 462 | −41.978 | −37.114 | −46.385 | 1.00 | 29.04 | C |
| ATOM | 15304 | C | GLY | B | 462 | −43.333 | −37.610 | −46.853 | 1.00 | 29.39 | C |
| ATOM | 15305 | O | GLY | B | 462 | −43.410 | −38.452 | −47.738 | 1.00 | 29.53 | O |
| ATOM | 15307 | N | ILE | B | 463 | −44.406 | −37.081 | −46.270 | 1.00 | 29.91 | N |
| ATOM | 15308 | CA | ILE | B | 463 | −45.764 | −37.552 | −46.572 | 1.00 | 30.27 | C |
| ATOM | 15310 | CB | ILE | B | 463 | −46.333 | −38.444 | −45.433 | 1.00 | 30.13 | C |
| ATOM | 15312 | CG1 | ILE | B | 463 | −46.308 | −37.706 | −44.092 | 1.00 | 30.22 | C |
| ATOM | 15315 | CD1 | ILE | B | 463 | −46.983 | −38.462 | −42.965 | 1.00 | 30.14 | C |
| ATOM | 15319 | CG2 | ILE | B | 463 | −45.558 | −39.740 | −45.340 | 1.00 | 29.85 | C |
| ATOM | 15323 | C | ILE | B | 463 | −46.775 | −36.429 | −46.881 | 1.00 | 30.75 | C |
| ATOM | 15324 | O | ILE | B | 463 | −46.595 | −35.270 | −46.495 | 1.00 | 30.52 | O |
| ATOM | 15326 | N | SER | B | 464 | −47.842 | −36.822 | −47.581 | 1.00 | 31.33 | N |
| ATOM | 15327 | CA | SER | B | 464 | −48.951 | −35.944 | −47.952 | 1.00 | 31.68 | C |
| ATOM | 15329 | CB | SER | B | 464 | −49.948 | −36.709 | −48.830 | 1.00 | 32.02 | C |
| ATOM | 15332 | OG | SER | B | 464 | −50.547 | −37.793 | −48.123 | 1.00 | 32.84 | O |
| ATOM | 15334 | C | SER | B | 464 | −49.705 | −35.396 | −46.747 | 1.00 | 31.62 | C |
| ATOM | 15335 | O | SER | B | 464 | −49.897 | −36.097 | −45.747 | 1.00 | 31.69 | O |
| ATOM | 15337 | N | GLU | B | 465 | −50.165 | −34.153 | −46.874 | 1.00 | 31.42 | N |
| ATOM | 15338 | CA | GLU | B | 465 | −50.881 | −33.466 | −45.803 | 1.00 | 31.20 | C |
| ATOM | 15340 | CB | GLU | B | 465 | −51.465 | −32.141 | −46.324 | 1.00 | 31.33 | C |
| ATOM | 15343 | CG | GLU | B | 465 | −52.441 | −31.455 | −45.359 | 1.00 | 31.42 | C |
| ATOM | 15346 | CD | GLU | B | 465 | −52.768 | −30.006 | −45.712 | 1.00 | 31.30 | C |
| ATOM | 15347 | OE1 | GLU | B | 465 | −52.325 | −29.490 | −46.765 | 1.00 | 30.56 | O |

TABLE 16-7-continued

Coordinates of *P. tremuloides* IspS

| ATOM | 15348 | OE2 | GLU | B | 465 | −53.487 | −29.380 | −44.906 | 1.00 | 31.84 | O |
|---|---|---|---|---|---|---|---|---|---|---|---|
| ATOM | 15349 | C | GLU | B | 465 | −51.985 | −34.325 | −45.202 | 1.00 | 30.97 | C |
| ATOM | 15350 | O | GLU | B | 465 | −52.175 | −34.327 | −43.992 | 1.00 | 30.72 | O |
| ATOM | 15352 | N | GLU | B | 466 | −52.709 | −35.052 | −46.055 | 1.00 | 30.98 | N |
| ATOM | 15353 | CA | GLU | B | 466 | −53.865 | −35.833 | −45.618 | 1.00 | 30.65 | C |
| ATOM | 15355 | CB | GLU | B | 466 | −54.553 | −36.541 | −46.788 | 1.00 | 30.62 | C |
| ATOM | 15358 | CG | GLU | B | 466 | −55.733 | −37.401 | −46.336 | 1.00 | 31.50 | C |
| ATOM | 15361 | CD | GLU | B | 466 | −56.353 | −38.240 | −47.446 | 1.00 | 33.14 | C |
| ATOM | 15362 | OE1 | GLU | B | 466 | −56.512 | −37.736 | −48.581 | 1.00 | 34.40 | O |
| ATOM | 15363 | OE2 | GLU | B | 466 | −56.699 | −39.413 | −47.173 | 1.00 | 33.21 | O |
| ATOM | 15364 | C | GLU | B | 466 | −53.477 | −36.851 | −44.564 | 1.00 | 30.17 | C |
| ATOM | 15365 | O | GLU | B | 466 | −54.215 | −37.049 | −43.606 | 1.00 | 30.46 | O |
| ATOM | 15367 | N | LEU | B | 467 | −52.333 | −37.506 | −44.726 | 1.00 | 29.59 | N |
| ATOM | 15368 | CA | LEU | B | 467 | −51.953 | −38.540 | −43.769 | 1.00 | 29.19 | C |
| ATOM | 15370 | CB | LEU | B | 467 | −51.640 | −39.869 | −44.476 | 1.00 | 29.27 | C |
| ATOM | 15373 | CG | LEU | B | 467 | −50.356 | −40.081 | −45.268 | 1.00 | 29.84 | C |
| ATOM | 15375 | CD1 | LEU | B | 467 | −49.341 | −40.761 | −44.357 | 1.00 | 31.06 | C |
| ATOM | 15379 | CD2 | LEU | B | 467 | −50.589 | −40.920 | −46.523 | 1.00 | 29.47 | C |
| ATOM | 15383 | C | LEU | B | 467 | −50.865 | −38.092 | −42.794 | 1.00 | 28.54 | C |
| ATOM | 15384 | O | LEU | B | 467 | −50.490 | −38.834 | −41.894 | 1.00 | 28.28 | O |
| ATOM | 15386 | N | ALA | B | 468 | −50.388 | −36.862 | −42.962 | 1.00 | 28.04 | N |
| ATOM | 15387 | CA | ALA | B | 468 | −49.682 | −36.158 | −41.893 | 1.00 | 27.54 | C |
| ATOM | 15389 | CB | ALA | B | 468 | −48.922 | −34.970 | −42.435 | 1.00 | 27.34 | C |
| ATOM | 15393 | C | ALA | B | 468 | −50.711 | −35.698 | −40.865 | 1.00 | 27.17 | C |
| ATOM | 15394 | O | ALA | B | 468 | −50.482 | −35.801 | −39.662 | 1.00 | 27.40 | O |
| ATOM | 15396 | N | THR | B | 469 | −51.841 | −35.182 | −41.349 | 1.00 | 26.57 | N |
| ATOM | 15397 | CA | THR | B | 469 | −52.957 | −34.795 | −40.490 | 1.00 | 25.87 | C |
| ATOM | 15399 | CB | THR | B | 469 | −54.130 | −34.297 | −41.328 | 1.00 | 25.53 | C |
| ATOM | 15401 | OG1 | THR | B | 469 | −53.737 | −33.111 | −42.025 | 1.00 | 24.99 | O |
| ATOM | 15403 | CG2 | THR | B | 469 | −55.316 | −33.993 | −40.453 | 1.00 | 24.62 | C |
| ATOM | 15407 | C | THR | B | 469 | −53.412 | −35.988 | −39.669 | 1.00 | 25.95 | C |
| ATOM | 15408 | O | THR | B | 469 | −53.551 | −35.925 | −38.450 | 1.00 | 25.80 | O |
| ATOM | 15410 | N | GLU | B | 470 | −53.618 | −37.091 | −40.367 | 1.00 | 26.06 | N |
| ATOM | 15411 | CA | GLU | B | 470 | −54.043 | −38.344 | −39.756 | 1.00 | 26.10 | C |
| ATOM | 15413 | CB | GLU | B | 470 | −54.057 | −39.436 | −40.848 | 1.00 | 26.60 | C |
| ATOM | 15416 | CG | GLU | B | 470 | −55.038 | −40.587 | −40.646 | 1.00 | 28.01 | C |
| ATOM | 15419 | CD | GLU | B | 470 | −54.553 | −41.897 | −41.286 | 1.00 | 29.05 | C |
| ATOM | 15420 | OE1 | GLU | B | 470 | −54.298 | −41.930 | −42.515 | 1.00 | 27.96 | O |
| ATOM | 15421 | OE2 | GLU | B | 470 | −54.435 | −42.892 | −40.536 | 1.00 | 30.42 | O |
| ATOM | 15422 | C | GLU | B | 470 | −53.148 | −38.746 | −38.557 | 1.00 | 25.28 | C |
| ATOM | 15423 | O | GLU | B | 470 | −53.629 | −39.266 | −37.556 | 1.00 | 25.08 | O |
| ATOM | 15425 | N | SER | B | 471 | −51.850 | −38.497 | −38.654 | 1.00 | 24.70 | N |
| ATOM | 15426 | CA | SER | B | 471 | −50.930 | −38.906 | −37.599 | 1.00 | 24.26 | C |
| ATOM | 15428 | CB | SER | B | 471 | −49.494 | −38.842 | −38.085 | 1.00 | 24.11 | C |
| ATOM | 15431 | OG | SER | B | 471 | −49.315 | −39.693 | −39.186 | 1.00 | 23.98 | O |
| ATOM | 15433 | C | SER | B | 471 | −51.085 | −38.029 | −36.377 | 1.00 | 23.92 | C |
| ATOM | 15434 | O | SER | B | 471 | −51.240 | −38.530 | −35.270 | 1.00 | 24.09 | O |
| ATOM | 15436 | N | VAL | B | 472 | −51.032 | −36.719 | −36.582 | 1.00 | 23.48 | N |
| ATOM | 15437 | CA | VAL | B | 472 | −51.279 | −35.774 | −35.510 | 1.00 | 23.15 | C |
| ATOM | 15439 | CB | VAL | B | 472 | −51.377 | −34.332 | −36.045 | 1.00 | 23.03 | C |
| ATOM | 15441 | CG1 | VAL | B | 472 | −51.739 | −33.347 | −34.929 | 1.00 | 21.74 | C |
| ATOM | 15445 | CG2 | VAL | B | 472 | −50.067 | −33.945 | −36.728 | 1.00 | 22.27 | C |
| ATOM | 15449 | C | VAL | B | 472 | −52.572 | −36.192 | −34.830 | 1.00 | 23.49 | C |
| ATOM | 15450 | O | VAL | B | 472 | −52.663 | −36.276 | −33.614 | 1.00 | 23.29 | O |
| ATOM | 15452 | N | MET | B | 473 | −53.573 | −36.508 | −35.626 | 1.00 | 24.34 | N |
| ATOM | 15453 | CA | MET | B | 473 | −54.850 | −36.901 | −35.070 | 1.00 | 24.93 | C |
| ATOM | 15455 | CB | MET | B | 473 | −55.816 | −37.266 | −36.190 | 1.00 | 25.09 | C |
| ATOM | 15458 | CG | MET | B | 473 | −57.191 | −36.788 | −35.912 | 1.00 | 26.94 | C |
| ATOM | 15461 | SD | MET | B | 473 | −57.328 | −35.035 | −36.251 | 1.00 | 29.69 | S |
| ATOM | 15462 | CE | MET | B | 473 | −58.316 | −35.080 | −37.775 | 1.00 | 29.12 | C |
| ATOM | 15466 | C | MET | B | 473 | −54.668 | −38.072 | −34.100 | 1.00 | 25.00 | C |
| ATOM | 15467 | O | MET | B | 473 | −55.135 | −38.018 | −32.963 | 1.00 | 24.78 | O |
| ATOM | 15469 | N | ASN | B | 474 | −53.965 | −39.110 | −34.556 | 1.00 | 25.30 | N |
| ATOM | 15470 | CA | ASN | B | 474 | −53.681 | −40.293 | −33.738 | 1.00 | 25.55 | C |
| ATOM | 15472 | CB | ASN | B | 474 | −53.143 | −41.439 | −34.601 | 1.00 | 25.82 | C |
| ATOM | 15475 | CG | ASN | B | 474 | −54.243 | −42.137 | −35.402 | 1.00 | 27.62 | C |
| ATOM | 15476 | OD1 | ASN | B | 474 | −54.238 | −42.102 | −36.638 | 1.00 | 29.33 | O |
| ATOM | 15477 | ND2 | ASN | B | 474 | −55.196 | −42.780 | −34.697 | 1.00 | 28.58 | N |
| ATOM | 15480 | C | ASN | B | 474 | −52.711 | −40.034 | −32.592 | 1.00 | 25.20 | C |
| ATOM | 15481 | O | ASN | B | 474 | −52.711 | −40.773 | −31.621 | 1.00 | 25.71 | O |
| ATOM | 15483 | N | LEU | B | 475 | −51.883 | −38.999 | −32.704 | 1.00 | 24.65 | N |
| ATOM | 15484 | CA | LEU | B | 475 | −50.987 | −38.595 | −31.614 | 1.00 | 24.04 | C |
| ATOM | 15486 | CB | LEU | B | 475 | −49.939 | −37.626 | −32.142 | 1.00 | 23.88 | C |
| ATOM | 15489 | CG | LEU | B | 475 | −48.837 | −37.285 | −31.164 | 1.00 | 23.70 | C |
| ATOM | 15491 | CD1 | LEU | B | 475 | −47.936 | −38.471 | −31.004 | 1.00 | 23.97 | C |
| ATOM | 15495 | CD2 | LEU | B | 475 | −48.088 | −36.104 | −31.679 | 1.00 | 23.99 | C |
| ATOM | 15499 | C | LEU | B | 475 | −51.747 | −37.940 | −30.453 | 1.00 | 23.65 | C |
| ATOM | 15500 | O | LEU | B | 475 | −51.323 | −38.014 | −29.299 | 1.00 | 23.74 | O |

TABLE 16-7-continued

Coordinates of *P. tremuloides* IspS

| ATOM | 15502 | N | ILE | B | 476 | −52.858 | −37.282 | −30.766 | 1.00 | 23.15 | N |
|---|---|---|---|---|---|---|---|---|---|---|---|
| ATOM | 15503 | CA | ILE | B | 476 | −53.728 | −36.711 | −29.742 | 1.00 | 22.50 | C |
| ATOM | 15505 | CB | ILE | B | 476 | −54.779 | −35.755 | −30.359 | 1.00 | 22.27 | C |
| ATOM | 15507 | CG1 | ILE | B | 476 | −54.099 | −34.508 | −30.910 | 1.00 | 20.55 | C |
| ATOM | 15510 | CD1 | ILE | B | 476 | −55.000 | −33.671 | −31.693 | 1.00 | 19.19 | C |
| ATOM | 15514 | CG2 | ILE | B | 476 | −55.817 | −35.363 | −29.336 | 1.00 | 22.15 | C |
| ATOM | 15518 | C | ILE | B | 476 | −54.398 | −37.849 | −28.985 | 1.00 | 22.40 | C |
| ATOM | 15519 | O | ILE | B | 476 | −54.316 | −37.900 | −27.767 | 1.00 | 22.32 | O |
| ATOM | 15521 | N | ASP | B | 477 | −55.023 | −38.777 | −29.708 | 1.00 | 22.37 | N |
| ATOM | 15522 | CA | ASP | B | 477 | −55.616 | −39.975 | −29.090 | 1.00 | 22.55 | C |
| ATOM | 15524 | CB | ASP | B | 477 | −55.996 | −41.007 | −30.151 | 1.00 | 22.67 | C |
| ATOM | 15527 | CG | ASP | B | 477 | −57.262 | −40.636 | −30.892 | 1.00 | 24.93 | C |
| ATOM | 15528 | OD1 | ASP | B | 477 | −57.690 | −39.458 | −30.818 | 1.00 | 28.87 | O |
| ATOM | 15529 | OD2 | ASP | B | 477 | −57.847 | −41.523 | −31.549 | 1.00 | 27.92 | O |
| ATOM | 15530 | C | ASP | B | 477 | −54.675 | −40.622 | −28.083 | 1.00 | 22.10 | C |
| ATOM | 15531 | O | ASP | B | 477 | −55.048 | −40.877 | −26.938 | 1.00 | 21.83 | O |
| ATOM | 15533 | N | GLU | B | 478 | −53.444 | −40.867 | −28.510 | 1.00 | 21.73 | N |
| ATOM | 15534 | CA | GLU | B | 478 | −52.472 | −41.506 | −27.645 | 1.00 | 21.69 | C |
| ATOM | 15536 | CB | GLU | B | 478 | −51.233 | −41.920 | −28.437 | 1.00 | 21.97 | C |
| ATOM | 15539 | CG | GLU | B | 478 | −50.786 | −43.360 | −28.150 | 1.00 | 24.18 | C |
| ATOM | 15542 | CD | GLU | B | 478 | −51.793 | −44.429 | −28.618 | 1.00 | 27.03 | C |
| ATOM | 15543 | OE1 | GLU | B | 478 | −51.599 | −45.627 | −28.285 | 1.00 | 29.15 | O |
| ATOM | 15544 | OE2 | GLU | B | 478 | −52.770 | −44.080 | −29.323 | 1.00 | 28.37 | O |
| ATOM | 15545 | C | GLU | B | 478 | −52.107 | −40.608 | −26.449 | 1.00 | 20.97 | C |
| ATOM | 15546 | O | GLU | B | 478 | −51.928 | −41.110 | −25.316 | 1.00 | 21.15 | O |
| ATOM | 15548 | N | THR | B | 479 | −52.031 | −39.291 | −26.687 | 1.00 | 19.82 | N |
| ATOM | 15549 | CA | THR | B | 479 | −51.787 | −38.319 | −25.604 | 1.00 | 18.59 | C |
| ATOM | 15551 | CB | THR | B | 479 | −51.587 | −36.897 | −26.129 | 1.00 | 17.95 | C |
| ATOM | 15553 | OG1 | THR | B | 479 | −50.291 | −36.779 | −26.712 | 1.00 | 17.43 | O |
| ATOM | 15555 | CG2 | THR | B | 479 | −51.654 | −35.938 | −25.009 | 1.00 | 17.90 | C |
| ATOM | 15559 | C | THR | B | 479 | −52.927 | −38.342 | −24.580 | 1.00 | 18.16 | C |
| ATOM | 15560 | O | THR | B | 479 | −52.695 | −38.339 | −23.383 | 1.00 | 18.06 | O |
| ATOM | 15562 | N | TRP | B | 480 | −54.160 | −38.390 | −25.057 | 1.00 | 17.77 | N |
| ATOM | 15563 | CA | TRP | B | 480 | −55.301 | −38.493 | −24.169 | 1.00 | 17.54 | C |
| ATOM | 15565 | CB | TRP | B | 480 | −56.605 | −38.464 | −24.970 | 1.00 | 17.49 | C |
| ATOM | 15568 | CG | TRP | B | 480 | −57.239 | −37.099 | −25.028 | 1.00 | 17.53 | C |
| ATOM | 15569 | CD1 | TRP | B | 480 | −57.150 | −36.186 | −26.041 | 1.00 | 17.04 | C |
| ATOM | 15571 | NE1 | TRP | B | 480 | −57.857 | −35.067 | −25.721 | 1.00 | 16.57 | N |
| ATOM | 15573 | CE2 | TRP | B | 480 | −58.423 | −35.236 | −24.484 | 1.00 | 16.41 | C |
| ATOM | 15574 | CD2 | TRP | B | 480 | −58.055 | −36.498 | −24.020 | 1.00 | 16.68 | C |
| ATOM | 15575 | CE3 | TRP | B | 480 | −58.507 | −36.914 | −22.765 | 1.00 | 16.92 | C |
| ATOM | 15577 | CZ3 | TRP | B | 480 | −59.300 | −36.076 | −22.039 | 1.00 | 16.97 | C |
| ATOM | 15579 | CH2 | TRP | B | 480 | −59.654 | −34.823 | −22.524 | 1.00 | 16.91 | C |
| ATOM | 15581 | CZ2 | TRP | B | 480 | −59.223 | −34.383 | −23.742 | 1.00 | 16.89 | C |
| ATOM | 15583 | C | TRP | B | 480 | −55.232 | −39.760 | −23.334 | 1.00 | 17.75 | C |
| ATOM | 15584 | O | TRP | B | 480 | −55.582 | −39.747 | −22.164 | 1.00 | 17.74 | O |
| ATOM | 15586 | N | LYS | B | 481 | −54.784 | −40.861 | −23.933 | 1.00 | 18.09 | N |
| ATOM | 15587 | CA | LYS | B | 481 | −54.721 | −42.124 | −23.210 | 1.00 | 18.10 | C |
| ATOM | 15589 | CB | LYS | B | 481 | −54.277 | −43.282 | −24.115 | 1.00 | 18.01 | C |
| ATOM | 15592 | CG | LYS | B | 481 | −55.311 | −43.803 | −25.114 | 1.00 | 16.89 | C |
| ATOM | 15595 | CD | LYS | B | 481 | −54.613 | −44.663 | −26.199 | 1.00 | 15.83 | C |
| ATOM | 15598 | CE | LYS | B | 481 | −55.587 | −45.500 | −27.025 | 1.00 | 14.74 | C |
| ATOM | 15601 | NZ | LYS | B | 481 | −55.119 | −45.725 | −28.413 | 1.00 | 12.34 | N |
| ATOM | 15605 | C | LYS | B | 481 | −53.750 | −41.970 | −22.054 | 1.00 | 18.46 | C |
| ATOM | 15606 | O | LYS | B | 481 | −53.976 | −42.494 | −20.969 | 1.00 | 18.44 | O |
| ATOM | 15608 | N | LYS | B | 482 | −52.662 | −41.252 | −22.279 | 1.00 | 18.80 | N |
| ATOM | 15609 | CA | LYS | B | 482 | −51.727 | −41.019 | −21.192 | 1.00 | 19.58 | C |
| ATOM | 15611 | CB | LYS | B | 482 | −50.425 | −40.424 | −21.727 | 1.00 | 20.03 | C |
| ATOM | 15614 | CG | LYS | B | 482 | −49.499 | −41.500 | −22.277 | 1.00 | 22.03 | C |
| ATOM | 15617 | CD | LYS | B | 482 | −48.706 | −41.063 | −23.506 | 1.00 | 24.87 | C |
| ATOM | 15620 | CE | LYS | B | 482 | −47.908 | −42.268 | −24.066 | 1.00 | 26.65 | C |
| ATOM | 15623 | NZ | LYS | B | 482 | −47.287 | −41.996 | −25.408 | 1.00 | 28.80 | N |
| ATOM | 15627 | C | LYS | B | 482 | −52.363 | −40.156 | −20.096 | 1.00 | 19.56 | C |
| ATOM | 15628 | O | LYS | B | 482 | −52.367 | −40.537 | −18.926 | 1.00 | 19.19 | O |
| ATOM | 15630 | N | MET | B | 483 | −52.922 | −39.013 | −20.483 | 1.00 | 20.00 | N |
| ATOM | 15631 | CA | MET | B | 483 | −53.677 | −38.165 | −19.552 | 1.00 | 20.37 | C |
| ATOM | 15633 | CB | MET | B | 483 | −54.426 | −37.057 | −20.295 | 1.00 | 20.25 | C |
| ATOM | 15636 | CG | MET | B | 483 | −53.529 | −35.951 | −20.807 | 1.00 | 20.52 | C |
| ATOM | 15639 | SD | MET | B | 483 | −54.461 | −34.483 | −21.225 | 1.00 | 20.47 | S |
| ATOM | 15640 | CE | MET | B | 483 | −55.361 | −35.084 | −22.649 | 1.00 | 22.07 | C |
| ATOM | 15644 | C | MET | B | 483 | −54.668 | −38.981 | −18.741 | 1.00 | 20.72 | C |
| ATOM | 15645 | O | MET | B | 483 | −54.809 | −38.779 | −17.543 | 1.00 | 20.37 | O |
| ATOM | 15647 | N | ASN | B | 484 | −55.345 | −39.910 | −19.403 | 1.00 | 21.57 | N |
| ATOM | 15648 | CA | ASN | B | 484 | −56.339 | −40.731 | −18.744 | 1.00 | 22.46 | C |
| ATOM | 15650 | CB | ASN | B | 484 | −57.042 | −41.631 | −19.765 | 1.00 | 22.23 | C |
| ATOM | 15653 | CG | ASN | B | 484 | −58.118 | −40.900 | −20.576 | 1.00 | 21.61 | C |
| ATOM | 15654 | OD1 | ASN | B | 484 | −58.412 | −39.722 | −20.362 | 1.00 | 20.25 | O |
| ATOM | 15655 | ND2 | ASN | B | 484 | −58.720 | −41.622 | −21.510 | 1.00 | 20.80 | N |

TABLE 16-7-continued

| | | | | Coordinates of *P. tremuloides* IspS | | | | | | |
|---|---|---|---|---|---|---|---|---|---|---|
| ATOM | 15658 | C | ASN | B | 484 | −55.723 | −41.555 | −17.598 | 1.00 | 23.83 | C |
| ATOM | 15659 | O | ASN | B | 484 | −56.262 | −41.591 | −16.484 | 1.00 | 23.76 | O |
| ATOM | 15661 | N | LYS | B | 485 | −54.585 | −42.190 | −17.868 | 1.00 | 25.69 | N |
| ATOM | 15662 | CA | LYS | B | 485 | −53.854 | −42.937 | −16.843 | 1.00 | 27.11 | C |
| ATOM | 15664 | CB | LYS | B | 485 | −52.679 | −43.712 | −17.447 | 1.00 | 27.13 | C |
| ATOM | 15667 | CG | LYS | B | 485 | −52.073 | −44.755 | −16.489 | 1.00 | 28.85 | C |
| ATOM | 15670 | CD | LYS | B | 485 | −51.643 | −46.082 | −17.187 | 1.00 | 31.17 | C |
| ATOM | 15673 | CE | LYS | B | 485 | −50.150 | −46.132 | −17.555 | 1.00 | 32.11 | C |
| ATOM | 15676 | NZ | LYS | B | 485 | −49.291 | −46.282 | −16.344 | 1.00 | 33.08 | N |
| ATOM | 15680 | C | LYS | B | 485 | −53.370 | −42.035 | −15.701 | 1.00 | 28.37 | C |
| ATOM | 15681 | O | LYS | B | 485 | −53.288 | −42.481 | −14.563 | 1.00 | 28.59 | O |
| ATOM | 15683 | N | GLU | B | 486 | −53.083 | −40.766 | −15.980 | 1.00 | 29.89 | N |
| ATOM | 15684 | CA | GLU | B | 486 | −52.683 | −39.849 | −14.910 | 1.00 | 31.09 | C |
| ATOM | 15686 | CB | GLU | B | 486 | −52.174 | −38.511 | −15.470 | 1.00 | 31.55 | C |
| ATOM | 15689 | CG | GLU | B | 486 | −51.059 | −37.851 | −14.643 | 1.00 | 32.69 | C |
| ATOM | 15692 | CD | GLU | B | 486 | −49.785 | −38.689 | −14.605 | 1.00 | 34.51 | C |
| ATOM | 15693 | OE1 | GLU | B | 486 | −49.104 | −38.682 | −13.557 | 1.00 | 36.35 | O |
| ATOM | 15694 | OE2 | GLU | B | 486 | −49.476 | −39.368 | −15.611 | 1.00 | 34.55 | O |
| ATOM | 15695 | C | GLU | B | 486 | −53.836 | −39.615 | −13.939 | 1.00 | 31.70 | C |
| ATOM | 15696 | O | GLU | B | 486 | −53.684 | −39.868 | −12.750 | 1.00 | 31.90 | O |
| ATOM | 15698 | N | LYS | B | 487 | −54.983 | −39.164 | −14.453 | 1.00 | 32.71 | N |
| ATOM | 15699 | CA | LYS | B | 487 | −56.177 | −38.856 | −13.629 | 1.00 | 33.57 | C |
| ATOM | 15701 | CB | LYS | B | 487 | −57.343 | −38.402 | −14.519 | 1.00 | 33.54 | C |
| ATOM | 15704 | CG | LYS | B | 487 | −58.703 | −38.196 | −13.823 | 1.00 | 33.45 | C |
| ATOM | 15707 | CD | LYS | B | 487 | −58.686 | −37.024 | −12.866 | 1.00 | 33.71 | C |
| ATOM | 15710 | CE | LYS | B | 487 | −59.906 | −36.996 | −11.931 | 1.00 | 34.48 | C |
| ATOM | 15713 | NZ | LYS | B | 487 | −61.123 | −36.378 | −12.526 | 1.00 | 35.03 | N |
| ATOM | 15717 | C | LYS | B | 487 | −56.626 | −40.046 | −12.802 | 1.00 | 34.60 | C |
| ATOM | 15718 | O | LYS | B | 487 | −57.126 | −39.892 | −11.681 | 1.00 | 34.55 | O |
| ATOM | 15720 | N | LEU | B | 488 | −56.453 | −41.233 | −13.371 | 1.00 | 35.94 | N |
| ATOM | 15721 | CA | LEU | B | 488 | −56.878 | −42.451 | −12.723 | 1.00 | 37.00 | C |
| ATOM | 15723 | CB | LEU | B | 488 | −57.280 | −43.489 | −13.778 | 1.00 | 36.90 | C |
| ATOM | 15726 | CG | LEU | B | 488 | −58.081 | −44.714 | −13.312 | 1.00 | 37.52 | C |
| ATOM | 15728 | CD1 | LEU | B | 488 | −58.758 | −44.536 | −11.946 | 1.00 | 38.76 | C |
| ATOM | 15732 | CD2 | LEU | B | 488 | −59.121 | −45.084 | −14.346 | 1.00 | 38.42 | C |
| ATOM | 15736 | C | LEU | B | 488 | −55.786 | −42.980 | −11.803 | 1.00 | 38.02 | C |
| ATOM | 15737 | O | LEU | B | 488 | −56.063 | −43.315 | −10.653 | 1.00 | 38.19 | O |
| ATOM | 15739 | N | GLY | B | 489 | −54.550 | −43.016 | −12.298 | 1.00 | 39.44 | N |
| ATOM | 15740 | CA | GLY | B | 489 | −53.441 | −43.710 | −11.621 | 1.00 | 40.62 | C |
| ATOM | 15743 | C | GLY | B | 489 | −52.563 | −42.837 | −10.740 | 1.00 | 41.76 | C |
| ATOM | 15744 | O | GLY | B | 489 | −51.357 | −42.703 | −10.988 | 1.00 | 41.83 | O |
| ATOM | 15746 | N | GLY | B | 490 | −53.183 | −42.230 | −9.726 | 1.00 | 43.10 | N |
| ATOM | 15747 | CA | GLY | B | 490 | −52.481 | −41.538 | −8.636 | 1.00 | 43.82 | C |
| ATOM | 15750 | C | GLY | B | 490 | −51.131 | −40.924 | −8.967 | 1.00 | 44.31 | C |
| ATOM | 15751 | O | GLY | B | 490 | −50.084 | −41.560 | −8.831 | 1.00 | 44.25 | O |
| ATOM | 15753 | N | SER | B | 491 | −51.161 | −39.672 | −9.396 | 1.00 | 44.87 | N |
| ATOM | 15754 | CA | SER | B | 491 | −49.939 | −38.892 | −9.575 | 1.00 | 45.22 | C |
| ATOM | 15756 | CB | SER | B | 491 | −50.224 | −37.723 | −10.537 | 1.00 | 45.34 | C |
| ATOM | 15759 | OG | SER | B | 491 | −51.411 | −37.032 | −10.166 | 1.00 | 45.38 | O |
| ATOM | 15761 | C | SER | B | 491 | −49.419 | −38.389 | −8.203 | 1.00 | 45.14 | C |
| ATOM | 15762 | O | SER | B | 491 | −49.896 | −38.824 | −7.140 | 1.00 | 45.11 | O |
| ATOM | 15764 | N | LEU | B | 492 | −48.429 | −37.491 | −8.227 | 1.00 | 44.77 | N |
| ATOM | 15765 | CA | LEU | B | 492 | −48.046 | −36.752 | −7.018 | 1.00 | 44.31 | C |
| ATOM | 15767 | CB | LEU | B | 492 | −46.726 | −35.971 | −7.188 | 1.00 | 44.55 | C |
| ATOM | 15770 | CG | LEU | B | 492 | −45.530 | −36.546 | −7.972 | 1.00 | 45.73 | C |
| ATOM | 15772 | CD1 | LEU | B | 492 | −44.373 | −35.556 | −7.859 | 1.00 | 46.25 | C |
| ATOM | 15776 | CD2 | LEU | B | 492 | −45.084 | −37.972 | −7.530 | 1.00 | 46.14 | C |
| ATOM | 15780 | C | LEU | B | 492 | −49.151 | −35.760 | −6.703 | 1.00 | 43.30 | C |
| ATOM | 15781 | O | LEU | B | 492 | −49.315 | −35.370 | −5.555 | 1.00 | 43.49 | O |
| ATOM | 15783 | N | PHE | B | 493 | −49.903 | −35.367 | −7.735 | 1.00 | 42.05 | N |
| ATOM | 15784 | CA | PHE | B | 493 | −50.822 | −34.239 | −7.668 | 1.00 | 41.03 | C |
| ATOM | 15786 | CB | PHE | B | 493 | −50.913 | −33.549 | −9.028 | 1.00 | 40.81 | C |
| ATOM | 15789 | CG | PHE | B | 493 | −49.696 | −32.771 | −9.408 | 1.00 | 38.96 | C |
| ATOM | 15790 | CD1 | PHE | B | 493 | −49.651 | −31.408 | −9.233 | 1.00 | 37.06 | C |
| ATOM | 15792 | CE1 | PHE | B | 493 | −48.543 | −30.697 | −9.603 | 1.00 | 36.41 | C |
| ATOM | 15794 | CZ | PHE | B | 493 | −47.471 | −31.341 | −10.158 | 1.00 | 35.87 | C |
| ATOM | 15796 | CE2 | PHE | B | 493 | −47.507 | −32.690 | −10.343 | 1.00 | 36.39 | C |
| ATOM | 15798 | CD2 | PHE | B | 493 | −48.612 | −33.400 | −9.977 | 1.00 | 37.36 | C |
| ATOM | 15800 | C | PHE | B | 493 | −52.240 | −34.603 | −7.268 | 1.00 | 40.76 | C |
| ATOM | 15801 | O | PHE | B | 493 | −52.686 | −35.733 | −7.419 | 1.00 | 40.35 | O |
| ATOM | 15803 | N | ALA | B | 494 | −52.943 | −33.584 | −6.790 | 1.00 | 40.72 | N |
| ATOM | 15804 | CA | ALA | B | 494 | −54.355 | −33.658 | −6.471 | 1.00 | 40.68 | C |
| ATOM | 15806 | CB | ALA | B | 494 | −54.786 | −32.362 | −5.770 | 1.00 | 40.70 | C |
| ATOM | 15810 | C | ALA | B | 494 | −55.175 | −33.851 | −7.744 | 1.00 | 40.59 | C |
| ATOM | 15811 | O | ALA | B | 494 | −55.013 | −33.099 | −8.716 | 1.00 | 40.95 | O |
| ATOM | 15813 | N | LYS | B | 495 | −56.071 | −34.835 | −7.733 | 1.00 | 40.12 | N |
| ATOM | 15814 | CA | LYS | B | 495 | −57.000 | −35.047 | −8.854 | 1.00 | 39.67 | C |
| ATOM | 15816 | CB | LYS | B | 495 | −58.008 | −36.166 | −8.520 | 1.00 | 39.98 | C |

TABLE 16-7-continued

Coordinates of *P. tremuloides* IspS

| ATOM | 15819 | CG  | LYS | B | 495 | −57.388 | −37.590 | −8.496  | 1.00 | 40.57 | C |
| ATOM | 15822 | CD  | LYS | B | 495 | −58.468 | −38.688 | −8.419  | 1.00 | 41.18 | C |
| ATOM | 15825 | CE  | LYS | B | 495 | −57.878 | −40.065 | −8.132  | 1.00 | 41.28 | C |
| ATOM | 15828 | NZ  | LYS | B | 495 | −58.736 | −41.159 | −8.671  | 1.00 | 41.39 | N |
| ATOM | 15832 | C   | LYS | B | 495 | −57.717 | −33.752 | −9.333  | 1.00 | 38.82 | C |
| ATOM | 15833 | O   | LYS | B | 495 | −57.847 | −33.535 | −10.537 | 1.00 | 38.70 | O |
| ATOM | 15835 | N   | PRO | B | 496 | −58.169 | −32.890 | −8.397  | 1.00 | 37.71 | N |
| ATOM | 15836 | CA  | PRO | B | 496 | −58.701 | −31.551 | −8.687  | 1.00 | 36.80 | C |
| ATOM | 15838 | CB  | PRO | B | 496 | −58.820 | −30.937 | −7.304  | 1.00 | 36.94 | C |
| ATOM | 15841 | CG  | PRO | B | 496 | −59.255 | −32.073 | −6.483  | 1.00 | 37.90 | C |
| ATOM | 15844 | CD  | PRO | B | 496 | −58.534 | −33.294 | −7.030  | 1.00 | 37.86 | C |
| ATOM | 15847 | C   | PRO | B | 496 | −57.845 | −30.625 | −9.536  | 1.00 | 35.57 | C |
| ATOM | 15848 | O   | PRO | B | 496 | −58.389 | −29.693 | −10.139 | 1.00 | 35.93 | O |
| ATOM | 15849 | N   | PHE | B | 497 | −56.527 | −30.836 | −9.546  | 1.00 | 33.52 | N |
| ATOM | 15850 | CA  | PHE | B | 497 | −55.654 | −30.083 | −10.439 | 1.00 | 31.34 | C |
| ATOM | 15852 | CB  | PHE | B | 497 | −54.355 | −29.710 | −9.750  | 1.00 | 30.86 | C |
| ATOM | 15855 | CG  | PHE | B | 497 | −53.394 | −28.989 | −10.634 | 1.00 | 29.04 | C |
| ATOM | 15856 | CD1 | PHE | B | 497 | −53.639 | −27.700 | −11.022 | 1.00 | 27.89 | C |
| ATOM | 15858 | CE1 | PHE | B | 497 | −52.752 | −27.028 | −11.834 | 1.00 | 27.39 | C |
| ATOM | 15860 | CZ  | PHE | B | 497 | −51.599 | −27.653 | −12.259 | 1.00 | 27.40 | C |
| ATOM | 15862 | CE2 | PHE | B | 497 | −51.341 | −28.941 | −11.877 | 1.00 | 27.44 | C |
| ATOM | 15864 | CD2 | PHE | B | 497 | −52.236 | −29.604 | −11.074 | 1.00 | 28.18 | C |
| ATOM | 15866 | C   | PHE | B | 497 | −55.390 | −30.870 | −11.714 | 1.00 | 30.24 | C |
| ATOM | 15867 | O   | PHE | B | 497 | −55.301 | −30.266 | −12.786 | 1.00 | 30.39 | O |
| ATOM | 15869 | N   | VAL | B | 498 | −55.295 | −32.200 | −11.630 | 1.00 | 28.50 | N |
| ATOM | 15870 | CA  | VAL | B | 498 | −55.076 | −32.983 | −12.854 | 1.00 | 27.54 | C |
| ATOM | 15872 | CB  | VAL | B | 498 | −54.778 | −34.472 | −12.611 | 1.00 | 27.34 | C |
| ATOM | 15874 | CG1 | VAL | B | 498 | −56.027 | −35.194 | −12.262 | 1.00 | 28.14 | C |
| ATOM | 15878 | CG2 | VAL | B | 498 | −53.731 | −34.649 | −11.530 | 1.00 | 27.04 | C |
| ATOM | 15882 | C   | VAL | B | 498 | −56.277 | −32.857 | −13.784 | 1.00 | 26.60 | C |
| ATOM | 15883 | O   | VAL | B | 498 | −56.129 | −32.864 | −14.995 | 1.00 | 26.33 | O |
| ATOM | 15885 | N   | GLU | B | 499 | −57.468 | −32.731 | −13.214 | 1.00 | 25.87 | N |
| ATOM | 15886 | CA  | GLU | B | 499 | −58.662 | −32.484 | −14.022 | 1.00 | 25.20 | C |
| ATOM | 15888 | CB  | GLU | B | 499 | −59.975 | −32.639 | −13.206 | 1.00 | 25.26 | C |
| ATOM | 15891 | CG  | GLU | B | 499 | −61.287 | −32.694 | −14.028 | 1.00 | 25.16 | C |
| ATOM | 15894 | CD  | GLU | B | 499 | −61.422 | −33.922 | −14.973 | 1.00 | 26.79 | C |
| ATOM | 15895 | OE1 | GLU | B | 499 | −60.607 | −34.880 | −14.928 | 1.00 | 26.39 | O |
| ATOM | 15896 | OE2 | GLU | B | 499 | −62.379 | −33.926 | −15.785 | 1.00 | 27.83 | O |
| ATOM | 15897 | C   | GLU | B | 499 | −58.542 | −31.097 | −14.641 | 1.00 | 24.27 | C |
| ATOM | 15898 | O   | GLU | B | 499 | −58.819 | −30.948 | −15.832 | 1.00 | 24.32 | O |
| ATOM | 15900 | N   | THR | B | 500 | −58.098 | −30.093 | −13.882 | 1.00 | 22.90 | N |
| ATOM | 15901 | CA  | THR | B | 500 | −58.027 | −28.764 | −14.487 | 1.00 | 22.29 | C |
| ATOM | 15903 | CB  | THR | B | 500 | −57.908 | −27.592 | −13.488 | 1.00 | 22.43 | C |
| ATOM | 15905 | OG1 | THR | B | 500 | −56.536 | −27.259 | −13.274 | 1.00 | 22.65 | O |
| ATOM | 15907 | CG2 | THR | B | 500 | −58.614 | −27.899 | −12.183 | 1.00 | 22.84 | C |
| ATOM | 15911 | C   | THR | B | 500 | −56.940 | −28.671 | −15.565 | 1.00 | 21.20 | C |
| ATOM | 15912 | O   | THR | B | 500 | −57.120 | −27.939 | −16.536 | 1.00 | 21.06 | O |
| ATOM | 15914 | N   | ALA | B | 501 | −55.845 | −29.414 | −15.422 | 1.00 | 19.88 | N |
| ATOM | 15915 | CA  | ALA | B | 501 | −54.906 | −29.574 | −16.537 | 1.00 | 19.24 | C |
| ATOM | 15917 | CB  | ALA | B | 501 | −53.704 | −30.393 | −16.115 | 1.00 | 19.22 | C |
| ATOM | 15921 | C   | ALA | B | 501 | −55.581 | −30.226 | −17.757 | 1.00 | 18.68 | C |
| ATOM | 15922 | O   | ALA | B | 501 | −55.427 | −29.768 | −18.881 | 1.00 | 18.32 | O |
| ATOM | 15924 | N   | ILE | B | 502 | −56.324 | −31.300 | −17.523 | 1.00 | 18.11 | N |
| ATOM | 15925 | CA  | ILE | B | 502 | −57.023 | −31.988 | −18.591 | 1.00 | 17.68 | C |
| ATOM | 15927 | CB  | ILE | B | 502 | −57.750 | −33.251 | −18.059 | 1.00 | 17.63 | C |
| ATOM | 15929 | CG1 | ILE | B | 502 | −56.713 | −34.350 | −17.769 | 1.00 | 18.16 | C |
| ATOM | 15932 | CD1 | ILE | B | 502 | −57.253 | −35.645 | −17.115 | 1.00 | 17.02 | C |
| ATOM | 15936 | CG2 | ILE | B | 502 | −58.756 | −33.762 | −19.063 | 1.00 | 16.93 | C |
| ATOM | 15940 | C   | ILE | B | 502 | −57.990 | −31.030 | −19.289 | 1.00 | 17.50 | C |
| ATOM | 15941 | O   | ILE | B | 502 | −58.153 | −31.071 | −20.512 | 1.00 | 17.62 | O |
| ATOM | 15943 | N   | ASN | B | 503 | −58.604 | −30.139 | −18.524 | 1.00 | 17.23 | N |
| ATOM | 15944 | CA  | ASN | B | 503 | −59.545 | −29.184 | −19.102 | 1.00 | 17.07 | C |
| ATOM | 15946 | CB  | ASN | B | 503 | −60.184 | −28.327 | −18.016 | 1.00 | 17.21 | C |
| ATOM | 15949 | CG  | ASN | B | 503 | −61.155 | −29.094 | −17.176 | 1.00 | 17.29 | C |
| ATOM | 15950 | OD1 | ASN | B | 503 | −61.721 | −30.097 | −17.609 | 1.00 | 16.66 | O |
| ATOM | 15951 | ND2 | ASN | B | 503 | −61.365 | −28.621 | −15.958 | 1.00 | 19.16 | N |
| ATOM | 15954 | C   | ASN | B | 503 | −58.920 | −28.270 | −20.149 | 1.00 | 16.59 | C |
| ATOM | 15955 | O   | ASN | B | 503 | −59.611 | −27.811 | −21.071 | 1.00 | 16.67 | O |
| ATOM | 15957 | N   | LEU | B | 504 | −57.629 | −27.992 | −20.014 | 1.00 | 15.79 | N |
| ATOM | 15958 | CA  | LEU | B | 504 | −56.948 | −27.204 | −21.031 | 1.00 | 15.44 | C |
| ATOM | 15960 | CB  | LEU | B | 504 | −55.530 | −26.865 | −20.609 | 1.00 | 15.07 | C |
| ATOM | 15963 | CG  | LEU | B | 504 | −54.933 | −25.837 | −21.552 | 1.00 | 14.21 | C |
| ATOM | 15965 | CD1 | LEU | B | 504 | −54.246 | −24.726 | −20.800 | 1.00 | 14.21 | C |
| ATOM | 15969 | CD2 | LEU | B | 504 | −54.000 | −26.538 | −22.462 | 1.00 | 14.27 | C |
| ATOM | 15973 | C   | LEU | B | 504 | −56.954 | −27.933 | −22.375 | 1.00 | 15.59 | C |
| ATOM | 15974 | O   | LEU | B | 504 | −57.177 | −27.323 | −23.414 | 1.00 | 15.30 | O |
| ATOM | 15976 | N   | ALA | B | 505 | −56.732 | −29.242 | −22.341 | 1.00 | 15.89 | N |
| ATOM | 15977 | CA  | ALA | B | 505 | −56.914 | −30.073 | −23.514 | 1.00 | 16.23 | C |

TABLE 16-7-continued

| | | | | | | | | | | | |
|---|---|---|---|---|---|---|---|---|---|---|---|
| ATOM | 15979 | CB | ALA | B | 505 | −56.608 | −31.483 | −23.188 | 1.00 | 16.05 | C |
| ATOM | 15983 | C | ALA | B | 505 | −58.352 | −29.955 | −24.010 | 1.00 | 16.69 | C |
| ATOM | 15984 | O | ALA | B | 505 | −58.598 | −29.738 | −25.204 | 1.00 | 16.88 | O |
| ATOM | 15986 | N | ARG | B | 506 | −59.300 | −30.071 | −23.090 | 1.00 | 16.88 | N |
| ATOM | 15987 | CA | ARG | B | 506 | −60.709 | −29.972 | −23.457 | 1.00 | 17.20 | C |
| ATOM | 15989 | CB | ARG | B | 506 | −61.630 | −30.170 | −22.248 | 1.00 | 17.34 | C |
| ATOM | 15992 | CG | ARG | B | 506 | −61.549 | −31.537 | −21.614 | 1.00 | 17.46 | C |
| ATOM | 15995 | CD | ARG | B | 506 | −62.837 | −31.917 | −20.962 | 1.00 | 17.48 | C |
| ATOM | 15998 | NE | ARG | B | 506 | −62.783 | −33.280 | −20.435 | 1.00 | 18.37 | N |
| ATOM | 16000 | CZ | ARG | B | 506 | −62.404 | −33.613 | −19.201 | 1.00 | 19.03 | C |
| ATOM | 16001 | NH1 | ARG | B | 506 | −62.008 | −32.690 | −18.324 | 1.00 | 18.83 | N |
| ATOM | 16004 | NH2 | ARG | B | 506 | −62.415 | −34.892 | −18.841 | 1.00 | 19.72 | N |
| ATOM | 16007 | C | ARG | B | 506 | −61.038 | −28.646 | −24.114 | 1.00 | 17.32 | C |
| ATOM | 16008 | O | ARG | B | 506 | −61.754 | −28.622 | −25.111 | 1.00 | 17.41 | O |
| ATOM | 16010 | N | GLN | B | 507 | −60.540 | −27.543 | −23.564 | 1.00 | 17.59 | N |
| ATOM | 16011 | CA | GLN | B | 507 | −60.864 | −26.233 | −24.139 | 1.00 | 18.05 | C |
| ATOM | 16013 | CB | GLN | B | 507 | −60.382 | −25.090 | −23.258 | 1.00 | 18.16 | C |
| ATOM | 16016 | CG | GLN | B | 507 | −60.798 | −23.709 | −23.764 | 1.00 | 17.57 | C |
| ATOM | 16019 | CD | GLN | B | 507 | −62.291 | −23.508 | −23.723 | 1.00 | 17.42 | C |
| ATOM | 16020 | OE1 | GLN | B | 507 | −62.953 | −23.959 | −22.800 | 1.00 | 17.55 | O |
| ATOM | 16021 | NE2 | GLN | B | 507 | −62.832 | −22.823 | −24.722 | 1.00 | 17.56 | N |
| ATOM | 16024 | C | GLN | B | 507 | −60.258 | −26.060 | −25.521 | 1.00 | 18.49 | C |
| ATOM | 16025 | O | GLN | B | 507 | −60.855 | −25.413 | −26.380 | 1.00 | 18.73 | O |
| ATOM | 16027 | N | SER | B | 508 | −59.066 | −26.619 | −25.724 | 1.00 | 18.85 | N |
| ATOM | 16028 | CA | SER | B | 508 | −58.427 | −26.621 | −27.037 | 1.00 | 19.07 | C |
| ATOM | 16030 | CB | SER | B | 508 | −57.108 | −27.364 | −26.969 | 1.00 | 19.04 | C |
| ATOM | 16033 | OG | SER | B | 508 | −56.304 | −26.772 | −25.979 | 1.00 | 20.10 | O |
| ATOM | 16035 | C | SER | B | 508 | −59.305 | −27.296 | −28.065 | 1.00 | 19.12 | C |
| ATOM | 16036 | O | SER | B | 508 | −59.438 | −26.827 | −29.187 | 1.00 | 19.00 | O |
| ATOM | 16038 | N | HIS | B | 509 | −59.905 | −28.409 | −27.674 | 1.00 | 19.26 | N |
| ATOM | 16039 | CA | HIS | B | 509 | −60.814 | −29.095 | −28.559 | 1.00 | 19.33 | C |
| ATOM | 16041 | CB | HIS | B | 509 | −61.275 | −30.412 | −27.959 | 1.00 | 19.30 | C |
| ATOM | 16044 | CG | HIS | B | 509 | −60.263 | −31.501 | −28.067 | 1.00 | 18.71 | C |
| ATOM | 16045 | ND1 | HIS | B | 509 | −59.941 | −32.089 | −29.267 | 1.00 | 18.57 | N |
| ATOM | 16047 | CE1 | HIS | B | 509 | −59.020 | −33.012 | −29.064 | 1.00 | 19.07 | C |
| ATOM | 16049 | NE2 | HIS | B | 509 | −58.738 | −33.044 | −27.774 | 1.00 | 18.52 | N |
| ATOM | 16051 | CD2 | HIS | B | 509 | −59.499 | −32.105 | −27.129 | 1.00 | 18.43 | C |
| ATOM | 16053 | C | HIS | B | 509 | −62.017 | −28.251 | −28.878 | 1.00 | 19.60 | C |
| ATOM | 16054 | O | HIS | B | 509 | −62.491 | −28.286 | −29.969 | 1.00 | 19.68 | O |
| ATOM | 16056 | N | CYS | B | 510 | −62.540 | −27.502 | −27.932 | 1.00 | 20.12 | N |
| ATOM | 16057 | CA | CYS | B | 510 | −63.748 | −26.738 | −28.216 | 1.00 | 20.63 | C |
| ATOM | 16059 | CB | CYS | B | 510 | −64.493 | −26.492 | −26.915 | 1.00 | 20.70 | C |
| ATOM | 16062 | SG | CYS | B | 510 | −64.856 | −28.020 | −26.065 | 1.00 | 22.93 | S |
| ATOM | 16064 | C | CYS | B | 510 | −63.465 | −25.422 | −28.950 | 1.00 | 20.55 | C |
| ATOM | 16065 | O | CYS | B | 510 | −64.338 | −24.881 | −29.622 | 1.00 | 20.16 | O |
| ATOM | 16067 | N | THR | B | 511 | −62.236 | −24.933 | −28.827 | 1.00 | 20.89 | N |
| ATOM | 16068 | CA | THR | B | 511 | −61.833 | −23.654 | −29.378 | 1.00 | 21.32 | C |
| ATOM | 16070 | CB | THR | B | 511 | −60.682 | −23.107 | −28.550 | 1.00 | 20.76 | C |
| ATOM | 16072 | OG1 | THR | B | 511 | −61.208 | −22.619 | −27.324 | 1.00 | 19.50 | O |
| ATOM | 16074 | CG2 | THR | B | 511 | −59.961 | −21.994 | −29.253 | 1.00 | 19.79 | C |
| ATOM | 16078 | C | THR | B | 511 | −61.417 | −23.735 | −30.851 | 1.00 | 23.11 | C |
| ATOM | 16079 | O | THR | B | 511 | −61.910 | −22.992 | −31.694 | 1.00 | 22.75 | O |
| ATOM | 16081 | N | TYR | B | 512 | −60.501 | −24.646 | −31.152 | 1.00 | 25.46 | N |
| ATOM | 16082 | CA | TYR | B | 512 | −59.867 | −24.704 | −32.462 | 1.00 | 27.09 | C |
| ATOM | 16084 | CB | TYR | B | 512 | −58.397 | −25.107 | −32.327 | 1.00 | 27.16 | C |
| ATOM | 16087 | CG | TYR | B | 512 | −57.598 | −24.056 | −31.582 | 1.00 | 27.26 | C |
| ATOM | 16088 | CD1 | TYR | B | 512 | −57.300 | −22.834 | −32.182 | 1.00 | 28.18 | C |
| ATOM | 16090 | CE1 | TYR | B | 512 | −56.583 | −21.844 | −31.511 | 1.00 | 27.98 | C |
| ATOM | 16092 | CZ | TYR | B | 512 | −56.164 | −22.068 | −30.226 | 1.00 | 27.72 | C |
| ATOM | 16093 | OH | TYR | B | 512 | −55.462 | −21.072 | −29.584 | 1.00 | 27.09 | O |
| ATOM | 16095 | CE2 | TYR | B | 512 | −56.453 | −23.281 | −29.602 | 1.00 | 27.52 | C |
| ATOM | 16097 | CD2 | TYR | B | 512 | −57.171 | −24.262 | −30.278 | 1.00 | 26.68 | C |
| ATOM | 16099 | C | TYR | B | 512 | −60.633 | −25.623 | −33.382 | 1.00 | 28.79 | C |
| ATOM | 16100 | O | TYR | B | 512 | −61.050 | −25.179 | −34.444 | 1.00 | 28.98 | O |
| ATOM | 16102 | N | HIS | B | 513 | −60.789 | −26.893 | −32.991 | 1.00 | 31.06 | N |
| ATOM | 16103 | CA | HIS | B | 513 | −61.865 | −27.800 | −33.492 | 1.00 | 33.07 | C |
| ATOM | 16105 | CB | HIS | B | 513 | −62.740 | −28.208 | −32.265 | 1.00 | 33.66 | C |
| ATOM | 16108 | CG | HIS | B | 513 | −64.181 | −28.602 | −32.535 | 1.00 | 34.73 | C |
| ATOM | 16109 | ND1 | HIS | B | 513 | −65.035 | −27.903 | −33.367 | 1.00 | 35.70 | N |
| ATOM | 16111 | CE1 | HIS | B | 513 | −66.234 | −28.464 | −33.343 | 1.00 | 35.40 | C |
| ATOM | 16113 | NE2 | HIS | B | 513 | −66.206 | −29.469 | −32.491 | 1.00 | 35.10 | N |
| ATOM | 16115 | CD2 | HIS | B | 513 | −64.943 | −29.565 | −31.956 | 1.00 | 35.07 | C |
| ATOM | 16117 | C | HIS | B | 513 | −62.692 | −27.179 | −34.623 | 1.00 | 34.03 | C |
| ATOM | 16118 | O | HIS | B | 513 | −63.003 | −27.848 | −35.627 | 1.00 | 34.55 | O |
| ATOM | 16120 | N | ASN | B | 514 | −63.047 | −25.906 | −34.444 | 1.00 | 34.65 | N |
| ATOM | 16121 | CA | ASN | B | 514 | −63.713 | −25.123 | −35.483 | 1.00 | 35.15 | C |
| ATOM | 16123 | CB | ASN | B | 514 | −63.845 | −23.643 | −35.070 | 1.00 | 35.01 | C |
| ATOM | 16126 | CG | ASN | B | 514 | −64.704 | −23.456 | −33.820 | 1.00 | 33.48 | C |

TABLE 16-7-continued

Coordinates of *P. tremuloides* IspS

| ATOM | 16127 | OD1 | ASN | B | 514 | −64.787 | −24.343 | −32.968 | 1.00 | 30.92 | O |
|------|-------|-----|-----|---|-----|---------|---------|---------|------|-------|---|
| ATOM | 16128 | ND2 | ASN | B | 514 | −65.327 | −22.295 | −33.703 | 1.00 | 32.16 | N |
| ATOM | 16131 | C   | ASN | B | 514 | −63.192 | −25.274 | −36.942 | 1.00 | 36.08 | C |
| ATOM | 16132 | O   | ASN | B | 514 | −62.010 | −25.051 | −37.254 | 1.00 | 35.69 | O |
| ATOM | 16134 | N   | GLY | B | 515 | −64.119 | −25.765 | −37.772 | 1.00 | 37.15 | N |
| ATOM | 16135 | CA  | GLY | B | 515 | −64.224 | −25.493 | −39.177 | 1.00 | 37.94 | C |
| ATOM | 16138 | C   | GLY | B | 515 | −65.269 | −24.384 | −39.284 | 1.00 | 39.01 | C |
| ATOM | 16139 | O   | GLY | B | 515 | −64.904 | −23.286 | −39.702 | 1.00 | 39.58 | O |
| ATOM | 16141 | N   | ASP | B | 516 | −66.550 | −24.585 | −38.909 | 1.00 | 39.95 | N |
| ATOM | 16142 | CA  | ASP | B | 516 | −67.167 | −25.810 | −38.349 | 1.00 | 40.65 | C |
| ATOM | 16144 | CB  | ASP | B | 516 | −67.296 | −25.652 | −36.836 | 1.00 | 41.09 | C |
| ATOM | 16147 | CG  | ASP | B | 516 | −66.318 | −26.511 | −36.063 | 1.00 | 43.63 | C |
| ATOM | 16148 | OD1 | ASP | B | 516 | −65.697 | −27.434 | −36.662 | 1.00 | 45.83 | O |
| ATOM | 16149 | OD2 | ASP | B | 516 | −66.152 | −26.246 | −34.843 | 1.00 | 47.12 | O |
| ATOM | 16150 | C   | ASP | B | 516 | −68.603 | −26.067 | −38.853 | 1.00 | 40.78 | C |
| ATOM | 16151 | O   | ASP | B | 516 | −69.134 | −25.301 | −39.660 | 1.00 | 41.28 | O |
| ATOM | 16153 | N   | ALA | B | 517 | −69.222 | −27.141 | −38.349 | 1.00 | 40.66 | N |
| ATOM | 16154 | CA  | ALA | B | 517 | −70.675 | −27.396 | −38.468 | 1.00 | 40.60 | C |
| ATOM | 16156 | CB  | ALA | B | 517 | −71.422 | −26.622 | −37.359 | 1.00 | 40.27 | C |
| ATOM | 16160 | C   | ALA | B | 517 | −71.295 | −27.106 | −39.862 | 1.00 | 40.79 | C |
| ATOM | 16161 | O   | ALA | B | 517 | −70.654 | −27.296 | −40.899 | 1.00 | 40.67 | O |
| ATOM | 16163 | N   | HIS | B | 518 | −72.562 | −26.696 | −39.874 | 1.00 | 41.13 | N |
| ATOM | 16164 | CA  | HIS | B | 518 | −73.162 | −26.033 | −41.039 | 1.00 | 41.60 | C |
| ATOM | 16166 | CB  | HIS | B | 518 | −74.446 | −26.756 | −41.480 | 1.00 | 42.24 | C |
| ATOM | 16169 | CG  | HIS | B | 518 | −74.207 | −28.179 | −41.910 | 1.00 | 45.54 | C |
| ATOM | 16170 | ND1 | HIS | B | 518 | −73.441 | −28.509 | −43.012 | 1.00 | 48.51 | N |
| ATOM | 16172 | CE1 | HIS | B | 518 | −73.392 | −29.825 | −43.140 | 1.00 | 48.79 | C |
| ATOM | 16174 | NE2 | HIS | B | 518 | −74.092 | −30.364 | −42.156 | 1.00 | 49.12 | N |
| ATOM | 16176 | CD2 | HIS | B | 518 | −74.608 | −29.357 | −41.369 | 1.00 | 48.28 | C |
| ATOM | 16178 | C   | HIS | B | 518 | −73.377 | −24.545 | −40.686 | 1.00 | 40.84 | C |
| ATOM | 16179 | O   | HIS | B | 518 | −74.487 | −23.997 | −40.769 | 1.00 | 40.60 | O |
| ATOM | 16181 | N   | THR | B | 519 | −72.261 | −23.932 | −40.275 | 1.00 | 40.10 | N |
| ATOM | 16182 | CA  | THR | B | 519 | −72.143 | −22.521 | −39.878 | 1.00 | 39.39 | C |
| ATOM | 16184 | CB  | THR | B | 519 | −72.561 | −22.263 | −38.393 | 1.00 | 39.40 | C |
| ATOM | 16186 | OG1 | THR | B | 519 | −71.823 | −23.131 | −37.517 | 1.00 | 39.55 | O |
| ATOM | 16188 | CG2 | THR | B | 519 | −74.074 | −22.460 | −38.178 | 1.00 | 38.98 | C |
| ATOM | 16192 | C   | THR | B | 519 | −70.654 | −22.164 | −40.059 | 1.00 | 38.81 | C |
| ATOM | 16193 | O   | THR | B | 519 | −69.800 | −23.050 | −40.067 | 1.00 | 38.48 | O |
| ATOM | 16195 | N   | SER | B | 520 | −70.338 | −20.881 | −40.199 | 1.00 | 38.19 | N |
| ATOM | 16196 | CA  | SER | B | 520 | −68.959 | −20.453 | −40.521 | 1.00 | 37.77 | C |
| ATOM | 16198 | CB  | SER | B | 520 | −68.983 | −18.976 | −40.960 | 1.00 | 37.76 | C |
| ATOM | 16201 | OG  | SER | B | 520 | −68.760 | −18.106 | −39.870 | 1.00 | 38.49 | O |
| ATOM | 16203 | C   | SER | B | 520 | −67.974 | −20.724 | −39.340 | 1.00 | 37.24 | C |
| ATOM | 16204 | O   | SER | B | 520 | −68.394 | −21.267 | −38.320 | 1.00 | 36.89 | O |
| ATOM | 16206 | N   | PRO | B | 521 | −66.671 | −20.350 | −39.472 | 1.00 | 36.96 | N |
| ATOM | 16207 | CA  | PRO | B | 521 | −65.692 | −20.638 | −38.396 | 1.00 | 36.80 | C |
| ATOM | 16209 | CB  | PRO | B | 521 | −64.320 | −20.354 | −39.041 | 1.00 | 36.68 | C |
| ATOM | 16212 | CG  | PRO | B | 521 | −64.599 | −19.593 | −40.309 | 1.00 | 37.19 | C |
| ATOM | 16215 | CD  | PRO | B | 521 | −66.091 | −19.469 | −40.507 | 1.00 | 37.10 | C |
| ATOM | 16218 | C   | PRO | B | 521 | −65.915 | −19.763 | −37.168 | 1.00 | 36.68 | C |
| ATOM | 16219 | O   | PRO | B | 521 | −66.233 | −20.289 | −36.105 | 1.00 | 36.90 | O |
| ATOM | 16220 | N   | ASP | B | 522 | −65.744 | −18.445 | −37.298 | 1.00 | 36.61 | N |
| ATOM | 16221 | CA  | ASP | B | 522 | −66.373 | −17.528 | −36.347 | 1.00 | 36.58 | C |
| ATOM | 16223 | CB  | ASP | B | 522 | −65.938 | −16.070 | −36.543 | 1.00 | 36.82 | C |
| ATOM | 16226 | CG  | ASP | B | 522 | −64.456 | −15.846 | −36.243 | 1.00 | 37.94 | C |
| ATOM | 16227 | OD1 | ASP | B | 522 | −63.848 | −16.627 | −35.473 | 1.00 | 39.62 | O |
| ATOM | 16228 | OD2 | ASP | B | 522 | −63.891 | −14.876 | −36.790 | 1.00 | 39.40 | O |
| ATOM | 16229 | C   | ASP | B | 522 | −67.836 | −17.718 | −36.681 | 1.00 | 36.12 | C |
| ATOM | 16230 | O   | ASP | B | 522 | −68.150 | −18.306 | −37.702 | 1.00 | 35.98 | O |
| ATOM | 16232 | N   | GLU | B | 523 | −68.732 | −17.249 | −35.830 | 1.00 | 35.69 | N |
| ATOM | 16233 | CA  | GLU | B | 523 | −70.152 | −17.605 | −35.927 | 1.00 | 35.46 | C |
| ATOM | 16235 | CB  | GLU | B | 523 | −70.703 | −17.560 | −37.379 | 1.00 | 35.51 | C |
| ATOM | 16238 | CG  | GLU | B | 523 | −70.535 | −16.175 | −38.061 | 1.00 | 36.11 | C |
| ATOM | 16241 | CD  | GLU | B | 523 | −70.854 | −16.136 | −39.572 | 1.00 | 36.72 | C |
| ATOM | 16242 | OE1 | GLU | B | 523 | −71.848 | −16.767 | −40.013 | 1.00 | 37.20 | O |
| ATOM | 16243 | OE2 | GLU | B | 523 | −70.101 | −15.452 | −40.314 | 1.00 | 35.53 | O |
| ATOM | 16244 | C   | GLU | B | 523 | −70.440 | −18.943 | −35.216 | 1.00 | 34.97 | C |
| ATOM | 16245 | O   | GLU | B | 523 | −71.557 | −19.148 | −34.765 | 1.00 | 35.02 | O |
| ATOM | 16247 | N   | LEU | B | 524 | −69.462 | −19.846 | −35.099 | 1.00 | 34.59 | N |
| ATOM | 16248 | CA  | LEU | B | 524 | −69.503 | −20.832 | −34.004 | 1.00 | 34.45 | C |
| ATOM | 16250 | CB  | LEU | B | 524 | −68.735 | −22.136 | −34.286 | 1.00 | 34.21 | C |
| ATOM | 16253 | CG  | LEU | B | 524 | −69.530 | −23.434 | −34.508 | 1.00 | 33.92 | C |
| ATOM | 16255 | CD1 | LEU | B | 524 | −68.657 | −24.627 | −34.227 | 1.00 | 32.21 | C |
| ATOM | 16259 | CD2 | LEU | B | 524 | −70.794 | −23.520 | −33.641 | 1.00 | 34.06 | C |
| ATOM | 16263 | C   | LEU | B | 524 | −68.901 | −20.162 | −32.791 | 1.00 | 34.38 | C |
| ATOM | 16264 | O   | LEU | B | 524 | −69.535 | −20.067 | −31.741 | 1.00 | 34.49 | O |
| ATOM | 16266 | N   | THR | B | 525 | −67.670 | −19.688 | −32.958 | 1.00 | 34.30 | N |
| ATOM | 16267 | CA  | THR | B | 525 | −66.913 | −19.073 | −31.874 | 1.00 | 34.23 | C |

TABLE 16-7-continued

Coordinates of *P. tremuloides* IspS

| ATOM | 16269 | CB | THR | B | 525 | −65.570 | −18.524 | −32.380 | 1.00 | 34.04 | C |
|---|---|---|---|---|---|---|---|---|---|---|---|
| ATOM | 16271 | OG1 | THR | B | 525 | −64.894 | −19.549 | −33.112 | 1.00 | 33.83 | O |
| ATOM | 16273 | CG2 | THR | B | 525 | −64.689 | −18.087 | −31.227 | 1.00 | 33.37 | C |
| ATOM | 16277 | C | THR | B | 525 | −67.702 | −17.960 | −31.184 | 1.00 | 34.46 | C |
| ATOM | 16278 | O | THR | B | 525 | −67.684 | −17.858 | −29.955 | 1.00 | 34.57 | O |
| ATOM | 16280 | N | ARG | B | 526 | −68.401 | −17.144 | −31.969 | 1.00 | 34.54 | N |
| ATOM | 16281 | CA | ARG | B | 526 | −69.200 | −16.056 | −31.418 | 1.00 | 34.60 | C |
| ATOM | 16283 | CB | ARG | B | 526 | −69.571 | −15.059 | −32.513 | 1.00 | 35.04 | C |
| ATOM | 16286 | CG | ARG | B | 526 | −70.256 | −13.800 | −32.013 | 1.00 | 37.13 | C |
| ATOM | 16289 | CD | ARG | B | 526 | −70.143 | −12.656 | −33.026 | 1.00 | 39.87 | C |
| ATOM | 16292 | NE | ARG | B | 526 | −70.353 | −13.075 | −34.420 | 1.00 | 42.28 | N |
| ATOM | 16294 | CZ | ARG | B | 526 | −71.543 | −13.292 | −35.000 | 1.00 | 44.26 | C |
| ATOM | 16295 | NH1 | ARG | B | 526 | −72.685 | −13.159 | −34.320 | 1.00 | 44.66 | N |
| ATOM | 16298 | NH2 | ARG | B | 526 | −71.593 | −13.658 | −36.279 | 1.00 | 44.49 | N |
| ATOM | 16301 | C | ARG | B | 526 | −70.448 | −16.593 | −30.735 | 1.00 | 33.91 | C |
| ATOM | 16302 | O | ARG | B | 526 | −70.848 | −16.074 | −29.704 | 1.00 | 33.74 | O |
| ATOM | 16304 | N | LYS | B | 527 | −71.048 | −17.637 | −31.306 | 1.00 | 33.39 | N |
| ATOM | 16305 | CA | LYS | B | 527 | −72.240 | −18.252 | −30.722 | 1.00 | 33.15 | C |
| ATOM | 16307 | CB | LYS | B | 527 | −72.837 | −19.332 | −31.639 | 1.00 | 33.42 | C |
| ATOM | 16310 | CG | LYS | B | 527 | −73.898 | −18.804 | −32.609 | 1.00 | 34.55 | C |
| ATOM | 16313 | CD | LYS | B | 527 | −74.643 | −19.919 | −33.358 | 1.00 | 35.43 | C |
| ATOM | 16316 | CE | LYS | B | 527 | −75.230 | −19.383 | −34.667 | 1.00 | 36.11 | C |
| ATOM | 16319 | NZ | LYS | B | 527 | −76.076 | −20.372 | −35.384 | 1.00 | 37.04 | N |
| ATOM | 16323 | C | LYS | B | 527 | −71.925 | −18.865 | −29.378 | 1.00 | 32.36 | C |
| ATOM | 16324 | O | LYS | B | 527 | −72.589 | −18.584 | −28.387 | 1.00 | 32.56 | O |
| ATOM | 16326 | N | ARG | B | 528 | −70.909 | −19.713 | −29.358 | 1.00 | 31.53 | N |
| ATOM | 16327 | CA | ARG | B | 528 | −70.502 | −20.401 | −28.138 | 1.00 | 30.77 | C |
| ATOM | 16329 | CB | ARG | B | 528 | −69.283 | −21.286 | −28.414 | 1.00 | 30.55 | C |
| ATOM | 16332 | CG | ARG | B | 528 | −69.624 | −22.519 | −29.252 | 1.00 | 29.48 | C |
| ATOM | 16335 | CD | ARG | B | 528 | −68.418 | −23.417 | −29.493 | 1.00 | 28.05 | C |
| ATOM | 16338 | NE | ARG | B | 528 | −68.811 | −24.774 | −29.880 | 1.00 | 26.55 | N |
| ATOM | 16340 | CZ | ARG | B | 528 | −67.968 | −25.719 | −30.288 | 1.00 | 25.87 | C |
| ATOM | 16341 | NH1 | ARG | B | 528 | −66.668 | −25.472 | −30.385 | 1.00 | 26.33 | N |
| ATOM | 16344 | NH2 | ARG | B | 528 | −68.424 | −26.920 | −30.615 | 1.00 | 25.49 | N |
| ATOM | 16347 | C | ARG | B | 528 | −70.225 | −19.415 | −27.004 | 1.00 | 30.42 | C |
| ATOM | 16348 | O | ARG | B | 528 | −70.721 | −19.582 | −25.885 | 1.00 | 30.30 | O |
| ATOM | 16350 | N | VAL | B | 529 | −69.455 | −18.376 | −27.307 | 1.00 | 29.96 | N |
| ATOM | 16351 | CA | VAL | B | 529 | −69.194 | −17.312 | −26.342 | 1.00 | 29.47 | C |
| ATOM | 16353 | CB | VAL | B | 529 | −68.261 | −16.227 | −26.932 | 1.00 | 29.40 | C |
| ATOM | 16355 | CG1 | VAL | B | 529 | −68.269 | −14.968 | −26.081 | 1.00 | 29.18 | C |
| ATOM | 16359 | CG2 | VAL | B | 529 | −66.845 | −16.782 | −27.062 | 1.00 | 28.90 | C |
| ATOM | 16363 | C | VAL | B | 529 | −70.516 | −16.723 | −25.841 | 1.00 | 28.98 | C |
| ATOM | 16364 | O | VAL | B | 529 | −70.759 | −16.682 | −24.641 | 1.00 | 28.97 | O |
| ATOM | 16366 | N | LEU | B | 530 | −71.384 | −16.308 | −26.752 | 1.00 | 28.54 | N |
| ATOM | 16367 | CA | LEU | B | 530 | −72.709 | −15.824 | −26.353 | 1.00 | 28.23 | C |
| ATOM | 16369 | CB | LEU | B | 530 | −73.631 | −15.604 | −27.559 | 1.00 | 28.09 | C |
| ATOM | 16372 | CG | LEU | B | 530 | −73.767 | −14.150 | −28.007 | 1.00 | 28.15 | C |
| ATOM | 16374 | CD1 | LEU | B | 530 | −72.412 | −13.570 | −28.406 | 1.00 | 27.99 | C |
| ATOM | 16378 | CD2 | LEU | B | 530 | −74.784 | −14.034 | −29.150 | 1.00 | 28.85 | C |
| ATOM | 16382 | C | LEU | B | 530 | −73.389 | −16.767 | −25.367 | 1.00 | 27.88 | C |
| ATOM | 16383 | O | LEU | B | 530 | −73.932 | −16.319 | −24.363 | 1.00 | 28.11 | O |
| ATOM | 16385 | N | SER | B | 531 | −73.352 | −18.066 | −25.652 | 1.00 | 27.28 | N |
| ATOM | 16386 | CA | SER | B | 531 | −74.081 | −19.049 | −24.849 | 1.00 | 26.68 | C |
| ATOM | 16388 | CB | SER | B | 531 | −74.209 | −20.363 | −25.612 | 1.00 | 26.68 | C |
| ATOM | 16391 | OG | SER | B | 531 | −72.970 | −21.033 | −25.681 | 1.00 | 26.67 | O |
| ATOM | 16393 | C | SER | B | 531 | −73.410 | −19.312 | −23.514 | 1.00 | 26.20 | C |
| ATOM | 16394 | O | SER | B | 531 | −74.076 | −19.550 | −22.511 | 1.00 | 25.86 | O |
| ATOM | 16396 | N | VAL | B | 532 | −72.085 | −19.281 | −23.512 | 1.00 | 25.86 | N |
| ATOM | 16397 | CA | VAL | B | 532 | −71.320 | −19.562 | −22.306 | 1.00 | 25.51 | C |
| ATOM | 16399 | CB | VAL | B | 532 | −69.891 | −20.055 | −22.651 | 1.00 | 25.34 | C |
| ATOM | 16401 | CG1 | VAL | B | 532 | −68.955 | −19.932 | −21.460 | 1.00 | 24.01 | C |
| ATOM | 16405 | CG2 | VAL | B | 532 | −69.950 | −21.484 | −23.158 | 1.00 | 24.95 | C |
| ATOM | 16409 | C | VAL | B | 532 | −71.271 | −18.357 | −21.373 | 1.00 | 25.52 | C |
| ATOM | 16410 | O | VAL | B | 532 | −71.377 | −18.523 | −20.164 | 1.00 | 25.82 | O |
| ATOM | 16412 | N | ILE | B | 533 | −71.137 | −17.158 | −21.935 | 1.00 | 25.39 | N |
| ATOM | 16413 | CA | ILE | B | 533 | −70.875 | −15.954 | −21.151 | 1.00 | 25.48 | C |
| ATOM | 16415 | CB | ILE | B | 533 | −69.666 | −15.185 | −21.732 | 1.00 | 25.30 | C |
| ATOM | 16417 | CG1 | ILE | B | 533 | −68.375 | −15.928 | −21.451 | 1.00 | 24.91 | C |
| ATOM | 16420 | CD1 | ILE | B | 533 | −68.118 | −16.120 | −19.989 | 1.00 | 25.00 | C |
| ATOM | 16424 | CG2 | ILE | B | 533 | −69.553 | −13.797 | −21.130 | 1.00 | 25.81 | C |
| ATOM | 16428 | C | ILE | B | 533 | −72.065 | −14.983 | −21.030 | 1.00 | 25.77 | C |
| ATOM | 16429 | O | ILE | B | 533 | −72.537 | −14.707 | −19.928 | 1.00 | 25.77 | O |
| ATOM | 16431 | N | THR | B | 534 | −72.541 | −14.442 | −22.142 | 1.00 | 25.98 | N |
| ATOM | 16432 | CA | THR | B | 534 | −73.446 | −13.295 | −22.064 | 1.00 | 26.31 | C |
| ATOM | 16434 | CB | THR | B | 534 | −73.094 | −12.253 | −23.143 | 1.00 | 26.21 | C |
| ATOM | 16436 | OG1 | THR | B | 534 | −72.914 | −12.909 | −24.397 | 1.00 | 26.72 | O |
| ATOM | 16438 | CG2 | THR | B | 534 | −71.795 | −11.535 | −22.781 | 1.00 | 25.97 | C |
| ATOM | 16442 | C | THR | B | 534 | −74.961 | −13.621 | −22.064 | 1.00 | 26.50 | C |

TABLE 16-7-continued

Coordinates of *P. tremuloides* IspS

| ATOM | 16443 | O   | THR | B | 534 | −75.713 | −12.974 | −21.344 | 1.00 | 26.67 | O  |
|------|-------|-----|-----|---|-----|---------|---------|---------|------|-------|----|
| ATOM | 16445 | N   | GLU | B | 535 | −75.410 | −14.616 | −22.829 | 1.00 | 26.55 | N  |
| ATOM | 16446 | CA  | GLU | B | 535 | −76.851 | −14.892 | −22.961 | 1.00 | 26.50 | C  |
| ATOM | 16448 | CB  | GLU | B | 535 | −77.197 | −15.197 | −24.426 | 1.00 | 26.68 | C  |
| ATOM | 16451 | CG  | GLU | B | 535 | −77.226 | −13.936 | −25.296 | 1.00 | 27.68 | C  |
| ATOM | 16454 | CD  | GLU | B | 535 | −78.193 | −14.014 | −26.475 | 1.00 | 28.75 | C  |
| ATOM | 16455 | OE1 | GLU | B | 535 | −79.370 | −13.588 | −26.330 | 1.00 | 27.72 | O  |
| ATOM | 16456 | OE2 | GLU | B | 535 | −77.762 | −14.492 | −27.549 | 1.00 | 30.06 | O  |
| ATOM | 16457 | C   | GLU | B | 535 | −77.355 | −16.019 | −22.056 | 1.00 | 26.19 | C  |
| ATOM | 16458 | O   | GLU | B | 535 | −77.021 | −17.171 | −22.279 | 1.00 | 26.15 | O  |
| ATOM | 16460 | N   | PRO | B | 536 | −78.186 | −15.697 | −21.047 | 1.00 | 26.05 | N  |
| ATOM | 16461 | CA  | PRO | B | 536 | −78.692 | −16.763 | −20.196 | 1.00 | 26.05 | C  |
| ATOM | 16463 | CB  | PRO | B | 536 | −79.495 | −16.018 | −19.118 | 1.00 | 25.87 | C  |
| ATOM | 16466 | CG  | PRO | B | 536 | −79.140 | −14.621 | −19.239 | 1.00 | 25.88 | C  |
| ATOM | 16469 | CD  | PRO | B | 536 | −78.760 | −14.402 | −20.660 | 1.00 | 26.21 | C  |
| ATOM | 16472 | C   | PRO | B | 536 | −79.608 | −17.717 | −20.943 | 1.00 | 26.14 | C  |
| ATOM | 16473 | O   | PRO | B | 536 | −80.173 | −17.359 | −21.973 | 1.00 | 25.99 | O  |
| ATOM | 16474 | N   | ILE | B | 537 | −79.746 | −18.924 | −20.411 | 1.00 | 26.38 | N  |
| ATOM | 16475 | CA  | ILE | B | 537 | −80.662 | −19.905 | −20.960 | 1.00 | 26.58 | C  |
| ATOM | 16477 | CB  | ILE | B | 537 | −80.443 | −21.292 | −20.333 | 1.00 | 26.47 | C  |
| ATOM | 16479 | CG1 | ILE | B | 537 | −79.023 | −21.789 | −20.600 | 1.00 | 26.38 | C  |
| ATOM | 16482 | CD1 | ILE | B | 537 | −78.709 | −23.102 | −19.907 | 1.00 | 26.40 | C  |
| ATOM | 16486 | CG2 | ILE | B | 537 | −81.430 | −22.300 | −20.890 | 1.00 | 26.71 | C  |
| ATOM | 16490 | C   | ILE | B | 537 | −82.072 | −19.420 | −20.657 | 1.00 | 26.93 | C  |
| ATOM | 16491 | O   | ILE | B | 537 | −82.347 | −18.965 | −19.545 | 1.00 | 26.81 | O  |
| ATOM | 16493 | N   | LEU | B | 538 | −82.963 | −19.491 | −21.641 | 1.00 | 27.36 | N  |
| ATOM | 16494 | CA  | LEU | B | 538 | −84.309 | −18.984 | −21.439 | 1.00 | 27.68 | C  |
| ATOM | 16496 | CB  | LEU | B | 538 | −85.181 | −19.094 | −22.698 | 1.00 | 27.75 | C  |
| ATOM | 16499 | CG  | LEU | B | 538 | −84.782 | −18.291 | −23.949 | 1.00 | 27.47 | C  |
| ATOM | 16501 | CD1 | LEU | B | 538 | −85.992 | −18.109 | −24.844 | 1.00 | 27.11 | C  |
| ATOM | 16505 | CD2 | LEU | B | 538 | −84.164 | −16.933 | −23.621 | 1.00 | 26.99 | C  |
| ATOM | 16509 | C   | LEU | B | 538 | −84.919 | −19.752 | −20.288 | 1.00 | 28.01 | C  |
| ATOM | 16512 | N   | PRO | B | 539 | −85.645 | −19.046 | −19.421 | 1.00 | 28.69 | N  |
| ATOM | 16513 | CA  | PRO | B | 539 | −86.028 | −19.631 | −18.152 | 1.00 | 29.05 | C  |
| ATOM | 16515 | CB  | PRO | B | 539 | −86.640 | −18.452 | −17.397 | 1.00 | 29.08 | C  |
| ATOM | 16518 | CG  | PRO | B | 539 | −87.144 | −17.548 | −18.447 | 1.00 | 28.86 | C  |
| ATOM | 16521 | CD  | PRO | B | 539 | −86.298 | −17.748 | −19.660 | 1.00 | 28.62 | C  |
| ATOM | 16524 | C   | PRO | B | 539 | −87.035 | −20.767 | −18.259 | 1.00 | 29.51 | C  |
| ATOM | 16525 | O   | PRO | B | 539 | −87.665 | −20.970 | −19.297 | 1.00 | 29.23 | O  |
| ATOM | 16526 | N   | PHE | B | 540 | −87.164 | −21.500 | −17.159 | 1.00 | 30.25 | N  |
| ATOM | 16527 | CA  | PHE | B | 540 | −88.089 | −22.613 | −17.070 | 1.00 | 30.56 | C  |
| ATOM | 16529 | CB  | PHE | B | 540 | −87.971 | −23.297 | −15.708 | 1.00 | 30.73 | C  |
| ATOM | 16532 | CG  | PHE | B | 540 | −88.848 | −24.499 | −15.567 | 1.00 | 30.49 | C  |
| ATOM | 16533 | CD1 | PHE | B | 540 | −89.910 | −24.505 | −14.683 | 1.00 | 30.32 | C  |
| ATOM | 16535 | CE1 | PHE | B | 540 | −90.718 | −25.614 | −14.568 | 1.00 | 30.59 | C  |
| ATOM | 16537 | CZ  | PHE | B | 540 | −90.475 | −26.722 | −15.346 | 1.00 | 30.55 | C  |
| ATOM | 16539 | CE2 | PHE | B | 540 | −89.420 | −26.720 | −16.234 | 1.00 | 30.68 | C  |
| ATOM | 16541 | CD2 | PHE | B | 540 | −88.619 | −25.617 | −16.342 | 1.00 | 30.43 | C  |
| ATOM | 16543 | C   | PHE | B | 540 | −89.507 | −22.120 | −17.257 | 1.00 | 30.76 | C  |
| ATOM | 16544 | O   | PHE | B | 540 | −89.967 | −21.257 | −16.508 | 1.00 | 30.59 | O  |
| ATOM | 16546 | N   | GLU | B | 541 | −90.184 | −22.677 | −18.259 | 1.00 | 31.13 | N  |
| ATOM | 16547 | CA  | GLU | B | 541 | −91.553 | −22.289 | −18.608 | 1.00 | 31.45 | C  |
| ATOM | 16549 | CB  | GLU | B | 541 | −91.525 | −21.186 | −19.680 | 1.00 | 31.60 | C  |
| ATOM | 16552 | CG  | GLU | B | 541 | −92.860 | −20.454 | −19.911 | 1.00 | 32.56 | C  |
| ATOM | 16555 | CD  | GLU | B | 541 | −93.773 | −21.133 | −20.935 | 1.00 | 33.64 | C  |
| ATOM | 16556 | OE1 | GLU | B | 541 | −93.261 | −21.922 | −21.771 | 1.00 | 35.06 | O  |
| ATOM | 16557 | OE2 | GLU | B | 541 | −95.002 | −20.868 | −20.901 | 1.00 | 32.44 | O  |
| ATOM | 16558 | C   | GLU | B | 541 | −92.326 | −23.510 | −19.105 | 1.00 | 31.31 | C  |
| ATOM | 16559 | O   | GLU | B | 541 | −92.860 | −24.286 | −18.310 | 1.00 | 31.30 | O  |
| ATOM | 16562 | MG  | MG  | C | 1   | −42.844 |  11.427 |  13.309 | 1.00 | 46.29 | MG |
| ATOM | 16561 | MG  | MG  | C | 2   | −46.615 | −18.454 | −33.231 | 1.00 | 48.45 | MG |
| ATOM | 16563 | O   | HOH | E | 1   | −50.507 |  −5.408 |  −4.491 | 1.00 | 17.42 | O  |
| ATOM | 16566 | O   | HOH | E | 2   | −64.748 | −36.007 | −11.725 | 1.00 |  2.00 | O  |
| ATOM | 16569 | O   | HOH | E | 3   | −40.643 |  −2.220 | −34.996 | 1.00 |  2.00 | O  |
| ATOM | 16572 | O   | HOH | E | 4   | −36.090 |  −9.757 | −37.074 | 1.00 | 17.20 | O  |
| ATOM | 16575 | O   | HOH | E | 5   | −46.117 | −37.662 | −22.916 | 1.00 | 17.03 | O  |
| ATOM | 16578 | O   | HOH | E | 6   | −49.541 |  35.476 |   6.921 | 1.00 | 14.03 | O  |
| ATOM | 16581 | O   | HOH | E | 7   | −32.288 |  27.572 |  16.443 | 1.00 | 13.16 | O  |
| ATOM | 16584 | O   | HOH | E | 8   | −50.706 |  10.207 | −15.061 | 1.00 | 18.73 | O  |
| ATOM | 16587 | O   | HOH | E | 9   | −77.188 |  36.767 |  −9.218 | 1.00 |  8.05 | O  |
| ATOM | 16590 | O   | HOH | E | 10  | −90.260 | −31.248 | −21.071 | 1.00 |  2.00 | O  |
| ATOM | 16593 | O   | HOH | E | 11  | −70.920 | −33.414 |  −3.884 | 1.00 |  9.35 | O  |
| ATOM | 16596 | O   | HOH | E | 12  | −37.761 | −21.294 |  −9.249 | 1.00 | 25.78 | O  |
| ATOM | 16599 | O   | HOH | E | 13  | −76.050 |  23.855 | −18.293 | 1.00 |  2.00 | O  |
| ATOM | 16602 | O   | HOH | E | 14  | −76.876 | −19.575 | −22.856 | 1.00 | 19.25 | O  |
| ATOM | 16605 | O   | HOH | E | 15  | −40.936 |  11.629 | −24.832 | 1.00 | 22.29 | O  |
| ATOM | 16608 | O   | HOH | E | 16  | −85.551 |  34.832 |   3.260 | 1.00 | 25.14 | O  |

TABLE 16-7-continued

| | | | Coordinates of *P. tremuloides* IspS | | | | | | | |
|---|---|---|---|---|---|---|---|---|---|---|
| ATOM | 16611 | O | HOH | E | 17 | −56.825 | 31.771 | −7.464 | 1.00 | 17.27 | O |
| ATOM | 16614 | O | HOH | E | 18 | −76.222 | 39.261 | −.613 | 1.00 | 25.47 | O |

Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention, which are obvious to those skilled in the relevant fields, are intended to be within the scope of the following claims.

We claim:

1. An isolated host cell comprising a heterologous polynucleotide sequence encoding a truncated isoprene synthase variant in operable combination with a promoter, wherein said truncated isoprene synthase variant comprises one or more amino acid substitution(s) at one or more amino acid residues corresponding to a poplar isoprene synthase having the sequence of SEQ ID NO: 120, wherein said substitution(s) are selected from the group consisting of V10M, F12S, T15A, E18G, V58I, V58F, L70Q, L70R, L70V, L70T, T71P, V79L, E89D, G94A, S119F, F120L, G127R, E175V, T212I, S257A, R262G, A266G, F280L, N297K, F305L, L319M, E323K, A328T, D342E, A359T, K366N, E368D, L374M, S396T, V418S, K438N, H440R, T442A, I449V, A469S, K500R, K505Q, G507S, S509N, F511Y, and N532K; and wherein the variant is capable of more effectively converting dimethylallyl diphosphate (DMAPP) to isoprene, as compared to an isoprene synthase variant without a substitution.

2. The host cell of claim 1 wherein at least one amino acid substitution is a L70R substitution.

3. The host cell of claim 1 wherein the variant comprises one of more amino acid substitutions selected from the group consisting of G127R/F511Y, L70Q/G94A/R262G/F305L, F12S/T15A/E18G/N297K, S396T/T442I, V10M/E323K, F120L/A266G, K438N/K500R, V79L/S509N, E175V/S257A/E368D/A469S, T71P/L374M, F280L/H440R, E89D/H440R, V58F/A328T/N532K, S119F/D342E/I449V, and K366N/G507S.

4. The host cell of claim 1 wherein the polynucleotide sequence is contained within a plasmid.

5. The host cell of claim 4 wherein the polynucleotide sequence is integrated into a chromosome of the host cell.

6. The host cell of claim 1 wherein the host is selected from the group consisting of gram-positive bacterial cells, gram-negative bacterial cells, filamentous fungal cells, and yeast cells.

7. The host cell of claim 1 wherein the host is selected from the group consisting of *Escherichia* sp. (*E. coli*), *Panteoa* sp. (*P. citrea*), *Bacillus* sp. (*B. subtilis*), *Yarrowia* sp. (*Y. lipolytica*), and *Trichoderma* (*T. reesei*).

8. The host cell of claim 1 wherein the host cell is cultured in a medium comprising a carbon source selected from the group consisting of glucose, glycerol, glycerine, dihydroxyacetone, yeast extract, biomass, molasses, sucrose, and oil.

9. The host cell of claim 1 wherein the host cell further comprises a heterologous or native nucleic acid encoding an isopentenyl-diphosphate delta-isomerase (IDI) polypeptide and/or a heterologous or native nucleic acid encoding a 1-Deoxyxylulose-5-phosphate synthase (DXS) polypeptide, optionally in combination with the native 1-deoxy-D-xylulose-5-phosphate (DXP) pathway.

10. The host cell of claim 1 wherein the host cell further comprises one or more nucleic acids encoding an IDI polypeptide and a DXS polypeptide.

11. The host cell of claim 1 wherein the host cell comprises one vector encoding the isoprene synthase variant, the IDI polypeptide, and the DXS polypeptide.

12. The host cell of claim 11 wherein the host cell further comprises a heterologous nucleic acid encoding a mevalonate (MVA) pathway polypeptide selected from the group consisting of an MVA pathway polypeptide from *Saccharomyces cerevisia* and *Enterococcus faecalis*.

13. The host cell of claim 1 wherein the host cell further comprises one or more nucleic acids encoding an MVA pathway polypeptide and a DXS polypeptide and wherein one vector encodes the isoprene synthase variant, the MVA pathway polypeptide, and the DXS polypeptide.

14. The host cell of claim 13 wherein the host cell further comprises one or more nucleic acids encoding a DXS polypeptide, an IDI polypeptide, or one or more of the rest of the DXP pathway polypeptides, and a MVA pathway polypeptide.

15. A method of producing isoprene, comprising:
(a) culturing the host cells of claim 1 under suitable culture conditions for production of isoprene; and
(b) producing the isoprene.

16. The method of claim 15 further comprising (c) recovering the isoprene.

17. The method of claim 16 further comprising (d) polymerizing isoprene.

18. The host cell of claim 1 wherein the variant is MEA variant having the sequence of SEQ ID NO: 122.

19. The host cell of claim 18 wherein the MEA variant comprises L70R amino acid substitution.

20. The host cell of claim 1 wherein at least one amino acid substitution is a G507S substitution.

21. The host cell of claim 18 wherein the MEA variant comprises G507S amino acid substitution.

22. The host cell of claim 1 wherein the host cell further comprises one or more heterologous nucleic acid(s) encoding an MVA pathway polypeptide.

* * * * *

```
                         SEQUENCE LISTING

<160> NUMBER OF SEQ ID NOS: 167

<210> SEQ ID NO 1
<211> LENGTH: 1695
<212> TYPE: DNA
<213> ORGANISM: Artificial Sequence
<220> FEATURE:
<223> OTHER INFORMATION: Synthetic Construct

<400> SEQUENCE: 1
atgtgtgcga cctcttctca atttactcag attaccgagc ataattcccg tcgttccgca      60
aactatcagc caaacctgtg gaatttcgaa ttcctgcaat ccctggagaa cgacctgaaa     120
gtggaaaagc tggaggagaa agcgaccaaa ctggaggaag aagttcgctg catgatcaac     180
cgtgtagaca cccagccgct gtccctgctg gagctgatcg acgatgtgca gcgcctgggt     240
ctgacctaca aatttgaaaa agacatcatt aaagccctgg aaaacatcgt actgctggac     300
gaaaacaaaa agaacaaatc tgacctgcac gcaaccgctc tgtcttttccg tctgctgcgt     360 cagcacggtt tcgaggtttc tcaggatgtt tttgagcgtt tcaaggataa agaaggtggt     420
ttcagcggtg aactgaaagg tgacgtccaa ggcctgctga gcctgtatga agcgtcttac     480 ctgggttcg agggtgagaa cctgctggag gaggcgcgta ccttttccat cacccacctg     540
aagaacaacc tgaaagaagg cattaatacc aaggttgcag aacaagtgag ccacgccctg     600
gaactgccat atcaccagcg tctgcaccgt ctggaggcac gttggttcct ggataaatac     660
gaaccgaaag aaccgcatca ccagctgctg ctggagctgg cgaagctgga ttttaacatg     720
gtacagaccc tgcaccagaa agagctgcaa gatctgtccc gctggtggac cgagatgggc     780
ctggctagca aactggattt tgtacgcgac cgcctgatgg aagtttattt ctgggcactg     840
ggtatggcgc cagacccgca gtttggtgaa tgtcgcaaag ctgttactaa aatgtttggt     900
ctggtgacga tcatcgatga cgtgtatgac gtttatggca ctctggacga actgcaactg     960
ttcaccgatg ctgtagagcg ctgggacgtt aacgctatta cacccctgcc ggactatatg    1020
aaactgtgtt tcctggcact gtacaacacc gttaacgaca cgtcctattc tattctgaaa    1080
gagaaaggtc ataacaacct gtcctatctg acgaaaagct ggcgtgaact gtgcaaagcc    1140
tttctgcaag aggcgaaatg gtccaacaac aaaattatcc cggctttctc caagtacctg    1200
gaaaacgcca gcgtttcctc ctccggtgta gcgctgctgg cgccgtctta cttttccgta    1260
tgccagcagc aggaagacat ctccgaccac gcgctgcgtt ccctgaccga cttccatggt    1320
ctggtgcgtt ctagctgcgt tatcttccgc ctgtgcaacg atctggccac ctctgcggcg    1380
gagctggaac gtggcgagac taccaattct atcattagct acatgcacga aaacgatggt    1440
accagcgagg aacaggcccg cgaagaactg cgtaaactga tcgacgccga atggaaaaag    1500
```

-continued

```
atgaatcgtg aacgcgttag cgactccacc ctgctgccta aagcgttcat ggaaatcgca    1560
gttaacatgg cacgtgtttc ccactgcacc taccagtatg gcgatggtct gggtcgccca    1620
gactacgcga ctgaaaaccg catcaaactg ctgctgattg accctttccc gattaaccag    1680
ctgatgtatg tctaa                                                      1695
```

<210> SEQ ID NO 2
<211> LENGTH: 564
<212> TYPE: PRT
<213> ORGANISM: Peuraria sp.

<400> SEQUENCE: 2

```
Met Cys Ala Thr Ser Ser Gln Phe Thr Gln Ile Thr Glu His Asn Ser
1               5                   10                  15

Arg Arg Ser Ala Asn Tyr Gln Pro Asn Leu Trp Asn Phe Glu Phe Leu
            20                  25                  30

Gln Ser Leu Glu Asn Asp Leu Lys Val Glu Lys Leu Glu Glu Lys Ala
        35                  40                  45

Thr Lys Leu Glu Glu Glu Val Arg Cys Met Ile Asn Arg Val Asp Thr
    50                  55                  60

Gln Pro Leu Ser Leu Leu Glu Leu Ile Asp Asp Val Gln Arg Leu Gly
65                  70                  75                  80

Leu Thr Tyr Lys Phe Glu Lys Asp Ile Ile Lys Ala Leu Glu Asn Ile
                85                  90                  95

Val Leu Leu Asp Glu Asn Lys Lys Asn Lys Ser Asp Leu His Ala Thr
            100                 105                 110

Ala Leu Ser Phe Arg Leu Leu Arg Gln His Gly Phe Glu Val Ser Gln
        115                 120                 125

Asp Val Phe Glu Arg Phe Lys Asp Lys Glu Gly Gly Phe Ser Gly Glu
    130                 135                 140

Leu Lys Gly Asp Val Gln Gly Leu Leu Ser Leu Tyr Glu Ala Ser Tyr
145                 150                 155                 160

Leu Gly Phe Glu Gly Glu Asn Leu Leu Glu Glu Ala Arg Thr Phe Ser
                165                 170                 175

Ile Thr His Leu Lys Asn Asn Leu Lys Glu Gly Ile Asn Thr Lys Val
            180                 185                 190

Ala Glu Gln Val Ser His Ala Leu Glu Leu Pro Tyr His Gln Arg Leu
        195                 200                 205

His Arg Leu Glu Ala Arg Trp Phe Leu Asp Lys Tyr Glu Pro Lys Glu
    210                 215                 220

Pro His His Gln Leu Leu Leu Glu Leu Ala Lys Leu Asp Phe Asn Met
225                 230                 235                 240

Val Gln Thr Leu His Gln Lys Glu Leu Gln Asp Leu Ser Arg Trp Trp
                245                 250                 255

Thr Glu Met Gly Leu Ala Ser Lys Leu Asp Phe Val Arg Asp Arg Leu
            260                 265                 270

Met Glu Val Tyr Phe Trp Ala Leu Gly Met Ala Pro Asp Pro Gln Phe
        275                 280                 285

Gly Glu Cys Arg Lys Ala Val Thr Lys Met Phe Gly Leu Val Thr Ile
    290                 295                 300

Ile Asp Asp Val Tyr Asp Val Tyr Gly Thr Leu Asp Glu Leu Gln Leu
305                 310                 315                 320

Phe Thr Asp Ala Val Glu Arg Trp Asp Val Asn Ala Ile Asn Thr Leu
                325                 330                 335

Pro Asp Tyr Met Lys Leu Cys Phe Leu Ala Leu Tyr Asn Thr Val Asn
```

-continued

```
                 340                 345                 350
Asp Thr Ser Tyr Ser Ile Leu Lys Glu Lys Gly His Asn Asn Leu Ser
            355                 360                 365

Tyr Leu Thr Lys Ser Trp Arg Glu Leu Cys Lys Ala Phe Leu Gln Glu
    370                 375                 380

Ala Lys Trp Ser Asn Asn Lys Ile Ile Pro Ala Phe Ser Lys Tyr Leu
385                 390                 395                 400

Glu Asn Ala Ser Val Ser Ser Gly Val Ala Leu Leu Ala Pro Ser
                405                 410                 415

Tyr Phe Ser Val Cys Gln Gln Gln Glu Asp Ile Ser Asp His Ala Leu
    420                 425                 430

Arg Ser Leu Thr Asp Phe His Gly Leu Val Arg Ser Ser Cys Val Ile
            435                 440                 445

Phe Arg Leu Cys Asn Asp Leu Ala Thr Ser Ala Ala Glu Leu Glu Arg
    450                 455                 460

Gly Glu Thr Thr Asn Ser Ile Ile Ser Tyr Met His Glu Asn Asp Gly
465                 470                 475                 480

Thr Ser Glu Glu Gln Ala Arg Glu Glu Leu Arg Lys Leu Ile Asp Ala
                485                 490                 495

Glu Trp Lys Lys Met Asn Arg Glu Arg Val Ser Asp Ser Thr Leu Leu
            500                 505                 510

Pro Lys Ala Phe Met Glu Ile Ala Val Asn Met Ala Arg Val Ser His
    515                 520                 525

Cys Thr Tyr Gln Tyr Gly Asp Gly Leu Gly Arg Pro Asp Tyr Ala Thr
    530                 535                 540

Glu Asn Arg Ile Lys Leu Leu Leu Ile Asp Pro Phe Pro Ile Asn Gln
545                 550                 555                 560

Leu Met Tyr Val

<210> SEQ ID NO 3
<211> LENGTH: 37
<212> TYPE: DNA
<213> ORGANISM: Artificial Sequence
<220> FEATURE:
<223> OTHER INFORMATION: Synthetic Construct

<400> SEQUENCE: 3
cgtgagatca tatgtgtgcg acctcttctc aatttac                              37

<210> SEQ ID NO 4
<211> LENGTH: 38
<212> TYPE: DNA
<213> ORGANISM: Artificial Sequence
<220> FEATURE:
<223> OTHER INFORMATION: Synthetic Construct

<400> SEQUENCE: 4
cggtcgacgg atccctgcag ttagacatac atcagctg                             38

<210> SEQ ID NO 5
<211> LENGTH: 41
<212> TYPE: DNA
<213> ORGANISM: Artificial Sequence
<220> FEATURE:
<223> OTHER INFORMATION: Synthetic Construct

<400> SEQUENCE: 5
catatgaaag cttgtatcga ttaaataagg aggaataaac c                         41
```

-continued

```
<210> SEQ ID NO 6
<211> LENGTH: 1680
<212> TYPE: DNA
<213> ORGANISM: Poplus alba x tremula

<400> SEQUENCE: 6
atgtgctctg tttctaccga gaacgtttcc ttcactgaga cggaaaccga ggcacgtcgt     60
agcgcgaact acgagccgaa tagctgggac tacgatttcc tgctgtcttc cgatactgac    120
gaatctattg aggtgtacaa agacaaagca agaaactgg aggctgaagt gcgccgcgaa    180
attaacaacg agaaagctga attcctgact ctgctggagc tgatcgataa cgtacagcgc    240
ctgggtctgg gttaccgctt cgaatctgat atccgtcgcg cactggatcg tttcgtaagc    300
agcggcggtt tcgatggcgt gaccaaaacg agcctgcacg ctaccgcgct gtccttccgt    360
ctgctgcgtc agcacggctt cgaagtttct caggaagcat tctccggttt caaagatcaa    420
aacggtaact tcctggaaaa cctgaaagaa gacactaagg cgatcctgag cctgtatgag    480
gcaagctttc tggccctgga gggtgagaac atcctggatg aggcgcgcgt attcgccatc    540
tcccatctga agagctgtc tgaagagaaa atcggtaagg aactggcaga gcaggttaat    600
cacgcactgg aactgccgct gcatcgtcgt acccagcgtc tggaggcggt ttggtccatc    660
gaagcgtacc gcaaaaagga ggatgctaac caggttctgc tggaactggc catcctggac    720
tacaacatga tccagtccgt ttaccagcgt gatctgcgtg aaacctcccg ttggtggcgc    780
cgtgtgggcc tggcgaccaa actgcacttc gctaaggacc gcctgattga gtctttttac    840
tgggcagtcg gcgttgcgtt cgaacctcag tattctgact gccgtaacag cgttgcgaaa    900
atgttcagct tcgttactat tatcgacgac atctacgacg tttacggtac tctggacgag    960 ctgaactgt ttaccgacgc tgtcgaacgt tgggatgtta acgccatcaa cgatctgcct   1020
gactacatga aactgtgctt cctggcactg tataacacga tcaacgaaat tgcatacgac   1080
aacctgaaag acaaaggtga aaacatcctg ccgtacctga ctaaagcgtg gcggatctg   1140 tgtaacgctt ttctgcaaga agcgaaatgg ctgtataaca atccactcc gacctttgac   1200 gattatttcg gcaatgcctg gaaatccagc tctggcccgc tgcaactgat cttcgcttat   1260
tttgcggttg tccaaaacat caaaaaggag gaaattgaaa acctgcaaaa ataccacgat   1320
atcattagcc gtccttctca tatctttcgc ctgtgcaacg acctggcaag cgcgtccgca   1380
gagatcgcac gtggcgaaac cgctaactct gtttcctgct acatgcgcac caagggcatt   1440
tccgaagagc tggcaaccga gagcgtaatg aatctgatcg acgaaacctg taagaaaatg   1500
aacaaagaaa aactgggtgg ctccctgttc gctaaaccgt tcgtagagac tgctattaac   1560
ctggcacgtc agagccactg cacctaccac aatggtgacg cacatactag cccggatgaa   1620
ctgactcgta aacgtgtact gtctgttatc accgaaccga ttctgccgtt cgaacgttaa   1680

<210> SEQ ID NO 7
<211> LENGTH: 559
<212> TYPE: PRT
<213> ORGANISM: Poplus alba x tremula

<400> SEQUENCE: 7

Met Cys Ser Val Ser Thr Glu Asn Val Ser Phe Thr Glu Thr Glu Thr
1               5                  10                  15

Glu Ala Arg Arg Ser Ala Asn Tyr Glu Pro Asn Ser Trp Asp Tyr Asp
                20                  25                  30

Phe Leu Leu Ser Ser Asp Thr Asp Glu Ser Ile Glu Val Tyr Lys Asp
            35                  40                  45
```

```
Lys Ala Lys Lys Leu Glu Ala Glu Val Arg Arg Glu Ile Asn Asn Glu
 50                  55                  60

Lys Ala Glu Phe Leu Thr Leu Leu Glu Leu Ile Asp Asn Val Gln Arg
 65                  70                  75                  80

Leu Gly Leu Gly Tyr Arg Phe Glu Ser Asp Ile Arg Arg Ala Leu Asp
                 85                  90                  95

Arg Phe Val Ser Ser Gly Gly Phe Asp Gly Val Thr Lys Thr Ser Leu
            100                 105                 110

His Ala Thr Ala Leu Ser Phe Arg Leu Leu Arg Gln His Gly Phe Glu
            115                 120                 125

Val Ser Gln Glu Ala Phe Ser Gly Phe Lys Asp Gln Asn Gly Asn Phe
            130                 135                 140

Leu Glu Asn Leu Lys Glu Asp Thr Lys Ala Ile Leu Ser Leu Tyr Glu
145                 150                 155                 160

Ala Ser Phe Leu Ala Leu Glu Gly Glu Asn Ile Leu Asp Glu Ala Arg
                165                 170                 175

Val Phe Ala Ile Ser His Leu Lys Glu Leu Ser Glu Glu Lys Ile Gly
                180                 185                 190

Lys Glu Leu Ala Glu Gln Val Asn His Ala Leu Glu Leu Pro Leu His
                195                 200                 205

Arg Arg Thr Gln Arg Leu Glu Ala Val Trp Ser Ile Glu Ala Tyr Arg
            210                 215                 220

Lys Lys Glu Asp Ala Asn Gln Val Leu Leu Glu Leu Ala Ile Leu Asp
225                 230                 235                 240

Tyr Asn Met Ile Gln Ser Val Tyr Gln Arg Asp Leu Arg Glu Thr Ser
                245                 250                 255

Arg Trp Trp Arg Arg Val Gly Leu Ala Thr Lys Leu His Phe Ala Lys
                260                 265                 270

Asp Arg Leu Ile Glu Ser Phe Tyr Trp Ala Val Gly Val Ala Phe Glu
                275                 280                 285

Pro Gln Tyr Ser Asp Cys Arg Asn Ser Val Ala Lys Met Phe Ser Phe
            290                 295                 300

Val Thr Ile Ile Asp Asp Ile Tyr Asp Val Tyr Gly Thr Leu Asp Glu
305                 310                 315                 320

Leu Glu Leu Phe Thr Asp Ala Val Glu Arg Trp Asp Val Asn Ala Ile
                325                 330                 335

Asn Asp Leu Pro Asp Tyr Met Lys Leu Cys Phe Leu Ala Leu Tyr Asn
            340                 345                 350

Thr Ile Asn Glu Ile Ala Tyr Asp Asn Leu Lys Asp Lys Gly Glu Asn
            355                 360                 365

Ile Leu Pro Tyr Leu Thr Lys Ala Trp Ala Asp Leu Cys Asn Ala Phe
            370                 375                 380

Leu Gln Glu Ala Lys Trp Leu Tyr Asn Lys Ser Thr Pro Thr Phe Asp
385                 390                 395                 400

Asp Tyr Phe Gly Asn Ala Trp Lys Ser Ser Ser Gly Pro Leu Gln Leu
                405                 410                 415

Ile Phe Ala Tyr Phe Ala Val Val Gln Asn Ile Lys Lys Glu Glu Ile
                420                 425                 430

Glu Asn Leu Gln Lys Tyr His Asp Ile Ile Ser Arg Pro Ser His Ile
                435                 440                 445

Phe Arg Leu Cys Asn Asp Leu Ala Ser Ala Ser Ala Glu Ile Ala Arg
            450                 455                 460

Gly Glu Thr Ala Asn Ser Val Ser Cys Tyr Met Arg Thr Lys Gly Ile
465                 470                 475                 480
```

```
Ser Glu Glu Leu Ala Thr Glu Ser Val Met Asn Leu Ile Asp Glu Thr
                485                 490                 495
Cys Lys Lys Met Asn Lys Glu Lys Leu Gly Gly Ser Leu Phe Ala Lys
            500                 505                 510
Pro Phe Val Glu Thr Ala Ile Asn Leu Ala Arg Gln Ser His Cys Thr
        515                 520                 525
Tyr His Asn Gly Asp Ala His Thr Ser Pro Asp Glu Leu Thr Arg Lys
    530                 535                 540
Arg Val Leu Ser Val Ile Thr Glu Pro Ile Leu Pro Phe Glu Arg
545                 550                 555
```

<210> SEQ ID NO 8
<211> LENGTH: 22
<212> TYPE: DNA
<213> ORGANISM: Artificial Sequence
<220> FEATURE:
<223> OTHER INFORMATION: Synthetic Construct

<400> SEQUENCE: 8
gagaaaatcg gtaaggaact gg                                         22

<210> SEQ ID NO 9
<211> LENGTH: 13
<212> TYPE: PRT
<213> ORGANISM: Artificial Sequence
<220> FEATURE:
<223> OTHER INFORMATION: Synthetic Construct

<400> SEQUENCE: 9

```
Leu Ala Ser Ala Ser Ala Glu Ile Ala Arg Gly Glu Thr
 1               5                   10
```

<210> SEQ ID NO 10
<211> LENGTH: 39
<212> TYPE: DNA
<213> ORGANISM: Artificial Sequence
<220> FEATURE:
<223> OTHER INFORMATION: Synthetic Construct

<400> SEQUENCE: 10
ctggaggaag aagttcgctc catgatcaac cgtgtagac                        39

<210> SEQ ID NO 11
<211> LENGTH: 47
<212> TYPE: DNA
<213> ORGANISM: Artificial Sequence
<220> FEATURE:
<223> OTHER INFORMATION: Synthetic Construct

<400> SEQUENCE: 11
cgccagaccc gcagtttggt gaatctcgca aagctgttac taaaatg               47

<210> SEQ ID NO 12
<211> LENGTH: 41
<212> TYPE: DNA
<213> ORGANISM: Artificial Sequence
<220> FEATURE:
<223> OTHER INFORMATION: Synthetic Construct

<400> SEQUENCE: 12
cgccgtctta cttttccgta tcccagcagc aggaagacat c                     41

<210> SEQ ID NO 13
<211> LENGTH: 42

```
<212> TYPE: DNA
<213> ORGANISM: Artificial Sequence
<220> FEATURE:
<223> OTHER INFORMATION: Synthetic Construct

<400> SEQUENCE: 13
catggtctgg tgcgttctag ctccgttatc ttccgcctgt gc                          42

<210> SEQ ID NO 14
<211> LENGTH: 41
<212> TYPE: DNA
<213> ORGANISM: Artificial Sequence
<220> FEATURE:
<223> OTHER INFORMATION: Synthetic Construct

<400> SEQUENCE: 14
gatgtcttcc tgctgctggg atacggaaaa gtaagacggc g                           41

<210> SEQ ID NO 15
<211> LENGTH: 28
<212> TYPE: DNA
<213> ORGANISM: Artificial Sequence
<220> FEATURE:
<223> OTHER INFORMATION: Synthetic Construct

<400> SEQUENCE: 15
gatcaagctt aaccggaatt gccagctg                                          28

<210> SEQ ID NO 16
<211> LENGTH: 33
<212> TYPE: DNA
<213> ORGANISM: Artificial Sequence
<220> FEATURE:
<223> OTHER INFORMATION: Synthetic Construct

<400> SEQUENCE: 16
gatccgatcg tcagaagaac tcgtcaagaa ggc                                    33

<210> SEQ ID NO 17
<211> LENGTH: 35
<212> TYPE: DNA
<213> ORGANISM: Artificial Sequence
<220> FEATURE:
<223> OTHER INFORMATION: Synthetic Construct

<400> SEQUENCE: 17
ccaaactgca cttcgctcgt gaccgcctga ttgag                                  35

<210> SEQ ID NO 18
<211> LENGTH: 30
<212> TYPE: DNA
<213> ORGANISM: Artificial Sequence
<220> FEATURE:
<223> OTHER INFORMATION: Synthetic Construct

<400> SEQUENCE: 18
atctttcgcc tgtgcgacga cctggcaagc                                        30

<210> SEQ ID NO 19
<211> LENGTH: 45
<212> TYPE: DNA
<213> ORGANISM: Artificial Sequence
<220> FEATURE:
<223> OTHER INFORMATION: Synthetic Construct

<400> SEQUENCE: 19
tgaatctgat cgacgaaacc tggaagaaaa tgaacaaaga aaaac                       45
```

<210> SEQ ID NO 20
<211> LENGTH: 60
<212> TYPE: DNA
<213> ORGANISM: Artificial Sequence
<220> FEATURE:
<223> OTHER INFORMATION: Synthetic Construct

<400> SEQUENCE: 20
gatcatgcat tcgcccttag gaggtaaaaa aacatgtgtg cgacctcttc tcaatttact    60

<210> SEQ ID NO 21
<211> LENGTH: 38
<212> TYPE: DNA
<213> ORGANISM: Artificial Sequence
<220> FEATURE:
<223> OTHER INFORMATION: Synthetic Construct

<400> SEQUENCE: 21
cggtcgacgg atccctgcag ttagacatac atcagctg    38

<210> SEQ ID NO 22
<211> LENGTH: 5679
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 3895
<223> OTHER INFORMATION: n = A,T,C or G

<400> SEQUENCE: 22
aagggcgaat tctgcagata tccatcacac tggcggccgc tcgagcatgc atctagaggg    60
cccaattcgc cctatagtga gtcgtattac aattcactgg ccgtcgtttt acaacgtcgt   120
gactgggaaa accctggcgt tacccaactt aatcgccttg cagcacatcc ccctttcgcc   180
agctggcgta atagcgaaga ggcccgcacc gatcgccctt cccaacagtt gcgcagcctg   240
aatggcgaat ggacgcgccc tgtagcggcg cattaagcgc ggcgggtgtg gtggttacgc   300
gcagcgtgac cgctacactt gccagcgccc tagcgcccgc tcctttcgct ttcttccctt   360
cctttctcgc cacgttcgcc ggctttcccc gtcaagctct aaatcggggg ctccctttag   420
ggttccgatt tagtgcttta cggcacctcg accccaaaaa acttgattag ggtgatggtt   480
cacgtagtgg gccatcgccc tgatagacgg ttttttcgccc tttgacgttg gagtccacgt   540
tctttaatag tggactcttg ttccaaactg gaacaacact caaccctatc tcggtctatt   600
cttttgattt ataagggatt ttgccgattt cggcctattg gttaaaaaat gagctgattt   660
aacaaaaatt taacgcgaat tttaacaaaa ttcagggcgc aagggctgct aaaggaagcg   720
gaacacgtag aaagccagtc cgcagaaacg gtgctgaccc cggatgaatg tcagctactg   780
ggctatctgg acaagggaaa acgcaagcgc aaagagaaag caggtagctt gcagtgggct   840
tacatggcga tagctagact gggcggtttt atgacagca agcgaaccgg aattgccagc   900
tggggcgccc tctggtaagg ttgggaagcc ctgcaaagta actggatgg ctttcttgcc   960 gccaaggatc tgatggcgca ggggatcaag atctgatcaa gagacaggat gaggatcgtt  1020
tcgcatgatt gaacaagatg gattgcacgc aggttctccg gccgcttggg tggagaggct  1080
attcggctat gactgggcac aacagacaat cggctgctct gatgccgccg tgttccggct  1140
gtcagcgcag gggcgcccgg ttcttttttgt caagaccgac ctgtccggtg ccctgaatga  1200
actgcaggac gaggcagcgc ggctatcgtg gctggccacg acgggcgttc cttgcgcagc  1260

```
tgtgctcgac gttgtcactg aagcgggaag ggactggctg ctattgggcg aagtgccggg    1320
gcaggatctc ctgtcatccc accttgctcc tgccgagaaa gtatccatca tggctgatgc    1380
aatgcggcgg ctgcatacgc ttgatccggc tacctgccca ttcgaccacc aagcgaaaca    1440
tcgcatcgag cgagcacgta ctcggatgga agccggtctt gtcgatcagg atgatctgga    1500
cgaagagcat caggggctcg cgccagccga actgttcgcc aggctcaagg cgcgcatgcc    1560
cgacggcgag gatctcgtcg tgacccatgg cgatgcctgc ttgccgaata tcatggtgga    1620
aaatggccgc ttttctggat tcatcgactg tggccggctg ggtgtggcgg accgctatca    1680
ggacatagcg ttggctaccc gtgatattgc tgaagagctt ggcggcgaat gggctgaccg    1740
cttcctcgtg ctttacggta tcgccgctcc cgattcgcag cgcatcgcct tctatcgcct    1800
tcttgacgag ttcttctgaa ttgaaaaagg aagagtatga gtattcaaca tttccgtgtc    1860
gcccttattc cctttttgc ggcattttgc cttcctgttt ttgctcaccc agaaacgctg    1920
gtgaaagtaa aagatgctga agatcagttg ggtgcacgag tgggttacat cgaactggat    1980
ctcaacagcg gtaagatcct tgagagtttt cgccccgaag aacgttttcc aatgatgagc    2040
acttttaaag ttctgctatg tggcgcggta ttatcccgta ttgacgccgg gcaagagcaa    2100
ctcggtcgcc gcatacacta ttctcagaat gacttggttg agtactcacc agtcacagaa    2160
aagcatctta cggatggcat gacagtaaga gaattatgca gtgctgccat aaccatgagt    2220
gataacactg cggccaactt acttctgaca acgatcggag gaccgaagga gctaaccgct    2280
tttttgcaca acatggggga tcatgtaact cgccttgatc gttgggaacc ggagctgaat    2340
gaagccatac caaacgacga gcgtgacacc acgatgcctg tagcaatggc aacaacgttg    2400
cgcaaactat taactggcga actacttact ctagcttccc ggcaacaatt aatagactgg    2460
atggaggcgg ataaagttgc aggaccactt ctgcgctcgg cccttccggc tggctggttt    2520
attgctgata atctggagcc ggtgagcgt gggtctcgcg gtatcattgc agcactgggg    2580
ccagatggta agccctcccg tatcgtagtt atctacacga cggggagtca ggcaactatg    2640
gatgaacgaa atagacagat cgctgagata ggtgcctcac tgattaagca ttggtaactg    2700
tcagaccaag tttactcata tatactttag attgatttaa aacttcattt ttaatttaaa    2760
aggatctagg tgaagatcct ttttgataat ctcatgacca aaatccctta acgtgagttt    2820
tcgttccact gagcgtcaga ccccgtagaa aagatcaaag gatcttcttg agatcctttt    2880
tttctgcgcg taatctgctg cttgcaaaca aaaaaaccac cgctaccagc ggtggtttgt    2940
ttgccggatc aagagctacc aactcttttt ccgaaggtaa ctggcttcag cagagcgcag    3000
ataccaaata ctgttcttct agtgtagccg tagttaggcc accacttcaa gaactctgta    3060
gcaccgccta catacctcgc tctgctaatc ctgttaccag tggctgctgc cagtggcgat    3120
aagtcgtgtc ttaccgggtt ggactcaaga cgatagttac cggataaggc gcagcggtcg    3180
ggctgaacgg ggggttcgtg cacacagccc agcttggagc gaacgaccta caccgaactg    3240
agatacctac agcgtgagct atgagaaagc gccacgcttc ccgaagggag aaaggcggac    3300
aggtatccgg taagcggcag ggtcggaaca ggagagcgca cgagggagct tccaggggga    3360
aacgcctggt atctttatag tcctgtcggg tttcgccacc tctgacttga gcgtcgattt    3420
ttgtgatgct cgtcaggggg gcggagccta tggaaaaacg ccagcaacgc ggcctttta    3480 cggttcctgg ccttttgctg gccttttgct cacatgttct ttcctgcgtt atcccctgat    3540
tctgtggata accgtattac cgcctttgag tgagctgata ccgctcgccg cagccgaacg    3600
accgagcgca gcgagtcagt gagcgaggaa gcggaagagc gcccaatacg caaaccgcct    3660
```

```
ctccccgcgc gttggccgat tcattaatgc agctggcacg acaggtttcc cgactggaaa   3720
gcgggcagtg agcgcaacgc aattaatgtg agttagctca ctcattaggc accccaggct   3780 ttacactttta tgcttccggc tcgtatgttg tgtggaattg tgagcggata acaatttcac   3840
acaggaaaca gctatgacca tgattacgcc aagcttggta ccgagctcgg atccnctagt   3900
aacggccgcc agtgtgctgg aattcgccct tgatcatgca ttcgcccta ggaggtaaaa   3960 aaacatgtgt gcgacctctt ctcaatttac tcagattacc gagcataatt cccgtcgttc   4020
cgcaaactat cagccaaacc tgtggaattt cgaattcctg caatccctgg agaacgacct   4080
gaaagtggaa aagctggagg agaaagcgac caaactggag gaagaagttc gctgcatgat   4140
caaccgtgta gacacccagc cgctgtccct gctggagctg atcgacgatg tgcagcgcct   4200
gggtctgacc tacaaatttg aaaagacat cattaaagcc ctggaaaaca tcgtactgct   4260
ggacgaaaac aaaagaaca atctgacct gcacgcaacc gctctgtctt ccgtctgct    4320 gcgtcagcac ggtttcgagg tttctcagga tgtttttgag cgtttcaagg ataaagaagg   4380
tggtttcagc ggtgaactga aggtgacgt ccaaggcctg ctgagcctgt atgaagcgtc   4440
ttacctgggt ttcgagggtg agaacctgct ggaggaggcg cgtacctttt ccatcaccca   4500
cctgaagaac aacctgaaag aaggcattaa taccaaggtt gcagaacaag tgagccacgc   4560
cctggaactg ccatatcacc agcgtctgca ccgtctggag gcacgttggt tcctggataa   4620
atacgaaccg aaagaaccgc atcaccagct gctgctggag ctggcgaagc tggattttaa   4680
catggtacag accctgcacc agaaagagct gcaagatctg tcccgctggt ggaccgagat   4740
gggcctggct agcaaactgg attttgtacg cgaccgcctg atggaagttt atttctgggc   4800
actgggtatg gcgccagacc gcagtttggg tgaatgtcgc aaagctgtta ctaaaatgtt   4860
tggtctggtg acgatcatcg atgacgtgta tgacgtttat ggcactctgg acgaactgca   4920
actgttcacc gatgctgtag agcgctggga cgttaacgct attaacaccc tgccggacta   4980
tatgaaactg tgtttcctgg cactgtacaa caccgttaac gacacgtcct attctattct   5040
gaaagagaaa ggtcataaca acctgtccta tctgacgaaa agctggcgtg aactgtgcaa   5100
agcctttctg caagaggcga atggtccaa caacaaaatt atcccggctt ctccaagta   5160 cctggaaaac gccagcgttt cctcctccgg tgtagcgctg ctggcgccgt cttacttttc   5220
cgtatgccag cagcaggaag acatctccga ccacgcgctg cgttccctga ccgacttcca   5280
tggtctggtg cgttctagct gcgttatctt ccgcctgtgc aacgatctgg ccacctctgc   5340
ggcggagctg gaacgtggcg agactaccaa ttctatcatt agctacatgc acgaaaacga   5400
tggtaccagc gaggaacagg cccgcgaaga actgcgtaaa ctgatcgacg ccgaatggaa   5460
aaagatgaat cgtgaacgcg ttagcgactc caccctgctg cctaaagcgt tcatggaaat   5520
cgcagttaac atggcacgtg tttcccactg cacctaccag tatggcgatg gtctgggtcg   5580
cccagactac gcgactgaaa accgcatcaa actgctgctg attgacccctt tcccgattaa   5640 ccagctgatg tatgtctaac tgcagggatc cgtcgaccg                         5679

<210> SEQ ID NO 23
<211> LENGTH: 6974
<212> TYPE: DNA
<213> ORGANISM: Artificial Sequence
<220> FEATURE:
<223> OTHER INFORMATION: Synthetic Construct

<400> SEQUENCE: 23
gtgcggccgc aagcttgtcg acggagctcg aattcggatc cctgcagtta gacatacatc    60
```

```
agctggttaa tcgggaaagg gtcaatcagc agcagtttga tgcggttttc agtcgcgtag    120
tctgggcgac ccagaccatc gccatactgg taggtgcagt gggaaacacg tgccatgtta    180
actgcgattt ccatgaacgc tttaggcagc agggtggagt cgctaacgcg ttcacgattc    240 atcttttttcc attcggcgtc gatcagttta cgcagttctt cgcgggcctg ttcctcgctg    300
gtaccatcgt tttcgtgcat gtagctaatg atagaattgg tagtctcgcc acgttccagc    360
tccgccgcag aggtggccag atcgttcac aggcggaaga taacgcagct agaacgcacc    420
agaccatgga agtcggtcag ggaacgcagc gcgtggtcgg agatgtcttc ctgctgctgg    480
catacggaaa agtaagacgg cgccagcagc gctacaccgg aggaggaaac gctggcgttt    540
tccaggtact tggagaaagc cgggataatt ttgttgttgg accatttcgc tcttgcaga    600 aaggctttgc acagttcacg ccagcttttc gtcagatagg acaggttgtt atgacctttc    660
tctttcagaa tagaatagga cgtgtcgtta acggtgttgt acagtgccag gaaacacagt    720
ttcatatagt ccggcagggt gttaatagcg ttaacgtccc agcgctctac agcatcggtg    780
aacagttgca gttcgtccag agtgccataa acgtcataca cgtcatcgat gatcgtcacc    840
agaccaaaca ttttagtaac agctttgcga cattcaccaa actgcgggtc tggcgccata    900
cccagtgccc agaaataaac ttccatcagg cggtcgcgta caaaatccag tttgctagcc    960
aggcccatct cggtccacca gcgggacaga tcttgcagct ctttctggtg cagggtctgt    1020
accatgttaa aatccagctt cgccagctcc agcagcagct ggtgatgcgg ttctttcggt    1080
tcgtatttat ccaggaacca acgtgcctcc agacggtgca gacgctggtg atatggcagt    1140
tccagggcgt ggctcacttg ttctgcaacc ttggtattaa tgccttcttt caggttgttc    1200
ttcaggtggg tgatggaaaa ggtacgcgcc tcctccagca ggttctcacc ctcgaaaccc    1260
aggtaagacg cttcatacag gctcagcagg ccttggacgt cacctttcag ttcaccgctg    1320
aaaccacctt ctttatcctt gaaacgctca aaaacatcct gagaaacctc gaaaccgtgc    1380
tgacgcagca gacggaaaga cagagcggtt gcgtgcaggt cagatttgtt ctttttgttt    1440
tcgtccagca gtacgatgtt ttccagggct taatgatgt ctttttcaaa tttgtaggtc    1500
agacccaggc gctgcacatc gtcgatcagc tccagcaggg acagcggctg ggtgtctaca    1560
cggttgatca tgcagcgaac ttcttcctcc agtttggtcg cttctcctc cagcttttcc    1620 actttcaggt cgttctccag ggattgcagg aattcgaaat tccacaggtt tggctgatag    1680
tttgcggaac gacgggaatt atgctcggta atctgagtaa attgagaaga ggtcgcacac    1740
atggtatatc tccttcttaa agttaaacaa aattatttct agaggggaat tgttatccgc    1800
tcacaattcc cctatagtga gtcgtattaa tttcgcggga tcgagatctc gatcctctac    1860
gccggacgca tcgtggccgg catcaccggc gccacaggtg cggttgctgg cgcctatatc    1920
gccgacatca ccgatgggga agatcgggct cgccacttcg ggctcatgag cgcttgtttc    1980
ggcgtgggta tggtggcagg ccccgtgcc ggggactgt tgggcgccat ctccttgcat    2040
gcaccattcc ttgcggcggc ggtgctcaac ggcctcaacc tactactggg ctgcttccta    2100
atgcaggagt cgcataaggg agagcgtcga gatcccggac accatcgaat ggcgcaaaac    2160
ctttcgcggt atggcatgat agcgcccgga agagagtcaa ttcagggtgg tgaatgtgaa    2220
accagtaacg ttatacgatg tcgcagagta tgccggtgtc tcttatcaga ccgtttcccg    2280
cgtggtgaac caggccagcc acgtttctgc gaaaacgcgg gaaaagtgg aagcggcgat    2340 ggcggagctg aattacattc ccaaccgcgt ggcacaacaa ctggcgggca aacagtcgtt    2400
gctgattggc gttgccacct ccagtctggc cctgcacgcg ccgtcgcaaa ttgtcgcggc    2460
```

-continued

```
gattaaatct cgcgccgatc aactgggtgc cagcgtggtg gtgtcgatgg tagaacgaag    2520
cggcgtcgaa gcctgtaaag cggcggtgca caatcttctc gcgcaacgcg tcagtgggct    2580
gatcattaac tatccgctgg atgaccagga tgccattgct gtggaagctg cctgcactaa    2640
tgttccggcg ttatttcttg atgtctctga ccagacaccc atcaacagta ttattttctc    2700
ccatgaagac ggtacgcgac tgggcgtgga gcatctggtc gcattgggtc accagcaaat    2760
cgcgctgtta gcgggcccat taagttctgt ctcggcgcgt ctgcgtctgg ctggctggca    2820
taaatatctc actcgcaatc aaattcagcc gatagcggaa cgggaaggcg actggagtgc    2880
catgtccggt tttcaacaaa ccatgcaaat gctgaatgag ggcatcgttc ccactgcgat    2940
gctggttgcc aacgatcaga tggcgctggg cgcaatgcgc gccattaccg agtccgggct    3000
gcgcgttggt gcggatatct cggtagtggg atacgacgat accgaagaca gctcatgtta    3060
tatcccgccg ttaaccacca tcaaacagga ttttcgcctg ctggggcaaa ccagcgtgga    3120
ccgcttgctg caactctctc agggccaggc ggtgaagggc aatcagctgt tgcccgtctc    3180
actggtgaaa agaaaaacca ccctggcgcc caatacgcaa accgcctctc cccgcgcgtt    3240
ggccgattca ttaatgcagc tggcacgaca ggtttcccga ctggaaagcg ggcagtgagc    3300
gcaacgcaat taatgtaagt tagctcactc attaggcacc gggatctcga ccgatgccct    3360
tgagagcctt caacccagtc agctccttcc ggtgggcgcg gggcatgact atcgtcgccg    3420
cacttatgac tgtcttcttt atcatgcaac tcgtaggaca ggtgccggca gcgctctggg    3480
tcattttcgg cgaggaccgc tttgctggag cgcgacgat gatcggcctg tcgcttgcgg    3540
tattcggaat cttgcacgcc ctcgctcaag ccttcgtcac tggtcccgcc accaaacgtt    3600
tcggcgagaa gcaggccatt atcgccgca tggcggcccc acgggtgcgc atgatcgtgc    3660
tcctgtcgtt gaggacccgg ctaggctggc ggggttgcct tactggttag cagaatgaat    3720
caccgatacg cgagcgaacg tgaagcgact gctgctgcaa aacgtctgcg acctgagcaa    3780
caacatgaat ggtcttcggt ttccgtgttt cgtaaagtct ggaaacgcgg aagtcagcgc    3840
cctgcaccat tatgttccgg atctgcatcg caggatgctg ctggctaccc tgtggaacac    3900
ctacatctgt attaacgaag cgctggcatt gaccctgagt gattttttctc tggtcccgcc    3960 gcatccatac cgccagttgt ttaccctcac aacgttccag taaccgggca tgttcatcat    4020
cagtaacccg tatcgtgagc atcctctctc gtttcatcgg tatcattacc cccatgaaca    4080
gaaatccccc ttacacgag gcatcagtga ccaaacagga aaaaaccgcc cttaacatgg    4140
cccgctttat cagaagccag acattaacgc ttctggagaa actcaacgag ctggacgcgg    4200
atgaacaggc agacatctgt gaatcgcttc acgaccacgc tgatgagctt taccgcagct    4260
gcctcgcgcg tttcggtgat gacggtgaaa acctctgaca catgcagctc ccggagacgg    4320
tcacagcttg tctgtaagcg gatgccggga gcagacaagc ccgtcagggc gcgtcagcgg    4380
gtgttggcgg gtgtcggggc gcagccatga cccagtcacg tagcgatagc ggagtgtata    4440
ctggcttaac tatgcggcat cagagcagat tgtactgaga gtgcaccata tatgcggtgt    4500
gaaataccgc acagatgcgt aaggagaaaa taccgcatca ggcgctcttc cgcttcctcg    4560
ctcactgact cgctgcgctc ggtcgttcgg ctgcggcgag cggtatcagc tcactcaaag    4620
gcggtaatac ggttatccac agaatcaggg gataacgcag gaaagaacat gtgagcaaaa    4680
ggccagcaaa aggccaggaa ccgtaaaaag gccgcgttgc tggcgttttt ccataggctc    4740
cgcccccctg acgagcatca caaaaatcga cgctcaagtc agaggtggcg aaacccgaca    4800
ggactataaa gataccaggc gtttccccct ggaagctccc tcgtgcgctc tcctgttccg    4860
```

```
accctgccgc ttaccggata cctgtccgcc tttctcccct cgggaagcgt ggcgctttct   4920
catagctcac gctgtaggta tctcagttcg gtgtaggtcg ttcgctccaa gctgggctgt   4980
gtgcacgaac cccccgttca gcccgaccgc tgcgccttat ccgqtaacta tcgtcttgag   5040
tccaacccgg taagacacga cttatcgcca ctggcagcag ccactggtaa caggattagc   5100
agagcgaggt atgtaggcgg tgctacagag ttcttgaagt ggtggcctaa ctacggctac   5160
actagaagga cagtatttgg tatctgcgct ctgctgaagc cagttacctt cggaaaaaga   5220
gttggtagct cttgatccgg caaacaaacc accgctggta gcggtggttt ttttgtttgc   5280
aagcagcaga ttacgcgcag aaaaaaagga tctcaagaag atcctttgat cttttctacg   5340
gggtctgacg ctcagtggaa cgaaaactca cgttaaggga ttttggtcat gaacaataaa   5400
actgtctgct tacataaaca gtaatacaag gggtgttatg agccatattc aacgggaaac   5460
gtcttgctct aggccgcgat taaattccaa catggatgct gatttatatg ggtataaatg   5520
ggctcgcgat aatgtcgggc aatcaggtgc gacaatctat cgattgtatg ggaagcccga   5580
tgcgccagag ttgtttctga acatggcaa aggtagcgtt gccaatgatg ttacagatga   5640
gatggtcaga ctaaactggc tgacggaatt tatgcctctt ccgaccatca agcattttat   5700
ccgtactcct gatgatgcat ggttactcac cactgcgatc cccgggaaaa cagcattcca   5760
ggtattagaa gaatatcctg attcaggtga aatatattgtt gatgcgctgg cagtgttcct   5820
gcgccggttg cattcgattc ctgtttgtaa ttgtcctttt aacagcgatc gcgtatttcg   5880
tctcgctcag gcgcaatcac gaatgaataa cggtttggtt gatgcgagtg attttgatga   5940
cgagcgtaat ggctggcctg ttgaacaagt ctggaaagaa atgcataaac ttttgccatt   6000
ctcaccggat tcagtcgtca ctcatggtga tttctcactt gataaccttta ttttttgacga   6060
ggggaaatta ataggttgta ttgatgttgg acgagtcgga atcgcagacc gataccagga   6120
tcttgccatc ctatggaact gcctcggtga gttttctcct tcattacaga aacggctttt   6180
tcaaaaatat ggtattgata atcctgatat gaataaattg cagtttcatt tgatgctcga   6240
tgagttttc taagaattaa ttcatgagcg gatacatatt tgaatgtatt tagaaaaata   6300
aacaaatagg ggttccgcgc acatttcccc gaaaagtgcc acctgaaatt gtaaacgtta   6360
atattttgtt aaaattcgcg ttaaattttt gttaaatcag ctcatttttt aaccaatagg   6420
ccgaaatcgg caaaatccct tataaatcaa aagaatagac cgagataggg ttgagtgttg   6480
ttccagtttg gaacaagagt ccactattaa agaacgtgga ctccaacgtc aaagggcgaa   6540
aaaccgtcta tcagggcgat ggcccactac gtgaaccatc accctaatca agttttttgg   6600
ggtcgaggtg ccgtaaagca ctaaatcgga accctaaagg gagcccccga tttagagctt   6660
gacggggaaa gccggcgaac gtggcgagaa aggaagggaa gaaagcgaaa ggagcgggcg   6720
ctagggcgct ggcaagtgta gcggtcacgc tgcgcgtaac caccacaccc gccgcgctta   6780
atgcgccgct acagggcgcg tcccattcgc caatccggat atagttcctc ctttcagcaa   6840
aaaacccctc aagacccgtt tagaggcccc aaggggttat gctagttatt gctcagcggt   6900
ggcagcagcc aactcagctt cctttcgggc tttgttagca gccggatctc agtggtggtg   6960
gtggtggtgc tcga                                                    6974
```

<210> SEQ ID NO 24
<211> LENGTH: 39
<212> TYPE: DNA
<213> ORGANISM: Artificial Sequence
<220> FEATURE:
<223> OTHER INFORMATION: Synthetic Construct

```
<220> FEATURE:
<221> NAME/KEY: misc_feature
<222> LOCATION: 19, 20
<223> OTHER INFORMATION: n = A,T,C or G

<400> SEQUENCE: 24
cataattccc gtcgttccnn saactatcag ccaaacctg                              39

<210> SEQ ID NO 25
<211> LENGTH: 41
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 22, 23
<223> OTHER INFORMATION: n = A,T,C or G

<400> SEQUENCE: 25
cataattccc gtcgttccgc annstatcag ccaaacctgt g                           41

<210> SEQ ID NO 26
<211> LENGTH: 41
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 18, 19
<223> OTHER INFORMATION: n = A,T,C or G

<400> SEQUENCE: 26
cccgtcgttc cgcaaacnns cagccaaacc tgtggaattt c                           41

<210> SEQ ID NO 27
<211> LENGTH: 38
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 18, 19
<223> OTHER INFORMATION: n = A,T,C or G

<400> SEQUENCE: 27
gtcgttccgc aaactatnns ccaaacctgt ggaatttc                               38

<210> SEQ ID NO 28
<211> LENGTH: 39
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 19, 20
<223> OTHER INFORMATION: n = A,T,C or G

<400> SEQUENCE: 28
ctggattttg tacgcgacnn sctgatggaa gtttatttc                              39

<210> SEQ ID NO 29
<211> LENGTH: 38
<212> TYPE: DNA
<213> ORGANISM: Artificial Sequence
<220> FEATURE:
<223> OTHER INFORMATION: Synthetic Construct
```

```
<220> FEATURE:
<221> NAME/KEY: misc_feature
<222> LOCATION: 19, 20
<223> OTHER INFORMATION: n = A,T,C or G

<400> SEQUENCE: 29
ctgatggaag tttatttcnn sgcactgggt atggcgcc                              38

<210> SEQ ID NO 30
<211> LENGTH: 40
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 20, 21
<223> OTHER INFORMATION: n = A,T,C or G

<400> SEQUENCE: 30
caaagctgtt actaaaatgn nsggtctggt gacgatcatc                            40

<210> SEQ ID NO 31
<211> LENGTH: 38
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 18, 19
<223> OTHER INFORMATION: n = A,T,C or G

<400> SEQUENCE: 31
ctaaaatgtt tggtctgnns acgatcatcg atgacgtg                              38

<210> SEQ ID NO 32
<211> LENGTH: 41
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 22, 23
<223> OTHER INFORMATION: n = A,T,C or G

<400> SEQUENCE: 32
gaaaacgcca gcgtttcctc cnnsggtgta gcgctgctgg c                          41

<210> SEQ ID NO 33
<211> LENGTH: 23
<212> TYPE: DNA
<213> ORGANISM: Artificial Sequence
<220> FEATURE:
<223> OTHER INFORMATION: Synthetic Construct

<400> SEQUENCE: 33
caccatgcgt tgtagcgtgt cca                                              23

<210> SEQ ID NO 34
<211> LENGTH: 52
<212> TYPE: DNA
<213> ORGANISM: Artificial Sequence
<220> FEATURE:
<223> OTHER INFORMATION: Synthetic Construct

<400> SEQUENCE: 34
gggcccgttt aaactttaac tagactctgc agttagcgtt caaacggcag aa              52
```

<210> SEQ ID NO 35
<211> LENGTH: 37
<212> TYPE: DNA
<213> ORGANISM: Artificial Sequence
<220> FEATURE:
<223> OTHER INFORMATION: Synthetic Construct

<400> SEQUENCE: 35
gaaggagata tacatatgag cgtgtccacc gaaaatg    37

<210> SEQ ID NO 36
<211> LENGTH: 37
<212> TYPE: DNA
<213> ORGANISM: Artificial Sequence
<220> FEATURE:
<223> OTHER INFORMATION: Synthetic Construct

<400> SEQUENCE: 36
cattttcggt ggacacgctc atatgtatat ctccttc    37

<210> SEQ ID NO 37
<211> LENGTH: 38
<212> TYPE: DNA
<213> ORGANISM: Artificial Sequence
<220> FEATURE:
<223> OTHER INFORMATION: Synthetic Construct

<400> SEQUENCE: 37
gaaggagata tacatatggt gtccaccgaa aatgtgtc    38

<210> SEQ ID NO 38
<211> LENGTH: 38
<212> TYPE: DNA
<213> ORGANISM: Artificial Sequence
<220> FEATURE:
<223> OTHER INFORMATION: Synthetic Construct

<400> SEQUENCE: 38
gacacatttt cggtggacac catatgtata tctccttc    38

<210> SEQ ID NO 39
<211> LENGTH: 38
<212> TYPE: DNA
<213> ORGANISM: Artificial Sequence
<220> FEATURE:
<223> OTHER INFORMATION: Synthetic Construct

<400> SEQUENCE: 39
gaaggagata tacatatgac cgaaaatgtg tctttcac    38

<210> SEQ ID NO 40
<211> LENGTH: 38
<212> TYPE: DNA
<213> ORGANISM: Artificial Sequence
<220> FEATURE:
<223> OTHER INFORMATION: Synthetic Construct

<400> SEQUENCE: 40
gtgaaagaca cattttcggt catatgtata tctccttc    38

<210> SEQ ID NO 41
<211> LENGTH: 38
<212> TYPE: DNA
<213> ORGANISM: Artificial Sequence
<220> FEATURE:
<223> OTHER INFORMATION: Synthetic Construct

<400> SEQUENCE: 41
gaaggagata tacatatgaa tgtgtctttc accgaaac         38

<210> SEQ ID NO 42
<211> LENGTH: 38
<212> TYPE: DNA
<213> ORGANISM: Artificial Sequence
<220> FEATURE:
<223> OTHER INFORMATION: Synthetic Construct

<400> SEQUENCE: 42
gtttcggtga aagacacatt catatgtata tctccttc         38

<210> SEQ ID NO 43
<211> LENGTH: 36
<212> TYPE: DNA
<213> ORGANISM: Artificial Sequence
<220> FEATURE:
<223> OTHER INFORMATION: Synthetic Construct

<400> SEQUENCE: 43
gaaggagata tacatatgga agctcgtcgt tctgcg           36

<210> SEQ ID NO 44
<211> LENGTH: 36
<212> TYPE: DNA
<213> ORGANISM: Artificial Sequence
<220> FEATURE:
<223> OTHER INFORMATION: Synthetic Construct

<400> SEQUENCE: 44
cgcagaacga cgagcttcca tatgtatatc tccttc           36

<210> SEQ ID NO 45
<211> LENGTH: 30
<212> TYPE: DNA
<213> ORGANISM: Artificial Sequence
<220> FEATURE:
<223> OTHER INFORMATION: Synthetic Construct

<400> SEQUENCE: 45
gaaggagata tacatatgcg ttgtagcgtg                  30

<210> SEQ ID NO 46
<211> LENGTH: 60
<212> TYPE: DNA
<213> ORGANISM: Artificial Sequence
<220> FEATURE:
<223> OTHER INFORMATION: Synthetic Construct

<400> SEQUENCE: 46
cccgcgctta ctcgaggccc tgaaaataca ggttttcgcg ttcaaacggc agaatcggtt    60

<210> SEQ ID NO 47
<211> LENGTH: 35
<212> TYPE: DNA
<213> ORGANISM: Artificial Sequence
<220> FEATURE:
<223> OTHER INFORMATION: Synthetic Construct

<400> SEQUENCE: 47
gaaactgaaa cccatatgga agctcgtcgt tctgc            35

<210> SEQ ID NO 48
<211> LENGTH: 43

```
<212> TYPE: DNA
<213> ORGANISM: Artificial Sequence
<220> FEATURE:
<223> OTHER INFORMATION: Synthetic Construct

<400> SEQUENCE: 48
gcatgctcga gcggccgctt ttaatcaaac atcctgccaa ctc              43

<210> SEQ ID NO 49
<211> LENGTH: 37
<212> TYPE: DNA
<213> ORGANISM: Artificial Sequence
<220> FEATURE:
<223> OTHER INFORMATION: Synthetic Construct

<400> SEQUENCE: 49
gatcgaaggg cgatcgtgtc acagtctggc gaaaccg                     37

<210> SEQ ID NO 50
<211> LENGTH: 43
<212> TYPE: DNA
<213> ORGANISM: Artificial Sequence
<220> FEATURE:
<223> OTHER INFORMATION: Synthetic Construct

<400> SEQUENCE: 50
ctgaattctg cagatatctg tttttccact cttcgttcac ttt              43

<210> SEQ ID NO 51
<211> LENGTH: 33
<212> TYPE: DNA
<213> ORGANISM: Artificial Sequence
<220> FEATURE:
<223> OTHER INFORMATION: Synthetic Construct

<400> SEQUENCE: 51
tctagagggc ccaagaaaaa tgccccgctt acg                         33

<210> SEQ ID NO 52
<211> LENGTH: 111
<212> TYPE: DNA
<213> ORGANISM: Artificial Sequence
<220> FEATURE:
<223> OTHER INFORMATION: Synthetic Construct

<400> SEQUENCE: 52
gatcgcggcc gcgcccttga cgatgccaca tcctgagcaa ataattcaac cactaattgt    60
gagcggataa cacaaggagg aaacagctat gtcattaccg ttcttaactt c            111

<210> SEQ ID NO 53
<211> LENGTH: 75
<212> TYPE: DNA
<213> ORGANISM: Artificial Sequence
<220> FEATURE:
<223> OTHER INFORMATION: Synthetic Construct

<400> SEQUENCE: 53
gatcgggccc caagaaaaaa ggcacgtcat ctgacgtgcc tttttatttt gtagacgcgt    60
tgttatagca ttcta                                                    75

<210> SEQ ID NO 54
<211> LENGTH: 81
<212> TYPE: DNA
<213> ORGANISM: Artificial Sequence
<220> FEATURE:
<223> OTHER INFORMATION: Synthetic Construct
```

<400> SEQUENCE: 54

```
aaagtagccg aagatgacgg tttgtcacat ggagttggca ggatgtttga ttaaaagcaa    60
ttaaccctca ctaaagggcg g                                              81
```

<210> SEQ ID NO 55
<211> LENGTH: 160
<212> TYPE: DNA
<213> ORGANISM: Artificial Sequence
<220> FEATURE:
<223> OTHER INFORMATION: Synthetic Construct

<400> SEQUENCE: 55

```
agagtgttca ccaaaaataa taacctttcc cggtgcagaa gttaagaacg gtaatgacat    60
agctgtttcc tccttgtgtt atccgctcac aattagtggt tgaattattt gctcaggatg   120
tggcatcgtc aagggctaat acgactcact atagggctcg                         160
```

<210> SEQ ID NO 56
<211> LENGTH: 445
<212> TYPE: DNA
<213> ORGANISM: Artificial Sequence
<220> FEATURE:
<223> OTHER INFORMATION: Synthetic Construct

<400> SEQUENCE: 56

```
aaagaccgac caagcgacgt ctgagagctc cctggcgaat tcggtaccaa taaaagagct    60
ttattttcat gatctgtgtg ttggttttg tgtgcggcgc ggaagttcct attctctaga   120
aagtatagga acttcctcga gccctatagt gagtcgtatt aaattcatat aaaaaacata   180
cagataacca tctgcggtga taaattatct ctggcggtgt tgacataaat accactggcg   240
gtgatactga gcacatcagc aggacgcact gaccaccatg aaggtgcaaa ggaggtaaaa   300
aaacatggta tcctgttctg cgccgggtaa gatttacctg ttcggtgaac acgccgtagt   360
ttatggcgaa actgcaattg cgtgtgcggt ggaactgcgt acccgtgttc gcgcggaact   420
caatgactct atcactattc agagc                                        445
```

<210> SEQ ID NO 57
<211> LENGTH: 445
<212> TYPE: DNA
<213> ORGANISM: Artificial Sequence
<220> FEATURE:
<223> OTHER INFORMATION: Synthetic Construct

<400> SEQUENCE: 57

```
aaagaccgac caagcgacgt ctgagagctc cctggcgaat tcggtaccaa taaaagagct    60
ttattttcat gatctgtgtg ttggttttg tgtgcggcgc ggaagttcct attctctaga   120
aagtatagga acttcctcga gccctatagt gagtcgtatt aaattcatat aaaaaacata   180
cagataacca tctgcggtga taaattatct ctggcggtgt tgacctaaat accactggcg   240
gtgatactga gcacatcagc aggacgcact gaccaccatg aaggtgcaaa ggaggtaaaa   300
aaacatggta tcctgttctg cgccgggtaa gatttacctg ttcggtgaac acgccgtagt   360
ttatggcgaa actgcaattg cgtgtgcggt ggaactgcgt acccgtgttc gcgcggaact   420
caatgactct atcactattc agagc                                        445
```

<210> SEQ ID NO 58
<211> LENGTH: 442
<212> TYPE: DNA
<213> ORGANISM: Artificial Sequence

```
<220> FEATURE:
<223> OTHER INFORMATION: Synthetic Construct

<400> SEQUENCE: 58
aaagaccgac caagcgacgt ctgagagctc cctggcgaat tcggtaccaa taaaagagct      60
ttattttcat gatctgtgtg ttggtttttg tgtgcggcgc ggaagttcct attctctaga     120
aagtatagga acttcctcga gccctatagt gagtcgtatt aaattcatat aaaaaacata     180
cagataacca tctgcggtga taaattatct ctggcggtgt tgacctaaat accactggcg     240
gtgatactga gcacatcagc aggacgcact gaccaccatg aaggtgcaaa ggtaaaaaaa     300
catggtatcc tgttctgcgc cgggtaagat ttacctgttc ggtgaacacg ccgtagttta     360
tggcgaaact gcaattgcgt gtgcggtgga actgcgtacc cgtgttcgcg cggaactcaa     420
tgactctatc actattcaga gc                                              442

<210> SEQ ID NO 59
<211> LENGTH: 445
<212> TYPE: DNA
<213> ORGANISM: Artificial Sequence
<220> FEATURE:
<223> OTHER INFORMATION: Synthetic Construct

<400> SEQUENCE: 59
aaagaccgac caagcgacgt ctgagagctc cctggcgaat tcggtaccaa taaaagagct      60
ttattttcat gatctgtgtg ttggtttttg tgtgcggcgc ggaagttcct attctctaga     120
aagtatagga acttcctcga gccctatagt gagtcgtatt aaattcatat aaaaaacata     180
cagataacca tctgcggtga taaattatct ctggcggtgt tgacgtaaat accactggcg     240
gtgatactga gcacatcagc aggacgcact gaccaccatg aaggtgcaaa ggaggtaaaa     300
aaacatggta tcctgttctg cgccgggtaa gatttacctg ttcggtgaac acgccgtagt     360
ttatggcgaa actgcaattg cgtgtgcggt ggaactgcgt acccgtgttc gcgcggaact     420
caatgactct atcactattc agagc                                           445

<210> SEQ ID NO 60
<211> LENGTH: 81
<212> TYPE: DNA
<213> ORGANISM: Artificial Sequence
<220> FEATURE:
<223> OTHER INFORMATION: Synthetic Construct

<400> SEQUENCE: 60
aaagtagccg aagatgacgg tttgtcacat ggagttggca ggatgtttga ttaaaagcaa      60
ttaaccctca ctaaagggcg g                                                81

<210> SEQ ID NO 61
<211> LENGTH: 22
<212> TYPE: DNA
<213> ORGANISM: Artificial Sequence
<220> FEATURE:
<223> OTHER INFORMATION: Synthetic Construct

<400> SEQUENCE: 61
gctctgaata gtgatagagt ca                                               22

<210> SEQ ID NO 62
<211> LENGTH: 199
<212> TYPE: DNA
<213> ORGANISM: Artificial Sequence
<220> FEATURE:
<223> OTHER INFORMATION: Synthetic Construct
```

```
<220> FEATURE:
<221> NAME/KEY: misc_feature
<222> LOCATION: 112
<223> OTHER INFORMATION: n = A,T,C or G

<400> SEQUENCE: 62
taaatcttac ccggcgcaga acaggatacc atgttttttt acctcctttg caccttcatg      60
gtggtcagtg cgtcctgctg atgtgctcag tatcaccgcc agtggtattt angtcaacac     120
cgccagagat aatttatcac cgcagatggt tatctgtatg tttttatat gaatttaata      180 cgactcacta tagggctcg                                                   199

<210> SEQ ID NO 63
<211> LENGTH: 24
<212> TYPE: DNA
<213> ORGANISM: Artificial Sequence
<220> FEATURE:
<223> OTHER INFORMATION: Synthetic Construct

<400> SEQUENCE: 63
aaagaccgac caagcgacgt ctga                                              24

<210> SEQ ID NO 64
<211> LENGTH: 22
<212> TYPE: DNA
<213> ORGANISM: Artificial Sequence
<220> FEATURE:
<223> OTHER INFORMATION: Synthetic Construct

<400> SEQUENCE: 64
caccatggta tcctgttctg cg                                                22

<210> SEQ ID NO 65
<211> LENGTH: 22
<212> TYPE: DNA
<213> ORGANISM: Artificial Sequence
<220> FEATURE:
<223> OTHER INFORMATION: Synthetic Construct

<400> SEQUENCE: 65
ttaatctact ttcagacctt gc                                                22

<210> SEQ ID NO 66
<211> LENGTH: 37
<212> TYPE: DNA
<213> ORGANISM: Artificial Sequence
<220> FEATURE:
<223> OTHER INFORMATION: Synthetic Construct

<400> SEQUENCE: 66
aggaggtggt ctcaaatgac tgccgacaac aatagta                                37

<210> SEQ ID NO 67
<211> LENGTH: 50
<212> TYPE: DNA
<213> ORGANISM: Artificial Sequence
<220> FEATURE:
<223> OTHER INFORMATION: Synthetic Construct

<400> SEQUENCE: 67
aggaggtggt ctcagcgctc tgcagttata gcattctatg aatttgcctg                  50

<210> SEQ ID NO 68
<211> LENGTH: 33
<212> TYPE: DNA
<213> ORGANISM: Artificial Sequence
```

```
<220> FEATURE:
<223> OTHER INFORMATION: Synthetic Construct
<220> FEATURE:
<221> NAME/KEY: misc_feature
<222> LOCATION: 16, 17
<223> OTHER INFORMATION: n = A,T,C or G

<400> SEQUENCE: 68
gaaaaagcag aatttnnkac cctgctggaa ctg                                    33

<210> SEQ ID NO 69
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 17, 18
<223> OTHER INFORMATION: n = A,T,C or G

<400> SEQUENCE: 69
cagttccagc agggtmnnaa attctgcttt ttc                                    33

<210> SEQ ID NO 70
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 16, 17
<223> OTHER INFORMATION: n = A,T,C or G

<400> SEQUENCE: 70
gagtctgata tccgtnnkgc gctggatcgc ttc                                    33

<210> SEQ ID NO 71
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 17, 18
<223> OTHER INFORMATION: n = A,T,C or G

<400> SEQUENCE: 71
gaagcgatcc agcgcmnnac ggatatcaga ctc                                    33

<210> SEQ ID NO 72
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 16, 17
<223> OTHER INFORMATION: n = A,T,C or G

<400> SEQUENCE: 72
tcccgttggt ggcgtnnkgt gggtctggcg acc                                    33

<210> SEQ ID NO 73
<211> LENGTH: 33
<212> TYPE: DNA
<213> ORGANISM: Artificial Sequence
```

```
<220> FEATURE:
<223> OTHER INFORMATION: Synthetic Construct
<220> FEATURE:
<221> NAME/KEY: misc_feature
<222> LOCATION: 17, 18
<223> OTHER INFORMATION: n = A,T,C or G

<400> SEQUENCE: 73
ggtcgccaga cccacmnnac gccaccaacg gga                                33

<210> SEQ ID NO 74
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 16, 17
<223> OTHER INFORMATION: n = A,T,C or G

<400> SEQUENCE: 74
tccgtcgcaa aaatgnnktc tttcgtaacc att                                33

<210> SEQ ID NO 75
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 17, 18
<223> OTHER INFORMATION: n = A,T,C or G

<400> SEQUENCE: 75
aatggttacg aaagamnnca ttttttgcgac gga                               33

<210> SEQ ID NO 76
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 16, 17
<223> OTHER INFORMATION: n = A,T,C or G

<400> SEQUENCE: 76
gcaaaaatgt tttctnnkgt aaccattatc gac                                33

<210> SEQ ID NO 77
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 17, 18
<223> OTHER INFORMATION: n = A,T,C or G

<400> SEQUENCE: 77
gtcgataatg gttacmnnag aaaacatttt tgc                                33

<210> SEQ ID NO 78
<211> LENGTH: 33
<212> TYPE: DNA
<213> ORGANISM: Artificial Sequence
```

```
<220> FEATURE:
<223> OTHER INFORMATION: Synthetic Construct
<220> FEATURE:
<221> NAME/KEY: misc_feature
<222> LOCATION: 16, 17
<223> OTHER INFORMATION: n = A,T,C or G

<400> SEQUENCE: 78
aaaatgtttt ctttcnnkac cattatcgac gat                                  33

<210> SEQ ID NO 79
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 17, 18
<223> OTHER INFORMATION: n = A,T,C or G

<400> SEQUENCE: 79
atcgtcgata atggtmnnga agaaaacat ttt                                   33

<210> SEQ ID NO 80
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 16, 17
<223> OTHER INFORMATION: n = A,T,C or G

<400> SEQUENCE: 80
gacctgtgca acgctnnkct gcaagaagcc aag                                  33

<210> SEQ ID NO 81
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 17, 18
<223> OTHER INFORMATION: n = A,T,C or G

<400> SEQUENCE: 81
cttggcttct tgcagmnnag cgttgcacag gtc                                  33

<210> SEQ ID NO 82
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 16, 17
<223> OTHER INFORMATION: n = A,T,C or G

<400> SEQUENCE: 82
gcatggaaat cctctnnkgg cccgctgcaa ctg                                  33

<210> SEQ ID NO 83
<211> LENGTH: 33
<212> TYPE: DNA
<213> ORGANISM: Artificial Sequence
```

```
<220> FEATURE:
<223> OTHER INFORMATION: Synthetic Construct
<220> FEATURE:
<221> NAME/KEY: misc_feature
<222> LOCATION: 17, 18
<223> OTHER INFORMATION: n = A,T,C or G

<400> SEQUENCE: 83
cagttgcagc gggccmnnag aggatttcca tgc                                33

<210> SEQ ID NO 84
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 16, 17
<223> OTHER INFORMATION: n = A,T,C or G

<400> SEQUENCE: 84
tcttctggcc cgctgnnkct ggtgttcgct tac                                33

<210> SEQ ID NO 85
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 17, 18
<223> OTHER INFORMATION: n = A,T,C or G

<400> SEQUENCE: 85
gtaagcgaac accagmnnca gcgggccaga aga                                33

<210> SEQ ID NO 86
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 16, 17
<223> OTHER INFORMATION: n = A,T,C or G

<400> SEQUENCE: 86
ggcccgctgc aactgnnktt cgcttacttc gct                                33

<210> SEQ ID NO 87
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 17, 18
<223> OTHER INFORMATION: n = A,T,C or G

<400> SEQUENCE: 87
agcgaagtaa gcgaamnnca gttgcagcgg gcc                                33

<210> SEQ ID NO 88
<211> LENGTH: 33
<212> TYPE: DNA
<213> ORGANISM: Artificial Sequence
```

```
<220> FEATURE:
<223> OTHER INFORMATION: Synthetic Construct
<220> FEATURE:
<221> NAME/KEY: misc_feature
<222> LOCATION: 16, 17
<223> OTHER INFORMATION: n = A,T,C or G

<400> SEQUENCE: 88
caaaaatacc atgacnnkat ctctcgtcct tcc                                33

<210> SEQ ID NO 89
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 17, 18
<223> OTHER INFORMATION: n = A,T,C or G

<400> SEQUENCE: 89
ggaaggacga gagatmnngt catggtattt ttg                                33

<210> SEQ ID NO 90
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 16, 17
<223> OTHER INFORMATION: n = A,T,C or G

<400> SEQUENCE: 90
cgtccttccc atatcnnkcg tctgtgcaat gac                                33

<210> SEQ ID NO 91
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 17, 18
<223> OTHER INFORMATION: n = A,T,C or G

<400> SEQUENCE: 91
gtcattgcac agacgmnnga tatgggaagg acg                                33

<210> SEQ ID NO 92
<211> LENGTH: 33
<212> TYPE: DNA
<213> ORGANISM: Artificial Sequence
<220> FEATURE:
<223> OTHER INFORMATION: Synthetic Construct

<400> SEQUENCE: 92
gaaggagata tacatatgac cgaagctcgt cgt                                33

<210> SEQ ID NO 93
<211> LENGTH: 33
<212> TYPE: DNA
<213> ORGANISM: Artificial Sequence
<220> FEATURE:
<223> OTHER INFORMATION: Synthetic Construct

<400> SEQUENCE: 93
```
acgacgagct tcggtcatat gtatatctcc ttc                                    33

<210> SEQ ID NO 94
<211> LENGTH: 33
<212> TYPE: DNA
<213> ORGANISM: Artificial Sequence
<220> FEATURE:
<223> OTHER INFORMATION: Synthetic Construct

<400> SEQUENCE: 94
gaaggagata tacatatgga aaccgaagct cgt                                    33

<210> SEQ ID NO 95
<211> LENGTH: 33
<212> TYPE: DNA
<213> ORGANISM: Artificial Sequence
<220> FEATURE:
<223> OTHER INFORMATION: Synthetic Construct

<400> SEQUENCE: 95
acgagcttcg gtttccatat gtatatctcc ttc                                    33

<210> SEQ ID NO 96
<211> LENGTH: 33
<212> TYPE: DNA
<213> ORGANISM: Artificial Sequence
<220> FEATURE:
<223> OTHER INFORMATION: Synthetic Construct

<400> SEQUENCE: 96
gaaggagata tacatatgac tgaaaccgaa gct                                    33

<210> SEQ ID NO 97
<211> LENGTH: 33
<212> TYPE: DNA
<213> ORGANISM: Artificial Sequence
<220> FEATURE:
<223> OTHER INFORMATION: Synthetic Construct

<400> SEQUENCE: 97
agcttcggtt tcagtcatat gtatatctcc ttc                                    33

<210> SEQ ID NO 98
<211> LENGTH: 33
<212> TYPE: DNA
<213> ORGANISM: Artificial Sequence
<220> FEATURE:
<223> OTHER INFORMATION: Synthetic Construct

<400> SEQUENCE: 98
gaaggagata tacatatgga aactgaaacc gaa                                    33

<210> SEQ ID NO 99
<211> LENGTH: 33
<212> TYPE: DNA
<213> ORGANISM: Artificial Sequence
<220> FEATURE:
<223> OTHER INFORMATION: Synthetic Construct

<400> SEQUENCE: 99
ttcggtttca gtttccatat gtatatctcc ttc                                    33

<210> SEQ ID NO 100
<211> LENGTH: 33
<212> TYPE: DNA
<213> ORGANISM: Artificial Sequence

```
<220> FEATURE:
<223> OTHER INFORMATION: Synthetic Construct

<400> SEQUENCE: 100
gaaggagata tacatatgac cgaaactgaa acc                           33

<210> SEQ ID NO 101
<211> LENGTH: 33
<212> TYPE: DNA
<213> ORGANISM: Artificial Sequence
<220> FEATURE:
<223> OTHER INFORMATION: Synthetic Construct

<400> SEQUENCE: 101
ggtttcagtt tcggtcatat gtatatctcc ttc                           33

<210> SEQ ID NO 102
<211> LENGTH: 39
<212> TYPE: DNA
<213> ORGANISM: Artificial Sequence
<220> FEATURE:
<223> OTHER INFORMATION: Synthetic Construct

<400> SEQUENCE: 102
agaaggagat ataccatgga agctcgtcgt tccgcaaac                     39

<210> SEQ ID NO 103
<211> LENGTH: 39
<212> TYPE: DNA
<213> ORGANISM: Artificial Sequence
<220> FEATURE:
<223> OTHER INFORMATION: Synthetic Construct

<400> SEQUENCE: 103
gtttgcggaa cgacgagctt ccatggtata tctccttct                     39

<210> SEQ ID NO 104
<211> LENGTH: 33
<212> TYPE: DNA
<213> ORGANISM: Artificial Sequence
<220> FEATURE:
<223> OTHER INFORMATION: Synthetic Construct

<400> SEQUENCE: 104
agaaggagat ataccatgga gcataattcc cgt                           33

<210> SEQ ID NO 105
<211> LENGTH: 33
<212> TYPE: DNA
<213> ORGANISM: Artificial Sequence
<220> FEATURE:
<223> OTHER INFORMATION: Synthetic Construct

<400> SEQUENCE: 105
acgggaatta tgctccatgg tatatctcct tct                           33

<210> SEQ ID NO 106
<211> LENGTH: 33
<212> TYPE: DNA
<213> ORGANISM: Artificial Sequence
<220> FEATURE:
<223> OTHER INFORMATION: Synthetic Construct

<400> SEQUENCE: 106
gaaggagata tacatatgga aacgcgtcgt tct                           33
```

<210> SEQ ID NO 107
<211> LENGTH: 33
<212> TYPE: DNA
<213> ORGANISM: Artificial Sequence
<220> FEATURE:
<223> OTHER INFORMATION: Synthetic Construct

<400> SEQUENCE: 107
agaacgacgc gtttccatat gtatatctcc ttc                33

<210> SEQ ID NO 108
<211> LENGTH: 23
<212> TYPE: DNA
<213> ORGANISM: Artificial Sequence
<220> FEATURE:
<223> OTHER INFORMATION: Synthetic Construct

<400> SEQUENCE: 108
cggtgaactg aaaggtgacg tcc                           23

<210> SEQ ID NO 109
<211> LENGTH: 25
<212> TYPE: DNA
<213> ORGANISM: Artificial Sequence
<220> FEATURE:
<223> OTHER INFORMATION: Synthetic Construct

<400> SEQUENCE: 109
ggacgttaac gctattaaca ccctg                         25

<210> SEQ ID NO 110
<211> LENGTH: 22
<212> TYPE: DNA
<213> ORGANISM: Artificial Sequence
<220> FEATURE:
<223> OTHER INFORMATION: Synthetic Construct

<400> SEQUENCE: 110
cacatcgtcg atcagctcca gc                            22

<210> SEQ ID NO 111
<211> LENGTH: 24
<212> TYPE: DNA
<213> ORGANISM: Artificial Sequence
<220> FEATURE:
<223> OTHER INFORMATION: Synthetic Construct

<400> SEQUENCE: 111
ggtcgtcaga ctgtcgatga agcc                          24

<210> SEQ ID NO 112
<211> LENGTH: 39
<212> TYPE: DNA
<213> ORGANISM: Artificial Sequence
<220> FEATURE:
<223> OTHER INFORMATION: Synthetic Construct

<400> SEQUENCE: 112
gcttatgaat tctgtgcgac ctcttctcaa tttactcag          39

<210> SEQ ID NO 113
<211> LENGTH: 38
<212> TYPE: DNA
<213> ORGANISM: Artificial Sequence
<220> FEATURE:
<223> OTHER INFORMATION: Synthetic Construct

<400> SEQUENCE: 113

```
gcttataagc ttagacatac atcagctggt taatcggg                              38
```

<210> SEQ ID NO 114
<211> LENGTH: 21
<212> TYPE: DNA
<213> ORGANISM: Artificial Sequence
<220> FEATURE:
<223> OTHER INFORMATION: Synthetic Construct

<400> SEQUENCE: 114

```
ctcctccagc aggttctcac c                                                21
```

<210> SEQ ID NO 115
<211> LENGTH: 52
<212> TYPE: DNA
<213> ORGANISM: Artificial Sequence
<220> FEATURE:
<223> OTHER INFORMATION: Synthetic Construct

<400> SEQUENCE: 115

```
gggcccgttt aaactttaac tagactctgc agttagcgtt caaacggcag aa              52
```

<210> SEQ ID NO 116
<211> LENGTH: 25
<212> TYPE: DNA
<213> ORGANISM: Artificial Sequence
<220> FEATURE:
<223> OTHER INFORMATION: Synthetic Construct

<400> SEQUENCE: 116

```
caccatgcgt cgttctgcga actac                                            25
```

<210> SEQ ID NO 117
<211> LENGTH: 25
<212> TYPE: DNA
<213> ORGANISM: Artificial Sequence
<220> FEATURE:
<223> OTHER INFORMATION: Synthetic Construct

<400> SEQUENCE: 117

```
caccatgcgt cgttctgcga actac                                            25
```

<210> SEQ ID NO 118
<211> LENGTH: 596
<212> TYPE: PRT
<213> ORGANISM: Artificial Sequence
<220> FEATURE:
<223> OTHER INFORMATION: Synthetic Construct

<400> SEQUENCE: 118

```
Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

His Pro Phe Thr Met Arg Cys Ser Val Ser Thr Glu Asn Val Ser Phe
        35                  40                  45

Thr Glu Thr Glu Thr Glu Ala Arg Arg Ser Ala Asn Tyr Glu Pro Asn
    50                  55                  60

Ser Trp Asp Tyr Asp Tyr Leu Leu Ser Ser Asp Thr Ser Glu Ser Ile
65                  70                  75                  80

Glu Val Tyr Lys Asp Lys Ala Lys Lys Leu Glu Ala Glu Val Arg Arg
                85                  90                  95

Glu Ile Asn Asn Glu Lys Ala Glu Phe Leu Thr Leu Leu Glu Leu Ile
```

-continued

```
              100                 105                 110
Asp Asn Val Gln Arg Leu Gly Leu Gly Tyr Arg Phe Glu Ser Asp Ile
              115                 120                 125

Arg Gly Ala Leu Asp Arg Phe Val Ser Ser Gly Gly Phe Asp Ala Val
              130                 135                 140

Thr Lys Thr Ser Leu His Gly Thr Ala Leu Ser Phe Arg Leu Leu Arg
145                 150                 155                 160

Gln His Gly Phe Glu Val Ser Gln Glu Ala Phe Ser Gly Phe Lys Asp
              165                 170                 175

Gln Asn Gly Asn Phe Leu Glu Asn Leu Lys Glu Asp Ile Lys Ala Ile
              180                 185                 190

Leu Ser Leu Tyr Glu Ala Ser Phe Leu Ala Leu Glu Gly Glu Asn Ile
              195                 200                 205

Leu Asp Glu Ala Lys Val Phe Ala Ile Ser His Leu Lys Glu Leu Ser
              210                 215                 220

Glu Glu Lys Ile Gly Lys Glu Leu Ala Glu Gln Val Asn His Ala Leu
225                 230                 235                 240

Glu Leu Pro Leu His Arg Arg Thr Gln Arg Leu Glu Ala Val Trp Ser
              245                 250                 255

Ile Glu Ala Tyr Arg Lys Lys Glu Asp Ala Asn Gln Val Leu Leu Glu
              260                 265                 270

Leu Ala Ile Leu Asp Tyr Asn Met Ile Gln Ser Val Tyr Gln Arg Asp
              275                 280                 285

Leu Arg Glu Thr Ser Arg Trp Trp Arg Arg Val Gly Leu Ala Thr Lys
              290                 295                 300

Leu His Phe Ala Arg Asp Arg Leu Ile Glu Ser Phe Tyr Trp Ala Val
305                 310                 315                 320

Gly Val Ala Phe Glu Pro Gln Tyr Ser Asp Cys Arg Asn Ser Val Ala
              325                 330                 335

Lys Met Phe Ser Phe Val Thr Ile Ile Asp Asp Ile Tyr Asp Val Tyr
              340                 345                 350

Gly Thr Leu Asp Glu Leu Glu Leu Phe Thr Asp Ala Val Glu Arg Trp
              355                 360                 365

Asp Val Asn Ala Ile Asn Asp Leu Pro Asp Tyr Met Lys Leu Cys Phe
370                 375                 380

Leu Ala Leu Tyr Asn Thr Ile Asn Glu Ile Ala Tyr Asp Asn Leu Lys
385                 390                 395                 400

Asp Lys Gly Glu Asn Ile Leu Pro Tyr Leu Thr Lys Ala Trp Ala Asp
              405                 410                 415

Leu Cys Asn Ala Phe Leu Gln Glu Ala Lys Trp Leu Tyr Asn Lys Ser
              420                 425                 430

Thr Pro Thr Phe Asp Asp Tyr Phe Gly Asn Ala Trp Lys Ser Ser Ser
              435                 440                 445

Gly Pro Leu Gln Leu Val Phe Ala Tyr Phe Ala Val Val Gln Asn Ile
              450                 455                 460

Lys Lys Glu Glu Ile Glu Asn Leu Gln Lys Tyr His Asp Thr Ile Ser
465                 470                 475                 480

Arg Pro Ser His Ile Phe Arg Leu Cys Asn Asp Leu Ala Ser Ala Ser
              485                 490                 495

Ala Glu Ile Ala Arg Gly Glu Thr Ala Asn Ser Val Ser Cys Tyr Met
              500                 505                 510

Arg Thr Lys Gly Ile Ser Glu Glu Leu Ala Thr Glu Ser Val Met Asn
              515                 520                 525
```

```
Leu Ile Asp Glu Thr Trp Lys Lys Met Asn Lys Glu Lys Leu Gly Gly
            530                 535                 540

Ser Leu Phe Ala Lys Pro Phe Val Glu Thr Ala Ile Asn Leu Ala Arg
545                 550                 555                 560

Gln Ser His Cys Thr Tyr His Asn Gly Asp Ala His Thr Ser Pro Asp
                565                 570                 575

Glu Leu Thr Arg Lys Arg Val Leu Ser Val Ile Thr Glu Pro Ile Leu
            580                 585                 590

Pro Phe Glu Arg
        595

<210> SEQ ID NO 119
<211> LENGTH: 7424
<212> TYPE: DNA
<213> ORGANISM: Artificial Sequence
<220> FEATURE:
<223> OTHER INFORMATION: Synthetic Construct

<400> SEQUENCE: 119
aagggcgagc tcaacgatcc ggctgctaac aaagcccgaa aggaagctga gttggctgct      60
gccaccgctg agcaataact agcataaccc cttggggcct ctaaacgggt cttgaggagt     120 ttttgctga aaggaggaac tatatccgga tatcccgcaa gaggcccggc agtaccggca     180
taaccaagcc tatgcctaca gcatccaggg tgacggtgcc gaggatgacg atgagcgcat     240
tgttagattt catacacggt gcctgactgc gttagcaatt taactgtgat aaactaccgc     300
attaaagctt atcgatgata agctgtcaaa catgagaatt aattcttgaa gacgaaaggg     360
cctcgtgata cgcctatttt tataggttaa tgtcatgata ataatggttt cttagacgtc     420
aggtggcact tttcggggaa atgtgcgcgg aaccccctatt tgtttatttt tctaaataca     480
ttcaaatatg tatccgctca tgagacaata accctgataa atgcttcaat aatattgaaa     540
aaggaagagt atgattgaac aagatggatt gcacgcaggt tctccggccg cttgggtgga     600
gaggctattc ggctatgact gggcacaact gacaatcggc tgctctgatg ccgccgtgtt     660
ccggctgtca gcgcagggc gcccggttct ttttgtcaag accgacctgt ccggtgccct     720
gaatgaactg caggacgagg cagcgcggct atcgtggctg gccacgacgg gcgttccttg     780
cgcagctgtg ctcgacgttg tcactgaagc gggaagggac tggctgctat tgggcgaagt     840
gccggggcag gatctcctgt catctcacct tgctcctgcc gagaaagtat ccatcatggc     900
tgatgcaatg cggcggctgc atacgcttga tccggctacc tgcccattcg accaccaagc     960
gaaacatcgc atcgagcggg cacgtactcg gatggaagcc ggtcttgtcg atcaggatga    1020
tctggacgaa gagcatcagg ggctcgcgcc agccgaactg ttcgccaggc tcaaggcgcg    1080
catgcccgac ggcgaggatc tcgtcgtgac acatggcgat gcctgcttgc cgaatatcat    1140
ggtggaaaat ggccgctttt ctggattcat cgactgtggc cggctgggtg tggcggaccg    1200
ctatcaggac atagcgttgg ctacccgtga tattgctgaa gagcttggcg gcgaatgggc    1260
tgaccgcttc ctcgtgcttt acggtatcgc cgctcccgat tcgcagcgca tcgccttcta    1320
tcgccttctt gacgagttct tctgagcggg actctggggt tcgaaatgac cgaccaagcg    1380
acgcctaact gtcagaccaa gtttactcat atatacttta gattgattta aaacttcatt    1440
tttaatttaa aaggatctag gtgaagatcc ttttgataa tctcatgacc aaaatcccctt    1500 aacgtgagtt ttcgttccac tgagcgtcag accccgtaga aagatcaaa ggatcttctt    1560 gagatccttt ttttctgcgc gtaatctgct gcttgcaaac aaaaaaacca ccgctaccag    1620
cggtggtttg tttgccggat caagagctac caactctttt tccgaaggta actggcttca    1680
```

```
gcagagcgca gataccaaat actgtccttc tagtgtagcc gtagttaggc caccacttca   1740
agaactctgt agcaccgcct acatacctcg ctctgctaat cctgttacca gtggctgctg   1800
ccagtggcga taagtcgtgt cttaccgggt tggactcaag acgatagtta ccggataagg   1860
cgcagcggtc gggctgaacg gggggttcgt gcacacagcc cagcttggag cgaacgacct   1920
acaccgaact gagatacct a cagcgtgagc tatgagaaag cgccacgctt cccgaaggga   1980
gaaaggcgga caggtatccg gtaagcggca gggtcggaac aggagagcgc acgagggagc   2040
ttccaggggg aaacgcctgg tatctttata gtcctgtcgg gtttcgccac ctctgacttg   2100
agcgtcgatt tttgtgatgc tcgtcagggg ggcggagcct atggaaaaac gccagcaacg   2160
cggccttttt acggttcctg gccttttgct ggccttttgc tcacatgttc tttcctgcgt   2220 tatccctga ttctgtggat aaccgtatta ccgcctttga gtgagctgat accgctcgcc   2280
gcagccgaac gaccgagcgc agcgagtcag tgagcgagga agcggaagag cgcctgatgc   2340
ggtattttct ccttacgcat ctgtgcggta tttcacaccg caatggtgca ctctcagtac   2400
aatctgctct gatgccgcat agttaagcca gtatacactc cgctatcgct acgtgactgg   2460
gtcatggctg cgccccgaca cccgccaaca cccgctgacg cgccctgacg gcttgtctg    2520 ctcccggcat ccgcttacag acaagctgtg accgtctccg ggagctgcat gtgtcagagg   2580
ttttcaccgt catcaccgaa acgcgcgagg cagctgcggt aaagctcatc agcgtggtcg   2640
tgaagcgatt cacagatgtc tgcctgttca tccgcgtcca gctcgttgag tttctccaga   2700
agcgttaatg tctggcttct gataaagcgg gccatgttaa gggcggtttt ttcctgtttg   2760
gtcactgatg cctccgtgta aggggatttc tgttcatgg gggtaatgat accgatgaaa    2820
cgagagagga tgctcacgat acgggttact gatgatgaac atgcccggtt actggaacgt   2880
tgtgagggta acaactggc ggtatggatg cggcgggacc agagaaaaat cactcagggt    2940
caatgccagc gcttcgttaa tacagatgta ggtgttccac agggtagcca gcagcatcct   3000
gcgatgcaga tccggaacat aatggtgcag gcgctgact tccgcgtttc cagactttac    3060
gaaacacgga aaccgaagac cattcatgtt gttgctcagg tcgcagacgt tttgcagcag   3120
cagtcgcttc acgttcgctc gcgtatcggt gattcattct gctaaccagt aaggcaaccc   3180
cgccagccta gccgggtcct caacgacagg agcacgatca tgcgcacccg tggccaggac   3240
ccaacgctgc ccgagatgcg ccgcgtgcgg ctgctggaga tggcggacgc gatggatatg   3300
ttctgccaag ggttggtttg cgcattcaca gttctccgca agaattgatt ggctccaatt   3360
cttggagtgg tgaatccgtt agcgaggtgc cgccggcttc cattcaggtc gaggtggccc   3420
ggctccatgc accgcgacgc aacgcgggga ggcagacaag gtatagggcg cgcctacaa    3480 tccatgccaa cccgttccat gtgctcgccg aggcggcata atcgccgtg acgatcagcg    3540 gtccaatgat cgaagttagg ctggtaagag ccgcgagcga tccttgaagc tgtccctgat   3600
ggtcgtcatc tacctgcctg gacagcatgg cctgcaacgc gggcatcccg atgccgccgg   3660
aagcgagaag aatcataatg gggaaggcca tccagcctcg cgtcgcgaac gccagcaaga   3720
cgtagcccag cgcgtcggcc gccatgccgg cgataatggc ctgcttctcg ccgaaacgtt   3780
tggtggcggg accagtgacg aaggcttgag cgagggcgtg caagattccg aataccgcaa   3840
gcgacaggcc gatcatcgtc gcgctccagc gaaagcggtc ctcgccgaaa atgacccaga   3900
gcgctgccgg cacctgtcct acgagttgca tgataaagaa gacagtcata agtgcggcga   3960
cgatagtcat gccccgcgcc caccggaagg agctgactgg gttgaaggct ctcaaggca    4020 tcggtcgaga tcccggtgcc taatgagtga gctaacttac attaattgcg ttgcgctcac   4080
```

```
tgcccgcttt ccagtcggga aacctgtcgt gccagctgca ttaatgaatc ggccaacgcg    4140
cggggagagg cggtttgcgt attgggcgcc agggtggttt ttcttttcac cagtgagacg    4200
ggcaacagct gattgccctt caccgcctgg ccctgagaga gttgcagcaa gcggtccacg    4260
ctggtttgcc ccagcaggcg aaaatcctgt ttgatggtgg ttaacggcgg gatataacat    4320
gagctgtctt cggtatcgtc gtatcccact accgagatat ccgcaccaac gcgcagcccg    4380
gactcggtaa tggcgcgcat tgcgcccagc gccatctgat cgttggcaac cagcatcgca    4440
gtgggaacga tgccctcatt cagcatttgc atggtttgtt gaaaaccgga catggcactc    4500
cagtcgcctt cccgttccgc tatcggctga atttgattgc gagtgagata tttatgccag    4560
ccagccagac gcagacgcgc cgagacagaa cttaatgggc ccgctaacag cgcgatttgc    4620
tggtgaccca atgcgaccag atgctccacg cccagtcgcg taccgtcttc atgggagaaa    4680
ataatactgt tgatgggtgt ctggtcagag acatcaagaa ataacgccgg aacattagtg    4740
caggcagctt ccacagcaat ggcatcctgg tcatccagcg gatagttaat gatcagccca    4800
ctgacgcgtt gcgcgagaag attgtgcacc gccgctttac aggcttcgac gccgcttcgt    4860
tctaccatcg acaccaccac gctggcaccc agttgatcgg cgcgagattt aatcgccgcg    4920
acaatttgcg acggcgcgtg cagggccaga ctggaggtgg caacgccaat cagcaacgac    4980
tgtttgcccg ccagttgttg tgccacgcgg ttgggaatgt aattcagctc cgccatcgcc    5040
gcttccactt tttcccgcgt tttcgcagaa acgtggctgg cctggttcac cacgcgggaa    5100
acggtctgat aagagacacc ggcatactct gcgacatcgt ataacgttac tggtttcaca    5160
ttcaccaccc tgaattgact ctcttccggg cgctatcatg ccataccgcg aaaggttttg    5220
cgccattcga tggtgtccgg gatctcgacg ctctccctta tgcgactcct gcattaggaa    5280
gcagcccagt agtaggttga ggccgttgag caccgccgcc gcaaggaatg gtgcatgcaa    5340
ggagatggcg cccaacagtc ccccggccac ggggcctgcc accataccca cgccgaaaca    5400
agcgctcatg agcccgaagt ggcgagcccg atcttcccca tcggtgatgt cggcgatata    5460
ggcgccagca accgcacctg tggcgccggt gatgccggcc acgatgcgtc cggcgtagag    5520
gatcgagatc tcgatcccgc gaaattaata cgactcacta tagggaatt gtgagcggat    5580 aacaattccc ctctagaaat aattttgttt aactttaaga aggagatata catatgcggg    5640
gttctcatca tcatcatcat catggtatgg ctagcatgac tggtggacag caaatgggtc    5700
gggatctgta cgacgatgac gataaggatc atcccttcac catgcgttgt agcgtgtcca    5760
ccgaaaatgt gtctttcacc gaaactgaaa ccgaagctcg tcgttctgcg aactacgaac    5820
ctaacagctg ggactatgat tacctgctgt cctccgacac ggacgagtcc atcgaagtat    5880
acaaagacaa agcgaaaaag ctggaagccg aagttcgtcg cgagattaat aacgaaaaag    5940
cagaatttct gaccctgctg gaactgattg acaacgtcca gcgcctgggc ctgggttacc    6000
gtttcgagtc tgatatccgt ggtgcgctgg atcgcttcgt ttcctccggc ggcttcgatg    6060
cggtaaccaa gacttccctg cacgtacgg cactgtcttt ccgtctgctg cgtcaacacg    6120
gttttgaggt ttctcaggaa gcgttcagcg gcttcaaaga ccaaaacggc aacttcctgg    6180
agaacctgaa ggaagatatc aaagctatcc tgagcctgta cgaggccagc ttcctggctc    6240
tggaaggcga aaacatcctg gacgaggcga aggttttcgc aatctctcat ctgaaagaac    6300
tgtctgaaga aaagatcggt aaagagctgg cagaacaggt gaaccatgca ctggaactgc    6360
cactgcatcg ccgtactcag cgtctggaag cagtatggtc tatcgaggcc taccgtaaaa    6420
aggaggacgc gaatcaggtt ctgctggagc tggcaattct ggattacaac atgatccagt    6480
```

```
ctgtatacca gcgtgatctg cgtgaaacgt cccgttggtg gcgtcgtgtg ggtctggcga    6540
ccaaactgca ctttgctcgt gaccgcctga ttgagagctt ctactgggcc gtgggtgtag    6600
cattcgaacc gcaatactcc gactgccgta actccgtcgc aaaaatgttt tctttcgtaa    6660
ccattatcga cgatatctac gatgtatacg gcaccctgga cgaactggag ctgtttactg    6720
atgcagttga gcgttgggac gtaaacgcca tcaacgacct gccggattac atgaaactgt    6780
gctttctggc tctgtataac actattaacg aaatcgccta cgacaacctg aaagataaag    6840
gtgagaacat cctgccgtat ctgaccaaag cctgggctga cctgtgcaac gcttttcctgc    6900 aagaagccaa gtggctgtac aacaaatcta ctccgacctt tgacgactac ttcggcaacg    6960
catggaaatc ctcttctggc ccgctgcaac tggtgttcgc ttacttcgct gtcgtgcaga    7020
acattaaaaa ggaagagatc gaaaacctgc aaaaatacca tgacaccatc tctcgtcctt    7080
cccatatctt ccgtctgtgc aatgacctgg ctagcgcgtc tgcggaaatt gcgcgtggtg    7140
aaaccgcaaa tagcgtttct tgttacatgc gcactaaagg tatctccgaa gaactggcta    7200
ccgaaagcgt gatgaatctg atcgatgaaa cctggaaaaa gatgaacaag gaaaaactgg    7260
gtggtagcct gttcgcgaaa ccgttcgtgg aaaccgcgat caacctggca cgtcaatctc    7320
actgcactta tcataacggc gacgcgcata cctctccgga tgagctgacc cgcaaacgcg    7380
ttctgtctgt aatcactgaa ccgattctgc cgtttgaacg ctaa                     7424
```

<210> SEQ ID NO 120
<211> LENGTH: 560
<212> TYPE: PRT
<213> ORGANISM: Poplus alba v tremula

<400> SEQUENCE: 120

```
Met Arg Cys Ser Val Ser Thr Glu Asn Val Ser Phe Thr Glu Thr Glu
1               5                   10                  15

Thr Glu Ala Arg Arg Ser Ala Asn Tyr Glu Pro Asn Ser Trp Asp Tyr
            20                  25                  30

Asp Tyr Leu Leu Ser Ser Asp Thr Asp Glu Ser Ile Glu Val Tyr Lys
        35                  40                  45

Asp Lys Ala Lys Lys Leu Glu Ala Glu Val Arg Arg Glu Ile Asn Asn
    50                  55                  60

Glu Lys Ala Glu Phe Leu Thr Leu Leu Glu Leu Ile Asp Asn Val Gln
65                  70                  75                  80

Arg Leu Gly Leu Gly Tyr Arg Phe Glu Ser Asp Ile Arg Gly Ala Leu
                85                  90                  95

Asp Arg Phe Val Ser Ser Gly Gly Phe Asp Ala Val Thr Lys Thr Ser
            100                 105                 110

Leu His Gly Thr Ala Leu Ser Phe Arg Leu Leu Arg Gln His Gly Phe
        115                 120                 125

Glu Val Ser Gln Glu Ala Phe Ser Gly Phe Lys Asp Gln Asn Gly Asn
    130                 135                 140

Phe Leu Glu Asn Leu Lys Glu Asp Ile Lys Ala Ile Leu Ser Leu Tyr
145                 150                 155                 160

Glu Ala Ser Phe Leu Ala Leu Glu Gly Glu Asn Ile Leu Asp Glu Ala
                165                 170                 175

Lys Val Phe Ala Ile Ser His Leu Lys Glu Leu Ser Glu Glu Lys Ile
            180                 185                 190

Gly Lys Glu Leu Ala Glu Gln Val Asn His Ala Leu Glu Leu Pro Leu
        195                 200                 205
```

```
His Arg Arg Thr Gln Arg Leu Glu Ala Val Trp Ser Ile Glu Ala Tyr
    210                 215                 220
Arg Lys Lys Glu Asp Ala Asn Gln Val Leu Glu Leu Ala Ile Leu
225                 230                 235                 240
Asp Tyr Asn Met Ile Gln Ser Val Tyr Gln Arg Asp Leu Arg Glu Thr
                245                 250                 255
Ser Arg Trp Trp Arg Arg Val Gly Leu Ala Thr Lys Leu His Phe Ala
                260                 265                 270
Arg Asp Arg Leu Ile Glu Ser Phe Tyr Trp Ala Val Gly Val Ala Phe
            275                 280                 285
Glu Pro Gln Tyr Ser Asp Cys Arg Asn Ser Val Ala Lys Met Phe Ser
    290                 295                 300
Phe Val Thr Ile Ile Asp Asp Ile Tyr Asp Val Tyr Gly Thr Leu Asp
305                 310                 315                 320
Glu Leu Glu Leu Phe Thr Asp Ala Val Glu Arg Trp Asp Val Asn Ala
                325                 330                 335
Ile Asn Asp Leu Pro Asp Tyr Met Lys Leu Cys Phe Leu Ala Leu Tyr
                340                 345                 350
Asn Thr Ile Asn Glu Ile Ala Tyr Asp Asn Leu Lys Asp Lys Gly Glu
            355                 360                 365
Asn Ile Leu Pro Tyr Leu Thr Lys Ala Trp Ala Asp Leu Cys Asn Ala
    370                 375                 380
Phe Leu Gln Glu Ala Lys Trp Leu Tyr Asn Lys Ser Thr Pro Thr Phe
385                 390                 395                 400
Asp Asp Tyr Phe Gly Asn Ala Trp Lys Ser Ser Gly Pro Leu Gln
                405                 410                 415
Leu Val Phe Ala Tyr Phe Ala Val Val Gln Asn Ile Lys Lys Glu Glu
            420                 425                 430
Ile Glu Asn Leu Gln Lys Tyr His Asp Thr Ile Ser Arg Pro Ser His
            435                 440                 445
Ile Phe Arg Leu Cys Asn Asp Leu Ala Ser Ala Ser Ala Glu Ile Ala
    450                 455                 460
Arg Gly Glu Thr Ala Asn Ser Val Ser Cys Tyr Met Arg Thr Lys Gly
465                 470                 475                 480
Ile Ser Glu Glu Leu Ala Thr Glu Ser Val Met Asn Leu Ile Asp Glu
                485                 490                 495
Thr Trp Lys Lys Met Asn Lys Glu Lys Leu Gly Gly Ser Leu Phe Ala
                500                 505                 510
Lys Pro Phe Val Glu Thr Ala Ile Asn Leu Ala Arg Gln Ser His Cys
            515                 520                 525
Thr Tyr His Asn Gly Asp Ala His Thr Ser Pro Asp Glu Leu Thr Arg
    530                 535                 540
Lys Arg Val Leu Ser Val Ile Thr Glu Pro Ile Leu Pro Phe Glu Arg
545                 550                 555                 560

<210> SEQ ID NO 121
<211> LENGTH: 6957
<212> TYPE: DNA
<213> ORGANISM: Artificial Sequence
<220> FEATURE:
<223> OTHER INFORMATION: Synthetic Construct

<400> SEQUENCE: 121
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
```

```
ctttctcgcc acgttcgccg gctttccccg tcaagctcta atcgggggc tccctttagg    180
gttccgattt agtgctttac ggcacctcga ccccaaaaaa cttgattagg gtgatggttc    240
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta tagggattt tgccgatttc ggcctattgg ttaaaaatg agctgattta       420
acaaaaattt aacgcgaatt ttaacaaaat attaacgttt acaatttcag gtggcacttt    480
tcggggaaat gtgcgcggaa cccctatttg tttattttc taaatacatt caaatatgta     540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga cgaaatac gcgatcgctg ttaaaaggac     960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa aatcccttaa    1440
cgtgagtttt cgttccactg agcgtcagac cccgtagaaa agatcaaagg atcttcttga    1500
gatcctttt ttctgcgcgt aatctgctgc ttgcaaacaa aaaaaccacc gctaccagcg     1560
gtggtttgtt tgccggatca agagctacca actctttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata agtcgtgtct taccgggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc gaagggaga    1920
aaggcggaca ggtatccggt aagcggcagg gtcggaacag gagagcgcac gagggagctt    1980
ccaggggga acgcctggta tctttatagt cctgtcgggt ttcgccacct ctgacttgag    2040
cgtcgatttt tgtgatgctc gtcagggggg cggagcctat ggaaaaacgc cagcaacgcg    2100
gccttttac ggttcctggc cttttgctgg ccttttgctc acatgttctt tcctgcgtta     2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
```

```
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aaggggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttcccccatc ggtgatgtcg gcgatatagg cgccagcaac cgcacctgtg   4920
```

-continued

```
gcgccggtga tgccggccac gatgcgtccg cgtagagga tcgagatctc gatcccgcga    4980
aattaatacg actcactata ggggaattgt gagcggataa caattcccct ctagaaataa    5040
ttttgtttaa ctttaagaag gagatataca tatgcgttgt agcgtgtcca ccgaaaatgt    5100
gtctttcacc gaaactgaaa ccgaagctcg tcgttctgcg aactacgaac ctaacagctg    5160
ggactatgat tacctgctgt cctccgacac ggacgagtcc atcgaagtat acaaagacaa    5220
agcgaaaaag ctggaagccg aagttcgtcg cgagattaat aacgaaaaag cagaatttct    5280
gaccctgctg gaactgattg acaacgtcca gcgcctgggc ctgggttacc gtttcgagtc    5340
tgatatccgt ggtgcgctgg atcgcttcgt ttcctccggc ggcttcgatg cggtaaccaa    5400
gacttccctg cacggtacgg cactgtcttt ccgtctgctg cgtcaacacg ttttgaggt     5460 ttctcaggaa gcgttcagcg gcttcaaaga ccaaaacggc aacttcctgg agaacctgaa    5520
ggaagatatc aaagctatcc tgagcctgta cgaggccagc ttcctggctc tggaaggcga    5580
aaacatcctg gacgaggcga aggttttcgc aatctctcat ctgaaagaac tgtctgaaga    5640
aaagatcggt aaagagctgg cagaacaggt gaaccatgca ctggaactgc cactgcatcg    5700
ccgtactcag cgtctggaag cagtatggtc tatcgaggcc taccgtaaaa aggaggacgc    5760
gaatcaggtt ctgctggagc tggcaattct ggattacaac atgatccagt ctgtatacca    5820
gcgtgatctc cgtgaaacgt cccgttggtg gcgtcgtgtg ggtctggcga ccaaactgca    5880
ctttgctcgt gaccgcctga ttgagagctt ctactgggcc gtgggtgtag cattcgaacc    5940
gcaatactcc gactgccgta actccgtcgc aaaaatgttt tctttcgtaa ccattatcga    6000
cgatatctac gatgtatacg gcaccctgga cgaactggag ctgtttactg atgcagttga    6060
gcgttgggac gtaaacgcca tcaacgacct gccggattac atgaaactgt gctttctggc    6120
tctgtataac actattaacg aaatcgccta cgacaacctg aaagataaag gtgagaacat    6180
cctgccgtat ctgaccaaag cctgggctga cctgtgcaac gctttcctgc aagaagccaa    6240
gtggctgtac aacaaatcta ctccgacctt tgacgactac ttcggcaacg catggaaatc    6300
ctcttctggc ccgctgcaac tggtgttcgc ttacttcgct gtcgtgcaga acattaaaaa    6360
ggaagagatc gaaaacctgc aaaaatacca tgacaccatc tctcgtcctt cccatatctt    6420
ccgtctgtgc aatgacctgg ctagcgcgtc tgcggaaatt gcgcgtggtg aaaccgcaaa    6480 tagcgttct tgttacatgc gcactaaagg tatctccgaa gaactggcta ccgaaagcgt    6540
gatgaatctg atcgatgaaa cctggaaaaa gatgaacaag gaaaaactgg tggtagcct     6600 gttcgcgaaa ccgttcgtgg aaaccgcgat caacctggca cgtcaatctc actgcactta    6660
tcataacggc gacgcgcata cctctccgga tgagctgacc cgcaaacgcg ttctgtctgt    6720
aatcactgaa ccgattctgc cgtttgaacg ctaaggatcc gaattcgagc tccgtcgaca    6780
agcttgcggc cgcactcgag caccaccacc accaccactg agatccggct gctaacaaag    6840
cccgaaagga agctgagttg gctgctgcca ccgctgagca ataactagca taaccccttg    6900
gggcctctaa acgggtcttg aggggttttt tgctgaaagg aggaactata tccggat       6957
```

<210> SEQ ID NO 122
<211> LENGTH: 544
<212> TYPE: PRT
<213> ORGANISM: Artificial Sequence
<220> FEATURE:
<223> OTHER INFORMATION: Synthetic Construct

<400> SEQUENCE: 122

Met Glu Ala Arg Arg Ser Ala Asn Tyr Glu Pro Asn Ser Trp Asp Tyr
1               5                   10                  15

```
Asp Tyr Leu Leu Ser Ser Asp Thr Asp Glu Ser Ile Glu Val Tyr Lys
                20                  25                  30

Asp Lys Ala Lys Leu Glu Ala Glu Val Arg Arg Glu Ile Asn Asn
            35                  40                  45

Glu Lys Ala Glu Phe Leu Thr Leu Leu Glu Leu Ile Asp Asn Val Gln
     50                  55                  60

Arg Leu Gly Leu Gly Tyr Arg Phe Glu Ser Asp Ile Arg Gly Ala Leu
 65              70                  75                      80

Asp Arg Phe Val Ser Ser Gly Gly Phe Asp Ala Val Thr Lys Thr Ser
                    85                  90                  95

Leu His Gly Thr Ala Leu Ser Phe Arg Leu Leu Arg Gln His Gly Phe
                100                 105                 110

Glu Val Ser Gln Glu Ala Phe Ser Gly Phe Lys Asp Gln Asn Gly Asn
                115                 120                 125

Phe Leu Glu Asn Leu Lys Glu Asp Ile Lys Ala Ile Leu Ser Leu Tyr
         130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                    165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
         195                 200                 205

Arg Lys Lys Glu Asp Ala Asn Gln Val Leu Leu Glu Leu Ala Ile Leu
210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
        275                 280                 285

Phe Val Thr Ile Ile Asp Asp Ile Tyr Asp Val Tyr Gly Thr Leu Asp
        290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
        355                 360                 365

Phe Leu Gln Glu Ala Lys Trp Leu Tyr Asn Lys Ser Thr Pro Thr Phe
    370                 375                 380

Asp Asp Tyr Phe Gly Asn Ala Trp Lys Ser Ser Gly Pro Leu Gln
385                 390                 395                 400

Leu Val Phe Ala Tyr Phe Ala Val Val Gln Asn Ile Lys Lys Glu Glu
                    405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ala Ser Ala Glu Ile Ala
```

435                 440                 445
Arg Gly Glu Thr Ala Asn Ser Val Ser Cys Tyr Met Arg Thr Lys Gly
        450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Gly Ser Leu Phe Ala
                485                 490                 495

Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
        515                 520                 525

Lys Arg Val Leu Ser Val Ile Thr Glu Pro Ile Leu Pro Phe Glu Arg
        530                 535                 540

<210> SEQ ID NO 123
<211> LENGTH: 6909
<212> TYPE: DNA
<213> ORGANISM: Artificial Sequence
<220> FEATURE:
<223> OTHER INFORMATION: Synthetic Construct

<400> SEQUENCE: 123

| | |
|---|---:|
| tggcgaatgg gacgcgccct gtagcggcgc attaagcgcg gcgggtgtgg tggttacgcg | 60 |
| cagcgtgacc gctacacttg ccagcgccct agcgcccgct cctttcgctt tcttcccttc | 120 |
| ctttctcgcc acgttcgccg gctttccccg tcaagctcta atcgggggc tcccctttagg | 180 |
| gttccgattt agtgctttac ggcacctcga ccccaaaaaa cttgattagg gtgatggttc | 240 |
| acgtagtggg ccatcgccct gatagacggt ttttcgccct ttgacgttgg agtccacgtt | 300 |
| ctttaatagt ggactcttgt tccaaactgg aacaacactc aaccctatct cggtctattc | 360 |
| ttttgattta agggatttt gccgatttc ggcctattgg ttaaaaaatg agctgattta | 420 |
| acaaaaattt aacgcgaatt ttaacaaaat attaacgttt acaatttcag gtggcacttt | 480 |
| tcggggaaat gtgcgcggaa cccctatttg tttatttttc taaatacatt caaatatgta | 540 |
| tccgctcatg aattaattct tagaaaaact catcgagcat caaatgaaac tgcaatttat | 600 |
| tcatatcagg attatcaata ccatattttt gaaaaagccg tttctgtaat gaaggagaaa | 660 |
| actcaccgag gcagttccat aggatggcaa gatcctggta tcggtctgcg attccgactc | 720 |
| gtccaacatc aatacaacct attaatttcc cctcgtcaaa aataaggtta tcaagtgaga | 780 |
| aatcaccatg agtgacgact gaatccggtg agaatggcaa aagtttatgc atttctttcc | 840 |
| agacttgttc aacaggccag ccattacgct cgtcatcaaa atcactcgca tcaaccaaac | 900 |
| cgttattcat tcgtgattgc gcctgagcga cgaaatac gcgatcgctg ttaaaaggac | 960 |
| aattacaaac aggaatcgaa tgcaaccggc gcaggaacac tgccagcgca tcaacaatat | 1020 |
| tttcacctga tcaggatat tcttctaata cctggaatgc tgttttcccg gggatcgcag | 1080 |
| tggtgagtaa ccatgcatca tcaggagtac ggataaaatg cttgatggtc ggaagaggca | 1140 |
| taaattccgt cagccagttt agtctgacca tctcatctgt aacatcattg gcaacgctac | 1200 |
| ctttgccatg tttcagaaac aactctggcg catcgggctt cccatacaat cgatagattg | 1260 |
| tcgcacctga ttgcccgaca ttatcgcgag cccatttata cccatataaa tcagcatcca | 1320 |
| tgttggaatt taatcgcggc ctagagcaag acgtttcccg ttgaatatgg ctcataacac | 1380 |
| cccttgtatt actgtttatg taagcagaca gttttattgt tcatgaccaa atcccttaa | 1440 |
| cgtgagtttt cgttccactg agcgtcagac cccgtagaaa agatcaaagg atcttcttga | 1500 |

```
gatccttttt ttctgcgcgt aatctgctgc ttgcaaacaa aaaaaccacc gctaccagcg    1560
gtggtttgtt tgccggatca agagctacca actcttttc cgaaggtaac tggcttcagc     1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata agtcgtgtct taccgggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcagggggg cggagcctat ggaaaaacgc cagcaacgcg    2100
gcctttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
```

```
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatggaagct cgtcgttctg cgaactacga   5100
acctaacagc tgggactatg attacctgct gtcctccgac acgacgagt ccatcgaagt   5160
atacaaagac aaagcgaaaa agctggaagc cgaagttcgt cgcgagatta ataacgaaaa   5220
agcagaattt ctgaccctgc tggaactgat tgacaacgtc cagcgcctgg gcctgggtta   5280
ccgtttcgag tctgatatcc gtggtgcgct ggatcgcttc gtttcctccg gcggcttcga   5340
tgcggtaacc aagacttccc tgcacggtac ggcactgtct ttccgtctgc tgcgtcaaca   5400
cggttttgag gtttctcagg aagcgttcag cggcttcaaa gaccaaaacg gcaacttcct   5460
ggagaacctg aaggaagata tcaaagctat cctgagcctg tacgaggcca gcttcctggc   5520
tctggaaggc gaaaacatcc tggacgaggc gaaggttttc gcaatctctc atctgaaaga   5580
actgtctgaa gaaaagatcg gtaaagagct ggcagaacag gtgaaccatg cactggaact   5640
gccactgcat cgccgtactc agcgtctgga agcagtatgg tctatcgagg cctaccgtaa   5700
aaaggaggac gcgaatcagg ttctgctgga gctggcaatt ctggattaca acatgatcca   5760
gtctgtatac cagcgtgatc tgcgtgaaac gtcccgttgg tggcgtcgtg tgggtctggc   5820
gaccaaactg cactttgctc gtgaccgcct gattgagagc ttctactggg ccgtgggtgt   5880
agcattcgaa ccgcaatact ccgactgccg taactccgtc gcaaaaatgt tttctttcgt   5940
aaccattatc gacgatatct acgatgtata cggcaccctg gacgaactgg agctgtttac   6000
tgatgcagtt gagcgttggg acgtaaacgc catcaacgac ctgccggatt acatgaaact   6060
gtgcttctg gctctgtata acactattaa cgaaatcgcc tacgacaacc tgaaagataa   6120
aggtgagaac atcctgccgt atctgaccaa agcctgggct gacctgtgca acgctttcct   6180
gcaagaagcc aagtggctgt acaacaaatc tactccgacc tttgacgact acttcggcaa   6240
cgcatggaaa tcctcttctg cccgctgca actggtgttc gcttacttcg ctgtcgtgca   6300
```

```
gaacattaaa aaggaagaga tcgaaaacct gcaaaaatac catgacacca tctctcgtcc    6360
ttcccatatc ttccgtctgt gcaatgacct ggctagcgcg tctgcggaaa ttgcgcgtgg    6420
tgaaaccgca aatagcgttt cttgttacat gcgcactaaa ggtatctccg aagaactggc    6480
taccgaaagc gtgatgaatc tgatcgatga aacctggaaa aagatgaaca aggaaaaact    6540
gggtggtagc ctgttcgcga aaccgttcgt ggaaaccgcg atcaacctgg cacgtcaatc    6600
tcactgcact tatcataacg gcgacgcgca tacctctccg gatgagctga cccgcaaacg    6660
cgttctgtct gtaatcactg aaccgattct gccgtttgaa cgctaaggat ccgaattcga    6720
gctccgtcga caagcttgcg gccgcactcg agcaccacca ccaccaccac tgagatccgg    6780
ctgctaacaa agcccgaaag gaagctgagt tggctgctgc caccgctgag caataactag    6840
cataacccct tggggcctct aaacgggtct gaggggtttt tttgctgaaa ggaggaacta    6900
tatccggat                                                           6909
```

<210> SEQ ID NO 124
<211> LENGTH: 558
<212> TYPE: PRT
<213> ORGANISM: Artificial Sequence
<220> FEATURE:
<223> OTHER INFORMATION: Synthetic Construct

<400> SEQUENCE: 124

Met Ser Val Ser Thr Glu Asn Val Ser Phe Thr Glu Thr Glu Thr Glu
1               5                   10                  15

Ala Arg Arg Ser Ala Asn Tyr Glu Pro Asn Ser Trp Asp Tyr Asp Tyr
            20                  25                  30

Leu Leu Ser Ser Asp Thr Asp Glu Ser Ile Glu Val Tyr Lys Asp Lys
        35                  40                  45

Ala Lys Lys Leu Glu Ala Glu Val Arg Arg Glu Ile Asn Asn Glu Lys
    50                  55                  60

Ala Glu Phe Leu Thr Leu Leu Glu Leu Ile Asp Asn Val Gln Arg Leu
65                  70                  75                  80

Gly Leu Gly Tyr Arg Phe Glu Ser Asp Ile Arg Gly Ala Leu Asp Arg
                85                  90                  95

Phe Val Ser Ser Gly Gly Phe Asp Ala Val Thr Lys Thr Ser Leu His
            100                 105                 110

Gly Thr Ala Leu Ser Phe Arg Leu Leu Arg Gln His Gly Phe Glu Val
        115                 120                 125

Ser Gln Glu Ala Phe Ser Gly Phe Lys Asp Gln Asn Gly Asn Phe Leu
    130                 135                 140

Glu Asn Leu Lys Glu Asp Ile Lys Ala Ile Leu Ser Leu Tyr Glu Ala
145                 150                 155                 160

Ser Phe Leu Ala Leu Glu Gly Glu Asn Ile Leu Asp Glu Ala Lys Val
                165                 170                 175

Phe Ala Ile Ser His Leu Lys Glu Leu Ser Glu Glu Lys Ile Gly Lys
            180                 185                 190

Glu Leu Ala Glu Gln Val Asn His Ala Leu Glu Leu Pro Leu His Arg
        195                 200                 205

Arg Thr Gln Arg Leu Glu Ala Val Trp Ser Ile Glu Ala Tyr Arg Lys
    210                 215                 220

Lys Glu Asp Ala Asn Gln Val Leu Leu Glu Leu Ala Ile Leu Asp Tyr
225                 230                 235                 240

Asn Met Ile Gln Ser Val Tyr Gln Arg Asp Leu Arg Glu Thr Ser Arg
                245                 250                 255

```
Trp Trp Arg Arg Val Gly Leu Ala Thr Lys Leu His Phe Ala Arg Asp
            260                 265                 270

Arg Leu Ile Glu Ser Phe Tyr Trp Ala Val Gly Val Ala Phe Glu Pro
        275                 280                 285

Gln Tyr Ser Asp Cys Arg Asn Ser Val Ala Lys Met Phe Ser Phe Val
    290                 295                 300

Thr Ile Ile Asp Asp Ile Tyr Asp Val Tyr Gly Thr Leu Asp Glu Leu
305                 310                 315                 320

Glu Leu Phe Thr Asp Ala Val Glu Arg Trp Asp Val Asn Ala Ile Asn
                325                 330                 335

Asp Leu Pro Asp Tyr Met Lys Leu Cys Phe Leu Ala Leu Tyr Asn Thr
            340                 345                 350

Ile Asn Glu Ile Ala Tyr Asp Asn Leu Lys Asp Lys Gly Glu Asn Ile
        355                 360                 365

Leu Pro Tyr Leu Thr Lys Ala Trp Ala Asp Leu Cys Asn Ala Phe Leu
    370                 375                 380

Gln Glu Ala Lys Trp Leu Tyr Asn Lys Ser Thr Pro Thr Phe Asp Asp
385                 390                 395                 400

Tyr Phe Gly Asn Ala Trp Lys Ser Ser Gly Pro Leu Gln Leu Val
                405                 410                 415

Phe Ala Tyr Phe Ala Val Val Gln Asn Ile Lys Lys Glu Ile Glu
            420                 425                 430

Asn Leu Gln Lys Tyr His Asp Thr Ile Ser Arg Pro Ser His Ile Phe
        435                 440                 445

Arg Leu Cys Asn Asp Leu Ala Ser Ala Ser Ala Glu Ile Ala Arg Gly
    450                 455                 460

Glu Thr Ala Asn Ser Val Ser Cys Tyr Met Arg Thr Lys Gly Ile Ser
465                 470                 475                 480

Glu Glu Leu Ala Thr Glu Ser Val Met Asn Leu Ile Asp Glu Thr Trp
                485                 490                 495

Lys Lys Met Asn Lys Glu Lys Leu Gly Gly Ser Leu Phe Ala Lys Pro
            500                 505                 510

Phe Val Glu Thr Ala Ile Asn Leu Ala Arg Gln Ser His Cys Thr Tyr
        515                 520                 525

His Asn Gly Asp Ala His Thr Ser Pro Asp Glu Leu Thr Arg Lys Arg
    530                 535                 540

Val Leu Ser Val Ile Thr Glu Pro Ile Leu Pro Phe Glu Arg
545                 550                 555

<210> SEQ ID NO 125
<211> LENGTH: 6951
<212> TYPE: DNA
<213> ORGANISM: Artificial Sequence
<220> FEATURE:
<223> OTHER INFORMATION: Synthetic Construct

<400> SEQUENCE: 125
tggcgaatgg gacgcgccct gtagcggcgc attaagcgcg gcgggtgtgg tggttacgcg    60
cagcgtgacc gctacacttg ccagcgccct agcgcccgct cctttcgctt tcttcccttc   120
ctttctcgcc acgttcgccg gctttccccg tcaagctcta atcggggggc tccctttagg   180
gttccgattt agtgctttac ggcacctcga ccccaaaaaa cttgattagg gtgatggttc   240
acgtagtggg ccatcgccct gatagacggt ttttcgccct ttgacgttgg agtccacgtt   300
ctttaatagt ggactcttgt tccaaactgg aacaacactc aaccctatct cggtctattc   360
ttttgattta taagggattt tgccgatttc ggcctattgg ttaaaaaatg agctgattta   420
```

```
acaaaaattt aacgcgaatt ttaacaaaat attaacgttt acaatttcag gtggcacttt      480
tcggggaaat gtgcgcggaa cccctatttg tttattttc taaatacatt caaatatgta      540
tccgctcatg aattaattct tagaaaaact catcgagcat caaatgaaac tgcaatttat      600
tcatatcagg attatcaata ccatattttt gaaaaagccg tttctgtaat gaaggagaaa      660
actcaccgag gcagttccat aggatggcaa gatcctggta tcggtctgcg attccgactc      720
gtccaacatc aatacaacct attaatttcc cctcgtcaaa aataaggtta tcaagtgaga      780
aatcaccatg agtgacgact gaatccggtg agaatggcaa aagtttatgc atttcttcc      840 agacttgttc aacaggccag ccattacgct cgtcatcaaa atcactcgca tcaaccaaac      900
cgttattcat tcgtgattgc gcctgagcga gacgaaatac gcgatcgctg ttaaaaggac      960
aattacaaac aggaatcgaa tgcaaccggc gcaggaacac tgccagcgca tcaacaatat     1020
tttcacctga atcaggatat tcttctaata cctggaatgc tgttttcccg gggatcgcag     1080
tggtgagtaa ccatgcatca tcaggagtac ggataaaatg cttgatggtc ggaagaggca     1140
taaattccgt cagccagttt agtctgacca tctcatctgt aacatcattg gcaacgctac     1200 cttttgccatg tttcagaaac aactctggcg catcgggctt cccatacaat cgatagattg     1260
tcgcacctga ttgcccgaca ttatcgcgag cccatttata cccatataaa tcagcatcca     1320
tgttggaatt taatcgcggc ctagagcaag acgtttcccg ttgaatatgg ctcataacac     1380
cccttgtatt actgtttatg taagcagaca gttttattgt tcatgaccaa aatcccttaa     1440
cgtgagtttt cgttccactg agcgtcagac cccgtagaaa agatcaaagg atcttcttga     1500 gatcctttt ttctgcgcgt aatctgctgc ttgcaaacaa aaaaaccacc gctaccagcg     1560
gtggtttgtt tgccggatca agagctacca actctttttc cgaaggtaac tggcttcagc     1620
agagcgcaga taccaaatac tgtccttcta gtgtagccgt agttaggcca ccacttcaag     1680
aactctgtag caccgcctac atacctcgct ctgctaatcc tgttaccagt ggctgctgcc     1740
agtggcgata agtcgtgtct taccgggttg gactcaagac gatagttacc ggataaggcg     1800
cagcggtcgg gctgaacggg gggttcgtgc acacagccca gcttggagcg aacgacctac     1860
accgaactga gatacctaca gcgtgagcta tgagaaagcg ccacgcttcc gaagggaga      1920 aaggcggaca ggtatccggt aagcggcagg gtcggaacag gagagcgcac gagggagctt     1980
ccagggggaa acgcctggta tctttatagt cctgtcgggt ttcgccacct ctgacttgag     2040
cgtcgatttt tgtgatgctc gtcagggggg cggagcctat ggaaaaacgc cagcaacgcg     2100 gccttttttac ggttcctggc cttttgctgg ccttttgctc acatgttctt tcctgcgtta     2160 tccccctgatt ctgtggataa ccgtattacc gcctttgagt gagctgatac cgctcgccgc     2220
agccgaacga ccgagcgcag cgagtcagtg agcgaggaag cggaagagcg cctgatgcgg     2280
tattttctcc ttacgcatct gtgcggtatt tcacaccgca tatatggtgc actctcagta     2340
caatctgctc tgatgccgca tagttaagcc agtatacact ccgctatcgc tacgtgactg     2400
ggtcatggct gcgccccgac acccgccaac acccgctgac gcgccctgac gggcttgtct     2460
gctcccggca tccgcttaca gacaagctgt gaccgtctcc gggagctgca tgtgtcagag     2520
gttttcaccg tcatcaccga aacgcgcgag gcagctgcgg taaagctcat cagcgtggtc     2580
gtgaagcgat tcacagatgt ctgcctgttc atccgcgtcc agctcgttga gtttctccag     2640
aagcgttaat gtctggcttc tgataaagcg ggccatgtta agggcggttt tttcctgttt     2700
ggtcactgat gcctccgtgt aagggggatt tctgttcatg ggggtaatga taccgatgaa     2760
acgagagagg atgctcacga tacgggttac tgatgatgaa catgcccggt tactggaacg     2820
```

-continued

```
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag gtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatgagcgtg tccaccgaaa atgtgtcttt    5100 caccgaaaact gaaaccgaag ctcgtcgttc tgcgaactac gaacctaaca gctgggacta    5160
tgattacctg ctgtcctccg acacggacga gtccatcgaa gtatacaaag acaaagcgaa    5220
```

```
aaagctggaa gccgaagttc gtcgcgagat taataacgaa aaagcagaat ttctgaccct    5280
gctggaactg attgacaacg tccagcgcct gggcctgggt taccgtttcg agtctgatat    5340
ccgtggtgcg ctggatcgct tcgtttcctc cggcggcttc gatgcggtaa ccaagacttc    5400
cctgcacggt acggcactgt ctttccgtct gctgcgtcaa cacggttttg aggtttctca    5460
ggaagcgttc agcggcttca agaccaaaaa cggcaacttc ctggagaacc tgaaggaaga    5520
tatcaaagct atcctgagcc tgtacgaggc cagcttcctg gctctggaag gcgaaaacat    5580
cctggacgag gcgaaggttt tcgcaatctc tcatctgaaa gaactgtctg aagaaaagat    5640
cggtaaagag ctggcagaac aggtgaacca tgcactggaa ctgccactgc atcgccgtac    5700
tcagcgtctg gaagcagtat ggtctatcga ggcctaccgt aaaaaggagg acgcgaatca    5760
ggttctgctg gagctggcaa ttctggatta caacatgatc cagtctgtat accagcgtga    5820
tctgcgtgaa acgtcccgtt ggtggcgtcg tgtgggtctg gcgaccaaac tgcactttgc    5880
tcgtgaccgc ctgattgaga gcttctactg ggccgtgggt gtagcattcg aaccgcaata    5940
ctccgactgc cgtaactccg tcgcaaaaat gttttctttc gtaaccatta tcgacgatat    6000
ctacgatgta tacggcaccc tggacgaact ggagctgttt actgatgcag ttgagcgttg    6060
ggacgtaaac gccatcaacg acctgccgga ttacatgaaa ctgtgctttc tggctctgta    6120
taacactatt aacgaaatcg cctacgacaa cctgaaagat aaaggtgaga catcctgcc    6180 gtatctgacc aaagcctggg ctgacctgtg caacgctttc ctgcaagaag ccaagtggct    6240
gtacaacaaa tctactccga cctttgacga ctacttcggc aacgcatgga atcctcttc    6300 tggcccgctg caactggtgt cgcttactt cgctgtcgtg cagaacatta aaaggaaga    6360 gatcgaaaac ctgcaaaaat accatgcaac catctctcgt ccttcccata tcttccgtct    6420
gtgcaatgac ctggctagcg cgtctgcgga aattgcgcgt ggtgaaaccg caaatagcgt    6480
ttcttgttac atgcgcacta aggtatctc gaagaactg gctaccgaaa gcgtgatgaa    6540
tctgatcgat gaaacctgga aaagatgaa caaggaaaaa ctgggtggta gcctgttcgc    6600
gaaaccgttc gtggaaaccg cgatcaacct ggcacgtcaa tctcactgca cttatcataa    6660
cggcgacgcg catacctctc cggatgagct gacccgcaaa cgcgttctgt ctgtaatcac    6720
tgaaccgatt ctgccgtttg aacgctaagg atccgaattc gagctccgtc gacaagcttg    6780
cggccgcact cgagcaccac caccaccacc actgagatcc ggctgctaac aaagcccgaa    6840
aggaagctga gttggctgct gccaccgctg agcaataact agcataaccc cttggggcct    6900
ctaaacgggt cttgaggggt ttttgctga aggaggaac tatatccgga t               6951
```

<210> SEQ ID NO 126
<211> LENGTH: 557
<212> TYPE: PRT
<213> ORGANISM: Artificial Sequence
<220> FEATURE:
<223> OTHER INFORMATION: Synthetic Construct

<400> SEQUENCE: 126

```
Met Val Ser Thr Glu Asn Val Ser Phe Thr Glu Thr Glu Thr Glu Ala
 1               5                  10                  15

Arg Arg Ser Ala Asn Tyr Glu Pro Asn Ser Trp Asp Tyr Asp Tyr Leu
            20                  25                  30

Leu Ser Ser Asp Thr Asp Glu Ser Ile Glu Val Tyr Lys Asp Lys Ala
        35                  40                  45

Lys Lys Leu Glu Ala Glu Val Arg Arg Glu Ile Asn Asn Glu Lys Ala
    50                  55                  60
```

```
Glu Phe Leu Thr Leu Leu Glu Leu Ile Asp Asn Val Gln Arg Leu Gly
 65                  70                  75                  80

Leu Gly Tyr Arg Phe Glu Ser Asp Ile Arg Gly Ala Leu Asp Arg Phe
                 85                  90                  95

Val Ser Ser Gly Gly Phe Asp Ala Val Thr Lys Thr Ser Leu His Gly
            100                 105                 110

Thr Ala Leu Ser Phe Arg Leu Leu Arg Gln His Gly Phe Glu Val Ser
        115                 120                 125

Gln Glu Ala Phe Ser Gly Phe Lys Asp Gln Asn Gly Asn Phe Leu Glu
130                 135                 140

Asn Leu Lys Glu Asp Ile Lys Ala Ile Leu Ser Leu Tyr Glu Ala Ser
145                 150                 155                 160

Phe Leu Ala Leu Glu Gly Glu Asn Ile Leu Asp Glu Ala Lys Val Phe
                165                 170                 175

Ala Ile Ser His Leu Lys Glu Leu Ser Glu Glu Lys Ile Gly Lys Glu
            180                 185                 190

Leu Ala Glu Gln Val Asn His Ala Leu Glu Leu Pro Leu His Arg Arg
        195                 200                 205

Thr Gln Arg Leu Glu Ala Val Trp Ser Ile Glu Ala Tyr Arg Lys Lys
210                 215                 220

Glu Asp Ala Asn Gln Val Leu Glu Leu Ala Ile Leu Asp Tyr Asn
225                 230                 235                 240

Met Ile Gln Ser Val Tyr Gln Arg Asp Leu Arg Glu Thr Ser Arg Trp
                245                 250                 255

Trp Arg Arg Val Gly Leu Ala Thr Lys Leu His Phe Ala Arg Asp Arg
            260                 265                 270

Leu Ile Glu Ser Phe Tyr Trp Ala Val Gly Val Ala Phe Glu Pro Gln
        275                 280                 285

Tyr Ser Asp Cys Arg Asn Ser Val Ala Lys Met Phe Ser Phe Val Thr
290                 295                 300

Ile Ile Asp Asp Ile Tyr Asp Val Tyr Gly Thr Leu Asp Glu Leu Glu
305                 310                 315                 320

Leu Phe Thr Asp Ala Val Glu Arg Trp Asp Val Asn Ala Ile Asn Asp
                325                 330                 335

Leu Pro Asp Tyr Met Lys Leu Cys Phe Leu Ala Leu Tyr Asn Thr Ile
            340                 345                 350

Asn Glu Ile Ala Tyr Asp Asn Leu Lys Asp Lys Gly Glu Asn Ile Leu
        355                 360                 365

Pro Tyr Leu Thr Lys Ala Trp Ala Asp Leu Cys Asn Ala Phe Leu Gln
370                 375                 380

Glu Ala Lys Trp Leu Tyr Asn Lys Ser Thr Pro Thr Phe Asp Asp Tyr
385                 390                 395                 400

Phe Gly Asn Ala Trp Lys Ser Ser Gly Pro Leu Gln Leu Val Phe
                405                 410                 415

Ala Tyr Phe Ala Val Val Gln Asn Ile Lys Lys Glu Ile Glu Asn
            420                 425                 430

Leu Gln Lys Tyr His Asp Thr Ile Ser Arg Pro Ser His Ile Phe Arg
        435                 440                 445

Leu Cys Asn Asp Leu Ala Ser Ala Ser Ala Glu Ile Ala Arg Gly Glu
450                 455                 460

Thr Ala Asn Ser Val Ser Cys Tyr Met Arg Thr Lys Gly Ile Ser Glu
465                 470                 475                 480

Glu Leu Ala Thr Glu Ser Val Met Asn Leu Ile Asp Glu Thr Trp Lys
```

```
                    485                 490                 495
Lys Met Asn Lys Glu Lys Leu Gly Gly Ser Leu Phe Ala Lys Pro Phe
            500                 505                 510

Val Glu Thr Ala Ile Asn Leu Ala Arg Gln Ser His Cys Thr Tyr His
        515                 520                 525

Asn Gly Asp Ala His Thr Ser Pro Asp Glu Leu Thr Arg Lys Arg Val
    530                 535                 540

Leu Ser Val Ile Thr Glu Pro Ile Leu Pro Phe Glu Arg
545                 550                 555

<210> SEQ ID NO 127
<211> LENGTH: 6948
<212> TYPE: DNA
<213> ORGANISM: Artificial Sequence
<220> FEATURE:
<223> OTHER INFORMATION: Synthetic Construct

<400> SEQUENCE: 127
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tccctttagg      180 gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta agggattt tgccgatttc ggcctattgg ttaaaaaatg agctgattta       420
acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg aattaattct tagaaaaact catcgagcat caaatgaaac tgcaatttat     600
tcatatcagg attatcaata ccatatttt gaaaagccg tttctgtaat gaaggagaaa      660
actcaccgag gcagttccat aggatggcaa gatcctggta tcggtctgcg attccgactc     720
gtccaacatc aatacaacct attaatttcc cctcgtcaaa aataaggtta tcaagtgaga     780
aatcaccatg agtgacgact gaatccggtg agaatggcaa agtttatgc atttctttcc      840 agacttgttc aacaggccag ccattacgct cgtcatcaaa atcactcgca tcaaccaaac     900
cgttattcat tcgtgattgc gcctgagcga cgaaatac gcgatcgctg ttaaaaggac       960
aattacaaac aggaatcgaa tgcaaccggc gcaggaacac tgccagcgca tcaacaatat    1020
tttcacctga atcaggatat tcttctaata cctggaatgc tgtttccg gggatcgcag      1080 tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa atcccttaa    1440 cgtgagtttt cgttccactg agcgtcagac cccgtagaaa agatcaaagg atcttcttga    1500
gatccttttt ttctgcgcgt aatctgctgc ttgcaaacaa aaaaccacc gctaccagcg    1560 gtggtttgtt tgccggatca agagctacca actctttttc cgaaggtaac tggcttcagc    1620
agagcgcaga taccaaatac tgtccttcta gtgtagccgt agttaggcca ccacttcaag    1680
```

```
aactctgtag caccgcctac atacctcgct ctgctaatcc tgttaccagt ggctgctgcc    1740
agtggcgata agtcgtgtct taccggggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacgcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
```

```
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa agacaccgg     4560 catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatggtgtcc accgaaaatg tgtctttcac    5100
cgaaactgaa accgaagctc gtcgttctgc gaactacgaa cctaacagct gggactatga    5160
ttacctgctg tcctccgaca cggacgagtc catcgaagta tacaaagaca aagcgaaaaa    5220
gctggaagcc gaagttcgtc gcgagattaa taacgaaaaa gcagaatttc tgaccctgct    5280
ggaactgatt gacaacgtcc agcgcctggg cctgggttac cgtttcgagt ctgatatccg    5340
tggtgcgctg gatcgcttcg tttcctccgg cggcttcgat gcggtaacca agacttccct    5400
gcacggtacg gcactgtctt tccgtctgct gcgtcaacac ggttttgagg tttctcagga    5460
agcgttcagc ggcttcaaag accaaaacgg caacttcctg gagaacctga aggaagatat    5520
caaagctatc ctgagcctgt acgaggccag cttcctggct ctggaaggcg aaaacatcct    5580
ggacgaggcg aaggttttcg caatctctca tctgaaagaa ctgtctgaag aaaagatcgg    5640
taaagagctg gcagaacagg tgaaccatgc actggaactg ccactgcatc gccgtactca    5700
gcgtctggaa gcagtatggt ctatcgaggc ctaccgtaaa aaggaggacg cgaatcaggt    5760
tctgctggag ctggcaattc tggattacaa catgatccag tctgtatacc agcgtgatct    5820
gcgtgaaacg tcccgttggt ggcgtcgtgt gggtctggcg accaaactgc actttgctcg    5880
tgaccgcctg attgagagct ctactgggc cgtgggtgta gcattcgaac cgcaatactc    5940
cgactgccgt aactccgtcg caaaaatgtt ttctttcgta accattatcg acgatatcta    6000
cgatgtatac ggcaccctgg acgaactgga gctgtttact gatgcagttg agcgttggga    6060
cgtaaacgcc atcaacgacc tgccggatta catgaaactg tgctttctgg ctctgtataa    6120
cactattaac gaaatcgcct acgacaacct gaaagataaa ggtgagaaca tcctgccgta    6180
tctgaccaaa gcctgggctg acctgtgcaa cgctttcctg caagaagcca gtggctgta    6240 caacaaatct actccgacct ttgacgacta cttcggcaac gcatggaaat cctcttctgg    6300
cccgctgcaa ctggtgttcg cttacttcgc tgtcgtgcag aacattaaaa aggaagagat    6360
cgaaaacctg caaaaatacc atgacaccat ctctcgtcct tcccatatct tccgtctgtg    6420
caatgacctg gctagcgcgt ctgcggaaat tgcgcgtggt gaaaccgcaa atagcgtttc    6480
```

```
ttgttacatg cgcactaaag gtatctccga agaactggct accgaaagcg tgatgaatct    6540
gatcgatgaa acctggaaaa agatgaacaa ggaaaaactg ggtggtagcc tgttcgcgaa    6600
accgttcgtg gaaaccgcga tcaacctggc acgtcaatct cactgcactt atcataacgg    6660
cgacgcgcat acctctccgg atgagctgac ccgcaaacgc gttctgtctg taatcactga    6720
accgattctg ccgtttgaac gctaaggatc cgaattcgag ctccgtcgac aagcttgcgg    6780
ccgcactcga gcaccaccac caccaccact gagatccggc tgctaacaaa gcccgaaagg    6840
aagctgagtt ggctgctgcc accgctgagc aataactagc ataaccccct ggggcctcta    6900
aacgggtctt gaggggtttt ttgctgaaag gaggaactat atccggat              6948
```

<210> SEQ ID NO 128
<211> LENGTH: 555
<212> TYPE: PRT
<213> ORGANISM: Artificial Sequence
<220> FEATURE:
<223> OTHER INFORMATION: Synthetic Construct

<400> SEQUENCE: 128

```
Met Thr Glu Asn Val Ser Phe Thr Glu Thr Glu Thr Glu Ala Arg Arg
 1               5                  10                  15

Ser Ala Asn Tyr Glu Pro Asn Ser Trp Asp Tyr Asp Tyr Leu Leu Ser
            20                  25                  30

Ser Asp Thr Asp Glu Ser Ile Glu Val Tyr Lys Asp Lys Ala Lys Lys
        35                  40                  45

Leu Glu Ala Glu Val Arg Arg Glu Ile Asn Asn Glu Lys Ala Glu Phe
    50                  55                  60

Leu Thr Leu Leu Glu Leu Ile Asp Asn Val Gln Arg Leu Gly Leu Gly
65                  70                  75                  80

Tyr Arg Phe Glu Ser Asp Ile Arg Gly Ala Leu Asp Arg Phe Val Ser
                85                  90                  95

Ser Gly Gly Phe Asp Ala Val Thr Lys Thr Ser Leu His Gly Thr Ala
            100                 105                 110

Leu Ser Phe Arg Leu Leu Arg Gln His Gly Phe Glu Val Ser Gln Glu
        115                 120                 125

Ala Phe Ser Gly Phe Lys Asp Gln Asn Gly Asn Phe Leu Glu Asn Leu
    130                 135                 140

Lys Glu Asp Ile Lys Ala Ile Leu Ser Leu Tyr Glu Ala Ser Phe Leu
145                 150                 155                 160

Ala Leu Glu Gly Glu Asn Ile Leu Asp Glu Ala Lys Val Phe Ala Ile
                165                 170                 175

Ser His Leu Lys Glu Leu Ser Glu Glu Lys Ile Gly Lys Glu Leu Ala
            180                 185                 190

Glu Gln Val Asn His Ala Leu Glu Leu Pro Leu His Arg Arg Thr Gln
        195                 200                 205

Arg Leu Glu Ala Val Trp Ser Ile Glu Ala Tyr Arg Lys Lys Glu Asp
    210                 215                 220

Ala Asn Gln Val Leu Leu Glu Leu Ala Ile Leu Asp Tyr Asn Met Ile
225                 230                 235                 240

Gln Ser Val Tyr Gln Arg Asp Leu Arg Glu Thr Ser Arg Trp Trp Arg
                245                 250                 255

Arg Val Gly Leu Ala Thr Lys Leu His Phe Ala Arg Asp Arg Leu Ile
            260                 265                 270

Glu Ser Phe Tyr Trp Ala Val Gly Val Ala Phe Glu Pro Gln Tyr Ser
        275                 280                 285
```

```
Asp Cys Arg Asn Ser Val Ala Lys Met Phe Ser Phe Val Thr Ile Ile
        290                 295                 300

Asp Asp Ile Tyr Asp Val Tyr Gly Thr Leu Asp Glu Leu Glu Leu Phe
305                 310                 315                 320

Thr Asp Ala Val Glu Arg Trp Asp Val Asn Ala Ile Asn Asp Leu Pro
            325                 330                 335

Asp Tyr Met Lys Leu Cys Phe Leu Ala Leu Tyr Asn Thr Ile Asn Glu
        340                 345                 350

Ile Ala Tyr Asp Asn Leu Lys Asp Lys Gly Glu Asn Ile Leu Pro Tyr
            355                 360                 365

Leu Thr Lys Ala Trp Ala Asp Leu Cys Asn Ala Phe Leu Gln Glu Ala
370                 375                 380

Lys Trp Leu Tyr Asn Lys Ser Thr Pro Thr Phe Asp Asp Tyr Phe Gly
385                 390                 395                 400

Asn Ala Trp Lys Ser Ser Ser Gly Pro Leu Gln Leu Val Phe Ala Tyr
                405                 410                 415

Phe Ala Val Val Gln Asn Ile Lys Lys Glu Ile Glu Asn Leu Gln
            420                 425                 430

Lys Tyr His Asp Thr Ile Ser Arg Pro Ser His Ile Phe Arg Leu Cys
        435                 440                 445

Asn Asp Leu Ala Ser Ala Ser Ala Glu Ile Ala Arg Gly Glu Thr Ala
450                 455                 460

Asn Ser Val Ser Cys Tyr Met Arg Thr Lys Gly Ile Ser Glu Glu Leu
465                 470                 475                 480

Ala Thr Glu Ser Val Met Asn Leu Ile Asp Glu Thr Trp Lys Lys Met
                485                 490                 495

Asn Lys Glu Lys Leu Gly Gly Ser Leu Phe Ala Lys Pro Phe Val Glu
            500                 505                 510

Thr Ala Ile Asn Leu Ala Arg Gln Ser His Cys Thr Tyr His Asn Gly
        515                 520                 525

Asp Ala His Thr Ser Pro Asp Glu Leu Thr Arg Lys Arg Val Leu Ser
        530                 535                 540

Val Ile Thr Glu Pro Ile Leu Pro Phe Glu Arg
545                 550                 555

<210> SEQ ID NO 129
<211> LENGTH: 6942
<212> TYPE: DNA
<213> ORGANISM: Artificial Sequence
<220> FEATURE:
<223> OTHER INFORMATION: Synthetic Construct

<400> SEQUENCE: 129
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggct ccctttagg      180 gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta agggatttt gccgatttc ggctattgg ttaaaaaatg agctgattta       420
acaaaaattt aacgcgaatt ttaacaaaat attaacgttt acaatttcag gtggcacttt      480
tcggggaaat gtgcgcggaa cccctatttg tttattttc taaatacatt caaatatgta      540
tccgctcatg aattaattct tagaaaaact catcgagcat caaatgaaac tgcaatttat     600
```

```
tcatatcagg attatcaata ccatatttt  gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa ataaggttat caagtgaga     780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gtttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actcttttc  cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata gtcgtgtct  taccggggttg gactcaagac gatagttacc ggataaggcg   1800
cagcggtcgg gctgaacggg gggttcgtgc acacagccca gcttggagcg aacgacctac   1860
accgaactga gataccataca gcgtgagcta tgagaaagcg ccacgcttcc cgaagggaga   1920
aaggcggaca ggtatccggt aagcggcagg gtcggaacag gagagcgcac gagggagctt   1980
ccaggggaa  acgcctggta tctttatagt cctgtcgggt ttcgccacct ctgacttgag   2040
cgtcgatttt tgtgatgctc gtcagggggg cggagcctat ggaaaaacgc cagcaacgcg   2100
gccttttac  ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt ttcctgtttt   2700
ggtcactgat gcctccgtgt aaggggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
```

```
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag gtggtttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc gcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg tgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa cttaagaag gagatataca tatgaccgaa aatgtgtctt tcaccgaaac   5100
tgaaaccgaa gctcgtcgtt ctgcgaacta cgaacctaac agctgggact atgattacct   5160
gctgtcctcc gacacggacg agtccatcga agtatacaaa gacaaagcga aaagctgga   5220
agccgaagtt cgtcgcgaga ttaataacga aaaagcagaa tttctgaccc tgctggaact   5280
gattgacaac gtccagcgcc tgggcctggg ttaccgtttc gagtctgata tccgtggtgc   5340
gctggatcgc ttcgtttcct ccggcggctt cgatgcggta accaagactt ccctgcacgg   5400
```

```
tacggcactg tctttccgtc tgctgcgtca acacggtttt gaggtttctc aggaagcgtt    5460
cagcggcttc aaagaccaaa acggcaactt cctggagaac ctgaaggaag atatcaaagc    5520
tatcctgagc ctgtacgagg ccagcttcct ggctctggaa ggcgaaaaca tcctggacga    5580
ggcgaaggtt ttcgcaatct ctcatctgaa agaactgtct gaagaaaaga tcggtaaaga    5640
gctggcagaa caggtgaacc atgcactgga actgccactg catcgccgta ctcagcgtct    5700
ggaagcagta tggtctatcg aggcctaccg taaaaaggag gacgcgaatc aggttctgct    5760
ggagctggca attctggatt acaacatgat ccagtctgta taccagcgtg atctgcgtga    5820
aacgtcccgt tggtggcgtc gtgtgggtct ggcgaccaaa ctgcactttg ctcgtgaccg    5880
cctgattgag agcttctact gggccgtggg tgtagcattc gaaccgcaat actccgactg    5940
ccgtaactcc gtcgcaaaaa tgttttcttt cgtaaccatt atcgacgata tctacgatgt    6000
atacggcacc ctggacgaac tggagctgtt tactgatgca gttgagcgtt gggacgtaaa    6060
cgccatcaac gacctgccgg attacatgaa actgtgcttt ctggctctgt ataacactat    6120
taacgaaatc gcctacgaca acctgaaaga taaggtgag aacatcctgc cgtatctgac    6180
caaagcctgg gctgacctgt gcaacgcttt cctgcaagaa gccaagtggc tgtacaacaa    6240
atctactccg acctttgacg actacttcgg caacgcatgg aaatcctctt ctggcccgct    6300
gcaactggtg ttcgcttact cgctgtcgt gcagaacatt aaaaaggaag atcgaaaa     6360 cctgcaaaaa taccatgaca ccatctctcg tccttcccat atcttccgtc tgtgcaatga    6420
cctggctagc gcgtctgcgg aaattgcgcg tggtgaaacc gcaaatagcg tttcttgtta    6480
catgcgcact aaaggtatct ccgaagaact ggctaccgaa agcgtgatga atctgatcga    6540
tgaaacctgg aaaagatga acaaggaaaa actgggtggt agcctgttcg cgaaaccgtt    6600
cgtggaaacc gcgatcaacc tggcacgtca atctcactgc acttatcata cggcgacgc     6660 gcatacctct ccggatgagc tgacccgcaa acgcgttctg tctgtaatca ctgaaccgat    6720
tctgccgttt gaacgctaag gatccgaatt cgagctccgt cgacaagctt gcggccgcac    6780
tcgagcacca ccaccaccac cactgagatc cggctgctaa caaagcccga aggaagctg     6840 agttggctgc tgccaccgct gagcaataac tagcataacc ccttggggcc tctaaacggg    6900
tcttgagggg ttttttgctg aaaggaggaa ctatatccgg at                       6942
```

<210> SEQ ID NO 130
<211> LENGTH: 553
<212> TYPE: PRT
<213> ORGANISM: Artificial Sequence
<220> FEATURE:
<223> OTHER INFORMATION: Synthetic Construct

<400> SEQUENCE: 130

```
Met Asn Val Ser Phe Thr Glu Thr Glu Thr Glu Ala Arg Arg Ser Ala
1               5                   10                  15

Asn Tyr Glu Pro Asn Ser Trp Asp Tyr Asp Tyr Leu Leu Ser Ser Asp
            20                  25                  30

Thr Asp Glu Ser Ile Glu Val Tyr Lys Asp Lys Ala Lys Lys Leu Glu
        35                  40                  45

Ala Glu Val Arg Arg Glu Ile Asn Asn Glu Lys Ala Glu Phe Leu Thr
    50                  55                  60

Leu Leu Glu Leu Ile Asp Asn Val Gln Arg Leu Gly Leu Gly Tyr Arg
65                  70                  75                  80

Phe Glu Ser Asp Ile Arg Gly Ala Leu Asp Arg Phe Val Ser Ser Gly
                85                  90                  95
```

```
Gly Phe Asp Ala Val Thr Lys Thr Ser Leu His Gly Thr Ala Leu Ser
                100                 105                 110

Phe Arg Leu Leu Arg Gln His Gly Phe Glu Val Ser Gln Glu Ala Phe
            115                 120                 125

Ser Gly Phe Lys Asp Gln Asn Gly Asn Phe Leu Asn Leu Lys Glu
130                 135                 140

Asp Ile Lys Ala Ile Leu Ser Leu Tyr Glu Ala Ser Phe Leu Ala Leu
145                 150                 155                 160

Glu Gly Glu Asn Ile Leu Asp Glu Ala Lys Val Phe Ala Ile Ser His
                165                 170                 175

Leu Lys Glu Leu Ser Glu Glu Lys Ile Gly Lys Glu Leu Ala Glu Gln
            180                 185                 190

Val Asn His Ala Leu Glu Leu Pro Leu His Arg Arg Thr Gln Arg Leu
        195                 200                 205

Glu Ala Val Trp Ser Ile Glu Ala Tyr Arg Lys Lys Glu Asp Ala Asn
    210                 215                 220

Gln Val Leu Leu Glu Leu Ala Ile Leu Asp Tyr Asn Met Ile Gln Ser
225                 230                 235                 240

Val Tyr Gln Arg Asp Leu Arg Glu Thr Ser Arg Trp Trp Arg Arg Val
                245                 250                 255

Gly Leu Ala Thr Lys Leu His Phe Ala Arg Asp Arg Leu Ile Glu Ser
            260                 265                 270

Phe Tyr Trp Ala Val Gly Val Ala Phe Glu Pro Gln Tyr Ser Asp Cys
        275                 280                 285

Arg Asn Ser Val Ala Lys Met Phe Ser Phe Val Thr Ile Ile Asp Asp
    290                 295                 300

Ile Tyr Asp Val Tyr Gly Thr Leu Asp Glu Leu Glu Leu Phe Thr Asp
305                 310                 315                 320

Ala Val Glu Arg Trp Asp Val Asn Ala Ile Asn Asp Leu Pro Asp Tyr
                325                 330                 335

Met Lys Leu Cys Phe Leu Ala Leu Tyr Asn Thr Ile Asn Glu Ile Ala
            340                 345                 350

Tyr Asp Asn Leu Lys Asp Lys Gly Glu Asn Ile Leu Pro Tyr Leu Thr
        355                 360                 365

Lys Ala Trp Ala Asp Leu Cys Asn Ala Phe Leu Gln Glu Ala Lys Trp
    370                 375                 380

Leu Tyr Asn Lys Ser Thr Pro Thr Phe Asp Asp Tyr Phe Gly Asn Ala
385                 390                 395                 400

Trp Lys Ser Ser Ser Gly Pro Leu Gln Leu Val Phe Ala Tyr Phe Ala
                405                 410                 415

Val Val Gln Asn Ile Lys Lys Glu Glu Ile Glu Asn Leu Gln Lys Tyr
            420                 425                 430

His Asp Thr Ile Ser Arg Pro Ser His Ile Phe Arg Leu Cys Asn Asp
        435                 440                 445

Leu Ala Ser Ala Ser Ala Glu Ile Ala Arg Gly Glu Thr Ala Asn Ser
    450                 455                 460

Val Ser Cys Tyr Met Arg Thr Lys Gly Ile Ser Glu Glu Leu Ala Thr
465                 470                 475                 480

Glu Ser Val Met Asn Leu Ile Asp Glu Thr Trp Lys Lys Met Asn Lys
                485                 490                 495

Glu Lys Leu Gly Gly Ser Leu Phe Ala Lys Pro Phe Val Glu Thr Ala
            500                 505                 510

Ile Asn Leu Ala Arg Gln Ser His Cys Thr Tyr His Asn Gly Asp Ala
```

```
                515                 520                 525
His Thr Ser Pro Asp Glu Leu Thr Arg Lys Arg Val Leu Ser Val Ile
            530                 535                 540

Thr Glu Pro Ile Leu Pro Phe Glu Arg
545                 550

<210> SEQ ID NO 131
<211> LENGTH: 6936
<212> TYPE: DNA
<213> ORGANISM: Artificial Sequence
<220> FEATURE:
<223> OTHER INFORMATION: Synthetic Construct

<400> SEQUENCE: 131
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcggggggc tccctttagg     180
gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta agggatttg ccgatttc ggcctattgg ttaaaaaatg agctgattta        420 acaaaatt aacgcgaatt ttaacaaaat attaacgttt acaatttcag gtggcacttt       480
tcggggaaat gtgcgcggaa cccctatttg tttattttc taaatacatt caaatatgta     540
tccgctcatg aattaattct tagaaaaact catcgagcat caaatgaaac tgcaatttat     600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga acgaaatac gcgatcgctg ttaaaaggac     960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa atcccttaa     1440 cgtgagtttt cgttccactg agcgtcagac cccgtagaaa agatcaaagg atcttcttga    1500 gatcctttt ttctgcgcgt aatctgctgc ttgcaaacaa aaaaaccacc gctaccagcg      1560
gtggtttgtt tgccggatca agagctacca actctttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata gtcgtgtct taccggggttg gactcaagac gatagttacc ggataaggcg    1800
cagcggtcgg gctgaacggg gggttcgtgc acacagccca gcttggagcg aacgacctac    1860
```

```
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980 ccaggggaa acgcctggta tctttatagt cctgtcgggt ttcgccacct ctgacttgag    2040
cgtcgatttt tgtgatgctc gtcagggggg cggagcctat ggaaaaacgc cagcaacgcg   2100 gccttttac ggttcctggc cttttgctgg ccttttgctc acatgttctt tcctgcgtta    2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccgaa cattagtgca ggcagcttcc acagcaatgg   4200
catcctggtc atccagcgga tagttaatga tcagcccact gacgcgttgc gcgagaagat   4260
```

```
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc aacagtccc    4800 ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatgaatgtg tctttcaccg aaactgaaac    5100
cgaagctcgt cgttctgcga actacgaacc taacagctgg gactatgatt acctgctgtc    5160
ctccgacacg gacgagtcca tcgaagtata caaagacaaa gcgaaaaagc tggaagccga    5220
agttcgtcgc gagattaata cgaaaaagc agaatttctg accctgctgg aactgattga    5280
caacgtccag cgcctgggcc tgggttaccg tttcgagtct gatatccgtg gtgcgctgga    5340
tcgcttcgtt tcctccggcg gcttcgatgc ggtaaccaag acttccctgc acggtacggc    5400
actgtctttc cgtctgctgc gtcaacacgg ttttgaggtt tctcaggaag cgttcagcgg    5460
cttcaaagac caaaacggca acttcctgga gaacctgaag gaagatatca agctatcct    5520 gagcctgtac gaggccagct tcctggctct ggaaggcgaa acatcctgg acgaggcgaa    5580 ggttttcgca atctctcatc tgaaagaact gtctgaagaa aagatcggta agagctggc    5640 agaacaggtg aacatgcac tggaactgcc actgcatcgc cgtactcagc gtctggaagc    5700
agtatggtct atcgaggcct accgtaaaaa ggaggacgcg aatcaggttc tgctggagct    5760
ggcaattctg gattacaaca tgatccagtc tgtataccag cgtgatctgc gtgaaacgtc    5820
ccgttggtgg cgtcgtgtgg gtctggcgac caaactgcac tttgctcgtg accgcctgat    5880
tgagagcttc tactgggccg tgggtgtagc attcgaaccg caatactccg actgccgtaa    5940
ctccgtcgca aaaatgtttt ctttcgtaac cattatcgac gatatctacg atgtatacgg    6000
caccctggac gaactggagc tgtttactga tgcagttgag cgttgggacg taaacgccat    6060
caacgacctg ccggattaca tgaaactgtg ctttctggct ctgtataaca ctattaacga    6120
aatcgcctac gacaacctga agataaagg tgagaacatc ctgccgtatc tgaccaaagc    6180
ctgggctgac ctgtgcaacg cttttcctgca agaagccaag tggctgtaca acaaatctac    6240
tccgaccttt gacgactact cggcaacgc atggaaatcc tcttctggcc cgctgcaact    6300
ggtgttcgct tacttcgctg tcgtgcagaa cattaaaaag gaagagatcg aaaacctgca    6360
aaaataccat gacaccatct ctcgtccttc ccatatcttc gtctgtgca atgacctggc    6420 tagcgcgtct gcgaaattg cgcgtggtga accgcaaat agcgtttctt gttacatgcg    6480
cactaaaggt atctccgaag aactggctac cgaaagcgtg atgaatctga tcgatgaaac    6540
ctggaaaaag atgaacaagg aaaaactggg tggtagcctg ttcgcgaaac cgttcgtgga    6600
aaccgcgatc aacctggcac gtcaatctca ctgcacttat cataacggcg acgcgcatac    6660
```

-continued

```
ctctccggat gagctgaccc gcaaacgcgt tctgtctgta atcactgaac cgattctgcc    6720
gtttgaacgc taaggatccg aattcgagct ccgtcgacaa gcttgcggcc gcactcgagc    6780
accaccacca ccaccactga gatccggctg ctaacaaagc ccgaaaggaa gctgagttgg    6840
ctgctgccac cgctgagcaa taactagcat aaccccttgg ggcctctaaa cgggtcttga    6900 ggggttttt gctgaaagga ggaactatat ccggat                              6936
```

<210> SEQ ID NO 132
<211> LENGTH: 559
<212> TYPE: PRT
<213> ORGANISM: Artificial Sequence
<220> FEATURE:
<223> OTHER INFORMATION: Synthetic Construct

<400> SEQUENCE: 132

```
Met Glu Ala Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
        275                 280                 285

Phe Val Thr Ile Ile Asp Asp Ile Tyr Asp Val Tyr Gly Thr Leu Asp
    290                 295                 300

Glu Leu Glu Leu Phe Thr Asp Ala Val Glu Arg Trp Asp Val Asn Ala
305                 310                 315                 320
```

```
Ile Asn Asp Leu Pro Asp Tyr Met Lys Leu Cys Phe Leu Ala Leu Tyr
            325                 330                 335

Asn Thr Ile Asn Glu Ile Ala Tyr Asp Asn Leu Lys Asp Lys Gly Glu
        340                 345                 350

Asn Ile Leu Pro Tyr Leu Thr Lys Ala Trp Ala Asp Leu Cys Asn Ala
            355                 360                 365

Phe Leu Gln Glu Ala Lys Trp Leu Tyr Asn Lys Ser Thr Pro Thr Phe
370                 375                 380

Asp Asp Tyr Phe Gly Asn Ala Trp Lys Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ala Ser Ala Glu Ile Ala
        435                 440                 445

Arg Gly Glu Thr Ala Asn Ser Val Ser Cys Tyr Met Arg Thr Lys Gly
    450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Gly Ser Leu Phe Ala
                485                 490                 495

Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
        515                 520                 525

Lys Arg Val Leu Ser Val Ile Thr Glu Pro Ile Leu Pro Phe Glu Arg
530                 535                 540

Glu Asn Leu Tyr Phe Gln Gly Leu Glu His His His His His His
545                 550                 555

<210> SEQ ID NO 133
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 133
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcggggggc tccctttagg     180
gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta agggattt tgccgatttc ggcctattgg ttaaaaaatg agctgattta      420
acaaaaattt aacgcgaatt ttaacaaaat attaacgttt acaatttcag gtggcactt     480 tcggggaaat gtgcgcggaa cccctatttg tttatttttc taaatacatt caaatatgta     540
tccgctcatg aattaattct tagaaaaact catcgagcat caaatgaaac tgcaatttat     600
tcatatcagg attatcaata ccatattttt gaaaaagccg tttctgtaat gaaggagaaa     660
actcaccgag gcagttccat aggatggcaa gatcctggta tcggtctgcg attccgactc     720
gtccaacatc aatacaacct attaatttcc cctcgtcaaa aataaggtta tcaagtgaga     780
```

```
aatcaccatg agtgacgact gaatccggtg agaatggcaa aagtttatgc atttctttcc      840
agacttgttc aacaggccag ccattacgct cgtcatcaaa atcactcgca tcaaccaaac      900
cgttattcat tcgtgattgc gcctgagcga gacgaaatac gcgatcgctg ttaaaaggac      960
aattacaaac aggaatcgaa tgcaaccggc gcaggaacac tgccagcgca tcaacaatat     1020
tttcacctga atcaggatat tcttctaata cctggaatgc tgttttcccg ggatcgcag      1080
tggtgagtaa ccatgcatca tcaggagtac ggataaaatg cttgatggtc ggaagaggca     1140
taaattccgt cagccagttt agtctgacca tctcatctgt aacatcattg caacgctac      1200
cttttgccatg tttcagaaac aactctggcg catcgggctt cccatacaat cgatagattg     1260
tcgcacctga ttgcccgaca ttatcgcgag cccatttata cccatataaa tcagcatcca     1320
tgttggaatt taatcgcggc ctagagcaag acgtttcccg ttgaatatgg ctcataacac     1380
cccttgtatt actgtttatg taagcagaca gttttattgt tcatgaccaa aatcccttaa     1440
cgtgagtttt cgttccactg agcgtcagac cccgtagaaa agatcaaagg atcttcttga     1500
gatcctttt ttctgcgcgt aatctgctgc ttgcaaacaa aaaaaccacc gctaccagcg     1560
gtggtttgtt tgccggatca agagctacca actcttttc cgaaggtaac tggcttcagc     1620
agagcgcaga taccaaatac tgtccttcta gtgtagccgt agttaggcca ccacttcaag     1680
aactctgtag caccgcctac atacctcgct ctgctaatcc tgttaccagt ggctgctgcc     1740
agtggcgata agtcgtgtct taccgggttg gactcaagac gatagttacc ggataaggcg     1800
cagcggtcgg gctgaacggg gggttcgtgc acacagccca gcttggagcg aacgacctac     1860
accgaactga gatacctaca gcgtgagcta tgagaaagcg ccacgcttcc gaagggaga     1920
aaggcggaca ggtatccggt aagcggcagg gtcggaacag gagagcgcac gagggagctt     1980
ccaggggaa acgcctggta tctttatagt cctgtcgggt ttcgccacct ctgacttgag     2040
cgtcgatttt tgtgatgctc gtcagggggg cggagcctat ggaaaaacgc cagcaacgcg     2100
gcctttttac ggttcctggc cttttgctgg cctttgctc acatgttctt tcctgcgtta     2160
tcccctgatt ctgtggataa ccgtattacc gcctttgagt gagctgatac cgctcgccgc     2220
agccgaacga ccgagcgcag cgagtcagtg agcgaggaag cggaagagcg cctgatgcgg     2280
tattttctcc ttacgcatct gtgcggtatt tcacaccgca tatatggtgc actctcagta     2340
caatctgctc tgatgccgca tagttaagcc agtatacact ccgctatcgc tacgtgactg     2400
ggtcatggct gcgccccgac acccgccaac accgctgac gcgccctgac gggcttgtct     2460
gctcccggca tccgcttaca gacaagctgt gaccgtctcc gggagctgca tgtgtcagag     2520
gttttcaccg tcatcaccga aacgcgcgag gcagctgcgg taaagctcat cagcgtggtc     2580
gtgaagcgat tcacagatgt ctgcctgttc atccgcgtcc agctcgttga gttctccag     2640
aagcgttaat gtctggcttc tgataaagcg ggccatgtta agggcggtt ttcctgttt      2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
```

```
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatggaagct cgtcgttctg cgaactacga   5100
acctaacagc tgggactatg attacctgct gtcctccgac acgacgagt ccatcgaagt   5160 atacaaagac aaagcgaaaa agctggaagc cgaagttcgt cgcgagatta ataacgaaaa   5220
agcagaattt ctgaccctgc tggaactgat tgacaacgtc cagcgcctgg gcctgggtta   5280
ccgtttcgag tctgatatcc gtggtgcgct ggatcgcttc gtttcctccg gcggcttcga   5340
tgcggtaacc aagacttccc tgcacggtac ggcactgtct ttccgtctgc tgcgtcaaca   5400
cggttttgag gtttctcagg aagcgttcag cggcttcaaa gaccaaaacg gcaacttcct   5460
ggagaacctg aaggaagata tcaaagctat cctgagcctg tacgaggcca gcttcctggc   5520
tctggaaggc gaaaacatcc tggacgaggc gaaggttttc gcaatctctc atctgaaaga   5580
```

-continued

```
actgtctgaa gaaaagatcg gtaaagagct ggcagaacag gtgaaccatg cactggaact    5640
gccactgcat cgccgtactc agcgtctgga agcagtatgg tctatcgagg cctaccgtaa    5700
aaaggaggac gcgaatcagg ttctgctgga gctggcaatt ctggattaca acatgatcca    5760
gtctgtatac cagcgtgatc tgcgtgaaac gtcccgttgg tggcgtcgtg tgggtctggc    5820
gaccaaactg cactttgctc gtgaccgcct gattgagagc ttctactggg ccgtgggtgt    5880
agcattcgaa ccgcaatact ccgactgccg taactccgtc gcaaaatgt tttctttcgt    5940 aaccattatc gacgatatct acgatgtata cggcaccctg gacgaactgg agctgtttac    6000
tgatgcagtt gagcgttggg acgtaaacgc catcaacgac ctgccggatt acatgaaact    6060 gtgcttctg gctctgtata acactattaa cgaaatcgcc tacgacaacc tgaaagataa    6120
aggtgagaac atcctgccgt atctgaccaa agcctgggct gacctgtgca acgctttcct    6180
gcaagaagcc aagtggctgt acaacaaatc tactccgacc tttgacgact acttcggcaa    6240
cgcatggaaa tcctcttctg gcccgctgca actggtgttc gcttacttcg ctgtcgtgca    6300
gaacattaaa aaggaagaga tcgaaaacct gcaaaaatac catgacacca tctctcgtcc    6360
ttcccatatc ttccgtctgt gcaatgacct ggctagcgcg tctgcggaaa ttgcgcgtgg    6420
tgaaaccgca aatagcgttt cttgttacat gcgcactaaa ggtatctccg aagaactggc    6480
taccgaaagc gtgatgaatc tgatcgatga aacctggaaa aagatgaaca aggaaaaact    6540
gggtggtagc ctgttcgcga aaccgttcgt ggaaaccgcg atcaacctgg cacgtcaatc    6600
tcactgcact tatcataacg cgacgcgca tacctctccg gatgagctga cccgcaaacg    6660
cgttctgtct gtaatcactg aaccgattct gccgtttgaa cgcgaaaacc tgtattttca    6720
gggcctcgag caccaccacc accaccactg agatccggct gctaacaaag cccgaaagga    6780
agctgagttg gctgctgcca ccgctgagca ataactagca taaccccttg ggcctctaa    6840 acgggtcttg aggggttttt tgctgaaagg aggaactata tccggat                  6887
```

<210> SEQ ID NO 134
<211> LENGTH: 575
<212> TYPE: PRT
<213> ORGANISM: Artificial Sequence
<220> FEATURE:
<223> OTHER INFORMATION: Synthetic Construct

<400> SEQUENCE: 134

```
Met Arg Cys Ser Val Ser Thr Glu Asn Val Ser Phe Thr Glu Thr Glu
 1               5                  10                  15

Thr Glu Ala Arg Arg Ser Ala Asn Tyr Glu Pro Asn Ser Trp Asp Tyr
            20                  25                  30

Asp Tyr Leu Leu Ser Ser Asp Thr Asp Glu Ser Ile Glu Val Tyr Lys
        35                  40                  45

Asp Lys Ala Lys Lys Leu Glu Ala Glu Val Arg Arg Glu Ile Asn Asn
    50                  55                  60

Glu Lys Ala Glu Phe Leu Thr Leu Leu Glu Leu Ile Asp Asn Val Gln
65                  70                  75                  80

Arg Leu Gly Leu Gly Tyr Arg Phe Glu Ser Asp Ile Arg Gly Ala Leu
                85                  90                  95

Asp Arg Phe Val Ser Ser Gly Gly Phe Asp Ala Val Thr Lys Thr Ser
            100                 105                 110

Leu His Gly Thr Ala Leu Ser Phe Arg Leu Leu Arg Gln His Gly Phe
        115                 120                 125

Glu Val Ser Gln Glu Ala Phe Ser Gly Phe Lys Asp Gln Asn Gly Asn
```

```
               130                 135                 140
Phe Leu Glu Asn Leu Lys Glu Asp Ile Lys Ala Ile Leu Ser Leu Tyr
145                 150                 155                 160

Glu Ala Ser Phe Leu Ala Leu Glu Gly Glu Asn Ile Leu Asp Glu Ala
                165                 170                 175

Lys Val Phe Ala Ile Ser His Leu Lys Glu Leu Ser Glu Glu Lys Ile
                180                 185                 190

Gly Lys Glu Leu Ala Glu Gln Val Asn His Ala Leu Glu Leu Pro Leu
                195                 200                 205

His Arg Arg Thr Gln Arg Leu Glu Ala Val Trp Ser Ile Glu Ala Tyr
                210                 215                 220

Arg Lys Lys Glu Asp Ala Asn Gln Val Leu Leu Glu Leu Ala Ile Leu
225                 230                 235                 240

Asp Tyr Asn Met Ile Gln Ser Val Tyr Gln Arg Asp Leu Arg Glu Thr
                245                 250                 255

Ser Arg Trp Trp Arg Arg Val Gly Leu Ala Thr Lys Leu His Phe Ala
                260                 265                 270

Arg Asp Arg Leu Ile Glu Ser Phe Tyr Trp Ala Val Gly Val Ala Phe
                275                 280                 285

Glu Pro Gln Tyr Ser Asp Cys Arg Asn Ser Val Ala Lys Met Phe Ser
290                 295                 300

Phe Val Thr Ile Ile Asp Asp Ile Tyr Asp Val Tyr Gly Thr Leu Asp
305                 310                 315                 320

Glu Leu Glu Leu Phe Thr Asp Ala Val Glu Arg Trp Asp Val Asn Ala
                325                 330                 335

Ile Asn Asp Leu Pro Asp Tyr Met Lys Leu Cys Phe Leu Ala Leu Tyr
                340                 345                 350

Asn Thr Ile Asn Glu Ile Ala Tyr Asp Asn Leu Lys Asp Lys Gly Glu
                355                 360                 365

Asn Ile Leu Pro Tyr Leu Thr Lys Ala Trp Ala Asp Leu Cys Asn Ala
                370                 375                 380

Phe Leu Gln Glu Ala Lys Trp Leu Tyr Asn Lys Ser Thr Pro Thr Phe
385                 390                 395                 400

Asp Asp Tyr Phe Gly Asn Ala Trp Lys Ser Ser Gly Pro Leu Gln
                405                 410                 415

Leu Val Phe Ala Tyr Phe Ala Val Val Gln Asn Ile Lys Lys Glu Glu
                420                 425                 430

Ile Glu Asn Leu Gln Lys Tyr His Asp Thr Ile Ser Arg Pro Ser His
                435                 440                 445

Ile Phe Arg Leu Cys Asn Asp Leu Ala Ser Ala Ser Ala Glu Ile Ala
450                 455                 460

Arg Gly Glu Thr Ala Asn Ser Val Ser Cys Tyr Met Arg Thr Lys Gly
465                 470                 475                 480

Ile Ser Glu Glu Leu Ala Thr Glu Ser Val Met Asn Leu Ile Asp Glu
                485                 490                 495

Thr Trp Lys Lys Met Asn Lys Glu Lys Leu Gly Gly Ser Leu Phe Ala
                500                 505                 510

Lys Pro Phe Val Glu Thr Ala Ile Asn Leu Ala Arg Gln Ser His Cys
                515                 520                 525

Thr Tyr His Asn Gly Asp Ala His Thr Ser Pro Asp Glu Leu Thr Arg
                530                 535                 540

Lys Arg Val Leu Ser Val Ile Thr Glu Pro Ile Leu Pro Phe Glu Arg
545                 550                 555                 560
```

Glu Asn Leu Tyr Phe Gln Gly Leu Glu His His His His His His
                565                 570                 575

<210> SEQ ID NO 135
<211> LENGTH: 6935
<212> TYPE: DNA
<213> ORGANISM: Artificial Sequence
<220> FEATURE:
<223> OTHER INFORMATION: Synthetic Construct

<400> SEQUENCE: 135

| | | | | |
|---|---|---|---|---|
| tggcgaatgg | gacgcgccct | gtagcggcgc | attaagcgcg | gcgggtgtgg | tggttacgcg | 60 |
| cagcgtgacc | gctacacttg | ccagcgccct | agcgcccgct | cctttcgctt | tcttcccttc | 120 |
| ctttctcgcc | acgttcgccg | gctttccccg | tcaagctcta | aatcgggggc | tccctttagg | 180 |
| gttccgattt | agtgctttac | ggcacctcga | ccccaaaaaa | cttgattagg | gtgatggttc | 240 |
| acgtagtggg | ccatcgccct | gatagacggt | ttttcgccct | ttgacgttgg | agtccacgtt | 300 |
| ctttaatagt | ggactcttgt | tccaaactgg | aacaacactc | aaccctatct | cggtctattc | 360 |
| ttttgattta | taagggattt | tgccgatttc | ggcctattgg | ttaaaaaatg | agctgattta | 420 |
| acaaaaattt | aacgcgaatt | ttaacaaaat | attaacgttt | acaatttcag | gtggcacttt | 480 |
| tcggggaaat | gtgcgcggaa | cccctatttg | tttatttttc | taaatacatt | caaatatgta | 540 |
| tccgctcatg | aattaattct | tagaaaaact | catcgagcat | caaatgaaac | tgcaatttat | 600 |
| tcatatcagg | attatcaata | ccatattttt | gaaaaagccg | tttctgtaat | gaaggagaaa | 660 |
| actcaccgag | gcagttccat | aggatggcaa | gatcctggta | tcggtctgcg | attccgactc | 720 |
| gtccaacatc | aatacaacct | attaatttcc | cctcgtcaaa | aataaggtta | tcaagtgaga | 780 |
| aatcaccatg | agtgacgact | gaatccggtg | agaatggcaa | aagtttatgc | atttctttcc | 840 |
| agacttgttc | aacaggccag | ccattacgct | cgtcatcaaa | atcactcgca | tcaaccaaac | 900 |
| cgttattcat | tcgtgattgc | gcctgagcga | gacgaaatac | gcgatcgctg | ttaaaaggac | 960 |
| aattacaaac | aggaatcgaa | tgcaaccggc | gcaggaacac | tgccagcgca | tcaacaatat | 1020 |
| tttcacctga | atcaggatat | tcttctaata | cctggaatgc | tgttttcccg | gggatcgcag | 1080 |
| tggtgagtaa | ccatgcatca | tcaggagtac | ggataaaatg | cttgatggtc | ggaagaggca | 1140 |
| taaattccgt | cagccagttt | agtctgacca | tctcatctgt | aacatcattg | gcaacgctac | 1200 |
| ctttgccatg | tttcagaaac | aactctggcg | catcgggctt | cccatacaat | cgatagattg | 1260 |
| tcgcacctga | ttgcccgaca | ttatcgcgag | cccatttata | cccatataaa | tcagcatcca | 1320 |
| tgttggaatt | taatcgcggc | ctagagcaag | acgtttcccg | ttgaatatgg | ctcataacac | 1380 |
| cccttgtatt | actgtttatg | taagcagaca | gttttattgt | tcatgaccaa | aatcccttaa | 1440 |
| cgtgagtttt | cgttccactg | agcgtcagac | cccgtagaaa | agatcaaagg | atcttcttga | 1500 |
| gatccttttt | ttctgcgcgt | aatctgctgc | ttgcaaacaa | aaaaaccacc | gctaccagcg | 1560 |
| gtggtttgtt | tgccggatca | agagctacca | actctttttc | cgaaggtaac | tggcttcagc | 1620 |
| agagcgcaga | taccaaatac | tgtccttcta | gtgtagccgt | agttaggcca | ccacttcaag | 1680 |
| aactctgtag | caccgcctac | atacctcgct | ctgctaatcc | tgttaccagt | ggctgctgcc | 1740 |
| agtggcgata | agtcgtgtct | taccgggttg | gactcaagac | gatagttacc | ggataaggcg | 1800 |
| cagcggtcgg | gctgaacggg | gggttcgtgc | acacagccca | gcttggagcg | aacgacctac | 1860 |
| accgaactga | gatacctaca | gcgtgagcta | tgagaaagcg | ccacgcttcc | cgaagggaga | 1920 |
| aaggcggaca | ggtatccggt | aagcggcagg | gtcggaacag | gagagcgcac | gagggagctt | 1980 |
| ccagggggaa | acgcctggta | tctttatagt | cctgtcgggt | ttcgccacct | ctgacttgag | 2040 |

```
cgtcgatttt tgtgatgctc gtcagggggg cggagcctat ggaaaaacgc cagcaacgcg   2100 gccttttac  ggttcctggc cttttgctgg ccttttgctc acatgttctt tcctgcgtta   2160 tccctgatt  ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt ttcctgtttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
```

```
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccgccac  gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatgcgttgt agcgtgtcca ccgaaaatgt    5100
gtctttcacc gaaactgaaa ccgaagctcg tcgttctgcg aactacgaac ctaacagctg    5160
ggactatgat tacctgctgt cctccgacac ggacgagtcc atcgaagtat acaaagacaa    5220
agcgaaaaag ctggaagccg aagttcgtcg cgagattaat aacgaaaaag cagaatttct    5280
gaccctgctg gaactgattg acaacgtcca gcgcctgggc ctgggttacc gtttcgagtc    5340
tgatatccgt ggtgcgctgg atcgcttcgt ttcctccggc ggcttcgatg cggtaaccaa    5400
gacttccctg cacggtacgg cactgtcttt ccgtctgctg cgtcaacacg ttttgaggt    5460 ttctcaggaa gcgttcagcg gcttcaaaga ccaaaacggc aacttcctgg agaacctgaa    5520
ggaagatatc aaagctatcc tgagcctgta cgaggccagc ttcctggctc tggaaggcga    5580
aaacatcctg gacgaggcga aggttttcgc aatctctcat ctgaaagaac tgtctgaaga    5640
aaagatcggt aaagagctgg cagaacaggt gaaccatgca ctggaactgc cactgcatcg    5700
ccgtactcag cgtctggaag cagtatggtc tatcgaggcc taccgtaaaa aggaggacgc    5760
gaatcaggtt ctgctggagc tggcaattct ggattacaac atgatccagt ctgtatacca    5820
gcgtgatctg cgtgaaacgt cccgttggtg gcgtcgtgtg ggtctggcga ccaaactgca    5880
ctttgctcgt gaccgcctga ttgagagctt ctactgggcc gtgggtgtag cattcgaacc    5940
gcaatactcc gactgccgta actccgtcgc aaaaatgttt tctttcgtaa ccattatcga    6000
cgatatctac gatgtatacg gcaccctgga cgaactggag ctgtttactg atgcagttga    6060
gcgttgggac gtaaacgcca tcaacgacct gccggattac atgaaactgt gctttctggc    6120
tctgtataac actattaacg aaatcgccta cgacaacctg aaagataaag gtgagaacat    6180
cctgccgtat ctgaccaaag cctgggctga cctgtgcaac gctttcctgc aagaagccaa    6240
gtggctgtac aacaaatcta ctccgacctt tgacgactac ttcggcaacg catggaaatc    6300
ctcttctggc ccgctgcaac tggtgttcgc ttacttcgct gtcgtgcaga acattaaaaa    6360
ggaagagatc gaaaacctgc aaaaatacca tgacaccatc tctcgtcctt cccatatctt    6420
ccgtctgtgc aatgacctgg ctagcgcgtc tgcggaaatt gcgcgtggtg aaaccgcaaa    6480 tagcgttct  tgttacatgc gcactaaagg tatctccgaa gaactggcta ccgaaagcgt    6540
gatgaatctg atcgatgaaa cctggaaaaa gatgaacaag gaaaactggg gtggtagcct    6600
gttcgcgaaa ccgttcgtgg aaaccgcgat caacctggca cgtcaatctc actgcactta    6660
tcataacggc gacgcgcata cctctccgga tgagctgacc cgcaaacgcg ttctgtctgt    6720
aatcactgaa ccgattctgc cgtttgaacg cgaaaacctg tattttcagg gcctcgagca    6780
ccaccaccac caccactgag atccggctgc taacaaagcc cgaaaggaag ctgagttggc    6840
```
tgctgccacc gctgagcaat aactagcata acccctgggg gcctctaaac gggtcttgag      6900
gggttttttg ctgaaaggag gaactatatc cggat      6935

<210> SEQ ID NO 136
<211> LENGTH: 545
<212> TYPE: PRT
<213> ORGANISM: Artificial Sequence
<220> FEATURE:
<223> OTHER INFORMATION: Synthetic Construct

<400> SEQUENCE: 136

Met Thr Glu Ala Arg Arg Ser Ala Asn Tyr Glu Pro Asn Ser Trp Asp
 1               5                  10                  15

Tyr Asp Tyr Leu Leu Ser Ser Asp Thr Asp Glu Ser Ile Glu Val Tyr
             20                  25                  30

Lys Asp Lys Ala Lys Lys Leu Glu Ala Glu Val Arg Arg Glu Ile Asn
         35                  40                  45

Asn Glu Lys Ala Glu Phe Leu Thr Leu Leu Glu Leu Ile Asp Asn Val
     50                  55                  60

Gln Arg Leu Gly Leu Gly Tyr Arg Phe Glu Ser Asp Ile Arg Gly Ala
 65                  70                  75                  80

Leu Asp Arg Phe Val Ser Ser Gly Gly Phe Asp Ala Val Thr Lys Thr
                 85                  90                  95

Ser Leu His Gly Thr Ala Leu Ser Phe Arg Leu Leu Arg Gln His Gly
            100                 105                 110

Phe Glu Val Ser Gln Glu Ala Phe Ser Gly Phe Lys Asp Gln Asn Gly
        115                 120                 125

Asn Phe Leu Glu Asn Leu Lys Glu Asp Ile Lys Ala Ile Leu Ser Leu
    130                 135                 140

Tyr Glu Ala Ser Phe Leu Ala Leu Glu Gly Glu Asn Ile Leu Asp Glu
145                 150                 155                 160

Ala Lys Val Phe Ala Ile Ser His Leu Lys Glu Leu Ser Glu Glu Lys
                165                 170                 175

Ile Gly Lys Glu Leu Ala Glu Gln Val Asn His Ala Leu Glu Leu Pro
            180                 185                 190

Leu His Arg Arg Thr Gln Arg Leu Glu Ala Val Trp Ser Ile Glu Ala
        195                 200                 205

Tyr Arg Lys Lys Glu Asp Ala Asn Gln Val Leu Leu Glu Leu Ala Ile
    210                 215                 220

Leu Asp Tyr Asn Met Ile Gln Ser Val Tyr Gln Arg Asp Leu Arg Glu
225                 230                 235                 240

Thr Ser Arg Trp Trp Arg Arg Val Gly Leu Ala Thr Lys Leu His Phe
                245                 250                 255

Ala Arg Asp Arg Leu Ile Glu Ser Phe Tyr Trp Ala Val Gly Val Ala
            260                 265                 270

Phe Glu Pro Gln Tyr Ser Asp Cys Arg Asn Ser Val Ala Lys Met Phe
        275                 280                 285

Ser Phe Val Thr Ile Ile Asp Asp Ile Tyr Asp Val Tyr Gly Thr Leu
    290                 295                 300

Asp Glu Leu Glu Leu Phe Thr Asp Ala Val Glu Arg Trp Asp Val Asn
305                 310                 315                 320

Ala Ile Asn Asp Leu Pro Asp Tyr Met Lys Leu Cys Phe Leu Ala Leu
                325                 330                 335

Tyr Asn Thr Ile Asn Glu Ile Ala Tyr Asp Asn Leu Lys Asp Lys Gly
            340                 345                 350

Glu Asn Ile Leu Pro Tyr Leu Thr Lys Ala Trp Ala Asp Leu Cys Asn
        355                 360                 365

Ala Phe Leu Gln Glu Ala Lys Trp Leu Tyr Asn Lys Ser Thr Pro Thr
    370                 375                 380

Phe Asp Asp Tyr Phe Gly Asn Ala Trp Lys Ser Ser Gly Pro Leu
385                 390                 395                 400

Gln Leu Val Phe Ala Tyr Phe Ala Val Val Gln Asn Ile Lys Lys Glu
                405                 410                 415

Glu Ile Glu Asn Leu Gln Lys Tyr His Asp Thr Ile Ser Arg Pro Ser
            420                 425                 430

His Ile Phe Arg Leu Cys Asn Asp Leu Ala Ser Ala Ser Ala Glu Ile
        435                 440                 445

Ala Arg Gly Glu Thr Ala Asn Ser Val Ser Cys Tyr Met Arg Thr Lys
    450                 455                 460

Gly Ile Ser Glu Glu Leu Ala Thr Glu Ser Val Met Asn Leu Ile Asp
465                 470                 475                 480

Glu Thr Trp Lys Lys Met Asn Lys Glu Lys Leu Gly Gly Ser Leu Phe
                485                 490                 495

Ala Lys Pro Phe Val Glu Thr Ala Ile Asn Leu Ala Arg Gln Ser His
            500                 505                 510

Cys Thr Tyr His Asn Gly Asp Ala His Thr Ser Pro Asp Glu Leu Thr
        515                 520                 525

Arg Lys Arg Val Leu Ser Val Ile Thr Glu Pro Ile Leu Pro Phe Glu
    530                 535                 540

Arg
545

<210> SEQ ID NO 137
<211> LENGTH: 6912
<212> TYPE: DNA
<213> ORGANISM: Artificial Sequence
<220> FEATURE:
<223> OTHER INFORMATION: Synthetic Construct

<400> SEQUENCE: 137
tggcgaatgg gacgcgccct gtagcggcgc attaagcgcg gcgggtgtgg tggttacgcg     60
cagcgtgacc gctacacttg ccagcgccct agcgcccgct cctttcgctt tcttcccttc    120
ctttctcgcc acgttcgccg gctttccccg tcaagctcta atcgggggc tccctttagg    180
gttccgattt agtgctttac ggcacctcga ccccaaaaaa cttgattagg gtgatggttc    240
acgtagtggg ccatcgccct gatagacggt ttttcgccct tgacgttgg agtccacgtt    300
ctttaatagt ggactcttgt tccaaactgg aacaacactc aaccctatct cggtctattc    360
ttttgattta aagggattt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttatttttc taaatacatt caaatatgta    540
tccgctcatg aattaattct tagaaaaact catcgagcat caaatgaaac tgcaatttat    600
tcatatcagg attatcaata ccatatttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa ataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900

```
cgttattcat tcgtgattgc gcctgagcga gacgaaatac gcgatcgctg ttaaaaggac      960
aattacaaac aggaatcgaa tgcaaccggc gcaggaacac tgccagcgca tcaacaatat     1020
tttcacctga atcaggatat tcttctaata cctggaatgc tgttttcccg gggatcgcag     1080
tggtgagtaa ccatgcatca tcaggagtac ggataaaatg cttgatggtc ggaagaggca     1140
taaattccgt cagccagttt agtctgacca tctcatctgt aacatcattg gcaacgctac     1200
cttttgccatg tttcagaaac aactctggcg catcgggctt cccatacaat cgatagattg     1260
tcgcacctga ttgcccgaca ttatcgcgag cccatttata cccatataaa tcagcatcca     1320
tgttggaatt taatcgcggc ctagagcaag acgtttcccg ttgaatatgg ctcataacac     1380
cccttgtatt actgtttatg taagcagaca gttttattgt tcatgaccaa aatcccttaa     1440
cgtgagtttt cgttccactg agcgtcagac cccgtagaaa agatcaaagg atcttcttga     1500
gatcctttt ttctgcgcgt aatctgctgc ttgcaaacaa aaaaaccacc gctaccagcg     1560
gtggtttgtt tgccggatca agagctacca actcttttc cgaaggtaac tggcttcagc     1620
agagcgcaga taccaaatac tgtccttcta gtgtagccgt agttaggcca ccacttcaag     1680
aactctgtag caccgcctac atacctcgct ctgctaatcc tgttaccagt ggctgctgcc     1740
agtggcgata agtcgtgtct taccgggttg gactcaagac gatagttacc ggataaggcg     1800
cagcggtcgg gctgaacggg gggttcgtgc acacagccca gcttggagcg aacgacctac     1860
accgaactga gatacctaca gcgtgagcta tgagaaagcg ccacgcttcc gaagggaga     1920
aaggcggaca ggtatccggt aagcggcagg gtcggaacag gagagcgcac gagggagctt     1980
ccaggggaa acgcctggta tctttatagt cctgtcgggt ttcgccacct ctgacttgag     2040
cgtcgatttt tgtgatgctc gtcaggggg cggagcctat ggaaaaacgc cagcaacgcg     2100
gccttttac ggttcctggc cttttgctgg ccttttgctc acatgttctt tcctgcgtta     2160
tcccctgatt ctgtggataa ccgtattacc gcctttgagt gagctgatac cgctcgccgc     2220
agccgaacga ccgagcgcag cgagtcagtg agcgaggaag cggaagagcg cctgatgcgg     2280
tattttctcc ttacgcatct gtgcggtatt tcacaccgca tatatggtgc actctcagta     2340
caatctgctc tgatgccgca tagttaagcc agtatacact ccgctatcgc tacgtgactg     2400
ggtcatggct gcgccccgac acccgccaac acccgctgac gcgccctgac gggcttgtct     2460
gctcccggca tccgcttaca gacaagctgt gaccgtctcc gggagctgca tgtgtcagag     2520
gttttcaccg tcatcaccga aacgcgcgag gcagctgcgg taaagctcat cagcgtggtc     2580
gtgaagcgat tcacagatgt ctgcctgttc atccgcgtcc agctcgttga gtttctccag     2640
aagcgttaat gtctggcttc tgataaagcg ggccatgtta agggcggttt ttcctgtttt     2700
ggtcactgat gcctccgtgt aagggggatt tctgttcatg ggggtaatga taccgatgaa     2760
acgagagagg atgctcacga tacgggttac tgatgatgaa catgcccggt tactggaacg     2820
ttgtgagggt aaacaactgg cggtatggat gcggcgggac cagagaaaaa tcactcaggg     2880
tcaatgccag cgcttcgtta atacagatgt aggtgttcca cagggtagcc agcagcatcc     2940
tgcgatgcag atccggaaca taatggtgca gggcgctgac ttccgcgttt ccagactttta     3000
cgaaacacgg aaaccgaaga ccattcatgt tgttgctcag gtcgcagacg ttttgcagca     3060
gcagtcgctt cacgttcgct cgcgtatcgg tgattcattc tgctaaccag taaggcaacc     3120
ccgccagcct agccgggtcc tcaacgacag gagcacgatc atgcgcaccc gtgggccgc      3180
catgccggcg ataatggcct gcttctcgcc gaaacgtttg gtggcgggac cagtgacgaa     3240
ggcttgagcg agggcgtgca agattccgaa taccgcaagc gacaggccga tcatcgtcgc     3300
```

```
gctccagcga aagcggtcct cgccgaaaat gacccagagc gctgccggca cctgtcctac      3360
gagttgcatg ataaagaaga cagtcataag tgcggcgacg atagtcatgc cccgcgccca      3420
ccggaaggag ctgactgggt tgaaggctct caagggcatc ggtcgagatc ccggtgccta      3480
atgagtgagc taacttacat taattgcgtt gcgctcactg cccgctttcc agtcgggaaa      3540
cctgtcgtgc cagctgcatt aatgaatcgg ccaacgcgcg gggagaggcg gtttgcgtat      3600
tgggcgccag ggtggttttt cttttcacca gtgagacggg caacagctga ttgcccttca      3660
ccgcctggcc ctgagagagt tgcagcaagc ggtccacgct ggtttgcccc agcaggcgaa      3720
aatcctgttt gatggtggtt aacggcggga tataacatga gctgtcttcg gtatcgtcgt      3780
atcccactac cgagatatcc gcaccaacgc gcagcccgga ctcggtaatg cgcgcattg       3840
cgcccagcgc catctgatcg ttggcaacca gcatcgcagt gggaacgatg ccctcattca      3900
gcatttgcat ggtttgttga aaaccggaca tggcactcca gtcgccttcc cgttccgcta      3960
tcggctgaat ttgattgcga gtgagatatt tatgccagcc agccgacgc agacgcgccg       4020
agacagaact taatgggccc gctaacagcg cgatttgctg gtgacccaat gcgaccagat      4080
gctccacgcc cagtcgcgta ccgtcttcat gggagaaaat aatactgttg atgggtgtct      4140
ggtcagagac atcaagaaat aacgccggaa cattagtgca ggcagcttcc acagcaatgg      4200
catcctggtc atccagcgga tagttaatga tcagcccact gacgcgttgc gcgagaagat      4260
tgtgcaccgc cgctttacag gcttcgacgc cgcttcgttc taccatcgac accaccacgc      4320
tggcacccag ttgatcggcg cgagatttaa tcgccgcgac aatttgcgac ggcgcgtgca      4380
gggccagact ggaggtggca acgccaatca gcaacgactg tttgcccgcc agttgttgtg      4440
ccacgcggtt gggaatgtaa ttcagctccg ccatcgccgc ttccacttt tcccgcgttt        4500
tcgcagaaac gtggctggcc tggttcacca cgcgggaaac ggtctgataa gagacaccgg      4560
catactctgc gacatcgtat aacgttactg gtttcacatt caccaccctg aattgactct      4620
cttccgggcg ctatcatgcc ataccgcgaa aggttttgcg ccattcgatg gtgtccggga      4680
tctcgacgct ctcccttatg cgactcctgc attaggaagc agcccagtag taggttgagg      4740
ccgttgagca ccgccgccgc aaggaatggt gcatgcaagg agatggcgcc caacagtccc      4800
ccggccacgg ggcctgccac catacccacg ccgaaacaag cgctcatgag cccgaagtgg      4860
cgagcccgat cttccccatc ggtgatgtcg gcgatatagg cgccagcaac cgcacctgtg      4920
gcgccggtga tgccggccac gatgcgtccg gcgtagagga tcgagatctc gatcccgcga      4980
aattaatacg actcactata ggggaattgt gagcggataa caattcccct ctagaaataa      5040
ttttgtttaa ctttaagaag gagatataca tatgaccgaa gctcgtcgtt ctgcgaacta      5100
cgaacctaac agctgggact atgattacct gctgtcctcc gacacggacg agtccatcga      5160
agtatacaaa gacaaagcga aaagctgga agccgaagtt cgtcgcgaga ttaataacga       5220
aaaagcagaa tttctgaccc tgctggaact gattgacaac gtccagcgcc tgggcctggg      5280
ttaccgtttc gagtctgata ccgtggtgc gctggatcgc ttcgtttcct ccggcggctt       5340
cgatgcggta accaagactt ccctgcacgg tacggcactg tctttccgtc tgctgcgtca      5400
acacggtttt gaggtttctc aggaagcgtt cagcggcttc aaagaccaaa acggcaactt      5460
cctggagaac ctgaaggaag atatcaaagc tatcctgagc ctgtacgagg ccagcttcct      5520
ggctctggaa ggcgaaaaca tcctggacga ggcgaaggtt ttcgcaatct ctcatctgaa      5580
agaactgtct gaagaaaaga tcggtaaaga gctggcagaa caggtgaacc atgcactgga      5640
actgccactg catcgccgta ctcagcgtct ggaagcagta tggtctatcg aggcctaccg      5700
```

-continued

```
taaaaaggag gacgcgaatc aggttctgct ggagctggca attctggatt acaacatgat      5760
ccagtctgta taccagcgtg atctgcgtga acgtcccgt tggtggcgtc gtgtgggtct       5820
ggcgaccaaa ctgcactttg ctcgtgaccg cctgattgag agcttctact gggccgtggg      5880
tgtagcattc gaaccgcaat actccgactg ccgtaactcc gtcgcaaaaa tgttttcttt      5940
cgtaaccatt atcgacgata tctacgatgt atacggcacc ctggacgaac tggagctgtt      6000
tactgatgca gttgagcgtt gggacgtaaa cgccatcaac gacctgccgg attacatgaa      6060
actgtgcttt ctggctctgt ataacactat taacgaaatc gcctacgaca acctgaaaga      6120
taaaggtgag aacatcctgc cgtatctgac caaagcctgg gctgacctgt gcaacgcttt      6180
cctgcaagaa gccaagtggc tgtacaacaa atctactccg acctttgacg actacttcgg      6240
caacgcatgg aaatcctctt ctggcccgct gcaactggtg ttcgcttact cgctgtcgt       6300 gcagaacatt aaaaaggaag agatcgaaaa cctgcaaaaa taccatgaca ccatctctcg      6360
tccttcccat atcttccgtc tgtgcaatga cctggctagc gcgtctgcgg aaattgcgcg      6420
tggtgaaacc gcaaatagcg tttcttgtta catgcgcact aaaggtatct ccgaagaact      6480
ggctaccgaa agcgtgatga atctgatcga tgaaacctgg aaaaagatga acaaggaaaa      6540
actgggtggt agcctgttcg cgaaaccgtt cgtggaaacc gcgatcaacc tggcacgtca      6600
atctcactgc acttatcata acggcgacgc gcatacctct ccggatgagc tgacccgcaa      6660
acgcgttctg tctgtaatca ctgaaccgat tctgccgttt gaacgctaag gatccgaatt      6720
cgagctccgt cgacaagctt gcggccgcac tcgagcacca ccaccaccac cactgagatc      6780
cggctgctaa caaagcccga aggaagctg agttggctgc tgccaccgct gagcaataac       6840
tagcataacc ccttggggcc tctaaacggg tcttgagggg ttttttgctg aaaggaggaa      6900
ctatatccgg at                                                          6912
```

<210> SEQ ID NO 138
<211> LENGTH: 546
<212> TYPE: PRT
<213> ORGANISM: Artificial Sequence
<220> FEATURE:
<223> OTHER INFORMATION: Synthetic Construct

<400> SEQUENCE: 138

```
Met Glu Thr Glu Ala Arg Arg Ser Ala Asn Tyr Glu Pro Asn Ser Trp
 1               5                  10                  15

Asp Tyr Asp Tyr Leu Leu Ser Ser Asp Thr Asp Glu Ser Ile Glu Val
            20                  25                  30

Tyr Lys Asp Lys Ala Lys Lys Leu Glu Ala Glu Val Arg Arg Glu Ile
        35                  40                  45

Asn Asn Glu Lys Ala Glu Phe Leu Thr Leu Leu Glu Leu Ile Asp Asn
    50                  55                  60

Val Gln Arg Leu Gly Leu Gly Tyr Arg Phe Glu Ser Asp Ile Arg Gly
65                  70                  75                  80

Ala Leu Asp Arg Phe Val Ser Ser Gly Gly Phe Asp Ala Val Thr Lys
                85                  90                  95

Thr Ser Leu His Gly Thr Ala Leu Ser Phe Arg Leu Leu Arg Gln His
            100                 105                 110

Gly Phe Glu Val Ser Gln Glu Ala Phe Ser Gly Phe Lys Asp Gln Asn
        115                 120                 125

Gly Asn Phe Leu Glu Asn Leu Lys Glu Asp Ile Lys Ala Ile Leu Ser
    130                 135                 140

Leu Tyr Glu Ala Ser Phe Leu Ala Leu Glu Gly Glu Asn Ile Leu Asp
```

```
            145                 150                 155                 160
        Glu Ala Lys Val Phe Ala Ile Ser His Leu Lys Glu Leu Ser Glu Glu
                        165                 170                 175
        Lys Ile Gly Lys Glu Leu Ala Glu Gln Val Asn His Ala Leu Glu Leu
                        180                 185                 190
        Pro Leu His Arg Arg Thr Gln Arg Leu Glu Ala Val Trp Ser Ile Glu
                        195                 200                 205
        Ala Tyr Arg Lys Lys Glu Asp Ala Asn Gln Val Leu Leu Glu Leu Ala
                        210                 215                 220
        Ile Leu Asp Tyr Asn Met Ile Gln Ser Val Tyr Gln Arg Asp Leu Arg
        225                 230                 235                 240
        Glu Thr Ser Arg Trp Trp Arg Arg Val Gly Leu Ala Thr Lys Leu His
                            245                 250                 255
        Phe Ala Arg Asp Arg Leu Ile Glu Ser Phe Tyr Trp Ala Val Gly Val
                        260                 265                 270
        Ala Phe Glu Pro Gln Tyr Ser Asp Cys Arg Asn Ser Val Ala Lys Met
                        275                 280                 285
        Phe Ser Phe Val Thr Ile Ile Asp Asp Ile Tyr Asp Val Tyr Gly Thr
                        290                 295                 300
        Leu Asp Glu Leu Glu Leu Phe Thr Asp Ala Val Glu Arg Trp Asp Val
        305                 310                 315                 320
        Asn Ala Ile Asn Asp Leu Pro Asp Tyr Met Lys Leu Cys Phe Leu Ala
                        325                 330                 335
        Leu Tyr Asn Thr Ile Asn Glu Ile Ala Tyr Asp Asn Leu Lys Asp Lys
                        340                 345                 350
        Gly Glu Asn Ile Leu Pro Tyr Leu Thr Lys Ala Trp Ala Asp Leu Cys
                        355                 360                 365
        Asn Ala Phe Leu Gln Glu Ala Lys Trp Leu Tyr Asn Lys Ser Thr Pro
                        370                 375                 380
        Thr Phe Asp Asp Tyr Phe Gly Asn Ala Trp Lys Ser Ser Ser Gly Pro
        385                 390                 395                 400
        Leu Gln Leu Val Phe Ala Tyr Phe Ala Val Val Gln Asn Ile Lys Lys
                        405                 410                 415
        Glu Glu Ile Glu Asn Leu Gln Lys Tyr His Asp Thr Ile Ser Arg Pro
                        420                 425                 430
        Ser His Ile Phe Arg Leu Cys Asn Asp Leu Ala Ser Ala Ser Ala Glu
                        435                 440                 445
        Ile Ala Arg Gly Glu Thr Ala Asn Ser Val Ser Cys Tyr Met Arg Thr
        450                 455                 460
        Lys Gly Ile Ser Glu Glu Leu Ala Thr Glu Ser Val Met Asn Leu Ile
        465                 470                 475                 480
        Asp Glu Thr Trp Lys Lys Met Asn Lys Glu Lys Leu Gly Gly Ser Leu
                        485                 490                 495
        Phe Ala Lys Pro Phe Val Glu Thr Ala Ile Asn Leu Ala Arg Gln Ser
                        500                 505                 510
        His Cys Thr Tyr His Asn Gly Asp Ala His Thr Ser Pro Asp Glu Leu
                        515                 520                 525
        Thr Arg Lys Arg Val Leu Ser Val Ile Thr Glu Pro Ile Leu Pro Phe
                        530                 535                 540
        Glu Arg
        545

<210> SEQ ID NO 139
<211> LENGTH: 6915
```

<212> TYPE: DNA
<213> ORGANISM: Artificial Sequence
<220> FEATURE:
<223> OTHER INFORMATION: Synthetic Construct

<400> SEQUENCE: 139

| | | | | | |
|---|---|---|---|---|---|
| tggcgaatgg | gacgcgccct | gtagcggcgc | attaagcgcg | gcgggtgtgg | tggttacgcg | 60 |
| cagcgtgacc | gctacacttg | ccagcgccct | agcgcccgct | cctttcgctt | tcttcccttc | 120 |
| ctttctcgcc | acgttcgccg | gctttccccg | tcaagctcta | atcgggggc | tccctttagg | 180 |
| gttccgattt | agtgctttac | ggcacctcga | ccccaaaaaa | cttgattagg | gtgatggttc | 240 |
| acgtagtggg | ccatcgccct | gatagacggt | ttttcgccct | ttgacgttgg | agtccacgtt | 300 |
| ctttaatagt | ggactcttgt | tccaaactgg | aacaacactc | aaccctatct | cggtctattc | 360 |
| ttttgattta | taagggattt | tgccgatttc | ggcctattgg | ttaaaaaatg | agctgattta | 420 |
| acaaaaattt | aacgcgaatt | ttaacaaaat | attaacgttt | acaatttcag | gtggcacttt | 480 |
| tcggggaaat | gtgcgcggaa | cccctatttg | tttattttc | taaatacatt | caaatatgta | 540 |
| tccgctcatg | aattaattct | tagaaaaact | catcgagcat | caaatgaaac | tgcaatttat | 600 |
| tcatatcagg | attatcaata | ccatattttt | gaaaagccg | tttctgtaat | gaaggagaaa | 660 |
| actcaccgag | gcagttccat | aggatggcaa | gatcctggta | tcggtctgcg | attccgactc | 720 |
| gtccaacatc | aatacaacct | attaatttcc | cctcgtcaaa | aataaggtta | tcaagtgaga | 780 |
| aatcaccatg | agtgacgact | gaatccggtg | agaatggcaa | aagtttatgc | atttctttcc | 840 |
| agacttgttc | aacaggccag | ccattacgct | cgtcatcaaa | atcactcgca | tcaaccaaac | 900 |
| cgttattcat | tcgtgattgc | gcctgagcga | gacgaaatac | gcgatcgctg | ttaaaaggac | 960 |
| aattacaaac | aggaatcgaa | tgcaaccggc | gcaggaacac | tgccagcgca | tcaacaatat | 1020 |
| tttcacctga | atcaggatat | tcttctaata | cctggaatgc | tgttttcccg | gggatcgcag | 1080 |
| tggtgagtaa | ccatgcatca | tcaggagtac | ggataaaatg | cttgatggtc | ggaagaggca | 1140 |
| taaattccgt | cagccagttt | agtctgacca | tctcatctgt | aacatcattg | gcaacgctac | 1200 |
| ctttgccatg | tttcagaaac | aactctggcg | catcgggctt | cccatacaat | cgatagattg | 1260 |
| tcgcacctga | ttgcccgaca | ttatcgcgag | cccatttata | cccatataaa | tcagcatcca | 1320 |
| tgttggaatt | taatcgcggc | ctagagcaag | acgtttcccg | ttgaatatgg | ctcataacac | 1380 |
| cccttgtatt | actgtttatg | taagcagaca | gttttattgt | tcatgaccaa | aatcccttaa | 1440 |
| cgtgagtttt | cgttccactg | agcgtcagac | cccgtagaaa | agatcaaagg | atcttcttga | 1500 |
| gatccttttt | ttctgcgcgt | aatctgctgc | ttgcaaacaa | aaaaaccacc | gctaccagcg | 1560 |
| gtggtttgtt | tgccggatca | agagctacca | actctttttc | cgaaggtaac | tggcttcagc | 1620 |
| agagcgcaga | taccaaatac | tgtccttcta | gtgtagccgt | agttaggcca | ccacttcaag | 1680 |
| aactctgtag | caccgcctac | atacctcgct | ctgctaatcc | tgttaccagt | ggctgctgcc | 1740 |
| agtggcgata | agtcgtgtct | taccgggttg | gactcaagac | gatagttacc | ggataaggcg | 1800 |
| cagcggtcgg | gctgaacggg | gggttcgtgc | acacagccca | gcttggagcg | aacgacctac | 1860 |
| accgaactga | gatacctaca | gcgtgagcta | tgagaaagcg | ccacgcttcc | cgaagggaga | 1920 |
| aaggcggaca | ggtatccggt | aagcggcagg | gtcggaacag | gagagcgcac | gagggagctt | 1980 |
| ccagggggaa | acgcctggta | tctttatagt | cctgtcgggt | ttcgccacct | ctgacttgag | 2040 |
| cgtcgatttt | tgtgatgctc | gtcaggggg | cggagcctat | ggaaaaacgc | cagcaacgcg | 2100 |
| gcctttttac | ggttcctggc | cttttgctgg | ccttttgctc | acatgttctt | tcctgcgtta | 2160 |
| tcccctgatt | ctgtggataa | ccgtattacc | gcctttgagt | gagctgatac | cgctcgccgc | 2220 |

```
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag gtggtttttc ttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat tgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
```

```
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatggaaacc gaagctcgtc gttctgcgaa   5100
ctacgaacct aacagctggg actatgatta cctgctgtcc tccgacacgg acagtccat    5160
cgaagtatac aaagacaaag cgaaaaagct ggaagccgaa gttcgtcgcg agattaataa   5220
cgaaaaagca gaatttctga ccctgctgga actgattgac aacgtccagc gcctgggcct   5280
gggttaccgt ttcgagtctg atatccgtgg tgcgctggat cgcttcgttt cctccggcgg   5340
cttcgatgcg gtaaccaaga cttccctgca cggtacggca ctgtctttcc gtctgctgcg   5400
tcaacacggt tttgaggttt ctcaggaagc gttcagcggc ttcaaagacc aaaacggcaa   5460
cttcctggag aacctgaagg aagatatcaa agctatcctg agcctgtacg aggccagctt   5520
cctggctctg gaaggcgaaa acatcctgga cgaggcgaag gttttcgcaa tctctcatct   5580
gaaagaactg tctgaagaaa gatcggtaa agagctggca gaacaggtga accatgcact   5640
ggaactgcca ctgcatcgcc gtactcagcg tctggaagca gtatggtcta tcgaggccta   5700
ccgtaaaaag gaggacgcga atcaggttct gctggagctg gcaattctgg attacaacat   5760
gatccagtct gtataccagc gtgatctgcg tgaaacgtcc cgttggtggc gtcgtgtggg   5820
tctggcgacc aaactgcact ttgctcgtga ccgcctgatt gagagcttct actgggccgt   5880
gggtgtagca ttcgaaccgc aatactccga ctgccgtaac tccgtcgcaa aaatgttttc   5940
tttcgtaacc attatcgacg atatctacga tgtatacggc accctggacg aactggagct   6000
gtttactgat gcagttgagc gttgggacgt aaacgccatc aacgacctgc cggattacat   6060
gaaactgtgc tttctggctc tgtataacac tattaacgaa atcgcctacg acaacctgaa   6120
agataaaggt gagaacatcc tgccgtatct gaccaaagcc tgggctgacc tgtgcaacgc   6180
tttcctgcaa gaagccaagt ggctgtacaa caaatctact ccgaccttg acgactactt    6240
cggcaacgca tggaaatcct cttctggccc gctgcaactg gtgttcgctt acttcgctgt   6300
cgtgcagaac attaaaaagg aagagatcga aaacctgcaa aaataccatg acaccatctc   6360
tcgtccttcc catatcttcc gtctgtgcaa tgacctggct agcgcgtctg cggaaattgc   6420
gcgtggtgaa accgcaaata gcgtttcttg ttacatgcgc actaaaggta tctccgaaga   6480
actggctacc gaaagcgtga tgaatctgat cgatgaaacc tggaaaaaga tgaacaagga   6540
aaaactgggt ggtagcctgt cgcgaaacc gttcgtggaa accgcgatca acctggcacg    6600
tcaatctcac tgcacttatc ataacggcga cgcgcatacc ctccggatg agctgacccg    6660
caaacgcgtt ctgtctgtaa tcactgaacc gattctgccg tttgaacgct aaggatccga   6720
attcgagctc cgtcgacaag cttgcggccg cactcgagca ccaccaccac caccactgag   6780
atccggctgc taacaaagcc cgaaaggaag ctgagttggc tgctgccacc gctgagcaat   6840
aactagcata accccttggg gcctctaaac gggtcttgag gggttttttg ctgaaaggag   6900
gaactatatc cggat                                                    6915
```

<210> SEQ ID NO 140
<211> LENGTH: 547
<212> TYPE: PRT
<213> ORGANISM: Artificial Sequence
<220> FEATURE:
<223> OTHER INFORMATION: Synthetic Construct

<400> SEQUENCE: 140

```
Met Thr Glu Thr Glu Ala Arg Arg Ser Ala Asn Tyr Glu Pro Asn Ser
1               5                   10                  15

Trp Asp Tyr Asp Tyr Leu Leu Ser Ser Asp Thr Asp Glu Ser Ile Glu
            20                  25                  30

Val Tyr Lys Asp Lys Ala Lys Lys Leu Glu Ala Glu Val Arg Arg Glu
        35                  40                  45

Ile Asn Asn Glu Lys Ala Glu Phe Leu Thr Leu Leu Glu Leu Ile Asp
50                  55                  60

Asn Val Gln Arg Leu Gly Leu Gly Tyr Arg Phe Glu Ser Asp Ile Arg
65                  70                  75                  80

Gly Ala Leu Asp Arg Phe Val Ser Ser Gly Gly Phe Asp Ala Val Thr
                85                  90                  95

Lys Thr Ser Leu His Gly Thr Ala Leu Ser Phe Arg Leu Leu Arg Gln
            100                 105                 110

His Gly Phe Glu Val Ser Gln Glu Ala Phe Ser Gly Phe Lys Asp Gln
        115                 120                 125

Asn Gly Asn Phe Leu Glu Asn Leu Lys Glu Asp Ile Lys Ala Ile Leu
130                 135                 140

Ser Leu Tyr Glu Ala Ser Phe Leu Ala Leu Gly Glu Asn Ile Leu
145                 150                 155                 160

Asp Glu Ala Lys Val Phe Ala Ile Ser His Leu Lys Glu Leu Ser Glu
                165                 170                 175

Glu Lys Ile Gly Lys Glu Leu Ala Glu Gln Val Asn His Ala Leu Glu
            180                 185                 190

Leu Pro Leu His Arg Arg Thr Gln Arg Leu Glu Ala Val Trp Ser Ile
        195                 200                 205

Glu Ala Tyr Arg Lys Lys Glu Asp Ala Asn Gln Val Leu Leu Glu Leu
210                 215                 220

Ala Ile Leu Asp Tyr Asn Met Ile Gln Ser Val Tyr Gln Arg Asp Leu
225                 230                 235                 240

Arg Glu Thr Ser Arg Trp Trp Arg Arg Val Gly Leu Ala Thr Lys Leu
                245                 250                 255

His Phe Ala Arg Asp Arg Leu Ile Glu Ser Phe Tyr Trp Ala Val Gly
            260                 265                 270

Val Ala Phe Glu Pro Gln Tyr Ser Asp Cys Arg Asn Ser Val Ala Lys
        275                 280                 285

Met Phe Ser Phe Val Thr Ile Ile Asp Asp Ile Tyr Asp Val Tyr Gly
290                 295                 300

Thr Leu Asp Glu Leu Glu Leu Phe Thr Asp Ala Val Glu Arg Trp Asp
305                 310                 315                 320

Val Asn Ala Ile Asn Asp Leu Pro Asp Tyr Met Lys Leu Cys Phe Leu
                325                 330                 335

Ala Leu Tyr Asn Thr Ile Asn Glu Ile Ala Tyr Asp Asn Leu Lys Asp
            340                 345                 350

Lys Gly Glu Asn Ile Leu Pro Tyr Leu Thr Lys Ala Trp Ala Asp Leu
        355                 360                 365

Cys Asn Ala Phe Leu Gln Glu Ala Lys Trp Leu Tyr Asn Lys Ser Thr
370                 375                 380
```

```
Pro Thr Phe Asp Asp Tyr Phe Gly Asn Ala Trp Lys Ser Ser Gly
385                 390                 395                 400

Pro Leu Gln Leu Val Phe Ala Tyr Phe Ala Val Gln Asn Ile Lys
            405                 410                 415

Lys Glu Glu Ile Glu Asn Leu Gln Lys Tyr His Asp Thr Ile Ser Arg
            420                 425                 430

Pro Ser His Ile Phe Arg Leu Cys Asn Asp Leu Ala Ser Ala Ser Ala
            435                 440                 445

Glu Ile Ala Arg Gly Glu Thr Ala Asn Ser Val Ser Cys Tyr Met Arg
            450                 455                 460

Thr Lys Gly Ile Ser Glu Glu Leu Ala Thr Glu Ser Val Met Asn Leu
465                 470                 475                 480

Ile Asp Glu Thr Trp Lys Lys Met Asn Lys Glu Lys Leu Gly Gly Ser
                485                 490                 495

Leu Phe Ala Lys Pro Phe Val Glu Thr Ala Ile Asn Leu Ala Arg Gln
                500                 505                 510

Ser His Cys Thr Tyr His Asn Gly Asp Ala His Thr Ser Pro Asp Glu
                515                 520                 525

Leu Thr Arg Lys Arg Val Leu Ser Val Ile Thr Glu Pro Ile Leu Pro
                530                 535                 540

Phe Glu Arg
545
```

<210> SEQ ID NO 141
<211> LENGTH: 6918
<212> TYPE: DNA
<213> ORGANISM: Artificial Sequence
<220> FEATURE:
<223> OTHER INFORMATION: Synthetic Construct

<400> SEQUENCE: 141

```
tggcgaatgg gacgcgccct gtagcggcgc attaagcgcg gcgggtgtgg tggttacgcg    60
cagcgtgacc gctacacttg ccagcgccct agcgcccgct cctttcgctt tcttcccttc   120
ctttctcgcc acgttcgccg gctttccccg tcaagctcta atcggggggc tcccttttagg   180
gttccgattt agtgctttac ggcacctcga ccccaaaaaa cttgattagg gtgatggttc   240
acgtagtggg ccatcgccct gatagacggt ttttcgccct tgacgttgg agtccacgtt    300
ctttaatagt ggactcttgt tccaaactgg aacaacactc aaccctatct cggtctattc   360
ttttgattta taagggattt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttatttttc taaatacatt caaatatgta   540
tccgctcatg aattaattct tagaaaaact catcgagcat caaatgaaac tgcaatttat   600
tcatatcagg attatcaata ccatattttt gaaaagccg tttctgtaat gaaggagaaa   660
actcaccgag gcagttccat aggatggcaa gatcctggta tcggtctgcg attccgactc   720
gtccaacatc aatacaacct attaatttcc cctcgtcaaa aataaggtta tcaagtgaga   780
aatcaccatg agtgacgact gaatccggtg agaatggcaa aagtttatgc atttctttcc   840
agacttgttc aacaggccag ccattacgct cgtcatcaaa atcactcgca tcaaccaaac   900
cgttattcat tcgtgattgc gcctgagcga gacgaaatac gcgatcgctg ttaaaaggac   960
aattacaaac aggaatcgaa tgcaaccggc gcaggaacac tgccagcgca tcaacaatat  1020
tttcacctga atcaggatat tcttctaata cctggaatgc tgttttcccg gggatcgcag  1080
```

```
tggtgagtaa ccatgcatca tcaggagtac ggataaaatg cttgatggtc ggaagaggca    1140
taaattccgt cagccagttt agtctgacca tctcatctgt aacatcattg caacgctac     1200
cttttgccatg tttcagaaac aactctggcg catcgggctt cccatacaat cgatagattg   1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa aatcccttaa    1440
cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actcttttc cgaaggtaac tggcttcagc     1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata gtcgtgtct taccggggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980
ccaggggggaa acgcctggta tctttatagt cctgtcgggt ttcgccacct ctgacttgag   2040
cgtcgatttt tgtgatgctc gtcagggggg cggagcctat ggaaaaacgc cagcaacgcg    2100
gccttttttac ggttcctggc cttttgctgg ccttttgctc acatgttctt tcctgcgtta   2160
tccccctgatt ctgtggataa ccgtattacc gcctttgagt gagctgatac cgctcgccgc   2220
agccgaacga ccgagcgcag cgagtcagtg agcgaggaag cggaagagcg cctgatgcgg    2280
tatttttctcc ttacgcatct gtgcggtatt tcacaccgca tatatggtgc actctcagta   2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt ttcctgtttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc ccgcgcccca    3420
ccggaaggag ctgactgggt tgaaggctct caagggcatc ggtcgagatc ccggtgccta    3480
```

```
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg cgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccgaaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa agacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa cttaagaag gagatataca tatgactgaa accgaagctc gtcgttctgc    5100
gaactacgaa cctaacagct gggactatga ttacctgctg tcctccgaca cggacgagtc    5160
catcgaagta tacaaagaca aagcgaaaaa gctggaagcc gaagttcgtc gcgagattaa    5220
taacgaaaaa gcagaatttc tgaccctgct ggaactgatt gacaacgtcc agcgcctggg    5280
cctgggttac cgtttcgagt ctgatatccg tggtgcgctg gatcgcttcg tttcctccgg    5340
cggcttcgat gcggtaacca agacttccct gcacggtacg gcactgtctt ccgtctgct    5400
gcgtcaacac ggttttgagg tttctcagga agcgttcagc ggcttcaaag accaaaacgg    5460
caacttcctg gagaacctga aggaagatat caaagctatc ctgagcctgt acgaggccag    5520
cttcctggct ctgaaggcg aaaacatcct ggacgaggcg aaggttttcg caatctctca    5580
tctgaaagaa ctgtctgaag aaaagatcgg taaagagctg gcagaacagg tgaaccatgc    5640
actggaactg ccactgcatc gccgtactca gcgtctggaa gcagtatggt ctatcgaggc    5700
ctaccgtaaa aaggaggacg cgaatcaggt tctgctggag ctggcaattc tggattacaa    5760
catgatccag tctgtatacc agcgtgatct gcgtgaaacg tcccgttggt ggcgtcgtgt    5820
gggtctggcg accaaactgc actttgctcg tgaccgcctg attgagagct tctactgggc    5880
```

-continued

```
cgtgggtgta gcattcgaac cgcaatactc cgactgccgt aactccgtcg caaaatgtt       5940 ttctttcgta accattatcg acgatatcta cgatgtatac ggcaccctgg acgaactgga      6000
gctgtttact gatgcagttg agcgttggga cgtaaacgcc atcaacgacc tgccggatta     6060
catgaaactg tgctttctgg ctctgtataa cactattaac gaaatcgcct acgacaacct     6120
gaaagataaa ggtgagaaca tcctgccgta tctgaccaaa gcctgggctg acctgtgcaa     6180
cgctttcctg caagaagcca gtggctgta caacaaatct actccgacct ttgacgacta      6240
cttcggcaac gcatggaaat cctcttctgg cccgctgcaa ctggtgttcg cttacttcgc     6300
tgtcgtgcag aacattaaaa aggaagagat cgaaaacctg caaaaatacc atgacaccat     6360
ctctcgtcct tcccatatct tccgtctgtg caatgacctg gctagcgcgt ctgcggaaat     6420
tgcgcgtggt gaaaccgcaa atagcgtttc ttgttacatg cgcactaaag gtatctccga     6480
agaactggct accgaaagcg tgatgaatct gatcgatgaa acctggaaaa agatgaacaa     6540
ggaaaaactg ggtggtagcc tgttcgcgaa accgttcgtg gaaaccgcga tcaacctggc     6600
acgtcaatct cactgcactt atcataacgg cgacgcgcat acctctccgg atgagctgac     6660
ccgcaaacgc gttctgtctg taatcactga accgattctg ccgtttgaac gctaaggatc     6720
cgaattcgag ctccgtcgac aagcttgcgg ccgcactcga gcaccaccac caccaccact     6780
gagatccggc tgctaacaaa gcccgaaagg aagctgagtt ggctgctgcc accgctgagc     6840
aataactagc ataaccccttt ggggcctcta acgggtctt gaggggtttt ttgctgaaag     6900
gaggaactat atccggat                                                    6918
```

<210> SEQ ID NO 142
<211> LENGTH: 548
<212> TYPE: PRT
<213> ORGANISM: Artificial Sequence
<220> FEATURE:
<223> OTHER INFORMATION: Synthetic Construct

<400> SEQUENCE: 142

```
Met Glu Thr Glu Thr Glu Ala Arg Arg Ser Ala Asn Tyr Glu Pro Asn
  1               5                  10                  15

Ser Trp Asp Tyr Asp Tyr Leu Leu Ser Ser Asp Thr Asp Glu Ser Ile
             20                  25                  30

Glu Val Tyr Lys Asp Lys Ala Lys Lys Leu Glu Ala Glu Val Arg Arg
         35                  40                  45

Glu Ile Asn Asn Glu Lys Ala Glu Phe Leu Thr Leu Leu Glu Leu Ile
     50                  55                  60

Asp Asn Val Gln Arg Leu Gly Leu Gly Tyr Arg Phe Glu Ser Asp Ile
 65                  70                  75                  80

Arg Gly Ala Leu Asp Arg Phe Val Ser Ser Gly Phe Asp Ala Val
                 85                  90                  95

Thr Lys Thr Ser Leu His Gly Thr Ala Leu Ser Phe Arg Leu Leu Arg
            100                 105                 110

Gln His Gly Phe Glu Val Ser Gln Glu Ala Phe Ser Gly Phe Lys Asp
        115                 120                 125

Gln Asn Gly Asn Phe Leu Glu Asn Leu Lys Glu Asp Ile Lys Ala Ile
    130                 135                 140

Leu Ser Leu Tyr Glu Ala Ser Phe Leu Ala Leu Glu Gly Glu Asn Ile
145                 150                 155                 160

Leu Asp Glu Ala Lys Val Phe Ala Ile Ser His Leu Lys Glu Leu Ser
                165                 170                 175

Glu Glu Lys Ile Gly Lys Glu Leu Ala Glu Gln Val Asn His Ala Leu
```

```
                    180                 185                 190
Glu Leu Pro Leu His Arg Arg Thr Gln Arg Leu Glu Ala Val Trp Ser
            195                 200                 205
Ile Glu Ala Tyr Arg Lys Lys Glu Asp Ala Asn Gln Val Leu Leu Glu
        210                 215                 220
Leu Ala Ile Leu Asp Tyr Asn Met Ile Gln Ser Val Tyr Gln Arg Asp
225                 230                 235                 240
Leu Arg Glu Thr Ser Arg Trp Trp Arg Arg Val Gly Leu Ala Thr Lys
                245                 250                 255
Leu His Phe Ala Arg Asp Arg Leu Ile Glu Ser Phe Tyr Trp Ala Val
            260                 265                 270
Gly Val Ala Phe Glu Pro Gln Tyr Ser Asp Cys Arg Asn Ser Val Ala
        275                 280                 285
Lys Met Phe Ser Phe Val Thr Ile Ile Asp Ile Tyr Asp Val Tyr
    290                 295                 300
Gly Thr Leu Asp Glu Leu Glu Leu Phe Thr Asp Ala Val Glu Arg Trp
305                 310                 315                 320
Asp Val Asn Ala Ile Asn Asp Leu Pro Asp Tyr Met Lys Leu Cys Phe
                325                 330                 335
Leu Ala Leu Tyr Asn Thr Ile Asn Glu Ile Ala Tyr Asp Asn Leu Lys
            340                 345                 350
Asp Lys Gly Glu Asn Ile Leu Pro Tyr Leu Thr Lys Ala Trp Ala Asp
        355                 360                 365
Leu Cys Asn Ala Phe Leu Gln Glu Ala Lys Trp Leu Tyr Asn Lys Ser
    370                 375                 380
Thr Pro Thr Phe Asp Asp Tyr Phe Gly Asn Ala Trp Lys Ser Ser
385                 390                 395                 400
Gly Pro Leu Gln Leu Val Phe Ala Tyr Phe Ala Val Val Gln Asn Ile
                405                 410                 415
Lys Lys Glu Glu Ile Glu Asn Leu Gln Lys Tyr His Asp Thr Ile Ser
            420                 425                 430
Arg Pro Ser His Ile Phe Arg Leu Cys Asn Asp Leu Ala Ser Ala Ser
        435                 440                 445
Ala Glu Ile Ala Arg Gly Glu Thr Ala Asn Ser Val Ser Cys Tyr Met
    450                 455                 460
Arg Thr Lys Gly Ile Ser Glu Glu Leu Ala Thr Glu Ser Val Met Asn
465                 470                 475                 480
Leu Ile Asp Glu Thr Trp Lys Lys Met Asn Lys Glu Lys Leu Gly Gly
                485                 490                 495
Ser Leu Phe Ala Lys Pro Phe Val Glu Thr Ala Ile Asn Leu Ala Arg
            500                 505                 510
Gln Ser His Cys Thr Tyr His Asn Gly Asp Ala His Thr Ser Pro Asp
        515                 520                 525
Glu Leu Thr Arg Lys Arg Val Leu Ser Val Ile Thr Glu Pro Ile Leu
    530                 535                 540
Pro Phe Glu Arg
545

<210> SEQ ID NO 143
<211> LENGTH: 6921
<212> TYPE: DNA
<213> ORGANISM: Artificial Sequence
<220> FEATURE:
<223> OTHER INFORMATION: Synthetic Construct

<400> SEQUENCE: 143
```

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta aatcggggc tcccttagg      180 gttccgattt agtgctttac ggcacctcga ccccaaaaaa cttgattagg gtgatggttc     240
acgtagtggg ccatcgccct gatagacggt ttttcgccct tgacgttgg agtccacgtt     300 ctttaatagt ggactcttgt tccaaactgg aacaacactc aaccctatct cggtctattc     360
ttttgattta aagggatttt tgccgatttc ggcctattgg ttaaaaaatg agctgattta     420
acaaaatttt aacgcgaatt ttaacaaaat attaacgttt acaatttcag gtggcacttt     480
tcggggaaat gtgcgcggaa cccctatttg tttattttc taaatacatt caaatatgta     540
tccgctcatg aattaattct tagaaaaact catcgagcat caaatgaaac tgcaatttat     600
tcatatcagg attatcaata ccatattttt gaaaaagccg tttctgtaat gaaggagaaa     660
actcaccgag gcagttccat aggatggcaa gatcctggta tcggtctgcg attccgactc     720
gtccaacatc aatacaacct attaatttcc cctcgtcaaa aataaggtta tcaagtgaga     780
aatcaccatg agtgacgact gaatccggtg agaatggcaa aagtttatgc atttctttcc     840
agacttgttc aacaggccag ccattacgct cgtcatcaaa atcactcgca tcaaccaaac     900
cgttattcat tcgtgattgc gcctgagcga acgaaatac gcgatcgctg ttaaaaggac     960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa atcccttaa     1440 cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actcttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata gtcgtgtct taccggggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcaggggg cggagcctat ggaaaaacgc cagcaacgcg    2100
gcctttttac ggttcctggc cttttgctgg cttttgctc acatgttctt cctgcgtta     2160 tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280 tatttttctcc ttacgcatct gtgcggtatt tcacaccgca tatatggtgc actctcagta    2340
caatctgctc tgatgccgca tagttaagcc agtatacact ccgctatcgc tacgtgactg    2400
```

```
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccgagag gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccgaaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
```

```
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatggaaact gaaaccgaag ctcgtcgttc    5100
tgcgaactac gaacctaaca gctgggacta tgattacctg ctgtcctccg acacggacga    5160
gtccatcgaa gtatacaaag acaaagcgaa aaagctggaa gccgaagttc gtcgcgagat    5220
taataacgaa aaagcagaat tctgacccct gctggaactg attgacaacg tccagcgcct    5280
gggcctgggt taccgtttcg agtctgatat ccgtggtgcg ctggatcgct tcgtttcctc    5340
cggcggcttc gatgcggtaa ccaagacttc cctgcacggt acggcactgt ctttccgtct    5400
gctgcgtcaa cacggttttg aggtttctca ggaagcgttc agcggcttca aagaccaaaa    5460
cggcaacttc ctggagaacc tgaaggaaga tatcaaagct atcctgagcc tgtacgaggc    5520
cagcttcctg gctctggaag gcgaaaacat cctggacgag gcgaaggttt cgcaatctc    5580 tcatctgaaa gaactgtctg aagaaagat cggtaaagag ctggcagaac aggtgaacca    5640
tgcactggaa ctgccactgc atcgccgtac tcagcgtctg gaagcagtat ggtctatcga    5700
ggcctaccgt aaaaggagg acgcgaatca ggttctgctg gagctggcaa ttctggatta    5760
caacatgatc cagtctgtat accagcgtga tctgcgtgaa acgtcccgtt ggtggcgtcg    5820
tgtgggtctg gcgaccaaac tgcactttgc tcgtgaccgc ctgattgaga gcttctactg    5880
ggccgtgggt gtagcattcg aaccgcaata ctccgactgc cgtaactccg tcgcaaaaat    5940
gttttctttc gtaaccatta tcgacgatat ctacgatgta tacggcaccc tggacgaact    6000
ggagctgttt actgatgcag ttgagcgttg ggacgtaaac gccatcaacg acctgccgga    6060
ttacatgaaa ctgtgctttt ggctctgta taacactatt aacgaaatcg cctacgacaa    6120
cctgaaagat aaaggtgaga acatcctgcc gtatctgacc aaagcctggg ctgacctgtg    6180
caacgctttc ctgcaagaag ccaagtggct gtacaacaaa tctactccga cctttgacga    6240
ctacttcggc aacgcatgga atcctcttc tggcccgctg caactggtgt tcgcttactt    6300
cgctgtcgtg cagaacatta aaaaggaaga gatcgaaaac ctgcaaaaat accatgacac    6360
catctctcgt ccttcccata tcttccgtct gtgcaatgac ctggctagcg cgtctgcgga    6420
aattgcgcgt ggtgaaaccg caaatagcgt ttcttgttac atgcgcacta aaggtatctc    6480
cgaagaactg gctaccgaaa gcgtgatgaa tctgatcgat gaaacctgga aaaagatgaa    6540
caaggaaaaa ctgggtggta gcctgttcgc gaaaccgttc gtggaaaccg cgatcaacct    6600
ggcacgtcaa tctcactgca cttatcataa cggcgacgcg catacctctc cggatgagct    6660
gacccgcaaa cgcgttctgt ctgtaatcac tgaaccgatt ctgccgtttg aacgctaagg    6720
atccgaattc gagctccgtc gacaagcttg cggccgcact cgagcaccac caccaccacc    6780
actgagatcc ggctgctaac aaagcccgaa aggaagctga gttggctgct gccaccgctg    6840
agcaataact agcataaccc cttggggcct ctaaacgggt cttgaggggt ttttgctga    6900 aaggaggaac tatatccgga t                                              6921
```

<210> SEQ ID NO 144
<211> LENGTH: 549
<212> TYPE: PRT
<213> ORGANISM: Artificial Sequence
<220> FEATURE:
<223> OTHER INFORMATION: Synthetic Construct

<400> SEQUENCE: 144

```
Met Thr Glu Thr Glu Thr Glu Ala Arg Arg Ser Ala Asn Tyr Glu Pro
 1               5                  10                  15

Asn Ser Trp Asp Tyr Asp Tyr Leu Leu Ser Ser Asp Thr Asp Glu Ser
             20                  25                  30

Ile Glu Val Tyr Lys Asp Lys Ala Lys Lys Leu Glu Ala Glu Val Arg
         35                  40                  45

Arg Glu Ile Asn Asn Glu Lys Ala Glu Phe Leu Thr Leu Leu Glu Leu
 50                  55                  60

Ile Asp Asn Val Gln Arg Leu Gly Leu Gly Tyr Arg Phe Glu Ser Asp
 65                  70                  75                  80

Ile Arg Gly Ala Leu Asp Arg Phe Val Ser Ser Gly Gly Phe Asp Ala
             85                  90                  95

Val Thr Lys Thr Ser Leu His Gly Thr Ala Leu Ser Phe Arg Leu Leu
        100                 105                 110

Arg Gln His Gly Phe Glu Val Ser Gln Glu Ala Phe Ser Gly Phe Lys
        115                 120                 125

Asp Gln Asn Gly Asn Phe Leu Glu Asn Leu Lys Glu Asp Ile Lys Ala
130                 135                 140

Ile Leu Ser Leu Tyr Glu Ala Ser Phe Leu Ala Leu Glu Gly Glu Asn
145                 150                 155                 160

Ile Leu Asp Glu Ala Lys Val Phe Ala Ile Ser His Leu Lys Glu Leu
                165                 170                 175

Ser Glu Glu Lys Ile Gly Lys Glu Leu Ala Gln Val Asn His Ala
                180                 185                 190

Leu Glu Leu Pro Leu His Arg Arg Thr Gln Arg Leu Glu Ala Val Trp
                195                 200                 205

Ser Ile Glu Ala Tyr Arg Lys Lys Glu Asp Ala Asn Gln Val Leu Leu
    210                 215                 220

Glu Leu Ala Ile Leu Asp Tyr Asn Met Ile Gln Ser Val Tyr Gln Arg
225                 230                 235                 240

Asp Leu Arg Glu Thr Ser Arg Trp Trp Arg Arg Val Gly Leu Ala Thr
                245                 250                 255

Lys Leu His Phe Ala Arg Asp Arg Leu Ile Glu Ser Phe Tyr Trp Ala
                260                 265                 270

Val Gly Val Ala Phe Glu Pro Gln Tyr Ser Asp Cys Arg Asn Ser Val
            275                 280                 285

Ala Lys Met Phe Ser Phe Val Thr Ile Ile Asp Asp Ile Tyr Asp Val
        290                 295                 300

Tyr Gly Thr Leu Asp Glu Leu Glu Leu Phe Thr Asp Ala Val Glu Arg
305                 310                 315                 320

Trp Asp Val Asn Ala Ile Asn Asp Leu Pro Asp Tyr Met Lys Leu Cys
                325                 330                 335

Phe Leu Ala Leu Tyr Asn Thr Ile Asn Glu Ile Ala Tyr Asp Asn Leu
            340                 345                 350

Lys Asp Lys Gly Glu Asn Ile Leu Pro Tyr Leu Thr Lys Ala Trp Ala
        355                 360                 365

Asp Leu Cys Asn Ala Phe Leu Gln Glu Ala Lys Trp Leu Tyr Asn Lys
    370                 375                 380

Ser Thr Pro Thr Phe Asp Asp Tyr Phe Gly Asn Ala Trp Lys Ser Ser
385                 390                 395                 400

Ser Gly Pro Leu Gln Leu Val Phe Ala Tyr Phe Ala Val Val Gln Asn
                405                 410                 415
```

```
Ile Lys Lys Glu Glu Ile Glu Asn Leu Gln Lys Tyr His Asp Thr Ile
            420                 425                 430

Ser Arg Pro Ser His Ile Phe Arg Leu Cys Asn Asp Leu Ala Ser Ala
        435                 440                 445

Ser Ala Glu Ile Ala Arg Gly Glu Thr Ala Asn Ser Val Ser Cys Tyr
    450                 455                 460

Met Arg Thr Lys Gly Ile Ser Glu Glu Leu Ala Thr Glu Ser Val Met
465                 470                 475                 480

Asn Leu Ile Asp Glu Thr Trp Lys Lys Met Asn Lys Glu Lys Leu Gly
            485                 490                 495

Gly Ser Leu Phe Ala Lys Pro Phe Val Glu Thr Ala Ile Asn Leu Ala
                500                 505                 510

Arg Gln Ser His Cys Thr Tyr His Asn Gly Asp Ala His Thr Ser Pro
            515                 520                 525

Asp Glu Leu Thr Arg Lys Arg Val Leu Ser Val Ile Thr Glu Pro Ile
        530                 535                 540

Leu Pro Phe Glu Arg
545

<210> SEQ ID NO 145
<211> LENGTH: 6924
<212> TYPE: DNA
<213> ORGANISM: Artificial Sequence
<220> FEATURE:
<223> OTHER INFORMATION: Synthetic Construct

<400> SEQUENCE: 145
tggcgaatgg gacgcgccct gtagcggcgc attaagcgcg gcgggtgtgg tggttacgcg     60
cagcgtgacc gctacacttg ccagcgccct agcgcccgct cctttcgctt tcttcccttc    120
ctttctcgcc acgttcgccg gctttccccg tcaagctcta atcgggggc tccctttagg     180 gttccgattt agtgctttac ggcacctcga ccccaaaaaa cttgattagg gtgatggttc    240
acgtagtggg ccatcgccct gatagacggt ttttcgccct tgacgttgg agtccacgtt     300 ctttaatagt ggactcttgt tccaaactgg aacaacactc aaccctatct cggtctattc    360
ttttgattta aagggatttt gccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttattttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
```

-continued

```
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actcttttt cgaaggtaac tggcttcagc    1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga atacctaca gcgtgagcta tgagaaagcg ccacgcttcc gaagggaga    1920 aaggcggaca ggtatccggt aagcggcagg gtcggaacag gagagcgcac gagggagctt   1980 ccaggggaa acgcctggta tctttatagt cctgtcgggt ttcgccacct ctgacttgag    2040
cgtcgatttt tgtgatgctc gtcagggggg cggagcctat ggaaaaacgc cagcaacgcg   2100
gcctttttac ggttcctggc cttttgctgg cctttgctc acatgttctt tcctgcgtta   2160 tccctgatt ctgtggataa ccgtattacc gcctttgagt gagctgatac cgctcgccgc    2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt ttcctgtttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagactta    3000 cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
```

```
ccgcctggcc ctgagagagt tgcagcaagc ggtccacgct ggtttgcccc agcaggcgaa    3720
aatcctgttt gatggtggtt aacgcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccgacgcg agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatgaccgaa actgaaaccg aagctcgtcg    5100
ttctgcgaac tacgaaccta acagctggga ctatgattac ctgctgtcct ccgacacgga    5160
cgagtccatc gaagtataca agacaaagc gaaaagctg gaagccgaag ttcgtcgcga    5220
gattaataac gaaaaagcag aatttctgac cctgctggaa ctgattgaca acgtccagcg    5280
cctgggcctg ggttaccgtt tcgagtctga tatccgtggt gcgctggatc gcttcgtttc    5340
ctccggcggc ttcgatgcgg taaccaagac ttccctgcac ggtacggcac tgtctttccg    5400
tctgctgcgt caacacggtt ttgaggtttc tcaggaagcg ttcagcggct tcaaagacca    5460
aaacggcaac ttcctggaga acctgaagga agatatcaaa gctatcctga gcctgtacga    5520
ggccagcttc ctggctctgg aaggcgaaaa catcctggac gaggcgaagg ttttcgcaat    5580
ctctcatctg aaagaactgt ctgaagaaaa gatcggtaaa gagctggcag aacaggtgaa    5640
ccatgcactg gaactgccac tgcatcgccg tactcagcgt ctggaagcag tatggtctat    5700
cgaggcctac cgtaaaaagg aggacgcgaa tcaggttctg ctggagctgg caattctgga    5760
ttacaacatg atccagtctg tataccagcg tgatctgcgt gaaacgtccc gttggtggcg    5820
tcgtgtgggt ctggcgacca aactgcactt tgctcgtgac cgcctgattg agagcttcta    5880
ctgggccgtg ggtgtagcat tcgaaccgca atactccgac tgccgtaact ccgtcgcaaa    5940
aatgttttct ttcgtaacca ttatcgacga tatctacgat gtatacggca ccctggacga    6000
actggagctg tttactgatg cagttgagcg ttgggacgta aacgccatca acgacctgcc    6060
```

```
ggattacatg aaactgtgct ttctggctct gtataacact attaacgaaa tcgcctacga    6120
caacctgaaa gataaaggtg agaacatcct gccgtatctg accaaagcct gggctgacct    6180
gtgcaacgct ttcctgcaag aagccaagtg gctgtacaac aaatctactc cgacctttga    6240
cgactacttc ggcaacgcat ggaaatcctc ttctggcccg ctgcaactgg tgttcgctta    6300
cttcgctgtc gtgcagaaca ttaaaaagga agagatcgaa aacctgcaaa ataccatga    6360 caccatctct cgtccttccc atatcttccg tctgtgcaat gacctggcta gcgcgtctgc    6420
ggaaattgcg cgtggtgaaa ccgcaaatag cgtttcttgt tacatgcgca ctaaaggtat    6480
ctccgaagaa ctggctaccg aaagcgtgat gaatctgatc gatgaaacct ggaaaaagat    6540
gaacaaggaa aaactgggtg gtagcctgtt cgcgaaaccg ttcgtggaaa ccgcgatcaa    6600
cctggcacgt caatctcact gcacttatca taacggcgac gcgcataccc tccggatga    6660 gctgacccgc aaacgcgttc tgtctgtaat cactgaaccg attctgccgt ttgaacgcta    6720
aggatccgaa ttcgagctcc gtcgacaagc ttgcggccgc actcgagcac caccaccacc    6780
accactgaga tccggctgct aacaaagccc gaaaggaagc tgagttggct gctgccaccg    6840
ctgagcaata actagcataa ccccttgggg cctctaaacg ggtcttgagg ggttttttgc    6900
tgaaaggagg aactatatcc ggat                                           6924
```

<210> SEQ ID NO 146  
<211> LENGTH: 544  
<212> TYPE: PRT  
<213> ORGANISM: Artificial Sequence  
<220> FEATURE:  
<223> OTHER INFORMATION: Synthetic Construct

<400> SEQUENCE: 146

```
Met Glu Thr Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val His Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Arg Ala Leu
65                  70                  75                  80

Asp Arg Phe Val Ser Ser Gly Gly Phe Asp Gly Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Ser His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
```

| | | | | | | | | | | | |
|---|---|---|---|---|---|---|---|---|---|---|---|
| | | | 210 | | | | 215 | | | | 220 |
| Asp | Tyr | Asn | Met | Ile | Gln | Ser | Val | Tyr | Gln | Arg | Asp | Leu | Arg | Glu | Thr |
| 225 | | | | 230 | | | | | 235 | | | | | 240 | |

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
            245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
        275                 280                 285

Phe Val Thr Ile Ile Asp Asp Ile Tyr Asp Val Tyr Gly Thr Leu Asp
290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
        355                 360                 365

Phe Leu Gln Glu Ala Lys Trp Leu Tyr Asn Lys Ser Thr Pro Thr Phe
370                 375                 380

Asp Asp Tyr Phe Gly Asn Ala Trp Lys Ser Ser Gly Pro Leu Gln
385                 390                 395                 400

Leu Ile Phe Ala Tyr Phe Ala Val Val Gln Asn Ile Lys Lys Glu Glu
                405                 410                 415

Ile Glu Asn Leu Gln Lys Tyr His Asp Ile Ile Ser Arg Pro Ser His
            420                 425                 430

Ile Phe Arg Leu Cys Asn Asp Leu Ala Ser Ala Ser Ala Glu Ile Ala
        435                 440                 445

Arg Gly Glu Thr Ala Asn Ser Val Ser Cys Tyr Met Arg Thr Lys Gly
450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Gly Ser Leu Phe Ala
                485                 490                 495

Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
        515                 520                 525

Lys Arg Val Leu Ser Val Ile Thr Glu Pro Ile Leu Pro Phe Glu Arg
530                 535                 540

<210> SEQ ID NO 147
<211> LENGTH: 6909
<212> TYPE: DNA
<213> ORGANISM: Artificial Sequence
<220> FEATURE:
<223> OTHER INFORMATION: Synthetic Construct

<400> SEQUENCE: 147
tggcgaatgg gacgcgccct gtagcggcgc attaagcgcg gcgggtgtgg tggttacgcg    60
cagcgtgacc gctacacttg ccagcgccct agcgcccgct cctttcgctt tcttcccttc   120
ctttctcgcc acgttcgccg gctttccccg tcaagctcta atcgggggc tcccttagg    180 gttccgattt agtgctttac ggcacctcga ccccaaaaaa cttgattagg gtgatggttc   240

```
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta aagggatttt tgccgatttc ggcctattgg ttaaaaaatg agctgattta    420 acaaaattt aacgcgaatt ttaacaaaat attaacgttt acaatttcag gtggcacttt     480
tcggggaaat gtgcgcggaa cccctatttg tttattttc taaatacatt caaatatgta     540
tccgctcatg aattaattct tagaaaaact catcgagcat caaatgaaac tgcaatttat    600
tcatatcagg attatcaata ccatatttt gaaaaagccg tttctgtaat aaggagaaa      660 actcaccgag gcagttccat aggatggcaa gatcctggta tcggtctgcg attccgactc    720
gtccaacatc aatacaacct attaattttcc cctcgtcaaa aataaggtta tcaagtgaga   780
aatcaccatg agtgacgact gaatccggtg agaatggcaa aagtttatgc atttcttcc    840 agacttgttc aacaggccag ccattacgct cgtcatcaaa atcactcgca tcaaccaaac    900
cgttattcat tcgtgattgc gcctgagcga acgaaatac gcgatcgctg ttaaaaggac     960
aattacaaac aggaatcgaa tgcaaccggc gcaggaacac tgccagcgca tcaacaatat   1020
tttcacctga atcaggatat tcttctaata cctggaatgc tgtttttccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500 gatcctttt ttctgcgcgt aatctgctgc ttgcaaacaa aaaaaccacc gctaccagcg    1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata gtcgtgtct accggggttg gactcaagac gatagttacc ggataaggcg    1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980 ccaggggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
```

```
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccgagag ctgccggca cctgtcctac    3360 gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccacttt tcccgcgttt    4500 tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
```

-continued

```
ttttgtttaa ctttaagaag gagatataca tatggaaacg cgtcgttctg cgaactacga   5100
acctaacagc tgggactatg attacctgct gtcctccgac acggacgagt ccatcgaagt   5160
acacaaagac aaagcgaaaa agctggaagc cgaagttcgt cgcgagatta ataacgaaaa   5220
agcagaattt ctgaccctgc tggaactgat tgacaacgtc cagcgcctgg gcctgggtta   5280
ccgtttcgag tctgatatcc gtcgtgcgct ggatcgcttc gtttcctccg cggcttcga   5340
tggcgtaacc aagacttccc tgcacggtac ggcactgtct ttccgtctgc tgcgtcaaca   5400
cggttttgag gtttctcagg aagcgttcag cggcttcaaa gaccaaaacg gcaacttcct   5460
ggagaacctg aaggaagata tcaaagctat cctgagcctg tacgaggcca gcttcctggc   5520
tctggaaggc gaaaacatcc tggacgaggc gaaggttttc gcaatctctc atctgaaaga   5580
actgtctgaa gaaagatcg gtaaagagct ggcagaacag gtgtcccatg cactggaact   5640
gccactgcat cgccgtactc agcgtctgga agcagtatgg tctatcgagg cctaccgtaa   5700
aaaggaggac gcgaaccagg ttctgctgga gctggcaatt ctggattaca acatgatcca   5760
gtctgtatac cagcgtgatc tgcgtgaaac gtcccgttgg tggcgtcgtg tgggtctggc   5820
gaccaaactg cactttgctc gtgaccgcct gattgagagc ttctactggg ccgtgggtgt   5880
agcattcgaa ccgcaatact ccgactgccg taactccgtc gcaaaaatgt tttctttcgt   5940
aaccattatc gacgatatct acgatgtata cggcaccctg gacgaactgg agctgtttac   6000
tgatgcagtt gagcgttggg acgtaaacgc catcaacgac ctgccggatt acatgaaact   6060
gtgcttctg gctctgtata acactattaa cgaaatcgcc tacgacaacc tgaaagataa   6120
aggtgagaac atcctgccgt atctgaccaa agcctgggct gacctgtgca acgctttcct   6180
gcaagaagcc aagtggctgt acaacaaatc tactccgacc tttgacgact acttcggcaa   6240
cgcatggaaa tcctcttctg cccgctgca actgatcttc gcttacttcg ctgtcgtgca   6300
gaacattaaa aaggaagaga tcgaaaacct gcaaaaatac catgacatca tctctcgtcc   6360
ttcccatatc ttccgtctgt gcaatgacct ggctagcgcg tctgcggaaa ttgcgcgtgg   6420
tgaaaccgca aatagcgttt cttgttacat gcgcactaaa ggtatctccg aagaactggc   6480
taccgaaagc gtgatgaatc tgatcgatga acctgaaa aagatgaaca aggaaaaact   6540
gggtggtagc ctgttcgcga aaccgttcgt ggaaaccgcg atcaacctgg cacgtcaatc   6600
tcactgcact tatcataacg gcgacgcgca tacctctccg gatgagctga cccgcaaacg   6660
cgttctgtct gtaatcactg aaccgattct gccgtttgaa cgctaaggat ccgaattcga   6720
gctccgtcga caagcttgcg gccgcactcg agcaccacca ccaccaccac tgagatccgg   6780
ctgctaacaa agcccgaaag gaagctgagt tggctgctgc caccgctgag caataactag   6840
cataacccct ggggcctct aaacgggtct gaggggttt ttgctgaaa ggaggaacta   6900
tatccggat                                                          6909
```

<210> SEQ ID NO 148
<211> LENGTH: 544
<212> TYPE: PRT
<213> ORGANISM: Artificial Sequence
<220> FEATURE:
<223> OTHER INFORMATION: Synthetic Construct

<400> SEQUENCE: 148

```
Met Glu Thr Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
            20                  25                  30
```

```
Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
 50                  55                  60

Arg Leu Gly Leu Gly Tyr Arg Phe Glu Ser Asp Ile Arg Arg Ala Leu
 65                  70                  75                  80

Asp Arg Phe Val Ser Ser Gly Gly Phe Asp Ala Val Thr Lys Thr Ser
                 85                  90                  95

Leu His Ala Thr Ala Leu Ser Phe Arg Leu Leu Arg Gln His Gly Phe
                100                 105                 110

Glu Val Ser Gln Glu Ala Phe Ser Gly Phe Lys Asp Gln Asn Gly Asn
            115                 120                 125

Phe Leu Glu Asn Leu Lys Glu Asp Ile Lys Ala Ile Leu Ser Leu Tyr
130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Asp Leu Ala Glu Gln Val Asn His Ala Leu Glu Leu Pro Leu
                180                 185                 190

His Arg Arg Thr Gln Arg Leu Glu Ala Val Leu Ser Ile Glu Ala Tyr
            195                 200                 205

Arg Lys Lys Glu Asp Ala Asp Gln Val Leu Leu Glu Leu Ala Ile Leu
210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
                260                 265                 270

Glu Pro Gln Tyr Ser Asp Cys Arg Asn Ser Val Ala Lys Met Phe Ser
            275                 280                 285

Phe Val Thr Ile Ile Asp Asp Ile Tyr Asp Val Tyr Gly Thr Leu Asp
290                 295                 300

Glu Leu Glu Leu Phe Thr Asn Ala Val Glu Arg Trp Asp Val Asn Ala
305                 310                 315                 320

Ile Asp Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Glu Lys Gly Glu
                340                 345                 350

Asn Ile Leu Pro Tyr Leu Thr Lys Ala Trp Ala Asp Leu Cys Asn Ala
            355                 360                 365

Phe Leu Gln Glu Ala Lys Trp Leu Tyr Asn Lys Ser Thr Pro Thr Phe
370                 375                 380

Asp Glu Tyr Phe Gly Asn Ala Trp Lys Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Ile Ile Ser Arg Pro Ser His
                420                 425                 430

Ile Phe Arg Leu Cys Asn Asp Leu Ala Ser Ala Ser Ala Glu Ile Ala
            435                 440                 445

Arg Gly Glu Thr Ala Asn Ser Val Ser Cys Tyr Met Arg Thr Lys Gly
450                 455                 460
```

```
Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Gly Ser Leu Phe Ala
            485                 490                 495

Lys Pro Phe Val Glu Thr Ala Ile Asn Leu Ala Arg Gln Ser His Cys
                500                 505                 510

Thr Tyr His Asn Gly Asp Ala His Thr Ser Pro Asp Glu Leu Thr Arg
            515                 520                 525

Lys Arg Val Leu Ser Val Ile Thr Glu Pro Ile Leu Pro Phe Glu Arg
            530                 535                 540

<210> SEQ ID NO 149
<211> LENGTH: 6909
<212> TYPE: DNA
<213> ORGANISM: Artificial Sequence
<220> FEATURE:
<223> OTHER INFORMATION: Synthetic Construct

<400> SEQUENCE: 149
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcggggggc tccctttagg     180
gttccgattt agtgctttac ggcacctcga ccccaaaaaa cttgattagg gtgatggttc     240
acgtagtggg ccatcgccct gatagacggt ttttcgccct tgacgttgga gtccacgtt     300 ctttaatagt ggactcttgt tccaaactgg aacaacactc aaccctatct cggtctattc     360
ttttgattta agggatttt gccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg aattaattct tagaaaaact catcgagcat caaatgaaac tgcaatttat     600
tcatatcagg attatcaata ccatattttt gaaaaagccg tttctgtaat gaaggagaaa     660
actcaccgag gcagttccat aggatggcaa gatcctggta tcggtctgcg attccgactc     720
gtccaacatc aatacaacct attaatttcc cctcgtcaaa ataaggttat caagtgaga     780 aatcaccatg agtgacgact gaatccggtg agaatggcaa agtttatgc atttctttcc     840 agacttgttc aacaggccag ccattacgct cgtcatcaaa atcactcgca tcaaccaaac     900
cgttattcat tcgtgattgc gcctgagcga cgaaatacg cgatcgctg ttaaaaggac     960 aattacaaac aggaatcgaa tgcaaccggc gcaggaacac tgccagcgca tcaacaatat    1020
tttcacctga tcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa atcccttaa    1440 cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actctttttc cgaaggtaac tggcttcagc    1620
```

```
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata agtcgtgtct taccgggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980 ccaggggaa acgcctggta tctttatagt cctgtcgggt ttcgccacct ctgacttgag    2040
cgtcgatttt tgtgatgctc gtcagggggg cggagcctat ggaaaaacgc cagcaacgcg    2100 gccttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
```

```
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040 tttttgtttaa ctttaagaag gagatataca tatggaaacg cgtcgttctg cgaactacga    5100
acctaacagc tgggactatg attacctgct gtcctccgac acgacgagt ccatcgaagt    5160 atacaaagac aaagcgaaaa agctggaagc cgaagttcgt cgcgagatta ataacgaaaa    5220
agcagaattt ctgaccctgc tggaactgat tgacaacgtc cagcgcctgg gcctgggtta    5280
ccgtttcgag tctgatatcc gtcgtgcgct ggatcgcttc gtttcctccg gcggcttcga    5340
tgcggtaacc aagacttccc tgcacgcgac ggcactgtct ttccgtctgc tgcgtcaaca    5400
cggttttgag gtttctcagg aagcgttcag cggcttcaaa gaccaaaacg gcaacttcct    5460
ggagaacctg aaggaagata tcaaagctat cctgagcctg tacgaggcca gcttcctggc    5520
tctggaaggc gaaaacatcc tggacgaggc gaaggttttc gcaatctctc atctgaaaga    5580
actgtctgaa gaaaagatcg gtaaagatct ggcagaacag gtgaaccatg cactggaact    5640
gccactgcat cgccgtactc agcgtctgga agcagtactg tctatcgagg cctaccgtaa    5700
aaaggaggac gcggatcagg ttctgctgga gctggcaatt ctggattaca acatgatcca    5760
gtctgtatac cagcgtgatc tgcgtgaaac gtcccgttgg tggcgtcgtg tgggtctggc    5820
gaccaaactg cactttgctc gtgaccgcct gattgagagc ttctactggg ccgtgggtgt    5880
agcattcgaa ccgcaatact ccgactgccg taactccgtc gcaaaaatgt ttctttcgt    5940 aaccattatc gacgatatct acgatgtata cggcaccctg gacgaactgg agctgtttac    6000
taacgcagtt gagcgttggg acgtaaacgc catcgacgat ctgccggatt acatgaaact    6060
gtgctttctg gctctgtata acactattaa cgaaatcgcc tacgacaacc tgaaagaaaa    6120
aggtgagaac atcctgccgt atctgaccaa agcctgggct gacctgtgca acgctttcct    6180
gcaagaagcc aagtggctgt acaacaaatc tactccgacc tttgacgaat acttcggcaa    6240
cgcatggaaa tcctcttctg gcccgctgca actggtgttc gcttacttcg ctgtcgtgca    6300
gaacattaaa aaggaagaga tcgaaaaacct gcaaaaatac catgcacatca tctctcgtcc    6360 ttcccatatc ttccgtctgt gcaatgacct ggctagcgcg tctgcggaaa ttgcgcgtgg    6420
```

-continued

```
tgaaaccgca aatagcgttt cttgttacat gcgcactaaa ggtatctccg aagaactggc      6480
taccgaaagc gtgatgaatc tgatcgatga aacctggaaa aagatgaaca aggaaaaact      6540
gggtggtagc ctgttcgcga aaccgttcgt ggaaaccgcg atcaacctgg cacgtcaatc      6600
tcactgcact tatcataacg cgacgcgca tacctctccg gatgagctga cccgcaaacg       6660
cgttctgtct gtaatcactg aaccgattct gccgtttgaa cgctaaggat ccgaattcga      6720
gctccgtcga caagcttgcg gccgcactcg agcaccacca ccaccaccac tgagatccgg      6780
ctgctaacaa agcccgaaag gaagctgagt tggctgctgc caccgctgag caataactag      6840
cataacccct tggggcctct aaacgggtct gagggggttt tttgctgaaa ggaggaacta      6900
tatccggat                                                              6909
```

<210> SEQ ID NO 150
<211> LENGTH: 551
<212> TYPE: PRT
<213> ORGANISM: Artificial Sequence
<220> FEATURE:
<223> OTHER INFORMATION: Synthetic Construct

<400> SEQUENCE: 150

```
Met Glu Ala Arg Arg Ser Ala Asn Tyr Gln Pro Asn Leu Trp Asn Phe
  1               5                  10                  15

Glu Phe Leu Gln Ser Leu Glu Asn Asp Leu Lys Val Glu Lys Leu Glu
             20                  25                  30

Glu Lys Ala Thr Lys Leu Glu Glu Val Arg Cys Met Ile Asn Arg
         35                  40                  45

Val Asp Thr Gln Pro Leu Ser Leu Leu Glu Leu Ile Asp Asp Val Gln
     50                  55                  60

Arg Leu Gly Leu Thr Tyr Lys Phe Glu Lys Asp Ile Ile Lys Ala Leu
 65                  70                  75                  80

Glu Asn Ile Val Leu Leu Asp Glu Asn Lys Lys Asn Lys Ser Asp Leu
                 85                  90                  95

His Ala Thr Ala Leu Ser Phe Arg Leu Leu Arg Gln His Gly Phe Glu
            100                 105                 110

Val Ser Gln Asp Val Phe Glu Arg Phe Lys Asp Lys Glu Gly Gly Phe
        115                 120                 125

Ser Gly Glu Leu Lys Gly Asp Val Gln Gly Leu Leu Ser Leu Tyr Glu
    130                 135                 140

Ala Ser Tyr Leu Gly Phe Glu Gly Glu Asn Leu Leu Glu Glu Ala Arg
145                 150                 155                 160

Thr Phe Ser Ile Thr His Leu Lys Asn Asn Leu Lys Glu Gly Ile Asn
                165                 170                 175

Thr Lys Val Ala Glu Gln Val Ser His Ala Leu Glu Leu Pro Tyr His
            180                 185                 190

Gln Arg Leu His Arg Leu Glu Ala Arg Trp Phe Leu Asp Lys Tyr Glu
        195                 200                 205

Pro Lys Glu Pro His His Gln Leu Leu Leu Glu Leu Ala Lys Leu Asp
    210                 215                 220

Phe Asn Met Val Gln Thr Leu His Gln Lys Glu Leu Gln Asp Leu Ser
225                 230                 235                 240

Arg Trp Trp Thr Glu Met Gly Leu Ala Ser Lys Leu Asp Phe Val Arg
                245                 250                 255

Asp Arg Leu Met Glu Val Tyr Phe Trp Ala Leu Gly Met Ala Pro Asp
            260                 265                 270

Pro Gln Phe Gly Glu Cys Arg Lys Ala Val Thr Lys Met Phe Gly Leu
```

```
                    275                 280                 285
Val Thr Ile Ile Asp Asp Val Tyr Asp Val Tyr Gly Thr Leu Asp Glu
            290                 295                 300

Leu Gln Leu Phe Thr Asp Ala Val Glu Arg Trp Asp Val Asn Ala Ile
305                 310                 315                 320

Asn Thr Leu Pro Asp Tyr Met Lys Leu Cys Phe Leu Ala Leu Tyr Asn
                325                 330                 335

Thr Val Asn Asp Thr Ser Tyr Ser Ile Leu Lys Glu Lys Gly His Asn
            340                 345                 350

Asn Leu Ser Tyr Leu Thr Lys Ser Trp Arg Glu Leu Cys Lys Ala Phe
        355                 360                 365

Leu Gln Glu Ala Lys Trp Ser Asn Asn Lys Ile Ile Pro Ala Phe Ser
    370                 375                 380

Lys Tyr Leu Glu Asn Ala Ser Val Ser Ser Ser Gly Val Ala Leu Leu
385                 390                 395                 400

Ala Pro Ser Tyr Phe Ser Val Cys Gln Gln Gln Glu Asp Ile Ser Asp
                405                 410                 415

His Ala Leu Arg Ser Leu Thr Asp Phe His Gly Leu Val Arg Ser Ser
            420                 425                 430

Cys Val Ile Phe Arg Leu Cys Asn Asp Leu Ala Thr Ser Ala Ala Glu
        435                 440                 445

Leu Glu Arg Gly Glu Thr Thr Asn Ser Ile Ile Ser Tyr Met His Glu
    450                 455                 460

Asn Asp Gly Thr Ser Glu Glu Gln Ala Arg Glu Glu Leu Arg Lys Leu
465                 470                 475                 480

Ile Asp Ala Glu Trp Lys Lys Met Asn Arg Glu Arg Val Ser Asp Ser
                485                 490                 495

Thr Leu Leu Pro Lys Ala Phe Met Glu Ile Ala Val Asn Met Ala Arg
            500                 505                 510

Val Ser His Cys Thr Tyr Gln Tyr Gly Asp Gly Leu Gly Arg Pro Asp
        515                 520                 525

Tyr Ala Thr Glu Asn Arg Ile Lys Leu Leu Leu Ile Asp Pro Phe Pro
    530                 535                 540

Ile Asn Gln Leu Met Tyr Val
545                 550

<210> SEQ ID NO 151
<211> LENGTH: 6935
<212> TYPE: DNA
<213> ORGANISM: Artificial Sequence
<220> FEATURE:
<223> OTHER INFORMATION: Synthetic Construct

<400> SEQUENCE: 151
tcgagcacca ccaccaccac cactgagatc cggctgctaa caaagcccga aaggaagctg      60
agttggctgc tgccaccgct gagcaataac tagcataacc ccttgggccc tctaaacggg     120
tcttgagggg ttttttgctg aaaggaggaa ctatatccgg attggcgaat gggacgcgcc     180
ctgtagcggc gcattaagcg cggcgggtgt ggtggttacg cgcagcgtga ccgctacact     240
tgccagcgcc ctagcgcccg ctcctttcgc tttcttccct ccttttctcg ccacgttcgc     300
cggctttccc cgtcaagctc taaatcgggg ctccctttta gggttccgat ttagtgcttt     360
acggcacctc gaccccaaaa aacttgatta gggtgatggt tcacgtagtg gccatcgcc     420 ctgatagacg gttttcgcc ctttgacgtt ggagtccacg ttctttaata gtggactctt     480
gttccaaact ggaacaacac tcaaccctat ctcggtctat tcttttgatt tataagggat     540
```

```
tttgccgatt tcggcctatt ggttaaaaaa tgagctgatt taacaaaaat ttaacgcgaa      600
ttttaacaaa atattaacgt ttacaatttc aggtggcact tttcggggaa atgtgcgcgg      660
aacccctatt tgtttatttt tctaaataca ttcaaatatg tatccgctca tgaattaatt      720
cttagaaaaa ctcatcgagc atcaaatgaa actgcaattt attcatatca ggattatcaa      780
taccatattt tgaaaaagc cgtttctgta atgaaggaga aaactcaccg aggcagttcc       840
ataggatggc aagatcctgg tatcggtctg cgattccgac tcgtccaaca tcaatacaac      900
ctattaattt cccctcgtca aaaataaggt tatcaagtga aaatcacca tgagtgacga       960
ctgaatccgg tgagaatggc aaaagtttat gcatttcttt ccagacttgt tcaacaggcc     1020
agccattacg ctcgtcatca aaatcactcg catcaaccaa accgttattc attcgtgatt     1080
gcgcctgagc gagacgaaat acgcgatcgc tgttaaaagg acaattacaa acaggaatcg     1140
aatgcaaccg cgcaggaac actgccagcg catcaacaat attttcaccct gaatcaggat     1200
attcttctaa tacctggaat gctgttttcc cggggatcgc agtggtgagt aaccatgcat     1260
catcaggagt acggataaaa tgcttgatgg tcggaagagg cataaattcc gtcagccagt     1320
ttagtctgac catctcatct gtaacatcat ggcaacgct acctttgcca tgtttcagaa      1380
acaactctgg cgcatcgggc ttcccataca atcgatagat tgtcgcacct gattgcccga    1440
cattatcgcg agcccattta tacccatata aatcagcatc catgttggaa tttaatcgcg     1500
gcctagagca agacgtttcc cgttgaatat ggctcataac ccccttgta ttactgttta      1560
tgtaagcaga cagttttatt gttcatgacc aaaatcccctt aacgtgagtt ttcgttccac    1620
tgagcgtcag accccgtaga aagatcaaa ggatcttctt gagatccttt ttttctgcgc      1680
gtaatctgct gcttgcaaac aaaaaaacca ccgctaccag cggtggtttg tttgccggat     1740
caagagctac caactctttt tccgaaggta actggcttca gcagagcgca gataccaaat     1800
actgtccttc tagtgtagcc gtagttaggc caccacttca agaactctgt agcaccgcct     1860
acatacctcg ctctgctaat cctgttacca gtggctgctg ccagtggcga taagtcgtgt     1920
cttaccgggt tggactcaag acgatagtta ccggataagg cgcagcggtc gggctgaacg     1980
gggggttcgt gcacacagcc cagcttggag cgaacgacct acaccgaact gagataccta     2040
cagcgtgagc tatgagaaag cgccacgctt cccgaaggga gaaaggcgga caggtatccg     2100
gtaagcggca gggtcggaac aggagagcgc acgagggagc ttccagggg aaacgcctgg      2160
tatctttata gtcctgtcgg gtttcgccac ctctgacttg agcgtcgatt tttgtgatgc     2220
tcgtcagggg ggcggagcct atggaaaaac gccagcaacg cggccttttt acggttcctg     2280
gccttttgct ggcctttgc tcacatgttc tttcctgcgt tatcccctga ttctgtggat      2340
aaccgtatta ccgcctttga gtgagctgat accgctcgcc gcagccgaac gaccgagcgc     2400
agcgagtcag tgagcgagga agcggaagag cgcctgatgc ggtattttct ccttacgcat     2460
ctgtgcggta tttcacaccg catatatggt gcactctcag tacaatctgc tctgatgccg     2520
catagttaag ccagtataca ctccgctatc gctacgtgac tgggtcatgg ctgcgccccg     2580
acacccgcca cacccgctg acgcgccctg acgggcttgt ctgctcccgg catccgctta     2640
cagacaagct gtgaccgtct ccgggagctg catgtgtcag aggttttcac cgtcatcacc     2700
gaaacgcgcg aggcagctgc ggtaaagctc atcagcgtgg tcgtgaagcg attcacagat     2760
gtctgcctgt tcatccgcgt ccagctcgtt gagtttctcc agaagcgtta atgtctggct     2820
tctgataaag cgggccatgt taagggcggt ttttcctgt ttggtcactg atgcctccgt     2880
gtaagggga tttctgttca tgggggtaat gataccgatg aaacgagaga ggatgctcac     2940
```

```
gatacgggtt actgatgatg aacatgcccg gttactggaa cgttgtgagg gtaaacaact    3000
ggcggtatgg atgcggcggg accagagaaa aatcactcag ggtcaatgcc agcgcttcgt    3060
taatacagat gtaggtgttc cacagggtag ccagcagcat cctgcgatgc agatccggaa    3120
cataatggtg cagggcgctg acttccgcgt ttccagactt tacgaaacac ggaaaccgaa    3180
gaccattcat gttgttgctc aggtcgcaga cgttttgcag cagcagtcgc ttcacgttcg    3240
ctcgcgtatc ggtgattcat tctgctaacc agtaaggcaa ccccgccagc ctagccgggt    3300
cctcaacgac aggagcacga tcatgcgcac ccgtggggcc gccatgccgg cgataatggc    3360
ctgcttctcg ccgaaacgtt tggtggcggg accagtgacg aaggcttgag cgagggcgtg    3420
caagattccg aataccgcaa gcgacaggcc gatcatcgtc gcgctccagc gaaagcggtc    3480
ctcgccgaaa atgacccaga gcgctgccgg cacctgtcct acgagttgca tgataaagaa    3540
gacagtcata agtgcggcga cgatagtcat gccccgcgcc caccggaagg agctgactgg    3600
gttgaaggct ctcaagggca tcggtcgaga tcccggtgcc taatgagtga gctaacttac    3660
attaattgcg ttgcgctcac tgcccgcttt ccagtcggga aacctgtcgt gccagctgca    3720
ttaatgaatc ggccaacgcg cggggagagg cggtttgcgt attgggcgcc agggtggttt    3780
ttcttttcac cagtgagacg ggcaacagct gattgccctt caccgcctgg ccctgagaga    3840
gttgcagcaa gcggtccacg ctggtttgcc ccagcaggcg aaaatcctgt ttgatggtgg    3900
ttaacggcgg gatataacat gagctgtctt cggtatcgtc gtatcccact accgagatat    3960
ccgcaccaac gcgcagcccg gactcggtaa tggcgcgcat tgcgcccagc gccatctgat    4020
cgttggcaac cagcatcgca gtgggaacga tgccctcatt cagcatttgc atggtttgtt    4080
gaaaaccgga catggcactc cagtcgcctt cccgttccgc tatcggctga atttgattgc    4140
gagtgagata tttatgccag ccagccagac gcagacgcgc cgagacagaa cttaatgggc    4200
ccgctaacag cgcgatttgc tggtgaccca atgcgaccag atgctccacg cccagtcgcg    4260
taccgtcttc atgggagaaa ataatactgt tgatgggtgt ctggtcagag acatcaagaa    4320
ataacgccgg aacattagtg caggcagctt ccacagcaat ggcatcctgg tcatccagcg    4380
gatagttaat gatcagccca ctgacgcgtt gcgcgagaag attgtgcacc gccgctttac    4440
aggcttcgac gccgcttcgt tctaccatcg acaccaccac gctggcaccc agttgatcgg    4500
cgcgagattt aatcgccgcg acaatttgcg acggcgcgtg cagggccaga ctggaggtgg    4560
caacgccaat cagcaacgac tgtttgcccg ccagttgttg tgccacgcgg ttgggaatgt    4620
aattcagctc cgccatcgcc gcttccactt ttcccgcgt tttcgcagaa acgtggctgg    4680
cctggttcac cacgcgggaa acggtctgat aagagacacc ggcatactct gcgacatcgt    4740
ataacgttac tggtttcaca ttcaccaccc tgaattgact ctcttccggg cgctatcatg    4800
ccataccgcg aaaggttttg cgccattcga tggtgtccgg gatctcgacg ctctcccta    4860 tgcgactcct gcattaggaa gcagcccagt agtaggttga ggccgttgag caccgccgcc    4920
gcaaggaatg gtgcatgcaa ggagatggcg cccaacagtc ccccgccac ggggcctgcc    4980 accatacccca cgccgaaaca gcgctcatg agcccgaagt ggcgagcccg atcttcccca    5040
tcggtgatgt cggcgatata ggcgccagca accgcacctg tggcgccggt gatgccggcc    5100
acgatgcgtc cggcgtagag gatcgagatc tcgatcccgc gaaattaata cgactcacta    5160
taggggaatt gtgagcggat aacaattccc ctctagaaat aattttgttt aactttaaga    5220
aggagatata ccatgaagc tcgtcgttcc gcaaactatc agccaaacct gtggaatttc    5280
gaattcctgc aatccctgga gaacgacctg aaagtggaaa agctggagga gaaagcgacc    5340
```

```
aaactggagg aagaagttcg ctgcatgatc aaccgtgtag acacccagcc gctgtccctg    5400
ctggagctga tcgacgatgt gcagcgcctg gtctgacct acaaatttga aaagacatc     5460 attaaagccc tggaaaacat cgtactgctg acgaaaaca aaaagaacaa atctgacctg    5520
cacgcaaccg ctctgtcttt ccgtctgctg cgtcagcacg gtttcgaggt ttctcaggat   5580 gttttgagc gtttcaagga taaagaaggt ggtttcagcg gtgaactgaa aggtgacgtc    5640
caaggcctgc tgagcctgta tgaagcgtct tacctgggtt tcgagggtga aacctgctg    5700 gaggaggcgc gtacctttc catcacccac ctgaagaaca acctgaaaga aggcattaat    5760
accaaggttg cagaacaagt gagccacgcc ctggaactgc catatcacca gcgtctgcac   5820
cgtctggagg cacgttggtt cctggataaa tacgaaccga agaaccgca tcaccagctg    5880 ctgctggagc tggcgaagct ggatttaac atggtacaga ccctgcacca gaaagagctg    5940
caagatctgt cccgctggtg gaccgagatg ggcctggcta gcaaactgga ttttgtacgc   6000
gaccgcctga tggaagttta tttctgggca ctgggtatgg cgccagaccc gcagtttggt   6060
gaatgtcgca aagctgttac taaaatgttt ggtctggtga cgatcatcga tgacgtgtat   6120
gacgtttatg gcactctgga cgaactgcaa ctgttcaccg atgctgtaga gcgctgggac   6180
gttaacgcta ttaacaccct gccggactat atgaaactgt gtttcctggc actgtacaac   6240
accgttaacg cacgtccta ttctattctg aagagaaag gtcataacaa cctgtcctat    6300
ctgacgaaaa gctggcgtga actgtgcaaa gcctttctgc aagaggcgaa atggtccaac   6360
aacaaaatta tcccggcttt ctccaagtac ctggaaaacg ccagcgtttc ctcctccggt   6420
gtagcgctgc tggcgccgtc ttacttttcc gtatgccagc agcaggaaga catctccgac   6480
cacgcgctgc gttccctgac cgacttccat ggtctggtgc gttctagctg cgttatcttc   6540
cgcctgtgca acgatctggc cacctctgcg gcggagctgg aacgtggcga gactaccaat   6600
tctatcatta gctacatgca cgaaaacgat ggtaccagcg aggaacaggc ccgcgaagaa   6660
ctgcgtaaac tgatcgacgc cgaatggaaa aagatgaatc gtgaacgcgt tagcgactcc   6720
accctgctgc ctaaagcgtt catggaaatc gcagttaaca tggcacgtgt ttcccactgc   6780
acctaccagt atggcgatgg tctgggtcgc ccagactacg cgactgaaaa ccgcatcaaa   6840
ctgctgctga ttgaccctt cccgattaac cagctgatgt atgtctaact gcagggatcc   6900
gaattcgagc tccgtcgaca agcttgcggc cgcac                              6935
```

<210> SEQ ID NO 152
<211> LENGTH: 553
<212> TYPE: PRT
<213> ORGANISM: Artificial Sequence
<220> FEATURE:
<223> OTHER INFORMATION: Synthetic Construct

<400> SEQUENCE: 152

Met Glu His Asn Ser Arg Arg Ser Ala Asn Tyr Gln Pro Asn Leu Trp
 1               5                  10                  15

Asn Phe Glu Phe Leu Gln Ser Leu Glu Asn Asp Leu Lys Val Glu Lys
            20                  25                  30

Leu Glu Glu Lys Ala Thr Lys Leu Glu Glu Glu Val Arg Cys Met Ile
        35                  40                  45

Asn Arg Val Asp Thr Gln Pro Leu Ser Leu Leu Glu Leu Ile Asp Asp
    50                  55                  60

Val Gln Arg Leu Gly Leu Thr Tyr Lys Phe Glu Lys Asp Ile Ile Lys
65                  70                  75                  80

-continued

```
Ala Leu Glu Asn Ile Val Leu Asp Glu Asn Lys Lys Asn Lys Ser
                 85                  90                  95

Asp Leu His Ala Thr Ala Leu Ser Phe Arg Leu Leu Arg Gln His Gly
            100                 105                 110

Phe Glu Val Ser Gln Asp Val Phe Glu Arg Phe Lys Asp Lys Glu Gly
        115                 120                 125

Gly Phe Ser Gly Glu Leu Lys Gly Asp Val Gln Gly Leu Leu Ser Leu
    130                 135                 140

Tyr Glu Ala Ser Tyr Leu Gly Phe Glu Gly Glu Asn Leu Leu Glu Glu
145                 150                 155                 160

Ala Arg Thr Phe Ser Ile Thr His Leu Lys Asn Asn Leu Lys Glu Gly
                165                 170                 175

Ile Asn Thr Lys Val Ala Glu Gln Val Ser His Ala Leu Glu Leu Pro
            180                 185                 190

Tyr His Gln Arg Leu His Arg Leu Glu Ala Arg Trp Phe Leu Asp Lys
        195                 200                 205

Tyr Glu Pro Lys Glu Pro His His Gln Leu Leu Glu Leu Ala Lys
    210                 215                 220

Leu Asp Phe Asn Met Val Gln Thr Leu His Gln Lys Glu Leu Gln Asp
225                 230                 235                 240

Leu Ser Arg Trp Trp Thr Glu Met Gly Leu Ala Ser Lys Leu Asp Phe
                245                 250                 255

Val Arg Asp Arg Leu Met Glu Val Tyr Phe Trp Ala Leu Gly Met Ala
            260                 265                 270

Pro Asp Pro Gln Phe Gly Glu Cys Arg Lys Ala Val Thr Lys Met Phe
        275                 280                 285

Gly Leu Val Thr Ile Ile Asp Asp Val Tyr Asp Val Tyr Gly Thr Leu
    290                 295                 300

Asp Glu Leu Gln Leu Phe Thr Asp Ala Val Glu Arg Trp Asp Val Asn
305                 310                 315                 320

Ala Ile Asn Thr Leu Pro Asp Tyr Met Lys Leu Cys Phe Leu Ala Leu
                325                 330                 335

Tyr Asn Thr Val Asn Asp Thr Ser Tyr Ser Ile Leu Lys Glu Lys Gly
            340                 345                 350

His Asn Asn Leu Ser Tyr Leu Thr Lys Ser Trp Arg Glu Leu Cys Lys
        355                 360                 365

Ala Phe Leu Gln Glu Ala Lys Trp Ser Asn Asn Lys Ile Ile Pro Ala
    370                 375                 380

Phe Ser Lys Tyr Leu Glu Asn Ala Ser Val Ser Ser Gly Val Ala
385                 390                 395                 400

Leu Leu Ala Pro Ser Tyr Phe Ser Val Cys Gln Gln Gln Glu Asp Ile
                405                 410                 415

Ser Asp His Ala Leu Arg Ser Leu Thr Asp Phe His Gly Leu Val Arg
            420                 425                 430

Ser Ser Cys Val Ile Phe Arg Leu Cys Asn Asp Leu Ala Thr Ser Ala
        435                 440                 445

Ala Glu Leu Glu Arg Gly Glu Thr Thr Asn Ser Ile Ile Ser Tyr Met
    450                 455                 460

His Glu Asn Asp Gly Thr Ser Glu Glu Gln Ala Arg Glu Glu Leu Arg
465                 470                 475                 480

Lys Leu Ile Asp Ala Glu Trp Lys Lys Met Asn Arg Glu Arg Val Ser
                485                 490                 495

Asp Ser Thr Leu Leu Pro Lys Ala Phe Met Glu Ile Ala Val Asn Met
            500                 505                 510
```

Ala Arg Val Ser His Cys Thr Tyr Gln Tyr Gly Asp Gly Leu Gly Arg
          515                 520                 525

Pro Asp Tyr Ala Thr Glu Asn Arg Ile Lys Leu Leu Leu Ile Asp Pro
      530                 535                 540

Phe Pro Ile Asn Gln Leu Met Tyr Val
545                 550

<210> SEQ ID NO 153
<211> LENGTH: 6941
<212> TYPE: DNA
<213> ORGANISM: Artificial Sequence
<220> FEATURE:
<223> OTHER INFORMATION: Synthetic Construct

<400> SEQUENCE: 153

| | | | | | |
|---|---|---|---|---|---|
| tcgagcacca | ccaccaccac | cactgagatc | cggctgctaa | caaagcccga | aggaagctg | 60 |
| agttggctgc | tgccaccgct | gagcaataac | tagcataacc | ccttgggcc | tctaaacggg | 120 |
| tcttgagggg | ttttttgctg | aaaggaggaa | ctatatccgg | attggcgaat | gggacgcgcc | 180 |
| ctgtagcggc | gcattaagcg | cggcgggtgt | ggtggttacg | cgcagcgtga | ccgctacact | 240 |
| tgccagcgcc | ctagcgcccg | ctcctttcgc | tttcttccct | tcctttctcg | ccacgttcgc | 300 |
| cggctttccc | cgtcaagctc | taaatcgggg | gctccctta | gggttccgat | ttagtgcttt | 360 |
| acggcacctc | gaccccaaaa | aacttgatta | gggtgatggt | tcacgtagtg | ggccatcgcc | 420 |
| ctgatagacg | ttttttcgcc | ctttgacgtt | ggagtccacg | ttctttaata | gtggactctt | 480 |
| gttccaaact | ggaacaacac | tcaaccctat | ctcggtctat | tcttttgatt | tataagggat | 540 |
| tttgccgatt | tcggcctatt | ggttaaaaaa | tgagctgatt | taacaaaaat | ttaacgcgaa | 600 |
| ttttaacaaa | atattaacgt | ttacaatttc | aggtggcact | tttcggggaa | atgtgcgcgg | 660 |
| aacccctatt | tgtttatttt | tctaaataca | ttcaaatatg | tatccgctca | tgaattaatt | 720 |
| cttagaaaaa | ctcatcgagc | atcaaatgaa | actgcaattt | attcatatca | ggattatcaa | 780 |
| taccatattt | ttgaaaaagc | cgtttctgta | atgaaggaga | aaactcaccg | aggcagttcc | 840 |
| ataggatggc | aagatcctgg | tatcggtctg | cgattccgac | tcgtccaaca | tcaatacaac | 900 |
| ctattaattt | cccctcgtca | aaaataaggt | tatcaagtga | gaaatcacca | tgagtgacga | 960 |
| ctgaatccgg | tgagaatggc | aaaagtttat | gcatttcttt | ccagacttgt | tcaacaggcc | 1020 |
| agccattacg | ctcgtcatca | aaatcactcg | catcaaccaa | accgttattc | attcgtgatt | 1080 |
| gcgcctgagc | gagacgaaat | acgcgatcgc | tgttaaaagg | acaattacaa | acaggaatcg | 1140 |
| aatgcaaccg | gcgcaggaac | actgccagcg | catcaacaat | attttcacct | gaatcaggat | 1200 |
| attcttctaa | tacctggaat | gctgttttcc | cggggatcgc | agtggtgagt | aaccatgcat | 1260 |
| catcaggagt | acggataaaa | tgcttgatgg | tcggaagagg | cataaattcc | gtcagccagt | 1320 |
| ttagtctgac | catctcatct | gtaacatcat | tggcaacgct | acctttgcca | tgtttcagaa | 1380 |
| acaactctgg | cgcatcgggc | ttcccataca | atcgatagat | tgtcgcacct | gattgcccga | 1440 |
| cattatcgcg | agcccattta | tacccatata | aatcagcatc | catgttggaa | tttaatcgcg | 1500 |
| gcctagagca | agacgtttcc | cgttgaatat | ggctcataac | accccttgta | ttactgttta | 1560 |
| tgtaagcaga | cagttttatt | gttcatgacc | aaaatccctt | aacgtgagtt | ttcgttccac | 1620 |
| tgagcgtcag | accccgtaga | aaagatcaaa | ggatcttctt | gagatccttt | ttttctgcgc | 1680 |
| gtaatctgct | gcttgcaaac | aaaaaaacca | ccgctaccag | cggtggtttg | tttgccggat | 1740 |
| caagagctac | caactctttt | tccgaaggta | actggcttca | gcagagcgca | gataccaaat | 1800 |

```
actgtccttc tagtgtagcc gtagttaggc caccacttca agaactctgt agcaccgcct    1860
acatacctcg ctctgctaat cctgttacca gtggctgctg ccagtggcga taagtcgtgt    1920
cttaccgggt tggactcaag acgatagtta ccggataagg cgcagcggtc gggctgaacg    1980
gggggttcgt gcacacagcc cagcttggag cgaacgacct acaccgaact gagataccta    2040
cagcgtgagc tatgagaaag cgccacgctt cccgaaggga gaaaggcgga caggtatccg    2100
gtaagcggca gggtcggaac aggagagcgc acgagggagc ttccagggggg aaacgcctgg    2160 tatctttata gtcctgtcgg gtttcgccac ctctgacttg agcgtcgatt tttgtgatgc    2220
tcgtcagggg ggcggagcct atggaaaaac gccagcaacg cggccttttt acggttcctg    2280
gccttttgct ggccttttgc tcacatgttc tttcctgcgt tatcccctga ttctgtggat    2340
aaccgtatta ccgcctttga gtgagctgat accgctcgcc gcagccgaac gaccgagcgc    2400
agcgagtcag tgagcgagga gcggaagag cgcctgatgc ggtattttct ccttacgcat    2460
ctgtgcggta tttcacaccg catatatggt gcactctcag tacaatctgc tctgatgccg    2520
catagttaag ccagtataca ctccgctatc gctacgtgac tgggtcatgg ctgcgccccg    2580
acacccgcca cacccgctg acgcgccctg acgggcttgt ctgctcccgg catccgctta    2640
cagacaagct gtgaccgtct ccgggagctg catgtgtcag aggttttcac cgtcatcacc    2700
gaaacgcgcg aggcagctgc ggtaaagctc atcagcgtgg tcgtgaagcg attcacagat    2760
gtctgcctgt tcatccgcgt ccagctcgtt gagtttctcc agaagcgtta atgtctggct    2820
tctgataaag cgggccatgt taagggcggt tttttcctgt ttggtcactg atgcctccgt    2880 gtaagggga tttctgttca tgggggtaat gataccgatg aaacgagaga ggatgctcac    2940
gatacgggtt actgatgatg aacatgcccg gttactggaa cgttgtgagg gtaaacaact    3000
ggcggtatgg atgcggcggg accagagaaa aatcactcag ggtcaatgcc agcgcttcgt    3060
taatacagat gtaggtgttc cacagggtag ccagcagcat cctgcgatgc agatccggaa    3120
cataatggtg cagggcgctg acttccgcgt ttccagactt tacgaaacac ggaaaccgaa    3180
gaccattcat gttgttgctc aggtcgcaga cgttttgcag cagcagtcgc ttcacgttcg    3240
ctcgcgtatc ggtgattcat tctgctaacc agtaaggcaa ccccgccagc ctagccgggt    3300
cctcaacgac aggagcacga tcatgcgcac ccgtggggcc gccatgccgg cgataatggc    3360
ctgcttctcg ccgaaacgtt tggtggcggg accagtgacg aaggcttgag cgagggcgtg    3420
caagattccg aataccgcaa gcgacaggcc gatcatcgtc gcgctccagc gaaagcggtc    3480
ctcgccgaaa atgacccaga gcgctgccgg cacctgtcct acgagttgca tgataaagaa    3540
gacagtcata agtgcggcga cgatagtcat gccccgcgcc caccggaagg agctgactgg    3600
gttgaaggct ctcaagggca tcggtcgaga tcccggtgcc taatgagtga gctaacttac    3660
attaattgcg ttgcgctcac tgcccgcttt ccagtcggga aacctgtcgt gccagctgca    3720
ttaatgaatc ggccaacgcg cggggagagg cggtttgcgt attgggcgcc agggtggttt    3780
ttcttttcac cagtgagacg ggcaacagct gattgccctt caccgcctgg ccctgagaga    3840
gttgcagcaa gcggtccacg ctggtttgcc ccagcaggcg aaaatcctgt ttgatggtgg    3900
ttaacggcgg gatataacat gagctgtctt cggtatcgtc gtatcccact accgagatat    3960
ccgcaccaac gcgcagcccg gactcggtaa tggcgcgcat tgcgcccagc gccatctgat    4020
cgttggcaac cagcatcgca gtgggaacga tgccctcatt cagcatttgc atggtttgtt    4080
gaaaaccgga catggcactc cagtcgcctt cccgttccgc tatcggctga atttgattgc    4140
gagtgagata tttatgccag ccagccagac gcagacgcgc cgagacagaa cttaatgggc    4200
```

```
ccgctaacag cgcgatttgc tggtgaccca atgcgaccag atgctccacg cccagtcgcg   4260
taccgtcttc atgggagaaa ataatactgt tgatgggtgt ctggtcagag acatcaagaa   4320
ataacgccgg aacattagtg caggcagctt ccacagcaat ggcatcctgg tcatccagcg   4380
gatagttaat gatcagccca ctgacgcgtt gcgcgagaaa attgtgcacc gccgctttac   4440
aggcttcgac gccgcttcgt tctaccatcg acaccaccac gctggcaccc agttgatcgg   4500
cgcgagattt aatcgccgcg acaatttgcg acggcgcgtg cagggccaga ctggaggtgg   4560
caacgccaat cagcaacgac tgtttgcccg ccagttgttg tgccacgcgg ttgggaatgt   4620
aattcagctc cgccatcgcc gcttccactt tttcccgcgt tttcgcagaa cgtggctgg   4680
cctggttcac cacgcgggaa acggtctgat aagagacacc ggcatactct gcgacatcgt   4740
ataacgttac tggtttcaca ttcaccaccc tgaattgact ctcttccggg cgctatcatg   4800
ccataccgcg aaaggttttg cgccattcga tggtgtccgg gatctcgacg ctctccctta   4860
tgcgactcct gcattaggaa gcagcccagt agtaggttga ggccgttgag caccgccgcc   4920
gcaaggaatg gtgcatgcaa ggagatggcg cccaacagtc ccccggccac ggggcctgcc   4980
accatacccca cgccgaaaca agcgctcatg agcccgaagt ggcgagcccg atcttcccca   5040
tcggtgatgt cggcgatata ggcgccagca accgcacctg tggcgccggt gatgccggcc   5100
acgatgcgtc cggcgtagag gatcgagatc tcgatcccgc gaaattaata cgactcacta   5160
taggggaatt gtgagcggat aacaattccc ctctagaaat aattttgttt aactttaaga   5220
aggagatata ccatggagca taattccgt cgttccgcaa actatcagcc aaacctgtgg   5280
aatttcgaat tcctgcaatc cctggagaac gacctgaaag tggaaaagct ggaggagaaa   5340
gcgaccaaac tggaggaaga agttcgctgc atgatcaacc gtgtagacac ccagccgctg   5400
tccctgctgg agctgatcga cgatgtgcag cgcctgggtc tgacctacaa atttgaaaaa   5460
gacatcatta agccctgga aaacatcgta ctgctggacg aaaacaaaaa gaacaaatct   5520
gacctgcacg caaccgctct gtcttttccgt ctgctgcgtc agcacggttt cgaggtttct   5580
caggatgttt ttgagcgttt caaggataaa gaaggtggtt tcagcggtga actgaaaggt   5640
gacgtccaag gcctgctgag cctgtatgaa gcgtcttacc tgggtttcga gggtgagaac   5700
ctgctggagg aggcgcgtac cttttccatc acccacctga gaacaacct gaaagaaggc   5760
attaatacca aggttgcaga acaagtgagc cacgccctgg aactgccata tcaccagcgt   5820
ctgcaccgtc tggaggcacg ttggttcctg gataaatacg aaccgaaaga accgcatcac   5880
cagctgctgc tggagctggc gaagctggat tttaacatgg tacagaccct gcaccagaaa   5940
gagctgcaag atctgtcccg ctggtggacc gagatgggcc tggctagcaa actggatttt   6000
gtacgcgacc gcctgatgga agtttatttc tgggcactgg gtatggcgcc agacccgcag   6060
tttggtgaat gtcgcaaagc tgttactaaa atgtttggtc tggtgacgat catcgatgac   6120
gtgtatgacg tttatggcac tctggacgaa ctgcaactgt tcaccgatgc tgtagagcgc   6180
tgggacgtta acgctattaa caccctgccg gactatatga actgtgttt cctggcactg   6240
tacaacaccg ttaacgacac gtcctattct attctgaaag agaaaggtca taacaacctg   6300
tcctatctga cgaaaagctg gcgtgaactg tgcaaagcct tctgcaaga ggcgaaatgg   6360
tccaacaaca aaattatccc ggctttctcc aagtacctgg aaaacgccag cgtttcctcc   6420
tccggtgtag cgctgctggc gccgtcttac ttttccgtat gccagcagca ggaagacatc   6480
tccgaccacg cgctgcgttc cctgaccgac ttccatggtc tggtgcgttc tagctgcgtt   6540
atcttccgcc tgtgcaacga tctggccacc tctgcgcgcgg agctgaacg tggcgagact   6600
```

| | |
|---|---|
| accaattcta tcattagcta catgcacgaa acgatggta ccagcgagga acaggcccgc | 6660 |
| gaagaactgc gtaaactgat cgacgccgaa tggaaaaaga tgaatcgtga acgcgttagc | 6720 |
| gactccaccc tgctgcctaa agcgttcatg gaaatcgcag ttaacatggc acgtgtttcc | 6780 |
| cactgcacct accagtatgg cgatggtctg ggtcgcccag actacgcgac tgaaaaccgc | 6840 |
| atcaaactgc tgctgattga ccctttcccg attaaccagc tgatgtatgt ctaactgcag | 6900 |
| ggatccgaat tcgagctccg tcgacaagct tgcggccgca c | 6941 |

<210> SEQ ID NO 154
<211> LENGTH: 4352
<212> TYPE: DNA
<213> ORGANISM: Artificial Sequence
<220> FEATURE:
<223> OTHER INFORMATION: Synthetic Construct

<400> SEQUENCE: 154

| | |
|---|---|
| tagaaaaact catcgagcat caaatgaaac tgcaatttat tcatatcagg attatcaata | 60 |
| ccatattttt gaaaaagccg tttctgtaat gaaggagaaa actcaccgag gcagttccat | 120 |
| aggatggcaa gatcctggta tcggtctgcg attccgactc gtccaacatc aatacaacct | 180 |
| attaatttcc cctcgtcaaa aataaggtta tcaagtgaga atcaccatg agtgacgact | 240 |
| gaatccggtg agaatggcaa aagtttatgc atttctttcc agacttgttc aacaggccag | 300 |
| ccattacgct cgtcatcaaa atcactcgca tcaaccaaac cgttattcat tcgtgattgc | 360 |
| gcctgagcga ggcgaaatac gcgatcgctg ttaaaaggac aattacaaac aggaatcgag | 420 |
| tgcaaccggc gcaggaacac tgccagcgca tcaacaatat tttcacctga atcaggatat | 480 |
| tcttctaata cctggaacgc tgtttttccg gggatcgcag tggtgagtaa ccatgcatca | 540 |
| tcaggagtac ggataaaatg cttgatggtc ggaagtggca taaattccgt cagccagttt | 600 |
| agtctgacca tctcatctgt aacatcattg gcaacgctac ctttgccatg tttcagaaac | 660 |
| aactctggcg catcgggctt cccatacaag cgatagattg tcgcacctga ttgcccgaca | 720 |
| ttatcgcgag cccatttata cccatataaa tcagcatcca tgttggaatt taatcgcggc | 780 |
| ctcgacgttt cccgttgaat atggctcata ttcttccttt ttcaatatta ttgaagcatt | 840 |
| tatcagggtt attgtctcat gagcggatac atatttgaat gtatttagaa aaataaacaa | 900 |
| atagggggtca gtgttacaac caattaacca attctgaaca ttatcgcgag ccatttata | 960 |
| cctgaatatg gctcataaca cccccttgttt gcctggcggc agtagcgcgg tggtcccacc | 1020 |
| tgaccccatg ccgaactcag aagtgaaacg ccgtagcgcc gatggtagtg tggggactcc | 1080 |
| ccatgcgaga gtagggaact gccaggcatc aaataaaacg aaaggctcag tcgaaagact | 1140 |
| gggcctttcg cccgggctaa ttaggggtg tcgcccttc gattgacgct gcagttagac | 1200 |
| atacatcagc tggttaatcg ggaaagggtc aatcagcagc agtttgatgc ggttttcagt | 1260 |
| cgcgtagtct gggcgaccca gaccatcgcc atactggtag gtgcagtggg aaacacgtgc | 1320 |
| catgttaact gcgatttcca tgaacgcttt aggcagcagg gtggagtcgc taacgcgttc | 1380 |
| acgattcatc ttttttccatt cggcgtcgat cagtttacgc agttcttcgc gggcctgttc | 1440 |
| ctcgctggta ccatcgtttt cgtgcatgta gctaatgata gaattggtag tctcgccacg | 1500 |
| ttccagctcc gccgcagagg tggccagatc gttgcacagg cggaagataa cgcagctaga | 1560 |
| acgcaccaga ccatggaagt cggtcaggga acgcagcgcg tggtcggaga tgtcttcctg | 1620 |
| ctgctggcat acgaaaagt aagacggcgc cagcagcgct acaccggagg aggaaacgct | 1680 |
| ggcgttttcc aggtacttgg agaaagccgg gataatttg ttgttggacc atttcgcctc | 1740 |

```
ttgcagaaag gctttgcaca gttcacgcca gcttttcgtc agataggaca ggttgttatg    1800
acctttctct ttcagaatag aataggacgt gtcgttaacg gtgttgtaca gtgccaggaa    1860
acacagtttc atatagtccg gcagggtgtt aatagcgtta acgtcccagc gctctacagc    1920
atcggtgaac agttgcagtt cgtccagagt gccataaacg tcatacacgt catcgatgat    1980
cgtcaccaga ccaaacattt tagtaacagc tttgcgacat tcaccaaact gcgggtctgg    2040
cgccataccc agtgcccaga aataaacttc catcaggcgg tcgcgtacaa aatccagttt    2100
gctagccagg cccatctcgg tccaccagcg ggacagatct tgcagctctt tctggtgcag    2160
ggtctgtacc atgttaaaat ccagcttcgc cagctccagc agcagctggt gatgcggttc    2220
tttcggttcg tatttatcca ggaaccaacg tgcctccaga cggtgcagac gctggtgata    2280
tggcagttcc agggcgtggc tcacttgttc tgcaaccttg gtattaatgc cttctttcag    2340
gttgttcttc aggtgggtga tggaaaaggt acgcgcctcc tccagcaggt tctcaccctc    2400
gaaacccagg taagacgctt catacaggct cagcaggcct tggacgtcac ctttcagttc    2460
accgctgaaa ccaccttctt tatccttgaa acgctcaaaa acatcctgag aaacctcgaa    2520
accgtgctga cgcagcagac ggaaagacag agcggttgcg tgcaggtcag atttgttctt    2580
tttgttttcg tccagcagta cgatgttttc cagggcttta atgatgtctt tttcaaattt    2640
gtaggtcaga cccaggcgct gcacatcgtc gatcagctcc agcagggaca gcggctgggt    2700
gtctacacgg ttgatcatgc agcgaacttc ttcctccagt ttggtcgctt tctcctccag    2760
cttttccact ttcaggtcgt tctccaggga ttgcaggaat tcgaaattcc acaggtttgg    2820
ctgatagttt gcggaacgac gggaattatg ctcggtaatc tgagtaaatt gagaagaggt    2880
cgcacacatg ttcagcgaca agggcgacac aaaatttatt ctaaatgcat aataaatact    2940
gataacatct tatagttttgt attatatttt gtattatcgt tgacatgtat aattttgata    3000
tcaaaaactg attttccctt tattattttc gagatttatt ttcttaattc tctttaacaa    3060
actagaaata ttgtatatac aaaaaatcat aaataataga tgaatagttt aatttataggt    3120
gttcatcaat cgaaaaagca acgtatctta tttaaagtgc gttgcttttt tctcatttat    3180
aaggttaaat aattctcata tatcaagcaa agtgacaggc gcccttaaat attctgacaa    3240
atgctctttc cctaaactcc ccccataaaa aaacccgccg aagcgggttt ttacgttatt    3300
tgcggattaa cgattactcg ttatcagaac cgcccagggg gcccgagctt aagactggcc    3360
gtcgttttac aacacagaaa gagtttgtag aaacgcaaaa aggccatccg tcaggggcct    3420
tctgcttagt ttgatgcctg gcagttccct actctcgcct tccgcttcct cgctcactga    3480
ctcgctgcgc tcggtcgttc ggctgcggcg agcggtatca gctcactcaa aggcggtaat    3540
acggttatcc acagaatcag gggataacgc aggaaagaac atgtgagcaa aaggccagca    3600
aaaggccagg aaccgtaaaa aggccgcgtt gctggcgttt ttccataggc tccgcccccc    3660
tgacgagcat cacaaaaatc gacgctcaag tcagaggtgg cgaaacccga caggactata    3720
aagataccag gcgtttcccc ctggaagctc cctcgtgcgc tctcctgttc cgaccctgcc    3780
gcttaccgga tacctgtccg cctttctccc ttcgggaagc gtggcgcttt ctcatagctc    3840
acgctgtagg tatctcagtt cggtgtaggt cgttcgctcc aagctgggct gtgtgcacga    3900
accccccgtt cagcccgacc gctgcgcctt atccggtaac tatcgtcttg agtccaaccc    3960
ggtaagacac gacttatcgc cactggcagc agccactggt aacaggatta gcagagcgag    4020
gtatgtaggc ggtgctacag agttcttgaa gtggtgggct aactacggct acactagaag    4080
aacagtattt ggtatctgcg ctctgctgaa gccagttacc ttcggaaaaa gagttggtag    4140
```

```
ctcttgatcc ggcaaacaaa ccaccgctgg tagcggtggt ttttttgttt gcaagcagca    4200
gattacgcgc agaaaaaaag gatctcaaga agatcctttg atcttttcta cggggtctga    4260
cgctcagtgg aacgacgcgc gcgtaactca cgttaaggga ttttggtcat gagcttgcgc    4320
cgtcccgtca agtcagcgta atgctctgct tt                                  4352

<210> SEQ ID NO 155
<211> LENGTH: 6080
<212> TYPE: DNA
<213> ORGANISM: Artificial Sequence
<220> FEATURE:
<223> OTHER INFORMATION: Synthetic Construct

<400> SEQUENCE: 155
gtttgacagc ttatcatcga ctgcacggtg caccaatgct tctggcgtca ggcagccatc      60
ggaagctgtg gtatggctgt gcaggtcgta aatcactgca taattcgtgt cgctcaaggc     120
gcactcccgt tctggataat gttttttgcg ccgacatcat aacggttctg gcaaatattc     180
tgaaatgagc tgttgacaat taatcatccg gctcgtataa tgtgtggaat tgtgagcgga     240
taacaatttc acacaggaaa cagcgccgct gagaaaaagc gaagcggcac tgctctttaa     300
caatttatca gacaatctgt gtgggcactc gaccggaatt atcgattaac tttattatta     360
aaaattaaag aggtatatat taatgtatcg attaaataag gaggaataaa ccatgtgtgc     420
gacctcttct caatttactc agattaccga gcataattcc cgtcgttccg caaactatca     480
gccaaacctg tggaatttcg aattcctgca atccctggag aacgacctga agtggaaaa     540 gctggaggag aaagcgacca aactggagga agaagttcgc tgcatgatca accgtgtaga     600
cacccagccg ctgtccctgc tggagctgat cgacgatgtg cagcgcctgg gtctgaccta     660
caaatttgaa aaagacatca ttaaagccct ggaaaacatc gtactgctgg acgaaaacaa     720
aaagaacaaa tctgacctgc acgcaaccgc tctgtctttc gtctgctgc gtcagcacgg     780 tttcgaggtt tctcaggatg tttttgagcg tttcaaggat aaagaaggtg gtttcagcgg     840
tgaactgaaa ggtgacgtcc aaggcctgct gagcctgtat gaagcgtctt acctgggttt     900
cgagggtgag aacctgctgg aggaggcgcg tacccttttcc atcacccacc tgaagaacaa     960
cctgaaagaa ggcattaata ccaaggttgc agaacaagtg agccacgccc tggaactgcc    1020
atatcaccag cgtctgcacc gtctggaggc acgttggttc ctggataaat acgaaccgaa    1080
agaaccgcat caccagctgc tgctggagct ggcgaagctg gatttttaaca tggtacagac    1140 cctgcaccag aaagagctgc aagatctgtc ccgctggtgg accagatggg cctggctag    1200 caaactggat tttgtacgcg accgcctgat ggaagtttat ttctgggcac tgggtatggc    1260
gccagacccg cagtttggtg aatgtcgcaa agctgttact aaaatgtttg gtctggtgac    1320
gatcatcgat gacgtgtatg acgtttatgg cactctggac gaactgcaac tgttcaccga    1380
tgctgtagag cgctgggacg ttaacgctat taacaccctg ccggactata tgaaactgtg    1440
tttcctggca ctgtacaaca ccgttaacga cacgtcctat tctattctga agagaaagg    1500 tcataacaac ctgtccctatc tgacgaaaag ctggcgtgaa ctgtgcaaag cctttctgca    1560
agaggcgaaa tggtccaaca caaaattat cccggctttc tccaagtacc tggaaaacgc    1620 cagcgttttcc tcctccggtg tagcgctgct ggcgccgtct tacttttccg tatgccagca    1680
gcaggaagac atctccgacc acgcgctgcg ttccctgacc gacttccatg gtctggtgcg    1740
ttctagctgc gttatcttcc gcctgtgcaa cgatctggcc acctctgcgg cggagctgga    1800
acgtggcgag actaccaatt ctatcattag ctacatgcac gaaaacgatg gtaccagcga    1860
```

-continued

```
ggaacaggcc cgcgaagaac tgcgtaaact gatcgacgcc gaatggaaaa agatgaatcg    1920
tgaacgcgtt agcgactcca ccctgctgcc taaagcgttc atggaaatcg cagttaacat    1980
ggcacgtgtt tcccactgca cctaccagta tggcgatggt ctgggtcgcc cagactacgc    2040
gactgaaaac cgcatcaaac tgctgctgat tgacccttc ccgattaacc agctgatgta    2100
tgtctaactg cagctggtac catatgggaa ttcgaagctt tctagaacaa aaactcatct    2160
cagaagagga tctgaatagc gccgtcgacc atcatcatca tcatcattga gtttaaacgg    2220
tctccagctt ggctgttttg gcggatgaga agattttc agcctgatac agattaaatc    2280
agaacgcaga agcggtctga taaaacagaa tttgcctggc ggcagtagcg cggtggtccc    2340
acctgacccc atgccgaact cagaagtgaa acgccgtagc gccgatggta gtgtggggtc    2400
tccccatgcg agagtaggga actgccaggc atcaaataaa acgaaaggct cagtcgaaag    2460
actgggcctt tcgttttatc tgttgtttgt cggtgaacgc tctcctgagt aggacaaatc    2520
cgccgggagc ggatttgaac gttgcgaagc aacggcccgg agggtggcgg gcaggacgcc    2580
cgccataaac tgccaggcat caaattaagc agaaggccat cctgacggat ggcctttttg    2640
cgtttctaca aactctttt gtttatttt ctaaatacat tcaaatatgt atccgctcat    2700
gagacaataa ccctgataaa tgcttcaata atattgaaaa aggaagagta tgagtattca    2760
acatttccgt gtcgccctta ttccctttt tgcggcattt tgccttcctg ttttgctca    2820 cccagaaacg ctggtgaaag taaaagatgc tgaagatcag ttgggtgcac gagtgggtta    2880
catcgaactg gatctcaaca gcggtaagat ccttgagagt tttcgccccg aagaacgttt    2940
tccaatgatg agcactttta agttctgcta tgtggcgcg gtattatccc gtgttgacgc    3000
cgggcaagag caactcggtc gccgcataca ctattctcag aatgacttgg ttgagtactc    3060
accagtcaca gaaaagcatc ttacggatgg catgacagta agagaattat gcagtgctgc    3120
cataaccatg agtgataaca ctgcggccaa cttacttctg acaacgatcg gaggaccgaa    3180
ggagctaacc gcttttttgc acaacatggg ggatcatgta actcgccttg atcgttggga    3240
accggagctg aatgaagcca taccaaacga cgagcgtgac accacgatgc ctgtagcaat    3300
ggcaacaacg ttgcgcaaac tattaactgg cgaactactt actctagctt cccggcaaca    3360
attaatagac tggatggagg cggataaagt tgcaggacca cttctgcgct cggcccttcc    3420
ggctggctgg tttattgctg ataaatctgg agccggtgag cgtgggtctc gcggtatcat    3480
tgcagcactg gggccagatg gtaagccctc ccgtatcgta gttatctaca cgacggggag    3540
tcaggcaact atggatgaac gaaatagaca gatcgctgag ataggtgcct cactgattaa    3600
gcattggtaa ctgtcagacc aagtttactc atatatactt tagattgatt taaaacttca    3660
tttttaattt aaaaggatct aggtgaagat cctttttgat aatctcatga ccaaaatccc    3720
ttaacgtgag ttttcgttcc actgagcgtc agaccccgta gaaaagatca aaggatcttc    3780
ttgagatcct ttttttctgc gcgtaatctg ctgcttgcaa acaaaaaaac caccgctacc    3840
agcggtggtt tgtttgccgg atcaagagct accaactctt tttccgaagg taactggctt    3900
cagcagagcg cagataccaa atactgtcct tctagtgtag ccgtagttag gccaccactt    3960
caagaactct gtagcaccgc ctacatacct cgctctgcta atcctgttac cagtggctgc    4020
tgccagtggc gataagtcgt gtcttaccgg gttggactca agacgatagt taccggataa    4080
ggcgcagcgg tcgggctgaa cggggggttc gtgcacacag cccagcttgg agcgaacgac    4140
ctacaccgaa ctgagatacc tacagcgtga gctatgagaa agcgccacgc ttcccgaagg    4200
gagaaaggcg gacaggtatc cggtaagcgg cagggtcgga acaggagagc gcacgaggga    4260
```

```
gcttccaggg ggaaacgcct ggtatcttta tagtcctgtc gggtttcgcc acctctgact    4320
tgagcgtcga ttttttgtgat gctcgtcagg ggggcggagc ctatggaaaa acgccagcaa    4380
cgcggccttt ttacggttcc tggccttttg ctggccttt gctcacatgt tctttcctgc     4440
gttatcccct gattctgtgg ataaccgtat taccgccttt gagtgagctg ataccgctcg    4500
ccgcagccga acgaccgagc gcagcgagtc agtgagcgag gaagcggaag agcgcctgat    4560
gcggtatttt ctccttacgc atctgtgcgg tatttcacac cgcatatggt gcactctcag    4620
tacaatctgc tctgatgccg catagttaag ccagtataca ctccgctatc gctacgtgac    4680
tgggtcatgg ctgcgccccg acacccgcca acacccgctg acgcgccctg acgggcttgt    4740
ctgctcccgg catccgctta cagacaagct gtgaccgtct ccgggagctg catgtgtcag    4800
aggttttcac cgtcatcacc gaaacgcgcg aggcagcaga tcaattcgcg cgcgaaggcg    4860
aagcggcatg catttacgtt gacaccatcg aatggtgcaa aacctttcgc ggtatggcat    4920
gatagcgccc ggaagagagt caattcaggg tggtgaatgt gaaaccagta acgttatacg    4980
atgtcgcaga gtatgccggt gtctcttatc agaccgtttc ccgcgtggtg aaccaggcca    5040
gccacgtttc tgcgaaaacg cgggaaaaag tggaagcggc gatggcggag ctgaattaca    5100
ttcccaaccg cgtggcacaa caactggcgg gcaaacagtc gttgctgatt ggcgttgcca    5160
cctccagtct ggccctgcac gcgccgtcgc aaattgtcgc ggcgattaaa tctcgcgccg    5220
atcaactggg tgccagcgtg gtggtgtcga tggtagaacg aagcggcgtc gaagcctgta    5280
aagcggcggt gcacaatctt ctcgcgcaac gcgtcagtgg gctgatcatt aactatccgc    5340
tggatgacca ggatgccatt gctgtggaag ctgcctgcac taatgttccg gcgttatttc    5400
ttgatgtctc tgaccagaca cccatcaaca gtattatttt ctcccatgaa gacggtacgc    5460
gactgggcgt ggagcatctg gtcgcattgg gtcaccagca aatcgcgctg ttagcgggcc    5520
cattaagttc tgtctcggcg cgtctgcgtc tggctggctg gcataaatat ctcactcgca    5580
atcaaattca gccgatagcg gaacgggaag gcgactggag tgccatgtcc ggttttcaac    5640
aaaccatgca aatgctgaat gagggcatcg ttcccactgc gatgctggtt gccaacgatc    5700
agatggcgct gggcgcaatg cgcgccatta ccgagtccgg gctgcgcgtt ggtgcggata    5760
tctcggtagt gggatacgac gataccgaag acagctcatg ttatatcccg ccgtcaacca    5820
ccatcaaaca ggattttcgc ctgctggggc aaaccagcgt ggaccgcttg ctgcaactct    5880
ctcagggcca ggcggtgaag ggcaatcagc tgttgcccgt ctcactggtg aaaagaaaaa    5940
ccaccctggc gcccaatacg caaaccgcct ctccccgcgc gttggccgat tcattaatgc    6000
agctggcacg acaggtttcc cgactggaaa gcgggcagtg agcgcaacgc aattaatgtg    6060
agttagcgcg aattgatctg                                               6080

<210> SEQ ID NO 156
<211> LENGTH: 6646
<212> TYPE: DNA
<213> ORGANISM: Artificial Sequence
<220> FEATURE:
<223> OTHER INFORMATION: Synthetic Construct

<400> SEQUENCE: 156
ccgacaccat cgaatggtgc aaaacctttc gcggtatggc atgatagcgc ccggaagaga      60
gtcaattcag ggtggtgaat gtgaaaccag taacgttata cgatgtcgca gagtatgccg     120
gtgtctctta tcagaccgtt tcccgcgtgg tgaaccaggc cagccacgtt tctgcgaaaa     180
cgcgggaaaa agtggaagcg gcgatggcgg agctgaatta cattcccaac cgcgtggcac     240
```

-continued

```
aacaactggc gggcaaacag tcgttgctga ttggcgttgc cacctccagt ctggccctgc    300
acgcgccgtc gcaaattgtc gcggcgatta atctcgcgc cgatcaactg ggtgccagcg     360
tggtggtgtc gatggtagaa cgaagcggcg tcgaagcctg taaagcggcg gtgcacaatc    420
ttctcgcgca acgcgtcagt gggctgatca ttaactatcc gctggatgac caggatgcca    480
ttgctgtgga agctgcctgc actaatgttc cggcgttatt tcttgatgtc tctgaccaga    540
cacccatcaa cagtattatt ttctcccatg aagacggtac gcgactgggc gtggagcatc    600
tggtcgcatt gggtcaccag caaatcgcgc tgttagcggg cccattaagt tctgtctcgg    660
cgcgtctgcg tctggctggc tggcataaat atctcactcg caatcaaatt cagccgatag    720
cggaacggga aggcgactgg agtgccatgt ccggttttca acaaaccatg caaatgctga    780
atgagggcat cgttcccact gcgatgctgg ttgccaacga tcagatggcg ctgggcgcaa    840
tgcgcgccat taccgagtcc gggctgcgcg ttggtgcgga tatctcggta gtgggatacg    900
acgataccga agacagctca tgttatatcc cgccgttaac caccatcaaa caggattttc    960
gcctgctggg gcaaaccagc gtggaccgct tgctgcaact ctctcagggc caggcggtga    1020
agggcaatca gctgttgccc gtctcactgg tgaaaagaaa aaccaccctg cgcccaata     1080 cgcaaaccgc ctctccccgc gcgttggccg attcattaat gcagctggca cgacaggttt    1140
cccgactgga aagcgggcag tgagcgcaac gcaattaatg taagttagct cactcattag    1200
gcacaattct catgtttgac agcttatcat cgactgcacg gtgcaccaat gcttctggcg    1260
tcaggcagcc atcggaagct gtggtatggc tgtgcaggtc gtaaatcact gcataattcg    1320
tgtcgctcaa ggcgcactcc cgttctggat aatgttttt gcgccgacat cataacggtt    1380
ctggcaaata ttctgaaatg agctgttgac aattaatcat cggctcgtat aatgtgtgga    1440
attgtgagcg gataacaatt tcacacagga aacagccagt ccgtttaggt gttttcacga    1500
gcacttcacc aacaaggacc atagcatatg aaaatcgaag aaggtaaact ggtaatctgg    1560
attaacggcg ataaaggcta taacggtctc gctgaagtcg gtaagaaatt cgagaaagat    1620
accggaatta aagtcaccgt tgagcatccg gataaactgg aagagaaatt cccacaggtt    1680
gcggcaactg gcgatggccc tgacattatc ttctgggcac acgaccgctt ggtggctac     1740 gctcaatctg gcctgttggc tgaaatcacc ccggacaaag cgttccagga caagctgtat    1800
ccgtttacct gggatgccgt acgttacaac ggcaagctga ttgcttaccc gatcgctgtt    1860
gaagcgttat cgctgatta taacaaagat ctgctgccga acccgccaaa aacctgggaa     1920
gagatcccgg cgctggataa agaactgaaa gcgaaggta agagcgcgct gatgttcaac    1980
ctgcaagaac cgtacttcac ctggccgctg attgctgctg acggggtta tgcgttcaag     2040 tatgaaaacg gcaagtacga cattaaagac gtgggcgtgg ataacgctgg cgcgaaagcg    2100
ggtctgacct tcctggttga cctgattaaa acaaacaca tgaatgcaga caccgattac     2160
tccatcgcag aagctgcctt taataaaggc gaaacagcga tgaccatcaa cggcccgtgg    2220
gcatggtcca acatcgacac cagcaaagtg aattatggtg taacggtact gccgaccttc    2280
aagggtcaac catccaaacc gttcgttggc gtgctgagcg caggtattaa cgccgccagt    2340
ccgaacaaag agctggcaaa agagttcctc gaaaactatc tgctgactga tgaaggtctg    2400
gaagcggtta ataaagacaa accgctgggt gcgtagcgc tgaagtctta cgaggaagag     2460
ttggtgaaag atccgcggat tgccgccact atggaaaacg cccagaaagg tgaaatcatg    2520
ccgaacatcc cgcagatgtc cgctttctgg tatgccgtgc gtactgcggt gatcaacgcc    2580
gccagcggtc gtcagactgt cgatgaagcc ctgaaagacg cgcagactaa ttcgagctcg    2640
```

-continued

```
aacaacaaca acaataacaa taacaacaac ctcgggatcg agggaaggat ttcagaattc    2700
ggatcctcta gagtcgacct gcaggcaagc ttggcactgg ccgtcgtttt acaacgtcgt    2760
gactgggaaa accctggcgt tacccaactt aatcgccttg cagcacatcc ccctttcgcc    2820
agctggcgta atagcgaaga ggcccgcacc gatcgccctt cccaacagtt gcgcagcctg    2880
aatggcgaat ggcagcttgg ctgttttggc ggatgagata gattttcag cctgatacag     2940
attaaatcag aacgcagaag cggtctgata aaacagaatt tgcctggcgg cagtagcgcg    3000
gtggtcccac ctgaccccat gccgaactca gaagtgaaac gccgtagcgc cgatggtagt    3060
gtggggtctc cccatgcgag agtagggaac tgccaggcat caaataaaac gaaaggctca    3120
gtcgaaagac tgggcctttc gttttatctg ttgtttgtcg gtgaacgctc tcctgagtag    3180
gacaaatccg ccgggagcgg atttgaacgt tgcgaagcaa cggcccggag ggtggcgggc    3240
aggacgcccg ccataaactg ccaggcatca aattaagcag aaggccatcc tgacggatgg    3300
cctttttgcg tttctacaaa ctcttttttgt ttattttttct aaatacattc aaatatgtat    3360
ccgctcatga dacaataacc ctgataaatg cttcaataat attgaaaaag gaagagtatg    3420
agtattcaac atttccgtgt cgcccttatt ccctttttttg cggcattttg ccttcctgtt    3480
tttgctcacc cagaaacgct ggtgaaagta aagatgctg aagatcagtt gggtgcacga     3540
gtgggttaca tcgaactgga tctcaacagc ggtaagatcc ttgagagttt tcgccccgaa    3600
gaacgttctc caatgatgag cacttttaaa gttctgctat gtggcgcggt attatcccgt    3660
gttgacgccg ggcaagagca actcggtcgc cgcatacact attctcagaa tgacttggtt    3720
gagtactcac cagtcacaga aaagcatctt acggatggca tgacagtaag agaattatgc    3780
agtgctgcca taaccatgag tgataacact gcggccaact tacttctgac aacgatcgga    3840
ggaccgaagg agctaaccgc ttttttgcac aacatggggg atcatgtaac tcgccttgat    3900
cgttgggaac cggagctgaa tgaagccata ccaaacgacg agcgtgacac cacgatgcct    3960
gtagcaatgg caacaacgtt gcgcaaacta ttaactggcg aactacttac tctagcttcc    4020
cggcaacaat taatagactg gatggaggcg gataaagttg caggaccact tctgcgctcg    4080
gcccttccgg ctggctggtt tattgctgat aaatctggag ccggtgagcg tgggtctcgc    4140
ggtatcattg cagcactggg gccagatggt aagccctccc gtatcgtagt tatctacacg    4200
acggggagtc aggcaactat ggatgaacga atagacaga tcgctgagat aggtgcctca     4260
ctgattaagc attggtaact gtcagaccaa gtttactcat atatacttta gattgattta    4320
ccccggttga taatcagaaa agccccaaaa acaggaagat tgtataagca aatatttaaa    4380
ttgtaaacgt taatattttg ttaaaattcg cgttaaattt tgttaaatc agctcatttt     4440
ttaaccaata ggccgaaatc ggcaaaatcc cttataaatc aaaagaatag accgagatag    4500
ggttgagtgt tgttccagtt tggaacaaga gtccactatt aaagaacgtg gactccaacg    4560
tcaaagggcg aaaaaccgtc tatcagggcg atggcccact acgtgaacca tcacccaaat    4620
caagtttttt ggggtcgagg tgccgtaaag cactaaatcg aaccctaaa gggagccccc     4680
gatttagagc ttgacgggga agccggcga acgtggcgag aaaggaaggg aagaaagcga     4740
aaggagcggg cgctagggcg ctggcaagtg tagcggtcac gctgcgcgta accaccacac    4800
ccgccgcgct taatgcgccg ctacaggggcg cgtaaaagga tctaggtgaa gatcctttttt    4860
gataatctca tgaccaaaat cccttaacgt gagttttcgt tccactgagc gtcagacccc    4920
gtagaaaaga tcaaaggatc ttcttgagat cctttttttc tgcgcgtaat ctgctgcttg    4980
caaacaaaaa aaccaccgct accagcggtg gtttgtttgc cggatcaaga gctaccaact    5040
```

-continued

| | |
|---|---|
| cttttttccga aggtaactgg cttcagcaga gcgcagatac caaatactgt ccttctagtg | 5100 |
| tagccgtagt taggccacca cttcaagaac tctgtagcac cgcctacata cctcgctctg | 5160 |
| ctaatcctgt taccagtggc tgctgccagt ggcgataagt cgtgtcttac cgggttggac | 5220 |
| tcaagacgat agttaccgga taaggcgcag cggtcgggct gaacggggg ttcgtgcaca | 5280 |
| cagcccagct tggagcgaac gacctacacc gaactgagat acctacagcg tgagctatga | 5340 |
| gaaagcgcca cgcttcccga agggagaaag cggacaggta tccggtaagc ggcagggtc | 5400 |
| ggaacaggag agcgcacgag ggagcttcca gggggaaacg cctggtatct ttatagtcct | 5460 |
| gtcgggtttc gccacctctg acttgagcgt cgatttttgt gatgctcgtc aggggggcgg | 5520 |
| agcctatgga aaaacgccag caacgcggcc ttttacggt tcctggcctt ttgctggcct | 5580 |
| tttgctcaca tgttctttcc tgcgttatcc cctgattctg tggataaccg tattaccgcc | 5640 |
| tttgagtgag ctgataccgc tcgccgcagc cgaacgaccg agcgcagcga gtcagtgagc | 5700 |
| gaggaagcgg aagagcgcct gatgcggtat tttctcctta cgcatctgtg cggtatttca | 5760 |
| caccgcatat atggtgcact ctcagtacaa tctgctctga tgccgcatag ttaagccagt | 5820 |
| atacactccg ctatcgctac gtgactgggt catggctgcg ccccgacacc cgccaacacc | 5880 |
| cgctgacgcg ccctgacggg cttgtctgct cccggcatcc gcttacagac aagctgtgac | 5940 |
| cgtctccggg agctgcatgt gtcagaggtt ttcaccgtca tcaccgaaac gcgcgaggca | 6000 |
| gctgcggtaa agctcatcag cgtggtcgtg cagcgattca cagatgtctg cctgttcatc | 6060 |
| cgcgtccagc tcgttgagtt ctctccagaag cgttaatgtc tggcttctga taaagcgggc | 6120 |
| catgttaagg gcggttttt cctgtttggt cactgatgcc tccgtgtaag ggggatttct | 6180 |
| gttcatgggg gtaatgatac cgatgaaacg agagaggatg ctcacgatac gggttactga | 6240 |
| tgatgaacat gcccggttac tggaacgttg tgagggtaaa caactggcgg tatggatgcg | 6300 |
| gcgggaccag agaaaaatca ctcagggtca atgccagcgc ttcgttaata cagatgtagg | 6360 |
| tgttccacag ggtagccagc agcatcctgc gatgcagatc cggaacataa tggtgcaggg | 6420 |
| cgctgacttc cgcgtttcca gactttacga aacacggaaa ccgaagacca ttcatgttgt | 6480 |
| tgctcaggtc gcagacgttt tgcagcagca gtcgcttcac gttcgctcgc gtatcggtga | 6540 |
| ttcattctgc taaccagtaa ggcaaccccg ccagcctagc cgggtcctca acgacaggag | 6600 |
| cacgatcatg cgcacccgtg gccaggaccc aacgctgccc gaaatt | 6646 |

<210> SEQ ID NO 157
<211> LENGTH: 8310
<212> TYPE: DNA
<213> ORGANISM: Artificial Sequence
<220> FEATURE:
<223> OTHER INFORMATION: Synthetic Construct

<400> SEQUENCE: 157

| | |
|---|---|
| ccgacaccat cgaatggtgc aaaacctttc gcggtatggc atgatagcgc ccggaagaga | 60 |
| gtcaattcag ggtggtgaat gtgaaaccag taacgttata cgatgtcgca gagtatgccg | 120 |
| gtgtctctta tcagaccgtt tcccgcgtgg tgaaccaggc cagccacgtt tctgcgaaaa | 180 |
| cgcgggaaaa agtggaagcg gcgatggcgg agctgaatta cattcccaac cgcgtggcac | 240 |
| aacaactggc gggcaaacag tcgttgctga ttggcgttgc cacctccagt ctggccctgc | 300 |
| acgcgccgtc gcaaattgtc gcggcgatta atctcgcgc cgatcaactg ggtgccagcg | 360 |
| tggtggtgtc gatggtagaa cgaagcggcg tcgaagcctg taaagcggcg gtgcacaatc | 420 |
| ttctcgcgca acgcgtcagt gggctgatca ttaactatcc gctggatgac caggatgcca | 480 |

-continued

```
ttgctgtgga agctgcctgc actaatgttc ggcgttatt tcttgatgtc tctgaccaga    540
cacccatcaa cagtattatt ttctcccatg aagacggtac gcgactgggc gtggagcatc    600
tggtcgcatt gggtcaccag caaatcgcgc tgttagcggg cccattaagt tctgtctcgg    660
cgcgtctgcg tctggctggc tggcataaat atctcactcg caatcaaatt cagccgatag    720
cggaacggga aggcgactgg agtgccatgt ccggttttca acaaaccatg caaatgctga    780
atgagggcat cgttcccact gcgatgctgg ttgccaacga tcagatggcg ctgggcgcaa    840
tgcgcgccat taccgagtcc gggctgcgcg ttggtgcgga tatctcggta gtgggatacg    900
acgataccga agacagctca tgttatatcc cgccgttaac caccatcaaa caggattttc    960
gcctgctggg gcaaaccagc gtggaccgct tgctgcaact ctctcagggc caggcggtga   1020
agggcaatca gctgttgccc gtctcactgg tgaaaagaaa aaccaccctg cgcccaata    1080
cgcaaaccgc ctctccccgc gcgttggccg attcattaat gcagctggca cgacaggttt   1140
cccgactgga aagcgggcag tgagcgcaac gcaattaatg taagttagct cactcattag   1200
gcacaattct catgtttgac agcttatcat cgactgcacg gtgcaccaat gcttctggcg   1260
tcaggcagcc atcggaagct gtggtatggc tgtgcaggtc gtaaatcact gcataattcg   1320
tgtcgctcaa ggcgcactcc cgttctggat aatgtttttt gcgccgacat cataacggtt   1380
ctggcaaata ttctgaaatg agctgttgac aattaatcat cggctcgtat aatgtgtgga   1440
attgtgagcg gataacaatt tcacacagga acagccagt ccgtttaggt gttttcacga   1500
gcacttcacc aacaaggacc atagcatatg aaaatcgaag aaggtaaact ggtaatctgg   1560
attaacggcg ataaaggcta taacggtctc gctgaagtcg gtaagaaatt cgagaaagat   1620
accggaatta aagtcaccgt tgagcatccg gataaactgg aagagaaatt cccacaggtt   1680
gcggcaactg gcgatggccc tgacattatc ttctgggcac acgaccgctt tggtggctac   1740
gctcaatctg gcctgttggc tgaaatcacc ccggacaaag cgttccagga caagctgtat   1800
ccgtttacct gggatgccgt acgttacaac ggcaagctga ttgcttaccc gatcgctgtt   1860
gaagcgttat cgctgattta taacaaagat ctgctgccga acccgccaaa aacctgggaa   1920
gagatcccgg cgctggataa agaactgaaa gcgaaaggta agagcgcgct gatgttcaac   1980
ctgcaagaac cgtacttcac ctggccgctg attgctgctg acgggggtta tgcgttcaag   2040
tatgaaaacg gcaagtacga cattaaagac gtgggcgtgg ataacgctgg cgcgaaagcg   2100
ggtctgacct tcctggttga cctgattaaa acaaacaca tgaatgcaga caccgattac   2160
tccatcgcag aagctgcctt taataaaggc gaaacagcga tgaccatcaa cggcccgtgg   2220
gcatggtcca acatcgacac cagcaaagtg aattatggtg taacggtact gccgaccttc   2280
aagggtcaac catccaaacc gttcgttggc gtgctgagcg caggtattaa cgccgccagt   2340
ccgaacaaag agctggcaaa agagttcctc gaaaactatc tgctgactga tgaaggtctg   2400
gaagcggtta ataaagacaa accgctgggt gccgtagcgc tgaagtctta cgaggaagag   2460
ttggtgaaag atccgcggat tgccgccact atggaaaacg cccagaaagg tgaaatcatg   2520
ccgaacatcc cgcagatgtc cgctttctgg tatgccgtgc gtactgcggt gatcaacgcc   2580
gccagcggtc gtcagactgt cgatgaagcc ctgaaagacg cgcagactaa ttcgagctcg   2640
aacaacaaca caataacaa taacaacaac ctcgggatcg agggaaggat ttcagaattc   2700
tgtgcgacct cttctcaatt tactcagatt accgagcata attcccgtcg ttccgcaaac   2760
tatcagccaa acctgtggaa tttcgaattc ctgcaatccc tggagaacga cctgaaagtg   2820
gaaaagctgg aggagaaagc gaccaaactg gaggaagaag ttcgctgcat gatcaaccgt   2880
```

```
gtagacaccc agccgctgtc cctgctggag ctgatcgacg atgtgcagcg cctgggtctg    2940
acctacaaat ttgaaaaaga catcattaaa gccctggaaa acatcgtact gctggacgaa    3000
aacaaaaaga acaaatctga cctgcacgca accgctctgt cttccgtct gctgcgtcag    3060 cacggtttcg aggtttctca ggatgttttt gagcgtttca aggataaaga aggtggtttc    3120
agcggtgaac tgaaaggtga cgtccaaggc ctgctgagcc tgtatgaagc gtcttacctg    3180
ggtttcgagg gtgagaacct gctggaggag gcgcgtacct tttccatcac ccacctgaag    3240
aacaacctga agaaggcat taataccaag gttgcagaac aagtgagcca cgccctggaa    3300
ctgccatatc accagcgtct gcaccgtctg gaggcacgtt ggttcctgga taaatacgaa    3360
ccgaaagaac cgcatcacca gctgctgctg agctggcga gctggattt taacatggta    3420 cagaccctgc accagaaaga gctgcaagat ctgtcccgct ggtggaccga gatgggcctg    3480
gctagcaaac tggattttgt acgcgaccgc ctgatggaag tttatttctg ggcactgggt    3540
atggcgccag acccgcagtt tggtaatgt cgcaaagctg ttactaaaat gtttggtctg    3600
gtgacgatca tcgatgacgt gtatgacgtt tatggcactc tggacgaact gcaactgttc    3660
accgatgctg tagagcgctg ggacgttaac gctattaaca ccctgccgga ctatatgaaa    3720
ctgtgtttcc tggcactgta caacaccgtt aacgacacgt cctattctat tctgaaagag    3780
aaaggtcata caacctgtc ctatctgacg aaaagctggc gtgaactgtg caaagccttt    3840
ctgcaagagg cgaaatggtc caacaacaaa attatcccgg cttttctccaa gtacctggaa    3900 aacgccagcg tttcctcctc cggtgtagcg ctgctggcgc cgtcttactt ttccgtatgc    3960
cagcagcagg aagacatctc cgaccacgcg ctgcgttccc tgaccgactt ccatggtctg    4020
gtgcgttcta gctgcgttat cttccgcctg tgcaacgatc tggccaccct gcggcggag    4080 ctggaacgtg gcgagactac caattctatc attagctaca tgcacgaaaa cgatggtacc    4140
agcgaggaac aggcccgcga agaactgcgt aaactgatcg acgccgaatg gaaaaagatg    4200
aatcgtgaac gcgttagcga ctccaccctg ctgcctaaag cgttcatgga aatcgcagtt    4260
aacatggcac gtgtttccca ctgcacctac cagtatggcg atggtctggg tcgcccagac    4320
tacgcgactg aaaaccgcat caaactgctg ctgattgacc ctttcccgat taaccagctg    4380
atgtatgtct aagcttggca ctggccgtcg ttttacaacg tcgtgactgg gaaaaccctg    4440
gcgttaccca acttaatcgc cttgcagcac atccccctt cgccagctgg cgtaatagcg    4500
aagaggcccg caccgatcgc ccttcccaac agttgcgcag cctgaatggc gaatggcagc    4560
ttggctgttt tggcggatga gataagattt tcagcctgat acagattaaa tcagaacgca    4620
gaagcggtct gataaaacag aatttgcctg gcggcagtag cgcggtggtc ccacctgacc    4680
ccatgccgaa ctcagaagtg aaacgccgta gcgccgatgg tagtgtgggg tctccccatg    4740
cgagagtagg gaactgccag gcatcaaata aaacgaaagg ctcagtcgaa agactgggcc    4800 tttcgttta tctgttgttt gtcggtgaac gctctcctga gtaggacaaa tccgccggga    4860
gcggatttga cgttgcgaa gcaacggccc ggagggtggc gggcaggacg cccgccataa    4920
actgccaggc atcaaattaa gcagaaggcc atcctgacgg atggcctttt tgcgtttcta    4980
caaactcttt tgttattt ttctaaatac attcaaatat gtatccgctc atgagacaat    5040
aaccctgata aatgcttcaa taatattgaa aaaggaagag tatgagtatt caacatttcc    5100
gtgtcgccct tattcccttt tttgcggcat tttgccttcc tgttttgct cacccagaaa    5160 cgctggtgaa agtaaaagat gctgaagatc agttgggtgc acgagtgggt tacatcgaac    5220
tggatctcaa cagcggtaag atccttgaga gttttcgccc cgaagaacgt tctccaatga    5280
```

```
tgagcacttt taaagttctg ctatgtggcg cggtattatc ccgtgttgac gccgggcaag    5340
agcaactcgg tcgccgcata cactattctc agaatgactt ggttgagtac tcaccagtca    5400
cagaaaagca tcttacggat ggcatgacag taagagaatt atgcagtgct gccataacca    5460
tgagtgataa cactgcggcc aacttacttc tgacaacgat cggaggaccg aaggagctaa    5520 ccgcttttt gcacaacatg ggggatcatg taactcgcct tgatcgttgg aaccggagc     5580 tgaatgaagc cataccaaac gacgagcgtg acaccacgat gcctgtagca atggcaacaa    5640
cgttgcgcaa actattaact ggcgaactac ttactctagc ttcccggcaa caattaatag    5700
actggatgga ggcggataaa gttgcaggac cacttctgcg ctcggccctt ccggctggct    5760
ggtttattgc tgataaatct ggagccggtg agcgtgggtc tcgcggtatc attgcagcac    5820
tggggccaga tggtaagccc tcccgtatcg tagttatcta cacgacgggg agtcaggcaa    5880
ctatggatga acgaaataga cagatcgctg agataggtgc ctcactgatt aagcattggt    5940
aactgtcaga ccaagtttac tcatatatac tttagattga tttacccccgg ttgataatca   6000 gaaaagcccc aaaaacagga agattgtata agcaaatatt taaattgtaa acgttaatat    6060
tttgttaaaa ttcgcgttaa attttttgtta aatcagctca ttttttaacc aataggccga    6120
aatcggcaaa atcccttata aatcaaaaga atagaccgag atagggttga gtgttgttcc    6180
agtttggaac aagagtccac tattaaagaa cgtggactcc aacgtcaaag ggcgaaaaac    6240
cgtctatcag ggcgatggcc cactacgtga accatcaccc aaatcaagtt ttttggggtc    6300
gaggtgccgt aaagcactaa atcggaaccc taaagggagc cccgatttta gagcttgacg    6360
gggaaagccg gcgaacgtgg cgagaaagga agggaagaaa gcgaaaggag cgggcgctag    6420
ggcgctggca agtgtagcgg tcacgctgcg cgtaaccacc cacccgccg cgcttaatgc     6480 gccgctacag ggcgcgtaaa aggatctagg tgaagatcct ttttgataat ctcatgacca    6540
aaatccctta acgtgagttt tcgttccact gagcgtcaga ccccgtagaa aagatcaaag    6600
gatcttcttg agatcctttt tttctgcgcg taatctgctg cttgcaaaca aaaaaaccac    6660
cgctaccagc ggtggtttgt ttgccggatc aagagctacc aactctttttt ccgaaggtaa    6720 ctggcttcag cagagcgcag ataccaaata ctgtccttct agtgtagccg tagttaggcc    6780
accacttcaa gaactctgta gcaccgccta catacctcgc tctgctaatc ctgttaccag    6840
tggctgctgc cagtggcgat aagtcgtgtc ttaccgggtt ggactcaaga cgatagttac    6900
cggataaggc gcagcggtcg ggctgaacgg ggggttcgtg cacacagccc agcttggagc    6960
gaacgaccta caccgaactg agatacctac agcgtgagct atgagaaagc gccacgcttc    7020
ccgaagggag aaaggcggac aggtatccgg taagcggcag ggtcggaaca ggagagcgca    7080
cgagggagct tccaggggga aacgcctggt atctttatag tcctgtcggg tttcgccacc    7140
tctgacttga gcgtcgattt ttgtgatgct cgtcaggggg gcggagccta tggaaaaacg    7200
ccagcaacgc ggcctttta cggttcctgg ccttttgctg gccttttgct cacatgttct     7260
ttcctgcgtt atcccctgat tctgtggata accgtattac cgcctttgag tgagctgata    7320
ccgctcgccg cagccgaacg accgagcgca gcgagtcagt gagcgaggaa gcggaagagc    7380
gcctgatgcg gtattttctc cttacgcatc tgtgcggtat ttcacaccgc atatatggtg    7440
cactctcagt acaatctgct ctgatgccgc atagttaagc cagtatacac tccgctatcg    7500
ctacgtgact gggtcatggc tgcgccccga cacccgccaa cacccgctga cgcgccctga    7560
cgggcttgtc tgctcccggc atccgcttac agacaagctg tgaccgtctc cgggagctgc    7620
atgtgtcaga ggttttcacc gtcatcaccg aaacgcgcga ggcagctgcg gtaaagctca    7680
```

-continued

```
tcagcgtggt cgtgcagcga ttcacagatg tctgcctgtt catccgcgtc cagctcgttg     7740
agttctccca gaagcgttaa tgtctggctt ctgataaagc gggccatgtt aagggcggtt     7800
ttttcctgtt tggtcactga tgcctccgtg taagggggat ttctgttcat gggggtaatg     7860
ataccgatga aacagagagag gatgctcacg atacgggtta ctgatgatga acatgcccgg     7920
ttactggaac gttgtgaggg taaacaactg gcggtatgga tgcggcggga ccagagaaaa     7980
atcactcagg gtcaatgcca gcgcttcgtt aatacagatg taggtgttcc acagggtagc     8040
cagcagcatc ctgcgatgca gatccggaac ataatggtgc agggcgctga cttccgcgtt     8100
tccagacttt acgaaacacg gaaaccgaag accattcatg ttgttgctca ggtcgcagac     8160
gttttgcagc agcagtcgct tcacgttcgc tcgcgtatcg gtgattcatt ctgctaacca     8220
gtaaggcaac cccgccagcc tagccgggtc ctcaacgaca ggagcacgat catgcgcacc     8280
cgtggccagg acccaacgct gcccgaaatt                                      8310
```

<210> SEQ ID NO 158
<211> LENGTH: 560
<212> TYPE: PRT
<213> ORGANISM: Populus tremuloides

<400> SEQUENCE: 158

```
Met Arg Cys Ser Val Ser Thr Glu Asn Val Ser Phe Ser Glu Thr Glu
 1               5                  10                  15

Thr Glu Thr Arg Arg Ser Ala Asn Tyr Glu Pro Asn Ser Trp Asp Tyr
             20                  25                  30

Asp Tyr Leu Leu Ser Ser Asp Thr Asp Glu Ser Ile Glu Val His Lys
         35                  40                  45

Asp Lys Ala Lys Lys Leu Glu Ala Glu Val Arg Arg Glu Ile Asn Asn
     50                  55                  60

Glu Lys Ala Glu Phe Leu Thr Leu Leu Glu Leu Ile Asp Asn Val Gln
 65                  70                  75                  80

Arg Leu Gly Leu Gly Tyr Arg Phe Glu Ser Asp Ile Arg Arg Ala Leu
                 85                  90                  95

Asp Arg Phe Val Ser Ser Gly Gly Phe Asp Gly Val Thr Lys Thr Ser
            100                 105                 110

Leu His Gly Thr Ala Leu Ser Phe Arg Leu Leu Arg Gln His Gly Phe
        115                 120                 125

Glu Val Ser Gln Glu Ala Phe Ser Gly Phe Lys Asp Gln Asn Gly Asn
    130                 135                 140

Phe Leu Glu Asn Leu Lys Glu Asp Ile Lys Ala Ile Leu Ser Leu Tyr
145                 150                 155                 160

Glu Ala Ser Phe Leu Ala Leu Glu Gly Glu Asn Ile Leu Asp Glu Ala
                165                 170                 175

Lys Val Phe Ala Ile Ser His Leu Lys Glu Leu Ser Glu Glu Lys Ile
            180                 185                 190

Gly Lys Glu Leu Ala Glu Gln Val Ser His Ala Leu Glu Leu Pro Leu
        195                 200                 205

His Arg Arg Thr Gln Arg Leu Glu Ala Val Trp Ser Ile Glu Ala Tyr
    210                 215                 220

Arg Lys Lys Glu Asp Ala Asn Gln Val Leu Leu Glu Leu Ala Ile Leu
225                 230                 235                 240

Asp Tyr Asn Met Ile Gln Ser Val Tyr Gln Arg Asp Leu Arg Glu Thr
                245                 250                 255

Ser Arg Trp Trp Arg Arg Val Gly Leu Ala Thr Lys Leu His Phe Ala
            260                 265                 270
```

Arg Asp Arg Leu Ile Glu Ser Phe Tyr Trp Ala Val Gly Val Ala Phe
         275                 280                 285

Glu Pro Gln Tyr Ser Asp Cys Arg Asn Ser Val Ala Lys Met Phe Ser
         290                 295                 300

Phe Val Thr Ile Ile Asp Asp Ile Tyr Asp Val Tyr Gly Thr Leu Asp
305                 310                 315                 320

Glu Leu Glu Leu Phe Thr Asp Ala Val Glu Arg Trp Asp Val Asn Ala
                 325                 330                 335

Ile Asn Asp Leu Pro Asp Tyr Met Lys Leu Cys Phe Leu Ala Leu Tyr
             340                 345                 350

Asn Thr Ile Asn Glu Ile Ala Tyr Asp Asn Leu Lys Asp Lys Gly Glu
         355                 360                 365

Asn Ile Leu Pro Tyr Leu Thr Lys Ala Trp Ala Asp Leu Cys Asn Ala
     370                 375                 380

Phe Leu Gln Glu Ala Lys Trp Leu Tyr Asn Lys Ser Thr Pro Thr Phe
385                 390                 395                 400

Asp Asp Tyr Phe Gly Asn Ala Trp Lys Ser Ser Gly Pro Leu Gln
                 405                 410                 415

Leu Ile Phe Ala Tyr Phe Ala Val Val Gln Asn Ile Lys Lys Glu Glu
             420                 425                 430

Ile Glu Asn Leu Gln Lys Tyr His Asp Ile Ile Ser Arg Pro Ser His
         435                 440                 445

Ile Phe Arg Leu Cys Asn Asp Leu Ala Ser Ala Ser Ala Glu Ile Ala
     450                 455                 460

Arg Gly Glu Thr Ala Asn Ser Val Ser Cys Tyr Met Arg Thr Lys Gly
465                 470                 475                 480

Ile Ser Glu Glu Leu Ala Thr Glu Ser Val Met Asn Leu Ile Asp Glu
                 485                 490                 495

Thr Trp Lys Lys Met Asn Lys Gly Lys Leu Gly Gly Ser Leu Phe Ala
             500                 505                 510

Lys Pro Phe Val Glu Thr Ala Ile Asn Leu Ala Arg Gln Ser His Cys
         515                 520                 525

Thr Tyr His Asn Gly Asp Ala His Thr Ser Pro Asp Glu Leu Thr Arg
     530                 535                 540

Lys Arg Val Leu Ser Val Ile Thr Glu Pro Ile Leu Pro Phe Glu Arg
545                 550                 555                 560

<210> SEQ ID NO 159
<211> LENGTH: 6957
<212> TYPE: DNA
<213> ORGANISM: Artificial Sequence
<220> FEATURE:
<223> OTHER INFORMATION: Synthetic Construct

<400> SEQUENCE: 159
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tcccttagg       180 gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta agggattt tgccgatttc ggcctattgg ttaaaaatg agctgattta       420 acaaaaattt aacgcgaatt ttaacaaaat attaacgttt acaatttcag gtggcacttt     480

```
tcggggaaat gtgcgcggaa cccctatttg tttattttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa ataaggttta tcaagtgaga    780
aatcaccatg agtgacgact gaatccggtg agaatggcaa aagtttatgc atttcttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgtttccc gggatcgcag     1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gtttattgt tcatgaccaa aatcccttaa    1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata gtcgtgtct taccggggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc gaagggaga    1920
aaggcggaca ggtatccggt aagcggcagg gtcggaacag gagagcgcac gagggagctt   1980
ccaggggaa acgcctggta tctttatagt cctgtcgggt ttcgccacct ctgacttgag    2040
cgtcgatttt tgtgatgctc gtcagggggg cggagcctat ggaaaaacgc cagcaacgcg   2100
gcctttttac ggttcctggc cttttgctgg cctttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
```

```
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag gtggtttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatgcgttgt agcgtgtcca ccgaaaatgt    5100
gtctttctct gaaactgaaa ccgaaacgcg tcgttctgcg aactacgaac ctaacagctg    5160
ggactatgat tacctgctgt cctccgacac ggacgagtcc atcgaagtac acaaagacaa    5220
agcgaaaaag ctggaagccg aagttcgtcg cgagattaat aacgaaaaag cagaatttct    5280
```

```
gaccctgctg gaactgattg acaacgtcca gcgcctgggc ctgggttacc gtttcgagtc   5340
tgatatccgt cgtgcgctgg atcgcttcgt ttcctccggc ggcttcgatg gcgtaaccaa   5400
gacttccctg cacggtacgg cactgtcttt ccgtctgctg cgtcaacacg gttttgaggt   5460
ttctcaggaa gcgttcagcg gcttcaaaga ccaaaacggc aacttcctgg agaacctgaa   5520
ggaagatatc aaagctatcc tgagcctgta cgaggccagc ttcctggctc tggaaggcga   5580
aaacatcctg gacgaggcga aggttttcgc aatctctcat ctgaaagaac tgtctgaaga   5640
aaagatcggt aaagagctgg cagaacaggt gtcccatgca ctggaactgc cactgcatcg   5700
ccgtactcag cgtctggaag cagtatggtc tatcgaggcc taccgtaaaa aggaggacgc   5760
gaaccaggtt ctgctggagc tgcaattct ggattacaac atgatccagt ctgtatacca   5820
gcgtgatctg cgtgaaacgt cccgttggtg gcgtcgtgtg ggtctggcga ccaaactgca   5880
ctttgctcgt gaccgcctga ttgagagctt ctactgggcc gtgggtgtag cattcgaacc   5940
gcaatactcc gactgccgta actccgtcgc aaaaatgttt ctttcgtaa ccattatcga   6000 cgatatctac gatgtatacg gcaccctgga cgaactggag ctgtttactg atgcagttga   6060
gcgttgggac gtaaacgcca tcaacgacct gccggattac atgaaactgt gctttctggc   6120
tctgtataac actattaacg aaatcgccta cgacaacctg aaagataaag gtgagaacat   6180
cctgccgtat ctgaccaaag cctgggctga cctgtgcaac gctttcctgc aagaagccaa   6240
gtggctgtac aacaaatcta ctccgacctt tgacgactac ttcggcaacg catggaaatc   6300
ctcttctggc ccgctgcaac tgatcttcgc ttacttcgct gtcgtgcaga acattaaaaa   6360
ggaagagatc gaaaacctgc aaaaatacca tgacatcatc tctcgtcctt cccatatctt   6420
ccgtctgtgc aatgacctgg ctagcgcgtc tgcggaaatt gcgcgtggtg aaaccgcaaa   6480
tagcgtttct tgttacatgc gcactaaagg tatctccgaa gaactggcta ccgaaagcgt   6540
gatgaatctg atcgatgaaa cctggaaaaa gatgaacaag gaaaaactgg gtggtagcct   6600
gttcgcgaaa ccgttcgtgg aaaccgcgat caacctggca cgtcaatctc actgcactta   6660
tcataacggc gacgcgcata cctctccgga tgagctgacc cgcaaacgcg ttctgtctgt   6720
aatcactgaa ccgattctgc cgtttgaacg ctaaggatcc gaattcgagc tccgtcgaca   6780
agcttgcggc cgcactcgag caccaccacc accaccactg agatccggct gctaacaaag   6840
cccgaaagga agctgagttg gctgctgcca ccgctgagca ataactagca taaccccttg   6900
gggcctctaa acgggtcttg aggggttttt tgctgaaagg aggaactata tccggat      6957
```

<210> SEQ ID NO 160
<211> LENGTH: 560
<212> TYPE: PRT
<213> ORGANISM: Populus trichocarpa

<400> SEQUENCE: 160

Met Arg Cys Ser Val Ser Thr Glu Asn Val Ser Phe Thr Glu Thr Glu
1               5                   10                  15

Thr Glu Thr Arg Arg Ser Ala Asn Tyr Glu Pro Asn Ser Trp Asp Tyr
            20                  25                  30

Asp Tyr Leu Leu Ser Ser Asp Thr Asp Glu Ser Ile Glu Val Tyr Lys
        35                  40                  45

Asp Lys Ala Lys Lys Leu Glu Ala Glu Val Arg Arg Glu Ile Asn Asn
    50                  55                  60

Glu Lys Ala Glu Phe Leu Thr Leu Leu Glu Leu Ile Asp Asn Val Gln
65                  70                  75                  80

-continued

Arg Leu Gly Leu Gly Tyr Arg Phe Glu Ser Asp Ile Arg Arg Ala Leu
                85                  90                  95

Asp Arg Phe Val Ser Ser Gly Gly Phe Asp Ala Val Thr Lys Thr Ser
            100                 105                 110

Leu His Ala Thr Ala Leu Ser Phe Arg Leu Leu Arg Gln His Gly Phe
            115                 120                 125

Glu Val Ser Gln Glu Ala Phe Ser Gly Phe Lys Asp Gln Asn Gly Asn
        130                 135                 140

Phe Leu Glu Asn Leu Lys Glu Asp Ile Lys Ala Ile Leu Ser Leu Tyr
145                 150                 155                 160

Glu Ala Ser Phe Leu Ala Leu Glu Gly Glu Asn Ile Leu Asp Glu Ala
                165                 170                 175

Lys Val Phe Ala Ile Ser His Leu Lys Glu Leu Ser Glu Glu Lys Ile
            180                 185                 190

Gly Lys Asp Leu Ala Glu Gln Val Asn His Ala Leu Glu Leu Pro Leu
        195                 200                 205

His Arg Arg Thr Gln Arg Leu Glu Ala Val Leu Ser Ile Glu Ala Tyr
210                 215                 220

Arg Lys Lys Glu Asp Ala Asp Gln Val Leu Leu Glu Leu Ala Ile Leu
225                 230                 235                 240

Asp Tyr Asn Met Ile Gln Ser Val Tyr Gln Arg Asp Leu Arg Glu Thr
                245                 250                 255

Ser Arg Trp Trp Arg Arg Val Gly Leu Ala Thr Lys Leu His Phe Ala
            260                 265                 270

Arg Asp Arg Leu Ile Glu Ser Phe Tyr Trp Ala Val Gly Val Ala Phe
        275                 280                 285

Glu Pro Gln Tyr Ser Asp Cys Arg Asn Ser Val Ala Lys Met Phe Ser
290                 295                 300

Phe Val Thr Ile Ile Asp Asp Ile Tyr Asp Val Tyr Gly Thr Leu Asp
305                 310                 315                 320

Glu Leu Glu Leu Phe Thr Asn Ala Val Glu Arg Trp Asp Val Asn Ala
                325                 330                 335

Ile Asp Asp Leu Pro Asp Tyr Met Lys Leu Cys Phe Leu Ala Leu Tyr
            340                 345                 350

Asn Thr Ile Asn Glu Ile Ala Tyr Asp Asn Leu Lys Glu Lys Gly Glu
        355                 360                 365

Asn Ile Leu Pro Tyr Leu Thr Lys Ala Trp Ala Asp Leu Cys Asn Ala
370                 375                 380

Phe Leu Gln Glu Ala Lys Trp Leu Tyr Asn Lys Ser Thr Pro Thr Phe
385                 390                 395                 400

Asp Glu Tyr Phe Gly Asn Ala Trp Lys Ser Ser Gly Pro Leu Gln
                405                 410                 415

Leu Val Phe Ala Tyr Phe Ala Val Val Gln Asn Ile Lys Lys Glu Glu
            420                 425                 430

Ile Glu Asn Leu Gln Lys Tyr His Asp Ile Ile Ser Arg Pro Ser His
        435                 440                 445

Ile Phe Arg Leu Cys Asn Asp Leu Ala Ser Ala Ser Ala Glu Ile Ala
450                 455                 460

Arg Gly Glu Thr Ala Asn Ser Val Ser Cys Tyr Met Arg Thr Lys Gly
465                 470                 475                 480

Ile Ser Glu Glu Leu Ala Thr Glu Ser Val Met Asn Leu Ile Asp Glu
                485                 490                 495

Thr Trp Lys Lys Met Asn Lys Glu Lys Leu Gly Gly Ser Leu Phe Ala
            500                 505                 510

```
Lys Pro Phe Val Glu Thr Ala Ile Asn Leu Ala Arg Gln Ser His Cys
        515                 520                 525

Thr Tyr His Asn Gly Asp Ala His Thr Ser Pro Asp Glu Leu Thr Arg
    530                 535                 540

Lys Arg Val Leu Ser Val Ile Thr Glu Pro Ile Leu Pro Phe Glu Arg
545                 550                 555                 560
```

<210> SEQ ID NO 161
<211> LENGTH: 6963
<212> TYPE: DNA
<213> ORGANISM: Artificial Sequence
<220> FEATURE:
<223> OTHER INFORMATION: Synthetic Construct

<400> SEQUENCE: 161

| | | | | | | |
|---|---|---|---|---|---|---|
| tggcgaatgg | gacgcgccct | gtagcggcgc | attaagcgcg | gcgggtgtgg | tggttacgcg | 60 |
| cagcgtgacc | gctacacttg | ccagcgccct | agcgcccgct | cctttcgctt | tcttcccttc | 120 |
| ctttctcgcc | acgttcgccg | gctttccccg | tcaagctcta | aatcgggggc | tccctttagg | 180 |
| gttccgattt | agtgctttac | ggcacctcga | ccccaaaaaa | cttgattagg | gtgatggttc | 240 |
| acgtagtggg | ccatcgccct | gatagacggt | ttttcgccct | ttgacgttgg | agtccacgtt | 300 |
| ctttaatagt | ggactcttgt | tccaaactgg | aacaacactc | aaccctatct | cggtctattc | 360 |
| ttttgattta | taagggattt | tgccgatttc | ggcctattgg | ttaaaaaatg | agctgattta | 420 |
| acaaaaattt | aacgcgaatt | ttaacaaaat | attaacgttt | acaatttcag | gtggcacttt | 480 |
| tcggggaaat | gtgcgcggaa | ccctatttg | tttattttc | taaatacatt | caaatatgta | 540 |
| tccgctcatg | aattaattct | tagaaaaact | catcgagcat | caaatgaaac | tgcaatttat | 600 |
| tcatatcagg | attatcaata | ccatattttt | gaaaaagccg | tttctgtaat | gaaggagaaa | 660 |
| actcaccgag | gcagttccat | aggatggcaa | gatcctggta | tcggtctgcg | attccgactc | 720 |
| gtccaacatc | aatacaacct | attaatttcc | cctcgtcaaa | aataaggtta | tcaagtgaga | 780 |
| aatcaccatg | agtgacgact | gaatccggtg | agaatggcaa | aagtttatgc | atttcttcc | 840 |
| agacttgttc | aacaggccag | ccattacgct | cgtcatcaaa | atcactcgca | tcaaccaaac | 900 |
| cgttattcat | tcgtgattgc | gcctgagcga | gacgaaatac | gcgatcgctg | ttaaaaggac | 960 |
| aattacaaac | aggaatcgaa | tgcaaccggc | gcaggaacac | tgccagcgca | tcaacaatat | 1020 |
| tttcacctga | atcaggatat | tcttctaata | cctggaatgc | tgttttcccg | gggatcgcag | 1080 |
| tggtgagtaa | ccatgcatca | tcaggagtac | ggataaaatg | cttgatggtc | ggaagaggca | 1140 |
| taaattccgt | cagccagttt | agtctgacca | tctcatctgt | aacatcattg | gcaacgctac | 1200 |
| ctttgccatg | tttcagaaac | aactctggcg | catcgggctt | cccatacaat | cgatagattg | 1260 |
| tcgcacctga | ttgcccgaca | ttatcgcgag | cccatttata | cccatataaa | tcagcatcca | 1320 |
| tgttggaatt | taatcgcggc | ctagagcaag | acgtttcccg | ttgaatatgg | ctcataacac | 1380 |
| cccttgtatt | actgtttatg | taagcagaca | gttttattgt | tcatgaccaa | aatcccttaa | 1440 |
| cgtgagtttt | cgttccactg | agcgtcagac | cccgtagaaa | agatcaaagg | atcttcttga | 1500 |
| gatcctttt | ttctgcgcgt | aatctgctgc | ttgcaaacaa | aaaaccacc | gctaccagcg | 1560 |
| gtggtttgtt | tgccggatca | agagctacca | actctttttc | cgaaggtaac | tggcttcagc | 1620 |
| agagcgcaga | taccaaatac | tgtccttcta | gtgtagccgt | agttaggcca | ccacttcaag | 1680 |
| aactctgtag | caccgcctac | atacctcgct | ctgctaatcc | tgttaccagt | ggctgctgcc | 1740 |
| agtggcgata | agtcgtgtct | taccgggttg | gactcaagac | gatagttacc | ggataaggcg | 1800 |

-continued

```
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag agagcgcac gagggagctt    1980
ccaggggaa acgcctggta tctttatagt cctgtcgggt ttcgccacct ctgacttgag    2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt ttcctgtttt   2700
ggtcactgat gcctccgtgt aagggggatt tctgttcatg gggtaatga taccgatgaa    2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
```

```
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatgcatatg cgttgtagcg tgtccaccga    5100
aaatgtgtct ttcaccgaaa ctgaaaccga acgcgtcgt tctgcgaact acgaacctaa    5160
cagctgggac tatgattacc tgctgtcctc cgacacggac gagtccatcg aagtatacaa    5220
agacaaagcg aaaagctgg aagccgaagt tcgtcgcgag attaataacg aaaaagcaga    5280
atttctgacc ctgctggaac tgattgacaa cgtccagcgc ctgggcctgg gttaccgttt    5340
cgagtctgat atccgtcgtg cgctggatcg cttcgtttcc tccggcgggct tcgatgcggt    5400
aaccaagact tccctgcacg cgacggcact gtctttccgt ctgctgcgtc aacacggttt    5460
tgaggtttct caggaagcgt tcagcggctt caaagaccaa aacggcaact tcctggagaa    5520
cctgaaggaa gatatcaaag ctatcctgag cctgtacgag gccagcttcc tggctctgga    5580
aggcgaaaac atcctggacg aggcgaaggt tttcgcaatc tctcatctga agaactgtc    5640
tgaagaaaag atcggtaaag atctggcaga acaggtgaac catgcactgg aactgccact    5700
gcatcgccgt actcagcgtc tggaagcagt actgtctatc gaggcctacc gtaaaaagga    5760
ggacgcggat caggttctgc tggagctggc aattctggat tacaacatga tccagtctgt    5820
ataccagcgt gatctgcgtg aaacgtcccg ttggtggcgt cgtgtgggtc tggcgaccaa    5880
actgcacttt gctcgtgacc gcctgattga gagcttctac tgggcgtgg gtgtagcatt    5940
cgaaccgcaa tactccgact gccgtaactc cgtcgcaaaa atgttttctt tcgtaaccat    6000
tatcgacgat atctacgatg tatacggcac cctggacgaa ctggagctgt ttactaacgc    6060
agttgagcgt tgggacgtaa acgccatcga cgatctgccg gattacatga aactgtgctt    6120
tctggctctg tataacacta ttaacgaaat cgcctacgac aacctgaaag aaaaaggtga    6180
gaacatcctg ccgtatctga ccaaagcctg gctgacctg tgcaacgctt tcctgcaaga    6240
agccaagtgg ctgtacaaca atctactcc gacctttgac gaatacttcg gcaacgcatg    6300
gaaatcctct tctggcccgc tgcaactggt gttcgcttac ttcgctgtcg tgcagaacat    6360
taaaaaggaa gagatcgaaa acctgcaaaa ataccatgac atcatctctc gtccttccca    6420
tatcttccgt ctgtgcaatg acctggctag cgcgtctgcg gaaattgcgc gtggtgaaac    6480
cgcaaatagc gtttcttgtt acatgcgcac taaaggtatc tccgaagaac tggctaccga    6540
aagcgtgatg aatctgatcg atgaaacctg gaaaagatg aacaaggaaa aactgggtgg    6600
```

-continued

```
tagcctgttc gcgaaaccgt tcgtggaaac cgcgatcaac ctggcacgtc aatctcactg    6660
cacttatcat aacggcgacg cgcataccct ccggatgag ctgacccgca aacgcgttct    6720
gtctgtaatc actgaaccga ttctgccgtt tgaacgctaa ggatccgaat tcgagctccg    6780
tcgacaagct tgcggccgca ctcgagcacc accaccacca ccactgagat ccggctgcta    6840
acaaagcccg aaaggaagct gagttggctg ctgccaccgc tgagcaataa ctagcataac    6900
cccttggggc ctctaaacgg gtcttgaggg gttttttgct gaaaggagga actatatccg    6960
gat    6963
```

<210> SEQ ID NO 162
<211> LENGTH: 578
<212> TYPE: PRT
<213> ORGANISM: Artificial Sequence
<220> FEATURE:
<223> OTHER INFORMATION: Synthetic Construct

<400> SEQUENCE: 162

```
Met Arg Gly Ser His His His His His His Gly Met Ala Ser Met Thr
  1               5                  10                  15

Gly Gly Gln Gln Met Gly Arg Asp Leu Tyr Asp Asp Asp Lys Asp
             20                  25                  30

His Pro Phe Thr Met Arg Arg Ser Ala Asn Tyr Glu Pro Asn Ser Trp
         35                  40                  45

Asp Tyr Asp Tyr Leu Leu Ser Ser Asp Thr Asp Glu Ser Ile Glu Val
     50                  55                  60

Tyr Lys Asp Lys Ala Lys Lys Leu Glu Ala Glu Val Arg Arg Glu Ile
 65                  70                  75                  80

Asn Asn Glu Lys Ala Glu Phe Leu Thr Leu Leu Glu Leu Ile Asp Asn
                 85                  90                  95

Val Gln Arg Leu Gly Leu Gly Tyr Arg Phe Glu Ser Asp Ile Arg Gly
            100                 105                 110

Ala Leu Asp Arg Phe Val Ser Ser Gly Gly Phe Asp Ala Val Thr Lys
        115                 120                 125

Thr Ser Leu His Gly Thr Ala Leu Ser Phe Arg Leu Leu Arg Gln His
    130                 135                 140

Gly Phe Glu Val Ser Gln Glu Ala Phe Ser Gly Phe Lys Asp Gln Asn
145                 150                 155                 160

Gly Asn Phe Leu Glu Asn Leu Lys Glu Asp Ile Lys Ala Ile Leu Ser
                165                 170                 175

Leu Tyr Glu Ala Ser Phe Leu Ala Leu Glu Gly Glu Asn Ile Leu Asp
            180                 185                 190

Glu Ala Lys Val Phe Ala Ile Ser His Leu Lys Glu Leu Ser Glu Glu
        195                 200                 205

Lys Ile Gly Lys Glu Leu Ala Glu Gln Val Asn His Ala Leu Glu Leu
    210                 215                 220

Pro Leu His Arg Arg Thr Gln Arg Leu Glu Ala Val Trp Ser Ile Glu
225                 230                 235                 240

Ala Tyr Arg Lys Lys Glu Asp Ala Asn Gln Val Leu Leu Glu Leu Ala
                245                 250                 255

Ile Leu Asp Tyr Asn Met Ile Gln Ser Val Tyr Gln Arg Asp Leu Arg
            260                 265                 270

Glu Thr Ser Arg Trp Trp Arg Arg Val Gly Leu Ala Thr Lys Leu His
        275                 280                 285

Phe Ala Arg Asp Arg Leu Ile Glu Ser Phe Tyr Trp Ala Val Gly Val
    290                 295                 300
```

```
Ala Phe Glu Pro Gln Tyr Ser Asp Cys Arg Asn Ser Val Ala Lys Met
305                 310                 315                 320

Phe Ser Phe Val Thr Ile Ile Asp Asp Ile Tyr Asp Val Tyr Gly Thr
                325                 330                 335

Leu Asp Glu Leu Glu Leu Phe Thr Asp Ala Val Glu Arg Trp Asp Val
            340                 345                 350

Asn Ala Ile Asn Asp Leu Pro Asp Tyr Met Lys Leu Cys Phe Leu Ala
        355                 360                 365

Leu Tyr Asn Thr Ile Asn Glu Ile Ala Tyr Asp Asn Leu Lys Asp Lys
370                 375                 380

Gly Glu Asn Ile Leu Pro Tyr Leu Thr Lys Ala Trp Ala Asp Leu Cys
385                 390                 395                 400

Asn Ala Phe Leu Gln Glu Ala Lys Trp Leu Tyr Asn Lys Ser Thr Pro
                405                 410                 415

Thr Phe Asp Asp Tyr Phe Gly Asn Ala Trp Lys Ser Ser Gly Pro
            420                 425                 430

Leu Gln Leu Val Phe Ala Tyr Phe Ala Val Val Gln Asn Ile Lys Lys
        435                 440                 445

Glu Glu Ile Glu Asn Leu Gln Lys Tyr His Asp Thr Ile Ser Arg Pro
450                 455                 460

Ser His Ile Phe Arg Leu Cys Asn Asp Leu Ala Ser Ala Ser Ala Glu
465                 470                 475                 480

Ile Ala Arg Gly Glu Thr Ala Asn Ser Val Ser Cys Tyr Met Arg Thr
                485                 490                 495

Lys Gly Ile Ser Glu Glu Leu Ala Thr Glu Ser Val Met Asn Leu Ile
            500                 505                 510

Asp Glu Thr Trp Lys Lys Met Asn Lys Glu Lys Leu Gly Gly Ser Leu
        515                 520                 525

Phe Ala Lys Pro Phe Val Glu Thr Ala Ile Asn Leu Ala Arg Gln Ser
530                 535                 540

His Cys Thr Tyr His Asn Gly Asp Ala His Thr Ser Pro Asp Glu Leu
545                 550                 555                 560

Thr Arg Lys Arg Val Leu Ser Val Ile Thr Glu Pro Ile Leu Pro Phe
                565                 570                 575

Glu Arg

<210> SEQ ID NO 163
<211> LENGTH: 7370
<212> TYPE: DNA
<213> ORGANISM: Artificial Sequence
<220> FEATURE:
<223> OTHER INFORMATION: Synthetic Construct

<400> SEQUENCE: 163
aagggcgagc tcaacgatcc ggctgctaac aaagcccgaa aggaagctga gttggctgct      60
gccaccgctg agcaataact agcataaccc cttggggcct ctaaacgggt cttgaggagt     120 ttttgctga aggaggaac tatatccgga tatcccgcaa gaggcccggc agtaccggca      180
taaccaagcc tatgcctaca gcatccaggg tgacggtgcc gaggatgacg atgagcgcat     240
tgttagattt catacacggt gcctgactgc gttagcaatt taactgtgat aaactaccgc     300
attaaagctt atcgatgata agctgtcaaa catgagaatt aattcttgaa gacgaaaggg     360
cctcgtgata cgcctatttt tataggttaa tgtcatgata ataatggttt cttagacgtc     420
aggtggcact tttcggggaa atgtgcgcgg aacccctatt tgtttatttt tctaaataca     480
```

-continued

```
ttcaaatatg tatccgctca tgagacaata accctgataa atgcttcaat aatattgaaa    540
aaggaagagt atgattgaac aagatggatt gcacgcaggt tctccggccg cttgggtgga    600
gaggctattc ggctatgact gggcacaact gacaatcggc tgctctgatg ccgccgtgtt    660
ccggctgtca gcgcagggc gcccggttct ttttgtcaag accgacctgt ccggtgccct     720
gaatgaactg caggacgagg cagcgcggct atcgtggctg gccacgacgg gcgttccttg    780
cgcagctgtg ctcgacgttg tcactgaagc gggaagggac tggctgctat tgggcgaagt    840
gccggggcag gatctcctgt catctcacct tgctcctgcc gagaaagtat ccatcatggc    900
tgatgcaatg cggcggctgc atacgcttga tccggctacc tgcccattcg accaccaagc    960
gaaacatcgc atcgagcggg cacgtactcg gatggaagcc ggtcttgtcg atcaggatga   1020
tctggacgaa gagcatcagg ggctcgcgcc agccgaactg ttcgccaggc tcaaggcgcg   1080
catgcccgac ggcgaggatc tcgtcgtgac acatggcgat gcctgcttgc cgaatatcat   1140
ggtgaaaaat ggccgctttt ctggattcat cgactgtggc cggctgggtg tggcggaccg   1200
ctatcaggac atagcgttgg ctacccgtga tattgctgaa gagcttggcg gcgaatgggc   1260
tgaccgcttc ctcgtgcttt acggtatcgc cgctcccgat tcgcagcgca tcgccttcta   1320
tcgccttctt gacgagttct tctgagcggg actctggggt tcgaaatgac cgaccaagcg   1380
acgcctaact gtcagaccaa gtttactcat atatacttta gattgattta aaacttcatt   1440
tttaatttaa aaggatctag gtgaagatcc ttttgataa tctcatgacc aaaatccctt   1500
aacgtgagtt ttcgttccac tgagcgtcag accccgtaga aaagatcaaa ggatcttctt   1560
gagatccttt ttttctgcgc gtaatctgct gcttgcaaac aaaaaaacca ccgctaccag   1620
cggtggtttg tttgccggat caagagctac caactctttt tccgaaggta actggcttca   1680
gcagagcgca gataccaaat actgtccttc tagtgtagcc gtagttaggc caccacttca   1740
agaactctgt agcaccgcct acatacctcg ctctgctaat cctgttacca gtggctgctg   1800
ccagtggcga taagtcgtgt cttaccgggt tggactcaag acgatagtta ccggataagg   1860
cgcagcggtc gggctgaacg gggggttcgt gcacacagcc cagcttggag cgaacgacct   1920
acaccgaact gagatacctta cagcgtgagc tatgagaaag cgccacgctt cccgaaggga   1980
gaaaggcgga caggtatccg gtaagcggca gggtcggaac aggagagcgc acgagggagc   2040
ttccagggg aaacgcctgg tatctttata gtcctgtcgg gtttcgccac ctctgacttg   2100
agcgtcgatt tttgtgatgc tcgtcagggg ggcggagcct atggaaaaac gccagcaacg   2160
cggccttttt acgttcctg gccttttgct ggccttttgc tcacatgttc tttcctgcgt   2220
tatcccctga ttctgtggat aaccgtatta ccgcctttga gtgagctgat accgctcgcc   2280
gcagccgaac gaccgagcgc agcgagtcag tgagcgagga agcggaagag cgcctgatgc   2340
ggtattttct ccttacgcat ctgtgcggta tttcacaccg caatggtgca ctctcagtac   2400
aatctgctct gatgccgcat agttaagcca gtatacactc cgctatcgct acgtgactgg   2460
gtcatggctg cgccccgaca cccgccaaca cccgctgacg cgccctgacg ggcttgtctg   2520
ctcccggcat ccgcttacag acaagctgtg accgtctccg ggagctgcat gtgtcagagg   2580
ttttcaccgt catcaccgaa acgcgcgagg cagctgcggt aaagctcatc agcgtggtcg   2640
tgaagcgatt cacagatgtc tgcctgttca tccgcgtcca gctcgttgag tttctccaga   2700
agcgttaatg tctggcttct gataaagcgg ccatgttaa gggcggtttt tcctgtttg    2760
gtcactgatg cctccgtgta agggggattt ctgttcatgg gggtaatgat accgatgaaa   2820
cgagagagga tgctcacgat acgggttact gatgatgaac atgcccggtt actggaacgt   2880
```

```
tgtgagggta aacaactggc ggtatggatg cggcgggacc agagaaaaat cactcagggt    2940
caatgccagc gcttcgttaa tacagatgta ggtgttccac agggtagcca gcagcatcct    3000
gcgatgcaga tccggaacat aatggtgcag ggcgctgact tccgcgtttc cagactttac    3060
gaaacacgga aaccgaagac cattcatgtt gttgctcagg tcgcagacgt tttgcagcag    3120
cagtcgcttc acgttcgctc gcgtatcggt gattcattct gctaaccagt aaggcaaccc    3180
cgccagccta gccgggtcct caacgacagg agcacgatca tgcgcacccg tggccaggac    3240
ccaacgctgc ccgagatgcg ccgcgtgcgg ctgctggaga tggcggacgc gatggatatg    3300
ttctgccaag ggttggtttg cgcattcaca gttctccgca agaattgatt ggctccaatt    3360
cttggagtgg tgaatccgtt agcgaggtgc cgccggcttc cattcaggtc gaggtggccc    3420
ggctccatgc accgcgacgc aacgcgggga ggcagacaag gtatagggcg cgcctacaa    3480 tccatgccaa cccgttccat gtgctcgccg aggcggcata aatcgccgtg acgatcagcg    3540
gtccaatgat cgaagttagg ctggtaagag ccgcgagcga tccttgaagc tgtccctgat    3600
ggtcgtcatc tacctgcctg acagcatgg cctgcaacgc gggcatcccg atgccgccgg    3660
aagcgagaag aatcataatg gggaaggcca tccagcctcg cgtcgcgaac gccagcaaga    3720
cgtagcccag cgcgtcggcc gccatgccgg cgataatggc ctgcttctcg ccgaaacgtt    3780
tggtggcggg accagtgacg aaggcttgag cgagggcgtg caagattccg aataccgcaa    3840
gcgacaggcc gatcatcgtc gcgctccagc gaaagcggtc ctcgccgaaa atgacccaga    3900
gcgctgccgg cacctgtcct acgagttgca tgataaagaa gacagtcata agtgcggcga    3960
cgatagtcat gccccgcgcc caccggaagg agctgactgg gttgaaggct ctcaagggca    4020
tcggtcgaga tccggtgcc taatgagtga gctaacttac attaattgcg ttgcgctcac    4080
tgcccgcttt ccagtcggga aacctgtcgt gccagctgca ttaatgaatc ggccaacgcg    4140
cggggagagg cggtttgcgt attgggcgcc agggtggttt ttcttttcac cagtgagacg    4200
ggcaacagct gattgccctt caccgcctgg ccctgagaga gttgcagcaa gcggtccacg    4260
ctggtttgcc ccagcaggcg aaaatcctgt ttgatggtgg ttaacggcgg gatataacat    4320
gagctgtctt cggtatcgtc gtatcccact accgagatat ccgcaccaac gcgcagcccg    4380
gactcggtaa tggcgcgcat tgcgcccagc gccatctgat cgttggcaac cagcatcgca    4440
gtgggaacga tgccctcatt cagcatttgc atggtttgtt gaaaaccgga catggcactc    4500
cagtcgcctt cccgttccgc tatcggctga atttgattgc gagtgagata tttatgccag    4560
ccagccagac gcagacgcgc cgagacagaa cttaatgggc ccgctaacag cgcgatttgc    4620
tggtgaccca atgcgaccag atgctccacg cccagtcgcg taccgtcttc atgggagaaa    4680
ataatactgt tgatgggtgt ctggtcagag acatcaagaa ataacgccgg aacattagtg    4740
caggcagctt ccacagcaat ggcatcctgg tcatccagcg atagttaat gatcagccca    4800 ctgacgcgtt gcgcgagaag attgtgcacc gccgctttac aggcttcgac gccgcttcgt    4860
tctaccatcg acaccaccac gctggcaccc agttgatcgg cgcgagattt aatcgccgcg    4920
acaatttgcg acgcgcgtg cagggccaga ctggaggtgg caacgccaat cagcaacgac    4980
tgtttgcccg ccagttgttg tgccacgcgg ttgggaatgt aattcagctc cgccatcgcc    5040
gcttccactt tttcccgcgt tttcgcagaa acgtggctgg cctggttcac cacgcgggaa    5100
acggtctgat aagagacacc ggcatactct gcgacatcgt ataacgttac tggtttcaca    5160
ttcaccaccc tgaattgact ctcttccggg gcgtatcatg ccataccgcg aaaggttttg    5220
cgccattcga tggtgtccgg gatctcgacg ctctcccctta tgcgactcct gcattaggaa    5280
```

```
gcagcccagt agtaggttga ggccgttgag caccgccgcc gcaaggaatg gtgcatgcaa   5340
ggagatggcg cccaacagtc ccccggccac ggggcctgcc accatacccca cgccgaaaca   5400 agcgctcatg agcccgaagt ggcgagcccg atcttcccca tcggtgatgt cggcgatata   5460
ggcgccagca accgcacctg tggcgccggt gatgccggcc acgatgcgtc cggcgtagag   5520
gatcgagatc tcgatcccgc gaaattaata cgactcacta tagggaatt gtgagcggat   5580 aacaattccc ctctagaaat aattttgttt aactttaaga aggagatata catatgcggg   5640
gttctcatca tcatcatcat catggtatgg ctagcatgac tggtggacag caaatgggtc   5700
gggatctgta cgacgatgac gataaggatc atcccttcac catgcgtcgt tctgcgaact   5760
acgaacctaa cagctgggac tatgattacc tgctgtcctc cgacacggac gagtccatcg   5820
aagtatacaa agacaaagcg aaaaagctgg aagccgaagt tcgtcgcgag attaataacg   5880
aaaaagcaga atttctgacc ctgctggaac tgattgacaa cgtccagcgc ctgggcctgg   5940
gttaccgttt cgagtctgat atccgtggtg cgctggatcg cttcgtttcc tccggcggct   6000
tcgatgcggt aaccaagact tccctgcacg gtacggcact gtcttttcgt ctgctgcgtc   6060
aacacggttt tgaggtttct caggaagcgt tcagcggctt caaagaccaa aacggcaact   6120
tcctggagaa cctgaaggaa gatatcaaag ctatcctgag cctgtacgag gccagcttcc   6180
tggctctgga aggcgaaaac atcctggacg aggcgaaggt tttcgcaatc tctcatctga   6240
aagaactgtc tgaagaaaag atcggtaaag agctggcaga acaggtgaac catgcactgg   6300
aactgccact gcatcgccgt actcagcgtc tggaagcagt atggtctatc gaggcctacc   6360
gtaaaaagga ggacgcgaat caggttctgc tggagctggc aattctggat acaacatga   6420 tccagtctgt ataccagcgt gatctgcgtg aaacgtcccg ttggtggcgt cgtgtgggtc   6480
tggcgaccaa actgcacttt gctcgtgacc gcctgattga gagcttctac tgggccgtgg   6540
gtgtagcatt cgaaccgcaa tactccgact gccgtaactc cgtcgcaaaa atgttttctt   6600
tcgtaaccat tatcgacgat atctacgatg tatacggcac cctggacgaa ctggagctgt   6660
ttactgatgc agttgagcgt tgggacgtaa acgccatcaa cgacctgccg gattacatga   6720
aactgtgctt tctggctctg tataacacta ttaacgaaat cgcctacgac aacctgaaag   6780
ataaaggtga aacatcctg ccgtatctga ccaaagcctg gctgacctg tgcaacgctt   6840 tcctgcaaga agccaagtgg ctgtacaaca atctactcc gacctttgac gactacttcg   6900
gcaacgcatg gaaatcctct tctggcccgc tgcaactggt gttcgcttac ttcgctgtcg   6960
tgcagaacat taaaaaggaa gagatcgaaa acctgcaaaa ataccatgac accatctctc   7020
gtccttccca tatcttccgt ctgtgcaatg acctggctag cgcgtctgcg gaaattgcgc   7080
gtggtgaaac cgcaaatagc gtttcttgtt acatgcgcac taaggtatc tccgaagaac   7140 tggctaccga aagcgtgatg aatctgatcg atgaaacctg gaaaaagatg aacaaggaaa   7200
aactgggtgg tagcctgttc gcgaaaccgt tcgtggaaac cgcgatcaac ctggcacgtc   7260
aatctcactg cacttatcat aacggcgacg cgcataccctc tccggatgag ctgacccgca   7320
aacgcgttct gtctgtaatc actgaaccga ttctgccgtt tgaacgctaa              7370
```

<210> SEQ ID NO 164
<211> LENGTH: 578
<212> TYPE: PRT
<213> ORGANISM: Artificial Sequence
<220> FEATURE:
<223> OTHER INFORMATION: Synthetic Construct

<400> SEQUENCE: 164

-continued

```
Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

His Pro Phe Thr Met Arg Arg Ser Ala Asn Tyr Glu Pro Asn Ser Trp
        35                  40                  45

Asp Tyr Asp Tyr Leu Leu Ser Ser Asp Thr Asp Glu Ser Ile Glu Val
    50                  55                  60

His Lys Asp Lys Ala Lys Lys Leu Glu Ala Glu Val Arg Arg Glu Ile
65                  70                  75                  80

Asn Asn Glu Lys Ala Glu Phe Leu Thr Leu Leu Glu Leu Ile Asp Asn
                85                  90                  95

Val Gln Arg Leu Gly Leu Gly Tyr Arg Phe Glu Ser Asp Ile Arg Arg
            100                 105                 110

Ala Leu Asp Arg Phe Val Ser Ser Gly Gly Phe Asp Gly Val Thr Lys
            115                 120                 125

Thr Ser Leu His Gly Thr Ala Leu Ser Phe Arg Leu Leu Arg Gln His
    130                 135                 140

Gly Phe Glu Val Ser Gln Glu Ala Phe Ser Gly Phe Lys Asp Gln Asn
145                 150                 155                 160

Gly Asn Phe Leu Glu Asn Leu Lys Glu Asp Ile Lys Ala Ile Leu Ser
                165                 170                 175

Leu Tyr Glu Ala Ser Phe Leu Ala Leu Glu Gly Glu Asn Ile Leu Asp
            180                 185                 190

Glu Ala Lys Val Phe Ala Ile Ser His Leu Lys Glu Leu Ser Glu Glu
            195                 200                 205

Lys Ile Gly Lys Glu Leu Ala Glu Gln Val Ser His Ala Leu Glu Leu
210                 215                 220

Pro Leu His Arg Arg Thr Gln Arg Leu Glu Ala Val Trp Ser Ile Glu
225                 230                 235                 240

Ala Tyr Arg Lys Lys Glu Asp Ala Asn Gln Val Leu Leu Glu Leu Ala
                245                 250                 255

Ile Leu Asp Tyr Asn Met Ile Gln Ser Val Tyr Gln Arg Asp Leu Arg
            260                 265                 270

Glu Thr Ser Arg Trp Trp Arg Arg Val Gly Leu Ala Thr Lys Leu His
            275                 280                 285

Phe Ala Arg Asp Arg Leu Ile Glu Ser Phe Tyr Trp Ala Val Gly Val
            290                 295                 300

Ala Phe Glu Pro Gln Tyr Ser Asp Cys Arg Asn Ser Val Ala Lys Met
305                 310                 315                 320

Phe Ser Phe Val Thr Ile Ile Asp Asp Ile Tyr Asp Val Tyr Gly Thr
                325                 330                 335

Leu Asp Glu Leu Glu Leu Phe Thr Asp Ala Val Glu Arg Trp Asp Val
            340                 345                 350

Asn Ala Ile Asn Asp Leu Pro Asp Tyr Met Lys Leu Cys Phe Leu Ala
            355                 360                 365

Leu Tyr Asn Thr Ile Asn Glu Ile Ala Tyr Asp Asn Leu Lys Asp Lys
    370                 375                 380

Gly Glu Asn Ile Leu Pro Tyr Leu Thr Lys Ala Trp Ala Asp Leu Cys
385                 390                 395                 400

Asn Ala Phe Leu Gln Glu Ala Lys Trp Leu Tyr Asn Lys Ser Thr Pro
                405                 410                 415

Thr Phe Asp Asp Tyr Phe Gly Asn Ala Trp Lys Ser Ser Ser Gly Pro
            420                 425                 430
```

```
Leu Gln Leu Ile Phe Ala Tyr Phe Ala Val Val Gln Asn Ile Lys Lys
            435                 440                 445

Glu Glu Ile Glu Asn Leu Gln Lys Tyr His Asp Ile Ile Ser Arg Pro
        450                 455                 460

Ser His Ile Phe Arg Leu Cys Asn Asp Leu Ala Ser Ala Ser Ala Glu
465                 470                 475                 480

Ile Ala Arg Gly Glu Thr Ala Asn Ser Val Ser Cys Tyr Met Arg Thr
                485                 490                 495

Lys Gly Ile Ser Glu Glu Leu Ala Thr Glu Ser Val Met Asn Leu Ile
            500                 505                 510

Asp Glu Thr Trp Lys Lys Met Asn Lys Glu Lys Leu Gly Gly Ser Leu
        515                 520                 525

Phe Ala Lys Pro Phe Val Glu Thr Ala Ile Asn Leu Ala Arg Gln Ser
    530                 535                 540

His Cys Thr Tyr His Asn Gly Asp Ala His Thr Ser Pro Asp Glu Leu
545                 550                 555                 560

Thr Arg Lys Arg Val Leu Ser Val Ile Thr Glu Pro Ile Leu Pro Phe
                565                 570                 575

Glu Arg

<210> SEQ ID NO 165
<211> LENGTH: 7370
<212> TYPE: DNA
<213> ORGANISM: Artificial Sequence
<220> FEATURE:
<223> OTHER INFORMATION: Synthetic Construct

<400> SEQUENCE: 165
cgtcgttctg cgaactacga acctaacagc tgggactatg attacctgct gtcctccgac    60
acggacgagt ccatcgaagt acacaaagac aaagcgaaaa agctggaagc cgaagttcgt   120
cgcgagatta ataacgaaaa agcagaattt ctgacccctgc tggaactgat tgacaacgtc   180
cagcgcctgg gcctgggtta ccgtttcgag tctgatatcc gtcgtgcgct ggatcgcttc   240
gtttcctccg gcggcttcga tggcgtaacc aagacttccc tgcacggtac ggcactgtct   300
ttccgtctgc tgcgtcaaca cggttttgag gtttctcagg aagcgttcag cggcttcaaa   360
gaccaaaacg gcaacttcct ggagaacctg aggaagata tcaaagctat cctgagcctg   420
tacgaggcca gcttcctggc tctggaaggc gaaaacatcc tggacgaggc gaaggttttc   480
gcaatctctc atctgaaaga actgtctgaa gaaaagatcg gtaaagagct ggcagaacag   540
gtgtcccatg cactggaact gccactgcat cgccgtactc agcgtctgga agcagtatgg   600
tctatcgagg cctaccgtaa aaaggaggac gcgaaccagg ttctgctgga gctggcaatt   660
ctggattaca acatgatcca gtctgtatac cagcgtgatc tgcgtgaaac gtcccgttgg   720
tggcgtcgtg tgggtctggc gaccaaactg cactttgctc gtgaccgcct gattgagagc   780
ttctactggg ccgtgggtgt agcattcgaa ccgcaatact ccgactgccg taactccgtc   840
gcaaaaatgt tttctttcgt aaccattatc gacgatatct acgatgtata cggcaccctg   900
gacgaactgg agctgtttac tgatgcagtt gagcgttggg acgtaaacgc catcaacgac   960
ctgccggatt acatgaaact gtgctttctg gctctgtata acactattaa cgaaatcgcc  1020
tacgacaacc tgaaagataa aggtgagaac atcctgccgt atctgaccaa agcctgggct  1080
gacctgtgca acgctttcct gcaagaagcc aagtggctgt acaacaaatc tactccgacc  1140
tttgacgact acttcggcaa cgcatggaaa tcctcttctg gcccgctgca actgatcttc  1200
```

```
gcttacttcg ctgtcgtgca gaacattaaa aaggaagaga tcgaaaacct gcaaaaatac    1260
catgacatca tctctcgtcc ttcccatatc ttccgtctgt gcaatgacct ggctagcgcg    1320
tctgcggaaa ttgcgcgtgg tgaaaccgca aatagcgttt cttgttacat gcgcactaaa    1380
ggtatctccg aagaactggc taccgaaagc gtgatgaatc tgatcgatga aacctggaaa    1440
aagatgaaca aggaaaaact gggtggtagc ctgttcgcga aaccgttcgt ggaaaccgcg    1500
atcaacctgg cacgtcaatc tcactgcact tatcataacg cgacgcgca tacctctccg     1560
gatgagctga cccgcaaacg cgttctgtct gtaatcactg aaccgattct gccgtttgaa    1620
cgctaaaagg gcgagctcaa cgatccggct gctaacaaag cccgaaagga agctgagttg    1680
gctgctgcca ccgctgagca ataactagca taaccccttg gggcctctaa acgggtcttg    1740
aggagttttt tgctgaaagg aggaactata tccggatatc ccgcaagagg cccggcagta    1800
ccggcataac caagcctatg cctacagcat ccagggtgac ggtgccgagg atgacgatga    1860
gcgcattgtt agatttcata cacggtgcct gactgcgtta gcaatttaac tgtgataaac    1920
taccgcatta aagcttatcg atgataagct gtcaaacatg agaattaatt cttgaagacg    1980
aaagggcctc gtgatacgcc tatttttata ggttaatgtc atgataataa tggtttctta    2040
gacgtcaggt ggcacttttc ggggaaatgt gcgcggaacc cctatttgtt tatttttcta    2100
aatacattca aatatgtatc cgctcatgag acaataaccc tgataaatgc ttcaataata    2160
ttgaaaaagg aagagtatga ttaacaaga tggattgcac gcaggttctc cggccgcttg     2220
ggtggagagg ctattcggct atgactgggc acaactgaca atcggctgct ctgatgccgc    2280
cgtgttccgg ctgtcagcgc aggggcgccc ggttcttttt gtcaagaccg acctgtccgg    2340
tgccctgaat gaactgcagg acgaggcagc gcggctatcg tggctggcca cgacgggcgt    2400
tccttgcgca gctgtgctcg acgttgtcac tgaagcggga agggactggc tgctattggg    2460
cgaagtgccg gggcaggatc tcctgtcatc tcaccttgct cctgccgaga agtatccat     2520
catggctgat gcaatgcggc ggctgcatac gcttgatccg gctacctgcc cattcgacca    2580
ccaagcgaaa catcgcatcg agcgggcacg tactcggatg aagccggtc ttgtcgatca     2640
ggatgatctg gacgaagagc atcaggggct cgcgccagcc gaactgttcg ccaggctcaa    2700
ggcgcgcatg cccgacggcg aggatctcgt cgtgacacat ggcgatgcct gcttgccgaa    2760
tatcatggtg gaaaatggcc gcttttctgg attcatcgac tgtggccggc tgggtgtggc    2820
ggaccgctat caggacatag cgttggctac ccgtgatatt gctgaagagc ttggcggcga    2880
atgggctgac cgcttcctcg tgctttacgg tatcgccgct cccgattcgc agcgcatcgc    2940
cttctatcgc cttcttgacg agttcttctg agcgggactc tggggttcga atgaccgac     3000
caagcgacgc ctaactgtca gaccaagttt actcatatat actttagatt gatttaaaac    3060
ttcattttta atttaaaagg atctaggtga agatccttt tgataatctc atgaccaaaa     3120
tcccttaacg tgagttttcg ttccactgag cgtcagaccc cgtagaaaag atcaaaggat    3180
cttcttgaga tccttttttt ctgcgcgtaa tctgctgctt gcaaacaaaa aaaccaccgc    3240
taccagcggt ggtttgtttg ccggatcaag agctaccaac tctttttccg aaggtaactg    3300
gcttcagcag agcgcagata ccaaatactg tccttctagt gtagccgtag ttaggccacc    3360
acttcaagaa ctctgtagca ccgcctacat acctcgctct gctaatcctg ttaccagtgg    3420
ctgctgccag tggcgataag tcgtgtctta ccgggttgga ctcaagacga tagttaccgg    3480
ataaggcgca gcggtcgggc tgaacggggg gttcgtgcac acagcccagc ttggagcgaa    3540
cgacctacac cgaactgaga tacctacagc gtgagctatg agaaagcgcc acgcttcccg    3600
```

```
aagggagaaa ggcggacagg tatccggtaa gcggcagggt cggaacagga gagcgcacga   3660
gggagcttcc aggggggaaac gcctggtatc tttatagtcc tgtcgggttt cgccacctct   3720
gacttgagcg tcgatttttg tgatgctcgt caggggggcg gagcctatgg aaaaacgcca   3780
gcaacgcggc cttttttacgg ttcctggcct tttgctggcc ttttgctcac atgttctttc   3840
ctgcgttatc ccctgattct gtggataacc gtattaccgc ctttgagtga gctgataccg   3900
ctcgccgcag ccgaacgacc gagcgcagcg agtcagtgag cgaggaagcg gaagagcgcc   3960
tgatgcggta ttttctcctt acgcatctgt gcggtatttc acaccgcaat ggtgcactct   4020
cagtacaatc tgctctgatg ccgcatagtt aagccagtat acactccgct atcgctacgt   4080
gactgggtca tggctgcgcc ccgacacccg ccaacacccg ctgacgcgcc ctgacgggct   4140
tgtctgctcc cggcatccgc ttacagacaa gctgtgaccg tctccgggag ctgcatgtgt   4200
cagaggtttt caccgtcatc accgaaacgc gcgaggcagc tgcggtaaag ctcatcagcg   4260
tggtcgtgaa gcgattcaca gatgtctgcc tgttcatccg cgtccagctc gttgagtttc   4320
tccagaagcg ttaatgtctg gcttctgata aagcgggcca tgttaagggc ggttttttcc   4380
tgtttggtca ctgatgcctc cgtgtaaggg ggatttctgt tcatgggggt aatgataccg   4440
atgaaacgag agaggatgct cacgatacgg gttactgatg atgaacatgc ccggttactg   4500
gaacgttgtg agggtaaaca actggcggta tggatgcggc gggaccagag aaaaatcact   4560
cagggtcaat gccagcgctt cgttaataca gatgtaggtg ttccacaggg tagccagcag   4620
catcctgcga tgcagatccg gaacataatg gtgcagggcg ctgacttccg cgtttccaga   4680
ctttacgaaa cacggaaacc gaagaccatt catgttgttg ctcaggtcgc agacgttttg   4740
cagcagcagt cgcttcacgt tcgctcgcgt atcggtgatt cattctgcta accagtaagg   4800
caaccccgcc agcctagccg ggtcctcaac gacaggagca cgatcatgcg cacccgtggc   4860
caggacccaa cgctgcccga gatgcgccgc gtgcggctgc tggagatggc ggacgcgatg   4920
gatatgttct gccaagggtt ggtttgcgca ttcacagttc tccgcaagaa ttgattggct   4980
ccaattcttg gagtggtgaa tccgttagcg aggtgccgcc ggcttccatt caggtcgagg   5040
tggcccggct ccatgcaccg cgacgcaacg cggggaggca gacaaggtat agggcggcgc   5100
ctacaatcca tgccaacccg ttccatgtgc tcgccgaggc ggcataaatc gccgtgacga   5160
tcagcggtcc aatgatcgaa gttaggctgg taagagccgc gagcgatcct tgaagctgtc   5220
cctgatggtc gtcatctacc tgcctggaca gcatggcctg caacgcgggc atcccgatgc   5280
cgccggaagc gagaagaatc ataatgggga aggccatcca gcctcgcgtc gcgaacgcca   5340
gcaagacgta gcccagcgcg tcggccgcca tgccggcgat aatggcctgc ttctcgccga   5400
aacgtttggt ggcgggacca gtgacgaagg cttgagcgag ggcgtgcaag attccgaata   5460
ccgcaagcga caggccgatc atcgtcgcgc tccagcgaaa gcggtcctcg ccgaaaatga   5520
cccagagcgc tgccggcacc tgtcctacga gttgcatgat aaagaagaca gtcataagtg   5580
cggcgacgat agtcatgccc gcgcccacc ggaaggagct gactgggttg aaggctctca   5640
agggcatcgg tcgagatccc ggtgcctaat gagtgagcta acttacatta attgcgttgc   5700
gctcactgcc cgctttccag tcgggaaacc tgtcgtgcca gctgcattaa tgaatcggcc   5760
aacgcgcggg gagaggcggt ttgcgtattg gcgccaggg tggttttttct tttcaccagt   5820
gagacgggca acagctgatt gcccttcacc gcctggccct gagagagttg cagcaagcgg   5880
tccacgctgg tttgccccag caggcgaaaa tcctgtttga tggtggttaa cggcgggata   5940
taacatgagc tgtcttcggt atcgtcgtat cccactaccg agatatccgc accaacgcgc   6000
```

```
agcccggact cggtaatggc gcgcattgcg cccagcgcca tctgatcgtt ggcaaccagc    6060
atcgcagtgg gaacgatgcc ctcattcagc atttgcatgg tttgttgaaa accggacatg    6120
gcactccagt cgccttcccg ttccgctatc ggctgaattt gattgcgagt gagatattta    6180
tgccagccag ccagacgcag acgcgccgag acagaactta atgggcccgc taacagcgcg    6240
atttgctggt gacccaatgc gaccagatgc tccacgccca gtcgcgtacc gtcttcatgg    6300
gagaaaataa tactgttgat gggtgtctgg tcagagacat caagaaataa cgccggaaca    6360
ttagtgcagg cagcttccac agcaatggca tcctggtcat ccagcggata gttaatgatc    6420
agcccactga cgcgttgcgc gagaagattg tgcaccgccg ctttacaggc ttcgacgccg    6480
cttcgttcta ccatcgacac caccacgctg gcacccagtt gatcggcgcg agatttaatc    6540
gccgcgacaa tttgcgacgg cgcgtgcagg gccagactgg aggtggcaac gccaatcagc    6600
aacgactgtt tgcccgccag ttgttgtgcc acgcggttgg gaatgtaatt cagctccgcc    6660
atcgccgctt ccacttttcc ccgcgttttc gcagaaacgt ggctggcctg gttcaccacg    6720
cgggaaacgg tctgataaga gacaccggca tactctgcga catcgtataa cgttactggt    6780
ttcacattca ccaccctgaa ttgactctct tccgggcgct atcatgccat accgcgaaag    6840
gttttgcgcc attcgatggt gtccgggatc tcgacgctct cccttatgcg actcctgcat    6900
taggaagcag cccagtagta ggttgaggcc gttgagcacc gccgccgcaa ggaatggtgc    6960
atgcaaggag atggcgccca acagtccccc ggccacgggg cctgccacca tacccacgcc    7020
gaaacaagcg ctcatgagcc cgaagtggcg agcccgatct tccccatcgg tgatgtcggc    7080
gatataggcg ccagcaaccg cacctgtggc gccggtgatg ccggccacga tgcgtccggc    7140
gtagaggatc gagatctcga tcccgcgaaa ttaatacgac tcactatagg ggaattgtga    7200
gcggataaca attcccctct agaaataatt ttgtttaact ttaagaagga gatatacata    7260
tgcggggttc tcatcatcat catcatcatg gtatggctag catgactggt ggacagcaaa    7320
tgggtcggga tctgtacgac gatgacgata aggatcatcc cttcaccatg                7370
```

<210> SEQ ID NO 166
<211> LENGTH: 578
<212> TYPE: PRT
<213> ORGANISM: Artificial Sequence
<220> FEATURE:
<223> OTHER INFORMATION: Synthetic Construct

<400> SEQUENCE: 166

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

His Pro Phe Thr Met Arg Arg Ser Ala Asn Tyr Glu Pro Asn Ser Trp
        35                  40                  45

Asp Tyr Asp Tyr Leu Leu Ser Ser Asp Thr Asp Glu Ser Ile Glu Val
    50                  55                  60

Tyr Lys Asp Lys Ala Lys Lys Leu Glu Ala Glu Val Arg Arg Glu Ile
65                  70                  75                  80

Asn Asn Glu Lys Ala Glu Phe Leu Thr Leu Leu Glu Leu Ile Asp Asn
                85                  90                  95

Val Gln Arg Leu Gly Leu Gly Tyr Arg Phe Glu Ser Asp Ile Arg Arg
            100                 105                 110

Ala Leu Asp Arg Phe Val Ser Ser Gly Gly Phe Asp Ala Val Thr Lys
        115                 120                 125

-continued

Thr Ser Leu His Ala Thr Ala Leu Ser Phe Arg Leu Leu Arg Gln His
    130                 135                 140

Gly Phe Glu Val Ser Gln Ala Phe Ser Gly Phe Lys Asp Gln Asn
145                 150                 155                 160

Gly Asn Phe Leu Glu Asn Leu Lys Glu Asp Ile Lys Ala Ile Leu Ser
            165                 170                 175

Leu Tyr Glu Ala Ser Phe Leu Ala Leu Glu Gly Glu Asn Ile Leu Asp
                180                 185                 190

Glu Ala Lys Val Phe Ala Ile Ser His Leu Lys Glu Leu Ser Glu Glu
        195                 200                 205

Lys Ile Gly Lys Asp Leu Ala Glu Gln Val Asn His Ala Leu Glu Leu
210                 215                 220

Pro Leu His Arg Arg Thr Gln Arg Leu Glu Ala Val Leu Ser Ile Glu
225                 230                 235                 240

Ala Tyr Arg Lys Lys Glu Asp Ala Asp Gln Val Leu Leu Glu Leu Ala
            245                 250                 255

Ile Leu Asp Tyr Asn Met Ile Gln Ser Val Tyr Gln Arg Asp Leu Arg
                260                 265                 270

Glu Thr Ser Arg Trp Trp Arg Arg Val Gly Leu Ala Thr Lys Leu His
        275                 280                 285

Phe Ala Arg Asp Arg Leu Ile Glu Ser Phe Tyr Trp Ala Val Gly Val
290                 295                 300

Ala Phe Glu Pro Gln Tyr Ser Asp Cys Arg Asn Ser Val Ala Lys Met
305                 310                 315                 320

Phe Ser Phe Val Thr Ile Ile Asp Ile Tyr Asp Val Tyr Gly Thr
            325                 330                 335

Leu Asp Glu Leu Glu Leu Phe Thr Asn Ala Val Glu Arg Trp Asp Val
                340                 345                 350

Asn Ala Ile Asp Asp Leu Pro Asp Tyr Met Lys Leu Cys Phe Leu Ala
        355                 360                 365

Leu Tyr Asn Thr Ile Asn Glu Ile Ala Tyr Asp Asn Leu Lys Glu Lys
370                 375                 380

Gly Glu Asn Ile Leu Pro Tyr Leu Thr Lys Ala Trp Ala Asp Leu Cys
385                 390                 395                 400

Asn Ala Phe Leu Gln Glu Ala Lys Trp Leu Tyr Asn Lys Ser Thr Pro
            405                 410                 415

Thr Phe Asp Glu Tyr Phe Gly Asn Ala Trp Lys Ser Ser Gly Pro
                420                 425                 430

Leu Gln Leu Val Phe Ala Tyr Phe Ala Val Val Gln Asn Ile Lys Lys
        435                 440                 445

Glu Glu Ile Glu Asn Leu Gln Lys Tyr His Asp Ile Ile Ser Arg Pro
450                 455                 460

Ser His Ile Phe Arg Leu Cys Asn Asp Leu Ala Ser Ala Ser Ala Glu
465                 470                 475                 480

Ile Ala Arg Gly Glu Thr Ala Asn Ser Val Ser Cys Tyr Met Arg Thr
            485                 490                 495

Lys Gly Ile Ser Glu Glu Leu Ala Thr Glu Ser Val Met Asn Leu Ile
                500                 505                 510

Asp Glu Thr Trp Lys Lys Met Asn Lys Glu Lys Leu Gly Gly Ser Leu
        515                 520                 525

Phe Ala Lys Pro Phe Val Glu Thr Ala Ile Asn Leu Ala Arg Gln Ser
530                 535                 540

His Cys Thr Tyr His Asn Gly Asp Ala His Thr Ser Pro Asp Glu Leu
545                 550                 555                 560

```
Thr Arg Lys Arg Val Leu Ser Val Ile Thr Glu Pro Ile Leu Pro Phe
            565                 570                 575
Glu Arg

<210> SEQ ID NO 167
<211> LENGTH: 7370
<212> TYPE: DNA
<213> ORGANISM: Artificial Sequence
<220> FEATURE:
<223> OTHER INFORMATION: Synthetic Construct

<400> SEQUENCE: 167
cgtcgttctg cgaactacga acctaacagc tgggactatg attacctgct gtcctccgac      60
acggacgagt ccatcgaagt atacaaagac aaagcgaaaa agctggaagc cgaagttcgt     120
cgcgagatta ataacgaaaa agcagaattt ctgaccctgc tggaactgat tgacaacgtc     180
cagcgcctgg gctgggtta ccgtttcgag tctgatatcc gtcgtgcgct ggatcgcttc      240
gtttcctccg gcggcttcga tgcggtaacc aagacttccc tgcacgcgac ggcactgtct     300
ttccgtctgc tgcgtcaaca cggttttgag gtttctcagg aagcgttcag cggcttcaaa     360
gaccaaaacg gcaacttcct ggagaacctg aaggaagata tcaaagctat cctgagcctg     420
tacgaggcca gcttcctggc tctggaaggc gaaacatcc tggacgaggc gaaggttttc      480
gcaatctctc atctgaaaga actgtctgaa gaaaagatcg gtaaagatct ggcagaacag     540
gtgaaccatg cactggaact gccactgcat cgccgtactc agcgtctgga agcagtactg     600
tctatcgagg cctaccgtaa aaaggaggac gcggatcagg ttctgctgga gctggcaatt     660
ctggattaca acatgatcca gtctgtatac agcgtgatc tgcgtgaaac gtcccgttgg      720
tggcgtcgtg tgggtctggc gaccaaactg cactttgctc gtgaccgcct gattgagagc     780
ttctactggg ccgtgggtgt agcattcgaa ccgcaatact ccgactgccg taactccgtc     840
gcaaaaatgt tttctttcgt aaccattatc gacgatatct acgatgtata cggcaccctg     900
gacgaactgg agctgtttac taacgcagtt gagcgttggg acgtaaacgc catcgacgat     960
ctgccggatt acatgaaact gtgctttctg gctctgtata acactattaa cgaaatcgcc    1020
tacgacaacc tgaaagaaaa aggtgagaac atcctgccgt atctgaccaa agcctgggct    1080
gacctgtgca acgcttttct gcaagaagcc aagtggctgt acaacaaatc tactccgacc    1140
tttgacgaat acttcggcaa cgcatggaaa tcctcttctg gcccgctgca actggtgttc    1200
gcttacttcg ctgtcgtgca gaacattaaa aggaagaga tcgaaaacct gcaaaaatac     1260
catgacatca tctctcgtcc ttcccatatc ttccgtctgt gcaatgacct ggctagcgcg    1320
tctgcggaaa ttgcgcgtgg tgaaaccgca aatagcgttt cttgttacat gcgcactaaa    1380
ggtatctccg aagaactggc taccgaaagc gtgatgaatc tgatcgatga aacctggaaa    1440
aagatgaaca aggaaaaact gggtggtagc ctgttcgcga aaccgttcgt ggaaaccgcg    1500
atcaacctgg cacgtcaatc tcactgcact tatcataacg cgacgcgca tacctctccg     1560
gatgagctga cccgcaaacg cgttctgtct gtaatcactg aaccgattct gccgtttgaa    1620
cgctaaaagg gcgagctcaa cgatccggct gctaacaaag cccgaaagga agctgagttg    1680
gctgctgcca ccgctgagca ataactagca taaccccttg ggcctctaa acgggtcttg    1740
aggagttttt tgctgaaagg aggaactata tccggatatc ccgcaagagg cccggcagta    1800
ccggcataac caagcctatg cctacagcat ccagggtgac ggtgccgagg atgacgatga    1860
gcgcattgtt agatttcata cacggtgcct gactgcgtta gcaatttaac tgtgataaac    1920
```

```
taccgcatta aagcttatcg atgataagct gtcaaacatg agaattaatt cttgaagacg   1980
aaagggcctc gtgatacgcc tattttata ggttaatgtc atgataataa tggtttctta    2040
gacgtcaggt ggcacttttc ggggaaatgt gcgcggaacc cctatttgtt tattttcta    2100
aatacattca aatatgtatc cgctcatgag acaataaccc tgataaatgc ttcaataata   2160
ttgaaaaagg aagagtatga ttaacaaga tggattgcac gcaggttctc cggccgcttg    2220
ggtggagagg ctattcggct atgactgggc acaactgaca atcggctgct ctgatgccgc   2280
cgtgttccgg ctgtcagcgc agggggcgccc ggttcttttt gtcaagaccg acctgtccgg  2340
tgccctgaat gaactgcagg acgaggcagc gcggctatcg tggctggcca cgacgggcgt   2400
tccttgcgca gctgtgctcg acgttgtcac tgaagcggga agggactggc tgctattggg   2460
cgaagtgccg gggcaggatc tcctgtcatc tcaccttgct cctgccgaga agtatccat    2520
catggctgat gcaatgcggc ggctgcatac gcttgatccg gctacctgcc cattcgacca   2580
ccaagcgaaa catcgcatcg agcgggcacg tactcggatg gaagccggtc ttgtcgatca   2640
ggatgatctg gacgaagagc atcaggggct cgcgccagcc gaactgttcg ccaggctcaa   2700
ggcgcgcatg cccgacggcg aggatctcgt cgtgacacat ggcgatgcct gcttgccgaa   2760
tatcatggtg gaaaatggcc gcttttctgg attcatcgac tgtggccggc tgggtgtggc   2820
ggaccgctat caggacatag cgttggctac ccgtgatatt gctgaagagc ttggcggcga   2880
atgggctgac cgcttcctcg tgctttacgg tatcgccgct cccgattcgc agcgcatcgc   2940
cttctatcgc cttcttgacg agttcttctg agcgggactc tggggttcga atgaccgac   3000
caagcgacgc ctaactgtca gaccaagttt actcatatat actttagatt gatttaaaac   3060
ttcatttta atttaaaagg atctaggtga agatcctttt tgataatctc atgaccaaaa    3120
tcccttaacg tgagttttcg ttccactgag cgtcagaccc cgtagaaaag atcaaaggat   3180
cttcttgaga tcctttttt ctgcgcgtaa tctgctgctt gcaaacaaaa aaaccaccgc    3240
taccagcggt ggtttgtttg ccggatcaag agctaccaac tctttttccg aaggtaactg   3300
gcttcagcag agcgcagata ccaaatactg tccttctagt gtagccgtag ttaggccacc   3360
acttcaagaa ctctgtagca ccgcctacat acctcgctct gctaatcctg ttaccagtgg   3420
ctgctgccag tggcgataag tcgtgtctta ccgggttgga ctcaagacga tagttaccgg   3480
ataaggcgca gcggtcgggc tgaacggggg gttcgtgcac acagcccagc ttggagcgaa   3540
cgacctacac cgaactgaga tacctacagc gtgagctatg agaaagcgcc acgcttcccg   3600
aagggagaaa ggcggacagg tatccggtaa gcggcagggt cggaacagga gagcgcacga   3660
gggagcttcc agggggaaac gcctggtatc tttatagtcc tgtcgggttt cgccacctct   3720
gacttgagcg tcgatttttg tgatgctcgt caggggggcg gagcctatgg aaaaacgcca   3780
gcaacgcggc cttttacgg ttcctggcct tttgctggcc ttttgctcac atgttctttc    3840
ctgcgttatc ccctgattct gtggataacc gtattaccgc ctttgagtga gctgataccg   3900
ctcgccgcag ccgaacgacc gagcgcagcg agtcagtgag cgaggaagcg gaagagcgcc   3960
tgatgcggta ttttctcctt acgcatctgt gcggtatttc acaccgcaat ggtgcactct   4020
cagtacaatc tgctctgatg ccgcatagtt aagccagtat acactccgct atcgctacgt   4080
gactgggtca tggctgcgcc ccgacacccg ccaacacccg ctgacgcgcc ctgacgggct   4140
tgtctgctcc cggcatccgc ttacagacaa gctgtgaccg tctccgggag ctgcatgtgt   4200
cagaggtttt caccgtcatc accgaaacgc gcgaggcagc tgcggtaaag ctcatcagcg   4260
tggtcgtgaa gcgattcaca gatgtctgcc tgttcatccg cgtccagctc gttgagtttc   4320
```

```
tccagaagcg ttaatgtctg gcttctgata aagcgggcca tgttaagggc ggttttttcc    4380
tgtttggtca ctgatgcctc cgtgtaaggg ggatttctgt tcatggggt  aatgataccg    4440
atgaaacgag agaggatgct cacgatacgg gttactgatg atgaacatgc ccggttactg    4500
gaacgttgtg agggtaaaca actggcgta  tggatgcggc gggaccagag aaaaatcact    4560
cagggtcaat gccagcgctt cgttaataca gatgtaggtg ttccacaggg tagccagcag    4620
catcctgcga tgcagatccg gaacataatg gtgcagggcg ctgacttccg cgtttccaga    4680
ctttacgaaa cacggaaacc gaagaccatt catgttgttg ctcaggtcgc agacgttttg    4740
cagcagcagt cgcttcacgt tcgctcgcgt atcggtgatt cattctgcta accagtaagg    4800
caaccccgcc agcctagccg ggtcctcaac gacaggagca cgatcatgcg cacccgtggc    4860
caggacccaa cgctgcccga gatgcgccgc gtgcggctgc tggagatggc ggacgcgatg    4920
gatatgttct gccaagggtt ggtttgcgca ttcacagttc tccgcaagaa ttgattggct    4980
ccaattcttg gagtggtgaa tccgttagcg aggtgccgcc ggcttccatt caggtcgagg    5040
tggcccggct ccatgcaccg cgacgcaacg cggggaggca gacaaggtat agggcggcgc    5100
ctacaatcca tgccaacccg ttccatgtgc tcgccgaggc ggcataaatc gccgtgacga    5160
tcagcggtcc aatgatcgaa gttaggctgg taagagccgc gagcgatcct tgaagctgtc    5220
cctgatggtc gtcatctacc tgcctggaca gcatggcctg caacgcgggc atcccgatgc    5280
cgccggaagc gagaagaatc ataatgggga aggccatcca gcctcgcgtc gcgaacgcca    5340
gcaagacgta gcccagcgcg tcggccgcca tgccggcgat aatggcctgc ttctcgccga    5400
aacgtttggt ggcgggacca gtgacgaagg cttgagcgag ggcgtgcaag attccgaata    5460
ccgcaagcga caggccgatc atcgtcgcgc tccagcgaaa gcggtcctcg ccgaaaatga    5520
cccagagcgc tgccggcacc tgtcctacga gttgcatgat aaagaagaca gtcataagtg    5580
cggcgacgat agtcatgccc cgcgcccacc ggaaggagct gactgggttg aaggctctca    5640
agggcatcgg tcgagatccc ggtgcctaat gagtgagcta acttacatta attgcgttgc    5700
gctcactgcc cgctttccag tcgggaaacc tgtcgtgcca gctgcattaa tgaatcggcc    5760
aacgcgcggg gagaggcggt ttgcgtattg ggcgccaggg tggttttttct tttcaccagt    5820
gagacgggca acagctgatt gcccttcacc gcctggccct gagagagttg cagcaagcgg    5880
tccacgctgg tttgccccag caggcgaaaa tcctgtttga tggtggttaa cggcgggata    5940
taacatgagc tgtcttcggt atcgtcgtat cccactaccg agatatccgc accaacgcgc    6000
agcccggact cggtaatggc gcgcattgcg cccagcgcca tctgatcgtt ggcaaccagc    6060
atcgcagtgg gaacgatgcc ctcattcagc atttgcatgg tttgttgaaa accggacatg    6120
gcactccagt cgccttcccg ttccgctatc ggctgaattt gattgcgagt gagatattta    6180
tgccagccag ccagacgcag acgcgccgag acagaactta atgggcccgc taacagcgcg    6240
atttgctggt gacccaatgc gaccagatgc tccacgccca gtcgcgtacc gtcttcatgg    6300
gagaaaataa tactgttgat gggtgtctgg tcagagacat caagaaataa cgccggaaca    6360
ttagtgcagg cagcttccac agcaatggca tcctggtcat ccagcggata gttaatgatc    6420
agcccactga cgcgttgcgc gagaagattg tgcaccgccg ctttacaggc ttcgacgccg    6480
cttcgttcta ccatcgacac caccacgctg cacccagtt  gatcggcgcg agatttaatc    6540
gccgcgacaa tttgcgacgg cgcgtgcagg gccagactgg aggtggcaac gccaatcagc    6600
aacgactgtt tgcccgccag ttgttgtgcc acgcggttgg gaatgtaatt cagctccgcc    6660
atcgccgctt ccactttttc ccgcgttttc gcagaaacgt ggctggcctg gttcaccacg    6720
```

```
cgggaaacgg tctgataaga gacaccggca tactctgcga catcgtataa cgttactggt    6780
ttcacattca ccaccctgaa ttgactctct tccgggcgct atcatgccat accgcgaaag    6840
gttttgcgcc attcgatggt gtccgggatc tcgacgctct cccttatgcg actcctgcat    6900
taggaagcag cccagtagta ggttgaggcc gttgagcacc gccgccgcaa ggaatggtgc    6960
atgcaaggag atggcgccca acagtccccc ggccacgggg cctgccacca tacccacgcc    7020
gaaacaagcg ctcatgagcc cgaagtggcg agcccgatct tccccatcgg tgatgtcggc    7080
gatataggcg ccagcaaccg cacctgtggc gccggtgatg ccggccacga tgcgtccggc    7140
gtagaggatc gagatctcga tcccgcgaaa ttaatacgac tcactatagg ggaattgtga    7200
gcggataaca attcccctct agaaataatt ttgtttaact ttaagaagga gatatacata    7260
tgcggggttc tcatcatcat catcatcatg gtatggctag catgactggt ggacagcaaa    7320
tgggtcggga tctgtacgac gatgacgata aggatcatcc cttcaccatg                7370
```